US012780820B2

(12) United States Patent
Xu et al.

(10) Patent No.: US 12,780,820 B2
(45) Date of Patent: *Nov. 3, 2026

(54) 3-(1H-IMIDAZOL-2-YL)-2,3,8,8A-TETRAHYDROINDOLIZIN-5(1H)-ONE DERIVATIVES USEFUL AS FACTOR XIA INHIBITORS

(71) Applicant: JANSSEN PHARMACEUTICA NV, Beerse (BE)

(72) Inventors: Guozhang Xu, Spring House, PA (US); Micheal D. Gaul, Spring House, PA (US); Tho V. Thieu, Spring House, PA (US); Jing Zhang, Spring House, PA (US); Mark Wall, Spring House, PA (US); Ling Hua Gao, Spring House, PA (US); Bin Zhu, Spring House, PA (US); Tianbao Lu, Spring House, PA (US); Boying Guo, Spring House, PA (US); Zhijie Liu, Spring House, PA (US); Ravi Nargund, Spring House, PA (US); Mark J. Macielag, Spring House, PA (US)

(73) Assignee: Janssen Pharmaceutica NV, Beerse (BE)

( * ) Notice: Subject to any disclaimer, the term of this patent is extended or adjusted under 35 U.S.C. 154(b) by 771 days.

This patent is subject to a terminal disclaimer.

(21) Appl. No.: 18/006,197

(22) PCT Filed: Jul. 22, 2021

(86) PCT No.: PCT/US2021/042693

§ 371 (c)(1),
(2) Date: Jan. 20, 2023

(87) PCT Pub. No.: WO2022/020546

PCT Pub. Date: Jan. 27, 2022

(65) Prior Publication Data

US 2023/0295157 A1 Sep. 21, 2023

Related U.S. Application Data

(60) Provisional application No. 63/054,826, filed on Jul. 22, 2020.

(51) Int. Cl.

| | |
|---|---|
| ***C07D 471/04*** | (2006.01) |
| ***A61K 31/437*** | (2006.01) |
| ***A61P 7/02*** | (2006.01) |
| ***C07D 487/04*** | (2006.01) |
| ***C07D 519/00*** | (2006.01) |
| ***C07F 9/6561*** | (2006.01) |

(52) U.S. Cl.

CPC .............. *C07D 471/04* (2013.01); *A61P 7/02* (2018.01); *C07D 487/04* (2013.01); *C07D 519/00* (2013.01); *C07F 9/6561* (2013.01); *C07B 2200/05* (2013.01)

(58) Field of Classification Search

CPC ............................ C07D 471/04; A61K 31/437
USPC .......................................... 546/112; 514/299
See application file for complete search history.

(56) References Cited

U.S. PATENT DOCUMENTS

| | | | |
|---|---|---|---|
| 4,808,405 | A | 2/1989 | Smith et al. |
| 4,845,079 | A | 7/1989 | Luly et al. |
| 4,885,292 | A | 12/1989 | Ryono et al. |
| 4,894,437 | A | 1/1990 | Tenbrink |
| 4,980,283 | A | 12/1990 | Huang et al. |
| 5,034,512 | A | 7/1991 | Hudspeth et al. |
| 5,036,053 | A | 7/1991 | Himmelsbach et al. |
| 5,036,054 | A | 7/1991 | Kaltenbronn et al. |
| 5,055,466 | A | 10/1991 | Weller et al. |
| 5,063,207 | A | 11/1991 | Doherty et al. |
| 5,063,208 | A | 11/1991 | Rosenberg et al. |
| 5,064,965 | A | 11/1991 | Ocain et al. |
| 5,066,643 | A | 11/1991 | Abeles et al. |
| 5,071,837 | A | 12/1991 | Doherty et al. |
| 5,075,451 | A | 12/1991 | Ocain et al. |
| 5,089,471 | A | 2/1992 | Hanson et al. |
| 5,095,119 | A | 3/1992 | Ocain et al. |
| 5,098,924 | A | 3/1992 | Poss |
| 5,104,869 | A | 4/1992 | Albright et al. |
| 5,106,835 | A | 4/1992 | Albright et al. |

(Continued)

FOREIGN PATENT DOCUMENTS

| | | | |
|---|---|---|---|
| CN | 103987697 | A | 8/2014 |
| CN | 104136431 | A | 11/2014 |

(Continued)

OTHER PUBLICATIONS

Pubchem Compound Summary for CID 146247689, 2-[4-[2-[(3S)-7-[5-chloro-2-(tetrazol-1-yl)phenyl]-5-oxo-2,3,8,8a-tetrahydro-1H-indolizin-3-yl]-1H-imidazol-5-yl]phenyl]acetic acida, PubChem, Create Date Jun. 27, 2020, https://pubchem.ncbi.nlm.nih.gov/compound/146247689 (Year: 2020).*
Bernatowicz et al., "Development of Potent Thrombin Receptor Antagonist Peptides", J. Med. Chem., 1996, vol. 39, 4879-4887.
Chou, "Theoretical Basis, Experimental Design, and Computerized Simulation of Synergism and Antagonism in Drug Combination Studies", Pharmacol. Rev., 2006, vol. 58, 621-681.
Database Pubchem, Database accession No. 153061176, Aug. 13, 2018, 9 pages.

(Continued)

*Primary Examiner* — Charanjit Aulakh

(57) ABSTRACT

The present invention is directed to 3-(1H-imidazol-2-yl)-2,3,8,8a-tetrahydroindolizin-5(1H)-one derivatives, stereoisomers, isotopologues, and pharmaceutically acceptable salts thereof, pharmaceutical compositions containing said compounds and the use of said compounds in the treatment and/or prophylaxis of thromboembolic disorders, inflammatory disorders and diseases or conditions in which plasma kallikrein activity is implicated.

14 Claims, No Drawings

(56) References Cited

U.S. PATENT DOCUMENTS

| | | | |
|---|---|---|---|
| 5,114,937 | A | 5/1992 | Hamby et al. |
| 5,116,835 | A | 5/1992 | Ruger et al. |
| 6,063,847 | A | 5/2000 | Chackalamannil et al. |
| 6,326,380 | B1 | 12/2001 | Chackalamannil et al. |
| 6,645,987 | B2 | 11/2003 | Chackalamannil et al. |
| 7,037,920 | B2 | 5/2006 | Chackalamannil et al. |
| 7,235,567 | B2 | 6/2007 | Wu |
| 7,304,078 | B2 | 12/2007 | Chackalamannil et al. |
| 7,713,999 | B2 | 5/2010 | Chackalamannil et al. |
| 9,944,625 | B2 | 4/2018 | Orwat et al. |
| 2006/0154915 | A1 | 7/2006 | Corte et al. |
| 2014/0275061 | A1 | 9/2014 | Orwat et al. |
| 2016/0185773 | A1 | 6/2016 | Edwards et al. |
| 2017/0305880 | A1 | 10/2017 | Orwat et al. |
| 2017/0305917 | A1 | 10/2017 | Courtney et al. |
| 2023/0312560 | A1 | 10/2023 | Xu et al. |

FOREIGN PATENT DOCUMENTS

| | | | |
|---|---|---|---|
| EP | 0028489 | A1 | 5/1981 |
| EP | 1495028 | A1 | 1/2005 |
| EP | 1294714 | B1 | 8/2007 |
| EP | 1495018 | B1 | 11/2007 |
| EP | 3290413 | A1 | 3/2018 |
| JP | 2017218449 | A | 12/2017 |
| WO | 94/03479 | A1 | 2/1994 |
| WO | 0129050 | A2 | 4/2001 |
| WO | 01/40231 | A1 | 6/2001 |
| WO | 01/96330 | A2 | 12/2001 |
| WO | 03/89435 | A1 | 10/2003 |
| WO | 2009124167 | A1 | 10/2009 |
| WO | 2013/055984 | A1 | 4/2013 |
| WO | 2014022767 | A1 | 2/2014 |
| WO | 2016093285 | A1 | 6/2016 |
| WO | 2017019819 | A1 | 2/2017 |
| WO | 2017023992 | A1 | 2/2017 |

OTHER PUBLICATIONS

Gailani et al., "Intrinsic Pathway of Coagulation and Arterial Thrombosis", Arterioscler. Thromb. Vasc. Biol., 2007, 27, 2507-2513.

Hoffman, "A cell-based model of coagulation and the role of factor Vlla", Blood Reviews, 2003, 17, S1-S5.

Howard et al., "Factor Ixa Inhibitors as Novel Anticoagulents", Arterioscler Thromb Vase Biol., 2007, 27, 722-727.

PubChem CID-146247689, "2-[4-[2-[(3S)-7-[5-chloro-2-(tetrazol-1-yl)phenyl]-5-oxo-2,3,8,8a-tetrahydro-1H-indolizin-3-yl]-1H-imidazol-5-yl]phenyl] acetic acid", Jun. 27, 2022, 9 Pages.

Quan et al., "Factor Xla Inhibitors as New Anticoagulant", J. Med. Chem., 2018, vol. 61, 7425-7447.

Xie et al., "Discovery and development of plasma kallikrein inhibitors for multiple diseases", European Journal of Medicinal Chemistry, 2020, 190, 112137.

Hanessian et al., "Synthesis of Diversely Functionalized Indolizidinones and Related Bicyclic Lactams Using Intramolecular Grubbs Olefin Metathesis and Dieckmann Condensation", The Journal of Organic Chemistry, vol. 68, No. 19, pp. 7219-7233, Sep. 19, 2003.

International Search Report and Written Opinion, received for PCT Application No. PCT/US2021/042693, mailed on Oct. 6, 2021, 15 pages.

International Search Report and Written Opinion, received for PCT Application No. PCT/EP2021/070430, mailed on Sep. 24, 2021, 13 pages.

Wong et al., "Nonpeptide Factor Xa Inhibitors III: Effects of Dpc423, an Orally-active Pyrazole Antithrombotic Agent, on Arterial Thrombosis in Rabbits", Journal of Pharmacology and Experimental Therapeutics, vol. 303, No. 03, pp. 993-1000, 2002.

Xiaoyong et al., "The Antithrombin Activity Detection of Eh in Vitro", China Biotechnology, vol. 31, No. 5, pp. 108-112, 2011. (English Abstract Attached).

* cited by examiner

3-(1H-IMIDAZOL-2-YL)-2,3,8,8A-TETRAHYDROINDOLIZIN-5(1H)-ONE DERIVATIVES USEFUL AS FACTOR XIA INHIBITORS

CROSS-REFERENCE TO RELATED APPLICATIONS

This application is the National Stage Application of International Patent Application No. PCT/US2021/042693, filed Jul. 22, 2021, which claims the benefit of U.S. Provisional Application No. 63/054,826, filed on Jul. 22, 2020, which is incorporated by reference herein in its entirety.

FIELD OF THE INVENTION

The present invention is directed 3-(1H-imidazol-2-yl)-2,3,8,8a-tetrahydroindolizin-5(1H)-one derivatives, stereoisomers, isotopologues, and pharmaceutically acceptable salts thereof, pharmaceutical compositions containing said compounds, and the use of said compounds in the treatment and/or prophylaxis of thromboembolic disorders, inflammatory disorders and diseases or conditions in which plasma kallikrein activity is implicated.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin inhibits the post-translational maturation of coagulation factors VII, IX, X and prothrombin, and has proven effective in both venous and arterial thrombosis. However, its usage is limited due to its narrow therapeutic index with respect to bleeding safety, slow onset of therapeutic effect, numerous dietary and drug-drug interactions, and a need for monitoring and dose adjustment. Novel oral anticoagulants directly targeting either thrombin or factor Xa, e.g., dabigatran, apixaban, betrixaban, edoxaban, rivaroxaban, have been approved for both venous and arterial indications. However, the risk of bleeding is not completely eliminated, and can be as high as 2-3% per year in patients with atrial fibrillation (Quan et al., J. Med. Chem. 2018, pp 7425-7447, Vol. 61). Thus, discovering and developing safe and efficacious oral anticoagulants with minimal impacts on hemostasis for the prevention and treatment of a wide range of thromboembolic disorders has become increasingly important.

SUMMARY OF THE INVENTION

The present invention is directed to compounds of formula (I)

(I)

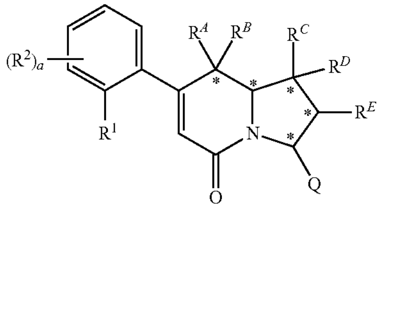

wherein $R^1$ is selected from the group consisting of halogen, hydroxy, $C_{1-4}$alkyl, fluorinated $C_{1-4}$ alkyl, $C_{1-4}$alkoxy, fluorinated $C_{1-4}$alkoxy, cyano, nitro, —$NR^AR^B$, —C(O)—$C_{1-4}$alkyl, $C_{3-6}$cycloalkyl, phenyl and 5 to 6 membered heterocycyl;

wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —$NR^AR^B$, —($C_{1-4}$alkyl)-$NR^AR^B$, $C_{3-7}$cycloalkyl and 5 to 6 membered heterocyclyl; and wherein $R^A$ and $R^B$ are each independently selected from the group consisting of hydrogen and $C_{1-4}$alkyl;

a is an integer from 0 to 3;

each $R^2$ is independently selected from the group consisting of chloro, fluoro, methyl and methoxy;

$R^A$ and $R^B$ are each independently selected from the group consisting of hydrogen and halogen; alternatively, $R^A$ and $R^B$ are taken together with the carbon atom to which they are bound to form oxo;

$R^C$ is selected from the group consisting of hydrogen and $C_{1-4}$alkyl;

$R^D$ is selected from the group consisting of hydrogen, $C_{1-4}$alkyl and $C_{1-4}$alkoxy;

$R^E$ is selected from the group consisting of hydrogen and $C_{1-4}$alkyl;

Q is selected from the group consisting of (a)

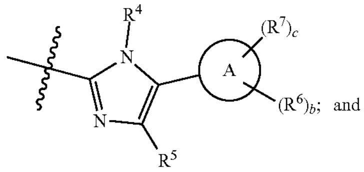

and (b)

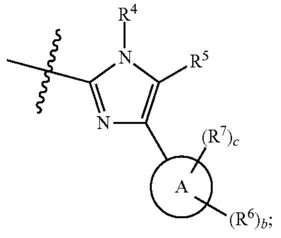

;

wherein $R^4$ is selected from the group consisting of hydrogen and $C_{1-4}$alkyl;

$R^5$ is selected from the group consisting of hydrogen, halogen and $C_{1-4}$alkyl;

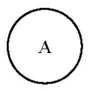

is selected from the group consisting of phenyl, 5-6 membered heteroaryl, and 9 to 10 membered heterocyclyl;

b is an integer from 0 to 1;

$R^8$ is selected from the group consisting of $C_{3-6}$cycloalkyl, —O—($C_{1-2}$alkylene)-$C_{3-8}$cycloalkyl, —C(O)—($C_{3-8}$cycloalkyl), —NH—($C_{3-8}$cycloalkyl), —NH—C(O)—($C_{3-8}$cycloalkyl), —C(O)—NH—($C_{3-6}$cycloalkyl), 4-6 membered heterocycloalkyl, —O—($C_{1-2}$alkylene)-(4-6 membered heterocycloalkyl), —C(O)-(4-6 membered heterocycloalkyl), —NH-(4-6 membered heterocycloalkyl), —C(O)—NH-(4-6 membered heterocycloalkyl), —NH—C(O)-(4-6 membered heterocycloalkyl), 5-6 membered heteroaryl, —O—($C_{1-2}$alkylene)-(5-6 membered heteroaryl), —C(O)-(5-6 membered heteroaryl), —NH-(5-6 membered heteroaryl), —NH—C(O)-(5-6 membered heteroaryl), —C(O)—NH-(5-6 membered heteroaryl), 2-oxa-6-azaspiro[3.3]hept-6-yl, 6-oxa-2-azaspiro[3.4]octan-2-yl, and 7-oxa-2-azaspiro[3.5]nonan-2-yl;

wherein the $C_{3-6}$cycloalkyl, 4-6 membered heterocycloalkyl, or 5-6 membered heteroaryl, whether alone or as part of a substituent group is optionally substituted with one or more substituents independently selected from the group consisting of halogen, $C_{1-4}$alkyl, hydroxy, oxo, cyano and $NR^PR^Q$; wherein $R^P$ and $R^Q$ are each independently selected from the group consisting of hydrogen and $C_{1-4}$alkyl;

c is an integer from 0 to 3;

each $R^7$ is independently selected from the group consisting of halogen, $C_{1-4}$alkyl, fluorinated $C_{1-4}$alkyl, hydroxy substituted $C_{1-6}$alkyl, hydroxy substituted fluorinated $C_{1-4}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-8}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-4}$alkyl), —C(O)—$NR^K$—$SO_2$—($C_{1-2}$alkyl), —($C_{1-2}$alkylene)-O—P(O)$(OH)_2$, and —($C_{1-2}$alkylene)-O—($C_{1-2}$alkylene)-P(O)$(OH)_2$; wherein $R^K$ and $R^L$ are each independently selected from hydrogen and $C_{1-4}$alkyl;

and wherein the heterocycyl, heteroaryl or heterocycloalkyl present as any part of the

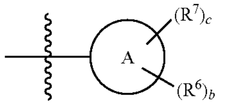

group contains a nitrogen atom, then said heterocyclyl, heteroaryl or heterocycloalkyl may be further substituted to form an N-oxide;

provided that when $R^1$ is 1,2,3,4-tetrazol-1-yl, a is 2, and the two $R^2$ groups are 2-fluoro and 3-chloro, then Q is other than (a)

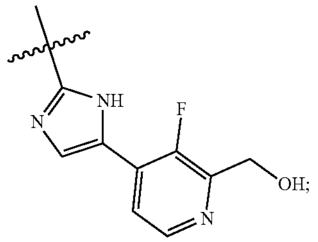

(b)

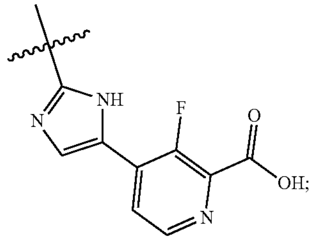

or (c)

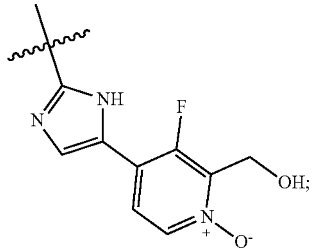

and tautomers, stereoisomers, isotopologues, and pharmaceutically acceptable salts thereof.

The present invention is further directed to a compound of formula (II)

(II)

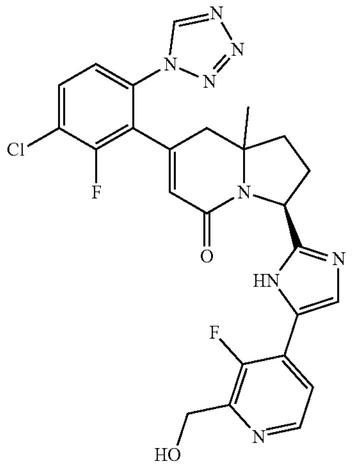

also known as (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-8a-methyl-2,3,8,8a-tetrahydroindolizin-5(1H)-one; and tautomers, stereoisomers, isotopologues, and pharmaceutically acceptable salts thereof.

The present invention is further directed to a compound of formula (III)

(III)

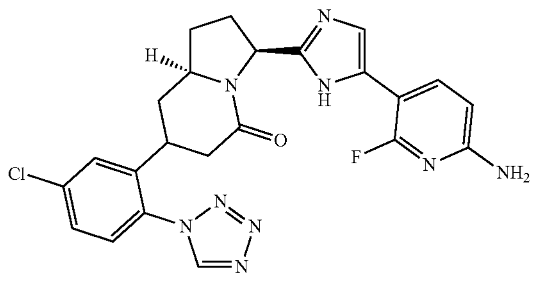

also known as (3S,8aR)-3-(5-(6-amino-2-fluoropyridin-3-yl)-1H-imidazol-2-yl)-7-(5-chloro-2-(1H-tetrazol-1-yl)phenyl)hexahydroindolizin-5(1H)-one; and tautomers, stereoisomers, isotopologues, and pharmaceutically acceptable salts thereof.

The present invention is further directed to a compound of formula (IV)

(IV)

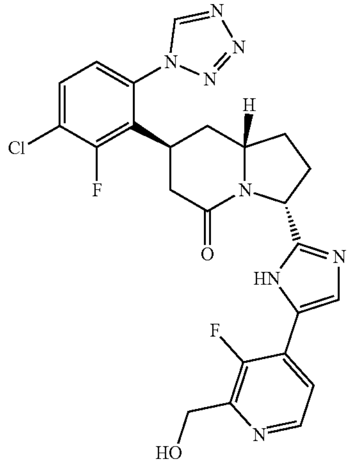

also known as (3S,7R,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)hexahydroindolizin-5(1H)-one: and tautomers, stereoisomers, isotopologues, and pharmaceutically acceptable salts thereof.

The present invention is further directed to processes for the preparation of the compounds of formula (I), compounds of formula (II), compounds of formula (III) and compounds of formula (IV). The present invention is further directed to a compound of formula (I), compound of formula (II), compound of formula (III) or compound of formula (IV) prepared according to any of the process(es) described herein.

Illustrative of the invention are pharmaceutical compositions comprising a pharmaceutically acceptable carrier and a compound of formula (I), compound of formula (II), compound of formula (III) or compound of formula (IV) as described herein. An illustration of the invention is a pharmaceutical composition made by mixing a compound of formula (I), compound of formula (II), compound of formula (III) or compound of formula (IV) as described herein and a pharmaceutically acceptable carrier. Illustrating the invention is a process for making a pharmaceutical composition comprising mixing a compound of formula (I), compound of formula (II), compound of formula (III) or compound of formula (IV) as described herein and a pharmaceutically acceptable carrier.

Exemplifying the invention are methods for the treatment and/or prophylaxis of thromboembolic disorders, inflammatory disorders or diseases or conditions in which plasma kallikrein activity is implicated, as described herein, comprising administering to a subject in need thereof a therapeutically effective amount of any of the compounds or pharmaceutical compositions described above.

Exemplifying the invention are methods or the treatment and/or prophylaxis of thromboembolic disorders, such as arterial cardiovascular thromboembolic disorders, venous cardiovascular thromboembolic disorders, arterial cerebrovascular thromboembolic disorders, and venous cerebrovascular thromboembolic disorders, comprising administering to a subject in need thereof a therapeutically effective amount of any of the compounds or pharmaceutical compositions described above. Examples of thromboembolic disorders include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In an embodiment, the present invention is directed to a compound of formula (I), compound of formula (II), compound of formula (III) or compound of formula (IV) for use as a medicament. In another embodiment, the present invention is directed to a compound of formula (I), compound of formula (II), compound of formula (III) or compound of formula (IV) for use in the treatment and/or prophylaxis of thromboembolic disorders, inflammatory disorders or diseases or conditions in which plasma kallikrein activity is implicated.

In another embodiment, the present invention is directed to a compound of formula (I), compound of formula (II), compound of formula (III) or compound of formula (IV) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a compound of formula (I), compound of formula (II), compound of formula (III) or compound of formula (IV) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention is directed to a compound of formula (I), compound of formula (II), compound of formula (III) or compound of formula (IV) for use in the treatment and/or prophylaxis of a thromboembolic disorder selected from the group consisting of hereditary angioedema (HAE) and diabetic macular edema (DME).

In another embodiment, the present invention is directed to a composition comprising a compound of formula (I), compound of formula (II), compound of formula (III) or compound of formula (IV) for use in the treatment and/or prophylaxis of a disorder, disease or condition as described herein. In another embodiment, the present invention is directed to a composition comprising a compound of formula (I), compound of formula (II), compound of formula (III) or compound of formula (IV) for use in the treatment and/or prophylaxis of a thromboembolic disorder, and inflammatory disorder or a disease or condition in which plasma kallikrein activity is implicated.

In another embodiment, the present invention is directed to a composition comprising a compound of formula (I), compound of formula (II), compound of formula (III) or compound of formula (IV) for use in the treatment and/or prophylaxis of a thromboembolic disorder, such as arterial cardiovascular thromboembolic disorders, venous cardiovascular thromboembolic disorders, arterial cerebrovascular thromboembolic disorders, and venous cerebrovascular thromboembolic disorders. In another embodiment, the present invention is directed to a composition comprising a compound of formula (I), compound of formula (II), compound of formula (III) or compound of formula (IV) for use in the treatment and/or prophylaxis of a thromboembolic disorder selected from the group consisting of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention is directed to a composition comprising a compound of formula (I), compound of formula (II), compound of formula (III) or compound of formula (IV) for use in the treatment and/or prophylaxis of a thromboembolic disorder such as hereditary angioedema (HAE) or diabetic macular edema (DME).

Another example of the invention is the use of any of the compounds described herein in the preparation of a medicament for the treatment and/or prophylaxis of a disorder, disease or condition as described herein. Another example of the invention is the use of any of the compounds described herein in the preparation of a medicament for the treatment and/or prophylaxis of a thromboembolic disorder, an inflammatory disorder or a disease or condition in which plasma kallikrein activity is implicated.

Another example of the invention is the use of any of the compounds described herein in the preparation of a medicament for the treatment and/or prophylaxis of a thromboembolic disorder selected from the group consisting of (a) arterial cardiovascular thromboembolic disorders, (b) venous cardiovascular thromboembolic disorders, (c) arterial cerebrovascular thromboembolic disorders, and (d) venous cerebrovascular thromboembolic disorders. Another example of the invention is the use of any of the compounds described herein in the preparation of a medicament for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (I) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis. Another example of the invention is the use of any of the compounds described herein in the preparation of a medicament for the treatment and/or prophylaxis of: (a) hereditary angioedema (HAE) or (b) diabetic macular edema (DME).

Another example of the invention is the use of any of the compounds described herein for use in a method for treating a thromboembolic, inflammatory or a disease or condition in which plasma kallikrein activity is implicated as described herein, in a subject in need thereof.

Another example of the invention is the use of any of the compounds described herein for use in a method for the treatment and/or prophylaxis of (a) arterial cardiovascular thromboembolic disorders, (b) venous cardiovascular thromboembolic disorders, (c) arterial cerebrovascular thromboembolic disorders, or (d) venous cerebrovascular thromboembolic disorders, in a subject in need thereof. Another example of the invention is the use of any of the compounds described herein for use in a method for the treatment and/or prophylaxis of (a) unstable angina, (b) an acute coronary syndrome, (c) atrial fibrillation, (d) first myocardial infarction, (e) recurrent myocardial infarction, (f) ischemic sudden death, (g) transient ischemic attack, (h) stroke, (i) atherosclerosis, (j) peripheral occlusive arterial disease, (k) venous thrombosis, (l) deep vein thrombosis, (m) thrombophlebitis, (n) arterial embolism, (o) coronary arterial thrombosis, (p) cerebral arterial thrombosis, (q) cerebral embolism, (r) kidney embolism, (s) pulmonary embolism, or (t) thrombosis resulting from medical implants, devices, or procedures in which blood is exposed to an artificial surface that promotes thrombosis, in a subject in need thereof. Another example of the invention is the use of any of the compounds described herein for use in a method for the treatment and/or prophylaxis of (a) hereditary angioedema (HAE) or (b) diabetic macular edema (DME), in a subject in need thereof.

In another example, the present invention is directed to a compound as described herein, for use in a method for the treatment and/or prophylaxis of disorders, diseases or conditions as described herein, in a subject in need thereof. In another example, the present invention is directed to a compound as described herein, for use in a method for the treatment and/or prophylaxis of a thromboembolic, inflammatory disorder, or a disease or condition in which plasma kallikrein activity is implicated, as described herein, in a subject in need thereof.

In another example, the present invention is directed to a compound as described herein, for use in methods for the treatment and/or prophylaxis of thromboembolic disorder, such as arterial cardiovascular thromboembolic disorders, venous cardiovascular thromboembolic disorders, arterial cerebrovascular thromboembolic disorders, and venous cerebrovascular thromboembolic disorders, in a subject in need thereof. In another example, the present invention is directed to a compound as described herein, for use in methods for the treatment and/or prophylaxis of unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis, in a subject in need thereof. In another example, the present invention is directed to a compound as described herein, for use in a method for the treatment and/or prophylaxis of hereditary angioedema (HAE) or diabetic macular edema (DME), in a subject in need thereof.

The present invention is further directed to a compound, composition (e.g. pharmaceutical composition), method of treatment, method of preparation or use, as herein described.

DETAILED DESCRIPTION OF THE INVENTION 1. 3-(1H-imidazol-2-yl)-2,3,8,8a-tetrahydroindolizin-5(1H)-one Derivatives Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood dot inside a blood vessel or cavity of the heart. Such a blood clot can lodge in a blood vessel blocking circulation and causing a heart attack or stroke. Thromboembolic disorders are the leading cause of mortality and disability in the industrialized world.

Blood clotting is a process of control of the bloodstream essential for the survival of mammals. The process of clotting, and the subsequent dissolution of the dot after wound healing has taken place, commences after vascular injury, and can be divided into four phases. The first phase, vasoconstriction or vasocontraction, can cause a decrease in blood loss in the injured area. In the next phase, platelet activation by thrombin, platelets attach to the site of the vessel wall damage and form a platelet aggregate. In the third phase, formation of dotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to yield a common final path of the clotting cascade. In this final path of clotting, dotting Factor X is activated. The activated Factor X is responsible for the formation of thrombin from the inactive precursor prothrombin circulating in the blood. The formation of a thrombus on the bottom of a vessel wall abnormality without a wound is the result of the intrinsic pathway. Fibrin dot formation as a response to tissue injury or an injury is the result of the extrinsic pathway. Both pathways comprise a relatively large number of proteins, which are known as dotting factors. The intrinsic pathway requires the dotting Factors V, VIII, IX, X, XI and XII and also prekallikrein, high molecular weight kininogen, calcium ions and phospholipids from platelets.

Factor XIa, a plasma serine protease involved in the regulation of blood coagulation, is initiated in vivo by the binding of tissue Factor (TF) to factor VII (FVII) to generate Factor Vila (FVIIa). The resulting TF:FVIIa complex activates Factor IX (FIX) and Factor X (FX) that leads to the production of Factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., Arterioscler. Thromb. Vasc. Biol., 27: 2507-2513 (2007)). The resulting burst of thrombin converts fibrinogen to fibrin that polymerizes to form the structural framework of a blood dot, and activates platelets, which are a key cellular component of coagulation (Hoffman, M., *Blood Reviews,* 17:S1-S5 (2003)). Factor XIa plays a key role in propagating this amplification loop. Epidemiological studies showed that increased circulating FXI levels in humans have been associated with increased risk for venous and arterial thrombosis, including stroke (see Quan et al. supra). In contrast, patients with congenital FXI deficiency (hemophilia C) are protected from ischemic stroke and venous thromboembolism. Therefore, Factor XIa is an attractive target for antithrombotic therapy.

In addition to stimulation via tissue factor, the coagulation system can be activated particularly on negatively charged surfaces, which include not only surface structures of foreign cells (e.g. bacteria) but also artificial surfaces such as vascular prostheses, stents and extracorporeal circulation. On the surface, initially Factor XII (FXII) is activated to Factor XIIa which subsequently activates Factor XI, attached to cell surfaces, to Factor XIa. This leads to further activation of the coagulation cascade as described above. In addition, Factor XIIa also activates bound plasma prokallikrein to plasma kallikrein (PK) which, in a potentiation loop, leads to further Factor XII activation, overall resulting in amplification of the initiation of the coagulation cascade. In addition, PK is an important bradykinin-releasing protease which leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

The present invention is directed to compounds of formula (I)

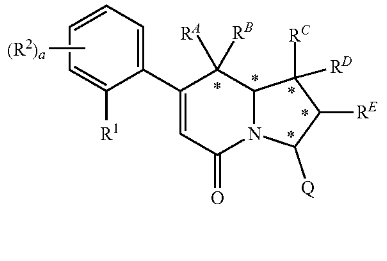

(I)

wherein a, $R^1$, $R^2$, $R^A$, $R^B$, $R^C$, $R^D$, $R^E$, Q, etc. are as described herein; and tautomers, stereoisomers, isotopologues, and pharmaceutically acceptable salts thereof. The present invention is further directed to compounds of formula (II)

(II)

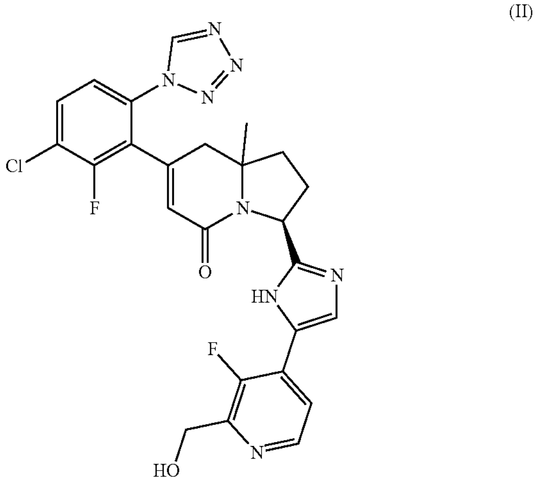 [SMILES: CC12CC[C@@H](c3ncc(-c4ccnc(CO)c4F)[nH]3)N1C(=O)C=C(c1c(-n3cnnn3)ccc(Cl)c1F)C2]

and tautomers, stereoisomers, isotopologues, and pharmaceutically acceptable salts thereof. The present invention is further directed to a compound of formula (III)

(III)

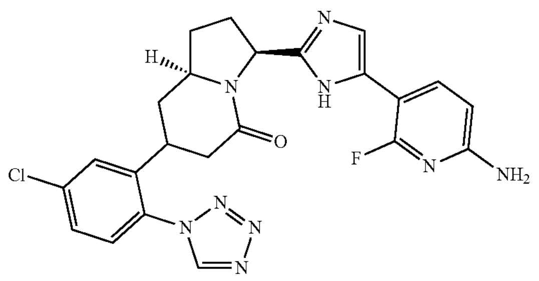

and tautomers, stereoisomers, isotopologues, and pharmaceutically acceptable salts thereof. The present invention is further directed to a compound of formula (IV)

(IV)

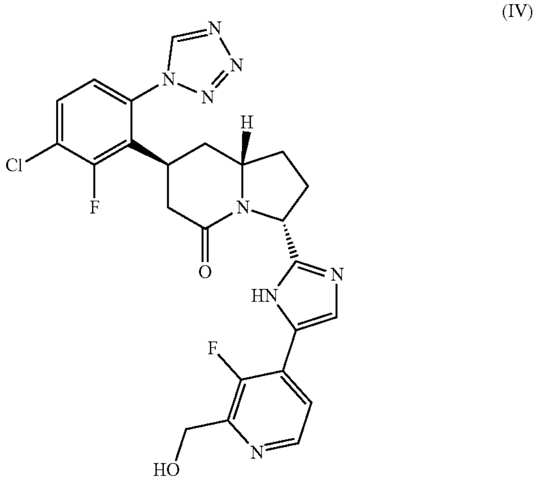 [SMILES: O=C1C[C@@H](c2c(-n3cnnn3)ccc(Cl)c2F)C[C@@H]2CC[C@H](c3ncc(-c4ccnc(CO)c4F)[nH]3)N12]

and tautomers, stereoisomers, isotopologues, and pharmaceutically acceptable salts thereof. The compounds of formula (I), compounds of formula (II), compounds of formula (III) and compounds of formula (IV) of the present invention are useful for the treatment and/or prophylaxis of thromboembolic disorders, inflammatory disorders and diseases or conditions in which plasma kallikrein activity is implicated.

EMBODIMENTS

In some embodiments, the present invention is directed to compounds of formula (I) having formula (I-A)

(I-A)

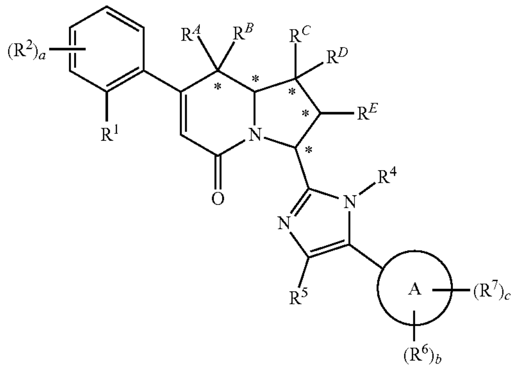

wherein $R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^AR^B$, —C(O)—$C_{1-4}$alkyl, $C_{3-6}$cycloalkyl, phenyl and 5 to 6 membered heterocyclyl;

wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —$NR^AR^B$, —($C_{1-4}$alkyl)-$NR^AR^B$, $C_{3-7}$cycloalkyl and 5 to 6 membered heterocyclyl; and wherein $R^A$ and $R^B$ are each independently selected from the group consisting of hydrogen and $C_{1-4}$alkyl;

a is an integer from 0 to 3;

each $R^2$ is independently selected from the group consisting of chloro, fluoro, methyl and methoxy;

$R^A$ and $R^B$ are each independently selected from the group consisting of hydrogen and halogen; alternatively, $R^A$ and $R^B$ are taken together with the carbon atom to which they are bound to form oxo;

$R^C$ is selected from the group consisting of hydrogen and $C_{1-4}$alkyl;

$R^D$ is selected from the group consisting of hydrogen, $C_{1-4}$alkyl and $C_{1-4}$alkoxy;

$R^E$ is selected from the group consisting of hydrogen and $C_{1-4}$alkyl;

Q is selected from the group consisting of (a)

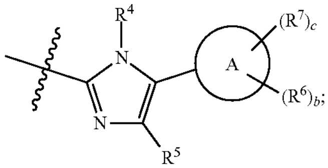

and (b)

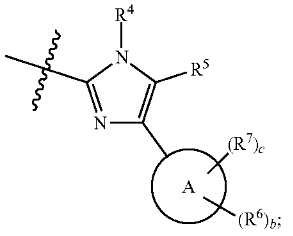

wherein $R^4$ is selected from the group consisting of hydrogen and $C_{1-4}$alkyl;

$R^5$ is selected from the group consisting of hydrogen, halogen and $C_{1-4}$alkyl;

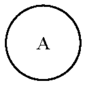

is selected from the group consisting of phenyl, 5-6 membered heteroaryl, and 9 to 10 membered heterocyclyl;

b is an integer from 0 to 1;

$R^6$ is selected from the group consisting of $C_{3-8}$cycloalkyl, —O—($C_{1-2}$alkylene)-$C_{3-8}$cycloalkyl, —C(O)—($C_{3-8}$cycloalkyl), —NH—($C_{3-8}$cycloalkyl), —NH—C(O)—($C_{3-8}$cycloalkyl), —C(O)—NH—($C_{3-8}$cycloalkyl), 4-6 membered heterocycloalkyl, —O—($C_{1-2}$alkylene)-(4-6 membered heterocycloalkyl), —C(O)-(4-6 membered heterocycloalkyl), —NH-(4-6 membered heterocycloalkyl), —C(O)—NH-(4-6 membered heterocycloalkyl), —NH—C(O)-(4-6 membered heterocycloalkyl), 5-6 membered heteroaryl, —O—($C_{1-2}$alkylene)-(5-6 membered heteroaryl), —C(O)-(5-6 membered heteroaryl), —NH-(5-6 membered heteroaryl), —NH—C(O)-(5-6 membered heteroaryl), —C(O)—NH-(5-6 membered heteroaryl), 2-oxa-6-azaspiro[3.3]hept-6-yl, 6-oxa-2-azaspiro[3.4]octan-2-yl, and 7-oxa-2-azaspiro[3.5]nonan-2-yl;

wherein the $C_{3-6}$cycloalkyl, 4-6 membered heterocycloalkyl, or 5-6 membered heteroaryl, whether alone or as part of a substituent group is optionally substituted with one or more substituents independently selected from the group consisting of halogen, $C_{1-4}$alkyl, hydroxy, oxo, cyano and $NR^PR^Q$; wherein $R^P$ and $R^Q$ are each independently selected from the group consisting of hydrogen and $C_{1-4}$alkyl;

c is an integer from 0 to 3;

each $R^7$ is independently selected from the group consisting of halogen, $C_{1-4}$alkyl, fluorinated $C_{1-4}$alkyl, hydroxy substituted $C_{1-4}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O) $NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-6}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-4}$alkyl), —C(O)—$NR^K$—$SO_2$—($C_{1-2}$alkyl), —($C_{1-2}$alkylene)-O—P(O)$(OH)_2$, and —($C_{1-2}$alkylene)-O—($C_{1-2}$alkylene)-P(O)$(OH)_2$; wherein $R^K$ and $R^L$ are each independently selected from hydrogen and $C_{1-4}$alkyl;

and wherein the heterocyclyl, heteroaryl or heterocycloalkyl present as any part of the

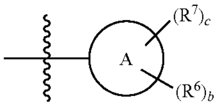

group contains a nitrogen atom, then said heterocyclyl, heteroaryl or heterocycloalkyl may be further substituted to form an N-oxide;

provided that when $R^1$ is 1,2,3,4-tetrazol-1-yl, a is 2, and the two $R^2$ groups are 2-fluoro and 3-chloro, then Q is other than (a)

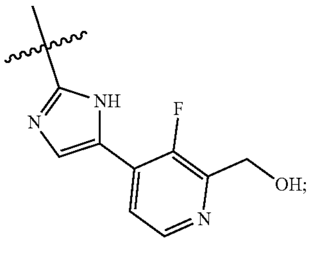

(b)

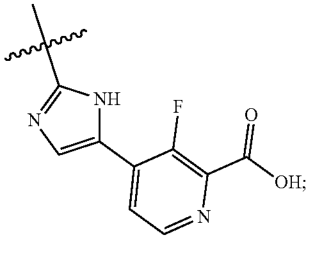

or (c)

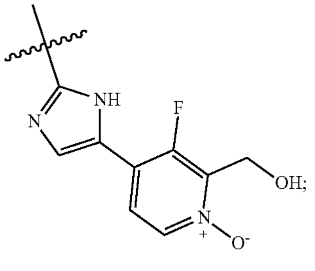

and stereoisomers, isotopologues, and pharmaceutically acceptable salts thereof. In some embodiments, the present invention is directed to compounds of formula (I) having formula (I-B)

(I-B)

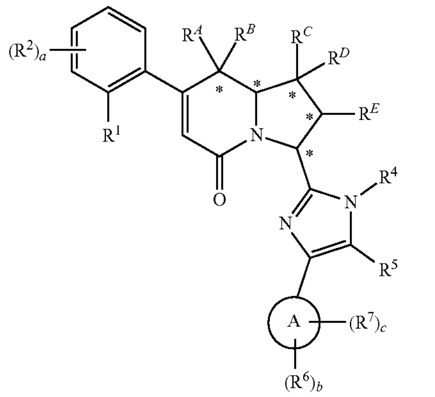

wherein $R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^AR^B$, —C(O)—$C_{1-4}$alkyl, $C_{3-8}$cycloalkyl, phenyl and 5 to 6 membered heterocycyl;

wherein the $C_{3-8}$cycloalkyl, phenyl or 5 to 6 membered heterocycyl is optionally substituted with one or more substituents independently selected from the group consisting of halogen, hydroxy, cyano, $C_{1-4}$alkyl, fluorinated $C_1$. 4alkyl, $C_{1-4}$alkoxy, fluorinated $C_{1-4}$alkoxy, —C(O)OH, —C(O)O—($C_{1-4}$alkyl), —$NR^AR^B$, —($C_{1-4}$alkyl)-$NR^AR^B$, $C_{3-7}$cycloalkyl and 5 to 6 membered heterocyclyl; and wherein $R^A$ and $R^B$ are each independently selected from the group consisting of hydrogen and $C_{1-4}$alkyl;

a is an integer from 0 to 3;

each $R^2$ is independently selected from the group consisting of chloro, fluoro, methyl and methoxy;

$R^A$ and $R^B$ are each independently selected from the group consisting of hydrogen and halogen; alternatively, $R^A$ and $R^B$ are taken together with the carbon atom to which they are bound to form oxo;

$R^C$ is selected from the group consisting of hydrogen and $C_{1-4}$alkyl;

$R^D$ is selected from the group consisting of hydrogen, $C_{1-4}$alkyl and $C_{1-4}$alkoxy;

$R^E$ is selected from the group consisting of hydrogen and $C_{1-4}$alkyl;

Q is selected from the group consisting of (a)

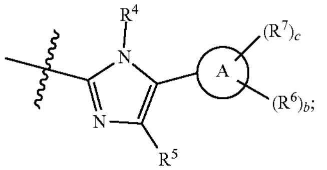

and

-continued (b)

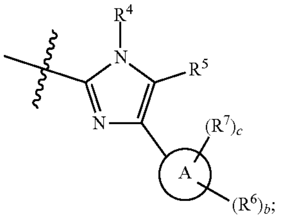

wherein $R^4$ is selected from the group consisting of hydrogen and $C_{1-4}$alkyl;

$R^5$ is selected from the group consisting of hydrogen, halogen and $C_{1-4}$alkyl,

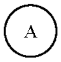

is selected from the group consisting of phenyl, 5-6 membered heteroaryl, and 9 to 10 membered heterocyclyl;

b is an integer from 0 to 1;

$R^6$ is selected from the group consisting of $C_{3-8}$cycloalkyl, —O—($C_{1-2}$alkylene)-$C_{3-8}$cycloalkyl, —C(O)—($C_{3-8}$cycloalkyl), —NH—($C_{3-8}$cycloalkyl), —NH—C(O)—($C_{3-8}$cycloalkyl), —C(O)—NH—($C_{3-8}$cycloalkyl), 4-6 membered heterocycloalkyl, —O—($C_{1-2}$alkylene)-(4-6 membered heterocycloalkyl), —C(O)-(4-6 membered heterocycloalkyl), —NH—(4-6 membered heterocycloalkyl), —C(O)—NH—(4-6 membered heterocycloalkyl), —NH—C(O)-(4-6 membered heterocycloalkyl), 5-6 membered heteroaryl, —O—($C_{1-2}$alkylene)-(5-6 membered heteroaryl), —C(O)-(5-6 membered heteroaryl), —NH—(5-6 membered heteroaryl), —NH—C(O)-(5-6 membered heteroaryl), —C(O)—NH—(5-6 membered heteroaryl), 2-oxa-6-azaspiro[3.3]hept-6-yl, 6-oxa-2-azaspiro[3.4]octan-2-yl, and 7-oxa-2-azaspiro[3.5]nonan-2-yl;

wherein the $C_{3-8}$cycloalkyl, 4-6 membered heterocycloalkyl, or 5-6 membered heteroaryl, whether alone or as part of a substituent group is optionally substituted with one or more substituents independently selected from the group consisting of halogen, $C_{1-4}$alkyl, hydroxy, oxo, cyano and $NR^PR^Q$; wherein $R^P$ and $R^Q$ are each independently selected from the group consisting of hydrogen and $C_{1-4}$alkyl;

c is an integer from 0 to 3;

each $R^7$ is independently selected from the group consisting of halogen, $C_{1-4}$alkyl, fluorinated $C_{1-4}$alkyl, hydroxy substituted $C_{1-6}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-4}$alkyl), —$NR^K$—C(O)O—($C_{1-4}$alkyl), —$NR^K$—C(O)—$C_{3-6}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_1$-~alkyl), —$NR^K$—$SO_2$—($C_{1-4}$alkyl), —C(O)—$NR^K$—$SO_2$—($C_{1-2}$alkyl), —($C_{1-2}$alkylene)-O—P(O)$(OH)_2$, and —($C_{1-2}$alkylene)-O—($C_{1-2}$alkylene)-P(O)$(OH)_2$; wherein $R^K$ and $R^L$ are each independently selected from hydrogen and $C_{1-4}$alkyl;

and wherein the heterocyclyl, heteroaryl or heterocycloalkyl present as any part of the

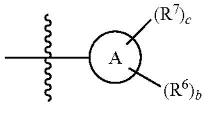

group contains a nitrogen atom, then said heterocyclyl, heteroaryl or heterocycloalkyl may be further substituted to form an N-oxide;

provided that when $R^1$ is 1,2,3,4-tetrazol-1-yl, a is 2, and the two $R^2$ groups are 2-fluoro and 3-chloro, then Q is other than (a)

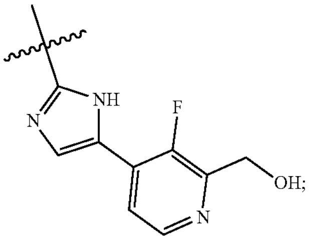

(b)

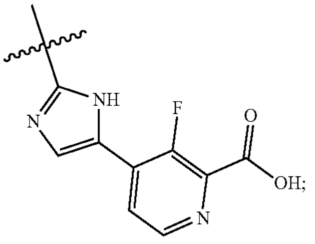

or (c)

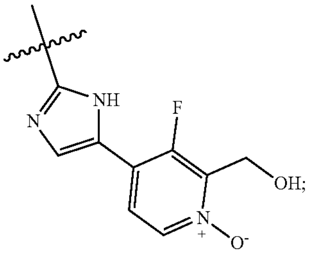

and stereoisomers, isotopologues, and pharmaceutically acceptable salts thereof.

In some embodiments, the present invention is directed to compounds of formula (I) wherein $R^1$ is selected from the group consisting of halogen, $C_{1-4}$alkyl, fluorinated $C_{1-4}$alkyl, $C_{1-4}$alkoxy, fluorinated $C_{1-4}$alkoxy, phenyl and 5 to 6 membered heterocyclyl; wherein the phenyl or 5 to 6 membered heterocyclyl is optionally substituted with one or more substituents independently selected from the group consisting of halogen, $C_{1-4}$alkyl, fluorinated $C_{1-4}$alkyl, $C_{1-4}$alkoxy, and fluorinated $C_{1-4}$alkoxy;

a is an integer from 0 to 2;

each $R^2$ is independently selected from the group consisting of chloro, fluoro, and methyl;

$R^A$ and $R^B$ are each independently selected from the group consisting of hydrogen and halogen; alternatively, $R^A$ and $R^B$ are taken together with the carbon atom to which they are bound to form oxo;

$R^C$ is selected from the group consisting of hydrogen and $C_{1-4}$alkyl;

$R^D$ is selected from the group consisting of hydrogen, $C_{1-4}$alkyl and $C_{1-4}$alkoxy;

$R^E$ is selected from the group consisting of hydrogen and $C_{1-4}$alkyl;

Q is selected from the group consisting of (a)

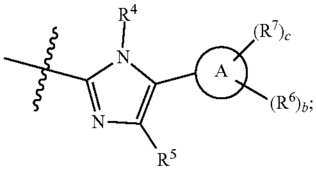

and (b)

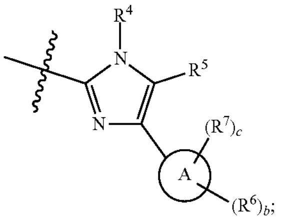

wherein $R^4$ is selected from the group consisting of hydrogen and $C_{1-4}$alkyl;

$R^5$ is selected from the group consisting of hydrogen, halogen and $C_{1-4}$alkyl;

b is an integer from 0 to 1;

$R^6$ is selected from the group consisting of $C_{3-8}$cycloalkyl, —O—($C_{1-2}$alkylene)-$C_{3-8}$cycloalkyl, —NH—($C_{3-8}$cycloalkyl), —NH—C(O)—($C_{3-8}$cycloalkyl), 4-6 membered heterocycloalkyl, —O—($C_{1-2}$alkylene)-(4-6 membered heterocycloalkyl), —C(O)-(4-6 membered heterocycloalkyl), —NH—(4-6 membered heterocycloalkyl), —C(O)—NH—(4-6 membered heterocycloalkyl), 5-6 membered heteroaryl, —O—($C_{1-2}$alkylene)-(5-6 membered heteroaryl), —NH—C(O)-(5-6 membered heteroaryl), and 2-oxa-6-azaspiro[3.3]hept-6-yl; wherein the $C_{3-6}$cycloalkyl, 4-6 membered heterocycloalkyl, or 5-6 membered heteroaryl, whether alone or as part of a substituent group is optionally substituted with one to two substituents independently selected from the group consisting of halogen, $C_{1-2}$alkyl, hydroxy, oxo, cyano and $NR^PR^Q$; wherein $R^P$ and $R^Q$ are each independently selected from the group consisting of hydrogen and $C_{1-4}$alkyl;

c is an integer from 0 to 2;

each $R^7$ is independently selected from the group consisting of halogen, $C_{1-2}$alkyl, fluorinated $C_{1-2}$alkyl, hydroxy substituted $C_{1-6}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$ (hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$C(O)O—($C_{1-4}$alkyl), —$NR^K$—C(O)—$C_{3-6}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_1$-~alkyl), —$NR^K$—$SO_2$—($C_{1-2}$alkyl), —C(O)—$NR^K$—$SO_2$—($C_{1-2}$alkyl), —($C_{1-2}$alkylene)-O—P(O)$(OH)_2$, and —($C_{1-2}$alkylene)-O—($C_{1-2}$alkylene)-P(O)$(OH)_2$; wherein $R^K$ and $R^L$ are each independently selected from hydrogen and $C_{1-4}$alkyl;

provided that when $R^1$ is 1,2,3,4-tetrazol-1-yl, a is 2, and the two $R^2$ groups are 2-fluoro and 3-chloro, then Q is other than (a)

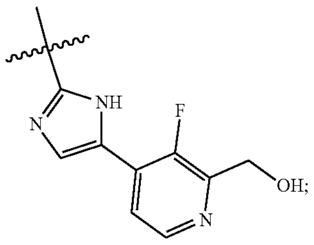

(b)

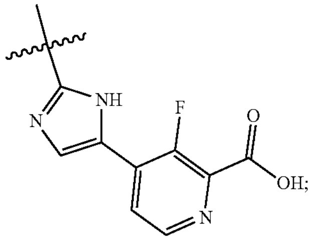

or (c)

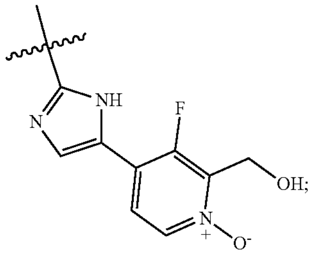

and tautomers, stereoisomers, isotopologues, and pharmaceutically acceptable salts thereof.

In some embodiments, the present invention is directed to compounds of formula (I) wherein $R^1$ is selected from the group consisting of fluorinated $C_{1-2}$alkyl, fluorinated $C_{1-2}$alkoxy, and 5-membered nitrogen containing heteroaryl; wherein the 5-membered nitrogen containing heteroaryl is optionally substituted with halogen or fluorinated $C_{1-2}$alkyl;

a is an integer from 1 to 2;

each $R^2$ is independently selected from the group consisting of chloro, fluoro and methyl;

$R^A$ and $R^B$ are each independently selected from the group consisting of hydrogen and halogen; alternatively, $R^A$ and $R^B$ are taken together with the carbon atom to which they are bound to form oxo;

$R^C$ is selected from the group consisting of hydrogen and $C_{1-2}$alkyl;

$R^D$ is selected from the group consisting of hydrogen, $C_{1-2}$alkyl and $C_{1-2}$alkoxy;

$R^E$ is selected from the group consisting of hydrogen and $C_{1-2}$alkyl;

Q is selected from the group consisting of (a)

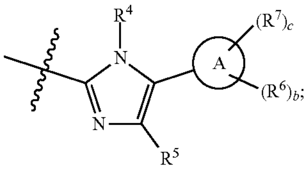

and (b)

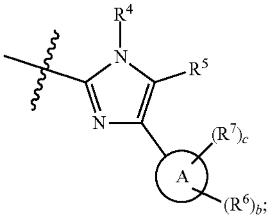

wherein $R^4$ is selected from the group consisting of hydrogen and $C_{1-2}$alkyl;

$R^5$ is selected from the group consisting of hydrogen, halogen and $C_{1-2}$alkyl;

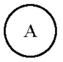

is selected from the group consisting of phenyl, 5 to 6 membered heteroaryl, and 9 to 10 membered heterocyclyl;

b is an integer from 0 to 1;

$R^6$ is selected from the group consisting of $C_{3-5}$cycloalkyl, —NH—C(O)—$C_{3-5}$cycloalkyl, 4-6 membered heterocycloalkyl, —O—($C_{1-2}$alkylene)-(4-6 membered heterocycloalkyl), —C(O)-(4-6 membered heterocycloalkyl), —NH—(4-6 membered heterocycloalkyl), —C(O)—NH—(5-6 membered heterocycloalkyl), 5-6 membered heteroaryl, —O—($C_{1-2}$alkylene)-(5-6 membered heteroaryl), —NH—C(O)-(5-6 membered heteroaryl), and 2-oxa-6-azaspiro[3.3]hept-6-yl; wherein the $C_{3-5}$cycloalkyl, 4-6 membered heterocycloalkyl, or 5-6 membered heteroaryl, whether alone or as part of a substituent group is optionally substituted with one to two substituents independently selected from the group consisting of halogen, $C_{1-2}$alkyl, hydroxy, oxo, cyano, and $NR^PR^Q$; wherein $R^P$ and $R^Q$ are each independently selected from the group consisting of hydrogen and $C_{1-4}$alkyl;

c is an integer from 0 to 2;

each $R^7$ is independently selected from the group consisting of halogen, $C_{1-2}$alkyl, fluorinated $C_{1-2}$alkyl, hydroxy substituted $C_{1-6}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-5}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-2}$alkyl), —C(O)—$NR^K$—$SO_2$—($C_{1-2}$alkyl), —($C_{1-2}$alkylene)-O—P(O)$(OH)_2$, and —($C_{1-2}$alkylene)-O—($C_{1-2}$alkylene)-P(O)$(OH)_2$; wherein $R^K$ and $R^L$ are each independently selected from hydrogen and $C_{1-2}$alkyl;

and wherein the heterocyclyl, heteroaryl or heterocycloalkyl present as any part of the

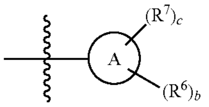

group contains a nitrogen atom, then said heterocyclyl, heteroaryl or heterocycloalkyl may be further substituted to form an N-oxide;

provided that when $R^1$ is 1,2,3,4-tetrazol-1-yl, a is 2, and the two $R^2$ groups are 2-fluoro and 3-chloro, then Q is other than (a)

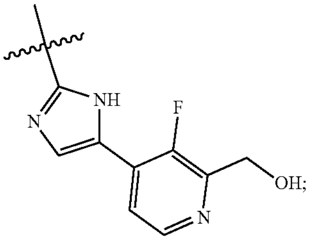

(b)

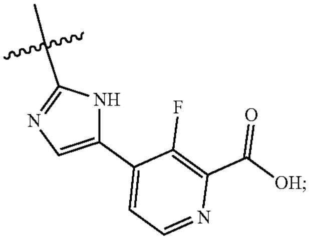

or (c)

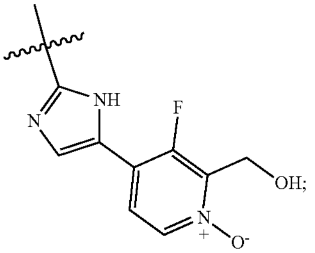

and tautomers, stereoisomers, isotopologues, and pharmaceutically acceptable salts thereof.

In some embodiments, the present invention is directed to compounds of formula (I) wherein $R^1$ is selected from the group consisting of difluoromethyl, difluoro-methoxy, 2,2,2-trifluoro-ethoxy, pyrazol-5-yl, imidazol-5-yl, 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, 3-chloro, 5-chloro and 3-methyl;

$R^A$ and $R^B$ are each independently selected from the group consisting of hydrogen, and fluoro; alternatively, $R^A$ and $R^B$ are taken together with the carbon atom to which they are bound to form oxo;

$R^C$ is selected from the group consisting of hydrogen, deutero and methyl;

$R^D$ is selected from the group consisting of hydrogen, deutero, methyl, S*-methyl, R*-methyl, S-methoxy, and R-methoxy;

$R^E$ is selected from the group consisting of hydrogen and methyl;

Q is selected from the group consisting of (a)

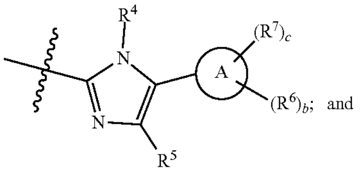

and (b)

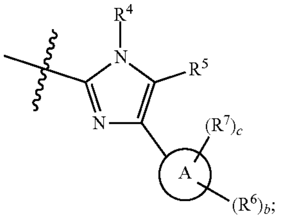

wherein $R^4$ is selected from the group consisting of hydrogen and methyl;

$R^5$ is selected from the group consisting of hydrogen, deutero, fluoro, chloro, bromo, and methyl;

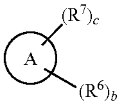

is selected from the group consisting of 2-methoxy-phenyl, 2-(isopropyloxy)-phenyl, 3-fluoro-4-carboxy-phenyl, 2-amino-phenyl, 2-(dimethyl-amino)-phenyl, 2-(amino-carbonyl)-phenyl, 2-fluoro-4-(amino-carbonyl)-phenyl, 2-fluoro-3-(amino-carbonyl)-phenyl, 3-(amino-carbonyl)-4-fluoro-phenyl, 3-fluoro-4-(amino-carbonyl)-phenyl, 2-(methyl-amino-carbonyl)-phenyl, 2-(dimethyl-amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 4-(1R-(methyl-carbonyl-amino)-ethyl)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl, 2-(methyl-sulfonyl-amino)-phenyl, 4-(oxazolidin-3-yl-2-one)-phenyl;

2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 2-(amino-carbonyl)-3-fluoro-thien-5-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 4-chloro-pyrazol-3-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, 1-methyl-3-(cyclopropyl-carbonyl-amino)-pyrazol-4-yl, 1-methyl-4-(cyclopropyl-carbonyl-amino)-pyrazol-5-yl, imidazol-2-yl, 2-(trifluoro-methyl)-imidazol-4-yl, 1-methyl-imidazol-2-yl, 4-(hydroxy-methyl)-thiazol-2-yl, 2-(hydroxy-methyl)-thiazol-4-yl, 2-(amino-carbonyl)-thiazol-5-yl, 1,2,4-triazol-3-yl, 1,2,3-triazol-5-yl, 1-methyl-(1,2,4-triazol-3-yl), 1-methyl-1,2,3-triazol-5-yl;

3-fluoro-pyridin-4-yl-2-one, 3-fluoro-pyridin-4-yl, 2-fluoro-5-chloro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R*-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1S-hydroxy-ethyl)-3-fluoro-pyridin-4-yl, 2-(1R-(hydroxy-methyl)-ethyl)-3-fluoro-pyridin-4-yl, 2-(1S*-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S*-cyano-ethyl)-3-fluoro-pyridin-4-yl, 2-(1R*-cyano-ethyl)-3-fluoro-pyridin-4-yl, 4-amino-pyridin-3-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-amino-6-(trifluoro-methyl)-pyridin-5-yl, 2-(methyl-amino)-pyridin-3-yl, 2-fluoro-6-(methyl-amino)-pyridin-3-yl, 2-fluoro-6-(dimethyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R'-hydroxy-n-propyl)-3-fluoro-pyridin-4-yl, 2-fluoro-4-deutero-6-amino-pyridin-3-yl, 2-fluoro-5-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-4-yl, 2-(amino-carbonyl)-pyridin-5-yl, 2-(amino-carbonyl)-3-fluoro-pyridin-3-yl, 2-chloro-6-(amino-carbonyl)-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 3-chloro-6-(methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 4-(ethoxy-carbonyl-amino)-pyridin-3-yl, 2-(ethoxy-carbonyl-amino-methyl)-3-fluoro-pyridin-4-yl, 3-(methyl-carbonyl-amino)-6-(trifluoro-methyl)-pyridin-4-yl, 3-(d3-methyl-carbonyl-amino)-6-(trifluoro-methyl)-pyridin-4-yl, 2-(1S-amino-isopropyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(2-cyano-cycloprop-1-yl)-3-fluoro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(oxetan-3-yl)-3-fluoro-pyridin-4-yl, 2-(3-cyano-oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(pyrrolidin-1-yl-2-one)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-2-yl, 2-(pyrazol-5-yl)-pyridin-4-yl, 2-(pyrazol-5-yl)-3-fluoro-pyridin-4-yl, 2-(5-amino-pyrazol-1-yl)-pyridin-4-yl, 2-(3-amino-pyrazol-1-yl)-3-fluoro-pyridin-4-yl, 2-(5-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 2-(1,2,3-triazol-1-yl)-pyridin-4-yl, 1-(1,2,5-triazol-1-yl)-pyridin-4-yl, 2-(1,2,3-triazol-1-yl)-3-fluoro-pyridin-4-yl, 2-(1,3,4-triazol-1-yl)-3-fluoro-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1R*-oxazol-2-yl-ethoxy)-3-fluoro-pyridin-4-yl, 2-(1S*-oxazol-2-yl-ethoxy)-3-fluoro-pyridin-4-yl, 2-(1S-(1,3,4-oxadiazol-2-yl)-ethoxy)-3-fluoro-pyridin-4-yl, 2-(3,3-difluoro-azetin-1-yl-carbonyl)-3-fluoro-pyridin-4-yl, 2-fluoro-6-(bicyclo[1.1.1]pentanyl-amino)-pyridin-3-yl, 2-(bicyclo[1.1.1]pentanyl-amino)-3-fluoro-pyridin-3-yl, 2-(bicyclo[1.1.1]pentanyl-amino-carbonyl)-3-fluoro-pyridin-3-yl, 3-(cyclopropyl-carbonyl-amino)-6-(trifluoro-methyl)-pyridin-4-yl, 2-(3-methyl-isoxazol-5-yl-carbonyl-amino)-3-fluoro-pyridin-4-yl, pyridin-4-yl-2-one, pyridin-4-yl-N-oxide, 2-(hydroxy-methyl)-3-fluoro-pyridin-4-yl-N-oxide indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-b]pyridin-5-yl, 1H-pyrrolo[2,3-c]pyridin-3-yl, 5-methyl-1H-pyrrolo[2,3-c]pyridin-3-yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, and 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

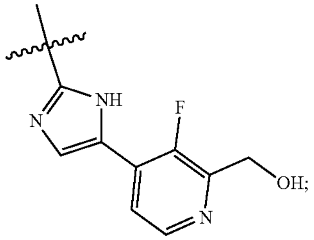

(b)

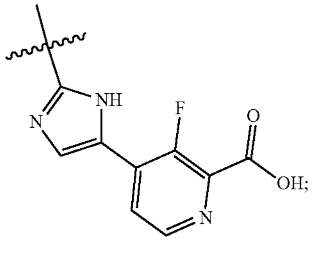

or (c)

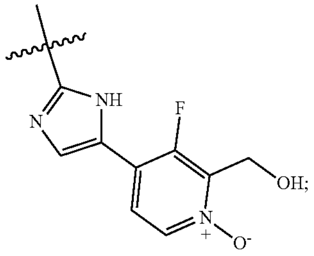

and tautomers, stereoisomers, isotopologues, and pharmaceutically acceptable salts thereof.

In some embodiments, the present invention is directed to compounds of formula (I) wherein $R^1$ is selected from the group consisting of 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is selected from the group consisting of hydrogen, and methyl;

$R^D$ is selected from the group consisting of hydrogen, methyl, S*-methyl, R*-methyl, S-methoxy, and R-methoxy;

$R^E$ is hydrogen;

Q is selected from the group consisting of (a)

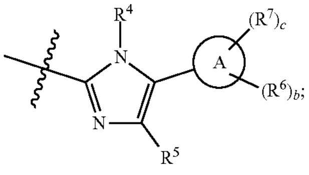

and (b)

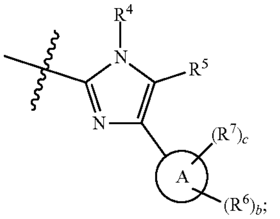

wherein $R^4$ is hydrogen;

$R^5$ is selected from the group consisting of hydrogen, deutero, fluoro, chloro, bromo, and methyl;

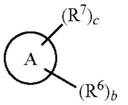

is selected from the group consisting of 2-methoxy-phenyl, 2-fluoro-4-(amino-carbonyl)-phenyl, 2-fluoro-3-(amino-carbonyl)-phenyl, 3-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl;

2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, 2-(amino-carbonyl)-thiazol-5-yl;

3-fluoro-pyridin-4-yl-2-one, 3-fluoro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R'-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1 S-hydroxy-ethyl)-3-fluoro-pyridin-4-yl, 2-(1R-(hydroxy-methyl)-ethyl)-3-fluoro-pyridin-4-yl, 2-(1S'-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S*-cyano-ethyl)-3-fluoro-pyridin-4-yl, 2 (1R*-cyano-ethyl)-3-fluoro-pyridin-4-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R'-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-5-yl, 2-(amino-carbonyl)-3-fluoro-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 2-(ethoxy-carbonyl-amino-methyl)-3-fluoro-pyridin-4-yl, 2-(1S-amino-isopropyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(3-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 1-(1,2,5-triazol-1-yl)-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1S*-oxazol-2-yl-ethoxy)-3-fluoro-pyridin-4-yl, 2-(1 S-(1,3,4-oxadiazol-2-yl)-ethoxy)-3-fluoro-pyridin-4-yl, 2-(bicyclo[1.1.1]pentanyl-amino)-3-fluoro-pyridin-3-yl, 3-(cyclopropyl-carbonyl-amino)-6-(trifluoro-methyl)-pyridin-4-yl, 2-(3-methyl-isoxazol-5-yl-carbonyl-amino)-3-fluoro-pyridin-4-yl, pyridin-4-yl-2-one;

indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-c]pyridin-3yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

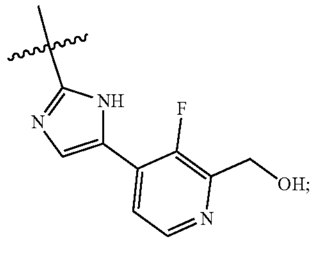

; or

-continued (b)

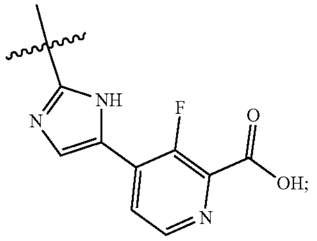

and tautomers, stereoisomers, isotopologues, and pharmaceutically acceptable salts thereof.

In some embodiments, the present invention is directed to compounds of formula (I) wherein $R^1$ is selected from the group consisting of 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is selected from the group consisting of hydrogen, and methyl;

$R^D$ is selected from the group consisting of hydrogen, methyl, S*-methyl, and R-methoxy;

$R^E$ is hydrogen;

Q is selected from the group consisting of (a)

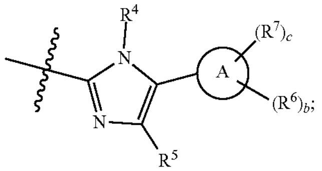

and (b)

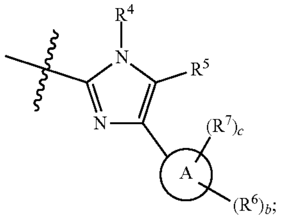

wherein $R^4$ is hydrogen;

$R^5$ is selected from the group consisting of hydrogen, deutero, fluoro, and chloro;

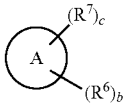

is selected from the group consisting of 2-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl;

2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 3-(trifluoro-methyl)-pyrrol-4-yl, 3-chloro-pyrazol-4-yl, 3-(trifluoromethyl)-pyrazol-4-yl, 5-chloro-pyrazol-4-yl, 1-methyl-4-(cyclopropyl-carbonyl-amino)-pyrazol-5-yl, 2-(amino-carbonyl)-thiazol-5-yl;

2-carboxy-3-fluoro-pyridin-4-yl, 2-(hydroxy-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-(hydroxy-d2-methyl)-3-chloro-pyridin-4-yl, \2-(1R-(hydroxy-methyl)-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(2-methyl-2-hydroxy-n-propyl-oxy)-3-fluoro-pyridin-4-yl, 2-chloro-6-amino-pyridin-3-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(methoxy-amino-carbonyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(ethoxy-carbonyl-amino)-pyridin-3-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(3-cyano-azetidin-1-yl)-3-fluoro-pyridin-4-yl, 2-(S-tetrahydrofuran-3-yl-amino)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(imidazol-2-yl)-3-fluoro-pyridin-4-yl, 1-(1,2,5-triazol-1-yl)-pyridin-4-yl, 2-(dioxan-2S-yl-ethoxy)-3-fluoro-pyridin-4-yl, pyridin-4-yl-2-one;

indol-5-yl-2-one, 7-fluoro-indol-6-yl, indazol-5-yl, 3-(methyl-amino)-indazol-6-yl, 3-amino-indazol-6-yl, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, benzoxazol-6-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-c]pyridin-3-yl, 1H-pyrrolo[2,3-c]pyridin-3yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

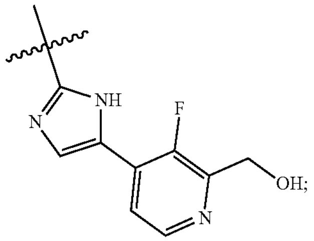

or (b)

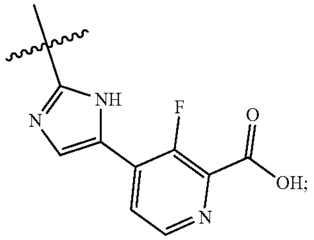

and tautomers, stereoisomers, isotopologues, and pharmaceutically acceptable salts thereof.

In some embodiments, the present invention is directed to compounds of formula (I) wherein $R^1$ is selected from the group consisting of 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is selected from the group consisting of hydrogen, and methyl;

$R^D$ is selected from the group consisting of hydrogen, methyl, and R-methoxy;

$R^E$ is hydrogen;

Q is selected from the group consisting of (a)

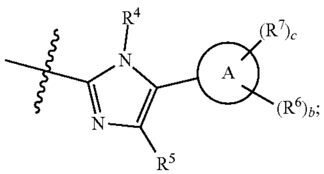

and

-continued (b)

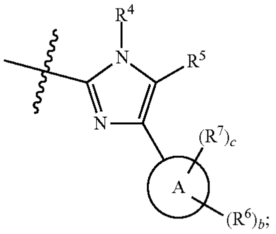

wherein $R^4$ is hydrogen;

$R^5$ is selected from the group consisting of hydrogen, deutero, fluoro, and chloro;

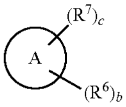

is selected from the group consisting of 2-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl;

2-carboxy-thien-5-yl, 2-carboxy-3-fluoro-thien-5-yl, 2-(amino-carbonyl)-thien-4-yl, 2-(amino-carbonyl)-thien-5-yl, 3-(trifluoro-methyl)-pyrrol-4-yl, 3-chloro-pyrazol-4-yl, 3-(trifluoromethyl)-pyrazol-4-yl, 1-methyl-4-(cyclopropyl-carbonyl-amino)-pyrazol-5-yl, 2-(amino-carbonyl)-thiazol-5-yl;

2-carboxy-3-fluoro-pyridin-4-yl, 2-(hydroxy-methyl)-3-fluoro-pyridin-4-yl, 2-(1R-(hydroxy-methyl)-ethyl)-3-fluoro-pyridin-4-yl, 2-(2-methyl-2-hydroxy-n-propyl-oxy)-3-fluoro-pyridin-4-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-chloro-6-amino-pyridin-3-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-fluoro-4-deutero-6-amino-pyridin-3-yl, 2-fluoro-4,5-dideutero-6-amino-pyridin-3-yl, 2-fluor-4,5-dideutero-6-(methyl-amino)-pyridin-3-yl, 2-(methyl-amino)-3-fluor-pyridin-4-yl, 5-(methoxy-carbonyl-amino)-pyridin-2-yl, 2-(methoxy-carbonyl-amino)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(S-tetrahydrofuran-3-yl-amino)-3-fluoro-pyridin-4-yl, 2-(pyrazol-5-yl)-pyridin-4-yl, 1-(1,2,5-triazol-1-yl)-pyridin-4-yl;

3-(methyl-amino)-indazol-6-yl, 3-amino-indazol-6-yl, benzimidazol-5-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 1H-pyrrolo[2,3-b]pyridin-4-yl, 6-methoxy-1H-pyrrolo[3,2-c]pyridin-3-yl, 7H-pyrrolo[2,3-d]pyrimidin-5-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

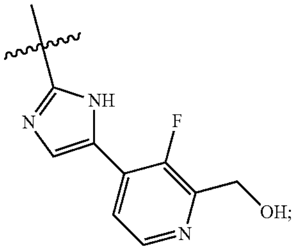

or (b)

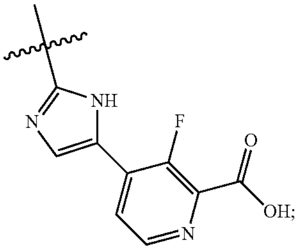 [SMILES: *c1ncc(-c2ccnc(C(=O)O)c2F)[nH]1]

and tautomers, stereoisomers, isotopologues, and pharmaceutically acceptable salts thereof.

In some embodiments, the present invention is directed to compounds of formula (I) wherein $R^1$ is selected from the group consisting of 4-chloro-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is hydrogen;

$R^D$ is hydrogen;

$R^E$ is hydrogen;

Q is selected from the group consisting of (a)

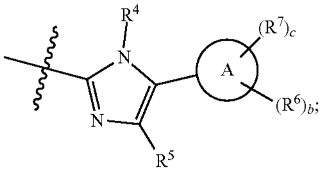

and

-continued (b)

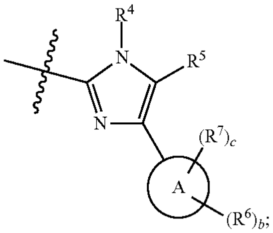

wherein $R^4$ is hydrogen;

$R^5$ is selected from the group consisting of hydrogen, deutero, fluoro, and chloro;

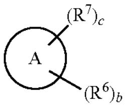

is selected from the group consisting of 4-(methoxy-carbonyl-amino)-phenyl, 2-(cyclopropyl-carbonyl-amino)-phenyl;

2-carboxy-thien-5-yl, 2-(amino-carbonyl)-thien-4-yl, 2-(amino-carbonyl)-thien-5-yl, 3-(trifluoro-methyl)-pyrrol-4-yl, 2-(amino-carbonyl)-thiazol-5-yl;

2-carboxy-3-fluoro-pyridin-4-yl, 2-fluoro-6-amino-pyridin-3-yl, 2-amino-3-fluoro-pyridin-4-yl, 2-fluoro-5-deutero-6-amino-pyridin-3-yl, 2-amino-pyridin-4-yl, 2-chloro-6-amino-pyridin-3-yl, 2-(ethyl-amino)-3-fluoro-pyridin-4-yl, 2-(2-methyl-2-hydroxy-n-propyl-amino)-3-fluoro-pyridin-4-yl, 2-fluoro-4,5-dideutero-6-amino-pyridin-3-yl, 2-(methyl-amino)-3-fluoro-pyridin-4-yl, 2-(methyl-sulfonyl-amino)-3-fluoro-pyridin-4-yl 2-(1-hydroxy-cycloprop-1-yl)-pyridin-4-yl, 3-(cyclopropyl-carbonyl-amino)-pyridin-4-yl;

3-(methyl-amino)-indazol-6-yl, 3-amino-indazol-6-yl, benzimidazol-5-yl-2-one, 2H-quinolin-6-yl-2-one, 3,4-dihydro-2H-quinolin-6-yl-2-one, 1H-pyrrolo[2,3-b]pyridin-4-yl, 1,4-dihydro-2H-benzo[d][1,3]oxazin-6-yl-2-one, and 5-fluoro-1,4-dihydro-2H-benzo[d][1,3]oxazin-6-yl-2-one;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than

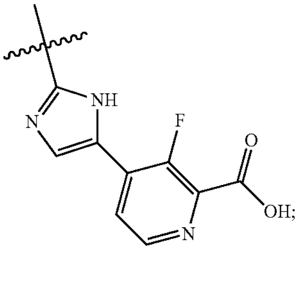

and tautomers, stereoisomers, isotopologues, and pharmaceutically acceptable salts thereof.

In some embodiments, the present invention is directed to compounds of formula (I) wherein $R^1$ is 1,2,3,4-tetrazol-1-yl; a is 2; the two $R^2$ are 2-fluoro, and 3-chloro; $R^A$ and $R^B$ are each hydrogen; $R^C$ is hydrogen; $R^D$ is hydrogen; $R^E$ is hydrogen; Q is selected from the group consisting of (a)

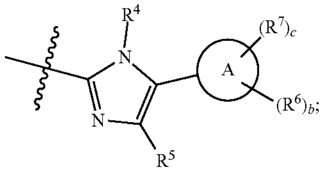

and (b)

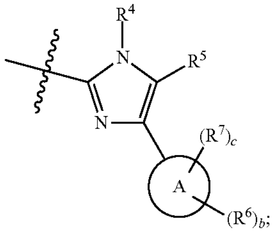

wherein $R^4$ is hydrogen; $R^5$ is selected from the group consisting of hydrogen, and chloro; and

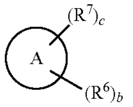

is selected from the group consisting of 4-(methoxy-carbonyl-amino)-phenyl, 2-(cyclopropyl-carbonyl-amino)-phenyl, 2-(amino-carbonyl)-thien-5-yl, 2-(amino-carbonyl)-thiazol-5-yl, 2-chloro-6-amino-pyridin-3-yl, 3-(cyclopropyl-carbonyl-amino)-pyridin-4-yl, 3-amino-indazol-6-yl, 2H-quinolin-6-yl-2-one, 1H-pyrrolo[2,3-b]pyridin-4-yl, and 1,4-dihydro-2H-benzo[d][1,3]oxazin-6-yl-2-one;

and tautomers, stereoisomers, isotopologues, and pharmaceutically acceptable salts thereof.

In some embodiments, the present invention is directed to compounds of formula (I) wherein $R^1$ is selected from the group consisting of halogen, $C_{1-4}$alkyl, fluorinated $C_{1-4}$alkyl, $C_{1-4}$alkoxy, fluorinated $C_{1-4}$alkoxy, phenyl and 5 to 6 membered heterocyclyl; wherein the phenyl or 5 to 6 membered heterocyclyl is optionally substituted with one or more substituents independently selected from the group consisting of halogen, $C_{1-4}$alkyl, fluorinated $C_{1-4}$alkyl, $C_{1-4}$alkoxy, and fluorinated $C_{1-4}$alkoxy. In some embodiments, the present invention is directed to compounds of formula (I) wherein $R^1$ is selected from the group consisting of fluorinated $C_{1-2}$alkyl, fluorinated $C_{1-2}$alkoxy, and 5-membered nitrogen containing heteroaryl; wherein the 5-membered nitrogen containing heteroaryl is optionally substituted with halogen or fluorinated $C_{1-2}$alkyl.

In some embodiments, the present invention is directed to compounds of formula (I) wherein $R^1$ is selected from the group consisting of difluoromethyl, difluoro-methoxy, 2,2,2-trifluoro-ethoxy, pyrazol-5-yl, imidazol-5-yl, 4-chloro-1,2,3-triazol-1-yl, 4-(trifluoromethyl)-1,2,3-triazol-1-yl, and 1,2,3,4-tetrazol-1-yl. In some embodiments, the present invention is directed to compounds of formula (I) wherein $R^1$ is selected from the group consisting of 4-chloro-1,2,3-triazol-1-yl, 4-(trifluoromethyl)-1,2,3-triazol-1-yl, and 1,2,3,4-tetrazol-1-yl. In some embodiments, the present invention is directed to compounds of formula (I) wherein $R^1$ is selected from the group consisting of 4-chloro-1,2,3-triazol-1-yl, and 1,2,3,4-tetrazol-1-yl. In some embodiments, the present invention is directed to compounds of formula (I) wherein $R^1$ is 1,2,3,4-tetrazol-1-yl.

In some embodiments, the present invention is directed to compounds of formula (I) wherein a is an integer from 0 to 2. In some embodiments, the present invention is directed to compounds of formula (I) wherein a is an integer from 1 to 2. In some embodiments, the present invention is directed to compounds of formula (I) wherein a is 0. In some embodiments, the present invention is directed to compounds of formula (I) wherein a is 1. In some embodiments, the present invention is directed to compounds of formula (I) wherein a is 2.

In some embodiments, the present invention is directed to compounds of formula (I) wherein each $R^2$ is independently selected from the group consisting of chloro, fluoro and methyl. In some embodiments, the present invention is directed to compounds of formula (I) wherein each $R^2$ is independently selected from the group consisting of 2-fluoro, 3-chloro, 5-chloro and 3-methyl. In some embodiments, the present invention is directed to compounds of formula (I) wherein each $R^2$ is independently selected from the group consisting of 2-fluoro, and 3-chloro. In some embodiments, the present invention is directed to compounds of formula (I) wherein the each $R^2$ is independently selected from the group consisting of 2-fluoro, and 3-chloro.

In some embodiments, the present invention is directed to compounds of formula (I) wherein a is 2, and the two $R^2$ groups are 2-fluoro and 3-chloro.

In some embodiments, the present invention is directed to compounds of formula (I) wherein $R^A$ is selected from the group consisting of hydrogen and halogen. In some embodiments, the present invention is directed to compounds of formula (I) wherein $R^A$ is selected from the group consisting of hydrogen and fluoro. In some embodiments, the present invention is directed to compounds of formula (I) wherein $R^A$ is selected from the group consisting of hydrogen (or deutero), and fluoro. In some embodiments, the present invention is directed to compounds of formula (I) wherein $R^A$ is hydrogen (or deutero). In some embodiments, the present invention is directed to compounds of formula (I) wherein $R^A$ is hydrogen. In some embodiments, the present invention is directed to compounds of formula (I) wherein $R^A$ is deutero. In some embodiments, the present invention is directed to compounds of formula (I) wherein $R^A$ is halogen. In some embodiments, the present invention is directed to compounds of formula (I) wherein $R^A$ is fluoro.

In some embodiments, the present invention is directed to compounds of formula (I) wherein $R^B$ is selected from the group consisting of hydrogen and halogen. In some embodiments, the present invention is directed to compounds of formula (I) wherein $R^B$ is selected from the group consisting of hydrogen and fluoro. In some embodiments, the present invention is directed to compounds of formula (I) wherein $R^B$ is hydrogen (or deutero) and fluoro. In some embodiments, the present invention is directed to compounds of formula (I) wherein $R^B$ is hydrogen (or deutero). In some embodiments, the present invention is directed to compounds of formula (I) wherein $R^B$ is hydrogen. In some embodiments, the present invention is directed to compounds of formula (I) wherein $R^B$ is deutero. In some embodiments, the present invention is directed to compounds of formula (I) wherein $R^B$ is halogen. In some embodiments, the present invention is directed to compounds of formula (I) wherein $R^B$ is fluoro.

In some embodiments, the present invention is directed to compounds of formula (I) wherein $R^A$ and $R^B$ are each hydrogen. In some embodiments, the present invention is directed to compounds of formula (I) wherein $R^A$ and $R^B$ are each deutero.

In some embodiments, the present invention is directed to compounds of formula (I) wherein $R^A$ and $R^B$ are taken together with the carbon atom to which they are bound to form oxo.

In some embodiments, the present invention is directed to compounds of formula (I) wherein $R^C$ is selected from the group consisting of hydrogen and $C_{1-2}$alkyl. In some embodiments, the present invention is directed to compounds of formula (I) wherein $R^C$ is selected from the group consisting of hydrogen (or deutero), and methyl. In some embodiments, the present invention is directed to compounds of formula (I) wherein $R^C$ is hydrogen (or deutero). In some embodiments, the present invention is directed to compounds of formula (I) wherein $R^C$ is selected from the group consisting of hydrogen and methyl. In some embodiments, the present invention is directed to compounds of formula (I) wherein $R^C$ is selected from the group consisting of methyl and ethyl. In some embodiments, the present invention is directed to compounds of formula (I) wherein $R^C$ is hydrogen. In some embodiments, the present invention is directed to compounds of formula (I) wherein $R^C$ is deutero. In some embodiments, the present invention is directed to compounds of formula (I) wherein $R^C$ is methyl.

In some embodiments, the present invention is directed to compounds of formula (I) wherein $R^D$ is selected from the group consisting of hydrogen, $C_{1-2}$alkyl and $C_{1-2}$alkoxy. In some embodiments, the present invention is directed to compounds of formula (I) wherein $R^D$ is selected from the group consisting of hydrogen (or deutero), methyl and methoxy. In some embodiments, the present invention is directed to compounds of formula (I) wherein $R^D$ is hydrogen (or deutero). In some embodiments, the present invention is directed to compounds of formula (I) wherein $R^D$ is hydrogen. In some embodiments, the present invention is directed to compounds of formula (I) wherein $R^D$ is deutero. In some embodiments, the present invention is directed to compounds of formula (I) wherein $R^D$ is selected from the group consisting of methyl and methoxy. In some embodiments, the present invention is directed to compounds of formula (I) wherein $R^D$ is methyl. In some embodiments, the present invention is directed to compounds of formula (I) wherein $R^D$ is methoxy.

In some embodiments, the present invention is directed to compounds of formula (I) wherein $R^D$ is selected from the group consisting of hydrogen (or deutero), methyl, S*-methyl, R*-methyl, methoxy, S-methoxy, and R-methoxy. In some embodiments, the present invention is directed to compounds of formula (I) wherein $R^D$ is selected from the group consisting of hydrogen (or deutero), methyl, S*-methyl, R*-methyl, S-methoxy, and R-methoxy. In some embodiments, the present invention is directed to compounds of formula (I) wherein $R^D$ is selected from the group consisting of hydrogen, methyl, S*-methyl, R*-methyl, S-methoxy, and R-methoxy. In some embodiments, the present invention is directed to compounds of formula (I) wherein $R^D$ is selected from the group consisting of hydrogen, methyl, S*-methyl, and R-methoxy. In some embodiments, the present invention is directed to compounds of formula (I) wherein $R^D$ is selected from the group consisting of hydrogen, methyl, and R-methoxy. In some embodiments, the present invention is directed to compounds of formula (I) wherein $R^D$ is hydrogen. In some embodiments, the present invention is directed to compounds of formula (I) wherein $R^D$ is deutero.

In some embodiments, the present invention is directed to compounds of formula (I) wherein $R^E$ is selected from the group consisting of hydrogen and $C_{1-2}$alkyl. In some embodiments, the present invention is directed to compounds of formula (I) wherein $R^E$ is selected from the group consisting of hydrogen and methyl. In some embodiments, the present invention is directed to compounds of formula (I) wherein $R^E$ is hydrogen. In some embodiments, the present invention is directed to compounds of formula (I) wherein $R^E$ is methyl.

In some embodiments, the present invention is directed to compounds of formula (I) wherein $R^A$ and $R^B$ are each hydrogen. In some embodiments, the present invention is directed to compounds of formula (I) wherein $R^C$ and $R^D$ are each hydrogen. In some embodiments, the present invention is directed to compounds of formula (I) wherein $R^A$, $R^B$ and $R^E$ are each hydrogen. In some embodiments, the present invention is directed to compounds of formula (I) wherein $R^C$, $R^D$ and $R^E$ are each hydrogen. In some embodiments, the present invention is directed to compounds of formula (I) wherein $R^A$, $R^B$, $R^C$ and $R^D$ are each hydrogen. In some embodiments, the present invention is directed to compounds of formula (I) wherein $R^A$, $R^B$, $R^C$, $R^D$ and $R^E$ are each hydrogen. In some embodiments, the present invention is directed to compounds of formula (I) wherein one of $R^A$, $R^B$, $R^C$, $R^D$ or $R^E$ is other than hydrogen.

In some embodiments, the present invention is directed to compounds of formula (I) wherein $R^4$ is selected from the group consisting of hydrogen and $C_{1-2}$alkyl. In some embodiments, the present invention is directed to compounds of formula (I) wherein $R^4$ is selected from the group consisting of hydrogen and methyl. In some embodiments, the present invention is directed to compounds of formula (I) wherein $R^4$ is hydrogen. In some embodiments, the present invention is directed to compounds of formula (I) wherein $R^4$ is methyl.

In some embodiments, the present invention is directed to compounds of formula (I) wherein $R^5$ is selected from the group consisting of hydrogen, halogen and $C_{1-2}$alkyl. In some embodiments, the present invention is directed to compounds of formula (I) wherein $R^5$ is hydrogen or deutero. In some embodiments, the present invention is directed to compounds of formula (I) wherein $R^5$ is halogen. In some embodiments, the present invention is directed to compounds of formula (I) wherein $R^5$ is selected from the group consisting of fluoro and chloro. In some embodiments, the present invention is directed to compounds of formula (I) wherein $R^5$ is chloro. In some embodiments, the present invention is directed to compounds of formula (I) wherein $R^5$ is $C_{1-2}$alkyl. In some embodiments, the present invention is directed to compounds of formula (I) wherein $R^5$ is methyl.

In some embodiments, the present invention is directed to compounds of formula (I) wherein $R^5$ is selected from the group consisting of hydrogen, deutero, fluoro, chloro, bromo, and methyl. In some embodiments, the present invention is directed to compounds of formula (I) wherein $R^5$ is selected from the group consisting of hydrogen (or deutero), fluoro, and chloro. In some embodiments, the present invention is directed to compounds of formula (I) wherein $R^5$ is selected from the group consisting of hydrogen (or deutero), and chloro.

In some embodiments, the present invention is directed to compounds of formula (I) wherein

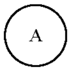

is phenyl. In some embodiments, the present invention is directed to compounds of formula (I) wherein

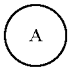

is 5-6 membered heteroaryl. In some embodiments, the present invention is directed to compounds of formula (I) wherein

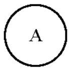

is 5 membered heteroaryl. In some embodiments, the present invention is directed to compounds of formula (I) wherein

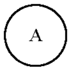

is 6 membered heteroaryl. In some embodiments, the present invention is directed to compounds of formula (I) wherein

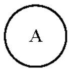

is 9 to 10 membered heterocyclyl. In some embodiments, the present invention is directed to compounds of formula (I) wherein

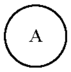

is 9 membered heterocyclyl. In some embodiments, the present invention is directed to compounds of formula (I) wherein

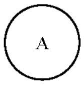

is 10 membered heterocydyl.

In some embodiments, the present invention is directed to compounds of formula (I) wherein b is 0. In some embodiments, the present invention is directed to compounds of formula (I) wherein b is 1.

In some embodiments, the present invention is directed to compounds of formula (I) wherein $R^6$ is selected from the group consisting of $C_{3-8}$cycloalkyl, —O—($C_{1-2}$alkylene)-$C_{3-8}$cycloalkyl, —NH—($C_{3-8}$cycloalkyl), —NH—C(O)—($C_{3-8}$cycloalkyl), 4-6 membered heterocycloalkyl, —O—($C_{1-2}$alkylene)-(4-6 membered heterocycloalkyl), —C(O)-(4-6 membered heterocycloalkyl), —NH—(4-6 membered heterocycloalkyl), —C(O)—NH—(4-6 membered heterocycloalkyl), 5-6 membered heteroaryl, —O—($C_{1-2}$alkylene)-(5-6 membered heteroaryl), —NH—C(O)-(5-6 membered heteroaryl), and 2-oxa-6-azaspiro[3.3]hept-6-yl; wherein the $C_{3-6}$cycloalkyl, 4-6 membered heterocycloalkyl, or 5-6 membered heteroaryl, whether alone or as part of a substituent group is optionally substituted with one to two substituents independently selected from the group consisting of halogen, $C_{1-2}$alkyl, hydroxy, oxo, cyano and $NR^PR^Q$; wherein $R^P$ and $R^Q$ are each independently selected from the group consisting of hydrogen and $C_{1-4}$alkyl.

In some embodiments, the present invention is directed to compounds of formula (I) wherein $R^6$ is selected from the group consisting of $C_{3-8}$cycloalkyl, —NH—C(O)—$C_{3-8}$cycloalkyl, 4-6 membered heterocycloalkyl, —O—($C_{1-2}$alkylene)-(4-6 membered heterocycloalkyl), —C(O)-(4-6 membered heterocycloalkyl), —NH—(4-6 membered heterocycloalkyl), —C(O)—NH—(5-6 membered heterocycloalkyl), 5-6 membered heteroaryl, —O—($C_{1-2}$alkylene)-(5-6 membered heteroaryl), —NH—C(O)-(5-6 membered heteroaryl), and 2-oxa-6-azaspiro[3.3]hept-6-yl; wherein the $C_{3-5}$cycloalkyl, 4-6 membered heterocycloalkyl, or 5-6 membered heteroaryl, whether alone or as part of a substituent group is optionally substituted with one to two substituents independently selected from the group consisting of halogen, $C_{1-2}$alkyl, hydroxy, oxo, cyano, and $NR^PR^Q$; wherein $R^P$ and $R^Q$ are each independently selected from the group consisting of hydrogen and $C_{1-4}$alkyl.

In some embodiments, the present invention is directed to compounds of formula (I) wherein c is an integer from 0 to 2. In some embodiments, the present invention is directed to compounds of formula (I) wherein c is an integer from 0 to 1. In some embodiments, the present invention is directed to compounds of formula (I) wherein c is an integer from 1 to 2. In some embodiments, the present invention is directed to compounds of formula (I) wherein c is 0. In some embodiments, the present invention is directed to compounds of formula (I) wherein c is 1. In some embodiments, the present invention is directed to compounds of formula (I) wherein c is 2.

In some embodiments, the present invention is directed to compounds of formula (I) wherein each $R^7$ is independently selected from the group consisting of halogen, $C_{1-2}$alkyl, fluorinated $C_{1-2}$alkyl, hydroxy substituted $C_{1-6}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-5}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-2}$alkyl), —C(O)—$NR^K$—$SO_2$—($C_{1-2}$alkyl), —($C_{1-2}$alkylene)-O—P(O)$(OH)_2$, and —($C_{1-2}$alkylene)-O—($C_{1-2}$alkylene)-P(O)$(OH)_2$; wherein $R^K$ and $R^L$ are each independently selected from hydrogen and $C_{1-4}$alkyl.

In some embodiments, the present invention is directed to compounds of formula (I) wherein each $R^7$ is independently selected from the group consisting of halogen, $C_{1-2}$alkyl, fluorinated $C_{1-2}$alkyl, hydroxy substituted $C_{1-4}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1}$-~alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, $NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-5}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-2}$alkyl), —C(O)—$NR^K$—$SO_2$—($C_{1-2}$alkyl), —($C_{1-2}$alkylene)-O—P(O)$(OH)_2$, and —($C_{1-2}$alkyene)-O—($C_{1-2}$alkylene)-P(O)$(OH)_2$; wherein $R^K$ and $R^L$ are each independently selected from hydrogen and $C_{1-2}$alkyl.

In some embodiments, the present invention is directed to compounds of formula (I) wherein

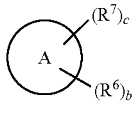

is selected from the group consisting of 2-methoxy-phenyl, 2-(isopropyloxy)-phenyl, 3-fluoro-4-carboxy-phenyl, 2-amino-phenyl, 2-(dimethyl-amino)-phenyl, 2-(amino-carbonyl)-phenyl, 2-fluoro-4-(amino-carbonyl)-phenyl, 2-fluoro-3-(amino-carbonyl)-phenyl, 3-(amino-carbonyl)-4-fluoro-phenyl, 3-fluoro-4-(amino-carbonyl)-phenyl, 2-(methyl-amino-carbonyl)-phenyl, 2-(dimethyl-amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 4-(1R-(methyl-carbonyl-amino)-ethyl)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl, 2-(methyl-sulfonyl-amino)-phenyl, 4-(oxazolidin-3-yl-2-one)-phenyl, 2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 2-(amino-carbonyl)-3-fluoro-thien-5-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 4-chloro-pyrazol-3-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, 1-methyl-3-(cyclopropyl-carbonyl-amino)-pyrazol-4-yl, 1-methyl-4-(cyclopropyl-carbonyl-amino)-pyrazol-5-yl, imidazol-2-yl, 2-(trifluoro-methyl)-imidazol-4-yl, 1-methyl-imidazol-2-yl, 4-(hydroxy-methyl)-thiazol-2-yl, 2-(hydroxy-methyl)-thiazol-4-yl, 2-(amino-carbonyl)-thiazol-5-yl, 1,2,4-triazol-3-yl, 1,2,3-triazol-5-yl, 1-methyl-(1,2,4-triazol-3-yl), 1-methyl-1,2,3-triazol-5-yl, 3-fluoro-pyridin-4-yl-2-one, 3-fluoro-pyridin-4-yl, 2-fluoro-5-chloro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R'-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1S-hydroxy-ethyl)-3-fluoro-pyridin-4-yl, 2-(1R-(hydroxy-methyl)-ethyl)-3-fluoro-pyridin-4-yl, 2-(1S*-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S*-cyan-ethyl)-3-fluoro-pyridin-4-yl, 2 (1R*-cyano-ethyl)-3-fluoro-pyridin-4-yl, 4-amino-pyridin-3-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-amino-6-(trifluoro-methyl)-pyridin-5-yl, 2-(methyl-amino)-pyridin-3-yl, 2-fluoro-6-(methyl-amino)-pyridin-3-yl, 2-fluoro-6-(dimethyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R'-hydroxy-n-propyl)-3-fluoro-pyridin-4-yl, 2-fluoro-4-deutero-6-amino-pyridin-3-yl, 2-fluoro-5-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-4-yl, 2-(amino-carbonyl)-pyridin-5-yl, 2-(amino-carbonyl)-3-fluoro-pyridin-3-yl, 2-chloro-6-(amino-carbonyl)-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 3-chloro-6-(methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 4-(ethoxy-carbonyl-amino)-pyridin-3-yl, 2-(ethoxy-carbonyl-amino-methyl)-3-fluoro-pyridin-4-yl, 3-(methyl-carbonyl-amino)-6-(trifluoro-methyl)-pyridin-4-yl, 3-(d3-methyl-carbonyl-amino)-6-(trifluoro-methyl)-pyridin-4-yl, 2-(1S-amino-isopropyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(2-cyano-cycloprop-1-yl)-3-fluoro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)- pyridin-3-yl, 2-(oxetan-3-yl)-3-fluoro-pyridin-4-yl, 2-(3-cyano-oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(pyrrolidin-1-yl-2-one)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-2-yl, 2-(pyrazol-5-yl)-pyridin-4-yl, 2-(pyrazol-5-yl)-3-fluoro-pyridin-4-yl, 2-(5-amino-pyrazol-1-yl)-pyridin-4-yl, 2-(3-amino-pyrazol-1-yl)-3-fluoro-pyridin-4-yl, 2-(5-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 2-(1,2,3-triazol-1-yl)-pyridin-4-yl, 1-(1,2,5-triazol-1-yl)-pyridin-4-yl, 2-(1,2,3-triazol-1-yl)-3-fluoro-pyridin-4-yl, 2-(1,3,4-triazol-1-yl)-3-fluoro-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1R*-oxazol-2-yl-ethoxy)-3-fluoro-pyridin-4-yl, 2-(1 S*-oxazol-2-yl-ethoxy)-3-fluoro-pyridin-4-yl, 2-(1S-(1,3,4-oxadiazol-2-yl)-ethoxy)-3-fluoro-pyridin-4-yl, 2-(3,3-difluoro-azetin-1-yl-carbonyl)-3-fluoro-pyridin-4-yl, 2-fluoro-6-(bicyclo[1.1.1]pentanyl-amino)-pyridin-3-yl, 2-(bicyclo[1.1.1]pentanyl-amino)-3-fluoro-pyridin-3-yl, 2-(bicyclo[1.1.1]pentanyl-amino-carbonyl)-3-fluoro-pyridin-3-yl, 3-(cyclopropyl-carbonyl-amino)-6-(trifluoro-methyl)-pyridin-4-yl, 2-(3-methyl-isoxazol-5-yl-carbonyl-amino)-3-fluoro-pyridin-4-yl, pyridin-4-yl-2-one, pyridin-4-yl-N-oxide, 2-(hydroxy-methyl)-3-fluoro-pyridin-4-yl-N-oxide, indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-b]pyridin-5-yl, 1H-pyrrolo[2,3-c]pyridin-3-yl, 5-methyl-1H-pyrrolo[2,3-c]pyridin-3-yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, and 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol.

In some embodiments, the present invention is directed to compounds of formula (I) wherein

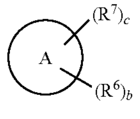

is selected from the group consisting of 2-methoxy-phenyl, 2-fluoro-4-(amino-carbonyl)-phenyl, 2-fluoro-3-(amino-carbonyl)-phenyl, 3-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl, 2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, 2-(amino-carbonyl)-thiazol-5-yl, 3-fluoro-pyridin-4-yl-2-one, 3-fluoro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R*-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1 S-hydroxy-ethyl)-3-fluoro-pyridin-4-yl, 2-(1R-(hydroxy-methyl)-ethyl)-3-fluoro-pyridin-4-yl, 2-(1S*-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S*-cyano-ethyl)-3-fluoro-pyridin-4-yl, 2-(1R'-cyano-ethyl)-3-fluoro-pyridin-4-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R*-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-5-yl, 2-(amino-carbonyl)-3-fluoro-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 2-(ethoxy-carbonyl-amino-methyl)-3-fluoro-pyridin-4-yl, 2 (1 S-amino-isopropyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(3-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 1-(1,2,5-triazol-1-yl)-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1 S*-oxazol-2-yl-ethoxy)-3-fluoro-pyridin-4-yl, 2-(1S-(1,3,4-oxadiazol-2-yl)-ethoxy)-3-fluoro-pyridin-4-yl, 2-(bicyclo[1.1.1]pentanyl-amino)-3-fluoro-pyridin-3-yl, 3-(cyclopropyl-carbonyl-amino)-6-(trifluoro-methyl)-pyridin-4-yl, 2-(3-methyl-isoxazol-5-yl-carbonyl-amino)-3-fluoro-pyridin-4-yl, pyridin-4-yl-2-one, indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-c]pyridin-3yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol.

In some embodiments, the present invention is directed to compounds of formula (I) wherein

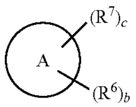

is selected from the group consisting of 2-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl, 2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 3-(trifluoro-methyl)-pyrrol-4-yl, 3-chloro-pyrazol-4-yl, 3 (trifluoromethyl)-pyrazol-4-yl, 5-chloro-pyrazol-4-yl, 1-methyl-4-(cyclopropyl-carbonyl-amino)-pyrazol-5-yl, 2-(amino-carbonyl)-thiazol-5-yl, 2-carboxy-3-fluoro-pyridin-4-yl, 2-(hydroxy-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-(hydroxy-d2-methyl)-3-chloro-pyridin-4-yl, 12-(1R-(hydroxy-methyl)-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(2-methyl-2-hydroxy-n-propyl-oxy)-3-fluoro-pyridin-4-yl, 2-chloro-6-amino-pyridin-3-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(methoxy-amino-carbonyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(ethoxy-carbonyl-amino)-pyridin-3-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(3-cyano-azetidin-1-yl)-3-fluoro-pyridin-4-yl, 2-(S-tetrahydrofuran-3-yl-amino)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(imidazol-2-yl)-3-fluoro-pyridin-4-yl, 1-(1,2,5-triazol-1-yl)-pyridin-4-yl, 2-(dioxan-2S-yl-ethoxy)-3-fluoro-pyridin-4-yl, pyridin-4-yl-2-one, indol-5-yl-2-one, 7-fluoro-indol-6-yl, indazol-5-yl, 3-(methyl-amino)-indazol-6-yl, 3-amino-indazol-6-yl, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, benzoxazol-6-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-c]pyridin-3-yl, 1H-pyrrolo[2,3-c]pyridin-3yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl.

In some embodiments, the present invention is directed to compounds of formula (I) wherein

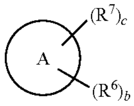

is selected from the group consisting of 2-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl, 2-carboxy-thien-5-yl, 2-carboxy-3-fluoro-thien-5-yl, 2-(amino-carbonyl)-thien-4-yl, 2-(amino-carbonyl)-thien-5-yl, 3-(trifluoro-methyl)-pyrrol-4-yl, 3-chloro-pyrazol-4-yl, 3-(trifluoromethyl)-pyrazol-4-yl, 1-methyl-4-(cyclopropyl-carbonyl-amino)-pyrazol-5-yl, 2-(amino-carbonyl)-thiazol-5-yl, 2-carboxy-3-fluoro-pyridin-4-yl, 2-(hydroxy-methyl)-3-fluoro-pyridin-4-yl, 2-(1R-(hydroxy-methyl)-ethyl)-3-fluoro-pyridin-4-yl, 2-(2-methyl-2-hydroxy-n-propyl-oxy)-3-fluoro-pyridin-4-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-chloro-6-amino-pyridin-3-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 5-(methoxy-carbonyl-amino)-pyridin-2-yl, 2-(methoxy-carbonyl-amino)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(S-tetrahydrofuran-3-yl-amino)-3-fluoro-pyridin-4-yl, 2-(pyrazol-5-yl)-pyridin-4-yl, 1-(1,2,5-triazol-1-yl)-pyridin-4-yl, 3-(methyl-amino)-indazol-6-yl, 3-amino-indazol-6-yl, benzimidazol-5-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 1H-pyrrolo[2,3-b]pyridin-4-yl, 6-methoxy-1H-pyrrolo[3,2-c]pyridin-3-yl, 7H-pyrrolo[2,3-d]pyrimidin-5-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl.

In some embodiments, the present invention is directed to compounds of formula (I) wherein

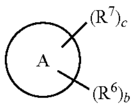

is selected from the group consisting of 4-(methoxy-carbonyl-amino)-phenyl, 2-(cyclopropyl-carbonyl-amino)-phenyl, 2-carboxy-thien-5-yl, 2-(amino-carbonyl)-thien-4-yl, 2-(amino-carbonyl)-thien-5-yl, 3-(trifluoro-methyl)-pyrrol-4-yl, 2-(amino-carbonyl)-thiazol-5-yl, 2-carboxy-3-fluoro-pyridin-4-yl, 2-fluoro-6-amino-pyridin-3-yl, 2-amino-3-fluoro-pyridin-4-yl, 2-fluoro-5-deutero-6-amino-pyridin-3-yl, 2-amino-pyridin-4-yl, 2-chloro-6-amino-pyridin-3-yl, 2-(ethyl-amino)-3-fluoro-pyridin-4-yl, 2-(2-methyl-2-hydroxy-n-propyl-amino)-3-fluoro-pyridin-4-yl, 2-fluoro-4,5-dideutero-6-amino-pyridin-3-yl, 2-(methyl-amino)-3-fluoro-pyridin-4-yl, 2-(methyl-sulfonyl-amino)-3-fluoro-pyridin-4-yl 2-(1-hydroxy-cycloprop-1-yl)-pyridin-4-yl, 3-(cyclopropyl-carbonyl-amino)-pyridin-4-yl, 3-(methyl-amino)-indazol-6-yl, 3-amino-indazol-6-yl, benzimidazol-5-yl-2-one, 2H-quinolin-6-yl-2-one, 3,4-dihydro-2H-quinolin-6-yl-2-one, 1H-pyrrolo[2,3-b]pyridin-4-yl, 1,4-dihydro-2H-benzo[d][1,3]oxazin-6-yl-2-one, and 5-fluoro-1,4-dihydro-2H-benzo[d][1,3]oxazin-6-yl-2-one.

In some embodiments, the present invention is directed to compounds of formula (I) wherein

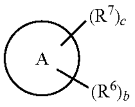

is selected from the group consisting of 4-(methoxy-carbonyl-amino)-phenyl, 2-(cyclopropyl-carbonyl-amino)-phenyl, 2-(amino-carbonyl)-thien-5-yl, 2-(amino-carbonyl)-thiazol-5-yl, 2-chloro-6-amino-pyridin-3-yl, 3-(cyclopropyl-carbonyl-amino)-pyridin-4-yl, 3-amino-indazol-6-yl, 2H-quinolin-6-yl-2-one, 1H-pyrrolo[2,3-b]pyridin-4-yl, and 1,4-dihydro-2H-benzo[d][1,3]oxazin-6-yl-2-one.

In some embodiments, the present invention is directed to compounds of formula (I) wherein

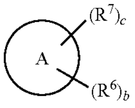

is selected from the group consisting of 2-methoxy-phenyl, 2-(isopropyloxy)-phenyl, 3-fluoro-4-carboxy-phenyl, 2-amino-phenyl, 2-(dimethyl-amino)-phenyl, 2-(amino-carbonyl)-phenyl, 2-fluoro-4-(amino-carbonyl)-phenyl, 2-fluoro-3-(amino-carbonyl)-phenyl, 3-(amino-carbonyl)-4-fluoro-phenyl, 3-fluoro-4-(amino-carbonyl)-phenyl, 2-(methyl-amino-carbonyl)-phenyl, 2-(dimethyl-amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 4-(1R-(methyl-carbonyl-amino)-ethyl)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl, 2-(methyl-sulfonyl-amino)-phenyl, and 4-(oxazolidin-3-yl-2-one)-phenyl.

In some embodiments, the present invention is directed to compounds of formula (I) wherein

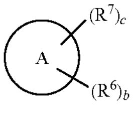

is selected from the group consisting of 2-methoxy-phenyl, 2-fluoro-4-(amino-carbonyl)-phenyl, 2-fluoro-3-(amino-carbonyl)-phenyl, 3-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, and 2-(cyclopropyl-carbonyl-amino)-4-methoxy-phenyl. In some embodiments, the present invention is directed to compounds of formula (I) wherein

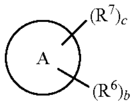

is selected from the group consisting of 2-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, and 2-(cyclopropyl-carbonyl-amino)-4-methoxy-phenyl. In some embodiments, the present invention is directed to compounds of formula (I) wherein

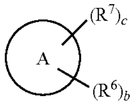

is selected from the group consisting of 4-(methoxy-carbonyl-amino)-phenyl, and 2-(cyclopropyl-carbonyl-amino)-phenyl.

In some embodiments, the present invention is directed to compounds of formula (I) wherein

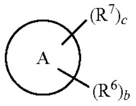

is selected from the group consisting of 2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 2-(amino-carbonyl)-3-fluoro-thien-5-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 4-chloro-pyrazol-3-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, 1-methyl-3-(cyclopropyl-carbonyl-amino)-pyrazol-4-yl, 1-methyl-4-(cyclopropyl-carbonyl-amino)-pyrazol-5-yl, imidazol-2-yl, 2-(trifluoro-methyl)-imidazol-4-yl, 1-methyl-imidazol-2-yl, 4-(hydroxy-methyl)-thiazol-2-yl, 2-(hydroxy-methyl)-thiazol-4-yl, 2-(amino-carbonyl)-thiazol-5-yl, 1,2,4-triazol-3-yl, 1,2,3-triazol-5-yl, 1-methyl-(1,2,4-triazol-3-yl), and 1-methyl-1,2,3-triazol-5-yl.

In some embodiments, the present invention is directed to compounds of formula (I) wherein

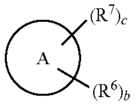

is selected from the group consisting of 2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, and 2-(amino-carbonyl)-thiazol-5-yl. In some embodiments, the present invention is directed to compounds of formula (I) wherein

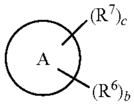

is selected from the group consisting of 2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 3-(trifluoro-methyl)-pyrrol-4-yl, 3-chloro-pyrazol-4-yl, 3-(trifluoromethyl)-pyrazol-4-yl, 5-chloro-pyrazol-4-yl, 1-methyl-4-(cyclopropyl-carbonyl-amino)-pyrazol-5-yl, and 2-(amino-carbonyl)-thiazol-5-yl.

In some embodiments, the present invention is directed to compounds of formula (I) wherein

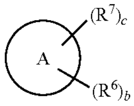

is selected from the group consisting of 2-carboxy-thien-5-yl, 2-carboxy-3-fluoro-thien-5-yl, 2-(amino-carbonyl)-thien-4-yl, 2-(amino-carbonyl)-thien-5-yl, 3-(trifluoro-methyl)-pyrrol-4-yl, 3-chloro-pyrazol-4-yl, 3-(trifluoromethyl)-pyrazol-4-yl, 1-methyl-4-(cyclopropyl-carbonyl-amino)-pyrazol-5-yl, and 2-(amino-carbonyl)-thiazol-5-yl. In some embodiments, the present invention is directed to compounds of formula (I) wherein

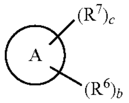

is selected from the group consisting of 2-carboxy-thien-5-yl, 2-(amino-carbonyl)-thien-4-yl, 2-(amino-carbonyl)-thien-5-yl, 3-(trifluoro-methyl)-pyrrol-4-yl, and 2-(amino-carbonyl)-thiazol-5-yl.

In some embodiments, the present invention is directed to compounds of formula (I) wherein

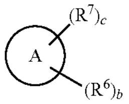

is selected from the group consisting of 3-fluoro-pyridin-4-yl-2-one, 3-fluoro-pyridin-4-yl, 2-fluoro-5-chloro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R*-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1S-hydroxy-ethyl)-3-fluoro-pyridin-4-yl, 2-(1R-(hydroxy-methyl)-ethyl)-3-fluoro-pyridin-4-yl, 2-(1S*-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S*-cyano-ethyl)-3-fluoro-pyridin-4-yl, 2-(1R*-cyano-ethyl)-3-fluoro-pyridin-4-yl, 4-amino-pyridin-3-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-amino-6-(trifluoro-methyl)-pyridin-5-yl, 2-(methyl-amino)-pyridin-3-yl, 2-fluoro-6-(methyl-amino)-pyridin-3-yl, 2-fluoro-6-(dimethyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R*-hydroxy-n-propyl)-3-fluoro-pyridin-4-yl, 2-fluoro-4-deutero-6-amino-pyridin-3-yl, 2-fluoro-5-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-4-yl, 2-(amino-carbonyl)-pyridin-5-yl, 2-(amino-carbonyl)-3-fluoro-pyridin-3-yl, 2-chloro-6-(amino-carbonyl)-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 3-chloro-6-(methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 4-(ethoxy-carbonyl-amino)-pyridin-3-yl, 2-(ethoxy-carbonyl-amino-methyl)-3-fluoro-pyridin-4-yl, 3-(methyl-carbonyl-amino)-6-(trifluoro-methyl)-pyridin-4-yl, 3-(d3-methyl-carbonyl-amino)-6-(trifluoro-methyl)-pyridin-4-yl, 2-(1S-amino-isopropyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(2-cyano-cycloprop-1-yl)-3-fluoro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(oxetan-3-yl)-3-fluoro-pyridin-4-yl, 2-(3-cyano-oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(pyrrolidin-1-yl-2-one)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-2-yl, 2-(pyrazol-5-yl)-pyridin-4-yl, 2-(pyrazol-5-yl)-3-fluoro-pyridin-4-yl, 2-(5-amino-pyrazol-1-yl)-pyridin-4-yl, 2-(3-amino-pyrazol-1-yl)-3-fluoro-pyridin-4-yl, 2-(5-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 2-(1,2,3-triazol-1-yl)-pyridin-4-yl, 1-(1,2,5-triazol-1-yl)-pyridin-4-yl, 2-(1,2,3-triazol-1-yl)-3-fluoro-pyridin-4-yl, 2-(1,3,4-triazol-1-yl)-3-fluoro-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1R*-oxazol-2-yl-ethoxy)-3-fluoro-pyridin-4-yl, 2-(1S*-oxazol-2-yl-ethoxy)-3-fluoro-pyridin-4-yl, 2-(1S-(1,3,4-oxadiazol-2-yl)-ethoxy)-3-fluoro-pyridin-4-yl, 2-(3,3-difluoro-azetin-1-yl-carbonyl)-3-fluoro-pyridin-4-yl, 2-fluoro-6-(bicyclo[1.1.1]pentanyl-amino)-pyridin-3-yl, 2-(bicyclo[1.1.1]pentanyl-amino)-3-fluoro-pyridin-3-yl, 2-(bicyclo[1.1.1]pentanyl-amino-carbonyl)-3-fluoro-pyridin-3-yl, 3-(cyclopropyl-carbonyl-amino)-6-(trifluoro-methyl)-pyridin-4-yl, 2-(3-methyl-isoxazol-5-yl-carbonyl-amino)-3-fluoro-pyridin-4-yl, pyridin-4-yl-2-one, pyridin-4-yl-N-oxide, and 2-(hydroxy-methyl)-3-fluoro-pyridin-4-yl-N-oxide.

In some embodiments, the present invention is directed to compounds of formula (I) wherein

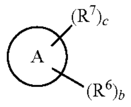

is selected from the group consisting of 3-fluoro-pyridin-4-yl-2-one, 3-fluoro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R'-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1S-hydroxy-ethyl)-3-fluoro-pyridin-4-yl, 2-(1R-(hydroxy-methyl)-ethyl)-3-fluoro-pyridin-4-yl, 2-(1S*-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S cyano-ethyl)-3-fluoro-pyridin-4-yl, 2-(1R*-cyano-ethyl)-3-fluoro-pyridin-4-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R'-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-5-yl, 2-(amino-carbonyl)-3-fluoro-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 2-(ethoxy-carbonyl-amino-methyl)-3-fluoro-pyridin-4-yl, 2-(1S-amino-iso-propyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(3-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 1-(1,2,5-triazol-1-yl)-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1S*-oxazol-2-yl-ethoxy)-3-fluoro-pyridin-4-yl, 2-(1S-(1,3,4-oxadiazol-2-yl)-ethoxy)-3-fluoro-pyridin-4-yl, 2-(bicyclo[1.1.1]pentanyl-amino)-3-fluoro-pyridin-3-yl, 3-(cyclopropyl-carbonyl-amino)-6-(trifluoromethyl)-pyridin-4-yl, 2-(3-methyl-isoxazol-5-yl-carbonyl-amino)-3-fluoro-pyridin-4-yl, and pyridin-4-yl-2-one.

In some embodiments, the present invention is directed to compounds of formula (I) wherein

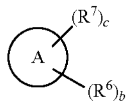

is selected from the group consisting of 2-carboxy-3-fluoro-pyridin-4-yl, 2-(hydroxy-methyl)-3-fluoro-pyridin-4-yl, 2-(1R-(hydroxy-methyl)-ethyl)-3-fluoro-pyridin-4-yl, 2-(2-methyl-2-hydroxy-n-propyl-oxy)-3-fluoro-pyridin-4-yl, 2-fluoro-6-amino-pyridin-3-yi, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-chloro-6-amino-pyridin-3-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 5-(methoxy-carbonyl-amino)-pyridin-2-yl, 2-(methoxy-carbonyl-amino)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(S tetrahydrofuran-3-yl-amino)-3-fluoro-pyridin-4-yl, 2-(pyrazol-5-yl)-pyridin-4-yl, and 1-(1,2,5-triazol-1-yl)-pyridin-4-yl.

In some embodiments, the present invention is directed to compounds of formula (I) wherein

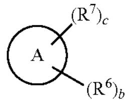

is selected from the group consisting of 2-carboxy-3-fluoro-pyridin-4-yl, 2-(hydroxy-methyl)-3-fluoro-pyridin-4-yl, 2-(2 hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-(hydroxy-d2-methyl)-3-chloro-pyridin-4-yl, \2-(1R-(hydroxy-methyl)-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(2-methyl-2-hydroxy-n-propyl-oxy)-3-fluoro-pyridin-4-yl, 2-chloro-6-amino-pyridin-3-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(methoxy-amino-carbonyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(ethoxy-carbonyl-amino)-pyridin-3-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(3-cyano-azetidin-1-yl)-3-fluoro-pyridin-4-yl, 2-(S-tetrahydrofuran-3-yl-amino)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(imidazol-2-yl)-3-fluoro-pyridin-4-yl, 1-(1,2,5-triazol-1-yl)-pyridin-4-yl, 2-(dioxan-2S-yl-ethoxy)-3-fluoro-pyridin-4-yl, and pyridin-4-yl-2-one.

In some embodiments, the present invention is directed to compounds of formula (I) wherein

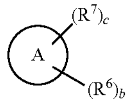

is selected from the group consisting of 2-carboxy-3-fluoro-pyridin-4-yl, 2-fluoro-6-amino-pyridin-3-yl, 2-amino-3-fluoro-pyridin-4-yl, 2-fluoro-5-deutero-6-amino-pyridin-3-yl, 2-amino-pyridin-4-yl, 2-chloro-6-amino-pyridin-3-yl, 2-(ethyl-amino)-3-fluoro-pyridin-4-yl, 2-(2-methyl-2-hydroxy-n-propyl-amino)-3-fluoro-pyridin-4-yl, 2-fluoro-4,5-dideutero-6-amino-pyridin-3-yl, 2-(methyl-amino)-3-fluoro-pyridin-4-yl, 2-(methyl-sulfonyl-amino)-3-fluoro-pyridin-4-yl 2-(1-hydroxy-cycloprop-1-yl)-pyridin-4-yl, and 3-(cyclopropyl-carbonyl-amino)-pyridin-4-yl.

In some embodiments, the present invention is directed to compounds of formula (I) wherein

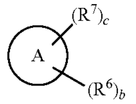

is selected from the group consisting of indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-b]pyridin-5-yl, 1H-pyrrolo[2,3-c]pyridin-3-yl, 5-methyl-1H-pyrrolo[2,3-c]pyridin-3-yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, and 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol.

In some embodiments, the present invention is directed to compounds of formula (I) wherein

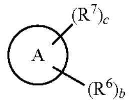

is selected from the group consisting of indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-c]pyridin-3yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol.

In some embodiments, the present invention is directed to compounds of formula (I) wherein

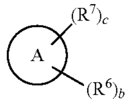

is selected from the group consisting of indol-5-yl-2-one, 7-fluoro-indol-6-yl, indazol-5-yl, 3-(methyl-amino)-indazol-6-yl, 3-amino-indazol-6-yl, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, benzoxazol-6-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-c]pyridin-3-yl, 1H-pyrrolo[2,3-c]pyridin-3yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl. In some embodiments, the present invention is directed to compounds of formula (I) wherein

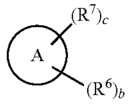

is selected from the group consisting of 3-(methyl-amino)-indazol-6-yl, 3-amino-indazol-6-yl, benzimidazol-5-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 1H-pyrrolo[2,3-b]pyridin-4-yl, 6-methoxy-1H-pyrrolo[3,2-c]pyridin-3-yl, 7H-pyrrolo[2,3-d]pyrimidin-5-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl. In some embodiments, the present invention is directed to compounds of formula (I) wherein

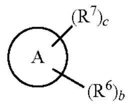

is selected from the group consisting of 3-(methyl-amino)-indazol-6-yl, 3-amino-indazol-6-yl, benzimidazol-5-yl-2-one, 2H-quinolin-6-yl-2-one, 3,4-dihydro-2H-quinolin-6-yl-2-one, 1H-pyrrolo[2,3-b]pyridin-4-yl, 1,4-dihydro-2H-benzo[d][1,3]oxazin-6-yl-2-one, and 5-fluoro-1,4-dihydro-2H-benzo[d][1,3]oxazin-6-yl-2-one.

In some embodiments, the present invention is directed to compounds of formula (I) wherein one or more, preferably one to two, more preferably one heterocyclyl, heteroaryl or heterocycloalkyl (present as any part of a substituent group, preferably an $R^5$ substituent group) contains a nitrogen atom is further substituted to form an N-oxide. In some embodiments, the present invention is directed to compounds of formula (I) wherein any one or more (preferably one to two, more preferably one) heterocyclyl, heteroaryl or heterocycloalkyl present as any part of the

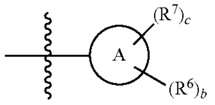

group contains a nitrogen atom, then said heterocyclyl, heteroaryl or heterocycloalkyl may be further substituted to form an N-oxide.

In some embodiments, the present invention is directed to compounds of formula (I) wherein one or more, (for example, one, two, three, four, five, six, seven, eight, nine, ten, eleven, etc.) hydrogen atoms are replaced with deuterium.

In some embodiments, the present invention is directed to compounds of formula (I) wherein a hydrogen atom on the

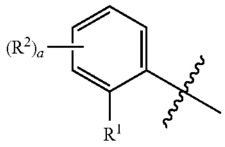

portion of the compound of formula (I) is replaced with deuterium. In some embodiments, the present invention is directed to compounds of formula (I) wherein the hydrogen atom at the 4-position of the

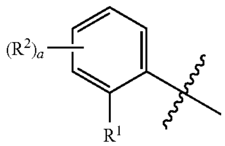

portion of the compound of formula (I) (i.e. in the meta-position to $R^1$) is replace with deuterium. In some embodiments, the present invention is directed to compounds of formula (I) wherein the

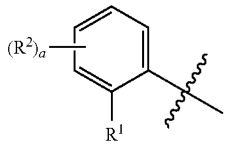

portion of the compound of formula (I) is selected from the group consisting of

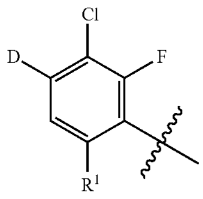

, and

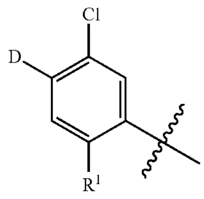

.

In some embodiments, the present invention is directed to compounds of formula (I) wherein $R^5$ is deutero. In some embodiments, the present invention is directed to compounds of formula (I) wherein $R^A$ and $R^B$ are each deutero. In some embodiments, the present invention is directed to compounds of formula (I) wherein $R^C$ and $R^D$ are each deutero. In some embodiments, the present invention is directed to compounds of formula (I) wherein $R^A$, $R^B$, $R^C$ and $R^D$ are each deutero.

In some embodiments, the present invention is directed to compounds of formula (I) wherein the hydrogen atom at the 8a position of the 2,3,8,8a-tetrahydroindolizin-5(1H)-one is replaced with deuterium. In some embodiments, the present invention is directed to compounds of formula (I) wherein one or more of $R^A$, $R^B$, $R^C$ and $R^D$ is deutero and wherein the hydrogen atom at the 8a position of the 2,3,8,8a-tetrahydroindolizin-5(1H)-one is replaced with deuterium.

In some embodiments, the present invention is directed to compounds of formula (I) wherein $R^5$ is deutero. In some embodiments, the present invention is directed to compounds of formula (I) wherein $R^5$ is deutero and the hydrogen atom at the 8a position of the 2,3,8,8a-tetrahydroindolizin-5(1H)-one is replaced with deuterium.

In some embodiments, the present invention is directed to compounds of formula (I) wherein the hydrogen atom at the 4-position of the

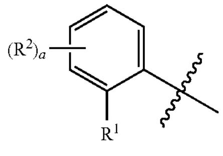

portion of the compound of formula (I) (i.e. in the meta-position to $R^1$) and the hydrogen atom at the 8a position of the 2,3,8,8a-tetrahydroindolizin-5(1H)-one are each replaced with deuterium. In some embodiments, the present invention is directed to compounds of formula (I) wherein the

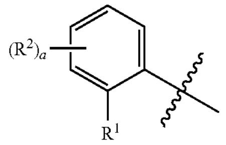

portion of the compound of formula (I) is selected from the group consisting of

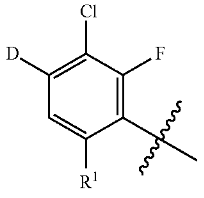

and

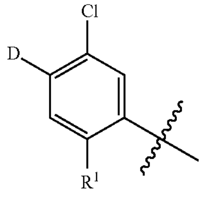

, and wherein the hydrogen atom at the 8a position of the 2,3,8,8a-tetrahydroindolizin-5(1H)-one are each replaced with deuterium.

In some embodiments, the present invention is directed to compounds of formula (I) wherein one or more (for example one, two, three, four, five, six, seven, eight, nine, ten, eleven, etc.), preferably one to six, more preferably one to three, hydrogen atoms on the Q portion of the compound of formula (I) is replaced with deuterium.

In some embodiments, the present invention is directed to a compound of formula (I) selected from the group consisting of

| Cmpd # | Compound IUPAC name |
|---|---|
| 358 | (3S,8aR)-3-[5-(6-amino-2-fluoro-3-pyridyl)-1H-imidazol-2-yl]-7-[3-chloro-2-fluoro-6-(tetrazol-1-yl)phenyl]-2,3,8,8a-tetrahydro-1H-indolizin-5-one; |
| 354 | (3S,8aR)-3-[5-(6-amino-2-chloro-3-pyridyl)-1H-imidazol-2-yl]-7-[3-chloro-2-fluoro-6-(tetrazol-1-yl)phenyl]-2,3,8,8a-tetrahydro-1H-indolizin-5-one; |
| 166 | (3S,8aR)-7-[3-chloro-2-fluoro-6-(tetrazol-1-yl)phenyl]-3-[5-[3-fluoro-2-(2-hydroxy-2-methyl-propoxy)-4-pyridyl]-1H-imidazol-2-yl]-2,3,8,8a-tetrahydro-1H-indolizin-5-one; |
| 162 | (35,8aR)-7-[3-chloro-2-fluoro-6-(tetrazol-1-yl)phenyl]-3-[5-[3-fluoro-2-(1-hydroxycyclopropyl)-4-pyridyl]-1H-imidazol-2-yl]-2,3,8,8a-tetrahydro-1H-indolizin-5-one; |
| 126 | (3S,8aR)-3-[5-(2-amino-3-fluoro-4-pyridyl)-1H-imidazol-2-yl]-7-[3-chloro-2-fluoro-6-(tetrazol-1-yl)phenyl]-2,3,8,8a-tetrahydro-1H-indolizin-5-one; |
| 107 | (3S,8aR)-7-[3-chloro-2-fluoro-6-(tetrazol-1-yl)phenyl]-3-[4-fluoro-5-[3-fluoro-2-(hydroxymethyl)-4-pyridyl]-1H-imidazol-2-yl]-2,3,8,8a-tetrahydro-1H-indolizin-5-one; |
| 80 | (3S,8aR)-7-[5-chloro-2-(tetrazol-1-yl)phenyl]-3-[4-fluoro-5-[3-fluoro-2-(hydroxymethyl)-4-pyridyl]-1H-imidazol-2-yl]-2,3,8,8a-tetrahydro-1H-indolizin-5-one; |
| 90 | (3S*,8aR)-3-[5-(2-amino-3-fluoro-4-pyridyl)-1H-imidazol-2-yl]-7-[5-chloro-2-(tetrazol-1-yl)phenyl]-2,3,8,8a-tetrahydro-1H-indolizin-5-one; |
| 44 | methyl N-[4-[2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]carbamate; |
| 361 | (3S,8aR)-7-[3-chloro-2-fluoro-6-(tetrazol-1-yl)phenyl]-3-[5-(2,3-dihydro-[1,4]dioxino[2,3-b]pyridin-8-yl)-1H-imidazol-2-yl]-2,3,8,8a-tetrahydro-1H-indolizin-5-one |

and isotopologues and pharmaceutically acceptable salts thereof.

In some embodiments, the present invention is directed to a compound of formula (Ix)

(Ix)

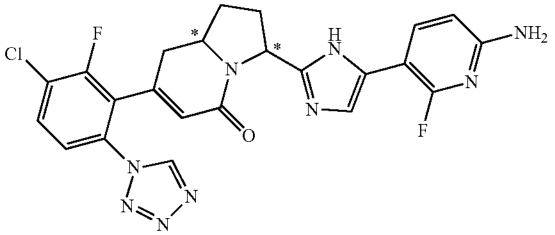

and tautomers, stereoisomers, isotopologues, and pharmaceutically acceptable salts or solvates thereof. In some embodiments, the present invention is directed to a compound of formula (Iy)

(Iy)

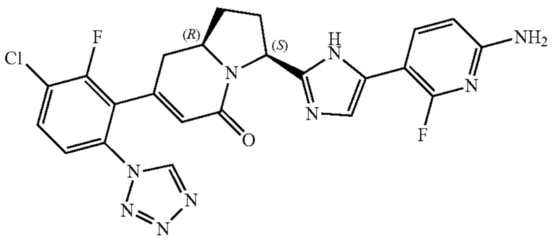

also known as (3S,8aR)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one and tautomers, isotopologues, and pharmaceutically acceptable salts or solvates thereof. In some embodiments, the present invention is directed to a compound of formula (Iz)

(Iz)

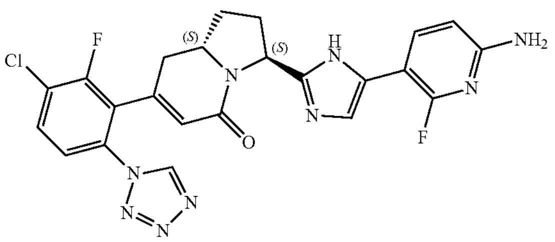

also known as (3S,8aS)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one, and tautomers, isotopologues, and pharmaceutically acceptable salts or solvates thereof.

One skilled in the art will recognize that, depending on substituent groups, the compounds of the present invention may contain one or more stereo-centers, including for example, the stereo-centers denoted by the "*" symbols in the structure of formula (I) shown below

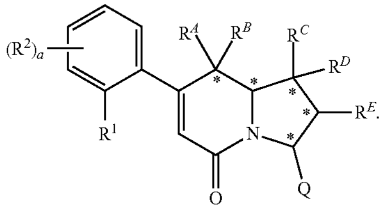

(I)

Unless otherwise noted, the starred ("*") stereo-center at the bridge carbon atom of the 2,3,8,8a-tetrahydroindolizin-5(1H)-one structure shall be referred to as the "Ring" stereo-center. One skilled in the art will further recognize that wherein the compound of formula (I) is present in a stereo-isomeric excess of one of the corresponding Ring stereo-isomers, then said compound may alternatively be referred to as the corresponding atropisomer.

Unless otherwise noted, the starred ("*") stereo-center at the carbon atom of the 2,3,8,8a-tetrahydroindolizin-5(1H)-one structure bound to $R^A$ and $R^E$ shall be referred to as the "$R^A/R^E$" stereo-center; the starred ("*") stereo-center at the carbon atom of the 2,3,8,8a-tetrahydroindolizin-5(1H)-one structure bound to $R^C$ and $R^D$ shall be referred to as the "$R^C/R^D$" stereo-center; the starred ("*") stereo-center at the carbon atom of the 2,3,8,8a-tetrahydroindolizin-5(1H)-one structure bound to $R^E$ shall be referred to as the "$R^E$" stereo-center, and the starred ("*") stereo-center at the carbon atom of the 2,3,8,8a-tetrahydroindolizin-5(1H)-one structure bound to the Q substituent group shall be referred to as the "Q" stereo-center.

In some embodiments, the present invention is directed to compounds of formula (I) wherein the Ring stereo-center is present as a racemic mixture. In some embodiments, the present invention is directed to compounds of formula (I) wherein the Ring stereo-center is present in an enantiomeric excess of the corresponding R-enantiomer. In some embodiments, the present invention is directed to compounds of formula (I) wherein the Ring stereocenter is present in an enantiomeric excess of the corresponding S-enantiomer.

In some embodiments, the present invention is directed to compounds of formula (I) wherein the Ring stereo-center is present in a stereo-isomeric excess of either the R- or S-enantiomer of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a stereo-isomeric excess at the Ring stereo-center of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) wherein the $R^A/R^B$ stereo-center is present as a racemic mixture. In some embodiments, the present invention is directed to compounds of formula (I) wherein the $R^A/R^B$ stereo-center is present in an enantiomeric excess of the corresponding R-enantiomer. In some embodiments, the present invention is directed to compounds of formula (I) wherein the $R^A/R^B$ stereocenter is present in an enantiomeric excess of the corresponding S-enantiomer.

In some embodiments, the present invention is directed to compounds of formula (I) wherein the $R^A/R^B$ stereo-center is present in a stereo-isomeric excess of either the R- or S-enantiomer of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a stereo-isomeric excess at the $R^A/R^B$ stereo-center of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) wherein the $R^C/R^D$ stereo-center is present as a racemic mixture. In some embodiments, the present invention is directed to compounds of formula (I) wherein the $R^C/R^D$ stereo-center is present in an enantiomeric excess of the corresponding R-enantiomer. In some embodiments, the present invention is directed to compounds of formula (I) wherein the $R^C/R^D$ stereocenter is present in an enantiomeric excess of the corresponding S-enantiomer.

In some embodiments, the present invention is directed to compounds of formula (I) wherein the $R^C/R^D$ stereo-center is present in a stereo-isomeric excess of either the R- or S-enantiomer of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a stereo-isomeric excess at the $R^C/R^D$ stereo-center of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) wherein the $R^E$ stereo-center is present as a racemic mixture. In some embodiments, the present invention is directed to compounds of formula (I) wherein the $R^E$ stereo-center is present in an enantiomeric excess of the corresponding R-enantiomer. In some embodiments, the present invention is directed to compounds of formula (I) wherein the $R^E$ stereocenter is present in an enantiomeric excess of the corresponding S-enantiomer.

In some embodiments, the present invention is directed to compounds of formula (I) wherein the $R^E$ stereo-center is present in a stereo-isomeric excess of either the R- or S-enantiomer of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a stereo-isomeric excess at the $R^E$ stereo-center of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) wherein the Q stereo-center is present as a racemic mixture. In some embodiments, the present invention is directed to compounds of formula (I) wherein the Q stereo-center is present in an enantiomeric excess of the corresponding R-enantiomer. In some embodiments, the present invention is directed to compounds of formula (I) wherein the Q stereocenter is present in an enantiomeric excess of the corresponding S-enantiomer.

In some embodiments, the present invention is directed to compounds of formula (I) wherein the Q stereo-center is present in an stereo-isomeric excess of either the R- or S-enantiomer of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I) is present in a stereo-isomeric excess at the Ring stereo-center of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I) wherein the Ring stereo-center is present in a stereo-isomeric excess of the R-configuration and the Q-stereo-center is present in a stereo-isomeric excess of the S-configuration.

Additional embodiments of the present invention include compounds of formula (I), compounds of formula (II), compounds of formula (III) and/or compounds of formula (IV) wherein the starred ("*") stereo-centers (i.e. Ring, $R^A/R^B$, $R^C/R^D$, $R^E$, Q, etc.) are each independently present in a racemic mixture or in a stereo-isomeric excess of either the corresponding R- or S-stereo-orientation. One skilled in the art will recognize that as such, additional embodiments of the present invention include compounds of formula (I), compounds of formula (II), compounds of formula (III) and/or compounds of formula (IV) wherein the starred ("*") stereo-centers (i.e. Ring, $R^A/R^B$, $R^C/R^D$, $R^E$, Q, etc.) are present in any combination of stereo-configurations and any combination of stereo-isomeric excess.

Additional embodiments of the present invention include those wherein the substituents selected for one or more of the variables defined herein (i.e. a, $R^1$, $R^2$, $R^A$, $R^B$, $R^C$, $R^D$, $R^E$, Q, etc.) are independently selected to be any individual substituent or any subset of substituents selected from the complete list as defined herein. Additional embodiments of the present invention include those wherein the substituents selected for one or more of the variables defined herein (a, $R^1$, $R^2$, $R^A$, $R^B$, $R^C$, $R^D$, $R^E$, Q, etc.) are independently selected to correspond to any of the embodiments as defined herein.

In some embodiments, the present invention is directed to any single compound or subset of compounds independently selected from the list of representative compounds in Tables 1 and 2, below.

Representative compounds of formula (I) of the present invention are as listed in Tables 1 and 2, below. Unless otherwise noted, the position of the $R^2$ group(s) as listed in the Table below using the following numbering scheme:

(I)

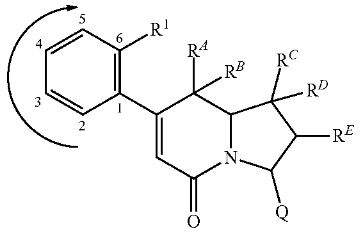

such that the $R^1$ substituent is bound at the 6-position and the $R^2$ substituents are bound at the 2-, 3-, 4- and/or 5-positions of the phenyl group.

In the Tables which follow hereinafter, wherein a column lists the stereo-orientation of a particular stereo-center (as indicated by the heading of the column), "RAC" shall indicate that the compound was prepared as a racemic mixture at the designated stereo-center. The S* and R* designations shall indicate that although the compound was prepared in a stereo-isomeric excess of one of the corresponding stereoisomers at the designated stereo-center, the exact stereo-configuration was not determined. The S and R designations indicate that the compound was prepared in a stereo-isomeric excess of the corresponding S or R stereoisomer at the designated stereo-center, with the exact stereo-configuration as noted.

TABLE 1

Representative Compounds of Formula (I)

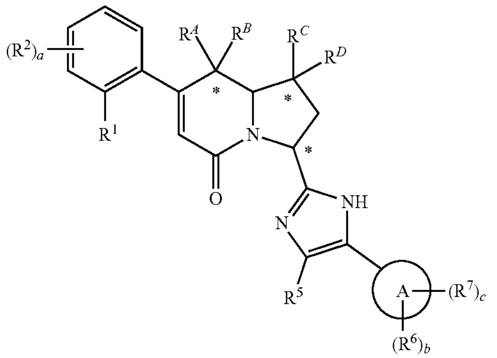

| ID No. | $R^1$ | $(R^2)_a$ | Ring Stereo | $R^A$, $R^B$ | $R^C$, $R^D$ | Q Stereo | $R^5$ | 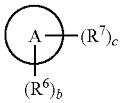 |
|---|---|---|---|---|---|---|---|---|
| 1 | 1,2,3,4-tetrazol-1-yl | 2-fluoro, 3-chloro | R | H, H | H, H | S | fluoro | 3-chloro-6-amino-pyridin-4-yl |
| 2 | 1,2,3,4-tetrazol-1-yl | 2-fluoro, 3-chloro | R | H, H | H, H | S | H | 2-(imidazol-2-yl)-3-fluoro-pyridin-4-yl |
| 4 | 1,2,3,4-tetrazol-1-yl | 2-fluoro, 3-chloro | R | H, H | H, H | RAC | H | 4-chloro-pyrazol-3-yl |
| 5 | 1,2,3,4-tetrazol-1-yl | 2-fluoro, 3-chloro | R | H, H | H, H | S | H | 2-(3-methyl-isoxazol-5-yl-carbonyl-amino)-3-fluoro-pyridin-4-yl |
| 6 | 1,2,3,4-tetrazol-1-yl | 2-fluoro, 3-chloro | RAC | H, H | H, H | RAC | fluoro | 2-(methyl-sulfonyl-amino)-pyridin-4-yl |
| 7 | 1,2,3,4-tetrazol-1-yl | 2-fluoro, 3-chloro | RAC | H, H | H, H | RAC | H | 2-(methyl-sulfonyl-amino)-pyridin-4-yl |
| 8 | 1,2,3,4-tetrazol-1-yl | 2-fluoro, 3-chloro | R | H, H | H, H | S | H | indol-6-yl |
| 11 | 1,2,3,4-tetrazol-1-yl | 2-fluoro, 3-chloro | RAC | H, H | H, H | S | fluoro | 4-(1R-(methyl-carbonyl-amino)-ethyl)-phenyl |
| 12 | 1,2,3,4-tetrazol-1-yl | 2-fluoro, 3-chloro | R | H, H | H, H | S | H | 2-(ethoxy-carbonyl-amino-methyl)-3-fluoro-pyridin-4-yl |
| 13 | 1,2,3,4-tetrazol-1-yl | 2-fluoro, 3-chloro | R | H, H | H, H | S | H | 2-(methyl-carbonyl-amino-methyl)-3-fluoro-pyridin-4-yl |
| 14 | 1,2,3,4-tetrazol-1-yl | 2-fluoro, 3-chloro | R | H, H | H, H | S | H | indol-5-yl |
| 15 | 1,2,3,4-tetrazol-1-yl | 2-fluoro, 3-chloro | R | H, H | H, H | S | H | 3-chloro-6-amino-pyridin-4-yl |
| 16 | 1,2,3,4-tetrazol-1-yl | 2-fluoro, 3-chloro | RAC | H, H | H, H | S | H | 4-(1R-(methyl-carbonyl-amino)-ethyl)-phenyl |
| 17 | 1,2,3,4-tetrazol-1-yl | 2-fluoro, 3-chloro | R | H, H | H, H | S | H | 3-fluoro-pyridin-4-yl |
| 18 | 1,2,3,4-tetrazol-1-yl | 2-fluoro, 3-chloro | RAC | H, H | H, H | S | H | 3-chloro-6-(methyl-cabonyl-amino)-pyridin-4-yl |
| 19 | 1,2,3,4-tetrazol-1-yl | 2-fluoro, 3-chloro | R* | H, H | H, H | S | H | 1H-pyrrolo[2,3-c]pyridin-3-yl |
| 20 | 1,2,3,4-tetrazol-1-yl | 2-fluoro, 3-chloro | R* | H, H | H, H | S | H | 1H-pyrrolo[2,3-c]pyridin-3-yl |
| 21 | 1,2,3,4-tetrazol-1-yl | 2-fluoro, 3-chloro | RAC | H, H | H, H | S | H | 2-amino-3-methyl-pyridin-4-yl |
| 23 | difluoro-methoxy | 2-fluoro, 3-chloro | R | H, H | H, H | S | fluoro | 2-(hydroxy-methyl)-3-fluoro-pyridin-4-yl |
| 24 | 1,2,3,4-tetrazol-1-yl | 2-fluoro, 3-chloro | R | H, H | H, H | S | H | 1H-pyrrolo[2,3-b]pyridin-5-yl |
| 25 | difluoro-methyl | 2-fluoro, 3-chloro | R | H, H | H, H | S | H | 2-(hydroxy-methyl)-3-fluoro-pyridin-4-yl |
| 26 | difluoro-methyl | 2-fluoro, 3-chloro | R | H, H | H, H | S | H | 2-(hydroxy-methyl)-3-fluoro-pyridin-4-yl |

TABLE 1-continued

| | | | | | | | | |
|---|---|---|---|---|---|---|---|---|
| 27 | difluoro-methyl | 2-fluoro, 3-chloro | R | H, H | H, H | S | fluoro | 2-(hydroxy-methyl)-3-fluoro-pyridin-4-yl |
| 28 | 1,2,3,4-tetrazol-1-yl | 2-fluoro, 3-chloro | S* | H, H | H, H | S* | H | 2-(2-hydroxy-n-propyl-oxy)-3-fluoro-pyridin-4-yl |
| 29 | 1,2,3,4-tetrazol-1-yl | 2-fluoro, 3-chloro | S* | H, H | H, H | S* | H | 2-(2-hydroxy-n-propyl-oxy)-3-fluoro-pyridin-4-yl |
| 30 | 1,2,3,4-tetrazol-1-yl | 2-fluoro, 3-chloro | R | H, H | H, H | S | H | 2-methyl-benzimidazol-6-yl |
| 31 | 1,2,3,4-tetrazol-1-yl | 2-fluoro, 3-chloro | R* | H, H | H, H | S* | fluoro | 2-(pyrazol-5-yl)-pyridin-4-yl |
| 34 | 4-(trifluoro-methyl)-1,2,3-triazol-1-yl | 2-fluoro, 3-chloro | R | H, H | H, H | S | fluoro | 2-carboxy-3-fluoro-pyridin-4-yl |
| 35 | 1,2,3,4-tetrazol-1-yl | 2-fluoro, 3-chloro | R | H, H | H, H | S* | methyl | 2-(hydroy-methyl)-3-fluoro-pyridin-4-yl |
| 37 | 1,2,3,4-tetrazol-1-yl | 2-fluoro, 3-chloro | R | H, H | H, H | R* | H | 2-(phosphono-methoxy-methyl)-3-fluoro-pyridin-4-yl |
| 40 | 1,2,3,4-tetrazol-1-yl | 2-fluoro, 3-chloro | R | H, H | H, H | S | fluoro | 2-(methoxy-carbonyl-amino)-3-fluoro-pyridin-4-yl |
| 44 | 1,2,3,4-tetrazol-1-yl | 2-fluoro, 3-chloro | R | H, H | H, H | S | H | 2-(methoxy-carbonyl-amino)-3-fluoro-pyridin-4-yl |
| 45 | 1,2,3,4-tetrazol-1-yl | 3-chloro | R | H, H | H, H | S | fluoro | 2-(1R-hydroxy-ethyl)-3-fluoro-pyridin-4-yl |
| 46 | 1,2,3,4-tetrazol-1-yl | 3-chloro | R | H, H | H, H | S | fluoro | 2-(1S-hydroxy-ethyl)-3-fluoro-pyridin-4-yl |
| 49 | 1,2,3,4-tetrazol-1-yl | 2-fluoro, 3-chloro | R | H, H | H, H | R* | H | 2-(5-amino-pyrazol-1-yl)-pyridin-4-yl |
| 50 | 4-chloro-1,2,3-triazol-1-yl | 2-fluoro, 3-chloro | R | H, H | H, H | S | H | 2-(methoxy-carbonyl)-3-fluoro-pyridin-4-yl |
| 52 | 1,2,3,4-tetrazol-1-yl | 2-fluoro, 3-chloro | R | H, H | H, H | S | H | 2-(methoxy-carbonyl)-3-fluoro-pyridin-4-yl |
| 53 | 1,2,3,4-tetrazol-1-yl | 2-fluoro, 3-chloro | RAC | H, H | H, H | RAC | H | 2-(pyrazol-5-yl)-pyridin-4-yl |
| 54 | 4-(trifluoro-methyl)-1,2,3-triazol-1-yl | 3-chloro | R | H, H | H, H | S* | H | 2-carboxy-3-fluoro-pyridin-4-yl |
| 56 | 1,2,3,4-tetrazol-1-yl | 3-chloro | RAC | fluoro, fluoro | H, H | S | H | 2-(hydroxy-methyl)-3-fluoro-pyridin-4-yl |
| 57 | 1,2,3,4-tetrazol-1-yl | 2-fluoro-3-methyl | R | H, H | H, H | S | H | 2-(hydroxy-methyl)-3-fluoro-pyridin-4-yl |
| 58 | 4-(trifluoro-methyl)-1,2,3-triazol-1-yl | 2-fluoro, 3-chloro | R | H, H | H, H | S | H | 2-carboxy-3-fluoro-pyridin-4-yl |
| 59 | 4-(trifluoro-methyl)-1,2,3-triazol-1-yl | 3-chloro | R* | H, H | H, H | S* | H | 6-methyl-quinoxalin-5-yl-2(1H)-one |
| 61 | 1,2,3,4-tetrazol-1-yl | 2-fluoro, 3-chloro | R | H, H | H, H | S | H | 2-(phosphono-oxy-methyl)-3-fluoro-pyridin-4-yl |
| 63 | 1,2,3,4-tetrazol-1-yl | 2-fluoro, 3-chloro | R | H, H | H, H | R* | H | 2-(3-amino-pyrazol-1-yl)-3-fluoro-pyridin-4-yl |
| 64 | 4-(trifluoro-methyl)-1,2,3-triazol-1-yl | 3-chloro | R | H, H | H, H | S | H | 2-(hydroxy-methyl)-3-fluoro-pyridin-4-yl |
| 65 | 1,2,3,4-tetrazol-1-yl | 2-fluoro, 3-chloro | R | H, H | H, H | S | H | 2-(hydroxy-methyl)-3-fluoro-pyridin-4-yl-N-oxide |
| 67 | 4-(trifluoro-methyl)-1,2,3-triazol-1-yl | 2-fluoro, 3-chloro | R | H, H | H, H | S | H | 2-(hydroxy-methyl)-3-fluoro-pyridin-4-yl |
| 68 | 1,2,3,4-tetrazol-1-yl | 2-fluoro, 3-chloro | R | H, H | H, H | S | H | 2-(5-amino-pyrazol-1-yl)-3-fluoro-pyridin-4-yl |

TABLE 1-continued

| | | | | | | | | |
|---|---|---|---|---|---|---|---|---|
| 69 | 1,2,3,4-tetrazol-1-yl | 3-chloro | R | H, H | H, H | S | fluoro | 2-fluoro-6-amino-pyridin-3-yl |
| 70 | 1,2,3,4-tetrazol-1-yl | 3-chloro | R | H, H | H, H | S* | fluoro | 2-amino-3-fluoro-pyridin-4-yl |
| 71 | 1,2,3,4-tetrazol-1-yl | 2-fluoro, 3-chloro | R | H, H | H, H | R* | H | 2-(1,2,3-triazol-1-yl)-3-fluoro-pyridin-4-yl |
| 72 | 1,2,3,4-tetrazol-1-yl | 2-fluoro, 3-chloro | R | H, H | H, H | R* | H | 2-(3-amino-pyrazol-1-yl)-pyridin-4-yl |
| 73 | 1,2,3,4-tetrazol-1-yl | 2-fluoro, 3-chloro | R* | H, H | H, H | S | H | 2-(S-tetrahydrofuran-3-yl-amino)-3-fluoro-pyridin-4-yl |
| 74 | 1,2,3,4-tetrazol-1-yl | 2-fluoro, 3-chloro | S* | H, H | H, H | S | H | 2-(S-tetrahydrofuran-3-yl-amino)-3-fluoro-pyridin-4-yl |
| 75 | 1,2,3,4-tetrazol-1-yl | 2-fluoro, 3-chloro | R | H, H | H, H | S | H | 2-(1S-amino-isopropyl-carbonyl-oxo-methyl)-3-fluoro-pyridin-4-yl |
| 76 | 1,2,3,4-tetrazol-1-yl | 2-fluoro, 3-chloro | RAC | H, H | H, H | S* | fluoro | 2-(S-tetrahydrofuran-3-yl-amino)-3-fluoro-pyridin-4-yl |
| 77 | 1,2,3,4-tetrazol-1-yl | 2-fluoro, 3-chloro | RAC | H, H | H, H | R* | fluoro | 2-(S-tetrahydrofuran-3-yl-amino)-3-fluoro-pyridin-4-yl |
| 78 | 1,2,3,4-tetrazol-1-yl | 2-fluoro, 3-chloro | R* | H, H | H, H | R* | H | 2-(1,3,4-triazol-1-yl)-3-fluoro-pyridin-4-yl |
| 79 | 1,2,3,4-tetrazol-1-yl | 3-chloro | R | H, H | H, H | S | H | 2-(1,1-dimethyl-2-hydroxy-ethyl-amino)-3-fluoro-pyridin-4-yl |
| 80 | 1,2,3,4-tetrazol-1-yl | 3-chloro | R | H, H | H, H | S | fluoro | 2-(hydroxy-methyl)-3-fluoro-pyridin-4-yl |
| 81 | 4-(trifluoro-methyl)-1,2,3-triazol-1-yl | 3-chloro | R | H, H | H, H | S | fluoro | 3,4-dihydro-2H-quinolin-6-yl-2-one |
| 83 | 1,2,3,4-tetrazol-1-yl | 3-chloro | R | H, H | H, H | S | H | 2-fluoro-6-(bicyclo[1.1.1]pentanyl-amino)-pyridin-3-yl |
| 84 | 1,2,3,4-tetrazol-1-yl | 3-chloro | R | H, H | H, H | S | fluoro | 2-(2-methyl-2-hydroxy-n-propyl-amino)-3-fluoro-pyridin-4-yl |
| 85 | 1,2,3,4-tetrazol-1-yl | 2-fluoro, 3-chloro | R | H, H | H, H | S | H | 2-(1,2,3-triazol-1-yl)-pyridin-4-yl |
| 86 | 1,2,3,4-tetrazol-1-yl | 2-fluoro, 3-chloro | R | H, H | H, H | S | H | 1-(1,2,5-triazol-1-yl)-pyridin-4-yl |
| 87 | 1,2,3,4-tetrazol-1-yl | 2-fluoro, 3-chloro | R | H, H | H, H | S | fluoro | 1-(1,2,5-triazol-1-yl)-pyridin-4-yl |
| 88 | 1,2,3,4-tetrazol-1-yl | 2-fluoro, 3-chloro | R | H, H | H, H | S | fluoro | 2-(pyrazol-1-yl)-pyridin-4-yl |
| 89 | 1,2,3,4-tetrazol-1-yl | 2-fluoro, 3-chloro | R | H, H | H, H | S | H | 2-(1,1-dimethyl-2-hydroxy-ethyl-amino)-3-fluoro-pyridin-4-yl |
| 90 | 1,2,3,4-tetrazol-1-yl | 3-chloro | R | H, H | H, H | S* | H | 2-amino-3-fluoro-pyridin-4-yl |
| 92 | 1,2,3,4-tetrazol-1-yl | 2-fluoro, 3-chloro | R | H, H | H, H | R* | fluoro | 2-(1,2,4-triazol-1-yl)-3-fluoro-pyridin-4-yl |
| 93 | 1,2,3,4-tetrazol-1-yl | 2-fluoro, 3-chloro | R | H, H | H, H | S | H | 2-(pyrazol-1-yl)-pyridin-4-yl |
| 94 | 1,2,3,4-tetrazol-1-yl | 2-fluoro, 3-chloro | R | H, H | H, H | S | H | 2-(3,3-difluoro-azetin-1-yl-carbonyl)-3-fluoro-pyridin-4-yl |
| 95 | 1,2,3,4-tetrazol-1-yl | 2-fluoro, 3-chloro | RAC | H, H | H, H | RAC | H | 7-methyl-6,7-dihydro-5H-cyclopenta[b]pyridin-4-yl-7-ol |

TABLE 1-continued

| | | | | | | | | |
|---|---|---|---|---|---|---|---|---|
| 96 | 1,2,3,4-tetrazol-1-yl | 3-chloro | R | H, H | H, H | S | H | 2-(bicyclo[1.1.1]pentanyl-amino)-3-fluoro-pyridin-3-yl |
| 97 | 4-(trifluoro-methyl)-1,2,3-triazol-1-yl | 3-chloro | R | H, H | H, H | S | H | 3,4-dihydro-2H-quinolin-6-yl-2-one |
| 98 | 1,2,3,4-tetrazol-1-yl | 3-chloro | R | H, H | H, H | S* | H | 2-fluoro-6-amino-pyridin-3-yl |
| 99 | 1,2,3,4-tetrazol-1-yl | 2-fluoro, 3-chloro | R | H, H | H, H | S | H | 2-(methoxy-carbonyl-amino)-pyridin-4-yl |
| 100 | 1,2,3,4-tetrazol-1-yl | 2-fluoro, 3-chloro | R | H, H | H, H | S* | H | 2-(3-cyano-azetidin-1-yl)-3-fluoro-pyridin-4-yl |
| 101 | 4-(trifluoro-methyl)-1,2,3-triazol-1-yl | 3-chloro | R | H, H | H, H | S | H | quinolin-5-yl-2-one |
| 102 | 1,2,3,4-tetrazol-1-yl | 2-fluoro, 3-chloro | R | H, H | H, H | R* | H | 2-(3-cyano-azetidin-1-yl)-3-fluoro-pyridin-4-yl |
| 103 | 1,2,3,4-tetrazol-1-yl | 2-fluoro, 3-chloro | R | H, H | H, H | S | H | 2-(methoxy-amino-carbonyl)-3-fluoro-pyridin-4-yl |
| 104 | 1,2,3,4-tetrazol-1-yl | 2-fluoro, 3-chloro | R | H, H | H, H | S | H | 2-(bicyclo[1.1.1] pentanyl-amino-carbonyl)-3-fluoro-pyridin-3-yl |
| 105 | 1,2,3,4-tetrazol-1-yl | 2-fluoro, 3-chloro | S | H, H | H, H | S | H | 2-(pyrrolidin-1-yl-2-one)-3-fluoro-pyridin-4-yl |
| 106 | 1,2,3,4-tetrazol-1-yl | 2-fluoro, 3-chloro | R | H, H | H, H | S | H | 2-(pyrrolidin-1-yl-2-one)-3-fluoro-pyridin-4-yl |
| 107 | 1,2,3,4-tetrazol-1-yl | 2-fluoro, 3-chloro | R | H, H | H, H | S | fluoro | 2-(hydroxy-methyl)-3-fluoro-pyridin-4-yl |
| 108 | 1,2,3,4-tetrazol-1-yl | 2-fluoro, 3-chloro | R | H, H | H, H | S* | H | 2-(2-oxa-6-azaspiro[3.3]hept-6-yl)-3-fluoro-pyridin-4-yl |
| 109 | 1,2,3,4-tetrazol-1-yl | 2-fluoro, 3-chloro | R | H, H | H, H | R* | fluoro | 2-(1-hydroxy-cycloprop-1-yl)-3-fluoro-pyridin-4-yl |
| 110 | 1,2,3,4-tetrazol-1-yl | 2-fluoro, 3-chloro | R | H, H | H, H | R* | H | 2-(azetidin-1-yl)-3-fluoro-pyridin-4-yl |
| 111 | 1,2,3,4-tetrazol-1-yl | 2-fluoro, 3-chloro | R | H, H | H, H | S* | H | 2-(azetidin-1-yl)-3-fluoro-pyridin-4-yl |
| 112 | 1,2,3,4-tetrazol-1-yl | 2-fluoro, 3-chloro | R | H, H | H, H | R* | H | 2-(1,2,4-triazol-1-yl)-3-fluoro-pyridin-4-yl |
| 113 | 1,2,3,4-tetrazol-1-yl | 2-fluoro, 3-chloro | R | H, H | H, H | S | deutero | 2-(hydroxy-d2-methyl)-3-fluoro-pyridin-4-yl |
| 114 | 1,2,3,4-tetrazol-1-yl | 2-fluoro, 3-chloro | R | H, H | H, H | S | H | 2-(oxazolidin-3-yl-2-one)-3-fluoro-pyridin-4-yl |
| 116 | 1,2,3,4-tetrazol-1-yl | 2-fluoro, 3-chloro | R | H, H | H, H | R* | deutero | 2-(1-hydroxy-cycloprop-1-yl)-3-fluoro-pyridin-4-yl |
| 117 | 1,2,3,4-tetrazol-1-yl | 2-fluoro, 3-chloro | R | H, H | H, H | S | deutero | 2-(hydroxy-methyl)-3-fluoro-pyridin-4-yl |
| 118 | 1,2,3,4-tetrazol-1-yl | 2-fluoro, 3-chloro | R* | H, H | H, H | S* | H | 5-fluoro-1,4-dihydro-2H-benzo[d][1,3]oxazin-6-yl-2-one |
| 119 | 1,2,3,4-tetrazol-1-yl | 3-chloro-4-deutero | R | H, H | H, H | R* | H | 2-fluoro-5-deutero-6-amino-pyridin-3-yl |
| 120 | 1,2,3,4-tetrazol-1-yl | 3-chloro-4-deutero | R | H, H | H, H | S* | H | 2-fluoro-5-deutero-6-amino-pyridin-3-yl |
| 121 | 1,2,3,4-tetrazol-1-yl | 3-chloro-4-deutero | R | H, H | H, H | R* | H | 2-fluoro-6-amino-pyridin-3-yl |
| 122 | 1,2,3,4-tetrazol-1-yl | 3-chloro-4-deutero | R | H, H | H, H | S* | H | 2-fluoro-6-amino-pyridin-3-yl |

TABLE 1-continued

| | | | | | | | | |
|---|---|---|---|---|---|---|---|---|
| 123 | 1,2,3,4-tetrazol-1-yl | 3-chloro | R | H, H | H, H | S | H | 2-fluoro-6-amino-pyridin-3-yl |
| 124 | 1,2,3,4-tetrazol-1-yl | 3-chloro | R | H, H | H, H | S | H | 2-fluoro-5-deutero-6-amino-pyridin-3-yl |
| 126 | 1,2,3,4-tetrazol-1-yl | 2-fluoro, 3-chloro | R | H, H | H, H | S | H | 2-amino-3-fluoro-pyridin-4-yl |
| 127 | 1,2,3,4-tetrazol-1-yl | 2-fluoro, 3-chloro | S* | H, H | H, H | S* | H | 2-(1S-(1,3,4-oxadiazol-2-yl)-ethoxy)-3-fluoro-pyridin-4-yl |
| 128 | 1,2,3,4-tetrazol-1-yl | 2-fluoro, 3-chloro | R* | H, H | H, H | S* | H | 2-(1S-(1,3,4-oxadiazol-2-yl)-ethoxy)-3-fluoro-pyridin-4-yl |
| 129 | 1,2,3,4-tetrazol-1-yl | 2-fluoro, 3-chloro, 4-deutero | R | H, H | H, H | S | deutero | 2-fluoro-6-amino-pyridin-3-yl |
| 130 | 1,2,3,4-tetrazol-1-yl | 2-fluoro, 3-chloro | R | H, H | H, H | S | H | 2-(oxetan-3-yl)-3-fluoro-pyridin-4-yl |
| 133 | 1,2,3,4-tetrazol-1-yl | 2-fluoro, 3-chloro | R | H, H | H, H | S | H | 2-fluoro-4,5-dideutero-6-(methyl-amino)-pyridin-3-yl |
| 134 | 1,2,3,4-tetrazol-1-yl | 2-fluoro, 3-chloro | R | H, H | H, H | S | H | 2-(methyl-amino)-3-fluoro-pyridin-4-yl |
| 135 | 1,2,3,4-tetrazol-1-yl | 2-fluoro, 3-chloro | S* | H, H | H, H | S | H | 2-(N-ethyl-N-2-hydroxy-ethyl-amino)-3-fluoro-pyridin-4-yl |
| 136 | 1,2,3,4-tetrazol-1-yl | 2-fluoro, 3-chloro | R* | H, H | H, H | S | H | 2-(N-ethyl-N-2-hydroxy-ethyl-amino)-3-fluoro-pyridin-4-yl |
| 137 | 1,2,3,4-tetrazol-1-yl | 2-fluoro, 3-chloro | R | H, H | H, H | R* | H | indol-3-yl |
| 138 | 1,2,3,4-tetrazol-1-yl | 2-fluoro, 3-chloro | R* | H, H | H, H | S | H | 2-(3-cyano-oxetan-3-yl)-3-fluoro-pyridin-4-yl |
| 139 | 1,2,3,4-tetrazol-1-yl | 2-fluoro, 3-chloro | R* | H, H | H, H | S | H | 2-(2-cyano-cycloprop-1-yl)-3-fluoro-pyridin-4-yl |
| 140 | 4-(trifluoro-methyl)-1,2,3-triazol-1-yl | 2-fluoro, 3-chloro | S | H, H | H, H | R* | H | 1H-pyrrolo[2,3-b]pyridin-3-yl |
| 141 | 1,2,3,4-tetrazol-1-yl | 2-fluoro, 3-chloro | R* | H, H | H, H | S* | H | 2-(1R*-oxazol-2-yl-ethoxy)-3-fluoro-pyridin-4-yl |
| 142 | 1,2,3,4-tetrazol-1-yl | 2-fluoro, 3-chloro | R* | H, H | H, H | S* | H | 2-(1S*-oxazol-2-yl-ethoxy)-3-fluoro-pyridin-4-yl |
| 143 | 1,2,3,4-tetrazol-1-yl | 2-fluoro, 3-chloro | R | H, H | H, H | S | H | 2-(3,3,3-trifluoro-2S*-hydroxy-n-propyl)-3-fluoro-pyridin-4-yl |
| 144 | 1,2,3,4-tetrazol-1-yl | 2-fluoro, 3-chloro | R | H, H | H, H | S | H | 2-(3,3,3-trifluoro-2R*-hydroxy-n-propyl)-3-fluoro-pyridin-4-yl |
| 145 | 1,2,3,4-tetrazol-1-yl | 2-fluoro, 3-chloro | R | H, H | H, H | S | deutero | 2-fluoro-5-deutero-6-amino-pyridin-3-yl |
| 147 | 1,2,3,4-tetrazol-1-yl | 2-fluoro, 3-chloro | R | H, H | H, H | S | H | 2-fluoro-5-deutero-6-amino-pyridin-3-yl |
| 148 | 1,2,3,4-tetrazol-1-yl | 2-fluoro, 3-chloro | R | H, H | H, H | S | deutero | 2-fluoro-4-deutero-6-amino-pyridin-3-yl |
| 149 | 1,2,3,4-tetrazol-1-yl | 2-fluoro, 3-chloro | R | H, H | H, H | S | deutero | 2-fluoro-4,5-dideutero-6-amino-pyridin-3-yl |
| 150 | 1,2,3,4-tetrazol-1-yl | 2-fluoro, 3-chloro | R | H, H | H, H | S | H | 2-fluoro-4-deutero-6-amino-pyridin-3-yl |
| 151 | 1,2,3,4-tetrazol-1-yl | 2-fluoro, 3-chloro | R | H, H | H, H | S | H | 2-fluoro-4,5-dideutero-6-amino-pyridin-3-yl |

TABLE 1-continued

| | | | | | | | | |
|---|---|---|---|---|---|---|---|---|
| 152 | 4-(trifluoro-methyl)-1,2,3-triazol-1-yl | 2-fluoro, 3-chloro | R | H, H | H, H | S | H | quinolin-6-yl-2-one |
| 154 | 1,2,3,4-tetrazol-1-yl | 2-fluoro, 3-chloro | R | H, H | H, H | S | deutero | 2-fluoro-6-amino-pyridin-3-yl |
| 155 | 1,2,3,4-tetrazol-1-yl | 2-fluoro, 3-chloro | R | H, H | H, H | S* | H | 2-(1-hydroxy-cycloprop-1-yl)-3-chloro-pyridin-4-yl |
| 156 | 1,2,3,4-tetrazol-1-yl | 2-fluoro, 3-chloro | R | H, H | H, H | R* | H | 2-(dioxan-2S-yl-ethoxy)-3-fluoro-pyridin-4-yl |
| 157 | 1,2,3,4-tetrazol-1-yl | 2-fluoro, 3-chloro | R | H, H | H, H | S* | H | 2-(dioxan-2S-yl-ethoxy)-3-fluoro-pyridin-4-yl |
| 158 | 1,2,3,4-tetrazol-1-yl | 2-fluoro, 3-chloro | R* | H, H | H, H | S* | H | 2-(3-hydroxy-3-methyl-n-butyl)-3-fluoro-pyridin-3-yl |
| 159 | 1,2,3,4-tetrazol-1-yl | 2-fluoro, 3-chloro | S* | H, H | H, H | S* | H | 2-(3-hydroxy-3-methyl-n-butyl)-3-fluoro-pyridin-3-yl |
| 160 | 1,2,3,4-tetrazol-1-yl | 2-fluoro, 3-chloro | R | H, H | H, H | S* | H | 2-(1,1-difluoro-2-hydroxy-ethyl)-3-fluoro-pyridin-4-yl |
| 161 | 1,2,3,4-tetrazol-1-yl | 2-fluoro, 3-chloro | RAC | H, H | H, H | S | H | 2-(methoxy-ethyl-amino)-3-fluoro-pyridin-4-yl |
| 162 | 1,2,3,4-tetrazol-1-yl | 2-fluoro, 3-chloro | R | H, H | H, H | S | H | 2-(1-hydroxy-cycloprop-1-yl)-3-fluoro-pyridin-4-yl |
| 163 | 1,2,3,4-tetrazol-1-yl | 2-fluoro, 3-chloro | RAC | H, H | H, H | S | H | 2-(1S*-cyano-ethyl)-3-fluoro-pyridin-4-yl |
| 164 | 1,2,3,4-tetrazol-1-yl | 2-fluoro, 3-chloro | RAC | H, H | H, H | S | H | 2-(1R*-cyano-ethyl)-3-fluoro-pyridin-4-yl |
| 165 | 4-(trifluoro-methyl)-1,2,3-triazol-1-yl | 2-fluoro, 3-chloro | R* | H, H | H, H | S* | H | 2-(amino-carbonyl-methyl)-3-fluoro-pyridin-4-yl |
| 166 | 1,2,3,4-tetrazol-1-yl | 2-fluoro, 3-chloro | R | H, H | H, H | S | H | 2-(2-methyl-2-hydroxy-n-propyl-oxy)-3-fluoro-pyridin-4-yl |
| 167 | 1,2,3,4-tetrazol-1-yl | 2-fluoro, 3-chloro | R* | H, H | H, H | S* | H | 2-amino-6-(trifluoro-methyl)-pyridin-5-yl |
| 168 | 1,2,3,4-tetrazol-1-yl | 2-fluoro, 3-chloro | R* | H, H | H, H | S | H | 2-(1R-(hydroxymethyl)-ethyl)-3-fluoro-pyridin-4-yl |
| 169 | 1,2,3,4-tetrazol-1-yl | 2-fluoro, 3-chloro | S* | H, H | H, H | S | H | 2-(1R-(hydroxymethyl)-ethyl)-3-fluoro-pyridin-4-yl |
| 170 | 1,2,3,4-tetrazol-1-yl | 2-fluoro, 3-chloro | S* | H, H | H, H | S* | H | 2-(1S*-hydroxy-2,2-difluoro-ethyl)-3-fluoro-pyridin-4-yl |
| 171 | 1,2,3,4-tetrazol-1-yl | 2-fluoro, 3-chloro | R* | H, H | H, H | S* | H | 2-(1R*-hydroxy-2,2-difluoro-ethyl)-3-fluoro-pyridin-4-yl |
| 172 | 1,2,3,4-tetrazol-1-yl | 2-fluoro, 3-chloro | S | H, H | H, H | S* | chloro | 2-(1S*-hydroxy-2,2-difluoro-ethyl)-3-fluoro-pyridin-4-yl |
| 173 | 1,2,3,4-tetrazol-1-yl | 2-fluoro, 3-chloro | R* | H, H | H, H | S* | chloro | 2-(1R*-hydroxy-2,2-difluoro-ethyl)-3-fluoro-pyridin-4-yl |
| 174 | 1,2,3,4-tetrazol-1-yl | 2-fluoro, 3-chloro | S* | H, H | H, H | S* | H | 2-(1S*-hydroxy-2,2-difluoro-ethyl)-3-fluoro-pyridin-4-yl |
| 175 | 1,2,3,4-tetrazol-1-yl | 2-fluoro, 3-chloro | R* | H, H | H, H | S* | H | 2-(1R*-hydroxy-2,2-difluoro-ethyl)-3-fluoro-pyridin-4-yl |
| 178 | 1,2,3,4-tetrazol-1-yl | 2-fluoro, 3-chloro | R | H, H | H, H | R* | chloro | 2-(1-hydroxy-cycloprop-1-yl)-pyridin-4-yl |
| 179 | 1,2,3,4-tetrazol-1-yl | 2-fluoro, 3-chloro | R | H, H | H, H | R | fluoro | 2-(1-hydroxy-cycloprop-1-yl)-pyridin-4-yl |

TABLE 1-continued

| | | | | | | | | |
|---|---|---|---|---|---|---|---|---|
| 180 | 1,2,3,4-tetrazol-1-yl | 2-fluoro, 3-chloro | R | H, H | H, H | S | H | 2-(2-methoxy-ethyl-amino-carbonyl)-3-fluoro-pyridin-4-yl |
| 181 | 1,2,3,4-tetrazol-1-yl | 2-fluoro, 3-chloro | R | H, H | H, H | S | H | 2-(amino-carbonyl)-3-fluoro-pyridin-3-yl |
| 182 | 1,2,3,4-tetrazol-1-yl | 2-fluoro, 3-chloro | R | H, H | H, H | S | H | 2-carboxy-3-fluoro-pyridin-4-yl |
| 183 | 1,2,3,4-tetrazol-1-yl | 2-fluoro, 3-chloro | R* | H, H | H, H | S | H | 2-(1-hydroxy-cycloprop-1-yl-methoxy)-3-fluoro-pyridin-4-yl |
| 184 | 1,2,3,4-tetrazol-1-yl | 3-chloro | R | H, H | H, H | S | bromo | 2-(hydroxy-d2-methyl)-3-fluoro-pyridin-4-yl |
| 185 | 1,2,3,4-tetrazol-1-yl | 2-fluoro, 3-chloro | R* | H, H | H, H | S | H | 2-(1R*-hydroxy-ethyl)-3-fluoro-pyridin-4-yl |
| 186 | 1,2,3,4-tetrazol-1-yl | 2-fluoro, 3-chloro | R* | H, H | H, H | S | H | 2-(1S*-hydroxy-ethyl)-3-fluoro-pyridin-4-yl |
| 187 | 1,2,3,4-tetrazol-1-yl | 2-fluoro, 3-chloro | R | H, H | H, H | R* | H | 2-(3S-hydroxy-piperidin-1-yl)-3-fluoro-pyridin-4-yl |
| 188 | 1,2,3,4-tetrazol-1-yl | 2-fluoro, 3-chloro | R | H, H | H, H | S* | H | 2-(3S-hydroxy-piperidin-1-yl)-3-fluoro-pyridin-4-yl |
| 189 | 1,2,3,4-tetrazol-1-yl | 2-fluoro, 3-chloro | RAC | H, H | H, H | S | H | 2-(hydroxy-d2-methyl)-3-fchloro-pyridin-4-yl |
| 199 | 1,2,3,4-tetrazol-1-yl | 2-fluoro, 3-chloro | RAC | H, H | H, H | S | chloro | pyridin-4-yl-2-one |
| 201 | 1,2,3,4-tetrazol-1-yl | 2-fluoro, 3-chloro | R | H, H | H, H | S | H | 3-amino-benzisoxazol-5-yl |
| 204 | 4-(trifluoro-methyl)-1,2,3-triazol-1-yl | 2-fluoro, 3-chloro | R* | H, H | H, H | S* | H | 2-(amino-carbonyl)-pyridin-4-yl |
| 206 | 1,2,3,4-tetrazol-1-yl | 2-fluoro, 3-chloro | R* | H, H | H, H | S* | H | 2-(amino-carbonyl)-pyridin-4-yl |
| 207 | 4-chloro-1,2,3-triazol-1-yl | 2-fluoro, 3-chloro | R | H, H | H, H | S | H | 2-(amino-carbonyl)-thien-5-yl |
| 208 | 4-chloro-1,2,3-triazol-1-yl | 2-fluoro, 3-chloro | R | H, H | H, H | S | H | 2-(amino-carbonyl)-thiazol-5-yl |
| 212 | 4-(trifluoro-methyl)-1,2,3-triazol-1-yl | 2-fluoro, 3-chloro | R* | H, H | H, H | S* | H | 2-(amino-carbonyl)-pyridin-5-yl |
| 213 | 4-(trifluoro-methyl)-1,2,3-triazol-1-yl | 2-fluoro, 3-chloro | S* | H, H | H, H | S* | H | 2-(amino-carbonyl)-pyridin-5-yl |
| 217 | 1,2,3,4-tetrazol-1-yl | 2-fluoro, 3-chloro | R | H, H | H, H | S | H | 3-fluoro-pyrazol-4-yl |
| 222 | 1,2,3,4-tetrazol-1-yl | 2-fluoro, 3-chloro | R | H, H | H, H | S | H | 2-(hydroxy-methyl)-3-fluoro-pyridin-4-yl |
| 223 | 4-(trifluoro-methyl)-1,2,3-triazol-1-yl | 2-fluoro, 3-chloro | R | H, H | H, H | S | H | 2-chloro-6-(hydroxy-methyl)-pyridin-3-yl |
| 224 | 1,2,3,4-tetrazol-1-yl | 2-fluoro, 3-chloro | R* | H, H | H, H | S | H | 3-chloro-pyrazol-4-yl |
| 225 | 1,2,3,4-tetrazol-1-yl | 2-fluoro, 3-chloro | R* | H, H | H, H | S* | H | 2-(amino-carbonyl)-pyridin-5-yl |
| 226 | 1,2,3,4-tetrazol-1-yl | 2-fluoro, 3-chloro | R* | H, H | H, H | R* | H | 2-(amino-carbonyl)-pyridin-5-yl |
| 227 | 1,2,3,4-tetrazol-1-yl | 2-fluoro, 3-chloro | R | H, H | H, H | S | H | 3-methoxy-pyrazol-4-yl |
| 228 | 1,2,3,4-tetrazol-1-yl | 2-fluoro, 3-chloro | R | H, H | H, H | S | H | 2-chloro-6-(amino-carbonyl)-pyridin-3-yl |
| 229 | 1,2,3,4-tetrazol-1-yl | 2-fluoro, 3-chloro | S | H, H | H, H | S | H | 2-chloro-6-(amino-carbonyl)-pyridin-3-yl |
| 230 | 1,2,3,4-tetrazol-1-yl | 2-fluoro, 3-chloro | R | H, H | H, H | S | H | 3-(trifluoro-methyl)-pyrrol-4-yl |
| 231 | 1,2,3,4-tetrazol-1-yl | 2-fluoro, 3-chloro | R | H, H | H, H | S | H | 2-(trifluoro-methyl)-imidazol-4-yl |
| 232 | 1,2,3,4-tetrazol-1-yl | 2-fluoro, 3-chloro | S | H, H | H, H | S | H | 3-(amino-carbonyl)-4-fluoro-phenyl |

TABLE 1-continued

| | | | | | | | | |
|---|---|---|---|---|---|---|---|---|
| 233 | 1,2,3,4-tetrazol-1-yl | 2-fluoro, 3-chloro | R | H, H | H, H | S | H | 3-(amino-carbonyl)-4-fluoro-phenyl |
| 234 | 1,2,3,4-tetrazol-1-yl | 2-fluoro, 3-chloro | R | H, H | H, H | S | H | 2-(amino-carbonyl)-thien-4-yl |
| 235 | 1,2,3,4-tetrazol-1-yl | 2-fluoro, 3-chloro | R* | H, H | H, H | S* | H | 2-fluoro-6-(hydroxy-methyl)-pyridin-3-yl |
| 236 | 1,2,3,4-tetrazol-1-yl | 2-fluoro, 3-chloro | R | H, H | H, H | S | H | 2-chloro-6-(hydroxy-methyl)-pyridin-3-yl |
| 237 | 1,2,3,4-tetrazol-1-yl | 2-fluoro, 3-chloro | R | H, H | H, H | S | H | 2-fluoro-3-(amino-carbonyl)-phenyl |
| 238 | 1,2,3,4-tetrazol-1-yl | 2-fluoro, 3-chloro | R | H, H | H, H | S* | H | 2-(amino-carbonyl)-thien-5-yl |
| 239 | 1,2,3,4-tetrazol-1-yl | 2-fluoro, 3-chloro | R* | H, H | H, H | R* | H | 3-(trifluoro-methyl)-pyrazol-4-yl |
| 240 | 1,2,3,4-tetrazol-1-yl | 2-fluoro, 3-chloro | R* | H, H | H, H | S* | H | 3-(trifluoro-methyl)-pyrazol-4-yl |
| 241 | 1,2,3,4-tetrazol-1-yl | 2-fluoro, 3-chloro | R | H, H | H, H | S | H | 3-(cyclopropyl-carbonyl-amino)-6-(trifluoro-methyl)-pyridin-4-yl |
| 242 | 1,2,3,4-tetrazol-1-yl | 2-fluoro, 3-chloro | S | H, H | H, H | S | H | 3-(cyclopropyl-carbonyl-amino)-6-(trifluoro-methyl)-pyridin-4-yl |
| 243 | 1,2,3,4-tetrazol-1-yl | 2-fluoro, 3-chloro | R | H, H | H, H | S | H | 3-(d3-methyl-carbonyl-amino)-6-(trifluoro-methyl)-pyridin-4-yl |
| 244 | 1,2,3,4-tetrazol-1-yl | 2-fluoro, 3-chloro | S | H, H | H, H | S | H | 3-(methyl-carbonyl-amino)-6-(trifluoro-methyl)-pyridin-4-yl |
| 245 | 1,2,3,4-tetrazol-1-yl | 2-fluoro, 3-chloro | R | H, H | H, H | S | H | 3-(methyl-carbonyl-amino)-6-(trifluoro-methyl)-pyridin-4-yl |
| 258 | 1,2,3,4-tetrazol-1-yl | 2-fluoro, 3-chloro | RAC | H, H | H, H | S | H | 3-(methyl-amino)-indazol-6-yl |
| 261 | 1,2,3,4-tetrazol-1-yl | 2-fluoro, 3-chloro | RAC | H, H | H, H | S | H | quinolin-6-yl-2-one |
| 265 | 1,2,3,4-tetrazol-1-yl | 2-fluoro, 3-chloro | S | H, H | H, H | S | H | 3-(methyl-amino)-indazol-6-yl |
| 269 | 1,2,3,4-tetrazol-1-yl | 2-fluoro, 3-chloro | S | H, H | H, H | S | H | 2-(methyl-amino)-pyridin-3-yl |
| 270 | 1,2,3,4-tetrazol-1-yl | 2-fluoro, 3-chloro | S | H, H | H, H | S | H | quinolin-6-yl-2-one |
| 273 | 1,2,3,4-tetrazol-1-yl | 2-fluoro, 3-chloro | RAC | H, H | H, H | S | H | quinazolin-6-yl-2-one |
| 277 | 1,2,3,4-tetrazol-1-yl | 2-fluoro, 3-chloro | R* | H, H | H, H | S | H | 1,4-dihydro-2H-benzo[d][1,3]oxazin-6-yl-2-one |
| 278 | 1,2,3,4-tetrazol-1-yl | 2-fluoro, 3-chloro | S* | H, H | H, H | S | H | 1,4-dihydro-2H-benzo[d][1,3]oxazin-6-yl-2-one |
| 280 | 1,2,3,4-tetrazol-1-yl | 2-fluoro, 3-chloro | S* | H, H | H, H | S | H | 3,4-dihydroquinolin-6-yl-2-one |
| 281 | 1,2,3,4-tetrazol-1-yl | 2-fluoro, 3-chloro | R* | H, H | H, H | S | H | 3,4-dihydroquinolin-6-yl-2-one |
| 282 | 1,2,3,4-tetrazol-1-yl | 2-fluoro, 3-chloro | R* | H, H | H, H | S | H | 2-fluoro-6-(methyl-amino)-pyridin-3-yl |
| 283 | 1,2,3,4-tetrazol-1-yl | 2-fluoro, 3-chloro | S* | H, H | H, H | S | H | indol-5-yl-2-one |
| 284 | 1,2,3,4-tetrazol-1-yl | 2-fluoro, 3-chloro | R* | H, H | H, H | S | H | indol-5-yl-2-one |
| 286 | 1,2,3,4-tetrazol-1-yl | 2-fluoro, 3-chloro | R* | H, H | H, H | S | H | benzimidazol-5-yl-2-one |
| 289 | 1,2,3,4-tetrazol-1-yl | 2-fluoro, 3-chloro | RAC | H, H | H, H | S | H | 2-(dimethyl-amino)-phenyl |
| 291 | 1,2,3,4-tetrazol-1-yl | 2-fluoro, 3-chloro | S* | H, H | H, H | S | H | 2-fluoro-6-(methyl-amino)-pyridin-3-yl |
| 292 | 1,2,3,4-tetrazol-1-yl | 2-fluoro, 3-chloro | S* | H, H | H, H | S | H | benzimidazol-5-yl-2-one |
| 297 | 1,2,3,4-tetrazol-1-yl | 2-fluoro, 3-chloro | RAC | H, H | H, H | S | H | 1,4-dihydro-2H-benzo[d][1,3]oxazin-6-yl-2-one |
| 299 | 1,2,3,4-tetrazol-1-yl | 2-fluoro, 3-chloro | S* | H, H | H, H | S | H | 1-methyl-benzimidazol-6-yl-2-one |

TABLE 1-continued

| | | | | | | | | |
|---|---|---|---|---|---|---|---|---|
| 300 | 1,2,3,4-tetrazol-1-yl | 2-fluoro, 3-chloro | R* | H, H | H, H | S | H | 1-methyl-benzimidazol-6-yl-2-one |
| 303 | 1,2,3,4-tetrazol-1-yl | 2-fluoro, 3-chloro | R | H, H | H, H | S | H | 1-methyl-benzimidazol-5-yl-2-one |
| 311 | 1,2,3,4-tetrazol-1-yl | 2-fluoro, 3-chloro | RAC | H, H | H, H | S | H | 3,4-dihydro-2H-quinolin-6-yl-2-one |
| 312 | 1,2,3,4-tetrazol-1-yl | 2-fluoro, 3-chloro | RAC | H, H | H, H | S | H | benzimidazol-5-yl-2-one |
| 313 | 1,2,3,4-tetrazol-1-yl | 2-fluoro, 3-chloro | RAC | H, H | H, H | S | H | 3-amino-indazol-6-yl |
| 314 | 1,2,3,4-tetrazol-1-yl | 2-fluoro, 3-chloro | RAC | H, H | H, H | S | H | indolin-5-yl-2-one |
| 315 | 1,2,3,4-tetrazol-1-yl | 2-fluoro, 3-chloro | RAC | H, H | H, H | S | H | 2-fluoro-6-(dimethyl-amino)-pyridin-3-yl |
| 316 | 1,2,3,4-tetrazol-1-yl | 2-fluoro, 3-chloro | R* | H, H | H, H | S | H | 5-(methoxy-carbonyl-amino)-pyridin-2-yl |
| 318 | 1,2,3,4-tetrazol-1-yl | 2-fluoro, 3-chloro | RAC | H, H | H, H | S | H | 4-(oxazolidin-3-yl-2-one)-phenyl |
| 319 | difluoro-methoxy | 2-fluoro, 5-chloro | S* | H, H | H, H | S | H | 4-(methoxy-carbonyl-amino)-phenyl |
| 320 | difluoro-methoxy | 2-fluoro, 3-chloro | S* | H, H | H, H | S | H | 4-(methoxy-carbonyl-amino)-phenyl |
| 321 | 1,2,3,4-tetrazol-1-yl | 2-fluoro, 3-chloro | S* | H, H | H, H | S | H | pyridin-4-yl-N-oxide |
| 322 | 1,2,3,4-tetrazol-1-yl | 2-fluoro, 3-chloro | S* | H, H | H, H | S | H | 5-(methoxy-carbonyl-amino)-pyridin-2-yl |
| 323 | difluoro-methoxy | 2-fluoro, 3-chloro | R* | H, H | H, H | S | H | 4-(methoxy-carbonyl-amino)-phenyl |
| 324 | 2,2,2-trifluoro-ethoxy | 2-fluoro, 3-chloro | RAC | H, H | H, H | S | H | 4-(methoxy-carbonyl-amino)-phenyl |
| 325 | 1,2,3,4-tetrazol-1-yl | 2-fluoro, 3-chloro | RAC | H, H | H, H | S | H | 2-(methoxy-carbonyl-amino)-pyridin-5-yl |
| 326 | 1,2,3,4-tetrazol-1-yl | 2-fluoro, 3-chloro | RAC | H, H | H, H | S | H | 5-(methoxy-carbonyl-amino)-pyridin-2-yl |
| 335 | 1,2,3,4-tetrazol-1-yl | 2-fluoro, 3-chloro | R* | H, H | methyl, methyl | S | H | 2-chloro-6-amino-pyridin-3-yl |
| 336 | 1,2,3,4-tetrazol-1-yl | 2-fluoro, 3-chloro | R* | H, H | methyl, methyl | S | H | 2-fluoro-6-amino-pyridin-3-yl |
| 337 | 1,2,3,4-tetrazol-1-yl | 2-fluoro, 3-chloro | S* | H, H | methyl, methyl | S | H | 2-fluoro-6-amino-pyridin-3-yl |
| 338 | 1,2,3,4-tetrazol-1-yl | 2-fluoro, 3-chloro | S* | H, H | methyl, methyl | S | H | 2-chloro-6-amino-pyridin-3-yl |
| 340 | 1,2,3,4-tetrazol-1-yl | 2-fluoro, 3-chloro | S | H, H | H, H | S | H | 4-(methoxy-carbonyl-amino)-phenyl |
| 341 | 1,2,3,4-tetrazol-1-yl | 2-fluoro, 3-chloro | R | H, H | H, H | S | H | 4-(methoxy-carbonyl-amino)-phenyl |
| 344 | 1,2,3,4-tetrazol-1-yl | 2-fluoro, 3-chloro | R* | H, H | H, S*-methyl | S | H | 2-fluoro-6-amino-pyridin-3-yl |
| 345 | 1,2,3,4-tetrazol-1-yl | 2-fluoro, 3-chloro | R* | H, H | H, R*-methyl | S | H | 2-fluoro-6-amino-pyridin-3-yl |
| 346 | 1,2,3,4-tetrazol-1-yl | 2-fluoro, 3-chloro | S* | H, H | H, S*-methyl | S | H | 2-fluoro-6-amino-pyridin-3-yl |
| 347 | 1,2,3,4-tetrazol-1-yl | 2-fluoro, 3-chloro | RAC | H, H | H, methyl | S | H | 2-chloro-6-amino-pyridin-3-yl |
| 348 | 1,2,3,4-tetrazol-1-yl | 2-fluoro, 3-chloro | RAC | H, H | H, methyl | S | H | 2-fluoro-6-amino-pyridin-3-yl |
| 349 | 1,2,3,4-tetrazol-1-yl | 2-fluoro, 3-chloro | RAC | H, H | methyl, methyl | S | H | 2-chloro-6-amino-pyridin-3-yl |
| 350 | 1,2,3,4-tetrazol-1-yl | 2-fluoro, 3-chloro | RAC | H, H | methyl, methyl | S | H | 2-fluoro-6-amino-pyridin-3-yl |
| 351 | 1,2,3,4-tetrazol-1-yl | 2-fluoro, 3-chloro | R | H, H | H, H | S | H | 2-(trifluoro-methyl)-pyridin-4-yl |
| 352 | 1,2,3,4-tetrazol-1-yl | 2-fluoro, 3-chloro | S | H, H | H, H | S | H | 2-chloro-6-amino-pyridin-3-yl |
| 353 | 1,2,3,4-tetrazol-1-yl | 2-fluoro, 3-chloro | S | H, H | H, H | S | H | 2-(trifluoro-methyl)-pyridin-4-yl |

TABLE 1-continued

| | | | | | | | | |
|---|---|---|---|---|---|---|---|---|
| 354 | 1,2,3,4-tetrazol-1-yl | 2-fluoro, 3-chloro | R | H, H | H, H | S | H | 2-chloro-6-amino-pyridin-3-yl |
| 355 | 1,2,3,4-tetrazol-1-yl | 2-fluoro, 3-chloro | RAC | H, H | H, H | S | H | 4-(methoxy-carbonyl-amino)-phenyl |
| 356 | 1,2,3,4-tetrazol-1-yl | 2-fluoro, 3-chloro | R | H, H | H, H | R | H | 2-fluoro-6-amino-pyridin-3-yl |
| 357 | 1,2,3,4-tetrazol-1-yl | 2-fluoro, 3-chloro | S | H, H | H, H | R | H | 2-fluoro-6-amino-pyridin-3-yl |
| 358 | 1,2,3,4-tetrazol-1-yl | 2-fluoro, 3-chloro | R | H, H | H, H | S | H | 2-fluoro-6-amino-pyridin-3-yl |
| 359 | 1,2,3,4-tetrazol-1-yl | 2-fluoro, 3-chloro | S | H, H | H, H | S | H | 2-fluoro-6-amino-pyridin-3-yl |
| 361 | 1,2,3,4-tetrazol-1-yl | 2-fluoro, 3-chloro | R | H, H | H, H | S | H | 2,3-dihydro-[1,4]dioxino[2,3-b]pyridin-8-yl |
| 362 | 1,2,3,4-tetrazol-1-yl | 2-fluoro, 3-chloro | R* | H, H | H, H | S | H | 1H-pyrrolo[2,3-b]pyridin-4-yl |
| 363 | pyrazol-5-yl | 2-fluoro, 3-chloro | RAC | H, H | H, H | S | H | 2-fluoro-6-amino-pyridin-3-yl |
| 365 | 4-(trifluoro-methyl)-1,2,3-triazol-1-yl | 2-fluoro, 3-chloro | RAC | H, H | H, H | S | H | 7H-pyrrolo[2,3-d]pyrimidin-5-yl |
| 366 | 1,2,3,4-tetrazol-1-yl | 2-fluoro, 3-chloro | RAC | H, H | H, H | S | H | 5-chloro-pyrazol-4-yl |
| 367 | 1,2,3,4-tetrazol-1-yl | 2-fluoro, 3-chloro | R* | H, H | H, H | S | H | 2-(methyl-sulfonyl-amino)-3-fluoro-pyridin-4-yl |
| 368 | 1,2,3,4-tetrazol-1-yl | 2-fluoro, 3-chloro | RAC | H, H | H, H | S | H | 2-fluoro-6-(methyl-amino)-pyridin-3-yl |
| 371 | 1,2,3,4-tetrazol-1-yl | 2-fluoro, 3-chloro | R | H, H | H, H | S | H | 2-fluoro-5-chloro-pyridin-4-yl |
| 372 | 1,2,3,4-tetrazol-1-yl | 2-fluoro, 3-chloro | R | H, H | H, H | S | chloro | 2-amino-pyridin-4-yl |
| 374 | 1,2,3,4-tetrazol-1-yl | 2-fluoro, 3-chloro | RAC | H, H | H, H | RAC | H | 7-methyl-5H-cyclopenta[b]pyridin-4-yl |
| 379 | 1,2,3,4-tetrazol-1-yl | 2-fluoro, 3-chloro | R* | H, H | H, H | S | H | 7H-pyrrolo[2,3-d]pyrimidin-5-yl |
| 380 | 1,2,3,4-tetrazol-1-yl | 2-fluoro, 3-chloro | R | H, H | H, H | S | H | 2-amino-3-chloro-pyridin-4-yl |
| 381 | 1,2,3,4-tetrazol-1-yl | 2-fluoro, 3-chloro | RAC | H, H | H, H | S | H | 5-methyl-1H-pyrrolo[2,3-c]pyridin-3-yl |
| 382 | 1,2,3,4-tetrazol-1-yl | 2-fluoro, 3-chloro | S | H, H | H, H | R* | H | 2-amino-3-methoxy-pyridin-4-yl |
| 383 | 1,2,3,4-tetrazol-1-yl | 2-fluoro, 3-chloro | RAC | H, H | H, H | S | H | 6-methyl-indolin-7-yl-2-one |
| 384 | 1,2,3,4-tetrazol-1-yl | 2-fluoro, 3-chloro | R | H, H | H, H | S | H | 7-fluoro-indol-6-yl |
| 385 | 4-(trifluoro-methyl)-1,2,3-triazol-1-yl | 2-fluoro, 3-chloro | R* | H, H | H, H | S | H | 1H-pyrrolo[3,2-c]pyridin-3-yl |
| 386 | 1,2,3,4-tetrazol-1-yl | 2-fluoro, 3-chloro | R | H, H | H, H | S | H | 2,3-dihydrofuro[2,3-b]pyridin-4-yl |
| 387 | 1,2,3,4-tetrazol-1-yl | 2-fluoro, 3-chloro | R | H, H | H, H | S | H | thieno[3,2-b]pyridin-7-yl |
| 388 | 1,2,3,4-tetrazol-1-yl | 2-fluoro, 3-chloro | R | H, H | H, H | S | H | 6-methoxy-1H-pyrrolo[3,2-c]pyridin-3-yl |
| 389 | 1,2,3,4-tetrazol-1-yl | 2-fluoro, 3-chloro | R | H, H | H, H | S | H | 2-amino-pyridin-4-yl |
| 390 | 1,2,3,4-tetrazol-1-yl | 2-fluoro, 3-chloro | R | H, H | H, H | S | H | 2-(ethyl-amino)-3-fluoro-pyridin-4-yl |

TABLE 1-continued

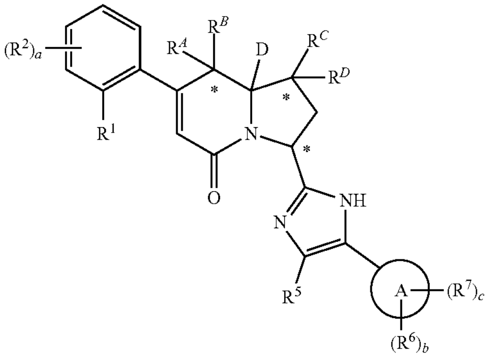

| ID No. | $R^1$ | $(R^2)_a$ | Ring Stereo | $R^A$, $R^B$ | $R^C$, $R^D$ | Q Stereo | $R^5$ | 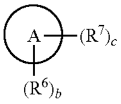 |
|---|---|---|---|---|---|---|---|---|
| 33 | 1,2,3,4-tetrazol-1-yl | 2-fluoro, 3-chloro | R | deutero, deutero | deutero, deutero | S | H | 2-(hydroxy-methyl)-3-fluoro-pyridin-4-yl |
| 36 | 1,2,3,4-tetrazol-1-yl | 2-fluoro, 3-chloro | R* | H, H | H, H | S | H | 2-(hydroxy-d2-methyl)-3-fluoro-pyridin-4-yl |
| 47 | 1,2,3,4-tetrazol-1-yl | 2-fluoro, 3-chloro | R | H, H | H, H | S | H | 2-(hydroxy-methyl)-3-fluoro-pyridin-4-yl |
| 48 | 1,2,3,4-tetrazol-1-yl | 2-fluoro, 3-chloro | S | H, H | H, H | S | H | 2-(hydroxy-methyl)-3-fluoro-pyridin-4-yl |
| 131 | 1,2,3,4-tetrazol-1-yl | 2-fluoro, 3-chloro | R* | H, H | H, H | R* | deutero | 2-fluoro-4,5-dideutero-6-amino-pyridin-3-yl |
| 132 | 1,2,3,4-tetrazol-1-yl | 2-fluoro, 3-chloro | R* | H, H | H, H | S* | deutero | 2-fluoro-4,5-dideutero-6-amino-pyridin-3-yl |
| 146 | 1,2,3,4-tetrazol-1-yl | 2-fluoro, 3-chloro | R | H, H | H, H | S | H | 2-fluoro-6-amino-pyridin-3-yl |

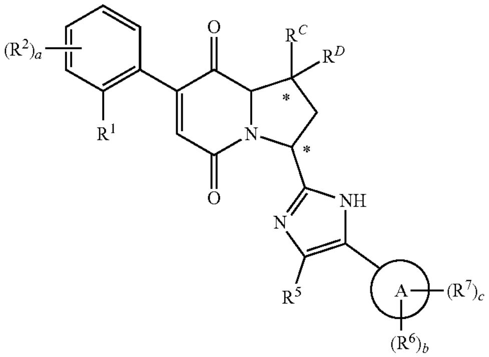

($R^A$ + $R^B$ = oxo)

| ID No. | $R^1$ | $(R^2)_a$ | $R^C$, $R^D$ | Q Stereo | $R^5$ | 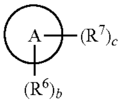 |
|---|---|---|---|---|---|---|
| 360 | 1,2,3,4-tetrazol-1-yl | 2-fluoro, 3-chloro | H, H | S* | H | 2-fluoro-6-amino-pyridin-3-yl |

TABLE 1-continued
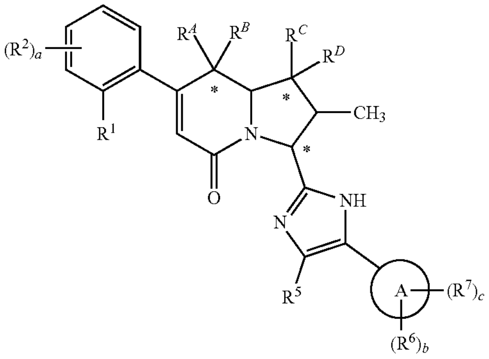
($R^E$ is methyl)
| ID No. | $R^1$ | $(R^2)_a$ | Ring Stereo | $R^A$, $R^B$ | $R^C$, $R^D$ | Q Stereo | $R^5$ | 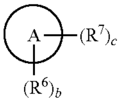 |
|---|---|---|---|---|---|---|---|---|
| 328 | 1,2,3,4-tetrazol-1-yl | 2-fluoro, 3-chloro | RAC | H, H | H, H | RAC | H | 2-fluoro-6-amino-pyridin-3-yl |
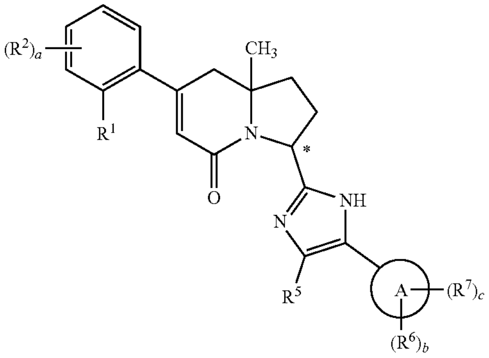
(Bridge methyl)
| ID No. | $R^1$ | $(R^2)_a$ | Q Stereo | $R^5$ | 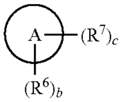 |
|---|---|---|---|---|---|
| 391 | 1,2,3,4-tetrazol-1-yl | 2-fluoro, 3-chloro | S | H | 2-(hydroxy-methyl)-3-fluoro-pyridin-4-yl |

TABLE 2

Representative Compounds of Formula (I)

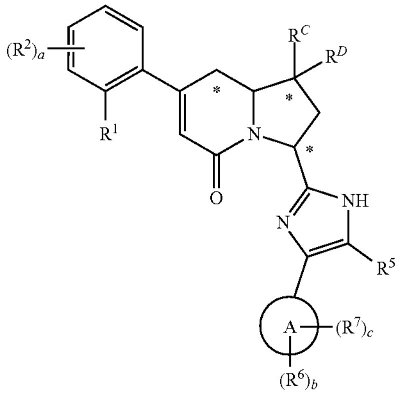

| ID No. | $R^1$ | $(R^2)_a$ | Ring Stereo | $R^C$, $R^D$ | Q Stereo | $R^5$ | 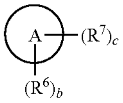 |
|---|---|---|---|---|---|---|---|
| 3 | 1,2,3,4-tetrazol-1-yl | 2-fluoro, 3-chloro | RAC | H, H | S* | fluoro | 2-(difluoro-methoxy)-pyridin-4-yl |
| 9 | 1,2,3,4-tetrazol-1-yl | 2-fluoro, 3-chloro | RAC | H, H | S* | H | 2-(2-hydroxy-ethyl-oxy)-pyridin-4-yl |
| 10 | 1,2,3,4-tetrazol-1-yl | 2-fluoro, 3-chloro | RAC | H, H | S* | H | 2-(difluoro-methoxy)-pyridin-4-yl |
| 22 | 1,2,3,4-tetrazol-1-yl | 2-fluoro, 3-chloro | S | H, H | S | H | 2-(hydroxy-methyl)-thiazol-4-yl |
| 32 | 1,2,3,4-tetrazol-1-yl | 2-fluoro, 3-chloro | R | H, H | S | H | 1H-pyrrolo[2,3-b]pyridin-4-yl |
| 38 | 1,2,3,4-tetrazol-1-yl | 2-fluoro, 3-chloro | R | H, H | S | H | 1H-pyrazolo[3,4-b]pyridin-4-yl |
| 39 | 1,2,3,4-tetrazol-1-yl | 2-fluoro, 3-chloro | R | H, H | S | H | 4-(hydroxy-methyl)-thiazol-2-yl |
| 41 | 1,2,3,4-tetrazol-1-yl | 2-fluoro, 3-chloro | R | H, H | S | H | 1H-pyrazolo[3,4-b]pyridin-5-yl |
| 42 | 1,2,3,4-tetrazol-1-yl | 2-fluoro, 3-chloro | R | H, H | S | H | benzimidiazol-5-yl |
| 43 | 1,2,3,4-tetrazol-1-yl | 2-fluoro, 3-chloro | R | H, H | S | H | indazol-5-yl |
| 51 | 1,2,3,4-tetrazol-1-yl | 2-fluoro, 3-chloro | R | H, H | S | H | indazol-4-yl |
| 66 | 1,2,3,4-tetrazol-1-yl | 2-fluoro, 3-chloro | RAC | H, H | S* | fluoro | 2-(pyrazol-5-yl)-pyridin-2-yl |
| 115 | 1,2,3,4-tetrazol-1-yl | 2-fluoro, 3-chloro | R* | H, H | S | H | 2-(pyrazol-5-yl)-3-fluoro-pyridin-4-yl |
| 125 | 1,2,3,4-tetrazol-1-yl | 2-fluoro, 3-chloro, 4-deutero | R | H, H | S | H | 2-fluoro-5-deutero-6-amino-pyridin-3-yl |
| 153 | 1,2,3,4-tetrazol-1-yl | 2-fluoro, 3-chloro, 4-deutero | R | H, H | S | H | 2-fluoro-6-amino-pyridin-3-yl |
| 176 | 1,2,3,4-tetrazol-1-yl | 2-fluoro, 3-chloro | R | H, H | S | H | 2-(cyano-methyl)-3-fluoro-pyridin-4-yl |
| 177 | 1,2,3,4-tetrazol-1-yl | 2-fluoro, 3-chloro | RAC | H, H | S | H | 2-(methoxy-methyl)-3-fluoro-pyridin-4-yl |
| 190 | 1,2,3,4-tetrazol-1-yl | 2-fluoro, 3-chloro | R* | H, H | S* | H | 2-(2-hydroxy-2-methyl-n-propyl-oxy)-3-fluoro-pyridin-4-yl |
| 191 | 4-(trifluoro-methyl)-1,2,3-triazol-1-yl | 2-fluoro, 3-chloro | R* | H, H | S* | H | 2-(2-hydroxy-2-methyl-n-propyl-oxy)-3-fluoro-pyridin-4-yl |
| 192 | 4-(trifluoro-methyl)-1,2,3-triazol-1-yl | 2-fluoro, 3-chloro | R | H, H | RAC | H | 2-(methyl-sulfonyl-amino-carbonyl)-3-fluoro-thien-5-yl |
| 193 | 4-chloro-1,2,3-triazol-1-yl | 2-fluoro, 3-chloro | RAC | H, H | S | H | 2-carboxy-thien-5-yl |

TABLE 2-continued

| | | | | | | | |
|---|---|---|---|---|---|---|---|
| 194 | 1,2,3,4-tetrazol-1-yl | 2-fluoro, 3-chloro | R* | H, H | S* | H | 2-(hydroxy-d2-methyl)-3-fluoro-pyridin-4-yl |
| 195 | 4-(trifluoro-methyl)-1,2,3-triazol-1-yl | 2-fluoro, 3-chloro | R | H, H | S* | H | 2-carboxy-3-fluoro-thien-5-yl |
| 196 | 1,2,3,4-tetrazol-1-yl | 2-fluoro, 3-chloro | R | H, H | S | H | 2-fluoro-4-(amino-carbonyl)-phenyl |
| 197 | 1,2,3,4-tetrazol-1-yl | 2-fluoro, 3-chloro | R | H, H | S | H | 3-fluoro-4-(amino-carbonyl)-phenyl |
| 198 | 1,2,3,4-tetrazol-1-yl | 2-fluoro, 3-chloro | S | H, H | S | H | 3-fluoro-4-(amino-carbonyl)-phenyl |
| 200 | 4-chloro-1,2,3-triazol-1-yl | 2-fluoro, 3-chloro | R | H, H | S | H | 3-fluoro-pyridin-4-yl-2-one |
| 202 | 4-(trifluoro-methyl)-1,2,3-triazol-1-yl | 2-fluoro, 3-chloro | S* | H, H | S | chloro | 2-(amino-carbonyl)-thien-5-yl |
| 203 | 4-(trifluoro-methyl)-1,2,3-triazol-1-yl | 2-fluoro, 3-chloro | R* | H, H | S | chloro | 2-(amino-carbonyl)-thien-5-yl |
| 205 | 1,2,3,4-tetrazol-1-yl | 2-fluoro, 3-chloro | R* | H, H | S* | H | 2-(amino-carbonyl)-thiazol-5-yl |
| 209 | 4-(trifluoro-methyl)-1,2,3-triazol-1-yl | 2-fluoro, 3-chloro | S* | H, H | S | H | 2-(amino-carbonyl)-thiazol-5-yl |
| 210 | 4-(trifluoro-methyl)-1,2,3-triazol-1-yl | 2-fluoro, 3-chloro | R* | H, H | S | H | 2-(amino-carbonyl)-thiazol-5-yl |
| 211 | 1,2,3,4-tetrazol-1-yl | 2-fluoro, 3-chloro | R* | H, H | S | chloro | 2-(amino-carbonyl)-thiazol-5-yl |
| 214 | 1,2,3,4-tetrazol-1-yl | 2-fluoro, 3-chloro | R | H, H | S | H | 2-(amino-carbonyl)-3-fluoro-thien-4-yl |
| 215 | 1,2,3,4 tetrazol-1-yl | 2-fluoro, 3-chloro | S | H, H | S | H | 2-(amino-carbonyl)-3-fluoro-thien-5-yl |
| 216 | 1,2,3,4-tetrazol-1-yl | 2-fluoro, 3-chloro | R | H, H | S | H | 2-(amino-carbonyl)-3-fluoro-thien-5-yl |
| 218 | 1,2,3,4-tetrazol-1-yl | 2-fluoro, 3-chloro | RAC | H, H | S | chloro | 2-(amino-carbonyl)-thien-4-yl |
| 219 | 1,2,3,4-tetrazol-1-yl | 2-fluoro, 3-chloro | RAC | H, H | S | H | 2-(amino-carbonyl)-thien-4-yl |
| 220 | 4-(trifluoro-methyl)-1,2,3-triazol-1-yl | 2-fluoro, 3-chloro | R* | H, H | S | H | 2-(amino-carbonyl)-thien-4-yl |
| 221 | 4-(trifluoro-methyl)-1,2,3-triazol-1-yl | 2-fluoro, 3-chloro | S* | H, H | S | H | 2-(amino-carbonyl)-thien-4-yl |
| 246 | 1,2,3,4-tetrazol-1-yl | 2-fluoro, 3-chloro | RAC | H, H | S | H | 3-(trifluoro-methyl-carbonyl-amino)-pyridin-4-yl |
| 247 | 1,2,3,4-tetrazol-1-yl | 2-fluoro, 3-chloro | S | H, H | S | H | 1-methyl-4-(cyclopropyl-carbonyl-amino)-pyrazol-5-yl |
| 248 | 1,2,3,4-tetrazol-1-yl | 2-fluoro, 3-chloro | RAC | H, H | S | H | 3-(cyclopropyl-carbonyl-amino)-thien-2-yl |
| 249 | 1,2,3,4-tetrazol-1-yl | 2-fluoro, 3-chloro | R* | H, H | S | H | 3-(cyclopropyl-carbonyl-amino)-pyridin-4-yl |
| 250 | 1,2,3,4-tetrazol-1-yl | 2-fluoro, 3-chloro | S* | H, H | S | H | 3-(cyclopropyl-carbonyl-amino)-pyridin-4-yl |
| 251 | 1,2,3,4-tetrazol-1-yl | 2-fluoro, 3-chloro | RAC | H, H | S | H | 4-(ethoxy-carbonyl-amino)-pyridin-3-yl |
| 252 | 1,2,3,4-tetrazol-1-yl | 2-fluoro, 3-chloro | RAC | H, H | S | H | 4-(cyclopropyl-carbonyl-amino)-pyridin-3-yl |
| 253 | 1,2,3,4-tetrazol-1-yl | 2-fluoro, 3-chloro | RAC | H, H | S | H | 4-amino-pyridin-3-yl |

TABLE 2-continued

| | | | | | | | |
|---|---|---|---|---|---|---|---|
| 254 | 1,2,3,4-tetrazol-1-yl | 2-fluoro, 3-chloro | R | H, H | S | H | 2-(ethoxy-carbonyl-amino)-pyridin-3-yl |
| 255 | 1,2,3,4-tetrazol-1-yl | 2-fluoro, 3-chloro | RAC | H, H | S | H | 1-methyl-(1,2,4-triazol-3-yl) |
| 256 | 1,2,3,4-tetrazol-1-yl | 2-fluoro, 3-chloro | RAC | H, H | S | H | 3-(d3-methyl-carbonyl-amino)-pyridin-4-yl |
| 257 | 1,2,3,4-tetrazol-1-yl | 2-fluoro, 3-chloro | R | H, H | S | H | 2-(cyclopropyl-carbonyl-amino)-5-methoxy-phenyl |
| 259 | 1,2,3,4-tetrazol-1-yl | 2-fluoro, 3-chloro | RAC | H, H | S | H | 1-methyl-3-(cyclopropyl-carbonyl-amino)-pyrazol-4-yl |
| 260 | 1,2,3,4-tetrazol-1-yl | 2-fluoro, 3-chloro | RAC | H, H | S | H | 2-(methyl-amino)-pyridin-3-yl |
| 262 | 1,2,3,4-tetrazol-1-yl | 2-fluoro, 3-chloro | S | H, H | S | H | 2-(ethoxy-carbonyl-amino)-pyridin-3-yl |
| 263 | 1,2,3,4-tetrazol-1-yl | 2-fluoro, 3-chloro | S | H, H | S | H | 2-(ethoxy-carbonyl-amino)-pyridin-3-yl |
| 264 | 1,2,3,4-tetrazol-1-yl | 2-fluoro, 3-chloro | S | H, H | S | H | 2-(cyclopropyl-carbonyl-amino)-4-methoxy-phenyl |
| 266 | 1,2,3,4-tetrazol-1-yl | 2-fluoro, 3-chloro | R* | H, H | S | H | 2-(cyclopropyl-carbonyl-amino)-4-methoxy-phenyl |
| 267 | 1,2,3,4-tetrazol-1-yl | 2-fluoro, 3-chloro | S | H, H | S | H | 4-(cyclopropyl-carbonyl-amino)-pyridin-3-yl |
| 268 | 1,2,3,4-tetrazol-1-yl | 2-fluoro, 3-chloro | S | H, H | S | H | 4-(ethoxy-carbonyl-amino)-pyridin-3-yl |
| 271 | 1,2,3,4-tetrazol-1-yl | 2-fluoro, 3-chloro | S | H, H | S | H | 2-(cyclopropyl-carbonyl-amino)-5-methoxy-phenyl |
| 272 | 1,2,3,4-tetrazol-1-yl | 2-fluoro, 3-chloro | S | H, H | S | H | 4-amino-pyridin-3-yl |
| 274 | 1,2,3,4-tetrazol-1-yl | 2-fluoro, 3-chloro | S | H, H | S | H | 1-methyl-(1,2,4-triazol-3-yl) |
| 275 | 1,2,3,4-tetrazol-1-yl | 2-fluoro, 3-chloro | S | H, H | S | H | 1-methyl-4-(cyclopropyl-carbonyl-amino)-pyrazol-5-yl |
| 276 | 1,2,3,4-tetrazol-1-yl | 2-fluoro, 3-chloro | RAC | H, H | S | H | 2-(cyclopropyl-carbonyl-amino)-4-methoxy-phenyl |
| 279 | 1,2,3,4-tetrazol-1-yl | 2-fluoro, 3-chloro | RAC | H, H | S | H | 2-(cyclopropyl-carbonyl-amino)-5-methoxy-phenyl |
| 285 | 1,2,3,4-tetrazol-1-yl | 2-fluoro, 3-chloro | RAC | H, S-methoxy | S | H | 2-fluoro-6-amino-pyridin-3-yl |
| 287 | 1,2,3,4-tetrazol-1-yl | 2-fluoro, 3-chloro | RAC | H, H | S | H | 2-(methyl-amino-carbonyl)-phenyl |
| 288 | 1,2,3,4-tetrazol-1-yl | 2-fluoro, 3-chloro | RAC | H, H | S | H | 2-(dimethyl-amino-carbonyl)-phenyl |
| 290 | 1,2,3,4-tetrazol-1-yl | 2-fluoro, 3-chloro | RAC | H, H | S | H | 2-(amino-carbonyl)-phenyl |
| 293 | 1,2,3,4-tetrazol-1-yl | 2-fluoro, 3-chloro | RAC | H, H | S | H | 2-(methyl-sulfonyl-amino)-phenyl |
| 294 | 1,2,3,4-tetrazol-1-yl | 2-fluoro, 3-chloro | RAC | H, H | S | H | 2-(isopropyloxy)-phenyl |
| 295 | 1,2,3,4-tetrazol-1-yl | 2-fluoro, 3-chloro | R* | H, H | S | H | 2-(ethyl-carbonyl-amino)-phenyl |
| 296 | 1,2,3,4-tetrazol-1-yl | 2-fluoro, 3-chloro | S | H, H | S | H | 2-(ethyl-carbonyl-amino)-phenyl |
| 301 | 1,2,3,4-tetrazol-1-yl | 2-fluoro, 3-chloro | R* | H, H | S | H | 2-(methoxy-carbonyl-amino)-phenyl |
| 302 | 1,2,3,4-tetrazol-1-yl | 2-fluoro, 3-chloro | S* | H, H | S | H | 2-(methoxy-carbonyl-amino)-phenyl |
| 305 | 1,2,3,4-tetrazol-1-yl | 2-fluoro, 3-chloro | R | H, H | S | H | 2-(isopropyl-carbonyl-amino)-phenyl |
| 306 | 1,2,3,4-tetrazol-1-yl | 2-fluoro, 3-chloro | R | H, H | S | H | 2-(methyl-carbonyl-amino)-phenyl |
| 307 | 1,2,3,4-tetrazol-1-yl | 2-fluoro, 3-chloro | R | H, H | S | H | 2-(cyclopropyl-carbonyl-amino)-phenyl |
| 308 | 1,2,3,4-tetrazol-1-yl | 2-fluoro, 3-chloro | S* | H, H | S | H | 2-amino-phenyl |
| 309 | 1,2,3,4-tetrazol-1-yl | 2-fluoro, 3-chloro | S | H, H | S | H | benzoxazol-6-yl-2-one |

TABLE 2-continued

| | | | | | | | |
|---|---|---|---|---|---|---|---|
| 310 | 1,2,3,4-tetrazol-1-yl | 2-fluoro, 3-chloro | R* | H, H | S | H | 2-amino-phenyl |
| 317 | 1,2,3,4-tetrazol-1-yl | 2-fluoro, 3-chloro | RAC | H, H | S | H | 2-methoxy-phenyl |
| 327 | 1,2,3,4-tetrazol-1-yl | 2-fluoro, 3-chloro | RAC | H, R-methoxy | S | H | 2-fluoro-6-amino-pyridin-3-yl |
| 329 | 1,2,3,4-tetrazol-1-yl | 2-fluoro, 3-chloro | RAC | H, H | S | H | 2-(isopropyl-carbonyl-amino)-phenyl |
| 330 | 1,2,3,4-tetrazol-1-yl | 2-fluoro, 3-chloro | RAC | H, H | S | H | 2-(cyclopentyl-carbonyl-amino)-phenyl |
| 331 | 1,2,3,4-tetrazol-1-yl | 2-fluoro, 3-chloro | RAC | H, H | S | H | 1,2,4-triazol-3-yl |
| 332 | 1,2,3,4-tetrazol-1-yl | 2-fluoro, 3-chloro | RAC | H, H | S | H | 1,2,3-triazol-5-yl |
| 333 | 1,2,3,4-tetrazol-1-yl | 2-fluoro, 3-chloro | RAC | H, H | S | H | imidazol-2-yl |
| 334 | 1,2,3,4-tetrazol-1-y | 2-fluoro, 3-chloro | RAC | H, H | S | H | 1-methyl-imidazol-2-yl |
| 339 | 1,2,3,4-tetrazol-1-yl | 2-fluoro, 3-chloro | RAC | H, H | S | H | 1-methyl-1,2,3-triazol-5-yl |
| 342 | 1,2,3,4-tetrazol-1-yl | 2-fluoro, 3-chloro | RAC | H, H | S | H | 3-fluoro-4-carboxy-phenyl |
| 364 | imidazol-5-yl | 2-fluoro, 3-chloro | RAC | H, H | S | H | 2-fluoro-6-amino-pyridin-3-yl |
| 369 | 1,2,3,4-tetrazol-1-yl | 2-fluoro, 3-chloro | R* | H, H | S | H | 2-(cyclopropyl-carbonyl-amino)-phenyl |
| 370 | 1,2,3,4-tetrazol-1-yl | 2-fluoro, 3-chloro | RAC | H, H | S | H | 2-(cyclopropyl-carbonyl-amino)-phenyl |
| 373 | 4-(trifluoro-methyl)-1,2,3-triazol-1-yl | 2-chloro | RAC | H, H | RAC | H | 2-carboxy-thien-5-yl |

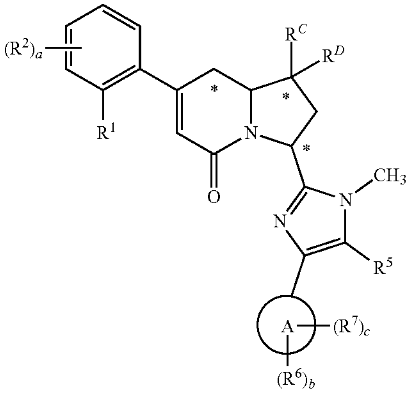

($R^4$ is methyl)

| ID No. | $R^1$ | $(R^2)_a$ | Ring Stereo | $R^C$, $R^D$ | Q Stereo | $R^5$ | 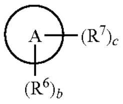 |
|---|---|---|---|---|---|---|---|
| 298 | 1,2,3,4-tetrazol-1-yl | 2-fluoro, 3-chloro | R* | H, H | S | H | 2-(cyclopropyl-carbonyl-amino)-phenyl |
| 304 | 1,2,3,4-tetrazol-1-yl | 2-fluoro, 3-chloro | S* | H, H | S | H | 2-(cyclopropyl-carbonyl-amino)-phenyl |

As used herein, the "*" symbol or notation shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. It is further understood that atropisomers (a specific type of stereoisomer resulting from steric or other hinderances to rotation) are also encompassed within the scope of the present invention.

Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer or stereoisomer, the diastereomer or stereoisomer is present at a diastereomeric or stereoisomeric excess of greater than or equal to about 80%, more preferably, at a diastereomeric or stereoisomeric excess of greater than or equal to about 90%, more preferably still, at a diastereomeric or stereoisomeric excess of greater than or equal to about 95%, more preferably still, at a diastereomeric or stereoisomeric excess of greater than or equal to about 98%, most preferably, at a diastereomeric or stereoisomeric excess of greater than or equal to about 99%.

In some embodiments, the present invention is directed to compounds of formula (I), compounds of formula (II), compounds of formula (III) and/or compounds of formula (IV) in an enantiomeric excess of one of the R- or S-enantiomers (at the $R^3$ stereocenter denoted with the "*"). In some embodiments of the present invention, the compound of formula (I) is present in an enantiomeric excess of one of the R- or S-enantiomers (at the $R^3$ stereocenter denoted with the "*") of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably the compound of formula (I), compounds of formula (II), compounds of formula (III) and/or compounds of formula (IV) is present in an enantiomeric excess of one of the R- or S-enantiomers (at the $R^3$stereocenter denoted with the "*") of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

In some embodiments, the present invention is directed to compounds of formula (I), compounds of formula (II), compounds of formula (III) and/or compounds of formula (IV) in a diastereomeric or stereoisomeric excess of one of the possible diastereomers or stereoisomers. In some embodiments of the present invention, the compound of formula (I), compounds of formula (II), compounds of formula (III) and/or compounds of formula (IV) is present in a diastereomeric or stereoisomeric excess of one of the possible diastereomers or stereoisomers, of about 55%, about 60%, about 65%, about 70%, about 75%, about 80%, about 85%, about 90%, about 91%, about 92%, about 93%, about 94%, about 95%, about 96%, about 97%, about 98% or about 99%. Preferably, the compound of formula (I), compounds of formula (II), compounds of formula (III) and/or compounds of formula (IV) is present in a diastereomeric or stereoisomeric excess of one of the possible diastereomers or stereoisomers of greater than or equal to about 80%, preferably greater than or equal to about 90%, more preferably greater than or equal to about 93%, more preferably greater than or equal to about 95%, more preferably greater than or equal to about 97%, more preferably greater than or equal to about 98%, more preferably greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isotopologues" shall mean molecules that differ only in their isotopic composition. More particularly, an isotopologue of a molecule differs from the parent molecule in that it contains at least one atom which is an isotope (i.e. has a different number of neutrons from its parent atom). For example, isotopologues of water include, but are not limited to, "light water" (HOH or $H_2O$), "semi-heavy water" with the deuterium isotope in equal proportion to protium (HDO or $^1H^2HO$), "heavy water" with two deuterium isotopes of hydrogen per molecule ($d_2O$ or $^2H_2O$), "super-heavy water" or tritiated water ($T_2O$ or $^3H_2O$), where the hydrogen atoms are replaced with tritium ($^3H$) isotopes, two heavy-oxygen water isotopologues ($H_2{}^{18}O$ and $H_2{}^{17}O$) and isotopologues where the hydrogen and oxygen atoms may each independently be replaced by isotopes, for example the doubly labeled water isotopologue $d_2{}^{18}O$.

It is intended that within the scope of the present invention, any one or more element(s), in particular when mentioned in relation to a compound of formula (I), shall comprise all isotopes and isotopic mixtures of said element (s), either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{18}O$ and $^{18}O$. The isotopes may be radioactive or non-radioactive. Radiolabelled compounds of formula (I) may comprise one or more radioactive isotope(s) selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

As used herein, unless otherwise noted, the term °isotopomer shall mean isomers with isotopic atoms, having the same number of each isotope of each element but differing in their position. Isotopomers include both constitutional isomers and stereoisomers solely based on isotopic location. For example, $CH_3CHDCH_3$ and $CH_3CH_2CH_2D$ are a pair of constitutional isotopomers of n-propane; whereas (R)-$CH_3CHDOH$ and (S)-$CH_3CHDOH$ or (Z)—$CH_3CH{=}CHD$ and (E)-$CH_3CH{=}CHD$ are examples of isotopic stereoisomers of ethanol and n-propene, respectively.

One skilled in the art will recognize that wherein the compound of formula (I) $R^4$ and $R^5$ are each hydrogen, then the compound of formula (I) may exist as any one or any mixture of its corresponding tautomers (i.e. structural isomers of that may readily interconvert), as shown below

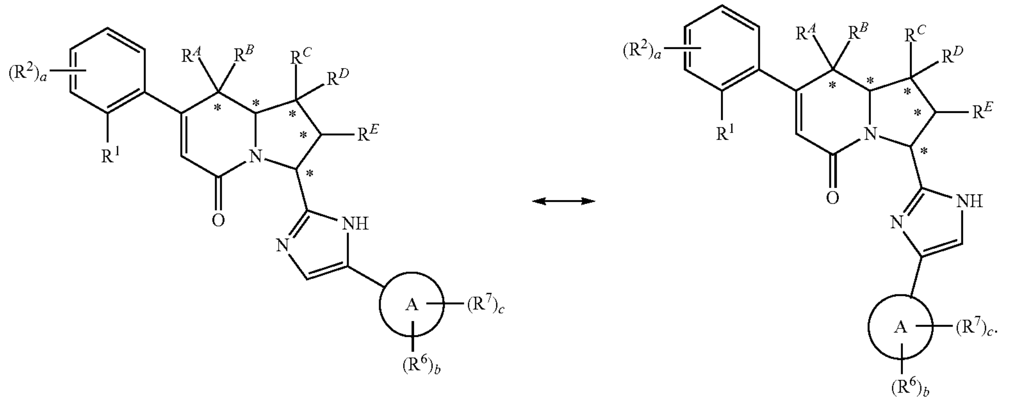

One skilled in the art will further recognize that compounds of formula (II), compounds of formula (III) and compounds of formula (IV) may similarly exist as any one of or any mixture of its corresponding tautomers. The present invention is intended to encompass any compound described herein, present in any of its corresponding tautomeric forms, or as a mixture of its tautomeric forms.

It is intended that the present invention includes the compounds described herein, including all isomers thereof (including, but not limited to stereoisomers, enantiomers, diastereomers, tautomers, isotopologues, atropisomers, and the like).

Under standard nomenclature used throughout this disclosure, the terminal portion of the designated side chain is described first, followed by the adjacent functionality toward the point of attachment. Thus, for example, a "phenyl-($C_1$-$C_6$alkylene)-amino-carbonyl-($C_1$-$C_6$alkylene)-" substituent refers to a group of the formula

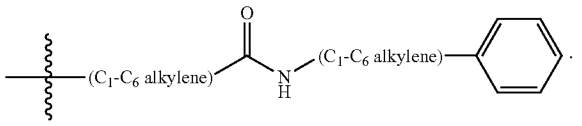

As used herein, unless otherwise noted, the term "isolated form" shall mean that the compound is present in a form which is separate from any solid mixture with another compound(s), solvent system or biological environment. In an embodiment of the present invention, the compound of formula (I), compound of formula (II), compound of formula (III) or compound of formula (IV) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I), compound of formula (II), compound of formula (III) or compound of formula (IV) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I), compound of formula (II), compound of formula (III) or compound of formula (IV) is present in a form which is substantially free of corresponding salt form(s).

2. General Synthesis Schemes

Compounds of formula (I) of the present invention may be prepared as described in the general synthesis schemes and Examples herein, selecting and substituting suitable reagents and conditions, as would be well within the skill of persons versed in the art. Additionally, the preparation of any starting materials used in the schemes and synthesis examples which follow herein is well within the skill of persons versed in the art.

One skilled in the art will further recognize that by selecting and substituting suitable starting reagent(s) (and then following or applying the processes described in the General Synthesis Schemes and Examples which follow herein) the compound of formula (I) (and any intermediates, such as the compound of formula (M1)) may be prepared as a racemate, may be prepared as a racemate and then separated into its corresponding stereo-isomers (according to known methods, for example, chiral separation or SFC), or may be prepared as a stereo-isomerically enriched or pure stereo-isomer.

Intermediates in the synthesis of the compounds of formula (I) of the present invention include compounds of formula (M1)

(M1)

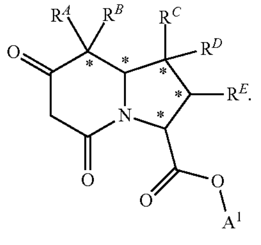

wherein $A^1$ is selected from $C_{1-4}$alkyl, preferably methyl or ethyl. Some compounds of formula (M1) are known or may be prepared according to known methods, as would be recognized by those skilled in the art.

Compounds of formula (M1) may be prepared for example, as described in Scheme 1, below.

Scheme 1

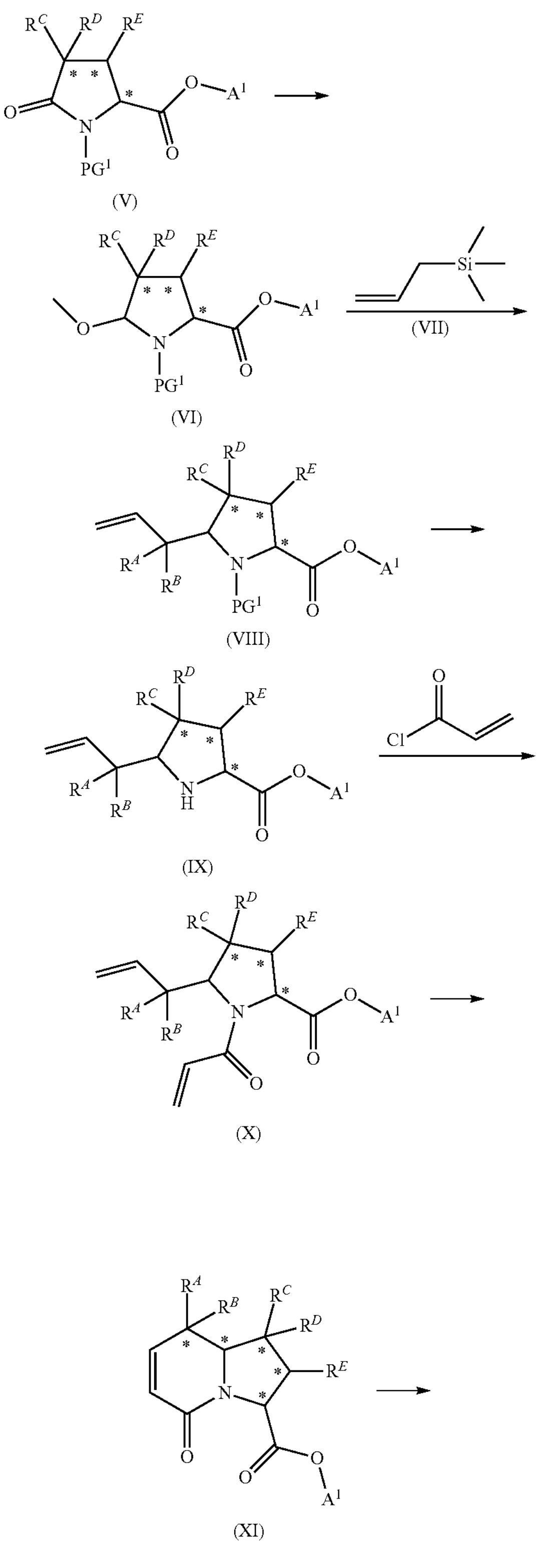

(V)

(VI)

(VIII)

(IX)

(X)

(XI)

-continued

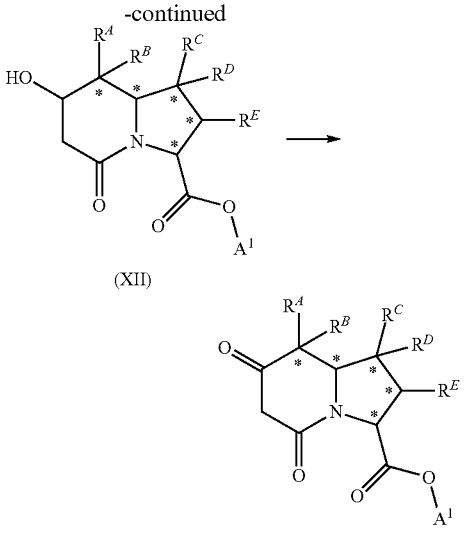

(XII)

(M1)

Accordingly, a suitably substituted compound of formula (V), wherein $A^1$ is $C_{1-4}$alkyl, preferably methyl or ethyl, and wherein $PG^1$ is a suitably selected nitrogen protecting group such as Boc, Benzyl, PMB, and the like, a known compound or compound prepared by known methods (for example, as described in the Examples which follow herein), is reacted with SUPER-HYDRIDE® (1.0M Lithium triethylborohydride in THF), a known solution; in a suitably selected solvent such as THF, 1,4-dioxane, and the like; at a reduced temperature, for example at about −78° C.; and then reacted with a suitably selected catalyst such as p-TsOH, and the like; in a suitably selected solvent such as MeOH, and the like; to yield the corresponding compound of formula (VI).

The compound of formula (VI) is reacted with a suitably substituted compound of formula (VII) (for example wherein $R^A$ and $R^B$ are each hydrogen then the compound of formula (VII) is allyltrimethylsilane), a known compound; in the presence of a suitably selected Lewis acid such as $BF_3 \cdot Et_2O$, $TiCl_4$, and the like; in a suitably selected solvent such as diethyl ether, THF, DCM, and the like; at a reduced temperature, for example at about −40° C.; to yield the corresponding compound of formula (VIII).

The compound of formula (VIII) is de-protected according to known methods; to yield the corresponding compound of formula (IX). For example, the compound of formula (VIII) may be reacted with a suitably selected acid such as HCl; in a suitably selected solvent such as 1,4-dioxane.

The compound of formula (IX) is reacted with acryloyl chloride, a known compound; in the presence of a suitably selected organic amine base such as TEA, pyridine, DIEA, and the like; in a suitably selected solvent such as THF, DCM, DMF, and the like; at a reduced temperature, for example at about −78° C.; to yield the corresponding compound of formula (X).

The compound of formula (X) is reacted with a suitably selected catalyst such as Grubb's $2^{nd}$ Generation Catalyst, Grubb's $3^{rd}$ Generation Catalyst, and the like; in a suitably selected solvent such a DCM, THF, toluene, and the like; at an elevated temperature, for example at about 45° C.; to yield the corresponding compound of formula (XI).

The compound of formula (XI) is reacted with a suitably selected hydroboronating agent such as bis(pinacolato)diboron, and the like; in the presence of a suitably selected copper reagent such as CuCl, and the like; in the presence of a suitably selected ligand such as BINAP, and the like; in the presence of a suitably selected base such a NaOt-Bu, and the like; in a suitably selected solvent or mixture of solvents, such as a mixture of THF and methanol, and the like; and then reacted with peroxide such as 30% $H_2O_2$, to yield the corresponding compound of formula (XII).

The compound of formula (XII) is reacted with a suitably selected oxidizing agent such as PCC, Dess-Martin periodonane (DMP), and the like; in a suitably selected solvent such as DCM, EtOAc, and the like; to yield the corresponding compound of formula (M1).

Compounds of formula (M1) may alternatively be prepared as described in Scheme 2, below.

Scheme 2

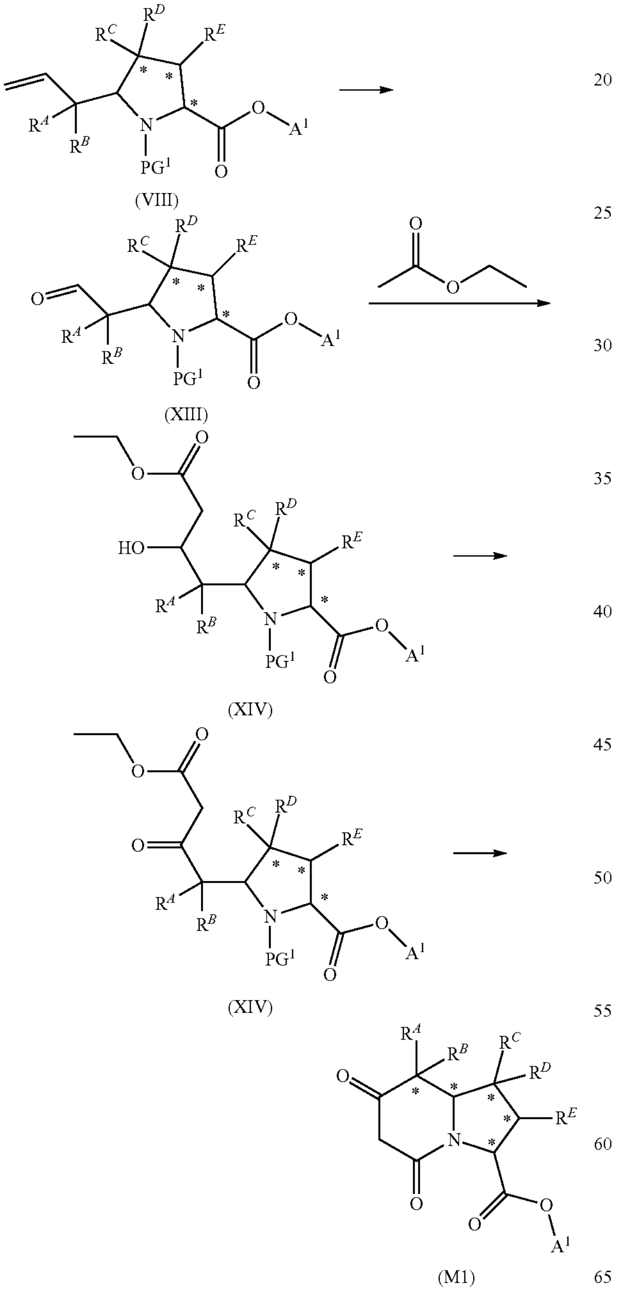

(VIII)

(XIII)

(XIV)

(XIV)

(M1)

Accordingly, a suitably substituted compound of formula (VIII), prepared for example as described in Scheme 1 above, is reacted with a suitably selected oxidizing agent or system such as a mixture of $OsO_4$ and $NalO_4$, $O_3$, and the like; in a suitably selected solvent or mixture of solvents such as a mixture of THE and water, DCM, and the like; at about room temperature; to yield the corresponding compound of formula (XIII).

The compound of formula (XIII) is reacted with ethyl acetate, a known compound; in the presence of a suitably selected base such as LiHMDS, $LiN(Pr\text{-}i)_2$, NaOEt, and the like; in a suitably selected solvent such as THF, toluene, EtOAc, and the like; at a reduced temperature, for example at about −78° C.; to yield the corresponding compound of formula (XIV).

The compound of formula (XIV) is reacted with a suitably selected oxidizing agent such as Dess-Martin periodonane (DMP), PCC, a mixture of $DMSO/(COCl)_2$, and the like; in a suitably selected solvent such as DCM, EtOAc, and the like; at about room temperature; to yield the corresponding compound of formula (XV).

The compound of formula (XV) is reacted with a suitably selected acid such as HCl, TFA, and the like; in a suitably selected solvent such as 1,4-dioxane, THF, DCM, and the like; and then reacted with a suitably selected base such as $NaHCO_3$, $Na_2CO_3$, $K_2CO_3$, and the like; in a suitably selected solvent such as toluene, xylene and the like; at an elevated temperature, for example, at about 110° C.; to yield the corresponding compound of formula (M1).

One skilled in the art will recognize that although the processes of Scheme 1 and 2 above describe the preparation of racemic mixtures of the compound of formula (M1), said processes may also be used to prepared specific stereo-isomer(s), by either using a stereo-isomerically enriched starting material, or by separating the prepared racemic mixture of the compound of formula (M1) and isolating the corresponding stereo-isomers, according to known methods, for example by chiral separation, SFC, and the like.

Some compounds of formula (M1), for example compounds of formula (M1) wherein $R^A$, $R^B$, $R^C$, $R^D$ and $R^E$ are each hydrogen, may alternatively be prepared as described in Scheme 3, below.

Scheme 3

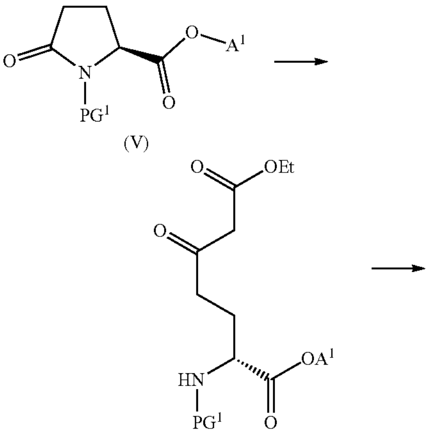

(V)

(XVI)

-continued

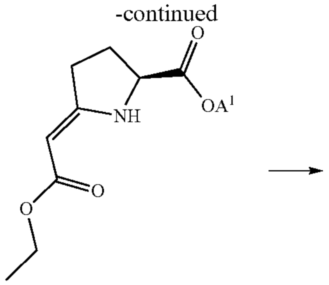

(XVII)

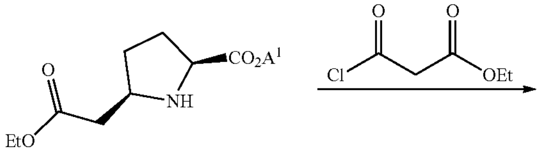

(XVIII)

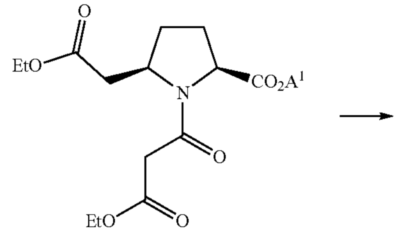

(XIX)

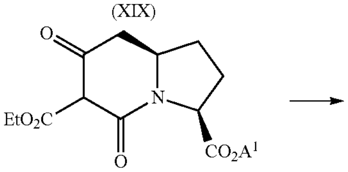

(XX)

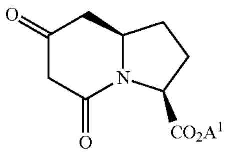

(M1a)

Accordingly, a suitably substituted compound of formula (V), a known compound or compound prepared by known methods is reacted with ethyl acetate, a known compound; in the presence of a suitably selected base such as LiHMDS, $LiN(Pr\text{-}i)_2$, NaOEt, and the like; in a suitably selected solvent such as THF, PhMe, EtOH, and the like; at a reduced temperature, for example at about −78° C.; to yield the corresponding compound of formula (XVI).

The compound of formula (XVI) is reacted with a suitably selected organic base such as TFA, HCl and the like; to effect de-protection and ring closure; to yield the corresponding compound of formula (XVII).

The compound of formula (XVII) is reacted with $H_2$; in the presence of a suitably selected catalyst such as $PtO_2$, Pd, Ni, $Pd(OH)_2$, and the like; in a suitably selected solvent such as HOAc, EtOH, DCM, and the like; to yield the corresponding compound of formula (XVIII).

The compound of formula (XVIII) is reacted with ethyl 3-chloro-3-oxopropanoate, a known compound; in the presence of a suitably selected organic amine base such as DIPEA, TEA, pyridine, and the like; in a suitably selected solvent such as DCM, THF, and the like; to yield the corresponding compound of formula (XIX).

The compound of formula (XIX) is reacted with a suitably selected base such as NaOEt, NaOMe, NaH, and the like; in a suitably selected solvent such as EtOH, MeOH, DMF, and the like; to yield the corresponding compound of formula (XX).

The compound of formula (XX) is reacted with a suitably selected reagent such as oxalic acid in water, 10% water in AcOH, HCl in water (at pH-2) or a mixture of ACN/water; at an elevated temperature, for example, at about 110° C.; to yield the corresponding compound of formula (M1a).

One skilled in the art will recognize that although the process of Scheme 3 above describes the preparation of a particular stereo-isomer of the compound of formula (M1), the process of Scheme 3 may also be used to prepared racemic mixtures and alternate specific stereo-isomer(s) of the compound of formula (M1), by either using a suitably selected racemic or stereo-isomerically enriched starting material, or by preparing a racemate of the compound of formula (M1) and then isolating the corresponding stereo-isomers according to known methods, for example by chiral separation, SFC, and the like.

Suitably substituted compounds of formula (M1) may be reacted as described in the Schemes and Examples which follow herein, to yield the compounds of formula (I) of the present invention.

Some compounds of formula (I) wherein $R^4$ is hydrogen, and $R^5$ is hydrogen may be prepared as described in Scheme 4, below.

Scheme 4

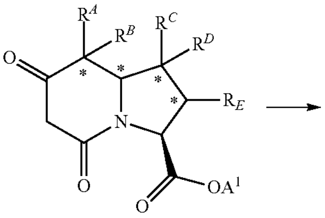

(M1b)

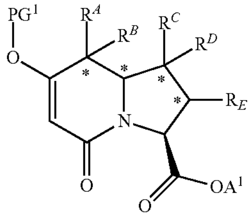

(XXI)

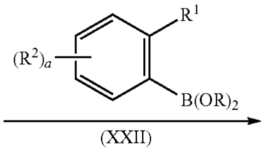

(XXII)

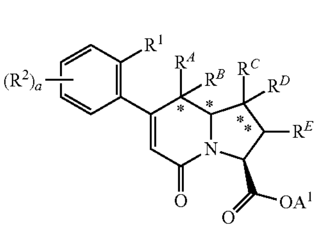

(XXII)

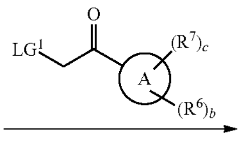

-continued

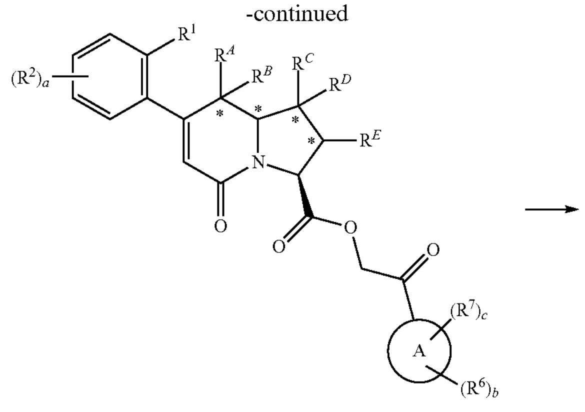

(XXIV)

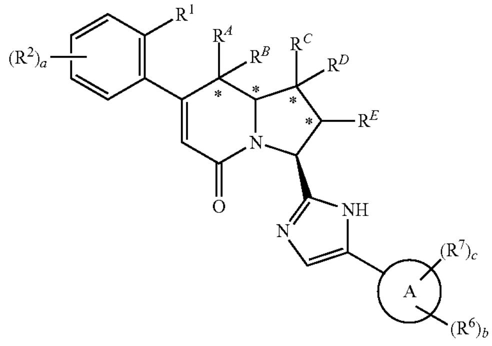

(Ia)

Accordingly, a suitably substituted compound of formula (M1b), wherein $A^1$ is $C_{1-4}$alkyl, preferably methyl or ethyl, prepared for example as described herein, is reacted with a suitably selected oxygen protecting reagent such as 1,1,1-trifluoro-N-phenyl-N-((trifluoromethyl)sulfonyl) methanesulfonamide, trifluoromethanesulfonic anhydride, and the like; in the presence of a suitably selected organic amine base such as TEA, pyridine, DIEA, and the like; in a suitably selected solvent such as DCM, THF, and the like; to yield the corresponding compound of formula (XXI), wherein $PG^2$ is the corresponding oxygen protecting group.

The compound of formula (XXI) is reacted with a suitably substituted compound of formula (XXII), and wherein $—B(OR)_2$ is for example, $—B(OH)_2$, $—B(OCH_3)_2$,

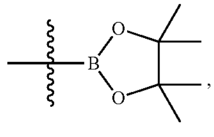 [SMILES: *B1OC(C)(C)C(C)(C)O1], and the like, a known compound or compound prepared by known methods; in the presence of a suitably selected coupling agent such as $Pd(dppf)Cl_2$, $Pd(PPh_3)_4$, $Pd(OAc)_2$, and the like; in the presence of a suitably selected base such as $K_2CO_3$, $Cs_2CO_3$, $K_3PO_4$, and the like; in a suitably selected solvent or mixture of solvents such as a mixture of 1,4-dioxane and water, DMF, toluene/water, and the like; at an elevated temperature, such as about 80° C.; to yield the corresponding compound of formula (XXIII).

The compound of formula (XXII) is reacted with a suitably substituted compound of formula (XXIII), wherein $LG^1$ is a suitably selected leaving group such as Cl, Br, I, and the like, a known compound, compound prepared by known methods, or compound prepared as described in the Examples which follow herein; in the presence of a suitably selected base such as $Cs_2CO_3$, $K_2CO_3$, $Na_2CO_3$, and the like; in a suitably selected solvent such as DMF, ACN, 1,4-dioxane, and the like; at about room temperature; to yield the corresponding compound of formula (XXIV).

The compound of formula (XXIV) is reacted with a suitably selected reagent such as $NH_4OAc$ and the like; in the presence of a suitably selected acid such as AcOH, and the like; in a suitably selected solvent such as toluene, xylene, and the like; at an elevated temperature, for example at about 110° C.; to yield the corresponding compound of formula (Ia).

Compounds of formula (I) wherein $R^5$ is halogen may be prepared from the corresponding compound of formula (Ia), by reacting with a suitably selected halogenating agent such as NCS (for chloro), NBS (for bromo), NIS (for iodo), Selectfluor (for fluoro), and the like, in a suitably selected solvent such as DCM, DCE, ACN, THE, $Et_2O$, and the like.

Compounds of formula (I) wherein $R^5$ is $C_{1-4}$alkyl may be similarly prepared as described in Scheme 4 above, by reacting the compound of formula (XXII) with a suitably substituted analog of the compound of formula (XXIII), such as a compound of formula (XXIII-ALT)

(XXIII-ALT)

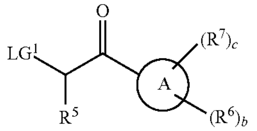

and then reacting the resulting intermediate to effect ring closure as described in Scheme 4.

One skilled in the art will recognize that although Scheme 4 describes the preparation of a specific stereoisomer of the compound of formula (I), the processes describe therein may be applied to the preparation of racemic mixtures and alternate stereo-isomers of the compounds of formula (I). Said racemates and/or alternate stereoisomers may be prepared by either using a suitably selected racemic or stereo-isomerically enriched starting material, or by preparing a racemate of the desired compound of formula (I) and then isolating the corresponding stereo-isomers according to known methods, for example by chiral separation, SFC, and the like.

Compounds of formula (I) wherein $R^1$ is 1,2,3,4-tetrazol-1-yl may alternatively be prepared from the corresponding compound of formula (Ia) where $R^1$ is $NH_2$, as described in Scheme 5, below.

Scheme 5

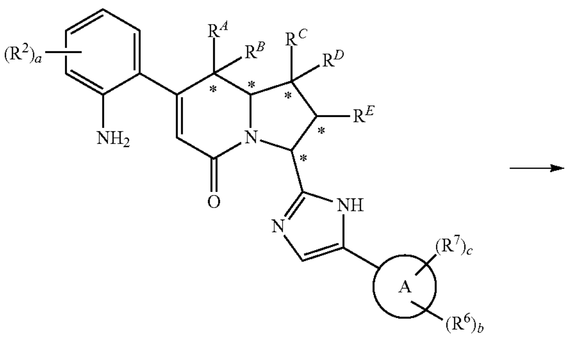

(Ib)

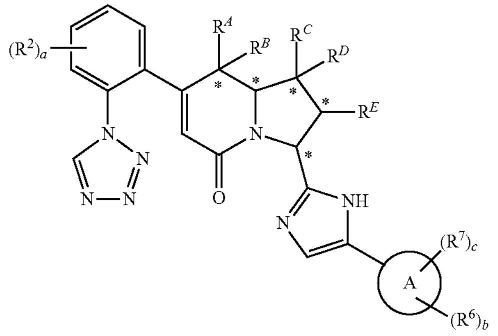

(Ic)

Accordingly, a suitably substituted compound of formula (Ib), prepared for example as described in Scheme 4 above, is reacted with a suitably selected reagent such as $TMSN_3$, $NaN_3$, and the like; in the presence of trimethoxymethane, and the like; in a suitably selected solvent such as AcOH, and the like; at an elevated temperature, for example at about 80° C.; to yield the corresponding compound of formula (Ic).

Compounds of formula (I) wherein $R^1$ is 1,2,3,4-tetrazol-1-yl may alternatively be prepared by reacting a compound of formula (XXII) wherein $R^1$ is $NH_2$, a compound of formula (XXIIa)

(XXIIa)

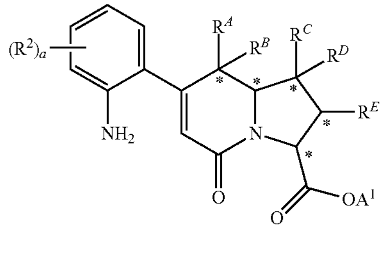

with a suitably reagent such as $TMSN_3$, $NaN_3$, and the like; in the presence of trimethoxymethane and the like; in a suitably selected solvent such as AcOH and the like; at an elevated temperature, for example at about 80° C.; as described Scheme 5, above; to yield the corresponding compound of formula (XXV)

(XXV)

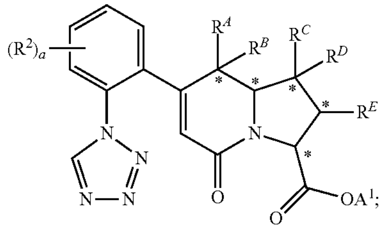

which compound of formula (XXV) is then substituted for the compound of formula (XXII) in Scheme 4 above, and reacted as described therein; to yield the corresponding compound of formula (Ic).

Compounds of formula (XXII) may alternatively be prepared as described in Scheme 6, below.

Scheme 6

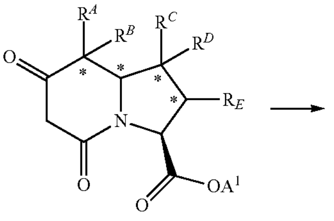

(M1b)

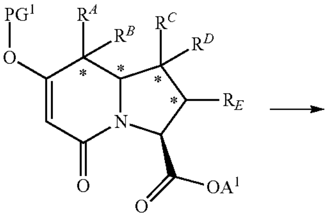

(XXI)

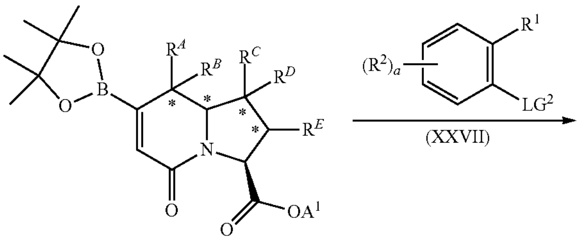

(XXVII)

(XXVI)

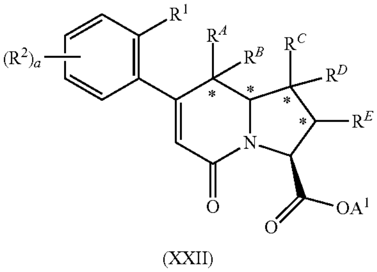

(XXII)

Accordingly, a suitably substituted compound of formula (M1b), wherein $A^1$ is $C_{1-4}$alkyl, preferably methyl or ethyl, a known compound or compound prepared as described in the Schemes and Examples herein, is reacted with a suitably selected oxygen protecting reagent such as 1,1,1-trifluoro- N-phenyl-N-((trifluoromethyl)sulfonyl)methanesulfonamide, trifluoromethanesulfonic anhydride, and the like; in the presence of a suitably selected organic amine base such as TEA, pyridine, DIEA, and the like; in a suitably selected solvent such as DCM, THF, and the like; to yield the corresponding compound of formula (XXI), wherein $PG^2$ is the corresponding oxygen protecting group.

The compound of formula (XXI) is reacted with bis(pinacolato)diboron, a known compound; in the presence of a suitably selected coupling agent such as $Pd(dppf)Cl_2$, $Pd(PPh_3)_4$, $Pd(OAc)_2$, and the like; in the presence of a suitably selected base such as KOAc, potassium ethylhexanoate ($n\text{-}BuCH(Et)CO_2K$), and the like; in a suitably selected solvent or mixture of solvents such as a mixture of 1,4-dioxane and water, DMF, toluene/water, and the like; at an elevated temperature, such as about reflux temperature; to yield the corresponding compound of formula (XXVI).

The compound of formula (XXVI) is reacted with a suitably substituted compound of formula (XXVII), wherein $LG^2$ is a suitably selected leaving group such as I, Br, Cl, OTf, and the like, a known compound, compound prepared by known methods, or compound prepared as described in the Examples which follow herein; in the presence of a suitably selected coupling agent such as $Pd(dppf)Cl_2$, $Pd(PPh_3)_4$, $Pd(OAc)_2$, and the like; in the presence of a suitably selected base such as $K_2CO_3$, $Cs_2CO_3$, $K_3PO_4$, and the like; in a suitably selected solvent or mixture of solvents such as a mixture of 1,4-dioxane and water, DMF, toluene/water, and the like; at an elevated temperature, for example reflux temperature; to yield the corresponding compound of formula (XXII).

One skilled in the art will recognize that although Scheme 6 describes the preparation of a specific stereoisomer of the compound of formula (XXII), the processes describe therein may be applied to the preparation of racemic mixtures and alternate stereo-isomers of the compounds of formula (XXII). Said racemates and/or alternate stereoisomers may be prepared by either using a suitably selected racemic or stereo-isomerically enriched starting material, or by preparing a racemate of the compound of formula (XXII) and then isolating the corresponding stereo-isomers according to known methods, for example by chiral separation.

Compounds of formula (XXII) wherein $R^1$ is 4-trifluoromethyl-1,2,3-triazol-1-yl may alternatively be prepared as described in Scheme 7, below.

Scheme 7

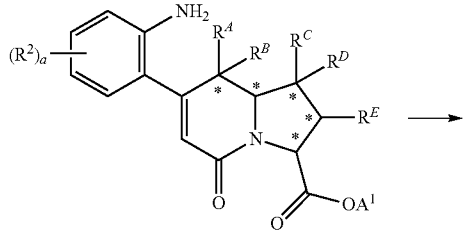

(XXIIa)

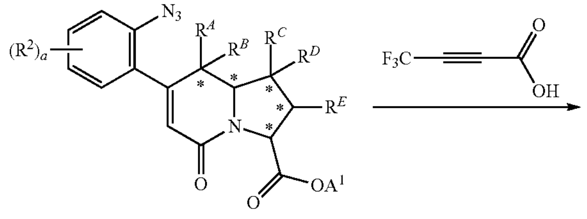

(XXVIII)

-continued

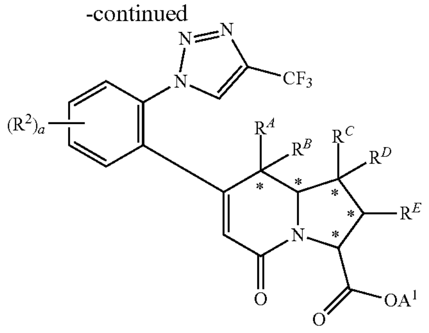

(XXIIb)

Accordingly, a suitably substituted compound of formula (XXIIa) wherein $R^1$ is $NH_2$, prepared for example as described in the Schemes and Examples herein, is reacted with a suitably selected agent such as $TMSN_3$, $NaN_3$, and the like; in the presence of a suitably selected agent such as t-butyl nitrite, $NaNO_2$/HCl, and the like; in a suitably selected solvent such as acetonitrile, EtOH, heptane, and the like; at about 0° C. to room temperature; to yield the corresponding compound of formula (XXVIII).

The compound of formula (XXVIII) is reacted with 4,4,4-trifluorobut-2-ynoic acid, a known compound; in the presence of a suitably selected agent such as $Cu_2O$, CuCl, and the like; in a suitably selected solvent such as acetonitrile, DCM, and the like; at an elevated temperature, for example at about reflux temperature; to yield the corresponding compound of formula (XXIIb).

One skilled in the art will recognize that the compound of formula (XXIIb) may then be further substituted for the compound of formula (XXII) in Scheme 4 above, and reacted as described therein, to yield the corresponding compound of formula (I) wherein $R^1$ is 4-trifluoromethyl-1,2,3-triazol-1-yl. One skilled in the art will further recognize that compounds of formula (I) wherein $R^1$ is 4-trifluoromethyl-1,2,3-triazol-1-yl may alternatively be prepared by substituting a suitably substituted compound of formula (Ia) wherein $R^1$ is $NH_2$, for the compound of formula (XXII) in Scheme 7 above, and reacting as described therein.

One skilled in the art will further recognize that although Scheme 7 describes the preparation of a racemate of the compound of formula (XXIIb), the processes describe therein may be applied to the preparation of specific stereo-isomers of the compounds of formula (XXIIb). Said alternate stereoisomers may be prepared by either using a suitably selected stereo-isomerically enriched starting material, or by preparing the racemic compound and then isolating the corresponding stereo-isomers according to known methods, for example by chiral separation, SFC, and the like.

Some compounds of formula (I) may alternatively be prepared as describe in Scheme 8, below.

Scheme 8

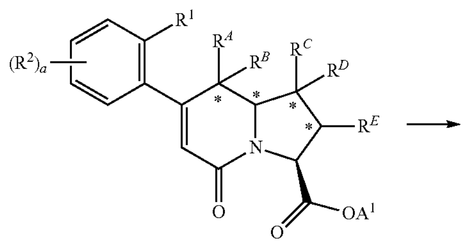

(XXII)

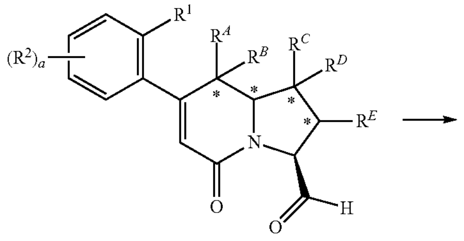

(XXIX)

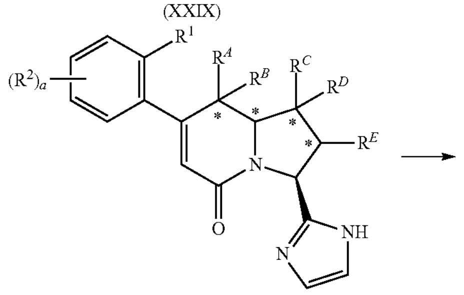

(XXX)

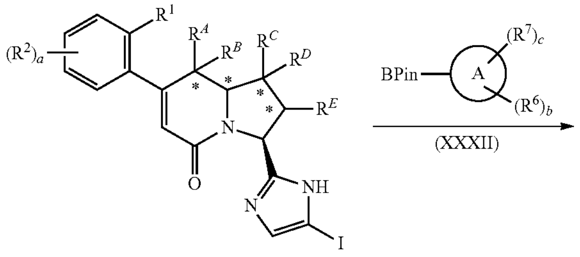

(XXXI)

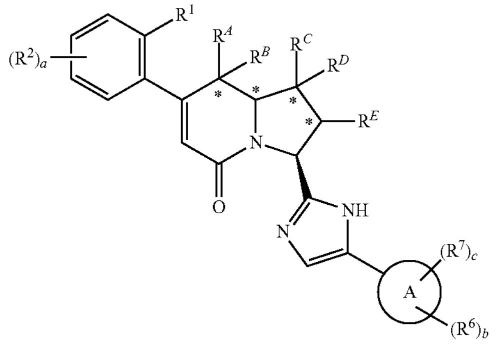

(Ia)

Accordingly, a suitably substituted compound of formula (XXII), prepared for example as described in the Schemes and Examples herein, is reacted with a suitably selected agent such as DABAL, $BH_3 \cdot Me_2S$, and the like; in a suitably selected solvent such as DCM, THF, and the like; at a reduced temperature, for example at −78° C.; to yield the corresponding compound of formula (XXIX).

The compound of formula (XXIX) is reacted with a suitably selected agent such as $NH_3 \cdot H_2O$, and the like; in the presence of a suitably selected agent such as glyoxal, and the like; in a suitably selected solvent such as methanol and the like; at about room temperature; to yield the corresponding compound of formula (XXX).

The compound of formula (XXX) is reacted with a suitably selected source of iodine such as NIS, 12, and the like; in a suitably selected solvent such as DCM, and the like; at about room temperature; and then reacted with a suitably selected agent such as $Na_2SO_3$, and the like; in a suitably selected solvent or mixture of solvents such as a mixture of ethanol/water, and the like; at an elevated temperature, for example at about 95° C.; to yield the corresponding compound of formula (XXXI).

The compound of formula (XXXI) is reacted with a suitably substituted compound of formula (XXXII), a known compound, compound prepared by known methods, or compound prepared as described herein, where BPin is bis(pinacolate)diboron; in the presence of a suitably selected palladium catalyst such as $Pd(dppf)Cl_2$, $Pd(PPh_3)_4$, and the like; in the presence of a suitably selected base such as $K_2CO_3$, $Cs_2CO_3$, and the like; in a suitably selected solvent or mixture of solvents such as a mixture of 1,4-dioxane/water, toluene/water, and the like; at an elevated temperature, for example at reflux temperature; to yield the corresponding compound of formula (Ia).

One skilled in the art will recognize that in the process as described in Scheme 8 above, wherein the compound of formula (XXII) $R^1$ is $NH_2$, said $NH_2$ group is preferably protected with a suitably selected nitrogen protecting group (for example, BOC, and the like), and subsequently, at the appropriate point in the synthesis, de-protected. One skilled in the art will further recognize that the synthesis as described in Scheme 8 may be modified at any appropriate step to effect conversion of any (intermediate or final) compound wherein $R^1$ is $NH_2$ to the corresponding compound wherein $R^1$ is for example a 1,2,3,4-tetrazol-1-yl, 4-trifluoromethyl-1,2,3-trazol-1-yl, etc. applying reaction steps and conditions as described in the Schemes and Examples herein.

One skilled in the art will further recognize that although Scheme 8 describes the preparation of a specific stereoisomer of the compound of formula (Ia), the processes describe therein may be applied to the preparation of racemic mixtures and alternate stereo-isomers of the compounds of formula (Ia). Said racemates and/or alternate stereoisomers may be prepared by either using a suitably selected racemic or stereo-isomerically enriched starting material, or by preparing a racemate of the compound of formula (Ia) and then isolating the corresponding stereo-isomers according to known methods, for example by chiral separation, SFC, and the like.

Compounds of formula (XXIII) are known compounds, compound which may be prepared by known methods, and/or compounds which may be prepared as described herein. Compounds of formula (XXIII) wherein $LG^2$ is for example bromo, may be prepared as described in Scheme 9, below.

Scheme 9

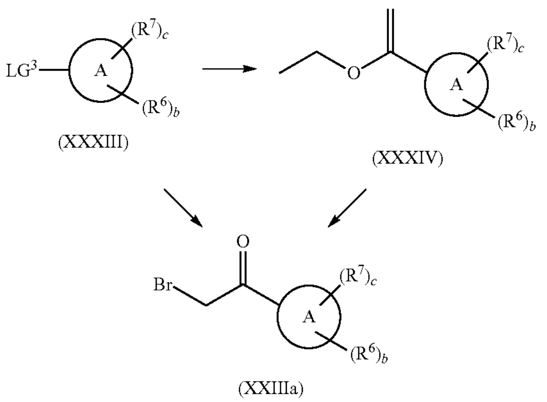

(XXXIII) (XXXIV) (XXIIIa)

Accordingly, a suitably substituted compound of formula (XXXIII), wherein $LG^3$ is a suitably selected leaving group such as Br, I, OTf, and the like, a known compound or compound prepared by known methods is reacted with dibutyl(1-ethoxyvinyl)(pentyl)stannane, a known compound; in the presence of a suitably selected coupling agent such as $Pd(dppf)Cl_2$, $Pd(PPh_3)Cl_2$, $Pd(PPh_3)_4$, and the like; in a suitably selected solvent such as 1,4-dioxane, toluene, and the like; at an elevated temperature, for example at about 90-100° C.; to yield the corresponding compound of formula (XXXIV).

The compound of formula (XXXIV) is reacted with a suitably selected source of bromine such as NBS, HBr, $Br_2$, pyridine·HBr, and the like; in a suitably selected solvent or mixture of solvents such as a mixture of THF/water, DCM, 1,4-dioxane/water, and the like; at about room temperature; to yield the corresponding compound of formula (XXIIIa). One skilled in the art will recognize that wherein the source of bromine is for example a mixture of HBr and $Br_2$, pyridine·HBr, and the like; then the reaction of the compound of formula (XXXIV) with the source of bromine is completed in the presence of a suitably selected acid such as AcOH, and the like. Compounds of formula (XXIII) wherein $LG^1$ is I, may be similarly prepared by reacting a suitably substituted compound of formula (XXXIV) with a suitably selected source of iodine, according to known methods.

Alternatively, the compound of formula (XXXIII), wherein $LG^3$ is —C(O)$C_1$, a known compound or compound prepared by known methods, is reacted with a suitably selected agent such as trimethylsilyldiazomethane ($TMSCHN_2$), and the like; in a suitably selected solvent such as acetonitrile, and the like; and then reacted with a suitably selected source of bromine such a HBr/water, $Br_2$, NBS, and the like; at about room temperature; to yield the corresponding compound of formula (XXIIIa).

One skilled in the art will recognize that any substituent group(s) and/or any portion(s) of a substitution group(s) (for example,

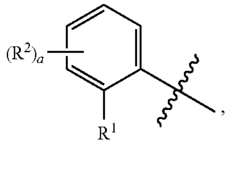

$R^1$, Q,

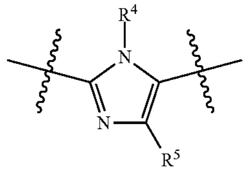

,

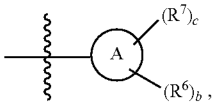

, etc.)

may be incorporated into the desired compound of formula (I) in any order, by applying the appropriate reaction steps in the desired order (for example, reaction steps under reaction conditions described in the Schemes and Examples herein).

One skilled in the art will further recognize that various substituent groups and/or functional groups on said substituent groups (for example —OH, —$NH_2$, etc.) may be protected prior to any reaction step described above, and then de-protected at a later step in the synthesis, as would be desirable or necessary, according to methods well known to those skilled in the art.

One skilled in the art will further recognize that any starting material, intermediate or compound of formula (I), (II), (III) or (IV) of the present invention may be prepared as a racemate or a stereo-isomerically enriched compound, by selecting and substituting suitable stereo-isomers into the processes described herein, or by preparing a racemic mixture and then isolating the stereo-isomers according to known methods, for example by chiral separation, SFC, and the like.

As more extensively provided in this written description, terms such as "reacting" and "reacted" are used herein in reference to a chemical entity that is any one of (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example, wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

One skilled in the art will recognize that wherein a reaction step of the present invention may be carried out in a variety of solvents or solvent systems, said reaction step may also be carried out in a mixture of the suitable solvents or solvent systems.

One skilled in the art will further recognize that the reaction or process step(s) as herein described are allowed to proceed for a sufficient period of time until the reaction is complete, as determined by any method known to one skilled in the art, for example, chromatography (e.g. HPLC). In this context a "completed reaction or process step" shall mean that the reaction mixture contains a significantly diminished amount of the starting material(s)/reagent(s) and a significantly reduced amount of the desired product(s), as compared to the amounts of each present at the beginning of the reaction.

To provide a more concise description, some of the quantitative expressions found herein are not qualified with the term "about". It is understood that whether the term "about" is used explicitly or not, every quantity found herein is meant to refer to the actual value, and it is also meant to refer to the approximation to such value that would reasonably be inferred based on the ordinary skill in the art, including approximations due to the experimental and/or measurement conditions for such value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$═CH—$CH_2$—, and the like; amides—groups of the formula —C(O)—R' wherein R' is for example methyl, phenyl, trifluoromethyl, and the like; N-sulfonyl derivatives— groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be measured in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be measured in texts such as T. W. Greene & P. G. M. Wuts, *Protective Groups in Organic Synthesis*, John Wiley & Sons, 1991.

Where the processes for the preparation of the compounds according to the invention yield rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-obs}]/[\alpha\text{-max}])\times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

3. Utility

The compounds of the present invention are useful for the treatment and/or prophylaxis of thromboembolic disorders, inflammatory disorders and diseases or conditions in which factor XIa and/or plasma kallikrein activity is implicated.

In some embodiments, the present invention is directed to methods for the treatment and/or prophylaxis of a thromboembolic disorder comprising administering to a patient in need of such treatment and/or prophylaxis a therapeutically effective amount of a least one of the compounds as described herein, or a stereoisomer, isotopologue, or pharmaceutically acceptable salt thereof.

As used herein, the term "thromboembolic disorders" includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In some embodiments, the term “thromboembolic disorders” includes acute coronary syndrome, stroke, deep vein thrombosis, and pulmonary embolism. In some embodiments, the “thromboembolic disorders” include hereditary angioedema (HAE) and diabetic macular edema (DME).

In some embodiments, the present invention is directed to methods for the treatment and/or prophylaxis of an inflammatory disorder comprising: administering to a patient in need of such treatment and/or prophylaxis a therapeutically effective amount of at least one of the compounds of the present invention or a stereoisomer, isotopologue, or pharmaceutically acceptable salt thereof. Examples of the inflammatory disorders include, but are not limited to, sepsis, acute respiratory distress syndrome, and systemic inflammatory response syndrome.

In some embodiments, the present invention is directed to methods for the treatment and/or prophylaxis of a disease or condition in which plasma kallikrein activity is implicated, comprising administering to a patient in need of such treatment and/or prophylaxis a therapeutically effective amount of at least one of the compounds of the present invention or a stereoisomer, isotopologue, or pharmaceutically acceptable salt thereof. The diseases or conditions in which plasma kallikrein activity is implicated include, but are not limited to, impaired visual acuity, diabetic retinopathy, diabetic macular edema, hereditary angioedema, diabetes, pancreatitis, nephropathy, cardiomyopathy, neuropathy, inflammatory bowel disease, arthritis, inflammation, septic shock, hypotension, cancer, adult respiratory distress syndrome, disseminated intravascular coagulation, and cardiopulmonary bypass surgery.

In some embodiments, the present invention provides a method for treating the primary prophylaxis of a thromboembolic disorder. In some embodiments, the present invention provides a method for the primary prophylaxis of a thromboembolic disorder wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In some embodiments, the present invention provides a method for the secondary prophylaxis of a thromboembolic disorder. In some embodiments, the present invention provides a method for the secondary prophylaxis of a thromboembolic disorder. wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

One skilled in the art will recognize that wherein the present invention is directed to methods of prophylaxis, the subject in need thereof (i.e. a subject in need of prophylaxis) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prophylaxis or prophylactic treatment) as a consequence of the subject’s medical history, including, but not limited to, family history, pre-disposition, co existing (comorbid) disorders or conditions, genetic testing, and the like.

The compounds of the present invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, for example, may occur when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components. Possible favorable outcomes of treatment with a synergistic combination include, but are not limited to, (a) increased efficacy of the therapeutic effect, (b) ability to administer decreased dosage while increasing or maintaining efficacy (which in turn may also result in decreased toxicity and/or adverse side effects), (c) minimized or slowed development of drug resistance, (d) selective synergism against the biological target (or efficacy synergism) versus host (toxicity antagonism).

In some embodiments of the present invention, the compound of formula (I), compound of formula (II), compound of formula (III) and/or compound of formula (IV) may be administered in combination with one or more anticoagulant, anti-thrombin agent, anti-platelet agent, fibrinolytic, hypolipidemic agent, antihypertensive agent, and/or anti-ischemic agent. Suitable examples include, but are not limited to warfarin, heparin, aprotinin, a synthetic pentasaccharide, a boroarginine derivative, a boropeptide, heparin, hirudin, argatroban, a thromboxane-A2-receptor antagonist, a thromboxane-A2-synthetase inhibitor, a PDE-III inhibitor, a PDE V inhibitor, an ADP receptor antagonist, an antagonist of the purinergic receptor P2Y1, an antagonist of the purinergic receptor P2Y12, tissue plasminogen activator and modified forms thereof, anistreplase, urokinase, streptokinase, tenecteplase, lanoteplase, a PAI-I inhibitor, an alpha-2-antiplasmin inhibitor, an anisoylated plasminogen streptokinase activator complex, a HMG-CoA reductase inhibitor, a squalene synthetase inhibitor, a fibrate, a bile acid sequestrant, an ACAT inhibitor, a MTP inhibitor, a lipooxygenase inhibitor, a cholesterol absorption inhibitor, a cholesterol ester transfer protein inhibitor, an alpha adrenergic blocker, a beta adrenergic blocker, a calcium channel blocker, a diuretic, a renin inhibitor, an angiotensin-converting enzyme inhibitor, an angiotensin-II-receptor antagonist, an ET receptor antagonist, a Dual ET/A11 antagonist, a neutral endopeptidase inhibitor, a vasopeptidase inhibitor, a Class I agent, a Class II agent, a Class III agent, a Class IV agent, an lach inhibitor, an Ikur inhibitor and a cardiac glycoside.

By "administered in combination" or "combination therapy" it is meant that the compound of the present invention and one or more additional therapeutic agents are administered concurrently or consecutively to the subject (preferably mammal, more preferably human) being treated. When administered in combination each component may be administered at the same time or sequentially in any order at different points in time. Thus, each component may be administered separately but sufficiently closely in time so as to provide the desired therapeutic effect. Chou, Theoretical Basis, Experimental Design, and Computerized Simulation of Synergism and Antagonism in Drug Combination Studies, Pharmacol Rev., 2006, vol. 58, 621-681.

4. Pharmaceutical Compositions

The present invention further comprises pharmaceutical compositions containing a compound of formula (I), compound of formula (II), compound of formula (III) and/or compound of formula (IV) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be administered at a dosage of from about 0.05 mg/day to about 1000 mg/day, or any amount or range therein, about 0.1 mg/day to about 500 mg/day, or any amount or range therein, preferably from about 1 mg/day to about 300 mg/day, or any amount or range therein.

The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof.

When referring to these pre-formulation compositions as homogeneous, it is meant that the active ingredient is dispersed evenly throughout the composition so that the composition may be readily subdivided into equally effective dosage forms such as tablets, pills and capsules. This solid pre-formulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of the treatment and/or prophylaxis of thromboembolic disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein, preferably from about 0.05 mg to about 300 mg of the compound, or any amount or range therein, more preferably from about 0.1 mg to about 100 mg of the compound, or any amount or range therein, more preferably from about 0.1 mg to about 50 mg of the compound, or any amount or range therein; and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I), compound of formula (II), compound of formula (III) and/or compound of formula (IV) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be measured in *The Handbook of Pharmaceutical Excipients*, published by the American Pharmaceutical Association and the Pharmaceutical Society of Great Britain. Methods of formulating pharmaceutical compositions have been described in numerous publications such as *Pharmaceutical Dosage Forms: Tablets. Second Edition. Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment or prophylaxis of thromboembolic disorders, inflammatory disorders or diseases or conditions in which plasma kallikrein activity is implicated is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug may be ordinarily supplied at a dosage level of from about 0.005 mg/kg to about 10 mg/kg of body weight per day, or any amount or range therein. Preferably, the range is from about 0.01 to about 5.0 mg/kg of body weight per day, or any amount or range therein, more preferably, from about 0.1 to about 1.0 mg/kg of body weight per day, or any amount or range therein, more preferably, from about 0.1 to about 0.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a disorder.

One skilled in the art will further recognize that human clinical trials including first-in-human, dose ranging and efficacy trials, in healthy patients and/or those suffering from a disorder, may be completed according to methods well known in the clinical and medical arts.

5. Combination Therapy

One or more additional pharmacologically active agents may be administered in combination with the compounds of the invention. The additional active agent (or agents) is intended to mean a pharmaceutically active agent (or agents) that is active in the body, including pro-drugs that convert to pharmaceutically active form after administration, which is different from the compound of formula (I), and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of formula (I), compound of formula (II), compound of formula (III) and/or compound of formula (IV) in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs (e.g., losartan i.e., COZAAR®, valsartan, candesartan, olmesartan, telmesartan, eprosartan, irbesartan and any of these drugs used in combination with hydrochlorothiazide such as HYZAAR®); diuretics, e.g. hydrochlorothiazide (HCTZ); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892 (CAS Registry Number 126222-34-2, also known as Remikiren); A 65317 (CAS Registry Number 119625-78-4); CP 80794 (CAS Registry Number 119625-78-4, also known as Terlakiren)); ES 1005 (CAS Registry Number 115404-79-0); ES 8891 (CAS Registry Number 129445-88-1); SQ 34017 (CAS Registry Number 695226-77-8); aliskiren (2(5),4(S),5(S),7(S)-N-(2-carbamoyl-2-methylpropyl)-5-amino-4-hydroxy-2,7-diisopropyl-8-[4-methoxy-3-(3-methoxypropoxy)-phenyl]-octanamide hemifumarate); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible. Compounds which can be alternatively or additionally administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Anticoagulant agents (or coagulation inhibitory agents) that may be used in combination with the compounds of this invention include warfarin, heparin (either unfractionated heparin or any commercially available low molecular weight heparin, for example enoxaparin and dalteparin), aprotinin, synthetic pentasaccharide inhibitors of Factor Xa such as fondaparinux and idraparinux, direct Factor Xa inhibitors such as rivaroxaban, apixaban, betrixaban, edoxaban, otamixaban, direct acting thrombin inhibitors including hirudin, dabigatran, argatroban, ximelagatran, melagatran, lepirudin, desirudin, and bivalirudin, as well as other factor Vila inhibitors, Villa inhibitors, Dca inhibitors, Xa inhibitors, XIa inhibitors, fibrinogen receptor antagonists (including abciximab, eptifibatide and tirofiban), TAFI inhibitors, and others known in the art. Factor Dca inhibitors include synthetic active-site blocked competitive inhibitors, oral inhibitors and RNA aptamers. These are described in Howard, E L, Becker K C, Rusconi, C P, Becker R C. Factor Ixa Inhibitors as Novel Anticoagulents. Arterioscler Thromb Vasc Biol, 2007; 27: 722-727.

The term "anti-platelet agents" or "platelet inhibitory agents", as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term "anti-platelet agents" or "platelet inhibitory agents", as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include tidopidine, prasugrel, dopidogrel, elinogrel, ticagrelor and cangrelor, including pharmaceutically acceptable salts or prodrugs thereof. Clopidogrel is an even more preferred agent. Tidopidine and clopidogrel are also preferred compounds since they are known to be gentle on the gastro-intestinal tract in use. The compounds of the present invention may also be dosed in combination with aprotinin.

The term "thrombin inhibitors" or "anti-thrombin agents", as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, dabigatran and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, omithine, arginine, homoarginine and corresponding isothiouronium analogs thereof. The term "hirudin", as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role. Thrombin receptor antagonist peptides have been identified based on structure-activity studies involving substitutions of amino acids on thrombin receptors. In Bematowicz et al, J Med. Chem., vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479. Substituted tricyclic thrombin receptor antagonists are disclosed in U.S. Pat. Nos. 6,063,847, 6,326,380 and WO 01/96330. Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor Vila inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes. The term urokinase, as used herein, is intended to denote both dual and single chain urokinase, the latter also being referred to herein as prourokinase. Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); lach inhibitors, and Ikur inhibitors (e.g., compounds such as those disclosed in WO01/40231).

6. Definitions

As used herein, unless otherwise noted, "halogen" shall mean chloro, bromo, fluoro and iodo, preferably bromo, fluoro or chloro, more preferably fluoro or chloro.

As used herein, unless otherwise noted, the term "oxo" shall mean a functional group of the structure =O (i.e. a substituent oxygen atom connected to another atom by a double bond).

As used herein, unless otherwise noted, the term "$C_{X-Y}$alkyl" wherein X and Y are integers, whether used alone or as part of a substituent group, include straight and branched chains containing between X and Y carbon atoms. For example, $C_{1-4}$alkyl radicals include straight and branched chains of between 1 and 4 carbon atoms, including methyl, ethyl, propyl, isopropyl, butyl, isobutyl, sec-butyl and t-butyl.

As used herein, unless otherwise noted, the terms "—($C_{X-Y}$alkylene)- and —$C_{X-Y}$alkylene-" wherein X and Y are integers, shall denote any $C_{X-Y}$alkyl carbon chain as herein defined, wherein said $C_{X-Y}$alkyl chain is divalent and is further bound through two points of attachment, preferably through two terminal carbon atoms.

As used herein, unless otherwise noted, the term "fluorinated $C_{1-4}$alkyl" shall mean any $C_{1-4}$alkyl group as defined above substituted with one or more fluoro groups, preferably one to three fluoro group. Suitably examples include, but are not limited to —$CH_2F$, —$CHF_2$, —$CF_3$, —$CH_2$—$CF_3$, —$CF_2$—$CH_3$, —$CH_2$—$CH_2$—$CH_2F$, —$CH_2$—$CH_2$—$CF_3$, —$C(CH_3)_2CF_3$, —$C(CF_3)_3$, and the like.

As used herein, unless otherwise noted, the term "hydroxy substituted $C_{1-4}$alkyl" shall mean any $C_{1-4}$alkyl group as defined above substituted with at one or more hydroxy (—OH) groups, preferably one to three, more preferably one to two hydroxy groups. Suitable examples include but are not limited to —$CH_2OH$, —$CH_2CH_2OH$, —$CH(OH)CH_3$, —$CH(OH)CH_2OH$, —$CH_2CH_2CH_2OH$, —$C(CH_2OH)_3$, and the like.

As used herein, unless otherwise noted, the term "hydroxy substituted fluorinated $C_{1-4}$alkyl" shall mean any fluorinated $C_{1-4}$alkyl group as defined above which is further substituted with at one or more hydroxy (—OH) groups, preferably one to three, more preferably one to two hydroxy groups. Suitable examples include but are not limited to —$CF_2OH$, —$CF_2CH_2OH$, —$CH(OH)CF_3$, and the like.

As used herein, unless otherwise noted, the term "amino substituted $C_{1-4}$alkyl" shall mean any $C_{1-4}$alkyl group as defined above substituted with one or more amino group, preferably one to two amino groups, more preferably one amino group. Suitably examples include, but are not limited to —CHF—$NH_2$, —$CF_2$—$NH_2$, —$CH_2$—$CF_2$—$NH_2$, —$CF_2$—$CH_2$—$NH_2$, —$CH_2$—CH(—$NH_2$)—$CH_2F$, —$CH_2$—$CH_2$—$CH_2$—$NH_2$, —CH(—$NH_2$)—$CH(CH_3)_2$, and the like.

As used herein, unless otherwise noted, the term "cyano substituted $C_{1-4}$alkyl" shall mean any $C_{1-4}$alkyl group as defined above substituted with one or more cyano group, preferably one to two cyano groups, more preferably one cyano group. Suitably examples include, but are not limited to —CHF—CN, —$CF_2$—CN, —$CH_2$—$CF_2$—CN, —$CF_2$—$CH_2$—CN, —$CH_2$—CH(—CN)—$CH_2F$, —$CH_2$—$CH_2$—$CH_2$—CN, —CH(—CN)—$CH(CH_3)_2$, and the like.

As used herein, unless otherwise noted, "$C_{X-Y}$alkoxy" wherein X and Y are integers, shall mean an oxygen ether radical of the above described straight or branched chain $C_{X-Y}$alkyl groups containing between X and Y carbon atoms. For example, $C_{1-4}$alkoxy shall include methoxy, ethoxy, n-propoxy, isopropoxy, n-butyloxy, iso-butyloxy, sec-butyloxy and tert butyloxy.

As used herein, unless otherwise noted, the term "fluorinated $C_{1-4}$alkoxy" shall mean any $C_{1-4}$alkoxy group as defined above substituted with one or more fluoro groups, preferably one to three fluoro group. Suitably examples include, but are not limited to —$OCH_2F$, —$OCHF_2$, —$OCF_3$, —$OCH_2$—$CF_3$, —$OCF_2$—$CH_3$, —$OCH_2$—$CH_2$—$CH_2F$, —$OCH_2$—$CH_2$—$CF_3$, —$OC(CH_3)_2CF_3$, —$OC(CF_3)_3$, and the like.

As used herein, unless otherwise noted, the term "hydroxy substituted $C_{1-4}$alkoxy" shall mean any $C_{1-4}$alkoxy group as defined above which is further substituted with one or more hydroxy (—OH) groups, preferably one to three, more preferably one to two hydroxy groups. Suitable examples include but are not limited to —$OCF_2OH$, —$OCF_2CH_2OH$, —$OCH(OH)CF_3$, and the like.

As used herein, unless otherwise noted, the term "$C_{X-Y}$cycloalkyl", wherein X and Y are integers, shall mean any stable X- to Y-membered monocyclic, bicyclic, polycyclic, bridged or spiro-cyclic saturated ring system, preferably a monocyclic, bicyclic, bridged or spiro-cyclic saturated ring system. For example, the term "$C_{3-8}$cycloalkyl" includes, but is not limited to cyclopropyl, cyclobutyl, cyclopentyl, cyclohexyl, cycloheptyl, bicyclo[2.2.1]hept 2-yl, cyclooctyl, bicyclo[2.2.2]octan-2-yl, and the like.

As used herein, unless otherwise noted, the term "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or nine or ten membered bicyclic aromatic ring structure containing at least one heteroatom selected from the group consisting of O, N and S, optionally containing one to four additional heteroatoms independently selected from the group consisting of O, N and S. The heteroaryl may be bound through any ring atom which results in a stable structure. Suitable examples include, but are not limited to, furanyl, thienyl, furazanyl, oxazolyl, imidazolyl, pyrrolyl, pyrazolyl, thiazolyl, isoxazolyl, isothiazolyl, triazolyl, thiadiazolyl, oxadiazolyl, pyrazyl, pyridyl, pyridazinyl, pyrimidinyl, pyrazinyl, triazinyl, indolyl, indolizinyl, isoindolinyl, indazolyl, benzofuranyl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, imidazo[1,2-a]pyridin-7-yl, [1,2,4]triazolo[4,3-a]pyridin-7-yl, and the like.

As used herein, unless otherwise noted, the term "5 to 6 membered heteroaryl" shall denote any five or six membered monocyclic aromatic ring structure containing at least one heteroatom selected from the group consisting of O, N and S, optionally containing one to three additional heteroatoms independently selected from the group consisting of O, N and S. Suitably examples include, but are not limited to furyl, thienyl, pyrrolyl, oxazolyl, thiazolyl, imidazolyl, pyrazolyl, isoxazolyl, isothiazolyl, oxadiazolyl, triazolyl, thidiazolyl, tetrazolyl, pyranyl, pyridinyl, pyridazinyl, pyrimidinyl, pyrazinyl, triazinyl, dioxinyl, oxazinyl, isoxazinyl, oxathiazinyl, oxadiazinyl, and the like The term "5 to 6 membered nitrogen containing heteroaryl" shall denote any five or six membered monocyclic aromatic ring structure containing at least one N atom, optionally containing one to three additional heteroatoms independently selected from the group consisting of O, N and S. Suitably examples include, but are not limited to pyrrolyl, oxazolyl, thiazolyl, imidazolyl, pyrazolyl, isoxazolyl, isothiazolyl, oxadiazolyl, triazolyl, thidiazolyl, tetrazolyl, pyridinyl, pyridazinyl, pyrimidinyl, pyrazinyl, triazinyl, oxazinyl, isoxazinyl, oxathiazinyl, oxadiazinyl, and the like.

Unless otherwise noted, any heteroaryl (regardless of the number of ring atoms, the number and identity of ring heteroatoms, etc.) may be bound through any ring atom which results in a stable structure.

In some embodiments of the present invention, the 5 to 6 membered heteroaryl is a 5 membered heteroaryl. In some embodiments of the present invention, the 5 to 6 membered heteroaryl is a 6 membered heteroaryl. In some embodiments of the present invention, the 5 to 6 membered heteroaryl is a 5 to 6 membered nitrogen containing heteroaryl. In some embodiments of the present invention, the 5 to 6 membered heteroaryl is a 5 membered nitrogen containing heteroaryl. In some embodiments of the present invention, the 5 to 6 membered heteroaryl is a 6 membered nitrogen containing heteroaryl.

As used herein, unless otherwise noted, the term "heterocyclyl" shall denote any monocyclic, saturated, partially unsaturated, or aromatic ring structure containing at least one heteroatom selected from the group consisting of 0, N and S, optionally containing one to three additional heteroatoms independently selected from the group consisting of O, N and S; or any saturated, partially unsaturated, partially aromatic or aromatic bicyclic, benzo-fused, bridged or spirocyclic ring system containing at least one heteroatom selected from the group consisting of O, N and S, optionally containing one to four additional heteroatoms independently selected from the group consisting of O, N and S. Suitable examples include, but are not limited to, azetidinyl, oxetanyl, thientanyl, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 2,3-dihydrobenzofuryl, 2,3-dihydrobenzo[b][1,4]dioxinyl, benzo[d][1,3]dioxolyl, and the like.

As used herein, unless otherwise noted, the term "5 to 6 membered heterocyclyl" shall denote 5 to 6 any monocyclic, saturated, partially unsaturated or aromatic ring structure containing at least one heteroatom selected from the group consisting of O, N and S, optionally containing one to three additional heteroatoms independently selected from the group consisting of O, N and S. Unless otherwise noted, the 5 to 6 membered heterocyclyl may be attached at any heteroatom or carbon atom of the ring such that the result is a stable structure. Suitable examples include, but are not limited to furyl, thiophenyl, pyrrolyl, pyrrolidinyl, oxazolyl, thiazolyl, isoxazolyl, pyrazolyl, imidazolyl, triazolyl, isothiazolyl, dioxolanyl, pyrazolidinyl, thiadiazolyl, pyranyl, pyridinyl, dioxanyl, morpholinyl, dithianyl, thiomorpholinyl, pyridazinyl, pyrimidinyl, pyrazinyl, piperidinyl, piperazinyl, triazinyl, oxazinyl, isoxazinyl, oxathiazinyl, and the like.

As used herein, unless otherwise noted, the term "5 membered heterocyclyl" shall denote 5 membered monocyclic, saturated, partially unsaturated or aromatic ring structure containing at least one heteroatom selected from the group consisting of O, N and S, optionally containing one to three additional heteroatoms independently selected from the group consisting of O, N and S. Unless otherwise noted, the 5 membered heterocyclyl may be attached at any heteroatom or carbon atom of the ring such that the result is a stable structure. Suitable examples include, but are not limited to furyl, thiophenyl, pyrrolyl, pyrrolidinyl, oxazolyl, thiazolyl, isoxazolyl, pyrazolyl, imidazolyl, triazolyl, isothiazolyl, dioxolanyl, pyrazolidinyl, thiadiazolyl, and the like.

As used herein, unless otherwise noted, the term "6 membered heterocyclyl" shall denote shall denote 5 membered monocyclic, saturated, partially unsaturated or aromatic ring structure containing at least one heteroatom selected from the group consisting of O, N and S, optionally containing one to three additional heteroatoms independently selected from the group consisting of O, N and S. Unless otherwise noted, the 6 membered heterocydyl may be attached at any heteroatom or carbon atom of the ring such that the result is a stable structure. Suitable examples include, but are not limited to pyranyl, pyridinyl, dioxanyl, morpholinyl, dithianyl, thiomorpholinyl, pyridazinyl, pyrimidinyl, pyrazinyl, piperidinyl, piperazinyl, triazinyl, oxazinyl, isoxazinyl, oxathiazinyl, and the like.

As used herein, unless otherwise noted, the term "9 to 10 membered heterocyclyl" shall denote 9 to 10 membered monocyclic, bicyclic, bridged, spiro, saturated, partially unsaturated, benzo-fused or aromatic ring structure containing at least one heteroatom selected from the group consisting of 0, N and S, optionally containing one to three additional heteroatoms independently selected from the group consisting of O, N and S. Unless otherwise noted, the 9 to 10 membered heterocyclyl may be attached at any heteroatom or carbon atom of the ring such that the result is a stable structure. Suitable examples include, but are not limited to indolenyl, indolyl, isoindolyl, indolizinyl, indolinyl, benzofuryl, benzothiophenyl, indazolyl, benzimidazolyl, benzthiazolyl, purinyl, quinolinyl, isoquinolinyl, quinolizinyl, quinazolinyl, cinnolinyl, phthalazinyl, quinoxalinyl, naphthyridinyl, pteridinyl, quinudidinyl, thionaphthenyl, isobenzazolyl, pyrano[3,4-b]pyrrolyl, anthranyl, benzopyranyl, chromenyl, coumarinyl, benzopyronyl, and the like.

As used herein, the term "4 to 6 membered heterocycloalkyl" shall mean any four to six membered saturated ring structure containing at least one heteroatom selected from the group consisting of O, N and S, optionally containing one to three additional heteroatoms independently selected from the group consisting of O, N and S. Unless otherwise noted, the 4 to 6 membered saturated heterocyclyl may be attached at any heteroatom or carbon atom of the ring such that the result is a stable structure. Suitable examples include, but are not limited to azetidinyl, oxetanyl, thientanyl, pyrrolidinyl, dioxolanyl, imidazolidinyl, pyrazolidinyl, piperidinyl, piperazinyl, morpholinyl, thiomorpholinyl, dithianyl, trithianyl, and the like.

When a particular group is "substituted" (e.g. $C_{X-Y}$alkyl, heteroaryl, etc.), that group may have one or more substituents, preferably from one to five substituents, more preferably from one to three substituents, most preferably from one to two substituents, independently selected from the list of substituents. With reference to substituents, the term "independently" means that when more than one of such substituents is possible, such substituents may be the same or different from each other.

Abbreviations used in the specification, particularly the Schemes and Examples, are as listed in the Table A, below:

TABLE A

| Abbreviations | |
|---|---|
| Ac= | Acetyl (i.e. —C(O)$CH_3$) |
| $Ac_2O$= | Acetic anhydride |
| AcOH= | Acetic Acid |
| ACN or MeCN= | Acetonitrile |
| aq.= | Aqueous |
| $BF_3$•$Et_2O$= | Boron trifluoride diethyl etherate |
| $BH_3$•$Me_2S$= | Borane Dimethyl Sulfide |
| BINAP= | (2,2'-Bis(diphenylphosphino)-1,1'-binaphthyl) |
| Boc or BOC= | tert-Butoxyloxycarbonyl (i.e. —C(O)—O—C($CH_3$)$_3$) |
| B(O—iPr)$_3$= | Tri(isopropyl) Borate |
| BPin= | Bis(pinacolate)diboron |
| BSA= | Bovine Serum Albumin |
| CHAPS= | 3-[(3-Cholamidopropyl)dimethylammonio]-1-propanesulfonate |
| DABAL= | Bis(trimethylaluminum)-1,4-diazabicyclo2.2.octane adduct |
| DBU= | 1,8-Diazabicyclo[5.4.0]undec-7-ene |
| DCE= | 1,2-Dichloroethane |
| DCM= | Dichloromethane |
| DEA= | Diethanolamine |
| DIEA or DIPEA= | Diisopropylethyl Amine |
| DME= | Diabetic Macular Edema |
| DMF= | N,N-Dimethylformamide |
| DMP or Dess Martin Periodinane= | 3-Oxo-1$\lambda^5$,2-benziodoxole-1,1,1(3H)-triyl triacetate |
| DMSO= | Dimethylsulfoxide |
| dppf= | 1,1'-Bis(diphenylphosphino)ferrocene |
| EA or EtOAc= | Ethyl Acetate |
| EDCI= | 1-Ethyl-3-(3-dimethylaminopropyl) carbodiimide |
| Ee= | Enantiomeric Excess |
| ER= | End Point Read (assay) |
| equiv.= | Equivalents |
| ES or ESI= | Electrospray ionization |
| Et= | Ethyl |
| EtOH= | Ethanol |
| $Et_2O$= | Diethyl Ether |
| $Et_3N$ or TEA= | Triethylamine |
| $Et_3$•3HF= | Triethylamine Trihydrofluoride |
| FA= | Formic Acid |
| FXIa= | Factor XIa |
| Grubbs Catalyst 1$^{st}$ generation= | Benzylidene-bis(tricyclohexylphosphine)dichlororuthenium |
| Grubbs Catalyst 2$^{nd}$ generation= | (1,3-Bis(2,4,6-trimethylphenyl)-2-imidazolidinylidene)dichloro(phenylmethylene)(tricyclohexylphosphine)ruthenium |
| Grubb's Catalyst 3$^{rd}$ generation= | Dichloro1,3-bis(2,4,6-trimethylphenyl)-2-imidazolidinylidene(benzylidene)bis(3-bromopyridine)ruthenium(II) |
| HAE= | Hereditary Angioedema |
| HATU= | (1-[Bis(dimethylamino)methylene]-1H-1,2,3-triazolo[4,5-b]pyridinium 3-oxide hexafluorophosphate |
| Hex= | Hexanes |
| HOAc= | Acetic Acid |
| HOBt or HOBT= | Hydroxybenzotriazole |
| HPLC= | High Performance Liquid Chromatography |
| IBX= | 2-Iodoxybenzoic acid |
| KIN= | Kinetic Read (assay) |
| KOAc= | Potassium Acetate |
| KOt-Bu or t-BuOK or tert-BuOK= | Potassium tert-Butoxide |
| LC-MS or LC/MS= | Liquid chromatography-mass spectrometry |
| LDA or LiN(Pr-i)$_2$= | Lithium Diisopropylamide |
| LiHMDS= | Lithium bis(trimethylsilyl)amide |
| Me= | Methyl |
| MeI= | Methyl Iodine |
| MeOH= | Methanol |
| MOM= | Methoxy methyl |
| Ms or mesyl= | Methylsulfonyl (i.e. —$SO_2$—$CH_3$) |
| MTBE= | Methyl tert-Butyl Ether |
| NaOEt= | Sodium Ethoxide |
| NaOMe= | Sodium Methoxide |
| NaOt-Bu or t-BuONa or tert-BuONa= | Sodium tert-Butoxide |
| NBS= | N-Bromosuccinimide |
| n-BuLi= | n-Butyl Lithium |

TABLE A-continued

| Abbreviations | |
|---|---|
| n-BuCH(Et)$CO_2$K= | Potassium ethylhexanoate |
| NCS= | N-Chlorosuccinimide |
| NFSI= | N-Fluorobenzenesulfonimide |
| $NH_4$OAc= | Ammonium Acetate |
| NIS= | N-Iodosuccinimide |
| NMR= | Nuclear Magnetic Resonance |
| Oms or mesylate= | Methanesulfonate (i.e. —O—$SO_2$—$CH_3$) |
| Otf or triflate= | Trifluoromethanesulfonyl (i.e. —O—SO═—$CF_3$) |
| Ots or tosylate= | p-Toluenesulfonate (i.e. —O—$SO_2$-(p-methylphenyl)) |
| PCC= | Pyridinium chlorochromate |
| Pd(dppf)$Cl_2$ or $PdCl_2$(dppf)= | [1,1'-Bis(diphenylphosphino)ferrocene] Palladium (II) Dichloride |
| Pd(dtbpf)$Cl_2$= | 1,1-Bis(di-tert-butylphosphino)ferrocenedichloro palladium (II) |
| $PdCl_2(PPh_3)_2$ or $Pd(PPh_3)_2Cl_2$= | Bis(triphenylphosphine)palladium (II) Dichloride |
| $Pd(PPh_3)_4$= | Tetrakis(triphenylphosphine)palladium(0) |
| PE= | Petroleum ether |
| Ph= | Phenyl |
| $PhI(Oac)_2$= | (Diacetoxyiodo)benzene |
| PhMe= | Toluene |
| PK= | Plasma Kallikrein |
| PMB= | para-Methoxybenzyl |
| PMBCl= | para-Methoxybenzyl Chloride |
| $PPh_3$= | Triphenylphosphine |
| PPTS= | Pyridinium p-toluenesulfonate |
| Py•$HBr_3$= | Pyridinium Perbromide |
| RFU= | Relative Fluorescence Unit |
| Selectfluor or F-TEDA= | 1-Chloromethyl-4-fluoro-1,4-diazoniabicyclo[2.2.2]octane bis(tetrafluoroborate) |
| SEMCl= | 2-(Trimethylsilyl)ethoxymethyl Chloride |
| SFC (purification)= | Supercritical Fluid Chromatography (purification) |
| TBAF= | Tetra-n-butylammonium fluoride |
| TBSCI or TBDMS-Cl= | tert-Butyldimethylsilyl chloride |
| TBSOTf= | tert-Butyldimethylsilyl triflate |
| TEA or $Et_3N$= | Triethylamine |
| Tf or triflyl= | Trifluoromethylsulfonyl (i.e. —$SO_2$—$CF_3$) |
| TFA= | Trifluoroacetic acid |
| TFAA= | Trifluoroacetic anhydride |
| THE= | Tetrahydrofuran |
| THP= | Tetrahydropyranyl |
| TMS= | Trimethysilyl |
| $TMSCHN_2$= | Trimethylsilyldiazomethane |
| TMSCl= | Trimethylsilyl Chloride |
| TMSCN= | Cyanotrimethylsilane |
| $TMSN_3$= | Trimethylsilyl azide |
| Tris (buffer)= | 2-Amino-2-(hydroxymethyl)-1,3-propanediol |
| Ts or tosyl= | —$SO_2$-(p-methylphenyl) |
| p-TsOH= | para-Toluenesulfonic Acid |
| wt % or wt %= | Weight Percent |
| X-Phos= | Dicyclohexyl[2',4',6'-tris(propan-2-yl)[1,1'-biphenyl]-2-yl]phosphane |
| X-Phos-Pd G2= | [2-(2-aminophenyl)phenyl]-chloro-palladium dicyclohexyl-[3-(2,4,6-triisopropylphenyl)phenyl]phosphane |
| X-Phos-Pd G3= | (2-Dicyclohexylphosphino-2',4',6'-triisopropyl-1,1'-biphenyl) [2-(2'-amino-1,1'-biphenyl)]palladium(II) methanesulfonate |

For use in medicine, the salts of the compounds of this invention refer to non-toxic “pharmaceutically acceptable salts”. Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (±)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

As used herein, the term "composition" is intended to encompass a product comprising the specified ingredients in the specified amounts, as well as any product which results, directly or indirectly, from combinations of the specified ingredients in the specified amounts.

As used herein, unless otherwise noted, the terms "treating", "treatment" and the like, shall include the management and care of a subject or patient, preferably a mammal, more preferably a human, for the purpose of combating a disease, condition, or disorder and includes the administration of a compound of the present invention to prevent the onset of the symptoms or complications, alleviate the symptoms or complications, slow the progression of the disease or disorder, or eliminate the disease, condition, or disorder. The terms "treating" or "treatment" further include: (a) inhibiting the disease-state, i.e., arresting its development; and/or (b) relieving the disease-state, i.e., causing regression of the disease state.

As used herein, "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population.

As used herein, "prophylaxis" is the protective treatment of a disease state to reduce and/or minimize the risk and/or reduction in the risk of recurrence of a disease state by administering to a patient a therapeutically effective amount of at least one of the compounds of the present invention or a stereoisomer, isotopologue, a pharmaceutically acceptable salt, thereof. Patients may be selected for prophylaxis therapy based on factors that are known to increase risk of suffering a clinical disease state compared to the general population. For prophylaxis treatment, conditions of the clinical disease state may or may not be presented yet. "Prophylaxis" treatment can be divided into (a) primary prophylaxis and (b) secondary prophylaxis. Primary prophylaxis is defined as treatment to reduce or minimize the risk of a disease state in a patient that has not yet presented with a clinical disease state, whereas secondary prophylaxis is defined as minimizing or reducing the risk of a recurrence or second occurrence of the same or similar clinical disease state.

As used herein, "risk reduction" covers therapies that lower the incidence of development of a clinical disease state. As such, primary and secondary prevention therapies are examples of risk reduction.

As used herein, the terms "combination" and "pharmaceutical combination" refer to either: 1) a fixed dose combination in one dosage unit form; or 2) a non-fixed dose combination, optionally packaged together for combined administration.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

EXAMPLES

The following Examples are set forth to aid in the understanding of the invention and are not intended and should not be construed to limit in any way the invention set forth in the claims which follow thereafter.

Where an Example which follow hereinafter lists only analytical measurements such as LC/MS, $^{1}H$ NMR, $^{19}F$ NMR, etc. (rather than reaction step details), it will be understood that the title compound was prepared according to the procedures as described in the synthesis schemes and Examples herein, selecting and substituting suitable reagents and reactants, as would be readily recognized by those skilled in the art.

Unless otherwise indicated in the examples, all temperature is expressed in Centigrade (° C.). All reactions were conducted under an inert atmosphere at ambient temperature unless otherwise noted. Unless otherwise specified, reaction solutions were stirred at room temperature under a $N_{2(g)}$ or Ara atmosphere. Reagents employed without synthetic details are commercially available or made according to known methods, for example according to literature procedures. When solutions were "concentrated to dryness", they were concentrated using a rotary evaporator under reduced pressure, when solutions were dried, they were typically dried over a drying agent such as $MgSO_4$ or $Na_2SO_4$. Where a synthesis product is listed as having been isolated as a residue, it will be understood by those skilled in the art that the term "residue" does not limit the physical state in which the product was isolated and may include, for example, a solid, an oil, a foam, a gum, a syrup, and the like.

In obtaining the compounds described in the examples below and the corresponding analytical data, the following experimental and analytical protocols were followed unless otherwise indicated.

LC-MS: Unless otherwise indicated, the analytical LC-MS system used consisted of a Shimadzu LCMS-2020 with electrospray ionization (ESI) in positive ion detection mode with 20ADXR pump, SIL-20ACXR autosampler, CTO-20AC column oven, M20A PDA Detector and LCMS 2020 MS detector. The column was a HALO a C18 30*5.0 mm, 2.7 μm. The mobile phase A was water containing 0.05% TFA and mobile phase B was acetonitrile containing 0.05% TFA. The gradient was from 5% mobile phase B to 100% (95%) in 2.0 min, hold 0.7 min, then revert to 5% mobile phase B over 0.05 min and maintain for 0.25 min. The Column Oven (CTO-20AC) was operated at a 40.0° C. The flow rate was 1.5 mL/min, and the injection volume was 1 μl. PDA (SPD-M20A) detection was in the range 190-400 nm. The MS detector, which was configured with electrospray ionization as ionizable source; Acquisition mode: Scan; Nebulizing Gas Flow: 1.5 L/min; Drying Gas Flow: 15 L/min; Detector Voltage: Tuning Voltage ±0.2 kv; DL Temperature: 250° C.; Heat Block Temperature: 250° C.; Scan Range: 90.00-900.00 m/z. ELSD (Alltech 3300) detector Parameters: Drift Tube Temperature: 60±5° C.; N2 Flow-Rate: 1.8±0.2 L/min. Mobile phase gradients were optimized for the individual compounds. Calculated mass corresponds to the exact mass.

Preparative HPLC: Unless otherwise noted, preparative HPLC purifications were performed with Waters Auto purification system (2545-2767) with a 2489 UV detector. The column was selected from one of the following: Waters C18, 19×150 mm, 5 μm; XBridge Prep OBD C18 Column, 30×150 mm 5 μm; XSelect CSH Prep C18 OBD Column, 5 μm, 19*150 mm; XBridge Shield RP18 OBD Column, 30×150 mm, 5 μm; Xselect CSH Fluoro Phenyl, 30×150 mm, 5 μm; or YMC-Actus Triart C18, 30×150 mm, 5 μm. The mobile phases consisted of mixtures of acetonitrile (5-95%) in water containing 0.1% FA or 10 mmol/L $NH_4HCO_3$. Flow rates were maintained at 25 mL/min, the injection volume was 1200 μL, and the UV detector used two channels 254 nm and 220 nm. Mobile phase gradients were optimized for the individual compounds.

Chiral chromatography: Chiral analytical chromatography was performed on one of Chiralpak AS, AD, Chiralcel OD, OJ Chiralpak IA, IB, IC, ID, IE, IF, IG, IH columns (Deice) Chemical Industries, Ltd.) (R,R)-Whelk-O1, (S,S)-Whelk-O1 columns (Regis technologies, Inc.) CHIRAL Cellulose-SB, SC, SA columns (YMC Co., Ltd.) as noted, at different column size (50×4.6 mm, 100×4.6 mm, 150×4.6 mm, 250×4.6 mm, 50×3.0 mm, 100×3.0 mm), with percentage of either ethanol in hexane (% Et/Hex) or isopropanol in hexane (% IPA/Hex) as isocratic solvent systems, or using supercritical fluid (SFC) conditions.

Normal phase flash chromatography: Unless otherwise noted, normal phase flash column chromatography (FCC) was performed on silica gel with pre-packaged silica gel columns (such as RediSep®), using ethyl acetate (EtOAc)/hexanes, ethyl acetate (EtOAc)/Petroleum ether (b.p. 60-90° C.), $CH_2Cl_2$/MeOH, or $CH_2Cl_{2/10}$% 2N $NH_3$ in MeOH, as eluent.

$^1$H NMR: Unless otherwise noted, $^1$H NMR spectra were acquired using 400 MHz spectrometers (or 300 MHz spectrometers) in DMSO-$d_6$ solutions. The nuclear magnetic resonance (NMR) spectral characteristics refer to chemical shifts (δ) are expressed in parts per million (ppm). Tetramethylsilane (TMS) was used as internal reference in DMSO-$d_6$ solutions, and residual $CH_3OH$ peak or TMS was used as internal reference in $CD_3OD$ solutions. Coupling constants (J) are reported in hertz (Hz). The nature of the shifts as to multiplicity is reported as s (singlet), d (doublet), t (triplet), q (quartet), dd (double doublet), dt (double triplet), m (multiplet), br (broad).

Synthesis Examples: Intermediates

Intermediate 1: (3S)-7-(6-Amino-3-chloro-2-fluorophenyl)-5-oxo-1,2,3,5,8,8a-hexahydroindolizine-3-carboxylic acid

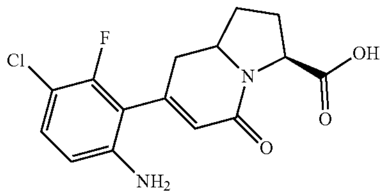 [SMILES: Nc1ccc(Cl)c(F)c1C1=CC(=O)N2C(CC[C@H]2C(=O)O)C1]

Step 1: 1-(Tert-butyl) 2-methyl (2S)-5-methoxypyrrolidine-1,2-dicarboxylate

To a solution of 1-(tert-butyl) 2-methyl (S)-5-oxopyrrolidine-1,2-dicarboxylate (2.1 g, 8.63 mmol, 1.0 equiv) in THF (40 mL), was added lithium triethylborohydride (13 mL, 13 mmol, 1.5 equiv, 1M in THF) drop-wise at −78° C. under $N_2$. The reaction mixture was stirred for 40 min at −78° C., then $Na_2CO_3$ (aq., 10 mL) was added at −78° C. and the mixture was warmed to 0° C. Hydrogen peroxide (1 mL, 30%) was added. The mixture was stirred for 30 min at room temperature. THF was removed under vacuum, and the resulting mixture was extracted with diethyl ether, washed with brine, dried, and concentrated under vacuum to yield a colorless oil. The oil was dissolved in methanol (40 mL), and p-toluenesulfonic acid (149 mg, 0.86 mmol, 0.1 equiv) was added. The resulting solution was stirred overnight at room temperature. The reaction was quenched with water and the resulting mixture was extracted with diethyl ether. The combined organic layer was washed with brine, dried over $Na_2SO_4$ and concentrated to yield 1-(tert-butyl) 2-methyl (2S)-5-methoxypyrrolidine-1,2-dicarboxylate as a colorless oil.

Step 2: 1-(Tert-butyl) 2-methyl (2S)-5-allylpyrrolidine-1,2-dicarboxylate

To a solution of 1-(tert-butyl) 2-methyl (2S)-5-methoxypyrrolidine-1,2-dicarboxylate (10.0 g, 38.60 mmol, 1.0 equiv) in $Et_2O$ (200 mL), were added allyltrimethylsilane (27 mL, 169.70 mmol, 4.4 equiv) and boron trifluoride etherate (6.6 g, 46.30 mmol, 1.2 equiv) at −40° C. in a $N_2$ atmosphere. The reaction mixture was stirred for 30 min at −40° C., and then warmed to room temperature and stirred for 40 min. The reaction was quenched with $Na_2CO_3$ (aq.) and the resulting mixture was extracted with ethyl acetate. The combined organic layer was washed with brine, dried over $Na_2SO_4$ and concentrated. The residue was purified by silica gel chromatography (0-20% EtOAc/petroleum ether)

to yield 1-(tert-butyl) 2-methyl (2S)-5-allylpyrrolidine-1,2-dicarboxylate as a yellow oil. LC/MS: mass calculated for $C_{14}H_{23}NO_4$: 269.16, measured: 270.20 $[M+H]^+$.

Step 3: 1-(Tert-butyl) 2-methyl (2S)-5-(2-oxoethyl) pyrrolidine-1,2-dicarboxylate To a solution of 1-(tert-butyl) 2-methyl (2S)-5-allylpyrrolidine-1,2-dicarboxylate (7.3 g, 27.10 mmol, 1.0 equiv) in THF/$H_2O$ (120 mL), was added 0504 (347 mg, 1.36 mmol, 0.05 equiv). The reaction mixture was stirred for 5 min at room temperature in the dark, and sodium periodate (14.5 g, 67.80 mmol, 2.5 equiv) was added. The reaction mixture was stirred for 4 h at room temperature. The reaction was quenched with water and the resulting mixture was extracted with ethyl acetate. The combined organic layer was washed with brine, dried over $Na_2SO_4$. The solids were filtered out. The filtrate was concentrated under vacuum. The residue was purified by silica gel chromatography (0-40% EA/PE) to yield 1-(tert-butyl) 2-methyl (2S)-5-(2-oxoethyl)pyrrolidine-1,2-dicarboxylate as a yellow oil. LC/MS: mass calculated for $C_{13}H_{21}NO_5$: 271.14, measured: 272.15 $[M+H]^+$.

Step 4: 1-(Tert-butyl) 2-methyl (2S)-5-(4-ethoxy-2-hydroxy-4-oxobutyl)pyrrolidine-1,2-dicarboxylate To a solution of tert-butyl acetate (3.9 g, 44.23 mmol, 2.0 equiv) in tetrahydrofuran (60 mL), was added lithium bis(trimethylsilyl)amide (44 mL, 44 mmol, 1.2 equiv) at −78° C. in a $N_2$ atmosphere. The resulting solution was stirred for 30 min at −78° C., then 1-(tert-butyl) 2-methyl (2S)-5-(2-oxoethyl)pyrrolidine-1,2-dicarboxylate (6 g, 22.1 mmol, 1.0 equiv) was added. The reaction mixture was stirred for 2 h at −78° C. The reaction was quenched with water and the resulting mixture was extracted with ethyl acetate. The combined organic layer was washed with brine, dried over $Na_2SO_4$. The solids were filtered out. The filtrate was concentrated under vacuum and concentrated. The residue was purified by silica gel chromatography (0-80% EA/PE) to yield 1-(tert butyl) 2-methyl (2S)-5-(4-ethoxy-2-hydroxy-4-oxobutyl)pyrrolidine-1,2-dicarboxylate as a yellow oil. LC/MS: mass calculated For $C_{17}H_{29}NO_7$: 359.19, measured: 360.10 $[M+H]^+$.

Step 5: 1-(Tert-butyl) 2-methyl (2S)-5-(4-ethoxy-2,4-dioxobutyl)pyrrolidine-1,2-dicarboxylate To a solution of 1-(tert butyl) 2-methyl (2S)-5-(4-ethoxy-2-hydroxy-4-oxobutyl)pyrrolidine-1,2-dicarboxylate (3.3 g, 9.20 mmol, 1.0 equiv) in acetonitrile (30 mL), was added IBX (10.3 g, 36.80 mmol, 4.0 equiv). The reaction mixture was stirred overnight at 50° C. The residue was purified by silica gel chromatography (0-80% EtOAc/petroleum ether) to yield 1-(tert-butyl) 2-methyl (2S)-5-(4-ethoxy-2,4-dioxobutyl)pyrrolidine-1,2-dicarboxylate as a yellow oil. LC/MS: mass calculated for $C_{17}H_{27}NO_7$: 357.18, measured: 380.15 $[M+Na]^+$.

Step 6: Methyl (3S)-5,7-dioxooctahydroindolizine-3-carboxylate

To a solution of 1-(tert butyl) 2-methyl (2S)-5-(4-ethoxy-2,4-dioxobutyl)pyrrolidine-1,2-dicarboxylate (900 mg, 2.50 mmol, 1.0 equiv) was added HCl (in 1,4-dioxane, 4 M)/dichloromethane (5 mL, 1/1) and the reaction mixture was stirred for 1 h at room temperature. The solvent was removed under vacuum to yield yellow oil. The oil was dissolved in toluene (5 mL), and sodium bicarbonate (2.1 g, 25.20 mmol, 10.0 equiv) was added. The reaction mixture was stirred over night at 110° C. The reaction was quenched with water and the resulting mixture was extracted with ethyl acetate. The combined organic layer was washed with brine, dried over $Na_2SO_4$ and concentrated. The residue was purified by silica gel chromatography (0-50% EtOAc/petroleum ether) to yield methyl (3S)-5,7-dioxooctahydroindolizine-3-carboxylate as a yellow solid. LC/MS: mass calculated for $C_{10}H_{13}NO_4$: 211.08, measured: 212.10 $[M+H]^+$.

Step 7: Methyl (3S)-5-oxo-7-(((trifluoromethyl) sulfonyl)oxy)-1,2,3,5,8,8a-hexahydroindolizine-3-carboxylate To a solution of methyl (3S)-5,7-dioxooctahydroindolizine-3-carboxylate (370 mg, 1.75 mmol, 1.0 equiv) in dichloromethane (5 mL), were added triethylamine (355 mg, 3.50 mmol, 2.0 equiv) and N,N-bis(trifluoromethylsulfonyl)aniline (751 mg, 2.10 mmol, 1.2 equiv). The reaction mixture was stirred over night at room temperature. The mixture was then concentrated. The residue was purified by silica gel chromatography (0-80% EA/PE) to yield methyl (3S)-5-oxo-7-(((trifluoromethyl)sulfonyl)oxy)-1,2,3,5,8,8a-hexahydroindolizine-3-carboxylate as a yellow solid. LC/MS: mass calculated for $C_{11}H_{12}F_3NO_6S$: 343.03, measured: 344.05 $[M+H]^+$.

Step 8: Methyl (3S)-7-(6-amino-3-chloro-2-fluorophenyl)-5-oxo-1,2,3,5,8,8a-hexahydroindolizine-3-carboxylate To a solution of ethyl methyl (3S)-5-oxo-7-(((trifluoromethyl)sulfonyl)oxy)-1,2,3,5,8,8a-hexahydroindolizine-3-carboxylate (350 mg, 1.02 mmol, 1.0 equiv), (6-amino-3-chloro-2-fluorophenyl)boronic acid (232 mg, 1.20 mmol, 1.2 equiv) and potassium carbonate (282 mg, 2.04 mmol 2.0 equiv) in 1,4-dioxane/$H_2O$ (5 mL, 10/1), was added [1,1'-bis(diphenylphosphino)ferrocene] dichloropalladium(II) (37 mg, 0.05 mmol, 0.1 equiv). The reaction mixture was stirred for 2 h at 80° C. under $N_2$. The reaction was quenched with water and extracted with ethyl acetate. The combined organic layer was washed with brine, dried over $Na_2SO_4$. The solids were filtered out. The filtrate was concentrated under vacuum. The residue was purified by silica gel chromatography (0-100% EtOAc/petroleum ether) to yield methyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{16}H_{16}ClFN_2O_3$: 338.08, measured: 339.10 $[M+H]^+$.

Step 9: (3S)-7-(6-Amino-3-chloro-2-fluorophenyl)-5-oxo-1,2,3,5,8,8a-hexahydroindolizine-3-carboxylic acid To a solution of methyl (3S)-7-(6-amino-3-chloro-2-fluorophenyl)-5-oxo-1,2,3,5,8,8a-hexahydroindolizine-3-carboxylate (210 mg, 0.62 mmol, 1.0 equiv) in THE/$H_2O$/MeOH (5 mL, 3/1/1), was added lithium hydroxide (124 mg, 3.10 mmol, 5.0 equiv). The reaction mixture was stirred for 1 h at room temperature. The residue was adjusted to pH 4 with HCl, then extracted with ethyl acetate and washed with brine, dried and concentrated under vacuum to yield (3S)-7-(6-amino-3-chloro-2-fluorophenyl)-5-oxo-1,2,3,5,8,8a-hexahydroindolizine-3-carboxylic acid as a yellow solid. LC/MS: mass calculated for $C_{15}H_{14}ClFN_2O_3$: 324.07, measured: 325.05 $[M+H]^+$.

Intermediate 2: Methyl (3S)-5,7-dioxooctahydroindolizine-3-carboxylate

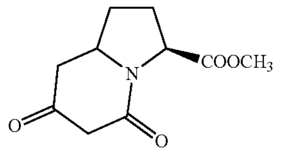 [SMILES: COC(=O)[C@@H]1CCC2CC(=O)CC(=O)N21]

Step 1: Methyl (2S)-5-allylpyrrolidine-2-carboxylate 1-(tert-Butyl) 2-methyl (2S)-5-allylpyrrolidine-1,2-dicarboxylate (10 g, 37.13 mmol, 1.0 eq) was dissolved in HCl solution (90 mL, 10.00 eq) (4 M in 1,4-dioxane). The resulting mixture was maintained at room temperature for 2 h. The solvent was removed under reduced pressure to yield methyl (2S)-5-allylpyrrolidine-2-carboxylate, which was used in the next step without further purification. LC/MS: mass calculated for $C_9H_{15}NO_2$: 169.11, measured: 170.20 $[M+H]^+$.

Step 2: Methyl (2S)-1-acryloyl-5-allylpyrrolidine-2-carboxylate

At −78° C., to a solution of methyl (2S)-5-allylpyrrolidine-2-carboxylate (6.0 g, 35.46 mmol, 1.0 eq) in THE (200 mL) was added TEA (23 mL, 177.28 mmol, 5.0 eq) followed by acryloyl chloride (3.2 g, 35.46 mmol, 1.0 eq). The resulting mixture was maintained at room temperature for 40 min. The reaction was then quenched with $NH_4C_1$ (aq.). The aqueous phase was extracted with EA. The organic layer was combined, dried over $Na_2SO_4$, filtered and concentrated. The residue was purified by silica gel chromatography (EA/PE) to yield methyl (2S)-1-acryloyl-5-allylpyrrolidine-2-carboxylate as a yellow oil. LC/MS: mass calculated for $C_{12}H_{17}NO_3$: 223.12, measured: 224.20 $[M+H]^+$.

Step 3: Methyl (3S)-5-oxo-1,2,3,5,8,8a-hexahydroindolizine-3-carboxylate

Under $N_2$, to a solution of methyl (2S)-1-acryloyl-5-allylpyrrolidine-2-carboxylate (7.2 g, 32.25 mmol, 1.0 eq) in DCM (100 mL) was added Grubbs' 2nd catalyst (2.7 g, 3.23 mmol, 0.1 eq). The resulting mixture was heated at 45° C. for 10 h and then the solvent was removed under reduced pressure. The residue was purified by silica gel column chromatography (EA/PE) to yield methyl (3S)-5-oxo-1,2,3,5,8,8a-hexahydroindolizine-3-carboxylate as brown oil. LC/MS: mass calculated for $C_{10}H_{13}NO_3$: 195.09, measured: 196.10 $[M+H]^+$.

Step 4: Methyl (3S)-7-hydroxy-5-oxooctahydroindolizine-3-carboxylate

Under $N_2$, to a solution of CuCl (0.102 g, 1.03 mmol, 0.2 eq) in THE (100 mL) was added BINAP (638 mg, 1.03 mmol, 0.2 eq). The mixture was maintained at room temperature for 15 min. Then t-BuONa (98 mg, 1.03 mmol, 0.2 eq) was added. 4,4,4',4',5,5,5',5'-Octamethyl-2,2'-bi(1,3,2-dioxaborolane) (1.6 g, 6.15 mmol, 1.2 eq) was added 30 min later, followed by addition of (3S)-methyl 5-oxo-1,2,3,5,8,8a-hexahydroindolizine-3-carboxylate (1.0 g, 5.12 mmol, 1.0 eq). MeOH (328 mg, 10.25 mmol, 2.0 eq) was then added dropwise. The resulting mixture was stirred for 16 h, then cooled to 0° C. $H_2O_2$ (6 mL, 51.23 mmol, 10.0 eq) was added and the reaction mixture was stirred for another 1 h. The solvent was removed under reduced pressure and the residue was purified through silica gel (DCM/MeOH) to yield methyl (3S)-7-hydroxy-5-oxooctahydroindolizine-3-carboxylate as a brown oil, which was used in the next step without further purification.

Step 5: Methyl (3S)-5,7-dioxooctahydroindolizine-3-carboxylate

To a solution of (3S)-methyl 7-hydroxy-5-oxo-octahydroindolizine-3-carboxylate (1.0 g) in DCM (100 mL) was added pyridinium chlorochromate (2.0 g, 9.38 mmol, 2.0 eq). The resulting mixture was stirred for 16 h. The solvent was removed under reduced pressure and the residue was purified through silica gel (EA/PE) to yield (3S)-methyl 5,7-dioxo-octahydroindolizine-3-carboxylate as a yellow oil. LC/MS: mass calculated for $C_{10}H_{13}NO_4$: 211.08, measured: 212.10 $[M+H]^+$.

Intermediate 3: Methyl (3S)-5,7-dioxooctahydroindolizine-3-carboxylate

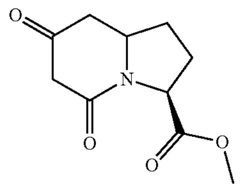

Step 1: Diethyl (S)-2-((tert-butoxycarbonyl)amino)-5-oxoheptanedioate

Into a 3-L 3-necked round-bottom flask purged and maintained with an inert atmosphere of nitrogen, was placed tetrahydrofuran (1.0 L), LDA (253 mL, 2 M in THF, 1.00 equiv). This was followed by the addition a solution of ethyl acetate (44.5 g, 505.2 mmol, 1.00 equiv) in THF (100 mL), dropwise with stirring at −78° C. and stirred for 30 min. To the resulting mixture was added a solution of 1-tert-butyl 2-ethyl (2S)-5-oxopyrrolidine-1,2-dicarboxylate (130 g, 505.2 mmol, 1.00 equiv) in THF (300 mL) with stirring at −78° C. The resulting solution was stirred overnight at room temperature. The reaction was then quenched by the addition of $NH_4C_1$ (aq., 50 mL). The resulting solution was extracted with DCM (3×1 L) and the organic layer was combined. The resulting mixture was washed with brine (2×500 mL). The resulting mixture was dried over anhydrous sodium sulfate and concentrated. The residue was applied onto a silica gel column with ethyl acetate to yield diethyl (S)-2-((tert butoxycarbonyl)amino)-5-oxoheptanedioate as a yellow oil. $^1$HNMR: (300 MHz, $CDCl_3$, ppm) δ 5.21-5.09 (m, 1H), 4.23-4.05 (m, 5H), 3.39 (s, 2H), 2.72-2.56 (m, 2H), 2.20-2.05 (m, 1H), 1.94-1.80 (m, 1H), 1.41 (s, 9H), 1.31-1.20 (m, 6H).

Step 2: Ethyl (S,Z)-5-(2-ethoxy-2-oxoethylidene)pyrrolidine-2-carboxylate

Into a 3-L 3-necked round-bottom flask purged and maintained with an inert atmosphere of nitrogen, was placed 1,7-diethyl (2S)-2-[(tert-butoxycarbonyl)amino]-5-oxoheptanedioate (105.0 g, 304.0 mmol, 1.00 equiv), and trifluoroacetic acid (59.6 g, 608.0 mmol, 2.00 equiv). The resulting solution was stirred for 3 h at 25° C. The resulting mixture was concentrated. The resulting solution was diluted with DCM (100 mL). The pH value of the solution was adjusted to 7 with $Na_2CO_3$. The resulting solution was extracted with DCM (3×500 mL), the organic layer was dried over anhydrous sodium sulfate and concentrated. The residue was applied onto a silica gel column with ethyl acetate/petroleum ether (1:4) to yield ethyl (S,Z)-5-(2-ethoxy-2-oxoethylidene)pyrrolidine-2-carboxylate as a light yellow oil. LC/MS: mass calculated for $C_{11}H_{17}NO_4$: 227.12, measured: 228.00 $[M+H]^+$.

Step 3: Ethyl (2S,5R)-5-(2-ethoxy-2-oxoethyl)pyrrolidine-2-carboxylate

Into a 500 ml round-bottom flask, was placed acetic acid (280 mL), ethyl (2S,5Z)-5-(2-ethoxy-2-oxoethylidene)pyrrolidine-2-carboxylate (35.0 g, 154.0 mmol, 1.00 equiv), $PtO_2$ (4.2 g, 18.5 mmol, 0.12 equiv). The mixture was stirred for 3 h under hydrogen atmosphere at room temperature. The mixture was concentrated and diluted with EA (3 L). $NaHCO_3$ aqueous solution added to adjust the pH of the mixture to pH 7. The resulting solution was extracted with ethyl acetate (3×2 L) acetate, dried over anhydrous sodium sulfate and concentrated to yield ethyl (2S,5R) 5-(2-ethoxy-2-oxoethyl)pyrrolidine-2-carboxylate as a yellow oil. $^1$HNMR (300 MHz, $CDCl_3$, ppm) δ 4.19 (dq, J=11.5, 7.1 Hz, 4H), 3.87 (dd, J=9.0, 5.5 Hz, 1H), 3.71 (s, 1H), 3.63-3.48 (m, 1H), 2.69-2.49 (m, 2H), 2.23-2.08 (m, 1H), 2.05-1.91 (m, 2H), 1.55-1.36 (m, 1H), 1.29 (dt, J=11.5, 7.1 Hz, 6H).

Step 4: Ethyl (2S,5R)-5-(2-ethoxy-2-oxoethyl)-1-(3-ethoxy-3-oxopropanoyl)pyrrolidi ne-2-carboxylate Into a 2-L 3-necked round-bottom flask purged and maintained with an inert atmosphere of nitrogen, was placed DCM (700 mL), DIPEA (39.4 g, 305.3 mmol, 2.00 equiv), ethyl (2S,5R)-5-(2-ethoxy-2-oxoethyl)pyrrolidine-2-carboxylate (35.0 g, 152.6 mmol, 1.00 equiv). This was followed by the addition of a solution of ethyl 3-chloro-3-oxopropanoate (29.9 g, 198.4 mmol, 1.30 equiv) in DCM (50 mL) dropwise with stirring at 0° C. The resulting solution was stirred for 1 h at room temperature. The resulting mixture was washed with water (2×200 mL). The mixture was dried over anhydrous sodium sulfate and concentrated. The residue was applied to a silica gel column with ethyl acetate/petroleum ether (1:20-1:2) to yield ethyl (2S,5R)-5-(2-ethoxy-2-oxoethyl)-1-(3-ethoxy-3-oxopropanoyl)pyrrolidine-2-carboxylate as a yellow oil. LC/MS: mass calculated for $C_{16}H_{25}NO_7$: 343.16, measured: 334.00 $[M+H]^+$.

Step 5: Diethyl (3S,8aR)-5,7-dioxooctahydroindolizine-3,6-dicarboxylate

Into a 1-L round-bottom flask purged and maintained with an inert atmosphere of nitrogen, was placed ethyl alcohol (500 mL), ethyl (2S,5R)-5-(2-ethoxy-2-oxoethyl)-1-(3-ethoxy-3-oxopropanoyl)pyrrolidine-2-carboxylate (38.6 g, 112.4 mmol, 1.00 equiv), sodium ethoxide (8.0 g, 118.0 mmol, 1.05 equiv). The resulting solution was stirred for 50 min at 60° C. The reaction mixture was cooled with a water/ice bath and concentrated. The mixture was poured into HCl (1 N, 300 mL). The resulting solution was extracted with ethyl acetate (2×200 mL) acetate, dried over anhydrous sodium sulfate and concentrated. The residue was applied onto a silica gel column with ethyl acetate/petroleum ether (1: 20-1:3) to yield diethyl (3S,8aR)-5,7-dioxooctahydroindolizine-3,6-dicarboxylate as a yellow oil. LC/MS: mass calculated for $C_{14}H_{19}NO_8$: 297.12, measured: 298.00 $[M+H]^+$.

Step 6: Ethyl (3S,8aR)-5,7-dioxooctahydroindolizine-3-carboxylate

Into a 2-L 3-necked round-bottom flask, was placed 3,6-diethyl (3S,8aR)-5,7-dioxo-hexahydroindolizine-3,6-dicarboxylate (28.0 g, 94.1 mmol, 1.00 equiv), and acetic acid (196 mL), $H_2O$ (20 mL). The resulting solution was stirred for 2 h at 110° C. The reaction mixture was cooled with a water/ice bath. The resulting mixture was concentrated to yield ethyl (3S,8aR)-5,7-dioxo-hexahydroindolizine-3-carboxylate as a yellow oil.

$^1$HNMR (300 MHz, $CDCl_3$, ppm) δ 4.63 (d, J=8.0 Hz, 1H), 4.23 (q, J=7.1 Hz, 2H), 4.08-3.90 (m, 1H), 3.32 (s, 2H), 2.88 (dd, J=16.6, 3.2 Hz, 1H), 2.65-2.54 (m, 1H), 2.41-2.09 (m, 3H), 1.99-1.79 (m, 1H), 1.31 (t, J=7.1 Hz, 3H).

Intermediate 4: (3S)-7-(3-chloro-6-(4-chloro-1H-1,2,3-triazol-1-yl)-2-fluorophenyl)-5-oxo-1,2,3,5,8,8a-hexahydroindolizine-3-carboxylic acid

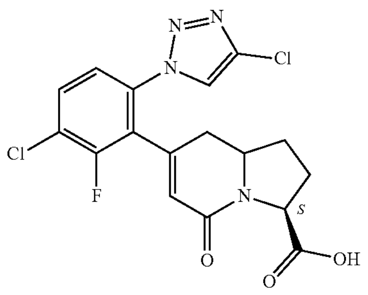

Step 1: 1-Azido-4-chloro-3-fluoro-2-iodobenzene

To a solution of 4-chloro-3-fluoro-2-iodoaniline (10 g, 36.83 mmol, 1.0 eq.) in $CH_3CN$ (100 mL) and azidotrimethylsilane (10 mL) was added tert-butyl nitrite (5.7 g, 55.25 mmol, 1.5 eq.) dropwise. The resulting mixture was stirred at room temperature overnight. The mixture was concentrated. The residue was applied onto a silica gel column to yield of 1-azido-4-chloro-3-fluoro-2-iodobenzene as a yellow solid. LC/MS: mass calculated for $C_6H_2ClFIN_3$: 296.90, measured: 297.00 $[M+H]^+$.

Step 2: 1-(4-Chloro-3-fluoro-2-iodophenyl)-4-(tri-tert-butylstannyl)-1H-1,2,3 triazole To 1-azido-4-chloro-3-fluoro-2-iodobenzene (5 g, 16.81 mmol, 1.0 eq.) in toluene (50 mL) was added tributyl (ethynyl)stannane (5.3 g, 16.81 mmol, 1 eq.). The resulting mixture was stirred at 100° C. for overnight. The mixture was concentrated. The residue was applied onto a silica gel column to yield 1-(4-chloro-3-fluoro-2-iodophenyl)-4-

(tributylstannyl)-1H-1,2,3-triazole as a yellow solid. LC/MS: mass calculated for $C_{20}H_{30}ClFIN_3Sn$: 613.02, measured: 614.00 $[M+H]^+$.

Step 3: 4-Chloro-1-(4-chloro-3-fluoro-2-iodophenyl)-1H-1,2,3-triazole

To 1-(4-chloro-3-fluoro-2-iodophenyl)-4-(tributylstannyl)-1H-1,2,3-triazole (10 g, 16.33 mmol, 1.0 eq.) in $CH_3CN$ (100 mL) was added NCS (2.2 g, 16.33 mmol, 1 eq.). The resulting mixture was stirred at 80° C. for 4 h, then concentrated. The residue was applied onto a silica gel column to yield 4-chloro-1-(4-chloro-3-fluoro-2-iodophenyl)-1H-1,2,3-triazole. LC/MS: mass calculated for $C_8H_3Cl_2FIN_3$: 356.87, measured: 358.10 $[M+H]^+$.

Step 4: Methyl (3S)-5-oxo-7-(((trifluoromethyl) sulfonyl)oxy)-1,2,3,5,8,8a-hexahydroindolizine-3-carboxylate To a solution of methyl (3S)-7-hydroxy-5-oxo-1,2,3,5,8,8a-hexahydroindolizine-3-carboxylate (1 g, 4.73 mmol, 1.0 equiv) in DCM (15 mL) was added 1,1,1-trifluoro-N-phenyl-N-((trifluoromethyl)sulfonyl)methanesulfonamide (1.9 g, 5.32 mmol, 1.1 equiv), and TEA (958 mg, 9.47 mmol, 2.0 equiv). The reaction mixture was stirred overnight at room temperature. The reaction mixture was concentrated to dryness under reduced pressure to yield a residue, which was purified by column chromatography on silica gel with EA/PE (0-100%) to yield methyl (3S)-5-oxo-7-(((trifluoromethyl)sulfonyl)oxy)-1,2,3,5,8,8a-hexahydroindolizine-3-carboxylate as a yellow solid. LC/MS: mass calculated for $C_{11}H_{12}F_3NO_6$: 343.03, measured: 344.10 $[M+H]^+$.

Step 5: Methyl (3S)-5-oxo-7-(4,4,5,5-tetramethyl-1,3,2-dioxaborolan-2-yl)-1,2,3,5,8,8a-hexahydroindolizine-3-carboxylate Under an inert atmosphere of nitrogen, to a solution of methyl (3S)-5-oxo-7-(((trifluoromethyl)sulfonyl)oxy)-1,2,3,5,8,8a-hexahydroindolizine-3-carboxylate (800 mg, 2.33 mmol, 1.0 equiv) in 1,4-dioxane (10 mL), were added 4,4,4',4',5,5,5',5'-octamethyl-2,2'-bi(1,3,2-dioxaborolane (888 mg, 3.49 mmol, 1.5 equiv), Pd(dppf)$Cl_2$ (171 mg, 0.23 mmol, 0.1 equiv), and KOAc (457 mg, 4.65 mmol, 2.0 equiv). The reaction mixture was stirred for 2 h at 90° C. The solids were filtered out by CELITE. The filtrate was concentrated under vacuum to yield methyl (3S)-5-oxo-7-(4,4,5,5-tetramethyl-1,3,2-dioxaborolan-2-yl)-1,2,3,5,8,8a-hexahydroindolizine-3-carboxylate as a yellow solid. LC/MS: mass calculated for $C_{16}H_{24}BNO_5$: 321.17, measured: 322.10 $[M+H]^+$.

Step 6: Methyl (3S)-7-(3-chloro-6-(4-chloro-1H-1,2,3-triazol-1-yl)-2-fluorophenyl)-5-oxo-1,2,3,5,8,8a-hexahydroindolizine-3-carboxylate Under an inert atmosphere of nitrogen, to a solution of methyl (3S)-5-oxo-7-(4,4,5,5-tetramethyl-1,3,2-dioxaborolan-2-yl)-1,2,3,5,8,8a-hexahydroindolizine-3-carboxylate (500 mg, 1.56 mmol, 1.0 equiv) in 1,4-dioxane (10 mL) with $H_2O$ (1.0 mL), were added 4-chloro-1-(4-chloro-3-fluoro-2-iodophenyl)-1H-1,2,3-triazole (613 mg, 1.71 mmol, 1.1 equiv), $Pd(PPh_3)_4$ (180 mg, 0.156 mmol, 0.1 equiv), $K_2CO_3$ (430 mg, 3.11 mmol, 2.0 equiv). The reaction mixture was stirred for 2 h at 90° C., then concentrated to dryness under reduced pressure to yield a residue, which was purified by column chromatography on silica gel with MeOH/DCM (0-15%) to yield methyl (3S)-7-(3-chloro-6-(4-chloro-1H-1,2,3-triazol-1-yl)-2-fluorophenyl)-5-oxo-1,2,3,5,8,8a-hexahydroindolizine-3-carboxylate as a yellow solid. LC/MS: mass calculated for $C_{18}H_{15}Cl_2FN_4O_3$: 424.05, measured: 425.05 $[M+H]^+$.

Step 7: (3S)-7-(3-Chloro-6-(4-chloro-1H-1,2,3-triazol-1-yl)-2-fluorophenyl)-5-oxo-1,2,3,5,8,8a-hexahydroindolizine-3-carboxylic acid To a solution of methyl (3S)-7-(3-chloro-6-(4-chloro-1H-1,2,3-triazol-1-yl)-2-fluorophenyl)-5-oxo-1,2,3,5,8,8a-hexahydroindolizine-3-carboxylate (300 mg, 0.70 mmol, 1.0 equiv) in THE (6 mL), MeOH (2 mL), and $H_2O$ (2 mL) was added LiOH (84 mg, 3.51 mmol, 5.0 equiv). The reaction mixture was stirred at room temperature for 3 h. The pH was adjusted to 5~6 by HCl (2 M) at 0° C. and the resulting mixture was extracted with ethyl acetate. The combined organic layer was washed with brine, dried over $Na_2SO_4$ and concentrated to yield (3S)-7-(3-chloro-6-(4-chloro-1H-1,2,3-triazol-1-yl)-2-fluorophenyl)-5-oxo-1,2,3,5,8,8a-hexahydroindolizine-3-carboxylic acid as a yellow solid. LC/MS: mass calculated for $C_{17}H_{13}Cl_2FN_4O_3$: 410.03, measured: 411.05 $[M+H]^+$.

Intermediate 5: (3S)-7-(3-Chloro-2-fluoro-6-(4-(trifluoromethyl)-1H-1,2,3-triazol-1-yl)phenyl)-5-oxo-1,2,3,5,8,8a-hexahydroindolizine-3-carboxylic acid

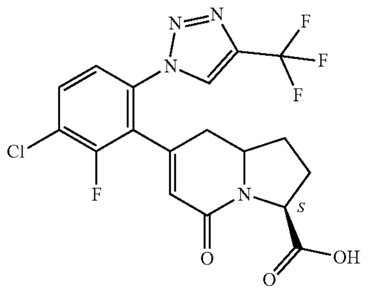

Step 1: Methyl (3S)-7-(6-amino-3-chloro-2-fluorophenyl)-5-oxo-1,2,3,5,8,8a-hexahydroindolizine-3-carboxylate To a mixture of methyl 5-oxo-7-(((trifluoromethyl)sulfonyl)oxy)-1,2,3,5,8,8a-hexahydroindolizine-3-carboxylate (5.0 g, 14.57 mmol, 1.0 equiv.) and (6-amino-3-chloro-2-fluorophenyl)boronic acid (5.5 g, 29.13 mmol, 2.0 equiv.) in 1,4-dioxane (50 mL) and water (10 mL) was added potassium phosphate (7.7 g, 36.41 mmol, 2.5 equiv.) and Pd(dppf) $Cl_2$ (1.1 g, 1.46 mmol, 0.1 equiv.). The flask was evacuated and flushed three times with nitrogen. The solution was stirred at 100° C. for 1 h under $N_2$. To the solution was added water and the resulting mixture was extracted with EA twice.

The combined organic layers were washed with brine, dried over $Na_2SO_4$ and concentrated under vacuum. The residue was purified by silica gel chromatography (0→80% EA/PE) to yield methyl 7-(6-amino-3-chloro-2-fluorophenyl)-5-oxo-1,2,3,5,8,8a-hexahydroindolizine-3-carboxylate as a yellow solid. LC/MS: mass calculated for $C_{18}H_{16}ClFN_2O_3$: 338.08, measured (ES, m/z): 339.10 [M+H]+.

Step 2: Methyl (3S)-7-(6-azido-3-chloro-2-fluorophenyl)-5-oxo-1,2,3,5,8,8a-hexahydroindolizine-3-carboxylate To a mixture of methyl 7-(6-amino-3-chloro-2-fluorophenyl)-5-oxo-1,2,3,5,8,8a-hexahydroindolizine-3-carboxylate (3.4 g, 10.04 mmol, 1.0 equiv.) and azidotrimethylsilane (2.6 mL, 20.07 mmol, 2.0 equiv.) in acetonitrile (35 mL) was added tert-butyl nitrite (2.4 mL, 20.07 mmol, 2.0 equiv.) at 0° C. The solution was stirred at room temperature for 1 h. To the mixture was added water and the resulting mixture was extracted with EA twice. The combined organic layers were washed with brine, dried over $Na_2SO_4$ and concentrated under vacuum. The residue was purified by silica gel chromatography (0→80% EA/PE) to yield methyl 7-(6-azido-3-chloro-2-fluorophenyl)-5-oxo-1,2,3,5,8,8a-hexahydroindolizine-3-carboxylate as a yellow solid. LC/MS: mass calculated for $C_{18}H_{14}ClFN_4O_3$: 364.07, measured (ES, m/z): 365.10 $[M+H]^+$.

Step 3: Methyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate To a mixture of methyl 7-(6-azido-3-chloro-2-fluorophenyl)-5-oxo-1,2,3,5,8,8a-hexahydroindolizine-3-carboxylate (2.9 g, 7.95 mmol, 1.0 equiv.) and 4,4,4-trifluorobut-2-ynoic acid (5.5 g, 39.75 mmol, 5.0 equiv.) in acetonitrile (30 mL) was added cuprous oxide (455 mg, 3.18 mmol, 0.4 equiv.). The flask was evacuated and flushed three times with nitrogen. The solution was stirred at 80° C. for 2 h under $N_2$. The solution was concentrated under vacuum and purified by silica gel chromatography (0→60% EA/PE) to yield methyl 7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate as a white solid. LC/MS: mass calculated for $C_{19}H_{15}ClF_4N_4O_3$: 458.08, measured (ES, m/z): 459.05 $[M+H]^+$.

Step 4: (3S)-7-(3-Chloro-2-fluoro-6-(4-(trifluoromethyl)-1H-1,2,3-triazol-1-yl)phenyl)-5-oxo-1,2,3,5,8,8a-hexahydroindolizine-3-carboxylic acid To a mixture of methyl 7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate (2.8 g, 6.10 mmol, 1.0 equiv.) in acetonitrile (30 mL) and water (0.2 mL) was added triethylamine (5.0 mL, 36.62 mmol, 6.0 equiv.) and lithium bromide (1.6 g, 18.31 mmol, 3.0 equiv.). The solution was stirred at 60° C. for 18 h. The mixture was concentrated under vacuum. The resulting residue was purified by reverse phase chromatography on C18 (330 g, $ACN/H_2O$ (0.05% $CF_3COOH$): 0→30%) to yield 7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylic acid as a yellow solid. LC/MS: mass calculated for $C_{18}H_{13}ClF_4N_4O_3$: 444.06, measured (ES, m/z): 445.15 $[M+H]^+$.

Intermediate 6: 7-(3-Chloro-2-fluoro-6-(1H-tetrazol-1-yl)phenyl)-2-methyl-5-oxo-1,2,3,5,8,8a-hexahydroindolizine-3-carboxylic acid

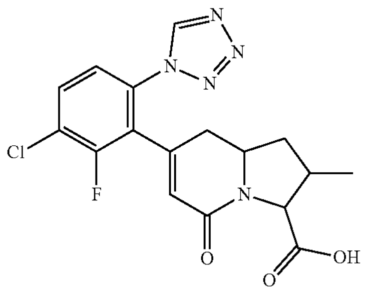 [SMILES: CC1CC2CC(c3c(-n4cnnn4)ccc(Cl)c3F)=CC(=O)N2C1C(=O)O]

Step 1: Ethyl (E)-2-((2,2-dimethylpropylidene)amino)acetate

To a solution of glycine ethyl ester hydrochloride (50.0 g, 358.22 mmol, 1.0 equiv.) in dichloroethane (500 mL), were added pivaldehyde (33.9 g, 394.04 mmol, 1.1 equiv.), $Et_3N$ (39.9 g, 394.04 mmol, 1.1 equiv.), $MgSO_4$ (43.1 g, 358.22 mmol, 1.0 equiv.). The reaction mixture was stirred at room temperature overnight. The reaction was filtrated and concentrated to yield ethyl (E)-2-((2,2-dimethylpropylidene)amino)acetate as a white solid.

Step 2: 1-Ethyl 5-methyl (E)-2-((2,2-dimethylpropylidene)amino)-3-methylpentanedioate To a solution of ethyl (E)-2-((2,2-dimethylpropylidene)amino)acetate (55.0 g, 321.19 mmol, 1.0 equiv.) in THE (450 mL) was added LiBr (30.7 g, 353.31 mmol, 1.1 equiv.). The reaction mixture was stirred for 10 minutes at room temperature. trans-Methyl crotonate (32.2 g, 321.19 mmol, 1.0 equiv) in THE (100 mL) and DBU (48.9 g, 321.19 mmol, 1.0 equiv.) were added to the reaction mixture. The reaction mixture was stirred for 10 minutes at room temperature. The reaction was quenched with water and extracted with EA. The combined organic layer was washed with brine, dried over $Na_2SO_4$ and concentrated. The residue was purified by silica gel chromatography (0-30% DCM/MeOH) to yield 1-ethyl 5-methyl (E)-2-((2,2-dimethylpropylidene)amino)-3-methylpentanedioate as a yellow oil.

Step 3: Ethyl 3-methyl-5-oxopyrrolidine-2-carboxylate

To a solution of 1-ethyl 5-methyl (E)-2-((2,2-dimethylpropylidene)amino)-3-methylpentanedioate (55.0 g, 202.69 mmol, 1.0 equiv.) in MeOH (400 mL) with $H_2O$ (100 mL) was added $CH_3COOH$ (5 mL). The reaction mixture was stirred overnight at 80° C. The reaction was quenched with water and extracted with ethyl acetate. The combined organic layer was washed with brine, dried over $Na_2SO_4$ and concentrated. The residue was purified by silica gel chromatography (0-30% DCM/MeOH) to yield ethyl 3-methyl-5-oxopyrrolidine-2-carboxylate as a yellow oil.

Step 4: 1-(Tert-butyl) 2-ethyl 3-methyl-5-oxopyrrolidine-1,2-dicarboxylate

To a solution of ethyl 3-methyl-5-oxopyrrolidine-2-carboxylate (27.0 g, 157.72 mmol, 1.0 equiv.) and di-tert-butyl dicarbonate (86.1 g, 394.29 mmol, 2.5 equiv.) in dichloromethane (500 mL), were added 4-dimethylaminopyridine (3.9 g, 31.54 mmol, 0.2 equiv.) and triethylamine (43.8 mL, 315.43 mmol, 2.0 equiv.). The reaction mixture was stirred over night at room temperature. The mixture was concentrated. The residue was purified by silica gel chromatography (0-30% EA/PE) to yield 1-(tert-butyl) 2-ethyl 3-methyl-5-oxopyrrolidine-1,2-dicarboxylate as a yellow oil. LC/MS: mass calculated for $C_{13}H_{21}NO_5$: 271.14, measured: 565.40 $[2M+Na]^+$.

Step 5: 1-(Tert-butyl) 2-ethyl 5-methoxy-3-methylpyrrolidine-1,2-dicarboxylate

To a solution of 1-(tert-butyl) 2-ethyl 3-methyl-5-oxopyrrolidine-1,2-dicarboxylate (20.0 g, 73.72 mmol, 1.0 equiv.) in THE (300 mL) was added lithium triethylborohydride (110.6 mL, 110.58 mmol, 1.5 equiv, 1M in THE) at 78° C. The reaction mixture was stirred for 40 min at −78° C., then $NaHCO_3$ (120 mL) was added at −78° C. and the mixture was warmed to 0° C. Hydrogen peroxide (15 mL, 30%) was then added. The mixture was stirred for 30 min at room temperature. THE was removed under vacuum, and the resulting mixture was extracted with diethyl ether, washed with brine, dried and concentrated under vacuum to yield a colorless oil. The oil was dissolved in methanol (300 mL), and p-toluenesulfonic acid (1.3 g, 7.37 mmol, 0.1 equiv.) was added. The solution was stirred over night at room temperature. The reaction was quenched with $NaHCO_3$ and extracted with diethyl ether. The combined organic layer was washed with brine, dried over $Na_2SO_4$ and concentrated to yield 1-(tert-butyl) 2-ethyl 5-methoxy-3-methylpyrrolidine-1,2-dicarboxylates a colorless oil.

Step 6: 1-(Tert-butyl) 2-ethyl 5-allyl-3-methylpyrrolidine-1,2-dicarboxylate

To a solution of 1-(tert-butyl) 2-ethyl 5-methoxy-3-methylpyrrolidine-1,2-dicarboxylate (20.0 g, 69.60 mmol, 1.0 equiv.) in diethyl ether (300 mL), were added allyltrimethylsilane (48.7 ml, 306.25 mmol, 4.4 equiv.) and boron trifluoride etherate (11.9 g, 83.5 mmol, 1.2 equiv.) at −40° C. The reaction mixture was stirred for 30 min at −40° C., and then warmed to room temperature and stirred for 40 min. The reaction was quenched with $Na_2CO_3$ and extracted with ethoxyethane. The combined organic layer was washed with brine, dried over $Na_2SO_4$ and concentrated. The residue was purified by silica gel chromatography (0-30% EtOAc/petroleum ether) to yield 1-(tert-butyl) 2-ethyl 5-allyl-3-methylpyrrolidine-1,2-dicarboxylate as a yellow oil. LC/MS: mass calculated for $C_{16}H_{27}NO_4$: 297.19, measured: 298.10 $[M+H]^+$.

Step 7: Ethyl 5-allyl-3-methylpyrrolidine-2-carboxylate

To a solution of 1-(tert-butyl) 2-ethyl 5-allyl-3-methylpyrrolidine-1,2-dicarboxylate (15.0 g, 50.44 mmol, 1.0 equiv.) in dichloromethane (200 mL), was added HCl in 1,4-dioxane (150 mL, 4N). The reaction mixture was stirred for 2 h at room temperature. The resulting solution was concentrated under vacuum to yield ethyl 5-allyl-3-methylpyrrolidine-2-carboxylate as a white solid. LC/MS: mass calculated for $C_{11}H_{19}NO_2$: 197.14, measured: 198.05 $[M+H]^+$.

Step 8: Ethyl 1-acryloyl-5-allyl-3-methylpyrrolidine-2-carboxylate

To a solution of ethyl 5-allyl-3-methylpyrrolidine-2-carboxylate (9.6 g, 41.07 mmol, 1.0 equiv.) in tetrahydrofuran (200 mL) was added triethylamine (28.5 mL, 205.36 mmol, 5.0 equiv.). The reaction mixture was stirred for −78° C. and acryloyl chloride (3.7 mL, 45.18 mmol, 1.1 equiv.) was drop-wise under $N_2$. The reaction mixture was stirred for 2 h at room temperature. The reaction was quenched by water (100 mL) and extracted with ethyl acetate (2×100 mL), and the organic layers combined and dried over anhydrous sodium sulfate. The residue was applied onto a silica gel column with ethyl acetate/petroleum ether (2:3) to yield ethyl 1-acryloyl-5-allyl-3-methylpyrrolidine-2-carboxylate as a yellow oil. LC/MS: mass calculated for $C_{14}H_{21}NO_3$: 251.15, measured: 252.10 $[M+H]^+$.

Step 9: Ethyl 2-methyl-5-oxo-1,2,3,5,8,8a-hexahydroindolizine-3-carboxylate

To a solution of ethyl 1-acryloyl-5-allyl-3-methylpyrrolidine-2-carboxylate (12.5 g, 49.74 mmol, 1.0 equiv.) in dichloromethane (400 mL) was added Grubbs catalyst 2nd generation (2.1 g, 2.49 mmol, 0.05 equiv.). The reaction mixture was stirred over night at 45° C. The residue was applied onto a silica gel column with ethyl acetate/petroleum ether (2:3) to yield ethyl 2-methyl-5-oxo-1,2,3,5,8,8a-hexahydroindolizine-3-carboxylate as a brown oil. LC/MS: mass calculated for $C_{12}H_{17}NO_3$: 223.12, measured: 224.05 $[M+H]^+$.

Step 10: Ethyl 7-hydroxy-2-methyl-5-oxooctahydroindolizine-3-carboxylate

A flask was charged with copper(I) chloride (0.53 g, 5.38 mmol, 0.2 equiv.) and BINAP (3.3 g, 5.38 mmol, 0.2 equiv.) under nitrogen. Freshly degassed (freeze-pump-thaw) THF (50 mL) was added, and the yellow reaction mixture was stirred for 15 min. Then sodium tert-butoxide (0.52 g, 5.38 mmol, 0.2 equiv.) was added in one portion and stirring was continued for 30 min. Bis(pinacolato)diboron (8.2 g, 32.25 mmol, 1.2 equiv.) was added and the reaction mixture was stirred for 10 min, then a solution of ethyl 2-methyl-5-oxo-1,2,3,5,8,8a-hexahydroindolizine-3-carboxylate (6.0 g, 26.87 mmol, 1.0 equiv.) in THF (10 mL) was added, followed by addition of MeOH (1.7 g, 53.75 mmol, 2.0 equiv.). After stirring overnight, 30% hydrogen peroxide (30.5 mL, 268.74 mmol, 10.0 equiv.) was added at 0° C. The resulting solution was stirred overnight at room temperature. The mixture was concentrated under vacuum. The residue was purified by silica gel column (0-10% MeOH/DCM) to yield ethyl 7-hydroxy-2-methyl-5-oxooctahydroindolizine-3-carboxylate as a yellow oil LC/MS: mass calculated for $C_{12}H_{19}NO_4$: 241.13, measured: 242.25 $[M+H]^+$, and ethyl 2-methyl-5-oxo-7-(4,4,5,5-tetramethyl-1,3,2-dioxaborolan-2-yl)octahydroindolizine-3-carboxylate as a brown solid. LC/MS: mass calculated for $C_{18}H_{30}BNO5$: 351.22, measured: 352.30 $[M+H]^+$.

Step 11: Ethyl 7-hydroxy-2-methyl-5-oxooctahydroindolizine-3-carboxylate

To a solution of ethyl 2-methyl-5-oxo-7-(4,4,5,5-tetramethyl-1,3,2-dioxaborolan-2-yl)octahydroindolizine-3-carboxylate (4.8 g, 13.67 mmol, 1.0 equiv. in THF/$H_2O$ (50 mL, 4/1), was added sodium perborate trihydrate (5.59 g, 68.33 mmol, 5.0 equiv.). The reaction mixture was stirred over night at room temperature. The mixture was concentrated under vacuum. The residue was purified by silica gel column (0-10% MeOH/DCM) to yield ethyl 7-hydroxy-2-methyl-5-oxooctahydroindolizine-3-carboxylate as a yellow oil. LC/MS: mass calculated for $C_{12}H_{19}NO_4$: 241.13, measured: 242.25 $[M+H]^+$.

Step 12: Ethyl 2-methyl-5,7-dioxooctahydroindolizine-3-carboxylate

To a solution of ethyl 7-hydroxy-2-methyl-5-oxooctahydroindolizine-3-carboxylate (5.9 g, 24.45 mmol, 1.0 equiv.) in dichloromethane (200 mL), was added pyridinium chlorochromate (10.5 g, 48.91 mmol, 2.0 equiv.). The reaction mixture was stirred over night at room temperature. The mixture was concentrated under vacuum. The residue was purified by silica gel column (0-10% MeOH/DCM) to yield ethyl 2-methyl-5,7-dioxooctahydroindolizine-3-carboxylate as a brown oil. LC/MS: mass calculated for $C_{12}H_{17}NO_4$: 239.12, measured: 240.25 $[M+H]^+$.

Step 13: Ethyl 2-methyl-5-oxo-7-(((trifluoromethyl)sulfonyl)oxy)-1,2,3,5,8,8a-hexahydroindolizine-3-carboxylate To a solution of ethyl 2-methyl-5,7-dioxooctahydroindolizine-3-carboxylate (4.0 g, 16.72 mmol, 1.0 equiv.) in dichloromethane (50 mL), were added triethylamine (3.4 g, 33.44 mmol, 2.0 equiv.) and 1,1,1-trifluoro-N-phenyl-N-((trifluoromethyl)sulfonyl)methanesulfonamide (7.2 g, 20.06 mmol, 1.2 equiv.). The reaction mixture was stirred overnight at room temperature and then concentrated under reduced pressure. The residue was purified by silica gel chromatography (0-60% EA/PE) to yield ethyl 2-methyl-5-oxo-7-(((trifluoromethyl)sulfonyl)oxy)-1,2,3,5,8,8a-hexahydroindolizine-3-carboxylate as a yellow oil. LC/MS: mass calculated for $C_{13}H_{16}F_3NO_6S$: 371.07, measured: 372.15 $[M+H]^+$.

Step 14: Ethyl 7-(6-amino-3-chloro-2-fluorophenyl)-2-methyl-5-oxo-1,2,3,5,8,8a-hexahydroindolizine-3-carboxylate To a solution of ethyl 2-methyl-5-oxo-7-(((trifluoromethyl)sulfonyl)oxy)-1,2,3,5,8,8a-hexahydroindolizine-3-carboxylate (6.0 g, 16.16 mmol, 1.0 equiv.), were added (6-amino-3-chloro-2-fluorophenyl)boronic acid (3.7 g, 19.39 mmol, 1.2 equiv.), potassium carbonate (4.5 g, 32.32 mmol 2.0 equiv.) in 1,4-dioxane/$H_2O$ (100 mL, 10/1), and [1,1'-bis(diphenylphosphino)ferrocene]dichloropalladium (II) (0.59 g, 0.81 mmol, 0.1 equiv.). The reaction mixture was stirred for 2 h at 80° C. The reaction was quenched with water and extracted with ethyl acetate. The combined organic layer was washed with brine, dried over $Na_2SO_4$ and concentrated. The residue was purified by silica gel chromatography (0-100% PE/EA) to yield ethyl 7-(6-amino-3-chloro-2-fluorophenyl)-2-methyl-5-oxo-1,2,3,5,8,8a-hexahydroindolizine-3-carboxylate as a brown solid. LC/MS: mass calculated for $C_{18}H_{20}ClFN_2O_3$: 366.11, measured: 367.20 $[M+H]^+$.

Step 15: 7-(6-Amino-3-chloro-2-fluorophenyl)-2-methyl-5-oxo-1,2,3,5,8,8a-hexahydroindolizine-3-carboxylic acid To a solution of ethyl 7-(6-amino-3-chloro-2-fluorophenyl)-2-methyl-5-oxo-1,2,3,5,8,8a-hexahydroindolizine-3-carboxylate (5.0 g, 13.63 mmol, 1.0 equiv.) in THF/$H_2O$/MeOH (100 mL, 3/1/1), was added lithium hydroxide (2.7 g, 68.15 mmol, 5.0 equiv.) The reaction mixture was stirred for 1 h at room temperature. The residue was adjusted to pH 4 with HCl, then extracted with ethyl acetate and washed with brine, dried and concentrated under vacuum to yield 7-(6-amino-3-chloro-2-fluorophenyl)-2-methyl-5-oxo-1,2,3,5,8,8a-hexahydroindolizine-3-carboxylic acid as a brown solid.

Step 16: 7-(3-Chloro-2-fluoro-6-(1H-tetrazol-1-yl)phenyl)-2-methyl-5-oxo-1,2,3,5,8,8a-hexahydroindolizine-3-carboxylic acid To a solution of 7-(6-amino-3-chloro-2-fluorophenyl)-2-methyl-5-oxo-1,2,3,5,8,8a-hexahydroindolizine-3-carboxylic acid (2.1 g, 6.20 mmol, 1.0 equiv.) in acetic acid (30 mL) were added azidotrimethylsilane (7.1 g, 61.99 mmol, 10.0 equiv.), and trimethoxymethane (6.6 g, 61.99 mmol, 10.0 equiv.). The reaction mixture was stirred at room temperature overnight. The reaction was diluted with water and extracted with EA. The combined extracts were washed with water, dried over $Na_2SO_4$, filtered and purified by silica gel chromatography (0-20% DCM/methanol) to yield 7-(3-chloro-2-fluoro-6-(1H-tetrazol-1-yl)phenyl)-2-methyl-5-oxo-1,2,3,5,8,8a-hexahydroindolizine-3-carboxylic acid as a yellow solid. LC/MS: mass calculated for $C_{17}H_{15}ClFN_5O_3$: 391.08, measured 392.10 $[M+H]^+$.

Intermediate 7: (3S)-7-(3-Chloro-2-fluoro-6-(1H-tetrazol-1-yl)phenyl)-1,1-dimethyl-5-oxo-1,2,3,5,8,8a-hexahydroindolizine-3-carboxylic acid

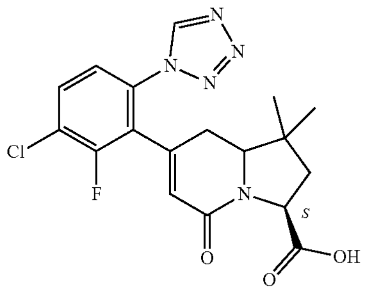

Step 1: 1-(Tert-butyl) 2-methyl (S)-4,4-dimethyl-5-oxopyrrolidine-1,2-dicarboxylate To a solution of 1-(tert-butyl) 2-methyl (S)-5-oxopyrrolidine-1,2-dicarboxylate (20.0 g, 82.20 mmol, 1.0 equiv.) in tetrahydrofuran (300 mL), was added lithium bis(trimethylsilyl)amide (86.0 mL, 86.30 mmol, 1.05 equiv.) at −78° C. The reaction mixture was stirred for 1 h at −78° C., then iodomethane (7.7 mL, 123.30 mmol, 1.5 equiv.) was added at −78° C. The reaction mixture was warmed to room temperature, then stirred for anther 1 h. The reaction was quenched by water (200 mL), extracted with ethyl acetate (2×200 mL) and the organic layers combined and dried over anhydrous sodium sulfate. The residue was applied onto a silica gel column with ethyl acetate/petroleum ether (1:5) to yield 1-(tert-butyl) 2-methyl (S)-4,4-dimethyl-5-oxopyrrolidine-1,2-dicarboxylate as a white solid. LC/MS: mass calculated for $C_{13}H_{21}NO_5$: 271.14, measured: 565.25 $[2M+Na]^+$.

Step 2: 1-(Tert-butyl) 2-methyl (2S)-5-methoxy-4,4-dimethylpyrrolidine-1,2-dicarboxylate To a solution of 1-(tert-butyl) 2-methyl (S)-4,4-dimethyl-5-oxopyrrolidine-1,2-dicarboxylate (10.0 g, 36.86 mmol, 1.0 equiv.) in THF (200 mL), was added lithium triethylborohydride (55.3 mL, 55.3 mmol, 1.5 equiv., 1M in THF) drop-wise at −78° C. The reaction mixture was stirred for 40 min at −78° C., then $Na_2CO_3$ (50 mL) was added at −78° C. and the mixture was warmed to 0° C. Hydrogen peroxide (10 mL, 30%) was added. The mixture was stirred for 30 min at room temperature. THF was removed under vacuum, and the resulting mixture was extracted with ethyl acetate, washed with brine, dried and concentrated under vacuum to yield a colorless oil. The oil was dissolved in methanol (200 mL), and p-toluenesulfonic acid (0.60 g, 3.69 mmol, 0.1 equiv.) was added. The resulting solution was stirred overnight at room temperature. The reaction was quenched with water and extracted with ethyl acetate. The combined organic layer was washed with brine, dried over $Na_2SO_4$ and concentrated to yield 1-(tert-butyl) 2-methyl (2S)-5-methoxy-4,4-dimethylpyrrolidine-1,2-dicarboxylate as a colorless oil.

Step 3: 1-(Tert-butyl) 2-methyl (2S)-5-allyl-4,4-dimethylpyrrolidine-1,2-dicarboxylate To a solution of 1-(tert-butyl) 2-methyl (2S)-5-methoxy-4,4-dimethylpyrrolidine-1,2-dicarboxylate (9.3 g, 32.36 mmol, 1.0 equiv.) in ethoxyethane (200 mL), were added allyltrimethylsilane (22.6 ml, 142.40 mmol, 4.4 equiv.) and boron trifluoride etherate (5.5 g, 38.80 mmol, 1.2 equiv.) at −40° C. The reaction mixture was stirred for 30 min at −40° C., and then warmed to room temperature and stirred for 40 min. The reaction was quenched with $Na_2CO_3$ and extracted with ethoxyethane. The combined organic layer was washed with brine, dried over $Na_2SO_4$ and concentrated. The residue was purified by silica gel chromatography (0-30% EtOAc/petroleum ether) to yield 1-(tert-butyl) 2-methyl (2S)-5-allyl-4,4-dimethylpyrrolidine-1,2-dicarboxylate as a colorless oil.

Step 4: Methyl (2S)-5-allyl-4,4-dimethylpyrrolidine-2-carboxylate

To a solution of 1-(tert-butyl) 2-methyl (2S)-5-ally)-4,4-dimethylpyrrolidine-1,2-dicarboxylate (5.2 g, 17.49 mmol, 1.0 equiv.) in dichloromethane (50 mL), was added HCl in 1,4-dioxane (50 mL, 4N). The reaction mixture was stirred for 2 h at room temperature. The solution was concentrated under vacuum to yield methyl (2S)-5-allyl-4,4-dimethylpyrrolidine-2-carboxylate as a white solid.

Step 5: Methyl (2S)-1-acryloyl-5-allyl-4,4-dimethylpyrrolidine-2-carboxylate

To a solution of methyl (2S)-5-ally)-4,4-dimethylpyrrolidine-2-carboxylate (3.2 g, 0.96 mmol, 1.0 equiv.) in tetrahydrofuran (50 mL), was added triethylamine (11.3 mL, 81.1 mmol, 5.0 equiv.). The reaction mixture was stirred for −78° C. and acryloyl chloride (1.5 mL, 17.80 mmol, 1.1 equiv.) was added drop-wise under $N_2$. The reaction mixture was stirred for 2 h at room temperature. The reaction was quenched by water and extracted with ethyl acetate, the organic layers combined and dried over anhydrous sodium sulfate. The residue was applied onto a silica gel column with ethyl acetate/petroleum ether (2:3) to yield methyl (2S)-1-acryloyl-5-allyl-4,4-dimethylpyrrolidine-2-carboxylate as a yellow oil. LC/MS: mass calculated for $C_{14}H_{21}NO_3$: 251.15, measured: 252.20 $[M+H]^+$.

Step 6: Methyl (3S)-1,1-dimethyl-5-oxo-1,2,3,5,8,8a-hexahydroindolizine-3-carboxylate To a solution of methyl (2S)-1-acryloyl-5-allyl-4,4-dimethylpyrrolidine-2-carboxylate (3.6 g, 14.30 mmol, 1.0 equiv.) in dichloromethane (100 mL), was added Grubbs Catalyst 2nd generation (609 mg, 0.70 mmol, 0.05 equiv.). The reaction mixture was stirred over night at 45° C. The residue was applied onto a silica gel column with ethyl acetate/petroleum ether (2:3) to yield methyl (3S)-1,1-dimethyl-5-oxo-1,2,3,5,8,8a-hexahydroindolizine-3-carboxylate as a brown oil. LC/MS: mass calculated for $C_{12}H_{17}NO_3$: 223.12, measured: 224.20 $[M+H]^+$.

Step 7: Methyl (3S)-7-hydroxy-1,1-dimethyl-5-oxooctahydroindolizine-3-carboxylate A flask was charged with copper (I) chloride (0.24 g, 2.42 mmol, 0.2 equiv.) and BINAP (1.5 g, 2.42 mmol, 0.2 equiv.) under nitrogen. Freshly degassed (freeze-pump-thaw) THF (40 mL) was added, and the yellow reaction mixture was stirred for 15 min. Then sodium tert-butoxide (0.23 g, 2.42 mmol, 0.2 equiv.) was added in one portion and stirring was continued for 30 min. Bis(pinacolato)diboron (3.7 g, 14.50 mmol, 1.2 equiv.) was added and the reaction mixture was stirred for 10 min, then a solution of methyl (3S)-1,1-dimethyl-5-oxo-1,2,3,5,8,8a-hexahydroindolizine-3-carboxylate (2.7 g, 12.10 mmol, 1.00 equiv.) in THF (10 mL) was added, followed by addition of MeOH (0.78 g, 24.20 mmol, 2 equiv.). After stirring overnight, 30% hydrogen peroxide (13.7 mL, 120.9 mmol, 10 eq) was added at 0° C. The resulting solution was stirred 1 h at room temperature. The mixture was concentrated under vacuum. The residue as purified by C18 (0-40% $H_2O/CH_3CN$) to yield methyl (3S)-7-hydroxy-1,1-dimethyl-5-oxooctahydroindolizine-3-carboxylate as a colorless oil. LC/MS: mass calculated for $C_{12}H_{19}NO_4$: 241.13, measured: 242.20 $[M+H]^+$.

Step 8: Methyl (3S)-1,1-dimethyl-5,7-dioxooctahydroindolizine-3-carboxylate

To a solution of methyl (3S)-7-hydroxy-1,1-dimethyl-5-oxooctahydroindolizine-3-carboxylate (2.2 g, 9.12 mmol, 1.0 equiv.) in dichloromethane (100 mL), was added pyridinium chlorochromate (3.9 g, 18.20 mmol, 2.0 equiv.). The reaction mixture was stirred overnight at room temperature. The residue was applied onto a silica gel column with DCM/MeOH (10:1) to yield methyl (3S)-1,1-dimethyl-5,7-dioxooctahydroindolizine-3-carboxylate as a brown oil. LC/MS: mass calculated for $C_{12}H_{17}NO_4$: 239.12, measured: 240.20 $[M+H]^+$.

Step 9: Methyl (3S)-1,1-dimethyl-5-oxo-7-(((trifluoromethyl)sulfonyl)oxy)-1,2,3,5,8,8a-hexahydroindolizine-3-carboxylate To a solution of methyl (3S)-1,1-dimethyl-5,7-dioxooctahydroindolizine-3-carboxylate (2.2 g, 9.20 mmol, 1.0 equiv.) in dichloromethane (50 mL), were added triethylamine (1.9 g, 18.40 mmol, 2.0 equiv.) and 1,1,1-trifluoro-N-phenyl-N-((trifluoromethyl)sulfonyl)methanesulfonamide (3.9 g, 11.0 mmol, 1.2 equiv.). The reaction mixture was stirred overnight at room temperature. The mixture was concentrated. The residue was purified by silica gel chromatography (0-80% EA/PE) to yield methyl (3S)-1,1-dimethyl-5-oxo-7-(((trifluoromethyl)sulfonyl)oxy)-1,2,3,5,8, 8a-hexahydroindolizine-3-carboxylate as a yellow oil. LC/MS: mass calculated for $C_{13}H_{16}F_3NO_6S$: 371.07, measured: 372.10 $[M+H]^+$.

Step 10: Methyl (3S)-7-(6-amino-3-chloro-2-fluorophenyl)-1,1-dimethyl-5-oxo-1,2,3,5,8,8a-hexahydroindolizine-3-carboxylate To a solution of methyl (3S)-1,1-dimethyl-5-oxo-7-(((trifluoromethyl)sulfonyl)oxy)-1,2,3,5,8,8a-hexahydroindolizine-3-carboxylate (2.0 g, 5.40 mmol, 1.0 equiv.), (6-amino-3-chloro-2-fluorophenyl) boronic acid (1.2 g, 6.50 mmol, 1.2 equiv.) and potassium carbonate (1.5 g, 10.77 mmol 2.0 equiv.) in 1,4-dioxane/$H_2O$ (50 mL, 10/1), was added [1,1'-bis(diphenylphosphino)ferrocene]dichloropalladium(I I) (197 mg, 0.27 mmol, 0.05 equiv.). The reaction mixture was stirred for 2 h at 80° C. The reaction was quenched with water and extracted with ethyl acetate. The combined organic layer was washed with brine, dried over $Na_2SO_4$ and concentrated. The residue was purified by silica gel chromatography (0-100% PE/EA) to yield methyl (3S)-7-(6-amino-3-chloro-2-fluorophenyl)-1,1-dimethyl-5-oxo-1,2,3,5,8,8a-hexahydroindolizine-3-carboxylate as a brown solid. LC/MS: mass calculated for $C_{18}H_{20}ClFN_2O_3$: 366.11, measured: 367.05 $[M+H]^+$.

Step 11: (3S)-7-(6-Amino-3-chloro-2-fluorophenyl)-1,1-dimethyl-5-oxo-1,2,3,5,8,8a-hexahydroindolizine-3-carboxylic acid To a solution of methyl (3S)-7-(6-amino-3-chloro-2-fluorophenyl)-1,1-dimethyl-5-oxo-1,2,3,5,8,8a-hexahydroindolizine-3-carboxylate (1.8 g, 4.90 mmol, 1.0 equiv.) in THE/$H_2O$/MeOH (20 mL, 3/1/1), was added lithium hydroxide (0.98 g, 24.5 mmol, 5.0 equiv.). The reaction mixture was stirred for 1 h at room temperature. The residue was adjusted to pH 4 with HCl, then extracted with ethyl acetate and washed with brine, dried and concentrated under vacuum to yield (3S)-7-(6-amino-3-chloro-2-fluorophenyl)-1,1-dimethyl-5-oxo-1,2,3,5,8,8a-hexahydroindolizine-3-carboxylic acid as a brown solid. LC/MS: mass calculated for $C_{17}H_{18}ClFN_2O_3$: 352.10, measured: 353.15 $[M+H]^+$.

Step 12: (3S)-7-(3-Chloro-2-fluoro-6-(1H-tetrazol-1-yl)phenyl)-1,1-dimethyl-5-oxo-1,2,3,5,8,8a-hexahydroindolizine-3-carboxylic acid To a solution of (3S)-7-(6-amino-3-chloro-2-fluorophenyl)-1,1-dimethyl-5-oxo-1,2,3,5,8,8a-hexahydroindolizine-3-carboxylic acid (300 mg, 0.85 mmol, 1.0 equiv.) in acetic acid (5 mL), were added azidotrimethylsilane (0.56 mL, 4.25 mmol, 5.0 equiv) and trimethoxymethane (0.46 mL, 4.25 mmol, 5.0 equiv.). The reaction mixture was stirred over night at room temperature. The residue was purified by silica gel chromatography (0-100% EtOAc/petroleum ether) to yield (3S)-7-(3-chloro-2-fluoro-6-(1H-tetrazol-1-yl)phenyl)-1,1-dimethyl-5-oxo-1,2,3,5,8,8a-hexahydroindolizine-3-carboxylic acid as a brown solid. LC/MS: mass calculated for $C_{18}H_{17}ClFN_5O_3$: 405.10, measured: 406.20 $[M+H]^+$.

Intermediate 8: (1S,3S)-7-(3-Chloro-2-fluoro-6-(1H-tetrazol-1-yl)phenyl)-1-methyl-5-oxo-1,2,3,5,8,8a-hexahydroindolizine-3-carboxylic acid

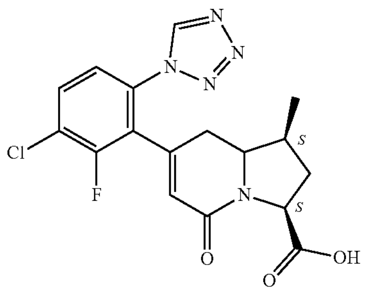

Step 1: 1-(Tert-butyl) 2-methyl (S,E)-4-((dimethylamino)methylene)-5-oxopyrrolidine-1,2-dicarboxylate To a solution of 1-(tert butyl) 2-methyl (S)-5-oxopyrrolidine-1,2-dicarboxylate (20.0 g, 82.22 mmol, 1.0 equiv.) in 1,2-dimethoxyethane (100 mL), was added 1-tert butoxy-N,N,N',N'-tetramethylmethanediamine (21.49 g, 123.33 mmol, 1.5 equiv.). The reaction mixture was stirred overnight at 70° C. The residue was applied onto a silica gel column with ethyl acetate/DCM (2:3) to yield 1-(tert-butyl) 2-methyl (S,E)-4-((dimethylamino)methylene)-5-oxopyrrolidine-1,2-dicarboxylate as a white solid.

$^1H$ NMR (300 MHz, Chloroform-d) δ 7.15 (t, J=1.7 Hz, 1H), 4.57 (dd, J=10.7, 3.7 Hz, 1H), 3.77 (s, 3H), 3.19-3.34 (m, 1H), 3.03 (s, 6H), 2.91 (ddd, J=14.7, 4.1, 1.5 Hz, 1H), 1.51 (s, 9H).

Step 2: 1-(Tert-butyl) 2-methyl (2S,4S)-4-methyl-5-oxopyrrolidine-1,2-dicarboxylate To a solution of 1-(tert-butyl) 2-methyl (S,E)-4-((dimethylamino)methylene)-5-oxopyrrolidine-1,2-dicarboxylate (10.0 g, 33.50 mmol, 1.0 equiv0) in isopropanol (1000 mL), was added Pd/C (2.0 g, 10%). The reaction mixture was stirred overnight at room temperature under an atmosphere of hydrogen. The solid was filtered out. The filtrate was concentrated under vacuum. The residue was applied onto a silica gel column with PE/EA (0~45%) to yield 1-(tert-butyl) 2-methyl (2S,4 S)-4-methyl-5-oxopyrrolidine-1,2-dicarboxylate as a white solid. LC/MS: mass calculated for $C_{12}H_{19}NO_5$: 257.13, measured: 537.25 $[2M+Na]^+$.

Step 3: 1-(Tert-butyl) 2-methyl (2S,4S)-5-methoxy-4-methylpyrrolidine-1,2-dicarboxylate To a solution of 1-(tert-butyl) 2-methyl (2S,4 S)-4-methyl-5-oxopyrrolidine-1,2-dicarboxylate (15.0 g, 58.30 mmol, 1.0 equiv.) in THE (300 mL), was added lithium triethylborohydride (87.5 mL, 87.50 mmol, 1.5 equiv., 1M in THF) drop-wise at −78° C. The reaction mixture was stirred for 40 min at −78° C., then $Na_2CO_3$ (100 mL) was added at −78° C. and the mixture was warmed to 0° C. Hydrogen peroxide (8 mL, 30%) was then added. The mixture was stirred for 30 min at room temperature. THF was removed under vacuum, and the resulting mixture was extracted with ethyl acetate, washed with brine, dried and concentrated under vacuum to yield a colorless oil. The oil was re-dissolved by methanol (300 mL), followed by the addition of p-toluenesulfonic acid (1.0 g, 5.83 mmol, 0.1 equiv.). The resulting solution was stirred overnight at room temperature. The reaction was quenched with water and extracted with ethyl acetate. The combined organic layer was washed with brine, dried over $Na_2SO_4$ and concentrated to yield 1-(tert-butyl) 2-methyl (2S,4S)-5-methoxy-4-methylpyrrolidine-1,2-dicarboxylate as a yellow oil.

Step 4: 1-(Tert-butyl) 2-methyl (2S,4S)-5-allyl-4-methylpyrrolidine-1,2-dicarboxylate To a solution of 1-(tert-butyl) 2-methyl (2S,4S)-5-methoxy-4-methylpyrrolidine-1,2-dicarboxylate (13.0 g, 47.60 mmol, 1.0 equiv.) in ethoxyethane (200 mL), were added allyltrimethylsilane (33.3 ml, 209.30 mmol, 4.4 equiv.) and boron trifluoride etherate (8.1 g, 57.10 mmol, 1.2 equiv.) at −40° C. The reaction mixture was stirred for 30 min at −40° C., and then warmed to room temperature and stirred for 40 min. The reaction was quenched with $Na_2CO_3$ and extracted with ethoxyethane. The combined organic layer was washed with brine, dried over $Na_2SO_4$ and concentrated. The residue was purified by silica gel chromatography (0-30% EtOAc/petroleum ether) to yield 1-(tert-butyl) 2-methyl (2S,4S)-5-ally)-4-methylpyrrolidine-1,2-dicarboxylate as a yellow oil. LC/MS: mass calculated for $C_{15}H_{25}NO_4$: 283.18, measured: 306.10 $[M+Na]^+$.

Step 5: Methyl (2S,4S)-5-allyl-4-methylpyrrolidine-2-carboxylate

To a solution of 1-(tart-butyl) 2-methyl (2S,4S)-5-ally)-4-methylpyrrolidine-1,2-dicarboxylate (9.6 g, 33.90 mmol, 1.0 equiv.) in dichloromethane (100 mL) was added HCl in 1,4-dioxane (100 mL, 4 N). The reaction mixture was stirred for 1 h at room temperature, then concentrated under vacuum to yield methyl (2S,4S)-5-allyl-4-methylpyrrolidine-2-carboxylate as a white solid. LC/MS: mass calculated for $C_{10}H_{17}NO_2$: 183.13, measured: 184.05 $[M+H]^+$.

Step 6: Methyl (2S,4S)-1-acryloyl-5-ally)-4-methylpyrrolidine-2-carboxylate

To a solution of methyl (2S,4S)-5-allyl-4-methylpyrrolidine-2-carboxylate (3.9 g, 21.10 mmol, 1.0 equiv.) in tetrahydrofuran (50 mL) was added triethylamine (14.6 mL, 105.30 mmol, 5.0 equiv.). The reaction mixture was stirred for −78° C. and acryloyl chloride (1.9 mL, 23.20 mmol, 1.1 equiv.) was added under $N_2$. The reaction mixture was stirred for 2 h at room temperature, quenched with water (50 mL) and extracted with ethyl acetate (2×50 mL), the organic layers were combined and dried over anhydrous sodium sulfate. The residue was applied onto a silica gel column with ethyl acetate/petroleum ether (2:3) to yield methyl (2S,4 S)-1-acryloyl-5-allyl-4-methylpyrrolidine-2-carboxylate as a yellow oil. LC/MS: mass calculated for $C_{12}H_{18}N_2O_3$: 237.14, measured: 238.10 $[M+H]^+$.

Step 7: Methyl (1S,3 S)-1-methyl-5-oxo-1,2,3,5,8,8a-hexahydroindolizine-3-carboxylate To a solution of methyl (2S,4S)-1-acryloyl-5-allyl-4-methylpyrrolidine-2-carboxylate (3.0 g, 12.64 mmol, 1.0 equiv.) in dichloromethane (50 mL), was added Grubbs Catalyst $2^{nd}$ generation (538 mg, 0.63 mmol, 0.05 equiv.). The reaction mixture was stirred overnight at 45° C. The residue was applied onto a silica gel column with ethyl acetate/petroleum ether (2:3) to yield methyl (3S)-5-oxo-1,2,3,5,8,8a-hexahydroindolizine-3-carboxylate as a brown oil. LC/MS: mass calculated for $C_{11}H_{15}NO_3$: 209.11, measured: 210.10 $[M+H]^+$.

Step 8: Methyl (1S,3S)-7-hydroxy-1-methyl-5-oxooctahydroindolizine-3-carboxylate A flask was charged with copper (I) chloride (242 mg, 2.40 mmol, 0.2 equiv.) and BINAP (1.5 g, 2.40 mmol, 0.2 equiv.) under nitrogen. Freshly degassed (freeze-pump-thaw) THE (40 mL) was added, and the yellow reaction mixture was stirred for 15 min. Then sodium tert-butoxide (235 mg, 2.40 mmol, 0.2 equiv.) was added in one portion and the stirring was continued for 30 min. Bis(pinacolato) diboron (3.7 g, 14.70 mmol, 1.2 equiv.) was added and the reaction mixture was stirred for 10 min, then a solution of methyl (1S,3S)-1-methyl-5-oxo-1,2,3,5,8,8a-hexahydroindolizine-3-carboxylate (2.6 g, 12.24 mmol, 1.0 equiv.) in THE (10 mL) was added, followed by addition of MeOH (784 mg, 24.50 mmol, 2.0 equiv.). After 16 h, 30% hydrogen peroxide (13.9 g, 122.30 mmol, 10.0 equiv.) was added at 0° C. The resulting solution was stirred 1 h at room temperature. The mixture was concentrated under vacuum. The residue was purified by $C_{18}$ (0-40% $H_2O/CH_3CN$) to yield methyl (1 S,3S)-7-hydroxy-1-methyl-5-oxooctahydroindolizine-3-carboxylate as a colorless oil. LC/MS: mass calculated for $C_{11}H_{17}NO_4$: 227.12, measured: 228.10 $[M+H]^+$.

Step 9: Methyl (1S,3S)-1-methyl-5,7-dioxooctahydroindolizine-3-carboxylate

To a solution of methyl (1S,3S)-7-hydroxy-1-methyl-5-oxooctahydroindolizine-3-carboxylate (2.6 g, 11.44 mmol, 1.0 equiv.) in dichloromethane (250 mL), was added pyridinium chlorochromate (4.9 g, 22.88 mmol, 2.0 equiv.). The reaction mixture was stirred overnight at room temperature. The residue was applied onto a silica gel column with DCM/MeOH (10:1) to yield methyl (1S,3S)-1-methyl-5,7-dioxooctahydroindolizine-3-carboxylate as a yellow oil. LC/MS: mass calculated for $C_{11}H_{15}NO_4$: 225.10, measured: 226.05 $[M+H]^+$.

Step 10: Methyl (1S,3S)-1-methyl-5-oxo-7-(((trifluoromethyl)sulfonyl)oxy)-1,2,3,5,8,8a-hexahydroindolizine-3-carboxylate To a solution of methyl (1S,3S)-1-methyl-5,7-dioxooctahydroindolizine-3-carboxylate (1.3 g, 5.80 mmol, 1.0 equiv.) in dichloromethane (30 mL), were added triethylamine (1.2 g, 11.50 mmol, 2.0 equiv.) and 1,1,1-trifluoro-N-phenyl-N-((trifluoromethyl)sulfonyl)methanesulfonamide (2.5 g, 6.90 mmol, 1.2 equiv.). The reaction mixture was stirred overnight at room temperature. The mixture was concentrated. The residue was purified by silica gel chromatography (0-40% EA/PE) to yield methyl (1S,3S)-1-methyl-5-oxo-7-(((trifluoromethyl)sulfonyl)oxy)-1,2,3,5,8,8a-hexahydroindolizine-3-carboxylate as a yellow oil. LC/MS: mass calculated for $C_{12}H_{14}F_3NO_6S$: 357.05, measured: 358.00 $[M+H]^+$.

Step 11: Methyl (1S,3S)-7-(6-amino-3-chloro-2-fluorophenyl)-1-methyl-5-oxo-1,2,3,5,8,8a-hexahydroindolizine-3-carboxylate To a solution of methyl (1S,3S)-1-methyl-5-oxo-7-(((trifluoromethyl)sulfonyl)oxy)-1,2,3,5,8,8a-hexahydroindolizine-3-carboxylate (1.5 g, 4.20 mmol, 1.0 equiv.), (6-amino-3-chloro-2-fluorophenyl) boronic acid (0.95 g, 5.00 mmol, 1.2 equiv.) and potassium carbonate (1.2 g, 8.40 mmol 2.0 equiv.) in 1,4-dioxane/$H_2O$ (20 mL, 10/1), was added [1,1'-Bis(diphenylphosphino)ferrocene] dichloropalladium(II) (154 mg, 0.21 mmol, 0.1 equiv.). The reaction mixture was stirred for 2 h at 80° C. The reaction was quenched with water and extracted with ethyl acetate. The combined organic layer was washed with brine, dried over $Na_2SO_4$ and concentrated. The residue was purified by silica gel chromatography (0-100% PE/EA) to yield methyl (1 S,3S)-7-(6-amino-3-chloro-2-fluorophenyl)-1-methyl-5-oxo-1,2,3,5,8,8a-hexahydroindolizine-3-carboxylate as a yellow solid. LC/MS: mass calculated for $C_{17}H_{18}ClFN_2O_3$: 352.10, measured: 353.10 $[M+H]^+$.

Step 12: (1 S,3S)-7-(6-Amino-3-chloro-2-fluorophenyl)-1-methyl-5-oxo-1,2,3,5,8,8a-hexahydroindolizine-3-carboxylic acid To a solution of methyl (1S,3S)-7-(6-amino-3-chloro-2-fluorophenyl)-1-methyl-5-oxo-1,2,3,5,8,8a-hexahydroindolizine-3-carboxylate (1.3 g, 3.69 mmol, 1.0 equiv.) in THE/$H_2O$/MeOH (15 mL, 3/1/1), was added lithium hydroxide (737 mg, 18.40 mmol, 5.0 equiv.). The reaction mixture was stirred for 1 h at room temperature. The residue was adjusted to pH 4 with HCl, then extracted with ethyl acetate and washed with brine, dried and concentrated under vacuum to yield (1S,3S)-7-(6-amino-3-chloro-2-fluorophenyl)-1-methyl-5-oxo-1,2,3,5,8,8a-hexahydroindolizine-3-carboxylic acid as a yellow solid. LC/MS: mass calculated for $C_{18}H_{16}ClFN_2O_3$: 338.08, measured: 339.05 $[M+H]^+$.

Step 13: (1S,3S)-7-(3-Chloro-2-fluoro-6-(1H-tetrazol-1-yl)phenyl)-1-methyl-5-oxo-1,2,3,5,8,8a-hexahydroindolizine-3-carboxylic acid To a solution of (1S,3S)-7-(6-amino-3-chloro-2-fluorophenyl)-1-methyl-5-oxo-1,2,3,5,8,8a-hexahydroindolizine-3-carboxylic acid (500 mg, 1.50 mmol, 1.0 equiv) in acetic acid (10 mL), were added azidotrimethylsilane (0.97 mL, 7.38 mmol, 5.0 equiv.) and trimethoxymethane (0.8 mL, 7.38 mmol, 5.0 equiv.). The reaction mixture was stirred over night at room temperature. The residue was purified by silica gel chromatography (0-100% EtOAc/petroleum ether) to yield (1S,3S)-7-(3-chloro-2-fluoro-6-(1H-tetrazol-1-yl) phenyl)-1-methyl-5-oxo-1,2,3,5,8,8a-hexahydroindolizine-3-carboxylic acid as a brown solid. LC/MS: mass calculated for $C_{17}H_{15}ClFN_5O_3$: 391.08, measured: 392.15 $[M+H]^+$.

Intermediate 9: (1R,3S)-7-(3-Chloro-2-fluoro-6-(1H-tetrazol-1-yl)phenyl)-1-methoxy-5-oxo-1,2,3,5,8,8a-hexahydroindolizine-3-carboxylic acid

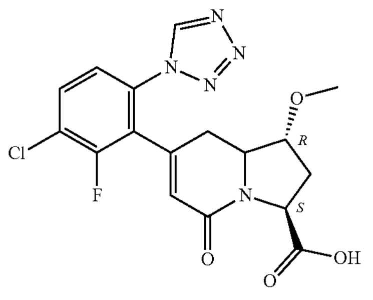

Step 1: 1-(Tert-butyl) 2-methyl (2S,4R)-4-methoxypyrrolidine-1,2-dicarboxylate

To a solution of 1-(tert-butyl) 2-methyl 4-hydroxypyrrolidine-1,2-dicarboxylate (10.0 g, 40.77 mmol, 1.0 equiv.) in N,N-dimethylformamide (150 mL), was added sodium hydride (1.8 g, 44.85 mmol, 1.1 equiv.) at 0° C. The reaction mixture was stirred for 30 min at 0° C. Iodomethane (11.6 g, 81. mmol, 2.0 equiv.) was added. The reaction mixture was stirred over night at room temperature. The reaction was quenched with water extracted with ethoxyethane. The combined organic layer was washed with brine, dried over $Na_2SO_4$ and concentrated. The residue was purified by silica gel chromatography (0-30% EtOAc/petroleum ether) to yield 1-(tert-butyl) 2-methyl 4-methoxypyrrolidine-1,2-dicarboxylate as a yellow oil. LC/MS: mass calculated for $C_{12}H_{21}NO_5$: 259.14, measured: 160.20 $[M-Boc]^+$.

Step 2: 1-(Tert-butyl) 2-methyl (2S,4R)-4-methoxy-5-oxopyrrolidine-1,2-dicarboxylate To a solution of sodium periodate (20.6 g, 96.41 mmol, 2.5 equiv.) in $H_2O$ (160 mL) was added ruthenium trichloride (1.6 g, 7.71 mmol, 0.2 equiv.) under nitrogen. The resulting solution was stirred for 5 minutes followed by addition of 1-(tert-butyl) 2-methyl 4-methoxypyrrolidine-1,2-dicarboxylate (10.0 g, 38.57 mmol, 1.0 equiv.) in EtOAc (88 mL) in one portion. The mixture was stirred overnight at room temperature. The reaction was extracted with ethyl acetate (2×100 mL) and washed with $Na_2SO_3$ solution (100 mL), the organic layers combined and dried over anhydrous sodium sulfate. The residue was applied onto a silica gel column with ethyl acetate/petroleum ether (1:3) to yield 1-(tert-butyl) 2-methyl (2S,4R)-4-methoxy-5-oxopyrrolidine-1,2-dicarboxylate as a yellow oil. LC/MS: mass calculated for $C_{12}H_{19}NO_8$: 273.12, measured: 569.30 $[2M+Na]^+$.

Step 3: 1-(Tert-butyl) 2-methyl (2S,4R)-4,5-dimethoxypyrrolidine-1,2-dicarboxylate To a solution of 1-(tert-butyl) 2-methyl (2S,4R)-4-methoxy-5-oxopyrrolidine-1,2-dicarboxylate (6.5 g, 23.79 mmol, 1.0 equiv.) in THF (100 mL), was added lithium triethylborohydride (35.7 mL, 35.7 mmol, 1.5 equiv., 1M in THF) at −78° C. The reaction mixture was stirred for 40 min at −78° C., then $NaHCO_3$ (40 mL) was added at −78° C. and the mixture was warmed to 0° C. Hydrogen peroxide (4 mL, 30%) was then added. The mixture was stirred for 30 min at room temperature. THF was removed under vacuum, and the residue was extracted with diethyl ether, washed with brine, dried and concentrated under vacuum to yield a colorless oil. The oil was re-dissolved in methanol (100 mL) followed by the addition of p-toluenesulfonic acid (410 mg, 2.38 mmol, 0.1 equiv.). The solution was stirred overnight at room temperature, quenched with $NaHCO_3$ and extracted with diethyl ether. The combined organic layer was washed with brine, dried over $Na_2SO_4$ and concentrated to yield 1-(tert-butyl) 2-methyl (2S,4R)-4,5-dimethoxypyrrolidine-1,2-dicarboxylate as a colorless oil.

Step 4: 1-(Tert-butyl) 2-methyl (2S,4R)-5-allyl-4-methoxypyrrolidine-1,2-dicarboxylate To a solution of 1-(tert-butyl) 2-methyl (2S,4R)-4,5-dimethoxypyrrolidine-1,2-dicarboxylate (5.0 g, 17.28 mmol, 1.0 equiv.) in diethyl ether (100 mL), were added allyltrimethylsilane (12.1 ml, 76.04 mmol, 4.4 equiv.) and boron trifluoride etherate (2.9 g, 20.74 mmol, 1.2 equiv.) at −40° C. The reaction mixture was stirred for 30 min at −40°

C., and then warmed to room temperature and stirred for 40 min. The reaction was quenched with $Na_2CO_3$ and extracted with ethoxyethane. The combined organic layer was washed with brine, dried over $Na_2SO_4$ and concentrated. The residue was purified by silica gel chromatography (0-30% EtOAc/petroleum ether) to yield 1-(tert-butyl) 2-methyl (2S)-5-allylpyrrolidine-1,2-dicarboxylate as a yellow oil.

Step 5: Methyl (2S,4R)-5-allyl-4-methoxypyrrolidine-2-carboxylate

To a solution of 1-(tert-butyl) 2-ethyl 5-allyl-3-methylpyrrolidine-1,2-dicarboxylate (12.6 g, 42.09 mmol, 1.0 equiv.) in dichloromethane (200 mL), was added HCl in 1,4-dioxane (120 mL, 4N). The reaction mixture was stirred for 2 h at room temperature. The solution was concentrated under vacuum to yield methyl (2S,4R)-5-allyl-4-methoxypyrrolidine-2-carboxylate as a white solid. LC/MS: mass calculated for $C_{10}H_{17}NO_3$: 199.12, measured: 200.05 $[M+H]^+$.

Step 6: Methyl (2S,4R)-1-acryloyl-5-allyl-4-methoxypyrrolidine-2-carboxylate To a solution of methyl (2S,4R)-5-allyl-4-methoxypyrrolidine-2-carboxylate (9.6 g, 40.73 mmol, 1.0 equiv.) in tetrahydrofuran (200 mL), was added triethylamine (28.3 mL, 203.64 mmol, 5.0 equiv.) added. The reaction mixture was stirred for −78° C. and acryloyl chloride (3.6 mL, 44.80 mmol, 1.1 equiv.) was added under $N_2$. The reaction mixture was stirred for 2 h at room temperature. The reaction was quenched with water (100 mL) and extracted with ethyl acetate (2×100 mL) and the organic layers were combined and dried over anhydrous sodium sulfate. The residue was applied onto a silica gel column with ethyl acetate/petroleum ether (2:3) to yield methyl (2S,4R)-1-acryloyl-5-allyl-4-methoxypyrrolidine-2-carboxylate as a yellow oil. LC/MS: mass calculated for $C_{13}H_{19}NO_4$: 253.13, measured: 254.10 $[M+H]^+$.

Step 7: Methyl (1R,3S)-1-methoxy-5-oxo-1,2,3,5,8,8a-hexahydroindolizine-3-carboxylate To a solution of methyl (2S,4R)-1-acryloyl-5-allyl-4-methoxypyrrolidine-2-carboxylate (8.5 g, 33.56 mmol, 1.0 equiv.) in dichloromethane (200 mL), was added Grubbs Catalyst $2^{nd}$ generation (1.4 g, 1.68 mmol, 0.05 equiv.). The reaction mixture was stirred over night at 45° C. The residue was applied onto a silica gel column with ethyl acetate/petroleum ether (2:3) to yield methyl (1R,3S)-1-methoxy-5-oxo-1,2,3,5,8,8a-hexahydroindolizine-3-carboxylate as a brown oil. LC/MS: mass calculated for $C_{11}H_{15}NO_4$: 223.12, measured: 226.10 $[M+H]^+$.

Step 8: Methyl (1R,3S)-7-hydroxy-1-methoxy-5-oxooctahydroindolizine-3-carboxylate A flask was charged with copper(I) chloride (264 mg, 2.66 mmol, 0.2 equiv.) and BINAP (1.7 g, 2.66 mmol, 0.2 equiv.) under nitrogen. Freshly degassed (freeze-pump-thaw) THF (200 mL) was added, and the yellow reaction mixture was stirred for 15 min. Then sodium tert-butoxide (256 mg, 2.66 mmol, 0.2 equiv.) was added in one portion and stirring was continued for 30 min. bis(pinacolato)diboron (4.1 g, 15.98 mmol, 1.2 equiv.) was added and the reaction mixture was stirred for 10 min, then a solution of methyl (1R,3S)-1-methoxy-5-oxo-1,2,3,5,8,8a-hexahydroindolizine-3-carboxylate (3.0 g, 13.32 mmol, 1.0 equiv.) in THF (40 mL) was added, followed by addition of MeOH (0.85 g, 26.64 mmol, 2.0 equiv.). After stirring overnight, 30% hydrogen peroxide (15.1 mL, 133.19 mmol, 10.0 equiv.) was added at 0° C. The resulting solution was stirred over night at room temperature. The mixture was concentrated under vacuum. The residue was purified by silica gel column (0-10% MeOH/DCM) to yield methyl (1R,3S)-7-hydroxy-1-methoxy-5-oxooctahydroindolizine-3-carboxylate as a yellow oil and LC/MS: mass calculated for $C_{11}H_{17}NO_5$: 243.11, measured: 244.10 $[M+H]^4$, methyl (1R,3S)-1-methoxy-5-oxo-7-(4,4,5,5-tetramethyl-1,3,2-dioxaborolan-2-yl)octahydroindolizine-3-carboxylate as a brown solid. LC/MS: mass calculated for $C_{17}H_{28}BNO_8$: 353.20, measured: 354.20 $[M+H]^+$.

Step 9: Methyl (1R,3S)-7-hydroxy-1-methoxy-5-oxooctahydroindolizine-3-carboxylate To a solution of methyl (1R,3S)-1-methoxy-5-oxo-7-(4,4,5,5-tetramethyl-1,3,2-dioxaborolan-2-yl)octahydroindolizine-3-carboxylate (3.8 g, 10.76 mmol, 1.0 equiv.) in THF/$H_2O$ (40 mL, 3/1), was added sodium perborate trihydrate (4.4 g, 53.79 mmol, 5.0 equiv.). The reaction mixture was stirred over night at room temperature. The mixture was concentrated under vacuum. The residue was purified by silica gel column (0-10% MeOH/DCM) to yield methyl (1R,3S)-7-hydroxy-1-methoxy-5-oxooctahydroindolizine-3-carboxylate as a yellow oil. LC/MS: mass calculated for $C_{11}H_{17}NO_5$: 243.11, measured: 244.20 $[M+H]^+$.

Step 10: Methyl (1R,3S)-1-methoxy-5,7-dioxooctahydroindolizine-3-carboxylate To a solution of methyl (1R,3S)-7-hydroxy-1-methoxy-5-oxooctahydroindolizine-3-carboxylate (3.4 g, 13.98 mmol, 1.0 equiv.) in dichloromethane (150 mL), was added pyridinium chlorochromate (6.0 g, 27.95 mmol, 2.0 equiv.). The reaction mixture was stirred over night at room temperature. The mixture was concentrated under vacuum. The residue was purified by silica gel column (0-10% MeOH/DCM) to yield methyl (1R,3S)-1-methoxy-5,7-dioxooctahydroindolizine-3-carboxylate as a brown solid. LC/MS: mass calculated for $C_{11}H_{15}NO_5$: 241.10, measured: 242.20 $[M+H]^+$.

Step 11: Methyl (1R,3S)-1-methoxy-5-oxo-7-(((trifluoromethyl)sulfonyl)oxy)-1,2,3,5,8,8a-hexahydroindolizine-3-carboxylate To a solution of methyl (1R,3S)-1-methoxy-5,7-dioxooctahydroindolizine-3-carboxylate (2.3 g, 9.53 mmol, 1.0 equiv.) in dichloromethane (30 mL), were added triethylamine (1.9 g, 19.07 mmol, 2.0 equiv.) and 1,1,1-trifluoro-N-phenyl-N-((trifluoromethyl)sulfonyl)methanesulfonamide (4.1 g, 11.44 mmol, 1.2 equiv.). The reaction mixture was stirred over night at room temperature. The mixture was concentrated. The residue was purified by silica gel chromatography (0-60% EA/PE) to yield methyl (1R,3S)-1-methoxy-5-oxo-7-(((trifluoromethyl)sulfonyl)oxy)-1,2,3,5,8,8a-hexahydroindolizine-3-carboxylate as a yellow oil. LC/MS: mass calculated for $C_{12}H_{14}F_3NO_7S$: 373.04, measured: 374.05 $[M+H]^+$.

Step 12: Methyl (1R,3S)-7-(6-amino-3-chloro-2-fluorophenyl)-1-methoxy-5-oxo-1,2,3,5,8,8a-hexahydroindolizine-3-carboxylate To a solution of methyl (1R,3S)-1-methoxy-5-oxo-7-(((trifluoromethyl)sulfonyl)oxy)-1,2,3,5,8,8a-hexahydroindolizine-3-carboxylate (3.0 g, 8.04 mmol, 1.0 equiv.), (6-amino-3-chloro-2-fluorophenyl)boronic acid (1.8 g, 9.64 mmol, 1.2 equiv.) and potassium carbonate (2.2 g, 16.07 mmol, 2.0 equiv.) in 1,4-dioxane/$H_2O$ (50 mL, 10/1), was added [1,1'-bis(diphenylphosphino)ferrocene]dichloropalladium(I I) (294 mg, 0.40 mmol, 0.1 equiv.). The reaction mixture was stirred for 2 h at 80° C. The reaction was quenched with water and extracted with ethyl acetate. The combined organic layer was washed with brine, dried over $Na_2SO_4$ and concentrated. The residue was purified by silica gel chromatography (0-100% PE/EA) to yield methyl (1R, 3S)-7-(6-amino-3-chloro-2-fluorophenyl)-1-methoxy-5-oxo-1,2,3,5,8,8a-hexahydroindolizine-3-carboxylate as a brown solid. LC/MS: mass calculated for $C_{17}H_{18}ClFN_2O_4$: 368.09, measured: 369.10 $[M+H]^+$.

Step 13: (1R,3S)-7-(6-Amino-3-chloro-2-fluorophenyl)-1-methoxy-5-oxo-1,2,3,5,8,8a-hexahydroindolizine-3-carboxylic acid To a solution of methyl (1R,3S)-7-(6-amino-3-chloro-2-fluorophenyl)-1-methoxy-5-oxo-1,2,3,5,8,8a-hexahydroindolizine-3-carboxylate (2.2 g, 5.97 mmol, 1.0 equiv.) in THF/$H_2O$/MeOH (50 mL, 3/1/1), was added lithium hydroxide (1.2 g, 29.83 mmol, 5.0 equiv.). The reaction mixture was stirred for 1 h at room temperature. The residue was adjusted to pH 4 with HCl, then extracted with ethyl acetate and washed with brine, dried and concentrated under vacuum to yield (1R,3S)-7-(6-amino-3-chloro-2-fluorophenyl)-1-methoxy-5-oxo-1,2,3,5,8,8a-hexahydroindolizine-3-carboxylic acid as a brown solid.

Step 14: (1R,3S)-7-(3-chloro-2-fluoro-6-(1H-tetrazol-1-yl)phenyl)-1-methoxy-5-oxo-1,2,3,5,8,8a-hexahydroindolizine-3-carboxylic acid To a mixture of methyl (3S)-7-(6-amino-3-chloro-2-fluorophenyl)-1-methoxy-5-oxo-1,2,3,5,8,8a-hexahydroindolizine-3-carboxylic acid (1.0 g, 2.82 mmol, 1.0 equiv.) in acetic acid (15 mL) were added trimethoxymethane (3.0 g, 28.19 mmol, 10.0 equiv.) and azidotrimethylsilane (3.2 g, 28.19 mmol, 10.0 equiv.). The reaction mixture was stirred at room temperature. overnight. The resulting mixture was then washed with water (3×20 mL), dried over $Na_2SO_4$, and concentrated. The residue was applied onto a silica gel column (MeOH/DCM: 1/10) to yield of methyl (3S)-5-oxo-7-(((trifluoromethyl)sulfonyl)oxy)-1,2,3,5,8,8a-hexahydroindolizine-3-carboxylate as a yellow oil. LC/MS: mass calculated for $C_{17}H_{15}ClFN_5O_4$: 407.08, measured: 408.10 $[M+H]^+$.

Intermediate 10: (6-amino-3-chloro-2-fluorophenyl)boronic acid

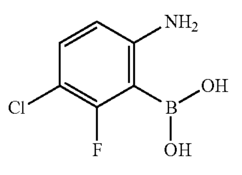 [SMILES: Nc1ccc(Cl)c(F)c1B(O)O]

Step 1: N-(4-Chloro-3-fluorophenyl)-2,2,2-trifluoroacetamide

To a mixture of 4-chloro-3-fluorobenzenamine (20 g, 137.398 mmol, 1.00 equiv) and $Na_2CO_3$ (24.7 g, 233.58 mmol, 1.70 equiv) in $Et_{20}$ (400 mL) was added TFAA (34.6 g, 164.88 mmol, 1.20 equiv) dropwise with stirring at −10° C. The mixture was slowly warmed to room temperature overnight. The mixture was then diluted with hexane (400 mL) and filtered. The filtrate was washed with saturated sodium bicarbonate solution (2×200 mL), brine (2×200 mL), dried over $Na_2SO_4$, and filtered. The filtrate was concentrated to yield N-(4-chloro-3-fluorophenyl)-2,22-trifluoroacetamide as a white solid.

Step 2: (6-Amino-3-chloro-2-fluorophenyl)boronic acid

Under an inert atmosphere of nitrogen, to a mixture of N-(4-chloro-3-fluorophenyl)-2,2,2-trifluoroacetamide (30 g, 124.19 mmol, 1.00 equiv) in THE (500 mL) was added n-BuLi (99 mL, 248.38 mmol, 2.00 equiv, 2.5 M in hexane) dropwise with stirring at −78° C., and the resulting mixture was then stirred at 78° C. for 15 min. The reaction mixture was slowly warmed to −50° C. The resulting clear brown solution was cooled to −78° C. and then $B(O-iPr)_3$ (51.3 g, 273.21 mmol, 2.20 equiv) was added dropwise. The reaction mixture was stirred at −78° C. for 10 mm and the reaction mixture was slowly allowed to warm to room temperature. The resulting orange suspension was stirred at room temperature for 4 h, then cooled in an ice bath and quenched with 1M HCl (300 mL). The resulting mixture was stirred at room temperature overnight, extracted with EtOAc (300 mL×3), dried over $Na_2SO_4$, and filtered. The filtrate was concentrated under reduced pressure. 6-Amino-3-chloro-2-fluorophenylboronic acid was recrystallized in EtOAc/PE (v/v 1/10) as a white solid.

Intermediate 11: 5-(4,4,5,5-Tetramethyl-1,3,2-dioxaborolan-2-yl)-7-((2-(trimethylsilyl)ethoxy)methyl)-7H-pyrrolo[2,3-d]pyrimidine

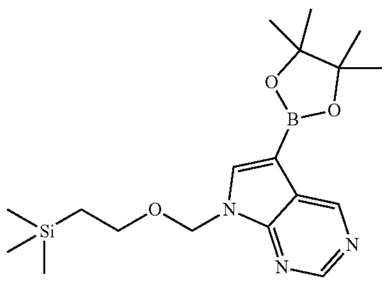

Step 1: 5-Bromo-7-((2-(trimethylsilyl)ethoxy) methyl)-7H-pyrrolo [2,3-d]pyrimidine To a solution of 5-bromo-7H-pyrrolo[2,3-d]pyrimidine (500 mg, 2.52 mmol, 1.0 equiv.) in N,N-dimethylformamide (10 mL) was added sodium hydride (131 mg, 3.28 mmol, 1.3 equiv.) at 0° C. The reaction mixture was stirred for 0.5 h. Then 2-(trimethylsilyl)ethoxymethyl chloride (505 mg, 3.03 mmol, 1.2 equiv.) was added and the reaction mixture was stirred at room temperature for 2 h. Water was added, the mixture was extracted with EA. The combined extracts were washed with brine and dried over anhydrous $Na_2SO_4$, then concentrated under reduced pressure. The residue was purified by column chromatography (0→20% EA/PE) to yield 5-bromo-7-((2-(trimethylsilyl)ethoxy)methyl)-7H-pyrrolo

[2,3-d]pyrimidine as a yellow oil. LC/MS (ES, m/z): mass calculated for $C_{12}H_{18}BrN_3OSi$: 327.04, measured: 327.95 $[M+H]^+$, 329.95 $[M+H+2]^+$.

Step 2: 5-(4,4,5,5-Tetramethyl-1,3,2-dioxaborolan-2-yl)-7-((2-(trimethylsilyl) ethoxy)methyl)-7H-pyrrolo[2,3-d]pyrimidine To a mixture of 5-bromo-7-((2-(trimethylsilyl)ethoxy)methyl)-7H-pyrrolo[2,3-d]pyrimidine (530 mg, 1.61 mmol, 1.0 equiv.) and 4,4,4',4',5,5,5',5' octamethyl-2,2'-bi(1,3,2-dioxaborolane) (820 mg, 3.23 mmol, 2.0 equiv.) in 1,4-dioxane (10 mL) were added potassium acetate (475 mg, 4.84 mmol, 3.0 equiv.) and 1,1'-bis(diphenylphosphino) ferrocene-palladium(II)dichloride dichloromethane complex (132 mg, 0.16 mmol, 0.1 equiv.). The reaction mixture was stirred at 100° C. for 3 h under $N_2$, then cooled to room temperature. Water was added, the resulting mixture was extracted with EA. The combined extracts were washed with brine and dried over anhydrous $Na_2SO_4$. The resulting mixture was concentrated under vacuum to yield 5-(4,4,5,5-tetramethyl-1,3,2-dioxaborolan-2-yl)-7-((2-(trimethylsilyl)ethoxy)methyl)-7H-pyrrolo[2,3-d]pyrimidine as a black oil (unpurified). LC/MS (ES, m/z): mass calculated for $C_{18}H_{30}BN_3O_3Si$: 375.21, measured: 376.20 $[M+H]^+$.

Intermediate 12: 2-Bromo-1-(2-(((tert-butyldimethylsilyl)oxy)methyl)-3-fluoropyridin-4-yl) ethan-1-one

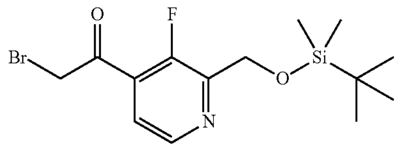 [SMILES: CC(C)(C)[Si](C)(C)OCc1nccc(C(=O)CBr)c1F]

Step 1: 2-(((tert-Butyldimethylsilyl)oxy)methyl)-3-fluoropyridine

To a solution of (3-fluoropyridin-2-yl)methanol (15.0 g, 118.002 mmol, 1.0 eq.) in DMF (200 mL) was added imidazole (16.1 g, 236.496 mmol, 2.0 eq.), followed by tert-butylchlorodimethylsilane (21.3 g, 141.32 mmol, 1.2 eq.). The resulting mixture was stirred at room temperature overnight. The reaction was quenched with water (200 mL). The resulting mixture was extracted with ethyl acetate (3×400 mL), then washed with water (3×200 mL). The organic layers were combined, dried over anhydrous sodium sulfate, and concentrated. The residue was purified by silica gel chromatography (0-30% PE/EA) to yield the 2-(((tert-butyldimethylsilyl)oxy)methyl)-3-fluoropyridine as a yellow oil. LC/MS: mass calculated for $C_{12}H_{20}FNOSi$: 241.13, measured: 242.10 $[M+H]^+$.

Step 2: 2-(((tert-butyldimethylsilyl)oxy)methyl)-3-fluoro-4-iodopyridine

To a solution of 2-(((tert-butyldimethylsilyl)oxy)methyl)-3-fluoropyridine (24.0 g, 99.43 mmol, 1.0 eq.) in THF (400 mL) was added LDA (59.7 mL, 119.4 mmol, 1.2 eq.) at −78° C. The resulting mixture was stirred at −78° C. for 0.5 h. A solution of iodine (30.3 g, 119.38 mmol, 1.2 eq.) in THF (60 mL) was then added to the mixture at −78° C. The resulting mixture was stirred at −78° C. for 3 h. The reaction was quenched with $NH_4C_1$ solution (200 mL), extracted with ethyl acetate (3×400 mL). The combined extracts were washed with water, dried over $Na_2SO_4$, filtered and concentrated. The resulting residue was purified by silica gel chromatography (0-30% EA/PE) to yield 2-(((tert-butyldimethylsilyl)oxy)methyl)-3-fluoro-4-iodopyridine as a white solid. LC/MS: mass calculated for $C_{12}H_{19}FINOSi$: 367.03, measured: 368.20 $[M+H]^+$.

Step 3: 2-(((tert-butyldimethylsilyl)oxy)methyl)-4-(1-ethoxyvinyl)-3-fluoro-pyridine To a solution of 2-(((tert-butyldimethylsilyl)oxy)methyl)-3-fluoro-4-iodopyridine (20.0 g, 54.45 mmol, 1.0 eq.) and bis(triphenylphosphine)palladium(II) chloride (3.8 g, 5.414 mmol, 0.1 eq.) in 1,4-dioxane (200 mL) was added tributyl (1-ethoxyvinyl)stannane (29.5 g, 81.68 mmol, 1.5 eq.). The mixture was stirred at 90° C. for 2 h. After cooling to room temperature, the reaction was quenched with water (200 mL), extracted with ethyl acetate (3×300 mL). The organic layers were combined, dried over anhydrous sodium sulfate, and concentrated. The residue was purified by $Al_2O_3$ chromatography (0-50% ethyl acetate/petroleum ether) to yield the 2-(((tert-butyldimethylsilyl)oxy)methyl)-4-(1-ethoxyvinyl)-3-fluoropyridine as a yellow oil. LC/MS: mass calculated for $C_{16}H_{26}FNO_2Si$: 311.17, measured 312.15 $[M+H]^+$.

Step 4: 2-bromo-1-(2-(((tert-butyldimethylsilyl)oxy)methyl)-3-fluoropyridin-4-yl)ethan-1-one To a mixture of 2-(((tert-butyldimethylsilyl)oxy)methyl)-4-(1-ethoxyvinyl)-3-fluoropyridine (15 g, 48.159 mmol, 1.0 equiv) in THF (120 mL) and $H_2O$ (30 mL) was added NBS (8.6 g, 48.319 mmol, 1.0 equiv). The reaction mixture was stirred at room temperature for 2 h. The resulting mixture was then diluted with EtOAc (700 mL), washed with brine (3×200 mL), dried over $Na_2SO_4$, concentrated to yield 2-bromo-1-(2-(((tert-butyldimethylsilyl)oxy)methyl)-3-fluoropyridin-4-yl)ethan-1-one as an off-white solid. LC/MS: mass calculated for $C_{14}H_{21}BrFNO_2Si$: 361.05, measured: 362.00 $[M+H]^+$ Intermediate 13: Methyl 4(1-ethoxyvinyl)-2-fluorobenzoate

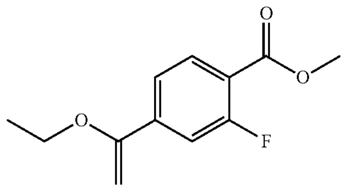 [SMILES: C=C(OCC)c1ccc(C(=O)OC)c(F)c1]

Step 1: Methyl 4-(1-ethoxyvinyl)-2-fluorobenzoate

To a mixture of 2-(((tert butyldimethylsilyl)oxy)methyl)-4-(1-ethoxyvinyl)-3-fluoropyridine (15 g, 48.16 mmol, 1.0 equiv) in THF (120 mL) and $H_2O$ (30 mL) was added NBS (8.6 g, 48.32 mmol, 1.0 equiv). The reaction mixture was stirred at room temperature for 2 h. The resulting mixture was then diluted with EtOAc (700 mL), washed with brine (3×200 mL), dried over $Na_2SO_4$, filtered and concentrated to yield 2-bromo-1-(2-(((tert butyldimethylsilyl)oxy)methyl)-

3-fluoropyridin-4-yl)ethan-1-one as an off-white solid. LC/MS: mass calculated for $C_{14}H_{21}BrFNO_2Si$: 361.05, measured: 362.00 $[M+H]^+$ Step 2: Methyl 4-(2-bromoacetyl)-2-fluorobenzoate To a solution of methyl 4-(1-ethoxyvinyl)-2-fluorobenzoate (4.5 g, 20.06 mmol, 1.0 equiv) in THF (50 mL) with $H_2O$ (10 mL) was added NBS (3.9 g, 22.07 mmol, 1.1 equiv) at 0° C. The reaction mixture was stirred for 1 h at room temperature. The reaction was quenched with brine, extracted with EA three times. The organic layer was washed with brine three times, concentrated under reduced pressure, and the residue purified on flash column chromatography on silica gel (EA/PE: 0%-20%) to yield methyl 4-(2-bromoacetyl)-2-fluorobenzoate as a yellow solid. LC/MS: mass calculated for $C_{10}H_8BrFO_3$: 275.071.

Intermediate 14: 2-Bromo-1-(2-(1-((tert-butyldimethylsilyl)oxy)cyclopropyl)-3-fluoropyridin-4-yl)ethan-1-one

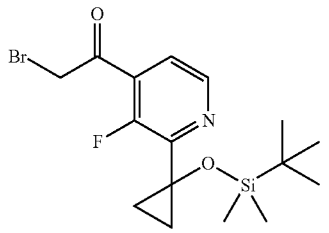 [SMILES: CC(C)(C)[Si](C)(C)OC1(c2nccc(C(=O)CBr)c2F)CC1]

Step 1: 2-(1-((Tert-butyldimethylsilyl)oxy)vinyl)-3-fluoropyridine

To a solution of 1-(3-fluoropyridin-2-yl)ethan-1-one (6.0 g, 43.12 mmol, 1.0 equiv.) and triethylamine (13.1 g, 129.37 mmol, 3.0 equiv.) in DCM (60 mL) was added TBSOTf (14.8 g, 56.06 mmol, 1.3 equiv.) at 0° C. The resulting mixture was stirred at room temperature for 1 h, then quenched with water (20 mL). The resulting mixture was extracted with DCM (3×50 mL) and combined, dried over anhydrous sodium sulfate, filtered and concentrated. The residue was purified by silica gel chromatography (0→20% ethyl acetate/petroleum ether) to yield the 2-(1-((tert-butyldimethylsilyl)oxy)vinyl)-3-fluoropyridine as a yellow oil.

Step 2: 2-(1-((Tert-butyldimethylsilyl)oxy)cyclopropyl)-3-fluoropyridine

To a solution of diethylzinc (52.6 mL, 78.93 mmol, 1.5 M in toluene, 4.0 equiv.) in DCM (80 mL) was added chloroiodomethane (20.9 g, 118.39 mmol, 6.0 equiv.) under nitrogen at 0° C. After 0.5 h, 2-(1-((tert-butyldimethylsilyl)oxy)vinyl)-3-fluoropyridine (5.0 g, 19.73 mmol, 1.0 equiv.) in DCM (10 mL) was added at 0° C. The resulting mixture was maintained under nitrogen and stirred at room temperature for 1 h, then quenched with saturated ammonium chloride solution (20 mL). The resulting mixture was extracted with ethyl acetate (3×20 mL) and the organic layers were combined, dried over anhydrous sodium sulfate, filtered and concentrated. The residue was purified by silica gel chromatography (0→0% ethyl acetate/petroleum ether) to yield the 2-(1-((tert-butyldimethylsilyl)oxy)cyclopropyl)-3-fluoropyridine as a yellow oil.

Step 3: 2-(1-((Tert-butyldimethylsilyl)oxy)cyclopropyl)-3-fluoro-4-iodopyridine

To a solution of 2-(1-((tert-butyldimethylsilyl)oxy)cyclopropyl)-3-fluoropyridine (1.4 g, 5.24 mmol, 1.0 equiv.) in THE (20 mL) was added lithium diisopropylamide (3.4 mL, 6.81 mmol, 2.0 M in THF/Hexane, 1.1 equiv.) at 78° C. After 0.5 h, a solution of 12 (1.5 g, 5.76 mmol, 1.3 equiv.) in THF (4 mL) was added at −78° C. The resulting mixture was maintained under nitrogen and stirred at −78° C. for 1 h. The reaction was quenched with saturated ammonium chloride solution (20 mL). The resulting mixture was extracted with ethyl acetate (3×20 mL). The organic layers were combined, dried over anhydrous sodium sulfate, filtered and concentrated. The residue was purified by silica gel chromatography (0→30% ethyl acetate/petroleum ether) to yield the 2-(1-((tert-butyldimethylsilyl)oxy)cyclopropyl)-3-fluoro-4-iodopyridine as a yellow oil.

Step 4: 2-(1-((Tert-butyldimethylsilyl)oxy)cyclopropyl)-4-(1-ethoxyvinyl)-3-fluoropyridine To a solution of 2-(1-((tert-butyldimethylsilyl)oxy)cyclopropyl)-3-fluoro-4-iodopyridine (1.0 g, 2.54 mmol, 1.0 equiv.) in 1,4-dioxane (10 mL) was added tributyl(1-ethoxyvinyl)stannane (1.8 g, 5.09 mmol, 2.0 equiv.) and $Pd(PPh_3)_4$ (294 mg, 0.25 mmol, 0.1 equiv.). The resulting mixture was stirred at 100° C. for 4 h under nitrogen. After cooling to room temperature, the resulting mixture was extracted with ethyl acetate (3×20 mL). The organic layers were combined, dried over anhydrous sodium sulfate, filtered and concentrated. The residue was purified by silica gel chromatography (0→50% ethyl acetate/petroleum ether) to yield the 2-(1-((tert butyldimethylsilyl)oxy)cyclopropyl)-4-(1-ethoxyvinyl)-3-fluoropyridine as a yellow oil.

Step 5: 2-Bromo-1-(2-(1-((tert-butyldimethylsilyl)oxy)cyclopropyl)-3-fluoropyridin-4-yl)ethan-1-one To a solution of 2-(1-((tert-butyldimethylsilyl)oxy)cyclopropyl)-4-(1-ethoxyvinyl)-3-fluoropyridine (1.0 g, 2.96 mmol, 1.0 equiv.) in THF (8 mL) was added $H_2O$ (2 mL) and NBS (422 mg, 2.37 mmol, 0.8 equiv.) at 0° C. The reaction mixture was stirred at room temperature for 1 h. The resulting mixture was extracted with ethyl acetate (2×20 mL). The organic layers were combined, dried over anhydrous sodium sulfate, filtered and concentrated to yield the 2-bromo-1-(2-(1-((tert-butyldimethylsilyl)oxy)cyclopropyl)-3-fluoropyridin-4-yl)ethan-1-one as a yellow oil.

Intermediate 15: 1-(4-(2-Bromoacetyl)-3-fluoropyridin-2-yl)cyclopropane-1-carbonitrile

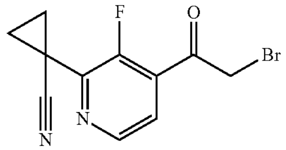 [SMILES: N#CC1(c2nccc(C(=O)CBr)c2F)CC1]

Step 1: 1-(3-Fluoro-4-iodopyridin-2-yl)cyclopropane-1-carbonitrile

To a solution of 2,3-difluoro-4-iodopyridine (0.50 g, 0.83 mmol, 1.0 equiv.) in toluene (10 mL) was added lithium bis(trimethylsilyl)amide solution 1.0 M in THE (3.1 mL, 3.10 mmol, 1.5 equiv.) dropwise under $N_2$ at −10° C. After stirring for 40 min at −10° C., cyclopropane carbonitrile (0.17 g, 2.49 mmol, 1.2 equiv.) was added dropwise. The reaction mixture was warmed to room temperature slowly and stirred for 2 h, then quenched with saturated $NH_4Cl$, extracted with EA, dried over $Na_2SO_4$ and concentrated under vacuum. The residue was purified by silica gel chromatography with EA/PE (0→40%) to yield 1-(3-fluoro-4-iodopyridin-2-yl)cyclopropane-1-carbonitrile as a white solid. LC/MS (ES, m/z): mass calculated for $C_9H_6FIN_2$: 287.96, measured: 280.95 $[M+H]^+$.

Step 2: 1-(4-(1-Ethoxyvinyl)-3-fluoropyridin-2-yl)cyclopropane-1-carbonitrile

To a solution of 1-(3-fluoro-4-iodopyridin-2-yl)cyclopropane-1-carbonitrile (0.50 g, 1.74 mmol, 1.0 equiv.) in 1,4-dioxane (10 mL) was added tributyl(1-ethoxyvinyl)tin (0.94 g, 2.60 mmol, 2.0 equiv.), bis(triphenylphosphine)palladium (II) chloride (90 mg, 0.13 mmol, 0.075 equiv.). The resulting mixture was maintained under nitrogen and stirred at 100° C. for 5 h, then cooled to room temperature and quenched with water. The reaction mixture was extracted with EA. The organic layers were combined, washed with brine, dried and concentrated under vacuum. The residue was purified by silica gel chromatography (0-(20% ethyl acetate/petroleum ether) to yield 1-(4-(1-ethoxyvinyl)-3-fluoropyridin-2-yl)cyclopropane-1-carbonitrile as a yellow solid. LC/MS (ES, m/z): mass calculated for $C_{13}H_{13}FN_2O$: 232.10, measured: 233.10 $[M+H]^+$.

Step 3: 1-(4-(2-Bromoacetyl)-3-fluoropyridin-2-yl)cyclopropane-1-carbonitrile

To a solution of 1-(4-(1-ethoxyvinyl)-3-fluoropyridin-2-yl)cyclopropane-1-carbonitrile (0.47 g, 2.02 mmol, 1.0 equiv.) in THF (10 mL) and water (0.3 mL) was added NBS (0.32 g, 1.82 mmol, 0.9 equiv.). The reaction mixture was stirred at room temperature for 0.5 h, then quenched with water. The reaction mixture was extracted with EA. The organic layers were combined, washed with brine, dried and concentrated under vacuum. The residue was purified by silica gel chromatography (0-(20% ethyl acetate/petroleum ether) to yield 1-(4-(2-bromoacetyl)-3-fluoropyridin-2-yl)cyclopropane-1-carbonitrile as a yellow oil. LC/MS (ES, m/z): mass calculated for $C_{11}H_8BrFN_2O$: 281.98, measured: 282.95 $[M+H]^+$.

Intermediate 16: 2-Bromo-1-(3-fluoro-2-(2-hydroxy-2-methylpropoxy)pyridin-4-yl)ethan-1-one

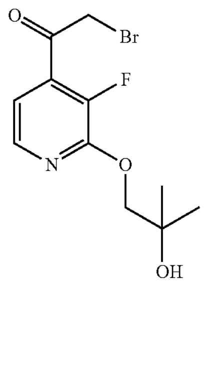 [SMILES: CC(C)(O)COc1nccc(C(=O)CBr)c1F]

Step 1: 1-((3-Fluoro-4-iodopyridin-2-yl)oxy)-2-methylpropan-2-ol

To a solution of 2-methylpropane-1,2-diol (1.3 g, 14.94 mmol, 1.2 equiv.) in DMF (40 mL) was added sodium hydride (359 mg, 14.94 mmol, 60%, 1.2 equiv.) at 0° C. The resulting mixture was stirred at 0° C. for 0.5 h. Then a solution of 2,3-difluoro-4-iodopyridine (3.0 g, 12.45 mmol, 1.0 equiv.) was added dropwise. The mixture was stirred at room temperature for 1 h, then quenched with saturated ammonium solution (50 mL), extracted with EA (3×100 mL) and washed with brine (2×50 mL). The organic layers were combined, dried over anhydrous sodium sulfate, filtered and concentrated. The residue was purified by silica gel chromatography (0→40% PE/EA) to yield 1-((3-fluoro-4-iodopyridin-2-yl)oxy)-2-methylpropan-2-ol. LC/MS (ES, m/z): mass calculated for $C_9H_{11}FINO_2$: 310.98, measured: 312.00 $[M+H]^+$.

Step 2: 1-((4-(1-Ethoxyvinyl)-3-fluoropyridin-2-yl)oxy)-2-methylpropan-2-ol

Under an inert atmosphere of nitrogen, to a solution of 1-((3-fluoro-4-iodopyridin-2-yl)oxy)-2-methylpropan-2-ol (2.4 g, 7.72 mmol, 1.0 equiv.) in 1,4-dioxane (30 mL) were added tributyl(1-ethoxyvinyl)stannane (3.6 g, 10.03 mmol, 1.3 equiv.) and $Pd(PPh_3)_2Cl_2$ (542 mg, 0.77 mmol, 0.1 equiv.). The reaction mixture was stirred for 8 h at 100° C., then concentrated. The residue was applied onto a silica gel column (EA/PE: 0→10%) to yield 1-((4-(1-ethoxyvinyl)-3-fluoropyridin-2-yl)oxy)-2-methylpropan-2-ol as a yellow oil. LC/MS (ES, m/z): mass calculated for $C_{13}H_{18}FNO_3$: 255.13, measured: 256.10 $[M+H]^+$.

Step 3: 2-Bromo-1-(3-fluoro-2-(2-hydroxy-2-methylpropoxy)pyridin-4-yl)ethan-1-one To a solution of 1-((4-(1-ethoxyvinyl)-3-fluoropyridin-2-yl)oxy)-2-methylpropan-2-ol (750 mg, 2.94 mmol, 1.0 equiv.) in THE (8 mL) and water (4 mL) at 0° C. was added NBS (523 mg, 2.94 mmol, 1.0 equiv.) in portions. The resulting mixture was stirred at room temperature for 1 h. The reaction was quenched with brine, extracted with EA for three times. The combined organic layer was washed with brine, concentrated under vacuum. The residue was purified on flash column chromatography on silica gel (EA/PE: 0,100%) to yield 2-bromo-1-(3-fluoro-2-(2-hydroxy-2-methylpropoxy)pyridin-4-yl)ethan-1-one as a yellow solid. LC/MS (ES, m/z): mass calculated for $C_{11}H_{13}BrFNO_3$: 305.01, measured: 306.05 $[M+H]^+$.

Intermediate 17: 2-Bromo-1-(2-(1-((tert-butyldimethylsilyl)oxy)-2,2,2-trifluoroethyl)-3-fluoropyridin-4-yl)ethan-1-one

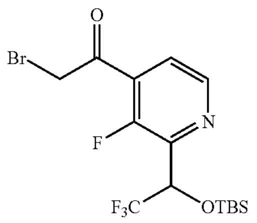 [SMILES: CC(C)(C)[Si](C)(C)OC(c1nccc(C(=O)CBr)c1F)C(F)(F)F]

Step 1: 2,2,2-Trifluoro-1-(3-fluoropyridin-2-yl) ethan-1-one

To a solution of 2-bromo-3-fluoropyridine (5.0 g, 28.41 mmol, 1.0 equiv.) in toluene (40 mL) was dropwise added n-butyllithium (14.78 mL, 36.94 mmol, 1.3 equiv.) under −65° C. under $N_2$. After 30 min, 2,2,2-trifluoro-n-methoxy-n-methylacetamide (6.7 g, 42.62 mmol, 1.5 equiv.) was added to the resulting mixture under −65° C. and the resulting mixture was kept stirring for 1 h. The resulting mixture was quenched with $NH_4C_1$ (aq.), diluted with EA (40 mL) and extracted with EA (2×40 mL). The organic layers were combined, washed with brine, dried over $Na_2SO_4$ and concentrated. The residue was purified by silica gel column (0→50%, EA/PE) to yield 2,2,2-trifluoro-1-(3-fluoropyridin-2-yl)ethan-1-one as a yellow oil. LC/MS (ES, m/z): mass calculated for $C_7H_3F_4NO$: 193.02, measured: 212.00 $[M+H_2O+H]^+$.

Step 2: 2,2,2-Trifluoro-1-(3-fluoropyridin-2-yl)ethan-1-ol

To a solution of 2,2,2-trifluoro-1-(3-fluoropyridin-2-yl) ethan-1-one (3.9 g, 20.04 mmol, 1.0 equiv.) in DCE (40 mL) was added sodium triacetoxyborohydride (5.5 g, 26.05 mmol, 1.3 equiv.) in several portions. The resulting mixture was stirred at room temperature overnight. The resulting mixture was diluted with water (50 mL), extracted with EA (3×30 mL). The organic layers were combined, washed with brine, dried over $Na_2SO_4$ and concentrated to yield 2,2,2-trifluoro-1-(5-nitroisoquinolin-1-yl)ethan-1-ol as a light yellow oil. LC/MS (ES, m/z): mass calculated for $C_7H_5F_4NO$: 195.03, measured: 196.05 $[M+H]^+$.

Step 3: 2-(1-((Tert-butyldimethylsilyl)oxy)-2,2,2-trifluoroethyl)-3-fluoropyridine To a solution of 2,2,2-trifluoro-1-(3-fluoropyridin-2-yl) ethan-1-ol (3.9 g, 19.84 mmol, 1.0 equiv.) in DCM (40 mL) were added 2,6-dimethylpyridine (6.9 mL, 59.50 mmol, 3.0 equiv.) and TBSOTf (13.7 mL, 59.50 mmol, 3.0 equiv.). The resulting mixture was stirred at 60° C. overnight. The resulting mixture was diluted with water (20 mL) and extracted with EA (3×20 mL). The organic layers were combined, washed with brine, dried over $Na_2SO_4$ and concentrated. The residue was purified by silica gel column (EA/PE, 0→50%) to yield 2-(1-((tart-butyldimethylsilyl) oxy)-2,2,2-trifluoroethyl)-3-fluoropyridine as a light yellow oil. LC/MS (ES, m/z): mass calculated for $C_{13}H_{19}F_4NOSi$: 309.12, measured: 310.00 $[M+H]^+$.

Step 4: 2-(1-((Tert-butyldimethylsilyl)oxy)-2,2,2-trifluoroethyl)-3-fluoro-5-iodopyridine To a solution of 2-(1-((tert butyldimethylsilyl)oxy)-2,2,2-trifluoroethyl)-3-fluoropyridine (1.0 g, 3.23 mmol, 1.0 equiv.) in THE (15 mL) was added LDA (2.4 mL, 4.85 mmol, 1.5 equiv.) dropwise at −55° C. under $N_2$. The resulting mixture was stirred at −55° C. for 30 min. 12 (1.6 g, 6.47 mmol, 2.0 equiv.) in THE was then added dropwise. The resulting mixture was stirred at −55° C. for 1 h, then diluted with aqueous $Na_2SO_3$ (20 mL), extracted with EA (3×20 mL). The organic layers were combined, washed with brine, dried over $Na_2SO_4$ and concentrated to yield 2-(1-((tert-butyldimethylsilyl)oxy)-2,2,2-trifluoroethyl)-3-fluoro-4-iodopyridine as a dark red oil. LC/MS (ES, m/z): mass calculated for $C_{13}H_{18}F_4INOSi$: 435.01, measured: 435.95 $[M+H]^+$.

Step 5: 2-(1-((Tert-butyldimethylsilyl)oxy)-2,2,2-trifluoroethyl)-4-(1-ethoxyvinyl)-3-fluoropyridine A mixture of 2-(1-((tert-butyldimethylsilyl)oxy)-2,2,2-trifluoroethyl)-3-fluoro-4-iodopyridine (1.7 g, 3.91 mmol, 1.0 equiv.), tributyl(1-ethoxyvinyl)stannane (2.1 g, 5.86 mmol, 1.5 equiv.) and $Pd(PPh_3)_4$ (451 mg, 0.39 mmol, 0.1 equiv.) in 1,4-dioxane (20 mL) was heated at 90° C. under $N_2$ for 1.5 h. The resulting mixture was evaporated and the residue diluted with DCM. Neutral $Al_2O_3$ was added and the resulting mixture was concentrated. The residue was purified by neutral $Al_2O_3$ column (EA/PE, 0→15%) to yield 2-(1-((tert-butyldimethylsilyl)oxy)-2,2,2-trifluoroethyl)-4-(1-ethoxyvinyl)-3-fluoropyridine as a light yellow oil. LC/MS (ES, m/z): mass calculated for $C_{17}H_{25}F_4NO_2Si$: 379.16, measured: 380.15 $[M+H]^+$.

Step 6: 2-Bromo-1-(2-(1-((tert-butyldimethylsilyl) oxy)-2,2,2-trifluoroethyl)-3-fluoropyridin-4-yl) ethan-1-one A mixture of 2-(1-((tert-butyldimethylsilyl)oxy)-2,2,2-trifluoroethyl)-4-(1-ethoxyvinyl)-3-fluoropyridine (850 mg, 2.24 mmol, 1.0 equiv.) and 1-bromopyrrolidine-2,5-dione (399 mg, 2.24 mmol, 1.0 equiv.) in $THF/H_2O$ (8 mL) was stirred at room temperature for 2 h. The reaction was diluted with water, then extracted with DCM (3×10 mL). The organic layers were combined, washed with brine, dried over $Na_2SO_4$ and added $CH_3CN$ to remove DCM. The residue-2-bromo-1-(2-(1-((tert-butyldimethylsilyl)oxy)-2,2,2-trifluoroethyl)-3-fluoropyridin-4-yl)ethan-1-one—was used in the next step without further concentration or purification. LC/MS (ES, m/z): mass calculated for $C_{15}H_{20}BrF_4NO_2Si$: 429.04, measured: 431.95 $[M+H]^+$.

Intermediate 18: 2-Bromo-1-(2-(((tert-butyldimethylsilyl)oxy)methyl-d2)-3-fluoropyridin-4-yl)ethan-1-one

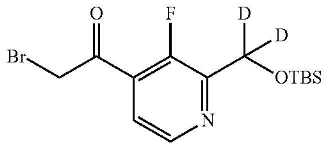 [SMILES: [2H]C([2H])(O[Si](C)(C)C(C)(C)C)c1nccc(C(=O)CBr)c1F]

Step 1: (3-Fluoropyridin-2-yl)methan-d2-ol

To a solution of methyl 3-fluoropicolinate (1.9 g, 12.25 mmol, 1.0 equiv.) in methanol-D (10 mL) was added $NaBD_4$ (767 mg, 18.37 mmol, 1.5 equiv.) at 0° C. The mixture was stirred at 0° C. for 1 h. The reaction was quenched with D20 (10 mL). The resulting mixture was extracted with ethyl acetate (2×100 mL). The organic layers were combined, dried over anhydrous sodium sulfate, filtered and concentrated to yield the (3-fluoropyridin-2-yl)methan-d2-ol as a yellow oil.

Step 2: 2-(((Tert-butyldimethylsilyl)oxy)methyl-d2)-3-fluoropyridine

To a solution of (3-fluoropyridin-2-yl)methan-d2-ol (1.2 g, 9.29 mmol, 1.0 equiv.) and 2,6-lutidine (1.5 g, 13.94 mmol, 1.5 equiv.) in DCM (15 mL) was added TBSOTf (3.2 g, 12.08 mmol, 1.3 equiv.) at 0° C. The mixture was stirred at room temperature for 1 h. The reaction was quenched with water (20 mL). The resulting mixture was extracted with DCM (1×50 mL) and washed with water and brine (30 mL). The organic layers were combined, dried over anhydrous sodium sulfate, filtered and concentrated. The residue was purified by silica gel chromatography (0→20% ethyl acetate/petroleum ether) to yield the 2-(((tert-butyldimethylsilyl)oxy)methyl-d2)-3-fluoropyridine as a yellow oil.

Step 3: 2-(((Tert-butyldimethylsilyl)oxy)methyl-d2)-3-fluoro-4-iodopyridine

To a solution of diisopropylamine (798 mg, 7.89 mmol, 1.2 equiv.) in tetrahydrofuran (20 mL) was added n-butyllithium (3.2 mL, 7.89 mmol, 2.5 M, 1.2 equiv.) at −20° C. After 0.5 h of stirring, 2-(((tert-butyldimethylsilyl)oxy)methyl-d2)-3-fluoropyridine (1.6 g, 6.57 mmol, 1.0 equiv.) was added at −78° C. and the mixture was maintained stirring at −78° C. for 1 h, then 12 (1.8 g, 7.23 mmol, 1.1 equiv.) in tetrahydrofuran (2 mL) was added. The resulting mixture was maintained under nitrogen and stirred at room temperature for 2 h. The reaction was then quenched with saturated ammonium chloride solution (20 mL), extracted with ethyl acetate (3×20 mL). The organic layers were combined, dried over anhydrous sodium sulfate, filtered and concentrated. The residue was purified by silica gel chromatography (0→10% ethyl acetate/petroleum ether) to yield the 2-(((tert-butyldimethylsilyl)oxy)methyl-d2)-3-fluoro-4-iodopyridine as a white solid.

Step 4: 2-(((Tert-butyldimethylsilyl)oxy)methyl-d2)-4-(1-ethoxyvinyl)-3-fluoropyridine To a solution of 2-(((tert-butyldimethylsilyl)oxy)methyl-d2)-3-fluoro-4-iodopyridine (1.8 g, 4.87 mmol, 1.0 equiv.) in 1,4-dioxane (20 mL) were added tributyl(1-ethoxyvinyl)stannane (2.6 g, 7.31 mmol, 1.5 equiv.), and $Pd(PPh_3)_2Cl_2$ (342 mg, 0.48 mmol, 0.1 equiv.). The resulting mixture was maintained under nitrogen and stirred at 90° C. for 2 h. After cooling to room temperature, the solvent was removed under vacuum and the residue was purified by silica gel column with EA/PE (0→50%) to yield the 2-(((tert-butyl-dimethylsilyl)oxy)methyl-d2)-4-(1-ethoxyvinyl)-3-fluoropyridine as a yellow oil.

Step 5: 2-Bromo-1-(2-(((tert-butyldimethylsilyl)oxy)methyl-d2)-3-fluoropyridin-4-yl)ethan-1-one To a solution of 2-(((tert-butyldimethylsilyl)oxy)methyl-d2)-4-(1-ethoxyvinyl)-3-fluoropyridine (550 mg, 1.76 mmol, 1.0 equiv.) in THE (8 mL) and $H_2O$ (2 mL) was added NBS (281 mg, 1.58 mmol, 0.9 equiv.) at 0° C. The reaction mixture was stirred at room temperature for 1 h. The resulting mixture was extracted with ethyl acetate (2×20 mL). The organic layers were combined, dried over anhydrous sodium sulfate, filtered and concentrated to yield the 2-bromo-1-(2-(((tert-butyldimethylsilyl)oxy)methyl-d2)-3-fluoropyridin-4-yl)ethan-1-one as a yellow oil.

Intermediate 19: 2-Bromo-1-(4-(trifluoromethyl)-1-((2-(trimethylsilyl)ethoxy)methyl)-1H-pyrrol-3-yl)ethan-1-one

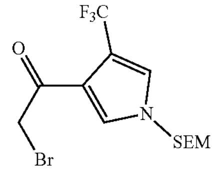 [SMILES: C[Si](C)(C)CCOCn1cc(C(=O)CBr)c(C(F)(F)F)c1]

Step 1: Ethyl 4-(trifluoromethyl)-1-((2-(trimethylsilyl)ethoxy)methyl)-1H-pyrrole-3-carboxylate To a solution of ethyl 4-(trifluoromethyl)-1H-pyrrole-3-carboxylate (0.50 g, 2.41 mmol, 1.0 equiv.) in THF (20 mL) were added NaH (0.12 g, 2.90 mmol, 1.2 equiv.) and SEMCl (0.60 g, 3.62 mmol, 1.5 equiv.). The resulting mixture was stirred for 3 h at 25° C. The reaction was quenched with $H_2O$, extracted with EtOAc. The organic layers were combined, dried over $Na_2SO_4$, filtered and concentrated. The residue was purified by silica gel chromatography (0→20% EA/PE) to yield ethyl 4-(trifluoromethyl)-1-((2-(trimethylsilyl)ethoxy)methyl)-1H-pyrrole-3-carboxylate as a yellow oil.

Step 2: 4-(Trifluoromethyl)-1-((2-(trimethylsilyl)ethoxy)methyl)-1H-pyrrole-3-carboxylic acid To a solution of ethyl 4-(trifluoromethyl)-1-((2-(trimethylsilyl)ethoxy)methyl)-1H-pyrrole-3-carboxylate (0.70 g, 2.08 mmol, 1.0 equiv.) in MeOH (10 mL) were added THF (10 mL) and LiOH (10.4 mL, 10.37 mmol, 1 M, 5.0 equiv.). The resulting mixture was stirred at 25° C. overnight. The resulting mixture was concentrated. The mixture was then poured onto HCl (2 N) adjusting to pH 2~3. The resulting mixture was extracted with EA. The organic layers were combined, dried over $Na_2SO_4$, filtered and concentrated to yield 4-(trifluoromethyl)-1-((2-(trimethylsilyl)ethoxy)methyl)-1H-pyrrole-3-carboxylic acid as a yellow oil.

Step 3: 4-(Trifluoromethyl)-1-((2-(trimethylsilyl)ethoxy)methyl)-1H-pyrrole-3-carbonyl chloride To a solution of 4-(trifluoromethyl)-1-((2-(trimethylsilyl)ethoxy)methyl)-1H-pyrrole-3-carboxylic acid (0.30 g, 0.97 mmol, 1.0 equiv.) in DCM (50 mL) was added oxalyl chloride (0.19 g, 1.46 mmol, 1.5 equiv.), followed by DMF (7 mg, 0.097 mmol, 0.1 equiv.). The resulting mixture was stirred for 1 h at 25° C., concentrated under vacuum to yield 4-(trifluoromethyl)-1-((2-(trimethylsilyl)ethoxy)methyl)-1H-pyrrole-3-carbonyl chloride as a yellow oil.

Step 4: 2-Bromo-1-(4-(trifluoromethyl)-1-((2-(trimethylsilyl)ethoxy)methyl)-1H-pyrrol-3-yl)ethan-1-one To a solution of 4-(trifluoromethyl)-1-((2-(trimethylsilyl)ethoxy)methyl)-1H-pyrrole-3-carbonyl chloride (0.31 g, 0.95 mmol, 1.0 equiv.) in MeCN (30 mL) was added $TMSCHN_2$ (1.4 mL, 2.84 mmol, 3.0 equiv.). The resulting mixture was stirred for 6 h at 25° C. Then HBr (0.80 g, 4.73 mmol, 5.0 equiv.) was added. The reaction mixture was stirred for 1 h at 25° C. The reaction was quenched with $H_2O$. The resulting mixture was extracted with EA. The organic layers were combined, dried over $Na_2SO_4$, filtered and concentrated to yield 2-bromo-1-(4-(trifluoromethyl)-1-((2-(trimethylsilyl)ethoxy)methyl)-1H-pyrrol-3-yl)ethanone as a yellow oil.

Intermediate 20: 2-Bromo-1-(1-(4-methoxybenzyl)-2-(trifluoromethyl)-1H-imidazol-4-yl)ethan-1-one

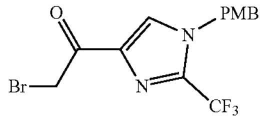

Step 1: Ethyl 1-(4-methoxybenzyl)-2-(trifluoromethyl)-1H-imidazole-4-carboxylate To a solution of ethyl 2-(trifluoromethyl)-1H-imidazole-4-carboxylate (2.1 g, 10.23 mmol, 1.0 equiv.) in DMF (30 mL) was added PMBCl (3.2 g, 20.47 mmol, 2.0 equiv.) and $K_2CO_3$ (4.2 g, 30.70 mmol, 3.0 equiv.). The resulting mixture stirred at room temperature for 9 h. The reaction progress was monitored by LCMS. LCMS showed the desired product was generated and the reaction was partitioned between $H_2O$ and EA. The organic layers were combined, dried over anhydrous sodium sulfate, filtered and concentrated. The residue was purified by silica gel chromatography (0→26% ethyl acetate/petroleum ether) to yield the ethyl 1-(4-methoxybenzyl)-2-(trifluoromethyl)-1H-imidazole-4-carboxylate as a white oil. LC/MS (ES, m/z): mass calculated for $C_{15}H_{15}F_3N_2O_3$: 328.10, measured: 329.05 $[M+H]^+$.

Step 2: 1-(4-Methoxybenzyl)-2-(trifluoromethyl)-1H-imidazole-4-carboxylic acid

To a solution of ethyl 1-(4-methoxybenzyl)-2-(trifluoromethyl)-1H-imidazole-4-carboxylate (2.1 g, 6.45 mmol, 1.0 equiv.) in THE/$H_2O$/EtOH (10/10/10 mL) was added LiOH (0.62 g, 25.95 mmol, 4.0 equiv.). The resulting mixture stirred at room temperature for 4 h. The reaction was quenched with HCl (2 M) solution and extract with EA to yield the 1-(4-methoxybenzyl)-2-(trifluoromethyl)-1H-imidazole-4-carboxylic acid as a white solid. LC/MS (ES, m/z): mass calculated for $C_{13}H_{11}F_3N_2O_3$: 300.07, measured: 301.25 $[M+H]^+$.

Step 3: 1-(4-Methoxybenzyl)-2-(trifluoromethyl)-1H-imidazole-4-carbonyl chloride To a solution of 1-(4-methoxybenzyl)-2-(trifluoromethyl)-1H-imidazole-4-carboxylic acid (600 mg, 2.00 mmol, 1.0 equiv.) in DCM (5 mL) was added oxalyl chloride (507 mg, 4.00 mmol, 2.0 equiv.) and DMF (0.001 mL). The resulting mixture was maintained under nitrogen and stirred at room temperature for 2 h. LCMS showed the desired product was generated and the mixture was used in the next step without any purifications.

Step 4: 2-Bromo-1-(1-(4-methoxybenzyl)-2-(trifluoromethyl)-1H-imidazol-4-yl)ethanone To a solution of 1-(4-methoxybenzyl)-2-(trifluoromethyl)-1H-imidazole-4-carbonyl chloride (600 mg, 1.88 mmol, 1.0 equiv.) in ACN (5 mL) was added (trimethylsilyl) diazomethane (860 mg, 7.53 mmol, 4.0 equiv.) slowly at 0° C. The resulting mixture was maintained under nitrogen and stirred at room temperature for 2 h. LCMS showed the desired product was generated and the mixture was used in the next step without any purifications.

Step 5. 2-bromo-1-(1-(4-methoxybenzyl)-2-(trifluoromethyl)-1H-imidazol-4-yl)ethanone To a solution of 2-diazo-1-(1-(4-methoxybenzyl)-2-(trifluoromethyl)-1H-imidazol-4-yl)ethanone (600 mg, 1.85 mmol, 1.0 equiv.) in ACN (5 mL) was added HBr/$H_2O$ (1.0 g, 12.95 mmol, 7.0 equiv.) at 0° C. The resulting mixture was stirred at room temperature for 4 h. LCMS showed the desired product was generated and after the reaction mixture was cooled to room temperature, and the reaction was quenched with water (50 mL). The resulting mixture was extracted with ethyl acetate (3×50 mL). The organic layers were combined, dried over anhydrous sodium sulfate, filtered and concentrated to yield the 2-bromo-1-(1-(4-methoxybenzyl)-2-(trifluoromethyl)-1H-imidazol-4-yl) ethanone.

Intermediate 21: 4-(2-Bromoacetyl)thiophene-2-carboxamide

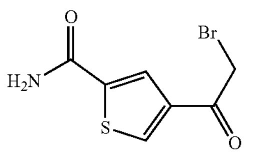 [SMILES: NC(=O)c1cc(C(=O)CBr)cs1]

Step 1: 4-Acetylthiophene-2-carboxamide

4-Bromothiophene-2-carboxamide (1.0 g, 4.85 mmol, 1.0 equiv.) and tributyl(1-ethoxyvinyl)stannane (1.9 g, 5.34 mmol, 1.2 equiv.) were dissolved in 1,4-dioxane (30 mL). $Pd(PPh_3)_4$ (561 mg, 0.49 mmol, 0.1 equiv.) was then added. The reaction mixture was stirred at 100° C. for 4 h. The reaction mixture was partitioned between ethyl acetate and water. The organic layers were separated and combined, dried over anhydrous sodium sulfate, filtered and concentrated. The residue was purified by silica gel chromatography (0→80% ethyl acetate/petroleum ether) to yield the 4-acetylthiophene-2-carboxamide as a yellowish oil. LC/MS (ES, m/z): mass calculated for $C_7H_7NO_2S$: 169.02, measured: 170.05 $[M+H]^+$.

Step 2: 4-(2-Bromoacetyl)thiophene-2-carboxamide

4-Acetylthiophene-2-carboxamide (600 mg, 3.55 mmol, 1.0 equiv.) and pyridinium tribromide (1.0 g, 3.19 mmol, 0.9 equiv.) were dissolved in dichloromethane (15 mL). HBr/HOAc (0.05 mL) was then added. The reaction mixture was stirred at room temperature for 5 h. LCMS showed the desired product was generated and the resulting mixture was extracted with ethyl acetate (3×50 mL). The organic layers were combined, dried over anhydrous sodium sulfate, filtered and concentrated. The residue was purified by silica gel chromatography (0→80% ethyl acetate/petroleum ether) to yield the 4-(2-bromoacetyl)thiophene-2-carboxamide as a white solid. LC/MS (ES, m/z): mass calculated for $C_7H_6BrNO_2S$: 246.93, measured: 247.95, 249.95 [M+H, M+H+2]$^+$.

Intermediate 22: 5-(2-Bromoacetyl)thiophene-2-carboxamide

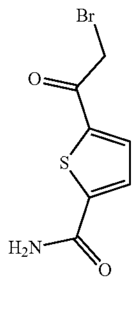 [SMILES: NC(=O)c1ccc(C(=O)CBr)s1]

Step 1: 5-(1-Ethoxyvinyl)thiophene-2-carboxamide

To a solution of 5-bromothiophene-2-carboxamide (5.0 g, 24.27 mmol, 1.0 equiv.) in 1,4-dioxane (50 mL) were added tributyl(1-ethoxyvinyl)stannane (13.1 g, 36.40 mmol, 1.5 equiv.) and $Pd(PPh_3)_4$ (2.8 g, 2.43 mmol, 0.1 equiv.). The resulting mixture was maintained under nitrogen and stirred at 100° C. for 3 h. After cooling to room temperature, the reaction was quenched with water (20 mL). The resulting mixture was extracted with ethyl acetate (3×20 mL). The organic layers were combined, dried over anhydrous sodium sulfate, filtered and concentrated to yield the 5-(1-ethoxyvinyl)thiophene-2-carboxamide as a green oil.

Step 2: 5-(2-Bromoacetyl)thiophene-2-carboxamide

To a solution of 5-(1-ethoxyvinyl)thiophene-2-carboxamide (2.1 g, 10.65 mmol, 1.0 equiv.) in THE (12 mL) and $H_2O$ (4 mL) was added NBS (2.1 g, 11.71 mmol, 1.1 equiv.). The mixture was stirred at room temperature for 1 h. The resulting mixture was extracted with ethyl acetate (2×20 mL). The organic layers were combined, dried over anhydrous sodium sulfate, filtered and concentrated to yield the 5-(2-bromoacetyl)thiophene-2-carboxamide as a white solid. LC/MS (ES, m/z): mass calculated for $C_7H_6BrNO_2S$: 246.93, measured: 248.00 [M+H]$^+$.

Intermediate 23: 5-(2-Bromoacetyl)-3-fluorothiophene-2-carboxamide

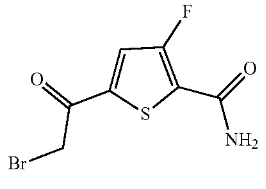 [SMILES: NC(=O)c1sc(C(=O)CBr)cc1F]

Step 1: 5-Bromo-3-fluorothiophene-2-carboxamide

To a solution of 5-bromo-3-fluorothiophene-2-carboxylic acid (900 mg, 3.99 mmol, 1.0 equiv.) in DMF (10 mL) were added HATU (1.8 g, 4.79 mmol, 1.2 equiv.), DIEA (1.5 g, 11.99 mmol, 3.0 equiv.) and ammonium chloride (256 mg, 4.79 mmol, 1.2 equiv.). The mixture was stirred at room temperature for 3 hours. The reaction was quenched with water (10 mL). The resulting mixture was extracted with ethyl acetate (20 mL×3). The organic layers were combined, washed with brine three times, dried over anhydrous sodium sulfate, filtered and concentrated. The residue was purified by gel chromatography (0→30% MeOH/DCM) to yield the 5-bromo-3-fluorothiophene-2-carboxamide. LC/MS (ES, m/z): mass calculated for $C_5H_3BrFNOS$: 222.91, measured: 223.90 [M+H]$^+$.

Step 2: 5-(1-Ethoxyvinyl)-3-fluorothiophene-2-carboxamide

A mixture of 5-bromo-3-fluorothiophene-2-carboxamide (360 mg, 1.67 mmol, 1.0 equiv.), tributyl (1-ethoxyvinyl)tin (724 mg, 2.00 mmol, 1.2 equiv.) and $Pd(PPh_3)_4$ (193 mg, 0.16 mmol, 0.1 equiv.) in 1,4-dioxane (10 mL) was degassed and then heated at 100° C. under $N_2$ for 4 hours before being cooled to room temperature. The mixture was concentrated under reduced pressure and the residue was purified by chromatography ($Al_2O_3$, EA/PE: 0→30%) to yield the desired compound 5-(1-ethoxyvinyl)-3-fluorothiophene-2-carboxamide as a yellow oil.

Step 3: 5-(2-Bromoacetyl)-3-fluorothiophene-2-carboxamide

To a solution of 5-(1-ethoxyvinyl)-3-fluorothiophene-2-carboxamide (350 mg, 1.62 mmol, 1.0 equiv.) in THE/$H_2O$ (9 mL/3 mL) was added NBS (347 mg, 1.95 mmol, 1.2 equiv.). The resulting mixture was stirred for 1 h, quenched the reaction with water and extracted with EA. The solvent was removed under reduced pressure. The residue was purified through silica gel. The residue was purified by gel chromatography (0-(30% EA/PE) to yield the 5-(2-bromoacetyl)-3-fluorothiophene-2-carboxamide.

Intermediate 24: 2-Bromo-1-(3-(trifluoromethyl)-1-((2-(trimethylsilyl)ethoxy)methyl)-1H-pyrazol-4-yl) ethan-1-one

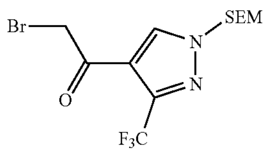 [SMILES: C[Si](C)(C)CCOCn1cc(C(=O)CBr)c(C(F)(F)F)n1]

Step 1: Ethyl 3-(trifluoromethyl)-1-((2-(trimethylsilyl)ethoxy)methyl)-1H-pyrazole-4-carboxylate To a solution of ethyl 3-(trifluoromethyl)-1H-pyrazole-4-carboxylate (4.0 g, 19.22 mmol, 1.0 equiv.) in DMF (40 mL) was added NaH (0.51 g, 21.14 mmol, 1.1 equiv.) at 0° C. for 15 min, then SEMCl (3.2 g, 19.22 mmol, 1.0 equiv.) was added. The resulting mixture was maintained under nitrogen and stirred at 25° C. for 3 h, then quenched with HCl (100 mL). The resulting mixture was extracted with EA (3×100 mL). The organic layers were combined, dried over anhydrous sodium sulfate, filtered and concentrated. Yield 4-(4-bromophenyl)-1-(4-(trifluoromethoxy) phenyl)butane-1,3-dione as a yellow oil. LC/MS (ES, m/z): mass calculated for $C_{13}H_{21}F_3N_2O_3Si$: 338.13, measured: 339.20 $[M+H]^+$.

Step 2: 3-(Trifluoromethyl)-1-((2-(trimethylsilyl) ethoxy)methyl)-1H-pyrazole-4-carboxylic acid To a solution of ethyl 3-(trifluoromethyl)-1-((2-(trimethylsilyl)ethoxy)methyl)-1H-pyrazole-4-carboxylate (3.3 g, 0.010 mol, 1.0 equiv.) in THE (10 mL), MeOH (10 mL), and $H_2O$ (10 mL) was added LiOH (1.2 g, 0.049 mol, 5.0 equiv.) at room temperature for 1 h. The reaction was quenched with HCl (50 mL). The resulting mixture was extracted with EA (3×50 mL). The organic layers were combined, dried over anhydrous sodium sulfate, filtered and concentrated to yield 3-(trifluoromethyl)-1-((2-(trimethylsilyl) ethoxy) methyl)-1H-pyrazole-4-carboxylic acid as a white solid. LC/MS (ES, m/z): mass calculated for $C_{11}H_{17}F_3N_2O_3Si$: 310.10, measured: 311.20 $[M+H]^+$.

Step 3: 3-(Trifluoromethyl)-1-((2-(trimethylsilyl) ethoxy) methyl)-1H-pyrazole-4-carbonyl chloride To a solution of 3-(trifluoromethyl)-1-((2-(trimethylsilyl) ethoxy)methyl)-1H-pyrazole-4-carboxylic acid (100 mg, 0.32 mmol, 1.0 equiv.) in DCM (5 mL), was added $(COCl)_2$ (61 mg, 0.48 mmol, 1.5 equiv.). The resulting mixture was maintained under nitrogen and stirred at 25° C. for 2 h. The reaction mixture containing the product was used in the next step reaction directly, without further purification or isolation.

Step 4: 2-Bromo-1-(3-(trifluoromethyl)-1-((2-(trimethylsilyl)ethoxy)methyl)-1H-pyrazol-4-yl)ethanone To a solution of 3-(trifluoromethyl)-1-((2-(trimethylsilyl) ethoxy)methyl)-1H-pyrazole-4-carbonyl chloride (20 mg, 0.061 mmol, 1.0 equiv.) in acetonitrile (3 mL) was added $TMSCHN_2$ (0.1 mL) at 0° C. The resulting mixture was maintained under nitrogen and stirred at 25° C. for 16 h, then concentrated under reduced pressure. The residue (300 mg, 0.89 mmol) was re-dissolved in ACN (3 mL). To the resulting solution was then added $HBr/H_2O$ (0.7 mL) at 0° C., and the resulting mixture was maintained under nitrogen and stirred at 25° C. for 1 h. The resulting mixture was concentrated under reduced pressure and the residue-2-bromo-1-(3-(trifluoromethyl)-1-((2-(trimethylsilyl)ethoxy) methyl)-1H-pyrazol-4-yl)ethanone-was used in the next step without further purification or isolation.

Intermediate 25: 6-(2-Bromoacetyl)-5-fluoro-1,4-dihydro-2H-benzo[d][1,3]oxazin-2-one

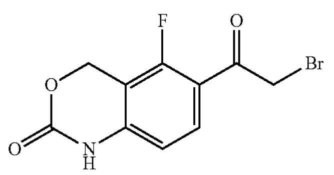 [SMILES: O=C1Nc2ccc(C(=O)CBr)c(F)c2CO1]

Step 1: 6-Amino-3-bromo-2-fluorobenzoic acid

To a mixture of 2-amino-6-fluorobenzoic acid (5.0 g, 32.23 mmol, 1.0 equiv.) in N,N-dimethylformamide (50 mL) was added N-bromosuccinimide (6.3 g, 35.45 mmol, 1.1 equiv.) at 0° C. The reaction mixture was stirred at room temperature overnight, then partitioned between EtOAc and water. The organic layer was separated, and the combined organic layers were washed with brine, dried over $Na_2SO_4$ and concentrated under vacuum to yield 6-amino-3-bromo-2-fluorobenzoic acid as a yellow solid. LC/MS (ES, m/z): mass calculated for $C_7H_5BrFNO_2$: 232.95, measured: 233.90, 235.90 $[M+H, M+H+2]^+$.

Step 2: (6-Amino-3-bromo-2-fluorophenyl)methanol

To a mixture of 6-amino-3-bromo-2-fluorobenzoic acid (7.0 g, 29.91 mmol, 1.0 equiv.) in THE (70 mL) was added borane-tetrahydrofuran complex (239 mL, 239.29 mmol, 1 M in THF, 8.0 equiv.) at room temperature. The reaction mixture was stirred at 50° C. for 4 h. The reaction was quenched with water and extracted with EA twice. The combined organic layers were washed with brine, dried over $Na_2SO_4$, concentrated under vacuum and the residue purified by silica gel chromatography (0→60% EA/PE) to yield (6-amino-3-bromo-2-fluorophenyl)methanol as a white solid. LC/MS (ES, m/z): mass calculated for $C_7H_7BrFNO$: 218.97, measured: 220.15, 222.15 $[M+H, M+H+2]^+$.

Step 3: 6-Bromo-5-fluoro-1,4-dihydro-2H-benzo[d][1,3]oxazin-2-one

To a mixture of (6-amino-3-bromo-2-fluorophenyl) methanol (6.0 g, 27.27 mmol, 1.0 equiv.) in THF (70 mL) was added triphosgene (16.2 g. 54.54 mmol. 2.0 equiv.). The reaction mixture was stirred at 60° C. for 1.5 h. The reaction was quenched with saturated $NaHCO_3$ and extracted with EA twice. The combined organic layers were washed with brine, dried over $Na_2SO_4$ and concentrated under vacuum. The residue was purified by silica gel chromatography (0→60% EA/PE) to yield 6-bromo-5-fluoro-1,4-dihydro-2H-benzo[d][1,3]oxazin-2-one as a yellow solid. LC/MS (ES, m/z): mass calculated for $C_8H_5BrFNO_2$: 244.95, measured: 246.10, 248.15 $[M+H, M+H+2]^+$.

Step 4: 6-(1-Ethoxyvinyl)-5-fluoro-1,4-dihydro-2H-benzo[d][1,3]oxazin-2-one

To a mixture of 6-bromo-5-fluoro-1,4-dihydro-2H-benzo [d][1,3]oxazin-2-one (2 g, 8.13 mmol, 1.0 equiv.) in 1,4-dioxane (20 mL) were added tributyl(1-ethoxyvinyl)stannane (3.3 mL, 9.75 mmol, 1.2 equiv.) and $Pd(PPh_3)_2Cl_2$ (0.60 g, 0.81 mmol, 0.1 equiv.). The resulting solution was stirred at 100° C. for 6 h under nitrogen. To the reaction mixture was then added water, and the mixture was extracted with EA twice. The combined organic layers were washed with brine, dried over $Na_2SO_4$ and concentrated under vacuum to yield 6-(1-ethoxyvinyl)-5-fluoro-1,4-dihydro-2H-benzo[d][1,3]oxazin-2-one as a yellow solid. LC/MS (ES, m/z): mass calculated for $C_{12}H_{12}FNO_3$: 237.08, measured: 238.15 $[M+H]^+$.

Step 5: 6-(2-Bromoacetyl)-5-fluoro-1,4-dihydro-2H-benzo[d][1,3]oxazin-2-one

To a mixture of 6-(1-ethoxyvinyl)-5-fluoro-1,4-dihydro-2H-benzo[d][1,3]oxazin-2-one (900 mg, 3.79 mmol, 1.0 equiv.) in THE (9 mL) and water (3 mL) was added N-bromosuccinimide (675 mg, 3.79 mmol, 1.0 equiv.). The reaction mixture was stirred at room temperature for 1.0 h. The mixture was diluted with $H_2O$, extracted with EA twice. The combined organic layers were washed with brine, dried over $Na_2SO_4$ and concentrated under vacuum. The residue was purified by silica gel chromatography (0→50% EA/PE) to yield 6-(2-bromoacetyl)-5-fluoro-1,4-dihydro-2H-benzo [d][1,3]oxazin-2-one as a yellow solid. LC/MS (ES, m/z): mass calculated for $C_{10}H7BrFNO_3$: 286.96, measured: 287.95, 289.95 $[M+H, M+H+2]^+$.

Intermediate 26: 2-Bromo-1-(2-fluoro-6-(methylamino)pyridin-3-yl)ethan-1-one

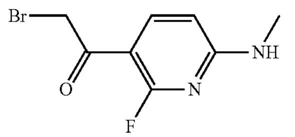

Step 1: 6-Fluoro-5-iodo-n-methylpyridin-2-amine

To a solution of 6-fluoro-5-iodopyridin-2-amine (4.0 g, 16.81 mmol, 1.0 equiv.) in tetrahydrofuran (50 mL) was added sodium hydride (807 mg, 20.17 mmol, 60%, 1.2 equiv.) at 0° C. After 30 min, $CH_3I$ (3.6 g, 25.21 mmol, 1.5 equiv.) was added to the above solution. The resulting mixture was stirred at 0° C. for 2 h, then quenched with ice water, extracted with EA twice, the organic layer was washed with brine, dried over $Na_2SO_4$, filtered and concentrated. The residue was purified by silica gel chromatography (0→100% ethyl acetate/petroleum ether) to yield the (3S)-7-(6-amino-3-chloro-2-fluorophenyl)-3-(4-(3-nitropyridin-4-yl)-1H-imidazol-2-yl)-2,3,8,8a-tetrahydroindolizin-5(1H) one as a yellow solid. LC/MS (ES, m/z): mass calculated for $C_8H_6FIN_2$: 251.96, measured: 253.03 $[M+H]^+$.

Step 2: 1-(2-Fluoro-6-(methylamino)pyridin-3-yl) ethan-1-one

To a solution of the 6-fluoro-5-iodopyridin-2-amine (1.5 g, 5.95 mmol, 1.0 equiv.) in 1,4-dioxane (30 mL) was added tributyl(1-ethoxyvinyl)stannane (4.30 g, 11.90 mmol, 2.0 equiv.), followed by tetrakis(triphenylphosphine) palladium (0) (688 mg, 0.60 mmol, 0.1 equiv.). The resulting mixture was stirred at 100° C. overnight. The residue was purified by silica gel chromatography (0→100% ethyl acetate/petroleum ether) to yield the 1-(2-fluoro-6-(methylamino)pyridin-3-yl)ethan-1-one as a yellow solid. LC/MS (ES, m/z): mass calculated for $C_8H_9FN_2O$: 168.07, measured: 169.10 $[M+H]^+$.

Step 3: 2-Bromo-1-(2-fluoro-6-(methylamino)pyridin-3-yl)ethan-1-one

To a solution of the 1-(2-fluoro-6-(methylamino)pyridin-3-yl)ethan-1-one (800 mg, 4.76 mmol, 1.0 equiv.) in glacial acetic acid (20 mL) and HBr (2 mL) was added $Br_2$ (380 mg, 2.38 mmol, 0.5 equiv.). The resulting mixture was stirred at room temperature for 2 h. The mixture was concentrated to yield 1-(2-fluoro-6-(methylamino)pyridin-3-yl)ethan-1-one as a yellow solid. LC/MS (ES, m/z): mass calculated for $C_8H_8BrFN_2O$: 245.98, measured: 247.10 $[M+H]^+$.

Intermediate 27: Methyl (6-(2-bromoacetyl)pyridin-3-yl)carbamate

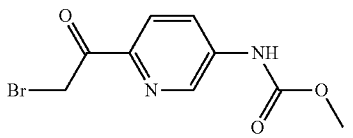

Step 1: Methyl n-(6-acetylpyridin-3-yl)carbamate

To a stirred solution of 1-(5-aminopyridin-2-yl)ethanone (680 mg, 4.99 mmol, 1.0 equiv.) in methylene chloride (20 mL) and pyridine (592 mg, 7.49 mmol, 1.5 equiv.) was added methyl chloroformate (566 mg, 5.99 mmol, 1.2 equiv.) dropwise at 0° C. The resulting mixture was stirred for 2 h at room temperature. The resulting mixture was concentrated under reduced pressure. The resulting mixture was diluted with water (15 mL). The resulting mixture was extracted with EtOAc (3x15 mL). The combined organic layers were dried over anhydrous $Na_2SO_4$. After filtration, the filtrate was concentrated under reduced pressure to yield methyl n-(6-acetylpyridin-3-yl)carbamate as a yellow solid.

Step 2: Methyl (6-(2-bromoacetyl)pyridin-3-yl)carbamate

To a mixture of methyl (6-acetylpyridin-3-yl)carbamate (300 mg, 1.54 mmol, 1.0 equiv.) in AcOH (5 mL) were added HBr (3 mL) and $Br_2$ (246 mg, 1.54 mmol, 1.0 equiv.). The reaction mixture was stirred at room temperature for 2 h, washed with water (3x20 mL), dried over $Na_2SO_4$, concentrated. The residue was applied onto a silica gel column (MeOH/DCM: 0-(10%) to yield methyl (6-(2-bromoacetyl)pyridin-3-yl)carbamate as a yellow solid. LC/MS (ES, m/z): mass calculated for $C_9H_9BrN_2O_3$: 271.98, measured: 273.10, 275.10 $[M+H, M+H+2]^+$.

Intermediate 28: N-(5-(2-bromoacetyl)-6-chloropyridin-2-yl)acetamide

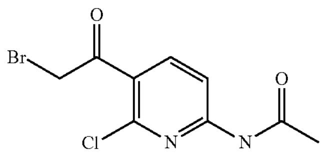

Step 1: N-(6-chloro-5-iodopyridin-2-yl)acetamide

6-Chloro-5-iodopyridin-2-amine (3.0 g, 11.79 mmol, 1.0 equiv.) was added in acetic anhydride (60 mL) at room temperature. The reaction was then stirred overnight at 40° C. After cooling to room temperature, the solid was collected by filtering to yield N-(6-chloro-5-iodopyridin-2-yl) acetamide as a yellow solid.

Step 2: N-(6-chloro-5-(1-ethoxyvinyl)pyridin-2-yl) acetamide

N-(6-chloro-5-iodopyridin-2-yl)acetamide (2.3 g, 7.58 mmol, 1.0 equiv.), tributyl(1-ethoxyvinyl)stannane (2.8 mL, 8.35 mmol. 1.1 equiv.), $Pd(PPh_3)_4$ (876 mg, 0.75 mmol. 0.1 equiv.) were placed in an oven-dried Schlenk tube under nitrogen and 1,4-dioxane (40 mL) was added. The reaction mixture was stirred for overnight at 100° C. After cooling to room temperature, the reaction was quenched by water (10 mL) and extracted with ethyl acetate (2×30 mL). The organic layers were combined and dried over anhydrous sodium sulfate, filtered and concentrated to yield the N-(6-chloro-5-(1-ethoxyvinyl)pyridin-2-yl)acetamide as a yellow solid.

Step 3: N-(5-(2-bromoacetyl)-6-chloropyridin-2-yl) acetamide

To a solution of N-(6-chloro-5-(1-ethoxyvinyl)pyridin-2-yl)acetamide (1.8 g, 7.56 mmol, 1.0 equiv.) in tetrahydrofuran/water (60 mL/20 mL) was added N-bromosuccinimide (2.0 g, 11.34 mmol, 1.5 equiv.) at room temperature. The reaction mixture was then stirred at room temperature for 3 h. The reaction was then concentrated and purified by silica gel chromatography (0→40% ethyl acetate/petroleum ether) to yield the n-(5-(2-bromoacetyl)-6-chloropyridin-2-yl)acetamide as a yellow solid.

Intermediate 29: N-(5-(2-bromoacetyl)-6-fluoropyridin-2-yl)acetamide

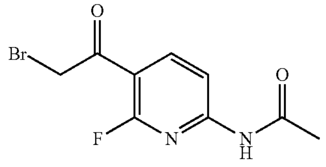

Step 1: N-(6-fluoro-5-iodopyridin-2-yl)acetamide

A suspension of 6-fluoro-5-iodopyridin-2-amine (10.0 g, 42.01 mmol, 1.0 equiv.) in acetic anhydride (20 mL) was stirred for 8 h. The resulting mixture was filtered to yield N-(6-fluoro-5-iodopyridin-2-yl)acetamide) as a white solid. LC/MS (ES, m/z): mass calculated for $C_7H_6FIN_2O$: 279.95, measured: 281.00 $[M+H]^+$.

Step 2: N-(5-(1-Ethoxyvinyl)-6-fluoropyridin-2-yl) acetamide

To a solution of N-(6-fluoro-5-iodopyridin-2-yl)acetamide (5.0 g, 17.85 mmol, 1.0 equiv.) and tributyl(1-ethoxyvinyl)stannane (7.7 g, 21.42 mmol, 1.2 equiv.) in 1,4-dioxane (100 mL) was added $Pd(PPh_3)_4$ (1.0 g, 0.89 mmol, 0.05 equiv.). The resulting mixture was maintained under nitrogen and stirred at 90° C. for 36 h. The solvent was removed under reduced pressure. The residue was purified by silica gel chromatography (EA:PE, 10→50%) to yield n-(5-(1-ethoxyvinyl)-6-fluoropyridin-2-yl)acetamide as a yellow solid. LC/MS (ES, m/z): mass calculated for $C_{11}H_{13}FN_2O_2$: 224.10, measured: 225.15 $[M+H]^+$.

Step 3: N-(5-(2-bromoacetyl)-6-fluoropyridin-2-yl) acetamide

To a solution of N-(5-(1-ethoxyvinyl)-6-fluoropyridin-2-yl)acetamide (3.0 g, 13.39 mmol, 1.0 equiv.) in THE/$H_2O$ (90/30 mL) was added NBS (2.9 g, 16.07 mmol, 1.2 equiv.) at 0° C. The resulting mixture was stirred for 20 min. The mixture was diluted with $H_2O$ (50 mL), then extracted with EA (50 mL×3). The organic layers were combined, dried over $Na_2SO_4$, filtered and concentrated. The residue was purified by silica gel chromotography (EA:PE, 10→50%) to yield n-(5-(2-bromoacetyl)-6-fluoropyridin-2-yl)acetamide as a brown solid.

Intermediate 30: 5-(2-Bromoacetyl)picolinamide

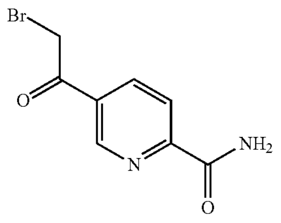 [SMILES: NC(=O)c1ccc(C(=O)CBr)cn1]

Step 1: 5-(1-Ethoxyvinyl)picolinamide

To a solution of 5-bromopicolinamide (1.5 g, 7.46 mmol, 1.0 equiv.) in 1,4-dioxane (15 mL) were added tributyl(1-ethoxyvinyl)stannane (4.0 g, 11.19 mmol, 1.5 equiv.), and tetrakis(triphenylphosphine)palladium (0.86 g, 0.75 mmol, 0.1 equiv.). The resulting mixture was maintained under nitrogen and stirred at 100° C. overnight. After cooling to room temperature, the organic layers were filtered and concentrated. The residue was purified by $Al_2O_3$ gel chromatography (0→60% EA/PE) to yield the 5-(1-ethoxyvinyl) picolinamide as a yellow oil.

Step 2: 5-(2-Bromoacetyl)picolinamide

To a solution of 5-(1-ethoxyvinyl)picolinamide (1.4 g, 7.28 mmol 1.0 equiv.) in THE/$H_2O$=3:1 (28 mL) was added N-bromosuccinimide (2.6 g, 14.57 mmol, 2.0 equiv.) at 0° C., and the reaction mixture was stirred at room temperature for 1 h. The reaction was quenched with aq. sodium hyposulfite (50 mL), The resulting mixture was extracted with ethyl acetate (3×50 mL). The organic layers were combined, dried over anhydrous sodium sulfate, filtered and concentrated. The residue was purified by silica gel chromatography (0→60% ethyl acetate/petroleum ether) to yield the 5-(2-bromoacetyl)picolinamide as a white solid.

Intermediate 31: (3S)-7-(6-Amino-3-chloro-2-fluorophenyl)-3-(5-iodo-1H-imidazol-2-yl)-2,3,8,8a-tetrahydroindolizin-5(1H)-one

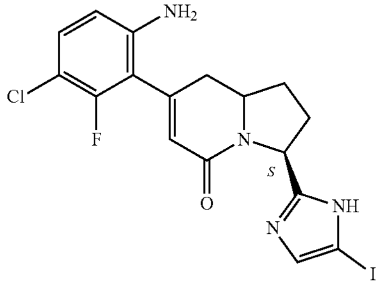

Step 1: Ethyl (3S)-7-(6-amino-3-chloro-2-fluorophenyl)-5-oxo-1,2,3,5,8,8a-hexahydroindolizine-3-carboxylate To a mixture of ethyl (3S)-5-oxo-7-(((trifluoromethyl)sulfonyl)oxy)-1,2,3,5,8,8a-hexahydroindolizine-3-carboxylate (5.0 g, 13.99 mmol, 1.0 equiv.) and (6-amino-3-chloro-2-fluorophenyl)boronic acid (4.770 g, 25.189 mmol, 1.8 equiv.) in 1,4-dioxane (50 mL) and water (10 mL) were added potassium phosphate (7.4 g, 34.98 mmol, 2.5 equiv.) and 1,1'-bis(diphenylphosphino)ferrocene-palladium(II)dichloride dichloromethane complex (1.1 g, 1.40 mmol, 0.1 equiv.). The resulting mixture was maintained under nitrogen and stirred at 100° C. for 1 h. After cooling to room temperature, the reaction was quenched with water and the mixture was extracted with EA. The combined extracts were dried over anhydrous $Na_2SO_4$ and concentrated. The residue was purified by silica gel chromatography (0→15% MeOH/DCM) to yield ethyl (3S)-7-(6-amino-3-chloro-2-fluorophenyl)-5-oxo-1,2,3,5,8,8a-hexahydroindolizine-3-carboxylate as a brown solid. LC/MS: mass calculated for $C_{17}H_{18}ClFN_2O_3$: 352.10, measured: 353.05 $[M+H]^+$.

Step 2: Ethyl (3S)-7-(6-((tert-butoxycarbonyl)amino)-3-chloro-2-fluorophenyl)-5-oxo-1,2,3,5,8,8a-hexahydroindolizine-3-carboxylate To a solution of ethyl (3S)-7-(6-amino-3-chloro-2-fluorophenyl)-5-oxo-1,2,3,5,8,8a-hexahydroindolizine-3-carboxylate (4.7 g, 13.32 mmol, 1.0 equiv.) in toluene (100 mL) was added di-tert butyl dicarbonate (17.45 g, 79.94 mmol, 6.0 equiv.). The reaction mixture was stirred at 100° C. for 48 h. After cooling to room temperature, the resulting mixture was concentrated under vacuum. The residue was purified by silica gel chromatography (0→55% EA/PE) to yield ethyl (3S)-7-(6-((tert-butoxycarbonyl)amino)-3-chloro-2-fluorophenyl)-5-oxo-1,2,3,5,8,8a-hexahydroindolizine-3-carboxylate as a yellow solid. LC/MS: mass calculated for $C_{22}H_{26}ClFN_2O_5$: 452.15, measured: 453.10 $[M+H]^+$.

Step 3: tert-Butyl (4-chloro-3-fluoro-2-((3S)-3-formyl-5-oxo-1,2,3,5,8,8a-hexahydroindolizin-7-yl)phenyl)carbamate To a solution of ethyl (3S)-7-(6-((tert-butoxycarbonyl)amino)-3-chloro-2-fluorophenyl)-5-oxo-1,2,3,5,8,8a-hexahydroindolizine-3-carboxylate (4.0 g, 8.83 mmol, 1.0 equiv.) in dichloromethane (40 mL) was added diisobutylaluminium hydride (19.4 mL, 1.0 M in DCM. 19.43 mmol. 2.2 equiv.) slowly at −78° C. under $N_2$. The reaction mixture was stirred for 2.5 h. Potassium sodium tartrate solution was added, and the mixture was extracted with EA. The combined extracts were dried over anhydrous $Na_2SO_4$. The resulting mixture was concentrated under vacuum. The residue was purified by silica gel chromatography with (0→55% EA/PE) to yield tert-butyl (4-chloro-3-fluoro-2-((3S)-3-formyl-5-oxo-1,2,3,5,8,8a-hexahydroindolizin-7-yl)phenyl)carbamate as a yellow solid. LC/MS: mass calculated for $C_{20}H_{22}ClFN_2O_4$: 408.13, measured: 409.10 $[M+H]^+$.

Step 4: tert-Butyl (2-((3S)-3-(1H-imidazol-2-yl)-5-oxo-1,2,3,5,8,8a-hexahydroindolizin-7-yl)-4-chloro-3-fluorophenyl)carbamate To a solution of tert-butyl (4-chloro-3-fluoro-2-((3S)-3-formyl-5-oxo-1,2,3,5,8,8a-hexahydroindolizin-7-yl)phenyl)carbamate (1.0 g. 2.45 mmol, 1.0 equiv.) in methanol (10 mL) and ammonium hydroxide (10 mL) was added glyoxal (1.8 g, 12.23 mmol, 5.0 equiv., 40% in water). The mixture was stirred at room temperature for 48 h, then concentrated under reduced pressure, extracted with EA, washed with brine and dried over anhydrous $Na_2SO_4$. The residue was purified by column chromatography (0→15% MeOH/DCM) to yield tert-butyl (2-((3S)-3-(1H-imidazol-2-yl)-5-oxo-1,2,3,5,8,8a-hexahydroindolizin-7-yl)-4-chloro-3-fluorophenyl)carbamate as a yellow solid. LC/MS: mass calculated for $C_{22}H_{24}ClFN_4O_3$: 446.15, measured: 447.10 $[M+H]^+$.

Step 5: tert-Butyl (4-chloro-3-fluoro-2-((3S)-3-(5-iodo-1H-imidazol-2-yl)-5-oxo-1,2,3,5,8,8a-hexahydroindolizin-7-yl)phenyl)carbamate To a solution of tert-butyl (2-((3S)-3-(1H-imidazol-2-yl)-5-oxo-1,2,3,5,8,8a-hexahydroindolizin-7-yl)-4-chloro-3-fluorophenyl)carbamate (450 mg, 1.01 mmol, 1.0 equiv) in DCM (10 mL) was added N-iodosuccinimide (453 mg. 2.01 mmol, 2.0 equiv). The reaction mixture was stirred at room temperature for 10 min. Water was added, and the mixture was extracted with EA. The combined extracts were washed with water, dried over anhydrous $Na_2SO_4$, then concentrated. EtOH (10 mL), $H_2O$ (10 mL) and sodium sulfite (1.0 g, 8.23 mmol, 10.0 equiv.) were added to residue. The mixture was stirred overnight at 95° C., then cooled to room temperature. Water was added, and the mixture was extracted with EA. The combined extracts were dried over anhydrous $Na_2SO_4$, filtered and concentrated to yield tert-butyl (4-chloro-3-fluoro-2-((3S)-3-(5-iodo-1H-imidazol-2-yl)-5-oxo-1,2,3,5,8,8a-hexahydroindolizin-7-yl)phenyl)carbamate as a brown solid, which was used in the next step without further purification. LC/MS (ES, m/z): mass calculated for $C_{22}H_{23}ClFIN_4O_3$: 572.05, measured: 573.00 $[M+H]^+$.

Step 6: (3S)-7-(6-Amino-3-chloro-2-fluorophenyl)-3-(5-iodo-1H-imidazol-2-yl)-2,3,8,8a-tetrahydroindolizin-5(1H)-one To a solution of tert-butyl (4-chloro-3-fluoro-2-((3S)-3-(5-iodo-1H-imidazol-2-yl)-5-oxo-1,2,3,5,8,8a-hexahydroindolizin-7-yl)phenyl)carbamate (580 mg) in dichloromethane (8 mL) was added trifluoroacetic acid (2 mL). The reaction mixture was stirred at room temperature. for 1 h. The resulting mixture was concentrated under vacuum. The residue was purified by silica gel column chromatography (0→10% MeOH/DCM) to yield (3S)-7-(6-amino-3-chloro-2-fluorophenyl)-3-(5-iodo-1H-imidazol-2-yl)-2,3,8,8a-tetrahydroindolizin-5(1H)-one as a yellow solid. LC/MS (ES, m/z): mass calculated for $C_{17}H_{15}ClFIN_4O$: 472.00, measured: 472.90 $[M+H]^+$.

Synthesis Examples: Compounds of Formula (I)

Example 1: (3S,8aR)-3-[5-(2-Amino-5-chloro-4-pyridyl)-4-fluoro-1H-imidazol-2-yl]-7-[3-chloro-2-fluoro-6-(tetrazol-1-yl)phenyl]-2,3,8,8a-tetrahydro-1H-indolizin-5-one

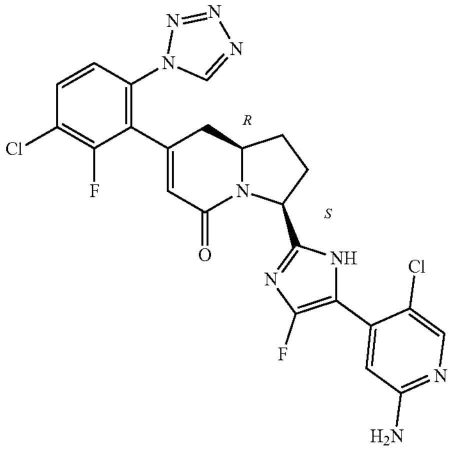

Step 1. To a mixture of N-(5-chloro-4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide 2,2,2-trifluoroacetate (400 mg, 0.501 mmol, 1.0 equiv) in DMF (9 mL) and $H_2O$ (0.9 mL) was added Selectfluor (142 mg, 0.401 mmol, 0.8 equiv) at 0° C. The resulting mixture was warmed to room temperature and then stirred at room temperature for 1 h. The mixture was then partitioned between EtOAc and water. The organic layer was separated, dried, and concentrated under reduced pressure. The residue was purified by $C_{18}$ reverse column chromatography (330 g, ACN/$H_2O$ (0.05% $NH_4HCO_3$): 5%>>>40%>>>45%) to yield N-(5-chloro-4-(2-((3S)-7-(3-chloro-2-fluoro-6-(1H-tetrazol-1-yl)phenyl)-5-oxo-1,2,3,5,8,8a-hexahydroindolizin-3-yl)-4-fluoro-1H-imidazol-5-yl) pyridin-2-yl)acetamide as a yellow solid. LC/MS: mass calculated for $C_{25}H_{19}Cl_2F_2N_6O_2$: 585.10, measured: 586.05 $[M+H]^+$.

Step 2. A mixture of N-(5-chloro-4-(2-((3S)-7-(3-chloro-2-fluoro-6-(1H-tetrazol-1-yl)phenyl)-5-oxo-1,2,3,5,8,8a-hexahydroindolizin-3-yl)-4-fluoro-1H-imidazol-5-yl)pyridin-2-yl)acetamide (60 mg, 0.102 mmol, 1.0 equiv) in THE (6 mL) and HCl (3 mL, 4N) was stirred at 50° C. for 1 h, then concentrated. The residue was applied onto a C18 reverse column (120 g, ACN/$H_2O$ (0.05% $NH_4HCO_3$): 5%>>>45%>>>50%) to yield (3S)-3-(5-(2-amino-5-chloropyridin-4-yl)-4-fluoro-1H-imidazol-2-yl)-7-(3-chloro-2-fluoro-6-(1H-tetrazol-1-yl)phenyl)-2,3,8,8a-tetrahydroindolizin-5(1H)-one as a white solid. The isolated solid was further purified by prep-Chiral-HPLC(Column: (R,R)-WHELK-01-Kromasil, 5*25 cm, 5 μm; Mobile Phase A: MeOH (0.5% 2M $NH_3$-MeOH)—-HPLC, Mobile Phase B: EtOH-HPLC; Flow rate: 20 mL/min) to yield (3S,8aR)-3-(5-(2-amino-5-chloropyridin-4-yl)-4-fluoro-1H-imidazol-2-yl)-7-(3-chloro-2-fluoro-6-(1H-tetrazol-1-yl)phenyl)-2,3,8,8a-tetrahydroindolizin-5(1H one as a white solid.

LC/MS: mass calculated for $C_{23}H_{17}Cl_2F_2N_9O$: 543.09, measured (ES, m/z): 544.10 $[M+H]^+$. $^1H$ NMR (300 MHz, DMSO-d6) δ 12.33 (s, 1H), 9.85 (s, 1H), 7.86-8.07 (m, 2H), 7.70-7.75 (m, 1H), 6.51 (s, 1H), 6.25 (s, 2H), 5.68 (s, 1H), 4.97 (d, J=8.6 Hz, 1H), 3.59-3.82 (m, 1H), 2.55-2.79 (m, 2H), 2.05-2.32 (m, 2H), 1.82-2.04 (m, 2H). $^{19}F$ NMR (282 MHz, DMSO-$d_6$) δ −112.93, −128.84.

Example 2: (3S,8aR)-7-[3-Chloro-2-fluoro-6-(tetrazol-1-yl)phenyl]-3-[5-[3-fluoro-2-(1H-imidazol-2-yl)-4-pyridyl]-1H-imidazol-2-yl]-2,3,8,8a-tetrahydro-1H-indolizin-5-one

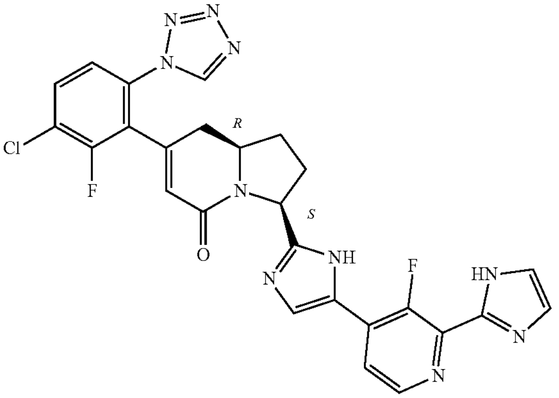

Step 1. A mixture of (3S)-7-(6-amino-3-chloro-2-fluorophenyl)-5-oxo-1,2,3,5,8,8a-hexahydroindolizine-3-carboxylic acid (330 mg, 1.016 mmol, 1.0 equiv) and $Cs_2CO_3$ (199 mg, 0.611 mmol, 0.6 equiv) in DMF (8 mL) was stirred at room temperature for 30 min. 2-Bromo-1-(3-fluoro-2-(1-((2-(trimethylsilyl)ethoxy)methyl)-1H-imidazol-2-yl)pyridin-4-yl)ethanone (463 mg, 1.117 mmol, 1.1 equiv) was then added to the mixture. The reaction mixture was stirred at room temperature for 4 h. The resulting mixture was then diluted with EtOAc (120 mL), washed with water (3×20 mL), brine (2×20 mL), dried over $Na_2SO_4$, and concentrated under reduced pressure. The residue was applied onto a silica gel column (40 g, MeOH/DCM: 1/20) to yield (3S)-2-(3-fluoro-2-(1-((2-(trimethylsilyl)ethoxy)methyl)-1H-imidazol-2-yl)pyridin-4-yl)-2-oxoethyl 7-(6-amino-3-chloro-2-fluorophenyl)-5-oxo-1,2,3,5,8,8a-hexahydroindolizine-3-carboxylate as a yellow solid. LC/MS: mass calculated for $C_{31}H_{34}ClF_2N_5O_5Si$: 657.20, measured: 658.15 $[M+H]^+$.

Step 2. To a mixture of (3S)-2-(3-fluoro-2-(1-((2-(trimethylsilyl)ethoxy)methyl)-1H-imidazol-2-yl)pyridin-4-yl)-2-oxoethyl 7-(6-amino-3-chloro-2-fluorophenyl)-5-oxo-1,2,3,5,8,8a-hexahydroindolizine-3-carboxylate (350 mg, 0.532 mmol, 1.0 equiv) and $NH_4OAc$ (410 mg, 5.319 mmol, 10.0 equiv) were added AcOH (5 mL) and toluene (50 mL). The reaction mixture was stirred at 110° C. for 1 h, then concentrated under reduced pressure. The residue was applied onto a silica gel column (40 g, MeOH/DCM: 1/15) to yield\(3S)-7-(6-amino-3-chloro-2-fluorophenyl)-3-(5-(3-fluoro-2-(1-((2-(trimethylsilyl)ethoxy)methyl)-1H-imidazol-2-yl)pyridin-4-yl)-1H-imidazol-2-yl)-2,3,8,8a-tetrahydroindolizin-5(1H)-one as a yellow solid.

Step 3. A mixture of (3S)-7-(6-amino-3-chloro-2-fluorophenyl)-3-(5-(3-fluoro-2-(1-((2-(trimethylsilyl)ethoxy)methyl)-1H-imidazol-2-yl)pyridin-4-yl)-1H-imidazol-2-yl)-2,3,8,8a-tetrahydroindolizin-5(1H)-one (180 mg, 0.282 mmol, 1.0 equiv), $TMSN_3$ (325 mg, 2.821 mmol, 10.0 equiv) and trimethoxymethane (300 mg, 2.827 mmol, 10.0 equiv) in AcOH (8 mL) was stirred at 65° C. for 2 h, then concentrated. The residue was applied onto a silica gel column (40 g, MeOH/DCM: 1/20) to yield (3S)-7-(3-chloro-2-fluoro-6-(1H-tetrazol-1-yl)phenyl)-3-(5-(3-fluoro-2-(1-((2-(trimethylsilyl)ethoxy)methyl)-1H-imidazol-2-yl)pyridin-4-yl)-1H-imidazol-2-yl)-2,3,8,8a-tetrahydroindolizin-5(1H)-one as a yellow solid. LC/MS: mass calculated for $C_{32}H_{33}ClF_2N_{10}O_2Si$: 690.22, measured: 691.20 $[M+H]^+$.

Step 4. To a mixture of (3S)-7-(3-chloro-2-fluoro-6-(1H-tetrazol-1-yl)phenyl)-3-(5-(3-fluoro-2-(1-((2-(trimethylsilyl)ethoxy)methyl)-1H-imidazol-2-yl)pyridin-4-yl)-1H-imidazol-2-yl)-2,3,8,8a-tetrahydroindolizin-5(1H)-one (130 mg, 0.188 mmol, 1.0 equiv) in DCM (8 mL) was added TFA (3 mL). The reaction mixture was stirred at room temperature for 4 h, then concentrated. The residue was applied onto a C18 reverse column (120 g, ACN/$H_2O$ (0.05% $NH_4HCO_3$): 5%>>>40%>>>45%) to yield (3S)-7-(3-chloro-2-fluoro-6-(1H-tetrazol-1-yl)phenyl)-3-(5-(3-fluoro-2-(1H-imidazol-2-yl)pyridin-4-yl)-1H-imidazol-2-yl)-2,3,8,8a-tetrahydroindolizin-5(1H)-one as a white solid. The solid was further purified by Prep-Chiral-HPLC(Column: CHIRALPAK IA, 2*25 cm, 5 um; Mobile Phase A:Hex: DCM=3:1 (0.5% 2M $NH_3$-MeOH)-HPLC, Mobile Phase B: EtOH—HPLC; Flow rate: 18 mL/min) to yield (3S,8aR)-7-(3-chloro-2-fluoro-6-(1H-tetrazol-1-yl)phenyl)-3-(5-(3-fluoro-2-(1H-imidazol-2-yl)pyridin-4-yl)-1H-imidazol-2-yl)-2,3,8,8a-tetrahydroindolizin-5(1H)-one as a white solid.

LC/MS: mass calculated for $C_{26}H_{19}ClF_2N_{10}O$: 560.14, measured (ES, m/z): 561.15$[M+H]^+$. $^1H$ NMR (400 MHz, DMSO-$d_6$) δ 12.77 (s, 1H), 12.31 (s, 1H), 9.85 (s, 1H), 8.44 (d, J=5.0 Hz, 1H), 7.92-8.01 (m, 2H), 7.65-7.75 (m, 2H), 7.28 (s, 1H), 7.14 (s, 1H), 5.71 (d, J=2.7 Hz, 1H), 5.06 (d, J=8.7 Hz, 1H), 3.64-3.85 (m, 1H), 2.64-2.80 (m, 1H), 2.54-2.59 (m, 1H), 2.16-2.35 (m, 1H), 2.06-2.15 (m, 1H), 1.91-2.05 (m, 2H). $^{19}F$ NMR (376 MHz, DMSO-$d_6$) δ −112.82, −124.37.

Example 3: (S)-7-[3-Chloro-2-fluoro-6-(tetrazol-1-yl)phenyl]-3-[4-[2-(difluoromethoxy)-4-pyridyl]-5-fluoro-1H-imidazol-2-yl]-2,3,8,8a-tetrahydro-1H-indolizin-5-one

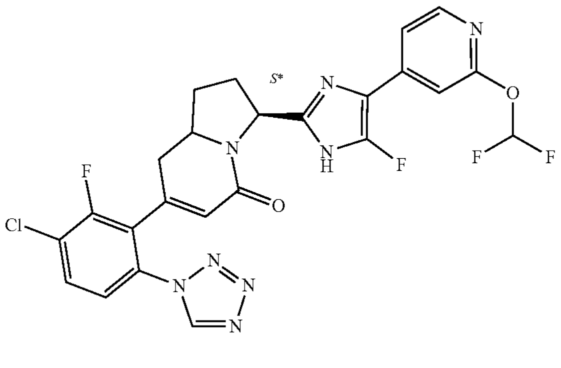

LC/MS: mass calculated for $C_{24}H_{17}ClF_4N_8O_2$: 560.11, measured (ES, m/z): 561.10 $[M+H]^+$. $^1H$ NMR (300 MHz, DMSO-$d_6$) δ 12.94 (s, 1H), 9.82 (s, 1H), 8.24 (d, J=5.5 Hz, 1H), 7.92-8.00 (m, 1H), 7.67-7.73 (m, 1H), 7.70 (t, J=72.6 Hz, 1H), 7.36 (dd, J=5.3, 1.5 Hz, 1H), 7.12 (d, J=1.5 Hz, 1H), 5.65 (s, 1H), 4.91 (d, J=8.4 Hz, 1H), 3.63-3.76 (m, 1H), 2.51-2.61 (m, 2H), 1.81-2.31 (m, 4H). $^{19}F$ NMR (282 MHz, DMSO-$d_6$) δ−87.05, −112.95, −125.18.

Example 4: (8aR)-7-[3-Chloro-2-fluoro-6-(tetrazol-1-yl)phenyl]-3-[5-(4-chloro-1H-pyrazol-3-yl)-1H-imidazol-2-yl]-2,3,8,8a-tetrahydro-1H-indolizin-5-one

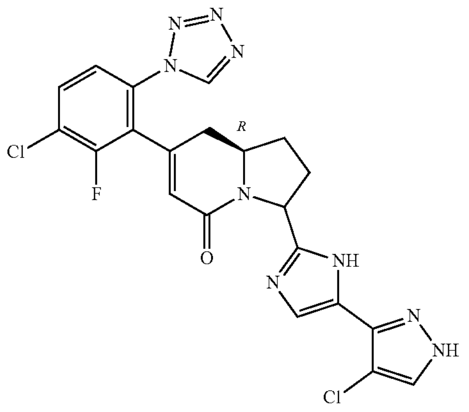

Step 1: 4-Chloro-1-(tetrahydro-2H-pyran-2-yl)-3-(4,4,5,5-tetramethyl-1,3,2-dioxaborolan-2-yl)-1H-pyrazole To a solution of 1-(tetrahydro-2H-pyran-2-yl)-3-(4,4,5,5-tetramethyl-1,3,2-dioxaborolan-2-yl)-1H-pyrazole (1.0 g, 3.60 mmol, 1.0 equiv.) in THF (10 mL) was added NCS (0.58 g, 4.31 mmol, 1.2 equiv.) at room temperature and the mixture was stirred for 2 h at 70° C. The reaction was diluted with $H_2O$ and extracted with ethyl acetate twice. The combined organic layers were washed with brine, dried over $Na_2SO_4$, concentrated and purified by silica gel chromatography (0→40% EA/PE) to yield 4-chloro-1-(tetrahydro-2H-pyran-2-yl)-3-(4,4,5,5-tetramethyl-1,3,2-dioxaborolan-2-yl)-1H-pyrazole as a light yellow oil. LC/MS: mass calculated for $C_{14}H_{22}BClN_2O_3$: 312.14, measured (ES, m/z): 313.10 $[M+H]^+$.

Step 2: (8aR)-7-(6-Amino-3-chloro-2-fluorophenyl)-3-(5-(4-chloro-1H-pyrazol-3-yl)-1H-imidazol-2-yl)-2,3,8,8a-tetrahydroindolizin-5(1H)-one A mixture of (8aR)-7-(6-amino-3-chloro-2-fluorophenyl)-3-(5-iodo-1H-imidazol-2-yl)-2,3,8,8a-tetrahydroindolizin-5(1H)-one (0.10 g, 0.21 mmol, 1.0 equiv.), 4-chloro-1-(tetrahydro-2H-pyran-2-yl)-3-(4,4,5,5-tetramethyl-1,3,2-dioxaborolan-2-yl)-1H-pyrazole (0.20 g, 0.64 mmol, 3.0 equiv.), Pd(dtbpf)$Cl_2$ (0.028 g, 0.042 mmol, 0.2 equiv.) and $K_2CO_3$ (0.088 g, 0.64 mmol, 3.0 equiv.) in 1,4-dioxane (2 mL) and water (0.4 mL) was refluxed at 100° C. under $N_2$ for 2 h. The mixture was diluted with $H_2O$ and extracted with ethyl acetate twice. The combined organic layers were washed with brine, dried over $Na_2SO_4$, concentrated and the residue was purified by silica gel chromatography (0→8%, MeOH/DCM) to yield (8aR)-7-(6-amino-3-chloro-2-fluorophenyl)-3-(5-(4-chloro-1H-pyrazol-3-yl)-1H-imidazol-2-yl)-2,3,8,8a-tetrahydroindolizin-5(1H)-one as a yellow solid. LC/MS: mass calculated for $C_{20}H_{17}Cl_2FN_6O$: 446.08, measured (ES, m/z): 447.00 $[M+H]^+$.

Step 3: (8aR)-7-[3-Chloro-2-fluoro-6-(tetrazol-1-yl)phenyl]-3-[5-(4-chloro-1H-pyrazol-3-yl)-1H-imidazol-2-yl]-2,3,8,8a-tetrahydro-1H-indolizin-5-one A mixture of (8aR)-7-(6-amino-3-chloro-2-fluorophenyl)-3-(5-(4-chloro-1-(tetrahydro-2H-pyran-2-yl)-1H-pyrazol-3-yl)-1H-imidazol-2-yl)-2,3,8,8a-tetrahydroindolizin-5(1H)-one (25 mg, 0.047 mmol, 1.0 equiv.), trimethoxymethane (0.2 mL), azidotrimethylsilane (0.2 mL) and acetic acid (0.5 mL) was stirred overnight at room temperature. The solution was concentrated and the residue was purified by reverse phase chromatography on C18 (0→50% ACN/$H_2O$) to yield (8aR)-3-(5-(4-chloro-1H-pyrazol-3-yl)-1H-imidazol-2-yl)-7-(3-chloro-2-fluoro-6-(1H-tetrazol-1-yl)phenyl)-2,3,8,8a-tetrahydroindolizin-5(1H)-one as a brown solid.

LC/MS: mass calculated for $C_{21}H_{16}Cl_2FN_9O$: 499.08, measured (ES, m/z): 500.05 $[M+H]^+$. $^1H$ NMR (300 MHz, DMSO-$d_6$) δ 9.79-9.90 (m, 1H), 7.90-8.04 (m, 2H), 7.68-7.77 (m, 2H), 5.62-5.74 (m, 1H), 5.05-5.17 (m, 1H), 3.59-3.80 (m, 1H), 2.52-2.60 (m, 2H), 1.92-2.18 (m, 4H). $^{19}F$ NMR (282 MHz, DMSO-$d_6$) δ −73.54, −112.86.

Example 5: N-[4-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]-3-methyl-isoxazole-5-carboxamide

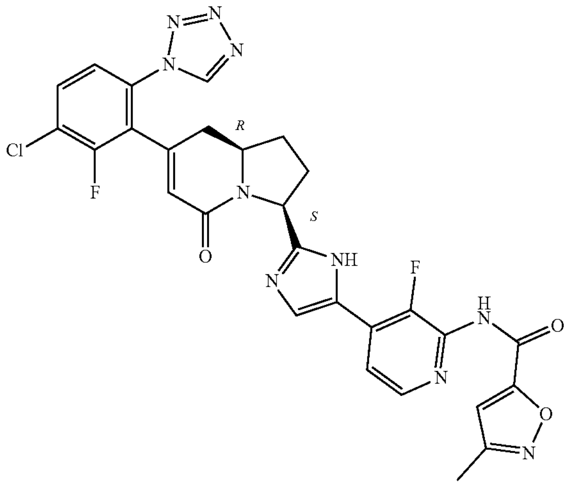

LC/MS: mass calculated for $C_{28}H_{21}ClF_2N_{10}O_3$: 618.15, measured (ES, m/z): 619.10 $[M+H]^+$. $^1H$ NMR (400 MHz, DMSO-$d_6$) δ 12.33 (d, J=2.2 Hz, 1H), 11.17 (s, 1H), 9.85 (s, 1H), 8.31 (d, J=5.1 Hz, 1H), 7.92-8.02 (m, 2H), 7.70-7.75 (m, 1H), 7.58-7.62 (m, 1H), 7.19 (s, 1H), 5.72 (d, J=2.7 Hz, 1H), 5.06 (d, J=8.7 Hz, 1H), 3.71-3.82 (m, 1H), 2.67-2.78 (m, 1H), 2.50-2.60 (m, 1H), 2.36 (s, 3H), 2.16-2.29 (m, 1H), 2.06-2.16 (m, 1H), 1.92-2.02 (m, 2H). $^{19}F$ NMR (376 MHz, DMSO-$d_6$) δ −112.82, −126.71.

Example 6: N-[4-[2-[7-[3-Chloro-2-fluoro-6-(tetrazol-1-yl)phenyl]-5-oxo-2,3,8,8a-tetrahydro-1H-indolizin-3-yl]-4-fluoro-1H-imidazol-5-yl]-2-pyridyl]methanesulfonamide

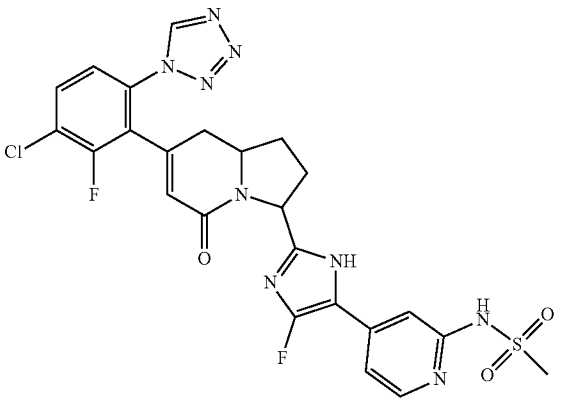 [SMILES: CS(=O)(=O)Nc1cc(-c2[nH]c(C3CCC4CC(c5c(-n6cnnn6)ccc(Cl)c5F)=CC(=O)N43)nc2F)ccn1]

LC/MS: mass calculated for $C_{24}H_{20}ClF_2N_9O_3S$: 587.11, measured (ES, m/z): 588.10 [M+H]+. $^1H$ NMR (300 MHz, DMSO-$d_6$) δ 9.84 (s, 1H), 8.06-8.26 (m, 1H), 7.89-8.05 (m, 1H), 7.63-7.80 (m, 1H), 7.17 (s, 1H), 7.04-7.12 (m, 1H), 5.67 (s, 1H), 4.94 (d, J=8.4 Hz, 1H), 3.59-3.82 (m, 1H), 3.20 (s, 3H), 2.55-2.62 (m, 2H), 1.82-2.38 (m, 4H). $^{19}F$ NMR (282 MHz, DMSO-$d_6$) δ 112.95.

Example 7: N-[4-[2-[7-[3-Chloro-2-fluoro-6-(tetrazol-1-yl)phenyl]-5-oxo-2,3,8,8a-tetrahydro-1H-indolizin-3-yl]-1H-imidazol-5-yl]-2-pyridyl]methanesulfonamide

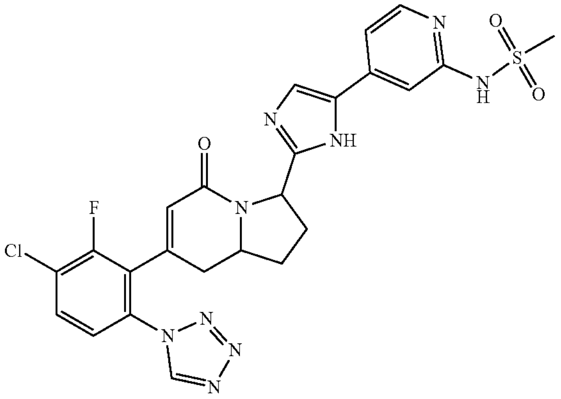 [SMILES: CS(=O)(=O)Nc1cc(-c2cnc(C3CCC4CC(c5c(-n6cnnn6)ccc(Cl)c5F)=CC(=O)N43)[nH]2)ccn1]

LC/MS: mass calculated for $C_{24}H_{21}ClFN_9O3S$: 569.12, measured (ES, m/z): 570.15 $[M+H]^+$. $^1H$ NMR (300 MHz, DMSO-$d_6$) δ(300 MHz, DMSO-$d_6$) δ-12.04-12.41 (m, 1H), 9.74-9.93 (m, 1H), 7.87-8.14 (m, 2H), 7.64-7.80 (m, 2H), 7.33-7.52 (m, 1H), 7.08-7.30 (m, 1H), 5.56-5.75 (m, 1H), 4.88-5.11 (m, 1H), 3.59-3.81 (m, 1H), 3.15 (s, 3H), 2.65-2.90 (m, 1H), 2.53-2.63 (m, 1H), 1.80-2.40 (m, 4H). $^{19}F$ NMR (282 MHz, DMSO-$d_6$) δ −112.99.

Example 8: (3S,8aR)-3-(5-(1H-indol-6-yl)-1H-imidazol-2-yl)-7-(3-chloro-2-fluoro-6-(1H-tetrazol-1-yl)phenyl-2,3,8,8a-tetrahydroindolizin-5(1H)-one

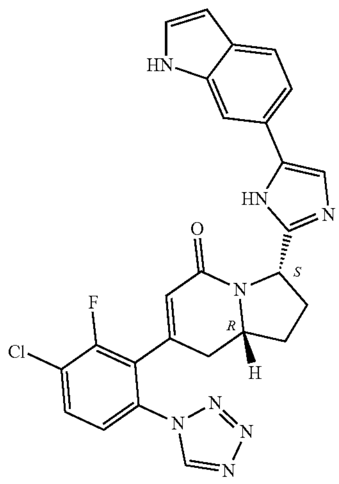

LC/MS: mass calculated for $C_{26}H_{20}ClFN_8O$: 514.1, measured (ES, m/z): 515.3 $[M+H]^+$. $^1H$ NMR (400 MHz, ACETONITRILE-$d_3$) δ ppm 9.42 (br s, 1H), 9.16 (5, 1H), 7.78 (s, 1H), 7.76-7.70 (m, 1H), 7.54 (d, J=8.3 Hz, 1H), 7.44 (dd, J=1.5, 8.8 Hz, 1H), 7.39 (dd, J=1.3, 8.3 Hz, 1H), 7.26-7.22 (m, 2H), 6.44 (br s, 1H), 5.73 (s, 1H), 5.09 (d, J=8.5 Hz, 1H), 3.86-3.77 (m, 1H), 2.60-2.49 (m, 2H), 2.22-2.10 (m, 2H), 1.92-1.84 (m, 2H).

Example 9: (S)-7-[3-Chloro-2-fluoro-6-(tetrazol-1-yl)phenyl]-3-[4-[2-(2-hydroxyethoxy)-4-pyridyl]-1H-imidazol-2-yl]-2,3,8,8a-tetrahydro-1H-indolizin-5-one

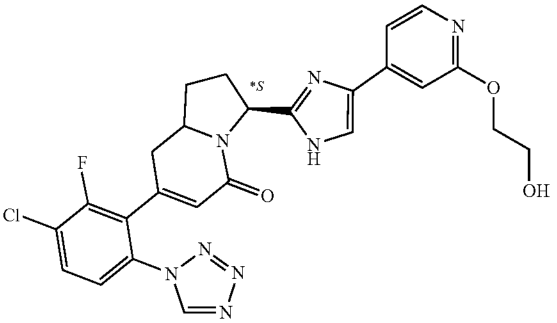

LC/MS: mass calculated for $C_{25}H_{22}ClFN_8O_3$: 536.15, measured (ES, m/z): 537.10 $[M+H]^+$. $^1H$ NMR (400 MHz, DMSO-$d_6$) δ 12.07 (s, 1H), 9.83 (s, 1H), 8.06 (d, J=5.4 Hz, 1H), 7.96 (t, J=8.2 Hz, 1H), 7.66-7.76 (m, 2H), 7.31 (d, J=5.5 Hz, 1H), 7.06-7.12 (m, 1H), 5.65-5.68 (m, 1H), 4.99 (d, J=8.6 Hz, 1H), 4.82 (t, J=5.5 Hz, 1H), 4.27 (t, J=5.2 Hz, 2H), 3.44-3.77 (m, 3H), 2.71-2.84 (m, 1H), 2.50-2.54 (m, 1H), 2.14-2.16 (m, 1H), 2.05-2.13 (m, 1H), 1.87-2.04 (m, 2H). $^{19}F$ NMR (376 MHz, DMSO-$d_6$) δ −112.78.

Example 10: (S)-7-[3-Chloro-2-fluoro-6-(tetrazol-1-yl)phenyl]-3-[4-[2-(difluoromethoxy)-4-pyridyl]-1H-imidazol-2-yl]-2,3,8,8a-tetrahydro-1H-indolizin-5-one

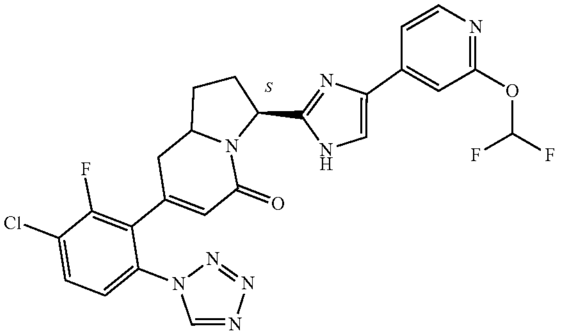

LC/MS: mass calculated for $C_{24}H_{18}ClF_3N_8O_2$: 542.12, measured (ES, m/z): 543.10 $[M+H]^+$. $^1H$ NMR (400 MHz, DMSO-$d_6$) δ 9.61 (s, 1H), 8.26 (d, J=5.4 Hz, 1H), 8.00 (s, 1H), 7.78-7.83 (m, 1H), 7.55 (t, J=72.6 Hz, 1H), 7.48-7.53 (m, 2H), 7.30-7.31 (m, 1H), 5.61 (d, J=2.8 Hz, 1H), 5.15 (dd, J=9.8, 1.6 Hz, 1H), 3.68-3.80 (m, 1H), 2.87 (t, J=15.6 Hz, 1H), 2.53-2.59 (m, 1H), 2.25-2.42 (m, 1H), 2.12-2.20 (m, 1H), 2.00-2.10 (m, 1H), 1.75-1.91 (m, 1H). $^{19}$FNMR (376 MHz, DMSO-$d_6$) δ −87.10, −112.77.

Example 11: N-[(1R)-1-[4-[2-[(3S)-7-[3-Chloro-2-fluoro-6-(tetrazol-1-yl)phenyl]-5-oxo-2,3,8,8a-tetrahydro-1H-indolizin-3-yl]-4-fluoro-1H imidazol-5-yl]phenyl]ethyl]acetamide

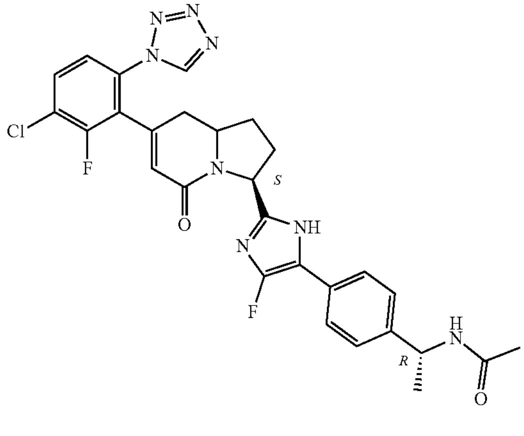

LC/MS: mass calculated for $C_{28}H_{25}ClF_2N_8O_2$: 578.18, measured (ES, m/z): 579.20 $[M+H]^+$. $^1H$ NMR (300 MHz, Methanol-$d_4$) δ 9.57 (s, 1H), 7.78-7.85 (m, 1H), 7.47-7.59 (m, 3H), 7.34-7.38 (m, 2H), 5.67 (d, J=2.7 Hz, 1H), 4.94-5.03 (m, 2H), 3.79-3.93 (m, 1H), 2.91-3.02 (m, 1H), 2.52-2.62 (m, 1H), 2.18-2.30 (m, 2H), 2.02-2.14 (m, 2H), 1.97 (s, 3H), 1.44 (d, J=7.0 Hz, 3H). $^{19}F$ NMR (282 MHz, Methanol-$d_4$) δ−113.30, −136.81.

Example 12: Ethyl-N-[[4-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]methyl]carbamate

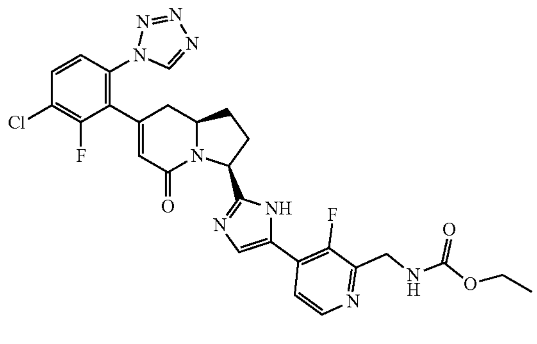 [SMILES: CCOC(=O)NCc1nccc(-c2cnc([C@@H]3CC[C@@H]4CC(c5c(-n6cnnn6)ccc(Cl)c5F)=CC(=O)N43)[nH]2)c1F]

Step 1: (3-Fluoro-4-iodopyridin-2-yl)methanamine

A solution of 3-fluoro-4-iodopicolinonitrile (3.0 g, 12.10 mmol, 1.0 equiv.) in DCM (50 mL) was cooled to −78° C., and diisobutylaluminium hydride (24.2 mL, 24.20 mmol, 2.0 equiv.) was then added slowly. The mixture was stirred at −78° C. for 2 h under $N_2$. The reaction was quenched with potassium sodium tartrate solution (50 mL). The resulting mixture was extracted with ethyl acetate (3×100 mL). The organic layers were combined, dried over anhydrous sodium sulfate, filtered, and concentrated. The residue was purified by silica gel chromatography (0→10% MeOH/DCM) to yield the (3-fluoro-4-iodopyridin-2-yl)methanamine as a yellow solid. LC/MS: mass calculated for $C_6H_6FIN_2$: 251.96, measured (ES, m/z): 252.95 $[M+H]^+$.

Step 2: Tert butyl ((3-fluoro-4-iodopyridin-2-yl)methyl)carbamate

A solution of (3-fluoro-4-iodopyridin-2-yl)methanamine (2.4 g, 9.52 mmol, 1.0 equiv.) in THE (30 mL) was cooled to 0° C., and then di-tert-butyl dicarbonate (2.5 g, 11.46 mmol, 1.2 equiv.) was added. The mixture was stirred at room temperature overnight. The reaction was quenched with water (50 mL). The resulting mixture was extracted with ethyl acetate (3×100 mL). The organic layers were combined, dried over anhydrous sodium sulfate, filtered, and concentrated. The residue was purified by silica gel chromatography (0→50% EA/PE) to yield the tert-butyl ((3-fluoro-4-iodopyridin-2-yl)methyl)carbamate as a yellow solid. LC/MS: mass calculated for $C_{11}H_{14}FIN_2O_2$: 352.01, measured (ES, m/z): 353.10 $[M+H]^+$.

Step 3: Tert butyl ((4-(1-ethoxyvinyl)-3-fluoropyridin-2-yl)methyl)carbamate

To a solution of tert-butyl ((3-fluoro-4-iodopyridin-2-yl)methyl)carbamate (3.0 g, 8.52 mmol, 1.0 equiv.), bis(triphenylphosphine)palladium(II) chloride (0.60 g, 0.86 mmol, 0.1 equiv.) in 1,4-dioxane (30 mL) was added tributyl(1-ethoxyvinyl)stannane (4.6 g, 12.74 mmol, 1.5 equiv.). The mixture was stirred at 95° C. for 3 h. After cooling to room temperature, the reaction was quenched with water (50 mL), then extracted with ethyl acetate (3×100 mL). The combined extracts were washed with water, dried over $Na_2SO_4$, filtered and purified by silica gel chromatography (0→30% EA/PE) to yield 1-(difluoromethyl)-5-(1-ethoxyvinyl)-1H-1,2,4-triazoleas a yellow oil. LC/MS: mass calculated for $C_{15}H_{21}FN_2O_3$: 296.15, measured (ES, m/z): 297.25 $[M+H]^+$.

Step 4: Tert-butyl ((4-(2-bromoacetyl)-3-fluoropyridin-2-yl)methyl)carbamate tert-Butyl ((4-(1-ethoxyvinyl)-3-fluoropyridin-2-yl)methyl)carbamate (3.0 g, 10.12 mmol, 1.0 equiv.) was dissolved in THE (40 mL) and $H_2O$ (10 mL). After cooling to 0° C., 1-bromopyrrolidine-2,5-dione (1.8 g, 10.12 mmol, 1.0 equiv.) was added. The reaction mixture was stirred at room temperature for 1 h, then diluted with water and extracted with EA. The organic layers were combined, dried over anhydrous sodium sulfate, filtered and concentrated to yield tert-butyl ((4-(2-bromoacetyl)-3-fluoropyridin-2-yl)methyl)carbamate as a yellow oil. LC/MS: mass calculated for $C_{13}H_{16}BrFN_2O_3$: 346.03, measured (ES, m/z): 347.10, 349.10 $[M+H, M+H+2]^+$.

Step 5: 2-(2-(((Teri butoxycarbonyl)amino)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (812 mg, 2.50 mmol, 1.0 equiv.) in DMF (15 mL) was added cesium carbonate (489 mg, 1.50 mmol, 0.6 equiv.). The mixture was stirred at room temperature for 0.5 h. Then tert-butyl ((4-(2-bromoacetyl)-3-fluoropyridin-2-yl)methyl)carbamate (1042 mg, 3.00 mmol, 1.2 equiv.) was added. The reaction mixture was stirred at room temperature for 2 h, quenched with water (50 mL), and extracted with ethyl acetate (3×100 mL). The combined extracts were washed with water, dried over $Na_2SO_4$, filtered and purified by silica gel chromatography (0→10% MeOH/DCM) to yield 2-(2-(((tert-butoxycarbonyl)amino)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{28}H_{29}ClF_2N_4O_8$: 590.17, measured (ES, m/z): 591.35 $[M+H]^+$.

Step 6: Tert-butyl ((4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)methyl)carbamate To a solution of 2-(2-(((tert-butoxycarbonyl)amino)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (1.1 g, 1.86 mmol, 1.0 equiv.) in toluene (20 mL) and acetic acid (2 mL) was added ammonium acetate (1.4 g, 18.16 mmol, 10.0 equiv.). The mixture was stirred at 90° C. for 4 h. After cooling to room temperature, the reaction was quenched with water (50 mL), extracted with ethyl acetate (3×100 mL). The organic layers were combined, dried over anhydrous sodium sulfate, filtered, and concentrated. The residue was purified by silica gel chromatography (0-(10% methanol/DCM) to yield the tert-butyl ((4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)methyl)carbamate as a yellow solid. LC/MS: mass calculated for $C_{28}H_{22}ClF_2N_6O_3$: 570.20, measured (ES, m/z): 571.40 $[M+H]^+$.

Step 7: Tert butyl ((4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methyl)carbamate To a solution of tert-butyl ((4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl) methyl)carbamate (872 mg, 1.53 mmol, 1.0 equiv.) in acetic acid (10 mL) was added azidotrimethylsilane (1759 mg, 15.27 mmol, 10.0 equiv.), followed by addition of trimethoxymethane (1621 mg, 15.27 mmol, 10.0 equiv.). The reaction mixture was stirred at 60° C. for 2 h. After cooling to room temperature, the reaction was quenched with water (50 mL), extracted with ethyl acetate (3×100 mL). The organic layers were combined, dried over anhydrous sodium sulfate, and concentrated. The residue was purified by silica gel chromatography (0→10% MeOH/DCM) to yield the tert-butyl ((4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methyl)carbamate as a yellow solid. LC/MS: mass calculated for $C_{29}H_{28}ClF_2N_9O_3$: 623.20, measured (ES, m/z): 624.40 $[M+H]^+$.

Step 8: (3S)-3-(5-(3-(Aminomethyl)-2-fluorophenyl)-1H-imidazol-2-yl)-7-(3-chloro-2-fluoro-6-(1H-tetrazol-1-yl)phenyl)-2,3,8,8a-tetrahydroindolizin-5 (1H)-one To a solution of tert-butyl ((4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methyl)carbamate (700 mg, 1.12 mmol) in DCM (4 mL) was added TFA (1 mL). The reaction mixture was stirred at room temperature for 2 h. The reaction was diluted with water and extracted with EA. The organic layers were combined, dried over anhydrous sodium sulfate, filtered and concentrated to yield (3S)-3-(5-(2-(aminomethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5 (1H)-one as a yellow oil. LC/MS: mass calculated for $C_{24}H_{20}ClF_2N_9O$: 523.14, measured (ES, m/z): 524.10 $[M+H]^+$.

Step 9: Ethyl ((4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methyl)carbamate To a solution of (3S)-3-(5-(2-(aminomethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5 (1H)-one (220 mg, 0.42 mmol, 1.0 equiv.) in DCM (5 mL) were added TEA (212 mg, 2.10 mmol, 5.0 equiv.) and ethyl carbonochloridate (137 mg, 1.26 mmol, 3.0 equiv.). The reaction mixture was stirred at 25° C. for 2 h. The reaction mixture was then diluted with water and extracted with EA. The organic layers were combined, dried over anhydrous sodium sulfate, filtered, and concentrated to dryness under reduced pressure to yield a residue. To the residue was added MeOH (5 mL) and $NH_3 \cdot H_2O$ (0.5 mL). The mixture was stirred at 35° C. for 0.5 h and concentrated to dryness under reduced pressure. The resulting residue was purified by C18 column chromatography ($CH_3CN/H_2O$) & chiral-HPLC (Column: (R,R)-WHELK-O1-Kromasil, 2.11*25 cm, 5 μm; Mobile Phase A: MTBE (0.5% 2M $NH_3$-MeOH)-HPLC, Mobile Phase B: EtOH-HPLC; Flow rate: 20 mL/min) to yield ethyl ((4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methyl)carbamate as a white solid.

LC/MS: mass calculated for $C_{27}H_{24}ClF_2N_9O_3$: 595.17, measured (ES, m/z): 596.20 $[M+H]^+$. $^1H$ NMR (400 MHz, DMSO-$d_6$) δ 12.27 (s, 1H), 9.84 (s, 1H), 8.32 (d, J=5.0 Hz, 1H), 7.93-8.02 (m, 1H), 7.86 (t, J=5.4 Hz, 1H), 7.69-7.72 (m, 1H), 7.55-7.58 (m, 1H), 7.47-7.52 (m, 1H), 5.70 (d, J=2.7 Hz, 1H), 5.04 (d, J=8.8 Hz, 1H), 4.32-4.42 (m, 2H), 4.00 (q, J=7.1 Hz, 2H), 3.69-3.78 (m, 1H), 2.67-2.77 (m, 1H), 2.52-2.55 (m, 1H), 2.15-2.24 (m, 1H), 2.07-2.14 (m, 1H), 1.90-1.99 (m, 2H), 1.16 (t, J=7.1 Hz, 3H). $^{19}F$ NMR (376 MHz, DMSO-$d_6$) δ −112.85, −130.28

Example 13: N-[[4 [2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]methyl]acetamide

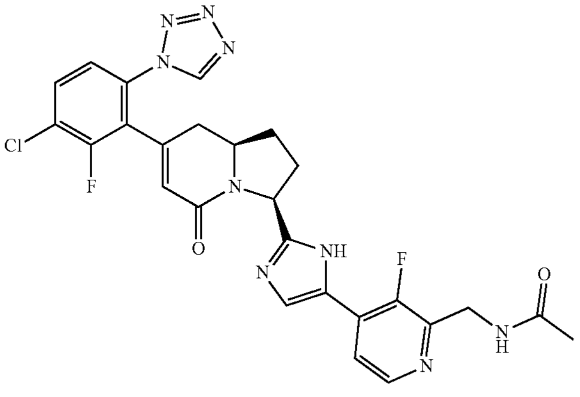 [SMILES: CC(=O)NCc1nccc(-c2cnc([C@@H]3CC[C@@H]4CC(c5c(-n6cnnn6)ccc(Cl)c5F)=CC(=O)N43)[nH]2)c1F]

LC/MS: mass calculated for $C_{26}H_{22}ClF_2N_9O_2$: 565.16, measured (ES, m/z): 566.15 $[M+H]^+$. $^1H$ NMR (300 MHz, DMSO-$d_6$) δ 12.26 (s, 1H), 9.82 (s, 1H), 8.29-8.32 (m, 2H), 7.95 (t, J=8.7 Hz, 1H), 7.86 (t, J=5.4 Hz, 1H), 7.65-7.75 (m, 1H), 7.56 (d, J=4.2 Hz, 1H), 5.68 (d, J=2.5 Hz, 1H), 5.02 (d, J=8.6 Hz, 1H), 4.43-4.46 (m, 2H), 3.67-3.77 (m, 1H), 2.66-2.76 (m, 1H), 2.50-2.55 (m, 1H), 2.04-2.26 (m, 2H), 1.89-1.97 (m, 2H), 1.85 (s, 3H). $^{19}F$ NMR (282 MHz, DMSO-$d_6$) δ−112.58, −129.79.

Example 14: (3S,8aR)-3-(5-(1H-indol-5-yl)-1H-imidazol-2-yl)-7-(3-chloro-2-fluoro-6-(1H-tetrazol-1-yl)phenyl)-2,3,8,8a-tetrahydroindolizin-5(1H)-one

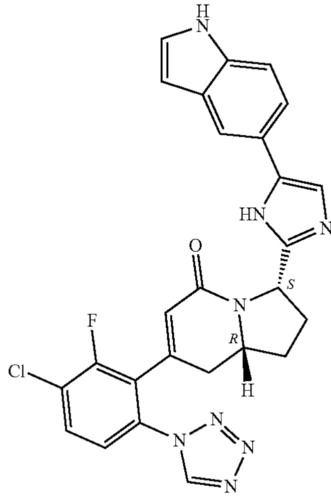

LC/MS: mass calculated for $C_{26}H_{20}ClFN_8O$: 514.1, measured (ES, m/z): 515.2 $[M+H]^+$. $^1H$ NMR (400 MHz, METHANOL-$d_4$) δ ppm 9.57 (s, 1H), 8.33 (s, 1H), 7.85-7.78 (m, 2H), 7.54 (dd, J=1.5, 8.8 Hz, 1H), 7.43-7.38 (m, 2H), 7.28-7.24 (m, 2H), 6.48 (d, J=3.0 Hz, 1H), 5.72 (d, J=2.8 Hz, 1H), 5.19 (d, J=8.8 Hz, 1H), 3.93-3.83 (m, 1H), 3.04-2.92 (m, 1H), 2.60 (dd, J=4.3, 16.8 Hz, 1H), 2.42-2.30 (m, 1H), 2.27-2.18 (m, 2H), 2.12-2.00 (m, 1H).

Example 15: (3S,8aR)-3-[5-(2-Amino-5-chloro-4-pyridyl)-1H-imidazol-2-yl]-7-[3-chloro-2-fluoro-6-(tetrazol-1-yl)phenyl]-2,3,8,8a-tetrahydro-1H-indolizin-5-one

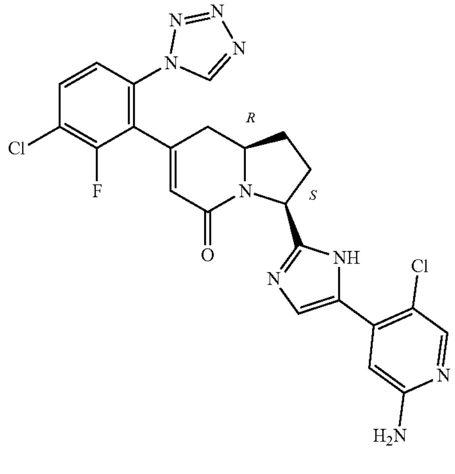

LC/MS: mass calculated for $C_{23}H_{18}Cl_2FN_9O$: 525.10, measured (ES, m/z): 526.00 $[M+H]^+$. $^1H$ NMR (300 MHz, DMSO-$d_6$) δ 12.09 (s, 1H), 9.85 (s, 1H), 7.97 (t, J=7.9 Hz, 1H), 7.89 (s, 1H), 7.68-7.75 (m, 2H), 7.19 (s, 1H), 6.05 (s, 2H), 5.70 (d, J=2.6 Hz, 1H), 5.01 (d, J=8.8 Hz, 1H), 3.65-3.78 (m, 1H), 2.59-2.79 (m, 1H), 2.52-2.56 (m, 1H), 2.15-2.26 (m, 1H), 2.05-2.14 (m, 1H), 1.88-2.04 (m, 2H). $^{19}F$ NMR (376 MHz, DMSO-$d_6$) δ −112.61.

Example 16: N-[(1R)-1-[4-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-5-yl]phenyl]ethyl]acetamide

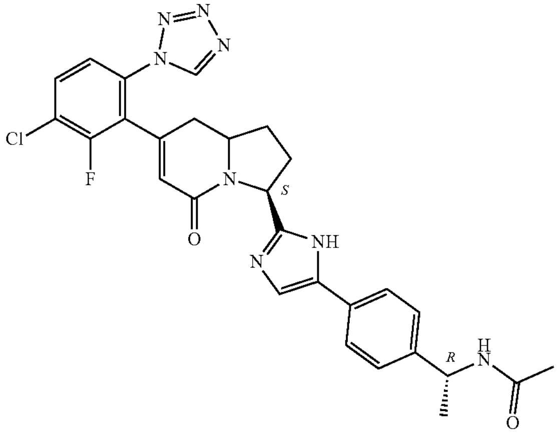

LC/MS: mass calculated for $C_{28}H_{26}ClFN_8O_2$: 560.19, measured (ES, m/z): 561.20$[M+H]^+$. $^1H$ NMR (400 MHz, DMSO-$d_6$) δ 11.76-11.92 (m, 1H), 9.84 (s, 1H), 8.28 (d, J=8.2 Hz, 1H), 7.98 (t, J=8.2 Hz, 1H), 7.60-7.75 (m, 3H), 7.42 (s, 1H), 7.25-7.30 (m, 2H), 5.68 (d, J=9.1 Hz, 1H), 5.00 (d, J=6.6 Hz, 1H), 4.86-4.92 (m, 1H), 3.65-4.13 (m, 1H), 2.70-2.87 (m, 1H), 2.29-2.44 (m, 1H), 2.16-2.27 (m, 1H), 1.90-2.05 (m, 2H), 1.84 (s, 3H), 1.64-1.74 (m, 1H), 1.33-1.38 (m, 3H). $^{19}F$ NMR (376 MHz, DMSO-$d_6$) δ 112.82, −113.06.

Example 17: (3S,8aR)-7-[3-Chloro-2-fluoro-6-(tetrazol-1-yl)phenyl]-3-[5-(3-fluoro-4-pyridyl)-1H-imidazol-2-yl]-2,3,8,8a-tetrahydro-1H-indolizin-5-one

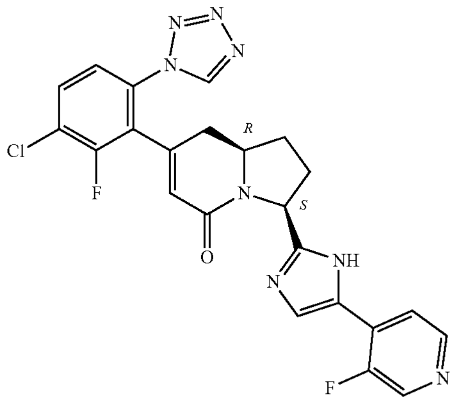

To a mixture of 2-(3-fluoropyridin-4-yl)-2-oxoethyl (3R,8aS)-7-(3-chloro-2-fluoro-6-(1H-tetrazol-1-yl)phenyl)-5-oxo-1,2,3,5,8,8a-hexahydroindolizine-3-carboxylate (43 mg, 0.07 mmol) and ammonium acetate (193.1 mg, 2.5 mmol) in a 20 ml scintillation vial was added HOAc (3.0 mL). The reaction mixture was stirred at 90° C. for 4 h, and the excess solvent was removed under reduced pressure. The residue was purified by HPLC to yield a white solid.

LC/MS calculated for $C_{23}H_{17}ClF_2N_8O$: 494.1, measured 495.1 (MH). $^1$H NMR (400 MHz, METHANOL-$d_4$) δ 9.61 (s, 1H), 8.69 (d, J=3.91 Hz, 1H), 8.57 (d, J=5.87 Hz, 1H), 8.27 (t, J=6.36 Hz, 1H), 7.91 (d, J=3.42 Hz, 1H), 7.81-7.88 (m, 1H), 7.58 (dd, J=1.47, 8.80 Hz, 1H), 5.78-5.81 (m, 1H), 5.25 (d, J=8.80 Hz, 1H), 3.93-4.06 (m, 1H), 2.81-2.92 (m, 1H), 2.74 (s, 1H), 2.36-2.47 (m, 1H), 2.20-2.34 (m, 2H), 2.01-2.13 (m, 1H).

Example 18: N-[5-Chloro-4-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-5-yl]-2-pyridyl]acetamide

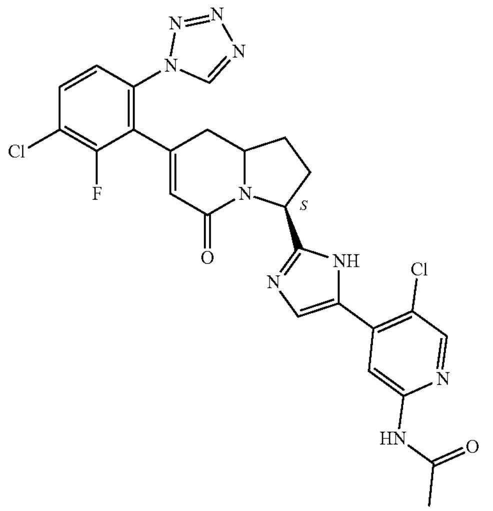

LC/MS: mass calculated for $C_{25}H_{20}Cl_2FN_9O_2$: 567.11, measured (ES, m/z): 568.10 $[M+H]^+$. $^1$H NMR (400 MHz, DMSO-$d_6$) δ 9.82 (s, 1H), 8.64 (s, 1H), 8.44 (s, 1H), 7.90-8.04 (m, 2H), 7.71 (d, J=8.7 Hz, 1H), 5.70 (d, J=2.7 Hz, 1H), 5.16 (d, J=9.2 Hz, 1H), 3.33-3.83 (m, 1H), 2.84-3.02 (m, 1H), 2.55-2.61 (m, 1H), 2.25-2.39 (m, 1H), 2.11-2.20 (m, 4H), 2.03-2.10 (m, 1H), 1.91-2.01 (m, 1H). $^{19}$F NMR (376 MHz, DMSO-$d_6$) δ −74.59, −112.42.

Example 19: (R)-7-[3-Chloro-2-fluoro-6-(tetrazol-1-yl)phenyl]-3-[5-(1H-pyrrolo[2,3-c]pyridin-3-yl)-1H-imidazol-2-yl]-2,3,8,8a-tetrahydro-1H-indolizin-5-one

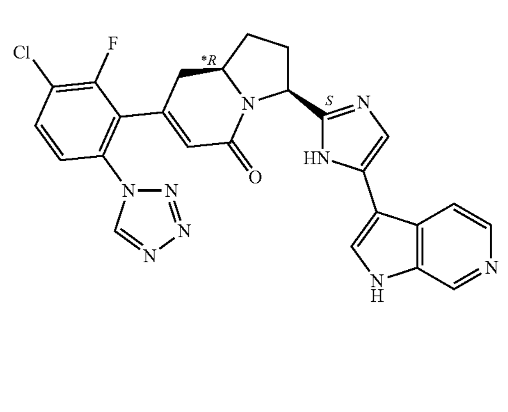

LC/MS: mass calculated for $C_{25}H_{19}ClFN_9O$: 515.14, measured (ES, m/z): 516.10 $[M+H]^+$. $^1$H NMR (400 MHz, Methanol-$d_4$) δ 9.58 (s, 1H), 8.71 (d, J=1.1 Hz, 1H), 8.14 (d, J=5.7 Hz, 1H), 7.75-7.93 (m, 3H), 7.52-7.59 (m, 1H), 7.26 (s, 1H), 5.72 (d, J=2.9 Hz, 1H), 5.10-5.21 (m, 1H), 3.82-3.95 (m, 1H), 2.91-3.03 (m, 1H), 2.55-2.64 (m, 1H), 2.27-2.39 (m, 1H), 2.18-2.27 (m, 2H), 2.02-2.16 (m, 1H). $^{19}$F NMR (376 MHz, Methanol-$d_4$) δ −113.30.

Example 20: (3S,8aR*)-3-(5-(1H-Pyrrolo[3,2-c]pyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

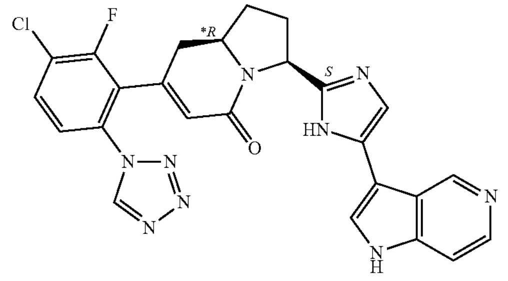

Step 1: tert-Butyl 3-(2-((3S)-7-(6-amino-3-chloro-2-fluorophenyl)-5-oxo-1,2,3,5,8,8a-hexahydroindolizin-3-yl)-1H-imidazol-5-yl)-1H-pyrrolo[3,2-c]pyridine-1-carboxylate To a mixture of (3S)-7-(6-amino-3-chloro-2-fluorophenyl)-3-(5-iodo-1H-imidazol-2-yl)-2,3,8,8a-tetrahydroindolizin-5(1H)-one (150 mg, 0.32 mmol, 1.0 equiv.) and tert-butyl 3-(4,4,5,5-tetramethyl-1,3,2-dioxaborolan-2-yl)-1H-pyrrolo[3,2-c]pyridine-1-carboxylate (218 mg, 0.63 mmol, 2.0 equiv.) in 1,4-dioxane (10 mL) and water (1 mL) were added potassium carbonate (132 mg, 0.95 mmol, 3.0 equiv.) and 1,1'-bis (di-t-butylphosphino)ferrocene palladium dichloride (21 mg, 0.03 mmol, 0.1 equiv.). The resulting mixture was maintained under nitrogen and stirred at 100° C. for 3 h. After cooling to room temperature, the reaction was quenched with water and the mixture was extracted with EA. The combined extracts were dried over anhydrous $Na_2SO_4$, concentrated. The residue was purified by silica gel column chromatography (0→8% MeOH/DCM) to yield tert-butyl 3-(2-((3S)-7-(6-amino-3-chloro-2-fluorophenyl)-5-oxo-1,2,3,5,8,8a-hexahydroindolizin-3-yl)-1H-imidazol-5-yl)-1H-pyrrolo[3,2-c]pyridine-1-carboxylate as a brown solid. LC/MS (ES, m/z): mass calculated for $C_{29}H_{28}ClFN_8O_3$:562.19, measured: 563.15 $[M+H]^+$.

Step 2: tert-Butyl 3-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-1H-pyrrolo[3,2-c]pyridine-1-carboxylate To a mixture of tert-butyl 3-(2-((3S)-7-(6-amino-3-chloro-2-fluorophenyl)-5-oxo-1,2,3,5,8,8a-hexahydroindolizin-3-yl)-1H-imidazol-5-yl)-1H-pyrrolo[3,2-c]pyridine-1-carboxylate (120 mg, 0.21 mmol, 1.0 equiv.) in acetic acid (5 mL) were added azidotrimethylsilane (2.5 mL) and trimethoxymethane (2.5 mL). The reaction mixture was stirred overnight at 50° C. The resulting mixture was concentrated under vacuum to yield tert butyl 3-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-1H-pyrrolo[3,2-c]pyridine-1-carboxylate as a brown solid, which was used in the next step without further purification. LC/MS (ES, m/z): mass calculated for $C_{30}H_{27}ClFN_9O_3$: 615.19, measured: 616.25 $[M+H]^+$.

Step 3: (3S,8a*R)-3-(5-(1H-Pyrrolo[3,2-c]pyridin-3-yl)-1H-imidazol-2-yl)-7-(3-chloro-2-fluoro-6-(1H-tetrazol-1-yl)phenyl)-2,3,8,8a-tetrahydroindolizin-5(1H) one A solution of tert-butyl 3-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-1H-pyrrolo[3,2-c]pyridine-1-carboxylate (157 mg) in dichloromethane (10 mL) and trifluoroacetic acid (3 mL) was stirred at room temperature for 1 h. The resulting mixture was concentrated under vacuum. The residue was dissolved into EA, washed with $NaHCO_3$ solution, dried over anhydrous $Na_2SO_4$, and concentrated. The residue was purified by chiral HPLC with MtBE (0.1% DEA):EtOH=70:30 to yield (3S,8a*R)-3-(5-(1H-pyrrolo[3,2-c]pyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one as a brown solid.

LC/MS: mass calculated for $C_{25}H_{19}ClFN_9O$: 515.14, measured (ES, m/z): 516.10 $[M+H]^+$. $^1H$ NMR (400 MHz, Methanol-$d_4$) δ 9.58 (s, 1H), 9.05 (s, 1H), 8.14-8.21 (m, 1H), 7.78-7.84 (m, 1H), 7.68 (s, 1H), 7.50-7.62 (m, 1H), 7.45 (dd, J=5.9, 1.1 Hz, 1H), 7.28 (s, 1H), 5.72 (d, J=2.8 Hz, 1H), 5.17 (d, J=8.8 Hz, 1H), 3.82-3.97 (m, 1H), 2.91-3.05 (m, 1H), 2.55-2.64 (m, 1H), 2.28-2.40 (m, 1H), 2.19-2.27 (m, 2H), 2.03-2.17 (m, 1H). $^{19}F$-NMR (376 MHz, Methanol-$d_4$) δ −113.25.

Example 21: (3S)-3-(5-(2-Amino-3-methylpyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

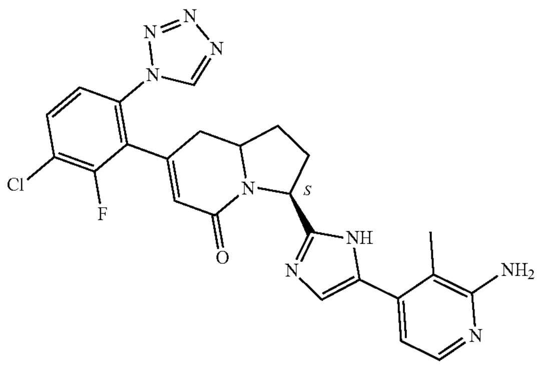

Step 1: 4-Iodo-3-methylpyridin-2-amine

To a solution of 2-fluoro-4-iodo-3-methylpyridine (500 mg, 2.11 mmol) in DMSO (5 mL) was added ammonium hydroxide (6 mL). The resulting mixture was stirred at 100° C. for 2 days. After cooling to room temperature, the resulting mixture was diluted with EA and washed with water three times. The organic layers were combined, dried over anhydrous sodium sulfate, filtered, and concentrated. The residue was purified by silica gel chromatography (0→50% ethyl acetate/petroleum ether) to yield the 4-iodo-3-methylpyridin-2-amine as a white solid. LC/MS: mass calculated for $C_6H_7IN_2$: 233.97, measured (ES, m/z): 234.95 $[M+H]^+$.

Step 2: N-(4-iodo-3-methylpyridin-2-yl)acetamide

A mixture of 4-iodo-3-methylpyridin-2-amine (540 mg, 2.31 mmol) and $Ac_2O$ (15 mL) was stirred at room temperature overnight. The resulting mixture was concentrated to yield the N-(4-iodo-3-methylpyridin-2-yl)acetamide as a yellow solid. LC/MS: mass calculated for $C_8H_9IN_2O$: 275.98, measured (ES, m/z): 276.95 $[M+H]^+$.

Step 3: N-(4-(1-ethoxyvinyl)-3-methylpyridin-2-yl)acetamide

To a solution of N-(4-iodo-3-methylpyridin-2-yl)acetamide (510 mg, 1.85 mmol, 1.0 equiv.) in 1,4-dioxane (35 mL) was added tributyl(1-ethoxyvinyl)tin (733 mg, 2.03 mmol, 1.1 equiv.), followed by addition of $Pd(dppf)Cl_2$ (75 mg, 0.092 mmol, 0.05 equiv.). The resulting mixture was maintained under nitrogen and stirred at 100° C. overnight. After cooling to room temperature, the reaction was quenched with water. The resulting mixture was extracted with ethyl acetate. The organic layers were combined, dried over anhydrous sodium sulfate, filtered, and concentrated. The residue was purified by alumina gel chromatography (0→80% ethyl acetate/petroleum ether) to yield the N-(4-(1-ethoxyvinyl)-3-methylpyridin-2-yl)acetamide as a yellow oil. LC/MS: mass calculated for $C_{12}H_{16}N_2O_2$: 220.12, measured (ES, m/z): 221.15 $[M+H]^+$.

Step 4: N-(4-(2-bromoacetyl)-3-methylpyridin-2-yl)acetamide

To a solution of N-(4-(1-ethoxyvinyl)-3-methylpyridin-2-yl)acetamide (270 mg, 1.23 mmol, 1.0 equiv.) in THE (6 mL) and $H_2O$ (2 mL) was added NBS (218 mg, 1.23 mmol, 1.0 equiv.). The resulting mixture was stirred at room temperature for 1 h. The reaction was quenched with water. The resulting mixture was extracted with ethyl acetate. The organic layers were combined, dried over anhydrous sodium sulfate, and concentrated. The residue was purified by silica gel chromatography (0→90% ethyl acetate/petroleum ether) to yield n-(4-(2-bromoacetyl)-3-methylpyridin-2-yl)acetamide as a yellow oil. LC/MS: mass calculated for $C_{10}H_{11}BrN_2O_2$: 270.00, measured (ES, m/z): 271.00, 273.00 $[M+H, M+H+2]^+$.

Step 5: 2-(2-Acetamido-3-methylpyridin-4-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (140 mg, 0.43 mmol, 1.0 equiv.) in ACN (4 mL) was added $K_2CO_3$ (119 mg, 0.86 mmol, 2.0 equiv.) at room temperature. After stirring for 30 min, N-(4-(2-bromoacetyl)-3-methylpyridin-2-yl)acetamide (175 mg, 0.65 mmol, 1.5 equiv.) was added. The resulting mixture was stirred at room temperature for 1 h. The resulting mixture was concentrated. The residue was purified by silica gel chromatography (0→10% MeOH/DCM) to yield the 2-(2-acetamido-3-methylpyridin-4-yl)-2-oxoethyl (3S)-7-(6-amino-3-chloro-2-fluorophenyl)-5-oxo-1,2,3,5,8,8a-hexahydroindolizine-3-carboxylate as a brown oil. LC/MS: mass calculated for $C_{25}H_{24}ClFN_4O_5$: 514.14, measured (ES, m/z): 515.15 $[M+H]^+$.

Step 6: N-(4-(2-((3S)-7-(6-amino-3-chloro-2-fluorophenyl)-5-oxo-1,2,3,5,8,8a-hexahydroindolizin-3-yl)-1H-imidazol-5-yl)-3-methylpyridin-2-yl)acetamide To a solution of 2-(2-acetamido-3-methylpyridin-4-yl)-2-oxoethyl (3S)-7-(6-amino-3-chloro-2-fluorophenyl)-5-oxo-1,2,3,5,8,8a-hexahydroindolizine-3-carboxylate (120 mg, 0.23 mmol, 1.0 equiv.) in toluene (8 mL) and HOAc (0.2 mL) was added $NH_4OAc$ (359 mg, 4.66 mmol, 20.0 equiv.). The resulting mixture was stirred at 100° C. for 1 h. The resulting mixture was concentrated. The residue was purified by silica gel chromatography (0→15% MeOH/DCM) to yield N-(4-(2-((3S)-7-(6-amino-3-chloro-2-fluorophenyl)-5-oxo-1,2,3,5,8,8a-hexahydroindolizin-3-yl)-1H-imidazol-5-yl)-3-methylpyridin-2-yl)acetamide as a yellow solid. LC/MS: mass calculated for $C_{25}H_{24}ClFN_6O_2$: 494.16, measured (ES, m/z): 495.30 $[M+H]^+$.

Step 7: N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-methylpyridin-2-yl)acetamide To a solution of N-(4-(2-((3S)-7-(6-amino-3-chloro-2-fluorophenyl)-5-oxo-1,2,3,5,8,8a-hexahydroindolizin-3-yl)-1H-imidazol-5-yl)-3-methylpyridin-2-yl)acetamide (73 mg, 0.15 mmol, 1.0 equiv.) in AcOH (8 mL) were added azidotrimethylsilane (340 mg, 2.95 mmol, 20.0 equiv.) and trimethoxymethane (313 mg, 2.95 mmol, 20.0 equiv.). The resulting mixture was stirred at 50° C. overnight. The resulting mixture was concentrated to yield N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-methylpyridin-2-yl)acetamide as a yellow oil, which was used in the next step without further purification. LC/MS: mass calculated for $C_{26}H_{23}ClFN_9O_2$: 547.16, measured (ES, m/z): 548.35 $[M+H]^+$.

Step 8: (3S)-3-(5-(2-Amino-3-methylpyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-methylpyridin-2-yl)acetamide (75 mg, 0.14 mmol) in THE (3 mL) was added HCl (3 mL, 2 M in $H_2O$). The resulting mixture was stirred at 60° C. overnight. After cooling to room temperature, the resulting mixture was concentrated. The residue was purified by prep-HPLC to yield the (3S)-3-(5-(2-amino-3-methylpyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC/MS: mass calculated for $C_{24}H_{21}ClFN_9O$: 505.15, measured (ES, m/z): 506.20 [M+H]. $^1H$ NMR (400 MHz, DMSO-$d_6$) δ 11.95-12.18 (m, 1H), 9.84 (s, 1H), 7.93-8.02 (m, 1H), 7.56-7.85 (m, 2H), 7.31 (s, 1H), 6.87 (d, J=5.4 Hz, 1H), 5.54-5.73 (m, 2H), 5.01 (d, J=8.4 Hz, 1H), 3.60-3.82 (m, 2H), 2.65-2.80 (m, 1H), 2.24 (s, 3H), 2.07-2.16 (m, 2H), 1.91-2.04 (m, 3H). $^{19}F$-NMR: (376 MHz, DMSO-$d_6$) δ −112.86.

Example 22: (3S,8aR)-7-(3-Chloro-2-fluoro-6-(1H-tetrazol-1-yl)phenyl)-3-(4-(2-(hydroxymethyl)thiazol-4-yl)-1H-imidazol-2-yl)-2,3,8,8a-tetrahydroindolizin-5(1H)-one

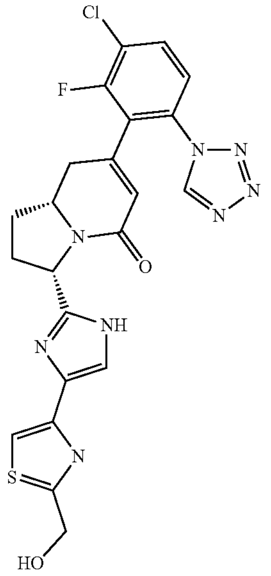

LC/MS: mass calculated for: $C_{22}H_{18}ClFN_8O_2S$: 512.1, measured (ES, m/z): 513.2 $[M+H]^+$. $^1H$ NMR (400 MHz, methanol-$d_4$) δ 9.58 (s, 1H), 7.89 (s, 1H), 7.84-7.75 (m, 1H), 7.79 (s, 1H), 7.58 (dd, J=8.8, 1.7 Hz, 1H), 5.76 (d, J=2.8 Hz, 1H), 5.28 (dd, J=10.2, 1.9 Hz, 1H), 4.90 (s, 2H), 2.98 (t, J=15.3 Hz, 1H), 2.71 (dd, J=17.0, 4.3 Hz, 1H), 2.57-2.47 (bm, 1H), 2.36-2.29 (bm, 1H), 2.26-2.19 (bm, 1H), 2.08-1.93 (bm, 1H), 190-1.80 (m, 1H). $^{19}F$ NMR (400 MHz, methanol-$d_4$) δ −113.5.

Example 23: (3S,8aR)-7-(3-Chloro-6-(difluoromethoxy)-2-fluorophenyl)-3-(4-fluoro-5-(3-fluoro-2-(hydroxymethyl)pyridin-4yl)-1H-imidazol-2-yl)-2,3,8,8a-tetrahydroindolizin-5(1H)-one

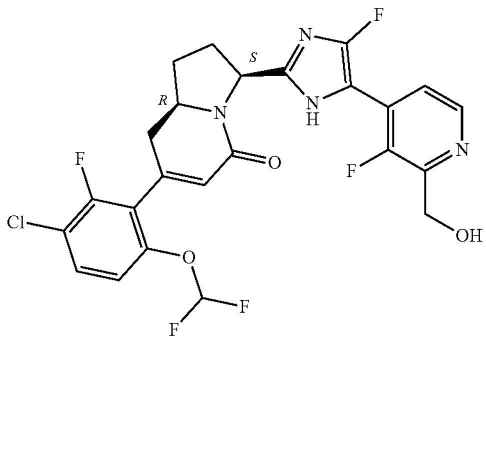

Step 1: 2-Bromo-4-chloro-3-fluorophenol

To a solution of 2-bromo-3-fluorophenol (5.0 g, 26.18 mmol, 1.0 equiv.) in ACN (200 mL) were added NCS (3.5 g, 26.21 mmol, 1.0 equiv.) and TFA (3.3 mL) at 0° C. The reaction mixture was stirred overnight at room temperature. The reaction mixture was concentrated. The residue was purified by silica gel chromatography (0→20% EA/PE) to yield 2-bromo-4-chloro-3-fluorophenol as a yellow oil. LC/MS: mass calculated for $C_6H_3BrClFO$: 223.90, measured (ES, m/z): 222.90 $[M-H]^-$.

Step 2: 2-Bromo-4-chloro-1-(difluoromethoxy)-3-fluorobenzene

To a solution of 2-bromo-4-chloro-3-fluorophenol (3.7 g, 16.41 mmol, 1.0 equiv.) in DMF (60 mL) were added $Cs_2CO_3$ (10.7 g, 32.84 mmol, 2.0 equiv.) and sodium 2-chloro-2,2-difluoroacetate (5.0 g, 32.80 mmol, 2.0 equiv.). The reaction mixture was stirred overnight at 90° C. After cooling to room temperature, the reaction mixture was poured into water (100 mL), then extracted with EA (3×100 mL). The organic layers were combined, washed with water (100 mL) and brine (100 mL), dried over $Na_2SO_4$, filtered and concentrated. The residue was purified by silica gel chromatography (0→20% EA/PE) to yield 2-bromo-4-chloro-1-(difluoromethoxy)-3-fluorobenzene as a colorless oil. $^1H$ NMR (300 MHz, Chloroform-d) δ 7.38 (dd, J=9.0, 7.8 Hz, 1H), 6.99-7.05 (m, 1H), 6.55 (t, J=72.5 Hz, 1H).

Step 3: Ethyl (3S)-5-oxo-7-(4,4,5,5-tetramethyl-1,3,2-dioxaborolan-2-yl)-1,2,3,5,8,8a-hexahydroindolizine-3-carboxylate Under an inert atmosphere of nitrogen, to a solution of ethyl (3S)-5-oxo-7-(((trifluoromethyl)sulfonyl)oxy)-1,2,3,5,8,8a-hexahydroindolizine-3-carboxylate (1.5 g, 4.20 mmol, 1.0 equiv.) in 1,4-dioxane (20 mL) were added 4,4,4',4',5,5,5',5'-octamethyl-2,2'-bi(1,3,2-dioxaborolane (1.6 g, 6.30 mmol, 1.5 equiv.), $Pd(dppf)Cl_2$ (307 mg, 0.42 mmol, 0.1 equiv.), and KOAc (824 mg. 8.40 mmol, 2.0 equiv.). The reaction mixture was stirred for 2 h at 90° C., then concentrated to dryness under reduced pressure to yield ethyl (3S)-5-oxo-7-(4,4,5,5-tetramethyl-1,3,2-dioxaborolan-2-yl)-1,2,3,5,8,8a-hexahydroindolizine-3-carboxylate as a yellow solid. LC/MS: mass calculated for $C_{17}H_{26}BNO_5$: 335.19, measured (ES, m/z): 336.15 $[M+H]^+$.

Step 4: Ethyl (3S)-7-(3-chloro-6-(difluoromethoxy)-2-fluorophenyl)-5-oxo-1,2,3,5,8,8a-hexahydroindolizine-3-carboxylate Under an inert atmosphere of nitrogen, to a solution of ethyl (3S)-5-oxo-7-(4,4,5,5-tetramethyl-1,3,2-dioxaborolan-2-yl)-1,2,3,5,8,8a-hexahydroindolizine-3-carboxylate (1.2 g, 3.58 mmol, 1.0 equiv.) in 1,4-dioxane (15 mL) with $H_2O$ (1.5 mL) were added 2-bromo-4-chloro-1-(difluoromethoxy)-3-fluorobenzene (1.1 g, 3.99 mmol, 1.1 equiv.), $Pd(dppf)Cl_2$ (262 mg, 0.36 mmol, 0.1 equiv.), and $K_2CO_3$ (990 mg, 7.16 mmol, 2.0 equiv.). The reaction mixture was stirred for 2 h at 90° C., then concentrated to dryness under reduced pressure to yield a residue, which was purified by column chromatography on silica gel with MeOH/DCM (0→15%) to yield ethyl (3S)-7-(3-chloro-6-(difluoromethoxy)-2-fluorophenyl)-5-oxo-1,2,3,5,8,8a-hexahydroindolizine-3-carboxylate as a yellow solid. LC/MS: mass calculated for $C_{18}H_{17}ClF_3NO_4$: 403.08, measured (ES, m/z): 404.10 $[M+H]^+$.

Step 5: (3S)-7-(3-Chloro-6-(difluoromethoxy)-2-fluorophenyl)-5-oxo-1,2,3,5,8,8a-hexahydroindolizine-3-carboxylic acid To a solution of ethyl (3S)-7-(3-chloro-6-(difluoromethoxy)-2-fluorophenyl)-5-oxo-1,2,3,5,8,8a-hexahydroindolizine-3-carboxylate (1.0 g, 2.48 mmol, 1.0 equiv.) in THF (10 mL), $H_2O$ (3 mL) was added LiOH (296 mg, 12.36 mmol, 5.0 equiv.). The reaction mixture was stirred overnight at room temperature, then adjusted to pH=5~6 by using HCl (2 M) at 0° C. and extracted with ethyl acetate. The combined organic layer was washed with brine, dried over $Na_2SO_4$ and concentrated to yield (3S)-7-(3-chloro-6-(difluoromethoxy)-2-fluorophenyl)-5-oxo-1,2,3,5,8,8a-hexahydroindolizine-3-carboxylic acid as a yellow solid. LC/MS: mass calculated for $C_{18}H_{13}ClF_3NO_4$: 375.05, measured (ES, m/z): 376.10 $[M+H]^+$.

Step 6: 2-(2-(((Teri butyldimethylsilyl)oxy)methyl)-3-fluoropyridin-4-yl)-2-oxoethyl (3S)-7-(3-chloro-6-(difluoromethoxy)-2-fluorophenyl)-5-oxo-1,2,3,5,8,8a-hexahydroindolizine-3-carboxylate To a mixture of (3S)-7-(3-chloro-6-(difluoromethoxy)-2-fluorophenyl)-5-oxo-1,2,3,5,8,8a-hexahydroindolizine-3-carboxylic acid (800 mg, 2.13 mmol, 1.0 equiv.) in DMF (15 mL) was added $Cs_2CO_3$ (416 mg, 1.28 mmol, 0.6 equiv.) and the mixture was stirred at room temperature for 30 min. 2-Bromo-1-(2-(((tert-butyldimethylsilyl)oxy)methyl)-3-fluoropyridin-4-yl)ethan-1-one (1.2 g, 3.31 mmol, 1.5 equiv.) was then added, and the resulting mixture was stirred at room temperature for 2 h. The reaction mixture was quenched with water (200 mL) and extracted with ethyl acetate (300 mL×3). The combined organic layer was washed with brine, dried over $Na_2SO_4$ and concentrated. The residue was purified by silica gel chromatography (0→20% MeOH/DCM) to yield 2-(2-(((tert-butyldimethylsilyl)oxy)methyl)-3-fluoropyridin-4-yl)-2-oxoethyl (3S)-7-(3-chloro-6-(difluoromethoxy)-2-fluorophenyl)-5-oxo-1,2,3,5,8,8a-hexahydroindolizine-3-carboxylate as a yellow solid. LC/MS: mass calculated for $C_{30}H_{33}ClF_4N_2O_6Si$: 656.17, measured (ES, m/z): 657.20 $[M+H]^+$.

Step 7: (3S)-3-(5-(2-(((Tert-butyldimethylsilyl)oxy)methyl)-3-fluoropyridin-4-yl)-1H-imidazol-2-yl)-7-(3-chloro-6-(difluoromethoxy)-2-fluorophenyl)-2,3,8,8a-tetrahydroindolizin-5(1H)-one To a solution of 2-(2-(((tert-butyldimethylsilyl)oxy)methyl)-3-fluoropyridin-4-yl)-2-oxoethyl (3S)-7-(3-chloro-6-(difluoromethoxy)-2-fluorophenyl)-5-oxo-1,2,3,5,8,8a-hexahydroindolizine-3-carboxylate (900 mg, 1.37 mmol, 1.0 equiv.) in toluene (15.0 mL) and $CH_3COOH$ (1.5 mL) was added $NH_4OAc$ (1.0 g, 12.97 mmol, 10.0 equiv.). The reaction mixture was stirred for 2 h at 110° C., then concentrated to dryness under reduced pressure to yield a residue, which was purified by column chromatography on silica gel with MeOH/DCM (0→15%) to yield (3S)-3-(5-(2-(((tert-butyldimethylsilyl)oxy)methyl)-3-fluoropyridin-4-yl)-1H-imidazol-2-yl)-7-(3-chloro-6-(difluoromethoxy)-2-fluorophenyl)-2,3,8,8a-tetrahydroindolizin-5(1H)-one as a yellow solid. LC/MS: mass calculated for $C_{30}H_{33}ClF_4N_4O_3Si$: 636.19, measured (ES, m/z): 637.25 $[M+H]^+$.

Step 8: (3S,8aR)-7-(3-Chloro-6-(difluoromethoxy)-2-fluorophenyl)-3-(5-(3-fluoro-2-(hydroxymethyl)pyridin-4-yl)-1H-imidazol-2-yl)-2,3,8,8a-tetrahydroindolizin-5(1H)-one To a solution of (3S)-3-(5-(2-(((tert-butyldimethylsilyl)oxy)methyl)-3-fluoropyridin-4-yl)-1H-imidazol-2-yl)-7-(3-chloro-6-(difluoromethoxy)-2-fluorophenyl)-2,3,8,8a-tetrahydroindolizin-5(1H)-one (700 mg, 1.10 mmol, 1.0 equiv.) in THE (10 mL) was added triethylamine trihydrofluoride (2.5 mL). The reaction mixture was stirred for 2 h at 70° C., then concentrated under vacuum and the residue was purified by C18 column (eluent: 5% to 50% (v/v) $CH_3CN$ and $H_2O$ with 0.05% $NH_4HCO_3$) to yield (3S)-7-(3-chloro-6-(difluoromethoxy)-2-fluorophenyl)-3-(5-(3-fluoro-2-(hydroxymethyl)pyridin-4-yl)-1H-imidazol-2-yl)-2,3,8,8a-tetrahydroindolizin-5(1H)-one as a yellow solid, which was further separated by preparative HPLC (Column: CHIRALPAK IG, 2*25 cm, 5 μm; Mobile Phase A: undefined, Mobile Phase B: undefined; Flow rate: 20 mL/min) to yield (3S,8aR)-7-(3-chloro-6-(difluoromethoxy)-2-fluorophenyl)-3-(5-(3-fluoro-2-(hydroxymethyl)pyridin-4-yl)-1H-imidazol-2-yl)-2,3,8,8a-tetrahydroindolizin-5(1H)-one as a white solid. LC/MS: mass calculated for $C_{24}H_{19}ClF_4N_4O_3$: 522.11, measured (ES, m/z): 523.15 $[M+H]^+$.

Step 9: (3S,8aR)-7-(3-Chloro-6-(difluoromethoxy)-2-fluorophenyl)-3-(4-fluoro-5-(3-fluoro-2-(hydroxymethyl)pyridin-4-yl)-1H-imidazol-2-yl)-2,3,8,8a-tetrahydroindolizin-5(1H)-one To a solution of (3S)-7-(3-chloro-6-(difluoromethoxy)-2-fluorophenyl)-3-(5-(3-fluoro-2-(hydroxymethyl)pyridin-4-yl)-1H-imidazol-2-yl)-2,3,8,8a-tetrahydroindolizin-5(1H)-one (200 mg, 0.38 mmol, 1.0 equiv.) in DMF (5 mL) with $H_2O$ (0.5 mL) was added Selectfluor (95 mg, 0.27 mmol, 0.7 equiv.). The reaction mixture was stirred 1 h at room temperature, then concentrated under reduced pressure. The residue was purified by preparative HPLC using a (Column: XBridge Prep OBD C18 Column, 19*250 mm, 5 um; Mobile Phase A: Water (10 MMOL/L $NH_4HCO_3$), Mobile Phase B: MeOH. Flow rate: 25 mL/min) to yield the (3S,8aR)-7-(3-Chloro-6-(difluoromethoxy)-2-fluorophenyl)-3-(4-fluoro-5-(3-fluoro-2-(hydroxymethyl)pyridin-4-yl)-1H-imidazol-2-yl)-2,3,8,8a-tetrahydroindolizin-5(1H)-one as a white solid.

LC/MS: mass calculated for $C_{24}H_{18}ClF_5N_4O_3$: 540.10, measured (ES, m/z): 541.10 $[M+H]^+$. $^1H$ NMR (300 MHz, DMSO-$d_6$) δ12.67 (s, 1H), 8.39 (d, J=5.1 Hz, 1H), 7.72 (t, J=8.7 Hz, 1H), 7.00-7.61 (m, 3H), 5.97 (d, J=1.9 Hz, 1H), 5.35 (brs, 1H), 5.12 (d, J=8.5 Hz, 1H), 4.64 (d, J=2.4 Hz, 2H), 3.88-4.01 (m, 1H), 2.65-2.74 (m, 2H), 2.14-2.29 (m, 2H), 1.95-2.07 (m, 2H). $^{19}F$-NMR: (282 MHz, DMSO-$d_6$) δ −82.38, −113.36, −125.75, −130.36.

Example 24: (3S,8aR)-3-(5-(1H-pyrrolo[2,3-b]pyridin-5-yl)-1H-imidazol-2-yl)-7-(3-chloro-2-fluoro-6-(1H-tetrazol-1-yl)phenyl)-2,3,8,8a-tetrahydroindolizin-5(1H)-one

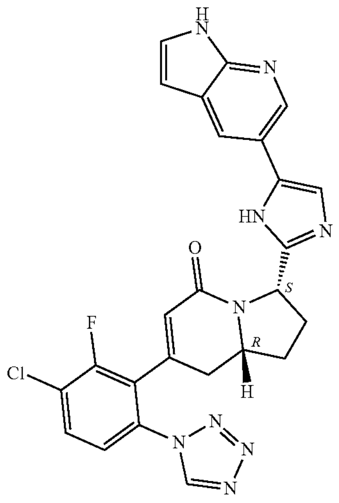

LC/MS: mass calculated for $C_{25}H_{19}ClFN_9O$: 515.1, measured (ES, m/z): 516.0 $[M+H]^+$. $^1H$ NMR (400 MHz, METHANOL-$d_4$) δ ppm 1.89 (s, 1H), 2.25 (s, 2H), 2.35-2.55 (m, 1H), 2.63 (dd, J=17.1, 4.4 Hz, 1H), 2.89 (br s, 1H), 3.76-3.97 (m, 1H), 5.17-5.26 (m, 1H), 5.27-5.34 (m, 1H), 5.67 (d, J=2.9 Hz, 1H), 5.84-5.92 (m, 1H), 6.52 (d, J=3.4 Hz, 1H), 7.42 (d, J=3.4 Hz, 2H), 7.66-7.81 (m, 2H), 8.12-8.15 (m, 1H), 8.23 (d, J=2.0 Hz, 1H), 8.45 (d, J=2.0 Hz, 1H), 9.49 (s, 1H).

Example 25: (3S,8aR)-7-(3-Chloro-6-(difluoromethoxy)-2-fluorophenyl)-3-(5-(3-fluoro-2-(hydroxymethyl)pyridin-4-yl)-1H-imidazol-2-yl)-2,3,8,8a-tetrahydroindolizin-5(1H)-one

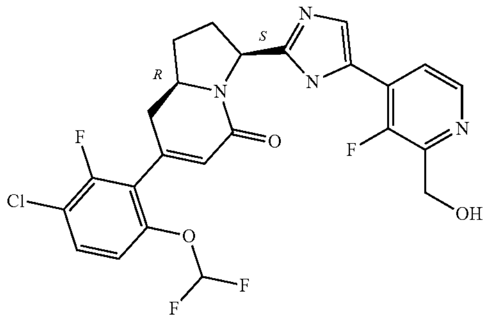

LC/MS: mass calculated for $C_{24}H_{19}ClF_4N_4O_3$: 522.11, measured (ES, m/z): 523.15 $[M+H]^+$. $^1H$ NMR (300 MHz, DMSO-$d_6$) δ12.32 (s, 1H), 8.30 (d, J=5.0 Hz, 1H), 7.90 (t, J=5.4 Hz, 1H), 7.72 (t, J=8.7 Hz, 1H), 7.05-7.65 (m, 3H), 5.98 (d, J=2.5 Hz, 1H), 5.28 (t, J=5.9 Hz, 1H), 5.13 (d, J=8.5 Hz, 1H), 4.59-4.68 (m, 2H), 3.92-4.03 (m, 1H), 2.85-2.96 (m, 1H), 2.62-2.70 (m, 1H), 2.13-2.28 (m, 2H), 2.01-2.08 (m, 2H). $^{19}F$-NMR: (282 MHz, DMSO-$d_6$) δ −82.38, −113.35, −130.06.

Example 26: (3S,8aR)-7-(3-Chloro-6-(difluoromethyl)-2-fluorophenyl)-3-(5-(3-fluoro-2-(hydroxymethyl)pyridin-4-yl)-1H-imidazol-2-yl)-2,3,8,8a-tetrahydroindolizin-5(1H)-one

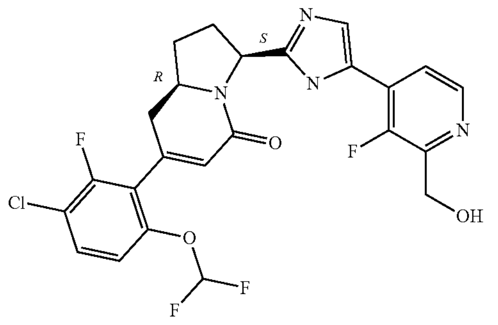

LC/MS: mass calculated for $C_{24}H_{19}ClF_4N_4O_2$: 506.11, measured (ES, m/z): 507.15 $[M+H]^+$. $^1H$ NMR (300 MHz, DMSO-$d_6$) δ12.26 (s, 1H), 8.32 (d, J=5.0 Hz, 1H), 7.91 (t, J=5.4 Hz, 1H), 7.75-7.85 (m, 1H), 7.54-7.65 (m, 2H), 7.09 (t, J=54.0 Hz, 1H), 5.91 (d, J=2.5 Hz, 1H), 5.29 (t, J=5.9 Hz, 1H), 5.14 (d, J=8.5 Hz, 1H), 4.64 (dd, J=5.9, 2.4 Hz, 2H), 4.00-4.13 (m, 1H), 2.65-2.98 (m, 1H), 2.62-2.73 (m, 1H), 2.16-2.32 (m, 2H), 1.96-2.10 (m, 2H). $^{19}F$-NMR: (282 MHz, DMSO-$d_6$) δ−109.38, −115.57, −130.01.

Example 27: (3S,8aR)-7-(3-Chloro-6-(difluoromethyl)-2-fluorophenyl)-3-(4-fluoro-5-(3-fluoro-2-(hydroxymethyl)pyridin-4-yl)-1H-imidazol-2-yl)-2,3,8,8a-tetrahydroindolizin-5(1H)-one

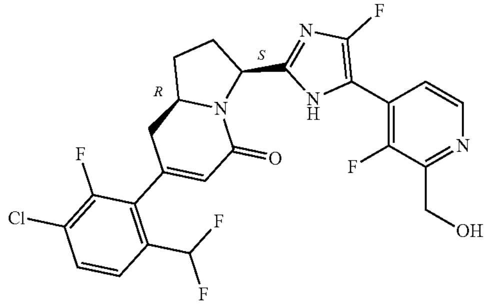

LC/MS: mass calculated for $C_{24}H_{18}ClF_5N_4O_2$: 524.12, measured (ES, m/z): 525.05 $[M+H]^+$. $^1H$ NMR (300 MHz, DMSO-$d_6$) (300 MHz, DMSO-$d_6$) δ 12.65 (s, 1H), 8.35-8.43 (m, 1H), 7.75-7.85 (m, 1H), 7.45-7.65 (m, 2H), 7.07 (t, J=54.0 Hz, 1H), 5.88-5.95 (m, 1H), 5.37 (t, J=5.8 Hz, 1H), 5.13 (d, J=8.5 Hz, 1H), 4.60-4.69 (m, 2H), 4.01-4.11 (m, 1H), 2.63-2.82 (m, 2H), 2.15-2.28 (m, 2H), 1.99-2.08 (m, 2H). $^{19}F$-NMR: (282 MHz, DMSO-$d_6$) δ 109.75, −115.57, −125.74, −130.35.

Example 28: (3S,8aR)-7-(3-Chloro-2-fluoro-6-(1H-tetrazol-1-yl)phenyl)-3-(5-(3-fluoro-2-(2-hydroxypropoxy)pyridin-4-yl)-1H-imidazol-2-yl)-2,3,8,8a-tetrahydroindolizin-5(1H)-one

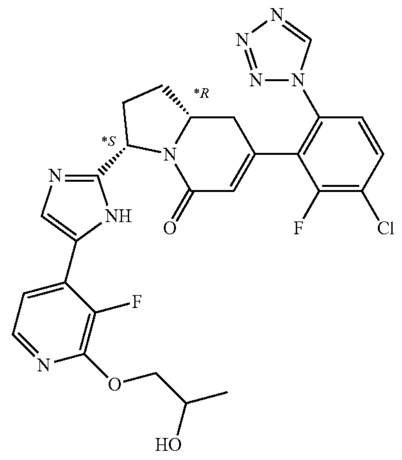 [SMILES: CC(O)COc1nccc(-c2cnc([C@@H]3CC[C@@H]4CC(c5c(-n6cnnn6)ccc(Cl)c5F)=CC(=O)N43)[nH]2)c1F]

LC/MS: mass calculated for $C_{26}H_{23}ClF_2N_8O_3$: 568.15, measured (ES, m/z): 569.15 $[M+H]^+$. $^1H$ NMR (300 MHz, DMSO-$d_6$) (300 MHz, DMSO-$d_6$) δ-12.26 (s, 1H), 9.84 (s, 1H), 7.86-8.06 (m, 2H), 7.66-7.76 (m, 1H), 7.47-7.64 (m, 2H), 5.70 (d, J=2.6 Hz, 1H), 5.04 (d, J=8.5 Hz, 1H), 4.89 (d, J=4.9 Hz, 1H), 4.19-4.29 (m, 1H), 4.09-4.19 (m, 1H), 3.93-4.07 (m, 1H), 3.63-3.85 (m, 1H), 2.63-2.84 (m, 1H), 2.53-2.62 (m, 1H), 2.05-2.32 (m, 2H), 1.89-2.04 (m, 2H), 1.16 (d, J=6.3 Hz, 3H). $^{19}F$-NMR: (282 MHz, DMSO-$d_6$) δ−112.22, −142.53.

Example 29: (3S,8aS)-7-(3-Chloro-2-fluoro-6-(1H-tetrazol-1-yl)phenyl)-3-(5-(3-fluoro-2-(2-hydroxypropoxy)pyridin-4-yl)-1H-imidazol-2-yl)-2,3,8,8a-tetrahydroindolizin-5(1H)-one

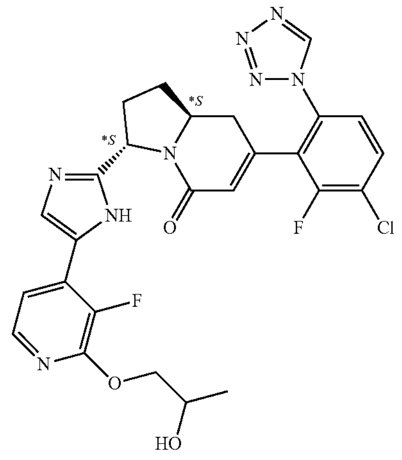 [SMILES: CC(O)COc1nccc(-c2cnc([C@@H]3CC[C@H]4CC(c5c(-n6cnnn6)ccc(Cl)c5F)=CC(=O)N43)[nH]2)c1F]

LC/MS: mass calculated for $C_{26}H_{23}ClF_2N_8O_3$: 568.15, measured (ES, m/z): 569.25 $[M+H]^+$. $^1H$ NMR (300 MHz, DMSO-$d_6$) (300 MHz, DMSO-$d_6$) δ-12.40 (s, 1H), 9.84 (s, 1H), 7.93-8.00 (m, 1H), 7.85-7.91 (m, 1H), 7.75-7.85 (m, 1H), 7.49-7.57 (m, 2H), 5.66-5.74 (m, 1H), 5.02 (t, J=7.4

Hz, 1H), 4.90 (d, J=4.9 Hz, 1H), 4.19-4.30 (m, 1H), 4.07-4.18 (m, 2H), 3.91-4.06 (m, 1H), 2.53-2.61 (m, 1H), 2.17-2.45 (m, 2H), 1.82-2.15 (m, 2H), 1.58-1.81 (m, 1H), 1.16 (d, J=6.3 Hz, 3H). $^{19}$F-NMR: (282 MHz, DMSO-$d_6$) δ −113.06, −143.10.

Example 30: (3S,8aR)-7-(3-chloro-2-fluoro-6-(1H-tetrazol-1-yl)phenyl)-3-(5-(2-methyl-1H-benzo[d]imidazol-6-yl)-1H-imidazol-2-yl)-2,3,8,8a-tetrahydroindolizin-5(1H)-one

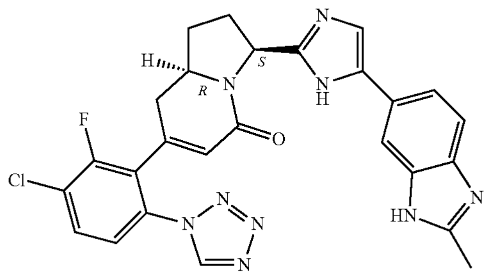

LC/MS: mass calculated for $C_{28}H_{21}ClFN_9O$: 529.1, measured (ES, m/z): 530.1 $[M+H]^+$. $^1$H NMR (400 MHz, DMSO-$d_6$) δ ppm 1.95-2.22 (m, 4H) 2.47-2.49 (m, 2H) 2.53-2.59 (m, 1H) 2.77 (br t, J=14.43 Hz, 1H) 3.17 (br s, 1H) 3.65-3.75 (m, 1H) 5.00 (d, J=8.31 Hz, 1H) 5.67 (d, J=2.45 Hz, 1H) 7.29-7.46 (m, 2H) 7.51 (br d, J=7.83 Hz, 1H) 7.64-7.82 (m, 2H) 7.97 (t, J=8.31 Hz, 1H) 9.84 (s, 1H) 11.91 (br s, 1H) 12.03 (br s, 1H).

Example 31: (3S,8aR)-3-(5-(2-(1H-Pyrazol-5-yl)pyridin-4-yl)-4-fluoro-1H-imidazol-2-yl)-7-(3-chloro-2-fluoro-6-(1H-tetrazol-1-yl)phenyl)-2,3,8,8a-tetrahydroindolizin-5(1H)-one

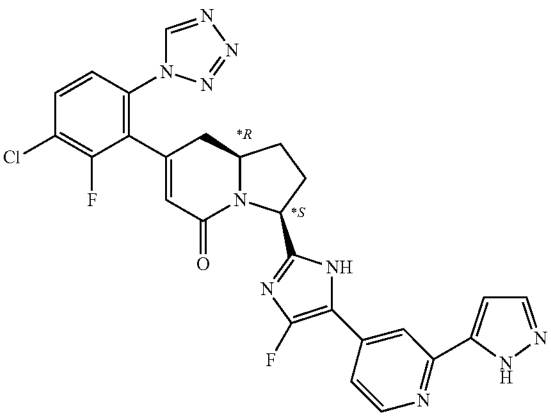 [SMILES: O=C1C=C(c2c(-n3cnnn3)ccc(Cl)c2F)C[C@H]2CC[C@@H](c3nc(F)c(-c4ccnc(-c5ccn[nH]5)c4)[nH]3)N12]

LC/MS: mass calculated for $C_{26}H_{19}ClF_2N_{10}O$: 560.14, measured (ES, m/z): 561.05 $[M+H]^+$. $^1$H NMR (400 MHz, DMSO-$d_6$) δ13.09 (s, 1H), 13.03-13.08 (m, 1H), 9.84 (s, 1H), 8.50-8.61 (m, 1H), 8.18 (s, 1H), 7.90-8.00 (m, 1H), 7.81-7.86 (m, 1H), 7.70-7.80 (m, 1H), 7.37-7.44 (m, 1H), 6.81-6.86 (m, 1H), 5.67 (s, 1H), 4.95 (d, J=8.6 Hz, 1H), 3.70-3.75 (m, 1H), 2.54-2.69 (m, 2H), 2.19-2.24 (m, 1H), 2.08-2.15 (m, 1H), 1.98-2.05 (m, 1H), 1.88-1.97 (m, 1H). $^{19}$F-NMR: (282 MHz, DMSO-$d_6$) δ−112.92, −126.88.

Example 32: (3S,8aR)-3-(4-(1H-pyrrolo[2,3-b]pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

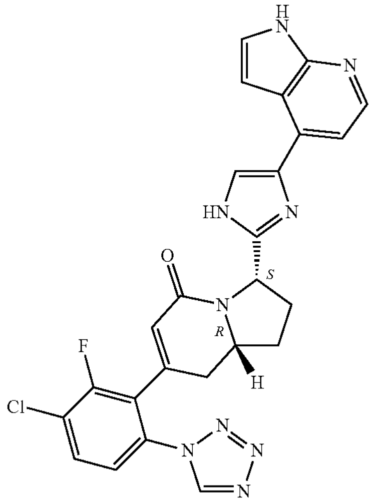

LC/MS: mass calculated for $C_{25}H_{19}ClFN_9O$: 515.1, measured (ES, m/z): 516.0 $[M+H]^+$. $^1$H NMR (400 MHz, METHANOL-$d_4$) δ ppm 1.91-2.89 (m, 7H), 3.80-3.99 (m, 1H), 5.13-5.21 (m, 1H), 5.23-5.30 (m, 1H), 5.68 (d, J=2.4 Hz, 1H), 5.86-5.91 (m, 1H), 7.09 (d, J=3.4 Hz, 1H), 7.40-7.81 (m, 4H), 8.02 (s, 1H), 8.10-8.16 (m, 1H), 8.22 (d, J=5.9 Hz, 1H), 9.49 (s, 1H).

Example 33: (3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5

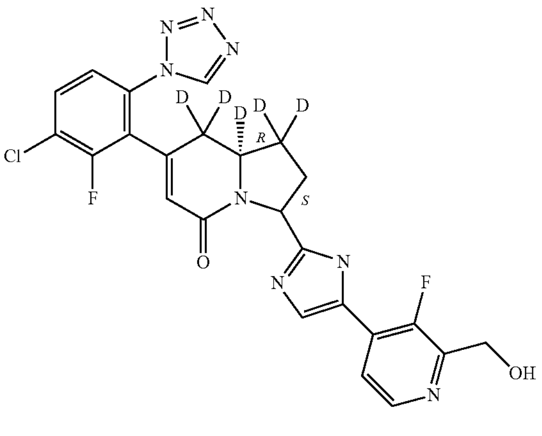

Step 1: 2-(2-(((Teri butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate-1,1,8,8,8a-d5

A mixture of (3S)-7-(6-amino-3-chloro-2-fluorophenyl)-5-oxo-1,2,3,5,8,8a-hexahydroindolizine-3-carboxylic-1,1,8, 8,8a-d5 acid (120 mg, 0.36 mmol, 1.0 equiv.) and $Cs_2CO_3$ (71 mg, 0.22 mmol, 0.6 equiv.) in DMF (8 mL) was stirred at room temperature for 30 min. 2-Bromo-1-(2-(((tert-butyldimethylsilyl)oxy)methyl)-3-fluoropyridin-4-yl)ethan-1-one (185 mg, 0.51 mmol, 1.4 equiv.) was then added to the mixture. The reaction mixture was stirred at room temperature for 4 h. The resulting mixture was then diluted with EtOAc (120 mL), washed with water (3×20 mL), brine (2×20 mL), dried over $Na_2SO_4$, and concentrated. The residue was purified by flash column chromatography on silica gel (40 g, MeOH/DCM: 1/20) to yield of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate-1,1,8,8,8a-d5 as a yellow solid. LC/MS: mass calculated for $C_{29}H_{29}ClD_5F_2N_3O_5Si$: 610.22, measured (ES, m/z): 611.15 $[M+H]^+$.

Step 2: (3S)-7-(6-Amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one-1,1,8,8,8a-d5

Under an inert atmosphere of nitrogen, a mixture of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate-1,1,8,8,8a-$d_5$ (130 mg, 0.21 mmol, 1.0 equiv.) and $NH_4OAc$ (164 mg, 2.13 mmol, 10.0 equiv.) in AcOH (2 mL) and toluene (20 mL) was stirred at 110° C. for 30 min and then concentrated. The residue was purified by flash column chromatography on silica gel (40 g, MeOH/DCM: 1/15) to yield (3S)-7-(6-amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one-1,1,8,8,8a-d5 as a yellow solid. LC/MS: mass calculated for $C_{29}H_{29}D5ClF_2N_5O_2Si$: 590.25, measured (ES, m/z): 591.30 $[M+H]^+$.

Step 3: (3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5

A mixture of (3S)-7-(6-amino-3-chloro-2-fluorophenyl)-3-(5-(2-(((tert butyldimethylsilyl)oxy)methyl)-3-fluoropyridin-4-yl)-1H-imidazol-2-yl)-2,3,8,8a-tetrahydroindolizin-5(1H)-one-1,1,8,8,8a-$d_5$ (80 mg, 0.14 mmol, 1.0 equiv.), $TMSN_3$ (156 mg, 1.35 mmol, 10.0 equiv.) and trimethoxymethane (143 mg, 1.35 mmol, 10.0 equiv.) in AcOH (8 mL) was stirred at 55° C. overnight. The solvent was removed under reduced pressure and the residue was applied onto a C18 reverse column (330 g, $ACN/H_2O$ (0.05% $NH_4HCO_3$): 5→50%) to yield (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5 as a white solid, which was further purified by prep-chiral-HPLC to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-1,1,8,8,8a-d5 as a white solid.

LC/MS: mass calculated for $C_{24}H_{14}D_5ClF_2N_8O_2$: 529.16, measured (ES, m/z): 530.10 $[M+H]^+$. $^1H$ NMR (400 MHz, DMSO-$d_6$) (400 MHz, DMSO-$d_6$) δ 12.26 (5, 1H), 9.84 (s, 1H), 8.34 (d, J=5.0 Hz, 1H), 7.90-8.00 (m, 1H), 7.90 (t, J=5.4 Hz, 1H), 7.75-7.85 (m, 1H), 7.51-7.62 (m, 1H), 5.70 (s, 1H), 5.27 (t, J=6.0 Hz, 1H), 5.04 (d, J=8.7 Hz, 1H), 4.58-4.69 (m, 2H), 2.13-2.30 (m, 1H), 1.84-2.00 (m, 1H). $^{19}F$-NMR: (376 MHz, DMSO-$d_6$) δ −112.86, 130.15.

Example 34: 4-(2-((3S,8aR)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-4-fluoro-1H-imidazol-5-yl)-3-fluoropicolinic acid

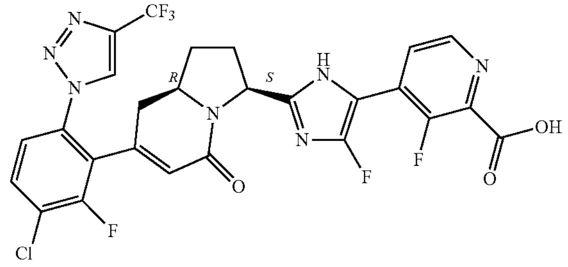

LC/MS: mass calculated for $C_{25}H_{16}ClF_6N_7O_3$: 623.09, measured (ES, m/z): 624.05 $[M+H]^+$. $^1H$ NMR (400 MHz, DMSO-$d_6$) (400 MHz, DMSO-$d_6$) δ 9.34 (s, 1H), 8.32 (d, J=4.9 Hz, 1H), 7.90-8.00 (m, 1H), 7.69-7.76 (m, 1H), 7.37-7.52 (m, 1H), 5.69 (s, 1H), 5.04 (d, J=8.6 Hz, 1H), 3.64-3.81 (m, 1H), 2.51-2.58 (m, 2H), 2.04-2.27 (m, 2H), 1.86-2.03 (m, 2H). $^{19}F$-NMR: (376 MHz, DMSO-$d_6$) δ −59.66, −112.99.

Example 35: (3S,8aR)-7-(3-Chloro-2-fluoro-6-(1H-tetrazol-1-yl)phenyl)-3-(5-(3-fluoro-2-(hydroxymethyl)pyridin-4-yl)-4-methyl-1H-imidazol-2-yl)-2,3,8,8a-tetrahydroindolizin-5(1H)-one

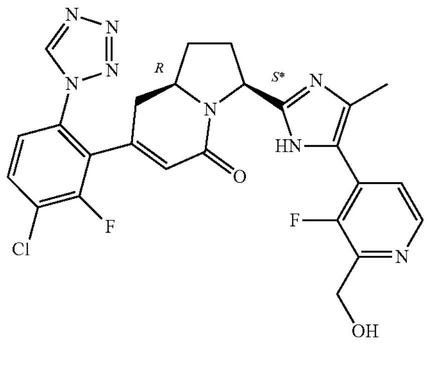

Step 1: 1-(2-(((Teri butyldimethylsilyl)oxy)methyl)-3-fluoropyridin-4-yl)propan-1-one To a solution of 2-(((tert-butyldimethylsilyl)oxy)methyl)-3-fluoropyridine (5.0 g, 20.71 mmol, 1.0 equiv.) in THE (50 mL) was added lithium diisopropylamide (13 mL, 26.93 mmol, 2 M, 1.3 equiv.) at −78° C. After 0.5 h, a solution of N-methoxy-N-methylpropionamide (2.9 g, 24.86 mmol, 1.2 equiv.) in THE (10 mL) was added at −78° C. The resulting mixture was maintained under nitrogen and stirred at room temperature for 1 h. The reaction was quenched with saturated ammonium chloride solution (50 mL). The resulting mixture was extracted with ethyl acetate (3×50 mL). The organic layers were combined, dried over anhydrous sodium sulfate, and concentrated under reduced pressure. The residue was purified by silica gel chromatography (0→30% ethyl acetate/petroleum ether) to yield the 1-(2-(((tert-butyldimethylsilyl)oxy)methyl)-3-fluoropyridin-4-yl)propan-1-one as a yellow oil. LC/MS: mass calculated for $C_{15}H_{24}FNO_2Si$: 297.16, measured (ES, m/z): 298.30 $[M+H]^+$.

Step 2: (4-(2-Bromopropanoyl)-3-fluoropyridin-2-yl)methyl acetate

To a solution of 1-(2-(((tert-butyldimethylsilyl)oxy) methyl)-3-fluoropyridin-4-yl)propan-1-one (1.4 g, 4.71 mmol, 1.0 equiv.) and HBr (2.3 g, 9.41 mmol, 2.0 equiv.) in AcOH (10 mL) was added pyridinium tribromide (1.2 g, 3.77 mmol, 0.8 equiv.). The mixture stirred at room temperature for 1 h. The resulting mixture was extracted with ethyl acetate (2×20 mL). The organic layers were combined, dried over anhydrous sodium sulfate, filtered and concentrated to yield the (4-(2-bromopropanoyl)-3-fluoropyridin-2-yl)methyl acetate as a yellow oil. LC/MS: mass calculated for $C_{11}H_{11}BrFNO_3$: 302.99, measured (ES, m/z): 304.00, 306.00 $[M+H, M+H+2]^+$.

Step 3: 1-(2-(Acetoxymethyl)-3-fluoropyridin-4-yl)-1-oxopropan-2-yl (8aR)-7-(3-chloro-2-fluoro-6-(1H-tetrazol-1-yl)phenyl)-5-oxo-1,2,3,5,8,8a-hexahydroindolizine-3-carboxylate To a solution of (8aR)-7-(3-chloro-2-fluoro-6-(1H-tetrazol-1-yl)phenyl)-5-oxo-1,2,3,5,8,8a-hexahydroindolizine-3-carboxylic acid (200 mg, 0.53 mmol, 1.0 equiv.) in $CH_3CN$ (8 mL) was added $K_2CO_3$ (109 mg, 0.80 mmol, 1.5 equiv.). After stirring at room temperature for 0.5 h, (4-(2-bromopropanoyl)-3-fluoropyridin-2-yl)methyl acetate (241 mg, 0.80 mmol, 1.5 equiv.) was added. The mixture was stirred at room temperature for 1 h. The residue was purified by silica gel chromatography (0→10% MeOH/DCM) to yield the 1-(2-(acetoxymethyl)-3-fluoropyridin-4-yl)-1-oxopropan-2-yl (8aR)-7-(3-chloro-2-fluoro-6-(1H-tetrazol-1-yl)phenyl)-5-oxo-1,2,3,5,8,8a-hexahydroindolizine-3-carboxylate as a yellow oil. LC/MS: mass calculated for $C_{27}H_{23}ClF_2N_6O_6$: 600.13, measured (ES, m/z): 601.30 $[M+H]^+$.

Step 4: (4-(2-((8aR)-7-(3-Chloro-2-fluoro-6-(1H-tetrazol-1-yl)phenyl)-5-oxo-1,2,3,5,8,8a-hexahydroindolizin-3-yl)-4-methyl-1H-imidazol-5-yl)-3-fluoropyridin-2-yl)methyl acetate To a solution of 1-(2-(acetoxymethyl)-3-fluoropyridin-4-yl)-1-oxopropan-2-yl (8aR)-7-(3-chloro-2-fluoro-6-(1H-tetrazol-1-yl)phenyl)-5-oxo-1,2,3,5,8,8a-hexahydroindolizine-3-carboxylate (140 mg, 0.23 mmol, 1.0 equiv.) in toluene (10 mL) and glacial acetic acid (1 mL) was added ammonium acetate (269 mg, 3.50 mmol, 15.0 equiv.). The mixture was stirred at 100° C. for 1 h. The solvent was removed under vacuum and the residue was purified by silica gel column with MeOH/DCM (0→10%) to yield (4-(2-((8aR)-7-(3-chloro-2-fluoro-6-(1H-tetrazol-1-yl)phenyl)-5-oxo-1,2,3,5,8,8a-hexahydroindolizin-3-yl)-4-methyl-1H-imidazol-5-yl)-3-fluoropyridin-2-yl)methyl acetate as a yellow solid.

LC/MS: mass calculated for $C_{27}H_{23}ClF_2N_8O_3$: 580.15, measured (ES, m/z): 581.10 $[M+H]^+$.

Step 5: (3'S,8aR)-7-(3-Chloro-2-fluoro-6-(1H-tetrazol-1-yl)phenyl)-3-(5-(3-fluoro-2-(hydroxymethyl) pyridin-4-yl)-4-methyl-1H-imidazol-2-yl)-2,3,8,8a-tetrahydroindolizin-5(1H)-one To a solution of (4-(2-((8aR)-7-(3-chloro-2-fluoro-6-(1H-tetrazol-1-yl)phenyl)-5-oxo-1,2,3,5,8,8a-hexahydroindolizin-3-yl)-4-methyl-1H-imidazol-5-yl)-3-fluoropyridin-2-yl)methyl acetate (90 mg, 0.16 mmol) in THE (3 mL) was added HCl (3 mL, 12.00 mmol, 4 M). The mixture was stirred at 60° C. for 1 h. The solvent was removed under vacuum and the residue was purified by C18 column [condition: ACN-water-6.5 mM $NH_4HCO_3$+$NH_3H_2O$ (5%→50%)] to yield a residue. The residue was purified by chiral HPLC to yield (3*S,8aR)-7-(3-chloro-2-fluoro-6-(1H-tetrazol-1-yl)phenyl)-3-(5-(3-fluoro-2-(hydroxymethyl)pyridin-4-yl)-4-methyl-1H-imidazol-2-yl)-2,3,8,8a-tetrahydroindolizin-5(1H)-one as an off-white solid.

LC/MS: mass calculated for $C_{25}H_{21}ClF_2N_8O_2$: 538.14, measured (ES, m/z): 539.15 $[M+H]^+$. $^1H$ NMR (400 MHz, DMSO-$d_6$) (400 MHz, DMSO-$d_6$) δ 11.98 (s, 1H), 9.83 (s, 1H), 8.30-8.40 (m, 1H), 7.91-8.03 (m, 1H), 7.68-7.75 (m, 1H), 7.49-7.59 (m, 1H), 5.68 (d, J=2.7 Hz, 1H), 5.17-5.40 (m, 1H), 4.96 (d, J=8.3 Hz, 1H), 4.60-4.67 (m, 2H), 3.64-3.79 (m, 1H), 2.61-2.77 (m, 1H), 2.53-2.57 (m, 1H), 2.21-2.37 (m, 3H), 2.14-2.20 (m, 1H), 2.03-2.12 (m, 1H), 1.89-2.03 (m, 2H). $^{19}F$-NMR: (376 MHz, DMSO-$d_6$) δ 112.81, −129.35.

Example 36: (3S,8aR)-7-(3-Chloro-2-fluoro-6-(1H-tetrazol-1-yl)phenyl)-3-(5-(3-fluoro-2-(hydroxymethyl-$d_2$)pyridin-4-yl)-1H-imidazol-2-yl)-2,3,8,8a-tetrahydroindolizin-5(1H)-one-8a-d

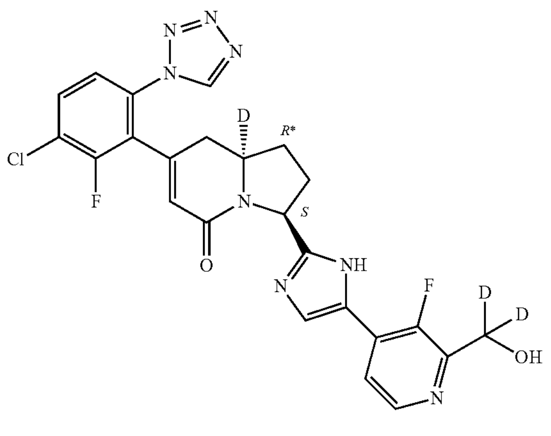

LC/MS: mass calculated for $C_{24}H_{16}D3ClF_2N_8O_2$: 527.15, measured (ES, m/z): 642.20 [M+H]+. $^1H$ NMR (400 MHz, DMSO-$d_6$) (400 MHz, DMSO-$d_6$) δ 12.29 (s, 1H), 9.84 (s, 1H), 8.34 (d, J=5.1 Hz, 1H), 7.93-8.02 (m, 1H), 7.84-7.92 (m, 1H), 7.70-7.75 (m, 1H), 7.58 (d, J=4.0 Hz, 1H), 5.69 (d, J=2.7 Hz, 1H), 5.12-5.32 (m, 1H), 5.04 (d, J=8.7 Hz, 1H), 2.63-2.80 (m, 1H), 2.50-2.56 (m, 1H), 2.17-2.31 (m, 1H), 2.05-2.15 (m, 1H), 1.90-2.01 (m, 2H). $^{19}F$-NMR: (376 MHz, DMSO-$d_6$) δ-112.86, −130.13.

Example 37: (((4-(24(3R*,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methoxy)methyl)phosphonic acid

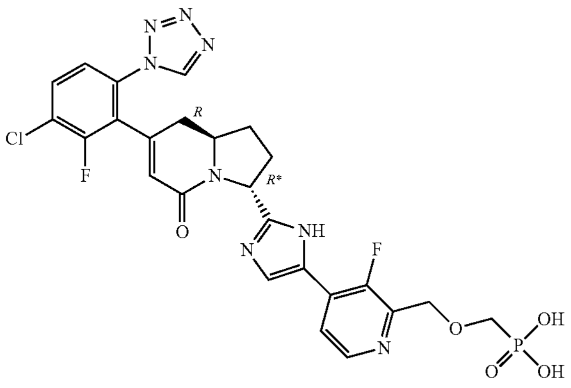

LC/MS: mass calculated for $C_{25}H_{22}ClF_2N_8O_5P$: 618.11, measured (ES, m/z): 619.05 $[M+H]^+$. $^1H$ NMR (400 MHz, DMSO-$d_6$) δ12.27 (s, 1H), 9.82 (s, 1 H), 8.33 (d, J=5.1 Hz, 1H), 7.90-7.98 (m, 2H), 7.68 (d, J=8.7 Hz, 1H), 7.55 (s, 1H), 5.67 (s, 1H), 5.01 (d, J=8.6 Hz, 1H), 4.68-4.72 (m, 2H), 3.61-3.87 (m, 5H), 2.62-2.73 (m, 2H), 1.83-2.24 (m, 4H). $^{19}F$ NMR (376 MHz, DMSO-$d_6$) δ −112.82.

Example 38: (3S,8aR)-3-(4-(1H-pyrazolo[3,4-b]pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

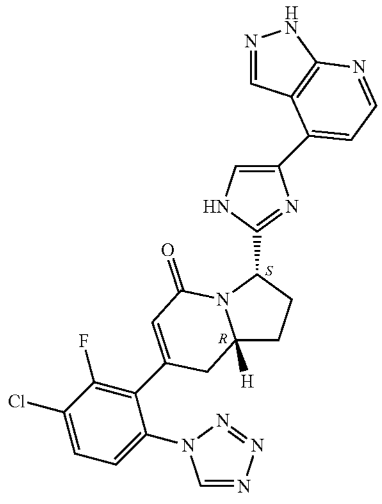

LC/MS: mass calculated for $C_{24}H_{18}ClFN_{10}O$: 516.1, measured (ES, m/z): 517.1 $[M+H]^+$. $^1H$ NMR (400 MHz, METHANOL-$d_4$) δ ppm 1.93-2.95 (m, 7H), 3.73-4.00 (m, 1H), 5.01-5.32 (m, 1H), 5.58-5.75 (m, 1H), 5.75-5.95 (m, 1H), 7.30-7.86 (m, 3H), 8.10-8.20 (m, 1H), 8.48-8.59 (m, 1H), 8.58-8.75 (m, 1H), 9.38-9.66 (m, 1H).

Example 39: (3S,8aR)-7-(3-Chloro-2-fluoro-6-(1H-tetrazol-1-yl)phenyl)-3-(4-(5-(hydroxymethyl)thiazol-2-yl)-1H-imidazol-2-yl)-2,3,8,8a-tetrahydroindolizin-5(1H)-one

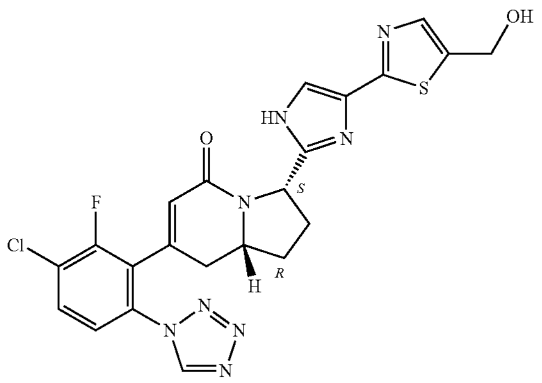

Step 1: 2-Bromo-5-(((tert butyldimethylsilyl)oxy)methyl)thiazole

To a solution of (2-bromothiazol-5-yl)methanol (1.70 g, 8.76 mmol) in DMF (20 mL), were added TBDMS-Cl (1.584 g, 10.51 mmol) and imidazole (1.1939, 17.52 mmol) under $N_2$. The reaction was heated at 50° C. overnight. The reaction mixture was partitioned with water and EA at room temperature. The organic was separated, washed with brine, and dried over $Na_2SO_4$. The solid was filtered and washed with EA. The filtrated was concentrated to yield a yellow solid. The yellow solid was purified by silica gel with heptane and EA as eluent (0% to 30% EA) to yield 2-bromo-5-(((tert-butyldimethylsilyl)oxy)methyl)thiazole as an off white oil. LC/MS: mass calculated for: $C_{10}H_{18}BrNOSSi$: 307.0, measured (ES, m/z): 308.1 $[M+H]^+$.

Step 2: 5-(((tert-Butyldimethylsilyl)oxy)methyl)-2-(1-ethoxyvinyl)thiazole

To a solution of 2-bromo-5-(((tert-butyldimethylsilyl)oxy)methyl)thiazole and tributyl(1-ethoxyvinyl)tin (0.843 g, 2.335 mmol) in 1,4-dioxane (12 mL), was added $Pd(PPh_3)_4$ (0.18 g, 0.156 mmol) under $N_2$. The reaction mixture was purged with $N_2$ for 10 minutes and heated at 100° C. overnight. The reaction was cooled to room temperature. The solid was filtered through CELITE and washed with EA. The filtrate was concentrated under vacuum. The residue was purified by silica gel with heptane and EA as eluent (0 to 20% EA) to yield 5-(((tert-butyldimethylsilyl)oxy)methyl)-2-(1-ethoxyvinyl)thiazole as a clear oil. LC/MS: mass calculated for $C_{14}H_{25}NO_2SSi$: 299.1, measured (ES, m/z): 300.1 $[M+H]^+$.

Step 3: 2-Bromo-1-(5-(((tert-butyldimethylsilyl)oxy)methyl)thiazol-2-yl)ethan-1-one To a solution of 5-(((tert-butyldimethylsilyl)oxy)methyl)-2-(1-ethoxyvinyl)thiazole (0.152 g, 0.507 mmol) in THF (10 mL) and water (1 mL), was added NBS (99 mg, 0.558 mmol) at room temperature and the resulting mixture was stirred for one hour. The reaction was partitioned with water and EA. The organic was separated, washed with brine, and dried over $Na_2SO_4$.

The solid was filtered and washed with EA. The filtrated was concentrated to yield 2-bromo-1-(5-(((tert-butyldimethylsilyl)oxy)methyl)thiazol-2-yl)ethan-1-one as a yellow solid. LC/MS: mass calculated for: $C_{12}H_{20}BrNO_2SSi$: 349.0, measured (ES, m/z): 350.1 $[M+H]^+$.

Step 4: 2-(5-(((tert-Butyldimethylsilyl)oxy)methyl)thiazol-2-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate To a solution of (3S,8aR)-7-(3-chloro-2-fluoro-6-(1H-tetrazol-1-yl)phenyl)-5-oxo-1,2,3,5,8,8a-hexahydroindolizine-3-carboxylic acid (0.08 g, 0.21 mmol) in ACN (6 mL), was added $Cs_2CO_3$ (0.207 g, 0.64 mmol) and the mixture was stirred at room temperature for 10 minutes. 2-Bromo-1-(5-(((tert-butyldimethylsilyl)oxy)methyl)thiazol-2-yl)ethan-1-one (0.089 g, 0.254 mmol) was then added. The reaction was heated at 50° C. for 2 hours. The solid was filtered through CELITE and washed with EA. The filtrate was concentrated to yield 2-(5-(((tert-butyldimethylsilyl)oxy)methyl)thiazol-2-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate as a yellow solid, which was used in the next step without further purification. LC/MS: mass calculated for: $C_{28}H_{32}ClFN_6O_5SSi$: 646.2, measured (ES, m/z): 647.3 $[M+H]^+$.

Step 5: (3S,8aR)-3-(4-(5-(((tert-butyldimethylsilyl)oxy)methyl)thiazol-2-yl)-1H-imidazol-2-yl)-7-(3-chloro-2-fluoro-6-(1H-tetrazol-1-yl)phenyl)-2,3,8,8a-tetrahydroindolizin-5(1H)-one Into a microwave vial, 2-(5-(((tert-butyldimethylsilyl)oxy)methyl)thiazol-2-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate (0.106 g, 0.164 mmol) in toluene (3 mL) and AcOH (0.188 ml), was added ammonium acetate (0.252 g, 3.3 mmol). The reaction was heated at 100° C. for 2.5 hours. The solvent was removed under vacuum to yield (3S,8aR)-3-(4-(5-(((tert-butyldimethylsilyl)oxy)methyl)thiazol-2-yl)-1H-imidazol-2-yl)-7-(3-chloro-2-fluoro-6-(1H-tetrazol-1-yl)phenyl)-2,3,8,8a-tetrahydroindolizin-5(1H)-one as a red residue, which was used in the next step without further purification. LC/MS: mass calculated for. $C_{28}H_{32}ClFN_8O_2SSi$: 626.2, measured (ES, m/z): 627.3 $[M+H]^+$.

Step 6: (3S,8aR)-7-(3-Chloro-2-fluoro-6-(1H-tetrazol-1-yl)phenyl)-3-(4-(5-(hydroxymethyl)thiazol-2-yl)-1H-imidazol-2-yl)-2,3,8,8a-tetrahydroindolizin-5(1H)-one To solution of (3S,8aR)-3-(4-(5-(((tert-butyldimethylsilyl)oxy)methyl)thiazol-2-yl)-1H-imidazol-2-yl)-7-(3-chloro-2-fluoro-6-(1H-tetrazol-1-yl)phenyl)-2,3,8,8a-tetrahydroindolizin-5(1H)-one (100 mg, 0.159 mmol) in THE (3 mL), was added 1M TBAF in THE (0.3 mL, 0.3 mmol). The reaction mixture was stirred at room temperature for 3 hours.

The reaction mixture was partitioned with water and EA. The organic was separated, washed with brine, and dried over $Na_2SO_4$. The solid was filtered and washed with EA. The filtrated was concentrated to yield a brown solid. The brown solid was purified via prep-HPLC with 0.1% TFA in water and 0.1% TFA in ACN as eluent (10% to 45% 0.1% TFA in ACN) to yield (3S,8aR)-7-(3-chloro-2-fluoro-6-(1H-tetrazol-1-yl)phenyl)-3-(4-(5-(hydroxymethyl)thiazol-2-yl)-1H-imidazol-2-yl)-2,3,8,8a-tetrahydroindolizin-5(1H)-one TFA adduct as an off white solid.

LC/MS: mass calculated for $C_{22}H_{18}ClFN_8O_2S$: 512.1, measured (ES, m/z): 513.2 $[M+H]^+$. $^1H$ NMR (400 MHz, methanol-$d_4$) δ 9.58 (s, 1H), 7.86 (s, 1H), 7.82 (d, J=8.2 Hz, 1H), 7.74 (s, 1H), 7.56 (dd, J=8.7, 1.7 Hz, 1H), 5.75 (d, J=2.9 Hz, 1H), 5.22 (d, J=9.3 Hz, 1H), 4.70 (bs, 2H), 3.88-3.98 (m, 1H), 2.95 (t, J=15.3 Hz, 1H), 2.67 (dd, J=16.9, 4.3 Hz, 1H), 2.50-2.40 (bm, 1H), 2.33-2.19 (bm, 2H), 2.08-1.96 (bm, 1H). $^{19}F$ NMR (376 MHz, methanol-$d_4$) δ 113.4.

Example 40: Methyl N-[4-[2-[(3S,8aR)-7-[3-chloro-2-fluoro-6-(tetrazol-1-yl)phenyl]-5-oxo-2,3,8,8a-tetrahydro-1H-indolizin-3-yl]-4-fluoro-1H-imidazol-5-yl]-3-fluoro-2-pyridyl]carbamate

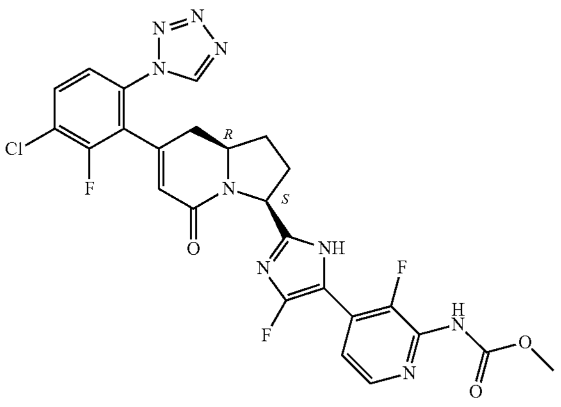

LC/MS: mass calculated for $C_{25}H_{19}ClF_3N_9O_3$: 585.13, measured (ES, m/z): 586.15 $[M+H]^+$. $^1H$ NMR (400 MHz, Methanol-$d_4$) δ 9.57 (s, 1H), 8.14 (d, J=5.3 Hz, 1H), 7.75-7.87 (m, 1H), 7.49-7.62 (m, 1H), 7.39-7.43 (m, 1H), 5.69 (d, J=2.8 Hz, 1H), 5.11 (d, J=8.7 Hz, 1H), 3.83-4.01 (m, 1H), 3.79 (s, 3H), 2.80-2.92 (m, 1H), 2.53-2.68 (m, 1H), 1.99-2.39 (m, 4H). $^{19}F$ NMR (376 MHz, Methanol-$d_4$) −113.42, −127.70.

Example 41: (3S,8aR)-3-(4-(1H-pyrazolo[3,4-b]pyridin-5-yl)-1H-imidazol-2-yl)-7-(3-chloro-2-fluoro-6-(1H-tetrazol-1-yl)phenyl)-2,3,8,8a-tetrahydroindolizin-5(1H)-one

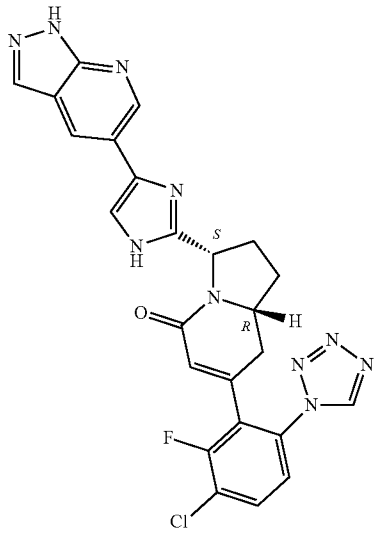

LC/MS: mass calculated for $C_{24}H_{18}ClFN_{10}O$: 516.1, measured (ES, m/z): 517.1 $[M+H]^+$. $^1H$ NMR (400 MHz, METHANOL-$d_4$) δ ppm 1.95-2.13 (m, 1H), 2.20-2.42 (m, 2H), 2.43-2.65 (m, 1H), 2.75 (s, 1H), 2.88-3.09 (m, 1H), 3.85-4.11 (m, 1H), 5.32 (dd, J=9.8, 1.5 Hz, 1H), 5.77 (d, J=2.9 Hz, 1H), 7.58 (dd, J=8.6, 1.7 Hz, 1H), 7.72-7.95 (m, 2H), 8.23 (s, 1H), 8.56 (d, J=2.4 Hz, 1H), 8.87 (d, J=2.0 Hz, 1H), 9.59 (s, 1H).

Example 42: (3S,8aR)-3-(4 (1H-benzo[d]imidazol-5-yl)-1H-imidazol-2-yl)-7-(3-chloro-2-fluoro-6-(1H-tetrazol-1-yl)phenyl)-2,3,8,8a-tetrahydroindolizin-5(1H)-one

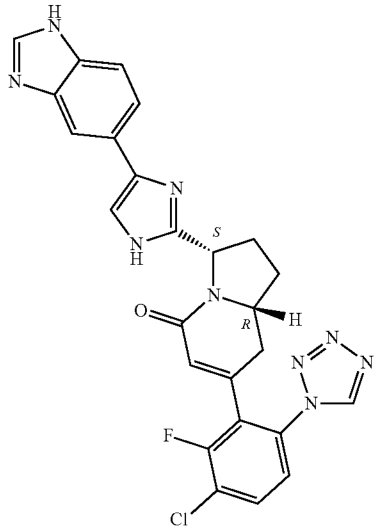

LC/MS: mass calculated for $C_{25}H_{19}ClFN_9O$: 515.1, measured (ES, m/z): 516.0 $[M+H]^+$. $^1H$ NMR (400 MHz, METHANOL-$d_4$) δ ppm 1.95-2.16 (m, 1H), 2.16-2.45 (m, 2H), 2.45-2.66 (m, 1H), 2.66-2.87 (m, 1H), 2.88-3.08 (m, 1H), 3.78-4.06 (m, 1H), 5.18-5.41 (m, 1H), 5.69-5.81 (m, 1H), 7.52-7.62 (m, 1H), 7.88 (s, 4H), 8.07-8.24 (m, 1H), 9.03-9.18 (m, 1H), 9.59 (s, 1H).

Example 43: (3S,8aR)-3-(4-(1H-indazol-5-yl)-1H-imidazol-2-yl)-7-(3-chloro-2-fluoro-6-(1H-tetrazol-1-yl)phenyl)-2,3,8,8a-tetrahydroindolizin-5(1H)-one

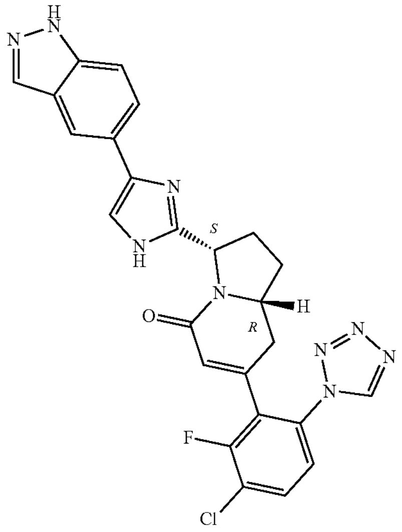

LC/MS: mass calculated for $C_{25}H_{19}ClFN_9O$: 515.1, measured (ES, m/z): 516.1 $[M+H]^+$. $^1H$ NMR (400 MHz, METHANOL-$d_4$) δ ppm 1.94-2.09 (m, 1H), 2.21-2.43 (m, 2H), 2.48-2.63 (m, 1H), 2.68-2.79 (m, 1H), 2.92-3.06 (m, 1H), 3.89-4.04 (m, 1H), 5.26-5.35 (m, 1H), 5.74-5.79 (m, 1H), 7.51-7.61 (m, 1H), 7.66-7.75 (m, 2H), 7.77-7.79 (m, 1H), 7.81-7.88 (m, 1H), 8.11-8.19 (m, 2H), 9.55-9.66 (m, 1H).

Example 44: Methyl(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)carbamate

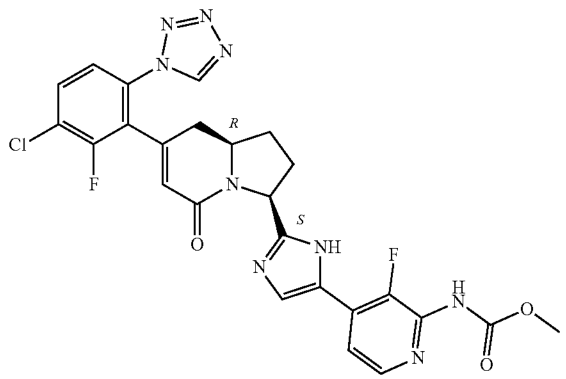

Step 1: 3-Fluoro-4-iodopyridin-2-amine

To a solution of 2,3-difluoro-4-iodopyridine (5.0 g, 20.75 mmol) in DMSO (50 mL) was added ammonium hydroxide (60 mL). The resulting mixture was stirred at 80° C. overnight. After cooling to room temperature, the resulting mixture was diluted with EA (800 mL) and washed with water three times. The organic layers were combined, dried over anhydrous sodium sulfate, and concentrated to yield the 3-fluoro-4-iodopyridin-2-amine as a yellow solid. LC/MS: mass calculated for $C_5H_4FIN_2$: 237.94, measured (ES, m/z): 239.00 $[M+H]^+$.

Step 2: Methyl (3-fluoro-4-iodopyridin-2-yl)carbamate

To a solution of 3-fluoro-4-iodopyridin-2-amine (2.0 g, 8.40 mmol 1.0 equiv.) in pyridine (30 mL) was added methyl chloroformate (4.0 g, 42.02 mmol, 5.0 equiv.) at 0° C. The reaction mixture was stirred 2 h. The reaction was quenched with water (50 mL). The resulting mixture was extracted with ethyl acetate (3×50 mL). The organic layers were combined and dried over anhydrous $Na_2SO_4$ and concentrated. The residue was purified by silica gel chromatography with EA/PE (0→55%) to yield methyl (3-fluoro-4-iodopyridin-2-yl)carbamate as a yellow solid. LC/MS: mass calculated for $C_7H_6FIN_2O_2$: 295.95, measured (ES, m/z): 296.95 $[M+H]^+$.

Step 3: Methyl (4(1-ethoxyvinyl)-3-fluoropyridin-2-yl)carbamate

To a mixture of methyl (3-fluoro-4-iodopyridin-2-yl)carbamate (1.1 g, 3.72 mmol, 1.0 equiv.) and tributyl(1-ethoxyvinyl)stannane (1.6 g, 4.46 mmol, 1.2 equiv.) in 1,4-dioxane (15 mL) was added bis(triphenylphosphine) palladium dichloride (0.26 g, 0.37 mmol, 0.1 equiv.). The resulting mixture was maintained under nitrogen and stirred at 100° C. for 3 h. After cooling to room temperature, the reaction was quenched with water (50 mL). The resulting mixture was extracted with ethyl acetate (3×50 mL). The organic layers were combined and dried over anhydrous $Na_2SO_4$ and concentrated. The residue was purified by silica gel chromatography with EA/PE (0→45%) to yield methyl (4(1-ethoxyvinyl)-3-fluoropyridin-2-yl)carbamate as a yellow solid. LC/MS: mass calculated for $C_{11}H_{13}FN_2O_3$: 240.09, measured (ES, m/z): 241.10 $[M+H]^+$.

Step 4: Methyl (4-(2-bromoacetyl)-3-fluoropyridin-2-yl)carbamate

To a mixture of methyl (4-(1-ethoxyvinyl)-3-fluoropyridin-2-yl)carbamate (870 mg, 3.62 mmol, 1.0 equiv.) in THE (9 mL) and $H_2O$ (3 mL) was added N-bromosuccinimide (645 mg, 3.62 mmol, 1.0 equiv.). The reaction mixture was stirred at room temperature for 1 h. The reaction was quenched with $H_2O$. The resulting mixture was extracted with EA. The organic layers were combined, dried over $Na_2SO_4$. The resulting mixture was concentrated under vacuum to yield methyl (4-(2-bromoacetyl)-3-fluoropyridin-2-yl)carbamate as a yellow solid. LC/MS: mass calculated for $C_9H_8BrFN_2O_3$: 289.97, measured (ES, m/z): 290.95, 292.95 $[M+H, M+H+2]^+$.

Step 5: 2-(3-Fluoro-2-((methoxycarbonyl)amino) pyridin-4-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (0.45 g, 1.39 mmol, 1.0 equiv.) in acetonitrile (10 mL) was added potassium carbonate (0.25 g, 1.80 mmol, 1.3 equiv.). The reaction mixture was stirred 0.5 h. Methyl (4-(2-bromoacetyl)-3-fluoropyridin-2-yl)carbamate (1.0 g, 3.46 mmol, 2.5 equiv.) was added and the reaction mixture was stirred at room temperature for 1 h. The resulting mixture was concentrated under vacuum. The residue was purified silica gel chromatography with MeOH/DCM (0→6%) to yield 2-(3-fluoro-2-((methoxycarbonyl)amino) pyridin-4-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{24}H_{21}ClF_2N_4O_6$: 534.11, measured (ES, m/z): 535.25 $[M+H]^+$.

Step 6: Methyl(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)carbamate To a solution of 2-(3-fluoro-2-((methoxycarbonyl)amino) pyridin-4-yl)-2-oxoethyl (3S)-7-(6-amino-3-chloro-2-fluorophenyl)-5-oxo-1,2,3,5,8,8a-hexahydroindolizine-3-carboxylate (0.63 g, 0.82 mmol, 1.0 equiv.) and ammonium acetate (1.3 g, 16.49 mmol, 20.0 equiv.) in toluene (10 mL) was added acetic acid (0.5 mL). The reaction mixture was stirred at 100° C. for 1 h. The resulting mixture was concentrated under vacuum. The residue was purified by silica gel chromatography with MeOH/DCM (0→7%) to yield methyl (4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)carbamate as a yellow solid. LC/MS: mass calculated for $C_{24}H_{21}ClF_2N_6O_3$: 514.13, measured (ES, m/z): 515.20 $[M+H]^+$.

Step 7: Methyl(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)carbamate To a solution of (3S)-3-(5-(2-(((tert-butyldimethylsilyl) oxy)methyl)-3-fluoropyridin-4-yl)-1H-imidazol-2-yl)-7-(5-chloro-2-(4-(trifluoromethyl)-1H-1,2,3-triazol-1-yl)phenyl)-1,2,3,8,9,9a-hexahydro-5H-pyrrolo[1,2-a]azepin-5-one (300 mg, 0.42 mmol, 1.0 equiv.) in THE (5 mL) was added triethylamine trihydrofluoride (335 mg, 2.08 mmol, 5.0 equiv.). The reaction mixture was stirred at 70° C. for 1 h, then purified by reverse phase chromatography with $CH_3CN$/water (5→55%) to yield (3S,9aS)-7-(5-chloro-2-(4-(trifluoromethyl)-1H-1,2,3-triazol-1-yl)phenyl)-3-(5-(3-fluoro-2-(hydroxymethyl)pyridin-4-yl)-1H-imidazol-2-yl)-1,2,3,8,9,9a-hexahydro-5H-pyrrolo[1,2-a]azepin-5-one as a white solid.

LC/MS: mass calculated for $C_{25}H_{20}ClF_2N_2O_3$: 567.13, measured (ES, m/z): 568.15 $[M+H]^+$. $^1H$ NMR (400 MHz, Methanol-$d_4$) δ 9.57 (5, 1H), 8.14 (d, J=5.3 Hz, 1H), 7.75-7.91 (m, 2H), 7.45-7.63 (m, 2H), 5.73 (d, J=2.8 Hz, 1H), 5.12-5.21 (m, 1H), 3.86-3.98 (m, 1H), 3.78 (s, 3H), 2.82-2.95 (m, 1H), 2.57-2.67 (m, 1H), 2.16-2.40 (m, 3H), 1.96-2.12 (m, 1H). $^{19F}$ NMR (376 MHz, Methanol-$d_4$) δ −113.49, −133.63.

Example 45: (3S,8aR)-7-(5-chloro-2-(1H-tetrazol-1-yl)phenyl)-3-(4-fluoro-5-(3-fluoro-2-((R*)-1-hydroxyethyl)pyridin-4-yl)-1H-imidazol-2-yl)-2,3,8,8a-tetrahydroindolizin-5(1H)-one

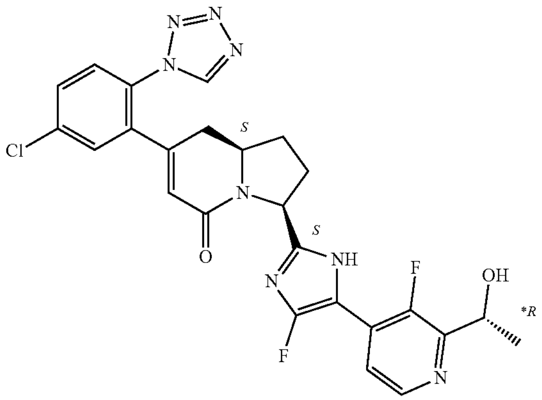

LC/MS: mass calculated for $C_{25}H_{21}ClF_2N_8O_2$: 538.14, measured (ES, m/z): 539.15 $[M+H]^+$. $^1H$ NMR (400 MHz, Methanol-$d_4$) δ 9.56 (5, 1H), 8.35 (d, J=5.2 Hz, 1H), 7.61-7.72 (m, 3H), 7.55 (t, J=5.5 Hz, 1H), 5.70 (d, J=2.8 Hz, 1H), 5.08-5.26 (m, 2H), 3.75-3.91 (m, 1H), 2.59-2.73 (m, 1H), 2.34-2.43 (m, 1H), 2.12-2.33 (m, 3H), 1.93-2.08 (m, 1H), 1.53 (d, J=6.6 Hz, 3H). $^{19}F$ NMR (376 MHz, Methanol-$d_4$) δ −127.79, −133.77.

Example 46: (3S,8aR)-7-(5-chloro-2-(1H-tetrazol-1-yl)phenyl)-3-(4-fluoro-5-(3-fluoro-2-((S*)-1-hydroxyethyl)pyridin-4-yl)-1H-imidazol-2-yl)-2,3,8,8a-tetrahydroindolizin-5(1H)-one

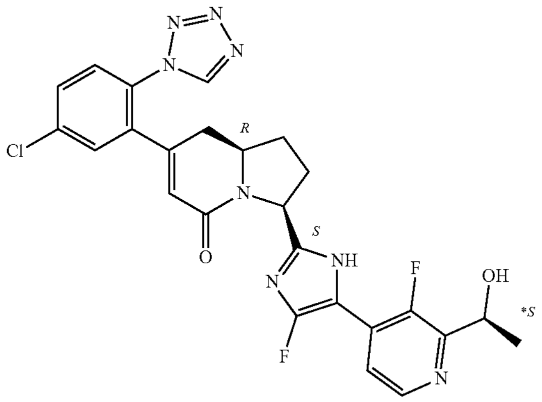

LC/MS: mass calculated for $C_{25}H_{21}ClF_2N_8O_2$: 538.14, measured (ES, m/z): 539.15 $[M+H]^+$. $^1H$ NMR (400 MHz, Methanol-$d_4$) δ 9.56 (s, 1H), 8.34 (d, J=5.2 Hz, 1H), 7.61-7.74 (m, 3H), 7.54 (t, J=5.5 Hz, 1H), 5.70 (d, J=2.8 Hz, 1H), 5.18-5.25 (m, 1H), 5.12 (d, J=8.8 Hz, 1H), 3.75-3.89 (m, 1H), 2.61-2.74 (m, 1H), 2.35-2.43 (m, 1H), 2.12-2.33 (m, 3H), 1.93-2.09 (m, 1H), 1.50-1.55 (m, 3H). $^{19}F$ NMR (376 MHz, Methanol-$d_4$) δ −128.08, −133.95.

Example 47: (3S,8aR*)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d

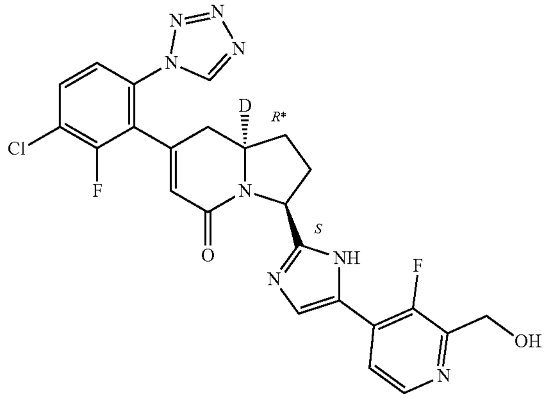

Step 1: 2-(2-(((Tert-butyldimethylsilyl)oxy)methyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate-8a-d To a solution of (3S)-7-(3-chloro-2-fluoro-6-(1H-tetrazol-1-yl)phenyl)-5-oxo-1,2,3,5,8,8a-hexahydroindolizine-3-carboxylic-8a-d acid (300 mg, 0.80 mmol, 1.0 equiv.) in $CH_3CN$ (10 mL) was added $K_2CO_3$ (142 mg, 1.03 mmol, 1.3 equiv.). After stirring at room temperature for 0.5 h, 2-bromo-1-(2-(((tert-butyldimethylsilyl)oxy)methyl)-3-fluoropyridin-4-yl)ethan-1-one (430 mg, 1.20 mmol, 1.5 equiv.) was added. The mixture was stirred at room temperature for 1 h. The resulting mixture was purified by silica gel column with MeOH/DCM (0→7%) to yield the 2-(2-(((tert-butyldimethylsilyl)oxy)methyl)-3-fluoropyridin-4-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate-8a-d as a yellow oil. LC/MS: mass calculated for $C_{30}H_{32}DClF_2N_6O_5Si$: 659.20, measured (ES, m/z): 660.15 $[M+H]^+$.

Step 2: (3S)-3-(5-(2-(((Tert-butyldimethylsilyl)oxy)methyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d To a solution of 2-(2-(((tert-butyldimethylsilyl)oxy)methyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate-8a-d (380 mg, 0.58 mmol, 1.0 equiv.) in toluene (10 mL) and acetic acid (1 mL) was added ammonium acetate (665 mg, 8.63 mmol, 15.0 equiv.). The mixture was stirred at 100° C. for 1 h. The solvent was removed under vacuum and the residue was purified by silica gel column with MeOH/DCM (0-(10%) to yield (3S)-3-(5-(2-(((tert butyldimethylsilyl)oxy)methyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d as a yellow oil. LC/MS: mass calculated for $C_{30}H_{32}DClF_2N_8O_2Si$: 639.22, measured (ES, m/z): 640.20 $[M+H]^+$.

Step 3: (3S,8aR*)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d To a solution of (3S)-3-(5-(2-(((tert-butyldimethylsilyl)oxy)methyl)-3-fluoropyridin-4-yl)-1H-imidazol-2-yl)-7-(3-Chloro-2-fluoro-6-(1H-tetrazol-1-yl)phenyl)-2,3,8,8a-tetrahydroindolizin-5(1H)-one-8a-d (280 mg, 0.44 mmol, 1.0 equiv.) in THE (5 mL) was added triethylamine trihydrofluoride (1.3 mL). The mixture was stirred at 70° C. for 1 h. The solvent was removed under vacuum and the residue was purified by C18 column [condition: ACN-water-6.5 mM $NH_4HCO_3$+$NH_3H_2O$ (5→50%)] to yield a second residue. The second residue was purified by chiral HPLC [column: (R,R) WHELK-01, 4.6*S0 mm, 3.5 um; mobile phase A: Hex (0.1% DEA): EtOH=55:45, mobile phase B; flow rate: 1 mL/min] to yield (3S,8a*R)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d as an off-white solid.

LC/MS: mass calculated for $C_{24}H_{18}ClDF_2N_8O_2$: 525.14, measured (ES, m/z): 526.10 $[M+H]^+$. $^1H$ NMR (400 MHz, DMSO-$d_6$) δ 12.25 (s, 1H), 9.84 (s, 1H), 8.34 (d, J=5.1 Hz, 1H), 7.94-8.00 (m, 1H), 7.86-7.90 (m, 1H), 7.71 (dd, J=8.6, 1.5 Hz, 1H), 7.57 (d, J=3.8 Hz, 1H), 5.70 (d, J=2.7 Hz, 1H), 5.23-5.29 (m, 1H), 5.04 (d, J=8.7 Hz, 1H), 4.63 (dd, J=6.0, 2.3 Hz, 2H), 2.65-2.77 (d, J=16.7 Hz, 1H), 2.52-2.58 (m, 1H), 2.16-2.29 (m, 1H), 2.06-2.14 (m, 1H), 2.90-2.02 (m, 2H). $^{19}F$ NMR (376 MHz, DMSO-$d_6$) δ −112.85, −130.16.

Example 48: (3S*,8aS)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one-8a-d

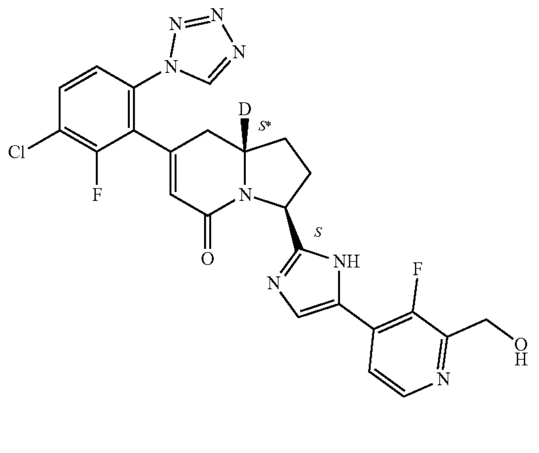

LC/MS: mass calculated for $C_{24}H_{18}DClF_2N_8O_2$: 525.14, measured (ES, m/z): 526.10 $[M+H]^+$. $^1H$ NMR (400 MHz, DMSO-$d_6$) δ 12.52 (s, 1H), 9.84 (s, 1H), 8.34 (d, J=5.1 Hz, 1H), 7.94-8.01 (m, 1H), 7.85-7.92 (m, 1H), 7.71 (dd, J=8.7, 1.5 Hz, 1H), 7.62 (d, J=3.7 Hz, 1H), 5.70 (d, J=2.7 Hz, 1H), 5.00-5.08 (m, 1H), 4.64 (d, J=2.2 Hz, 2H), 2.42-2.46 (m, 1H), 2.31-2.41 (m, 1H), 2.20-2.30 (m, 1H), 1.95-2.08 (m, 1H), 1.64-1.78 (m, 1H), 1.14-1.28 (m, 1H). $^{19}F$ NMR (376 MHz, DMSO-$d_6$) δ −113.06, −129.81.

Example 49: (3R*,8aR)-3-(5-(2-(5-amino-1H-pyrazol-1-yl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

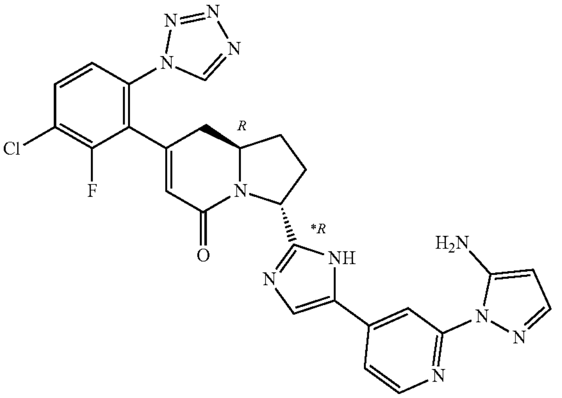

LC/MS: mass calculated for $C_{26}H_{21}ClFN_{11}O$: 557.16, measured (ES, m/z): 558.20 $[M+H]^+$. $^1H$ NMR (400 MHz, DMSO-$d_6$) δ 12.10-12.14 (m, 1H), 9.81 (5, 1H), 8.29 (d, J=5.3 Hz, 1H), 8.17 (d, J=1.8 Hz, 1H), 7.90-7.98 (m, 1H), 7.84 (d, J=2.2 Hz, 1H), 7.65-7.72 (m, 1H), 7.51-7.59 (m, 1H), 7.31-7.39 (m, 1H), 6.76-6.83 (m, 2H), 5.61-5.67 (m, 1H), 5.36-5.40 (m, 1H), 4.96-5.03 (m, 1H), 2.72-2.84 (m, 1H), 2.51-2.55 (m, 1H), 2.46-2.50 (m, 1H), 2.13-2.23 (m, 1H), 2.06-2.12 (m, 1H), 1.87-2.02 (m, 2H). $^{19}F$ NMR (376 MHz, DMSO-$d_6$) δ −112.57.

Example 50: Methyl 4 [2-[(3S,8aR)-7-[3-chloro-6-(4-chlorothiazol-1-yl)-2-fluoro-phenyl]-5-oxo-2,3,8,8a-tetrahydro-1H-indolizin-3-yl]-1H-imidazol-5-yl]-3-fluoro-pyridine-2-carboxylate

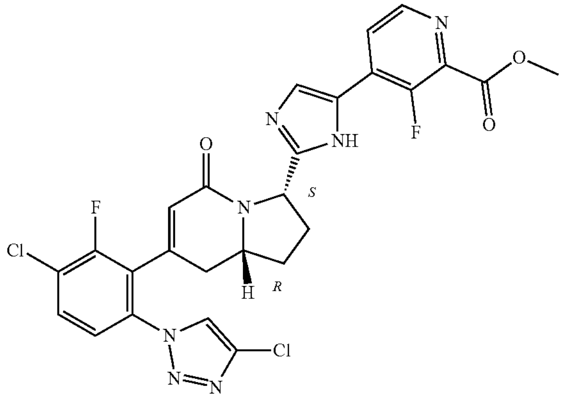

2-(3-Fluoro-2-(methoxycarbonyl)pyridin-4-yl)-2-oxoethyl (3R,8aS)-7-(3-chloro-6-(4-chloro-1H-1,2,3-triazol-1-yl)-2-fluorophenyl)-5-oxo-1,2,3,5,8,8a-hexahydroindolizine-3-carboxylate (55 mg, 0.091 mmol) was dissolved in HOAc. To the resulting solution was then added ammonium acetate (69.9 mg, 0.91 mmol) and the reaction mixture was stirred at 80° C. for 75 mins. The solvent was removed under reduced pressure and the residue was purified by HPLC to yield methyl 4-[2-[(3S,8aR)-7-[3-chloro-6-(4-chlorothiazol- 1-yl)-2-fluoro-phenyl]-5-oxo-2,3,8,8a-tetrahydro-1H-indolizin-3-yl]-1H-imidazol-5-yl]-3-fluoro-pyridine-2-carboxylate as a white solid.

LC/MS calculated for $C_{26}H_{19}Cl_2F_2N_7O_3$: 585.1, measured 586.2 ($MH^+$).

$^1$H NMR (400 MHz, METHANOL-$d_4$) δ 8.42-8.44 (m, 1H), 8.41 (s, 1H), 8.09 (s, 1H), 7.73 (d, J=3.42 Hz, 1H), 7.69 (dd, J=7.83, 8.80 Hz, 1H), 7.41 (dd, J=1.71, 8.56 Hz, 1H), 5.65 (d, J=2.45 Hz, 1H), 5.14-5.18 (m, 1H), 3.91 (s, 3H), 2.77-2.87 (m, 1H), 2.53-2.60 (m, 1H), 2.26-2.37 (m, 1H), 2.13-2.23 (m, 2H), 1.93-2.02 (m, 1H).

Example 51: (3S,8aR)-3-(4-(1H-indazol-4-yl)-1H-imidazol-2-yl)-7-(3-chloro-2-fluoro-6-(1H-tetrazol-1-yl)phenyl)-2,3,8,8a-tetrahydroindolizin-5(1H)-one

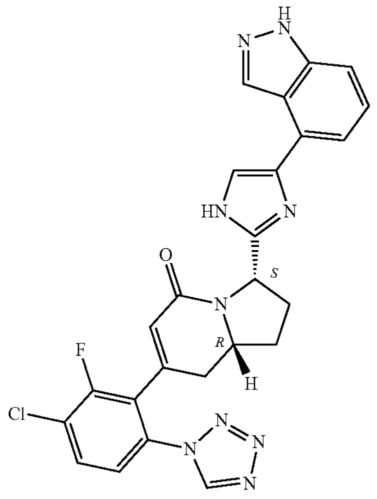

LC/MS: mass calculated for $C_{25}H_{19}ClFN_9O$: 515.1, measured (ES, m/z): 516.1 $[M+H]^+$. $^1$H NMR (400 MHz, METHANOL-$d_4$) δ ppm 1.91-2.12 (m, 1H), 2.24-2.42 (m, 2H), 2.48-2.67 (m, 1H), 2.67-2.80 (m, 1H), 2.93-3.08 (m, 1H), 3.88-4.09 (m, 1H), 5.25-5.44 (m, 1H), 5.74-5.81 (m, 1H), 7.42-7.61 (m, 3H), 7.65-7.74 (m, 1H), 7.78-7.91 (m, 1H), 7.99 (s, 1H), 8.28-8.40 (m, 1H), 9.59 (s, 1H).

Example 52: Methyl 4 [2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-5-yl]-3-fluoro-pyridine-2-carboxylate

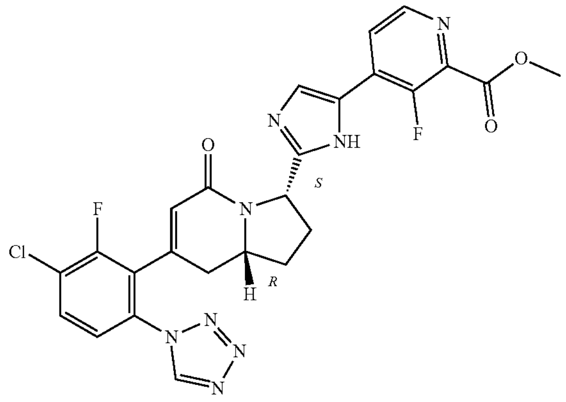

2-(3-Fluoro-2-(methoxycarbonyl)pyridin-4-yl)-2-oxoethyl (3R,8aS)-7-(3-chloro-2-fluoro-6-(1H-tetrazol-1-yl)phenyl)-5-oxo-1,2,3,5,8,8a-hexahydroindolizine-3-carboxylate (44 mg, 0.077 mmol) was dissolved in HOAc. To the resulting solution was added ammonium acetate (59.2 mg, 0.77 mmol) and the reaction mixture was stirred at 80° C. for 75 mins. The solvent was removed under reduced pressure and the residue was purified by HPLC to yield methyl 4 [2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-5-yl]-3-fluoro-pyridine-2-carboxylate as an off-white solid.

LC/MS calculated for $C_{25}H_{19}ClF_2N_8O_3$: 552.1, measured 553.2 ($MH^+$). $^1$H NMR (400 MHz, METHANOL-$d_4$) δ 9.60 (s, 1H), 8.55 (d, J=4.89 Hz, 1H), 8.20 (t, J=5.38 Hz, 1H), 7.81-7.89 (m, 2H), 7.58 (dd, J=1.47, 8.80 Hz, 1H), 5.76-5.80 (m, 1H), 5.23 (s, 1H), 4.02-4.05 (m, 3H), 3.94-4.01 (m, 1H), 2.86-2.98 (m, 1H), 2.65-2.74 (m, 1H), 2.37-2.51 (m, 1H), 2.21-2.34 (m, 2H), 2.02-2.14 (m, 1H).

Example 53: 3-(5-(2-(1H-pyrazol-5-yl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

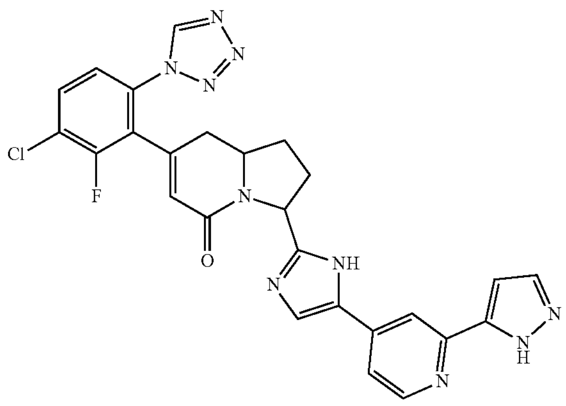 [SMILES: O=C1C=C(c2c(-n3cnnn3)ccc(Cl)c2F)CC2CCC(c3ncc(-c4ccnc(-c5ccn[nH]5)c4)[nH]3)N12]

LC/MS: mass calculated for $C_{26}H_{20}ClFN_{10}O$: 542.15, measured (ES, m/z): 543.15 $[M+H]^+$. $^1H$ NMR (400 MHz, DMSO-$d_6$) δ 12.99-13.04 (m, 1H), 12.10 (s, 1H), 9.83 (s, 1H), 8.47-8.52 (m, 1H), 8.26 (s, 1H), 7.92-8.01 (m, 1H), 7.54-7.91 (m, 4H), 6.85 (s, 1H), 5.67 (d, J=2.7 Hz, 1H), 5.02 (d, J=8.8 Hz, 1H), 3.63-3.75 (m, 1H), 2.74-2.86 (m, 2H), 2.18-2.24 (m, 1H), 2.08-2.14 (m, 1H), 1.92-2.04 (m, 2H)

Example 54: 4-(2-((3S*,8aR)-7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-5-yl)-3-fluoropicolinic acid

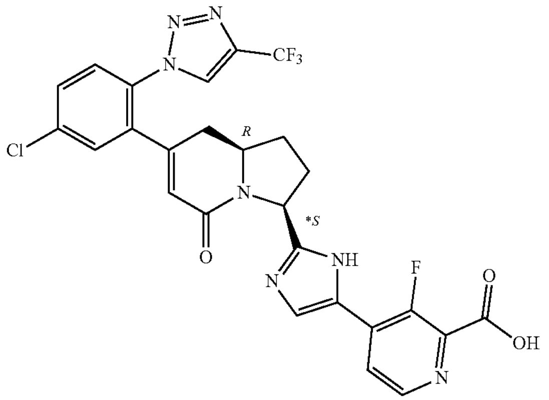

LC/MS: mass calculated for $C_{26}H_{18}ClF_4N_7O_3$: 587.11, measured (ES, m/z): 588.15 $[M+H]^+$. $^1H$ NMR (400 MHz, Methanol-$d_4$) δ 9.00 (s, 1H), 8.18-8.55 (m, 2H), 7.62-7.73 (m, 4H), 5.80 (d, J=2.4 Hz, 1H), 5.20 (d, J=8.6 Hz, 1H), 3.78-3.98 (m, 1H), 2.57-2.74 (m, 1H), 2.13-2.45 (m, 4H), 1.97-2.10 (m, 1H). $^{19}F$ NMR (376 MHz, Methanol-$d_4$) δ −62.52.

Example 56: (3S)-7-(5-chloro-2-(1H-tetrazol-1-yl)phenyl)-8,8-difluoro-3-(5-(3-fluoro-2-(hydroxymethyl)pyridin-4-yl)-1H-imidazol-2-yl)-2,3,8,8a-tetrahydroindolizin-5(1H)-one

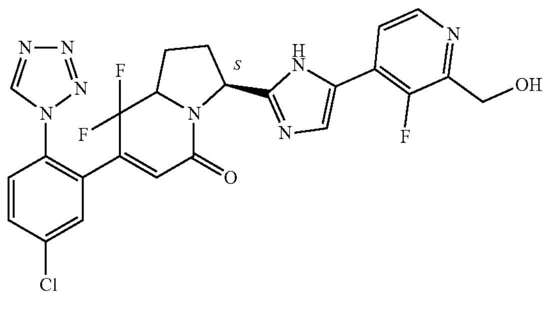

Step 1: 1-(Tert-butyl) 2-methyl (2R)-5-(2-ethoxy-1,1-difluoro-2-oxoethyl)pyrrolidine-1,2-dicarboxylate Zinc dust (6.4 g, 97.85 mmol, 2.0 equiv.) was placed in a bottle and heated to 100° C. under vacuum. After being cooled to room temperature, the reaction bottle was filled with $N_2$. Then, $CH_3CN$ (8 mL), TMSCl (0.4 g), and 1,2-dibromoethane (56 mg) were successively added, and the mixture was stirred for 30 min. The mixture was cooled to −10° C., and a solution of ethyl bromodifluoroacetate (10 g, 49.27 mmol, 1.0 equiv.) in MeCN (16 mL) was added over 40 min. After the completion of the addition, the mixture was allowed to warm to room temperature and stirred for 1 h. Then, the mixture was cooled to 0° C., TMSCl (8.5 g, 78.27 mmol, 1.6 equiv.) was added dropwise, and the mixture was allowed to warm to room temperature over 45 min. Under $N_2$, the mixture was extracted with pentane (4×12 mL, pentane phase was decanted using a cannula). To the above mixture was added a solution of 1-(tert-butyl) 2-methyl (2S)-5-methoxypyrrolidine-1,2-dicarboxylate (3.2 g, 12.34 mmol, 0.50 equiv.) in tert-butyl methyl ether (100 mL) followed by the addition of solution of ((1-ethoxy-2,2-difluorovinyl)oxy)trimethylsilane at −40° C. Boron trifluoride etherate (4.1 g, 28.89 mmol, 0.60 equiv.) was added to the solution at −40° C. under $N_2$ and the mixture was stirred for 40 min, then allowed to warm to ambient temperature over 40 min. The reaction was quenched with $Na_2CO_3$ (aq.). The resulting solution was extracted with ethyl acetate and the organic layers were combined and dried with $Na_2SO_4$. The solids were filtered out. The resulting organic phase was concentrated under vacuum. The residue was purified by flash column chromatography on silica gel (PE/EA=3:1) to yield 1-(tert-butyl) 2-methyl (2S)-5-(2-ethoxy-1,1-difluoro-2-oxoethyl)pyrrolidine-1,2-dicarboxylate as a yellow oil. LC/MS: mass calculated for $C_{15}H_{23}F_2NO_6$: 351.15, measured (ES, m/z): 252.10 $[M-Boc+H]^+$.

Step 2: Methyl (2R)-5-(2-ethoxy-1,1-difluoro-2-oxoethyl)pyrrolidine-2-carboxylate To a solution of 1-(tert butyl) 2-methyl (2S)-5-(2-ethoxy-1,1-difluoro-2-oxoethyl)pyrrolidine-1,2-dicarboxylate (2.2 g, 6.26 mmol, 1.0 equiv.) in DCM (30 mL) was added TFA (10 mL). The reaction mixture was stirred for 3 h. The mixture was concentrated under vacuum to yield methyl (2S)-5-(2-ethoxy-1,1-difluoro-2-oxoethyl)pyrrolidine-2-carboxylate (TFA salt) as a yellow oil. LC/MS: mass calculated for $C_{10}H_{15}F_2NO_4$: 251.10, measured (ES, m/z): 252.15 $[M+H]^+$.

Step 3: Methyl (2R)-5-(2-ethoxy-1,1-difluoro-2-oxoethyl)-1-(3-ethoxy-3-oxopropanoyl)pyrrolidine-2-carboxylate To a solution of methyl (2S)-5-(2-ethoxy-1,1-difluoro-2-oxoethyl)pyrrolidine-2-carboxylate (TFA salt) (2.3 g, 6.30 mmol, 1.0 equiv.) in DCM (30 mL) was added TEA (3.5 g, 34.59 mmol, 5.5 equiv.) followed by slow addition of ethyl 3-chloro-3-oxopropanoate (1.0 g, 6.64 mmol, 1.0 equiv.) with stirring at 0° C. The reaction mixture was stirred for 1.5 h at 0° C. Another portion of ethyl 3-chloro-3-oxopropanoate (1.8 g, 11.96 mmol, 1.9 equiv.) was added to the mixture at 0° C. The reaction mixture was stirred for 1.5 h, then was quenched with water (60 mL) and extracted with EA (100 mL×3). The combined organic layer was washed with brine, dried over $Na_2SO_4$. The solids were filtered out. The resulting organic phase was concentrated under vacuum. The residue was purified by flash column chromatography on silica gel (PE/EA=2:1) to yield methyl (2S)-5-(2-ethoxy-1,1-difluoro-2-oxoethyl)-1-(3-ethoxy-3-oxopropanoyl)pyrrolidine-2-carboxylate as a yellow oil. LC/MS: mass calculated for $C_{15}H_{21}F_2NO_7$: 365.13, measured (ES, m/z): 366.30 $[M+H]^+$.

Step 4: 6-Ethyl 3-methyl (3R)-8,8-difluoro-7-hydroxy-5-oxo-1,2,3,5,8,8a-hexahydroindolizine-3,6-dicarboxylate To a solution of methyl (2S)-5-(2-ethoxy-1,1-difluoro-2-oxoethyl)-1-(3-ethoxy-3-oxopropanoyl)pyrrolidine-2-carboxylate (1.4 g, 3.832 mmol, 1.0 equiv.) in EtOH (30 mL) was added NaH (60% in mineral oil, 200 mg, 5.00 mmol, 1.3 equiv.) with stirring at 0° C. The reaction was then stirred at room temperature for 1.5 h. The mixture was quenched with water (50 mL) and extracted with EA (100 mL×3). The combined organic layer was washed with brine, dried over $Na_2SO_4$. The solids were filtered out. The resulting organic phase was concentrated under vacuum. The residue was purified by flash column chromatography on silica gel (PE/EA=1:1) to yield 6-ethyl 3-methyl (3S)-8,8-difluoro-7-hydroxy-5-oxo-1,2,3,5,8,8a-hexahydroindolizine-3,6-dicarboxylate (containing diethyl (3S)-8,8-difluoro-7-hydroxy-5-oxo-1,2,3,5,8,8a-hexahydroindolizine-3,6-dicarboxylate) as a yellow oil. LC/MS: mass calculated for $C_{13}H_{15}F_2NO_6$: 319.09, measured (ES, m/z): 320.20 $[M+H]^+$.

Step 5: Methyl (3R)-8,8-difluoro-7-hydroxy-5-oxo-1,2,3,5,8,8a-hexahydroindolizine-3-carboxylate To a solution of 6-ethyl 3-methyl (3S)-8,8-difluoro-7-hydroxy-5-oxo-1,2,3,5,8,8a-hexahydroindolizine-3,6-dicarboxylate (0.80 g, 2.51 mmol, 1.0 equiv.) in HOAc (20 mL) was added $H_2O$ (4 mL). The reaction mixture was stirred for 5 h at 90° C. The resulting mixture was concentrated under vacuum. The residue was applied onto a C18 column for purification ($CH_3CN/H_2O$) to yield methyl (3S)-8,8-difluoro-7-hydroxy-5-oxo-1,2,3,5,8,8a-hexahydroindolizine-3-carboxylate as a yellow oil (containing ethyl (3S)-8,8-difluoro-7-hydroxy-5-oxo-1,2,3,5,8,8a-hexahydroindolizine-3-carboxylate). LC/MS: mass calculated for $C_{10}H_{11}F_2NO_4$: 247.07, measured (ES, m/z): 248.25 $[M+H]^+$.

Step 6: Methyl (3R)-8,8-difluoro-5-oxo-7-(((trifluoromethyl)sulfonyl)oxy)-1,2,3,5,8,8a-hexahydroindolizine-3-carboxylate To a solution of methyl (3S)-8,8-difluoro-7-hydroxy-5-oxo-1,2,3,5,8,8a-hexahydroindolizine-3-carboxylate (containing ethyl (3S)-8,8-difluoro-7-hydroxy-5-oxo-1,2,3,5,8,8a-hexahydroindolizine-3-carboxylate) (0.50 g, 2.02 mmol, 1.0 equiv.) in DCM (10 mL) were added 1,1,1-trifluoro-N-phenyl-N-((trifluoromethyl)sulfonyl)methanesulfonamide (0.80 g, 2.24 mmol, 1.1 equiv.) and TEA (0.5 g, 4.94 mmol, 2.4 equiv.). The reaction mixture was stirred for 16 h at 25° C. The reaction was quenched with water (20 mL) and extracted with EA (30 mL×3). The combined organic layer was washed with brine, dried over $Na_2SO_4$. The solids were filtered out. The resulting organic phase was concentrated under vacuum. The residue was purified by flash column chromatography on silica gel (PE/EA=2:1) to yield methyl (3S)-8,8-difluoro-5-oxo-7-(((trifluoromethyl)sulfonyl)oxy)-1,2,3,5,8,8a-hexahydroindolizine-3-carboxylate (containing ethyl (3S)-8,8-difluoro-5-oxo-7-(((trifluoromethyl)sulfonyl)oxy)-1,2,3,5,8,8a-hexahydroindolizine-3-carboxylate) as a yellow oil. LC/MS: mass calculated for $C_{11}H_{10}F_5NO_6S$: 379.01, measured (ES, m/z): 380.10 $[M+H]^+$.

Step 7: Methyl (3S)-7-(5-chloro-2-nitrophenyl)-8,8-difluoro-5-oxo-1,2,3,5,8,8a-hexahydroindolizine-3-carboxylate To a solution of methyl (3S)-8,8-difluoro-5-oxo-7-(((trifluoromethyl)sulfonyl)oxy)-1,2,3,5,8,8a-hexahydroindolizine-3-carboxylate (0.30 g, 0.79 mmol, 1.0 equiv.) in 1,4-dioxane (5 mL) and $H_2O$ (1 mL) were added (5-chloro-2-nitrophenyl)boronic acid (175 mg, 0.87 mmol, 1.1 equiv.) and Pd(dppf)$Cl_2$ (38 mg, 0.052 mmol, 0.06 equiv.). The reaction mixture was stirred for 2.5 h at 90° C. under $N_2$. The reaction was quenched with water (10 mL) and extracted with EA (20 mL×3). The combined organic layer was washed with brine, dried over $Na_2SO_4$. The solids were filtered out. The resulting organic phase was concentrated under vacuum. The residue was purified by flash column chromatography on silica gel (PE/EA=2:1) to yield methyl (3S)-7-(5-chloro-2-nitrophenyl)-8,8-difluoro-5-oxo-1,2,3,5,8,8a-hexahydroindolizine-3-carboxylate as a yellow oil. LC/MS: mass calculated for $C_{16}H_{13}ClF_2N_2O_5$: 386.05, measured (ES, m/z): 387.20 $[M+H]^+$.

Step 8: (3S)-7-(5-Chloro-2-nitrophenyl)-8,8-difluoro-5-oxo-1,2,3,5,8,8a-hexahydroindolizine-3-carboxylic acid To a mixture of (3S)-methyl 7-(5-chloro-2-nitrophenyl)-8,8-difluoro-5-oxo-1,2,3,5,8,8a-hexahydroindolizine-3-carboxylate (65 mg, 0.17 mmol, 1.0 equiv.) in MeOH (2 mL) and THE (2 mL) was added a solution of LiOH (20 mg, 0.84 mmol, 5.0 equiv.) in $H_2O$ (2 mL). The reaction mixture was stirred at room temperature for 1 h. The resulting mixture was diluted with water (10 mL), the pH value of the aqueous phase was adjusted to 6 with HCl solution (1 M). The mixture was extracted with EtOAc (3×30 mL), dried over $Na_2SO_4$, and concentrated to yield (3S)-7-(5-chloro-2-nitrophenyl)-8,8-difluoro-5-oxo-1,2,3,5,8,8a-hexahydroindolizine-3-carboxylic acid as a yellow solid. LC/MS: mass calculated for $C_{15}HClF_2N_2O_5$: 372.03, measured (ES, m/z): 373.00 $[M+H]^+$.

Step 9: 2-(2-(((Teri butyldimethylsilyl)oxy)methyl)-3-fluoropyridin-4-yl)-2-oxoethyl (3S)-7-(5-chloro-2-nitrophenyl)-8,8-difluoro-5-oxo-1,2,3,5,8,8a-hexahydroindolizine-3-carboxylate A mixture of (3S)-7-(5-chloro-2-nitrophenyl)-8,8-difluoro-5-oxo-1,2,3,5,8,8a-hexahydroindolizine-3-carboxylic acid (55 mg, 0.15 mmol, 1.0 equiv.) and $Cs_2CO_3$ (29 mg, 0.089 mmol, 0.6 equiv.) in DMF (6 mL) was stirred at room temperature for 30 min. 2-Bromo-1-(2-(((tert-butyldimethylsilyl)oxy)methyl)-3-fluoropyridin-4-yl)ethan-1-one (80 mg, 0.22 mmol, 1.5 equiv.) was then added to the mixture. The reaction mixture was stirred at room temperature for 4 h. The resulting mixture was then diluted with EtOAc (110 mL), washed with water (3×20 mL), brine (2×20 mL), dried over $Na_2SO_4$, and concentrated to yield (3S)-2-(2-((tert-butyldimethylsilyloxy)methyl)-3-fluoropyridin-4-yl)-2-oxoethyl 7-(5-chloro-2-nitrophenyl)-8,8-difluoro-5-oxo-1,2,3,5,8,8a-hexahydroindolizine-3-carboxylate as a yellow solid. LC/MS: mass calculated for $C_{29}H_{31}ClF_3N_3O_7Si$: 653.16, measured (ES, m/z): 654.05 $[M+H]^+$.

Step 10: (3S)-3-(5-(2-(((Tert-butyldimethylsilyl)oxy)methyl)-3-fluoropyridin-4-yl)-1H-imidazol-2-yl)-7-(5-chloro-2-nitrophenyl)-8,8-difluoro-2,3,8,8a-tetrahydroindolizin-5(1H)-one A mixture of $NH_4OAc$ (77 mg, 1.00 mmol, 10.0 equiv.) and (3S)-2-(2-((tert-butyldimethyl silyloxy)methyl)-3-fluoropyridin-4-yl)-2-oxoethyl 7-(5-chloro-2-nitrophenyl)-8,8-difluoro-5-oxo-1,2,3,5,8,8a-hexahydroindolizine-3-carboxylate (65 mg, 0.099 mmol, 1.0 equiv.) in AcOH (2 mL)

and toluene (20 mL) was stirred at 110° C. for 30 min, then concentrated under reduced pressure. The residue was purified by flash column chromatography on silica gel (40 g, MeOH/DCM: 1/15) to yield (3S)-3-(5-(2-((tert-butyldimethylsilyloxy)methyl)-3-fluoropyridin-4-yl)-1H-imidazol-2-yl)-7-(5-chloro-2-nitrophenyl)-8,8-difluoro-2,3,8,8a-tetrahydroindolizin-5(1H)-one as a yellow solid. LC/MS: mass calculated for $C_{29}H_{31}ClF_3N_5O_4Si$: 633.18, measured (ES, m/z): 634.10 $[M+H]^+$.

Step 11: (3S)-7-(2-Amino-5-chlorophenyl)-3-(5-(2-(((tert-butyldimethylsilyl)oxy)methyl)-3-fluoropyridin-4-yl)-1H-imidazol-2-yl)-8,8-difluoro-2,3,8,8a-tetrahydroindolizin-5(1H)-one To a mixture of (3S)-3-(5-(2-((tert-butyldimethylsilyloxy)methyl)-3-fluoropyridin-4-yl)-1H-imidazol-2-yl)-7-(5-chloro-2-nitrophenyl)-8,8-difluoro-2,3,8,8a-tetrahydroindolizin-5(1H)-one (55 mg, 0.087 mmol, 1.0 equiv.) in MeOH (2 mL), THE (2 mL) and $H_2O$ (2 mL) was added sodium dithionite (76 mg, 0.44 mmol, 5.0 equiv.). The reaction mixture was stirred at room temperature for 1 h. The resulting mixture was diluted with EtOAc (100 mL), then washed with brine (3×20 mL), dried over $Na_2SO_4$, and concentrated. The residue was purified by flash column chromatography on silica gel (40 g, MeOH/DCM: 1/15) to yield (3S)-7-(2-amino-5-chlorophenyl)-3-(5-(2-((tert butyldimethylsilyloxy)methyl)-3-fluoropyridin-4-yl)-1H-imidazol-2-yl)-8,8-difluoro-2,3,8,8a-tetrahydroindolizin-5(1H)-one as a yellow solid. LC/MS: mass calculated for $C_{29}H_{33}ClF_3N_5O_2Si$: 603.20, measured (ES, m/z): 604.15 $[M+H]^+$.

Step 12: (3S)-3-(5-(2-(((Tert-butyldimethylsilyl)oxy)methyl)-3-fluoropyridin-4-yl)-1H-imidazol-2-yl)-7-(5-chloro-2-(1H-tetrazol-1-yl)phenyl)-8,8-difluoro-2,3,8,8a-tetrahydroindolizin-5(1H)-one A mixture of (3S)-7-(2-amino-5-chlorophenyl)-3-(5-(2-((tert-butyldimethylsilyloxy)methyl)-3-fluoropyridin-4-yl)-1H-imidazol-2-yl)-8,8-difluoro-2,3,8,8a-tetrahydroindolizin-5(1H)-one (45 mg, 0.074 mmol, 1.0 equiv.), $TMSN_3$ (85 mg, 0.75 mmol, 10.0 equiv.) and trimethoxymethane (79 mg, 0.75 mmol, 10.0 equiv.) in AcOH (5 mL) was stirred at 65° C. for 2 h and then concentrated under reduced pressure. The residue was purified by flash column chromatography on silica gel (40 g, MeOH/DCM: 1/15) to yield (3S)-3-(5-(2-((tert-butyldimethylsilyloxy)methyl)-3-fluoropyridin-4-yl)-1H-imidazol-2-yl)-7-(5-chloro-2-(1H-tetrazol-1-yl)phenyl)-8,8-difluoro-2,3,8,8a-tetrahydroindolizin-5(1H)-one as a yellow solid. LC/MS: mass calculated for $C_{30}H32ClF_3N_8O_2Si$: 656.21, measured (ES, m/z): 657.20 $[M+H]^+$.

Step 13: (3S)-7-(5-Chloro-2-(1H-tetrazol-1-yl)phenyl)-8,8-difluoro-3-(5-(3-fluoro-2-(hydroxymethyl)pyridin-4-yl)-1H-imidazol-2-yl)-2,3,8,8a-tetrahydroindolizin-5(1H)-one A mixture of (3S)-3-(5-(2-(((tert-butyldimethylsilyl)oxy)methyl)-3-fluoropyridin-4-yl)-1H-imidazol-2-yl)-7-(5-chloro-2-(1H-tetrazol-1-yl)phenyl)-8,8-difluoro-2,3,8,8a-tetrahydroindolizin-5(1H)-one (40 mg, 0.061 mmol, 1.0 equiv.) in THE (6 mL) and HCl (2 mL, 4 M) was stirred at 55° C. for 1 h. The solvent was removed under reduced pressure and the residue was applied onto a C18 reverse column (330 g, ACN/$H_2O$ (0.05% $NH_4HCO_3$): 5%>>>40%>>>45%, 40 min) to yield (3S)-7-(5-chloro-2-(1H-tetrazol-1-yl)phenyl)-8,8-difluoro-3-(5-(3-fluoro-2-(hydroxymethyl)pyridin-4-yl)-1H-imidazol-2-yl)-2,3,8,8a-tetrahydroindolizin-5(1H)-one as a white solid.

LC/MS: mass calculated for $C_{24}H_{18}ClF_3NBO_2$: 542.12, measured (ES, m/z): 543.05 $[M+H]^+$. $^1H$ NMR (400 MHz, DMSO-$d_6$) δ 12.55 (s, 1H), 9.80 (s, 1H), 8.33 (d, J=5.1 Hz, 1H), 7.81-7.95 (m, 3H), 7.76 (d, J=2.2 Hz, 1H), 7.54-7.68 (m, 1H), 6.38 (d, J=3.9 Hz, 1H), 5.23-5.38 (m, 1H), 5.02-5.22 (m, 1H), 4.59-4.62 (m, 2H), 4.40-4.57 (m, 1H), 2.31-2.44 (m, 1H), 2.19-2.31 (m, 1H), 2.09-2.18 (m, 2H). $^{19}F$ NMR (376 MHz, DMSO-$d_6$) δ−103.81, −115.32, −130.15.

Example 57: (3S,8aR)-3-(5-(3-fluoro-2-(hydroxymethyl)pyridin-4-yl)-1H-imidazol-2-yl)-7-(2-fluoro-3-methyl-6-(1H-tetrazol-1-yl)phenyl)-2,3,8,8a-tetrahydroindolizin-5(1H)-one

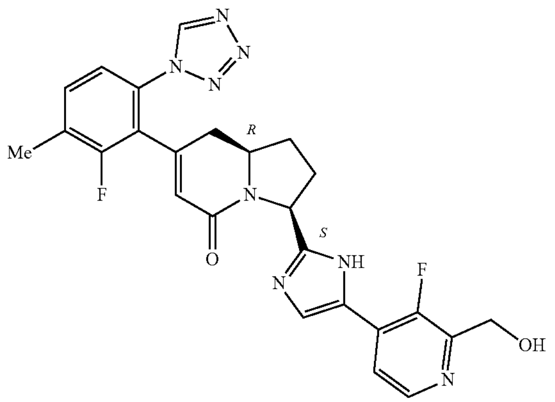

Step 1: Methyl (3S)-7-(6-amino-2-fluoro-3-methylphenyl)-5-oxo-1,2,3,5,8,8a-hexahydroindolizine-3-carboxylate To a mixture of methyl (3S)-7-(6-amino-3-chloro-2-fluorophenyl)-5-oxo-1,2,3,5,8,8a-hexahydroindolizine-3-carboxylate (600 mg, 1.77 mmol, 1.0 equiv.) and methylboronic acid (530 mg, 8.86 mmol, 5.0 equiv.) in 1,4-dioxane (10 mL) was added potassium phosphate (1128 mg, 5.31 mmol, 3.0 equiv.), palladium (II) acetate (80 mg, 0.35 mmol, 0.1 equiv.) and tricyclohexylphosphonium tetrafluoroborate (130 mg, 0.35 mmol, 0.1 equiv.). The resulting mixture was maintained under nitrogen and stirred at 100° C. for 5 h. Water was added, the mixture was extracted with EA. The combined extracts were washed with water, saturated brine, dried over $Na_2SO_4$, filtered and concentrated. The residue was purified by flash column chromatography on silica gel with MeOH/DCM (0→8%) to yield methyl (3S)-7-(6-amino-2-fluoro-3-methylphenyl)-5-oxo-1,2,3,5,8,8a-hexahydroindolizine-3-carboxylate a brown solid. LC/MS: mass calculated for $C_{17}H_{19}FN_2O_3$: 318.14, measured (ES, m/z): 319.10 $[M+H]^+$.

Step 2: (3S)-7-(6-Amino-2-fluoro-3-methylphenyl)-5-oxo-1,2,3,5,8,8a-hexahydroindolizine-3-carboxylic acid To a solution of methyl (3S)-7-(6-amino-2-fluoro-3-methylphenyl)-5-oxo-1,2,3,5,8,8a-hexahydroindolizine-3-carboxylate (500 mg, 1.57 mmol, 1.0 equiv.) in acetic acid (9 mL) was added hydrochloric acid (3 mL). The reaction mixture was stirred at 90° C. for 1 h. The resulting mixture was concentrated under vacuum. The residue was purified by reverse phase chromatography with $CH_3CN/H_2O$ (5→45%) to yield (3S)-7-(6-amino-2-fluoro-3-methylphenyl)-5-oxo-1,2,3,5,8,8a-hexahydroindolizine-3-carboxylic acid as a yellow solid. LC/MS: mass calculated for $C_{10}H_{17}FN_2O_3$: 304.12, measured (ES, m/z): 305.10 $[M+H]^+$.

Step 3: 2-(2-(((Tert-butyldimethylsilyl)oxy)methyl)-3-fluoropyridin-4-yl)-2-oxoethyl (3S)-7-(6-amino-2-fluoro-3-methylphenyl)-5-oxo-1,2,3,5,8,8a-hexahydroindolizine-3-carboxylate To a solution of (3S)-7-(6-amino-2-fluoro-3-methylphenyl)-5-oxo-1,2,3,5,8,8a-hexahydroindolizine-3-carboxylic acid (250 mg, 0.82 mmol, 1.0 equiv.) in N,N-dimethylformamide (5 mL) was added potassium carbonate (148 mg, 1.07 mmol, 1.3 equiv.). The reaction mixture was stirred for 0.5 h. 2-(((tert-Butyldimethylsilyl)oxy)methyl)-4-(1-ethoxyvinyl)-3-fluoropyridine (595 mg, 1.64 mmol, 2.0 equiv.) was added and the reaction mixture was stirred at room temperature for 1 h. Water was added, the mixture was extracted with EA. The combined extracts were washed with water, saturated brine, dried over $Na_2SO_4$, filtered and concentrated. The residue was purified by flash column chromatography on silica gel with MeOH/DCM (0→6%) to yield 2-(2-(((tert-butyldimethylsilyl)oxy)methyl)-3-fluoropyridin-4-yl)-2-oxoethyl (3S)-7-(6-amino-2-fluoro-3-methylphenyl)-5-oxo-1,2,3,5,8,8a-hexahydroindolizine-3-carboxylate as a yellow solid. LC/MS: mass calculated for $C_{30}H_{37}F_2N_3O_5Si$: 585.25, measured (ES, m/z): 586.45 $[M+H]^+$.

Step 4: (3S)-7-(6-Amino-2-fluoro-3-methylphenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one To a solution of 2-(2-(((tert-butyldimethylsilyl)oxy)methyl)-3-fluoropyridin-4-yl)-2-oxoethyl (3S)-7-(6-amino-2-fluoro-3-methylphenyl)-5-oxo-1,2,3,5,8,8a-hexahydroindolizine-3-carboxylate (160 mg, 0.27 mmol, 1.0 equiv.) and ammonium acetate (421 mg, 5.46 mmol, 20.0 equiv.) in toluene (10 mL) was added acetic acid (0.5 mL). The reaction mixture was stirred at 100° C. for 1 h. The resulting mixture was concentrated under vacuum. The residue was purified by flash column chromatography on silica gel with MeOH/DCM (0→6%) to yield (3S)-7-(6-amino-2-fluoro-3-methylphenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one as a yellow solid. LC/MS: mass calculated for $C_{30}H_{37}F_2N_5O_2Si$: 565.27, measured (ES, m/z): 566.45 $[M+H]^+$.

Step 5: (3S)-3-(5-(2-(((Tert-butyldimethylsilyl)oxy)methyl)-3-fluoropyridin-4-yl)-1H-imidazol-2-yl)-7-(2-fluoro-3-methyl-6-(1H-tetrazol-1-yl)phenyl)-2,3,8,8a-tetrahydroindolizin-5(1H)-one To a mixture of (3S)-7-(6-amino-2-fluoro-3-methylphenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one (50 mg, 0.088 mmol, 1.0 equiv.) in acetic acid (3 mL) were added azidotrimethylsilane (102 mg, 0.88 mmol, 10.0 equiv.) and trimethoxymethane (98 mg, 0.88 mmol, 10.0 equiv.). The reaction mixture was stirred overnight at 60° C. The resulting mixture was concentrated under vacuum to yield (3S)-3-(5-(2-(((tert-butyldimethylsilyl)oxy)methyl)-3-fluoropyridin-4-yl)-1H-imidazol-2-yl)-7-(2-fluoro-3-methyl-6-(1H-tetrazol-1-yl)phenyl)-2,3,8,8a-tetrahydroindolizin-5(1H)-one as a brown solid. LC/MS: mass calculated for $C_{31}H_{36}F_2N_8O_2Si$: 618.27, measured (ES, m/z): 619.20 $[M+H]^+$.

Step 6: (3S,8aR)-3-(5-(3-Fluoro-2-(hydroxymethyl)pyridin-4-yl)-1H-imidazol-2-yl)-7-(2-fluoro-3-methyl-6-(1H-tetrazol-1-yl)phenyl)-2,3,8,8a-tetrahydroindolizin-5(1H)-one To a solution of (3S)-3-(5-(2-(((tert-butyldimethylsilyl)oxy)methyl)-3-fluoropyridin-4-yl)-1H-imidazol-2-yl)-7-(2-fluoro-3-methyl-6-(1H-tetrazol-1-yl)phenyl)-2,3,8,8a-tetrahydroindolizin-5(1H)-one (70 mg) in THE (5 mL) was added triethylamine trihydrofluoride (64 mg, 0.40 mmol, 5.0 equiv.). The reaction mixture was stirred at 70° C. for 1 h, then purified by reverse phase chromatography with $CH_3CN$/water (5-(25%) to yield racemic product, which was purified by HPLC to yield (3S,8aR)-3-(5-(3-fluoro-2-(hydroxymethyl)pyridin-4-yl)-1H-imidazol-2-yl)-7-(2-fluoro-3-methyl-6-(1H-tetrazol-1-yl)phenyl)-2,3,8,8a-tetrahydroindolizin-5(1H)-one as a white solid.

LC/MS: mass calculated for $C_{25}H_{22}F_2N_8O_2$: 504.18, measured (ES, m/z): 505.20 $[M+H]^+$. $^1H$ NMR (400 MHz, Methanol-$d_4$) δ 9.44 (s, 1H), 8.24 (dd, J=5.1, 0.6 Hz, 1H), 7.91 (s, 1H), 7.51 (d, J=4.0 Hz, 1H), 7.42-7.48 (m, 1H), 7.27-7.32 (m, 1H), 5.56 (d, J=2.7 Hz, 1H), 5.02-5.11 (m, 1H), 4.69 (d, J=2.3 Hz, 2H), 3.74-3.88 (m, 1H), 2.72-2.88 (m, 1H), 2.46-2.56 (m, 1H), 2.31-2.36 (m, 3H), 2.07-2.29 (m, 3H), 1.89-2.03 (m, 1H). $^{19}F$ NMR (376 MHz, Methanol-$d_4$) 5-116.25, −131.26.

Example 58: 4-(2-((3S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)-3-fluoropicolinic acid

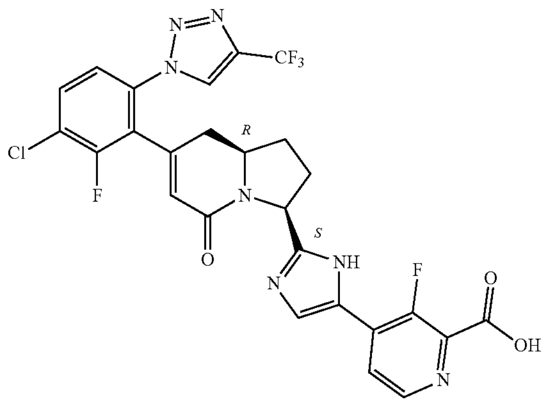

Step 1: Methyl (3S)-7-(6-amino-3-chloro-2-fluorophenyl)-5-oxo-1,2,3,5,8,8a-hexahydroindolizine-3-carboxylate To a mixture of methyl 5-oxo-7-(((trifluoromethyl)sulfonyl)oxy)-1,2,3,5,8,8a-hexahydroindolizine-3-carboxylate (5.0 g, 14.57 mmol, 1.0 equiv.) and (6-amino-3-chloro-2-fluorophenyl)boronic acid (5.5 g, 29.13 mmol, 2.0 equiv.) in 1,4-dioxane (50 mL) and water (10 mL) was added potassium phosphate (7.7 g, 36.41 mmol, 2.5 equiv.) and Pd(dppf) $Cl_2$ (1.1 g, 1.46 mmol, 0.1 equiv.). The flask was evacuated and flushed three times with nitrogen. The solution was stirred at 100° C. for 1 h under $N_2$, then diluted with water and extracted with EA twice. The combined organic layers were washed with brine, dried over $Na_2SO_4$, and concentrated under vacuum. The residue was purified by flash column chromatography on silica gel (0→80% EA/PE) to yield methyl 7-(6-amino-3-chloro-2-fluorophenyl)-5-oxo-1,2,3,5,8,8a-hexahydroindolizine-3-carboxylate as a yellow solid. LC/MS: mass calculated for $C_{16}H_{16}ClFN_2O_3$: 338.08, measured (ES, m/z): 339.10 $[M+H]^+$.

Step 2: Methyl (3S)-7-(6-azido-3-chloro-2-fluorophenyl)-5-oxo-1,2,3,5,8,8a-hexahydroindolizine-3-carboxylate To a mixture of methyl 7-(6-amino-3-chloro-2-fluorophenyl)-5-oxo-1,2,3,5,8,8a-hexahydroindolizine-3-carboxylate (3.4 g, 10.04 mmol, 1.0 equiv.) and azidotrimethylsilane (2.6 mL, 20.07 mmol, 2.0 equiv.) in acetonitrile (35 mL) was added tert-butyl nitrite (2.4 mL, 20.07 mmol, 2.0 equiv.) at 0° C. The solution was stirred at room temperature for 1 h, diluted with water and extracted with EA twice. The combined organic layers were washed with brine, dried over $Na_2SO_4$, and concentrated under vacuum. The residue was purified by silica gel chromatography (0-(80% EA/PE) to yield methyl 7-(6-azido-3-chloro-2-fluorophenyl)-5-oxo-1,2,3,5,8,8a-hexahydroindolizine-3-carboxylate as a yellow solid. LC/MS: mass calculated for $C_{16}H_{14}ClFN_4O_3$: 364.07, measured (ES, m/z): 365.10 $[M+H]^+$.

Step 3: Methyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate To a mixture of methyl 7-(6-azido-3-chloro-2-fluorophenyl)-5-oxo-1,2,3,5,8,8a-hexahydroindolizine-3-carboxylate (2.9 g, 7.95 mmol, 1.0 equiv.) and 4,4,4-trifluorobut-2-ynoic acid (5.5 g, 39.75 mmol, 5.0 equiv.) in acetonitrile (30 mL) was added cuprous oxide (455 mg, 3.18 mmol, 0.4 equiv.). The flask was evacuated and flushed three times with nitrogen. The solution was stirred at 80° C. for 2 h under $N_2$. The solution was concentrated under vacuum and purified by silica gel chromatography (0-(60% EA/PE) to yield methyl 7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate as a white solid. LC/MS: mass calculated for $C_{19}H_{15}ClF_4N_4O_3$: 458.08, measured (ES, m/z): 459.05 $[M+H]^+$.

Step 4: (3S)-7-(3-Chloro-2-fluoro-6-(4-(trifluoromethyl)-1H-1,2,3-triazol-1-yl)phenyl)-5-oxo-1,2,3,5,8,8a-hexahydroindolizine-3-carboxylic acid To a mixture of methyl 7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate (2.8 g, 6.10 mmol, 1.0 equiv.) in acetonitrile (30 mL) and water (0.2 mL) was added triethylamine (5.0 mL, 36.62 mmol, 6.0 equiv.) and lithium bromide (1.6 g, 18.31 mmol, 3.0 equiv.). The solution was stirred at 60° C. for 18 h, then concentrated under vacuum. The residue was purified by reverse phase chromatography on C18 column ($ACN/H_2O$ (0.05% $CF_3COOH$): 0→30%) to yield 7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylic acid as a yellow solid. LC/MS: mass calculated for $C_{18}H_{13}ClF_4N_4O_3$: 444.06, measured (ES, m/z): 445.15 $[M+H]^+$.

Step 5: 2-(2-(((Teri butyldimethylsilyl)oxy)methyl)-3-fluoropyridin-4-yl)-2-oxoethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate To a solution of (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylic acid (500 mg, 1.12 mmol, 1.0 equiv.) in N,N-dimethylformamide (10 mL) was added potassium carbonate (202 mg, 1.46 mmol, 1.3 equiv.). The reaction mixture was stirred for 0.5 h. 2-(((tert-Butyldimethylsilyl)oxy)methyl)-4-(1-ethoxyvinyl)-3-fluoropyridine (815 mg, 2.25 mmol, 2.0 equiv.) was added and the reaction mixture was stirred at room temperature for 1 h. Water was added, the mixture was extracted with EA. The combined extracts were washed with water, saturated brine, dried over $Na_2SO_4$, filtered and concentrated. The residue was purified by silica gel chromatography with EA/PE (0→70%) to yield 2-(2-(((tert butyldimethylsilyl)oxy)methyl)-3-fluoropyridin-4-yl)-2-oxoethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate as a yellow solid. LC/MS: mass calculated for $C_{32}H_{33}ClF_5N_5O_5Si$: 725.19, measured (ES, m/z): 726.35 $[M+H]^+$.

Step 6: (3S)-3-(5-(2-(((Tert-butyldimethylsilyl)oxy)methyl)-3-fluoropyridin-4-yl) 1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one To a solution of 2-(2-(((tert-butyldimethylsilyl)oxy)methyl)-3-fluoropyridin-4-yl)-2-oxoethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate (0.60 g, 0.83 mmol, 1.0 equiv.) and ammonium acetate (1.3 g, 16.53 mmol, 20.0 equiv.) in toluene (10 mL) was added acetic acid (0.5 mL). The reaction mixture was stirred at 100° C. for 1.5 h. The resulting mixture was concentrated under vacuum. The residue was purified by silica gel chromatography with MeOH/DCM (07%) to yield (3S)-3-(5-(2-(((tert-butyldimethylsilyl)oxy)methyl)-3-fluoropyridin-4-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one as a yellow solid. LC/MS: mass calculated for $C_{32}H_{33}ClF_5N_7O_2Si$: 705.21, measured (ES, m/z): 706.20 $[M+H]^+$.

Step 7: (3S,8aR)-7-(3-Chloro-2-fluoro-6-(4-(trifluoromethyl)-1H-1,2,3-triazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one To a solution of (3S)-3-(5-(2-(((tert-butyldimethylsilyl)oxy)methyl)-3-fluoropyridin-4-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one (0.49 g, 0.69 mmol, 1.0 equiv.) in THE (5 mL) was added triethylamine trihydrofluoride (0.56 g, 3.47 mmol, 5.0 equiv.). The reaction mixture was stirred at 70° C. for 1 h, then diluted with water and the organic layer was separated and concentrated. The residue was purified by reverse phase chromatography with $CH_3CN$/water (5→55%) to yield (3S,8aR)-7-(3-chloro-2-fluoro-6-(4-(trifluoromethyl)-1H-1,2,3-triazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one as a yellow solid. LC/MS: mass calculated for $C_{26}H_{19}ClF_5N_7O_2$: 591.12, measured (ES, m/z): 592.10 $[M+H]^+$.

Step 8: 4-(2-((3S,8aR)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)-3-fluoropicolinic acid To a mixture of (3S,8aR)-7-(3-chloro-2-fluoro-6-(4-(trifluoromethyl)-1H-1,2,3-triazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one (80 mg, 0.14 mmol, 1.0 equiv.) in DCM (5 mL) and $H_2O$ (0.25 mL) was added TEMPO (21 mg, 0.14 mmol, 1.0 equiv.) and $Phl(OAc)_2$ (2.2 g, 6.83 mmol, 3.0 equiv.). The reaction mixture was stirred at room temperature for 2 h and concentrated under reduced pressure. The residue was applied onto a C18 reverse column ($ACN/H_2O$ (0.05% $NH_4HCO_3$): 5→35%) to yield 4-(2-((3S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)-3-fluoropicolinic acid as a white solid.

LC/MS: mass calculated for $C_{28}H_{17}ClF_5N_7O_3$: 605.10, measured (ES, m/z): 606.15 $[M+H]^+$. $^1H$ NMR (400 MHz, Methanol-$d_4$) δ 8.99 (d, J=1.0 Hz, 1H), 8.38 (d, J=5.1 Hz, 1H), 8.18 (t, J=5.4 Hz, 1H), 7.74-7.85 (m, 1H), 7.67 (d, J=4.1 Hz, 1H), 7.48-7.58 (m, 1H), 5.72 (d, J=2.7 Hz, 1H), 5.19 (d, J=8.6 Hz, 1H), 3.85-4.02 (m, 1H), 2.86-2.99 (m, 1H), 2.57-2.70 (m, 1H), 2.16-2.39 (m, 3H), 1.98-2.16 (m, 1H). $^{19}F$ NMR (376 MHz, Methanol-$d_4$) δ 62.53, −113.68, −124.91.

Example 59: 6-(2-((3S*,8aR*)-7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-5-yl)-5-fluoroquinoxalin-2(1H)-one

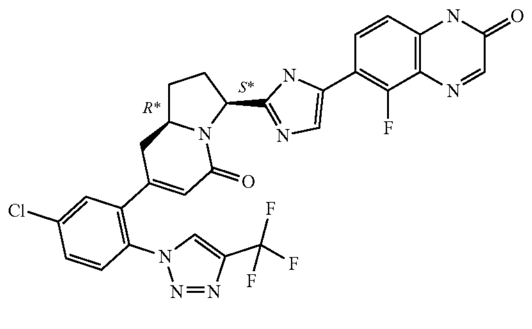 [SMILES: O=C1C=C(c2cc(Cl)ccc2-n2cc(C(F)(F)F)nn2)C[C@H]2CC[C@@H](c3ncc(-c4ccc5[nH]c(=O)cnc5c4F)[nH]3)N12]

LC/MS: mass calculated for $C_{28}H_{19}ClF_4N_8O_2$: 610.13, measured (ES, m/z): 611.15 $[M+H]^+$. $^1H$ NMR (300 MHz, DMSO-$d_6$) δ 12.59 (s, 1H), 11.97 (s, 1H), 9.35 (s, 1H), 8.15-8.24 (m, 2H), 7.71-7.81 (m, 3H), 7.38 (d, J=3.8 Hz, 1H), 7.17 (d, J=8.8 Hz, 1H), 5.70 (d, J=2.4 Hz, 1H), 5.03 (d, J=8.4 Hz, 1H), 3.61-3.76 (m, 1H), 2.32-2.49 (m, 1H), 2.11-2.30 (m, 2H), 1.87-2.07 (m, 3H). $^{19F}$ NMR (282 MHz, DMSO-$d_6$) δ −59.56, −126.68.

Example 61: (4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methyl dihydrogen phosphate

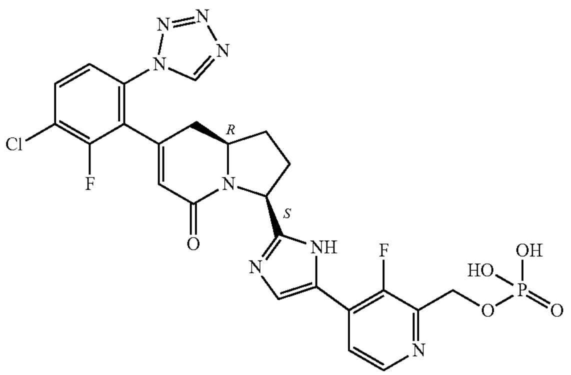

LC/MS: mass calculated for $C_{24}H_{20}ClF_2NBO_5P$: 604.10, measured (ES, m/z): 605.05 $[M+H]^+$. $^1H$ NMR (300 MHz, DMSO-$d_6$) δ 9.87 (s, 1H), 8.58 (d, J=5.1 Hz, 1H), 8.08-8.19 (m, 2H), 8.00 (t, J=8.4 Hz, 1H), 7.73 (dd, J=8.7, 1.5 Hz, 1H), 5.71 (d, J=2.6 Hz, 1H), 5.30 (d, J=9.6 Hz, 1H), 5.09 (dd, J=6.6, 2.0 Hz, 2H), 3.73-3.87 (m, 1H), 3.01-3.19 (m, 1H), 2.54-2.66 (m, 1H), 2.25-2.46 (m, 1H), 1.91-2.23 (m, 3H). $^{19}F$ NMR (282 MHz, DMSO-$d_6$) δ-112.48, −126.39.

Example 63: (3R',8aR)-3-(5-(2-(3-amino-1H-pyrazol-1-yl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

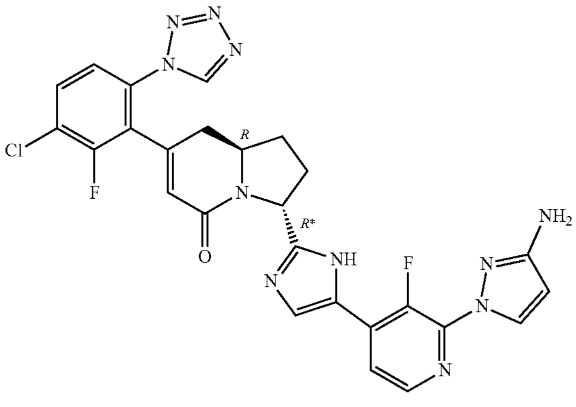

LC/MS: mass calculated for $C_{26}H_{20}ClF_2N_{11}O$: 575.15, measured (ES, m/z): 576.15 $[M+H]^+$. $^1H$ NMR (400 MHz, DMSO-$d_6$) δ 12.29 (s, 1H), 9.82 (s, 1H), 8.08-8.20 (m, 2H), 7.91-7.99 (m, 1H), 7.75-7.82 (m, 1H), 7.69 (dd, J=8.7, 1.5 Hz, 1H), 7.60 (d, J=3.6 Hz, 1H), 5.81 (d, J=2.7 Hz, 1H), 5.68 (d, J=2.7 Hz, 1H), 5.11-5.20 (m, 2H), 5.03 (d, J=8.8 Hz, 1H), 3.66-3.79 (m, 1H), 2.64-2.78 (m, 1H), 2.50-2.56 (m, 1H), 2.03-2.28 (m, 2H), 1.87-2.01 (m, 2H). $^{19}F$ NMR (376 MHz, DMSO-$d_6$) δ-112.84, −131.49.

Example 64: (3S,8aR*)-7-(5-chloro-2-(4-(trifluoromethyl)-1H-1,2,3-triazol-1-yl)phenyl)-3-(5-(3-fluoro-2-(hydroxymethyl)pyridin-4-yl)-1H-imidazol-2-yl)-2 3,8,8a-tetrahydroindolizin-1H-one

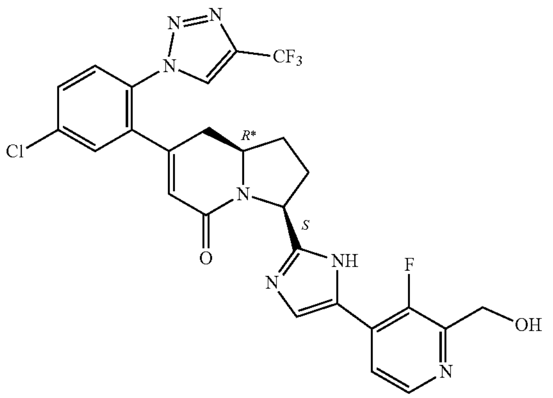

LC/MS: mass calculated for $C_{26}H_2OClF_4N_7O_2$: 573.13, measured (ES, m/z): 574.15 $[M+H]^+$. $^1H$ NMR (400 MHz, Methanol-$d_4$) δ 9.00 (s, 1H), 8.34 (d, J=5.3 Hz, 1H), 8.03 (t, J=5.7 Hz, 1H), 7.65-7.75 (m, 4H), 5.79 (d, J=2.7 Hz, 1H), 5.19 (d, J=8.7 Hz, 1H), 4.79-4.82 (m, 2H). 3.79-3.95 (m, 1H), 2.58-2.73 (m, 1H), 2.25-2.40 (m, 2H), 2.11-2.25 (m, 2H), 1.91-2.07 (m, 1H). 19F NMR (376 MHz, DMSO-$d_6$) δ −62.52, −76.94, −130.74.

Example 65: 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-2-(hydroxymethyl)pyridine 1-oxide

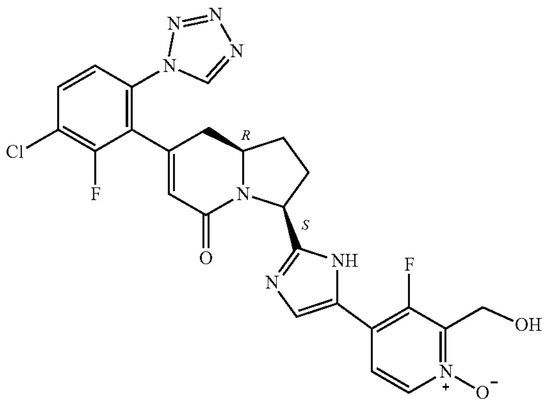

LC/MS: mass calculated for $C_{24}H_{19}ClF_2NBO_3$: 540.12, measured (ES, m/z): 541.15 $[M+H]^+$. $^1H$ NMR (400 MHz, Methanol-$d_4$): δ 9.57 (s, 1H), 8.29 (d, J=6.9 Hz, 1H), 8.10 (t, J=7.9 Hz, 1H), 7.77-7.85 (m, 1H), 7.60 (d, J=4.1 Hz, 1H), 7.55 (dd, J=8.7, 1.6 Hz, 1H), 5.76 (d, J=2.7 Hz, 1H), 5.16 (d, J=8.6 Hz, 1H), 4.94 (d, J=3.2 Hz, 2H), 3.88-4.01 (m, 1H), 2.72-2.89 (m, 1H), 2.56-2.69 (m, 1H), 2.14-2.39 (m, 3H), 1.97-2.12 (m, 1H). $^{19}F$ NMR (376 MHz, Methanol-$d_4$): δ−113.62, −124.02.

Example 66: (3S*)-3-(4-(6-(1H-pyrazol-5-yl)pyridin-2-yl)-5-fluoro-1H-imidazol-2-yl)-7-(3-chloro-2-fluoro-6-(1H-tetrazol-1-yl)phenyl)-2,3,8,8a-tetrahydroindolizin-5(1H)-one

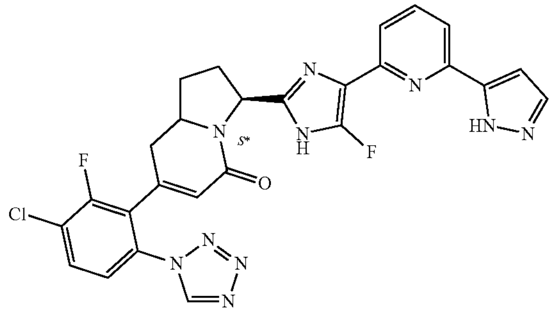 [SMILES: O=C1C=C(c2c(-n3cnnn3)ccc(Cl)c2F)CC2CC[C@@H](c3nc(-c4cccc(-c5ccn[nH]5)n4)c(F)[nH]3)N12]

LC/MS: mass calculated for $C_{28}H_{19}ClF_2N_{10}O$: 560.14, measured (ES, m/z): 561.15 $[M+H]^+$. $^1H$ NMR (400 MHz, DMSO-$d_6$) δ 12.96-13.61 (m, 1H), 12.35-12.67 (m, 1H), 9.83 (s, 1H), 7.92-7.99 (m, 1H), 7.75-7.91 (m, 2H), 7.68-7.72 (m, 1H), 7.61 (s, 1H), 7.34-7.41 (m, 1H), 6.91-7.21 (m, 1H), 5.67 (s, 1H), 4.91-5.17 (m, 1H), 3.65-3.80 (m, 1H), 2.51-2.63 (m, 2H), 1.88-2.29 (m, 4H). $^{19}F$ NMR (376 MHz, DMSO-$d_6$) δ −112.92, −128.21.

Example 67: (3S,8aR)-7-(3-chloro-2-fluoro-6-(4-(trifluoromethyl)-1H-1,2,3-triazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one

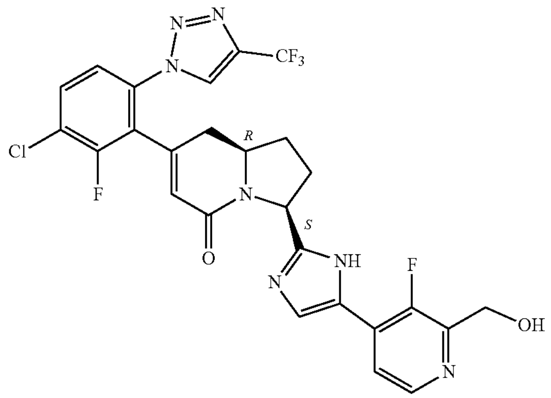

Step 1: 2-(2-(((Tert-butyldimethylsilyl)oxy)methyl)-3-fluoropyridin-4-yl)-2-oxoethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate To a solution of (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylic acid (500 mg, 1.12 mmol, 1.0 equiv.) in N,N-dimethylformamide (10 mL) was added potassium carbonate (202 mg, 1.46 mmol, 1.3 equiv.). The reaction mixture was stirred for 0.5 h, then 2-(((tert-butyldimethylsilyl)oxy)methyl)-4-(1-ethoxyvinyl)-3-fluoropyridine (815 mg, 2.25 mmol, 2.0 equiv.) was added and the reaction mixture was stirred at room temperature for 1 h. The resulting mixture was diluted with water and extracted with EA. The combined extracts were washed with water, saturated brine, dried over $Na_2SO_4$, filtered and concentrated. The residue was purified by flash column chromatography on silica gel with EA/PE (0→70%) to yield 2-(2-(((tert-butyldimethylsilyl)oxy)methyl)-3-fluoropyridin-4-yl)-2-oxoethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate as a yellow solid. LC/MS: mass calculated for $C_{32}H_{33}ClF_5N_5O_5Si$: 725.19, measured (ES, m/z): 726.35 $[M+H]^+$.

Step 2: (3S)-3-(5-(2-(((Tert-butyldimethylsilyl)oxy) methyl)-3-fluoropyridin-4-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5 (1H)-one To a solution of 2-(2-(((tert-butyldimethylsilyl)oxy) methyl)-3-fluoropyridin-4-yl)-2-oxoethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate (0.60 g, 0.83 mmol 1.0 equiv.) and ammonium acetate (1.3 g, 16.53 mmol, 20.0 equiv.) in toluene (10 mL) was added acetic acid (0.5 mL). The reaction mixture was stirred at 100° C. for 1.5 h. The resulting mixture was concentrated under vacuum. The residue was purified by silica gel chromatography with MeOH/DCM (0→7%) to yield (3S)-3-(5-(2-(((tert-butyldimethylsilyl)oxy)methyl)-3-fluoropyridin-4-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one as a yellow solid. LC/MS: mass calculated for $C_{32}H_{33}ClF_5N_7O_2Si$: 705.21, measured (ES, m/z): 706.20 $[M+H]^+$.

Step 3: (3S,8aR)-7-(3-Chloro-2-fluoro-6-(4-(trifluoromethyl)-1H-12,3-triazol-1-yl) phenyl)-3-(5-(3-fluoro-2-(hydroxymethyl)pyridin-4-yl)-1H-imidazol-2-yl)-2,3,8,8a-tetrahydroindolizin-5(1H)-one To a solution of (3S)-3-(5-(2-(((tert-butyldimethylsilyl) oxy)methyl)-3-fluoropyridin-4-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one (0.49 g, 0.69 mmol, 1.0 equiv.) in THE (5 mL) was added triethylamine trihydrofluoride (0.56 g, 3.47 mmol, 5.0 equiv.). The reaction mixture was stirred at 70° C. for 1 h, then purified by reverse phase chromatography with $CH_3CN$/water (5→55%) to yield (3S,8aR)-7-(3-chloro-2-fluoro-6-(4-(trifluoromethyl)-1H-1,2,3-triazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one as a yellow solid.

LC/MS: mass calculated for $C_{26}H_{19}ClF_5N_7O_2$: 591.12, measured (ES, m/z): 592.10 $[M+H]^+$. $^1H$ NMR (400 MHz, Methanol-$d_4$) δ 8.97-9.01 (m, 1H), 8.33 (d, J=5.2 Hz, 1H), 8.01 (t, J=5.6 Hz, 1H), 7.76-7.83 (m, 1H), 7.63 (d, J=3.9 Hz, 1H), 7.54 (dd, J=8.7, 1.6 Hz, 1H), 5.72 (d, J=2.8 Hz, 1H), 5.16-5.21 (m, 1H), 4.80 (d, J=2.3 Hz, 2H), 3.87-3.99 (m, 1H), 2.84-2.98 (m, 1H), 2.58-2.68 (m, 1H), 2.18-2.40 (m, 3H), 1.99-2.14 (m, 1H). $^{19}F$ NMR (376 MHz, methanol-$d_4$) δ −62.58, −113.68, −130.98.

Example 68: (3S,8aR)-3-(4-(2-(5-amino-1H-pyrazol-1-yl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-1H)-one

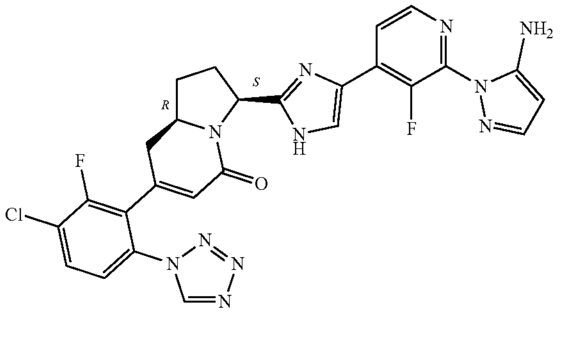

LC/MS: mass calculated for $C_{28}H_{20}ClF_2N_{11}O$: 575.15, measured (ES, m/z): 576.15 $[M+H]^+$. $^1H$ NMR (400 MHz, DMSO-$d_6$) δ 12.33 (s, 1H), 9.82 (s, 1H), 8.29 (d, J=5.1 Hz, 1H), 7.90-8.00 (m, 2H), 7.60-7.73 (m, 2H), 7.33 (d, J=1.8 Hz, 1H), 5.64-5.77 (m, 3H), 5.44 (d, J=1.8 Hz, 1H), 5.04 (d, J=8.8 Hz, 1H), 3.66-3.82 (m, 1H), 2.64-2.79 (m, 1H), 2.50-2.60 (m, 1H), 2.04-2.25 (m, 2H), 1.88-2.02 (m, 2H). $^{19}F$ NMR (376 MHz, DMSO-$d_6$) δ −112.82, 128.53.

Example 69: (3S,8aR)-3-(5-(6-amino-2-fluoropyridin-3-yl)-4-fluoro-1H-imidazol-2-yl)-7-(5-chloro-2-(1H-tetrazol-1-yl)phenyl)-2,3,8,8a-tetrahydroindolizin-5(1H)-one

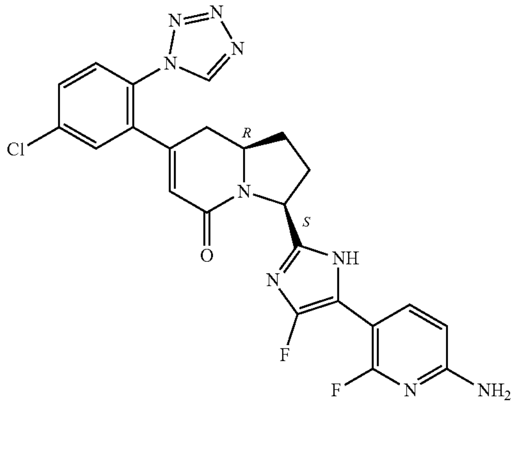

LC/MS: mass calculated for $C_{23}H_{18}ClF_2N_9O$: 509.13, measured (ES, m/z): 510.15 $[M+H]^+$. $^1H$ NMR (400 MHz, DMSO-$d_6$) δ 11.95 (s, 1H), 9.84 (s, 1H), 7.74-7.85 (m, 3H), 7.50-7.61 (m, 1H), 6.52 (s, 2H), 6.40 (dd, J=8.3, 2.0 Hz, 1H), 5.55 (d, J=2.6 Hz, 1H), 4.93 (d, J=8.6 Hz, 1H), 3.56-3.76 (m, 1H), 2.40-2.50 (m, 1H), 2.24-2.38 (m, 1H), 2.07-2.21 (m, 1H), 1.98-2.06 (m, 1H), 1.80-1.96 (m, 2H). $^{19}F$ NMR (376 MHz, DMSO-$d_6$) δ −71.32, −136.14.

Example 70: (3S*,8aR)-3-(5-(2-amino-3-fluoropyridin-4-yl)-4-fluoro-1H-imidazol-2-yl)-7-(5-chloro-2-(1H-tetrazol-1-yl)phenyl)-2,3,8,8a-tetrahydroindolizin-5(1H)-one

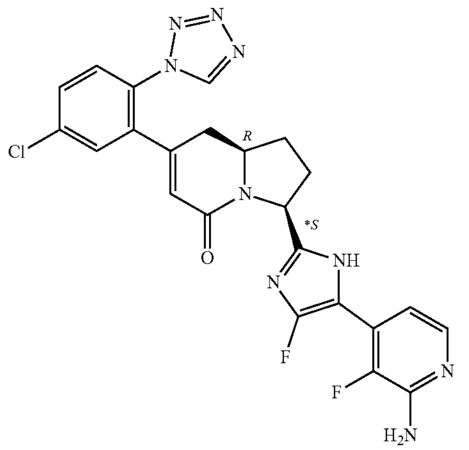

Step 1: 2-(2-Acetamido-3-fluoropyridin-4-yl)-2-oxoethyl (8aR)-7-(5-chloro-2-(1H-tetrazol-1-yl)phenyl)-5-oxo-1,2,3,5,8,8a-hexahydroindolizine-3-carboxylate To a solution of (8aR)-7-(5-chloro-2-(1H-tetrazol-1-yl)phenyl)-5-oxo-1,2,3,5,8,8a-hexahydroindolizine-3-carboxylic acid (2.0 g, 5.56 mmol, 1.0 equiv.) in $CH_3CN$ (20 mL) was added $K_2CO_3$ (1.2 g, 8.34 mmol, 1.5 equiv.). After stirring at room temperature for 0.5 h, N-(4-(2-bromoacetyl)-3-fluoropyridin-2-yl)acetamide (2.3 g, 8.34 mmol, 1.5 equiv.) was added. The mixture was stirred at room temperature for 1 h. The residue was purified by silica gel chromatography (0→10% MeOH/DCM) to yield the 2-(2-acetamido-3-fluoropyridin-4-yl)-2-oxoethyl (8aR)-7-(5-chloro-2-(1H-tetrazol-1-yl)phenyl)-5-oxo-1,2,3,5,8,8a-hexahydroindolizine-3-carboxylate as a yellow solid. LC/MS: mass calculated for $C_{25}H_{21}ClFN_7O_5$: 553.13, measured (ES, m/z): 554.05 $[M+H]^+$.

Step 2: N-(4-(2-((8aR)-7-(5-chloro-2-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide To a solution of 2-(2-acetamido-3-fluoropyridin-4-yl)-2-oxoethyl (8aR)-7-(5-chloro-2-(1H-tetrazol-1-yl)phenyl)-5-oxo-1,2,3,5,8,8a-hexahydroindolizine-3-carboxylate (2.5 g, 4.51 mmol, 1.0 equiv.) in toluene (30 mL) and acetic acid (3 mL) was added ammonium acetate (5.2 g, 67.70 mmol, 15.0 equiv.). The mixture was stirred at 100° C. for 1 h. The solvent was removed under vacuum and the residue was purified by silica gel column with MeOH/DCM (0→10%) to yield N-(4-(2-((8aR)-7-(5-chloro-2-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide as a yellow solid. LC/MS: mass calculated for $C_{25}H_{21}ClFN_9O_2$: 533.13, measured (ES, m/z): 534.40 $[M+H]^+$.

Step 3: N-(4-(2-((8aR)-7-(5-chloro-2-(1H-tetrazol-1-yl)phenyl)-5-oxo-1,2,3,5,8,8a-hexahydroindolizin-3-yl)-4-fluoro-1H-imidazol-5-yl)-3-fluoropyridin-2-yl)acetamide To a solution of n-(4-(2-((8aR)-7-(5-chloro-2-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide (120 mg, 0.23 mmol, 1.0 equiv.) in DCM (5 mL) and acetone (5 mL) were added NFSI (637 mg, 2.02 mmol, 9.0 equiv.), and $NaHCO_3$ (283 mg, 3.37 mmol, 15.0 equiv.). The resulting mixture was maintained under nitrogen and stirred at 60° C. for 3 days. The residue was purified by C18 column with $CH_3CN$/0.05% TFA water (5→50%) to yield the N-(4-(2-((8aR)-7-(5-chloro-2-(1H-tetrazol-1-yl)phenyl)-5-oxo-1,2,3,5,8,8a-hexahydroindolizin-3-yl)-4-fluoro-1H-imidazol-5-yl)-3-fluoropyridin-2-yl)acetamide as a yellow solid. LC/MS: mass calculated for $C_{25}H_{20}ClF_2N_9O_2$: 551.14, measured (ES, m/z): 552.35 $[M+H]^+$.

Step 4: (3S',8aR)-3-(5-(2-Amino-3-fluoropyridin-4-yl)-4-fluoro-1H-imidazol-2-yl)-7-(5-chloro-2-(1H-tetrazol-1-yl)phenyl)-2,3,8,8a-tetrahydroindolizin-5(1H)-one To a solution of N-(4-(2-((8aR)-7-(5-chloro-2-(1H-tetrazol-1-yl)phenyl)-5-oxo-1,2,3,5,8,8a-hexahydroindolizin-3-yl)-4-fluoro-1H-imidazol-5-yl)-3-fluoropyridin-2-yl)acetamide (45 mg, 0.08 mmol) in THE (2 mL) was added HCl (2 mL, 2 M). The mixture was stirred at 50° C. for 2 h. The solvent was removed under vacuum and the residue was purified by C18 column [condition: ACN-water-6.5 mM $NH_4HCO_3+NH_3H_2O$ (5→50%)] to yield a residue. The residue was purified by chiral HPLC [Column: CHIRAL ART cellulose-SB, 4.6*100 mm, 3 um; mobile phase A: MtBE (0.1% DEA): EtOH=50:50, mobile phase B; flow rate: 1 mL/min] to yield (3'S,8aR)-3-(5-(2-amino-3-fluoropyridin-4-yl)-4-fluoro-1H-imidazol-2-yl)-7-(5-chloro-2-(1H-tetrazol-1-yl)phenyl)-2,3,8,8a-tetrahydroindolizin-5(1H)-one as an off-white solid.

LC/MS: mass calculated for $C_{23}H_{18}ClF_2N_9O$: 509.13, measured (ES, m/z): 510.15 $[M+H]^+$. $^1H$ NMR (400 MHz, DMSO-$d_6$) δ 12.36 (s, 1H), 9.84 (s, 1H), 7.81-7.84 (m, 1H), 7.71-7.80 (m, 3H), 6.62-6.66 m, 1H), 6.28 (s, 2H), 5.55 (d, J=2.7 Hz, 1H), 5.01 (d, J=8.7 Hz, 1H), 3.64-3.76 (m, 1H), 2.41-2.48 (m, 1H), 2.29-2.39 (m, 1H), 2.10-2.22 (m, 1H), 2.00-2.08 (m, 1H), 1.82-1.99 (m, 2H). $^{19}F$ NMR (376 MHz, DMSO-$d_6$) δ-127.18, −143.05.

Example 71: (3R*,8aR)-7-(3-chloro-2-fluoro-6-(1H-tetrazol-1-yl)phenyl)-3-(5-(3-fluoro-2-(1H-1,2,3-triazol-1-yl)pyridin-4-yl)-1H-imidazol-2-yl)-2,3,8,8a-tetrahydroindolizin-5(1H)-one

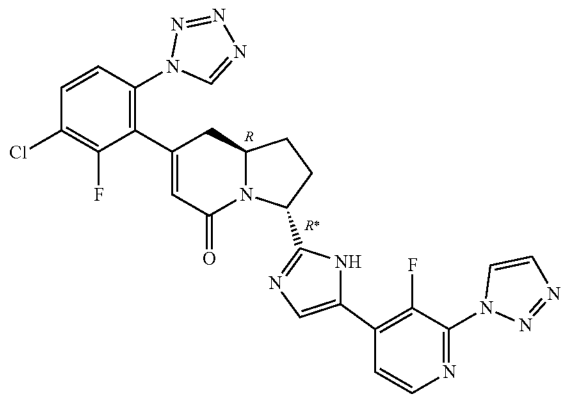

Step 1: 3-Fluoro-4-iodo-2-(1H-1,2,3-triazol-1-yl)pyridine

To a solution of 2,3-difluoro-4-iodopyridine (2.0 g, 8.30 mmol, 1.0 equiv.) in DMSO (20 mL) was added 2H-1,2,3-triazole (573 mg, 8.30 mmol, 1.0 equiv.) and $Cs_2CO_3$ (4.1 g, 12.45 mmol, 1.5 equiv.). The resulting mixture was stirred at 25° C. for 1 h. The mixture was extracted with EA (60 mL) and $H_2O$ (40 mL). The organic layers were combined, dried over anhydrous sodium sulfate, filtered and concentrated. The residue was purified by silica gel chromatography (10→30% EA/PE) to yield 3-fluoro-4-iodo-2-(1H-1,2,3-triazol-1-yl)pyridine as a white solid. LC/MS: mass calculated for $C_7H_4FIN_4$: 289.95, measured (ES, m/z): 291.10 $[M+H]^+$.

Step 2: 4-(1-Ethoxyvinyl)-3-fluoro-2-(1H-1,2,3-triazol-1-yl)pyridine

To a solution of 3-fluoro-4-iodo-2-(1H-1,2,3-triazol-1-yl)pyridine (900 mg, 3.10 mmol, 1.0 equiv.) in 1,4-dioxane (20 mL) was added tributyl(1-ethoxyvinyl)stannane (2.2 g, 6.20 mmol, 2.0 equiv.) and $Pd(PPh_3)_4$ (359 mg, 0.31 mmol, 0.1 equiv.). The resulting mixture was stirred at 100° C. for 6 h. The mixture was extracted with EA (50 mL) and $H_2O$ (30 mL). The organic layers were combined, dried over anhydrous sodium sulfate, and concentrated. The residue was purified by silica gel chromatography (30-(50% ethyl acetate/petroleum ether) to yield 4-(1-ethoxyvinyl)-3-fluoro-2-(1H-1,2,3-triazol-1-yl)pyridine as a yellow oil. LC/MS: mass calculated for $C_{11}H_{11}FN_4O$: 234.09, measured (ES, m/z): 235.25 $[M+H]^+$.

Step 3: 2-Bromo-1-(3-fluoro-2-(1H-1,2,3-triazol-1-yl)pyridin-4-yl)ethan-1-one

To a solution of 4-(1-ethoxyvinyl)-3-fluoro-2-(1H-1,2,3-triazol-1-yl)pyridine (700 mg, 2.90 mmol, 1.0 equiv.) in THE (8 mL) and $H_2O$ (2 mL) was added NBS (479 mg, 2.61 mmol, 0.9 equiv.). The resulting mixture was stirred at 25° C. for 1 h. The resulting mixture was extracted with ethyl acetate (30 mL). The organic layers were combined, dried over anhydrous sodium sulfate, filtered and concentrated to yield 2-bromo-1-(3-fluoro-2-(1H-1,2,3-triazol-1-yl)pyridin-4-yl)ethan-1-one as a yellow solid. LC/MS: mass calculated for $C_9H_8BrFN_4O$: 283.97, measured (ES, m/z): 284.95 $[M+H]^+$.

Step 4: 2-(3-Fluoro-2-(1H-1,2,3-triazol-1-yl)pyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate To a solution of (8aR)-7-(3-chloro-2-fluoro-6-(1H-tetrazol-1-yl)phenyl)-5-oxo-1,2,3,5,8,8a-hexahydroindolizine-3-carboxylic acid (186 mg, 0.49 mmol, 1.0 equiv.) in ACN (5 mL) was added $K_2CO_3$ (145 mg, 1.05 mmol, 2.1 equiv.). The resulting mixture was stirred at 25° C. for 0.5 h. 2-Bromo-1-(3-fluoro-2-(1H-1,2,3-triazol-1-yl)pyridin-4-yl)ethan-1-one (200 mg, 0.70 mmol, 1.4 equiv.) was then added to the mixture. The resulting mixture was stirred at 25° C. for 1 h, then concentrated under vacuum. The residue was purified by silica gel chromatography (0→20% MeOH/DCM) to yield 2-(3-fluoro-2-(1H-1,2,3-triazol-1-yl)pyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylates a yellow solid. LC/MS: mass calculated for $C_{25}H_{18}ClF_2N_9O_4$: 581.11, measured (ES, m/z): 582.30 $[M+H]^+$.

Step 5: (3R,8aR)-7-(3-Chloro-2-fluoro-6-(1H-tetrazol-1-yl)phenyl)-3-(5-(3-fluoro-2-(1H-1,2,3-triazol-1-yl)pyridin-4-yl)-1H-imidazol-2-yl)-2,3,8,8a-tetrahydroindolizin-5(1H)-one To a solution of 2-(3-fluoro-2-(1H-1,2,3-triazol-1-yl)pyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate (290 mg, 0.50 mmol, 1.0 equiv.) in AcOH (0.3 mL) and toluene (3 mL) was added ammonium acetate (576 mg, 7.50 mmol, 15.0 equiv.). The resulting mixture was stirred at 90° C. for 1 h, concentrated under vacuum. The residue was purified by silica gel chromatography (0→10% MeOH/DCM) and chiral-HPLC with [Column: (R,R)-WHELK-O1-Kromasil, 2.12*25 cm, 5 um; Mobile Phase A: MTBE(0.5% 2M $NH_3$-MeOH)—HPLC, Mobile Phase B: EtOH—HPLC; Flow rate: 20 mL/min; Gradient: 50 B to 50 B in 16 min; 220/254 nm; RT1:9.558; RT2:14.518; Injection Volume: 1.5 ml; Number Of Runs: 7] to yield (3R*,8aR)-7-(3-chloro-2-fluoro-6-(1H-tetrazol-1-yl)phenyl)-3-(5-(3-fluoro-2-(1H-1,2,3-triazol-1-yl)pyridin-4-yl)-1H-imidazol-2-yl)-2,3,8,8a-tetrahydroindolizin-5(1H)-one as a white solid.

LC/MS: mass calculated for $C_{25}H_{18}ClF_2N_{11}O$: 561.14, measured (ES, m/z): 562.10 $[M+H]^+$. $^1H$ NMR (400 MHz, DMSO-$d_6$) δ 12.42 (s, 1H), 9.83 (s, 1H), 8.73-8.75 (m, 1H), 8.43 (d, J=5.0 Hz, 1H), 8.11-8.18 (m, 1H), 7.91-8.03 (m, 2H), 7.66-7.76 (m, 2H), 5.69 (d, J=2.7 Hz, 1H), 5.05 (d, J=8.7 Hz, 1H), 3.67-3.82 (m, 1H), 2.63-2.81 (m, 1H), 2.49-2.58 (m, 1H), 2.11-2.32 (m, 2H), 1.88-2.03 (m, 2H). $^{19}F$ NMR (376 MHz, DMSO-$d_6$) δ −112.83, −131.19.

Example 72: (3R*,8aR)-3-(5-(2-(3-amino-1H-pyrazol-1-yl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

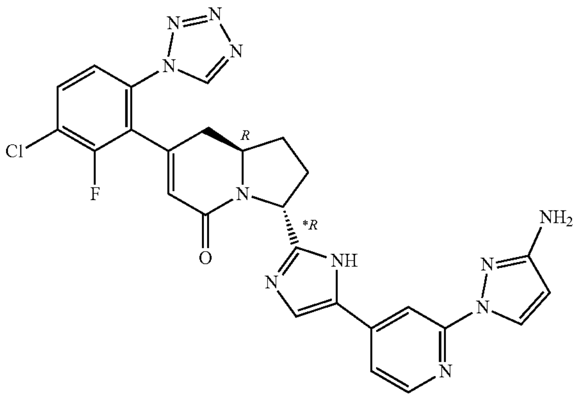

LC/MS: mass calculated for $C_{26}H_{21}ClFN_{11}O$: 557.16, measured (ES, m/z): 558.10 $[M+H]^+$. $^1H$ NMR (400 MHz, DMSO-$d_6$) δ 12.05 (s, 1H), 9.80-9.84 (m, 1H), 8.18-8.28 (m, 2H), 7.91-8.01 (m, 2H), 7.76 (d, J=2.2 Hz, 1H), 7.65-7.73 (m, 1H), 7.38-7.52 (m, 1H), 5.77 (d, J=2.6 Hz, 1H), 5.62-5.70 (m, 1H), 5.15-5.26 (m, 2H), 4.97-5.02 (m, 1H), 3.61-3.73 (m, 1H), 2.71-2.83 (m, 1H), 2.50-2.55 (m, 1H), 2.03-2.34 (m, 2H), 1.85-2.04 (m, 2H). $^{19}F$ NMR (376 MHz, DMSO-$d_6$) δ −73.40, −112.67.

Example 73: (3S,8aR*)-7-(3-chloro-2-fluoro-6-(1H-tetrazol-1-yl)phenyl)-3-(5-(3-fluoro-2-(((S)-tetrahydrofuran-3-yl)amino)pyridin-4-yl)-1H-imidazol-2-yl)-2,3,8,8a-tetrahydroindolizin-5(1H)-one

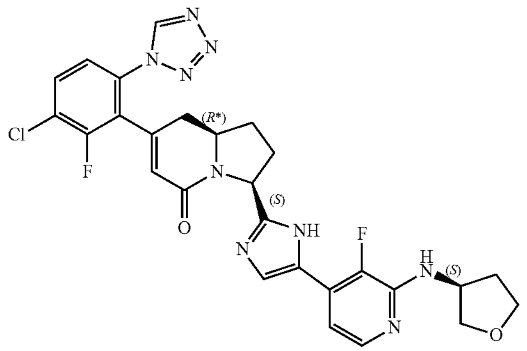

Step 1: (S)-3-Fluoro-4-iodo-n-(tetrahydrofuran-3-yl)pyridin-2-amine

To a solution of 2,3-difluoro-4-iodopyridine (1.0 g, 4.15 mmol, 1.0 equiv.) in DMSO (15 mL) was added (S)-tetrahydrofuran-3-amine hydrochloride (1.5 g, 12.45 mmol, 3.0 equiv.) and $Et_3N$ (2.5 g, 24.90 mmol, 6.0 equiv.). The resulting mixture was stirred at 100° C. overnight. After cooling to room temperature, the reaction was quenched with water. The resulting mixture was extracted with ethyl acetate. The organic layers were combined, dried over anhydrous sodium sulfate, and concentrated. The residue was purified by silica gel chromatography (0→30% ethyl acetate/petroleum ether) to yield the (S)-3-fluoro-4-iodo-n-(tetrahydrofuran-3-yl)pyridin-2-amine as a yellow oil. LC/MS: mass calculated for $C_9H_{10}FIN_2O$: 307.98, measured (ES, m/z): 308.90 $[M+H]^+$.

Step 2: (S)-4-(1-Ethoxyvinyl)-3-fluoro-n-(tetrahydrofuran-3-yl)pyridin-2-amine

To a solution of (S)-3-fluoro-4-iodo-n-(tetrahydrofuran-3-yl)pyridin-2-amine (550 mg, 1.79 mmol, 1.0 equiv.) in 1,4-dioxane (10 mL) were added tributyl(1-ethoxyvinyl)tin (1.0 g, 2.86 mmol, 1.6 equiv.), $Pd(PPh_3)_4$ (103 mg, 0.089 mmol, 0.05 equiv.). The resulting mixture was maintained under nitrogen and stirred at 100° C. overnight. After cooling to room temperature, the reaction was quenched with water. The resulting mixture was extracted with ethyl acetate. The organic layers were combined, dried over anhydrous sodium sulfate, and concentrated. The residue was purified by silica gel chromatography (0→30% ethyl acetate/petroleum ether) to yield the (S)-4-(1-ethoxyvinyl)-3-fluoro-N-(tetrahydrofuran-3-yl)pyridin-2-amine as a red oil. LC/MS: mass calculated for $C_{13}H_{17}FN_2O_2$: 252.13, measured (ES, m/z): 253.25 $[M+H]^+$.

Step 3: (S)-2-Bromo-1-(3-fluoro-2-((tetrahydrofuran-3-yl)amino)pyridin-4-yl)ethan-1-one To a solution of (S)-4-(1-ethoxyvinyl)-3-fluoro-n-(tetrahydrofuran-3-yl)pyridin-2-amine (420 mg, 1.67 mmol, 1.0 equiv.) in THE (3 mL) and $H_2O$ (1 mL) was added NBS (296 mg, 1.67 mmol, 1.0 equiv.). The resulting mixture was maintained under nitrogen and stirred at room temperature for 1 h. The reaction was quenched with water. The resulting mixture was extracted with ethyl acetate. The organic layers were combined, dried over anhydrous sodium sulfate, and concentrated. The residue was purified by silica gel chromatography (0→40% ethyl acetate/petroleum ether) to yield the (S)-2-bromo-1-(3-fluoro-2-((tetrahydrofuran-3-yl)amino)pyridin-4-yl)ethan-1-one as a yellow oil. LC/MS: mass calculated for $C_{11}H_{12}BrFN_2O_2$: 302.01, measured (ES, m/z): 303.00, 305.00 [M+H, M+H+2]$^+$.

Step 4: 2-(3-Fluoro-2-(((S)-tetrahydrofuran-3-yl)amino)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate To a solution of (3S,8aR)-7-(6-amino-3-chloro-2-fluorophenyl)-5-oxo-1,2,3,5,8,8a-hexahydroindolizine-3-carboxylic acid (357 mg, 1.10 mmol, 1.0 equiv.) in ACN (13 mL) was added $K_2CO_3$ (304 mg, 2.20 mmol, 2.0 equiv.) at room temperature. After stirring for 30 min, (S)-2-bromo-1-(3-fluoro-2-((tetrahydrofuran-3-yl)amino)pyridin-4-yl)ethan-1-one (400 mg, 1.32 mmol, 1.2 equiv.) was added. The resulting mixture was stirred at room temperature overnight, then concentrated under reduced pressure. The residue was purified by silica gel chromatography (0→5% MeOH/DCM) to yield the 2-(3-fluoro-2-(((S)-tetrahydrofuran-3-yl)amino)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate as a yellow solid. LC/MS: mass calculated for $C_{26}H_{25}ClF_2N_4O_5$: 546.15, measured (ES, m/z): 547.35 $[M+H]^+$.

Step 5: (3S)-7-(6-Amino-3-chloro-2-fluorophenyl)-3-(5-(3-fluoro-2-(((S)-tetrahydrofuran-3-yl)amino)pyridin-4-yl)-1H-imidazol-2-yl)-2,3,8,8a-tetrahydroindolizin-5(1H)-one To a solution of 2-(3-fluoro-2-(((S)-tetrahydrofuran-3-yl)amino)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate (20 mg, 0.037 mmol, 1.0 equiv.) in toluene (1 mL) and HOAc (0.05 mL) was added $NH_4OAc$ (56 mg, 0.73 mmol, 20.0 equiv.). The resulting mixture was stirred at 100° C. for 2 h, then concentrated. The residue was purified by silica gel chromatography (0-(10% MeOH/DCM) to yield (3S)-7-(6-amino-3-chloro-2-fluorophenyl)-3-(5-(3-fluoro-2-(((S)-tetrahydrofuran-3-yl)amino)pyridin-4-yl)-1H-imidazol-2-yl)-2,3,8,8a-tetrahydroindolizin-5(1H)-one as a yellow solid. LC/MS: mass calculated for $C_{26}H_{25}ClF_2N_6O_2$: 526.17, measured (ES, m/z): 527.35 $[M+H]^+$.

Step 6: (3S,8aR*)-7-(3-Chloro-2-fluoro-6-(1H-tetrazol-1-yl)phenyl)-3-(5-(3-fluoro-2-(((S)-tetrahydrofuran-3-yl)amino)pyridin-4-yl)-1H-imidazol-2-yl)-2,3,8,8a-tetrahydroindolizin-5(1H)-one To a solution of (3S)-7-(6-amino-3-chloro-2-fluorophenyl)-3-(5-(3-fluoro-2-(((S)-tetrahydrofuran-3-yl)amino)pyridin-4-yl)-1H-imidazol-2-yl)-2,3,8,8a-tetrahydroindolizin-5(1H)-one (413 mg, 0.78 mmol, 1.0 equiv.) in AcOH (15 mL) was added azidotrimethylsilane (1.8 g, 15.68 mmol, 20.0 equiv.), followed by addition of trimethoxymethane (1.7 g, 15.68 mmol, 20.0 equiv.). The resulting mixture was stirred at 80° C. for 3 h, then concentrated. The residue was purified by reversed phase chromatography on C18 column ($MeCN/H_2O$ (0.05% $NH_4HCO_3$): 0→45%) and prep-chiral HPLC to yield the (3S,8aR*)-7-(3-chloro-2-fluoro-6-(1H-tetrazol-1-yl)phenyl)-3-(5-(3-fluoro-2-(((S)-tetrahydrofuran-3-yl)amino)pyridin-4-yl)-1H-imidazol-2-yl)-2,3,8,8a-tetrahydroindolizin-5(1H)-one as a white solid.

LC/MS: mass calculated for $C_{27}H_{24}ClF_2N_9O_2$: 579.17, measured: 580.20 $[M+H]^+$. $^1H$ NMR (400 MHz, DMSO-$d_6$) δ 12.11 (s, 1H), 9.81 (s, 1H), 7.95 (dd, J=8.7, 7.8 Hz, 1H), 7.78 (d, J=5.3 Hz, 1H), 7.69 (dd, J=8.7, 1.5 Hz, 1H), 7.41 (dd, J=3.9, 1.9 Hz, 1H), 7.11-7.13 (m, 1H), 6.55 (dd, J=6.1, 1.6 Hz, 1H), 5.66 (d, J=2.7 Hz, 1H), 5.01 (d, J=8.6 Hz, 1H), 4.37-4.52 (m, 1H), 3.77-3.94 (m, 2H), 3.62-3.77 (m, 3H), 3.55 (dd, J=8.7, 4.6 Hz, 1H), 2.71-2.73 (m, 1H), 2.02-2.27 (m, 3H), 1.82-2.01 (m, 3H). $^{19}F$ NMR (376 MHz, DMSO-$d_6$) δ −112.86, −142.49.

Example 74: (3S,8aS*)-7-(3-chloro-2-fluoro-6-(1H-tetrazol-1-yl)phenyl)-3-(5-(3-fluoro-2-(((S)-tetrahydrofuran-3-yl)amino)pyridin-4-yl)-1H-imidazol-2-yl)-2,3,8,8a-tetrahydroindolizin-5(1H)-one

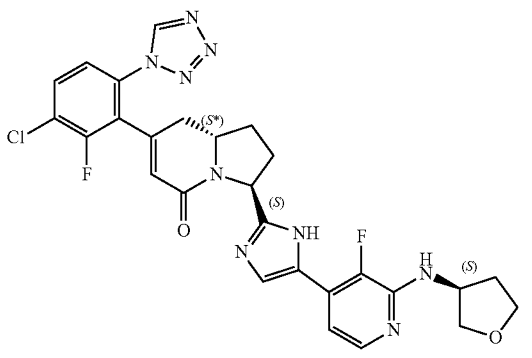

LC/MS: mass calculated for $C_{27}H_{24}ClF_2N_9O_2$: 597.17, measured: 598.20 $[M+H]^+$. $^1H$ NMR (400 MHz, DMSO-$d_6$) δ 12.11 (s, 1H), 9.81 (s, 1H), 7.95 (dd, J=8.7, 7.8 Hz, 1H), 7.78 (d, J=5.3 Hz, 1H), 7.69 (dd, J=8.7, 1.5 Hz, 1H), 7.41 (dd, J=3.9, 1.9 Hz, 1H), 7.11-7.13 (m, 1H), 6.55 (dd, J=6.1, 1.6 Hz, 1H), 5.66 (d, J=2.7 Hz, 1H), 5.01 (d, J=8.6 Hz, 1H), 4.37-4.52 (m, 1H), 4.11-4.18 (m, 1H), 3.77-3.94 (m, 3H), 3.62-3.76 (m, 1H), 3.55 (dd, J=8.7, 4.6 Hz, 1H), 2.71-2.73 (m, 1H), 2.42-2.49 (m, 1H), 2.18-2.34 (m, 2H), 1.82-2.01 (m, 2H), 1.73-1.79 (m, 1H). $^{19}F$ NMR (376 MHz, DMSO-$d_6$) δ −113.05, −142.51.

Example 75: [4-[2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]methyl (2S)-2-amino-3-methyl-butanoate

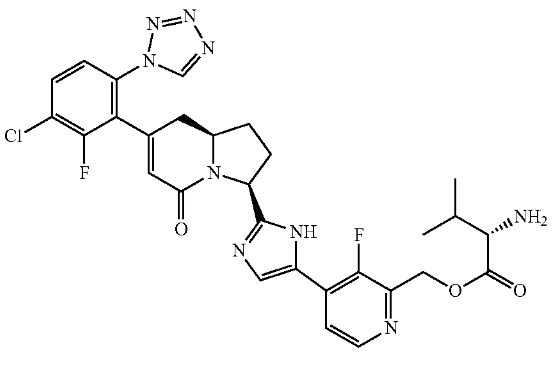 [SMILES: CC(C)[C@H](N)C(=O)OCc1nccc(-c2cnc([C@@H]3CC[C@@H]4CC(c5c(-n6cnnn6)ccc(Cl)c5F)=CC(=O)N43)[nH]2)c1F]

LC/MS: mass calculated for $C_{29}H_{28}ClF_2N_9O_3$: 623.20, measured: 624.30 [M+H]. $^1H$ NMR (400 MHz, DMSO-$d_6$) δ 12.32 (brs, 1H), 9.84 (s, 1H), 8.37 (d, J=5.0 Hz, 1H), 7.88-8.03 (m, 2H), 7.72 (d, J=8.7 Hz, 1H), 7.59 (d, J=3.9 Hz, 1H), 5.70 (d, J=2.7 Hz, 1H), 5.19-5.39 (m, 2H), 5.04 (d, J=8.8 Hz, 1H), 3.64-3.81 (m, 1H), 3.19 (d, J=5.2 Hz, 1H), 2.63-2.82 (m, 1H), 2.53-2.61 (m, 1H), 2.05-2.30 (m, 3H), 1.78-2.05 (m, 4H), 0.87 (d, J=6.8 Hz, 3H), 0.81 (d, J=6.7 Hz, 3H). $^{19}F$ NMR (376 MHz, DMSO-$d_6$) δ −112.87, −128.90.

Example 76: (3S*)-7-(3-chloro-2-fluoro-6-(1H-tetrazol-1-yl)phenyl)-3-(4-fluoro-5-(3-fluoro-2-(((S)-tetrahydrofuran-3-yl)amino)pyridin-4-yl)-1H-imidazol-2-yl)-2,3,8,8a-tetrahydroindolizin-5(1H)-one

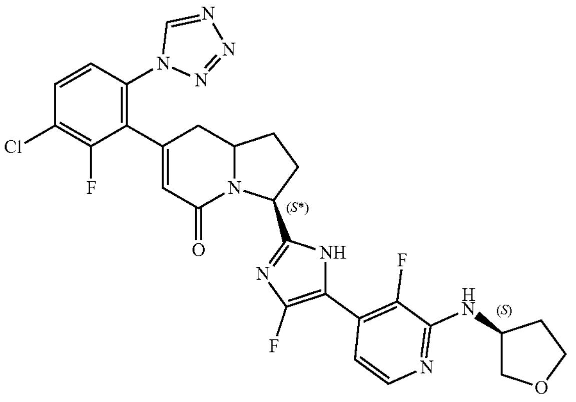

LC/MS: mass calculated for $C_{27}H_{23}ClF_3N_9O_2$: 597.16, measured: 598.15 [M+H]. $^1$H NMR (400 MHz, DMSO-$d_6$) δ 12.39 (s, 1H), 9.82 (s, 1H), 7.95 (dd, J=8.7, 7.8 Hz, 1H), 7.82 (d, J=5.4 Hz, 1H), 7.70 (dd, J=8.7, 1.5 Hz, 1H), 6.77-6.86 (m, 1H), 6.65-6.69 (m, 1H), 5.65 (d, J=2.2 Hz, 1H), 4.98 (d, J=8.6 Hz, 1H), 4.41-4.52 (m, 1H), 3.78-3.94 (m, 2H), 3.62-3.75 (m, 2H), 3.56 (dd, J=8.8, 4.6 Hz, 1H), 2.53 (d, J=5.3 Hz, 2H), 2.03-2.23 (m, 3H), 1.84-2.00 (m, 3H). $^{19}$F NMR (376 MHz, DMSO-$d_6$) δ −112.88, −127.01, −142.75.

Example 77: (3R*)-7-(3-chloro-2-fluoro-6-(1H-tetrazol-1-yl)phenyl)-3-(4-fluoro-5-(3-fluoro-2-(((S)-tetrahydrofuran-3-yl)amino)pyridin-4-yl)-1H-imidazol-2-yl)-2,3,8,8a-tetrahydroindolizin-5(1H)-one

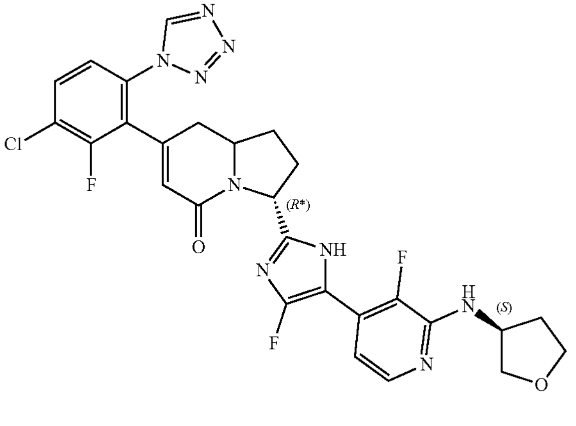

LC/MS: mass calculated for $C_{27}H_{23}ClF_3N_9O_2$: 597.16, measured: 598.20 [M+H]$^+$. $^1$H NMR (400 MHz, DMSO-$d_6$) δ 12.48 (s, 1H), 9.82 (s, 1H), 7.95 (dd, J=8.7, 7.8 Hz, 1H), 7.82 (d, J=5.3 Hz, 1H), 7.69 (dd, J=8.7, 1.5 Hz, 1H), 6.82 (dd, J=6.1, 1.7 Hz, 1H), 6.64-6.66 (m, 1H), 5.67 (d, J=2.7 Hz, 1H), 4.94-4.97 (m, 1H), 4.38-4.52 (m, 1H), 3.94-4.07 (m, 1H), 3.77-3.92 (m, 2H), 3.63-3.74 (m, 1H), 3.55 (dd, J=8.8, 4.6 Hz, 1H), 2.50-2.55 (m, 1H), 2.26-2.38 (m, 2H), 2.07-2.25 (m, 2H), 1.84-2.00 (m, 2H), 1.59-1.75 (m, 1H). $^{19}$F NMR (376 MHz, DMSO-$d_6$) δ −113.06, −127.13, −142.57.

Example 78: (3R*,8aR)-7-(3-chloro-2-fluoro-6-(1H-tetrazol-1-yl)phenyl)-3-(5-(3-fluoro-2-(4H-1,2,4-triazol-4-yl)pyridin-4-yl)-1H-imidazol-2-yl)-2,3,8,8a-tetrahydroindolizin-5(1H)-one

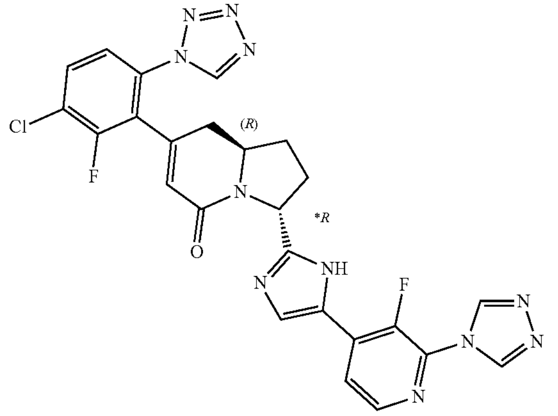

LC/MS: mass calculated for $C_{25}H_{18}ClF_2N_{11}O$: 561.14, measured: 562.10 [M+H]. $^1$H NMR (400 MHz, DMSO-$d_6$) δ12.42 (s, 1H), 9.83 (s, 1H), 9.12 (d, J=1.5 Hz, 2H), 8.37 (d, J=5.1 Hz, 1H), 8.00-8.07 (m, 1H), 7.91-8.00 (m, 1H), 7.64-7.74 (m, 2H), 5.65-5.71 (m, 1H), 4.99-5.08 (m, 1H), 3.70-3.90 (m, 1H), 2.60-2.70 (m, 1H), 2.52-2.57 (m, 1H), 2.15-2.26 (m, 1H), 2.06-2.14 (m, 1H), 1.89-1.99 (m, 2H). $^{19}$F NMR: (376 MHz, DMSO-$d_6$) δ −112.84, 132.82.

Example 79: (3S,8aR)-7-[5-chloro-2-(tetrazol-1-yl)phenyl]-3-[5-[3-fluoro-2-[(2-hydroxy-1,1-dimethyl-ethyl)amino]-4-pyridyl]-1H-imidazol-2-yl]-2,3,8,8a-tetrahydro-1H-indolizin-5-one

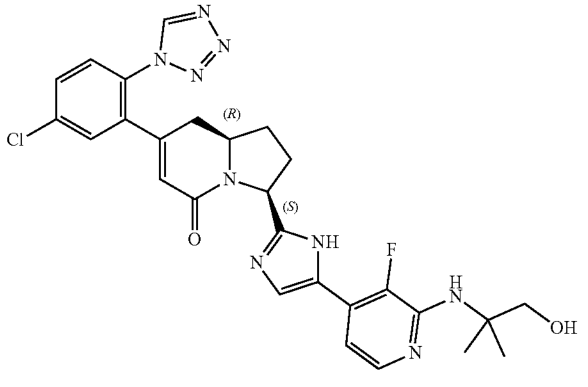

LC/MS: mass calculated for $C_{27}H_{27}ClFN_9O_2$: 563.20, measured: 564.25 [M+H]$^+$. $^1$H NMR: (400 MHz, Methanol-$d_4$) δ 9.59 (s, 1H), 7.85-7.99 (m, 1H), 7.79-7.84 (m, 1H), 7.45-7.78 (m, 3H), 7.50-7.60 (m, 1H), 5.85 (d, J=2.5 Hz, 1H), 5.22 (d, J=8.9 Hz, 1H), 3.90-4.00 (m, 1H), 3.78 (s, 2H), 2.35-2.59 (m, 3H), 2.15-2.29 (m, 2H), 1.92-2.05 (m, 1H), 1.49 (s, 6H). $^{19}$F NMR: (376 MHz, Methanol-$d_4$) δ −77.25.

Example 80: (3S,8aR)-7-[5-chloro-2-(tetrazol-1-yl)phenyl]-3-[4-fluoro-5-[3-fluoro-2-(hydroxymethyl)-4-pyridyl]-1H-imidazol-2-yl]-2,3,8,8a-tetrahydro-1H-indolizin-5-one

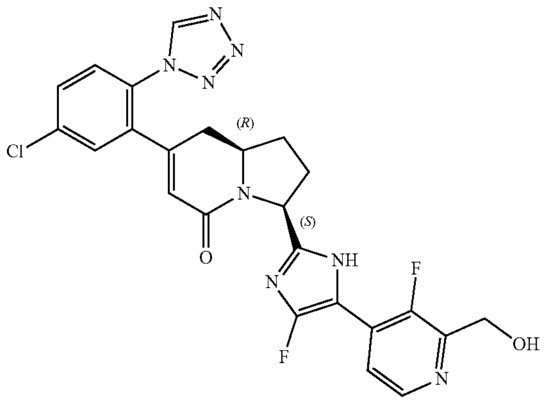

LC/MS: mass calculated for $C_{24}H_{19}ClF_2N_8O_2$: 524.13, measured: 525.10 $[M+H]^+$. $^1$H NMR (400 MHz, DMSO-$d_6$) δ 12.59 (brs., 1H), 9.85 (s, 1H), 8.38 (d, J=5.1 Hz, 1H), 7.84 (s, 1H), 7.77 (d, J=1.6 Hz, 2H), 7.49-7.51 (m, 1H), 5.56 (d, J=2.4 Hz, 1H), 5.36-5.41 (m, 1H), 5.03 (d, J=8.6 Hz, 1H), 4.64 (dd, J=5.7, 2.4 Hz, 2H), 3.60-3.80 (m, 1H), 2.31-2.46 (m, 1H), 1.79-2.31 (m, 4H). $^{19}$F NMR (376 MHz, DMSO-$d_6$) δ −125.71, −130.38.

Example 81: 6-[2-[(3S,8aR)-7-[5-chloro-2-[4-(trifluoromethyl)triazol-1-yl]phenyl]-5-oxo-2,3,8,8a-tetrahydro-1H-indolizin-3-yl]-4-fluoro-1H-imidazol-5-yl]-3,4-dihydro-1H-quinolin-2-one

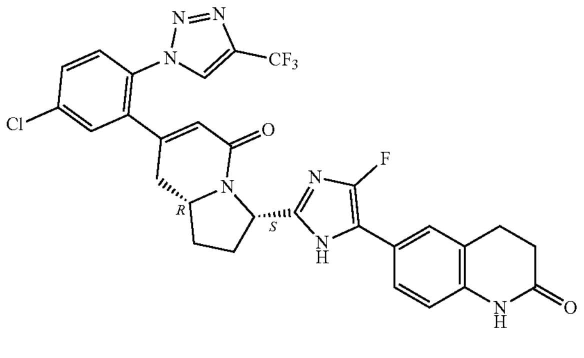

LC/MS: mass calculated for $C_{29}H_{22}ClF_4N_7O_2$: 611.15, measured: 612.10 $[M+H]^+$. $^1$H-NMR: (400 MHz, Methanol-$d_4$) δ 9.00 (d, J=1.0 Hz, 1H), 7.63-7.72 (m, 3H), 7.32-7.42 (m, 2H), 6.92 (d, J=8.2 Hz, 1H), 5.71 (d, J=2.7 Hz, 1H), 5.06 (d, J=8.9 Hz, 1H), 3.76-3.89 (m, 1H), 3.01-3.03 (m, 2H), 2.69-2.84 (m, 1H), 2.57-2.66 (m, 2H), 2.21-2.38 (m, 2H), 1.97-2.20 (m, 3H). $^{19}$F NMR: (376 MHz, Methanol-$d_4$) δ −62.34, −77.00, −137.84.

Example 83: (3S,8aR)-3-[5-[6-(3-bicyclo[1.1.1]pentanoylamino)-2-fluoro-3-pyridyl]-1H-imidazol-2-yl]-7-[5-chloro-2-(tetrazol-1-yl)phenyl]-2,3,8,8a-tetrahydro-1H-indolizin-5-one

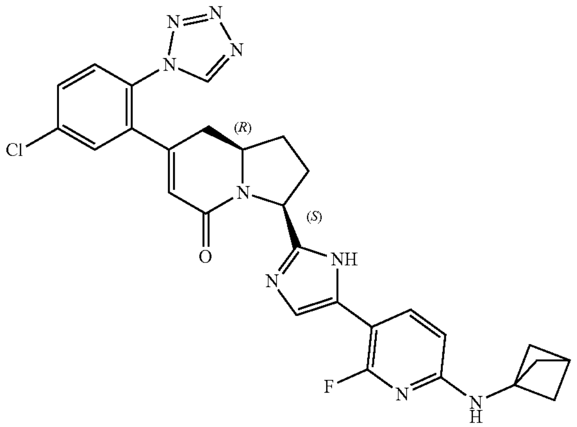

LC/MS: mass calculated for $C_{28}H_{25}ClFN_9O$: 557.19, measured: 558.20 [M+H]. $^1$H NMR: (400 MHz, Methanol-$d_4$): δ 9.56 (s, 1H), 8.05 (s, 1H), 7.61-7.71 (m, 3H), 7.11 (s, 1H), 6.48 (d, J=8.4 Hz, 1H), 5.74 (s, 1H), 5.14 (d, J=8.9 Hz, 1H), 3.75-3.87 (m, 1H), 2.62-2.75 (m, 1H), 2.45 (s, 1H), 2.33-2.42 (m, 1H), 2.21-2.32 (m, 1H), 2.09-2.21 (m, 8H), 1.85-2.03 (m, 1H). $^{19F}$ NMR: (376 MHz, Methanol-$d_4$): δ −71.58.

Example 84: (3S,8aR)-7-[5-chloro-2-(tetrazol-1-yl)phenyl]-3-[4-fluoro-5-[3-fluoro-2-[(2-hydroxy-2-methyl-propyl)amino]-4-pyridyl]-1H-imidazol-2-yl]-2,3,8,8a-tetrahydro-1H-indolizin-5-one

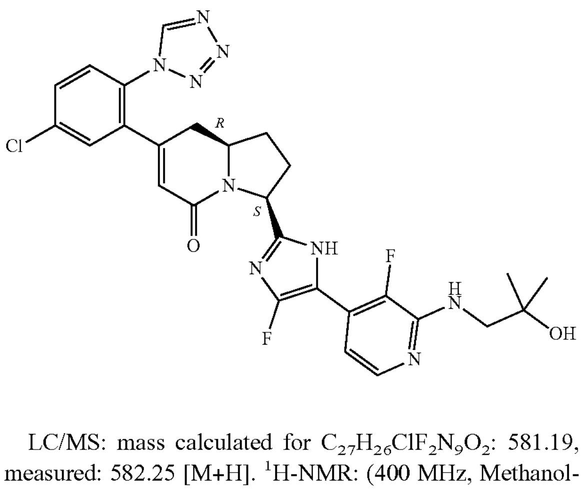

LC/MS: mass calculated for $C_{27}H_{26}ClF_2N_9O_2$: 581.19, measured: 582.25 [M+H]. $^1$H-NMR: (400 MHz, Methanol-$d_4$) δ 9.46 (s, 1H), 7.51-7.68 (m, 4H), 6.62-6.71 (m, 1H), 5.60 (d, J=2.8 Hz, 1H), 5.02 (d, J=8.5 Hz, 1H), 3.66-3.79 (m, 1H), 3.36 (s, 2H), 2.52-2.63 (m, 1H), 2.24-2.32 (m, 1H), 2.02-2.22 (m, 3H), 1.82-1.96 (m, 1H), 1.14 (s, 6H). $^{19}$F NMR (376 MHz, Methanol-$d_4$) δ −129.59, −147.43.

Example 85: (3S,8aR)-7-[3-chloro-2-fluoro-6-(tetrazol-1-yl)phenyl]-3-[5-[2-(triazol-1-yl)-4-pyridyl]-1H-imidazol-2-yl]-2,3,8,8a-tetrahydro-1H-indolizin-5-one

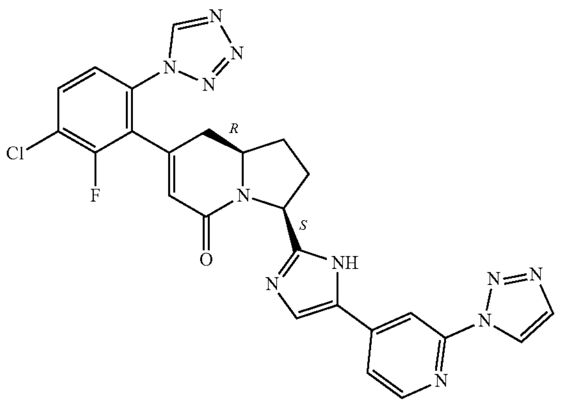

LC/MS: mass calculated for $C_{25}H_{19}ClFN_{11}O$: 543.14, measured: 544.15 [M+H]. $^1H$ NMR (400 MHz, DMSO-$d_6$) δ 12.25 (s, 1H), 9.83 (s, 1H), 8.86 (s, 1H), 8.51 (d, J=5.3 Hz, 1H), 8.42 (d, J=1.5 Hz, 1H), 7.95-8.01 (m, 3H), 7.85 (d, J=5.2 Hz, 1H), 7.68-7.79 (m, 1H), 5.68 (d, J=2.7 Hz, 1H), 5.03 (d, J=8.9 Hz, 1H), 3.67-3.75 (m, 1H), 2.75-2.85 (m, 1H), 2.52-2.56 (m, 1H), 2.18-2.27 (m, 1H), 2.08-2.13 (m, 1H), 1.92-2.00 (m, 2H). $^{19}F$ NMR (376 MHz, DMSO-$d_6$) δ −112.71.

Example 86: (3S,8aR)-7-[3-chloro-2-fluoro-6-(tetrazol-1-yl)phenyl]-3-[5-[2-(triazol-2-yl)-4-pyridyl]-1H-imidazol-2-yl]-2,3,8,8a-tetrahydro-1H-indolizin-5-one

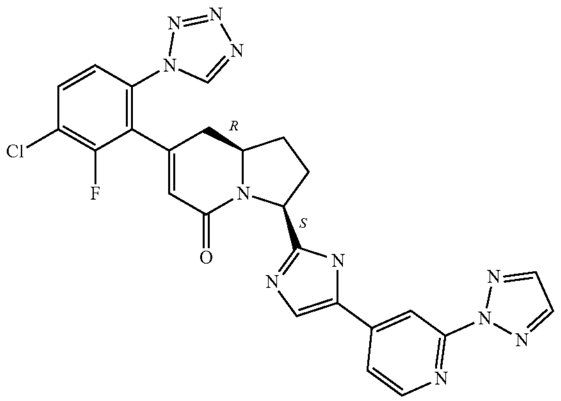

LC/MS: mass calculated for $C_{25}H_{19}ClFN_{11}O$: 543.14, measured: 544.10 $[M+H]^+$. $^1H$ NMR (400 MHz, DMSO-$d_6$) δ12.22 (s, 1H), 9.83 (s, 1H), 8.48 (d, J=5.2 Hz, 1H), 8.32 (s, 1H), 8.17 (s, 2H), 7.93-8.01 (m, 2H), 7.80 (d, J=5.2 Hz, 1H), 7.71 (d, J=8.7 Hz, 1H), 5.67 (d, J=2.7 Hz, 1H), 5.02 (d, J=8.8 Hz, 1H), 3.67-3.78 (m, 1H), 2.77-2.85 (m, 1H), 2.52-2.57 (m, 1H), 2.17-2.27 (m, 1H), 2.10-2.15 (m, 1H), 1.92-2.02 (m, 2H). $^{19}F$ NMR (376 MHz, DMSO-$d_6$) δ −112.66.

Example 87: (3S,8aR)-7-[3-chloro-2-fluoro-6-(tetrazol-1-yl)phenyl]-3-[4-fluoro-5-[2-(triazol-2-yl)-4-pyridyl]-1H-imidazol-2-yl]-2,3,8,8a-tetrahydro-1H-indolizin-5-one

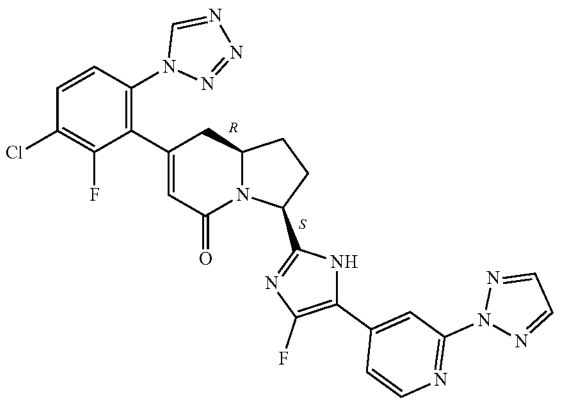

LC/MS: mass calculated for $C_{25}H_{18}ClF_2N_{11}O$: 561.14, measured: 562.20 $[M+H]^+$. $^1H$ NMR (300 MHz, DMSO-$d_6$) δ13.21 (s, 1H), 9.85 (s, 1H), 8.55 (d, J=5.3 Hz, 1H), 8.19-8.24 (m, 3H), 7.98-8.02 (m, 1H), 7.72 (d, J=8.7 Hz, 1H), 7.59 (d, J=5.3 Hz, 1H), 5.68 (d, J=1.4 Hz, 1H), 4.95 (d, J=8.4 Hz, 1H), 3.66-3.80 (m, 1H), 2.52-2.58 (m, 2H), 2.20-2.28 (m, 1H), 2.10-2.17 (m, 1H), 1.99-2.08 (m, 1H), 1.90-1.96 (m, 1H). $^{19}F$ NMR (282 MHz, DMSO-$d_6$) δ −112.93, −124.95.

Example 88: (3S,8aR)-7-[3-chloro-2-fluoro-6-(tetrazol-1-yl)phenyl]-3-[4 fluoro-5-(2-pyrazol-1-yl-4-pyridyl)-1H-imidazol-2-yl]-2,3,8,8a-tetrahydro-1H-indolizin-5-one

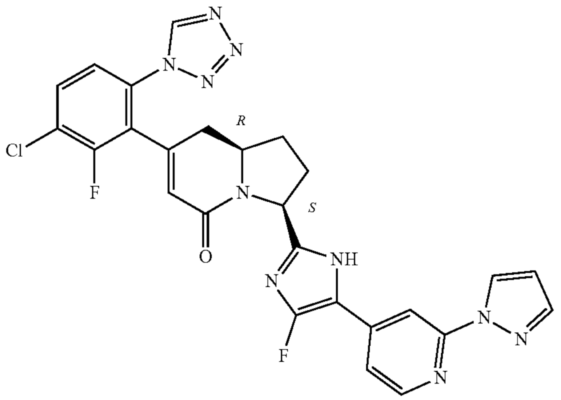

LC/MS: mass calculated for $C_{26}H_{19}ClF_2N_{10}O$: 560.14, measured: 561.15 [M+H]. $^1H$ NMR (300 MHz, DMSO-$d_6$) δ 13.19 (s, 1H), 9.85 (s, 1H), 8.64 (d, J=2.6 Hz, 1H), 8.46 (d, J=5.4 Hz, 1H), 8.15 (s, 1H), 7.98-8.03 (m, 1H), 7.86 (s, 1H), 7.72 (d, J=8.7 Hz, 1H), 7.46 (d, J=5.2 Hz, 1H), 6.60 (dd, J=2.6, 1.7 Hz, 1H), 5.68 (s, 1H), 4.91-5.00 (m, 1H), 3.67-3.78 (m, 1H), 2.52-2.58 (m, 2H), 2.19-2.27 (m, 1H), 2.10-2.16 (m, 1H), 2.00-2.07 (m, 1H), 1.90-1.99 (m, 1H). $^{19}F$ NMR (282 MHz, DMSO-$d_6$) δ −112.93, −125.31.

Example 89: (3S,8aR)-7-[3-chloro-2-fluoro-6-(tetrazol-1-yl)phenyl]-3-[5-[3-fluoro-2-[(2-hydroxy-1,1-dimethyl-ethyl)amino]-4-pyridyl]-1H-imidazol-2-yl]-2,3,8,8a-tetrahydro-1H-indolizin-5-one

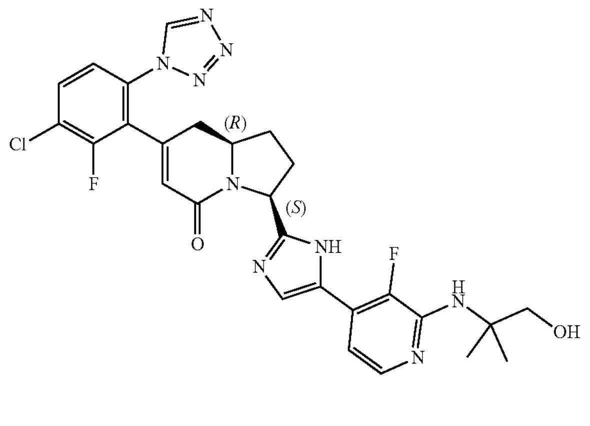

Step 1: 2-(3-Fluoro-2-(n-(1-hydroxy-2-methylpropan-2-yl)acetamido)pyridin-4-yl)-2-oxoethyl (3S, 8aR)-7-(6-amino-3-chloro-2-fluorophenyl)-5-oxo-1,2,3,5,8,8a-hexahydroindolizine-3-carboxylate To a solution of (3S,8aR)-7-(6-amino-3-chloro-2-fluorophenyl)-5-oxo-1,2,3,5,8,8a-hexahydroindolizine-3-carboxylic acid (0.25 g, 0.77 mmol, 1.0 equiv.) in ACN (10 mL) was added potassium carbonate (0.14 g, 1.00 mmol, 2.0 equiv.). After the reaction mixture was stirred at room temperature for 0.5 h, N-(4-(2-bromoacetyl)-3-fluoropyridin-2-yl)-N-(1-((tert-butyldimethylsilyl)oxy)-2-methylpropan-2-yl)acetamide (0.50 g, 1.08 mmol, 1.4 equiv.) was added. The reaction mixture was stirred at room temperature for 2 h, then concentrated under reduced pressure. The residue was purified by silica gel chromatography with MeOH/DCM (0→10%) to yield 2-(3-fluoro-2-(n-(1-hydroxy-2-methylpropan-2-yl)acetamido)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate. LC/MS: mass calculated for $C_{28}H_{29}ClF_2N_4O_6$: 590.17, measured (ES, m/z): 591.15 $[M+H]^+$.

Step 2: N-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-n-(1-hydroxy-2-methylpropan-2-yl)acetamide To a solution of 2-(2-(n-(1-((tert-butyldimethylsilyl)oxy)-2-methylpropan-2-yl)acetamido)-3-fluoropyridin-4-yl)-2-oxoethyl (3S,8aR)-7-(6-amino-3-chloro-2-fluorophenyl)-5-oxo-1,2,3,5,8,8a-hexahydroindolizine-3-carboxylate (0.22 g, 0.38 mmol, 1.0 equiv.) in toluene (5 mL) and acetic acid (0.25 mL) was added ammonium acetate (0.58 g, 7.57 mmol, 20.0 equiv.). The reaction mixture was stirred at 100° C. for 1 h, concentrated under vacuum. The residue was purified by silica gel chromatography (0-(10% DCM/MeOH) to yield N-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-N-(1-hydroxy-2-methylpropan-2-yl)acetamide as a yellow solid. LC/MS: mass calculated for $C_{28}H_{29}ClF_2NeO_3$: 570.20, measured (ES, m/z): 571.25 $[M+H]^+$.

Step 3: N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-n-(1-hydroxy-2-methylpropan-2-yl) acetamide To a solution of N-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-n-(1-hydroxy-2-methylpropan-2-yl)acetamide (0.10 g, 0.18 mmol, 1.0 equiv.) in acetic acid (5 mL) was added azidotrimethylsilane (0.20 g, 1.75 mmol, 10.0 equiv.), then, tert-butyl nitrite (0.18 g, 1.75 mmol, 10.0 equiv.) was slowly added. The reaction mixture was stirred at 40° C. overnight. The solvent was removed under reduced pressure and the residue was diluted with DCM, washed with $NaHCO_3$ water, filtered and concentrated to yield N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-n-(1-hydroxy-2-methylpropan-2-yl)acetamide as a yellow solid. LC/MS: mass calculated for $C_{29}H_{28}ClF_2N_9O_3$: 623.20, measured (ES, m/z): 624.30 $[M+H]^+$.

Step 4: N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-n-(1-hydroxy-2-methylpropan-2-yl) acetamide To a solution of N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-n-(1-hydroxy-2-methylpropan-2-yl)acetamide (0.12 g, 0.19 mmol, 1.0 equiv.) in THE (3 mL) was added 2 M HCl (3 mL). The reaction mixture was stirred at 60° C. for 1 h. The pH value of the solution was adjusted to 7~8 with $NaHCO_3$ solution, extracted with EA, the organic layer was dried over anhydrous sodium sulfate and concentrated. The residue was purified by reverse column chromatography on C18 column ($CH_3CN$/water (0.05% TFA): 5→70%) to yield (3S,8aR)-7-(3-chloro-2-fluoro-6-(1H-tetrazol-1-yl)phenyl)-3-(5-(3-fluoro-2-((1-hydroxy-2-methylpropan-2-yl)amino)pyridin-4-yl)-1H-imidazol-2-yl)-2,3,8,8a-tetrahydroindolizin-5(1H)-one as a white solid.

LC/MS: mass calculated for $C_{27}H_{26}ClF_2N_9O_2$: 581.19, measured: 582.25 $[M+H]^+$. $^1H$ NMR (300 MHz, Methanol-$d_4$) δ 9.48 (s, 1H), 7.67-7.85 (m, 3H), 7.38-7.50 (m, 2H), 5.67 (d, J=2.7 Hz, 1H), 5.11 (d, J=8.6 Hz, 1H), 3.76-3.89 (m, 1H), 3.66 (s, 2H), 2.47-2.79 (m, 2H), 2.01-2.33 (m, 3H), 1.81-1.98 (m, 1H), 1.38 (s, 6H). $^{19}F$ NMR (282 MHz, Methanol-$d_4$) δ −77.34, −113.67, 137.09.

Example 90: (3S*,8aR)-3-(5-(2-amino-3-fluoropyridin-4-yl)-1H-imidazol-2-yl)-7-(5-chloro-2-(1H-tetrazol-1-yl)phenyl)-2,3,8,8a-tetrahydroindolizin-5(1H)-one

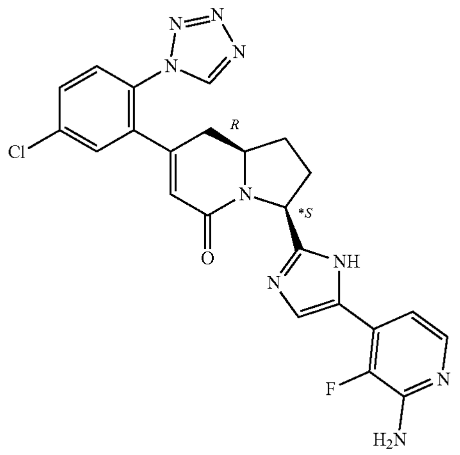

Step 1: 2-(2-Acetamido-3-fluoropyridin-4-yl)-2-oxoethyl (8aR)-7-(5-chloro-2-(1H-tetrazol-1-yl)phenyl)-5-oxo-1,2,3,5,8,8a-hexahydroindolizine-3-carboxylate To a solution of (8aR)-7-(5-chloro-2-(1H-tetrazol-1-yl) phenyl)-5-oxo-1,2,3,5,8,8a-hexahydroindolizine-3-carboxylic acid (2.0 g, 5.56 mmol, 1.0 equiv.) in $CH_3CN$ (20 mL) was added $K_2CO_3$ (1.2 g, 8.34 mmol, 1.5 equiv.). After stirring at room temperature for 0.5 h, N-(4-(2-bromoacetyl)-3-fluoropyridin-2-yl)acetamide (2.3 g, 8.34 mmol, 1.5 equiv.) was added to the mixture. The reaction mixture was stirred at room temperature for 1 h and then concentrated under reduced pressure. The residue was purified by silica gel chromatography (0→10% MeOH/DCM) to yield the 2-(2-acetamido-3-fluoropyridin-4-yl)-2-oxoethyl (8aR)-7-(5-chloro-2-(1H-tetrazol-1-yl)phenyl)-5-oxo-1,2,3,5,8,8a-hexahydroindolizine-3-carboxylate as a yellow solid. LC/MS: mass calculated for $C_{25}H_{21}ClFN_7O_5$: 553.13, measured (ES, m/z): 554.05 $[M+H]^+$.

Step 2: N-(4-(2-((8aR)-7-(5-chloro-2-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide To a solution of 2-(2-acetamido-3-fluoropyridin-4-yl)-2-oxoethyl (8aR)-7-(5-chloro-2-(1H-tetrazol-1-yl)phenyl)-5-oxo-1,2,3,5,8,8a-hexahydroindolizine-3-carboxylate (2.5 g, 4.51 mmol, 1.0 equiv.) in toluene (30 mL) and acetic acid (3 mL) was added ammonium acetate (5.2 g, 67.70 mmol, 15.0 equiv.). The mixture was stirred at 100° C. for 1 h. The solvent was removed under vacuum and the residue was purified by silica gel column with MeOH/DCM (0→10%) to yield n-(4-(2-((8aR)-7-(5-chloro-2-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide as a yellow solid. LC/MS: mass calculated for $C_{25}H_{21}ClFN_9O_2$: 533.15, measured (ES, m/z): 534.40 $[M+H]^+$.

Step 3: (3S',8aR)-3-(5-(2-Amino-3-fluoropyridin-4-yl)-1H-imidazol-2-yl)-7-(5-chloro-2-(1H-tetrazol-1-yl)phenyl)-2,3,8,8a-tetrahydroindolizin-5(1H)-one To a solution of n-(4-(2-((8aR)-7-(5-chloro-2-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide (1.3 g, 2.44 mmol, 1.0 equiv.) in THE (10 mL) was added HCl (10 mL, 20 mmol, 2 M, 8.2 equiv.). The mixture was stirred at 50° C. for 2 h. The solvent was removed under vacuum and the residue was purified by $C_{18}$ column [condition: ACN-water-6.5 mM $NH_4HCO_3$+$NH_3H_2O$ (5→50%)] to yield a residue. The residue was purified by chiral HPLC [column: CHIRAL ART cellulose-SB, 4.6*100 mm, 3 um; mobile phase A: MtBE (0.1% DEA): EtOH=70:30, mobile phase B; flow rate: 1 mL/min] to yield (3*S,8aR)-3-(5-(2-amino-3-fluoropyridin-4-yl)-1H-imidazol-2-yl)-7-(5-chloro-2-(1H-tetrazol-1-yl)phenyl)-2,3,8,8a-tetrahydroindolizin-5(1H)-one as an off-white solid.

LC/MS: mass calculated for $C_{23}H_{19}ClFN_9O$: 491.14, measured: 492.10 [M+H]. $^1H$ NMR (400 MHz, DMSO-$d_6$) δ 12.05 (s, 1H), 9.84 (s, 1H), 7.74-7.83 (m, 4H), 7.43 (d, J=3.6 Hz, 1H), 7.12-7.16 (m, 1H), 6.03 (s, 2H), 5.61 (d, J=2.6 Hz, 1H), 5.01 (d, J=8.6 Hz, 1H), 3.64-3.78 (m, 1H), 2.54-2.59 (m, 1H), 2.28-2.39 (m, 1H), 2.11-2.23 (m, 1H), 1.83-2.09 (m, 3H). $^{19}F$ NMR (376 MHz, DMSO-$d_6$) δ −142.41.

Example 92: 7-[3-Chloro-2-fluoro-6-(tetrazol-1-yl) phenyl]-3-[4-fluoro-5-[3-fluoro-2-(1,2,4-triazol-1-yl)-4-pyridyl]-1H-imidazol-2-yl]-2,3,8,8a-tetrahydro-1H-indolizin-5-one

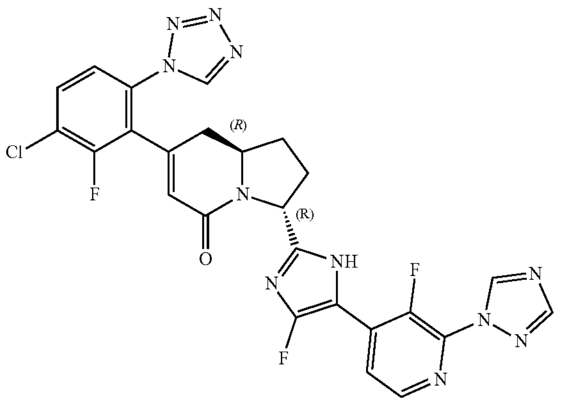

LC/MS: mass calculated for $C_{25}H_{17}ClF_3N_{11}O$: 579.13, measured: 580.10 [M+H]. $^1H$ NMR (400 MHz, DMSO-$d_6$) δ 12.81 (s, 1H), 9.81 (s, 1H), 9.20 (s, 1H), 8.41 (d, J=5.2 Hz, 1H), 8.34 (s, 1H), 7.90-7.99 (m, 1H), 7.65-7.73 (m, 2H), 5.66 (d, J=1.8 Hz, 1H), 5.03 (d, J=8.7 Hz, 1H), 3.64-3.76 (m, 1H), 2.50-2.58 (m, 2H), 2.26-2.03 (m, 2H), 1.88-2.01 (m, 2H). $^{19}F$ NMR (376 MHz, DMSO-$d_6$) δ −112.89, −123.46, −131.53.

Example 93: (3S,8aR)-3-(5-(2-(1H-pyrazol-1-yl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

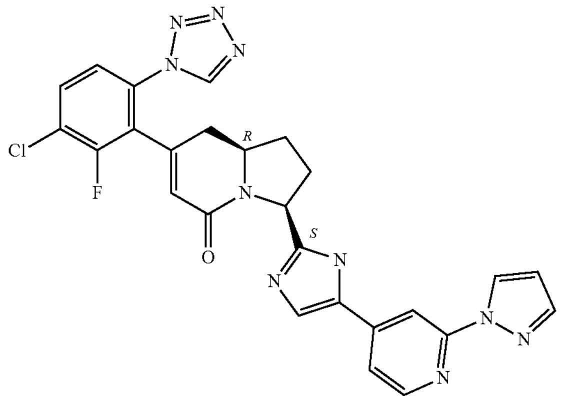

LC/MS: mass calculated for $C_{26}H_{20}ClFN_{10}O$: 542.15, measured (ES, m/z): 543.20 $[M+H]^+$ $^1H$ NMR (300 MHz, DMSO-$d_6$) δ 12.19 (s, 1H), 9.84 (s, 1H), 8.59-8.65 (m, 1H), 8.38 (d, J=5.3 Hz, 1H), 8.26 (s, 1H), 7.94-8.02 (m, 1H), 7.92 (d, J=2.1 Hz, 1H), 7.80-7.87 (m, 1H), 7.63-7.77 (m, 2H), 6.54-6.61 (m, 1H), 5.68 (d, J=2.6 Hz, 1H), 5.03 (d, J=8.6 Hz, 1H), 3.66-3.77 (m, 1H), 2.71-2.88 (m, 1H), 2.53-2.58 (m, 1H), 2.19-2.28 (m, 1H), 2.08-2.14 (m, 1H), 1.94-2.03 (m, 2H). $^{19}F$ NMR (282 MHz, DMSO-$d_6$) δ −112.60.

Example 94 (3S,8aR)-7-(3-Chloro-2-fluoro-6-(1H-tetrazol-1-yl)phenyl)-3-(5-(2-(3,3-difluoroazetidine-1-carbonyl)-3-fluoropyridin-4-yl)-1H-imidazol-2-yl)-2,3,8,8a-tetrahydroindolizin-5(1H)-one

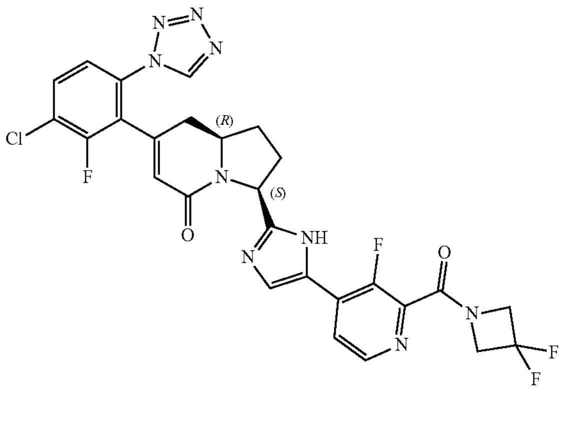

LC/MS: mass calculated for $C_{27}H_{20}ClF_4N_8O_2$: 613.14, measured (ES, m/z): 614.10 $[M+H]^+$ $^1H$ NMR (400 MHz, DMSO-$d_6$) δ 12.37 (s, 1H), 9.84 (s, 1H), 8.42 (d, J=4.9 Hz, 1H), 8.10 (t, J=5.3 Hz, 1H), 7.98 (t, J=8.2 Hz, 1H), 7.68-7.75 (m, 1H), 7.62-7.68 (m, 1H), 5.71 (d, J=2.6 Hz, 1H), 5.04 (d, J=8.8 Hz, 1H), 4.69-4.80 (m, 2H), 4.49-4.60 (m, 2H), 3.70-3.79 (m, 1H), 2.67-2.74 (m, 1H), 2.53-2.56 (m, 1H), 2.17-2.25 (m, 1H), 2.08-2.13 (m, 1H), 1.90-2.00 (m, 2H). $^{19}F$ NMR (376 MHz, DMSO-$d_6$) δ −100.09, −112.87, −125.46.

Example 95 7-(3-Chloro-2-fluoro-6-(1H-tetrazol-1-yl)phenyl)-3-(5-(7-hydroxy-7-methyl-6,7-dihydro-5H-cyclopenta[b]pyridin-4-yl)-1H-imidazol-2-yl)-2,3,8,8a-tetrahydroindolizin-5(1H)-one

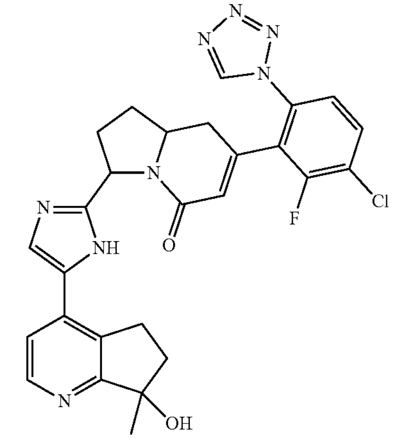 [SMILES: CC1(O)CCc2c(-c3cnc(C4CCC5CC(c6c(-n7cnnn7)ccc(Cl)c6F)=CC(=O)N54)[nH]3)ccnc21]

LC/MS: mass calculated for $C_{27}H_{24}ClFN_8O_2$: 546.17, measured (ES, m/z): 547.20 $[M+H]^+$. $^1H$ NMR (400 MHz, DMSO-$d_6$) δ 9.72-9.80 (m, 1H), 8.36 (d, J=5.3 Hz, 1H), 7.88-7.92 (m, 1H), 7.53-7.70 (m, 3H), 5.61-5.66 (m, 1H), 4.98-5.03 (m, 1H), 3.78-3.82 (m, 1H), 3.27-3.36 (m, 1H), 3.04-3.15 (m, 1H), 2.88-2.96 (m, 1H), 2.64-2.73 (m, 1H), 2.07-2.22 (m, 4H), 1.87-1.98 (m, 2H), 1.45 (d, J=4.2 Hz, 3H). $^{19}F$ NMR (376 MHz, DMSO-$d_6$) δ −73.43, −112.95.

Example 96: (3S,8aR)-3-(5-(2-(Bicyclo[1.1.1]pentan-1-ylamino)-3-fluoropyridin-4-yl)-1H-imidazol-2-yl)-7-(5-chloro-2-(1H-tetrazol-1-yl)phenyl)-2,3,8,8a-tetrahydroindolizin-5(1H)-one

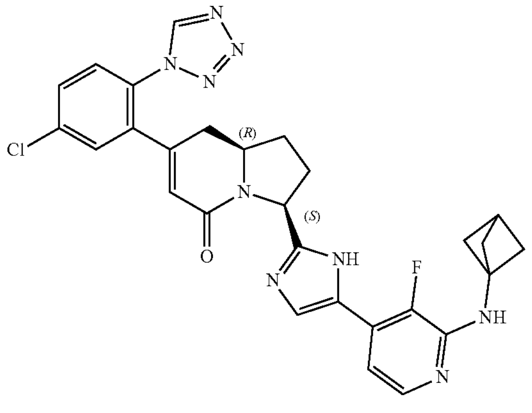

Step 1: 2-(2-(N-(bicyclo[1.1.1]pentan-1-yl)acetamido)-3-fluoropyridin-4-yl)-2-oxoethyl (3S,8aR)-7-(2-amino-5-chlorophenyl)-5-oxo-1,2,3,5,8,8a-hexahydroindolizine-3-carboxylate To a solution of (3S)-7-(2-amino-5-chlorophenyl)-5-oxo-1,2,3,5,8,8a-hexahydroindolizine-3-carboxylic acid (0.22 g, 0.72 mmol, 1.0 equiv.) in MeCN (10 mL) was added potassium carbonate (0.20 g, 1.43 mmol, 2.0 equiv.). After the mixture was stirred for 30 min, N-(bicyclo[1.1.1]pentan-1-yl)-n-(4-(2-bromoacetyl)-3-fluoropyridin-2-yl)acetamide (0.37 g, 1.08 mmol, 1.5 equiv.) was added. The reaction mixture was stirred at room temperature for 2 h, then concentrated under vacuum. The residue was purified by silica gel chromatography with MeOH/DCM (0→10%) to yield 2-(2-(n-(bicyclo[1.1.1]pentan-1-yl)acetamido)-3-fluoropyridin-4-yl)-2-oxoethyl (3S)-7-(2-amino-5-chlorophenyl)-5-oxo-1,2,3,5,8,8a-hexahydroindolizine-3-carboxylate as a light yellow solid. LC/MS: mass calculated for $C_{29}H_{28}ClFN_4O_5$: 566.17, measured (ES, m/z): 567.15 $[M+H]^+$.

Step 2: N-(4-(2-((3S)-7-(2-amino-5-chlorophenyl)-5-oxo-1,2,3,5,8,8a-hexahydroindolizin-3-yl)-1H-imidazol-5-yl)-3-fluoropyridin-2-yl)-n-(bicyclo[1.1.1]pentan-1-yl)acetamide To a solution of 2-(2-(n-(bicyclo[1.1.1]pentan-1-yl)acetamido)-3-fluoropyridin-4-yl)-2-oxoethyl (3S)-7-(2-amino-5-chlorophenyl)-5-oxo-1,2,3,5,8,8a-hexahydroindolizine-3-carboxylate (0.27 g, 0.48 mmol, 1.0 equiv.) in toluene (15 mL) was added ammonium acetate (0.73 g, 9.52 mmol, 20.0 equiv.) followed by the addition of acetic acid (0.5 mL) under $N_2$. The reaction mixture was stirred for 1.5 h at 100° C., then cooled to room temperature and concentrated under vacuum. The residue was purified by silica gel chromatography with MeOH/DCM (0→10%) to yield N-(4-(2-((3S)-7-(2-amino-5-chlorophenyl)-5-oxo-1,2,3,5,8,8a-hexahydroindolizin-3-yl)-1H-imidazol-5-yl)-3-fluoropyridin-2-yl)-n-(bicyclo[1.1.1]pentan-1-yl)acetamide as a light yellow solid. LC/MS: mass calculated for $C_{29}H_{28}ClFN_6O_2$: 546.19, measured (ES, m/z): 547.35 $[M+H]^+$.

Step 3: N-(bicyclo[1.1.1]pentan-1-yl)-n-(4-(2-((3S)-7-(5-chloro-2-(1H-tetrazol-1-yl)phenyl)-5-oxo-1,2,3,5,8,8a-hexahydroindolizin-3-yl)-1H-imidazol-4-yl)-3-fluoropyridin-2-yl)acetamide To a solution of N-(4-(2-((3S)-7-(2-amino-5-chlorophenyl)-5-oxo-1,2,3,5,8,8a-hexahydroindolizin-3-yl)-1H-imidazol-5-yl)-3-fluoropyridin-2-yl)-n-(bicyclo[1.1.1]pentan-1-yl)acetamide (0.15 g, 0.27 mmol, 1.0 equiv.) in acetic acid (10 mL) were added trimethoxymethane (0.29 g, 2.74 mmol, 10.0 equiv.), and $TMSN_3$ (0.32 g, 2.74 mmol, 10.0 equiv.). The resulting mixture was stirred overnight at 50° C., then concentrated under vacuum to yield N-(bicyclo[1.1.1]pentan-1-yl)-n-(4-(2-((3S)-7-(5-chloro-2-(1H-tetrazol-1-yl)phenyl)-5-oxo-1,2,3,5,8,8a-hexahydroindolizin-3-yl)-1H-imidazol-4-yl)-3-fluoropyridin-2-yl)acetamide as a light yellow solid. LC/MS: mass calculated for $C_{30}H_{27}ClFN_9O_2$: 599.20, measured (ES, m/z): 600.25 $[M+H]^+$.

Step 4: (3S,8aR)-3-(5-(2-(Bicyclo[1.1.1]pentan-1-ylamino)-3-fluoropyridin-4-yl)-1H-imidazol-2-yl)-7-(5-chloro-2-(1H-tetrazol-1-yl)phenyl)-2,3,8,8a-tetrahydroindolizin-5(1H)-one To a solution of N-(bicyclo[1.1.1]pentan-1-yl)-n-(4-(2-((3S)-7-(5-chloro-2-(1H-tetrazol-1-yl)phenyl)-5-oxo-1,2,3,5,8,8a-hexahydroindolizin-3-yl)-1H-imidazol-4-yl)-3-fluoropyridin-2-yl)acetamide (0.15 g, 0.25 mmol, 1.0 equiv.) in THE (5 mL) was added 2M HCl (5 mL). The mixture was stirred for 5 h at 70° C., then cooled to room temperature and concentrated under vacuum. The residue was purified by reverse column chromatography with ACN-Water-5 mM $NH_4HCO_3$ (5→60%) to yield (3S,8aR)-3-(5-(2-(bicyclo[1.1.1]pentan-1-ylamino)-3-fluoropyridin-4-yl)-1H-imidazol-2-yl)-7-(5-chloro-2-(1H-tetrazol-1-yl)phenyl)-2,3,8,8a-tetrahydroindolizin-5(1H)-one as a white solid.

LC/MS: mass calculated for $C_{28}H_{25}ClFN_9O$: 557.19, measured (ES, m/z): 558.15 $[M+H]^+$. $^1H$ NMR (400 MHz, Methanol-$d_4$): δ 9.46 (s, 1H), 7.71 (d, J=5.4 Hz, 1H), 7.52-7.62 (m, 3H), 7.35 (s, 1H), 7.07 (s, 1H), 5.66 (s, 1H), 5.07 (d, J=8.8 Hz, 1H), 3.67-3.80 (m, 1H), 2.48-2.68 (m, 1H), 2.34 (s, 1H), 2.20-2.29 (m, 1H), 2.13-2.23 (m, 1H), 2.00-2.13 (m, 8H), 1.77-1.94 (m, 1H). $^{19}F$ NMR (376 MHz, Methanol-$d_4$): δ −144.42.

Example 97: 6-(2-((3S,8aR)-7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-5-yl)-3,4-dihydroquinolin-2(1H)-one

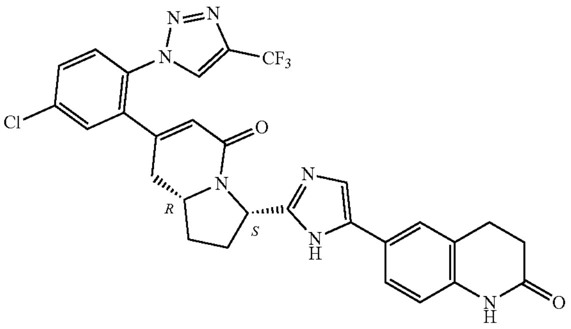

LC/MS: mass calculated for $C_{29}H_{23}ClF_3N_7O_2$: 593.16, measured (ES, m/z): 594.20$[M+H]^+$ $^1H$ NMR (400 MHz, Methanol-$d_4$) δ 8.86-9.00 (m, 1H), 7.61-7.70 (m, 3H), 7.37-7.41 (m, 2H), 7.19 (s, 1H), 6.86 (d, J=8.2 Hz, 1H), 5.73 (d, J=2.7 Hz, 1H), 5.02-5.09 (m, 1H), 3.56-3.78 (m, 1H), 2.84-2.93 (m, 2H), 2.58-2.71 (m, 1H), 2.44-2.52 (m, 2H), 2.17-2.27 (m, 2H), 1.98-2.13 (m, 2H), 1.85-1.92 (m, 1H). $^{19}$FNMR: (376 MHz, Methanol-$d_4$) δ 62.48.

Example 98: (3S*,8aR)-7-(5-chloro-2-(1H-tetrazol-1-yl)phenyl)-3-(5-(2-fluoro-6-(methylamino)pyridin-3-yl)-1H-imidazol-2-yl)-2,3,8,8a-tetrahydroindolizin-5(1H)-one

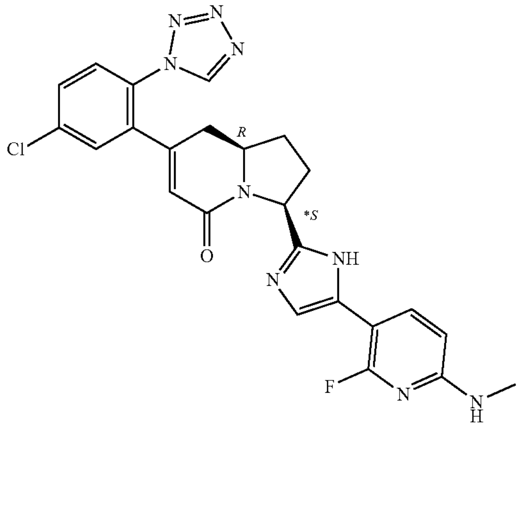

LC/MS: mass calculated for $C_{24}H_{21}ClFN_9O$: 505.15, measured (ES, m/z): 506.15 $[M+H]^+$ $^1H$ NMR (400 MHz, DMSO-$d_6$) δ 11.70 (s, 1H), 9.84 (s, 1H), 8.06 (s, 1H), 7.74-7.80 (m, 3H), 6.99-7.06 (m, 1H), 6.83 (s, 1H), 6.42 (dd, J=8.4, 2.1 Hz, 1H), 5.62 (d, J=2.6 Hz, 1H), 4.98 (d, J=8.5 Hz, 1H), 3.62-3.77 (m, 1H), 2.75 (d, J=4.8 Hz, 3H), 2.42-2.53 (m, 1H), 2.26-2.37 (m, 1H), 2.08-2.21 (m, 1H), 1.82-2.06 (m, 3H). $^{19}F$ NMR (376 MHz, DMSO-$d_6$) δ −70.44.

Example 99: Methyl (4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)carbamate

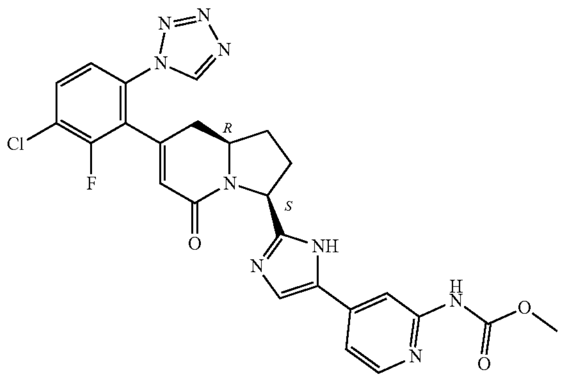

LC/MS: mass calculated for $C_{25}H_{21}ClFN_9O_3$: 549.14, measured (ES, m/z): 550.15 $[M+H]^+$ $^1H$ NMR (300 MHz, DMSO-$d_6$) δ 12.03 (s, 1H), 10.01 (s, 1H), 9.81 (s, 1H), 8.11-8.21 (m, 2H), 7.89-8.00 (m, 1H), 7.61-7.79 (m, 2H), 7.35 (d, J=5.3 Hz, 1H), 5.65 (d, J=2.5 Hz, 1H), 4.99 (d, J=8.6 Hz, 1H), 3.66 (s, 4H), 2.70-2.85 (m, 1H), 2.51-2.54 (m, 1H), 2.04-2.23 (m, 2H), 1.90-1.99 (m, 2H). $^{19}F$ NMR (282 MHz, DMSO-$d_6$) δ −112.50.

Example 1001-(4-(2-((3S*,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)azetidine-3-carbonitrile

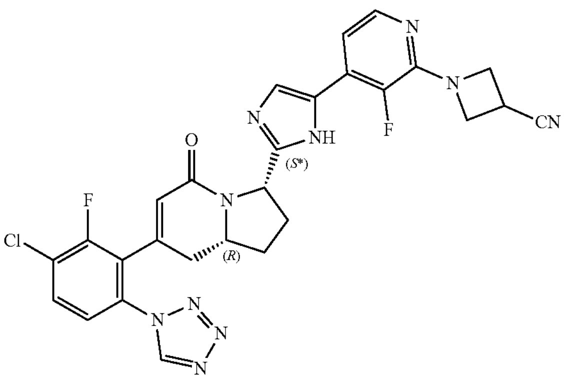

LC/MS: mass calculated for $C_{27}H_{21}ClF_2N_{10}O$: 574.16, measured (ES, m/z): 575.15 $[M+H]^+$ $^1H$ NMR (300 MHz, DMSO-$d_6$) δ 12.21 (s, 1H), 9.84 (s, 1H), 7.91-8.02 (m, 2H), 7.72 (dd, J=8.7, 1.5 Hz, 1H), 7.49 (d, J=3.5 Hz, 1H), 7.25-7.39 (m, 1H), 5.69 (d, J=2.7 Hz, 1H), 5.03 (d, J=8.5 Hz, 1H), 4.31-4.42 (m, 2H), 4.15-4.27 (m, 2H), 3.82-3.93 (m, 1H), 3.69-3.79 (m, 1H), 2.66-2.82 (m, 1H), 2.52-2.56 (m, 1H), 2.05-2.26 (m, 2H), 1.87-2.05 (m, 2H). $^{19}F$ NMR (282 MHz, DMSO-$d_6$) δ −112.85, −142.54.

Example 101 6-(2-((3S,8aR)-7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-5-yl)quinolin-2(1H)-one

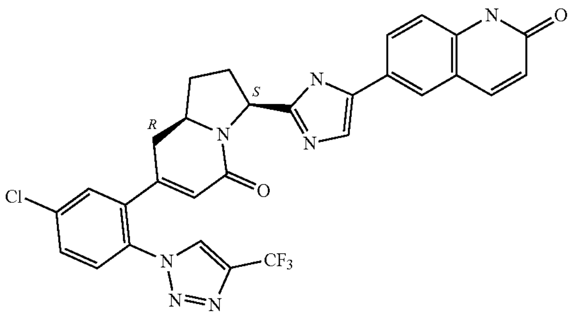

LC/MS: mass calculated for $C_{29}H_{21}ClF_3N_7O_2$: 591.14, measured (ES, m/z): 592.20 $[M+H]^+$ $^1H$ NMR (300 MHz, Methanol-$d_4$) δ 9.02 (d, J=1.0 Hz, 1H), 7.97-8.07 (m, 2H), 7.91 (dd, J=8.6, 1.9 Hz, 1H), 7.65-7.72 (m, 3H), 7.35-7.44 (m, 2H), 6.65 (d, J=9.5 Hz, 1H), 5.78 (d, J=2.7 Hz, 1H), 5.20 (d, J=8.7 Hz, 1H), 3.78-3.97 (m, 1H), 2.68-2.86 (m, 1H), 2.30-2.44 (m, 2H), 2.12-2.39 (m, 2H), 1.95-2.09 (m, 1H). $^{19}F$NMR: (282 MHz, Methanol-$d_4$) δ −62.54.

Example 1021-(4-(24(3R*,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)azetidine-3-carbonitrile

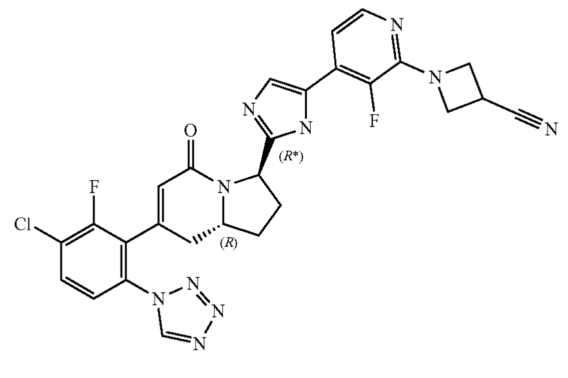

LC/MS: mass calculated for $C_{27}H_{21}ClF_2N_{10}O$: 574.16, measured (ES, m/z): 575.15 $[M+H]^+$ $^1H$ NMR (300 MHz, DMSO-$d_6$) δ 12.36 (s, 1H), 9.84 (s, 1H), 7.86-8.03 (m, 2H), 7.71 (dd, J=8.7, 1.5 Hz, 1H), 7.50 (d, J=3.9 Hz, 1H), 7.29-7.36 (m, 1H), 5.70 (d, J=2.5 Hz, 1H), 4.95-5.05 (m, 1H), 4.31-4.42 (m, 2H), 4.15-4.26 (m, 2H), 4.03-4.14 (m, 1H), 3.82-3.96 (m, 1H), 2.41-2.46 (m, 1H), 2.15-2.49 (m, 3H), 1.92-2.11 (m, 1H), 1.61-1.79 (m, 1H). $^{19}F$ NMR (282 MHz, DMSO-$d_6$) δ −113.05, −142.49.

Example 103: 4-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-3-fluoro-N-methoxy-pyridine-2-carboxamide

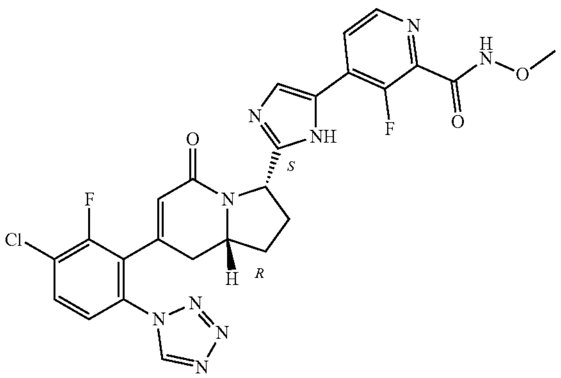

To a mixture of 4-(2-((3R,8aS)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid (37 mg, 0.07 mmol), O-methylhydroxyamine hydrochloride (8.5 mg, 0.1 mmol), and EDCl (19.5 mg, 0.1 mmol) was added pyridine (3 ml). The resulting mixture was maintained stirring at room temperature for 3 h. The solvent was removed under reduced pressure and the residue was purified by HPLC to yield 4-[2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-5-yl]-3-fluoro-N-methoxy-pyridine-2-carboxamide as a white solid.

$^1$H NMR (400 MHz, METHANOL-$d_4$) δ 9.50 (s, 1H), 8.40-8.48 (m, 1H), 7.97 (t, J=5.14 Hz, 1H), 7.82 (d, J=2.93 Hz, 1H), 7.74 (t, J=8.31 Hz, 1H), 7.47 (d, J=8.31 Hz, 1H), 5.64-5.69 (m, 1H), 5.14-5.21 (m, 1H), 3.81-3.95 (m, 1H), 3.75 (s, 3H), 2.77-2.90 (m, 1H), 2.55-2.64 (m, 1H), 2.30-2.43 (m, 1H), 2.10-2.25 (m, 2H), 1.86-2.01 (m, 1H). LC/MS calculated for $C_{25}H_{20}ClF_2N_9O_3$ 567.14, measured 568.2 ($MH^+$).

Example 104 N-(bicyclo[1.1.1]pentan-1-yl)-4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinamide

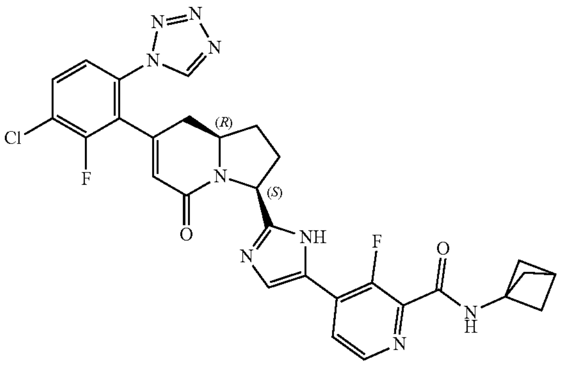

LC/MS: mass calculated for $C_{29}H_{24}ClF_2N_6O_2$: 603.17, measured (ES, m/z): 604.10[M+H]$^+$ $^1$H NMR (400 MHz, DMSO-$d_6$) δ−12.33 (s, 1H), 9.84 (s, 1H), 9.10 (s, 1H), 8.39 (d, J=5.0 Hz, 1H), 8.04-8.11 (m, 1H), 7.93-8.01 (m, 1H), 7.71 (d, J=8.7 Hz, 1H), 7.60-7.66 (m, 1H), 5.70 (d, J=2.7 Hz, 1H), 5.04 (d, J=8.8 Hz, 1H), 3.72-3.78 (m, 1H), 2.66-2.75 (m, 1H), 2.54-2.56 (m, 1H), 2.46 (s, 1H), 2.16-2.26 (m, 1H), 2.07-2.13 (m, 7H), 1.91-1.99 (m, 2H). $^{19}$F NMR (376 MHz, DMSO-$d_6$) δ −112.84, −126.53.

Example 105 (3S,8aS)-7-(3-chloro-2-fluoro-6-(1H-tetrazol-1-yl)phenyl)-3-(5-(3-fluoro-2-(2-oxopyrrolidin-1-yl)pyridin-4-yl)-1H-imidazol-2-yl)-2,3,8,8a-tetrahydroindolizin-5(1H)-one

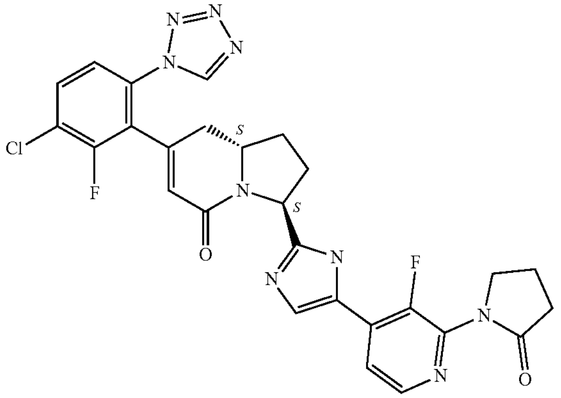

LC/MS: mass calculated for $C_{27}H_{22}ClF_2N_9O_2$: 577.16 measured (ES, m/z): 578.15 [M+H]$^+$ $^1$H NMR (400 MHz, DMSO-$d_6$) δ 12.43 (s, 1H), 9.83 (s, 1H), 8.23 (d, J=5.1 Hz, 1H), 7.94-8.01 (m, 1H), 7.86 (t, J=5.2 Hz, 1H), 7.70 (dd, J=8.7, 1.5 Hz, 1H), 7.58 (d, J=4.0 Hz, 1H), 5.70 (d, J=2.6 Hz, 1H), 5.02 (t, J=7.5 Hz, 1H), 4.08-4.19 (m, 1H), 3.90 (t, J=7.0 Hz, 2H), 2.52-2.55 (m, 1H), 2.46-2.49 (m, 2H), 2.32-2.44 (m, 2H), 2.21-2.28 (m, 1H), 2.10-2.19 (m, 2H), 1.96-2.06 (m, 1H), 1.67-1.75 (m, 1H). $^{19}$F NMR (376 MHz, DMSO-$d_6$) δ −113.05, −126.03.

Example 106 (3S,8aR)-7-(3-chloro-2-fluoro-6-(1H-tetrazol-1-yl)phenyl)-3-(5-(3-fluoro-2-(2-oxopyrrolidin-1-yl)pyridin-4-yl)-1H-imidazol-2-yl)-2,3,8,8a-tetrahydroindolizin-5(1H)-one

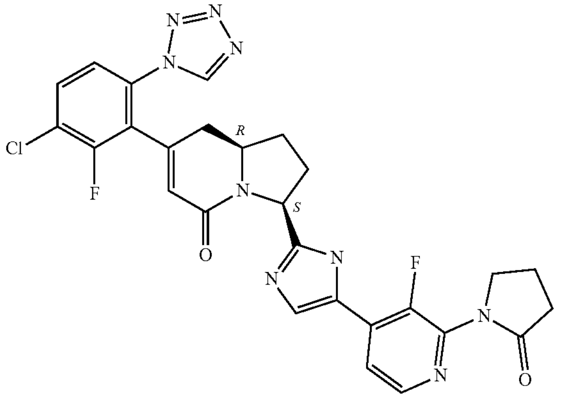

Step 1: 1-(3-Fluoro-4-iodopyridin-2-yl)pyrrolidin-2-one

To a mixture of methyl 4-((3-fluoro-4-iodopyridin-2-yl) amino)butanoate (720 mg, 2.13 mmol, 1.0 equiv.) in THE (120 mL) was added NaHMDS (2.6 mL, 2.60 mmol, 1.2 equiv.) at −78° C. under $N_2$. The reaction mixture was stirred at room temperature for 2 h. The reaction was then quenched by the addition of $NH_4Cl$, extracted with EtOAc (3×300 mL), dried over $Na_2SO_4$, concentrated. The residue was applied onto a silica gel column (EtOAc/PE: 0→70%) to yield 1-(3-fluoro-4-iodopyridin-2-yl)pyrrolidin-2-one as a light yellow oil. LC/MS: mass calculated for $C_9H_8FIN_2O$: 305.97, measured (ES, m/z): 306.90 $[M+H]^+$.

Step 2: 1-(4-(1-Ethoxyvinyl)-3-fluoropyridin-2-yl) pyrrolidin-2-one

To a solution of 1-(3-fluoro-4-iodopyridin-2-yl)pyrrolidin-2-one (530 mg, 1.73 mmol, 1.0 equiv.) in 1,4-dioxane (8 mL) were added tributyl(1-ethoxyvinyl)stannane (938 mg, 2.60 mmol, 1.5 equiv.) and $Pd(dppf)Cl_2$ (121 mg, 0.17 mmol, 0.1 equiv.) The mixture was stirred 2 h at 95° C. under an atmosphere of $N_2$ (balloon). The reaction mixture was cooled to room temperature. The resulting solution was extracted with water (5 mL) and ethyl acetate (20×3 mL). The organic layers were combined, washed with sodium carbonate (aq.) and brine, dried and concentrated under vacuum. The residue was applied on a $Al_2O_3$ column and eluted with ethyl acetate/hexane (1/3) to yield 1-(4-(1-ethoxyvinyl)-3-fluoropyridin-2-yl)pyrrolidin-2-one.

LC/MS: mass calculated for $C_{13}H_{15}FN_2O_2$: 250.11, measured (ES, m/z): 251.10 $[M+H]^+$.

Step 3: 1-(4-(2-Bromoacetyl)-3-fluoropyridin-2-yl) pyrrolidin-2-one

To a solution of 1-(4-(1-ethoxyvinyl)-3-fluoropyridin-2-yl)pyrrolidin-2-one (427 mg, 1.70 mmol, 1.0 equiv.) in THE/$H_2O$ 4 mL (3:1) was slowly added NBS (455 mg, 2.56 mmol, 1.5 equiv.) and the resulting mixture was stirred at 0° C. for 30 min. The mixture was concentrated under vacuum. The resulting residue was dissolved by the addition of $H_2O$. The resulting solution was extracted with of ethyl acetate (3×15 mL). The organic layers were combined, washed with brine, dried and concentrated under vacuum to yield 1-(4-(2-bromoacetyl)-3-fluoropyridin-2-yl)pyrrolidin-2-one as a yellow oil. LC/MS: mass calculated for $C_{11}H_{10}BrFN_2O_2$: 299.99, measured (ES, m/z): 301.10, 303.10 $[M+H, M+H+2]^+$.

Step 4: 2-(3-Fluoro-2-(2-oxopyrrolidin-1-yl)pyridin-4-yl)-2-oxoethyl (3S)-7-(6-amino-3-chloro-2-fluorophenyl)-5-oxo-1,2,3,5,8,8a-hexahydroindolizine-3-carboxylate To a mixture of (3S)-7-(6-amino-3-chloro-2-fluorophenyl)-5-oxo-1,2,3,5,8,8a-hexahydroindolizine-3-carboxylic acid (300 mg, 0.92 mmol, 1.0 equiv.) in DMF (5 mL) was added 1-(4-(2-bromoacetyl)-3-fluoropyridin-2-yl)pyrrolidin-2-one (417 mg, 1.39 mmol, 1.5 equiv.), followed by addition of $Cs_2CO_3$ (180 mg, 0.55 mmol, 0.6 equiv.). The reaction mixture was stirred at room temperature overnight, then partitioned between water and ethyl acetate (3×15 mL). The organic layers were combined, washed with sodium carbonate (aq.) and brine, dried and concentrated under vacuum. The residue was applied on a silica gel column and eluted with MeOH/DCM (010%) to yield of 2-(3-fluoro-2-(2-oxopyrrolidin-1-yl)pyridin-4-yl)-2-oxoethyl (3S)-7-(6-amino-3-chloro-2-fluorophenyl)-5-oxo-1,2,3,5,8,8a-hexahydroindolizine-3-carboxylate as an off-white solid. LC/MS: mass calculated for $C_{26}H_{23}ClF_2N_4O_5$: 544.13, measured (ES, m/z): 545.30 $[M+H]^+$.

Step 5: (3S,8aR)-7-(6-Amino-3-chloro-2-fluorophenyl)-3-(5-(3-fluoro-2-(2-oxopyrrolidin-1-yl)pyridin-4-yl)-1H-imidazol-2-yl)-2,3,8,8a-tetrahydroindolizin-5(1H)-one To a solution of 2-(3-fluoro-2-(2-oxopyrrolidin-1-yl)pyridin-4-yl)-2-oxoethyl (3S)-7-(6-amino-3-chloro-2-fluorophenyl)-5-oxo-1,2,3,5,8,8a-hexahydroindolizine-3-carboxylate (260 mg, 0.48 mmol, 1.0 equiv.) in AcOH/toluene 6 mL (5:1) was added $CH_3COONH_4$ (735 mg, 9.54 mmol, 20.0 equiv.). The reaction mixture was stirred 2 h at 110° C. The excess solvent was removed under reduced pressure. The residue was applied on a silica gel column and elided with MeOH/DCM (0→10%) to yield (3S)-7-(6-amino-3-chloro-2-fluorophenyl)-3-(5-(3-fluoro-2-(2-oxopyrrolidin-1-yl)pyridin-4-yl)-1H-imidazol-2-yl)-2,3,8,8a-tetrahydroindolizin-5(1H)-one as a yellow solid. LC/MS: mass calculated for $C_{26}H_{23}ClF_2N_4O_5$: 524.15, measured (ES, m/z): 525.30 $[M+H]^+$.

Step 6: (3S,8aR)-7-(3-Chloro-2-fluoro-6-(1H-tetrazol-1-yl)phenyl)-3-(5-(3-fluoro-2-(2-oxopyrrolidin-1-yl)pyridin-4-yl)-1H-imidazol-2-yl)-2,3,8,8a-tetrahydroindolizin-5(1H)-one To a solution of (3S)-7-(6-amino-3-chloro-2-fluorophenyl)-3-(5-(3-fluoro-2-(2-oxopyrrolidin-1-yl)pyridin-4-yl)-1H-imidazol-2-yl)-2,3,8,8a-tetrahydroindolizin-5(1H)-one (200 mg, 0.38 mmol, 1.0 equiv.) in AcOH (2 mL) was added trimethoxymethane (2 mL) followed by $TMSN_3$ (2 mL). The resulting solution was stirred at room temperature overnight. The residue was applied onto a prep-HPLC (80 g, MeOH/$H_2O$ (0.05% $NH_4HCO_3$): 0→55%) to yield (3S,8aR)-7-(3-chloro-2-fluoro-6-(1H-tetrazol-1-yl)phenyl)-3-(5-(3-fluoro-2-(2-oxopyrrolidin-1-yl)pyridin-4-yl)-1H-imidazol-2-yl)-2,3,8,8a-tetrahydroindolizin-5(1H)-one as a white solid.

LC/MS: mass calculated for $C_{27}H_{22}ClF_2N_9O_2$: 577.16, measured (ES, m/z): 578.15 $[M+H]^+$ $^1H$ NMR (400 MHz, DMSO-$d_6$) δ–12.29 (s, 1H), 9.84 (s, 1H), 8.25 (d, J=5.1 Hz, 1H), 7.97 (t, J=8.2 Hz, 1H), 7.88 (t, J=5.3 Hz, 1H), 7.71 (d, J=8.7 Hz, 1H), 7.57 (s, 1H), 5.70 (s, 1H), 5.04 (d, J=8.5 Hz, 1H), 3.80-3.92 (m, 2H), 3.70-3.79 (m, 1H), 2.66-2.76 (m, 1H), 2.51-2.56 (m, 3H), 2.09-2.24 (m, 4H), 1.91-2.00 (m, 2H). $^{19}F$ NMR (376 MHz, DMSO-$d_6$) δ-112.83, −126.08.

Example 107: (3S,8aR)-7-(3-chloro-2-fluoro-6-(1H-tetrazol-1-yl)phenyl)-3-(4-fluoro-5-(3-fluoro-2-(hydroxymethyl)pyridin-4-yl)-1H-imidazol-2-yl)-2,3,8,8a-tetrahydroindolizin-5(1H)-one

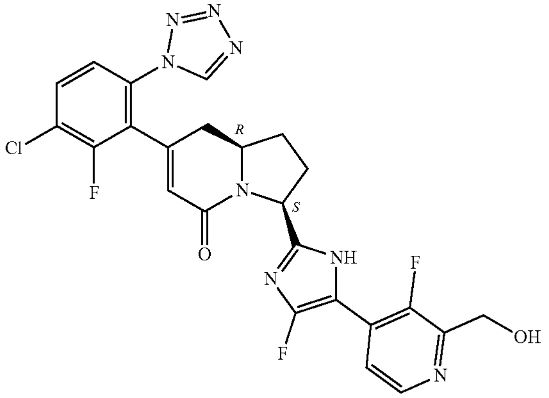

To a mixture of (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5 (1H)-one (250 mg, 0.48 mmol, 1.0 equiv.) and pyridine (377 mg, 4.77 mmol, 10.0 equiv.) in THE (7 mL) and ACN (21 mL) under $N_2$ was added F-TEDA (236 mg, 0.67 mmol, 1.4 equiv.) at 0° C. The reaction mixture was stirred at 0° C. for 2 h, then quenched with water (30 mL), extracted with EtOAc (3×30 mL), dried over $Na_2SO_4$, concentrated. The residue was applied onto a C18 reverse column (ACN/$H_2O$ (0.05% $NH_4HCO_3$): 5%→42%→45%) to (3S,8aR)-7-(3-chloro-2-fluoro-6-(1H-tetrazol-1-yl)phenyl)-3-(4-fluoro-5-(3-fluoro-2-(hydroxymethyl)pyridin-4-yl)-1H-imidazol-2-yl)-2,3,8,8a-tetrahydroindolizin-5(1H)-one as a light yellow solid.

LC/MS: mass calculated for $C_{24}H_{18}ClF_3N_8O_2$: 542.12, measured (ES, m/z): 543.10 $[M+H]^+$ $^1H$ NMR (400 MHz, DMSO-$d_6$) δ 12.60 (s, 1H), 9.83 (s, 1H), 8.38 (d, J=5.1 Hz, 1H), 7.92-8.00 (m, 1H), 7.71 (dd, J=8.7 Hz, 1.5 Hz, 1H), 7.44-7.52 (m, 1H), 5.68 (d, J=2.1 Hz, 1H), 5.34 (t, J=6.0 Hz, 1H), 5.03 (d, J=8.6 Hz, 1H), 4.63 (dd, J=6.0, 2.3 Hz, 2H), 3.63-3.82 (m, 1H), 2.53-2.66 (m, 2H), 2.16-2.28 (m, 1H), 2.04-2.16 (m, 1H), 1.88-2.03 (m, 2H). $^{19}F$ NMR (376 MHz, DMSO-$d_6$) δ −112.89, −125.70, −130.37.

Example 108 (3S*,8aR)-7-(3-chloro-2-fluoro-6-(1H-tetrazol-1-yl)phenyl)-3-(5-(3-fluoro-2-(2-oxa-6-azaspiro[3.3]heptan-6-yl)pyridin-4-yl)-1H-imidazol-2-yl)-2,3,8,8a-tetrahydroindolizin-5(1H)-one

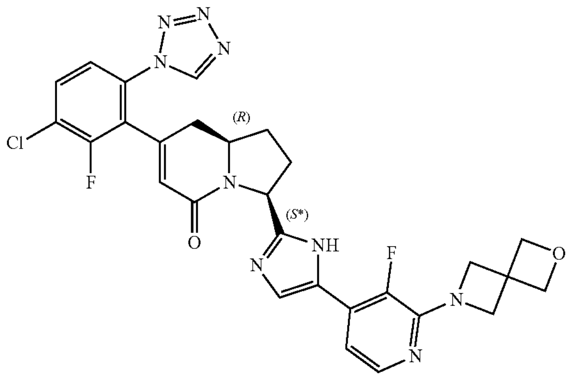

Step 1: 2-(3-Fluoro-2-(2-oxa-6-azaspiro[3.3]heptan-6-yl)pyridin-4-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate To a solution of (8aR)-7-(3-chloro-2-fluoro-6-(1H-tetrazol-1-yl)phenyl)-5-oxo-1,2,3,5,8,8a-hexahydroindolizine-3-carboxylic acid (180 mg, 0.47 mmol, 1.0 equiv.) in DMF (5 mL) was added $K_2CO_3$ (131 mg, 0.95 mmol, 2.0 equiv.). After stirring at room temperature for 0.5 h, 2-bromo-1-(3-fluoro-2-(2-oxa-6-azaspiro[3.3]heptan-6-yl)pyridin-4-yl) ethan-1-one (450 mg, 1.43 mmol, 3.0 equiv.) was added. The mixture was stirred at room temperature for 1 h. The resulting mixture was extracted with ethyl acetate (3×20 mL). The organic layers were combined, dried over anhydrous sodium sulfate, filtered and concentrated. The residue was purified by silica gel chromatography (0→7% MeOH/DCM) to yield the 2-(3-fluoro-2-(2-oxa-6-azaspiro[3.3]heptan-6-yl)pyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate as a yellow oil. LC/MS: mass calculated for $C_{28}H_{24}ClF_2N_7O_5$: 611.15, measured (ES, m/z): 612.35 $[M+H]^+$.

Step 2: (3S',8aR)-7-(3-Chloro-2-fluoro-6-(1H-tetrazol-1-yl)phenyl)-3-(5-(3-fluoro-2-(2-oxa-6-azaspiro[3.3]heptan-6-yl)pyridin-4-yl)-1H-imidazol-2-yl)-2,3,8,8a-tetrahydroindolizin-5(1H)-one To a solution of 2-(3-fluoro-2-(2-oxa-6-azaspiro[3.3]heptan-6-yl)pyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate (150 mg, 0.25 mmol, 1.0 equiv.) in toluene (10 mL) and acetic acid (1 mL) was added ammonium acetate (378 mg, 4.90 mmol, 20.0 equiv.). The mixture was stirred at 100° C. for 1 h. The residue was purified by reverse phase chromatography on C18 column with $CH_3CN$/0.05% TFA water (5→50%) to yield a second residue, which was purified by Chiral-HPLC with MtBE (0.1% DEA):EtOH=70:30 to yield (3*S,8aR)-7-(3-chloro-2-fluoro-6-(1H-tetrazol-1-yl)phenyl)-3-(5-(3-fluoro-2-(2-oxa-6-azaspiro[3.3]heptan-6-yl)pyridin-4-yl)-1H-imidazol-2-yl)-2,3,8,8a-tetrahydroindolizin-5(1H)-one as an off-white solid.

LC/MS: mass calculated for $C_{28}H_{24}ClF_2N_6O_2$: 591.17, measured (ES, m/z): 592.15 $[M+H]^+$ $^1H$ NMR (400 MHz, DMSO-$d_6$) δ −12.17 (s, 1H), 9.83 (s, 1H), 7.93-8.00 (m, 1H), 7.86 (d, J=5.2 Hz, 1H), 7.71 (dd, J=8.7, 1.5 Hz, 1H), 7.44-7.47 (m, 1H), 7.22-7.29 (m, 1H), 5.68 (d, J=2.7 Hz, 1H), 5.01 (d, J=8.7 Hz, 1H), 4.73 (s, 4H), 4.21-4.27 (m, 4H), 3.65-3.78 (m, 1H), 2.64-2.83 (m, 1H), 2.53-2.57 (m, 1H), 2.14-2.29 (m, 1H), 2.04-2.13 (m, 1H), 1.88-2.01 (m, 2H). $^{19}F$ NMR (376 MHz, DMSO-$d_6$) δ −112.85, −142.71.

Example 109 (3*R,8aR)-3-(5-(2-(1-((tert-butyldimethylsilyl)oxy)cyclopropyl)-3-fluoropyridin-1-yl)-4-fluoro-1H-imidazol-2-yl)-7-(3-chloro-2-fluoro-6-(1H-tetrazol-1-yl)phenyl)-2,3,8,8a-tetrahydroindolizin-5(1H)-one

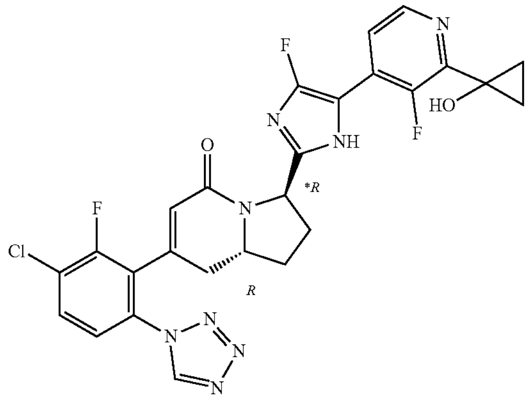

LC/MS: mass calculated for $C_{26}H_{20}ClF_3N_8O_2$: 568.13, measured (ES, m/z): 569.15 $[M+H]^+$. $^1H$ NMR (400 MHz, DMSO-$d_6$) δ 12.59 (s., 1H), 9.83 (s, 1H), 8.28 (d, J=5.1 Hz, 1H), 7.92-8.00 (m, 1H), 7.71 (dd, J=8.7, 1.5 Hz, 1H), 7.40-7.44 (m, 1H), 6.15 (s, 1H), 5.67 (d, J=2.1 Hz, 1H), 5.00-5.08 (m, 1H), 3.65-3.79 (m, 1H), 2.07-2.28 (m, 2H), 1.87-2.03 (m, 2H), 1.20-1.25 (m, 2H), 1.08-1.17 (m, 2H), 0.97-1.06 (m, 2H). $^{19}F$ NMR (376 MHz, DMSO-$d_6$) δ −112.88, 125.91, −126.75.

Example 110 (3*R,8aR)-3-(5-(2-(azetidin-1-yl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

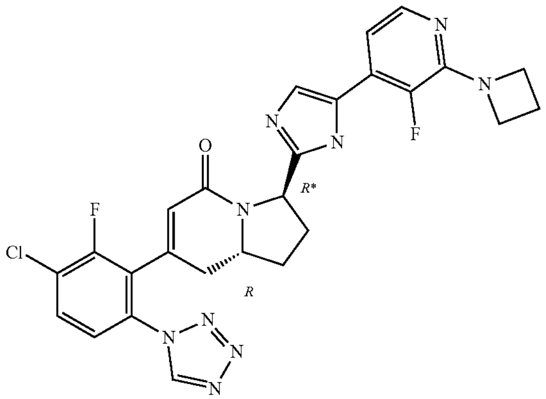

LC/MS: mass calculated for $C_{26}H_{22}ClF_2N_9O$: 549.16, measured (ES, m/z): 550.15 $[M+H]^+$. $^1H$ NMR (300 MHz, DMSO-$d_6$) δ 12.33 (s, 1H), 9.84 (s, 1H), 7.93-8.03 (m, 1H), 7.85 (d, J=5.2 Hz, 1H), 7.71 (dd, J=8.7, 1.5 Hz, 1H), 7.47 (d, J=3.9 Hz, 1H), 7.22 (s, 1H), 5.70 (d, J=2.5 Hz, 1H), 4.93-5.05 (m, 1H), 4.01-4.18 (m, 5H), 2.52-2.56 (m, 1H), 2.23-2.49 (m, 5H), 1.98-2.09 (m, 1H), 1.61-1.72 (m, 1H). $^{19}F$ NMR (282 MHz, DMSO-$d_6$) δ −113.05, −142.65.

Example 111 (3*S,8aR)-3-(5-(2-(azetidin-1-yl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

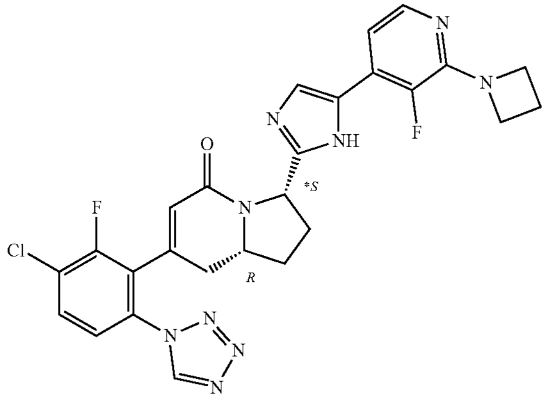

Step 1: 2-(2-(Azetidin-1-yl)-3-fluoropyridin-4-yl)-2-oxoethyl (3S,8aR)-7-(6-amino-3-chloro-2-fluorophenyl)-5-oxo-1,2,3,5,8,8a-hexahydroindolizine-3-carboxylate 7-(6-Amino-3-chloro-2-fluorophenyl)-5-oxo-1,2,3,5,8,8a-hexahydroindolizine-3-carboxylic acid (300 mg, 0.92 mmol, 1.0 equiv.) and potassium carbonate (192 mg, 1.39 mmol, 1.5 equiv.) were added to acetonitrile (20 mL). The mixture was stirred at room temperature for 0.5 h and then 1-(2-(azetidin-1-yl)-3-fluoropyridin-4-yl)-2-bromoethan-1-one (378 mg, 1.39 mmol, 1.5 equiv.) was added. The reaction mixture was stirred at room temperature for 4 h, diluted with water (50 mL), then extracted with EA (10.0 mL×3). The organic layers were combined, washed with brine (50 mL), dried and concentrated under reduced pressure. The residue was purified by silica gel chromatography (0→20% MeOH/DCM) to yield the 2-(2-(azetidin-1-yl)-3-fluoropyridin-4-yl)-2-oxoethyl 7-(6-amino-3-chloro-2-fluorophenyl)-5-oxo-1,2,3,5,8,8a-hexahydroindolizine-3-carboxylate as a yellow solid. C/MS: mass calculated for $C_{25}H_{23}ClF_2N_4O_4$: 516.14, measured (ES, m/z): 517.20 $[M+H]^+$.

Step 2: (3S,8aR)-7-(6-Amino-3-chloro-2-fluorophenyl)-3-(5-(2-(azetidin-1-yl)-3-fluoropyridin-4-yl)-1H-imidazol-2-yl)-2,3,8,8a-tetrahydroindolizin-5(1H)-one 2-(2-(Azetidin-1-yl)-3-fluoropyridin-4-yl)-2-oxoethyl 7-(6-amino-3-chloro-2-fluorophenyl)-5-oxo-1,2,3,5,8,8a-hexahydroindolizine-3-carboxylate (300 mg, 0.58 mmol, 1.0 equiv.), ammonium acetate (447 mg, 5.80 mmol, 10.0 equiv.) were dissolved in toluene (10 mL) and acetic acid (1 mL). The resulting mixture was stirred at 90° C. for 1 h, then concentrated under reduced pressure. The residue was purified by silica gel chromatography (0→20% MeOH/DCM) to yield 7-(6-amino-3-chloro-2-fluorophenyl)-3-(5-(2-(azetidin-1-yl)-3-fluoropyridin-4-yl)-1H-imidazol-2-yl)-2,3,8,8a-tetrahydroindolizin-5(1H)-one as a yellow oil. LC/MS: mass calculated for $C_{25}H_{23}ClF_2N_6O$: 496.94, measured (ES, m/z): 497.30 $[M+H]^+$.

Step 3: (3'S,8aR)-3-(5-(2-(Azetidin-1-yl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of 7-(6-amino-3-chloro-2-fluorophenyl)-3-(5-(2-(azetidin-1-yl)-3-fluoropyridin-4-yl)-1H-imidazol-2-yl)-2,3,8,8a-tetrahydroindolizin-5(1H)-one (300 mg, 0.60 mmol, 1.0 equiv.) in acetic acid (4 mL) was added azidotrimethylsilane (2 mL) and trimethoxymethane (2 mL). The resulting mixture was stirred at room temperature for 16 h. The mixture was concentrated under reduced pressure. The residue was purified by reverse phase chromatography on C18 column with (MeCN/$H_2O$ (0.05%): 0→40%) to yield a yellow solid, which was further purified by Chiral HPLC with MeOH:ACN:DCM=1:1:1 (0.1% DEA) to yield (3S',8aR)-3-(5-(2-(azetidin-1-yl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one.

LC/MS: mass calculated for $C_{26}H_{22}ClF_2N_9O$: 549.16, measured (ES, m/z): 550.15 $[M+H]^+$. $^1H$ NMR (300 MHz, DMSO-$d_6$) δ12.17 (s, 1H), 9.83 (s, 1H), 7.92-8.02 (m, 1H), 7.86 (d, J=5.2 Hz, 1H), 7.71 (dd, J=8.7, 1.5 Hz, 1H), 7.40-7.50 (m, 1H), 7.25 (s, 1H), 5.69 (d, J=2.5 Hz, 1H), 5.03 (d, J=8.4 Hz, 1H), 4.03-4.14 (m, 4H), 3.62-3.81 (m, 1H), 2.65-2.81 (m, 1H), 2.50-2.52 (m, 1H), 2.29-2.39 (m, 2H), 2.05-2.26 (m, 2H), 1.88-2.02 (m, 2H). $^{19}F$ NMR (282 MHz, DMSO-$d_6$) δ −112.85, −142.72.

Example 112 (3*R,8aR)-7-(3-chloro-2-fluoro-6-(1H-tetrazol-1-yl)phenyl)-3-(5-(3-fluoro-2-(1H-1,2,4-triazol-1-yl)pyridin-4-yl)-1H-imidazol-2-yl)-2,3,8,8a-tetrahydroindolizin-5(1H)-one

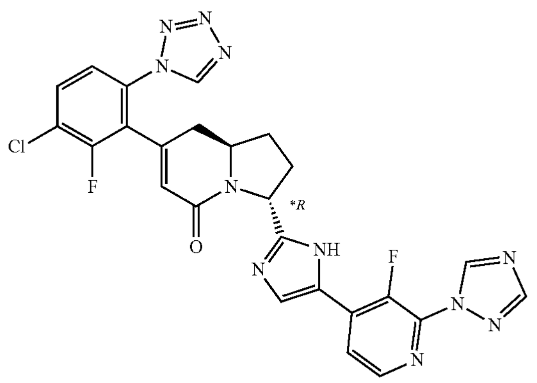

LC/MS: mass calculated for $C_{25}H_{18}ClF_2N_{11}O$: 561.14, measured (ES, m/z): 562.15 $[M+H]^+$. $^1H$ NMR (400 MHz, DMSO-$d_6$) δ 12.41 (s, 1H), 9.83 (s, 1H), 9.19 (s, 1H), 8.37-8.45 (m, 1H), 8.33 (s, 1H), 8.06-8.12 (m, 1H), 7.91-7.99 (m, 1H), 7.67-7.74 (m, 2H), 5.69 (d, J=2.7 Hz, 1H), 5.04 (d, J=8.8 Hz, 1H), 3.69-3.80 (m, 1H), 2.65-2.77 (m, 1H), 2.49-2.58 (m, 1H), 2.14-2.28 (m, 1H), 2.03-2.13 (m, 1H), 1.87-2.02 (m, 2H). $^{19}F$ NMR (376 MHz, DMSO-$d_6$) δ −112.83, −131.41.

Example 113: (3S,8aR)-7-[3-Chloro-2-fluoro-6-(tetrazol-1-yl)phenyl]-3-[4-deuterio-5-[2-[dideuterio(hydroxy)methyl]-3-fluoro-4-pyridyl]-1H-imidazol-2-yl]-2,3,8,8a-tetrahydro-1H-indolizin-5-one

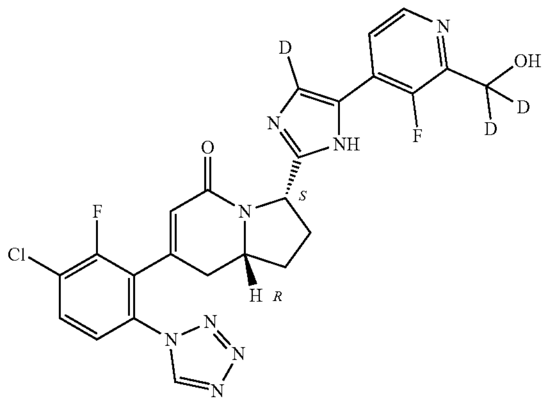

To a mixture of (3R,8aS)-7-(3-chloro-2-fluoro-6-(1H-tetrazol-1-yl)phenyl)-3-(5-(3-fluoro-2-(hydroxymethyl-$d_2$) pyridin-4-yl)-4-iodo-1H-imidazol-2-yl)-2,3,8,8a-tetrahydroindolizin-5(1H)-one (25 mg, 0.038 mmol) and Zn dust (25 mg, 0.38 mmol) was added $CD_3COOD$ (1.5 g) and the mixture was stirred at room temperature for 2 h. The mixture was stirred for another 2 h and the resulting precipitate was filtered off. The filtrate was concentrated under reduced pressure and the residue was purified by Gilson HPLC to yield (3S,8aR)-7-[3-chloro-2-fluoro-6-(tetrazol-1-yl)phenyl]-3-[4-deuterio-5-[2-[dideuterio(hydroxy)methyl]-3-fluoro-4-pyridyl]-1H-imidazol-2-yl]-2,3,8,8a-tetrahydro-1H-indolizin-5-one as a light yellow solid.

LC/MS calculated for $C_{24}H_{19}ClF_2NBO_2$: 527.1, measured 528.3 ($MH^+$). $^1H$ NMR (400 MHz, METHANOL-$d_4$) δ 9.62 (s, 1H), 8.56 (s, 1H), 8.46 (s, 1H), 7.85 (dd, J=7.83, 8.80 Hz, 1H), 7.58 (dd, J=1.71, 8.56 Hz, 1H), 5.77-5.85 (m, 1H), 5.21-5.30 (m, 1H), 3.96-4.13 (m, 1H), 2.75-2.88 (m, 1H), 2.66-2.73 (m, 1H), 2.35-2.45 (m, 1H), 2.27-2.33 (m, 1H), 2.16-2.24 (m, 1H), 2.02-2.12 (m, 1H).

Example 114 3-[4-[2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]oxazolidin-2-one

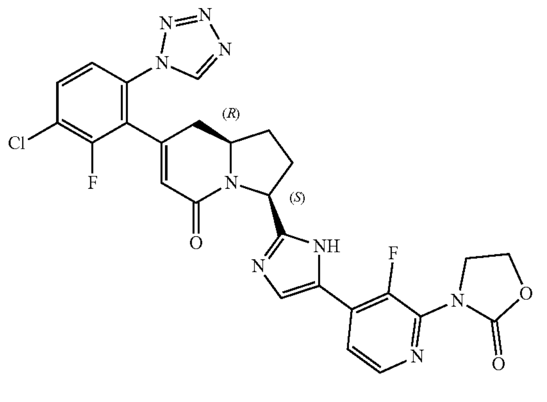

Step 1: 2-(3-Fluoro-2-(2-oxooxazolidin-3-yl)pyridin-4-yl)-2-oxoethyl (3S)-7-(6-amino-3-chloro-2-fluorophenyl)-5-oxo-1,2,3,5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) in DMF (5 mL), 3-(4-(2-bromoacetyl)-3-fluoropyridin-2-yl)oxazolidin-2-one (300 mg, 0.99 mmol, 1.5 equiv.), and $K_2CO_3$ (51 mg, 0.37 mmol, 0.6 equiv.) was stirred at room temperature overnight. The resulting solution was partitioned between water and ethyl acetate (3×15 mL). The organic layers were combined, washed with sodium carbonate (aq.) and brine, dried and concentrated under vacuum. The residue was applied on a silica gel column and eluted with MeOH/DCM (0→10%) to yield 2-(3-fluoro-2-(2-oxooxazolidin-3-yl)pyridin-4-yl)-2-oxoethyl (3S)-7-(6-amino-3-chloro-2-fluorophenyl)-5-oxo-1,2,3,5,8,8a-hexahydroindolizine-3-carboxylate as an off-white solid. LC/MS: mass calculated for $C_{25}H_{21}ClF_2N_4O_6$: 546.11, measured (ES, m/z): 547.30 $[M+H]^+$.

Step 2: 3-(4-(2-((3S,8aR)-7-(6-Amino-3-chloro-2-fluorophenyl)-5-oxo-1,2,3,5,8,8a-hexahydroindolizin-3-yl)-1H-imidazol-5-yl)-3-fluoropyridin-2-yl)oxazolidin-2-one A mixture of 2-(3-fluoro-2-(2-oxooxazolidin-3-yl)pyridin-4-yl)-2-oxoethyl (3S)-7-(6-amino-3-chloro-2-fluorophenyl)-5-oxo-1,2,3,5,8,8a-hexahydroindolizine-3-carboxylate (360 mg, 0.66 mmol, 1.0 equiv.) in AcOH/toluene (6 mL, 5:1) and $CH_3COONH_4$ (1.0 g, 12.99 mmol, 20.0 equiv.) was stirred 2 h at 110° C. The reaction mixture was concentrated under vacuum. The residue was applied on a silica gel column and eluted with MeOH/DCM (1/10) to yield 3-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)oxazolidin-2-one as a yellow solid. LC/MS: mass calculated for $C_{25}H_{21}ClF_2NeO_3$: 526.13, measured (ES, m/z): 527.30 $[M+H]^+$.

Step 3: 3-[4-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]oxazolidin-2-one To a solution of 3-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)oxazolidin-2-one (130 mg, 0.25 mmol, 1.0 equiv.) in AcOH (2 mL) was added trimethoxymethane (2 mL) and $TMSN_3$ (2 mL). The resulting solution was stirred at room temperature overnight. The residue was purified by prep-HPLC on C18 column (MeOH/$H_2O$ (0.05% $NH_4HCO_3$): 0→55%) to yield 3-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)oxazolidin-2-one as a white solid.

LC/MS: mass calculated for $C_{28}H_{20}ClF_2NeO_3$: 579.13, measured (ES, m/z): 580.20 $[M+H]^+$. $^1H$ NMR (400 MHz, DMSO-$d_6$) δ12.32 (s, 1H), 9.84 (s, 1H), 8.25 (d, J=5.1 Hz, 1H), 7.94-8.00 (m, 1H), 7.90 (t, J=5.2 Hz, 1H), 7.71 (dd, J=8.7, 1.5 Hz, 1H), 7.58-7.63 (m, 1H), 5.70 (d, J=2.7 Hz, 1H), 5.05 (d, J=8.7 Hz, 1H), 4.55 (t, J=7.7 Hz, 2H), 4.16 (t, J=7.7 Hz, 2H), 3.71-3.78 (m, 1H), 2.67-2.76 (m, 1H), 2.54-2.56 (m, 1H), 2.16-2.25 (m, 1H), 2.07-2.14 (m, 1H), 1.94-1.99 (m, 2H). $^{19}F$ NMR (376 MHz, DMSO-$d_6$) δ −112.84, −127.74.

Example 115 (3S,8a*R)-7-(3-chloro-2-fluoro-6-(1H-tetrazol-1-yl)phenyl)-3-(4-(3-fluoro-2-(1H-pyrazol-5-yl)pyridin-4-yl)-1H-imidazol-2-yl)-2,3,8,8a-tetrahydroindolizin-5(1H)-one

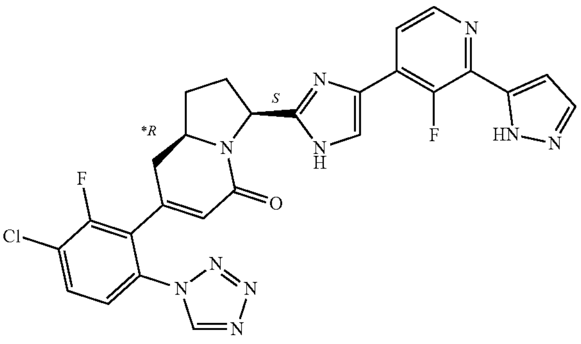

LC/MS: mass calculated for $C_{26}H_{19}ClF_2N_{10}O$: 560.14, measured (ES, m/z): 561.20 $[M+H]^+$. $^1H$ NMR (400 MHz, DMSO-$d_6$) δ 13.10–13.69 (m, 1H), 12.22-12.43 (m, 1H), 9.85 (s, 1H), 8.45 (s, 1H), 7.79-8.04 (m, 2H), 7.58-7.76 (m, 3H), 6.85 (s, 1H), 5.71 (d, J=2.7 Hz, 1H), 5.06 (d, J=8.7 Hz, 1H), 3.69-3.83 (m, 1H), 2.64-2.83 (m, 1H), 2.54-2.59 (m, 1H), 2.07-2.29 (m, 2H), 1.90-2.04 (m, 2H). $^{19}F$ NMR (376 MHz, DMSO-$d_6$) δ −112.83, −124.93, 126.03.

Example 116 (3*R,8aR)-7-(3-chloro-2-fluoro-6-(1H-tetrazol-1-yl)phenyl)-3-(5-(3-fluoro-2-(1-hydroxycyclopropyl)pyridin-4-yl)-1H-imidazol-2-yl-4-d)-2,3,8,8a-tetrahydroindolizin-5(1H)-one

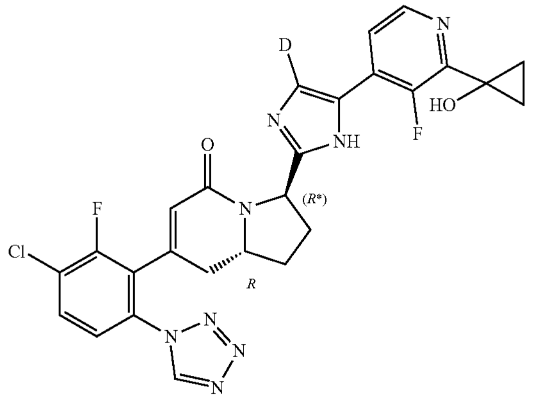

LC/MS: mass calculated for $C_{26}H_{20}ClDF_2N_8O_2$: 551.15, measured (ES, m/z): 552.10 $[M+H]^+$. $^1H$ NMR (400 MHz, Methanol-$d_4$) δ 9.59 (s, 1H), 8.28 (d, J=5.1 Hz, 1H), 7.99 (s, 1H), 7.80-7.87 (m, 1H), 7.56 (dd, J=8.7, 1.6 Hz, 1H), 5.76 (s, 1H), 5.19 (d, J=8.7 Hz, 1H), 3.87-4.00 (m, 1H), 2.82-2.95 (m, 1H), 2.55-2.70 (m, 1H), 2.31-2.40 (m, 1H), 2.16-2.30 (m, 2H), 2.00-2.15 (m, 1H), 1.20-1.26 (m, 2H), 1.13-1.19 (m, 2H). $^{19}F$ NMR (376 MHz, Methanol-$d_4$) δ −113.49, −127.60.

Example 117 (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl-4-d)-2,3,8,8a-tetrahydroindolizin-5(1H)-one

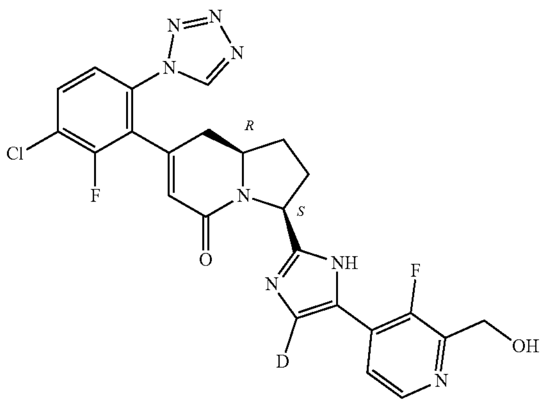

LC/MS: mass calculated for $C_{24}H_{18}ClDF_2N_8O_2$: 525.14, measured (ES, m/z): 526.15 $[M+H]^+$. $^1H$ NMR (400 MHz, DMSO-$d_6$) δ−12.30 (brs, 1H), 9.84 (s, 1H), 8.30-8.40 (m, 1H), 7.95-8.01 (m, 1H), 7.89 (t, J=5.4 Hz, 1H), 7.71 (dd, J=8.7, 1.5 Hz, 1H), 5.70 (d, J=2.7 Hz, 1H), 5.13-5.50 (m, 1H), 5.05 (d, J=8.7 Hz, 1H), 4.64 (d, J=2.3 Hz, 2H), 3.65-3.83 (m, 1H), 2.62-2.83 (m, 1H), 2.53-2.60 (m, 1H), 2.05-2.30 (m, 2H), 1.83-2.04 (m, 2H). $^{19}F$ NMR (376 MHz, DMSO-$d_6$) δ −112.51, −130.07.

Example 118 6-(24(3*S,8a*R)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-5-fluoro-1,4-dihydro-2H-benzo[d][1,3]oxazin-2-one

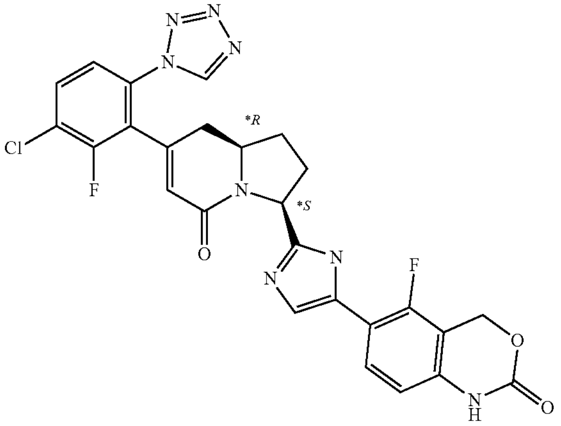

Step 1: 2-(5-Fluoro-2-oxo-1,4-dihydro-2H-benzo[d][1,3]oxazin-6-yl)-2-oxoethyl (3S)-7-(6-amino-3-chloro-2-fluorophenyl)-5-oxo-1,2,3,5,8,8a-hexahydroindolizine-3-carboxylate To a solution of 7-(6-amino-3-chloro-2-fluorophenyl)-5-oxo-1,2,3,5,8,8a-hexahydroindolizine-3-carboxylic acid (200 mg, 0.62 mmol, 1.0 equiv.) in N,N-dimethylformamide (5 mL) was added cesium carbonate (220 mg, 0.68 mmol, 1.1 equiv.). To the resulting solution was added 6-(2-bromoacetyl)-5-fluoro-1,4-dihydro-2H-benzo[d][1,3]oxazin-2-one (267 mg, 0.92 mmol, 1.5 equiv.), and the resulting mixture was stirred at room temperature for 1.5 h, then diluted with water and extracted with ethyl acetate twice. The combined organic layers was washed with brine, dried over $Na_2SO_4$, concentrated to yield 2-(5-fluoro-2-oxo-1,4-dihydro-2H-benzo[d][1,3]oxazin-6-yl)-2-oxoethyl 7-(6-amino-3-chloro-2-fluorophenyl)-5-oxo-1,2,3,5,8,8a-hexahydroindolizine-3-carboxylate as a yellow oil. LC/MS: mass calculated for $C_{25}H_{20}ClF_2N_3O_6$: 531.10, measured (ES, m/z): 532.15 $[M+H]^+$.

Step 2: 6-(2-((3S)-7-(6-Amino-3-chloro-2-fluorophenyl)-5-oxo-1,2,3,5,8,8a-hexahydroindolizin-3-yl)-1H-imidazol-5-yl)-5-fluoro-1,4-dihydro-2H-benzo[d][1,3]oxazin-2-one To a mixture of 2-(5-fluoro-2-oxo-1,4-dihydro-2H-benzo[d][1,3]oxazin-6-yl)-2-oxoethyl 7-(6-amino-3-chloro-2-fluorophenyl)-5-oxo-1,2,3,5,8,8a-hexahydroindolizine-3-carboxylate (200 mg, 0.38 mmol, 1.0 equiv.) in toluene (3 mL) and acetic acid (0.3 mL) was added ammonium acetate (290 mg, 3.76 mmol, 10.0 equiv.). The reaction mixture was stirred at 100° C. for 1.0 h and concentrated under vacuum. The residue was purified by reverse phase chromatography on C18 (ACN/$H_2O$ (0.05% $CF_3COOH$): 0→28%) to yield 6-(2-(7-(6-amino-3-chloro-2-fluorophenyl)-5-oxo-1,2,3,5,8,8a-hexahydroindolizin-3-yl)-1H-imidazol-5-yl)-5-fluoro-1,4-dihydro-2H-benzo[d][1,3]oxazin-2-one as a yellow solid. LC/MS: mass calculated for $C_{25}H_{20}ClF_2N_5O_3$: 511.12, measured (ES, m/z): 512.25 $[M+H]^+$.

Step 3: 6-(2-((3*S,8a*R)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-5-fluoro-1,4-dihydro-2H-benzo[d][1,3]oxazin-2-one To a mixture of 6-(2-(7-(6-amino-3-chloro-2-fluorophenyl)-5-oxo-1,2,3,5,8,8a-hexahydroindolizin-3-yl)-1H-imidazol-5-yl)-5-fluoro-1,4-dihydro-2H-benzo[d][1,3]oxazin-2-one (140 mg, 0.27 mmol) in acetic acid (1.5 mL) were added trimethoxymethane (1.5 mL) and azidotrimethylsilane (1.5 mL). The reaction mixture was stirred at room temperature overnight. The mixture was concentrated under vacuum and the resulting residue was purified by reverse phase chromatography on C18 (120 g, ACN/$H_2O$ (0.05% $CF_3COOH$): 0→35%) to yield 100 a residue, which was further purified with prep-chiral-HPLC. This resulted in 6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-5-fluoro-1,4-dihydro-2H-benzo[d][1,3]oxazin-2-one as a white solid.

LC/MS: mass calculated for $C_{26}H_{19}ClF_2NBO_3$: 564.12, measured (ES, m/z): 565.10 [M+H]+. $^1H$ NMR (400 MHz, DMSO-$d_6$) δ 11.92 (s, 1H), 10.38 (s, 1H), 9.84 (s, 1H), 7.94-8.01 (m, 1H), 7.86-7.93 (m, 1H), 7.68-7.75 (m, 1H), 7.21-7.26 (m, 1H), 6.79 (d, J=8.4 Hz, 1H), 5.69 (d, J=2.6 Hz, 1H), 5.43 (s, 2H), 5.01 (d, J=8.6 Hz, 1H), 3.66-3.80 (m, 1H), 2.64-2.78 (m, 1H), 2.51-2.56 (m, 1H), 2.05-2.24 (m, 2H), 1.87-2.04 (m, 2H). $^{19F}$ NMR (376 MHz, DMSO-$d_6$) δ−112.87, −122.02.

Example 119 (3*R,8aR)-3-(5-(6-amino-2-fluoropyridin-3-yl-5-d)-1H-imidazol-2-yl)-7-(5-chloro-2-(1H-tetrazol-1-yl)phenyl-3-d)-2,3,8,8a-tetrahydroindolizin-5(1H)-one

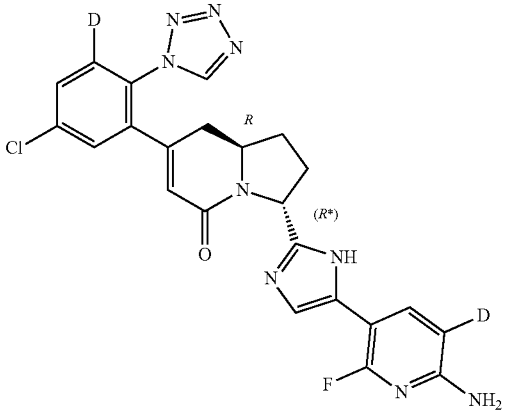

LC/MS: mass calculated for $C_{23}H_{17}ClD_2FN_9O$: 493.15, measured (ES, m/z): 494.10 $[M+H]^+$. $^1H$ NMR (400 MHz, DMSO-$d_6$) δ 11.71 (s, 1H), 9.84 (s, 1H), 7.95-8.10 (m, 1H), 7.65-7.82 (m, 2H), 7.03 (d, J=3.8 Hz, 1H), 6.25 (s, 2H), 5.62 (d, J=2.6 Hz, 1H), 4.99 (d, J=8.5 Hz, 1H), 3.63-3.78 (m, 1H), 2.41-2.47 (m, 1H), 2.24-2.37 (m, 1H), 2.07-2.20 (m, 1H), 1.83-2.06 (m, 3H). $^{19}F$ NMR (376 MHz, DMSO-$d_6$) δ−70.83.

Example 120 (3*S,8aR)-3-(5-(6-amino-2-fluoropyridin-3-yl-5-d)-1H-imidazol-2-yl)-7-(5-chloro-2-(1H-tetrazol-1-yl)phenyl-3-d)-2,3,8,8a-tetrahydroindolizin-5(1H)-one

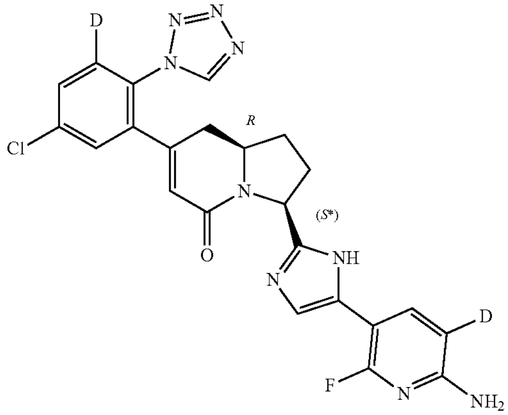

LC/MS: mass calculated for $C_{23}H_{17}ClD_2FN_9O$: 493.15, measured (ES, m/z): 494.10 $[M+H]^+$. $^1H$ NMR (400 MHz, DMSO-$d_6$) δ 9.83 (s, 1H), 7.94 (d, J=10.4 Hz, 1H), 7.74-7.83 (m, 2H), 7.20 (s, 1H), 6.41 (s, 2H), 5.61 (d, J=2.6 Hz, 1H), 5.00 (t, J=7.5 Hz, 1H), 4.01-4.14 (m, 1H), 2.29-2.40 (m, 2H), 2.16-2.28 (m, 2H), 1.96-2.12 (m, 1H), 1.54-1.72 (m, 1H). $^{19}F$ NMR (376 MHz, DMSO-$d_6$) δ −70.26, −73.44.

Example 121: (3'R,8aR)-3-(5-(6-amino-2-fluoropyridin-3-yl)-1H-imidazol-2-yl)-7-(5-chloro-2-(1H-tetrazol-1-yl)phenyl-3-d)-2,3,8,8a-tetrahydroindolizin-5(1H)-one

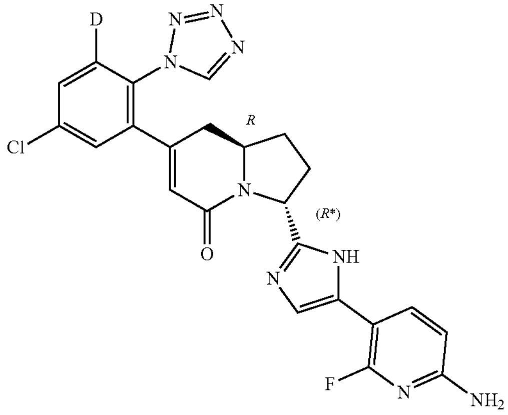

LC/MS: mass calculated for $C_{23}H_{18}ClDFN_9O$: 492.14, measured (ES, m/z): 493.20 [M+H]+. $^1H$ NMR (400 MHz, DMSO-d6) δ 11.69 (s, 1H), 9.84 (s, 1H), 8.00-8.11 (m, 1H), 7.72-7.81 (m, 2H), 6.90-7.07 (m 1H), 6.35-6.47 (m, 1H), 6.23 (s, 2H), 5.63 (d, J=2.6 Hz, 1H), 4.98 (d, J=8.5 Hz, 1H), 3.63-3.79 (m, 1H), 2.23-2.39 (m, 1H), 2.08-2.19 (m, 1H), 1.81-2.07 (m, 4H). $^{19}F$ NMR (376 MHz, DMSO-$d_6$) δ −70.84.

Example 122 (3*S,8aR)-3-(5-(6-amino-2-fluoro-pyridin-3-yl)-1H-imidazol-2-yl)-7-(5-chloro-2-(1H-tetrazol-1-yl)phenyl-3-d)-2,3,8,8a-tetrahydroindolizin-5(1H)-one

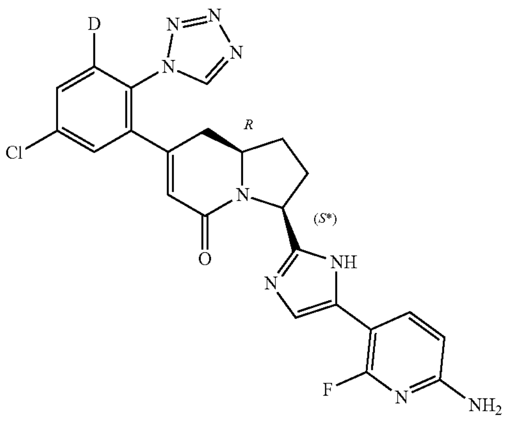

LC/MS: mass calculated for $C_{23}H_{18}ClDFN_9O$: 492.14, measured (ES, m/z): 493.20 $[M+H]^+$. $^1H$ NMR (400 MHz, DMSO-$d_6$) δ 11.91 (s, 1H), 9.83 (s, 1H), 7.95-8.05 (m, 1H), 7.64-7.86 (m, 2H), 7.04 (s, 1H), 6.37 (dd, J=8.3, 2.1 Hz, 1H), 6.25 (s, 2H), 5.59 (d, J=2.7 Hz, 1H), 4.97 (t, J=7.1 Hz, 1H), 3.97-4.15 (m, 1H), 2.16-2.41 (m, 4H), 1.92-2.13 (m, 1H), 1.52-1.70 (m, 1H). $^{19}F$ NMR (376 MHz, DMSO-$d_6$) δ−70.75.

Example 123 (3S,8aR)-3-[5-(6-amino-2-fluoro-3-pyridyl)-1H-imidazol-2-yl]-7-[5-chloro-2-(tetrazol-1-yl)phenyl]-2,3,8,8a-tetrahydro-1H-indolizin-5-one

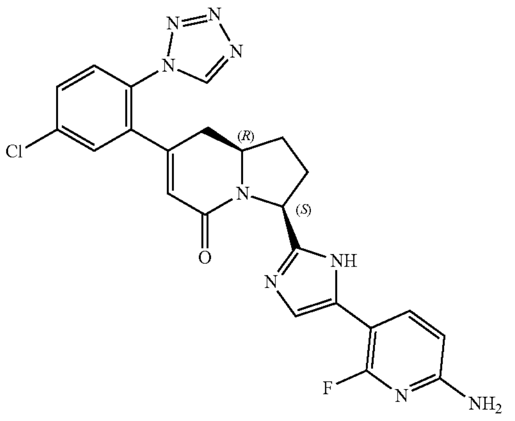

Step 1: Methyl (3S)-7-(2-amino-5-chlorophenyl)-5-oxo-1,2,3,5,8,8a-hexahydroindolizine-3-carboxylate Under an inert atmosphere of nitrogen, a mixture of (3S)-methyl 5-oxo-7-(trifluoromethylsulfonyloxy)-1,2,3,5,8,8a-hexahydroindolizine-3-carboxylate (14.0 g, 40.78 mmol, 1.0 equiv.), 4-chloro-2-(4,4,5,5-tetramethyl-1,3,2-dioxaborolan-2-yl)benzenamine (12.4 g, 48.91 mmol, 1.2 equiv.), $K_2CO_3$ (11.3 g, 81.76 mmol, 2.0 equiv.) and $Pd(dppf)Cl_2$ (3.0 g, 4.10 mmol, 0.1 equiv.) in 1,4-dioxane (350 mL) and $H_2O$ (35 mL) was stirred at 90° C. for 2 h. After cooling to room temperature, the resulting mixture was diluted with EtOAc (800 mL), washed with water (3×200 mL), brine (2×200 mL), dried over $Na_2SO_4$, and concentrated under reduced pressure. The residue was applied onto a silica gel column (120 g, MeOH/DCM: 0→5%) to yield (3S)-methyl 7-(2-amino-5-chlorophenyl)-5-oxo-1, 2, 3,5,8,8a-hexahydroindolizine-3-carboxylate as a brown solid. LC/MS: mass calculated for $C_{16}HClN_2O_3$: 320.09, measured (ES, m/z): 321.05 $[M+H]^+$.

Step 2: (3S)-7-(2-Amino-5-chlorophenyl)-5-oxo-1,2,3,5,8,8a-hexahydroindolizine-3-carboxylic acid To a solution of methyl (3S)-7-(2-amino-5-chlorophenyl)-5-oxo-1,2,3,5,8,8a-hexahydroindolizine-3-carboxylate (1.5 g, 4.68 mmol, 1.0 equiv.) in $THF/H_2O$ (20 mL/4 mL) was added LiOH (374 mg, 18.71 mmol, 4.0 equiv.). The reaction mixture was stirred at room temperature for 2 h, adjusted to pH 5 with HCl solution (2 N), then extracted by EA. The organic layer was concentrated under vacuum to yield (3S)-7-(2-amino-5-chlorophenyl)-5-oxo-1,2,3,5,8,8a-hexahydroindolizine-3-carboxylic acid as a colorless oil. LC/MS: mass calculated for $C_{15}H_{15}ClN_2O_3$: 306.08, measured (ES, m/z): 307.05 $[M+H]^+$.

Step 3: 2-(6-Acetamido-2-fluoropyridin-3-yl)-2-oxoethyl (3S)-7-(2-amino-5-chlorophenyl)-5-oxo-1,2,3,5,8,8a-hexahydroindolizine-3-carboxylate To a solution of (3S)-7-(2-amino-5-chlorophenyl)-5-oxo-1,2,3,5,8,8a-hexahydroindolizine-3-carboxylic acid (937 mg, 3.05 mmol, 1.2 equiv.) in $CH_3CN$ (10 mL) was added $K_2CO_3$ (351 mg, 2.55 mmol, 1.0 equiv.) followed by addition of N-(5-(2-bromoacetyl)-6-fluoropyridin-2-yl)acetamide (700 mg, 2.55 mmol, 1.0 equiv.). The reaction mixture was stirred overnight at room temperature and concentrated under vacuum. The residue was purified by silica gel column chromatography to yield 2-(6-acetamido-2-fluoropyridin-3-yl)-2-oxoethyl (3S)-7-(2-amino-5-chlorophenyl)-5-oxo-1,2,3,5,8,8a-hexahydroindolizine-3-carboxylate as a yellow oil. LC/MS: mass calculated for $C_{24}H_{22}ClFN_4O_5$: 500.13, measured (ES, m/z): 501.10 $[M+H]^+$.

Step 4: N-(5-(2-((3S)-7-(2-amino-5-chlorophenyl)-5-oxo-1,2,3,5,8,8a-hexahydroindolizin-3-yl)-1H-imidazol-5-yl)-6-fluoropyridin-2-yl)acetamide Under an inert atmosphere of nitrogen, a mixture of (3S)-2-(6-acetamido-2-fluoropyridin-3-yl)-2-oxoethyl 7-(2-amino-5-chlorophenyl)-5-oxo-1,2,3,5,8,8a-hexahydroindolizine-3-carboxylate (7.0 g, 13.98 mmol, 1.0 equiv.) and $NH_4OAc$ (10.7 g, 138.81 mmol, 10.0 equiv.) in AcOH (30 mL) and toluene (300 mL) was heated at 110° C. with stirring for 1 h, then concentrated under reduced pressure. The residue was applied onto a silica gel column (120 g, MeOH/DCM: 1/15) to yield N-(5-(2-((3S)-7-(2-amino-5-chlorophenyl)-5-oxo-1,2,3,5,8,8a-hexahydroindolizin-3-yl)-1H-imidazol-5-yl)-6-fluoropyridin-2-yl)acetamide as a yellow solid. LC/MS: mass calculated for $C_{24}H_{22}ClFN_8O_2$: 480.15, measured (ES, m/z): 481.15 $[M+H]^+$.

Step 5: N-(5-(2-((3S)-7-(5-chloro-2-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide To a solution of N-(5-(2-((3S)-7-(2-amino-5-chlorophenyl)-5-oxo-1,2,3,5,8,8a-hexahydroindolizin-3-yl)-1H-imidazol-5-yl)-6-fluoropyridin-2-yl)acetamide (365 mg, 0.76 mmol, 1.0 equiv.) in AcOH (4 mL) was added trimethoxymethane (2 mL), followed by addition of $TMSN_3$ (2.0 mL). The resulting solution was stirred at room temperature overnight. The mixture was concentrated under vacuum. The residue was purified by flash column chromatography on silica gel (DCM/MeOH v/v 10:1) to yield N-(5-(2-((3S)-7-(5-chloro-2-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide as a yellow solid. LC/MS: mass calculated for $C_{25}H_{21}ClFN_9O_2$: 533.15, measured (ES, m/z): 534.05 $[M+H]^+$.

Step 6: (3S,8aR)-3-[5-(6-Amino-2-fluoro-3-pyridyl)-1H-imidazol-2-yl]-7-[5-chloro-2-(tetrazol-1-yl)phenyl]-2,3,8,8a-tetrahydro-1H-indolizin-5-one A mixture of N-(5-(2-((3S)-7-(5-chloro-2-(2H-tetrazol-2-yl)phenyl)-5-oxo-1,2,3,5,8,8a-hexahydroindolizin-3-yl)-1H-imidazol-5-yl)-6-fluoropyridin-2-yl)acetamide (345 mg, 0.65 mmol, 1.0 equiv.) in THE (8 mL) and 4 N HCl (8 mL) was stirred at 53° C. for 1.5 h. The mixture was concentrated under vacuum. The resulting residue was purified by prep-HPLC followed by chiral-HPLC to yield (3S,8aR)-3-(5-(6-amino-2-fluoropyridin-3-yl)-1H-imidazol-2-yl)-7-(5-chloro-2-(1H-tetrazol-1-yl)phenyl)-2,3,8,8a-tetrahydroindolizin-5(1H)-one as an off-white solid.

LC/MS: mass calculated for $C_{23}H_{19}ClFN_9O$: 491.14, measured (ES, m/z): 492.10 $[M+H]^+$. $^1H$ NMR (400 MHz, DMSO-$d_6$) δ 9.85 (s, 1H), 7.95-8.05 (m, 1H), 7.76-7.78 (m, 3H), 7.00-7.32 (m, 2H), 6.30-6.54 (m, 2H), 5.62 (s, 1H), 5.06 (d, J=8.9 Hz, 1H), 3.66-3.75 (m, 1H), 2.58-2.66 (m, 1H), 2.29-2.36 (m, 1H), 2.15-2.26 (m, 1H), 1.97-2.06 (m, 2H), 1.85-1.94 (m, 1H). $^{19}F$ NMR (376 MHz, DMSO-$d_6$) δ−70.37.

Example 124 (3S,8aR)-3-[5-(6-amino-5-deuterio-2-fluoro-3-pyridyl)-1H-imidazol-2-yl]-7-[5-chloro-2-(tetrazol-1-yl)phenyl]-2,3,8,8a-tetrahydro-1H-indolizin-5-one

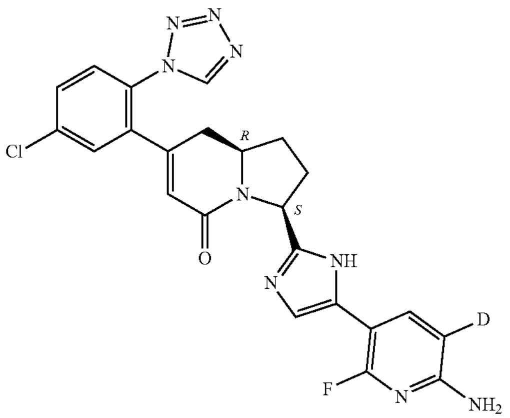

LC/MS: mass calculated for $C_{23}H_{19}ClDFN_9O$: 492.14, measured (ES, m/z): 493.15 $[M+H]^+$. $^1H$ NMR (400 MHz, DMSO-d6) δ 11.65-11.95 (m, 1H), 9.84 (s, 1H), 8.05 (d, J=10.5 Hz, 1H), 7.75-7.78 (m, 3H), 7.00-7.08 (m, 1H), 6.23 (s, 2H), 5.63 (d, J=2.6 Hz, 1H), 4.98 (d, J=8.6 Hz, 1H), 3.65-3.74 (m, 1H), 2.43-2.48 (m, 1H), 2.28-2.33 (m, 1H), 1.85-2.18 (m, 4H). $^{19}F$ NMR (376 MHz, DMSO-$d_6$) δ −70.85.

Example 125 (3S,8aR)-3-(4-(6-amino-2-fluoropyridin-3-yl-5-d)-1H-imidazol-2-yl)-7-(3-chloro-2-fluoro-6-(1H-tetrazol-1-yl)phenyl-5-d)-2,3,8,8a-tetrahydroindolizin-5(1H)-one

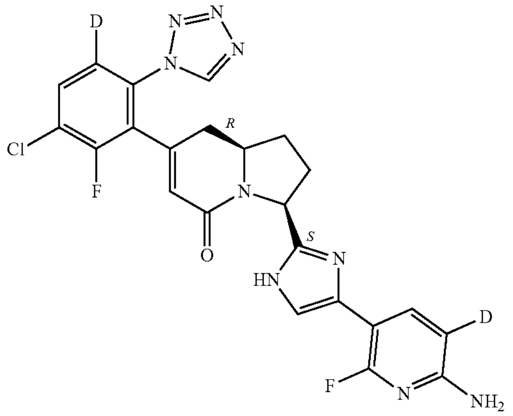

LC/MS: mass calculated for $C_{23}H_{16}ClD_2F_2N_9O$: 511.14, measured (ES, m/z): 512.15 $[M+H]^+$. $^1H$ NMR (400 MHz, DMSO-$d_6$) δ11.77 (s, 1H), 9.84 (s, 1H), 8.04 (d, J=10.4 Hz, 1H), 7.97 (d, J=7.7 Hz, 1H), 6.90-7.08 (m, 1H), 6.15-6.50 (m, 2H), 5.60-5.77 (m, 1H), 4.98 (d, J=8.6 Hz, 1H), 3.57-3.86 (m, 1H), 2.58-2.77 (m, 1H), 2.40-2.45 (m, 1H), 2.01-2.29 (m, 2H), 1.85-2.02 (m, 2H). $^{19}F$ NMR (376 MHz, DMSO-$d_6$) δ−70.81, −112.92.

Example 126 (3S,8aR)-3-(5-(2-amino-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

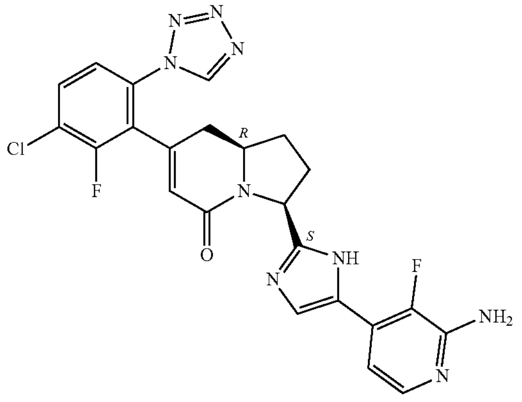

Step 1: 3-Fluoro-4-iodopyridin-2-amine

To a solution of 2,3-difluoro-4-iodopyridine (1.8 g, 7.47 mmol, 1.0 equiv.) in DMSO (10 mL) was added ammonia hydrate (5 mL). The resulting mixture was stirred at 80° C. overnight, diluted with water, and extracted with EA (3×20 mL). The organic layers were combined, washed with brine, dried over $Na_2SO_4$ and concentrated under vacuum to yield 3-fluoro-4-iodopyridin-2-amine as a brown solid. LC/MS: mass calculated for $C_5H_4FIN_2$: 237.94, measured (ES, m/z): 238.90 $[M+H]^+$.

Step 2: N-acetyl-n-(3-fluoro-4-iodopyridin-2-yl)acetamide

A solution of 3-fluoro-4-iodopyridin-2-amine (2.0 g, 8.40 mmol, 1.0 equiv.) in $Ac_2O$ (20 mL) was stirred at 60° C. for 36 h. The resulting mixture was diluted with water (20 mL) extracted with EA (3×20 mL). The organic layers were combined, washed with brine, dried over $Na_2SO_4$ and concentrated. The residue was purified by silica gel column chromatography (EA/PE 0-(100%) to yield N-acetyl-n-(3-fluoro-4-iodopyridin-2-yl)acetamide as a white solid. LC/MS: mass calculated for $C_7H_6FIN_2O$: 321.96, measured (ES, m/z): 322.85 $[M+H]^+$.

Step 3: N-(4-(1-ethoxyvinyl)-3-fluoropyridin-2-yl) acetamide

A mixture of N-acetyl-N-(3-fluoro-4-iodopyridin-2-yl)acetamide (1.6 g, 4.88 mmol, 1.0 equiv.), tributyl(1-ethoxyvinyl)stannane (2.6 g, 7.31 mmol, 1.5 equiv.) and $Pd(PPh_3)_4$ (563 mg, 0.49 mmol, 0.1 equiv.) in 1,4-dioxane (20 mL) was heated at 90° C. with stirring under $N_2$ overnight. The resulting mixture was concentrated and the residue was purified on neutral $Al_2O_3$ column (EA/PE, 0→15%) to yield N-(5-(1-ethoxyvinyl)-6-fluoropyridin-2-yl-4-d)acetamide as a light yellow solid. LC/MS: mass calculated for $C_{11}H_{13}FN_2O_2$: 224.10, measured (ES, m/z): 225.05 $[M+H]^+$.

Step 4: N-(4-(2-bromoacetyl)-3-fluoropyridin-2-yl) acetamide

A mixture of N-(4-(1-ethoxyvinyl)-3-fluoropyridin-2-yl) acetamide (750 mg, 3.35 mmol, 1 equiv.) and NBS (298 mg, 1.67 mmol, 0.5 equiv.) in $THF/H_2O$ (V/V=3:1, 6 mL) was stirred at room temperature for 30 min. The resulting mixture was diluted with water (10 mL), extracted with EA (3×10 mL). The organic layers were combined, dried over $Na_2SO_4$ and concentrated to yield a light yellow liquid of N-(4-(2-bromoacetyl)-3-fluoropyridin-2-yl)acetamide. LC/MS: mass calculated for $C_9H_8BrFN_2O_2$: 273.98, measured (ES, m/z): 274.90, 276.90 $[M+H, M+H+2]^+$.

Step 5: 2-(2-Acetamido-3-fluoropyridin-4-yl)-2-oxoethyl (3S,8aR)-7-(6-amino-3-chloro-2-fluorophenyl)-5-oxo-1,2,3,5,8,8a-hexahydroindolizine-3-carboxylate A mixture of (3S,8aR)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) in DMF (5 mL) was added cesium carbonate (100 mg, 0.31 mmol, 0.5 equiv.). The resulting mixture was stirred at room temperature for 30 min. Then N-(4-(2-bromoacetyl)-3-fluoropyridin-2-yl)acetamide (213 mg, 0.92 mmol, 1.5 equiv.) was added. The resulting mixture was stirred at room temperature overnight, diluted with water, and extracted with EA (3×20 mL). The organic layers were combined, washed with brine, dried over $Na_2SO_4$ and concentrated under reduced pressure. The residue was purified by flash column chromatography on silica gel (MeOH/DCM, 0→8%) to yield 2-(2-acetamido-3-fluoropyridin-4-yl)-2-oxoethyl (3R,8aS)-7-(6-amino-3-chloro-2-fluorophenyl)-5-oxo-1,2,3,5,8,8a-hexahydroindolizine-3-carboxylate as a yellow solid. LC/MS: mass calculated for $C_{24}H_{21}ClF_2N_4O_5$: 518.12, measured (ES, m/z): 519.10 $[M+H]^+$.

Step 6: N-(4-(2-((3S,8aR)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)acetamide To a mixture of 2-(2-acetamido-3-fluoropyridin-4-yl)-2-oxoethyl (3R,8aS)-7-(6-amino-3-chloro-2-fluorophenyl)-5-oxo-1,2,3,5,8,8a-hexahydroindolizine-3-carboxylate (216 mg, 0.42 mmol, 1.0 equiv.) and ammonium acetate (321 mg, 4.16 mmol, 10.0 equiv.) in toluene (4 mL) was added acetic acid (1 mL). The resulting mixture was stirred at 100° C. for 1 h. The solvent was evaporated under reduced pressure. The residue was purified by silica gel column (MeOH/DCM, 0→10%) to yield N-(4-(2-((3S,8aR)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)acetamide as a yellow oil. LC/MS: mass calculated for $C_{24}H_{21}ClF_2N_6O_2$. 498.14, measured (ES, m/z): 499.10 $[M+H]^+$.

Step 7: N-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide A mixture of N-(4-(2-((3S,8aR)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)acetamide (150 mg, 0.30 mmol, 1.0 equiv.), trimethoxymethane (2 mL), azidotrimethylsilane (2 mL) and acetic acid (3 mL) was stirred at room temperature overnight. The reaction mixture was concentrated under reduced pressure to yield N-(4-(2-((3S,8aR)-7-(3-chloro-2-fluor-6-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide as a yellow solid. LC/MS: mass calculated for $C_{25}H_{20}ClF_2N_9O_2$. 551.14, measured (ES, m/z): 552.10 $[M+H]^+$.

Step 8: (3S,8aR)-3-(5-(2-Amino-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of N-(4-(2-((3R,8aS)-7-(3S-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)acetamide (140 mg, 0.25 mmol, 1.0 equiv.) in THE (2 mL) was added HCl (1 mL). The resulting mixture was stirred at room temperature for 2 h and concentrated under reduced pressure. The residue was purified by reversal phase chromatography on C18 ($MeCN/H_2O$ (0.05% $CF_3COOH$)) to yield (3R,8aS)-3-(5-(2-amino-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid. The racemic product (60 mg) was separated by chiral-HPLC to yield (3R,8aS)-3-(5-(2-amino-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC/MS: mass calculated for $C_{23}H_{18}ClF_2N_9O$: 509.13, measured (ES, m/z): 510.10 $[M+H]^+$. $^1H$ NMR (300 MHz, DMSO-d6) δ 12.05-12.27 (m, 1H), 9.84 (s, 1H), 7.97 (t, J=8.2 Hz, 1H), 7.67-7.76 (m, 2H), 7.45 (d, J=3.8 Hz, 1H), 6.99-7.17 (m, 1H), 6.12 (s, 2H), 5.69 (d, J=2.5 Hz, 1H), 5.03

(d, J=8.4 Hz, 1H), 3.60-3.80 (m 1H), 2.62-2.84 (m, 1H), 2.50-2.60 (m, 1H), 2.08-2.26 (m, 2H), 1.93-2.02 (m, 2H). $^{19}$F NMR (282 MHz, DMSO-d6) δ −112.86, −142.19.

Example 127 (3S*,8aS*)-3-(5-(2-((S*)-1-(1,3,4-oxadiazol-2-yl)ethoxy)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

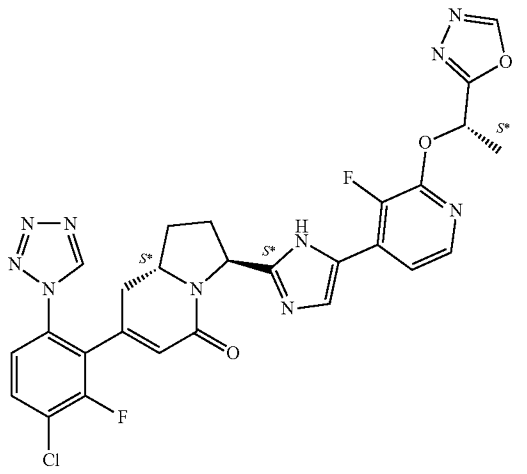 [SMILES: C[C@H](Oc1nccc(-c2cnc([C@@H]3CC[C@H]4CC(c5c(-n6cnnn6)ccc(Cl)c5F)=CC(=O)N43)[nH]2)c1F)c1nnco1]

LC/MS: mass calculated for $C_{27}H_{21}ClF_2N_{10}O_3$: 606.15, measured (ES, m/z): 607.10 [M+H]$^+$. $^1$H NMR (300 MHz, DMSO-d$_6$) δ 9.83 (s, 1H), 9.24 (s, 1H), 7.89-8.01 (m, 2H), 7.63-7.76 (m, 2H), 7.48-7.61 (m, 1H), 6.49 (q, J=6.7 Hz, 1H), 5.67 (d, J=2.6 Hz, 1H), 5.08 (d, J=8.8 Hz, 1H), 3.64-3.80 (m, 1H), 2.71-2.87 (m, 1H), 2.55-2.64 (m, 1H), 2.04-2.34 (m, 2H), 1.85-2.03 (m, 2H), 1.76 (d, J=6.7 Hz, 3H). $^{19}$F NMR (282 MHz, DMSO-d6) δ −142.45, −112.77.

Example 128 (3S*,8aR*)-3-(5-(2-((S*)-1-(1,3,4-oxadiazol-2-yl)ethoxy)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

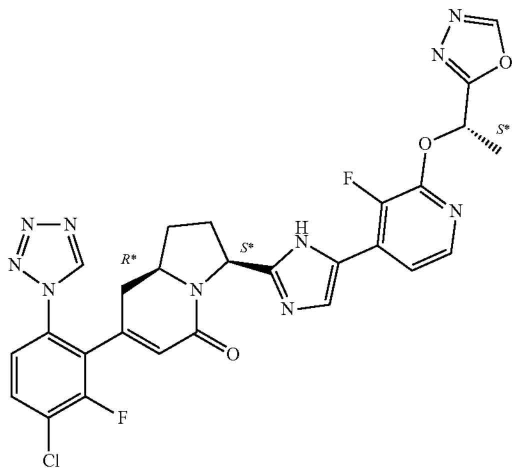 [SMILES: C[C@H](Oc1nccc(-c2cnc([C@@H]3CC[C@@H]4CC(c5c(-n6cnnn6)ccc(Cl)c5F)=CC(=O)N43)[nH]2)c1F)c1nnco1]

LC/MS: mass calculated for $C_{27}H_{21}ClF_2N_{10}O_3$: 606.15, measured (ES, m/z): 607.15 [M+H]$^+$. $^1$H NMR (300 MHz, DMSO-d6) δ 9.81 (s, 1H), 9.23 (s, 1H), 7.85-8.00 (m, 2H), 7.63-7.76 (m, 1H), 7.52-7.64 (m, 2H), 6.48 (q, J=6.6 Hz, 1H), 5.67 (d, J=2.5 Hz, 1H), 5.02 (d, J=8.4 Hz, 1H), 3.63-3.81 (m, 1H), 2.62-2.79 (m, 2H), 2.03-2.29 (m, 2H), 1.87-2.02 (m, 2H), 1.75 (d, J=6.7 Hz, 3H). $^{19}$F NMR (282 MHz, DMSO-d$_6$) δ −143.01, −112.86.

Example 129 (3S,8aR)-3-(5-(6-amino-2-fluoropyridin-3-yl)-1H-imidazol-2-yl-4-d)-7-(3-chloro-2-fluoro-6-(1H-tetrazol-1-yl)phenyl-5-d)-2,3,8,8a-tetrahydroindolizin-5(1H)-one

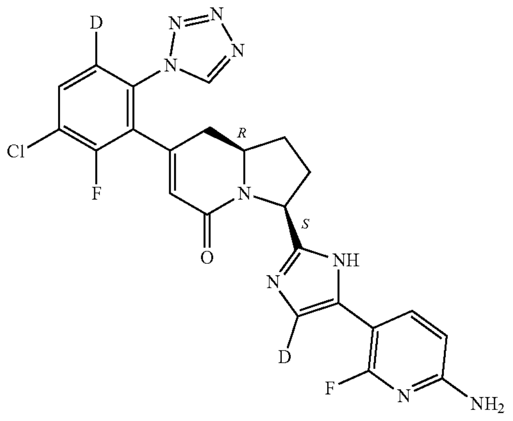

LC/MS: mass calculated for $C_{23}H_{16}D_2ClF_2N_9O$: 511.14, measured (ES, m/z): 512.10 [M+H]$^+$. $^1$H NMR (300 MHz, DMSO-d$_6$) δ 11.58-11.97 (m, 1H), 9.81 (s, 1H), 8.03 (dd, J=10.5, 8.2 Hz, 1H), 7.94 (d, J=7.8 Hz, 1H), 6.39 (dd, J=8.2, 2.3 Hz, 1H), 6.22 (s, 2H), 5.60-5.72 (m, 1H), 4.97 (d, J=8.4 Hz, 1H), 3.62-3.72 (m, 1H), 2.61-2.74 (m, 1H), 2.49-2.53 (m, 1H), 2.03-2.16 (m, 2H), 1.92-1.98 (m, 2H). $^{19}$F NMR (282 MHz, DMSO-d$_6$) δ −70.83, 112.88.

Example 130 (3S,8aR)-7-(3-chloro-2-fluoro-6-(1H-tetrazol-1-yl)phenyl)-3-(5-(3-fluoro-2-(oxetan-3-yl)pyridin-4-yl)-1H-imidazol-2-yl)-2,3,8,8a-tetrahydroindolizin-5(1H)-one

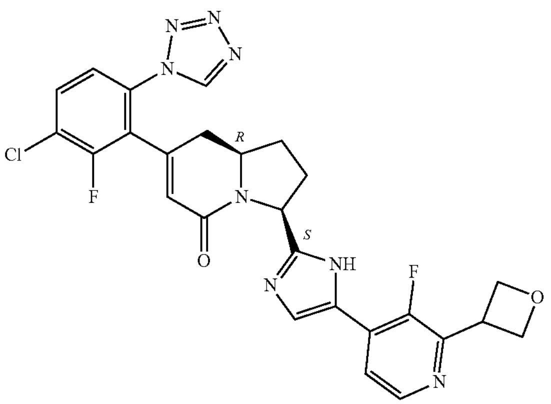

Step 1: 3-Fluoro-2-(oxetan-3-yl)pyridine

A mixture of 2-bromo-3-fluoropyridine (2.0 g, 11.37 mmol, 1.0 equiv.), 3-bromooxetane (1.9 g, 13.64 mmol, 1.2 equiv.), sodium iodide (0.43 g, 2.84 mmol, 0.25 equiv.), zinc powder (1.5 g, 22.73 mmol, 2.0 equiv.), pyridine-2,6-bis (carboximidamide) (0.093 g, 0.57 mmol, 0.05 equiv.), $NiCl_2$ (dry) (0.11 g, 0.57 mmol, 0.05 equiv.) and TFA (0.13 g, 1.14 mmol, 0.1 equiv.) in DMAc (30 mL) was stirred at 60° C. under $N_2$ atmosphere for 15 h. The resulting mixture was filtered out. The filtrate was diluted with water, extracted with EA (3×30 mL). The organic layers were combined and washed with brine, dried over $Na_2SO_4$ and concentrated. The residue was purified by silica gel column (EA/PE, 0→30%) to yield 3-fluoro-2-(oxetan-3-yl)pyridine as a light yellow oil. LC/MS: mass calculated for $C_8H_8FNO$: 153.06, measured (ES, m/z): 154.10 $[M+H]^+$.

Step 2: 3-Fluoro-4-iodo-2-(oxetan-3-yl)pyridine

To a solution of 3-fluoro-2-(oxetan-3-yl)pyridine (370 mg, 2.42 mmol, 1.0 equiv.) in THF (10 mL) was dropwise added LDA (1.6 mL, 3.14 mmol, 1.3 equiv.) under −65° C. The mixture was stirred at that temperature for 30 min. To the resulting mixture was then added 12 (920 mg, 3.62 mmol, 1.5 equiv.) in THF (3 mL). The resulting mixture was stirred for additional 1 h, diluted with water, and extracted with EA (3×20 mL). The organic layers were combined, washed with brine and dried over $Na_2SO_4$ and concentrated. The residue was purified by flash silica gel column EA/PE (0→80%) to yield 3-fluoro-4-iodo-2-(oxetan-3-yl)pyridine as an off-white solid. LC/MS: mass calculated for $C_8H_7FINO$: 278.96, measured (ES, m/z): 279.95 $[M+H]^+$.

Step 3: 4-(1-Ethoxyvinyl)-3-fluoro-2-(oxetan-3-yl) pyridine

A mixture of 3-fluoro-4-iodo-2-(oxetan-3-yl)pyridine (278 mg, 1.00 mmol, 1.0 equiv.), tributyl(1-ethoxyvinyl) stannane (540 mg, 1.49 mmol, 1.5 equiv.) and $Pd(PPh_3)_4$ (115 mg, 0.10 mmol, 0.1 equiv.) in 1,4-dioxane (5 mL) was refluxed at 90° C. under $N_2$ overnight. The resulting mixture was concentrated. The residue was purified by flash column chromatography on neutral $Al_2O_3$ column (EA/PE, 0-(15%) to yield 4-(1-ethoxyvinyl)-3-fluoro-2-(oxetan-3-yl)pyridine as a colorless oil. LC/MS: mass calculated for $C_{12}H_{14}FNO_2$: 223.10, measured (ES, m/z): 224.05 $[M+H]^+$.

Step 4: 2-Bromo-1-(3-fluoro-2-(oxetan-3-yl)pyridin-4-yl)ethan-1-one

A mixture of 4-(1-ethoxyvinyl)-3-fluoro-2-(oxetan-3-yl) pyridine (600 mg, 2.69 mmol, 1.0 equiv.) and NBS (239 mg, 1.34 mmol, 0.5 equiv.) in THF/$H_2O$ (V/V=6 mL) was stirred at room temperature for 30 min. The resulting mixture was diluted with water (10 mL), extracted with EA (3×10 mL). The organic layers were combined, dried over $Na_2SO_4$ and concentrated to yield a light yellow liquid of 2-bromo-1-(3-fluoro-2-(oxetan-3-yl)pyridin-4-yl)ethan-1-one. LC/MS: mass calculated for $C_{12}H_{14}FNO_2$: 272.98, measured (ES, m/z): 273.90, 275.90 $[M+H, M+H+2]^+$.

Step 5: 2-(3-Fluoro-2-(oxetan-3-yl)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate To a mixture of (3S,8aR)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) in DMF (5 mL) was added cesium carbonate (120 mg, 0.37 mmol, 0.6 equiv.). The resulting mixture was stirred at room temperature for 30 min. To the resulting mixture was then added 2-bromo-1-(3-fluoro-2-(oxetan-3-yl)pyridin-4-yl)ethan-1-one (253 mg, 0.92 mmol, 1.5 equiv.). The resulting mixture was stirred at room temperature overnight, diluted with water and extracted with EA (3×20 mL). The organic layers were combined, washed with brine, dried over $Na_2SO_4$ and concentrated under reduced pressure. The residue was purified by flash column chromatography on silica gel (MeOH/DCM, 0→8%) to yield 2-(3-fluoro-2-(oxetan-3-yl)pyridin-4-yl)-2-oxoethyl (3R,8aS)-7-(6-amino-3-chloro-2-fluorophenyl)-5-oxo-1,2,3,5,8,8a-hexahydroindolizine-3-carboxylate as a yellow solid. LC/MS: mass calculated for $C_{25}H_{22}ClF_2N_3O_5$: 517.12, measured (ES, m/z): 518.05 $[M+H]^+$.

Step 6: (3S,8aR)-7-(6-Amino-3-chloro-2-fluorophenyl)-3-(5-(3-fluoro-2-(oxetan-3-yl)pyridin-4-yl)-1H-imidazol-2-yl)-2,3,8,8a-tetrahydroindolizin-5(1H)-one To a mixture of 2-(3-fluoro-2-(oxetan-3-yl)pyridin-4-yl)-2-oxoethyl (3R,8aS)-7-(6-amino-3-chloro-2-fluorophenyl)-5-oxo-1,2,3,5,8,8a-hexahydroindolizine-3-carboxylate (195 mg, 0.38 mmol, 1.0 equiv.) and ammonium acetate (290 mg, 3.77 mmol, 10.0 equiv.) in toluene (5 mL) was added acetic acid (1 mL). The resulting reaction mixture was heated at 100° C. with stirring for 1 h. The solvent was evaporated under reduced pressure and the residue was purified by flash column chromatography on silica gel (MeOH/DCM, 0→10%) to yield (3S,8aR)-7-(6-amino-3-chloro-2-fluorophenyl)-3-(5-(3-fluoro-2-(oxetan-3-yl)pyridin-4-yl)-1H-imidazol-2-yl)-2,3,8,8a-tetrahydroindolizin-5(1H)-one as a yellow solid. LC/MS: mass calculated for $C_{25}H_{22}ClF_2NSO_2$: 497.14, measured (ES, m/z): 498.10 $[M+H]^+$.

Step 7: (3S,8aR)-7-(3-Chloro-2-fluoro-6-(1H-tetrazol-1-yl)phenyl)-3-(5-(3-fluoro-2-(oxetan-3-yl)pyridin-4-yl)-1H-imidazol-2-yl)-2,3,8,8a-tetrahydroindolizin-5(1H) one A mixture of (3R,8aS)-7-(6-amino-3-chloro-2-fluorophenyl)-3-(5-(3-fluoro-2-(oxetan-3-yl)pyridin-4-yl)-1H-imidazol-2-yl)-2,3,8,8a-tetrahydroindolizin-5(1H)-one (140 mg, 0.28 mmol, 1.0 equiv.), trimethoxymethane (2 mL), azidotrimethylsilane (2 mL) and acetic acid (3 mL) was stirred at room temperature overnight. The solvent was evaporated under reduced pressure. The residue was purified by reversal phase chromatography on C18 (MeCN/$H_2O$ (0.05% $CF_3COOH$)) to yield (3R,8aS)-7-(3-chloro-2-fluoro-6-(1H-tetrazol-1-yl)phenyl)-3-(5-(3-fluoro-2-(oxetan-3-yl)pyridin-4-yl)-1H-imidazol-2-yl)-2,3,8,8a-tetrahydroindolizin-5(1H)-one as a yellow solid. The racemic product (78 mg) was further separated by chiral-HPLC to yield (3R,8aS)-7-(3-chloro-2-fluoro-6-(1H-tetrazol-1-yl)phenyl)-3-(5-(3-fluoro-2-(oxetan-3-yl)pyridin-4-yl)-1H-imidazol-2-yl)-2,3,8,8a-tetrahydroindolizin-5(1H)-one as a white solid.

LC/MS: mass calculated for $C_{26}H_{21}ClF_2N_8O_2$: 550.14, measured (ES, m/z): 551.05 $[M+H]^+$. $^1H$ NMR (300 MHz, DMSO-$d_6$) δ 12.05-12.78 (m, 1H), 9.84 (5, 1H), 8.43 (d, J=5.0 Hz, 1H), 7.82-8.03 (m, 2H), 7.72 (dd, J=8.7, 1.5 Hz, 1H), 7.51-7.59 (m, 1H), 5.70 (d, J=2.5 Hz, 1H), 5.04 (d, J=8.5 Hz, 1H), 4.85-4.97 (m, 4H), 4.58-4.77 (m, 1H), 3.65-3.85 (m, 1H), 2.62-2.83 (m, 1H), 2.50-2.60 (m, 1H), 2.03-2.31 (m, 2H), 1.85-2.02 (m, 2H). $^{19}$F NMR (282 MHz, DMSO-$d_6$) δ−112.86, −130.28.

Example 131 (3R*,8aR*)-3-(5-(6-amino-2-fluoropyridin-3-yl-4,5-d2)-1H-imidazol-2-yl-4-d)-7-(3-chloro-2-fluoro-6-(1H-tetrazol-1-yl)phenyl)-2,3,8,8a-tetrahydroindolizin-5(1H)-one-8a-d

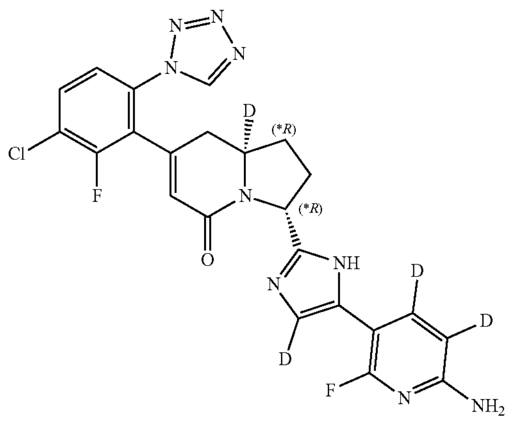 [SMILES: [2H]c1nc([C@H]2CC[C@]3([2H])CC(c4c(-n5cnnn5)ccc(Cl)c4F)=CC(=O)N23)[nH]c1-c1c(F)nc(N)c([2H])c1[2H]]

LC/MS: mass calculated for $C_{23}H_{14}D_4ClF_2N_9O$: 513.15, measured (ES, m/z): 514.15 $[M+H]^+$. $^1$H NMR (400 MHz, DMSO-$d_6$) δ 9.81 (s, 1H), 7.90-7.99 (m, 1H), 7.68 (dd, J=8.7, 1.4 Hz, 1H), 5.66 (dd, J=8.0, 2.6 Hz, 1H), 4.97 (t, J=7.4 Hz, 1H), 2.30-2.38 (m, 3H), 2.20-2.23 (m, 1H), 1.95-2.08 (m, 1H), 1.65-1.67 (m, 1H). $^{19}$F NMR (376 MHz, DMSO-$d_6$) δ−70.81, −113.06.

Example 132 (3S*,8aR*)-3-(5-(6-amino-2-fluoropyridin-3-yl-4,5-d2)-1H-imidazol-2-yl-4-d)-7-(3-chloro-2-fluoro-6-(1H-tetrazol-1-yl)phenyl)-2,3,8,8a-tetrahydroindolizin-5(1H)-one-8a-d

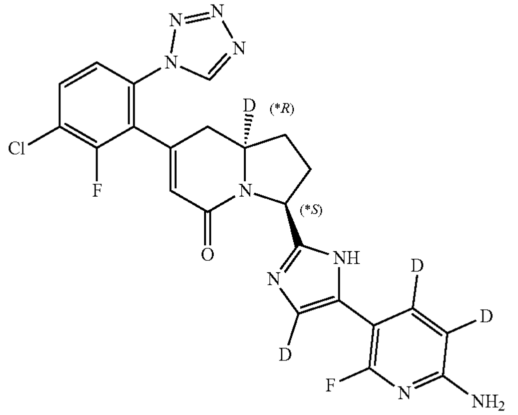 [SMILES: [2H]c1nc([C@@H]2CC[C@]3([2H])CC(c4c(-n5cnnn5)ccc(Cl)c4F)=CC(=O)N23)[nH]c1-c1c(F)nc(N)c([2H])c1[2H]]

LC/MS: mass calculated for $C_{23}H_{14}D_4ClF_2N_9O$: 513.15 measured (ES, m/z): 514.15 $[M+H]^+$. $^1$H NMR (400 MHz, DMSO-$d_6$) δ 9.81 (s, 1H), 7.88-7.97 (m, 1H), 7.67 (dd, J=8.7, 1.5 Hz, 1H), 5.66 (d, J=2.7 Hz, 1H), 5.01 (d, J=8.8 Hz, 1H), 2.60-2.73 (m, 1H), 2.43-2.46 (m, 1H), 2.14-2.22 (m, 1H), 2.02-2.07 (m, 1H), 1.91-1.96 (m, 1H). $^{19}$F NMR (376 MHz, DMSO-$d_6$) δ 70.64, −112.75.

Example 133 (3R*,8aR)-7-(3-chloro-2-fluoro-6-(1H-tetrazol-1-yl)phenyl)-3-(5-(2-fluoro-6-(methylamino)pyridin-3-yl-4,5-d2)-1H-imidazol-2-yl)-2,3,8,8a-tetrahydroindolizin-5(1H)-one

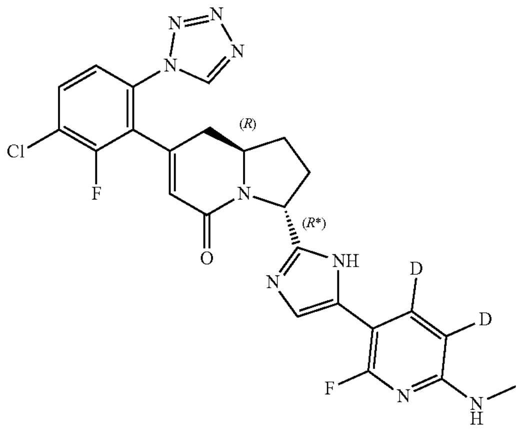

LC/MS: mass calculated for $C_{24}H_{18}D_2ClF_2N_9O$: 525.16, measured (ES, m/z): 526.10 $[M+H]^+$. $^1$H NMR (400 MHz, DMSO-$d_6$) δ 9.82 (s, 1H), 7.90-8.10 (m, 1H), 7.70 (dd, J=8.7, 1.5 Hz, 1H), 7.18 (s, 1H), 6.98 (s, 1H), 5.67 (d, J=2.7 Hz, 1H), 5.03 (d, J=8.9 Hz, 1H), 3.68-3.81 (m, 1H), 2.72-2.88 (m, 4H), 2.50-2.54 (m, 1H), 2.08-2.29 (m, 2H), 1.91-2.07 (m, 2H). $^{19}$F NMR (376 MHz, DMSO-$d_6$) δ−70.44, −112.86.

Example 134 (3S,8aR)-7-(3-chloro-2-fluoro-6-(1H-tetrazol-1-yl)phenyl)-3-(5-(3-fluoro-2-(methylamino)pyridin-4-yl)-1H-imidazol-2-yl)-2,3,8,8a-tetrahydroindolizin-5(1H)-one

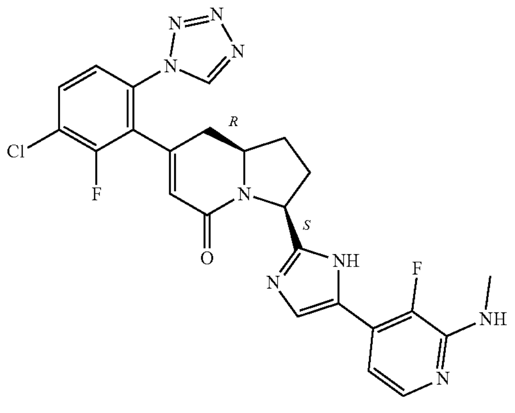

Step 1: 2-(3-Fluoro-2-(n-methylacetamido)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate To a mixture of (3S,8aR)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) in DMF (5 mL) was added cesium carbonate (120 mg, 0.37 mmol, 0.6 equiv.), followed by addition of N-(4-(2-bromoacetyl)-3-fluoropyridin-2-yl)-N-methylacetamide (226 mg, 0.92 mmol, 1.5 equiv.). The resulting mixture was stirred at room temperature overnight, diluted with water, and extracted with EA (3×20 mL). The organic layers were combined, washed with brine, dried over $Na_2SO_4$ and concentrated under reduced pressure. The residue was purified by flash column chromatography on silica gel (MeOH/DCM, 0→8%) to yield 2-(3-fluoro-2-(n-methylacetamido)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate as a yellow solid. LC/MS: mass calculated for $C_{25}H_{23}ClF_2N_4O_5$: 532.13, measured (ES, m/z): 533.10 $[M+H]^+$.

Step 2: 2-(3-Fluoro-2-(n-methylacetamido)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate To a mixture of 2-(3-fluoro-2-(n-methylacetamido)pyridin-4-yl)-2-oxoethyl (3S,8aR)-7-(6-amino-3-chloro-2-fluorophenyl)-5-oxo-1,2,3,5,8,8a-hexahydroindolizine-3-carboxylate (275 mg, 0.52 mmol, 1.0 equiv.) and ammonium acetate (398 mg, 5.16 mmol, 10.0 equiv.) in 1,4-dioxane (5 mL) was added acetic acid (1 mL). The resulting mixture was stirred at 100° C. for 1 h. The excess solvent was evaporated under reduced pressure. The residue was purified by flash column chromatography on silica gel (MeOH/DCM, 0→10%) to yield N-(4-(2-((3S,8aR)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-n-methylacetamide as a yellow solid. LC/MS: mass calculated for $C_{25}H_{23}ClF_2N_6O_2$: 512.15, measured (ES, m/z): 513.15 $[M+H]^+$.

Step 3: N-(4-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-n-methylacetamide A mixture of N-(4-(2-((3S,8aR)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-N-methylacetamide (150 mg, 0.29 mmol, 1.0 equiv.), trimethoxymethane (2 mL) and azidotrimethylsilane (2 mL) in acetic acid (2 mL) was stirred at room temperature overnight. The solvent was evaporated under reduced pressure to yield N-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-n-methylacetamide as a yellow oil. LC/MS: mass calculated for $C_{28}H_{22}ClF_2NaO_2$: 565.16, measured (ES, m/z): 566.15 $[M+H]^+$.

Step 4: (3S,8aR)-7-(3-Chloro-2-fluoro-6-(1H-tetrazol-1-yl)phenyl)-3-(5-(3-fluoro-2-(methylamino)pyridin-4-yl)-1H-imidazol-2-yl)-2,3,8,8a-tetrahydroindolizin-5(1H)-one To a solution of N-(4-(2-((3R,8aS)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-n-methylacetamide (190 mg, 0.34 mmol, 1.0 equiv.) in THE (2 mL) was added HCl (1 mL, 2 M). The resulting mixture was stirred at 50° C. for 2 h, then concentrated under reduced pressure. The residue was purified by reversal phase chromatography on C18 (MeCN/$H_2O$ (0.05% $CF_3COOH$)) to yield (3R,8aS)-7-(3-Chloro-2-fluoro-6-(1H-tetrazol-1-yl)phenyl)-3-(5-(3-fluoro-2-(methylamino)pyridin-4-yl)-1H-imidazol-2-yl)-2,3,8,8a-tetrahydroindolizin-5(1H)-as a yellow solid. The racemic product (78 mg) was further separated by chiral-HPLC to yield (3R,8aS)-7-(3-chloro-2-fluoro-6-(1H-tetrazol-1-yl)phenyl)-3-(5-(3-fluoro-2-(methylamino)pyridin-4-yl)-1H-imidazol-2-yl)-2,3,8,8a-tetrahydroindolizin-5(1H)-one as a white solid.

LC/MS: mass calculated for $C_{24}H_{20}ClF_2N_9O$: 523.14, measured (ES, m/z): 524.05 $[M+H]^+$. $^1H$ NMR (300 MHz, DMSO-$d_6$) δ 12.15 (s, 1H), 9.84 (s, 1H), 7.92-8.03 (m, 1H), 7.68-7.84 (m, 2H), 7.45 (d, J=3.7 Hz, 1H), 7.08 (s, 1H), 6.57 (s, 1H), 5.69 (d, J=2.5 Hz, 1H), 5.04 (d, J=8.4 Hz, 1H), 3.60-3.80 (m, 1H), 2.82-2.94 (m, 3H), 2.65-2.80 (m, 1H), 2.56-2.60 (m, 1H), 1.88-2.26 (m, 4H). $^{19}F$ NMR (282 MHz, DMSO-$d_6$) δ−112.85, −143.81.

Example 135 (3S,8a*S)-7-(3-chloro-2-fluoro-6-(1H-tetrazol-1-yl)phenyl)-3-(5-(2-(ethyl(2-hydroxyethyl)amino)-3-fluoropyridin-4-yl)-1H-imidazol-2-yl)-2,3,8,8a-tetrahydroindolizin-5(1H)-one

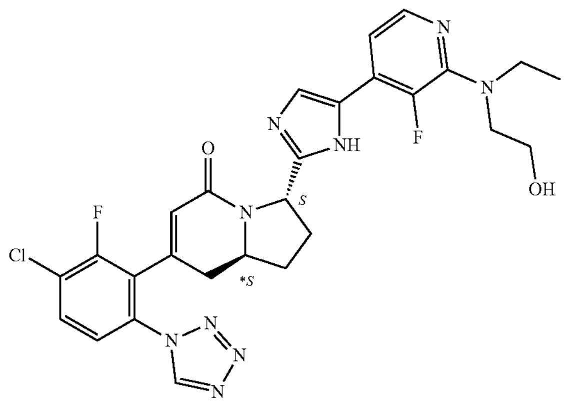

LC/MS: mass calculated for $C_{27}H_{28}ClF_2N_6O_2$: 581.19, measured (ES, m/z): 582.20 $[M+H]^+$. $^1H$ NMR (400 MHz, Methanol-d4) δ 9.57 (s, 1H), 7.90 (d, J=5.7 Hz, 1H), 7.75-7.85 (m, 2H), 7.50-7.57 (m, 1H), 7.24-7.31 (m, 1H), 5.73 (d, J=2.6 Hz, 1H), 5.15-5.22 (m, 1H), 4.26-4.38 (m, 1H), 3.76-3.86 (m, 2H), 3.62-3.74 (m, 4H), 2.61-2.73 (m, 3H), 2.36-2.47 (m, 1H), 2.07-2.23 (m, 1H), 1.80-1.94 (m, 1H), 1.28 (t, J=7.0 Hz, 3H). $^{19}F$ NMR (376 MHz, Methanol-d4) δ −76.98, −113.88, −134.07.

Example 136 (3S,8a*R)-7-(3-chloro-2-fluoro-6-(1H-tetrazol-1-yl)phenyl)-3-(5-(2-(ethyl(2-hydroxyethyl)amino)-3-fluoropyridin-4-yl)-1H-imidazol-2-yl)-2,3,8,8a-tetrahydroindolizin-5(1H)-one

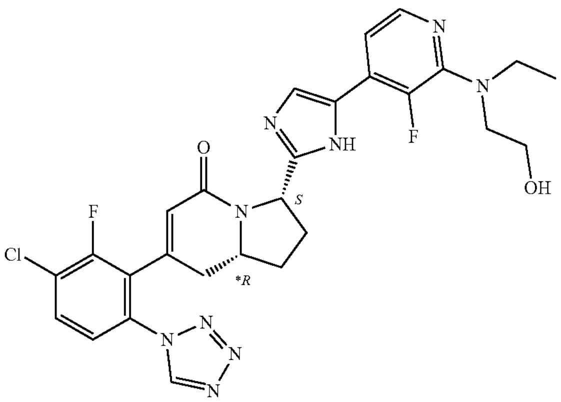

LC/MS: mass calculated for $C_{27}H_{26}ClF_2N_9O_2$: 581.19, measured (ES, m/z): 582.20 $[M+H]^+$. $^1H$ NMR (400 MHz, Methanol-d4) δ 9.57 (s, 1H), 7.75-7.90 (m, 2H), 7.48-7.57 (m, 2H), 7.24-7.33 (m, 1H), 5.73 (d, J=2.8 Hz, 1H), 5.14-5.21 (m, 1H), 3.84-3.97 (m, 1H), 3.74-3.80 (m, 2H), 3.56-3.67 (m, 4H), 2.84-2.95 (m, 1H), 2.56-2.65 (m, 1H), 2.16-2.40 (m, 3H), 1.98-2.12 (m, 1H), 1.23 (t, J=7.0 Hz, 3H). $^{19}F$ NMR (376 MHz, Methanol-d4) δ 76.92, −113.16, −135.42.

Example 137 (3R*,8aR)-3-(5-(1H-indol-3-yl)-1H-imidazol-2-yl)-7-(3-chloro-2-fluoro-6-(1H-tetrazol-1-yl)phenyl)-2,3,8,8a-tetrahydroindolizin-5(1H)-one

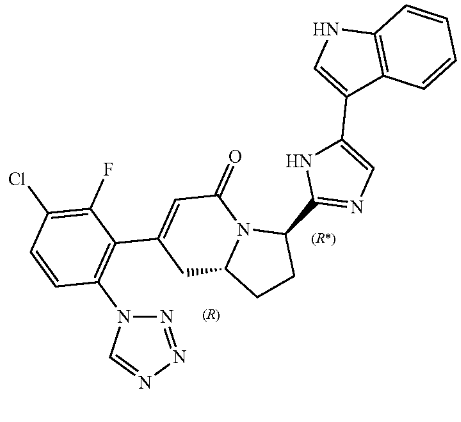

LC/MS: mass calculated for $C_{26}H_{20}ClFN_8O$: 514.14, measured (ES, m/z): 515.10 $[M+H]^+$. $^1H$ NMR (400 MHz, DMSO-$d_6$) δ 11.33-12.05 (m, 1H), 10.56-11.22 (m, 1H), 9.78 (s, 1H), 7.88-8.08 (m, 2H), 7.64-7.76 (m, 1H), 7.41-7.52 (m, 1H), 7.22-7.40 (m, 1H), 6.93-7.18 (m, 3H), 5.40-5.60 (m, 1H), 4.94-4.96 (m, 1H), 3.59-3.71 (m, 1H), 2.61-2.91 (m, 2H), 1.78-2.10 (m, 4H). $^{19}F$ NMR (376 MHz, DMSO-$d_6$) δ−112.81.

Example 138 3-(4-(2-((3S,8aR*)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)oxetane-3-carbonitrile

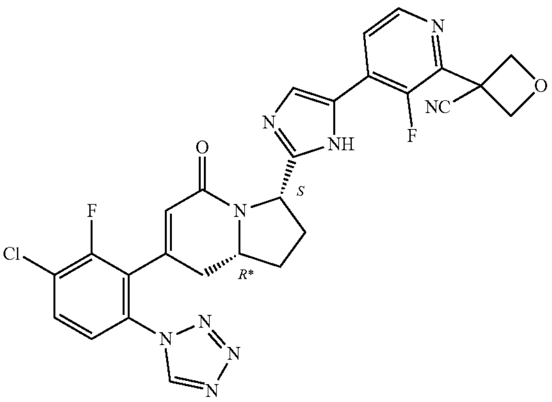

Step 1: 3-(3-Fluoro-4-iodopyridin-2-yl)oxetane-3-carbonitrile

To a solution of 2,3-difluoro-4-iodopyridine (1.0 g, 4.15 mmol, 1.0 equiv.) in toluene (15 mL) was added lithium bis(trimethylsilyl)amide solution 1.0 M in THF (6.2 mL, 6.23 mmol, 1.5 equiv.) dropwise under $N_2$ at −10° C. After stirring for 40 min at −10° C., oxetane-3-carbonitrile (0.41 g, 4.98 mmol, 1.2 equiv.) was added dropwise. The reaction mixture was warmed to room temperature slowly and stirred for 2 h, then quenched with saturated $NH_4Cl$, extracted with EA, dried over $Na_2SO_4$ and concentrated under vacuum. The residue was purified by silica gel chromatography with EA/PE (0→40%) to yield 3-(3-fluoro-4-iodopyridin-2-yl)oxetane-3-carbonitrile as a white solid. LC/MS: mass calculated for $C_9H_6FIN_2O$: 303.95, measured (ES, m/z): 305.00 $[M+H]^+$.

Step 2: 3-(4-(1-Ethoxyvinyl)-3-fluoropyridin-2-yl)oxetane-3-carbonitrile

To a solution of 3-(3-fluoro-4-iodopyridin-2-yl)oxetane-3-carbonitrile (1.8 g, 5.31 mmol, 1.0 equiv.) in 1,4-dioxane (20 mL) was added tributyl(1-ethoxyvinyl)tin (3.8 g, 10.62 mmol, 2.0 equiv.), bis(triphenylphosphine) palladium(II) chloride (0.28 g, 0.40 mmol, 0.075 equiv.). The resulting mixture was maintained under nitrogen and stirred at 100° C. overnight, then cooled to room temperature and quenched with water. The reaction mixture was extracted with EA. The organic layers were combined, washed with brine, dried and concentrated under vacuum. The residue was purified by silica gel chromatography on silica gel (0-20% ethyl acetate/petroleum ether) to yield (S)-2-((1,4-dioxan-2-yl)methoxy)-4-(1-ethoxyvinyl)-3-fluoropyridine as a yellow solid. LC/MS: mass calculated for $C_{13}H_{13}FN_2O_2$: 248.10, measured (ES, m/z): 249.25 $[M+H]^+$.

Step 3: 3-(4-(2-Bromoacetyl)-3-fluoropyridin-2-yl)oxetane-3-carbonitrile

To a solution of 3-(4-(1-ethoxyvinyl)-3-fluoropyridin-2-yl)oxetane-3-carbonitrile (0.40 g, 1.61 mmol, 1.0 equiv.) in tetrahydrofuran (6 mL) and water (2 mL) was added N-bromosuccinimide (0.26 g, 1.45 mmol, 1.0 equiv.). The reaction mixture was stirred at room temperature for 0.5 h, quenched with water and extracted with EA. The organic layers were combined, washed with brine, dried and concentrated under vacuum. The residue was purified by silica gel chromatography on silica gel (0→20% ethyl acetate/petroleum ether) to yield 3-(4-(2-bromoacetyl)-3-fluoropyridin-2-yl)oxetane-3-carbonitrile as a yellow oil. LC/MS: mass calculated for $C_{11}H_8BrFN_2O_2$: 297.98, measured (ES, m/z): 298.95, 300.95 $[M+H, M+H+2]^+$.

Step 4: 2-(2-(3-Cyanooxetan-3-yl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (0.20 g, 0.53 mmol, 1.0 equiv.) in DMF (5 mL) was added potassium carbonate (0.11 g, 0.79 mmol, 1.5 equiv.), followed by 3-(4-(2-bromoacetyl)-3-fluoropyridin-2-yl)oxetane-3-carbonitrile (0.24 g, 0.79 mmol, 1.5 equiv.). The reaction mixture was stirred at room temperature for 2 h and concentrated under reduced pressure. The residue was purified by reverse column chromatography on C18 with ($CH_3CN$/water (0.05% TFA): 5-(70%) to yield 2-(2-(3-cyanooxetan-3-yl)-3-fluoropyridin-4-yl)-2-oxoethyl (3R)-7-(3-chloro-2-fluoro-6-(1H-tetrazol-1-yl)phenyl)-5-oxo-1,2,3,5,8,8a-hexahydroindolizine-3-carboxylate as a brown solid. LC/MS: mass calculated for $C_{27}H_{20}ClF_2N_7O5$. 595.12, measured (ES, m/z): 596.05 $[M+H]^+$.

Step 5: 3-(4-(2-((3S,8aR*)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)oxetane-3-carbonitrile To a solution of 2-(2-(3-cyanooxetan-3-yl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate (0.12 g, 0.20 mmol, 1.0 equiv.) in toluene (5 mL) and acetic acid (0.25 mL) was added ammonium acetate (0.31 g, 4.03 mmol, 20.0 equiv.). The reaction mixture was stirred at 100° C. for 1 h, concentrated under vacuum. The residue was purified by flash column chromatography on silica gel (0→10% MeOH/DCM) to yield 1-(4-(2-((3S,8aR)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)cyclopropane-1-carbonitrile as a brown solid. The racemic mixture was purified by prep-chiral-HPLC with MeOH (0.1% DEA) to yield 3-(4-(2-((3S, 8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)oxetane-3-carbonitrile as a white solid.

LC/MS: mass calculated for $C_{27}H_{20}ClF_2N_9O_2$: 575.14, measured (ES, m/z): 576.10 $[M+H]^+$. $^1H$ NMR (300 MHz, DMSO-$d_6$) δ12.40 (s, 1H), 9.85 (s, 1H), 8.38-8.53 (m, 1H), 7.81-8.20 (m, 2H), 7.60-7.78 (m, 2H), 5.71 (d, J=2.5 Hz, 1H), 5.11-5.32 (m, 4H), 5.05 (d, J=8.5 Hz, 1H), 3.69-3.89 (m, 1H), 2.62-2.84 (m, 1H), 2.57-2.61 (m, 1H), 2.09-2.29 (m, 2H), 1.96-2.09 (m, 2H). $^{19}F$ NMR (282 MHz, DMSO-$d_6$) δ −112.85, −127.22.

Example 139 1-(4-(2-((3S,8a*R)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)cyclopropane-1-carbonitrile

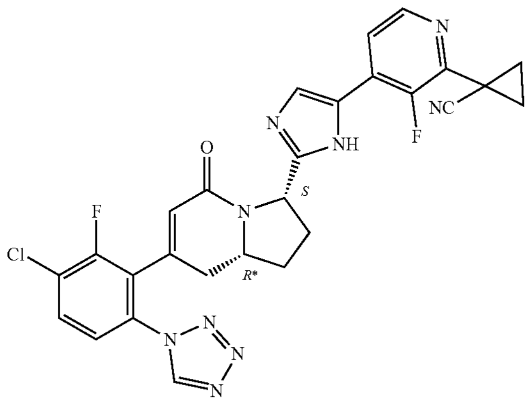

LC/MS: mass calculated for $C_{27}H_{20}ClF_2N_9O$: 559.14, measured (ES, m/z): 560.15 $[M+H]^+$. $^1H$ NMR (300 MHz, Methanol-d4) δ 9.60 (s, 1H), 8.37-8.43 (m, 1H), 7.79-7.94 (m, 3H), 7.54-7.63 (m, 1H), 5.78 (d, J=2.8 Hz, 1H), 5.20-5.35 (m, 1H), 3.90-4.10 (m, 1H), 2.91-3.08 (m, 1H), 2.65-2.83 (m, 1H), 2.41-2.58 (m, 1H), 2.15-2.39 (m, 2H), 1.93-2.17 (m, 1H), 1.73-1.91 (m, 4H)/$^{19}F$ NMR (282 MHz, Methanol-d4) 5-77.25, −113.59, −126.83.

Example 140 (3*R,8aS)-3-(5-(1H-pyrrolo[2,3-b]pyridin-3-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one

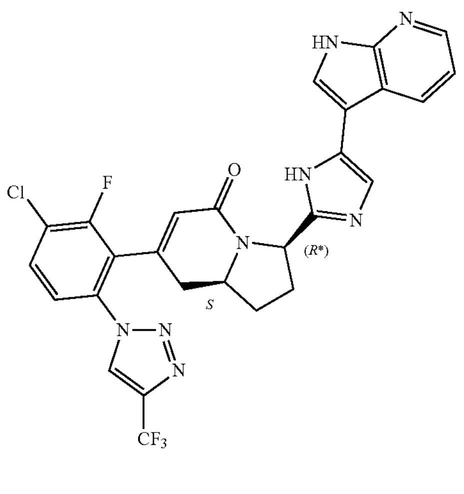

LC/MS: mass calculated for $C_{27}H_{19}ClF_4N_8O$: 582.13, measured (ES, m/z): 583.05 $[M+H]^+$. $^1H$ NMR (400 MHz, DMSO-$d_6$) δ 9.32 (d, J=1.1 Hz, 1H), 8.30-8.40 (m, 2H), 7.91-8.01 (m, 3H), 7.71 (dd, J=8.7, 1.5 Hz, 1H), 7.23-7.29 (m, 1H), 5.72 (d, J=2.8 Hz, 1H), 5.20-5.26 (m, 1H), 3.70-3.84 (m, 1H), 2.94-3.09 (m, 1H), 2.53-2.67 (m, 1H), 2.31-2.47 (m, 1H), 2.09-2.22 (m, 2H), 1.89-2.02 (m, 1H)/$^{19}F$ NMR (376 MHz, DMSO-$d_6$) δ −59.52, −74.06, −112.65.

Example 141 (3*S,8a*R)-7-(3-chloro-2-fluoro-6-(1H-tetrazol-1-yl)phenyl)-3-(5-(3-fluoro-2-((*R)-1-(oxazol-2-yl)ethoxy)pyridin-4-yl)-1H-imidazol-2-yl)-2,3,8,8a-tetrahydroindolizin-5(1H)-one

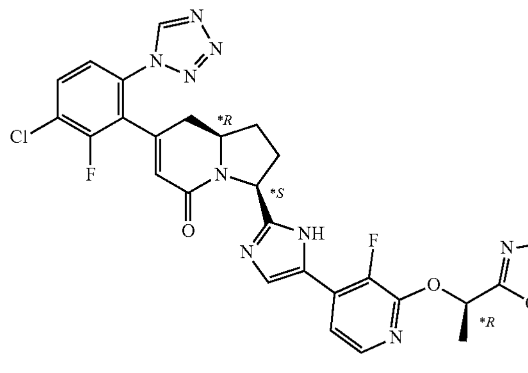

LC/MS: mass calculated for $C_{28}H_{22}ClF_2N_9O_3$: 605.15, measured (ES, m/z): 606.10 $[M+H]^+$. $^1H$ NMR (300 MHz, DMSO-$d_6$) δ 9.82 (s, 1H), 8.08 (s, 1H), 7.83-8.02 (m, 2H), 7.64-7.74 (m, 1H), 7.50-7.61 (m, 2H), 7.20 (s, 1H), 6.33 (q, J=6.6 Hz, 1H), 5.67 (d, J=2.5 Hz, 1H), 5.02 (d, J=8.4 Hz, 1H), 3.65-3.79 (m, 1H), 2.60-2.79 (m, 1H), 2.03-2.29 (m, 3H), 1.86-2.03 (m, 2H), 1.69 (d, J=6.6 Hz, 3H)/$^{19}F$ NMR (282 MHz, DMSO-$d_6$) δ −142.97, −112.90.

Example 142 (3*S,8a*R)-7-(3-chloro-2-fluoro-6-(1H-tetrazol-1-yl)phenyl)-3-(5-(3-fluoro-2-((*S)-1-(oxazol-2-yl)ethoxy)pyridin-4-yl)-1H-imidazol-2-yl)-2,3,8,8a-tetrahydroindolizin-5(1H)-one

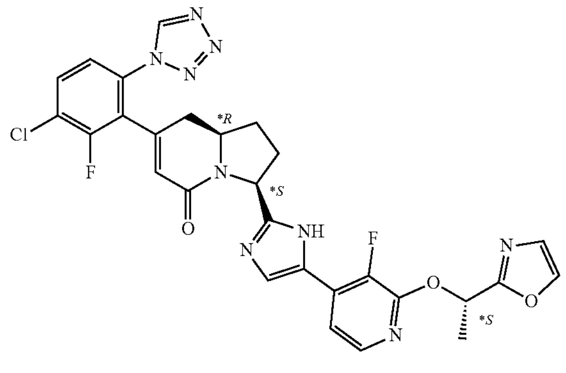

LC/MS: mass calculated for $C_{28}H_{22}ClF_2N_9O_3$: 605.15, measured (ES, m/z): 606.10 $[M+H]^+$. $^1H$ NMR (300 MHz, DMSO-$d_6$) δ 9.82 (s, 1H), 8.08 (s, 1H), 7.79-8.02 (m, 2H), 7.69 (dd, J=8.6, 1.5 Hz, 1H), 7.50-7.61 (m, 2H), 7.20 (s, 1H), 6.34 (q, J=6.6 Hz, 1H), 5.68 (d, J=2.5 Hz, 1H), 5.02 (d, J=8.4 Hz, 1H), 3.66-3.79 (m, 1H), 2.61-2.78 (m, 1H), 2.03-2.34 (m, 3H), 1.86-2.20 (m, 2H), 1.69 (d, J=6.7 Hz, 3H)/$^{19}F$ NMR (282 MHz, DMSO-$d_6$) δ −142.99, −112.90.

Example 143 (3S,8aR)-7-(3-chloro-2-fluoro-6-(1H-tetrazol-1-yl)phenyl)-3-(5-(3-fluoro-2-((*S)-3,3,3-trifluoro-2-hydroxypropyl)pyridin-4-yl)-1H-imidazol-2-yl)-2,3,8,8a-tetrahydroindolizin-5(1H)-one

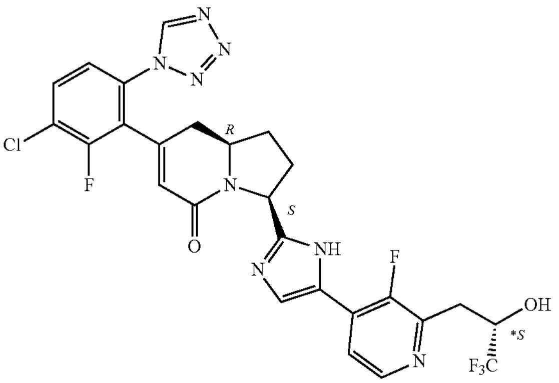

Step 1: 2-(2-(2-((Tert-butyldimethylsilyl)oxy)-3,3,3-trifluoropropyl)-3-fluoropyridin-4-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate To a solution of (3S)-7-(3-chloro-2-fluoro-6-(1H-tetrazol-1-yl)phenyl)-5-oxo-1,2,3,5,8,8a-hexahydroindolizine-3-carboxylic acid (0.20 g, 0.53 mmol, 1.0 equiv.) in N,N-dimethylformamide (5 mL) was added potassium carbonate (0.11 g, 0.79 mmol, 1.5 equiv.), followed by addition of 2-bromo-1-(2-(2-((tert-butyldimethylsilyl)oxy)-3,3,3-trifluoropropyl)-3-fluoropyridin-4-yl)ethan-1-one (0.44 g). The reaction mixture was stirred at room temperature for 1 h, then purified by reverse phase chromatography on C18 with $CH_3CN$/water (5→100%) to yield 2-(2-(2-((tert-butyldimethylsilyl)oxy)-3,3,3-trifluoropropyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate as a yellow solid. LC/MS: mass calculated for $C_{32}H_{34}ClF_5N_6O_5Si$: 740.20, measured (ES, m/z): 741.05 $[M+H]^+$.

Step 2: (3S,8aR)-7-(3-Chloro-2-fluoro-6-(1H-tetrazol-1-yl)phenyl)-3-(5-(3-fluoro-2-(3,3,3-trifluoro-2-hydroxypropyl)pyridin-4-yl)-1H-imidazol-2-yl)-2,3,8,8a-tetrahydroindolizin-5(1H)-one To a mixture of 2-(2-(2-((tert-butyldimethylsilyl)oxy)-3,3,3-trifluoropropyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate (180 mg, 0.24 mmol 1.0 equiv.) and ammonium acetate (374 mg, 4.86 mmol, 20.0 equiv.) in toluene (10 mL) was added acetic acid (0.3 mL). The reaction mixture was stirred at 100° C. for 1 h, then concentrated under vacuum. The residue was purified by flash column chromatography on silica gel with MeOH/DCM (0→10%) to yield (3S)-3-(5-(2-(2-((tert-butyldimethylsilyl)oxy)-3,3,3-trifluoropropyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow solid. LC/MS: mass calculated for $C_{26}H_{20}ClF_5N_8O_2$: 720.22, measured (ES, m/z): 721.40 $[M+H]^+$.

Step 3: (3S,8aR)-7-(3-Chloro-2-fluoro-6-(1H-tetrazol-1-yl)phenyl)-3-(5-(3-fluoro-2-(('S)-3,3,3-trifluoro-2-hydroxypropyl)pyridin-4-yl)-1H-imidazol-2-yl)-2,3,8,8a-tetrahydroindolizin-5(1H)-one To a solution of (3S,8aR)-3-(5-(2-(2-((tert-butyldimethylsilyl)oxy)-3,3,3-trifluoropropyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (110 mg, 0.15 mmol, 1.0 equiv.) in THE (5 mL) was added triethylamine trihydrofluoride (123 mg, 0.76 mmol, 5.0 equiv.). The reaction mixture was stirred at 70° C. for 1.5 h, then concentrated under reduced pressure and the residue was purified by reverse phase chromatography with $CH_3CN$/water (5→35%) to yield a racemic product, which was further purified by chiral HPLC with Hex(0.1% DEA): EtOH=50:50 to yield (3S,8aR)-7-(3-chloro-2-fluoro-6-(1H-tetrazol-1-yl)phenyl)-3-(5-(3-fluoro-2-(('S)-3,3,3-trifluoro-2-hydroxypropyl)pyridin-4-yl)-1H-imidazol-2-yl)-2,3,8,8a-tetrahydroindolizin-5(1H)-one as a white solid.

LC/MS: mass calculated for $C_{26}H_{20}ClF_5N_8O_2$: 606.13, measured (ES, m/z): 607.10 $[M+H]^+$. $^1H$ NMR (400 MHz, Methanol-d4) δ 9.57 (s, 1H), 8.32 (d, J=5.1 Hz, 1H), 7.92-8.01 (m, 1H), 7.77-7.86 (m, 1H), 7.64-7.51 (m, 2H), 5.74 (d, J=2.6 Hz, 1H), 5.17 (d, J=8.8 Hz, 1H), 4.43-4.55 (m, 1H), 3.85-3.99 (m, 1H), 3.19-3.26 (m, 1H), 3.05-3.15 (m, 1H), 2.80-2.97 (m, 1H), 2.56-2.68 (m, 1H), 2.15-2.37 (m, 3H), 1.97-2.14 (m, 1H)/$^{19}F$ NMR (376 MHz, Methanol-d4) δ −81.18, −113.52, −129.57.

Example 144 (3S,8aR)-7-(3-chloro-2-fluoro-6-(1H-tetrazol-1-yl)phenyl)-3-(5-(3-fluoro-2-((*R)-3,3,3-trifluoro-2-hydroxypropyl)pyridin-4-yl)-1H-imidazol-2-yl)-2,3,8,8a-tetrahydroindolizin-5(1H)-one

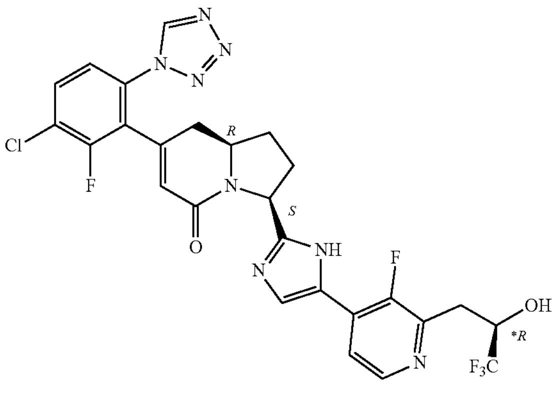

LC/MS: mass calculated for $C_{28}H_{20}ClF_5N_6O_2$: 606.13, measured (ES, m/z): 607.05 $[M+H]^+$. $^1H$ NMR (400 MHz, Methanol-d4) δ 9.57 (s, 1H), 8.32 (d, J=5.2 Hz, 1H), 7.91-8.01 (m, 1H), 7.79-8.88 (m, 1H), 7.61 (d, J=4.1 Hz, 1H), 7.55 (dd, J=8.7, 1.6 Hz, 1H), 5.74 (d, J=2.7 Hz, 1H), 5.17 (d, J=8.7 Hz, 1H), 4.42-4.57 (m, 1H), 3.82-4.07 (m, 1H), 3.20-3.28 (m, 1H), 3.07-3.17 (m, 1H), 2.80-2.95 (m, 1H), 2.56-2.68 (m, 1H), 2.16-2.39 (m, 3H), 2.00-2.14 (m, 1H). $^{19}F$ NMR (376 MHz, Methanol-$d_4$) δ−81.18, −113.52, −129.56.

Example 145 (3S,8aR)-3-[5-(6-amino-5-deuterio-2-fluoro-3-pyridyl)-4-deuterio-1H-imidazol-2-yl]-7-[3-chloro-2-fluoro-6-(tetrazol-1-yl)phenyl]-2,3,8,8a-tetrahydro-1H-indolizin-5-one

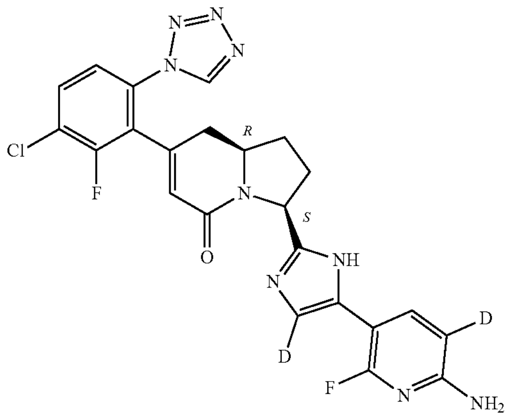

LC/MS: mass calculated for $C_{23}H_{16}ClD_2F_2N_9O$: 511.14, measured (ES, m/z): 512.10 $[M+H]^+$. $^1H$ NMR (400 MHz, DMSO-$d_6$) δ 9.82 (s, 1H), 7.91-8.03 (m, 2H), 7.67-7.73 (m, 1H), 5.68 (d, J=2.7 Hz, 1H), 5.00 (d, J=8.7 Hz, 1H), 3.62-3.75 (m, 1H), 2.60-2.78 (m, 1H), 2.50-2.52 (m, 1H), 2.03-2.20 (m, 2H), 1.90-2.00 (m, 2H)/$^{19}F$ NMR (376 MHz, DMSO-$d_6$) δ−70.74, −112.84.

Example 146 (3S,8aR)-3-[5-(6-amino-2-fluoro-3-pyridyl)-1H-imidazol-2-yl]-7-[3-chloro-2-fluoro-6-(tetrazol-1-yl)phenyl]-8a-deuterio-1,2,3,8-tetrahydroindolizin-5-one

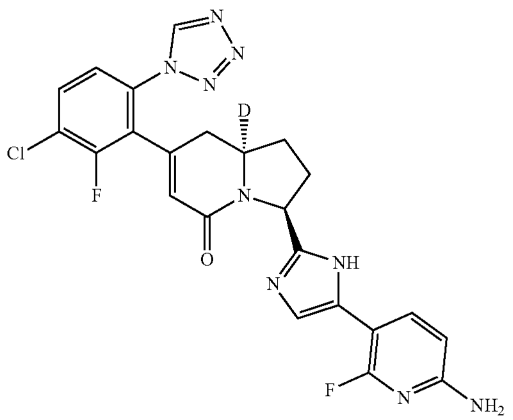 [SMILES: [2H][C@]12CC[C@@H](c3ncc(-c4ccc(N)nc4F)[nH]3)N1C(=O)C=C(c1c(-n3cnnn3)ccc(Cl)c1F)C2]

Step 1: 1-(Tert-butyl) 2-methyl (2S)-5-hydroxypyrrolidine-1,2-dicarboxylate-5-d

To a solution of 1-(tert-butyl) 2-methyl (S)-5-oxopyrrolidine-1,2-dicarboxylate (20 g, 82.22 mmol, 1.0 equiv) in methanol-d (120 mL) was added $NaBD_4$ (5.16 g, 123.33 mmol, 1.5 equiv) at 0° C. The mixture was stirred at 0° C. for 1 h. The reaction was quenched with D20 (10 mL). The resulting mixture was extracted with ethyl acetate (2×100 mL). The organic layers were combined, dried over anhydrous sodium sulfate, and concentrated. The residue was purified by silica gel chromatography (0-35% ethyl acetate/petroleum ether) to yield the 1-(tert-butyl) 2-methyl (2S)-5-hydroxypyrrolidine-1,2-dicarboxylate-5-d as a yellow oil.

Step 2: 1-(Tert-butyl) 2-methyl (2S)-5-methoxypyrrolidine-1,2-dicarboxylate-5-d

To a solution of 1-(tert butyl) 2-methyl (2S)-5-hydroxypyrrolidine-1,2-dicarboxylate-5-d (10 g, 40.61 mmol, 1.0 equiv) in MeOH (100 mL) was added p-toluenesulfonic acid monohydrate (1.9 g, 10.15 mmol, 0.25 equiv). The mixture was stirred at room temperature overnight. The solvent was removed under vacuum and the residue was purified by silica gel column with EA/PE (0%-35%) to yield the 1-(tert-butyl)2-methyl-(2S)-5-methoxypyrrolidine-1,2-dicarboxylate-5-d as a yellow oil.

Step 3: 1-(Tert-butyl) 2-methyl (2S)-5-((2,2-dimethyl-4-oxo-4H-1,3-dioxin-6-yl)methyl) pyrrolidine-1,2-dicarboxylate-5-d To a solution of 1-(tert-butyl) 2-methyl (2S)-5-methoxypyrrolidine-1,2-dicarboxylate-5-d (2.5 g, 10.151 mmol, 1.0 eq.), ((2,2-dimethyl-4-methylene-4H-1,3-dioxin-6-yl)oxy) trimethylsilane (3.3 g, 15.397 mmol, 1.5 eq.) in MTBE (30 mL) at −78° C. was added boron trifluoride etherate (1.7 g, 11.978 mmol, 1.2 eq.). The resulting mixture was maintained stirring at −78° C. for 1 h then warmed to room temperature and maintained stirring for 1 h, then quenched with $NaHCO_3$ solution (100 mL) and the aqueous layer was extracted with MTBE (3×100 mL). The organic layers were combined, dried over anhydrous sodium sulfate, and concentrated under reduced pressure. The residue was purified by silica gel chromatography (0-50% EA/PE) to yield the 1-(tert-butyl) 2-methyl (2S)-5-((2,2-dimethyl-4-oxo-4H-1,3-dioxin-6-yl)methyl)pyrrolidine-1,2-dicarboxylate-5-d as a yellow solid. LC/MS: mass calculated for $C_{18}H_{26}DNO_7$: 370.19, measured: 371.20 $[M+H]^+$.

Step 4: Methyl (2S)-5-((2,2-dimethyl-4-oxo-4H-1,3-dioxin-6-yl)methyl)pyrrolidine-2-carboxylate-5-d To a solution of 1-(tert-butyl) 2-methyl (2S)-5-((2,2-dimethyl-4-oxo-4H-1,3-dioxin-6-yl)methyl)pyrrolidine-1,2-dicarboxylate-5-d (1.5 g, 4.05 mmol, 1.0 eq.) in DCM (22.5 mL) was added TFA (4.5 mL). The mixture was stirred at room temperature for 4 h and then concentrated under reduced pressure to yield the methyl (2S)-5-((2,2-dimethyl-4-oxo-4H-1,3-dioxin-6-yl)methyl)pyrrolidine-2-carboxylate-5-d as a yellow oil. LC/MS: mass calculated for $C_{13}H_{18}DNO_5$: 270.13, measured: 271.30 $[M+H]^+$.

Step 5: Methyl (3S)-5,7-dioxooctahydroindolizine-3-carboxylate-8a-d

A solution of methyl (2S)-5-((2,2-dimethyl-4-oxo-4H-1,3-dioxin-6-yl)methyl)pyrrolidine-2-carboxylate-5-d (1.0 g, 3.70 mmol, 1.0 eq.) in toluene (10 mL) was heated at 110° C. with stirring for 1 h. The mixture was quenched with water (50 mL) and extracted with EA (3×100 mL). The organic layers were combined, dried over anhydrous sodium sulfate, and concentrated under reduced pressure. The residue was purified by flash column chromatography on silica gel (0-10% methanol/DCM) to yield the methyl (3S)-5,7-dioxooctahydroindolizine-3-carboxylate-8a-d as a yellow oil. LC/MS: mass calculated for $C_{10}H_{12}DNO_4$: 212.09, measured: 213.10 $[M+H]^+$.

Step 6: Methyl (3S)-5-oxo-7-(((trifluoromethyl) sulfonyl)oxy)-1,2,3,5,8,8a-hexahydro indolizine-3-carboxylate-8a-d To a solution of methyl (3S)-5,7-dioxooctahydroindolizine-3-carboxylate-8a-d (472 mg, 2.22 mmol, 1.0 eq.) in DCM (10 mL) was added N-phenyl-bis(trifluoromethanesulfonimide) (1193 mg, 3.34 mmol, 1.5 eq.) followed by triethylamine (450 mg, 4.447 mmol, 2.0 eq.). The reaction mixture was stirred at room temperature overnight, quenched with water (100 mL), and extracted with ethyl acetate (3×100 mL). The organic layers were combined, dried over anhydrous sodium sulfate, and concentrated under reduced pressure. The residue was purified by flash column chromatography on silica gel (0-100% EA/PE) to yield the methyl (3S)-5-oxo-7-(((trifluoromethyl)sulfonyl)oxy)-1,2,3,5,8,8a-hexahydroindolizine-3-carboxylate-8a-d as a yellow oil. LC/MS: mass calculated for $C_{11}H_{11}DF_3NO_6S$: 344.04, measured 345.05 $[M+H]^+$.

Step 7: Methyl (3S)-7-(6-amino-3-chloro-2-fluorophenyl)-5-oxo-1,2,3,5,8,8a-hexahydro indolizine-3-carboxylate-8a-d To a mixture of methyl (3S)-5-oxo-7-(((trifluoromethyl)sulfonyl)oxy)-1,2,3,5,8,8a-hexahydroindolizine-3-carboxylate-8a-d (673 mg, 1.95 mmol, 1.0 eq.), $Pd(dppf)Cl_2$ (149 mg, 0.196 mmol, 0.1 eq.) in 1,4-dioxane (10 mL) and $H_2O$ (1 mL) was added (6-amino-3-chloro-2-fluorophenyl)boronic acid (555 mg, 2.93 mmol, 1.5 eq.), $K_2CO_3$ (810 mg, 5.86 mmol, 3.0 eq.). The mixture was stirred at 90° C. for 4 h. After cooling to room temperature, the reaction mixture was quenched with water (50 mL) and the aqueous layer was extracted with ethyl acetate (3×100 mL). The organic layers were combined, dried over anhydrous sodium sulfate, and concentrated under reduced pressure. The residue was purified by flash column chromatography on silica gel (0-10% methanol/DCM) to yield the methyl (3S)-7-(6-amino-3-chloro-2-fluorophenyl)-5-oxo-1,2,3,5,8,8a-hexahydroindolizine-3-carboxylate-8a-d as a yellow solid. LC/MS: mass calculated for $C_{16}H_{15}ClDFN_2O_3$: 339.09, measured 340.10 $[M+H]^+$.

Step 8: (3S)-7-(6-amino-3-chloro-2-fluorophenyl)-5-oxo-1,2,3,5,8,8a-hexahydroindolizine-3-carboxylic-8a-d acid To a solution of methyl (3S)-7-(6-amino-3-chloro-2-fluorophenyl)-5-oxo-1,2,3,5,8,8a-hexahydroindolizine-3-carboxylate-8a-d (602 mg, 1.77 mmol, 1.0 eq.) in THE (10 mL) and $H_2O$ (5 mL) was added lithium hydroxide (212 mg, 8.85 mmol, 5.0 eq.). The reaction mixture was stirred at room temperature for 2 h, adjusted pH 5 with HCl (1M), and then extracted with ethyl acetate (3×100 mL). The organic layers were combined, dried over anhydrous sodium sulfate, filtered and concentrated under reduced pressure to yield the (3S)-7-(6-amino-3-chloro-2-fluorophenyl)-5-oxo-1,2,3,5,8,8a-hexahydroindolizine-3-carboxylic-8a-d acid as a yellow solid. LC/MS: mass calculated for $C_{15}H_{13}ClDFN_2O_3$: 325.07, measured 326.20 $[M+H]^+$.

Step 9: 2-(6-acetamido-2-fluoropyridin-3-yl)-2-oxoethyl (3S)-7-(6-amino-3-chloro-2-fluorophenyl)-5-oxo-1,2,3,5,8,8a-hexahydroindolizine-3-carboxylate-8a-d To a solution of (3S)-7-(6-amino-3-chloro-2-fluorophenyl)-5-oxo-1,2,3,5,8,8a-hexahydroindolizine-3-carboxylic-8a-d acid (465 mg, 1.428 mmol, 1.0 eq.) in DMF (5 mL) was added cesium carbonate (279 mg, 0.856 mmol, 0.6 eq.) followed by N-(5-(2-bromoacetyl)-6-fluoropyridin-2-yl)acetamide (472 mg, 1.716 mmol, 1.0 eq.). The reaction mixture was stirred at room temperature for 2 hours, quenched with water (50 mL), and extracted with ethyl acetate (3×100 mL). The organic layers were combined, dried over anhydrous sodium sulfate, and concentrated under reduced pressure. The residue was purified by flash column chromatography on silica gel (0-10% methanol/DCM) to yield the 2-(6-acetamido-2-fluoropyridin-3-yl)-2-oxoethyl (3S)-7-(6-amino-3-chloro-2-fluorophenyl)-5-oxo-1,2,3,5,8,8a-hexahydroindolizine-3-carboxylate-8a-d as a yellow solid. LC/MS: mass calculated for $C_{24}H_{20}ClDF_2N_4O_5$: 519.12, measured: 520.30 $[M+H]^+$.

Step 10: N-(5-(2-((3S)-7-(6-amino-3-chloro-2-fluorophenyl)-5-oxo-1,2,3,5,8,8a-hexahydroindolizin-3-yl-8a-d)-1H-imidazol-5-yl)-6-fluoropyridin-2-yl)acetamide To a solution of 2-(6-acetamido-2-fluoropyridin-3-yl)-2-oxoethyl (3S)-7-(6-amino-3-chloro-2-fluorophenyl)-5-oxo-1,2,3,5,8,8a-hexahydroindolizine-3-carboxylate-8a-d (541 mg, 1.04 mmol, 1.0 eq.) in toluene (10 mL) and acetic acid (1 mL) was added ammonium acetate (803 mg, 10.42 mmol, 10.0 eq.). The mixture was stirred at 90° C. for 2 h. After cooling to room temperature, the reaction mixture was quenched with water (50 mL) and extracted with ethyl acetate (3×50 mL). The organic layers were combined, dried over anhydrous sodium sulfate, filtered and concentrated under reduced pressure. The residue was purified by flash column chromatography on silica gel (0-10% MeOH/DCM) to yield the N-(5-(2-((3S)-7-(6-amino-3-chloro-2-fluorophenyl)-5-oxo-1,2,3,5,8,8a-hexahydroindolizin-3-yl-8a-d)-1H-imidazol-5-yl)-6-fluoropyridin-2-yl)acetamide as a yellow solid. LC/MS: mass calculated for $C_{24}H_{20}ClDF_2N_6O_2$: 499.14, measured: 500.30 $[M+H]^+$.

Step 11: N-(5-(2-((3S)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-6-fluoropyridin-2-yl)acetamide To a solution of N-(5-(2-((3S)-7-(6-amino-3-chloro-2-fluorophenyl)-5-oxo-1,2,3,5,8,8a-hexahydroindolizin-3-yl-8a-d)-1H-imidazol-5-yl)-6-fluoropyridin-2-yl)acetamide (341 mg, 0.682 mmol, 1.0 eq.) in acetic acid (10 mL) were added azidotrimethylsilane (787 mg, 6.831 mmol, 10.0 eq.) and trimethoxymethane (724 mg, 6.822 mmol, 10.0 eq.). The reaction mixture was stirred at 60° C. for 4 h. After cooling to room temperature, the reaction mixture was quenched with water (50 mL) and extracted with ethyl acetate (3×50 mL). The organic layers were combined, dried over anhydrous sodium sulfate, and concentrated. The residue was purified by silica gel chromatography (0-10% MeOH/DCM) to yield the N-(5-(2-((3S)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-6-fluoropyridin-2-yl)acetamide as a yellow solid. LC/MS: mass calculated for $C_{25}H_{19}ClDF_2N_9O_2$: 552.15, measured: 553.35 $[M+H]^+$.

Step 12: (3S)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d To a solution of N-(5-(2-((3S)-7-(3-chloro-2-fluoro-6-(1H-tetrazol-1-yl)phenyl)-5-oxo-1,2,3,5,8,8a-hexahydroindolizin-3-yl-8a-d)-1H-imidazol-5-yl)-6-fluoropyridin-2-yl)acetamide (152 mg, 0.275 mmol, 1.0 eq.) in THE (1 mL) was added 4 N HCl solution (1 mL). The mixture was stirred at 50° C. for 3 h. After cooling to room temperature, the reaction was diluted with water and extracted with EA. The organic layers were combined, dried over anhydrous sodium sulfate, filtered and concentrated to dryness under reduced pressure to yield a residue, which was purified by reverse phase chromatography on a C18 column (eluent: 5% to 50% (v/v) $CH_3CN$ and $H_2O$ with 0.05% $NH_4HCO_3$) and chiral-HPLC using a column: CHIRALPAK IA-3, 4.6*50 mm, 3 μm; Mobile Phase A: Hex (0.1% DEA): EtOH=50:50, Mobile Phase B; Flow rate: 1 mL/min to yield (3S,8aR)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one-8a-d as a white solid.

LC/MS: mass calculated for $C_{23}H_{17}ClDF_2N_9O$: 510.14, measured (ES, m/z): 511.15 $[M+H]^+$. $^1H$ NMR (300 MHz, DMSO-$d_6$) δ 11.78 (s, 1H), 9.83 (s, 1H), 7.92-8.07 (m, 2H), 7.71 (dd, J=8.7, 1.5 Hz, 1H), 7.04 (d, J=3.9 Hz, 1H), 6.41 (dd, J=8.2, 2.2 Hz, 1H), 6.25 (s, 2H), 5.69 (d, J=2.5 Hz, 1H), 5.00 (d, J=8.3 Hz, 1H), 2.65-2.73 (m, 1H), 2.47-2.50 (m, 1H), 1.91-2.19 (m, 4H)/$^{19}F$ NMR (282 MHz, DMSO-$d_6$) δ−70.80, −112.87.

Example 147 (3S,8aR)-3-[5-(6-amino-5-deuterio-2-fluoro-3-pyridyl)-1H-imidazol-2-yl]-7-[3-chloro-2-fluoro-6-(tetrazol-1-yl)phenyl]-2,3,8,8a-tetrahydro-1H-indolizin-5-one

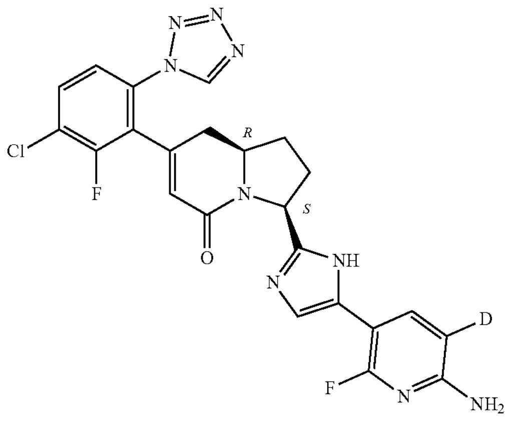

Step 1: 2-(6-Acetamido-2-fluoropyridin-3-yl-5-d)-2-oxoethyl (3S)-7-(6-amino-3-chloro-2-fluorophenyl)-5-oxo-1,2,3,5,8,8a-hexahydroindolizine-3-carboxylate To a solution of 2-(2-(2-((tert-butyldimethylsilyl)oxy)-3,3,3-trifluoropropyl)-3-fluoropyridin-4-yl)-2-oxoethyl (3S)-

7-(3-chloro-2-fluoro-6-(1H-tetrazol-1-yl)phenyl)-5-oxo-1,2,3,5,8,8a-hexahydroindolizine-3-carboxylate (180 mg, 0.24 mmol, 1.0 equiv.) and ammonium acetate (374 mg, 4.86 mmol, 20.0 equiv.) in toluene (10 mL) was added acetic acid (0.3 mL). The reaction mixture was stirred at 100° C. for 1 h. The resulting mixture was concentrated under vacuum. The residue was purified by silica gel chromatography with MeOH/DCM (0→10%) to yield (3S)-3-(5-(2-(2-((tert-butyldimethylsilyl)oxy)-3,3,3-trifluoropropyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow solid. LC/MS: mass calculated for $C_{24}H_{20}DClF_2N_4O_5$: 519.12, measured (ES, m/z): 520.05 $[M+H]^+$.

Step 2: N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl-3-d)acetamide Under an inert atmosphere of nitrogen, a mixture of 2-(6-acetamido-2-fluoropyridin-3-yl-5-d)-2-oxoethyl(3S)-7-(6-amino-3-chloro-2-fluorophenyl)-5-oxo-1,2,3,5,8,8a-hexahydroindolizine-3-carboxylate (700 mg, 1.35 mmol, 1.0 equiv.) and $NH_4OAc$ (1.0 g, 13.46 mmol, 10.0 equiv.) in AcOH (8 mL) and toluene (80 mL) was stirred at 110° C. for 1 h. The solvent was removed under vacuum and the residue was applied onto a silica gel column (40 g, MeOH/DCM: 1/20) to yield N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl-3-d)acetamide as a yellow solid.

Step 3: N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-3-d)acetamide A mixture of N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl-3-d)acetamide (520 mg, 1.040 mmol, 1.00 equiv), $TMSN_3$ (1.2 g, 10.40 mmol, 10.0 equiv.) and trimethoxymethane (1.1 g, 10.40 mmol, 10.0 equiv.) in AcOH (15 mL) was stirred at 65° C. for 3 h. The solvent was removed and the residue was purified by flash column chromatography on silica gel (40 g, MeOH/DCM: 1/20) to yield N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-3-d)acetamide as a light yellow solid. LC/MS: mass calculated for $C_{25}H_{19}DClF_2N_9O_2$: 552.15, measured (ES, m/z): 553.05 $[M+H]^+$.

Step 4: (3S,8aR)-3-[5-(6-Amino-5-deuterio-2-fluoro-3-pyridyl)-1H-imidazol-2-yl]-7-[3-chloro-2-fluoro-6-(tetrazol-1-yl)phenyl]-2,3,8,8a-tetrahydro-1H-indolizin-5-one A mixture of N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-3-d)acetamide (200 mg, 0.36 mmol, 1.0 equiv.) in THE (4 mL) and HCl (4 mL, 4 M) was stirred at 50° C. for 1 h. The reaction mixture was concentrated and the residue was purified by silica gel column chromatography (40 g, MeOH/DCM: 1/15) to yield (3S)-3-(5-(6-amino-2-fluoropyridin-3-yl-5-d)-1H-imidazol-2-yl)-7-(3-chloro-2-fluoro-6-(1H-tetrazol-1-yl)phenyl)-2,3,8,8a-tetrahydroindolizin-5(1H)-one as a white solid. The solid was further purified by prep-chiral-HPLC (Column: CHIRALPAK IA, 2*25 cm, 5 um; Mobile Phase A:Hex:DCM=3:1 (0.5% 2 M $NH_3$-MeOH)-HPLC, Mobile Phase B: EtOH—HPLC; Flow rate: 18 mL/min; Gradient: 20 B to 20 B in 21 min; 220/254 nm; RT1:14.048; RT2:16.708; Injection Volume: 1 ml; Number Of Runs: 5) to yield (3S,8aR)-3-(5-(6-amino-2-fluoropyridin-3-yl-5-d)-1H-imidazol-2-yl)-7-(3-chloro-2-fluor-6-(1H-tetrazol-1-yl)phenyl)-2,3,8,8a-tetrahydroindolizin-5(1H)-one as a white solid.

LC/MS: mass calculated for $C_{23}H_{17}ClDF_2N_9O$: 510.14, measured (ES, m/z): 511.10 $[M+H]^+$. $^1H$ NMR (400 MHz, DMSO-$d_6$) δ 11.76 (s, 1H), 9.83 (s, 1H), 7.90-8.10 (m, 2H), 7.71 (dd, J=8.7, 1.5 Hz, 1H), 7.04 (s, 1H), 6.23 (s, 2H), 5.69 (d, J=2.6 Hz, 1H), 4.99 (d, J=8.5 Hz, 1H), 3.69-3.76 (m, 1H), 2.67-2.73 (m, 1H), 2.50-2.53 (m, 1H), 2.05-2.21 (m, 2H), 1.94-2.01 (m, 2H)/$^{19}F$ NMR (376 MHz, DMSO-$d_6$) −70.92, −112.87.

Example 148 (3S,8aR)-3-[5-(6-amino-4-deuterio-2-fluoro-3-pyridyl)-4-deuterio-1H-imidazol-2-yl]-7-[3-chloro-2-fluoro-6-(tetrazol-1-yl)phenyl]-2,3,8,8a-tetrahydro-1H-indolizin-5-one

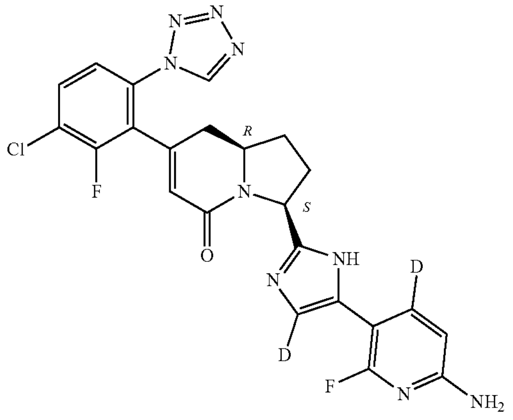

LC/MS: mass calculated for $C_{23}H_{16}ClD_2F_2N_9O$: 511.14, measured (ES, m/z): 512.10 $[M+H]^+$. $^1H$ NMR (300 MHz, DMSO-$d_6$) δ 11.79 (s, 1H), 9.84 (s, 1H), 7.94-8.02 (m 1H), 7.67-7.77 (m, 1H), 6.41 (d, J=2.2 Hz, 1H), 6.26 (s, 2H), 5.69 (d, J=2.6 Hz, 1H), 4.99 (d, J=8.3 Hz, 1H), 3.77-3.66 (m, 1H), 2.61-2.80 (m, 1H), 2.54-2.58 (m, 1H), 1.95-2.23 (m, 4H)/$^{19}F$ NMR (282 MHz, DMSO-$d_6$) δ −70.87, −112.88.

Example 149 (3S,8aR)-3-[5-(6-amino-4,5-dideuterio-2-fluoro-3-pyridyl)-4-deuterio-1H-imidazol-2-yl]-7-[3-chloro-2-fluoro-6-(tetrazol-1-yl)phenyl]-2,3,8,8a-tetrahydro-1H-indolizin-5-one

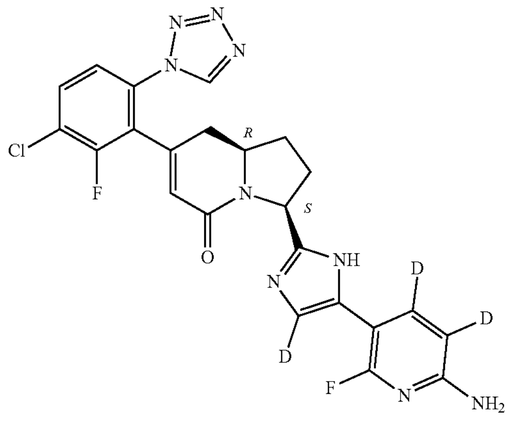

Step 1: (3S,8aR)-3-(5-(6-Amino-2-fluoro-5-iodopyridin-3-yl-4-d)-4-iodo-1H-imidazol-2-yl)-7-(3-chloro-2-fluoro-6-(1H-tetrazol-1-yl)phenyl)-2,3,8,8a-tetrahydroindolizin-5(1H)-one A mixture of (3R,8aS)-3-(5-(6-amino-2-fluoropyridin-3-yl-4-d)-1H-imidazol-2-yl)-7-(3-chloro-2-fluoro-6-(1H-tetrazol-1-yl)phenyl)-2,3,8,8a-tetrahydroindolizin-5(1H)-one (322 mg, 0.63 mmol, 1.0 equiv.) and NIS (255 mg, 1.13 mmol, 1.8 equiv.) in $CH_3COOH$/TFA (V/V=10:1, 5.5 mL) was stirred at room temperature for 2 h. The resulting mixture was diluted with water (20 mL) and extracted with EA (3×20 mL). Then the organic layers were combined, washed with brine, and dried over $Na_2SO_4$ and concentrated under reduced pressure. The residue was purified by flash column chromatography on silica gel with MeOH/DCM (0→10%) to yield (3R,8aS)-3-(5-(6-amino-2-fluoro-5-iodopyridin-3-yl-4-d)-4-iodo-1H-imidazol-2-yl)-7-(3-chloro-2-fluoro-6-(1H-tetrazol-1-yl)phenyl)-2,3,8,8a-tetrahydroindolizin-5(1H)-one as a brown solid. LC/MS: mass calculated for $C_{23}H_{15}DClF_2I_2N_9O$: 761.93, measured (ES, m/z): 762.85 $[M+H]^+$.

Step 2: (3S,8aR)-3-[5-(6-Amino-4,5-dideuterio-2-fluoro-3-pyridyl)-4-deuterio-1H-imidazol-2-yl]-7-[3-chloro-2-fluoro-6-(tetrazol-1-yl)phenyl]-2,3,8,8a-tetrahydro-1H-indolizin-5-one To a mixture of (3R,8aS)-3-(5-(6-amino-2-fluoro-5-iodopyridin-3-yl-4-d)-4-iodo-1H-imidazol-2-yl)-7-(3-chloro-2-fluoro-6-(1H-tetrazol-1-yl)phenyl)-2,3,8,8a-tetrahydroindolizin-5(1H)-one (333 mg, 0.44 mmol, 1.0 equiv.) and zinc powder (828 mg, 12.66 mmol, 29.0 equiv.) was added $CD_3COOD$ (7 mL) followed by D20 (7 mL) under $N_2$ atmosphere. The resulting mixture was stirred at room temperature for 2 h. The solid was filtered off and the filtrate was concentrated under reduced pressure. The residue was purified by reversal phase chromatography on C18 (MeCN/$H_2O$ (0.05% $CF_3COOH$)) to yield (3R,8aS)-3-(5-(6-amino-2-fluoropyridin-3-yl-4,5-d2)-1H-imidazol-2-yl-4-d)-7-(3-chloro-2-fluoro-6-(1H-tetrazol-1-yl)phenyl)-2,3,8,8a-tetrahydroindolizin-5(1H one as a white solid. The racemic product (230 mg) was separated by Chiral-HPLC to yield (3R,8aS)-3-(5-(6-amino-2-fluoropyridin-3-yl-4,5-d2)-1H-imidazol-2-yl-4-d)-7-(3-chloro-2-fluoro-6-(1H-tetrazol-1-yl)phenyl)-2,3,8,8a-tetrahydroindolizin-5(1H)-one as a white solid.

LC/MS: mass calculated for $C_{23}H_{15}ClD_3F_2N_9O$: 512.15, measured (ES, m/z): 513.15 $[M+H]^+$. $^1H$ NMR (300 MHz, DMSO-$d_6$) δ 11.79 (s, 1H), 9.84 (s, 1H), 7.93-8.01 (m, 1H), 7.68-7.76 (m, 1H), 6.27 (s, 2H), 5.69 (d, J=2.5 Hz, 1H), 5.00 (d, J=8.4 Hz, 1H), 3.77-3.66 (m, 1H), 2.62-2.80 (m, 1H), 2.55-2.59 (m, 1H), 1.89-2.23 (m, 4H)/$^{19}F$ NMR (282 MHz, DMSO-$d_6$) δ −70.87, 112.87.

Example 150 (3S,8aR)-3-[5-(6-amino-4-deuterio-2-fluoro-3-pyridyl)-1H-imidazol-2-yl]-7-[3-chloro-2-fluoro-6-(tetrazol-1-yl)phenyl]-2,3,8,8a-tetrahydro-1H-indolizin-5-one

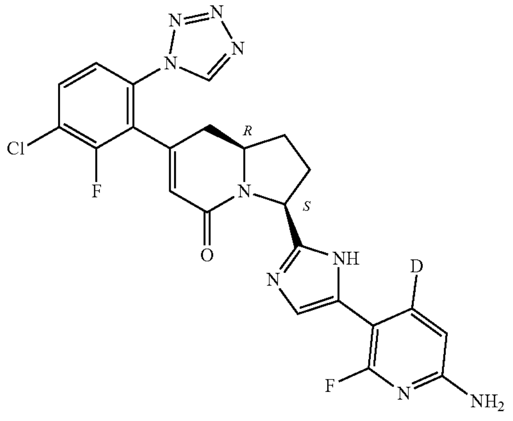

Step 1: 2-(6-Acetamido-2-fluoropyridin-3-yl-4-d)-2-oxoethyl (3S,8aR)-7-(6-amino-3-chloro-2-fluorophenyl)-5-oxo-1,2,3,5,8,8a-hexahydroindolizine-3-carboxylate To a solution of (3R)-7-(6-amino-3-chloro-2-fluorophenyl)-5-oxo-1,2,3,5,8,8a-hexahydroindolizine-3-carboxylic acid (800 mg, 2.46 mmol, 1.0 equiv.) in DMF (10 mL) was added cesium carbonate (482 mg, 1.48 mmol, 0.6 equiv.), followed by N-(5-(2-bromoacetyl)-6-fluoropyridin-2-yl-4-d)acetamide (816 mg, 2.96 mmol, 1.2 equiv.). The resulting mixture was stirred at room temperature overnight, diluted with water, and extracted with EA (3×20 mL). The organic layers were combined, washed with brine, dried over $Na_2SO_4$ and concentrated. The resulting residue was purified by flash column chromatography on silica gel (MeOH/DCM, 0→8%) to yield 2-(6-acetamido-2-fluoropyridin-3-yl-4-d)-2-oxoethyl (3S,8aR)-7-(6-amino-3-chloro-2-fluorophenyl)-5-oxo-1,2,3,5,8,8a-hexahydroindolizine-3-carboxylate as a yellow solid. LC/MS: mass calculated for $C_{24}H_{20}DClF_2N_4O_5$: 519.12, measured (ES, m/z): 520.15 $[M+H]^+$.

Step 2: N-(5-(2-((3S,8aR)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl-4-d)acetamide To a mixture of 2-(6-acetamido-2-fluoropyridin-3-yl-4-d)-2-oxoethyl (3S,8aR)-7-(6-amino-3-chloro-2-fluorophenyl)-5-oxo-1,2,3,5,8,8a-hexahydroindolizine-3-carboxylate (1.4 g, 2.69 mmol, 1.0 equiv.) and ammonium acetate (2.1 g, 26.93 mmol, 10.0 equiv.) in 1,4-dioxane (15 mL) was added acetic acid (5 mL). The resulting mixture was stirred at 100° C. for 1 h. The solvent was evaporated under reduced pressure. The residue was purified by flash column chromatography on silica gel (MeOH/DCM, 010%) to yield N-(5-(2-((3S,8aR)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl-4-d)acetamide as a yellow solid. LC/MS: mass calculated for $C_{24}H_{20}DClF_2N_6O_2$: 499.14, measured (ES, m/z): 500.10 $[M+H]^+$.

Step 3: N-(5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-4-d)acetamide A mixture of N-(5-(2-((3S,8aR)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl-4-d)acetamide (1.1 g, 2.10 mmol, 1.0 equiv.), trimethoxymethane (5 mL), azidotrimethylsilane (5 mL) and acetic acid (10 mL) was stirred at room temperature overnight. The reaction mixture was concentrated under reduced pressure to yield N-(5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-4-d)acetamide as a yellow solid. LC/MS: mass calculated for $C_{25}H_{19}DClF_2N_9O_2$: 552.15, measured (ES, m/z): 553.10 $[M+H]^+$.

Step 4: (3S,8aR)-3-[5-(6-Amino-4-deuterio-2-fluoro-3-pyridyl)-1H-imidazol-2-yl]-7-[3-chloro-2-fluoro-6-(tetrazol-1-yl)phenyl]-2,3,8,8a-tetrahydro-1H-indolizin-5-one To a solution of N-(5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-4-d)acetamide (520 mg, 0.94 mmol, 1.0 equiv.) in THE (2 ml) was added HCl (4 mL). The resulting mixture was stirred at 50° C. for 2 h, then concentrated under reduced pressure and the resulting residue was purified by reversal phase chromatography on C18 column (MeCN/$H_2O$ (0.05% $CF_3COOH$)) to yield (3R,8aS)-3-(5-(6-amino-2-fluoropyridin-3-yl-4-d)-1H-imidazol-2-yl)-7-(3-chloro-2-fluoro-6-(1H-tetrazol-1-yl)phenyl)-2,3,8,8a-tetrahydroindolizin-5 (1H)-one as a white solid. The racemic product (150 mg) was further separated by chiral-HPLC to yield (3R,8aS)-3-(5-(6-amino-2-fluoropyridin-3-yl-4-d)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC/MS: mass calculated for $C_{23}HClDF_2N_9O$: 510.14, measured (ES, m/z): 511.10 $[M+H]^+$. $^1H$ NMR (300 MHz, DMSO-$d_6$) δ 11.78 (s, 1H), 9.84 (s, 1H), 7.94-8.02 (m, 1H), 7.72 (dd, J=8.7, 1.5 Hz, 1H), 7.04 (dd, J=4.2, 1.9 Hz, 1H), 6.41 (d, J=2.2 Hz, 1H), 6.25 (s, 2H), 5.70 (d, J=2.5 Hz, 1H), 4.99 (d, J=8.4 Hz, 1H), 3.66-3.77 (m, 1H), 2.66-2.76 (m, 1H), 2.47-2.54 (m, 1H), 1.95-2.23 (m, 4H)/$^{19}F$ NMR (282 MHz, DMSO-$d_6$) δ−70.81, −112.83.

Example 151 (3S,8aR)-3-[5-(6-amino-4,5-dideuterio-2-fluoro-3-pyridyl)-1H-imidazol-2-yl]-7-[3-chloro-2-fluoro-6-(tetrazol-1-yl)phenyl]-2,3,8,8a-tetrahydro-1H-indolizin-5-one

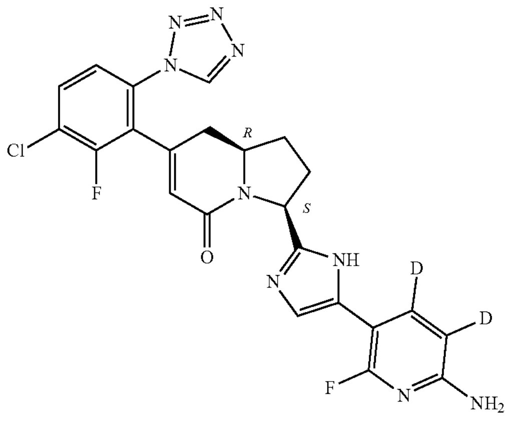

Step 1: 6-Fluoro-3,4,5-triiodopyridine-2-amine

N-Iodosuccinimide (NIS, 9.5 g, 42.02 mmol, 2.0 equiv.) was added to a solution of 6-fluoro-4-iodopyridin-2-amine (5.0 g, 21.01 mmol, 1.0 equiv.) in AcOH (50 mL) and TFA (5 mL). The resulting mixture was maintained stirring at room temperature overnight, quenched with water (30 mL), adjusted to pH 8 with ammonium hydroxide solution, and extracted with EA (200 mL). The organic layer was separated and dried over $Na_2SO_4$, filtered, and concentrated under reduced pressure. The residue was purified by flash column chromatography on silica gel with PE/EA from 0% to 60% to yield 6-fluoro-3,4,5-triiodopyridin-2-amine as a yellow solid. LC/MS: mass calculated for $C_5H_2FI_3N_2$: 489.73, measured (ES, m/z): 490.75 $[M+H]^+$ Step 2: 6-Fluoropyridin-3,4,5-$d_3$-2-amine 6-Fluoro-3,4,5-triiodopyridin-2-amine (1.0 g, 2.04 mmol, 1.0 equiv.) and Zn (668 mg, 10.21 mmol, 5.0 equiv.) were added to a solution of $CD_3COOD$ (8.0 mL) and D20 (8.0 mL). The resulting mixture was maintained stirring at room temperature overnight, diluted with EA (100 mL) and washed with $NaHCO_3$ solution (30 mL). The organic phase was dried by $Na_2SO_4$ and concentrated under reduced pressure. The residue was purified by silica gel column with PE/EA 0-50% to yield 6-fluoropyridin-3,4,5-$d_3$-2-amine as a yellow solid. LC/MS: mass calculated for $C_5H_2D_3FN_2$: 115.06, measured (ES, m/z): 116.10 $[M+H]^+$ Step 3: 6-Fluoro-5-iodopyridin-3,4-$d_2$-2-amine 6-Fluoropyridin-3,4,5-$d_3$-2-amine (460 mg, 4.00 mmol, 1.0 equiv.) was dissolved in DMF (5 mL) and then NIS (899 mg, 4.00 mmol, 1.0 equiv.) was added at 0° C. The resulting mixture was maintained stirring at room temperature for 2 h, extracted with EA (100 mL). The organic layer was dried over $Na_2SO_4$ and concentrated under reduced pressure. The residue-6-fluoro-5-iodopyridin-3,4-$d_2$-2-amine—was used in the next step without further purification. LC/MS: mass calculated for $C_5H_2D2FIN_2$: 239.95, measured (ES, m/z): 240.95 $[M+H]^+$.

Step 4: N-(6-fluoro-5-iodopyridin-2-yl-3,4-d2)acetamide

6-Fluoro-5-iodopyridin-3,4-$d_2$-2-amine (700 mg, 2.92 mmol, 1.0 equiv.) was added to $Ac_2O$ (10 mL) and the mixture was stirred at room temperature overnight, diluted with water, extracted with EA (100 mL) and washed with $NaHCO_3$ (aq.) solution. The organic phase was dried by $Na_2SO_4$ and concentrated under reduced pressure. The residue—of N-(6-fluoro-5-iodopyridin-2-yl-3,4-d2)acetamide—was used in the next step without further purification. LC/MS: mass calculated for $C_7H_4D2FIN_2O$: 281.96, measured (ES, m/z): 282.95 [M+H]+

Step 5: N-(5-(1-ethoxyvinyl)-6-fluoropyridin-2-yl-3,4-d2)acetamide

To a mixture of N-(6-fluoro-5-iodopyridin-2-yl-3,4-d2) acetamide (1.4 g, 5.03 mmol, 1.0 equiv.) and tributyl(ethynyl)stannane (2.7 g, 7.54 mmol, 1.5 equiv.) and $Pd(PPh_3)_4$ (581 mg, 0.50 mmol, 0.1 equiv.) was added 1,4-dioxane (25.0 mL). The mixture was stirred at 100° C. for 17.0 h under an atmosphere of nitrogen. The solvent was removed under vacuum. The residue was purified by silica gel column chromatography with ethyl acetate/petroleum ether (1:1) to yield N-(5-(1-ethoxyvinyl)-6-fluoropyridin-2-yl-3,4-d2)acetamide as a yellow solid. LC/MS: mass calculated for $C_{11}H_{11}D_2FN_2O_2$: 226.25, measured (ES, m/z): 227.10 $[M+H]^+$ Step 6: N-(5-(2-bromoacetyl)-6-fluoropyridin-2-yl-3,4-d2)acetamide NBS (378 mg, 2.12 mmol, 0.8 equiv.) added to a solution of N-(5-(1-ethoxyvinyl)-6-fluoropyridin-2-yl-3,4-d2)acetamide (600 mg, 2.65 mmol, 1.0 equiv.) was dissolved in THF (4 mL) and water (1 mL) at 0° C. and the resulting mixture was stirred at room temperature for 2 h. The resulting mixture was then diluted with water and extracted with EA (100 mL). The organic layer was dried by $Na_2SO_4$ and concentrated under reduced pressure. The residue—N-(5-(2-bromoacetyl)-6-fluoropyridin-2-yl-3,4-d2)acetamide—was used for the next step without further purification. LC/MS: mass calculated for $C_9H_6D_2BrFN_2O_2$: 275.99, measured (ES, m/z): 278.95 $[M+H+2]^+$ Step 7: 2-(6-Acetamido-2-fluoropyridin-3-yl-4,5-d2)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate A mixture of (3S,8aR)-7-(3-chloro-2-fluoro-6-(1H-tetrazol-1-yl)phenyl)-5-oxo-1,2,3,5,8,8a-hexahydroindolizine-3-carboxylic acid (302 mg, 0.80 mmol, 1.0 equiv.) and $K_2CO_3$ (166 mg, 1.20 mmol, 1.5 equiv.) in $CH_3CN$ (5 mL) was stirred at room temperature for 0.5 h. To the resulting mixture was added a solution of N-(5-(2-bromoacetyl)-6-fluoropyridin-2-yl-3,4-d2)acetamide (332 mg, 1.20 mmol, 1.0 equiv.) in $CH_3CN$ (5 mL). The reaction mixture was stirred for 2 h at room temperature and the solvent was removed under reduced pressure. The residue was purified by silica gel column chromatography (0-10% DCM/MeOH) to yield 2-(6-acetamido-2-fluoropyridin-3-yl-4,5-d2)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate as a yellow solid. LC/MS: mass calculated for $C_{25}H_{18}D_2ClF_2N_7O_5$:573.13, measured (ES, m/z): 574.20 $[M+H]^+$ Step 8: N-(5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-3,4-d2)acetamide 2-(6-Acetamido-2-fluoropyridin-3-yl-4,5-d2)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate (300 mg, 0.52 mmol, 1.0 equiv.), ammonium acetate (806 mg, 10.45 mmol, 20.0 equiv.) and acetic acid (0.25 mL) were dissolved in toluene (10.0 mL) and the reaction mixture was stirred at 90° C. for 1.5 h. The solvent was removed under vacuum and the residue was purified by flash column chromatography on silica gel with DCM/MeOH from 0-10% to yield N-(5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-3,4-$d_2$)acetamide as a yellow solid. LC/MS: mass calculated for $C_{25}H_{18}D_2ClF_2N_9O_2$: 553.15, measured (ES, m/z): 554.25 $[M+H]^+$ Step 9: (3S,8aR)-3-(5-(6-amino-2-fluoropyridin-3-yl-4,5-d2)-1H-imidazol-2-yl)-7-(3-chloro-2-fluoro-6-(1H-tetrazol-1-yl)phenyl)-2,3,8,8a-tetrahydroindolizin-5(1H)-one N-(5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl-3,4-d2)acetamide (150 mg, 0.27 mmol, 1.0 equiv.) was dissolved in HCl (4 M, 2.5 mL) and THF (2.5 mL) and the mixture was stirred at 50° C. for 1 h. The solvent was removed under reduced pressure and the residue was purified by reverse phase chromatography on C18 column with $MeCN/H_2O$ (0-60%) to yield 3-(5-(6-amino-2-fluoropyridin-3-yl-4,5-d2)-1H-imidazol-2-yl)-7-(3-chloro-2-fluoro-6-(1H-tetrazol-1-yl) phenyl)-2,3,8,8a-tetrahydroindolizin-5(1H)-one as a yellow solid, which was further purified by chiral-HPLC with (Hex:DCM=3:1)(0.1% DEA):EtOH=80:20 to yield (3S, 8aR)-3-(5-(6-amino-2-fluoropyridin-3-yl-4,5-d2)-1H-imidazol-2-yl)-7-(3-chloro-2-fluoro-6-(1H-tetrazol-1-yl)phenyl)-2,3,8,8a-tetrahydroindolizin-5(1H)-one as an off-white solid.

LC/MS: mass calculated for $C_{23}H_{16}ClD_2F_2N_9O$: 510.14, measured (ES, m/z): 512.10 $[M+H]^+$. $^1H$ NMR (400 MHz, DMSO-$d_6$) δ 9.69 (s, 1H), 7.72-7.91 (m, 1H), 7.56-7.62 (m, 1H), 7.33 (d, J=2.6 Hz, 1H), 5.63 (d, J=2.7 Hz, 1H), 5.08 (d, J=9.4 Hz, 1H), 3.65-3.76 (m, 1H), 2.74-2.91 (m, 1H), 2.50-2.52 (m, 1H), 2.20-2.32 (m, 1H), 2.06-2.18 (m, 1H), 1.90-1.97 (m, 1H), 1.80-1.92 (m, 1H)/$^{19}F$ NMR (376 MHz, DMSO-$d_6$) δ−70.14, −73.83, −112.39.

Example 152 6-[2-[(3S,8a*R)-7-[3-chloro-2-fluoro-6-[4-(trifluoromethyl)triazol-1-yl]phenyl]-5-oxo-2,3,8,8a-tetrahydro-1H-indolizin-3-yl]-1H-imidazol-5-yl]-1H-quinolin-2-one

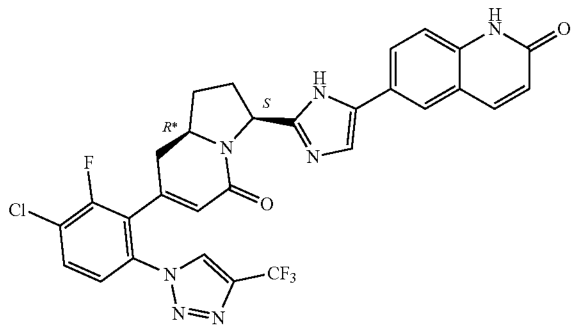

LC/MS: mass calculated for $C_{29}H_{20}ClF_4N_7O_2$: 609.13, measured (ES, m/z): 610.20 $[M+H]^+$. $^1H$ NMR (300 MHz, Methanol-d4) δ 9.06 (s, 1H), 7.96-8.09 (m, 2H), 7.91 (dd, J=8.6, 2.0 Hz, 1H), 7.81 (dd, J=8.7, 7.6 Hz, 1H), 7.56 (dd, J=8.7, 1.6 Hz, 1H), 7.36-7.41 (m, 2H), 6.64 (d, J=9.5 Hz, 1H), 5.73 (d, J=2.7 Hz, 1H), 5.19 (d, J=8.6 Hz, 1H), 3.84-4.00 (m, 1H), 2.95-3.11 (m, 1H), 2.59-2.70 (m, 1H), 2.00-2.45 (m, 4H)/$^{19}F$ NMR (282 MHz, Methanol-d4) δ-62.57, −113.49.

Example 153 (3S,8aR)-3-[4-(6-amino-2-fluoro-3-pyridyl)-1H-imidazol-2-yl]-7-[3-chloro-5-deuterio-2-fluoro-6-(tetrazol-1-yl)phenyl]-2,3,8,8a-tetrahydro-1H-indolizin-5-one

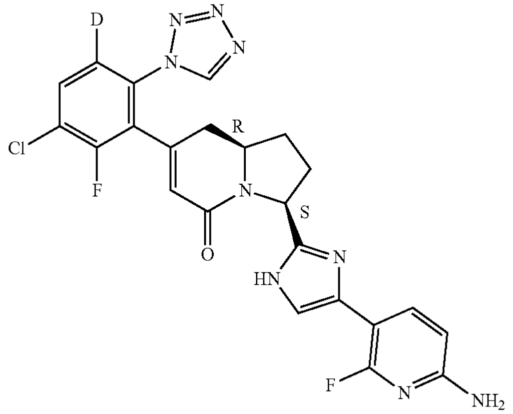

LC/MS: mass calculated for $C_{23}H_{17}ClDF_2N_9O$: 510.14, measured (ES, m/z): 511.10 $[M+H]^+$. $^1H$ NMR (300 MHz, DMSO-$d_6$) δ 11.77 (s, 1H), 9.84 (s, 1H), 7.96-8.07 (m, 2H), 7.04 (s, 1H), 6.41 (dd, J=8.3, 2.2 Hz, 1H), 6.25 (s, 2H), 5.69 (d, J=2.5 Hz, 1H), 4.99 (d, J=8.3 Hz, 1H), 3.65-3.79 (m, 1H), 2.65-2.77 (m, 1H), 2.51-2.56 (m, 1H), 2.07-2.22 (m, 2H), 1.93-1.99 (m, 2H)/$^{19}F$ NMR (282 MHz, Methanol-d4) δ −70.82, −112.89.

Example 154 (3S,8aR)-3-[5-(6-amino-2-fluoro-3-pyridyl)-4-deuterio-1H-imidazol-2-yl]-7-[3-chloro-2-fluoro-6-(tetrazol-1-yl)phenyl]-2,3,8,8a-tetrahydro-1H-indolizin-5-one

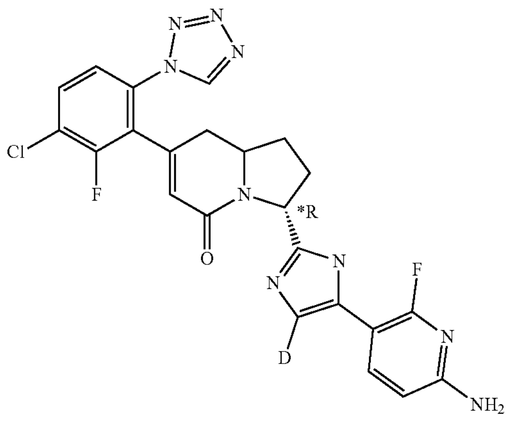 [SMILES: [2H]c1nc([C@H]2CCC3CC(c4c(-n5cnnn5)ccc(Cl)c4F)=CC(=O)N32)[nH]c1-c1ccc(N)nc1F]

LC/MS: mass calculated for $C_{23}H_{17}ClDF_2N_9O$: 510.14, measured (ES, m/z): 511.10 $[M+H]^+$. $^1H$ NMR (300 MHz, DMSO-$d_6$) δ 11.79 (brs., 1H), 9.82 (s, 1H), 7.90-8.13 (m, 2H), 7.69 (dd, J=8.7, 1.5 Hz, 1H), 6.39 (dd, J=8.3, 2.2 Hz, 1H), 6.27 (brs., 2H), 5.67 (d, J=2.7 Hz, 1H), 4.98 (d, J=8.5 Hz, 1H), 3.62-3.75 (m, 1H), 2.60-2.75 (m, 1H), 2.50-2.52 (m, 1H), 2.20-2.24 (m, 2H), 1.83-7.98 (m, 2H)/$^{19}F$ NMR (376 MHz, DMSO-$d_6$) δ −70.84, −112.87.

Example 155 (3*S,8aR)-3-(5-(3-chloro-2-(1-hydroxycyclopropyl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

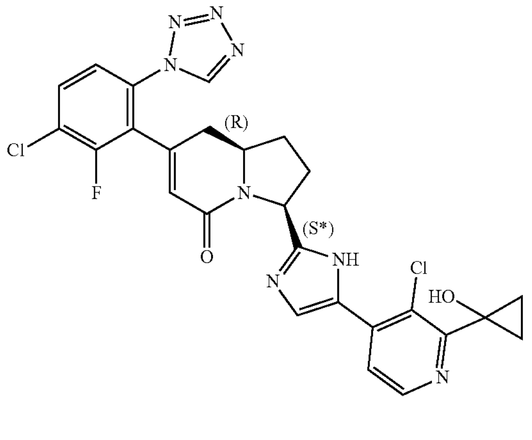

Step 1: 2-(1-((Tert-butyldimethylsilyl)oxy)vinyl)-3-chloropyridine

To a solution of 1-(3-chloropyridin-2-yl)ethan-1-one (2.0 g, 12.86 mmol, 1.0 equiv.) and triethylamine (13.9 g, 38.57 mmol, 3.0 equiv.) in DCM (20 mL) was added TBSOTf (4.4 g, 16.71 mmol, 1.3 equiv.) at 0° C. The mixture was stirred at room temperature for 1 h. The reaction was quenched with water (20 mL). The resulting mixture was extracted with DCM (1×50 mL) and washed with water and brine (30 mL). The organic layers were combined, dried over anhydrous sodium sulfate, and concentrated under reduced pressure. The residue was purified by flash column chromatography on silica gel (0→100% ethyl acetate/petroleum ether) to yield the 2-(1-((tert-butyldimethylsilyl)oxy)vinyl)-3-chloropyridine as a yellow oil. LC/MS: mass calculated for $C_{13}H_{20}ClNOSi$: 269.10, measured (ES, m/z): 270.05 $[M+H]^+$.

Step 2: 2-(1-((Tert-butyldimethylsilyl)oxy)cyclopropyl)-3-chloropyridine

To a solution of diethylzinc (5.6 mL, 8.34 mmol, 1.5 equiv.) in DCM (20 mL) was added chloroiodomethane (2.5 g, 13.90 mmol, 2.5 equiv.) under nitrogen at 0° C. After 0.5 h of stirring, 2-(1-((tert-butyldimethylsilyl)oxy)vinyl)-3-chloropyridine (1.5 g, 5.56 mmol, 1.0 equiv.) in DCM (5 mL) was added at 0° C. The resulting mixture was maintained under nitrogen and stirred at room temperature for 1 h. The reaction was quenched with saturated ammonium chloride solution (20 mL) and extracted with ethyl acetate (3×20 mL). The organic layers were combined, dried over anhydrous sodium sulfate, and concentrated under reduced pressure. The residue was purified by flash column chromatography on silica gel (0→20% ethyl acetate/petroleum ether) to yield the 2-(1-((tert-butyldimethylsilyl)oxy)cyclopropyl)-3-chloropyridine as a yellow oil. LC/MS: mass calculated for $C_{14}H_{22}ClNOSi$: 283.12, measured (ES, m/z): 284.20 $[M+H]^+$.

Step 3: 2-(1-((Tert-butyldimethylsilyl)oxy)cyclopropyl)-3-chloro-4-iodopyridine

To a solution of diisopropylamine (342 mg, 3.38 mmol, 1.2 equiv.) in tetrahydrofuran (10 mL) was added n-butyllithium (1.4 mL, 3.38 mmol, 1.2 equiv.). After 0.5 h of stirring, 2-(1-((tert-butyldimethylsilyl)oxy)cyclopropyl)-3-chloropyridine (800 mg, 2.82 mmol, 1.0 equiv.) was added the above mixture at −78° C. The mixture was maintained stirring at −78° C. for 1 h, to which was added 12 (787 mg, 3.10 mmol, 1.1 equiv.) in tetrahydrofuran (2 mL). The resulting mixture was maintained under nitrogen and stirred at room temperature for 2 h, then quenched with saturated ammonium chloride solution (20 mL) and the aqueous layer was extracted with ethyl acetate (3×20 mL). The organic layers were combined, dried over anhydrous sodium sulfate, filtered and concentrated under reduced pressure. The residue was purified by flash column chromatography on silica gel (0→20% ethyl acetate/petroleum ether) to yield the 2-(1-((tert-butyldimethylsilyl)oxy)cyclopropyl)-3-chloropyridine as a yellow oil. LC/MS: mass calculated for $C_{14}H_{21}ClINOSi$: 409.01, measured (ES, m/z): 410.15 $[M+H]^+$.

Step 4: 2-(1-((Tert-butyldimethylsilyl)oxy)cyclopropyl)-3-chloro-4-(1-ethoxyvinyl)pyridine To a solution of 2-(1-((tert-butyldimethylsilyl)oxy)cyclopropyl)-3-chloro-4-iodopyridine (780 mg, 1.90 mmol, 1.0 equiv.) in 1,4-dioxane (10 mL) was added tributyl(1-ethoxyvinyl)stannane (1.4. g, 3.81 mmol, 2.0 equiv.), $Pd(PPh_3)_4$ (220 mg, 0.19 mmol, 0.1 equiv.). The resulting mixture was maintained under nitrogen and stirred at 100° C. for 4 h. After cooling to room temperature, the resulting mixture was extracted with ethyl acetate (3×20 mL). The organic layers were combined, dried over anhydrous sodium sulfate, filtered and concentrated. The residue was purified by silica gel chromatography (0→30% ethyl acetate/petroleum ether) to yield the 2-(1-((tert-butyldimethylsilyl)oxy)cyclopropyl)-3-chloro-4-(1-ethoxyvinyl)pyridine as a yellow oil. LC/MS: mass calculated for $C_{18}H_{28}ClNO_2Si$: 353.16, measured (ES, m/z): 354.30 $[M+H]^+$.

Step 5: 2-Bromo-1-(2-(1-((tert-butyldimethylsilyl)oxy)cyclopropyl)-3-chloropyridin-4-yl)ethan-1-one To a solution of 2-(1-((tert-butyldimethylsilyl)oxy)cyclopropyl)-3-chloro-4-(1-ethoxyvinyl)pyridine (600 mg, 1.70 mmol, 1.0 equiv.) in THE (8 mL) was added $H_2O$ (2 mL) was added NBS (241 mg, 1.36 mmol, 0.8 equiv.) at 0° C. The mixture was stirred at room temperature for 1 h and extracted with ethyl acetate (2×20 mL). The organic layers were combined, dried over anhydrous sodium sulfate, filtered and concentrated to yield the 2-bromo-1-(2-(1-((tert-butyldimethylsilyl)oxy)cyclopropyl)-3-chloropyridin-4-yl)ethan-1-one as a yellow oil. LC/MS: mass calculated for $C_{16}H_{23}BrClNO_2Si$: 403.04, measured (ES, m/z): 404.05, 406.05 $[M+H, M+H+2]^+$.

Step 6: 2-(2-(1-((Tert-butyldimethylsilyl)oxy)cyclopropyl)-3-chloropyridin-4-yl)-2-oxoethyl(8aR)-7-(3-chloro-2-fluoro-6-(1H-tetrazol-1-yl)phenyl)-5-oxo-1,2,3,5,8,8a-hexahydroindolizine-3-carboxylate To a solution of 2-(1-((tert-butyldimethylsilyl)oxy)cyclopropyl)-3-chloro-4-iodopyridine (780 mg, 1.90 mmol, 1.0 equiv.) in 1,4-dioxane (10 mL) was added tributyl(1-ethoxyvinyl)stannane (1.4. g, 3.81 mmol, 2.0 equiv.) followed by $Pd(PPh_3)_4$ (220 mg, 0.19 mmol, 0.1 equiv.). The resulting mixture was maintained under nitrogen and stirred at 100° C. for 4 h. After cooling to room temperature, the resulting mixture was diluted with water and extracted with ethyl acetate (3×20 mL). The organic layers were combined, dried over anhydrous sodium sulfate, filtered and concentrated. The residue was purified by flash column chromatography on silica gel (0→30% ethyl acetate/petroleum ether) to yield the 2-(1-((tert-butyldimethylsilyl)oxy)cyclopropyl)-3-chloro-4-(1-ethoxyvinyl)pyridine as a yellow oil. LC/MS: mass calculated for $C_{32}H_{35}Cl_2FN_6O_5Si$: 700.18, measured (ES, m/z): 701.15 $[M+H]^+$.

Step 7: (8aR)-3-(5-(2-(1-((Tert-butyldimethylsilyl)oxy)cyclopropyl)-3-chloropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of 2-(2-(1-((tert butyldimethylsilyl)oxy)cyclopropyl)-3-chloropyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate (340 mg, 0.49 mmol, 1.0 equiv.) in toluene (10 mL) and acetic acid (1 mL) was added ammonium acetate (748 mg, 9.69 mmol, 20.0 equiv.). The mixture was stirred at 100° C. for 1 h and the solvent was removed under vacuum. The residue was purified by flash column chromatography on silica gel with MeOH/DCM (0→10%) to yield (8aR)-3-(5-(2-(1-((tert-butyldimethylsilyl)oxy)cyclopropyl)-3-chloropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow oil. LC/MS: mass calculated for $C_{32}H_{35}C_{12}FN_8O_2Si$: 680.20, measured (ES, m/z): 681.15 $[M+H]^+$.

Step 8: (3*S,8aR)-3-(5-(3-Chloro-2-(1-hydroxycyclopropyl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of (8aR)-3-(5-(2-(1-((tert-butyldimethylsilyl)oxy)cyclopropyl)-3-chloropyridin-4-yl)-1H-imidazol-2-yl)-7-(3-chloro-2-fluoro-6-(1H-tetrazol-1-yl)phenyl)-2,3,8,8a-tetrahydroindolizin-5(1H one (290 mg, 0.43 mmol, 1.0 equiv.) in THE (4 mL) was added triethylamine trihydrofluoride (1 mL). The mixture was stirred at 70° C. for 1 h and then concentrated. The residue was purified by reverse phase chromatography on C18 column with $CH_3CN$/0.05% TFA water (5-(50%) to yield a residue, which was further purified by chiral-HPLC with MtBE (0.1% DEA):EtOH=70:30 to yield (3*S,8aR)-3-(5-(3-chloro-2-(1-hydroxycyclopropyl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as an off-white solid.

LC/MS: mass calculated for $C_{26}H_{21}Cl_2FN_8O_2$: 566.11, measured (ES, m/z): 567.10 $[M+H]^+$. $^1H$ NMR (400 MHz, DMSO-$d_6$) δ 9.83 (s, 1H), 8.40 (d, J=5.1 Hz, 1H), 7.90-8.01 (m, 3H), 7.71 (dd, J=8.7, 1.5 Hz, 1H), 5.70 (d, J=2.7 Hz, 1H), 5.06 (d, J=8.7 Hz, 1H), 3.69-3.85 (m, 1H), 2.65-2.70 (m, 2H), 2.18-2.29 (m, 1H), 2.07-2.16 (m, 1H), 1.90-2.04 (m, 2H), 0.96-1.09 (m, 4H). $^{19}F$ NMR (376 MHz, DMSO-$d_6$) δ−73.66, −112.86.

Example 156 (3*R,8aR)-3-(5-(2-(((S)-1,4-dioxan-2-yl)methoxy)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

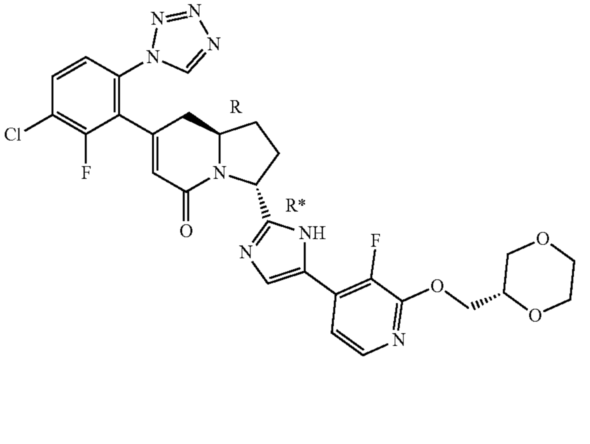

LC/MS: mass calculated for $C_{28}H_{25}ClF_2N_6O_4$: 610.17, measured (ES, m/z): 611.15 $[M+H]^+$. $^1H$-NMR: (400 MHz, Methanol-d4) δ 9.58 (s, 1H), 8.00 (d, J=5.3 Hz, 1H), 7.79-7.89 (m, 2H), 7.57 (dd, J=8.7, 1.6 Hz, 1H), 7.38 (t, J=5.0 Hz, 1H), 5.75 (d, J=2.8 Hz, 1H), 5.19-5.24 (m, 1H), 4.35-4.47 (m, 2H), 3.49-4.05 (m, 8H), 2.87-3.02 (m, 1H), 2.63-2.78 (m, 1H), 2.35-2.59 (m, 1H), 2.19-2.32 (m, 2H), 1.90-2.03 (m, 1H). $^{19}F$ NMR (376 MHz, Methanol-d4) δ −77.09, −113.93, −143.30

Example 157 (3*S,8aR)-3-(5-(2-(((S)-1,4-dioxan-2-yl)methoxy)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

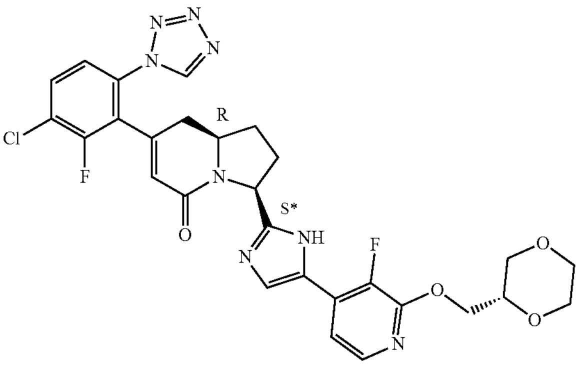

LC/MS: mass calculated for $C_{28}H_{25}ClF_2N_8O_4$: 610.17, measured (ES, m/z): 611.15 $[M+H]^+$. $^1H$-NMR: (400 MHz, Methanol-d4) δ 9.58 (s, 1H), 8.00 (d, J=5.3 Hz, 1H), 7.79-7.89 (m, 2H), 7.57 (dd, J=8.7, 1.6 Hz, 1H), 7.38 (t, J=5.0 Hz, 1H), 5.75 (d, J=2.8 Hz, 1H), 5.28 (dd, J=9.9, 1.7 Hz, 1H), 4.35-4.47 (m, 2H), 3.49-4.05 (m, 8H), 2.87-3.02 (m, 1H), 2.63-2.78 (m, 1H), 2.35-2.59 (m, 1H), 2.19-2.32 (m, 2H), 1.90-2.03 (m, 1H). $^{19}F$ NMR (376 MHz, Methanol-d4) δ −77.19, −113.52, −143.29.

Example 158 (3*S,8a*R)-7-(3-chloro-2-fluoro-6-(1H-tetrazol-1-yl)phenyl)-3-(5-(3-fluoro-2-(3-hydroxy-3-methylbutyl)pyridin-4-yl)-1H-imidazol-2-yl)-2,3,8,8a-tetrahydroindolizin-5(1H)-one

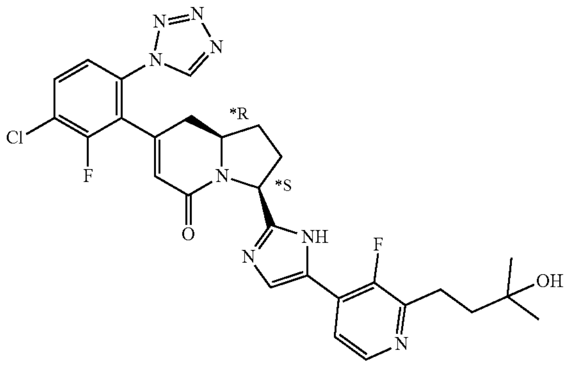 [SMILES: CC(C)(O)CCc1nccc(-c2cnc([C@@H]3CC[C@@H]4CC(c5c(-n6cnnn6)ccc(Cl)c5F)=CC(=O)N43)[nH]2)c1F]

Step 1: 2-(2-(3-((Tert-butyldimethylsilyl)oxy)-3-methylbutyl)-3-fluoropyridin-4-yl)-2-oxoethyl (3S, 8aR)-7-(3-chloro-2-fluoro-6-(1H-tetrazol-1-yl)phenyl)-5-oxo-1,2,3,5,8,8a-hexahydroindolizine-3-carboxylate To a mixture of 7-(3-chloro-2-fluoro-6-(1H-tetrazol-1-yl)phenyl)-5-oxo-1,2,3,5,8,8a-hexahydroindolizine-3-carboxylic acid (170 mg, 0.45 mmol, 1.0 equiv.) and potassium carbonate (81 mg, 0.59 mmol, 1.3 equiv.) in acetonitrile (5.0 mL) was added 2-bromo-1-(2-(3-((tert-butyldimethylsilyl)oxy)-3-methylbutyl)-3-fluoropyridin-4-yl)ethan-1-one (282 mg, 0.68 mmol, 1.5 equiv.). The reaction mixture was stirred at room temperature for 2 h, quenched with water and extracted with EA twice. The combined organic layers were washed with brine, dried over $Na_2SO_4$ and concentrated under vacuum. The residue was purified by flash column chromatography on silica gel (0→10% methanol/dichloromethane) to yield 2-(2-(3-((tert-butyldimethylsilyl)oxy)-3-methylbutyl)-3-fluoropyridin-4-yl)-2-oxoethyl 7-(3-chloro-2-fluoro-6-(1H-tetrazol-1-yl)phenyl)-5-oxo-1,2,3,5,8,8a-hexahydroindolizine-3-carboxylate as a yellow solid. LC/MS: mass calculated for $C_{34}H_{41}ClF_2N_6O_5Si$: 714.26, measured (ES, m/z): 715.15 $[M+H]^+$.

Step 2: (3S)-3-(5-(2-(3-((Tert-butyldimethylsilyl)oxy)-3-methylbutyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a mixture of 2-(2-(3-((tert-butyldimethylsilyl)oxy)-3-methylbutyl)-3-fluoropyridin-4-yl)-2-oxoethyl 7-(3-chloro-2-fluoro-6-(1H-tetrazol-1-yl)phenyl)-5-oxo-1,2,3,5,8,8a-hexahydroindolizine-3-carboxylate (210 mg, 0.29 mmol, 1.0 equiv.) in toluene (3 mL) and acetic acid (0.3 mL) was added ammonium acetate (226 mg, 2.94 mmol, 10.0 equiv.). The reaction mixture was stirred at 100° C. for 2.0 h, quenched with water and extracted with EA twice. The combined organic layers were washed with brine, dried over $Na_2SO_4$ and concentrated under vacuum. The residue was purified by flash column chromatography on silica gel (0→10% MeOH/DCM) to yield 3-(5-(2-(3-((tert-butyldimethylsilyl)oxy)-3-methylbutyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow solid. LC/MS: mass calculated for $C_{34}H_{41}ClF_2N_8O_2Si$: 694.28, measured (ES, m/z): 695.40 $[M+H]^+$.

Step 3: (3*S,8a*R)-7-(3-Chloro-2-fluoro-6-(1H-tetrazol-1-yl)phenyl)-3-(5-(3-fluoro-2-(3-hydroxy-3-methylbutyl)pyridin-4-yl)-1H-imidazol-2-yl)-2,3,8,8a-tetrahydroindolizin-5(1H)-one A mixture of 3-(5-(2-(3-((tert-butyldimethylsilyl)oxy)-3-methylbutyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (180 mg, 0.26 mmol, 1.0 equiv.) in THE (1.0 mL) and hydrochloric acid (1.0 mL, 4 M) was stirred at room temperature for 2 h. The reaction mixture was concentrated and the resulting residue was purified by reverse phase chromatography on C18 column (120 g, $ACN/H_2O$ (0.05% $CF_3COOH$): 0→35%) and further purified by prep-chiral-HPLC to yield (3S,8aR)-7-(3-chloro-2-fluoro-6-(1H-tetrazol-1-yl)phenyl)-3-(5-(3-fluoro-2-(3-hydroxy-3-methylbutyl)pyridin-4-yl)-1H-imidazol-2-yl)-2,3,8,8a-tetrahydroindolizin-5(1H)-one as a white solid.

LC/MS: mass calculated for $C_{28}H_{27}ClF_2N_8O_2$: 580.19, measured (ES, m/z): 581.25 $[M+H]^+$. $^1$H-NMR: (300 MHz, DMSO-$d_6$) δ 9.78 (s, 1H), 8.34 (d, J=5.3 Hz, 1H), 7.81-7.97 (m, 2H), 7.55-7.75 (m, 2H), 5.67 (d, J=2.5 Hz, 1H), 5.06 (d, J=8.8 Hz, 1H), 3.86-3.90 (m, 1H), 2.85-2.89 (m, 2H), 2.73 (t, J=15.0 Hz, 1H), 2.55-2.62 (m, 1H), 2.06-2.32 (m, 2H), 1.83-2.02 (m, 2H), 1.67-1.79 (m, 2H), 1.15 (s, 6H). $^{19}$F NMR (282 MHz, DMSO-$d_6$) δ−73.92, −113.11, −128.94.

Example 159 (3*S,8a*S)-7-(3-chloro-2-fluoro-6-(1H-tetrazol-1-yl)phenyl)-3-(5-(3-fluoro-2-(3-hydroxy-3-methylbutyl)pyridin-4-yl)-1H-imidazol-2-yl)-2,3,8,8a-tetrahydroindolizin-5(1H)-one

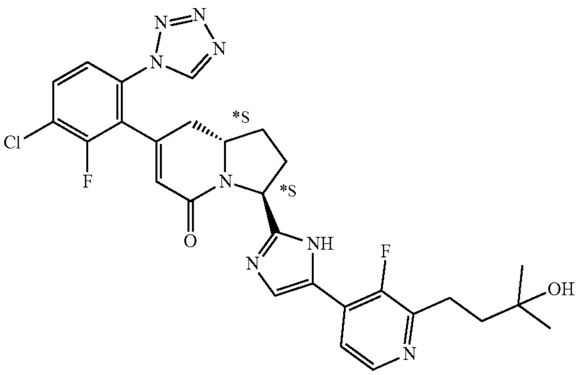 [SMILES: CC(C)(O)CCc1nccc(-c2cnc([C@@H]3CC[C@H]4CC(c5c(-n6cnnn6)ccc(Cl)c5F)=CC(=O)N43)[nH]2)c1F]

LC/MS: mass calculated for $C_{28}H_{27}ClF_2N_8O_2$: 580.19, measured (ES, m/z): 581.25 $[M+H]^+$. $^1$H-NMR: (300 MHz, DMSO-$d_6$) δ 9.76 (s, 1H), 8.34 (d, J=5.4 Hz, 1H), 7.76-7.95 (m, 3H), 7.57-7.70 (m, 1H), 5.67 (d, J=2.5 Hz, 1H), 5.04 (t, J=7.8 Hz, 1H), 4.05-4.23 (m, 1H), 2.84-2.96 (m, 2H), 2.56-2.65 (m, 1H), 2.32-2.48 (m, 2H), 2.20-2.30 (m, 1H), 1.86-2.06 (m, 1H), 1.64-1.79 (m, 3H), 1.15 (s, 6H). $^{19}$F NMR (282 MHz, DMSO-$d_6$) δ−73.86, 113.06, −129.05.

Example 160 (3*S,8aR)-7-(3-chloro-2-fluoro-6-(1H-tetrazol-1-yl)phenyl)-3-(5-(2-(1,1-difluoro-2-hydroxyethyl)-3-fluoropyridin-4-yl)-1H-imidazol-2-yl)-2,3,8,8a-tetrahydroindolizin-5(1H)-one

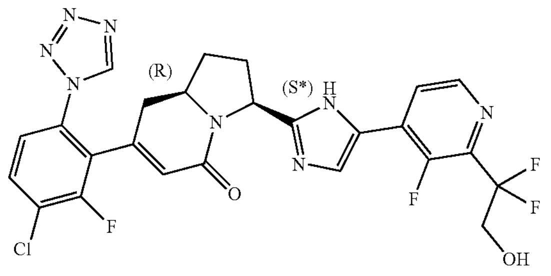

Step 1: Ethyl 2,2-difluoro-2-(3-fluoropyridin-2-yl)acetate

To a solution of 2-bromo-3-fluoropyridine (5.0 g, 28.40 mmol, 1.0 equiv.) in DMSO (70 mL) were added ethyl 2-bromo-2,2-difluoroacetate (8.6 g, 42.60 mmol, 1.5 equiv.) and Cu (3.6 g, 56.80 mmol, 2.0 equiv.). The resulting mixture was stirred at 50° C. for 8 h, then diluted with EA and $KH_2PO_4$ solution, and stirred for 0.5 h at 25° C. The resulting mixture was filtered and washed with EA (200 mL). The organic layers were combined, dried over anhydrous sodium sulfate, filtered and concentrated under reduced pressure. The residue was purified by silica gel chromatography (0→20% ethyl acetate/petroleum ether) to yield ethyl 2,2-difluoro-2-(3-fluoropyridin-2-yl)acetate as a yellow oil. LC/MS: mass calculated for $C_9H_8F_3NO_2$: 219.05, measured (ES, m/z): 220.20 $[M+H]^+$.

Step 2: 2,2-Difluoro-2-(3-fluoropyridin-2-yl)ethan-1-ol

To a solution of ethyl 2,2-difluoro-2-(3-fluoropyridin-2-yl)acetate (4.3 g, 19.60 mmol, 1.0 equiv.) in EtOH (80 mL) was added $NaBH_4$ (0.70 g, 19.60 mmol, 1.0 equiv.). The resulting mixture was stirred at 25° C. for 1 h. The solvent was removed under vacuum and the residue was partitioned between water and EA. The organic layer was separated, dried over anhydrous sodium sulfate, filtered and concentrated under reduced pressure to yield 2,2-difluoro-2-(3-fluoropyridin-2-yl)ethan-1-ol. LC/MS: mass calculated for $C_7H_6F_3NO$: 177.04, measured (ES, m/z): 178.15 $[M+H]^+$.

Step 3: 2-(2-((Tert-butyldimethylsilyl)oxy)-1,1-difluoroethyl)-3-fluoropyridine

To a solution of 2,2-difluoro-2-(3-fluoropyridin-2-yl)ethan-1-ol (1.6 g, 9.00 mmol, 1.0 equiv.) in DCM (30 mL) were added TBSOTf (3.1 g, 11.70 mmol, 1.3 equiv.) and 2,6-lutidine (2.9 g, 27.10 mmol, 3.0 equiv.). The resulting mixture was stirred at 25° C. for 1 h. The mixture was partitioned between DCM (100 mL) and water. The organic layers were combined, dried over anhydrous sodium sulfate, filtered and concentrated. The residue was purified by flash column chromatography on silica gel (0→10% ethyl acetate/petroleum ether) to yield 2-(2-((tert-butyldimethylsilyl)oxy)-1,1-difluoroethyl)-3-fluoropyridine as a yellow oil. LC/MS: mass calculated for $C_{13}H_{20}F_3NOSi$: 291.13, measured (ES, m/z): 292.05 $[M+H]^+$.

Step 4: 2-(2-((Tert-butyldimethylsilyl)oxy)-1,1-difluoroethyl)-3-fluoro-4-iodopyridine To a solution of 2-(2-((tert-butyldimethylsilyl)oxy)-1,1-difluoroethyl)-3-fluoropyridine (2.3 g, 7.80 mmol, 1.0 equiv.) in THE (30 mL) was added LDA (0.90 g, 8.60 mmol, 1.1 equiv.). The resulting mixture was stirred at −70° C. for 0.5 h. To the mixture was then added 12 (2.0 g, 7.80 mmol, 1.0 equiv.). The resulting mixture was stirred at 25° C. for 1 h, quenched with $NH_4Cl$ and extracted with EA. The organic layers were combined, dried over anhydrous sodium sulfate, filtered and concentrated. The residue was purified by flash column chromatography on silica gel (0→10% ethyl acetate/petroleum ether) to yield 2-(2-((tert-butyldimethylsilyl)oxy)-1,1-difluoroethyl)-3-fluoro-4-iodopyridine. LC/MS: mass calculated for $C_{13}H_{19}F_3INOSi$: 417.02, measured (ES, m/z): 418.10 $[M+H]^+$.

Step 5: 2-(2-((Tert-butyldimethylsilyl)oxy)-1,1-difluoroethyl)-4-(1-ethoxyvinyl)-3-fluoropyridine To a solution of 2-(2-((tert-butyldimethylsilyl)oxy)-1,1-difluoroethyl)-3-fluoro-4-iodopyridine (1.5 g, 3.60 mmol, 1.0 equiv.) in 1,4-dioxane (40 mL) were added trimethyl((tributylstannyl)ethynyl)silane (2.0 g, 5.40 mmol, 1.5 equiv.) and $Pd(PPh_3)_4$ (0.4 g, 0.36 mmol, 0.1 equiv.). The resulting mixture was stirred at 90° C. for 16 h. The mixture was extracted with EA (150 mL). The organic layers were combined, dried over anhydrous sodium sulfate, filtered and concentrated. The residue was purified by flash column chromatography on $Al_2O_3$ column (0→10% ethyl acetate/petroleum ether) to yield 2-(2-((tert-butyldimethylsilyl)oxy)-1,1-difluoroethyl)-4-(1-ethoxyvinyl)-3-fluoropyridine as a yellow oil. LC/MS: mass calculated for $C_{17}H_{26}F_3NO_2Si$: 361.17, measured (ES, m/z): 362.30 $[M+H]^+$.

Step 6: 2-Bromo-1-(2-(2-((tert-butyldimethylsilyl)oxy)-1,1-difluoroethyl)-3-fluoropyridin-4-yl)ethan-1-one To a solution of 2-(2-((tert-butyldimethylsilyl)oxy)-1,1-difluoroethyl)-4-(1-ethoxyvinyl)-3-fluoropyridin (1.3 g, 3.50 mmol, 1.0 equiv.) in THE (20 mL) and $H_2O$ (5 mL) was added NBS (0.50 g, 3.20 mmol, 0.9 equiv.). The resulting mixture was stirred at 25° C. for 1 h, diluted with water and extracted with EA (100 mL). The organic layers were combined, dried over anhydrous sodium sulfate, filtered and concentrated to yield 2-bromo-1-(2-(2-((tert-butyldimethylsilyl)oxy)-1,1-difluoroethyl)-3-fluoropyridin-4-yl)ethan-1-one. LC/MS: mass calculated for $C_{15}H_{21}BrF_3NO_2Si$: 411.05, measured (ES, m/z): 412.20, 414.20 $[M+H, M+H+2]^+$.

Step 7: 2-(2-(2-((Tert-butyldimethylsilyl)oxy)-1,1-difluoroethyl)-3-fluoropyridin-4-yl)-2-oxoethyl (8aR)-7-(6-amino-3-chloro-2-fluorophenyl)-5-oxo-1,2,3,5,8,8a-hexahydroindolizine-3-carboxylate To a solution of (8aR)-7-(6-amino-3-chloro-2-fluorophenyl)-5-oxo-1,2,3,5,8,8a-hexahydroindolizine-3-carboxylic acid (299 mg, 0.90 mmol, 1.0 equiv.) in ACN (3 mL) was added $K_2CO_3$ (191 mg, 1.40 mmol, 1.5 equiv.). The resulting mixture was stirred at 25° C. for 0.5 h. To the mixture was then added 2-bromo-1-(2-(2-((tert-butyldimethylsilyl)oxy)-1,1-difluoroethyl)-3-fluoropyridin-4-yl)ethan-1-one (380 mg, 0.90 mmol, 1.0 equiv.). The resulting mixture was stirred at 25° C. for 16 h and extracted with EA (50 mL). The organic layers were combined, dried over anhydrous sodium sulfate, filtered and concentrated. The residue was purified by silica gel chromatography (5→70% ethyl acetate/petroleum ether) to yield 2-(2-(2-((tert-butyldimethylsilyl)oxy)-1,1-difluoroethyl)-3-fluoropyridin-4-yl)-2-oxoethyl (8aR)-7-(6-amino-3-chloro-2-fluorophenyl)-5-oxo-1,2,3,5,8,8a-hexahydroindolizine-3-carboxylate as a yellow oil. LC/MS: mass calculated for $C_{30}H_{34}ClF_4N_3O_5Si$: 655.19, measured (ES, m/z): 656.15 $[M+H]^+$.

Step 8: (8aR)-7-(6-Amino-3-chloro-2-fluorophenyl)-3-(5-(2-(2-((tert-butyldimethylsilyl)oxy)-1,1-difluoroethyl)-3-fluoropyridin-4-yl)-1H-imidazol-2-yl)-2,3,8,8a-tetrahydroindolizin-5(1H)-one To a solution of 2-(2-(2-((tert-butyldimethylsilyl)oxy)-1,1-difluoroethyl)-3-fluoropyridin-4-yl)-2-oxoethyl (8aR)-7-(6-amino-3-chloro-2-fluorophenyl)-5-oxo-1,2,3,5,8,8a-hexahydroindolizine-3-carboxylate (200 mg, 0.30 mmol, 1.0 equiv.) in acetic acid (0.3 mL) and toluene (3 mL) was added ammonium acetate (470 mg, 6.00 mmol, 20.0 equiv.). The resulting mixture was heated at 100° C. with stirring for 1 h, then cooled to room temperature and concentrated under vacuum. The residue was purified by flash column chromatography on silica gel (0-010% MeOH/DCM) to yield (8aR)-7-(6-amino-3-chloro-2-fluorophenyl)-3-(5-(2-(2-((tert-butyldimethylsilyl)oxy)-1,1-difluoroethyl)-3-fluoropyridin-4-yl)-1H-imidazol-2-yl)-2,3,8,8a-tetrahydroindolizin-5(1H)-one as a yellow oil. LC/MS: mass calculated for $C_{30}H_{34}ClF_4N_5O_2Si$: 635.21, measured (ES, m/z): 636.40 $[M+H]^+$.

Step 9: (8aR)-3-(5-(2-(2-((Tert-butyldimethylsilyl)oxy)-1,1-difluoroethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of (8aR)-7-(6-amino-3-chloro-2-fluorophenyl)-3-(5-(2-(2-((tert-butyldimethylsilyl)oxy)-1,1-difluoroethyl)-3-fluoropyridin-4-yl)-1H-imidazol-2-yl)-2,3,8,8a-tetrahydroindolizin-5(1H)-one (170 mg, 0.20 mmol, 1.0 equiv.) in AcOH (2 mL) was added $TMSN_3$ (1 mL) followed by addition of trimethoxymethane (1 mL). The resulting mixture was stirred at 25° C. for 16 h, then concentrated under reduced pressure and the residue was purified by reverse phase chromatography on C18 column with ACN/water (0.05% TFA) (5-090%) to yield (8aR)-3-(5-(2-(2-((tert-butyldimethylsilyl)oxy)-1,1-difluoroethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow oil. LC/MS: mass calculated for $C_{31}H_{33}ClF_4N_8O_2Si$: 688.21, measured (ES, m/z): 689.35 $[M+H]^+$.

Step 10: (3*S,8aR)-7-(3-Chloro-2-fluoro-6-(1H-tetrazol-1-yl)phenyl)-3-(5-(2-(1,1-difluoro-2-hydroxyethyl)-3-fluoropyridin-4-yl)-1H-imidazol-2-yl)-2,3,8,8a-tetrahydroindolizin-5(1H)-one To a solution of (8aR)-3-(5-(2-(2-((tert-butyldimethylsilyl)oxy)-1,1-difluoroethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (90 mg, 0.10 mmol, 1.0 equiv.) in THE (2 mL) was added triethylamine trihydrofluoride (0.5 mL). The resulting mixture was stirred at 80° C. for 1 h, then concentrated and the residue was purified by reverse phase chromatography on C18 column with ACN/water (0.05% TFA) (5-+50%) and chiral-HPLC with hexanes (0.1% DEA): EtOH=50:50 to yield (3S*,,8aR)-7-(3-chloro-2-fluoro-6-(1H-tetrazol-1-yl)phenyl)-3-(5-(2-(1,1-difluoro-2-hydroxyethyl)-3-fluoropyridin-4-yl)-1H-imidazol-2-yl)-2,3,8,8a-tetrahydroindolizin-5(1H)-one as a white solid.

LC/MS: mass calculated for $C_{25}H_{19}ClF_4N_8O_2$: 574.13, measured (ES, m/z): 575.10 $[M+H]^+$. $^1$H-NMR: (400 MHz, DMSO-$d_6$) δ12.38 (s, 1H), 9.84 (s, 1H), 8.45-8.46 (m, 1H), 8.10-8.13 (m, 1H), 7.95-7.99 (m, 1H), 7.66-7.73 (m, 2H), 5.69-5.70 (m, 1H), 5.59-5.60 (m, 1H), 5.03-5.06 (m, 1H), 4.03-4.12 (m, 2H), 3.71-3.86 (m, 1H), 2.68-2.82 (m, 1H), 2.53-2.58 (m, 1H), 2.18-2.29 (m, 1H), 2.07-2.12 (m, 1H), 1.88-1.97 (m, 2H). $^{19}$F NMR (376 MHz, DMSO-$d_6$) δ 105.46, −112.85, −126.96.

Example 161 (3S)-7-(3-chloro-2-fluoro-6-(1H-tetrazol-1-yl)phenyl)-3-(5-(3-fluoro-2-((2-methoxyethyl)amino)pyridin-4-yl)-1H-imidazol-2-yl)-2,3,8,8a-tetrahydroindolizin-5(1H)-one

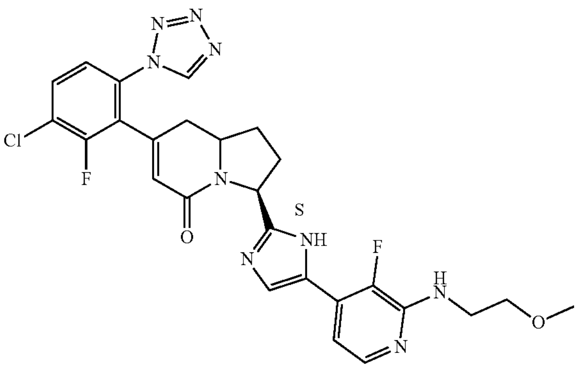

LC/MS: mass calculated for $C_{26}H_{24}ClF_2N_6O_2$: 567.17, measured (ES, m/z): 568.10 $[M+H]^+$. $^1$H-NMR: (300 MHz, DMSO-$d_6$) δ 12.10 (s, 1H), 9.81 (s, 1H), 7.95 (dd, J=8.7, 7.8 Hz, 1H), 7.77 (d, J=5.3 Hz, 1H), 7.69 (dd, J=8.7, 1.5 Hz, 1H), 7.42 (s, 1H), 7.02-7.19 (m, 1H), 6.32-6.57 (m, 1H), 5.67 (d, J=2.5 Hz, 1H), 4.90-5.10 (m, 1H), 3.64-3.76 (m, 1H), 3.44-3.54 (m, 4H), 3.25 (s, 3H), 2.64-2.77 (m, 1H), 2.50-2.55 (m, 1H), 2.06-2.23 (m, 2H), 1.92-2.00 (m, 2H). $^{19}$F NMR (282 MHz, DMSO-$d_6$) δ −112.84, −143.76.

Example 162 (3*R,8aR)-7-(3-chloro-2-fluoro-6-(1H-tetrazol-1-yl)phenyl)-3-(5-(3-fluoro-2-(1-hydroxycyclopropyl)pyridin-4-yl)-1H-imidazol-2-yl)-2,3,8,8a-tetrahydroindolizin-5(1H)-one

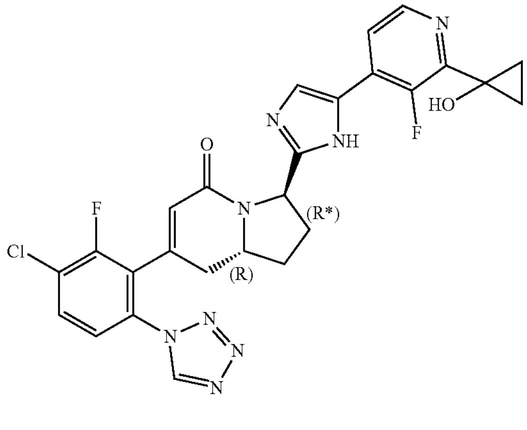

Step 1: 2-(2-(3-((Tert-butyldimethylsilyl)oxy)-3-methylbutyl)-3-fluoropyridin-4-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate To a solution of (8aR)-7-(3-chloro-2-fluoro-6-(1H-tetrazol-1-yl)phenyl)-5-oxo-1,2,3,5,8,8a-hexahydroindolizine-3-carboxylic acid (300 mg, 0.80 mmol, 1.0 equiv.) in $CH_3CN$ (10 mL) was added $K_2CO_3$ (220 mg, 1.59 mmol, 2.0 equiv.)

followed by addition of 2-bromo-1-(2-(1-((tert-butyldimethylsilyl)oxy)cyclopropyl)-3-fluoropyridin-4-yl)ethan-1-one (925 mg, 2.38 mmol, 3.0 equiv.). The mixture was stirred at room temperature for 1 h, diluted with water and extracted with ethyl acetate (3×20 mL). The organic layers were combined, dried over anhydrous sodium sulfate, filtered and concentrated. The residue was purified by flash column chromatography on silica gel (0→20% MeOH/DCM) to yield the 2-(2-(1-((tert butyldimethylsilyl)oxy)cyclopropyl)-3-fluoropyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate as a yellow oil. LC/MS: mass calculated for $C_{32}H_{35}ClF_2N_6O_5Si$: 684.21, measured (ES, m/z): 685.30 $[M+H]^+$.

Step 2: (8aR)-3-(5-(2-(1-((Tert-butyldimethylsilyl)oxy)cyclopropyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of 2-(2-(1-((tert butyldimethylsilyl)oxy)cyclopropyl)-3-fluoropyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate (780 mg, 0.14 mmol, 1.0 equiv.) in toluene (1 mL) and acetic acid (0.1 mL) was added ammonium acetate (1.8 g, 22.77 mmol, 20.0 equiv.). The mixture was stirred at 100° C. for 1 h. The solvent was removed under vacuum and the residue was purified by flash column chromatography on silica gel with MeOH/DCM (0→20%) to yield (8aR)-3-(5-(2-(1-((tert-butyldimethylsilyl)oxy)cyclopropyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow oil. LC/MS: mass calculated for $C_{32}H_{35}ClF_2N_8O_2Si$: 664.23, measured (ES, m/z): 665.40 $[M+H]^+$.

Step 3: (3'R,8aR)-7-(3-Chloro-2-fluoro-6-(1H-tetrazol-1-yl)phenyl)-3-(5-(3-fluoro-2-(1-hydroxycyclopropyl)pyridin-4-yl)-1H-imidazol-2-yl)-2,3,8,8a-tetrahydroindolizin-5(1H)-one To a solution of (8aR)-3-(5-(2-(1-((tert-butyldimethylsilyl)oxy)cyclopropyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (380 mg, 0.57 mmol, 1.0 equiv.) in THE (4 mL) was added triethylamine trihydrofluoride (1 mL). The mixture stirred at 70° C. for 1 h. The residue was purified by reverse phase chromatography on C18 column with $CH_3CN$/0.05% TFA water (5→50%) to yield a residue, which was further purified by chiral-HPLC with MtBE (0.1% DEA):EtOH=50:50 to yield (3'R,8aR)-7-(3-chloro-2-fluoro-6-(1H-tetrazol-1-yl)phenyl)-3-(5-(3-fluoro-2-(1-hydroxycyclopropyl)pyridin-4-yl)-1H-imidazol-2-yl)-2,3,8,8a-tetrahydroindolizin-5(1H)-one as a light yellow solid.

LC/MS: mass calculated for $C_{26}H_{21}ClF_2N_6O_2$: 550.14, measured (ES, m/z): 551.10 $[M+H]^+$. $^1H$-NMR: (400 MHz, DMSO-$d_6$) δ 12.20 (s, 1H), 9.81 (s, 1H), 8.23 (d, J=5.0 Hz, 1H), 7.88-7.98 (m, 1H), 7.80-7.88 (m, 1H), 7.66-7.73 (m, 1H), 7.52-7.59 (m, 1H), 6.05 (s, 1H), 5.68 (d, J=2.6 Hz, 1H), 5.02 (d, J=8.6 Hz, 1H), 3.64-3.82 (m, 1H), 2.61-2.82 (m, 1H), 2.29-2.46 (m, 1H), 2.15-2.26 (m, 1H), 2.03-2.12 (m, 1H), 1.89-2.00 (m, 2H), 1.07-1.17 (m, 2H), 0.92-1.06 (m, 2H). $^{19}F$ NMR (376 MHz, DMSO-$d_6$) δ −112.87, −126.26.

Example 163 (2*S)-2-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)propanenitrile

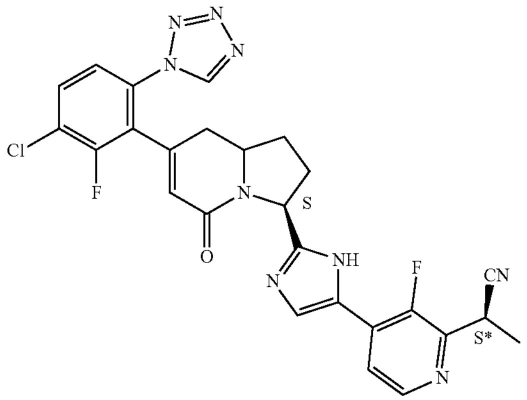

LC/MS: mass calculated for $C_{26}H_{20}ClF_2N_9O$: 547.14, measured (ES, m/z): 548.15 $[M+H]^+$. $^1H$-NMR: (400 MHz, DMSO-$d_6$) δ 12.36 (brs, 1H), 9.84 (s, 1H), 8.41 (d, J=5.0 Hz, 1H), 7.92-8.01 (m, 2H), 7.69-7.80 (m, 1H), 7.63 (d, J=4.0 Hz, 1H), 5.70 (d, J=2.6 Hz, 1H), 5.05 (d, J=8.8 Hz, 1H), 4.71 (q, J=7.1 Hz, 1H), 3.66-3.85 (m, 1H), 2.64-2.82 (m, 1H), 2.56 (d, J=4.2 Hz, 1H), 2.04-2.31 (m, 2H), 1.86-2.05 (m, 2H), 1.61 (d, J=7.1 Hz, 3H). $^{19}F$ NMR (376 MHz, DMSO-$d_6$) δ−112.85, −128.95.

Example 164 (2*R)-2-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)propanenitrile

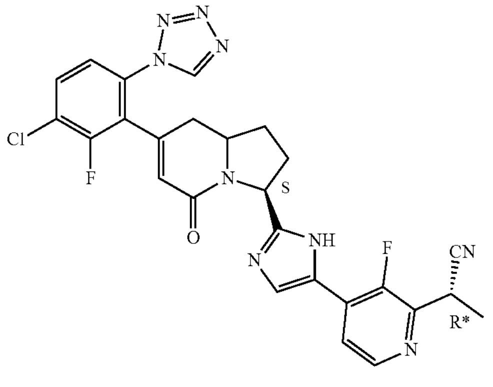

LC/MS: mass calculated for $C_{26}H_{20}ClF_2N_9O$: 547.14, measured (ES, m/z): 548.15 $[M+H]^+$. $^1H$-NMR: (400 MHz, DMSO-$d_6$) δ 12.39 (brs, 1H), 9.84 (s, 1H), 8.42 (d, J=5.0 Hz, 1H), 7.92-8.04 (m, 2H), 7.69-7.82 (m, 1H), 7.64 (d, J=4.0 Hz, 1H), 5.70 (d, J=2.7 Hz, 1H), 5.05 (d, J=8.8 Hz, 1H), 4.71 (q, J=7.1 Hz, 1H), 3.67-3.86 (m, 1H), 2.72 (t, J=15.1 Hz, 1H), 2.56 (d, J=4.2 Hz, 1H), 2.05-2.31 (m, 2H), 1.90-2.04 (m, 2H), 1.61 (d, J=7.2 Hz, 3H). $^{19}F$ NMR (376 MHz, DMSO-$d_6$) δ−112.87, −128.93.

Example 165 2-(4-(24(3*S,8a*R)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)-3-fluoropyridin-2-yl)acetamide

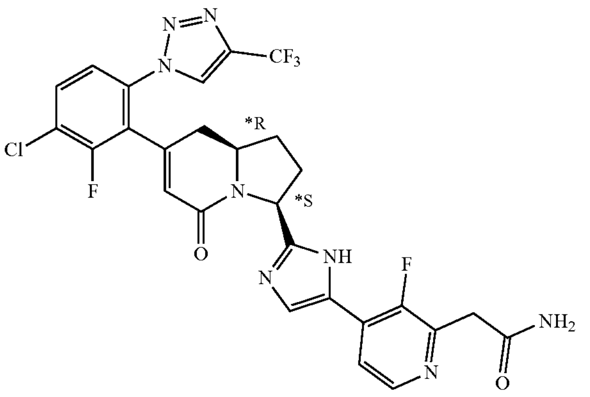 [SMILES: NC(=O)Cc1nccc(-c2cnc([C@@H]3CC[C@@H]4CC(c5c(-n6cc(C(F)(F)F)nn6)ccc(Cl)c5F)=CC(=O)N43)[nH]2)c1F]

LC/MS: mass calculated for $C_{27}H_{20}ClF_5N_8O_2$: 618.13, measured (ES, m/z): 619.15 $[M+H]^+$. $^1$H-NMR: (400 MHz, DMSO-$d_6$) 12.02-12.70 (m, 1H), 9.34 (s, 1H), 8.24 (d, J=5.0 Hz, 1H), 7.98-8.05 (m, 1H), 7.82-7.88 (m, 1H), 7.71-7.76 (m, 1H), 7.42-7.58 (m, 2H), 7.00 (s, 1H), 5.70 (d, J=2.6 Hz, 1H), 5.03 (d, J=8.7 Hz, 1H), 3.68-3.77 (m, 3H), 2.30-2.50 (m, 2H), 2.09-2.19 (m, 2H), 1.91-2.00 (m, 2H). $^{19}$F NMR (376 MHz, DMSO-$d_6$) δ−127.59, −112.90, −59.57.

Example 166 (3S,8aR)-7-[3-chloro-2-fluoro-6-(tetrazol-1-yl)phenyl]-3-[5-[3-fluoro-2-(2-hydroxy-2-methyl-propoxy)-4-pyridyl]-1H-imidazol-2-yl]-2,3,8,8a-tetrahydro-1H-indolizin-5-one

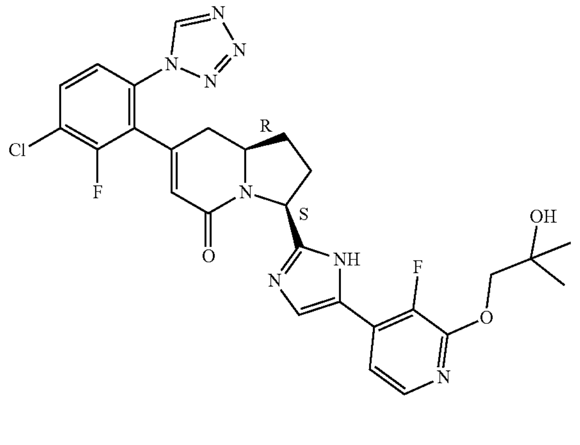

Step 1: 2-(3-Fluoro-2-(2-hydroxy-2-methylpropoxy)pyridin-4-yl)-2-oxoethyl (3S)-7-(6-amino-3-chloro-2-fluorophenyl)-5-oxo-1,2,3,5,8,8a-hexahydroindolizine-3-carboxylate To a solution of 7-(6-amino-3-chloro-2-fluorophenyl)-5-oxo-1,2,3,5,8,8a-hexahydroindolizine-3-carboxylic acid (200 mg, 0.62 mmol, 1.0 equiv.) in DMF (5 mL) were added 2-bromo-1-(3-fluoro-2-(2-hydroxy-2-methylpropoxy)pyridin-4-yl)ethan-1-one (226 mg, 0.74 mmol, 1.0 equiv.) and $Cs_2CO_3$ (120 mg, 0.37 mmol, 0.6 equiv.). The reaction mixture was stirred overnight at room temperature. The reaction was quenched with water and extracted with ethyl acetate. The combined organic layer was washed with brine, dried over $Na_2SO_4$ and concentrated. The residue was purified by silica gel chromatography (0→30% MeOH/DCM) to yield 2-(3-fluoro-2-(2-hydroxy-2-methylpropoxy)pyridin-4-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{26}H_{26}ClF_2N_3O_6$: 549.15, measured (ES, m/z): 550.20 $[M+H]^+$.

Step 2: (3S)-7-(6-Amino-3-chloro-2-fluorophenyl)-3-(4-(3-fluoro-2-(2-hydroxy-2-methylpropoxy)pyridin-4-yl)-1H-imidazol-2-yl)-2,3,8,8a-tetrahydroindolizin-5(1H)-one To a solution of 2-(3-fluoro-2-(2-hydroxy-2-methylpropoxy)pyridin-4-yl)-2-oxoethyl (3S)-7-(6-amino-3-chloro-2-fluorophenyl)-5-oxo-1,2,3,5,8,8a-hexahydroindolizine-3-carboxylate (250 mg, 0.46 mmol, 1.0 equiv.) in toluene (5.0 mL) and $CH_3COOH$ (0.5 mL) was added $NH_4OAc$ (350 mg, 4.55 mmol, 10.0 equiv.). The reaction mixture was stirred for 2 h at 110° C., quenched with water and extracted with ethyl acetate. The combined organic layer was washed with brine, dried over $Na_2SO_4$ and concentrated. The residue was purified by flash column chromatography on silica gel (0→30% MeOH/DCM) to yield 2-(3-fluoro-2-(2-hydroxy-2-methylpropoxy)pyridin-4-yl)-2-oxoethyl (3S)-7-(6-amino-3-chloro-2-fluorophenyl)-5-oxo-1,2,3,5,8,8a-hexahydroindolizine-3-carboxylate as a yellow oil. LC/MS: mass calculated for $C_{26}H_{26}ClF_2N_5O_3$: 529.17, measured (ES, m/z): 530.15 $[M+H]^+$.

Step 3: (3S,8aR)-7-[3-Chloro-2-fluoro-6-(tetrazol-1-yl)phenyl]-3-[5-[3-fluoro-2-(2-hydroxy-2-methylpropoxy)-4-pyridyl]-1H-imidazol-2-yl]-2,3,8,8a-tetrahydro-1H-indolizin-5-one To a solution of (3S)-7-(6-amino-3-chloro-2-fluorophenyl)-3-(4-(3-fluoro-2-(2-hydroxy-2-methylpropoxy)pyridin-4-yl)-1H-imidazol-2-yl)-2,3,8,8a-tetrahydroindolizin-5(1H)-one (100 mg, 0.19 mmol, 1.0 equiv.) in AcOH (3 mL) were added $TMSN_3$ (217 mg, 1.89 mmol, 10.0 equiv.) and trimethoxymethane (200 mg, 1.89 mmol, 10.0 equiv.). The reaction mixture was stirred overnight at room temperature, quenched with water and extracted with ethyl acetate. The combined organic layer was washed with brine, dried over $Na_2SO_4$ and concentrated under reduced pressure. The residue was purified by reverse phase chromatography on C18 column to yield (3S,8aR)-7-(3-chloro-2-fluoro-6-(1H-tetrazol-1-yl)phenyl)-3-(4-(3-fluoro-2-(2-hydroxy-2-methylpropoxy)pyridin-4-yl)-1H-imidazol-2-yl)-2,3,8,8a-tetrahydroindolizin-5(1H)-one as a white solid.

LC/MS: mass calculated for $C_{27}H_{25}ClF_2N_8O_3$: 582.17, measured (ES, m/z): 583.15 $[M+H]^+$. $^1$H-NMR: (400 MHz, DMSO-$d_6$) δ 12.22 (s, 1H), 9.81 (s, 1H), 7.90-8.00 (m, 1H), 7.88 (d, J=5.3 Hz, 1H), 7.69 (dd, J=8.7, 1.5 Hz, 1H), 7.48-7.57 (m, 2H), 5.67 (d, J=2.7 Hz, 1H), 5.02 (d, J=8.7 Hz, 1H), 4.63 (s, 1H), 4.11 (s, 2H), 3.67-3.74 (m, 1H), 2.70-2.80 (m, 1H), 2.49-2.52 (m, 1H), 2.14-2.23 (m, 1H), 2.05-2.13

(m, 1H), 1.89-1.98 (m, 2H), 1.20 (s, 6H). $^{19}$F NMR (376 MHz, DMSO-$d_6$) δ−112.86, −143.22.

Example 167 (3S,8aR)-3-(5-(6-amino-2-(trifluoromethyl)pyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

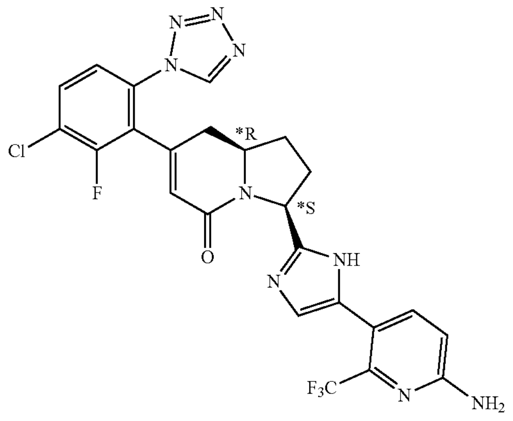 [SMILES: Nc1ccc(-c2cnc([C@@H]3CC[C@@H]4CC(c5c(-n6cnnn6)ccc(Cl)c5F)=CC(=O)N43)[nH]2)c(C(F)(F)F)n1]

Step 1: 5-(1-Ethoxyvinyl)-6-(trifluoromethyl)pyridin-2-amine

To a mixture of 5-bromo-6-(trifluoromethyl)pyridin-2-amine (3.0 g, 12.45 mmol, 1.0 equiv.) in 1,4-dioxane (30 mL) was added tributyl(1-ethoxyvinyl)stannane (5 mL, 14.94 mmol, 1.2 equiv.), followed by addition of $Pd(PPh_3)_4$ (1.4 g, 1.25 mmol, 0.1 equiv.) under $N_2$. The solution was stirred for at 90° C. overnight under nitrogen, then diluted with water and extracted with EA twice. The combined organic layers were washed with brine, dried over $Na_2SO_4$ and concentrated under vacuum. The residue was purified by flash column chromatography on $Al_2O_3$ column (0→40% EA/PE) to yield 5-(1-ethoxyvinyl)-6-(trifluoromethyl)pyridin-2-amine as a yellow oil. LC/MS: mass calculated for $C_{10}H_{11}F_3N_2O$: 232.08, measured (ES, m/z): 233.05 $[M+H]^+$.

Step 2: 1-(6-Amino-2-(trifluoromethyl)pyridin-3-yl)-2-bromoethan-1-one

To a mixture of 5-(1-ethoxyvinyl)-6-(trifluoromethyl) pyridin-2-amine (1.5 g, 6.46 mmol, 1.0 equiv.) in THF (15 mL) and water (5 mL) was added N-bromosuccinimide (0.92 g, 5.17 mmol, 0.8 equiv.). The reaction mixture was stirred at room temperature for 30 min, diluted with $H_2O$ and extracted with EA twice. The combined organic layers were washed with brine, dried over $Na_2SO_4$ and concentrated under vacuum. The residue was purified by flash column chromatography on silica gel (0→50% EA/PE) to yield 1-(6-amino-2-(trifluoromethyl)pyridin-3-yl)-2-bromoethan-1-one as a yellow solid. LC/MS: mass calculated for $C_8H_6BrF_3N_2O$: 281.96, measured (ES, m/z): 282.95, 284.95 $[M+H, M+H+2]^+$.

Step 3: 2-(6-Amino-2-(trifluoromethyl)pyridin-3-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate A mixture of 7-(3-chloro-2-fluoro-6-(1H-tetrazol-1-yl) phenyl)-5-oxo-1,2,3,5,8,8a-hexahydroindolizine-3-carboxylic acid (300 mg. 0.79 mmol, 1.0 equiv.) and potassium carbonate (143 mg, 1.03 mmol, 1.3 equiv.) in acetonitrile (5 mL) was stirred at room temperature for 20 min. 1-(6-Amino-2-(trifluoromethyl)pyridin-3-yl)-2-bromoethan-1-one (292 mg, 1.03 mmol, 1.3 equiv.) was added and the resulting solution was stirred at room temperature overnight. The reaction mixture was diluted with water and extracted with EA twice. The combined organic layers were washed with brine, dried over $Na_2SO_4$ and concentrated under vacuum to yield 2-(6-amino-2-(trifluoromethyl)pyridin-3-yl)-2-oxoethyl 7-(3-chloro-2-fluoro-6-(1H-tetrazol-1-yl) phenyl)-5-oxo-1,2,3,5,8,8a-hexahydroindolizine-3-carboxylate as a light yellow solid. LC/MS: mass calculated for $C_{24}H_{18}ClF_4N_7O_4$: 579.10, measured (ES, m/z): 580.10 $[M+H]^+$.

Step 4: (3S,8aR)-3-(5-(6-Amino-2-(trifluoromethyl) pyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one To a mixture of 3-(5-(2-(3-((tert-butyldimethylsilyl)oxy)-3-methylbutyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (320 mg, 0.55 mmol, 1.0 equiv.) in toluene (5 mL) and acetic acid (0.5 mL) was added ammonium acetate (425 mg, 5.52 mmol, 10.0 equiv.). The reaction mixture was stirred at 100° C. for 2.0 h, diluted with water and extracted with EA twice. The combined organic layers were washed with brine, dried over $Na_2SO_4$, concentrated under vacuum. The residue was purified by reverse phase chromatography on C18 column (330 g, ACN/$H_2O$ (0.05% $CF_3COOH$): 0-40%) and the residue was further purified by prep-chiral-HPLC to yield (3S,8aR)-3-(5-(6-amino-2-(trifluoromethyl)pyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC/MS: mass calculated for $C_{24}H_{18}ClF_4N_9O$: 559.13, measured (ES, m/z): 560.10 $[M+H]^+$. $^1$H-NMR: (400 MHz, DMSO-$d_6$) δ 12.31 (brs., 1H), 9.83 (s, 1H), 7.90-8.10 (m, 1H), 7.67-7.81 (m, 2H), 7.10-7.23 (m, 1H), 6.75 (d, J=8.6 Hz, 1H), 6.54 (s, 2H), 5.68 (d, J=2.7 Hz, 1H), 5.03 (d, J=8.7 Hz, 1H), 3.63-3.80 (m, 1H), 2.66-2.79 (m, 1H), 2.53-2.56 (m, 1H), 2.05-2.30 (m, 2H), 1.89-2.04 (m, 2H). $^{19}$F NMR (376 MHz, DMSO-$d_6$) δ −61.88, −73.47, −112.82

Example 168 (3S,8a*R)-7-(3-chloro-2-fluoro-6-(1H-tetrazol-1-yl)phenyl)-3-(5-(3-fluoro-2-(((R)-1-hydroxypropan-2-yl)oxy)pyridin-4-yl)-1H-imidazol-2-yl)-2,3,8,8a-tetrahydroindolizin-5(1H)-one

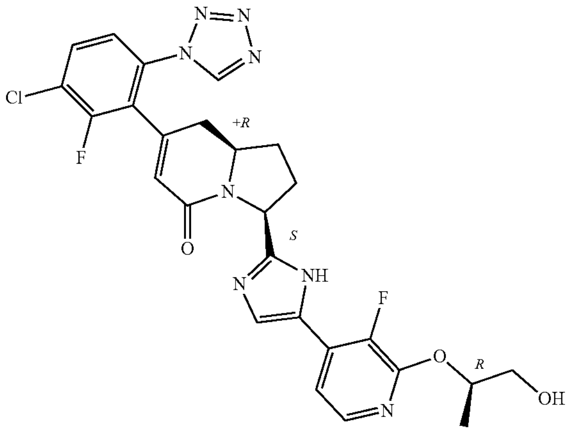

Step 1: (R)-2-((1-(benzyloxy)propan-2-yl)oxy)-3-fluoro-4-iodopyridine

To a solution of (R)-1-(benzyloxy)propan-2-ol in THE (50 mL) was added NaH (1.9, 16.60 mmol, 2.0 equiv.) at 0° C. The mixture was stirred at 0° C. for 1 h, then 2,3-difluoro-4-iodopyridine (2.0 g, 8.30 mmol, 1.0 equiv.) was added. The mixture was slowly warmed to room temperature. and stirred for 5 h, then quenched with water (100 mL) and extracted with EA (50 mL×3). The combined organic extracts were washed with brine, dried over anhydrous $Na_2SO_4$, filtered and concentrated to dryness under reduced pressure to yield a residue, which was purified by flash column chromatography on silica gel to yield (R)-2-((1-(benzyloxy)propan-2-yl)oxy)-3-fluoro-4-iodopyridine as colorless oil. LC/MS: mass calculated for $C_{15}H_{15}FINO_2$: 387.01, measured: 387.90 $[M+H]^+$.

Step 2: (R)-2-((3-fluoro-4-iodopyridin-2-yl)oxy)propan-1-ol

To a solution of (R)-2-((1-(benzyloxy)propan-2-yl)oxy)-3-fluoro-4-iodopyridine in DCM (50 mL) was added $BBr_3$ in DCM (5.2 mL, 2.0 equiv.) at 78° C. The mixture was stirred at −78° C. for 2 h until the starting material was totally converted. The reaction was quenched with water (6 mL) and extracted with EA (6 mL×3). The combined organic extracts were washed with brine, dried over anhydrous $Na_2SO_4$, filtered and concentrated to dryness under reduced pressure to yield a residue, which was purified by silica gel chromatography to yield (R)-2-((3-fluoro-4-iodopyridin-2-yl)oxy)propan-1-ol as colorless oil. LC/MS: mass calculated for $C_8H_9FINO_2$: 296.97, measured: 298.00 $[M+H]^+$.

Step 3: (R)-2-((4-(1-ethoxyvinyl)-3-fluoropyridin-2-yl)oxy)propan-1-ol

To a solution of methyl (R)-2-((3-fluoro-4-iodopyridin-2-yl)oxy)propan-1-ol (248 mg, 0.83 mmol, 1.2 equiv.) in 1,4-dioxane (10 mL) was added tributyl(1-ethoxyvinyl)stannane (363 mg, 1.00 mmol, 1.2 equiv.) at room temperature. followed by addition of $Pd(PPh_3)_4$ (193 mg, 0.16 mmol, 0.2 equiv.). The mixture was stirred at 100° C. for 2 h till the starting material fully consumed. The reaction was quenched with $H_2O$ (2 mL) and extracted with EA (50 mL). The solvent was removed under reduced pressure and the residue was purified by flash column chromatography on $Al_2O_3$ column to yield (R)-2-((4-(1-ethoxyvinyl)-3-fluoropyridin-2-yl)oxy)propan-1-ol as a yellow oil. LC/MS: mass calculated for $C_{12}H_{16}FNO_3$: 241.11, measured: 242.05 $[M+H]^+$.

Step 4: (R)-2-bromo-1-(3-fluoro-2-((1-hydroxypropan-2-yl)oxy)pyridin-4-yl)ethan-1-one To a solution of (R)-2-((4-(1-ethoxyvinyl)-3-fluoropyridin-2-yl)oxy)propan-1-01 (628 mg, 2.61 mmol, 1.0 equiv.) in THE/$H_2O$ (3:1) (15 mL) was added NBS (N-bromosuccinimide) (556 mg, 3.12 mmol, 1.2 equiv.) at room temperature. The mixture was stirred at room temperature. for 4 h, diluted with water and then extracted with EA (100 mL). The organic layer was washed with water, saturated aqueous sodium bicarbonate solution and brine, dried over anhydrous magnesium sulfate and concentrated under reduced pressure to yield (R)-2-bromo-1-(3-fluoro-2-((1-hydroxypropan-2-yl)oxy)pyridin-4-yl)ethan-1-one as a residue. The residue was used directly in the next step without any purification. LC/MS: mass calculated for $C_{10}H_{11}BrFNO_3$: 290.99, measured: 292.10 $[M+H]^+$, 294.10 $[M+H+2]^+$.

Step 5: 2-(3-fluoro-2-(((R)-1-hydroxypropan-2-yl)oxy)pyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate To a solution of (3S)-7-(3-chloro-2-fluoro-6-(1H-tetrazol-1-yl)phenyl)-5-oxo-1,2,3,5,8,8a-hexahydroindolizine-3-carboxylic acid in DMF (5 mL) was added $Cs_2CO_3$ (92 mg, 0.28 mmol, 0.6 equiv.). The mixture was stirred at room temperature. for 1 h. Then, (R)-2-bromo-1-(3-fluoro-2-((1-hydroxypropan-2-yl)oxy)pyridin-4-yl)ethan-1-one (275 mg, 0.94 mmol, 2.0 equiv.) was added. The resulting mixture was stirred at room temperature. for 3 h, diluted with water (6 mL) and extracted with EA (6 mL×3). The combined organic extracts were washed with brine, dried over anhydrous $Na_2SO_4$, filtered and concentrated to dryness under reduced pressure to yield a residue, which was purified by flash column chromatography on silica gel to yield 2-(3-fluoro-2-(((R)-1-hydroxypropan-2-yl)oxy)pyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate as a yellow solid. LC/MS: mass calculated for $C_{26}H_{23}ClF_2N_6O_6$: 588.13, measured: 589.15 $[M+H]^+$.

Step 6: (3S,8a*R)-7-(3-chloro-2-fluoro-6-(1H-tetrazol-1-yl)phenyl)-3-(5-(3-fluoro-2-(((R)-1-hydroxypropan-2-yl)oxy)pyridin-4-yl)-1H-imidazol-2-yl)-2,3,8,8a-tetrahydroindolizin-5(1H)-one To a solution of 2-(3-fluoro-2-(((R)-1-hydroxypropan-2-yl)oxy)pyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate (217 mg, 0.37 mmol, 1.0 equiv.) in toluene (10 mL) and AcOH (1 mL) was added ammonium acetate (284 mg, 3.69 mmol, 10.0 equiv.) and the reaction mixture was heated to reflux with stirring for 4 h. The resulting mixture was diluted with water (50 mL) and extracted with EA (50 mL×3). The combined organic extracts were washed with brine, dried over anhydrous $Na_2SO_4$, filtered and concentrated to dryness under reduced pressure to yield a residue, which was purified by flash column chromatography on silica gel and preparative HPLC using a XBridge Prep OBD C18 150 mm×30 mm×5 μm column (eluent: 36% to 66% (v/v) $CH_3CN$ and $H_2O$ with 0.05% $NH_4HCO_3$) to yield the (3S,8a*R)-7-(3-chloro-2-fluoro-6-(1H-tetrazol-1-yl)phenyl)-3-(5-(3-fluoro-2-(((R)-1-hydroxypropan-2-yl)oxy)pyridin-4-yl)-1H-imidazol-2-yl)-2,3,8,8a-tetrahydroindolizin-5(1H)-one as a white solid.

LC/MS: mass calculated for $C_{26}H_{23}ClF_2N_8O_3$: 568.15, measured (ES, m/z): 569.05 $[M+H]^+$. $^1H$-NMR: 1H NMR (300 MHz, DMSO-$d_6$) δ 12.27 (brs, 1H), 9.83 (s, 1H), 7.90-8.10 (m, 2H), 7.69 (dd, J=8.7, 1.5 Hz, 1H), 7.45-7.60 (m, 2H), 5.67 (d, J=2.5 Hz, 1H), 4.60-5.10 (m, 2H), 4.18-4.35 (m, 1H), 4.07-4.18 (m, 1H), 3.91-4.07 (m, 1H), 3.82-3.63 (m, 1H), 2.54-2.85 (m, 2H), 2.05-2.40 (m, 2H), 1.80-2.05 (m, 2H), 1.14 (d, J=6.2 Hz, 3H). $^{19}F$ NMR (282 MHz, DMSO-$d_6$) δ −112.84, −143.07.

Example 169 (3S,8a*S)-7-(3-chloro-2-fluoro-6-(1H-tetrazol-1-yl)phenyl)-3-(5-(3-fluoro-2-(((R)-1-hydroxypropan-2-yl)oxy)pyridin-4-yl)-1H-imidazol-2-yl)-2,3,8,8a-tetrahydroindolizin-5(1H)-one

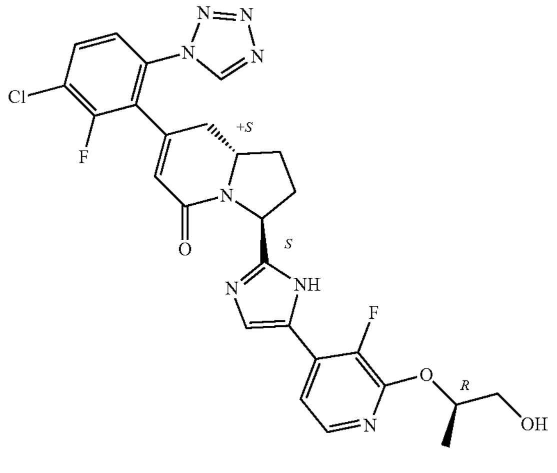

LC/MS: mass calculated for $C_{26}H_{23}ClF_2N_8O_3$: 568.15, measured (ES, m/z): 569.05 $[M+H]^+$. $^1H$-NMR: (300 MHz, DMSO-$d_6$) δ 12.31 (brs, 1H), 9.83 (s, 1H), 7.86-8.01 (m, 2H), 7.69 (d, J=8.7 Hz, 1H), 7.43-7.56 (m, 2H), 5.67 (d, J=2.5 Hz, 1H), 5.15-5.35 (m 1H), 5.03 (d, J=8.5 Hz, 1H), 3.65-3.89 (m, 1H), 3.45-3.64 (m, 3H), 2.65-2.89 (m, 2H), 2.01-2.45 (m, 2H), 1.87-2.01 (m, 2H), 1.15-1.35 (m, 3H). $^{19}F$ NMR (282 MHz, DMSO-$d_6$) δ −112.84, −142.52.

Example 170 (3*S,8a*R)-7-(3-chloro-2-fluoro-6-(1H-tetrazol-1-yl)phenyl)-3-(5-(2-((*S)-2,2,2-trifluoro-1-hydroxyethyl)pyridin-4-yl)-1H-imidazol-2-yl)-2,3,8,8a-tetrahydroindolizin-5(1H)-one

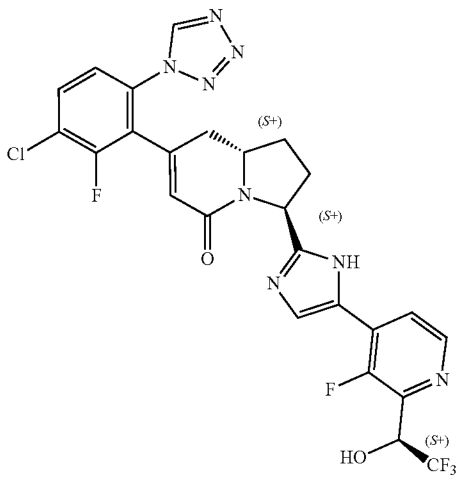

LC/MS: mass calculated for $C_{25}H_{18}ClF_5N_8O_2$: 592.12, measured (ES, m/z): 593.05 $[M+H]^+$. $^1H$-NMR: (400 MHz, DMSO-$d_6$) δ 9.82 (s, 1H), 8.46 (d, J=5.0 Hz, 1H), 7.90-8.15 (m, 2H), 7.55-7.75 (m, 2H), 5.70 (d, J=2.7 Hz, 1H), 5.42-5.50 (m, 1H), 5.05-5.10 (m, 1H), 3.76-3.85 (m, 1H), 2.71-2.80 (m, 1H), 2.58-2.60 (m, 1H), 2.07-2.26 (m, 2H), 1.91-2.00 (m, 2H). $^{19}F$ NMR (376 MHz, DMSO-$d_6$) δ −75.11, −112.82, −128.57.

Example 171 (3*S,8a*R)-7-(3-chloro-2-fluoro-6-(1H-tetrazol-1-yl)phenyl)-3-(5-(3-fluoro-2-((*R)-2,2,2-trifluoro-1-hydroxyethyl)pyridin-4-yl)-1H-imidazol-2-yl)-2,3,8,8a-tetrahydroindolizin-5(1H)-one

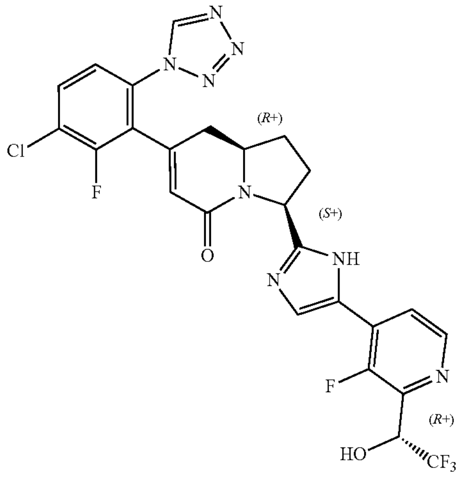

Step 1: 2,2,2-trifluoro-1-(3-fluoropyridin-2-yl)ethan-1-one

To a solution of 2-bromo-3-fluoropyridine (5.0 g, 28.41 mmol, 1.0 equiv.) in toluene (40 mL) was dropwise added n-butyllithium (14.8 mL, 36.94 mmol, 1.3 equiv.) under −65° C. under $N_2$. After 30 min, 2,2,2-trifluoro-N-methoxy-N-methylacetamide (6.69 g, 42.62 mmol, 1.5 equiv.) was added to the mixture under −65° C. The resulting mixture was maintained with stirring for additional 1 h, then quenched with $NH_4Cl$ (aq.), diluted with EA (40 mL) and extracted with EA (2×40 mL). The organic layers were combined, washed with brine, dried over $Na_2SO_4$ and concentrated. The residue was purified by flash column chromatography on silica gel (0→50% EA/PE) to yield 2,2,2-trifluoro-1-(3-fluoropyridin-2-yl)ethan-1-one as a yellow oil. LC/MS: mass calculated for $C_7H_3F_4NO$: 193.02, measured: 212.00 $[M+H+H_2O]^+$.

Step 2: 2,2,2-trifluoro-1-(3-fluoropyridin-2-yl)ethan-1-ol

To a solution of 2,2,2-trifluoro-1-(3-fluoropyridin-2-yl)ethan-1-one (3.9 g, 20.04 mmol, 1.0 equiv.) in DCE (40 mL) was added sodium triacetoxyborohydride (5.5 g, 26.05 mmol, 1.3 equiv.) in several portions. The resulting mixture was stirred at room temperature overnight and diluted with water (50 mL), extracted with EA (3×30 mL). The organic layers were combined, washed with brine, dried over $Na_2SO_4$, and concentrated to yield 2,2,2-trifluoro-1-(3-fluoropyridin-2-yl)ethan-1-ol as a light yellow oil. LC/MS: mass calculated for $C_7H_5F_4NO$: 195.03, measured: 196.02 $[M+H]^+$.

Step 3: 2-(1-((tert-butyldimethylsilyl)oxy)-2,2,2-trifluoroethyl)-3-fluoropyridine To a solution of 2,2,2-trifluoro-1-(3-fluoropyridin-2-yl)ethan-1-ol (3.5 g) in DCM (40 mL) were added 2,6-dimethylpyridine (6.9 mL, 59.50 mmol, 3.0 equiv.) and TBSOTf (13.7 mL, 59.50 mmol, 3.0 equiv.). The resulting mixture was stirred at 60° C. overnight, diluted with water (20 mL) and extracted with EA (3×20 mL). The organic layers were combined, washed with brine, dried over $Na_2SO_4$ and concentrated under reduced pressure. The residue was purified by flash column chromatography on silica gel (0→50% EA/PE) to yield 2-(1-((tert-butyldimethylsilyl)oxy)-2,2,2-trifluoroethyl)-3-fluoropyridine as a light yellow oil. LC/MS: mass calculated for $C_{13}H_{19}F_4NOSi$: 309.12, measured: 310.00 $[M+H]^+$.

Step 4: 2-(1-((tart-butyldimethylsilyl)oxy)-2,2,2-trifluoroethyl)-3-fluoro-5-iodopyridine To a solution of 2-(1-((tert-butyldimethylsilyl)oxy)-2,2,2-trifluoroethyl)-3-fluoropyridine (1.0 g, 3.23 mmol, 1.0 equiv.) in THE (15 mL) was added LDA (2.4 mL, 4.85 mmol, 1.5 equiv.) at −55° C. under $N_2$. After 30 min. 12 (1.6 g, 6.46 mmol, 2.0 equiv.) in THE was added. The resulting mixture was maintained stirring at −55° C. for 1 h, diluted with aqueous $Na_2SO_3$ (20 mL), and extracted with EA (3×20 mL). The organic layers were combined, washed with brine, dried over $Na_2SO_4$. and concentrated to yield 2-(1-((tert-butyldimethylsilyl)oxy)-2,2,2-trifluoroethyl)-3-fluoro-4-iodopyridine as a dark red oil. LC/MS: mass calculated for $C_{13}H_{18}F_4INOSi$: 435.01, measured: 435.95 $[M+H]^+$.

Step 5: 2-(1-((tert-butyldimethylsilyl)oxy)-2,2,2-trifluoroethyl)-4-(1-ethoxyvinyl)-3-fluoropyridine A mixture of 2-(1-((tert-butyldimethylsilyl)oxy)-2,2,2-trifluoroethyl)-3-fluoro-4-iodopyridine (1.7 g, 3.91 mmol, 1.0 equiv.), tributyl(1-ethoxyvinyl)stannane (2.1 g, 5.86 mmol, 1.5 equiv.) and $Pd(PPh_3)_4$ (451 mg, 0.39 mmol, 0.1 equiv.) in 1,4-dioxane (20 mL) was heated at 90° C. under $N_2$ for 1.5 h. Upon cooling to room temperature, the solvent was removed and the residue was purified by flash column chromatography on neutral $Al_2O_3$ column (0→15% EA/PE) to yield 2-(1-((tert butyldimethylsilyl)oxy)-2,2,2-trifluoroethyl)-4-(1-ethoxyvinyl)-3-fluoropyridine as a light yellow oil. LC/MS: mass calculated for $C_{17}H_{25}F_4NO_2Si$: 379.16, measured: 380.15 $[M+H]^+$.

Step 6: 2-bromo-1-(2-(1-((tert-butyldimethylsilyl)oxy)-2,2,2-trifluoroethyl)-3-fluoropyridin-4-yl)ethan-1-one A mixture of 2-(1-((tert-butyldimethylsilyl)oxy)-2,2,2-trifluoroethyl)-4-(1-ethoxyvinyl)-3-fluoropyridine (850 mg, 2.24 mmol, 1.0 equiv.) and 1-bromopyrrolidine-2,5-dione (399 mg, 2.24 mmol, 1.0 equiv.) in $THF/H_2O$ (8 mL) was stirred at room temperature for 2 h. The reaction mixture was diluted with water, extracted with DCM (3×10 mL). The organic layers were combined, washed with brine, dried over $Na_2SO_4$ and concentrated under reduced pressure. The residue was used in the next step reaction without further purification. LC/MS: mass calculated for $C_{15}H_{20}BrF_4NO_2Si$: 429.04, measured: 429.95 $[M+H]^+$, 431.95 $[M+H+2]^+$.

Step 7: 2-bromo-1-(2-(1-((tert-butyldimethylsilyl)oxy)-2,2,2-trifluoroethyl)-3-fluoropyridin-4-yl)ethan-1-one To a solution of (3S)-7-(6-amino-3-chloro-2-fluorophenyl)-5-oxo-1,2,3,5,8,8a-hexahydroindolizine-3-carboxylic acid (250 mg, 0.77 mmol, 1.0 equiv.) in $CH_3CN$ (3 mL) was added potassium carbonate (128 mg, 0.92 mmol, 1.2 equiv.), followed by addition of 2-bromo-1-(2-(1-((tert-butyldimethylsilyl)oxy)-2,2,2-trifluoroethyl)-3-fluoropyridin-4-yl)ethan-1-one (397 mg, 0.92 mmol, 1.2 equiv.), and the resulting mixture was stirred at room temperature overnight. The resulting mixture was then diluted with water and extracted with EA (3×20 mL). The organic layers were combined, washed with brine, dried over $Na_2SO_4$ and concentrated. The residue was purified by flash column chromatography on silica gel (0→8% MeOH/DCM) to yield 2-(2-(1-((tert-butyldimethylsilyl)oxy)-2,2,2-trifluoroethyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as a light yellow oil. LC/MS: mass calculated for $C_{30}H_{34}ClF_4N_3O_5Si$: 673.18, measured: 674.20 $[M+H]^+$.

Step 8: (3S)-7-(6-amino-3-chloro-2-fluorophenyl)-3-(5-(2-(1-((tert-butyldimethylsilyl)oxy)-2,2,2-trifluoroethyl)-3-fluoropyridin-4-yl)-1H-imidazol-2-yl)-2,3,8,8a-tetrahydroindolizin-5(1H)-one To a mixture of 2-(2-(1-((tert-butyldimethylsilyl)oxy)-2,2,2-trifluoroethyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (130 mg, 0.19 mmol, 1.0 equiv.) and ammonium acetate (149 mg, 1.93 mmol, 10.0 equiv.) in toluene (3 mL) was added acetic acid (23 mg, 0.38 mmol, 2.0 equiv.). The resulting mixture was stirred at 100°

C. for 2 h and concentrated under reduced pressure. The residue was purified by flash column chromatography on silica gel (0→10% MeOH/DCM) to yield (3S)-7-(6-amino-3-chloro-2-fluorophenyl)-3-(5-(2-(1-((tert-butyldimethylsilyl)oxy)-2,2,2-trifluoroethyl)-3-fluoropyridin-4-yl)-1H-imidazol-2-yl)-2,3,8,8a-tetrahydroindolizin-5(1H)-one as a light yellow oil. LC/MS: mass calculated for $C_{30}H_{33}ClF_5N_5O_2Si$: 653.20, measured: 655.20 $[M+H]^+$.

Step 9: (3S)-3-(5-(2-(1-((tert-butyldimethylsilyl)oxy)-2,2,2-trifluoroethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one A mixture of (3S)-7-(6-amino-3-chloro-2-fluorophenyl)-3-(5-(2-(1-((tert-butyldimethylsilyl)oxy)-2,2,2-trifluoroethyl)-3-fluoropyridin-4-yl)-1H-imidazol-2-yl)-2,3,8,8a-tetrahydroindolizin-5(1H)-one (100 mg, 0.15 mmol, 1.0 equiv.), trimethoxymethane (1 mL), azidotrimethylsilane (1 mL) and acetic acid (2 mL) was stirred at room temperature for 24 h. The solvent was removed under reduced pressure to yield (3S)-3-(5-(2-(1-((tert-butyldimethylsilyl)oxy)-2,2,2-trifluoroethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a light yellow oil, which was used in the next step without further purification. LC/MS: mass calculated for $C_{31}H_{32}ClF_5NBO_2Si$: 706.20, measured: 707.10 $[M+H]^+$.

Step 10: (3*S,8a*R)-7-(3-chloro-2-fluoro-6-(1H-tetrazol-1-yl)phenyl)-3-(5-(2-((*R)-2,2,2-trifluoro-1-hydroxyethyl)pyridin-4-yl)-1H-imidazol-2-yl)-2,3,8,8a-tetrahydroindolizin-5(1H)-one To a solution of (3S)-3-(5-(2-(1-((tert-butyldimethylsilyl)oxy)-2,2,2-trifluoroethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (175 mg, 0.25 mmol, 1.0 equiv.) in THE (4 mL) was added $Et_3N·3HF$ (1 mL). The resulting mixture was stirred at 50° C. for 2 h. The resulting mixture was concentrated and purified by reverse phase chromatography on C18 column (80 g, 0→50% MeCN/$H_2O$ (0.05% $CF_3COOH$)) to yield a residue. The racemic product was further separated by chiral-HPLC to yield (3S*,8aR*)-7-(3-chloro-2-fluoro-6-(1H-tetrazol-1-yl)phenyl)-3-(5-(3-fluoro-2-((R*)-2,2,2-trifluoro-1-hydroxyethyl)pyridin-4-yl)-1H-imidazol-2-yl)-2,3,8,8a-tetrahydroindolizin-5(1H)-one as a white solid.

LC/MS: mass calculated for $C_{25}H_{18}ClF_5N_8O_2$: 592.12, measured (ES, m/z): 593.05 $[M+H]^+$. $^1$H-NMR: (400 MHz, DMSO-$d_6$) δ 9.78 (s, 1H), 8.47 (d, J=5.0 Hz, 1H), 7.89-8.07 (m, 1H), 7.97-7.88 (m, 1H), 7.58-7.70 (m, 2H), 5.68 (d, J=2.6 Hz, 1H), 5.40-5.53 (m, 1H), 5.05-5.07 (m, 1H), 3.76-3.85 (m, 1H), 2.65-2.72 (m, 1H), 2.55-2.58 (m, 1H), 2.20-2.30 (m, 1H), 2.07-2.16 (m, 1H), 1.85-2.00 (m, 2H). $^{19}$F NMR (376 MHz, DMSO-$d_6$) δ −73.84, −75.17, 112.73, −128.28.

Example 172 (3*S,8a*S)-7-(3-chloro-2-fluoro-6-(1H-tetrazol-1-yl)phenyl)-3-(4-chloro-5-(2-((*S)-2,2,2-trifluoro-1-hydroxyethyl)pyridin-4-yl)-1H-imidazol-2-yl)-2,3,8,8a-tetrahydroindolizin-5(1H)-one

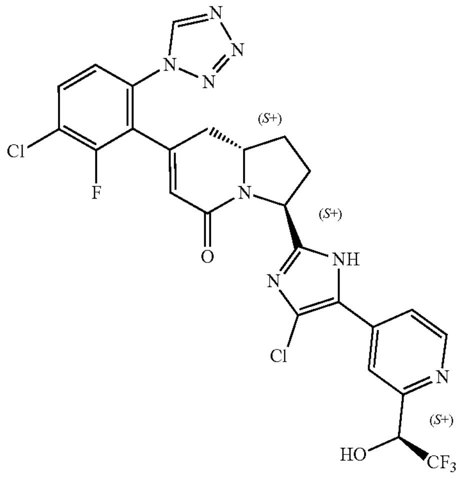

LC/MS: mass calculated for $C_{25}H_{18}Cl_2F_4N_8O_2$: 608.09, measured (ES, m/z): 609.05 $[M+H]^+$. $^1$H-NMR: (400 MHz, DMSO-$d_6$) δ 13.19 (s, 1H), 9.82 (s, 1H), 8.50 (d, J=5.2 Hz, 1H), 8.71 (s, 1H), 7.81-8.02 (m, 2H), 7.66-7.77 (m, 2H), 7.05-7.25 (m, 1H), 5.67 (d, J=2.6 Hz, 1H), 5.17 (q, J=7.2 Hz, 1H), 5.00 (d, J=8.7 Hz, 1H), 3.77-3.80 (m, 1H), 2.56-2.67 (m, 2H), 2.05-2.31 (m, 2H), 1.92-2.02 (m, 2H). $^{19}$F NMR (282 MHz, DMSO-$d_6$) δ −73.55, −75.66, −112.73.

Example 173 (3S,8aR)-7-(3-chloro-2-fluoro-6-(1H-tetrazol-1-yl)phenyl)-3-(4-chloro-5-(2-((R)-2,2,2-trifluoro-1-hydroxyethyl)pyridin-4-yl)-1H-imidazol-2-yl)-2,3,8,8a-tetrahydroindolizin-5(1H)-one

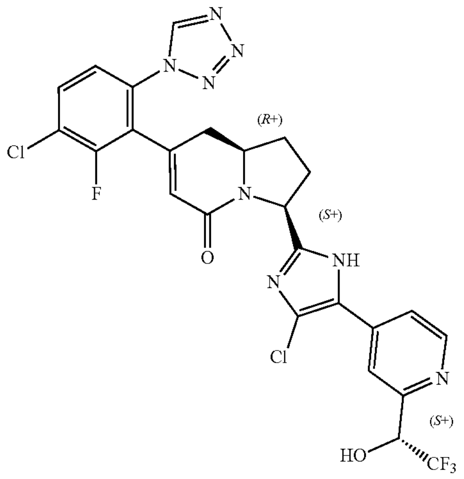

LC/MS: mass calculated for $C_{25}H_{18}Cl_2F_4N_8O_2$: 608.09, measured (ES, m/z): 609.05 $[M+H]^+$. $^1$H-NMR: (400 MHz, DMSO-$d_6$) δ 13.19 (s, 1H), 9.85 (s, 1H), 8.63 (d, J=5.3 Hz, 1H), 7.95-8.08 (m, 2H), 7.69-7.85 (m, 1H), 7.67-7.69 (m, 1H), 7.05-7.25 (m, 1H), 5.68 (d, J=2.2 Hz, 1H), 5.10-5.30

(m, 1H), 4.99 (d, J=8.7 Hz, 1H), 3.77-3.80 (m, 1H), 2.51-2.67 (m, 2H), 2.19-2.27 (m, 1H), 2.10-2.18 (m, 1H), 1.98-2.09 (m, 1H), 1.92-1.96 (m, 1H). $^{19}F$ NMR (376 MHz, DMSO-$d_6$) δ−73.89, −75.66, −112.87

Example 174 (3S*,8aS*)-7-(3-chloro-2-fluoro-6-(1H-tetrazol-1-yl)phenyl)-3-(5-(2-((S*)-2,2,2-trifluoro-1-hydroxyethyl)pyridin-4-yl)-1H-imidazol-2-yl)-2,3,8,8a-tetrahydroindolizin-5(1H)-one

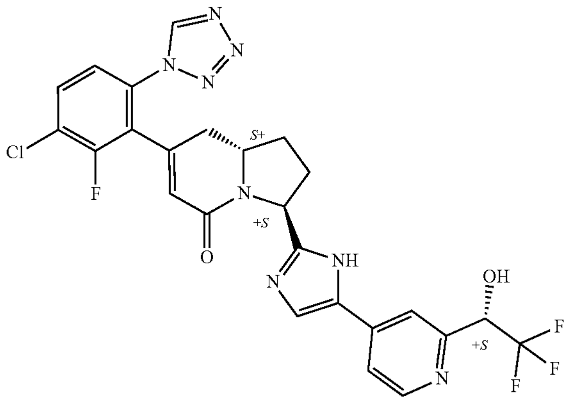

LC/MS: mass calculated for $C_{25}H_{19}ClF_4N_8O_2$:574, measured (ES, m/z): 575.05 $[M+H]^+$. $^1H$ NMR: (300 MHz, DMSO-$d_6$) δ 9.82 (s, 1H), 8.58 (d, J=5.4 Hz, 1H), 7.91-8.09 (m, 3H), 7.65-7.84 (m, 2H), 5.68 (d, J=2.6 Hz, 1H), 5.05-5.26 (m, 2H), 3.68-3.72 (m, 1H), 2.70-2.90 (m, 1H), 2.56-2.73 (m, 1H), 1.85-2.33 (m, 4H). $^{19}F$ NMR: (282 MHz, DMSO-$d_6$) δ−73.78, −75.71, −112.76.

Example 175 (3S*,8 aR*)-7-(3-chloro-2-fluoro-6-(1H-tetrazol-1-yl)phenyl)-3-(5-(2-((R*)-2,2,2-trifluoro-1-hydroxyethyl)pyridin-4-yl)-1H-imidazol-2-yl)-2,3,8,8a-tetrahydroindolizin-5(1H)-one

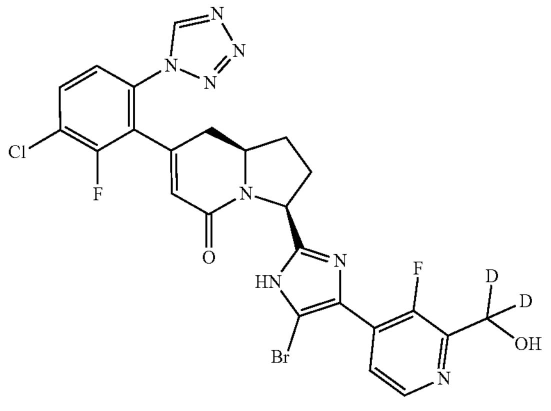 [SMILES: [2H]C([2H])(O)c1nccc(-c2nc([C@@H]3CC[C@@H]4CC(c5c(-n6cnnn6)ccc(Cl)c5F)=CC(=O)N43)[nH]c2Br)c1F]

To a solution of (3S)-3-(5-(2-(1-(tert-butyldimethylsilyloxy)-2,2,2-trifluoroethyl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (150 mg, 0.218 mmol, 1 equiv.) in THE (4 ml) was added $Et_3N·3HF$ (1 ml). The resulting mixture was stirred at 50° C. for 2 h. The resulting mixture was concentrated and purified by reverse phase chromatography on C18 (MeCN/$H_2O$ (0.05% $CF_3COOH$)) to yield 7-(3-chloro-2-fluoro-6-(1H-tetrazol-1-yl)phenyl)-3-(5-(2-((R)-2,2,2-trifluoro-1-hydroxyethyl)pyridin-4-yl)-1H-imidazol-2-yl)-2,3,8,8a-tetrahydroindolizin-5(1H)-one. The racemic product was further separated by chiral-HPLC to yield (3S',8aR*)-7-(3-chloro-2-fluoro-6-(1H-tetrazol-1-yl)phenyl)-3-(5-(2-((S*)-2,2,2-trifluoro-1-hydroxyethyl)pyridin-4-yl)-1H-imidazol-2-yl)-2,3,8,8a-tetrahydroindolizin-5(1H)-one as a white solid.

LC/MS: mass calculated for $C_{25}H_{19}ClF_4N_8O_2$:574, measured: 575.05 $[M+H]^+$ and (3S*,8aS*)-7-(3-chloro-2-fluoro-6-(1H-tetrazol-1-yl)phenyl)-3-(5-(2-((R*)-2,2,2-trifluoro-1-hydroxyethyl)pyridin-4-yl)-1H-imidazol-2-yl)-2,3,8,8a-tetrahydroindolizin-5(1H)-one as a white solid.

LC/MS: mass calculated for $C_{25}H_{19}ClF_4N_8O_2$:574, measured: 575.10 $[M+H]^+$. $^1H$ NMR (300 MHz, DMSO-$d_6$) δ 9.82 (s, 1H), 8.50 (d, J=5.2 Hz, 1H), 8.02-7.81 (m, 3H), 7.77-7.66 (m, 2H), 5.67 (d, J=2.6 Hz, 1H), 5.19-4.97 (m, 2H), 3.71 (s, 1H), 2.87-2.71 (m, 1H), 2.56 (d, J=4.3 Hz, 1H), 2.31-2.05 (m, 2H), 2.02-1.92 (m, 2H)/$^{19}F$ NMR (282 MHz, DMSO-$d_6$) δ−73.55, −75.66, −112.73.

Example 176 2-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-3-fluoropyridin-2-yl)acetonitrile

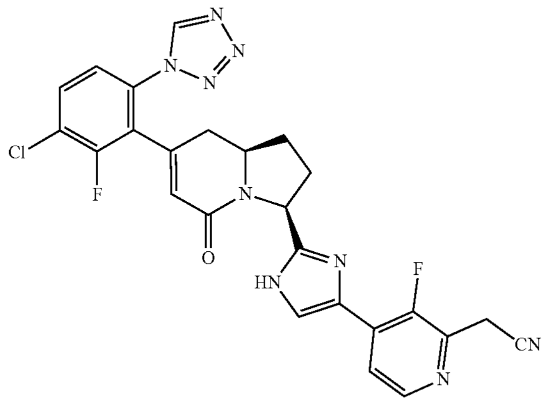 [SMILES: N#CCc1nccc(-c2c[nH]c([C@@H]3CC[C@@H]4CC(c5c(-n6cnnn6)ccc(Cl)c5F)=CC(=O)N43)n2)c1F]

Step 1: 2-(bromomethyl)-3-fluoro-4-iodopyridine

Under an inert atmosphere of nitrogen, to a mixture of (3-fluoro-4-iodopyridin-2-yl)methanol (1.1 g, 4.35 mmol, 1.0 equiv.) and $CBr_4$ (2.3 g, 6.96 mmol, 1.6 equiv.) in DCM (50 mL) was added $PPh_3$ (1.4 g, 5.22 mmol, 1.2 equiv.) in portions at 0° C., and the resulting mixture stirred at 0° C. for 1 h. The reaction was then quenched with water (50 mL), extracted with DCM (3×50 mL), dried over $Na_2SO_4$, concentrated. The residue was purified by flash column chromatography on silica gel (0→25% EA/PE) to yield 2-(bromomethyl)-3-fluoro-4-iodopyridine as a light yellow solid.

Step 2: 2-(3-fluoro-4-iodopyridin-2-yl)acetonitrile

Under an inert atmosphere of nitrogen, to a mixture of 2-(bromomethyl)-3-fluoro-4-iodopyridine (1.2 g, 3.80 mmol, 1.0 equiv.) and TMSCN (490 mg, 4.94 mmol, 1.3 equiv.) in THE (35 mL) was added TBAF (4.9 mL, 4.94 mmol, 1.3 equiv., 1 M in THF) at 0° C. The reaction mixture was stirred at 70° C. for 1 h and concentrated under vacuum. The residue was purified by flash column chromatography on silica gel (0→20% EA/PE) to yield 2-(3-fluoro-4-iodopyridin-2-yl)acetonitrile as a light yellow solid.

Step 3: 2-(4-(1-ethoxyvinyl)-3-fluoropyridin-2-yl) acetonitrile

Under an inert atmosphere of nitrogen, a mixture of 2-(3-fluoro-4-iodopyridin-2-yl)acetonitrile (900 mg, 3.44 mmol, 1.0 equiv.), tributyl(1-ethoxyvinyl)stannane (2.5 g, 6.87 mmol, 2.0 equiv.) and $Pd(PPh_3)_2Cl_2$ (241 mg, 0.34 mmol, 0.1 equiv.) in 1,4-dioxane (20 mL) was stirred at 100° C. for 2 h, then cooled to room temperature, and concentrated under vacuum. The residue was purified by flash column chromatography on silica gel (0→25% EA/PE) to yield 2-(4-(1-ethoxyvinyl)-3-fluoropyridin-2-yl)acetonitrile as a light yellow solid.

Step 4: 2-(4-(2-bromoacetyl)-3-fluoropyridin-2-yl) acetonitrile

To a mixture of 2-(4-(1-ethoxyvinyl)-3-fluoropyridin-2-yl)acetonitrile (650 mg, 3.15 mmol, 1.0 equiv.) in THE (20 mL) and $H_2O$ (6 mL) was added NBS (561 mg, 3.15 mmol, 1.0 equiv.). The reaction mixture was stirred at room temperature. for 1 h, diluted with EA (100 mL), washed with brine (3×30 mL), dried over $Na_2SO_4$, and concentrated to yield 2-(4-(2-bromoacetyl)-3-fluoropyridin-2-yl)acetonitrile as a yellow solid.

Step 5: 2-(2-(cyanomethyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate A mixture of (3S)-7-(3-chloro-2-fluoro-6-(1H-tetrazol-1-yl)phenyl)-5-oxo-1,2,3,5,8,8a-hexahydroindolizine-3-carboxylic acid (320 mg, 0.85 mmol, 1.0 equiv.) and $Cs_2CO_3$ (166 mg, 0.51 mmol, 0.6 equiv.) in DMF (10 mL) was stirred at 40° C. for 30 min. Then, 2-(4-(2-bromoacetyl)-3-fluoropyridin-2-yl)acetonitrile (326 mg, 1.27 mmol, 1.5 equiv.) was added to the mixture. The reaction mixture was maintained with stirring at room temperature for 4 h, then diluted with EA (100 mL), washed with water (3×20 mL), brine (2×20 mL), dried over $Na_2SO_4$, and concentrated. The residue was purified by flash column chromatography on silica gel (0-010% MeOH/DCM) to yield 2-(2-(cyanomethyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate. LC/MS: mass calculated for $C_{25}H_{18}ClF_2N_7O_4$: 553.11, measured: 554.05 $[M+H]^+$.

Step 6: 2-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-3-fluoropyridin-2-yl)acetonitrile Under an inert atmosphere of nitrogen, a mixture of 2-(2-(cyanomethyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate (330 mg, 0.59 mmol, 1.0 equiv.) and $NH_4OAc$ (459 mg, 5.96 mmol, 10.0 equiv.) in AcOH (2 mL) and toluene (20 mL) was stirred at 110° C. for 1 h, then concentrated under reduced pressure. The residue was purified by flash column chromatography on silica gel (0→10% MeOH/DCM) to yield 2-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-3-fluoropyridin-2-yl)acetonitrile as a yellow solid, which was further purified by prep-chiral-HPLC to yield 2-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-3-fluoropyridin-2-yl)acetonitrile as an off-white solid.

LC/MS: mass calculated for $C_{25}H_{18}ClF_2N_9O$: 533.13, measured (ES, m/z): 534.15 $[M+H]^+$. $^1H$ NMR: (300 MHz, DMSO-$d_6$) δ 12.35 (s, 1H), 9.85 (s, 1H), 8.39 (d, J=5.1 Hz, 1H), 7.92-8.06 (m, 2H), 7.73 (dd, J=8.7, 1.5 Hz, 1H), 7.55-7.67 (m, 1H), 5.72 (d, J=2.6 Hz, 1H), 5.06 (d, J=8.5 Hz, 1H), 4.35 (d, J=2.0 Hz, 2H), 3.65-3.87 (m, 1H), 2.65-2.85 (m, 1H), 2.55-2.65 (m, 1H), 2.06-2.34 (m, 2H), 1.85-2.07 (m, 2H). $^{19}F$ NMR (282 MHz, DMSO-$d_6$) δ −112.84, −127.82.

Example 177 (3S)-7-(3-chloro-2-fluoro-6-(1H-tetrazol-1-yl)phenyl)-3-(4-(3-fluoro-2-(methoxymethyl)pyridin-4-yl)-1H-imidazol-2-yl)-2,3,8,8a-tetrahydroindolizin-5(1H)-one

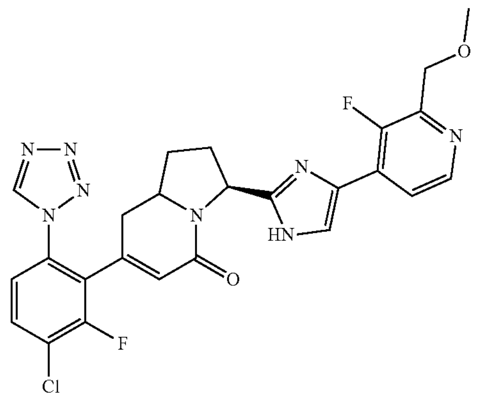 [SMILES: COCc1nccc(-c2c[nH]c([C@@H]3CCC4CC(c5c(-n6cnnn6)ccc(Cl)c5F)=CC(=O)N43)n2)c1F]

Step 1: 2-(((tert-butyldimethylsilyl)oxy)methyl)-3-fluoropyridine

To a mixture of (3-fluoropyridin-2-yl)methanol (9.0 g, 70.80 mmol, 1.0 equiv.) and imidazole (9.6 g, 142 mmol, 2.0 equiv.) in DMF (90 mL) was added TBSCl (12.8 g, 84.96 mmol, 1.2 equiv.). The reaction mixture was stirred at room temperature. for 4 h. The resulting mixture was then diluted with EA (700 mL), washed with water (3×150 mL), brine (2×150 mL), dried over $Na_2SO_4$, and concentrated. The residue was purified by flash column chromatography on silica gel (0→25% EA/PE) to yield 2-(((tert-butyldimethylsilyl)oxy)methyl)-3-fluoropyridine as a light yellow oil. LC/MS: mass calculated for $C_{12}H_{20}FNOSi$: 241.13, measured: 242.10 $[M+H]^+$.

Step 2: 2-(((tert-butyldimethylsilyl)oxy)methyl)-3-fluoro-4-iodopyridine

Under an inert atmosphere of nitrogen, to a mixture of 2-(((tert-butyldimethylsilyl)oxy)methyl)-3-fluoropyridine (16.0 g, 66.28 mmol, 1.0 equiv.) in THF (350 mL) was added LDA (39.8 mL, 79.54 mmol, 1.2 equiv., 2 M in THF) at −78° C. The mixture was stirred at −78° C. for 30 min., and then a solution of 12 (20.2 g, 79.54 mmol, 1.2 equiv.) in THF (80 mL) was added to the mixture at −78° C. The reaction mixture was stirred at −78° C. for another 1 h, then quenched with saturated ammonium chloride solution (300 mL), extracted with EA (3×300 mL), dried over $Na_2SO_4$, and concentrated under reduced pressure. The residue was purified by flash column chromatography on silica gel (0→20% EA/PE) to yield 2-(((tert-butyldimethylsilyl)oxy)methyl)-3-fluoro-4-iodopyridine as a light yellow oil. LC/MS: mass calculated for $C_{12}H_{19}FINOSi$: 367.03, measured: 367.90 $[M+H]^+$.

Step 3: (3-fluoro-4-iodopyridin-2-yl)methanol

To a mixture of 2-(((tert-butyldimethylsilyl)oxy)methyl)-3-fluoro-4-iodopyridine (4.0 g, 10.89 mmol, 1.0 equiv.) in THF (60 mL) was added TBAF (12.0 mL, 11.98 mmol, 1.1 equiv., 1 M in THF). The reaction mixture was stirred at room temperature. for 2 h, diluted with water, extracted with EA (150 mL), washed with brine (3×60 mL), dried over $Na_2SO_4$, and concentrated under reduced pressure. The residue was purified by flash column chromatography on silica gel (0→50% EA/PE) to yield (3-fluoro-4-iodopyridin-2-yl)methanol as a light yellow oil.

Step 4: 3-fluoro-4-iodo-2-(methoxymethyl)pyridine

To a mixture of (3-fluoro-4-iodopyridin-2-yl)methanol (1.0 g, 3.95 mmol, 1.0 equiv.) in THF (18 mL) was added NaH (205 mg, 5.14 mmol, 1.3 equiv., 60%) at 0° C., the reaction mixture was stirred at 0° C. for 20 min. To the resulting mixture was then added MeI (729 mg, 5.14 mmol, 1.3 equiv.) and the reaction mixture was maintained stirring at room temperature. for 3 h. The reaction was quenched with ice water (40 mL), extracted with EA (3×60 mL), dried over $Na_2SO_4$, concentrated under reduced pressure. The residue was purified by flash column chromatography on silica gel (0→25% EA/PE) to yield 3-fluoro-4-iodo-2-(methoxymethyl)pyridine as a light yellow solid.

Step 5: 4-(1-ethoxyvinyl)-3-fluoro-2-(methoxymethyl)pyridine

A mixture of 3-fluoro-4-iodo-2-(methoxymethyl)pyridine (950 mg, 3.56 mmol, 1.0 equiv.), tributyl(1-ethoxyvinyl) stannane (2.6 g, 7.11 mmol, 2.0 equiv.) and $Pd(PPh_3)_2Cl_2$ (250 mg, 0.36 mmol, 0.1 equiv.) in 1,4-dioxane (20 mL) was stirred at 100° C. under $N_2$ for 2 h, then cooled to room temperature, and concentrated under reduced pressure. The residue was purified by flash column chromatography (0→25% EA/PE) to yield 4-(1-ethoxyvinyl)-3-fluoro-2-(methoxymethyl)pyridine as a light yellow solid.

Step 6: 2-bromo-1-(3-fluoro-2-(methoxymethyl) pyridin-4-yl)ethan-1-one

To a mixture of 4-(1-ethoxyvinyl)-3-fluoro-2-(methoxymethyl)pyridine (700 mg, 3.31 mmol, 1.0 equiv.) in THE (15 mL) and $H_2O$ (5 mL) was added NBS (590 mg, 3.31 mmol, 1.00 equiv.). The mixture was stirred at room temperature. for 1 h. The resulting mixture was diluted with water and extracted with EA (100 mL), washed with brine (3×30 mL), dried over $Na_2SO_4$, and concentrated under reduced pressure to yield 2-bromo-1-(3-fluoro-2-(methoxymethyl)pyridin-4-yl)ethan-1-one as a yellow solid. LC/MS: mass calculated for $C_9H_9BrFNO_2$: 260.98, measured: 261.95 $[M+H]^+$, 263.95 $[M+H+2]^+$.

Step 7: 2-(3-fluoro-2-(methoxymethyl)pyridin-4-yl)-2-oxoethyl (3S)-7-(6-amino-3-chloro-2-fluorophenyl)-5-oxo-1,2,3,5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (300 mg, 0.92 mmol, 1.0 equiv.) and $Cs_2CO_3$ (181 mg, 0.55 mmol, 0.6 equiv.) in DMF (8 mL) was stirred at 40° C. for 30 min. To the resulting mixture was then added 2-bromo-1-(3-fluoro-2-(methoxymethyl)pyridin-4-yl)ethanone (315 mg, 1.20 mmol, 1.3 equiv.) and the reaction mixture was stirred at room temperature. for 4 h. The reaction mixture was diluted with EA (100 mL), washed with water (3×20 mL), brine (2×20 mL), dried over $Na_2SO_4$, concentrated. The residue was purified by flash column chromatography (0→5% MeOH/DCM) to yield 2-(3-fluoro-2-(methoxymethyl)pyridin-4-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{24}H_{22}ClF_2N_3O_5$: 505.12, measured: 506.05 $[M+H]^+$.

Step 8: (3S)-7-(6-amino-3-chloro-2-fluorophenyl)-3-(4-(3-fluoro-2-(methoxymethyl)pyridin-4-yl)-1H-imidazol-2-yl)-2,3,8,8a-tetrahydroindolizin-5(1H)-one Under an inert atmosphere of nitrogen, a mixture of 2-(3-fluoro-2-(methoxymethyl)pyridin-4-yl)-2-oxoethyl (3S)-7-(6-amino-3-chloro-2-fluorophenyl)-5-oxo-1,2,3,5,8,8a-hexahydroindolizine-3-carboxylate (310 mg, 0.61 mmol, 1.0 equiv.) and $NH_4OAc$ (472 mg, 6.13 mmol, 10.0 equiv.) in AcOH (2 mL) and toluene (20 mL) was stirred at 110° C. for 1 h. The solvent was removed under reduced pressure. The residue was purified by flash column chromatography on silica gel (0→10% MeOH/DCM) to yield (3S)-7-(6-amino-3-chloro-2-fluorophenyl)-3-(4-(3-fluoro-2-(methoxymethyl)pyridin-4-yl)-1H-imidazol-2-yl)-2,3,8,8a-tetrahydroindolizin-5(1H)-one as a yellow solid. LC/MS: mass calculated for $C_{24}H_{22}ClF_2N_5O_2$: 485.14, measured: 486.10 $[M+H]^+$.

Step 9: (3S)-7-(3-chloro-2-fluoro-6-(1H-tetrazol-1-yl)phenyl)-3-(4-(3-fluoro-2-(methoxymethyl)pyridin-4-yl)-1H-imidazol-2-yl)-2,3,8,8a-tetrahydroindolizin-5(1H)-one A mixture of (3S)-7-(6-amino-3-chloro-2-fluorophenyl)-3-(4-(3-fluoro-2-(methoxymethyl)pyridin-4-yl)-1H-imidazol-2-yl)-2,3,8,8a-tetrahydroindolizin-5(1H)-one (120 mg, 0.25 mmol, 1.0 equiv.), $TMSN_3$ (284 mg, 2.47 mmol, 10.0 equiv.) and trimethoxymethane (262 mg, 2.47 mmol, 10.0 equiv.) in AcOH (8 mL) was stirred at 65° C. for 2 h, then concentrated under reduced pressure. The residue was applied onto a C18 reverse column (40 g, ACN/$H_2O$ (0.05% TFA): 0→45%) for purification to yield (3S)-7-(3-chloro-2-fluoro-6-(1H-tetrazol-1-yl)phenyl)-3-(4-(3-fluoro-2-(methoxymethyl)pyridin-4-yl)-1H-imidazol-2-yl)-2,3,8,8a-tetrahydroindolizin-5(1H)-one as a yellow solid.

LC/MS: mass calculated for $C_{25}H_{21}ClF_2N_8O_2$:538.14, measured (ES, m/z): 539.20 $[M+H]^+$. $^1H$ NMR (300 MHz, DMSO-$d_6$) δ 9.86 (s, 1H), 8.46 (d, J=5.2 Hz, 1H), 7.89-8.05 (m, 2H), 7.84 (d, J=3.6 Hz, 1H), 7.73 (dd, J=8.7, 1.5 Hz, 1H), 5.73 (d, J=2.6 Hz, 1H), 5.13 (d, J=8.9 Hz, 1H), 4.64 (d, J=2.3 Hz, 2H), 3.74-3.84 (m, 1H), 3.36 (s, 3H), 2.70-2.92 (m, 1H), 2.55-2.65 (m, 1H), 2.21-2.40 (m, 1H), 2.09-2.20 (m, 1H), 1.85-2.08 (m, 2H). $^{19}$F NMR (282 MHz, DMSO-$d_6$) δ −74.60, −112.80, −128.08.

Example 178 (3R,8aR)-7-(3-chloro-2-fluoro-6-(1H-tetrazol-1-yl)phenyl)-3-(4-chloro-5-(2-(1-hydroxycyclopropyl)pyridin-4-yl)-1H-imidazol-2-yl)-2,3,8,8a-tetrahydroindolizin-5(1H)-one

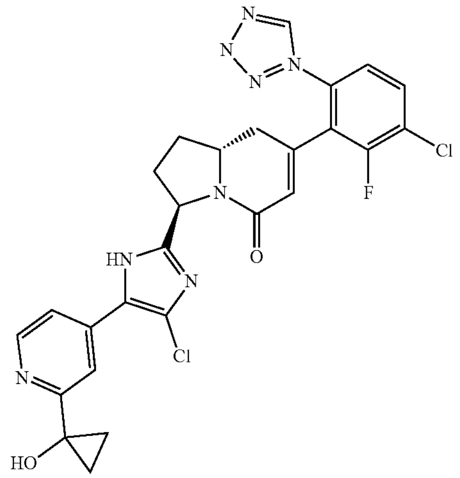

LC/MS: mass calculated for $C_{26}H_{21}Cl_2FN_8O_2$:566.11, measured (ES, m/z): 567.05 $[M+H]^+$. $^1$H NMR (300 MHz, DMSO-$d_6$) δ13.07 (s, 1H), 9.84 (s, 1H), 8.46 (d, J=5.3 Hz, 1H), 8.13 (d, J=1.8 Hz, 1H), 7.92-8.02 (m, 1H), 7.72 (dd, J=8.7, 1.5 Hz, 1H), 7.37-7.52 (m, 1H), 6.22 (s, 1H), 5.63-5.71 (m, 1H), 5.00 (d, J=8.4 Hz, 1H), 3.63-3.80 (m, 1H), 2.54-2.76 (m, 2H), 1.86-2.33 (m, 4H), 1.20-1.31 (m, 2H), 1.05-1.19 (m, 2H). $^{19}$F NMR (282 MHz, DMSO-$d_6$) δ−112.84.

Example 179 (3R,8aR)-7-(3-chloro-2-fluoro-6-(1H-tetrazol-1-yl)phenyl)-3-(4-fluoro-5-(2-(1-hydroxycyclopropyl)pyridin-4-yl)-1H-imidazol-2-yl)-2,3,8,8a-tetrahydroindolizin-5(1H)-one

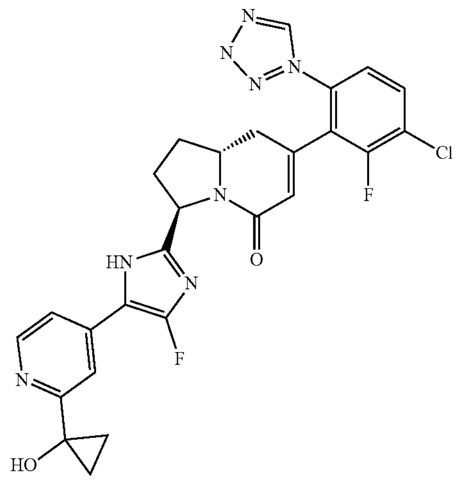

Step 1: 2-(2-(1-((tert-butyldimethylsilyl)oxy)cyclopropyl)pyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate To a solution of (8aR)-7-(3-chloro-2-fluoro-6-(1H-tetrazol-1-yl)phenyl)-5-oxo-1,2,3,5,8,8a-hexahydroindolizine-3-carboxylic acid (300 mg, 0.79 mmol, 1.0 equiv.) in $CH_3CN$ (6 mL) was added $K_2CO_3$ (165 mg, 1.19 mmol, 1.5 equiv.), followed by 2-bromo-1-(2-(1-((tert-butyldimethylsilyl)oxy)cyclopropyl)pyridin-4-yl)ethan-1-one (441 mg, 1.19 mmol, 1.5 equiv.). The mixture was stirred at room temperature for 1 h and then extracted with ethyl acetate (3×20 mL). The organic layers were combined, dried over anhydrous sodium sulfate, filtered, and concentrated under reduced pressure. The residue was purified by flash column chromatography on silica gel (0→20% MeOH/DCM) to yield 2-(2-(1-((tert-butyldimethylsilyl)oxy)cyclopropyl)pyridin-4-yl)-2-oxoethyl (8aR)-7-(3-chloro-2-fluoro-6-(1H-tetrazol-1-yl)phenyl)-5-oxo-1,2,3,5,8,8a-hexahydroindolizine-3-carboxylate as a yellow solid. LC/MS: mass calculated for $C_{32}H_{36}ClFN_6O_5Si$: 666.22, measured: 667.30 $[M+H]^+$.

Step 2: (8aR)-3-(5-(2-(1-((tert-butyldimethylsilyl)oxy)cyclopropyl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of 2-(2-(1-((tert butyldimethylsilyl)oxy)cyclopropyl)pyridin-4-yl)-2-oxoethyl (3S,8aR)-7-(3-chloro-2-fluoro-6-(1H-tetrazol-1-yl)phenyl)-5-oxo-1,2,3,5,8,8a-hexahydroindolizine-3-carboxylate (390 mg, 0.59 mmol, 1.0 equiv.) in toluene (10 mL) and acetic acid (1 mL) was added ammonium acetate (901 mg, 11.69 mmol, 20.0 equiv.). The mixture was stirred at 100° C. for 1 h. The solvent was removed under vacuum and the residue was purified by flash column chromatography on silica gel (0→20% MeOH/DCM) to yield (8aR)-3-(5-(2-(1-((tert-butyldimethylsilyl)oxy)cyclopropyl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow solid. LC/MS: mass calculated for $C_{32}H_{38}ClFN_8O_2Si$: 646.24, measured: 647.35 $[M+H]^+$.

Step 3: (8aR)-3-(5-(2-(1-((tert-butyldimethylsilyl)oxy)cyclopropyl)pyridin-4-yl)-4-fluoro-1H-imidazol-2-yl)-7-(3-chloro-2-fluoro-6-(1H-tetrazol-1-yl)phenyl)-2,3,8,8a-tetrahydroindolizin-5(1H)-one To a solution of (8aR)-3-(5-(2-(1-((tert-butyldimethylsilyl)oxy)cyclopropyl)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (150 mg, 0.23 mmol, 1.0 equiv.) in $CH_3CN$ (5 mL) was added 1-chloromethyl-4-fluoro-1,4-diazoniabicyclo[2.2.2]octane bis(tetrafluoroborate) (82 mg, 0.23 mmol, 1.0 equiv.). The mixture was stirred at 60° C. for 1 h, partitioned between water and EtOAc (3×20 mL). The organic layers were combined, dried over anhydrous sodium sulfate, filtered, and concentrated under reduced pressure. The residue was purified by flash column chromatography on silica gel (0→20% MeOH/DCM) to yield the (8aR)-3-(5-(2-(1-((tert-butyldimethylsilyl)oxy)cyclopropyl)pyridin-4-yl)-4-fluoro-1H-imidazol-2-yl)-7-(3-chloro-2-fluoro-6-(1H-tetrazol-1-yl)phenyl)-2,3,8,8a-tetrahydroindolizin-5 (1H one as a yellow solid. LC/MS: mass calculated for $C_{32}H_{35}ClF_2N_8O_2Si$: 664.23, measured: 656.40 $[M+H]^+$.

Step 4: (3'R,8aR)-7-(3-chloro-2-fluoro-6-(1H-tetrazol-1-yl)phenyl)-3-(4-fluoro-5-(2-(1-hydroxycyclopropyl)pyridin-4-yl)-1H-imidazol-2-yl)-2,3,8,8a-tetrahydroindolizin-5(1H)-one To a solution of 8aR)-3-(5-(2-(1-((tert-butyldimethylsilyl)oxy)cyclopropyl)pyridin-4-yl)-4-fluoro-1H-imidazol-2-yl)-7-(3-chloro-2-fluoro-6-(1H-tetrazol-1-yl)phenyl)-2,3,8,8a-tetrahydroindolizin-5(1H-one (80 mg, 0.12 mmol, 1.0 equiv.) in THE (4 mL) was added triethylamine trihydrofluoride (1 mL). The residue was purified by reverse phase chromatography on C18 ($CH_3CN$/water (0.05% TFA) 5%→50%) to yield a residue, which was purified by chiral-HPLC with Hex (0.1% DEA):EtOH=50:50 to yield (3'R, 8aR)-7-(3-chloro-2-fluoro-6-(1H-tetrazol-1-yl)phenyl)-3-(4-fluoro-5-(2-(1-hydroxycyclopropyl)pyridin-4-yl)-1H-imidazol-2-yl)-2,3,8,8a-tetrahydroindolizin-5(1H)-one as an off-white solid.

LC/MS: mass calculated for $C_{26}H_{21}ClF_2N_8O_2$:550.14, measured (ES, m/z): 551.0 $[M+H]^+$. $^1H$ NMR (300 MHz, DMSO-$d_6$) δ 12.96 (s, 1H), 9.84 (s, 1H), 8.40 (d, J=5.3 Hz, 1H), 7.88-8.04 (m, 2H), 7.72 (dd, J=8.7, 1.5 Hz, 1H), 7.23-7.35 (m, 1H), 6.23 (s, 1H), 5.64-5.71 (m, 1H), 4.96 (d, J=8.4 Hz, 1H), 3.63-3.81 (m, 1H), 2.54-2.62 (m, 2H), 2.21-2.31 (m, 1H), 2.08-2.20 (m, 1H), 1.95-2.07 (m, 1H), 1.87-1.94 (m, 1H), 1.19-1.30 (m, 2H), 0.99-1.18 (m, 2H). $^{19}F$ NMR (282 MHz, DMSO-$d_6$) δ −112.93, −127.09.

Example 180 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoro-N-(2-methoxyethyl)picolinamide

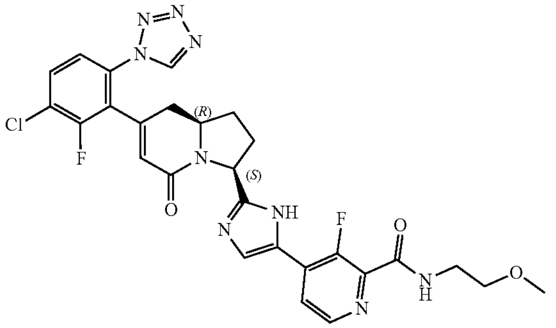

LC/MS: mass calculated for $C_{27}H_{24}ClF_2N_9O_3$: 595.17, measured: (ES, m/z) 596.15 $[M+H]^+$. $^1H$ NMR (300 MHz, DMSO-$d_6$) δ 9.84 (s, 1H), 8.66 (d, J=5.4 Hz, 1H), 8.46 (d, J=5.0 Hz, 1H), 8.05-8.15 (m, 1H), 7.98 (dd, J=8.7, 7.8 Hz, 1H), 7.67-7.79 (m, 2H), 5.71 (d, J=2.6 Hz, 1H), 5.09 (d, J=8.8 Hz, 1H), 3.62-3.81 (m, 3H), 3.25-3.50 (m, 5H), 2.53-2.83 (m, 2H), 1.91-2.29 (m, 4H). $^{19}F$ NMR (282 MHz, DMSO-$d_6$) δ −112.81, −125.50.

Example 181 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinamide

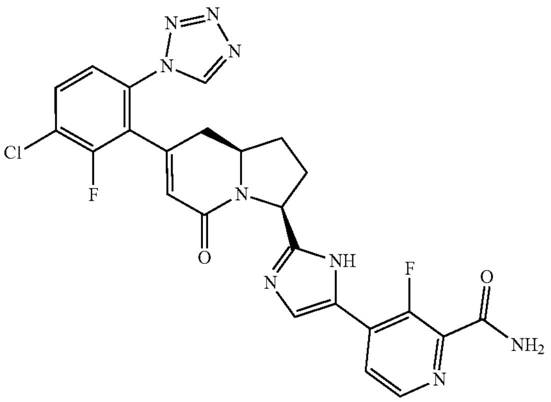 [SMILES: NC(=O)c1nccc(-c2cnc([C@@H]3CC[C@@H]4CC(c5c(-n6cnnn6)ccc(Cl)c5F)=CC(=O)N43)[nH]2)c1F]

LC/MS: mass calculated for $C_{24}H_{18}ClF_2N_6O_2$: 537.12, measured (ES, m/z): 538.10 $[M+H]^+$. $^1H$ NMR (300 MHz, DMSO-$d_6$) δ 9.84 (s, 1H), 8.46 (d, J=4.9 Hz, 1H), 8.03-8.12 (m, 2H), 7.98 (dd, J=8.7, 7.8 Hz, 1H), 7.80 (d, J=3.8 Hz, 1H), 7.68-7.72 (m, 2H), 5.72 (d, J=2.6 Hz, 1H), 5.11 (d, J=8.9 Hz, 1H), 3.03-3.18 (m, 1H), 2.73-2.91 (m, 1H), 2.51-2.57 (m, 1H), 2.23-2.29 (m, 1H), 2.07-2.16 (m, 1H), 1.92-2.05 (m, 2H). $^{19}F$ NMR (282 MHz, DMSO-$d_6$) δ −112.80, −125.36.

Example 182 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid

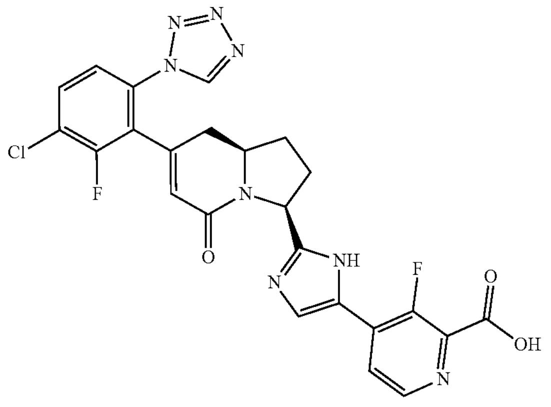 [SMILES: O=C(O)c1nccc(-c2cnc([C@@H]3CC[C@@H]4CC(c5c(-n6cnnn6)ccc(Cl)c5F)=CC(=O)N43)[nH]2)c1F]

Step 1: 2-(((tert-butyldimethylsilyl)oxy)methyl)-4-(1-ethoxyvinyl)-3-fluoropyridine Under an inert atmosphere of nitrogen, a mixture of 2-(((tert-butyldimethylsilyl)oxy)methyl)-3-fluoro-4-iodopyridine (24.0 g, 65.35 mmol, 1.0 equiv.), tributyl(1-ethoxyvinyl)stannane (47.2 g, 130.69 mmol, 2.0 equiv.) and $Pd(PPh_3)_2Cl_2$ (4.6 g, 6.53 mmol, 0.1 equiv.) in 1,4-dioxane (300 mL) was stirred at 100° C. for 2 h, cooled to room temperature, and concentrated. The residue was purified by flash column chromatography on silica gel (0→20% EA/PE) to yield 2-(((tert-butyldimethylsilyl)oxy)methyl)-4-(1-ethoxyvinyl)-3-fluoropyridine as a light yellow oil.

Step 2: 2-bromo-1-(2-(((tert-butyldimethylsilyl)oxy)methyl)-3-fluoropyridin-4-yl)ethan-1-one To a mixture of 2-(((tert butyldimethylsilyl)oxy)methyl)-4-(1-ethoxyvinyl)-3-fluoropyridine (5.6 g, 17.98 mmol, 1.0 equiv.) in THE (100 mL) and $H_2O$ (30 mL) was added NBS (3.2 g, 17.98 mmol, 1.0 equiv.). The reaction mixture was stirred at room temperature for 1 h. The reaction mixture was diluted with EA (500 mL), washed with brine (3×100 mL), dried over $Na_2SO_4$, and concentrated to yield 2-bromo-1-(2-(((tert-butyldimethylsilyl)oxy)methyl)-3-fluoropyridin-4-yl)ethan-1-one as an off-white solid.

Step 3: 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (2.4 g, 7.39 mmol, 1.0 equiv.) and $Cs_2CO_3$ (1.4 g, 4.43 mmol, 0.6 equiv.) in DMF (60 mL) was stirred at 40° C. for 30 min. Then 2-bromo-1-(2-(((tert-butyldimethylsilyl)oxy)methyl)-3-fluoropyridin-4-yl)ethan-1-one (4.0 g, 11.08 mmol, 1.5 equiv.) was added to the mixture. The reaction mixture was stirred at room temperature. for 4 h. The resulting mixture was then diluted with EA (600 mL), washed with water (3×150 mL), brine (2×150 mL), dried over $Na_2SO_4$, and concentrated under reduced pressure. The residue was purified by flash column chromatography on silica gel (0→10% MeOH/DCM) to yield 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as a light yellow solid. LC/MS: mass calculated for $C_{29}H_{34}ClF_2N_3O_5Si$: 605.19, measured: 606.15 $[M+H]^+$.

Step 4: (3S)-7-(6-amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one Under an inert atmosphere of nitrogen, a mixture of 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (3.0 g, 4.95 mmol, 1.0 equiv.) and $NH_4OAc$ (3.0 g, 39.59 mmol, 8.0 equiv.) in AcOH (10 mL) and toluene (100 mL) was stirred at 110° C. for 1 h, then cooled to room temperature, and concentrated under reduced pressure. The residue was purified by flash column chromatography on silica gel (0→8% MeOH/DCM) to yield (3S)-7-(6-amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one as a light yellow solid.

Step 5: (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one A mixture of (3S)-7-(6-amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one (1.8 g, 3.07 mmol, 1.0 equiv.), $TMSN_3$ (3.5 g, 30.71 mmol, 10.0 equiv.) and trimethoxymethane (3.2 g, 30.70 mmol, 10. 0 equiv.) in AcOH (60 mL) was stirred at 55° C. overnight, then concentrated under reduced pressure. The residue was purified by reverse phase chromatography on C18 column (ACN/$H_2O$ (0.05% $NH_4HCO_3$): 0→40%) and purified to yield a residue, which was further purified by prep-SFC to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one as a white solid. LC/MS: mass calculated for $C_{24}H_{19}ClF_2N_8O_2$: 524.13, measured: 525.05 $[M+H]^+$.

Step 6: 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid To a mixture of (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one (1.2 g, 2.28 mmol, 1.0 equiv.) in DCM (60 mL) and $H_2O$ (30 mL) was added TEMPO (179 mg, 1.15 mmol, 0.5 equiv.) and $PhI(OAc)_2$ (2.2 g, 6.83 mmol, 3.0 equiv.). The reaction mixture was stirred at room temperature for 2 h, concentrated under reduced pressure. The residue was loaded onto a C18 reverse column (330 g, ACN/$H_2O$ (0.05% $NH_4HCO_3$): 0→25%) and purified to yield 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropicolinic acid as a white solid.

LC/MS: mass calculated for $C_{24}H_{17}ClF_2N_8O_3$: 538.11, measured (ES, m/z): 539.05 $[M+H]^+$. $^1H$ NMR (400 MHz, DMSO-$d_6$) δ 12.30 (br, 1H), 9.85 (s, 1H), 8.28 (d, J=8.0 Hz, 1H), 7.93-8.01 (m, 1H), 7.84-7.92 (m, 1H), 7.71 (d, J=8.7 Hz, 1H), 7.55 (d, J=4.0 Hz, 1H), 5.69 (d, J=2.7 Hz, 1H), 5.05 (d, J=8.8 Hz, 1H), 3.65-3.85 (m, 1H), 2.63-2.86 (m, 1H), 2.52-2.62 (m, 1H), 2.15-2.19 (m, 1H), 2.05-2.14 (m, 1H), 1.89-2.05 (m, 2H). $^{19}F$ NMR (376 MHz, DMSO-$d_6$) δ −112.81, −127.49.

Example 183 (3S,8aR)-7-(3-chloro-2-fluoro-6-(1H-tetrazol-1-yl)phenyl)-3-(5-(3-fluoro-2-((1-hydroxycyclopropyl)methoxy)pyridin-4-yl)-1H-imidazol-2-yl)-2,3,8,8a-tetrahydroindolizin-5(1H)-one

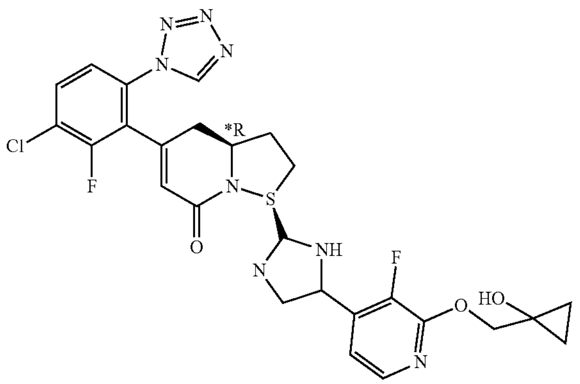

Step 1: Methyl 1-((tetrahydro-2H-pyran-2-yl)oxy)cyclopropane-1-carboxylate

To a solution of methyl 1-hydroxycyclopropane-1-carboxylate (1.0 g, 8.61 mmol, 1.0 equiv.) in DCM (20 mL) was added 3,4-dihydro-2H-pyran (0.8 g, 9.47 mmol, 1.1 equiv.), PPTS (0.2 g, 0.86 mmol, 0.1 equiv.). The reaction mixture was stirred at room temperature for 3 h, then concentrated under vacuum to yield a clear oil, which was dissolved in diethyl ether (50 mL), washed with saturated aqueous brine solution (25 mL), dried over sodium sulfate and concentrated under reduced pressure to yield methyl 1-((tetrahydro-2H-pyran-2-yl)oxy)cyclopropane-1-carboxylate as colorless oil.

Step 2: (1-((tetrahydro-2H-pyran-2-yl)oxy)cyclopropyl)methanol

To a solution of methyl 1-((tetrahydro-2H-pyran-2-yl)oxy)cyclopropane-1-carboxylate (1.1 g, 5.49 mmol, 1 equiv.) in diethyl ether (20 mL) was added 1 M lithium aluminum hydride in THE (5.8 mL, 5.77 mmol, 1.05 equiv.). The reaction was heated at reflux under nitrogen for 2 h. Upon cooling to 25° C., the mixture was poured into ice water. The organic layer was separated, washed with water (2×20 mL), dried over $Na_2SO_4$ and concentrated under reduced pressure to yield (1-((tetrahydro-2H-pyran-2-yl)oxy)cyclopropyl)methanol as colorless oil.

Step 3: 3-fluoro-4-iodo-2-((1-((tetrahydro-2H-pyran-2-yl)oxy)cyclopropyl)methoxy)pyridine A solution of (1-((tetrahydro-2H-pyran-2-yl)oxy)cyclopropyl)methanol (650 mg, 3.77 mmol, 1.2 equiv.) in DMF (8 mL) was added to sodium hydride (150 mg, 3.77 mmol, 1.2 equiv.) under $N_2$. After the mixture was stirred for 30 min, 2,3-difluoro-4-iodopyridine (758 mg, 3.14 mmol, 1.0 equiv.) was added to the mixture. The resulting mixture was stirred at room temperature for 2 h, then quenched with water, extracted with EA. The combined organic layer was washed with brine, dried over $Na_2SO_4$, and concentrated under vacuum. The residue was purified by flash column chromatography on silica gel (0-080% EA/PE) to yield 3-fluoro-4-iodo-2-((1-((tetrahydro-2H-pyran-2-yl)oxy)cyclopropyl)methoxy)pyridine as colorless oil. LC/MS: mass calculated for $C_{14}H_{17}FI_2NO_3$: 393.02, measured: 394.00 $[M+H]^+$.

Step 4: 4-(1-ethoxyvinyl)-3-fluoro-2-((1-((tetrahydro-2H-pyran-2-yl)oxy)cyclopropyl)methoxy)pyridine To a solution of 3-fluoro-4-iodo-2-((1-((tetrahydro-2H-pyran-2-yl)oxy)cyclopropyl)methoxy)pyridine (0.9 g, 2.29 g, 1.0 equiv.) in 1,4-dioxane (15 mL) was added 1-ethoxyvinyl-tri-n-butyltin (0.9 g, 2.52 mmol, 1.1 equiv.) followed by $Pd(PPh_3)_4$ (0.26 g, 0.23 mmol, 0.1 equiv.) under $N_2$. The reaction mixture was stirred overnight at 100° C., then cooled to room temperature, quenched with water, extracted with EA, dried over $Na_2SO_4$. and concentrated under vacuum. The residue was purified by flash column chromatography on silica gel with (0→20% EA/PE) to yield 4-(1-ethoxyvinyl)-3-fluoro-2-((1-((tetrahydro-2H-pyran-2-yl)oxy)cyclopropyl)methoxy)pyridine as colorless oil. LC/MS: mass calculated for $C_{18}H_{24}FNO_4$: 337.17, measured: 338.10 $[M+H]^+$.

Step 5: 2-bromo-1-(3-fluoro-2-((1-((tetrahydro-2H-pyran-2-yl)oxy)cyclopropyl)methoxy)pyridin-4-yl)ethan-1-one To a solution of 4-(1-ethoxyvinyl)-3-fluoro-2-((1-((tetrahydro-2H-pyran-2-yl)oxy)cyclopropyl)methoxy)pyridine (620 mg, 1.84 mmol, 1.0 equiv.) in THE (10 mL) and water (3 mL) was added NBS (392 mg, 2.21 mmol, 1.2 equiv.). The mixture was stirred at room temperature for 2 h, then quenched with water, extracted with EA, washed with brine, dried over $Na_2SO_4$, and concentrated under vacuum. The residue was purified by flash column chromatography on silica gel with (0→50% EA/PE) to yield 2-bromo-1-(3-fluoro-2-((1-((tetrahydro-2H-pyran-2-yl)oxy)cyclopropyl)methoxy)pyridin-4-yl)ethan-1-one as colorless oil. LC/MS: mass calculated for $C_{16}H_{19}BrFNO_4$: 387.05, measured: 388.00 $[M+H]^+$, 390.00 $[M+H+2]^+$ Step 6: 2-(3-fluoro-2-((1-((tetrahydro-2H-pyran-2-yl)oxy)cyclopropyl)methoxy)pyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate To a solution of (3S)-7-(3-chloro-2-fluoro-6-(1H-tetrazol-1-yl)phenyl)-5-oxo-1,2,3,5,8,8a-hexahydroindolizine-3-carboxylic acid (200 mg, 0.53 mmol, 1.0 equiv.) in DMF (5 mL) was added potassium carbonate (88 mg, 0.64 mmol, 1.2 equiv.), followed by 2-bromo-1-(3-fluoro-2-((1-((tetrahydro-2H-pyran-2-yl)oxy)cyclopropyl)methoxy)pyridin-4-yl)ethan-1-one (267 mg, 0.69 mmol, 1.3 equiv.). The reaction mixture was stirred at room temperature for 2 h, then purified by reverse column chromatography on C18 column (330 g, $CH_3CN$/water (0.05% $CH_3COOH$): 5→70%) to yield 2-(3-fluoro-2-((1-((tetrahydro-2H-pyran-2-yl)oxy)cyclopropyl)methoxy)pyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate as an off-white solid. LC/MS: mass calculated for $C_{32}H_{31}ClF_2N_6O_7$: 684.19, measured: 685.10 $[M+H]^+$.

Step 7: (3S)-7-(3-chloro-2-fluoro-6-(1H-tetrazol-1-yl)phenyl)-3-(5-(3-fluoro-2-((1-((tetrahydro-2H-pyran-2-yl)oxy)cyclopropyl)methoxy)pyridin-4-yl)-1H-imidazol-2-yl)-2,3,8,8a-tetrahydroindolizin-5(1H)-one To a solution of 2-(3-fluoro-2-((1-((tetrahydro-2H-pyran-2-yl)oxy)cyclopropyl)methoxy)pyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate (210 mg, 0.31 mmol, 1.0 equiv.) in toluene (15 mL) was added ammonium acetate (473 mg, 6.13 mmol, 20.0 equiv.) followed by the addition of acetic acid (0.4 mL) under $N_2$. The reaction mixture was stirred for 1 h at 100° C., then cooled to room temperature. and concentrated under vacuum. The residue was purified by silica gel chromatography with (0→10% MeOH/DCM) to yield (3S)-7-(3-chloro-2-fluoro-6-(1H-tetrazol-1-yl)phenyl)-3-(5-(3-fluoro-2-((1-((tetrahydro-2H-pyran-2-yl)oxy)cyclopropyl)methoxy)pyridin-4-yl)-1H-imidazol-2-yl)-2,3,8,8a-tetrahydroindolizin-5(1H)-one as a light yellow solid. LC/MS: mass calculated for $C_{32}H_{31}ClF_2N_8O_4$: 664.21, measured: 665.10 $[M+H]^+$.

Step 8: (3S,8a*R)-7-(3-chloro-2-fluoro-6-(1H-tetrazol-1-yl)phenyl)-3-(5-(3-fluoro-2-((1-hydroxycyclopropyl)methoxy)pyridin-4-yl)-1H-imidazol-2-yl)-2,3,8,8a-tetrahydroindolizin-5(1H)-one To a solution of (3S)-7-(3-chloro-2-fluoro-6-(1H-tetrazol-1-yl)phenyl)-3-(5-(3-fluoro-2-((1-((tetrahydro-2H-pyran-2-yl)oxy)cyclopropyl)methoxy)pyridin-4-yl)-1H-imidazol-2-yl)-2,3,8,8a-tetrahydroindolizin-5(1H)-one (150 mg, 0.23 mmol, 1.0 equiv.) in THE (5 mL) was added 2 M HCl (1 mL). The mixture was stirred at room temperature for 1 h, then purified by reverse column chromatography on C18 column (330 g, $CH_3CN$/water (5 mM $NH_4HCO_3$): 5→70%) to yield (3S,8a*R)-7-(3-chloro-2-fluoro-6-(1H-tetrazol-1-yl)phenyl)-3-(5-(3-fluoro-2-((1-hydroxycyclopropyl)methoxy)pyridin-4-yl)-1H-imidazol-2-yl)-2,3,8,8a-tetrahydroindolizin-5(1H)-one as a white solid.

LC/MS: mass calculated for. $C_{27}H_{23}ClF_2N_8O_3$:580.15, measured: (ES, m/z): 581.10 $[M+H]^+$. NMR: (400 MHz, DMSO-$d_6$): δ 12.27 (s, 1H), 9.84 (s, 1H), 7.97 (dd, J=8.7, 7.8 Hz, 1H), 7.89 (d, J=5.3 Hz, 1H), 7.71 (dd, J=8.7, 1.5 Hz, 1H), 7.49-7.58 (m, 2H), 5.69 (d, J=2.7 Hz, 1H), 5.60 (s, 1H), 5.03 (d, J=8.7 Hz, 1H), 4.36 (s, 2H), 3.65-3.80 (m, 1H), 2.65-2.79 (m, 1H), 2.55 (d, J=4.2 Hz, 1H), 2.06-2.26 (m, 2H), 1.90-2.05 (m, 2H), 0.61-0.73 (m, 4H). $^{19}F$ NMR: (376 MHz, DMSO-$d_6$): δ −112.88, −142.68.

Example 184 (3S,8aR)-3-(5-bromo-4-(3-fluoro-2-(hydroxymethyl-d2)pyridin-4-yl)-1H-imidazol-2-yl)-7-(3-choro-2-fluoro-6-(1H-tetrazol-1-yl)phenyl)-2,3,8,8a-tetrahydroindolizin-5(1H)-one

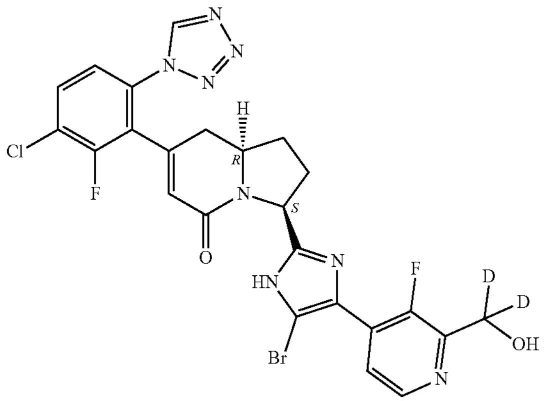

LC/MS calculated for $C_{24}H_{18}BrClF_2N_8O_2$ 604.1, measured 605.1 ($MH^+$) and 607.0 $(MH+2)^+$. $^1H$ NMR (400 MHz, METHANOL-d4) δ 9.60 (s, 1H), 8.54 (d, J=5.87 Hz, 1H), 8.13-8.20 (m, 1H), 7.81-7.90 (m, 1H), 7.53-7.63 (m, 1H), 5.74 (d, J=2.93 Hz, 1H), 5.16 (d, J=8.80 Hz, 1H), 3.87-4.03 (m, 1H), 2.86-3.00 (m, 1H), 2.60-2.71 (m, 1H), 2.07-2.43 (m, 4H).

Example 185 (3S,8aR)-7-(3-chloro-2-fluoro-6-(1H-tetrazol-1-yl)phenyl)-3-(5-(3-fluoro-2-((R)-1-hydroxyethyl)pyridin-4-yl)-1H-imidazol-2-yl)-2,3,8,8a-tetrahydroindolizin-5(1H)-one

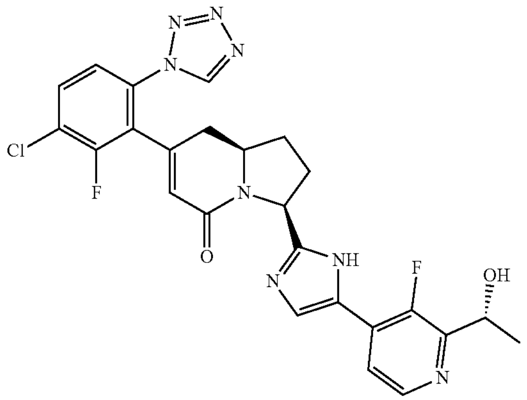 [SMILES: C[C@@H](O)c1nccc(-c2cnc([C@@H]3CC[C@@H]4CC(c5c(-n6cnnn6)ccc(Cl)c5F)=CC(=O)N43)[nH]2)c1F]

LC/MS: mass calculated for: $C_{25}H_{21}ClF_2N_8O_2$:538.14, (ES, m/z): 539.15 $[M+H]^+$. $^1H$ NMR (300 MHz, DMSO-$d_6$) δ12.25 (s, 1H), 9.84 (s, 1H), 8.35 (dd, J=5.1, 0.9 Hz, 1H), 7.98 (dd, J=8.7, 7.7 Hz, 1H), 7.82-7.92 (m, 1H), 7.72 (dd, J=8.7, 1.6 Hz, 1H), 7.57 (d, J=3.3 Hz, 1H), 5.70 (d, J=2.6 Hz, 1H), 5.15-5.29 (m, 1H), 5.01-5.10 (m, 2H), 3.67-3.79 (m, 1H), 2.69-2.78 (m, 1H), 2.53-2.58 (m, 1H), 2.06-2.27 (m, 2H), 1.92-2.01 (m, 2H), 1.44 (d, J=6.4 Hz, 3H). $^{19}F$ NMR (282 MHz, DMSO-$d_6$) δ−112.91, −130.78.

Example 186 (3S,8aR)-7-(3-chloro-2-fluoro-6-(1H-tetrazol-1-yl)phenyl)-3-(5-(3-fluoro-2-((S)-1-hydroxyethyl)pyridin-4-yl)-1H-imidazol-2-yl)-2,3,8,8a-tetrahydroindolizin-5(1H)-one

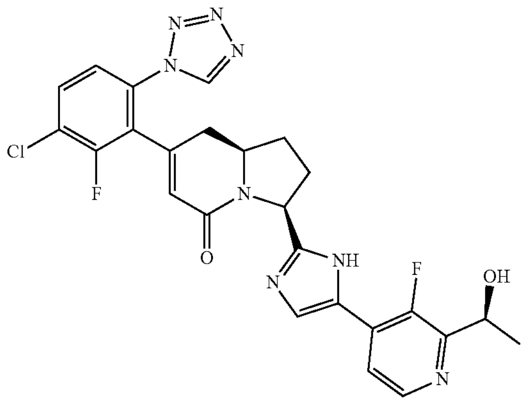 [SMILES: C[C@H](O)c1nccc(-c2cnc([C@@H]3CC[C@@H]4CC(c5c(-n6cnnn6)ccc(Cl)c5F)=CC(=O)N43)[nH]2)c1F]

Step 1: 1-(3-fluoropyridin-2-yl)ethan-1-ol

Under an inert atmosphere of nitrogen, $CH_3MgBr$ (80 mL) was added to a solution of 3-fluoropicolinaldehyde (10.0 g, 79.98 mmol, 1.0 equiv.) in THF (150 mL) 0° C. The reaction mixture was stirred overnight at room temperature, then quenched with water and extracted with ethyl acetate. The combined organic layer was washed with brine, dried over $Na_2SO_4$, and concentrated under reduced pressure. The residue was purified by flash column chromatography on silica gel (0-00% MeOH/DCM) to yield 1-(3-fluoropyridin-2-yl)ethan-1-ol as a yellow solid.

Step 2: 2-(1-((tert-butyldimethylsilyl)oxy)ethyl)-3-fluoropyridine

To a solution of 1-(3-fluoropyridin-2-yl)ethan-1-ol (8.5 g, 60.22 mmol, 1.0 equiv.) in DMF (300 mL) were added TBSCl (13.6 g, 90.33 mmol, 1.0 equiv.) and 1H-imidazole (6.1 g, 90.33 mmol, 1.5 equiv.). The reaction mixture was stirred overnight at room temperature and then quenched with water and extracted with ethyl acetate. The combined organic layer was washed with brine, dried over $Na_2SO_4$ and concentrated. The residue was purified by flash column chromatography on silica gel (0-000% EA/PE) to yield 2-(1-((tert butyldimethylsilyl)oxy)ethyl)-3-fluoropyridine as a yellow solid.

Step 3: 2-(1-((tert-butyldimethylsilyl)oxy)ethyl)-3-fluoro-4-iodopyridine

LDA (4.7 mL, 2.0 M) was added to a solution of 2-(1-((tert-butyldimethylsilyl)oxy)ethyl)-3-fluoropyridine (2.0 g, 7.83 mol, 1.0 equiv.) in THF (30 mL) at −78° C. under $N_2$. After 30 min, 12 (2.4 g, 9.40 mmol, 1.2 equiv.) in THF (5 mL) was added to the above mixture and the resulting mixture was stirred for 1 h, then quenched by the addition of saturated ammonium chloride aqueous solution and extracted with ethyl acetate twice. The combined organic layers were washed with brine, dried over $Na_2SO_4$, concentrated under reduced pressure. The residue was purified by flash column chromatography on silica gel (0→100% EA/PE) to yield 2-(1-((tert-butyldimethylsilyl)oxy)ethyl)-3-fluoro-4-iodopyridine as a yellow solid.

Step 4: 2-(1-((tert butyldimethylsilyl)oxy)ethyl)-4-(1-ethoxyvinyl)-3-fluoropyridine Under an inert atmosphere of nitrogen, to a solution of 2-(1-((tert-butyldimethylsilyl)oxy)ethyl)-3-fluoro-4-iodopyridine (1.6 g, 4.20 mmol, 1.0 equiv.) in 1,4-dioxane (20 mL) were added tributyl(1-ethoxyvinyl)stannane (2.0 g, 5.46 mmol, 1.3 equiv.) and $Pd(PPh_3)_4$ (485 mg, 0.42 mmol, 0.1 equiv.). The reaction mixture was stirred for 8 h at 100° C., cooled to room temperature, and concentrated under reduced pressure. The residue was purified by flash column chromatography on silica gel (0→10% EA/PE) to yield 2-(1-((tert-butyldimethylsilyl)oxy)ethyl)-3-fluoro-4-iodopyridine as a yellow oil.

Step 5: 2-bromo-1-(2-(1-((tert-butyldimethylsilyl)oxy)ethyl)-3-fluoropyridin-4-yl)ethan-1-one NBS (601 mg, 3.38 mmol, 1.0 equiv.) was added to a solution of 2-(1-((tert-butyldimethylsilyl)oxy)ethyl)-4-(1-ethoxyvinyl)-3-fluoropyridine (1.0 g, 3.38 mmol, 1.0 equiv.) in THF (10 mL) with $H_2O$ (5 mL) at 0° C. The reaction mixture was stirred at room temperature for 1 h, quenched with brine, and extracted with EA three times. The organic layer was washed with brine three times, concentrated under reduced pressure. The residue was purified on flash column chromatography on silica gel (0→100% EA/PE) to yield 2-bromo-1-(2-(1-((tert-butyldimethylsilyl)oxy)ethyl)-3-fluoropyridin-4-yl)ethan-1-one as a yellow solid.

Step 6: 2-(2-(1-((tert-butyldimethylsilyl)oxy)ethyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate To a solution of (3S)-7-(3-chloro-2-fluoro-6-(1H-tetrazol-1-yl)phenyl)-5-oxo-1,2,3,5,8,8a-hexahydroindolizine-3-carboxylic acid (500 mg, 1.32 mmol, 1.0 equiv.) in DMF (10 mL) were added 2-bromo-1-(2-(1-((tert-butyldimethylsilyl)oxy)ethyl)-3-fluoropyridin-4-yl)ethan-1-one (598 mg, 1.59 mmol, 1 equiv.) and $Cs_2CO_3$ (259 mg, 0.79 mmol, 0.6 equiv.). The reaction mixture was stirred overnight at room temperature, then quenched with water and extracted with ethyl acetate. The combined organic layer was washed with brine, dried over $Na_2SO_4$ and concentrated. The residue was purified on flash column chromatography on silica gel (0→30% MeOH/DCM) to yield 2-(2-(1-((tert-butyldimethylsilyl)oxy)ethyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate as a yellow solid.

Step 7: (3S)-3-(5-(2-(1-((tert butyldimethylsilyl)oxy)ethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of 2-(2-(1-((tert-butyldimethylsilyl)oxy)ethyl)-3-fluoropyridin-4-yl)-2-oxoethyl (3S)-7-(3-chloro-2-fluoro-6-(1H-tetrazol-1-yl)phenyl)-5-oxo-1,2,3,5,8,8a-hexahydroindolizine-3-carboxylate (250 mg, 0.37 mmol, 1.0 equiv) in toluene (5.0 mL) with $CH_3COOH$ (0.5 mL) was added $NH_4OAc$ (286 mg, 3.71 mmol, 10.0 equiv.). The reaction mixture was stirred for 2 h at 110° C., then quenched with water and extracted with ethyl acetate. The combined organic layer was washed with brine, dried over $Na_2SO_4$ and concentrated. The residue was purified by silica gel chromatography (0→30% MeOH/DCM) to yield (3S)-3-(5-(2-(1-((tert-butyldimethylsilyl)oxy)ethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow oil.

Step 8: (3S,8a*R)-7-(3-chloro-2-fluoro-6-(1H-tetrazol-1-yl)phenyl)-3-(5-(3-fluoro-2-((*S)-1-hydroxyethyl)pyridin-4-yl)-1H-imidazol-2-yl)-2,3,8,8a-tetrahydroindolizin-5(1H)-one $Et_3N \cdot 3HF$ (50 mg, 0.34 mmol, 2.0 equiv.) was added to a solution of (3S)-3-(5-(2-(1-((tert-butyldimethylsilyl)oxy)ethyl)-3-fluoropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (110 mg, 0.17 mmol, 1.0 equiv.) in THE (3.0 mL). The reaction mixture was stirred at 80° C. for 3 h, then quenched with brine, extracted with MeOH/DCM=1:10 (v/v) three times. The organic layer was washed with brine three times, concentrated under reduced pressure. The residue was purified by flash column chromatography on silica gel (0→10% MeOH/DCM) to yield (3S,8a*R)-7-(3-chloro-2-fluoro-6-(1H-tetrazol-1-yl)phenyl)-3-(5-(3-fluoro-2-(('S)-1-hydroxyethyl)pyridin-4-yl)-1H-imidazol-2-yl)-2,3,8,8a-tetrahydroindolizin-5(1H)-one of yellow solid.

LC/MS: mass calculated for. $C_{25}H_{21}ClF_2N_8O_2$:538.14, measured: (ES, m/z): 539.15 $[M+H]^+$. $^1H$ NMR (300 MHz, DMSO-$d_6$) δ 12.25 (s, 1H), 9.84 (s, 1H), 8.35 (d, J=5.0 Hz, 1H), 7.98 (dd, J=8.7, 7.8 Hz, 1H), 7.90-7.85 (m, 1H), 7.72 (dd, J=8.7, 1.5 Hz, 1H), 7.57 (d, J=3.6 Hz, 1H), 5.70 (d, J=2.5 Hz, 1H), 5.20 (d, J=5.9 Hz, 1H), 5.02-5.11 (m, 2H), 3.68-3.79 (m, 1H), 2.65-2.77 (m, 1H), 2.53-2.57 (m, 1H), 2.09-2.29 (m, 2H), 1.94-2.01 (m, 2H), 1.44 (d, J=6.5 Hz, 3H). $^{19}F$ NMR (282 MHz, DMSO-$d_6$) δ−112.86, −130.80.

Example 187 (3R,8aS)-7-(3-chloro-2-fluoro-6-(1H-tetrazol-1-yl)phenyl)-3-(5-(3-fluoro-2-((R)-3-hydroxypiperidin-1-yl)pyridin-4-yl)-1H-imidazol-2-yl)-2,3,8,8a-tetrahydroindolizin-5(1H)-one

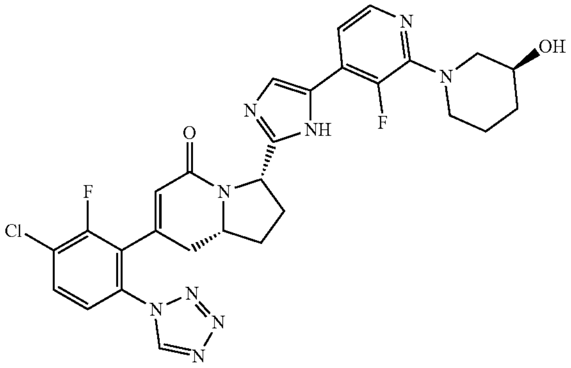 [SMILES: O=C1C=C(c2c(-n3cnnn3)ccc(Cl)c2F)C[C@H]2CC[C@@H](c3ncc(-c4ccnc(N5CCC[C@H](O)C5)c4F)[nH]3)N12]

LC/MS: mass calculated for. $C_{28}H_{26}ClF_2N_9O_2$:593.19, measured: (ES, m/z): 594.15 $[M+H]^+$. $^1H$ NMR: (400 MHz, Acetic Acid-$d_4$) δ 9.33 (s, 1H), 7.88 (d, J=5.9 Hz, 1H), 7.58-7.72 (m, 2H), 7.38 (dd, J=8.7, 1.5 Hz, 1H), 7.31-7.28 (m, 1H), 5.82 (d, J=2.0 Hz, 1H), 5.24 (t, J=8.0 Hz, 1H), 4.12-4.25 (m, 1H), 3.85-3.93 (m, 1H), 3.65-3.72 (m, 1H), 3.45-3.59 (m, 1H), 3.23-3.35 (m, 2H), 2.42-2.55 (m, 3H), 2.18-2.35 (m, 2H), 1.83-1.85 (m, 2H), 1.72-1.76 (m, 1H), 1.47-1.61 (m, 2H). $^{19}F$ NMR: (376 MHz, Acetic Acid-$d_4$) δ−76.41, −112.74, −129.56

Example 188 (3R,8aR)-7-(3-chloro-2-fluoro-6-(1H-tetrazol-1-yl)phenyl)-3-(5-(3-fluoro-2-((S)-3-hydroxypiperidin-1-yl)pyridin-4-yl)-1H-imidazol-2-yl)-2,3,8,8a-tetrahydroindolizin-5(1H)-one

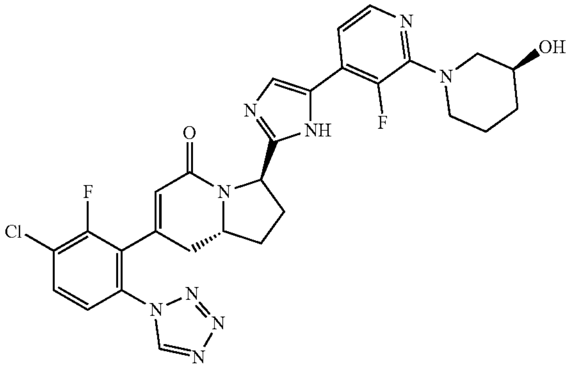 [SMILES: O=C1C=C(c2c(-n3cnnn3)ccc(Cl)c2F)C[C@H]2CC[C@H](c3ncc(-c4ccnc(N5CCC[C@H](O)C5)c4F)[nH]3)N12]

LC/MS: mass calculated for. $C_{28}H_{26}ClF_2N_9O_2$:593.19, measured: (ES, m/z): 594.20 $[M+H]^+$. $^1H$ NMR (400 MHz, Acetic Acid-$d_4$) δ 9.33 (s, 1H), 7.88 (d, J=6.2 Hz, 1H), 7.72 (d, J=3.1 Hz, 1H), 7.55-7.65 (m, 1H), 7.33-7.44 (m, 2H), 5.84 (d, J=2.5 Hz, 1H), 5.26 (d, J=8.9 Hz, 1H), 3.83-3.98 (m, 2H), 3.37-3.40 (m, 1H), 3.50-3.61 (m, 1H), 3.33-3.45 (m, 2H), 2.59-2.71 (m, 1H), 2.40-2.56 (m, 2H), 2.13-2.33 (m, 2H), 1.95-2.05 (m, 1H), 1.82-1.84 (m, 2H), 1.51-1.66 (m, 2H). $^{19}F$ NMR (376 MHz, Acetic Acid-$d_4$) δ −76.47, −112.59, −129.23.

Example 189 (3S)-3-(5-(3-chloro-2-(hydroxymethyl-d2)pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

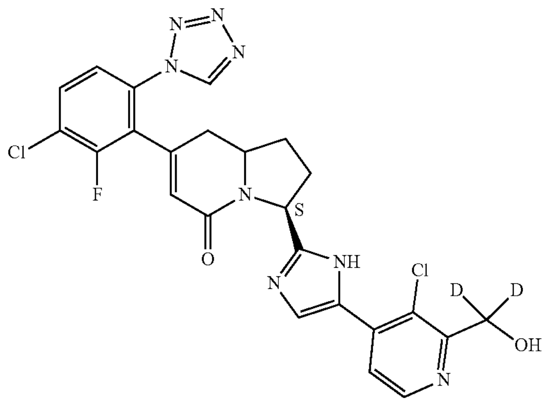

LC/MS: mass calculated for $C_{24}HC_{17}D_2FN_8O_2$: 542.11, measured (ES, m/z): 543.10 $[M+H]^+$. $^1H$ NMR (400 MHz, DMSO-$d_6$) δ 12.69 (brs., 1H), 9.84 (s, 1H), 8.53 (d, J=5.5 Hz, 1H), 8.05-8.11 (m, 2H), 7.95-8.00 (m, 1H), 7.70-7.75 (m, 1H), 5.70-5.75 (m, 1H), 5.07 (d, J=8.8 Hz, 1H), 4.57 (q, J=7.0 Hz, 1H), 3.73-3.80 (m, 1H), 2.64-2.74 (m, 1H), 2.51-2.58 (m, 1H), 2.17-2.30 (m, 1H), 2.09-2.16 (m, 1H), 1.91-2.00 (m, 2H)/$^{19}F$ NMR (376 MHz, DMSO-$d_6$) δ−74.03, −112.85.

Example 190 (3S,8aR)-7-(3-Chloro-2-fluoro-6-(4-(trifluoromethyl)-1H-1,2,3-triazol-1-yl)phenyl)-3-(4-(3-fluoro-2-(2-hydroxy-2-methylpropoxy)pyridin-4-yl)-1H-imidazol-2-yl)-2,3,8,8a-tetrahydroindolizin-5(1H)-one

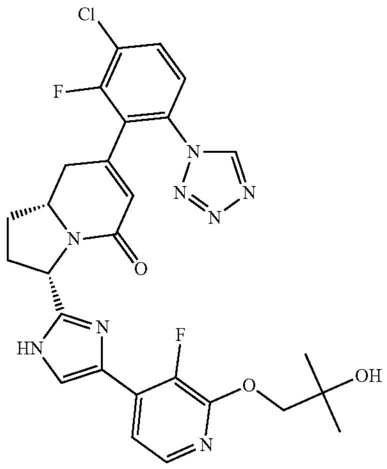 [SMILES: CC(C)(O)COc1nccc(-c2c[nH]c([C@@H]3CC[C@@H]4CC(c5c(-n6cnnn6)ccc(Cl)c5F)=CC(=O)N43)n2)c1F]

LC/MS: mass calculated for. $C_{27}H_{25}ClF_2N_8O_3$: 582.2, measured (ES, m/z): 583.2 $[M+H]^+$. $^1H$ NMR (400 MHz, methanol-d4) δ 9.60-9.57 (s, 1H), 7.98-7.93 (m, 1H), 7.97-

7.87 (m, 1H), 7.88-7.80 (m, 1H), 7.60-7.55 (m, 1H), 7.39-7.30 (m, 1H), 5.80-5.72 (m, 1H), 5.32-5.23 (m, 1H), 4.25 (s, 2H), 4.02-3.85 (m, 1H), 2.97 (t, J=15.5 Hz, 1H), 2.78-1.90 (m, 5H), 1.34 (s, 6H). $^{19}F$ NMR (376 MHz, methanol-$d_4$) δ−113.5, −142.7.

Example 191 (3S,8aR)-7-(3-Chloro-2-fluoro-6-(4-(trifluoromethyl)-1H-1,2,3-triazol-1-yl)phenyl)-3-(4-(3-fluoro-2-(2-hydroxy-2-methylpropoxy)pyridin-4-yl)-1H-imidazol-2-yl)-2,3,8,8a-tetrahydroindolizin-5(1H)-one

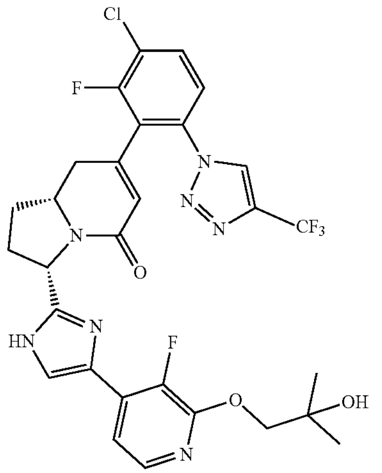

Step 1: 1-((3-Fluoro-4-iodopyridin-2-yl)oxy)-2-methylpropan-2-ol

A mixture of 2,3-difluoro-4-iodopyridine (1.200 g, 4.89 mmol), 2-methylpropane diol (0.494 g, 5.48 mmol), and $Cs_2CO_3$ (1.7859, 5.478 mmol) in DMF (25 ml) was heated at 110° C. for one hour. The reaction was cooled to room temperature and partitioned with water and EA. The organic was separated, washed with brine, and dried over $Na_2SO_4$. The solid was filtered and washed with EA. The filtrated was concentrated to yield a yellow solid, which was purified by ISCO normal phase column chromatography with heptane and EA as eluent (20% to 90% EA) to yield 1-((3-fluoro-4-iodopyridin-2-yl)oxy)-2-methylpropan-2-ol as an oil. LC/MS: mass calculated for. $C_9H_{11}FINO_2$: 310.98, measured (ES, m/z): 312.0 $[M+H]^+$.

Step 2: 1-(3-Fluoro-2-(2-hydroxy-2-methylpropoxy)pyridin-4-yl)ethan-1-one

A mixture of 1-((3-fluoro-4-iodopyridin-2-yl)oxy)-2-methylpropan-2-ol (0.45 g, 1.45 mmol), tributyl(1-ethoxyvinyl)stannane (0.78 g, 2.17 mmol), and $Pd(PPh_3)_4$ (167.1 mg, 0.145 mmol) in 1,4-dioxane (10 mL) was purged with $N_2$ for 10 minutes and heated at reflux overnight. The reaction mixture was cooled to room temperature, quenched with 2N HCl (5 mL) and stirred for 30 minutes, then partitioned between water and EA. The organic was separated, washed with brine, and dried over $Na_2SO_4$. The solid was filtered and concentrated to yield a yellow solid. The residue was purified by flash column chromatography on silica gel with heptane and EA as eluent (10% to 80% EA) to yield 1-(3-fluoro-2-(2-hydroxy-2-methylpropoxy)pyridin-4-yl)ethan-1-one as a yellow solid. LC/MS: mass calculated for. $C_{11}H_{14}FNO_3$: 227.1, measured (ES, m/z): 228.1 $[M+H]^+$.

Step 3: 2-Bromo-1-(3-fluoro-2-(2-hydroxy-2-methylpropoxy)pyridin-4-yl)ethan-1-one To a solution of 1-(3-fluoro-2-(2-hydroxy-2-methylpropoxy)pyridin-4-yl)ethan-1-one (314 mg, 1.382 mmol), in AcOH (2 mL), pyridine·$HBr_3$ (441.936 mg, 1.382 mmol) and $HBr/CH_3COOH$ (0.5 mL, 2.764 mmol) were added at room temperature. The reaction mixture was stirred at room temperature for 2 hours. The solvent was removed under vacuum. The residue was partitioned with water and EA. The organic layer was separated, washed with water, then brine and dried over $Na_2SO_4$. The solid was filtered and concentrated to yield a clear oil. The oil was triturated with heptane. The residue was concentrated to yield 2-bromo-1-(3-fluoro-2-(2-hydroxy-2-methylpropoxy)pyridin-4-yl) ethan-1-one (~90% purity) as a clear oi. $^1H$ NMR (400 MHz, $CDCl_3$) δ 8.01-7.27 (d, J=8.2 Hz, 1H), 7.25-7.29 (m, 1H), 4.49 (d, J=1.96 Hz, 2H), 4.30 (s, 2H), 1.37 (s, 6H)

Step 4: 2-(3-Fluoro-2-(2-hydroxy-2-methylpropoxy)pyridin-4-yl)-2-oxoethyl (3S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate To a solution of (3S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylic acid in ACN (5 mL), was added $Cs_2CO_3$ (114.1 mg, 0.35 mmol) and the mixture stirred at room temperature for 10 minutes. 2-Bromo-1-(3-fluoro-2-(2-hydroxy-2-methylpropoxy)pyridin-4-yl)ethan-1-one was then added. The reaction was heated at 40° C. for one hour. The reaction was cooled to room temperature. The solid was filtered through CELITE and washed with EA. The solvent was removed under vacuum to yield 2-(3-fluoro-2-(2-hydroxy-2-methylpropoxy)pyridin-4-yl)-2-oxoethyl (3S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate as a red oil. The red oil was used in the next step without further purification. LC/MS: mass calculated for: $C_{29}H_{25}ClF_5N_5O_8$: 669.1, measured (ES, m/z): 670.1 $[M+H]^+$.

Step 5: (3S,8aR)-7-(3-Chloro-2-fluoro-6-(4-(trifluoromethyl)-1H-1,2,3-triazol-1-yl)phenyl)-3-(4-(3-fluoro-2-(2-hydroxy-2-methylpropoxy)pyridin-4-yl)-1H-imidazol-2-yl)-2,3,8,8a-tetrahydroindolizin-5(1H)-one To a solution of 2-(3-fluoro-2-(2-hydroxy-2-methylpropoxy)pyridin-4-yl)-2-oxoethyl (3S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate (91 mg, 0.136 mmol) in toluene (6 mL) and AcOH (0.23 mL) was added $NH_4OAc$ (157 mg, 2.043 mmol). The reaction mixture was heated at 100° C. for 2 hours. The solvent was removed under vacuum. The residue was partitioned between water and DCM. The organic layer was washed with brine, dried over $Na_2SO_4$, and concentrated under reduced pressure. The residue was purified via high throughput mass directed reverse phase column chromatography to yield (3S,8aR)-7-(3-chloro-2-fluoro-6-(4-(trifluoromethyl)-1H-1,2,3-triazol-1-yl)phenyl)-3-(4-(3-fluoro-2-(2-hydroxy- 2-methylpropoxy)pyridin-4-yl)-1H-imidazol-2-yl)-2,3,8,8a-tetrahydroindolizin-5(1H)-one as a white solid.

LC/MS: mass calculated for. $C_{29}H_{25}ClF_5N_7O_3$: 649.2, measured (ES, m/z): 650.3 $[M+H]^+$. $^1H$ NMR (400 MHz, methanol-$d_4$) δ 9.01 (s, 1H), 7.88 (d, J=5.4 Hz, 1H), 7.83-7.76 (m, 1H), 7.62-7.47 (m, 3H), 5.72 (d, J=2.8 Hz, 1H), 5.18 (d, J=8.8 Hz, 1H), 4.21 (s, 2H), 3.85-4.00 (m, 1H), 2.95 (t, J=15.5 Hz, 1H), 2.63 (dd, J=16.6, 4.2 Hz, 1H), 1.96-2.45 (m, 4H), 1.34 (s, 6H). $^{19}F$ NMR (376 MHz, methanol-$d_4$) δ −62.3, −113.6, −144.1.

Example 192: 5-(2-((8aR)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-4-yl)-3-fluoro-N-(methylsulfonyl)thiophene-2-carboxamide

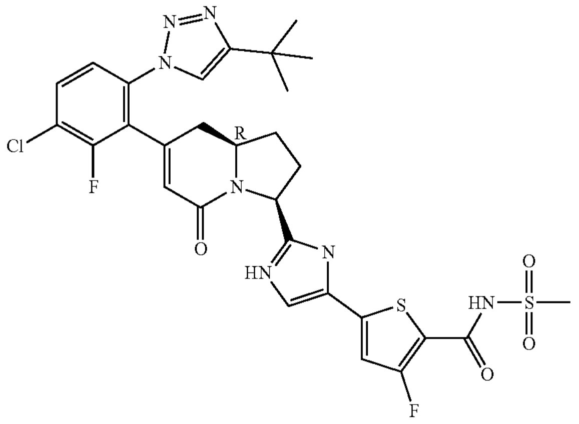

LC/MS: mass calculated for $C_{26}H_{19}ClF_5N_7O_4S_2$: 687.05, measured (ES, m/z): 688.05 $[M+H]^+$. $^1H$ NMR (300 MHz, DMSO-$d_6$) δ 9.34 (s, 1H), 7.90-8.05 (m, 1H), 7.77-7.65 (m, 2H), 7.31 (s, 1H), 5.69 (d, J=2.5 Hz, 1H), 4.99 (d, J=8.8 Hz, 1H), 3.92-4.05 (m, 1H), 3.34 (s, 3H), 2.85-2.66 (m, 1H), 2.40-2.45 (m, 1H), 2.32-2.05 (m, 2H), 2.03-1.86 (m, 2H)/$^{19}F$ NMR (282 MHz, DMSO) δ −59.54, −74.05, −112.84.

Example 193: 5-(2-((3S)-7-(3-chloro-6-(4-chloro-1H-1,2,3-triazol-1-yl)-2-fluorophenyl)-5-oxo-1,2,3,5,8,8a-hexahydroindolizin-3-yl)-1H-imidazol-4-yl)thiophene-2-carboxylic acid

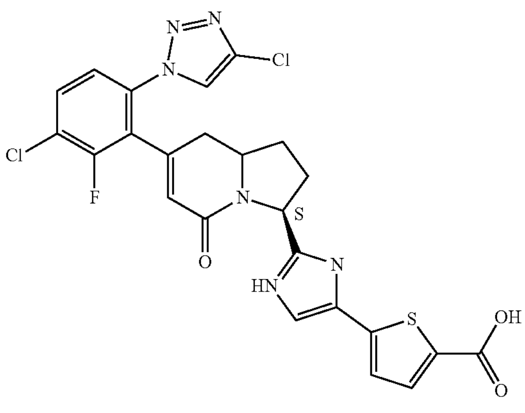

LC/MS: mass calculated for $C_{24}H_{17}Cl_2FN_6O_3S$: 558.04 measured (ES, m/z): 559.05 $[M+H]^+$. $^1H$ NMR (400 MHz, DMSO-$d_6$) δ 8.83 (s, 1H), 7.87-7.96 (m, 2H), 7.69-7.73 (m, 1H), 7.53-7.64 (m, 2H), 5.65-5.75 (m, 1H), 5.09-5.16 (m, 1H), 3.69-3.79 (m, 1H), 2.93-3.02 (m, 1H), 2.24-2.37 (m, 2H), 1.94-2.15 (m, 3H). $^{19}F$ NMR (376 MHz, DMSO-$d_6$) δ −74.58, −112.86.

Example 194 (3*S,8a*R)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one

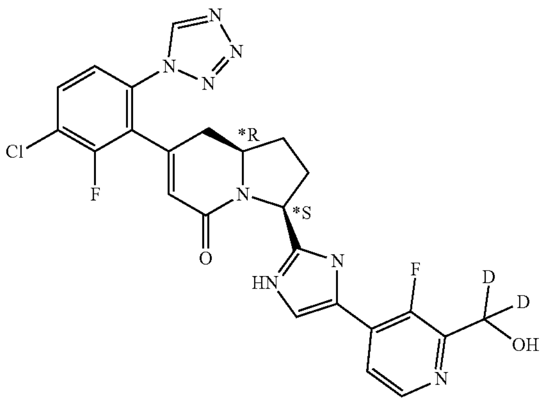 [SMILES: [2H]C([2H])(O)c1nccc(-c2cnc([C@@H]3CC[C@@H]4CC(c5c(-n6cnnn6)ccc(Cl)c5F)=CC(=O)N43)[nH]2)c1F]

Step 1: 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate A mixture of ((3S)-7-(6-amino-3-chloro-2-fluorophenyl)-5-oxo-1,2,3,5,8,8a-hexahydroindolizine-3-carboxylic acid (260 mg, 0.80 mmol, 1.0 equiv.) and $Cs_2CO_3$ (156 mg, 0.48 mmol, 0.6 equiv.) in DMF (12 mL) was stirred at 40° C. for 30 min. 2-Bromo-1-(2-(((tert-butyldimethylsilyl)oxy)methyl-d2)-3-fluoropyridin-4-yl)ethan-1-one (437 mg, 1.20 mmol, 1.5 equiv.) was then added to the mixture. The reaction mixture was stirred at room temperature. for 4 h. The resulting mixture was then diluted with EA (120 mL), washed with water (3×30 mL), brine (2×20 mL), dried over $Na_2SO_4$, and concentrated. The residue was purified by flash column chromatography on silica gel (0→10% MeOH/DCM) to yield 2-(2-(((tert-butyldimethylsilyl)oxy)methyl-d2)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{29}H_{32}ClD_2F_2N_3O_5Si$: 607.20, measured: 608.10 $[M+H]^+$.

Step 2: (3S)-7-(6-amino-3-chloro-2-fluorophenyl)-3-(4-(3-fluoro-2-(hydroxymethyl-d2)pyridin-4-yl)-1H-imidazol-2-yl)-2,3,8,8a-tetrahydroindolizin-5(1H)-one A mixture of 2-(2-(((tert-butyldimethylsilyl)oxy)methyl-$d_2$)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (280 mg, 0.46 mmol, 1.0 equiv.) and $NH_4OAc$ (355 mg, 4.60 mmol, 10.0 equiv.) in AcOH (3 mL) and toluene (30 mL) was stirred at 110° C. for 1 h, then cooled to room temperature, and concentrated under reduced pressure. The residue was purified by flash column chromatography on silica gel (0→9% MeOH/DCM) to yield (3S)-7-(6-amino-3-chloro-2-fluorophenyl)-3-(4-(3-fluoro-2-(hydroxymethyl-d2)pyridin-4-yl)-1H-imidazol-2-yl)-2,3,8,8a-tetrahydroindolizin-5(1H)-one as a yellow solid. LC/MS: mass calculated for $C_{23}H_{18}ClD_2F_2N_5O_2$: 473.14, measured: 474.05 $[M+H]^+$.

Step 3: (3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one A mixture of ((3S)-7-(6-amino-3-chloro-2-fluorophenyl)-3-(4-(3-fluoro-2-(hydroxymethyl-d2)pyridin-4-yl)-1H-imidazol-2-yl)-2,3,8,8a-tetrahydroindolizin-5(1H)-one (200 mg, 0.422 mmol, 1.00 equiv), $TMSN_3$ (486 mg, 4.22 mmol, 10.0 equiv.) and trimethoxymethane (448 mg, 4.22 mmol, 10.0 equiv.) in AcOH (10 mL) was stirred at 50° C. for 4 h, then concentrated under reduced pressure. The residue was purified by flash column chromatography on silica gel (0→10% MeOH/DCM) to yield (3S)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one as a light yellow solid, which was further purified by chiral-HPLC with to yield (3S,8aR)-7-(3-chloro-2-fluoro-6-(1H-tetrazol-1-yl)phenyl)-3-(4-(3-fluoro-2-(hydroxymethyl-d2)pyridin-4-yl)-1H-imidazol-2-yl)-2,3,8,8a-tetrahydroindolizin-5(1H)-one as a white solid.

LC/MS: mass calculated for $C_{24}H_{17}ClD_2F_2N_8O_2$: 526.14, measured (ES, m/z): 527.05 $[M+H]^+$. $^1H$ NMR (400 MHz, DMSO-$d_6$) δ 12.27 (s, 1H), 9.85 (s, 1H), 8.35 (d, J=5.0 Hz, 1H), 7.98 (t, J=8.0 Hz, 1H), 7.90 (t, J=5.4 Hz, 1H), 7.72 (dd, J=8.7, 1.5 Hz, 1H), 7.58 (d, J=1.6 Hz, 1H), 5.71 (d, J=2.8 Hz, 1H), 5.24 (s, 1H), 5.05 (d, J=8.7 Hz, 1H), 3.65-3.84 (m, 1H), 2.73 (t, J=15.4 Hz, 1H), 2.54-2.62 (m, 1H), 2.17-2.30 (m, 1H), 2.06-2.16 (m, 1H), 1.89-2.05 (m, 2H). $^{19}F$ NMR (376 MHz, DMSO-$d_6$) δ −112.85, −130.23

Example 195: 5-(2-((3*S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-yl)-3-fluorothiophene-2-carboxylic acid

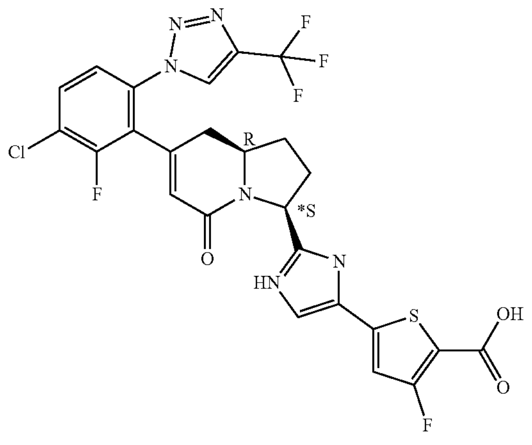

LC/MS: mass calculated for $C_{25}H_{16}ClF_5N_8O_3S$: 610.06, measured (ES, m/z): 611.00 $[M+H]^+$. $^1H$ NMR (300 MHz, DMSO-$d_6$) δ 9.28 (s, 1H), 7.88-7.98 (m, 1H), 7.59-7.72 (m, 2H), 7.25 (s, 1H), 5.66 (d, J=2.5 Hz, 1H), 4.99 (d, J=8.7 Hz, 1H), 3.67-3.77 (m, 1H), 2.65-2.85 (m, 1H), 2.40-2.48 (m, 1H), 2.04-2.30 (m, 2H), 1.83-2.01 (m, 2H). $^{19}F$ NMR (282 MHz, DMSO) δ−59.58, −73.96, −112.82, −113.48.

Example 196: 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-3-fluorobenzamide

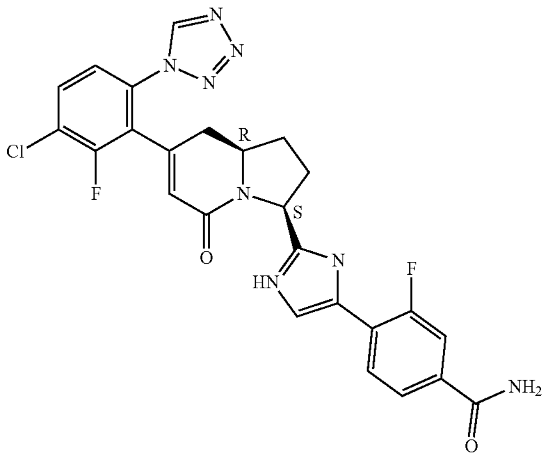

LC/MS: mass calculated for $C_{25}H_{19}ClF_2N_8O_2$: 536.13, measured (ES, m/z): 537.10 $[M+H]^+$. $^1H$ NMR (400 MHz, DMSO-$d_6$) δ 12.15 (brs., 1H), 9.82 (s, 1H), 7.90-8.10 (m, 3H), 7.75-7.83 (m, 3H), 7.30-7.40 (m, 2H), 5.68-5.73 (m, 1H), 5.01 (d, J=8.7 Hz, 1H), 3.70-3.80 (m, 1H), 2.71-2.85 (m, 1H), 2.55-260 (m, 1H), 2.10-2.25 (m, 2H), 1.90-2.04 (m, 2H). $^{19}F$ NMR (376 MHz, DMSO-$d_6$) δ−114.60, −112.91.

Example 197 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-2-fluorobenzamide

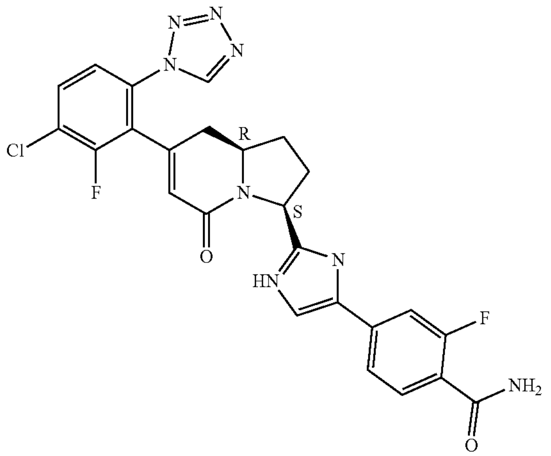

Step 1: 4-(1-ethoxyvinyl)-2-fluorobenzamide

A mixture of 4-bromo-3-fluorobenzamide (500 mg, 1.89 mmol, 1.0 equiv.) and tributyl(1-ethoxyvinyl)tin (818 mg, 2.26 mmol, 1.2 equiv.) and $Pd(PPh_3)_4$ (218 mg, 0.19 mmol, 0.1 equiv.) in 1,4-dioxane (20 mL) was purged with $N_2$ and then stirred at 100° C. for 3 hours. The mixture was quenched with water (1000 mL) and extracted with EA (1000 mL×3). The combined organic extracts were washed with brine, dried over anhydrous $Na_2SO_4$, filtered and concentrated to dryness under reduced pressure to yield a residue, which was purified by column chromatography on silica gel with (0→50% EA/PE) to yield 4-(1-ethoxyvinyl)-2-fluorobenzamide as a yellow solid.

Step 2: 4-(2-bromoacetyl)-2-fluorobenzamide

NBS (1.4 g, 7.89 mmol, 5.0 equiv.) was added to a mixture of 4-(1-ethoxyvinyl)-2-fluorobenzamide (330 mg, 1.58 mmol, 1.0 equiv.) in THE (6 mL) and $H_2O$ (2 mL) and the mixture was stirred at room temperature for 3 hours, quenched with water (1000 mL) and extracted with EA (1000 mL×3). The combined organic extracts were washed with brine, dried over anhydrous $Na_2SO_4$, filtered and concentrated to dryness under reduced pressure to yield a residue, which was purified by column chromatography on silica gel (0→50% EA/PE) to yield 4-(2-bromoacetyl)-2-fluorobenzamide as a yellow solid.

Step 3: 2-(4-carbamoyl-3-fluorophenyl)-2-oxoethyl (3S)-7-(6-amino-3-chloro-2-fluorophenyl)-5-oxo-1,2,3,5,8,8a-hexahydroindolizine-3-carboxylate To a mixture of (3S)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) and $Cs_2CO_3$ (120 mg, 0.37 mmol, 0.6 equiv.) in DMF (15 mL) was added 4-(2-bromoacetyl)-2-fluorobenzamide (192 mg, 0.74 mmol, 1.2 equiv.). After 3 hours, the mixture was quenched with water (1000 mL) and extracted with EA (1000 mL×3). The combined organic extracts were washed with brine, dried over anhydrous $Na_2SO_4$. The solid was filtered and the filtrate was concentrated to dryness under reduced pressure to yield a residue, which was purified by column chromatography on silica gel (0→50% EA/PE) to yield 2-(4-carbamoyl-3-fluorophenyl)-2-oxoethyl (3S)-7-(6-amino-3-chloro-2-fluorophenyl)-5-oxo-1,2,3,5,8,8a-hexahydroindolizine-3-carboxylate as a yellow solid.

Step 4: 4-(2-((3S)-7-(6-amino-3-chloro-2-fluorophenyl)-5-oxo-1,2,3,5,8,8a-hexahydroindolizin-3-yl)-1H-imidazol-4-yl)-2-fluorobenzamide To 2-(4-carbamoyl-3-fluorophenyl)-2-oxoethyl (3S)-7-(6-amino-3-chloro-2-fluorophenyl)-5-oxo-1,2,3,5,8,8a-hexahydroindolizine-3-carboxylate (260 mg, 0.52 mmol, 1.0 equiv.) in AcOH (1 mL) and toluene (10 mL) was added $CH_3COONH_4$ (459 mg, 5.95 mmol, 10.0 equiv.). The reaction mixture was stirred at 100° C. for 3 hours, then quenched with water (1000 mL) and extracted with EA (1000 mL×3). The combined organic extracts were washed with brine, dried over anhydrous $Na_2SO_4$, filtered and concentrated to dryness under reduced pressure to yield a residue, which was purified by column chromatography on silica gel with (0→50% EA/PE) to yield 4-(2-((3S)-7-(6-amino-3-chloro-2-fluorophenyl)-5-oxo-1,2,3,5,8,8a-hexahydroindolizin-3-yl)-1H-imidazol-4-yl)-2-fluorobenzamide as a yellow solid.

Step 5: 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-2-fluorobenzamide A solution of 4-(2-((3S)-7-(6-amino-3-chloro-2-fluorophenyl)-5-oxo-1,2,3,5,8,8a-hexahydroindolizin-3-yl)-1H-imidazol-4-yl)-2-fluorobenzamid (200 mg, 0.413 mmol, 1.0 equiv.) in AcOH (6 mL) were added trimethoxymethane (438 mg, 4.13 mmol, 10.0 equiv.) and $TMSN_3$ (476 mg, 4.13 mmol, 10.0 equiv.). The reaction mixture was stirred at 60° C. for 1 h and then concentrated under reduced pressure. The residue was purified by prep-HPLC with Mobile Phase A: Water (0.05% $NaHCO_3$), Mobile Phase B: ACN to yield the racemic product, which was separated by chiral-HPLC to yield 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-2-fluorobenzamide as a white solid.

LC/MS: mass calculated for $C_{24}H_{17}D2ClF_2N_8O_2$: 526.14, measured (ES, m/z): 527.05 $[M+H]^+$. $^1H$ NMR (400 MHz, DMSO-$d_6$) δ 12.31 (brs., 1H), 9.84 (s, 1H), 8.35 (d, J=5.1 Hz, 1H), 7.95-8.05 (m, 1H), 7.82-7.93 (m, 1H), 7.70-7.80 (m, 1H), 7.55-7.85 (m, 1H), 5.70 (d, J=2.7 Hz, 1H), 5.10-5.45 (m, 1H), 5.05 (d, J=8.8 Hz, 1H), 3.66-3.85 (m, 1H), 2.63-2.84 (m, 1H), 2.52-2.60 (m, 1H), 2.05-2.30 (m, 2H), 1.85-2.05 (m, 2H). $^{19}F$ NMR (376 MHz, DMSO-$d_6$) δ −112.86, −130.05.

Example 198 4-(2-((3S,8aS)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-2-fluorobenzamide

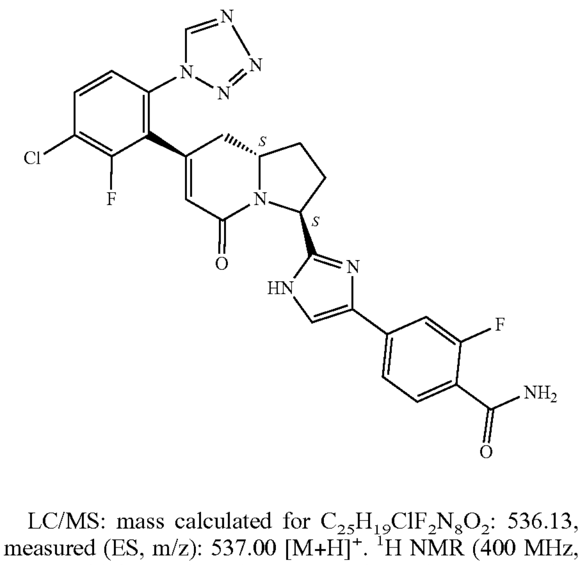

LC/MS: mass calculated for $C_{25}H_{19}ClF_2N_8O_2$: 536.13, measured (ES, m/z): 537.00 $[M+H]^+$. $^1H$ NMR (400 MHz, DMSO-$d_6$) δ 9.82 (s, 1H), 7.90-8.10 (m, 1H), 7.40-7.90 (m, 5H), 5.68 (d, J=2.6 Hz, 1H), 4.90-5.00 (m, 1H), 4.02-4.12 (m, 1H), 2.30-2.35 (m, 3H), 2.21-2.30 (m, 1H), 1.90-2.02 (m, 1H), 1.65-1.72 (m, 1H). $^{19}F$ NMR (376 MHz, DMSO-$d_6$) δ −73.46, −113.05.

Example 199 (3S)-7-(3-chloro-2-fluoro-6-(1H-tetrazol-1-yl)phenyl)-3-(4 chloro-5-(2-oxo-1,2-dihydropyridin-4-yl)-1H-imidazol-2-yl)-2,3,8,8a-tetrahydroindolizin-5(1H)-one

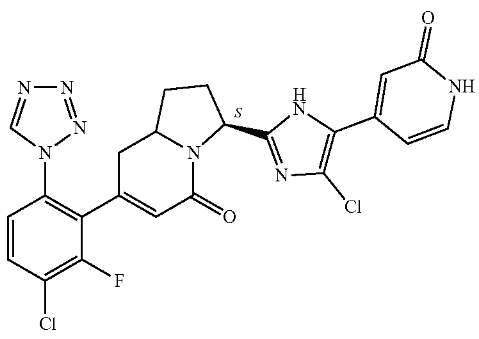

LC/MS: mass calculated for $C_{23}H_{17}Cl_2FN_8O_2$: 526.08, measured (ES, m/z): 527.20 $[M+H]^+$. $^1H$ NMR (300 MHz, DMSO-$d_6$) δ 12.33 (s, 1H), 11.80 (s, 1H), 9.84 (s, 1H), 7.92-8.03 (m, 2H), 7.70-7.75 (m, 1H), 7.30-7.40 (m, 1 H), 7.00-7.05 (m, 1H), 5.71 (d, J=2.5 Hz, 1H), 5.03 (d, J=8.4 Hz, 1H), 3.67-3.80 (m, 1H), 2.54-2.73 (m, 2H), 2.05-2.26 (m, 2H), 1.89-2.20 (m, 2H)/$^{19}F$ NMR (282 MHz, DMSO-$d_6$) δ −112.86.

Example 200 (3S,8aR)-7-(3-chloro-6-(4-chloro-1H-1,2,3-triazol-1-yl)-2-fluorophenyl)-3-(4-(3-fluoro-2-oxo-1,2-dihydropyridin-4-yl)-1H-imidazol-2-yl)-2,3,8,8a-tetrahydroindolizin-5(1H)-one

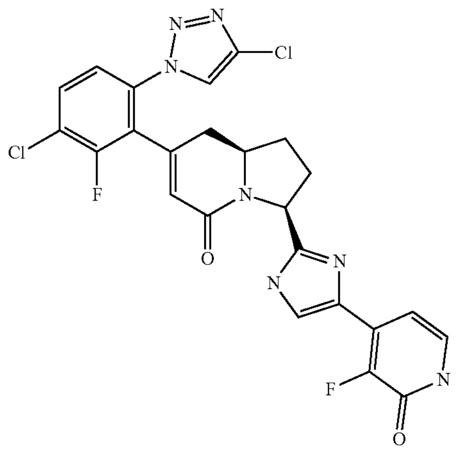 [SMILES: O=C1C=C(c2c(-n3cc(Cl)nn3)ccc(Cl)c2F)C[C@H]2CC[C@@H](c3nc(-c4cc[nH]c(=O)c4F)c[nH]3)N12]

LC/MS: mass calculated for $C_{24}H_{17}C_{12}F_2N_7O_2$: 543.08, measured (ES, m/z): 544.15 $[M+H]^+$. $^1H$ NMR (400 MHz, DMSO-$d_6$) δ 12.18 (brs., 1H), 8.85 (s, 1H), 7.93-7.95 (m, 2H), 7.60-7.70 (m, 1H), 7.31-7.38 (m, 1H), 6.70-6.80 (m, 1H), 5.68-5.72 (m, 1H), 5.22 (d, J=9.4 Hz, 1H), 3.72-3.88 (m, 1H), 2.87-3.03 (m, 1H), 2.47-2.49 (m, 1H), 2.27-2.39 (m, 1H), 1.93-2.15 (m, 3H). $^{19}F$ NMR (376 MHz, DMSO-$d_6$) δ −112.87.

Example 201 (3S,8aR)-3-(5-(3-aminobenzo[d]isoxazol-5-yl)-1H-imidazol-2-yl)-7-(3-chloro-2-fluoro-6-(1H-tetrazol-1-yl)phenyl)-2,3,8,8a-tetrahydroindolizin-5(1H)-one

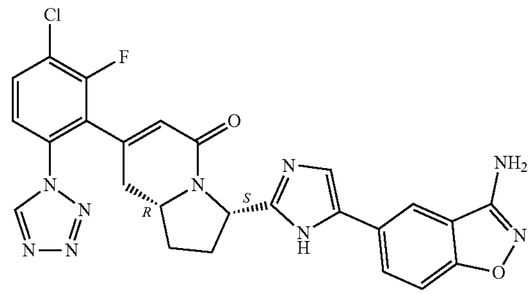

LC/MS: mass calculated for $C_{25}H_{19}ClFN_9O_2$: 531.13, measured (ES, m/z): 532.05 $[M+H]^+$. $^1H$ NMR (400 MHz, DMSO-$d_6$+$D_2O$) δ 9.74 (s, 1H), 8.07 (s, 1H), 7.80-7.92 (m, 3H), 7.58-7.70 (m, 2H), 5.66-5.67 (m, 1H), 5.16 (d, J=4.8 Hz, 1H), 3.68-3.81 (m, 2H), 2.89-2.97 (m, 1H), 2.57-2.58 (m, 1H), 2.35-2.39 (m, 1H), 2.05-2.10 (m, 2H), 1.89-1.92 (m, 1H). $^{19}F$ NMR (376 MHz, DMSO-$d_6$) δ −73.80, −112.68.

Example 202 5-(5-Chloro-2-((3S,8aS)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxamide

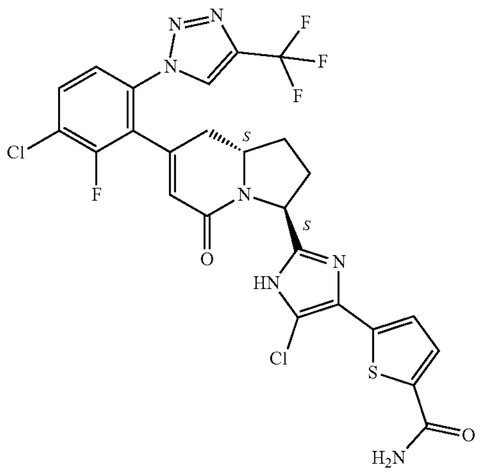

LC/MS: mass calculated for $C_{25}H_{17}Cl_2F_4N_7O_2S$: 625.05, measured (ES, m/z): 626.05 $[M+H]^+$. $^1H$ NMR (400 MHz, DMSO-$d_6$) δ12.86 (s, 1H), 9.32 (d, J=1.1 Hz, 1H), 7.89-8.05 (m, 2H), 7.65-7.72 (m, 2H), 7.31-7.41 (m, 2H), 5.67 (d, J=2.3 Hz, 1H), 4.87-4.95 (d, J=8.7 Hz, 1H), 3.63-3.74 (m, 1H), 3.20-3.22 (m, 1H), 2.55-2.65 (m, 1H), 2.11-2.28 (m, 1H), 2.02-2.10 (m, 1H), 1.93-2.01 (m, 1H), 1.89-1.92 (m, 1H). $^{19}F$ NMR (376 MHz, DMSO-$d_6$) δ −59.61, −112.95

Example 203 5-(5-Chloro-2-((3S,8aR)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxamide

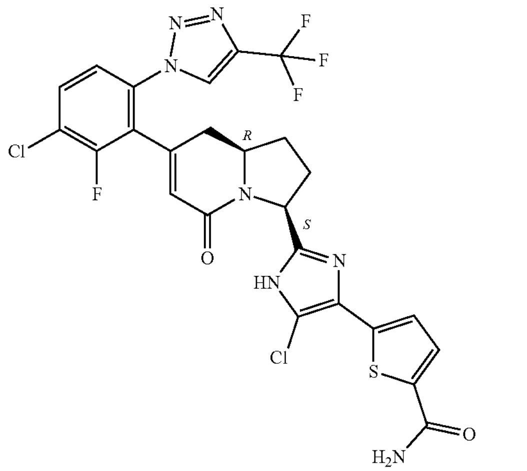

LC/MS: mass calculated for $C_{20}H_{17}Cl_2F_4N_7O_2S$: 625.05, measured (ES, m/z): 626.00 $[M+H]^+$. $^1H$ NMR (400 MHz, DMSO-$d_6$) δ 12.75-12.98 (m, 1H), 9.25-9.36 (m, 1H), 7.85-8.02 (m, 2H), 7.62-7.72 (m, 2H), 7.31-7.45 (m, 2H), 5.60-5.75 (m, 1H), 4.80-4.99 (m, 1H), 3.95-4.10 (m, 1H), 3.20-3.25 (m, 1H), 2.30-2.39 (m, 2H), 2.08-2.28 (m, 1H), 1.86-1.98 (m, 1H), 1.62-1.73 (m, 1H). $^{19}F$ NMR (376 MHz, DMSO-$d_6$) δ −59.64, −73.57, −113.12

Example 204 4-(2-((3S,8aR)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)picolinamide

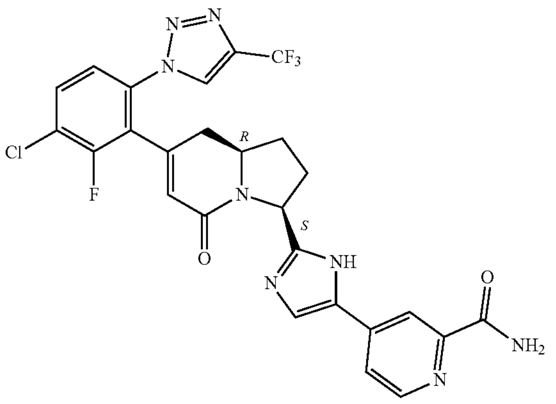

LC/MS: mass calculated for $C_{26}H_{19}ClF_4N_8O_2$: 586.13, measured (ES, m/z): 587.10 $[M+H]^+$. $^1H$ NMR (300 MHz, DMSO-$d_6$) δ12.13 (s, 1H), 9.33 (s, 1H), 8.51 (d, J=5.1 Hz, 1H), 8.32 (s, 1H), 8.07 (s, 1H), 7.94 (t, J=8.2 Hz, 1H), 7.82-7.90 (m, 2H), 7.70 (dd, J=8.7, 1.5 Hz, 1H), 7.59 (s, 1H), 5.68 (d, J=2.5 Hz, 1H), 5.00 (d, J=8.5 Hz, 1H), 3.60-3.77 (m, 1H), 2.66-2.82 (m, 1H), 2.41-2.45 (m, 1H), 1.87-2.30 (m, 4H). $^{19}F$ NMR (300 MHz, DMSO-$d_6$) δ 59.52, −112.77.

Example 205 5-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)thiazole-2-carboxamide

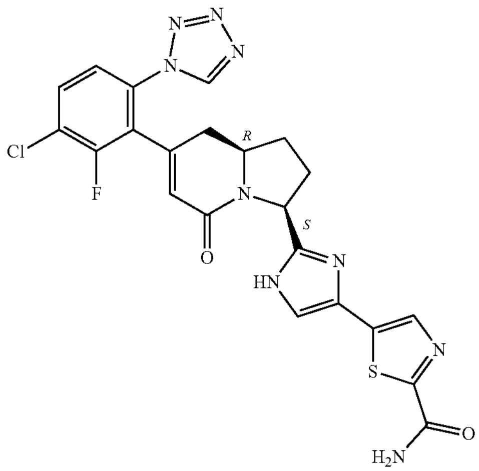

Step 1: 5-bromothiazole-2-carboxamide

A mixture of 5-bromothiazole-2-carboxylic acid (1.4 g, 6.73 mmol, 1.0 equiv.), ammonium chloride (1.8 g, 33.65 mmol, 5.0 equiv.), N,N-diisopropylethylamine (1.0 g, 8.07 mmol, 1.2 equiv.) and HATU (3.1 g, 8.08 mmol, 1.2 equiv.) in N,N-dimethylformamide (14 mL) was stirred at room temperature for 2 h. The resulting mixture was diluted with water, extracted with EA (3×10 ml). The organic layers were combined, washed with brine, dried over $Na_2SO_4$ and concentrated under reduced pressure. The residue was purified by flash column chromatography on silica gel (0→35% EA/PE) to yield 5-bromothiazole-2-carboxamide as a yellow solid.

Step 2: 5-(1-ethoxyvinyl)thiazole-2-carboxamide

A mixture of 5-bromothiazole-2-carboxamide (960 mg, 4.64 mmol, 1.0 equiv.), tributyl(1-ethoxyvinyl)stannane (2.5 g, 6.95 mmol, 1.5 equiv.) and $Pd(PPh_3)_4$ (536 mg, 0.46 mmol, 0.1 equiv.) in 1,4-dioxane (10 mL) was heated at 90° C. under $N_2$ for 3 h. The resulting mixture was diluted with water, extracted with EA (3×10 ml). The organic layers were combined, washed with brine, dried over $Na_2SO_4$. The residue was purified by silica gel column (0→50% EA/PE) to yield 5-(1-ethoxyvinyl)thiazole-2-carboxamide as a brown solid.

Step 3: 5-acetylthiazole-2-carboxamide

2M HCl (4 mL). was added to a solution of 5-(1-ethoxyvinyl)thiazole-2-carboxamide (900 mg, 4.54 mmol, 1.0 equiv.) in THE (4 ml). The resulting mixture was stirred at room temperature for 1 h and evaporated under vacuum. The residue was purified by flash column chromatography on silica gel (0→50% EA/PE) to yield 5-acetylthiazole-2-carboxamide as an orange solid.

Step 4: 5-(2-bromoacetyl)thiazole-2-carboxamide

Hydrogen bromide (190 mg, 2.35 mmol, 1.0 equiv.). was added to a mixture of 5-acetylthiazole-2-carboxamide (400 mg, 2.35 mmol, 1.0 equiv.) and pyridinium tribromide (676 mg, 2.11 mmol, 0.9 equiv.) in acetic acid (5 ml). The resulting mixture was stirred at room temperature for 2 h. The solid was filtered out, washed with water and dried in vacuo to yield 5-(2-bromoacetyl)thiazole-2-carboxamide as an orange solid.

Step 5: 2-(2-carbamoylthiazol-5-yl)-2-oxoethyl (3S,8aR)-7-(6-amino-3-chloro-2-fluorophenyl)-5-oxo-1,2,3,5,8,8a-hexahydroindolizine-3-carboxylate A mixture of (3S,8aR)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) and potassium carbonate (941 mg, 0.68 mmol, 1.1 equiv.) in $CH_3CN$ (3 mL) was stirred at room temperature for 1 h. 2-Bromo-1-(2-fluoro-6-(hydroxymethyl)pyridin-3-yl)ethan-1-one (184 mg, 0.74 mmol, 1.2 equiv.) was then added to the mixture. After 2 h, the resulting mixture was concentrated and purified by flash column chromatography on silica gel (0→100% EA/PE) to yield 2-(2-carbamoylthiazol-5-yl)-2-oxoethyl (3S,8aR)-7-(6-amino-3-chloro-2-fluorophenyl)-5-oxo-1,2,3,5,8,8a-hexahydroindolizine-3-carboxylate as an orange solid.

Step 6: 5-(2-((3S,8aR)-7-(6-amino-3-chloro-2-fluorophenyl)-5-oxo-1,2,3,5,8,8a-hexahydroindolizin-3-yl)-1H-imidazol-4-yl)thiazole-2-carboxamide To a mixture of 2-(2-carbamoylthiazol-5-yl)-2-oxoethyl (3S,8aR)-7-(6-amino-3-chloro-2-fluorophenyl)-5-oxo-1,2,3,5,8,8a-hexahydroindolizine-3-carboxylate (198 mg, 0.40 mmol, 1.0 equiv.) and ammonium acetate (310 mg, 4.02 mmol, 10.0 equiv.) in toluene (3 ml) was added acetic acid (48 mg, 0.80 mmol, 2.0 equiv.). The resulting mixture was heated at reflux for 1 h, then concentrated and the residue was purified by flash column chromatography on silica gel (0→10% MeOH/DCM) to yield 5-(2-((3S,8aR)-7-(6-amino-3-chloro-2-fluorophenyl)-5-oxo-1,2,3,5,8,8a-hexahydroindolizin-3-yl)-1H-imidazol-4-yl)thiazole-2-carboxamide as a light yellow solid.

Step 7: 5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)thiazole-2-carboxamide A mixture of 5-(2-((3S,8aR)-7-(6-amino-3-chloro-2-fluorophenyl)-5-oxo-1,2,3,5,8,8a-hexahydroindolizin-3-yl)-1H-imidazol-4-yl)thiazole-2-carboxamide (200 mg, 0.42 mmol, 1.0 equiv.), trimethoxymethane (1 mL), azidotrimethylsilane (1 mL) and acetic acid (2 ml) was stirred 48 h at 30° C. The excess solvent was removed under vacuum and the residue was purified by reversal chromatography on C18 (MeCN/$H_2O$ (0.05% $CF_3COOH$): 0-050%) to yield a white solid. The racemic product (30 mg) was further separated by chiral-HPLC to yield 5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)thiazole-2-carboxamide as a white solid.

LC/MS: mass calculated for $C_{22}H_{17}ClFN_9O_2S$: 525.09, measured (ES, m/z): 526.00 $[M+H]^+$. $^1H$ NMR (300 MHz, DMSO-$d_6$) δ 12.09 (s, 1H), 9.80 (s, 1H), 8.07 (s, 1H), 8.04 (s, 1H), 7.95 (dd, J=8.7, 7.8 Hz, 1H), 7.67-7.74 (m, 2H), 7.58 (d, J=2.1 Hz, 1H), 5.64 (d, J=2.6 Hz, 1H), 4.96 (d, J=8.6 Hz, 1H), 3.62-3.74 (m, 1H), 2.69-2.85 (m, 1H), 2.51-2.53 (m, 1H), 2.03-2.24 (m, 2H), 1.85-1.98 (m, 2H). $^{19}F$ NMR (282 MHz, DMSO-$d_6$) δ −73.41, −112.81, −112.86, −112.94, −113.33

Example 206 4-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)picolinamide

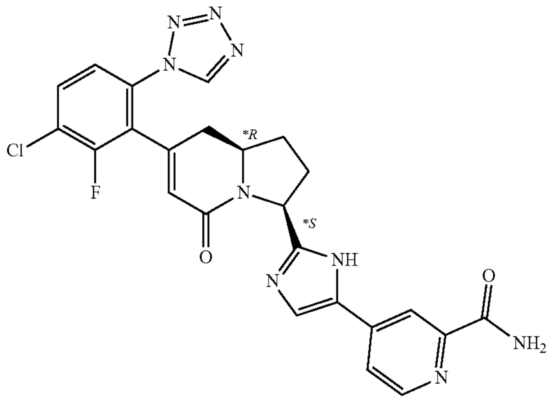

LC/MS: mass calculated for $C_{24}H_{19}ClFN_9O_2$: 519.13, measured (ES, m/z): 520.10 $[M+H]^+$. $^1H$ NMR (300 MHz, DMSO-$d_6$) δ 9.72 (s, 1H), 8.60 (d, J=5.2 Hz, 1H), 8.33 (s, 1H), 7.99 (s, 1H), 7.80-7.91 (m, 2H), 7.59 (d, J=8.7 Hz, 1H), 5.62 (s, 1H), 5.07 (d, J=9.0 Hz, 1H), 3.63-3.74 (m, 1H), 2.69-2.91 (m, 1H), 2.53-2.59 (m, 1H), 2.20-2.38 (m, 1H), 2.05-2.17 (m, 1H), 1.77-2.05 (m, 2H). $^{19}F$ NMR (300 MHz, DMSO-$d_6$) δ−73.79, −112.69.

Example 207 5-(2-((3S,8aR)-7-(3-Chloro-6-(4-chloro-1H-1,2,3-triazol-1-yl)-2-fluorophenyl)-5-oxo-1,2,3,5,8,8a-hexahydroindolizin-3-yl)-1H-imidazol-5-yl)thiophene-2-carboxamide

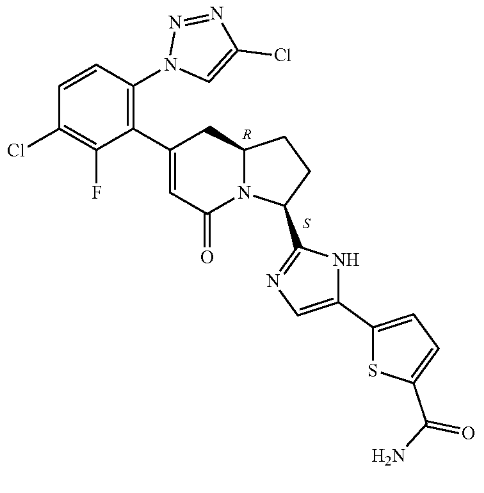

LC/MS: mass calculated for $C_{24}H_{18}Cl_2FN_7O_2S$: 557.06, measured (ES, m/z): 557.90 $[M+H]^+$. $^1H$ NMR (400 MHz, DMSO-$d_6$) δ 11.94 (s, 1H), 8.81 (s, 1H), 7.90 (t, J=8.4 Hz, 1H), 7.75-7.86 (m, 1H), 7.58-7.65 (m, 2H), 7.42 (s, 1H), 7.16-7.25 (m, 2H), 5.66 (d, J=2.7 Hz, 1H), 4.97 (d, J=8.8 Hz, 1H), 3.63-3.73 (m, 1H), 2.66-2.79 (m, 1H), 2.40-2.46 (m, 1H), 2.13-2.21 (m, 1H), 2.02-2.10 (m, 1H), 1.90-1.98 (m, 2H). $^{19}$F NMR (376 MHz, DMSO-$d_6$) δ −112.98.

Example 208 5-(2-((3S,8aR)-7-(3-Chloro-6-(4-chloro-1H-1,2,3-triazol-1-yl)-2-fluorophenyl)-5-oxo-1,2,3,5,8,8a-hexahydroindolizin-3-yl)-1H-imidazol-5-yl)thiazole-2-carboxamide

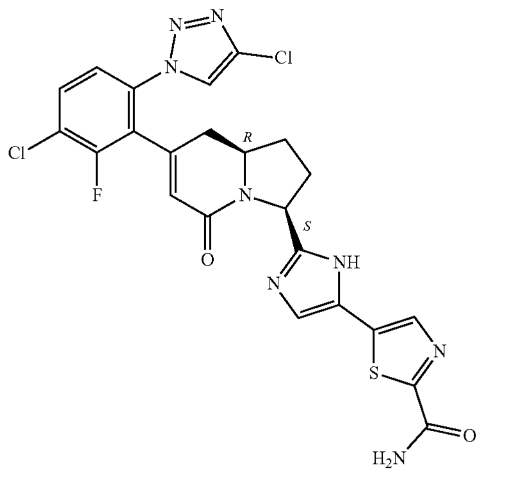

Step 1: 2-(2-carbamoylthiazol-5-yl)-2-oxoethyl (3S)-7-(3-chloro-6-(4-chloro-1H-1,2,3-triazol-1-yl)-2-fluorophenyl)-5-oxo-1,2,3,5,8,8a-hexahydroindofizine-3-carboxylate $Cs_2CO_3$ (95 mg, 0.29 mmol, 0.6 equiv.) was added to a solution of (3S)-7-(3-chloro-6-(4-chloro-1H-1,2,3-triazol-1-yl)-2-fluorophenyl)-5-oxo-1,2,3,5,8,8a-hexahydroindolizine-3-carboxylic acid (200 mg, 0.48 mmol, 1.0 equiv.) in DMF (3 mL). After stirring at room temperature. for 30 min, 5-(2-bromoacetyl)thiazole-2-carboxamide (182 mg, 0.73 mmol, 2.0 equiv.) was added and the resulting mixture was stirred at room temperature for 2 h. The reaction was quenched with water (100 mL) and extracted with ethyl acetate (100 mL×3). The combined organic layer was washed with brine, dried over $Na_2SO_4$ and concentrated. The residue was purified by purified by flash column chromatography on silica gel (0→20% MeOH/DCM) to yield 2-(2-carbamoylthiazol-5-yl)-2-oxoethyl (3S)-7-(3-chloro-6-(4-chloro-1H-1,2,3-triazol-1-yl)-2-fluorophenyl)-5-oxo-1,2,3,5,8,8a-hexahydroindolizine-3-carboxylate as a yellow solid. LC/MS: mass calculated for $C_{23}H_{17}Cl_2FN_6O_5S$: 578.03, measured: 579.05 $[M+H]^+$.

Step 2: 5-(2-((3S,8aR)-7-(3-chloro-6-(4-chloro-1H-1,2,3-triazol-1-yl)-2-fluorophenyl)-5-oxo-1,2,3,5,8,8a-hexahydroindolizin-3-yl)-1H-imidazol-5-yl)thiazole-2-carboxamide To a solution of 2-(2-carbamoylthiazol-5-yl)-2-oxoethyl (3S)-7-(3-chloro-6-(4-chloro-1H-1,2,3-triazol-1-yl)-2-fluorophenyl)-5-oxo-1,2,3,5,8,8a-hexahydroindolizine-3-carboxylate (120 mg, 0.21 mmol, 1.0 equiv.) in toluene (5 mL) were added $CH_3COOH$ (0.5 mL) and $NH_4OAc$ (160 mg, 2.07 mmol, 10.0 equiv.). The reaction mixture was stirred for 2 h at 110° C., cooled to room temperature, quenched with water, and extracted with ethyl acetate. The combined organic layer was washed with brine, dried over $Na_2SO_4$ and concentrated under reduced pressure. The residue was purified by reverse phase chromatography on C18 column to yield 5-(2-((3S,8aR)-7-(3-chloro-6-(4-chloro-1H-1,2,3-triazol-1-yl)-2-fluorophenyl)-5-oxo-1,2,3,5,8,8a-hexahydroindolizin-3-yl)-1H-imidazol-5-yl)thiazole-2-carboxamide as a white solid.

LC/MS: mass calculated for $C_{23}H_{17}C_{12}FN_8O_2S$: 558.06, measured (ES, m/z): 559.00 $[M+H]^+$. $^1$H NMR (300 MHz, DMSO-$d_6$) δ 12.13 (s, 1H), 8.83 (s, 1H), 8.10 (s, 1H), 8.05-8.08 (m, 1H), 7.93 (t, J=8.3 Hz, 1H), 7.73 (s, 1H), 7.58-7.69 (m, 2H), 5.68 (d, J=2.5 Hz, 1H), 5.00 (d, J=8.6 Hz, 1H), 3.65-3.77 (m, 1H), 2.69-2.81 (m, 1H), 1.91-2.26 (m, 5H). $^{19}$F NMR (282 MHz, DMSO-$d_6$) δ −113.04

Example 209 5-(2-((3S,8aS)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H imidazol-4-yl)thiazole-2-carboxamide

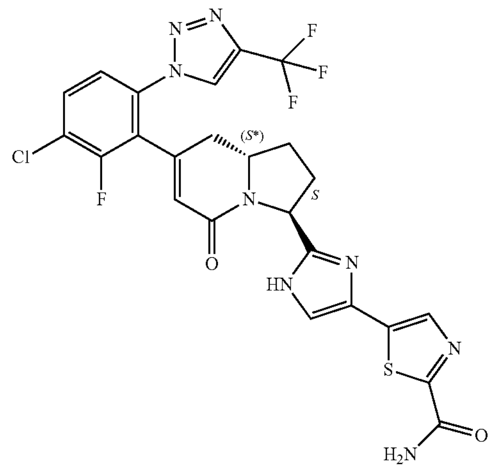

LC/MS: mass calculated for $C_{24}H_{17}ClF_4N_8O_2S$: 592.08, measured (ES, m/z): 593.00 $[M+H]^+$. $^1$H NMR (400 MHz, DMSO-$d_6$) δ 9.35 (d, J=1.0 Hz, 1H), 8.08-8.19 (m, 2H), 7.75-8.03 (m, 1H), 7.76 (s, 1H), 7.71 (dd, J=8.7, 1.5 Hz, 1H), 7.62 (s, 1H), 5.70 (d, J=2.7 Hz, 1H), 4.97 (t, J=7.5 Hz, 1H), 4.02-4.17 (m, 1H), 2.53-2.54 (m, 1H), 2.31-2.42 (m, 2H), 2.17-2.28 (m, 1H), 1.96-2.13 (m, 1H), 1.60-1.78 (m, 1H). $^{19}$F NMR (376 MHz, DMSO-$d_6$) δ −59.59, −113.15.

Example 210 5-(2-((3S,8aR)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-4-yl)thiazole-2-carboxamide

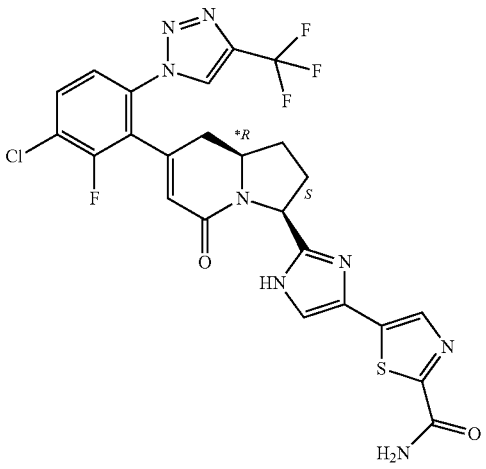

LC/MS: mass calculated for $C_{24}H_{17}ClF_4N_8O_2S$: 592.08, measured (ES, m/z): 593.00 $[M+H]^+$. $^1H$ NMR (400 MHz, DMSO-$d_6$) δ 11.88-12.40 (m, 1H), 9.32 (d, J=1.1 Hz, 1H), 8.06-8.10 (m, 2H), 7.95-7.99 (m, 1H), 7.74 (s, 1H), 7.70 (dd, J=8.7, 1.5 Hz, 1H), 7.61 (s, 1H), 5.66 (d, J=2.7 Hz, 1H), 4.98 (d, J=9.0 Hz, 1H), 3.69-3.70 (m, 1H), 2.78-2.86 (m, 1H), 2.53-2.54 (m, 1H), 2.18-2.26 (m, 1H), 2.03-2.12 (m, 1H), 1.91-2.02 (m, 2H). $^{19F}$ NMR (376 MHz, DMSO-$d_6$) δ −59.56, −112.89

Example 211 5-(5-Chloro-2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)thiophene-2-carboxamide

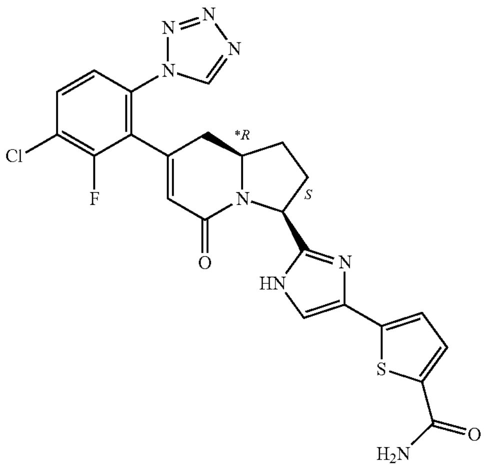

LC/MS: mass calculated for $C_{23}H_{17}Cl_2FN_8O_2S$: 558.06, measured (ES, m/z): 558.95 $[M+H]^+$. $^1H$ NMR (400 MHz, DMSO-$d_6$) δ 12.96 (s, 1H), 9.84 (s, 1H), 7.95-8.00 (m, 2H), 7.70-7.72 (m, 2H), 7.42 (s, 1H), 7.35 (d, J=3.9 Hz, 1H), 5.65 (d, J=2.3 Hz, 1H), 4.91 (d, J=8.7 Hz, 1H), 3.67-3.74 (m, 1H), 2.59-2.63 (m, 1H), 1.92-2.33 (m, 5H). $^{19}F$ NMR (376 MHz, DMSO-$d_6$) δ −113.55.

Example 212 5-(2-((3S,8aR)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)picolinamide

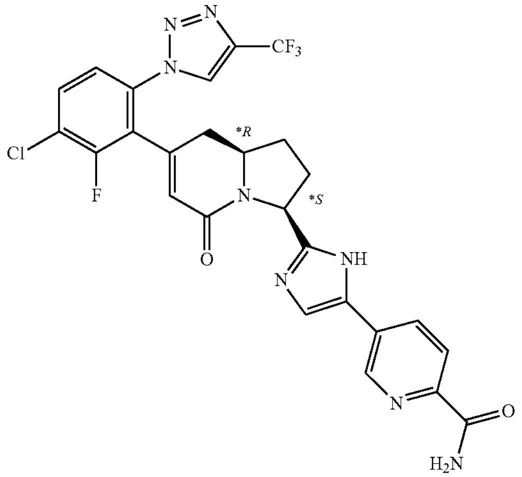 [SMILES: NC(=O)c1ccc(-c2cnc([C@@H]3CC[C@@H]4CC(c5c(-n6cc(C(F)(F)F)nn6)ccc(Cl)c5F)=CC(=O)N43)[nH]2)cn1]

LC/MS: mass calculated for $C_{26}H_{19}ClF_4N_8O_2$: 586.13, measured (ES, m/z): 587.20 $[M+H]^+$. $^1H$ NMR (300 MHz, DMSO-$d_6$) δ 12.13 (s, 1H), 9.33 (d, J=1.1 Hz, 1H), 8.96 (d, J=2.1 Hz, 1H), 8.23 (dd, J=8.1, 2.2 Hz, 1H), 7.90-8.07 (m, 3H), 7.74 (s, 1H), 7.70 (dd, J=8.7, 1.5 Hz, 1H), 7.54 (s, 1H), 5.69 (d, J=2.5 Hz, 1H), 5.01 (d, J=8.4 Hz, 1H), 3.64-3.77 (m, 1H), 2.63-2.78 (m, 1H), 2.42-2.46 (m, 1H), 1.83-2.33 (m, 4H). $^{19}F$ NMR (300 MHz, DMSO-$d_6$) δ −59.59, −112.90.

Example 213 5-(2-((3S,8aS)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)picolinamide

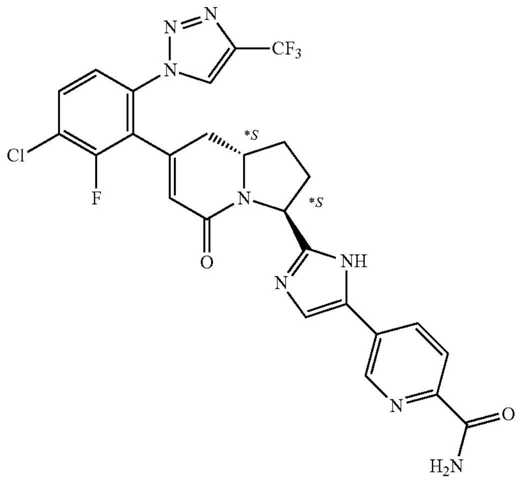 [SMILES: NC(=O)c1ccc(-c2cnc([C@@H]3CC[C@H]4CC(c5c(-n6cc(C(F)(F)F)nn6)ccc(Cl)c5F)=CC(=O)N43)[nH]2)cn1]

LC/MS: mass calculated for $C_{26}H_{19}ClF_4N_8O_2$: 586.13, measured (ES, m/z): 587.10 $[M+H]^+$. $^1H$ NMR (300 MHz, DMSO-$d_6$) δ 12.88-12.94 (m, 1H), 9.33 (s, 1H), 8.95 (s, 1H), 8.21 (d, J=8.2 Hz, 1H), 7.89-8.08 (m, 3H), 7.80 (s, 1H), 7.69 (d, J=8.7 Hz, 1H), 7.56 (s, 1H), 5.69 (5, 1H), 5.01 (t, J=7.5 Hz, 1H), 4.02-4.19 (m, 1H), 2.17-2.43 (m, 4H), 1.91-2.12 (m, 1H), 1.61-1.78 (m, 1H). $^{19}$F NMR (300 MHz, DMSO-$d_6$) δ −59.64, −73.57, −113.19.

Example 214 4-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-3-fluorothiophene-2-carboxamide

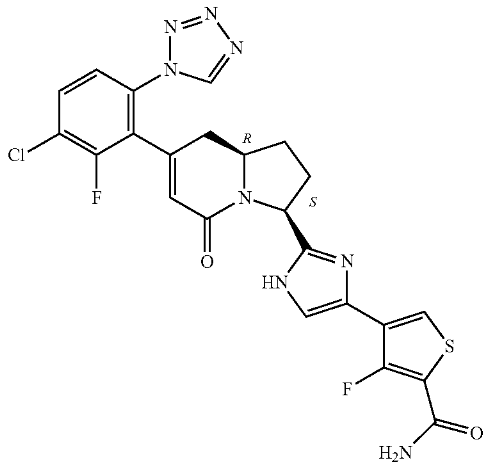

LC/MS: mass calculated for $C_{23}H_{17}ClF_2N_8O_2S$: 542.09, measured (ES, m/z): 543.00 $[M+H]^+$. $^1$H-NMR (400 MHz, DMSO-$d_6$) δ 11.76-12.57 (m, 1H), 9.84 (s, 1H), 7.97 (t, J=8.2 Hz, 1H), 7.60-7.80 (m, 3H), 7.36 (s, 1H), 7.20 (s, 1H), 5.69 (s, 1H), 5.01 (d, J=8.6 Hz, 1H), 3.67-3.77 (m, 1H), 2.65-2.75 (m, 1H), 2.15-2.20 (m, 1H), 2.06-2.14 (m, 1H), 1.86-1.97 (m, 2H), 1.03-1.14 (m, 1H). $^{19}$F-NMR (376 MHz, DMSO-$d_6$) δ −112.71, −120.00.

Example 215 5-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-3-fluorothiophene-2-carboxamide

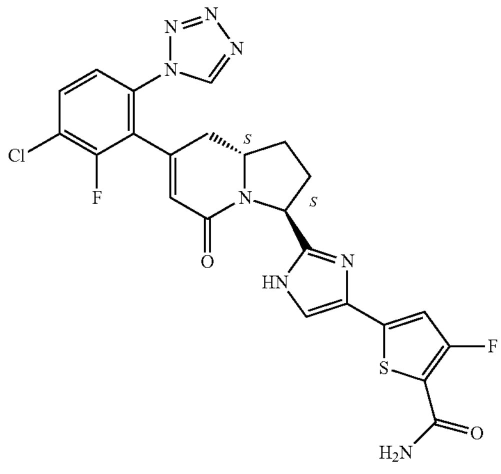

LC/MS: mass calculated for $C_{23}H_{17}ClF_2N_8O_2S$: 542.09, measured (ES, m/z): 543.05 $[M+H]^+$. $^1$H NMR (400 MHz, DMSO-$d_6$) δ 9.84 (s, 1H), 7.99 (dd, J=8.4, 8.0 Hz, 1H), 7.66-7.74 (m, 2H), 7.20-7.35 (m, 1H), 5.71 (d, J=2.8 Hz, 1H), 4.97 (t, J=7.7 Hz, 1H), 4.08-4.19 (m, 1H), 2.70-2.80 (m, 1H), 2.50-2.53 (m, 1H), 2.31-2.40 (m, 1H), 2.19-2.30 (m, 1H), 1.89-2.02 (m, 1H), 1.75-1.83 (m, 1H). $^{19}$F NMR (376 MHz, DMSO-$d_6$) δ −113.03, −117.76.

Example 216 5-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-3-fluorothiophene-2-carboxamide

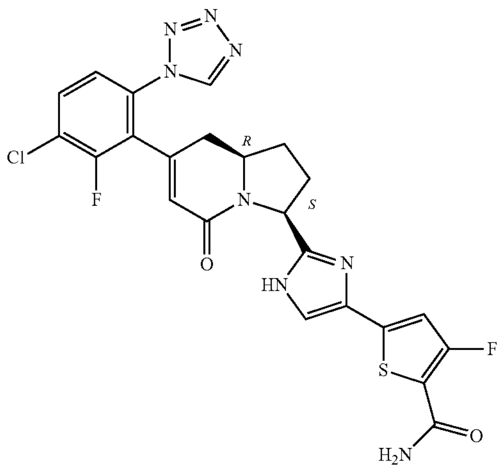

Step 1: 2-(5-carbamoyl-4-fluorothiophen-2-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (222 mg, 0.68 mmol, 1.0 equiv.) in DMF (8 mL) was added $Cs_2CO_3$ (133 mg, 0.41 mmol, 0.6 equiv.), followed by methyl 4-(2-bromoacetyl)-3-fluorothiophene-2-carboxylate (200 mg, 0.75 mmol, 1.1 equiv.). The resulting mixture was stirred at room temperature. for 2 h, diluted with water (10 mL), and extracted with ethyl acetate (20 mL×3). The organic layers were combined, washed with brine three times, dried over anhydrous sodium sulfate, filtered, and concentrated. The residue was purified by purified by flash column chromatography on silica gel (0→20% MeOH/DCM) to yield the 2-(5-carbamoyl-4-fluorothiophen-2-yl)-2-oxoethyl (3S)-7-(6-amino-3-chloro-2-fluorophenyl)-5-oxo-1,2,3,5,8,8a-hexahydroindolizine-3-carboxylate. LC/MS: mass calculated for $C_{22}H_{18}ClF_2N_3O_5S$: 509.06, measured: 510.20 $[M+H]^+$.

Step 2: 5-(2-((3S)-7-(6-amino-3-chloro-2-fluorophenyl)-5-oxo-1,2,3,5,8,8a-hexahydroindolizin-3-yl)-1H-imidazol-4-yl)-3-fluorothiophene-2-carboxamide To a mixture of 2-(5-carbamoyl-4-fluorothiophen-2-yl)-2-oxoethyl (3S)-7 (6-amino-3-chloro-2-fluorophenyl)-5-oxo-1,2,3,5,8,8a-hexahydroindolizine-3-carboxylate (230 mg, 0.45 mmol, 1.0 equiv.) in toluene (10 mL) and acetic acid (1 mL) was added ammonium acetate (352 mg, 4.51 mmol, 10.0 equiv.) in portions at room temperature. The resulting mixture was stirred at 100° C. for 2 h, allowed to cool to room temperature, and concentrated under reduced pressure. The residue was purified by purified by flash column chromatography on silica gel (0→20% MeOH/DCM) to yield 5-(2-((3S)-7-(6-amino-3-chloro-2-fluorophenyl)-5-oxo-1,2,3,5,8,8a-hexahydroindolizin-3-yl)-1H-imidazol-4-yl)-3-fluorothiophene-2-carboxamide as a yellow solid. LC/MS: mass calculated for $C_{22}H_{18}ClF_2N_5O_2S$: 489.08, measured: 490.20 $[M+H]^+$.

Step 3: 5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-3-fluorothiophene-2-carboxamide To a solution of 5-(2-((3S)-7-(6-amino-3-chloro-2-fluorophenyl)-5-oxo-1,2,3,5,8,8a-hexahydroindolizin-3-yl)-1H-imidazol-4-yl)-3-fluorothiophene-2-carboxamide (210 mg, 0.43 mmol, 1.0 equiv.) in AcOH (10 mL) was added $TMSN_3$ (492.933 mg, 4.28 mmol) followed by addition of trimethoxymethane (455 mg, 4.28 mmol, 10.0 equiv.). The resulting mixture was maintained at 60° C. for 2 h. The solvent was removed under reduced pressure and the residue was purified by prep-HPLC with Mobile Phase A: Water (0.05% TFA), Mobile Phase B: ACN to yield the racemic product, which was further separated by Chiral-HPLC to yield 5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-3-fluorothiophene-2-carboxamide as a white solid.

LC/MS: mass calculated for $C_{23}H_{17}ClF_2N_8O_2S$: 542.09, measured (ES, m/z): 543.05 $[M+H]^+$. $^1H$ NMR (400 MHz, DMSO-$d_6$) δ 9.83 (s, 1H), 7.98 (dd, J=8.4, 8.0 Hz, 1H), 7.66-7.74 (m, 3H), 7.20-7.30 (m, 2H), 5.67 (d, J=2.8 Hz, 1H), 5.02 (d, J=9.2 Hz, 1H), 3.65-3.72 (m, 1H), 2.81 (t, J=15.3 Hz, 1H), 2.50-2.53 (m, 1H), 2.19-2.30 (m, 1H), 2.09-2.15 (m, 1H), 1.84-2.03 (m, 2H). $^{19}F$ NMR (376 MHz, DMSO-$d_6$) δ −112.75, −117.79.

Example 217 (3S,8aR)-7-(3-Chloro-2-fluoro-6-(1H-tetrazol-1-yl)phenyl)-3-(5-(3-fluoro-1H-pyrazol-4-yl)-1H-imidazol-2-yl)-2,3,8,8a-tetrahydroindolizin-5(1H)-one

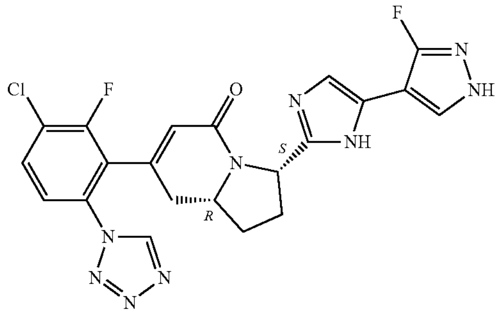

Step 1: 2-(3-fluoro-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate Potassium carbonate (400 mg, 2.90 mmol, 3.0 equiv.) was added to a solution of (3S)-7-(6-amino-3-chloro-2-fluorophenyl)-5-oxo-1,2,3,5,8,8a-hexahydroindolizine-3-carboxylic acid (314 mg, 0.97 mmol, 1.0 equiv.) in DMF (5 mL). The reaction mixture was stirred at 25° C. for 0.5 h, then 2-bromo-1-(3-fluoro-1H-pyrazol-4-yl)ethanone (200 mg) was added and the resulting mixture was stirred at room temperature for 1.5 h. The solvent was removed under reduced pressure and the residue was purified by reverse phase chromatography on C18 column (MeCN/$H_2O$ (0.05% TFA): 0→60%) to yield 2-(3-fluoro-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate as a yellow oil. LC/MS: mass calculated for $C_{20}H_{17}ClF_2N_4O_4$: 450.09, measured: 451.10 $[M+H]^+$.

Step 2: (3S)-7-(6-amino-3-chloro-2-fluorophenyl)-3-(5-(3-fluoro-1H-pyrazol-4-yl)-1H-imidazol-2-yl)-2,3,8,8a-tetrahydroindolizin-5(1H)-one To a solution of 2-(3-fluoro-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate (180 mg, 0.40 mmol, 1.0 equiv.) in AcOH (0.5 mL) and toluene (5 mL) was added $NH_4OAc$ (307 mg, 3.99 mmol, 10.0 equiv.). The resulting mixture was maintained under nitrogen and stirred at 110° C. for 3 h, then concentrated under vacuum. The residue was purified by purified by flash column chromatography on silica gel (0→10% MeOH/DCM) to yield the (3S)-7-(6-amino-3-chloro-2-fluorophenyl)-3-(5-(3-fluoro-1H-pyrazol-4-yl)-1H-imidazol-2-yl)-2,3,8,8a-tetrahydroindolizin-5(1H)-one as a yellow solid. LC/MS: mass calculated for $C_{20}H_{17}ClF_2N_6O$: 430.11, measured: 431.10 $[M+H]^+$.

Step 3: (3S,8aR)-7-(3-chloro-2-fluoro-6-(1H-tetrazol-1-yl)phenyl)-3-(5-(3-fluoro-1H-pyrazol-4-yl)-1H-imidazol-2-yl)-2,3,8,8a-tetrahydroindolizin-5(1H)-one To a solution of (3S)-7-(6-amino-3-chloro-2-fluorophenyl)-3-(5-(3-fluoro-1H-pyrazol-4-yl)-1H-imidazol-2-yl)-2,3,8,8a-tetrahydroindolizin-5(1H)-one (60 mg, 0.14 mmol, 1.0 equiv.) in HOAc (3 mL) were added trimethoxymethane (148 mg, 1.39 mmol, 10.0 equiv.), and $TMSN_3$ (160 mg, 1.39 mmol, 10.0 equiv.). The resulting mixture was stirred at 25° C. overnight and concentrated under reduced pressure. The residue was purified by purified by flash column chromatography on silica gel (0→10% MeOH/DCM) and then separated by Chiral Prep-SEC with Mobile Phase A: Hex: DCM=1:1 (10 mM $NH_3$-MeOH), Mobile Phase B: EtOH to yield (3S,8aR)-7-(3-chloro-2-fluoro-6-(1H-tetrazol-1-yl)phenyl)-3-(5-(3-fluoro-1H-pyrazol-4-yl)-1H-imidazol-2-yl)-2,3,8,8a-tetrahydroindolizin-5(1H)-one as an white solid.

LC/MS: mass calculated for $C_{21}H_{16}ClF_2N_9O$: 483.11, measured (ES, m/z): 484.00 $[M+H]^+$. $^1H$ NMR (400 MHz, DMSO-$d_6$) δ 12.21-12.53 (m, 1H), 11.68 (br, 1H), 9.82 (s, 1H), 7.96 (t, J=8.0 Hz, 1H), 7.81 (s, 1H), 7.70 (d, J=8.8 Hz, 1H), 6.98 (s, 1H), 5.67 (s, 1H), 4.97 (d, J=8.4 Hz, 1H), 3.62-3.75 (m, 1H), 2.71-2.81 (m, 1H), 2.52-2.67 (m, 1H), 2.01-2.22 (m, 2H), 1.86-2.00 (m, 2H). $^{19}F$ NMR (376 MHz, DMSO-$d_6$) δ −135.64, −112.76.

Example 218 4-(5-Chloro-2-((3S)-7-(3-chloro-2-fluoro-6-(1H-tetrazol-1-yl)phenyl)-5-oxo-1,2,3,5,8,8a-hexahydroindolizin-3-yl)-1H-imidazol-4-yl)thiophene-2-carboxamide

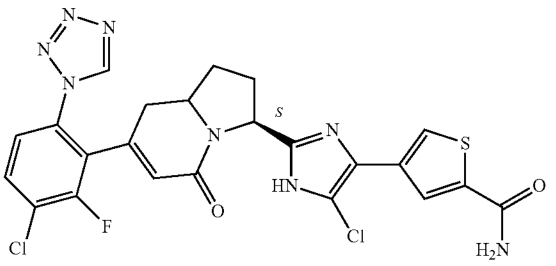

LC/MS: mass calculated for $C_{23}H_{17}Cl_2FN_8O_2S$: 558.06, measured (ES, m/z): 559.00 $[M+H]^+$. $^1H$ NMR (400 MHz, DMSO-$d_6$) δ 12.63 (br, 1H), 9.83 (s, 1H), 8.06-8.14 (m, 2H), 7.96 (t, J=8.2 Hz, 1H), 7.85 (s, 1H), 7.71 (d, J=8.7 Hz, 1H), 7.44 (s, 1H), 5.66 (s, 1H), 4.92 (d, J=8.6 Hz, 1H), 3.62-3.76 (m, 1H), 2.49-2.66 (m, 2H), 2.15-2.23 (m, 1H), 2.07-2.11 (m, 1H), 1.96-2.05 (m, 1H), 1.87-1.92 (m, 1H). $^{19}F$ NMR (376 MHz, DMSO-$d_6$) δ −112.81.

Example 219 4-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)thiophene-2-carboxamide

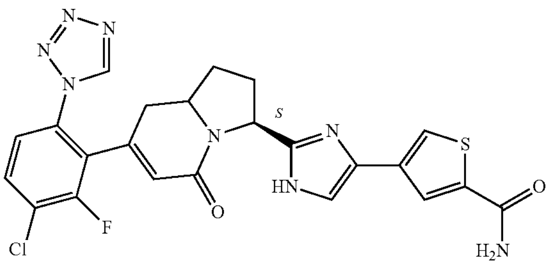

LC/MS: mass calculated for $C_{23}H_{18}ClFN_8O_2S$: 524.09, measured (ES, m/z): 525.00 $[M+H]^+$. $^1H$ NMR (400 MHz, DMSO-$d_6$) δ 11.67-11.93 (m, 1H), 9.83 (s, 1H), 8.02 (s, 1H), 8.00-7.89 (m, 2H), 7.74-7.67 (m, 2H), 7.30-7.42 (m, 1H), 7.24 (s, 1H), 5.70-5.63 (m, 1H), 4.98 (d, J=8.6 Hz, 1H), 3.63-4.13 (m, 1H), 2.67-2.82 (m, 1H), 2.49-2.58 (m, 1H), 2.13-2.22 (m, 1H), 2.03-2.11 (m, 1H), 1.85-2.02 (m, 2H). $^{19}F$ NMR (376 MHz, DMSO-$d_6$) δ −112.66, −112.90, −113.05

Example 220 5-(2-((3S,8aR)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H imidazol-4-yl)thiophene-2-carboxamide

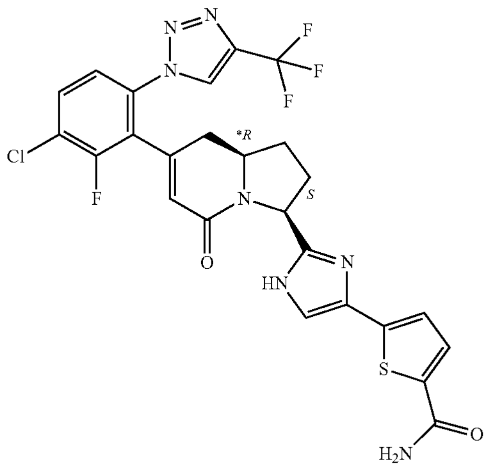

LC/MS: mass calculated for $C_{25}H_{18}ClF_4N_7O_2S$: 591.09, measured (ES, m/z): 592.00 $[M+H]^+$. $^1H$ NMR (400 MHz, DMSO-$d_6$) δ 11.92-12.26 (m, 1H), 9.20-9.42 (m, 1H), 7.90-8.01 (m, 1H), 7.77-7.89 (m, 1H), 7.66-7.76 (m, 1H), 7.61 (d, J=3.8 Hz, 1H), 7.39-7.49 (m, 1H), 7.10-7.38 (m, 2H), 5.65-5.82 (m, 1H), 4.89-5.10 (m, 1H), 3.99-4.35 (m, 1H), 2.30-2.40 (m, 2H), 2.10-2.20 (m, 1H), 1.92-2.09 (m, 2H), 1.60-1.75 (m, 1H). $^{19}F$ NMR (376 MHz, DMSO-$d_6$) δ −59.60, −113.75

Example 221 5-(2-((3S,8aS)-7-(3-Chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxamide

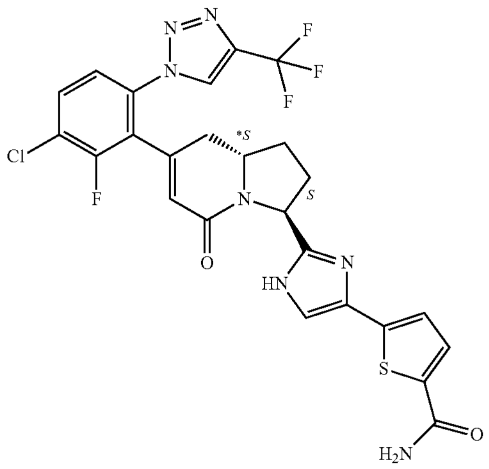

LC/MS: mass calculated for $C_{25}H_{18}ClF_4N_7O_2S$: 591.09, measured (ES, m/z): 592.00 $[M+H]^+$. $^1H$ NMR (400 MHz, DMSO-$d_6$) δ 11.93 (s, 1H), 9.33 (s, 1 H), 7.96 (t, J=8.2 Hz, 1H), 7.81 (s, 1H), 7.71 (d, J=8.7 Hz, 1H), 7.62 (d, J=3.9 Hz, 1H), 7.43 (s, 1H), 7.21 (d, J=3.9 Hz, 1H), 5.68 (s, 1H), 4.97

(d, J=8.6 Hz, 1H), 3.60-3.80 (m, 1H), 2.77 (t, J=15.2 Hz, 1H), 2.40-2.45 (m, 1H), 2.13-2.28 (m, 1H), 2.01-2.12 (m, 1H), 1.85-2.00 (m, 2H). $^{19}$F NMR (376 MHz, DMSO-$d_6$) δ −59.56, −112.77.

Example 222 (3S,8aR)-7-(3-Chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one

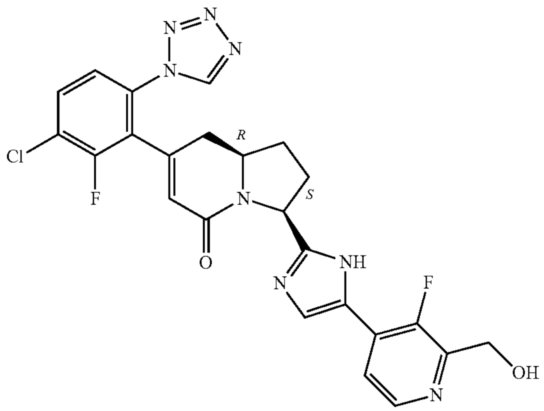

Step 1: 2-(2-(((tert-butyldimethylsilyl)oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (9.3 g, 28.64 mmol, 1.0 equiv) and $Cs_2CO_3$ (5.6 g, 17.18 mmol, 0.6 equiv) in DMF (90 mL) was stirred at 40° C. for 30 min. 2-Bromo-1-(2-(((tert-butyldimethylsilyl)oxy) methyl)-3-fluoropyridin-4-yl)ethan-1-one (14.5 g, 40.09 mmol, 1.4 equiv) was then added to the mixture. The resulting mixture was stirred at room temperature for 4 h, then diluted with EtOAc (900 mL), washed with water (3×150 mL), brine (2×150 mL), dried over $Na_2SO_4$, and concentrated under reduced pressure. The residue was purified by flash column chromatography on silica gel (330 g, MeOH/DCM: 1/20) to yield 2-(2-(((tert butyldimethylsilyl) oxy)methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate as a light yellow solid. LC/MS: mass calculated for $C_{29}H_{34}ClF_2N_3O_5Si$: 605.19, measured: 606.15 [M+H]$^+$.

Step 2: (3S)-7-(6-amino-3-chloro-2-fluorophenyl)-3-(5-(2-(((tert-butyldimethylsilyl)oxy)methyl)-3-fluoropyridin-4-yl)-1H-imidazol-2-yl)-2,3,8,8a-tetrahydroindolizin-5(1H)-one To a solution of 2-(2-(((tert-butyldimethylsilyl)oxy) methyl)-3-fluoropyridin-4-yl)-2-oxoethyl (3S)-7-(6-amino-3-chloro-2-fluorophenyl)-5-oxo-1,2,3,5,8,8a-hexahydroindolizine-3-carboxylate (15 g, 24.75 mmol, 1.0 equiv) in AcOH (30 mL) and toluene (300 mL) was added $NH_4OAc$ (19.08 g, 247.47 mmol, 10.0 equiv) and the mixture was stirred at 110° C. under $N_2$ for 1 h. The solvent was removed under reduced pressure and the residue was purified by flash column chromatography on silica gel (330 g, MeOH/DCM: 1/15) to yield (3S)-7-(6-amino-3-chloro-2-fluorophenyl)-3-(5-(2-((tert-butyldimethylsilyloxy)methyl)-3-fluoropyridin-4-yl)-1H-imidazol-2-yl)-2,3,8,8a-tetrahydroindolizin-5 (1H)-one as a light yellow solid. LC/MS: mass calculated for $C_{29}H_{34}ClF_2N_5O_2Si$: 585.21, measured: 586.15 [M+H]$^+$.

Step 3: (3S,8aR)-7-(3-chloro-2-fluoro-6-(1H-tetrazol-1-yl)phenyl)-3-(5-(3-fluoro-2-(hydroxymethyl) pyridin-4-yl)-1H-imidazol-2-yl)-2,3,8,8a-tetrahydroindolizin-5(1H)-one A mixture of (3S)-7-(6-amino-3-chloro-2-fluorophenyl)-3-(5-(2-((tert-butyldimethyl-silyloxy)methyl)-3-fluoropyridin-4-yl)-1H-imidazol-2-yl)-2,3,8,8a-tetrahydroindolizin-5 (1H)-one (8.0 g, 13.65 mmol, 1.00 equiv), $TMSN_3$ (15.7 g, 136.48 mmol, 10.0 equiv) and trimethoxymethane (14.48 g, 136.48 mmol, 10.00 equiv) in AcOH (60 mL) was stirred at 55° C. overnight, then concentrated under reduced pressure. The resulting residue was purified by flash column chromatography on silica gel to yield (3S)-7-(3-chloro-2-fluoro-6-(1H-tetrazol-1-yl)phenyl)-3-(5-(3-fluoro-2-(hydroxyl methyl)pyridin-4-yl)-1H-imidazol-2-yl)-2,3,8,8a-tetrahydroindolizin-5(1H)-one as a white solid, which was further purified by prep-SFC(Column: Exsil Chieal-NR, 250 mm*30 mm, 8 um; Mobile Phase A: $CO_2$, Mobile Phase B: MeOH (0.1% 2M $NH_3$-MeOH); Flow rate: 100 mL/min; Gradient: 50% B; 220 nm; RT1:6.78; RT2:8.45; Injection Volume: 3 ml; Number Of Runs: 37) to yield (3S,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-2,3,8,8a-tetrahydroindolizin-5(1H)-one as a white solid.

LC/MS: mass calculated for $C_{24}H_{19}ClF_2N_8O_2$: 524.13, measured (ES, m/z): 525.00 [M+H]$^+$. 1H NMR (300 MHz, DMSO-$d_6$) δ 12.22 (s, 1H), 9.81 (s, 1 H), 8.32 (d, J=5.0 Hz, 1H), 7.96 (dd, J=8.7, 7.8 Hz, 1H), 7.90-7.83 (m, 1H), 7.69 (dd, J=8.7, 1.5 Hz, 1H), 7.54 (d, J=4.0 Hz, 1H), 5.68 (d, J=2.5 Hz, 1H), 5.30-5.17 (m, 1H), 5.03 (d, J=8.5 Hz, 1H), 4.62 (s, 2H), 3.80-3.65 (m, 1H), 2.78-2.62 (m, 1H), 2.57-2.52 (m, 1H), 2.28-2.03 (m, 2H), 2.04-1.87 (m, 2H). $^{19}$F NMR (300 MHz, DMSO-$d_6$) δ −112.84, −130.18.

Example 223 (3S,8aR)-7-(3-Chloro-2-fluoro-6-(4-(trifluoromethyl)-1H-1,2,3-triazol-1-yl)phenyl)-3-(5-(2-chloro-6-(hydroxymethyl)pyridin-3-yl)-1H-imidazol-2-yl)-2,3,8,8a-tetrahydroindolizin-5(1H)-one

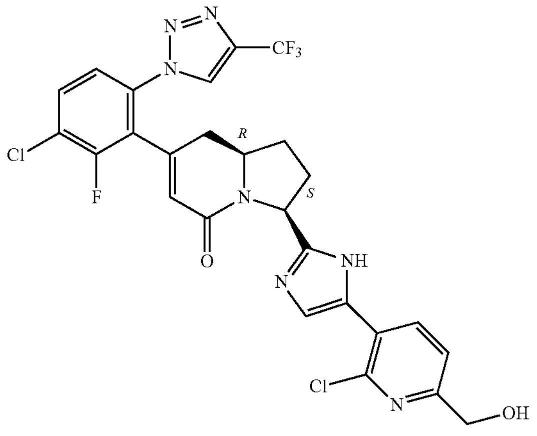

LC/MS: mass calculated for $C_{28}H_{19}Cl_2F_4N_7O_2$: 607.09, measured (ES, m/z): 608.00 $[M+H]^+$. $^1H$ NMR (400 MHz, DMSO-$d_6$) δ 12.14 (br, 1H), 9.34 (s, 1H), 8.44 (br, 1H), 7.96 (t, J=8.1 Hz, 1H), 7.68-7.72 (m, 2H), 7.54 (d, J=8.0 Hz, 1H), 5.72 (s, 1H), 5.03-5.06 (m, 1H), 4.54 (s, 2H), 3.69-3.76 (m, 1H), 2.65-2.75 (m, 1H), 2.48-2.57 (m, 1H), 2.16-2.30 (m, 1H), 2.05-2.12 (m, 1H), 1.95-2.03 (m, 2H). $^{19}F$ NMR (376 MHz, DMSO-$d_6$) δ −59.58, −112.95.

Example 224: (3S,8aR)-3-(5-(3-Chloro-1H-pyrazol-4-yl)-1H-imidazol-2-yl)-7-(3-chloro-2-fluoro-6-(1H-tetrazol-1-yl)phenyl)-2,3,8,8a-tetrahydroindolizin-1H_-one

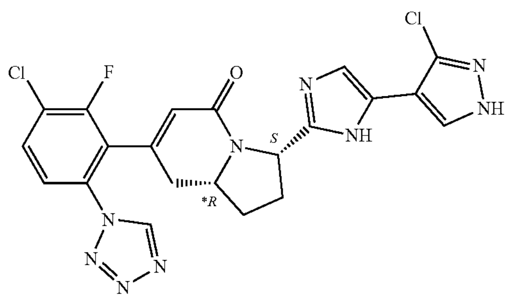

Step 1: 4-bromo-3-chloro-1-(tetrahydro-2H-pyran-2-yl)-1H-pyrazole

NBS (2.8 g, 16.07 mmol, 1.5 equiv.) was added to a solution of 3-chloro-1-(tetrahydro-2H-pyran-2-yl)-1H-pyrazole (2.0 g, 10.72 mmol, 1.0 equiv.) in DMF(20 mL) and the resulting mixture was stirred at 25° C. under nitrogen for 2 h. The reaction was quenched with water (50 mL) and extracted with EA (3×50 mL). The organic layers were combined, dried over anhydrous sodium sulfate, filtered, and concentrated to yield 4-bromo-3-chloro-1-(tetrahydro-2H-pyran-2-yl)-1H-pyrazole as a white oil. LC/MS: mass calculated for $C_8H_{10}BrClN_2O$: 263.97, measured: 264.90 $[M+H]^+$, 266.90 $[M+H+2]^+$.

Step 2: 1-(3-chloro-1-(tetrahydro-2H-pyran-2-yl)-1H-pyrazol-4-yl)ethan-1-one

Tributyl(1-ethoxyvinyl)stannane (204 mg, 0.56 mmol, 1.5 equiv.) and Pd(pph$_3$)$_4$ (44 mg, 0.04 mmol, 0.1 equiv.) were added to a solution of 4-bromo-3-chloro-1-(tetrahydro-2H-pyran-2-yl)-1H-pyrazole (100 mg, 0.38 mmol, 1.0 equiv.) in 1,4-dioxane (2 mL) and the resulting mixture was stirred at 100° C. for 3 h under nitrogen. After being cooled to room temperature, the reaction mixture was quenched with water (50 mL), extracted with EA (3×50 mL). The organic layers were combined, dried over anhydrous sodium sulfate, filtered, and concentrated. The residue was purified by flash column chromatography on silica gel (0→20% PE/EA) to yield 1-(3-chloro-1-(tetrahydro-2H-pyran-2-yl)-1H-pyrazol-4-yl)ethanone as an yellow oil. LC/MS: mass calculated for $C_{10}H_{13}ClN_2O_2$: 228.07, measured: 229.05 $[M+H]^+$.

Step 3: 2-bromo-1-(3-chloro-1H-pyrazol-4-yl)ethan-1-one

To a solution of 1-(3-chloro-1-(tetrahydro-2H-pyran-2-yl)-1H-pyrazol-4-yl)ethanone (650 mg, 2.84 mmol, 1.0 equiv.) in DCM (5 mL) was added Py·HBr$_3$ (819 mg, 2.56 mmol, 0.9 equiv.) followed by AcOH/HBr (0.02 mL). The resulting mixture was stirred at 25° C. for 16 h under nitrogen. The mixture was concentrated under vacuum to yield 2-bromo-1-(3-chloro-1H-pyrazol-4-yl)ethanone as a brown solid. LC/MS: mass calculated for $C_5H_4BrClN_2O$: 221.92, measured: 223.05 $[M+H]^+$, 225.05 $[M+H+2]^+$.

Step 4: 2-(3-chloro-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate Potassium carbonate (153 mg, 1.12 mmol, 2.0 equiv.) was added to a solution of (3S)-7-(6-amino-3-chloro-2-fluorophenyl)-5-oxo-1,2,3,5,8,8a-hexahydroindolizine-3-carboxylic acid (180 mg, 0.55 mmol, 1.0 equiv.) in DMF (5 mL) and the mixture was stirred at room temperature for 0.5 h. 2-Bromo-1-(3-chloro-1H-pyrazol-4-yl)ethanone (124 mg) was then added to the mixture. The resulting mixture was maintained under nitrogen and stirred at 25° C. for 2 h and then concentrated. The resulting residue was purified by prep-HPLC to yield 2-(3-chloro-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate as a brown solid.

Step 5: (3S)-7-(6-amino-3-chloro-2-fluorophenyl)-3-(5-(3-chloro-1H-pyrazol-4-yl)-1H-imidazol-2-yl)-2,3,8,8a-tetrahydroindolizin-5(1H)-one NH$_4$OAc (495 mg, 6.42 mmol, 10.0 equiv.) was added to a solution of 2-(3-chloro-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate (300 mg, 0.64 mmol, 1.0 equiv.) in toluene (5 mL) and AcOH (0.2 mL). The resulting mixture was maintained under nitrogen and stirred at 100° C. for 3 h. then cooled to room temperature, and concentrated. The residue was purified by flash column chromatography on silica gel (0→20% MeOH/DCM) to yield the (3S)-7-(6-amino-3-chloro-2-fluorophenyl)-3-(5-(3-chloro-1H-pyrazol-4-yl)-1H-imidazol-2-yl)-2,3,8,8a-tetrahydroindolizin-5(1H)-one as a brown solid. LC/MS: mass calculated for $C_{20}H_{17}Cl_2FN_6O$: 446.08, measured: 447.00 $[M+H]^+$.

Step 6: (3S,8aR)-3-(5-(3-chloro-1H-pyrazol-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of (3S)-7-(6-amino-3-chloro-2-fluorophenyl)-3-(5-(3-chloro-1H-pyrazol-4-yl)-1H-imidazol-2-yl)-2,3,8,8a-tetrahydroindolizin-5(1H)-one (190 mg, 0.42 mmol, 1.0 equiv.) in AcOH (5 mL) were added trimethoxymethane (451 mg, 4.25 mmol, 1.0 equiv.) and TMSN$_3$ (489 mg, 4.25 mmol, 10.0 equiv.), the resulting mixture was maintained under nitrogen and stirred at 25° C. for 16 h, concentrated under vacuum and the residue was purified by flash column chromatography on silica gel (0→20% MeOH/DCM) to yield a racemic product, which was separated by chiral-HPLC to yield (3S,8aR)-3-(5-(3-chloro-1H-pyrazol-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC/MS: mass calculated for $C_{21}H_{16}Cl_2FN_9O$: 499.08, measured (ES, m/z): 500.00 $[M+H]^+$. $^1H$ NMR (400 MHz, DMSO-$d_6$) δ 13.02-12.97 (m, 1H), 11.72-11.93 (m, 1H), 9.82 (s, 1H), 7.94-7.98 (m, 2H), 7.70 (d, J=8.4 Hz, 1H), 7.17 (s, 1H), 5.67 (s, 1H), 4.97 (d, J=8.4 Hz, 1H), 3.61-3.78 (m, 1H), 2.69-2.79 (m, 1H), 2.45-2.49 (m, 1H), 2.02-2.27 (m, 2H), 1.89-2.01 (m, 2H). $^{19}$F NMR (376 MHz, DMSO-$d_6$) δ−112.79.

Example 225: 5-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)picolinamide

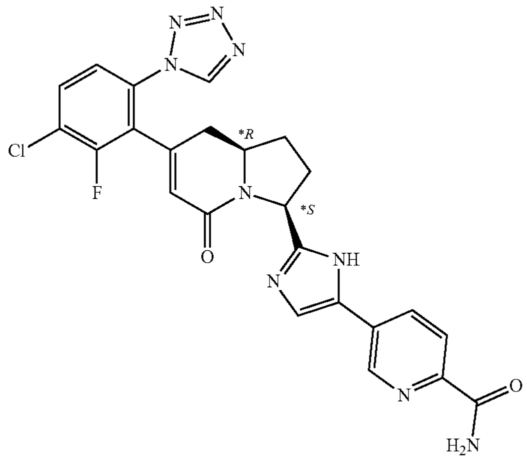 [SMILES: NC(=O)c1ccc(-c2cnc([C@@H]3CC[C@@H]4CC(c5c(-n6cnnn6)ccc(Cl)c5F)=CC(=O)N43)[nH]2)cn1]

LC/MS: mass calculated for $C_{24}H_{19}ClFN_9O_2$: 519.13, measured (ES, m/z): 520.05 $[M+H]^+$. $^1$H NMR (300 MHz, DMSO-$d_6$) δ 12.06 (s, 1H), 9.81 (s, 1H), 8.97 (dd, J=2.1, 0.8 Hz, 1H), 8.23 (dd, J=8.2, 2.2 Hz, 1H), 7.90-8.04 (m, 3H), 7.74 (d, J=2.1 Hz, 1H), 7.69 (dd, J=8.7, 1.5 Hz, 1H), 7.48-7.54 (m, 1H), 5.67 (d, J=2.6 Hz, 1H), 5.00 (d, J=8.6 Hz, 1H), 3.63-3.81 (m, 1H), 2.66-2.81 (m, 1H), 2.51-2.57 (m, 1H), 2.15-2.27 (m, 1H), 2.04-2.15 (m, 1H), 1.87-2.03 (m, 2H). $^{19}$F NMR (300 MHz, DMSO-$d_6$) δ −112.82.

Example 226 5-(2-((3R,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)picolinamide

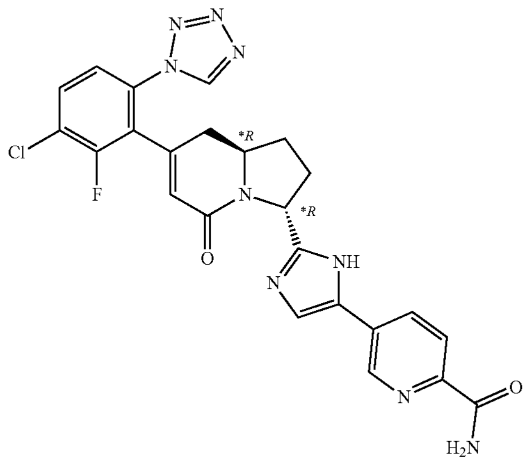 [SMILES: NC(=O)c1ccc(-c2cnc([C@H]3CC[C@@H]4CC(c5c(-n6cnnn6)ccc(Cl)c5F)=CC(=O)N43)[nH]2)cn1]

LC/MS: mass calculated for $C_{24}H_{19}ClFN_6O_2$: 519.13, measured (ES, m/z): 520.05 $[M+H]^+$. $^1$H NMR (300 MHz, DMSO-$d_6$) δ12.21 (s, 1H), 9.80 (s, 1H), 8.95 (d, J=2.1 Hz, 1H), 8.21 (dd, J=8.2, 2.2 Hz, 1H), 7.87-8.01 (m, 3H), 7.73 (s, 1H), 7.67 (dd, J=8.7, 1.5 Hz, 1H), 7.46-7.53 (m, 1H), 5.67 (d, J=2.5 Hz, 1H), 4.99 (t, J=7.3 Hz, 1H), 4.04-4.14 (m, 1H), 2.15-2.45 (m, 4H), 1.89-2.11 (m, 1H), 1.58-1.77 (m, 1H). $^{19}$F NMR (300 MHz, DMSO-$d_6$) δ 113.03.

Example 227: (3S,8aR)-7-(3-chloro-2-fluoro-6-(1H-tetrazol-1-yl)phenyl)-3-(5-(3-methoxy-1H-pyrazol-4-yl)-1H-imidazol-2-yl)-2,3,8,8a-tetrahydroindolizin-5(1H)-one

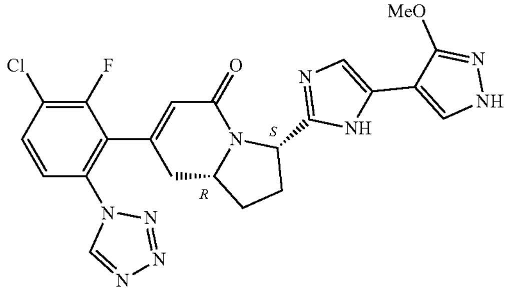

Step 1: ethyl 3-methoxy-1-(4-methoxybenzyl)-1H-pyrazole-4-carboxylate

To a solution of ethyl 3-methoxy-1H-pyrazole-4-carboxylate (100 mg, 0.59 mmol, 1.0 equiv.) in $CH_3CN$ (3 mL) was added $K_2CO_3$ (243 mg, 1.76 mmol, 3.0 equiv.) followed by addition of PMBCl (183 mg, 1.17 mmol, 2.0 equiv.). The resulting mixture was maintained under nitrogen and stirred at 50° C. for 3 h, and concentrated. The residue was purified by silica gel chromatography (0→20% PE/EA) to yield the ethyl 3-methoxy-1-(4-methoxybenzyl)-1H-pyrazole-4-carboxylate as a white solid. LC/MS: mass calculated for $C_{15}H_{18}N_2O_4$: 290.13, measured: 291.10 $[M+H]^+$.

Step 2: 3-methoxy-1-(4-methoxybenzyl)-1H-pyrazole-4-carboxylic acid

LiOH (868 mg, 20.67 mmol, 4.0 equiv.) was added to a solution of ethyl 3-methoxy-1-(4-methoxybenzyl)-1H-pyrazole-4-carboxylate (1.5 g, 5.17 mmol, 1.0 equiv.) in EtOH (3 mL), THE (3 mL) and $H_2O$ (3 mL). The resulting mixture was maintained under nitrogen and stirred at 25° C. for 4 h., adjusted to pH 3-4 with HCl solution (2 M). The resulting mixture was filtered and the solid was dried in vacuo to yield the 3-methoxy-1-(4-methoxybenzyl)-1H-pyrazole-4-carboxylic acid as a white solid. LC/MS: mass calculated for $C_{13}H_{14}N_2O_4$: 262.10, measured: 547.30 $[2M+Na]^+$.

Step 3: 3-methoxy-1-(4-methoxybenzyl)-1H-pyrazole-4-carbonyl chloride

To a solution of 3-methoxy-1-(4-methoxybenzyl)-1H-pyrazole-4-carboxylic acid (400 mg, 1.52 mmol, 1.0 equiv.) in DCM (5 mL) was added $(COCl)_2$ (384 mg, 3.05 mmol, 2.0 equiv.) followed by addition of DMF (0.05 mL). The resulting mixture was stirred at 25° C. for 2 h, then concentrated under reduced pressure to yield 3-methoxy-1-(4-methoxybenzyl)-1H-pyrazole-4-carbonyl chloride as a yellow solid.

Step 4: 2-diazo-1-(3-methoxy-1-(4-methoxybenzyl)-1H-pyrazol-4-yl)ethan-1-one

To a solution of 3-methoxy-1-(4-methoxybenzyl)-1H-pyrazole-4-carbonyl chloride (300 mg, 1.07 mmol, 1.0 equiv.) in ACN (5 mL) at 0° C. was added $TMSCHN_2$ (2.3 mL, 3.0 equiv.). The resulting mixture was stirred at 25° C. overnight and then concentrated under vacuum. The resulting residue was used in the next step without further purification.

Step 5: 2-bromo-1-(3-methoxy-1-(4-methoxybenzyl)-1H-pyrazol-4-yl)ethan-1-one

To a solution of 2-diazo-1-(3-methoxy-1-(4-methoxybenzyl)-1H-pyrazol-4-yl)ethanone (400 mg) in ACN (5 mL) at 0° C. was added $HBr/H_2O$ (1.2 mL, 6.0 equiv.). The resulting mixture was stirred at 25° C. for 2 h, quenched with water (20 mL) and extracted with ethyl acetate (3×20 mL). The organic layers were combined, dried over anhydrous sodium sulfate, filtered, and concentrated to yield 2-bromo-1-(3-methoxy-1-(4-methoxybenzyl)-1H-pyrazol-4-yl)ethanone as a yellow oil. LC/MS: mass calculated for $C_{14}H_{15}BrN_2O_3$: 338.02, measured: 339.00 $[M+H]^+$, 341.00 $[M+H+2]^+$.

Step 6: 2-(3-methoxy-1-(4-methoxybenzyl)-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate $K_2CO_3$ (366 mg, 2.65 mmol, 3.0 equiv.). was added to a solution of (3S)-7-(6-amino-3-chloro-2-fluorophenyl)-5-oxo-1,2,3,5,8,8a-hexahydroindolizine-3-carboxylic acid (287 mg, 0.88 mmol, 1.0 equiv.) in DMF (5 mL). The mixture was stirred at 25° C. for 1 h. To the resulting mixture was then added 2-bromo-1-(3-methoxy-1-(4-methoxybenzyl)-1H-pyrazol-4-yl)ethanone (300 mg). The resulting mixture was stirred 4 h, then purified by reverse phase chromatography on C18 column ($MeCN/H_2O$ (0.05% TFA): 0-060%) to yield 2-(3-methoxy-1-(4-methoxybenzyl)-1H-pyrazol-4-yl)-2-oxoethyl (3S)-7-(6-amino-3-chloro-2-fluorophenyl)-5-oxo-1,2,3,5,8,8a-hexahydroindolizine-3-carboxylate as a yellow oil. LC/MS: mass calculated for $C_{29}H_{28}ClFN_4O_6$: 582.17, measured: 583.30 $[M+H]^+$.

Step 7: (3S)-7-(6-amino-3-chloro-2-fluorophenyl)-3-(5-(3-methoxy-1-(4-methoxybenzyl)-1H-pyrazol-4-yl)-1H-imidazol-2-yl)-2,3,8,8a-tetrahydroindolizin-5(1H)-one To a solution of (3S)-2-(3-methoxy-1-(4-methoxybenzyl)-1H-pyrazol-4-yl)-2-oxoethyl 7-(6-amino-3-chloro-2-fluorophenyl)-5-oxo-1,2,3,5,8,8a-hexahydroindolizine-3-carboxylate (310 mg, 0.53 mmol, 1.0 equiv.) in AcOH (0.5 mL) and toluene (5 mL) was added $NH_4OAc$ (409 mg, 5.32 mmol, 10.0 equiv.). The resulting mixture was maintained under nitrogen and stirred at 100° C. for 3 h, then concentrated under vacuum and the residue was purified by reverse phase chromatography on C18 column ($MeCN/H_2O$ (0.05% TFA): 0-060%) to yield (3S)-7-(6-amino-3-chloro-2-fluorophenyl)-3-(5-(3-methoxy-1-(4-methoxybenzyl)-1H-pyrazol-4-yl)-1H-imidazol-2-yl)-2,3,8,8a-tetrahydroindolizin-5(1H)-one as a yellow oil. LC/MS: mass calculated for $C_{29}H_{28}ClFN_6O_3$: 562.19, measured: 563.30 $[M+H]^+$.

Step 8: (3S)-7-(3-chloro-2-fluoro-6-(1H-tetrazol-1-yl)phenyl)-3-(5-(3-methoxy-1-(4-methoxybenzyl)-1H-pyrazol-4-yl)-1H-imidazol-2-yl)-2,3,8,8a-tetrahydroindolizin-5(1H)-one To a solution of (3S)-7-(6-amino-3-chloro-2-fluorophenyl)-3-(5-(3-methoxy-1-(4-methoxybenzyl)-1H-pyrazol-4-yl)-1H-imidazol-2-yl)-2,3,8,8a-tetrahydroindolizin-5(1H)-one (120 mg, 0.21 mmol, 1.0 equiv.) in AcOH (5 mL) was added $TMSN_3$ (246 mg, 2.13 mmol, 10.0 equiv.) followed by addition of trimethoxymethane (226 mg, 2.13 mmol, 10.0 equiv.). The resulting mixture was maintained under nitrogen and stirred at 25° C. for 3 h, concentrated under vacuum and the residue was purified by flash column chromatography on silica gel (0→010% MeOH/DCM) to yield the (3S)-7-(3-chloro-2-fluoro-6-(1H-tetrazol-1-yl)phenyl)-3-(5-(3-methoxy-1-(4-methoxybenzyl)-1H-pyrazol-4-yl)-1H-imidazol-2-yl)-2,3,8,8a-tetrahydroindolizin-5(1H)-one as an yellow oil. LC/MS: mass calculated for $C_{30}H_{27}ClFN_9O_3$: 615.19, measured: 616.10 $[M+H]^+$.

Step 9: (3S,8aR)-7-(3-chloro-2-fluoro-6-(1H-tetrazol-1-yl)phenyl)-3-(5-(3-methoxy-1H-pyrazol-4-yl)-1H-imidazol-2-yl)-2,3,8,8a-tetrahydroindolizin-5(1H one To a solution of (3S)-7-(3-chloro-2-fluoro-6-(1H-tetrazol-1-yl)phenyl)-3-(5-(3-methoxy-1-(4-methoxybenzyl)-1H-pyrazol-4-yl)-1H-imidazol-2-yl)-2,3,8,8a-tetrahydroindolizin-5(1H)-one (40 mg, 0.065 mmol, 1.0 equiv.) in TFA (1 mL) was added anisole (0.1 mL). The resulting mixture was maintained under nitrogen and stirred at 70° C. overnight, concentrated in a vacuum and the residue was purified by silica gel chromatography (0→10% MeOH/DCM). The resulting racemic product was further separated by chiral Prep-SFC with Mobile Phase A: Hex:DCM=1:1 (10 mM $NH_3$-MeOH), Mobile Phase B: EtOH to yield (3S,8aR)-7-(3-chloro-2-fluoro-6-(1H-tetrazol-1-yl)phenyl)-3-(5-(3-methoxy-1H-pyrazol-4-yl)-1H-imidazol-2-yl)-2,3,8,8a-tetrahydroindolizin-5(1H)-one as a white solid.

LC/MS: mass calculated for $C_{22}H_{19}ClFN_9O_2$: 495.13, measured (ES, m/z): 496.10 $[M+H]^+$. $^1H$ NMR (400 MHz, DMSO-$d_6$) δ 11.30-12.10 (m, 2H), 9.82 (s 1H), 7.96 (t, J=8.4 Hz, 1H), 7.70 (d, J=8.4 Hz, 2H), 6.88 (s, 1H), 5.67 (s, 1H), 4.97 (d, J=8.0 Hz, 1H), 3.88 (s, 3H), 3.63-3.73 (m, 1H), 2.54-2.77 (m, 2H), 1.96-2.07 (m, 4H). $^{19}F$ NMR (376 MHz, DMSO-$d_6$) δ −112.82.

Example 228: 6-Chloro-5-(2-((3S,8aS)-7-(3-chloro-2-fluoro-6-(1H-tetrazol-1-yl)phenyl)-5-oxo-1,2,3,5,8,8a-hexahydroindolizin-3-yl)-1H-imidazol-5-yl)picolinamide

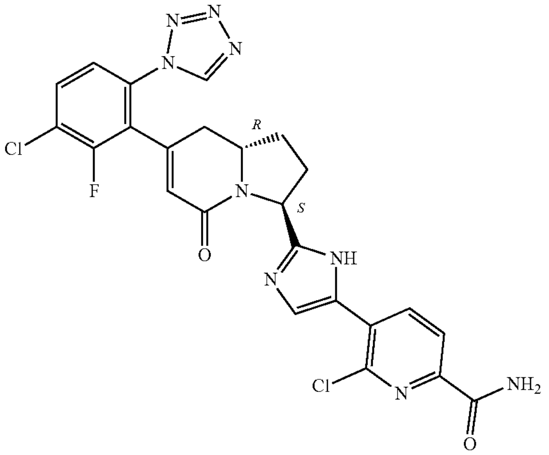

LC/MS: mass calculated for $C_{24}H_{18}Cl_2FN_9O_2$: 553.09, measured (ES, m/z): 554.05 $[M+H]^+$. $^1H$ NMR (400 MHz, DMSO-$d_6$) δ 9.83 (s, 1H), 8.76 (br, 1H), 8.51 (d, J=8.0 Hz, 1H), 8.11 (d, J=8.0 Hz, 1H), 8.01 (s, 1H), 7.97 (d, J=8.3 Hz, 1H), 7.94 (d, J=2.8 Hz, 1H), 7.75 (s, 1H), 7.70 (dd, J=8.7, 1.5 Hz, 1H), 5.70 (d, J=2.7 Hz, 1H), 5.09 (d, J=9.0 Hz, 1H), 3.69-3.92 (m, 1H), 2.66-2.79 (m, 1H), 2.49-2.60 (m, 1H), 2.21-2.32 (m, 1H), 1.92-2.14 (m, 3H). $^{19}F$ NMR (376 MHz, DMSO-$d_6$) δ−112.84.

Example 229: 6-Chloro-5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)picolinamide

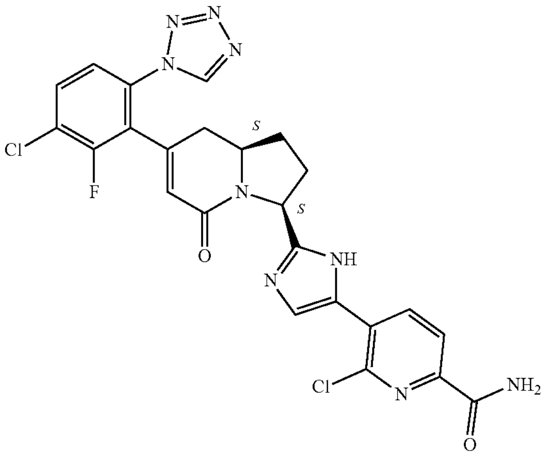

LC/MS: mass calculated for $C_{24}H_{18}Cl_2FN_9O_2$: 553.09, measured (ES, m/z): 554.05 $[M+H]^+$. $^1H$ NMR (400 MHz, DMSO-$d_6$) δ 9.82 (s, 1H), 8.73 (br, 1H), 8.53 (d, J=7.8 Hz, 1H), 8.07 (d, J=8.0 Hz, 1H), 7.88-8.00 (m, 3H), 7.60-7.75 (m, 2H), 5.69 (d, J=2.7 Hz, 1H), 5.04 (t, J=7.6 Hz, 1H), 4.04-4.16 (m, 1H), 2.36-2.57 (m, 3H), 2.17-2.32 (m, 1H), 1.93-2.09 (m, 1H), 1.64-1.76 (m, 1H). $^{19}F$ NMR (376 MHz, DMSO-$d_6$) δ −113.07

Example 230 (3S,8aR)-7-(3-Chloro-2-fluoro-6-(1H-tetrazol-1-yl)phenyl)-3-(5-(4-(trifluoromethyl)-1H-pyrrol-3-yl)-1H-imidazol-2-yl)-2,3,8,8a-tetrahydroindolizin-5(1H)-one

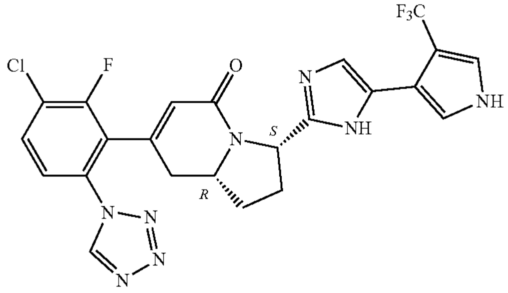

Step 1: 2-oxo-2-(4-(trifluoromethyl)-1-((2-(trimethylsilyl)ethoxy)methyl)-1H-pyrrol-3-yl)ethyl (3S,8aR)-7-(6-amino-3-chloro-2-fluorophenyl)-5-oxo-1,2,3,5,8,8a-hexahydroindolizine-3-carboxylate To a solution of (3S,8aR)-7-(6-amino-3-chloro-2-fluorophenyl)-5-oxo-1,2,3,5,8,8a-hexahydroindolizine-3-carboxylic acid (150 mg, 0.47 mmol, 1.0 equiv.) in DMF (10 mL) was added $K_2CO_3$ (193 mg, 1.40 mmol, 3.0 equiv.), followed by addition of 2-bromo-1-(4-(trifluoromethyl)-1-((2-(trimethylsilyl)ethoxy)methyl)-1H-pyrrol-3-yl)ethanone (180 mg, 0.47 mmol, 1.0 equiv.). The resulting mixture was stirred overnight, quenched with $H_2O$ and extracted with EA. The organic layers were combined, dried over $Na_2SO_4$, filtered, and concentrated. The residue was purified by silica gel chromatography (0→10% MeOH/DCM) to yield 2-oxo-2-(4-(trifluoromethyl)-1-((2-(trimethylsilyl)ethoxy)methyl)-1H-pyrrol-3-yl)ethyl (3S,8aR)-7-(6-amino-3-chloro-2-fluorophenyl)-5-oxo-1,2,3,5,8,8a-hexahydroindolizine-3-carboxylate as a yellow oil. LC/MS: mass calculated for $C_{28}H_{32}ClF_4N_3O_5Si$: 629.17, measured: 630.10 $[M+H]^+$.

Step 2: (3S,8aR)-7-(6-amino-3-chloro-2-fluorophenyl)-3-(5-(4-(trifluoromethyl)-1-((2-(trimethylsilyl)ethoxy)methyl)-1H-pyrrol-3-yl)-1H-imidazol-2-yl)-2,3,8,8a-tetrahydroindolizin-5(1H)-one To a solution of 2-oxo-2-(4-(trifluoromethyl)-1-((2-(trimethylsilyl)ethoxy)methyl)-1H-pyrrol-3-yl)ethyl (3S,8aR)-7-(6-amino-3-chloro-2-fluorophenyl)-5-oxo-1,2,3,5,8,8a-hexahydroindolizine-3-carboxylate (220 mg, 0.32 mmol, 1.0 equiv.) in toluene (10 mL) was added $NH_4OAc$ (254 mg, 3.17 mmol, 10.0 equiv.) followed by addition of AcOH (1 mL). The resulting mixture was stirred for 3 h at 110° C. After being cooled to room temperature, the resulting mixture was concentrated under vacuum. The residue was purified by flash column chromatography on silica gel (0-0100% EA/PE) to yield (3S,8aR)-7-(6-amino-3-chloro-2-fluorophenyl)-3-(5-(4-(trifluoromethyl)-1-((2-(trimethylsilyl)ethoxy)methyl)-1H-pyrrol-3-yl)-1H-imidazol-2-yl)-2,3,8,8a-tetrahydroindolizin-5(1H)-one as a yellow oil. LC/MS: mass calculated for $C_{28}H_{32}ClF_4NSO_2Si$: 609.19, measured: 610.10 $[M+H]^+$.

Step 3: (3S,8aR)-7-(3-chloro-2-fluoro-6-(1H-tetrazol-1-yl)phenyl)-3-(5-(4-(trifluoromethyl)-1-((2-(trimethylsilyl)ethoxy)methyl)-1H-pyrrol-3-yl)-1H-imidazol-2-yl)-2,3,8,8a-tetrahydroindolizin-5(1H)-one To a solution of (3S)-7-(6-amino-3-chloro-2-fluorophenyl)-3-(5-(4-(trifluoromethyl)-1-((2-(trimethylsilyl)ethoxy)methyl)-1H-pyrrol-3-yl)-1H-imidazol-2-yl)-2,3,8,8a-tetrahydroindolizin-5(1H)-one (100 mg, 0.16 mmol, 1.0 equiv.) in AcOH (5 mL) was added trimethoxymethane (174 mg, 1.64 mmol, 10.0 equiv.), followed by addition of $TMSN_3$ (189 mg, 1.64 mmol, 10.0 equiv.). The resulting mixture was stirred at 25° C. overnight, concentrated under vacuum and the residue was purified by silica gel chromatography (0→10% MeOH/DCM) to yield (3S,8aR)-7-(3-chloro-2-fluoro-6-(1H-tetrazol-1-yl)phenyl)-3-(5-(4-(trifluoromethyl)-1-((2-(trimethylsilyl)ethoxy)methyl)-1H-pyrrol-3-yl)-1H-imidazol-2-yl)-2,3,8,8a-tetrahydroindolizin-5(1H)-one as a yellow oil. LC/MS: mass calculated for $C_{29}H_{31}ClF_4N_8O_2Si$: 662.20, measured: 663.10 $[M+H]^+$.

Step 4: (3S,8aR)-7-(3-chloro-2-fluoro-6-(1H-tetrazol-1-yl)phenyl)-3-(5-(4-(trifluoromethyl)-1H-pyrrol-3-yl)-1H-imidazol-2-yl)-2,3,8,8a-tetrahydroindolizin-5(1H)-one To a solution of (3S,8aR)-7-(3-chloro-2-fluoro-6-(1H-tetrazol-1-yl)phenyl)-3-(5-(4-(trifluoromethyl)-1-((2-(trimethylsilyl)ethoxy)methyl)-1H-pyrrol-3-yl)-1H-imidazol-2-yl)-2,3,8,8a-tetrahydroindolizin-5(1H)-one (75 mg, 0.11 mmol, 1.0 equiv.) in DCM (1 mL) was added TFA (1 mL). The resulting mixture was stirred for 3 h at 25° C., then concentrated under vacuum. The residue was neutralized with $NH_3$/MeOH (2 mL) and the solvent was removed. The residue was purified by chiral-HPLC to yield (3S,8aR)-7-(3-chloro-2-fluoro-6-(1H-tetrazol-1-yl)phenyl)-3-(5-(4-(trifluoromethyl)-1H-pyrrol-3-yl)-1H-imidazol-2-yl)-2,3,8,8a-tetrahydroindolizin-5(1H)-one.

LC/MS: mass calculated for $C_{23}H_{17}ClF_4N_8O$: 532.11, measured (ES, m/z): 533.20 $[M+H]^+$. 1H NMR (400 MHz, DMSO-$d_6$) δ 9.77 (s, 1H), 7.89-7.93 (m, 1H), 7.70 (dd, J=8.7, 1.5 Hz, 1H), 7.25 (s, 1H), 7.14 (s, 1H), 6.85 (s, 1H), 5.63 (d, J=2.8 Hz, 1H), 4.96 (d, J=8.8 Hz, 1H), 3.66-3.70 (m, 1H), 2.68-2.78 (m, 1H), 2.46-2.50 (m, 1H), 2.04-2.17 (m, 2H), 1.94-1.99 (m, 2H). $^{19}F$ NMR (376 MHz, DMSO-$d_6$) δ−55.32, −112.83.

Example 231 (3S,8aR)-7-(3-Chloro-2-fluoro-6-(1H-tetrazol-1-yl)phenyl)-3-(2-(trifluoromethyl)-1H,3'H-[4,4'-biimidazol]-2'-yl)-2,3,8,8a-tetrahydroindolizin-5(1H)-one

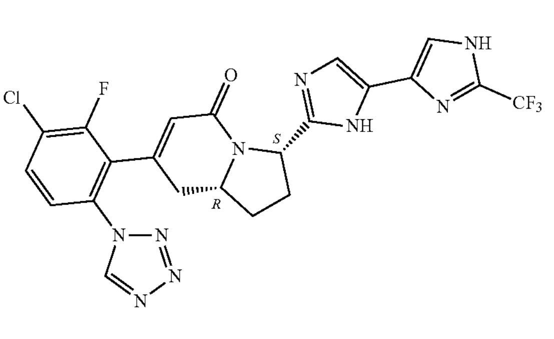

Step 1: 2-(1-(4-methoxybenzyl)-2-(trifluoromethyl)-1H-imidazol-4-yl)-2-oxoethyl (3S,8aR)-7-(6-amino-3-chloro-2-fluorophenyl)-5-oxo-1,2,3,5,8,8a-hexahydroindolizine-3-carboxylate To a solution of (3S,8aR)-7-(6-amino-3-chloro-2-fluorophenyl)-5-oxo-1,2,3,5,8,8a-hexahydroindolizine-3-carboxylic acid (453 mg, 1.39 mmol, 1.0 equiv.) in DMF (10 mL) was added $K_2CO_3$ (578 mg, 4.18 mmol, 3.0 equiv.), followed by 2-bromo-1-(1-(4-methoxybenzyl)-2-(trifluoromethyl)-1H-imidazol-4-yl)ethanone (526 mg, 1.39 mmol, 1.0 equiv.) and the resulting mixture was stirred for 11.5 h, then quenched with $H_2O$, and extracted with EA. The organic layers were combined, dried over $Na_2SO_4$, filtered and concentrated. The residue was purified by flash column chromatography on silica gel (0→10% MeOH/DCM) to yield 12-(1-(4-methoxybenzyl)-2-(trifluoromethyl)-1H-imidazol-4-yl)-2-oxoethyl (3S,8aR)-7-(6-amino-3-chloro-2-fluorophenyl)-5-oxo-1,2,3,5,8,8a-hexahydroindolizine-3-carboxylate as a yellow oil. LC/MS: mass calculated for $C_{29}H_{25}ClF_4N_4O_5$: 620.14, measured: 621.05 $[M+H]^+$.

Step 2: (3S,8aR)-7-(6-amino-3-chloro-2-fluorophenyl)-3-(1-(4-methoxybenzyl)-2-(trifluoromethyl)-1H,3'H-[4,4'-biimidazol]-2'-yl)-2,3,8,8a-tetrahydroindolizin-5(1H)-one To a solution of 2-(1-(4-methoxybenzyl)-2-(trifluoromethyl)-1H-imidazol-4-yl)-2-oxoethyl (3S,8aR)-7-(6-amino-3-chloro-2-fluorophenyl)-5-oxo-1,2,3,5,8,8a-hexahydroindolizine-3-carboxylate (1.0 g, 1.61 mmol, 1.0 equiv.) in AcOH/toluene (1 mL/10 mL) was added ammonium acetate (1.2 g, 16.1 mmol, 10.0 equiv.). The resulting mixture was stirred at 100° C. for 2 h under nitrogen. After being cooled to room temperature. The resulting mixture was concentrated under vacuum. The residue was purified by reverse phase HPLC (0→83% MeCN/$H_2O$) to yield the (3S,8aR)-7-(6-amino-3-chloro-2-fluorophenyl)-3-(1-(4-methoxybenzyl)-2-(trifluoromethyl)-1H,3'H-[4,4'-biimidazol]-2'-yl)-2,3,8,8a-tetrahydroindolizin-5(1H)-one as a white solid. LC/MS: mass calculated for $C_{29}H_{25}ClF_4N_6O_2$: 600.17, measured: 601.36 $[M+H]^+$.

Step 3: (3S,8aR)-7-(3-chloro-2-fluoro-6-(1H-tetrazol-1-yl)phenyl)-3-(1-(4-methoxybenzyl)-2-(trifluoromethyl)-1H,3'H-[4,4'-biimidazol]-2'-yl)-2,3,8,8a-tetrahydroindolizin-5(1H)-one To a solution of (3S,8aR)-7-(6-amino-3-chloro-2-fluorophenyl)-3-(1-(4-methoxybenzyl)-2-(trifluoromethyl)-1H,3'H-[4,4'-biimidazol]-2'-yl)-2,3,8,8a-tetrahydroindolizin-5(1H)-one (300 mg, 0.50 mmol, 1.0 equiv.) in acetic acid (5 mL) were added trimethoxymethane (530 mg, 4.99 mmol, 10.0 equiv.) and azidotrimethylsilane (575 mg, 4.99 mmol, 10.0 equiv.). The resulting mixture was maintained stirring at 70° C. for 2 h. The resulting mixture was concentrated under vacuum. The residue was purified by reverse phase HPLC (0→46% MeCN/$H_2O$) to yield the (3S,8aR)-7-(3-chloro-2-fluoro-6-(1H-tetrazol-1-yl)phenyl)-3-(1-(4-methoxybenzyl)-2-(trifluoromethyl)-1H,3'H-[4,4'-biimidazol]-2'-yl)-2,3,8,8a-tetrahydroindolizin-5(1H)-one as a yellow oil. LC/MS: mass calculated for $C_{30}H_{24}ClF_4N_9O_2$: 653.17, measured: 654.30 $[M+H]^+$.

Step 4: (3S,8aR)-7-(3-chloro-2-fluoro-6-(1H-tetrazol-1-yl)phenyl)-3-(2-(trifluoromethyl)-1H,3'H-[4,4'-biimidazol]-2'-yl)-2,3,8,8a-tetrahydroindolizin-5(1H)-one To a solution of (3S,8aR)-7-(3-chloro-2-fluoro-6-(1H-tetrazol-1-yl)phenyl)-3-(1-(4-methoxybenzyl)-2-(trifluoromethyl)-1H,3'H-[4,4'-biimidazol]-2'-yl)-2,3,8,8a-tetrahydroindolizin-5(1H)-one (200 mg, 0.31 mmol, 1.0 equiv.) in TFA (5 mL) was added anisole (198 mg, 1.83 mmol, 6.0 equiv.). The resulting mixture was stirred at 50° C. for 2 h. The solution was concentrated and purified by silica gel chromatography (0→5% MeOH/DCM) to yield the racemic product, which was further separated by chiral-HPLC to yield (3S,8aR)-7-(3-chloro-2-fluoro-6-(1H-tetrazol-1-yl)phenyl)-3-(2-(trifluoromethyl)-1H,3'H-[4,4'-biimidazol]-2'-yl)-2,3,8,8a-tetrahydroindolizin-5(1H)-one as an off-white solid.

LC/MS: mass calculated for $C_{23}H_{17}ClF_4N_8O$: 533.11, measured (ES, m/z): 534.00 $[M+H]^+$. 1H NMR (400 MHz, DMSO-$d_6$) δ 13.58 (br, 1H), 11.88 (br, 1H), 9.83 (s, 1H), 7.95-7.99 (m, 1H), 7.72 (dd, J=8.7, 1.5 Hz, 1H), 7.23-7.54 (m, 2H), 5.68 (d, J=2.6 Hz, 1H), 5.00 (d, J=8.8 Hz, 1H), 3.67-3.73 (m, 1H), 2.67-2.74 (m, 1H), 2.52-2.53 (m, 1H), 2.20-2.34 (m, 1H), 2.08-2.18 (m, 1H), 1.94-2.06 (m, 2H). $^{19}$F NMR (282 MHz, DMSO-$d_6$) δ−61.16, −112.77

Example 232 5-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-2-fluorobenzamide

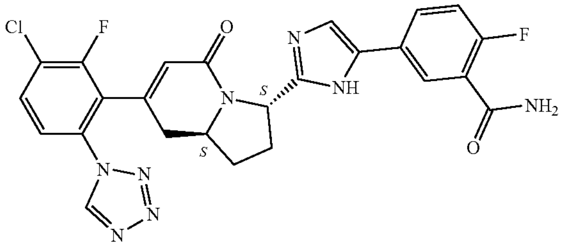

LC/MS: mass calculated for $C_{25}H_{19}ClF_2N_8O_2$: 536.13, measured (ES, m/z): 537.05 $[M+H]^+$. $^1$H NMR (400 MHz, DMSO-$d_6$) δ 12.03 (br, 1H), 9.83 (s, 1 H), 7.97-7.98 (m, 2H), 7.80-7.87 (m, 1H), 7.54-7.71 (m, 4H), 7.20-7.31 (m, 1H), 5.70 (s, 1H), 4.91-5.13 (m, 1H), 4.10-4.12 (m, 1H), 2.37-2.46 (m, 3H), 2.21-2.31 (m, 1H), 1.97-2.10 (m, 1H), 1.68-1.73 (m, 1H). $^{19}$F NMR (376 MHz, DMSO-$d_6$) δ −113.00, −117.91.

Example 233 5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-2-fluorobenzamide

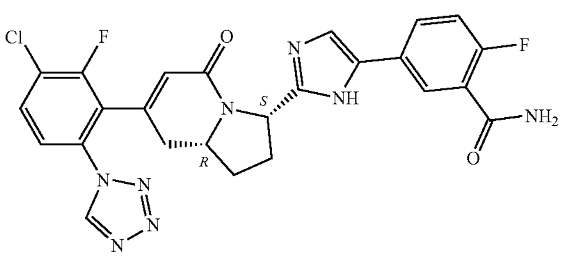

LC/MS: mass calculated for $C_{25}H_{19}ClF_2N_8O_2$: 536.13, measured (ES, m/z): 537.05 $[M+H]^+$. $^1$H NMR (400 MHz, DMSO-$d_6$) δ 11.78-12.54 (m, 1H), 9.82 (s 1H), 7.94-7.98 (m, 2H), 7.82-7.89 (m, 1H), 7.71 (d, J=8.0 Hz, 2H), 7.61 (s, 1H), 7.51 (s, 1H), 7.23-7.26 (m, 1H), 5.66 (s, 1H), 4.98 (d, J=8.8 Hz, 1H), 3.63-3.76 (m, 1H), 2.71-2.83 (m, 1H), 2.53-2.61 (m, 1H), 2.17-2.20 (m, 1H), 2.01-2.10 (m, 1H), 1.97-1.99 (m, 2H). $^{19}$F NMR (376 MHz, DMSO-$d_6$) δ −112.70, −117.92.

Example 234: 4 (2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)thiophene-2-carboxamide

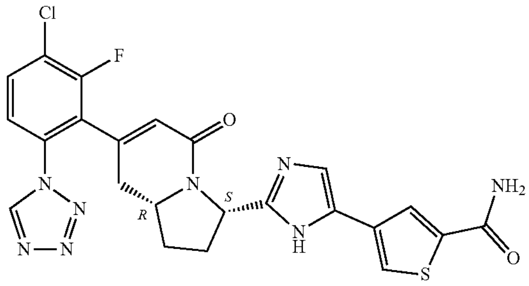

Step 1: 2-(5-carbamoylthiophen-3-yl)-2-oxoethyl (3S,8aR)-7-(6-amino-3-chloro-2-fluorophenyl)-5-oxo-1,2,3,5,8,8a-hexahydroindolizine-3-carboxylate To a solution of (3S,8aR)-7-(6-amino-3-chloro-2-fluorophenyl)-5-oxo-1,2,3,5,8,8a-hexahydroindolizine-3-carboxylic acid (654 mg, 2.01 mmol, 1.0 equiv.) in DMF (8 mL) was added $K_2CO_3$ (557 mg, 4.03 mmol, 2.0 equiv.). The mixture was stirred at 25° C. for 0.5 h. To the resulting mixture was then added 4-(2-bromoacetyl)thiophene-2-carboxamide (500 mg, 2.01 mmol, 1.0 equiv.) and the resulting mixture was stirred for 3.5 h. The solid was filtered out. The filtrate was concentrated under vacuum and the residue was purified by HPLC (20%→100% MeCN/$H_2O$) to yield the 2-(5-carbamoylthiophen-3-yl)-2-oxoethyl (3S,8aR)-7-(6-amino-3-chloro-2-fluorophenyl)-5-oxo-1,2,3,5,8,8a-hexahydroindolizine-3-carboxylate as a yellowish oi. LC/MS: mass calculated for $C_{22}H_{19}ClFN_3O_5S$: 491.07, measured: 492.10 $[M+H]^+$.

Step 2: 4-(2-((3S,8aR)-7-(6-amino-3-chloro-2-fluorophenyl)-5-oxo-1,2,3,5,8,8a-hexahydroindolizin-3-yl)-1H-imidazol-5-yl)thiophene-2-carboxamide To a solution of 2-(5-carbamoylthiophen-3-yl)-2-oxoethyl (3S,8aR)-7-(6-amino-3-chloro-2-fluorophenyl)-5-oxo-1,2,3,5,8,8a-hexahydroindolizine-3-carboxylate (500 mg, 1.02 mmol, 1.0 equiv.) in toluene (10 mL) were added AcOH (1 mL) and $NH_4OAc$ (783 mg, 10.16 mmol, 10.0 equiv.). The reaction mixture was stirred for 3 h at 100° C. After being cooled to room temperature. The resulting mixture was concentrated under vacuum. The residue was purified by flash column chromatography on silica gel (20%→100% EA/PE) to yield the 4-(2-((3S,8aR)-7-(6-amino-3-chloro-2-fluorophenyl)-5-oxo-1,2,3,5,8,8a-hexahydroindolizin-3-yl)-1H-imidazol-5-yl)thiophene-2-carboxamide as a yellow oil. LC/MS: mass calculated for $C_{22}H_{19}ClFN_5O_2S$: 471.09, measured: 472.10 $[M+H]^+$.

Step 3: 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)thiophene-2-carboxamide To a solution of 4-(2-((3S,8aR)-7-(6-amino-3-chloro-2-fluorophenyl)-5-oxo-1,2,3,5,8,8a-hexahydroindolizin-3-yl)-1H-imidazol-5-yl)thiophene-2-carboxamide (100 mg, 0.21 mmol, 1.0 equiv.) in AcOH (10 mL) were added trimethoxymethane (225 mg, 2.12 mmol, 10.0 equiv.) and $TMSN_3$ (244 mg, 2.12 mmol, 10.0 equiv.). The resulting mixture was stirred at room temperature. for 16 h. The residue was purified by Prep-HPLC and then separated by prep-SFC with Mobile Phase A: Hex:DCM=3:1 (10 mM $NH_3$-MeOH), Mobile Phase B: EtOH to yield 4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)thiophene-2-carboxamide as a white solid.

LC/MS: mass calculated for $C_{23}H_{18}ClFN_8O_2S$: 524.09, measured (ES, m/z): 525.00 $[M+H]^+$. $^1H$ NMR (400 MHz, $DMSO-d_6+H_2O$) δ 9.75 (s, 1H), 7.97 (d, J=1.2 Hz, 1H), 7.89 (t, J=6.3 Hz, 1H), 7.84 (d, J=1.4 Hz, 1H), 7.63 (dd, J=8.7, 1.4 Hz, 1H), 7.42 (s, 1H), 5.64 (d, J=2.8 Hz, 1H), 5.03 (d, J=9.2 Hz, 1H), 3.67-3.72 (m, 1H), 2.78-2.86 (m, 1H), 2.51-2.54 (m, 1H), 2.21-2.27 (m, 1H), 2.09-2.14 (m, 1H), 1.95-1.99 (m, 2H). $^{19}F$ NMR (376 MHz, $DMSO-d_6$) δ−73.50, −112.71.

Example 235 (3S,8aR)-7-(3-chloro-2-fluoro-6-(1H-tetrazol-1-yl)phenyl)-3-(5-(2-fluoro-6-(hydroxymethyl)pyridin-3-yl)-1H-imidazol-2-yl)-2,3,8,8a-tetrahydroindolizin-5(1H)-one

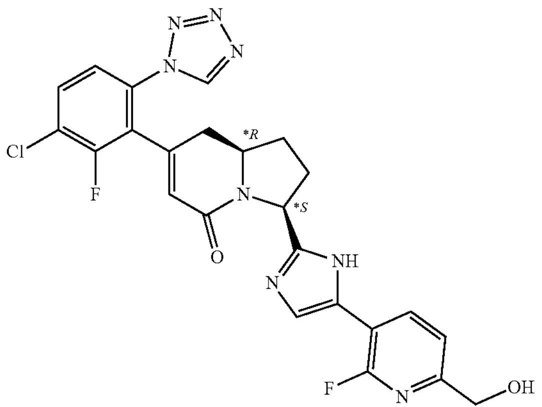 [SMILES: O=C1C=C(c2c(-n3cnnn3)ccc(Cl)c2F)C[C@H]2CC[C@@H](c3ncc(-c4ccc(CO)nc4F)[nH]3)N12]

LC/MS: mass calculated for $C_{24}H_{19}ClF_2N_8O_2$: 524.13, measured (ES, m/z): 525.00 $[M+H]^+$. $^1H$ NMR (300 MHz, $DMSO-d_6$) δ 12.08 (br, 1H), 9.82 (s, 1H), 8.42 (t, J=8.8 Hz, 1H), 7.95 (t, J=8.2 Hz, 1H), 7.69 (dd, J=8.7, 1.5 Hz, 1H), 7.46 (dd, J=7.7, 2.2 Hz, 1H), 7.35 (d, J=4.1 Hz, 1H), 5.68 (d, J=2.5 Hz, 1H), 5.44-5.57 (m, 1H), 5.01 (d, J=8.4 Hz, 1H), 4.48 (s, 2H), 3.64-3.81 (m, 1H), 2.59-2.76 (m, 1H), 2.55-2.50 (m, 1H), 2.24-2.02 (m, 2H), 2.00-1.85 (m, 2H). $^{19}F$ NMR (282 MHz, $DMSO-d_6$) δ −69.11, −73.4, −112.88.

Example 236 (3S,8aR)-7-(3-Chloro-2-fluoro-6-(1H-tetrazol-1-yl)phenyl)-3-(5-(2-chloro-6-(hydroxymethyl)pyridin-3-yl)-1H-imidazol-2-yl)-2,3,8,8a-tetrahydroindolizin-5(1H)-one

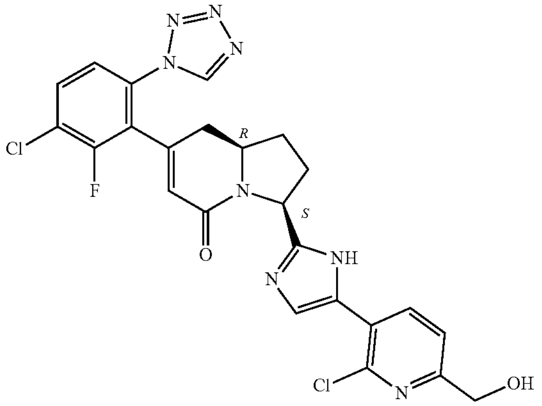

Step 1: 2-(2-chloro-6-(methoxycarbonyl)pyridin-3-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (250 mg, 0.77 mmol, 1.0 equiv.) in DMF (5 mL) was added $Cs_2CO_3$ (150 mg, 0.46 mmol, 0.6 equiv.). After 0.5 h., methyl 5-(2-bromoacetyl)-6-chloropicolinate (338 mg, 1.16 mmol, 1.5 equiv.) was added to the mixture and the reaction mixture was stirred overnight, then quenched with water and extracted with ethyl acetate. The combined organic layer was washed with brine, dried over $Na_2SO_4$ and concentrated. The residue was purified by silica gel chromatography (0%→30% MeOH/DCM) to yield 2-(2-chloro-6-(methoxycarbonyl)pyridin-3-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{22}H_{20}Cl_2FN_3O_6$: 535.07, measured: 536.10 $[M+H]^+$.

Step 2: methyl 5-(2-((3S)-7-(6-amino-3-chloro-2-fluorophenyl)-5-oxo-1,2,3,5,8,8a-hexahydroindolizin-3-yl)-1H-imidazol-5-yl)-6-chloropicolinate To a solution of 2-(2-chloro-6-(methoxycarbonyl)pyridin-3-yl)-2-oxoethyl (3S)-7-(6-amino-3-chloro-2-fluorophenyl)-5-oxo-1,2,3,5,8,8a-hexahydroindolizine-3-carboxylate (300 mg, 0.56 mmol, 1.0 equiv.) in toluene (5 mL) and AcOH (0.5 mL) was added $NH_4OAc$ (431 mg, 1.15 mmol, 2.0 equiv.). The reaction mixture was stirred for 2 h at 110° C., then quenched with water and extracted with ethyl acetate. The combined organic layer was washed with brine, dried over $Na_2SO_4$ and concentrated. The residue was purified by silica gel chromatography (0%→30% MeOH/DCM) to yield methyl 5-(2-((3S)-7-(6-amino-3-chloro-2-fluorophenyl)-5-oxo-1,2,3,5,8,8a-hexahydroindolizin-3-yl)-1H-imidazol-5-yl)-6-chloropicolinate as a yellow oil. LC/MS: mass calculated for $C_{22}H_{20}Cl_2FN_5O_3$: 515.09, measured: 516.10 $[M+H]^+$.

Step 3: methyl 6-chloro-5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)picolinate To a solution of methyl 5-(2-((3S)-7-(6-amino-3-chloro-2-fluorophenyl)-5-oxo-1,2,3,5,8,8a-hexahydroindolizin-3-yl)-1H-imidazol-5-yl)-6-chloropicolinate (200 mg, 0.39 mmol, 1.0 equiv.) in AcOH (3 mL) were added $TMSN_3$ (448 mg, 3.87 mmol, 10 equiv.) and trimethoxymethane (411 mg, 3.87 mmol, 10.0 equiv.). The reaction mixture was stirred overnight at room temperature, quenched with water, and extracted with ethyl acetate. The combined organic layer was washed with brine, dried over $Na_2SO_4$ and concentrated. The residue was purified by silica gel chromatography (0%→30% MeOH/DCM) to yield methyl 6-chloro-5-(2-((3S)-7-(3-chloro-2-fluor-6-(1H-tetrazol-1-yl)phenyl)-5-oxo-1,2,3,5,8,8a-hexahydroindolizin-3-yl)-1H-imidazol-5-yl)picolinate as a yellow solid. LC/MS: mass calculated for $C_{25}H_{19}Cl_2FN_8O_3$: 568.09, measured: 569.05 $[M+H]^+$.

Step 4: (3S,8aR)-7-(3-chloro-2-fluoro-6-(1H-tetrazol-1-yl)phenyl)-3-(5-(2-chloro-6-(hydroxymethyl)pyridin-3-yl)-1H-imidazol-2-yl)-2,3,8,8a-tetrahydroindolizin-5(1H)-one To a solution of methyl 6-chloro-5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)picolinate (200 mg, 0.39 mmol, 1.0 equiv.) in THE (5 mL) was added sodium borohydride (122 mg, 3.88 mmol, 10.0 equiv.). The reaction mixture was stirred at room temperature. for 2 h. The reaction was quenched with water and extracted with ethyl acetate. The combined organic layer was washed with brine, dried over $Na_2SO_4$ and concentrated. The residue was purified by silica gel chromatography (0%-30% MeOH/DCM) to yield the racemic product, which was further purified by SFC to yield the (3S,8aR)-7-(3-chloro-2-fluoro-6-(1H-tetrazol-1-yl)phenyl)-3-(5-(2-chloro-6-(hydroxymethyl)pyridin-3-yl)-1H-imidazol-2-yl)-2,3,8,8a-tetrahydroindolizin-5(1H)-one as a yellow solid.

LC/MS: mass calculated for $C_{24}H_{19}Cl_2FN_8O_2$: 540.10, measured (ES, m/z): 541.10 $[M+H]^+$. $^1H$ NMR (300 MHz, DMSO-$d_6$) δ 12.07-12.25 (m, 1H), 9.85 (s, 1H), 8.41-8.51 (m, 1H), 7.92-8.04 (m, 1H), 7.72 (dd, J=8.7, 1.5 Hz, 1H), 7.68 (s, 1H), 7.57 (d, J=8.0 Hz, 1H), 5.71 (d, J=2.5 Hz, 1H), 5.04 (d, J=8.4 Hz, 1H), 4.55 (s, 2H), 3.67-3.81 (m, 1H), 2.61-2.77 (m, 1H), 2.51-2.57 (m, 1H), 2.05-2.27 (m, 2H), 1.94-2.03 (m, 2H). $^{19}F$ NMR (282 MHz, DMSO-$d_6$) δ −112.907.

Example 237 3-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-2-fluorobenzamide

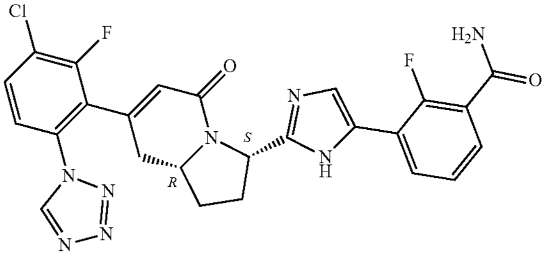

LC/MS: mass calculated for $C_{25}H_{19}ClF_2N_8O_2$: 536.13, measured (ES, m/z): 537.05 $[M+H]^+$. $^1H$ NMR (300 MHz, DMSO-$d_6$+$D_2O$) δ: 9.81 (s, 1H), 8.04-8.12 (m, 1H), 7.94 (t, J=8.4 Hz, 1H), 7.83 (s, 1H), 7.65 (dd, J=8.7, 1.5 Hz, 1H), 7.61 (s, 1H), 7.47-7.39 (m, 1H), 7.37 (d, J=4.6 Hz, 1H), 7.28 (t, J=7.7 Hz, 1H), 5.66 (d, J=2.5 Hz, 1H), 5.05 (d, J=8.4 Hz, 1H), 3.72-3.81 (m, 1H), 2.57-2.83 (m, 2H), 2.05-2.28 (m, 2H), 1.73-2.00 (m, 2H). $^{19}F$-NMR (376 MHz, DMSO-$d_6$) δ −112.86, −116.62.

Example 238 5-(2-((3*S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)thiophene-2-carboxamide

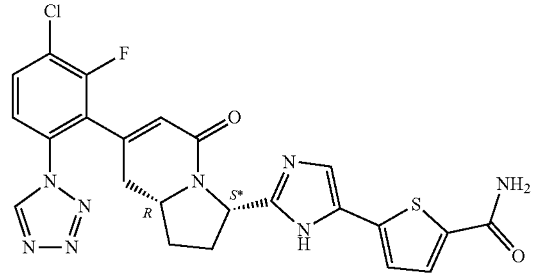

Step 1: 2-(5-carbamoylthiophen-2-yl)-2-oxoethyl (3S,8aR)-7-(6-amino-3-chloro-2-fluorophenyl)-5-oxo-1,2,3,5,8,8a-hexahydroindolizine-3-carboxylate To a solution of (3S,8aR)-7-(6-amino-3-chloro-2-fluorophenyl)-5-oxo-1,2,3,5,8,8a-hexahydroindolizine-3-carboxylic acid (262 mg, 0.81 mmol, 1.0 equiv.) in DMF (3 mL) was added $K_2CO_3$ (222 mg, 1.612 mmol, 2.0 equiv.). The mixture was stirred at 25° C. for 0.5 h. To which 5-(2-bromoacetyl)thiophene-2-carboxamide (200 mg, 0.81 mmol, 1.0 equiv.) was added. The resulting mixture was stirred 1.5 h, quenched with water (10 mL) and extracted with ethyl acetate (3×10 mL). The organic layers were combined, dried over anhydrous sodium sulfate, filtered, and concentrated. The residue was purified by silica gel chromatography (0→50% EA/PE) to yield the 2-(5-carbamoylthiophen-2-yl)-2-oxoethyl (3S,8aR)-7-(6-amino-3-chloro-2-fluorophenyl)-5-oxo-1,2,3,5,8,8a-hexahydroindolizine-3-carboxylate as a yellow oil. LC/MS: mass calculated for $C_{22}H_{19}ClFN_3O_5S$: 491.07, measured: 492.10 $[M+H]^+$.

Step 2: 5-(2-((3S,8aR)-7-(6-amino-3-chloro-2-fluorophenyl)-5-oxo-1,2,3,5,8,8a-hexahydroindolizin-3-yl)-1H-imidazol-5-yl)thiophene-2-carboxamide To a solution of 2-(5-carbamoylthiophen-2-yl)-2-oxoethyl (3S,8aR)-7-(6-amino-3-chloro-2-fluorophenyl)-5-oxo-1,2,3,5,8,8a-hexahydroindolizine-3-carboxylate (170 mg, 0.35 mmol, 1.0 equiv.) in toluene/AcOH (10:1) (3 mL) was added ammonium acetate (266 mg, 3.5 mmol, 10.0 equiv.). The resulting mixture was stirred 2 hours at 100° C. After being cooled to room temperature. The resulting mixture was concentrated under vacuum. The residue was purified by flash column chromatography on silica gel (0%→50% EA/PE) to yield the 5-(2-((3S,8aR)-7-(6-amino-3-chloro-2-fluorophenyl)-5-oxo-1,2,3,5,8,8a-hexahydroindolizin-3-yl)-

1H-imidazol-5-yl)thiophene-2-carboxamide as a yellow oil. LC/MS: mass calculated for $C_{22}H_{19}ClFN_5O_2S$: 471.09, measured: 472.10 [M+H]$^+$.

Step 3: 5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)thiophene-2-carboxamide To a solution of 5-(2-((3S,8aR)-7-(6-amino-3-chloro-2-fluorophenyl)-5-oxo-1,2,3,5,8,8a-hexahydroindolizin-3-yl)-1H-imidazol-5-yl)thiophene-2-carboxamide (90 mg, 0.19 mmol, 1.0 equiv.) in acetic acid (5 mL) were added trimethoxymethane (202 mg, 1.91 mmol, 10.0 equiv.) and $TMSN_3$ (220 mg 1.91 mmol, 10.0 equiv.). The resulting mixture was stirred at room temperature for 2 h. The residue was purified by Prep-HPLC and then separated by Chiral Prep-SEC with Mobile Phase A: Hex:DCM=3:1 (10 mM $NH_3$-MeOH), Mobile Phase B: EtOH to yield 5-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)thiophene-2-carboxamide as a white solid.

LC/MS: mass calculated for $C_{23}H_{18}ClFN_8O_2S$: 524.09, measured (ES, m/z): 525.10 [M+H]$^+$. $^1$H NMR (400 MHz, DMSO-$d_6$) δ 11.96 (s, 1H), 9.82 (s, 1H), 7.97 (t, J=8.4 Hz, 1H), 7.76-7.91 (m, 1H), 7.70-7.72 (m, 1H), 7.62 (d, J=3.8 Hz, 1H), 7.44 (d, J=2.2 Hz, 1H), 7.20-7.21 (m, 2H), 5.66 (d, J=2.8 Hz, 1H), 4.96 (d, J=8.8 Hz, 1H), 3.66-3.71 (m, 1H), 2.74-2.81 (m, 1H), 2.17-2.20 (m, 1H), 2.06-2.12 (m, 1H), 1.95-1.96 (m, 2H). $^{19}$F NMR (376 MHz, DMSO-$d_6$) δ −112.73.

Example 239 (3*R,8a*R)-7-(3-Chloro-2-fluoro-6-(1H-tetrazol-1-yl)phenyl)-3-(5-(3-(trifluoromethyl)-1H-pyrazol-4-yl)-1H-imidazol-2-yl)-2,3,8,8a-tetrahydroindolizin-5(1H)-one

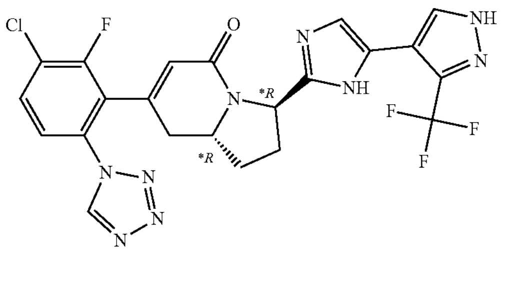 [SMILES: O=C1C=C(c2c(-n3cnnn3)ccc(Cl)c2F)C[C@H]2CC[C@H](c3ncc(-c4c[nH]nc4C(F)(F)F)[nH]3)N12]

LC/MS: mass calculated for $C_{22}H_{16}ClF_4N_6O$: 533.11, measured (ES, m/z): 534.10 [M+H]$^+$. $^1$H NMR (400 MHz, DMSO-$d_6$) δ 13.51 (br, 1H), 11.92 (br, 1H), 9.83 (s, 1H), 8.09 (s, 1H), 7.97 (t, J=8.2 Hz, 1H), 7.70-7.72 (m, 1H), 6.99 (s, 1H), 5.66 (d, J=2.4 Hz, 1H), 4.98 (t, J=7.2 Hz, 1H), 3.98-4.22 (m, 1H), 2.18-2.38 (m, 4H), 1.93-2.12 (m, 2H). $^{19}$F NMR (376 MHz, DMSO-$d_6$) δ −60.09, −113.10.

Example 296: (3*S,8a*R)-7-(3-Chloro-2-fluoro-6-(1H-tetrazol-1-yl)phenyl)-3-(5-(3-(trifluoromethyl)-1H-pyrazol-4-yl)-1H-imidazol-2-yl)-2,3,8,8a-tetrahydroindolizin-5(1H)-one

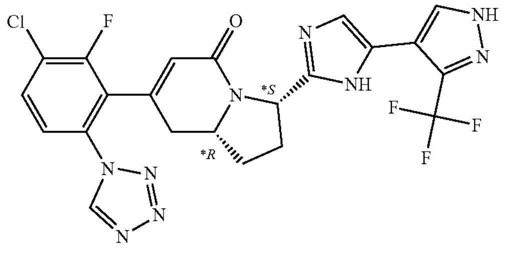 [SMILES: O=C1C=C(c2c(-n3cnnn3)ccc(Cl)c2F)C[C@H]2CC[C@@H](c3ncc(-c4c[nH]nc4C(F)(F)F)[nH]3)N12]

Step 1: 2-oxo-2-(3-(trifluoromethyl)-1-(trimethylsilyl)ethoxy)methyl)-1H-pyrazol-4-yl)ethyl (3S,8aR)-7-(6-amino-3-chloro-2-fluorophenyl)-5-oxo-1,2,3,5,8,8a-hexahydroindolizine-3-carboxylate To a solution of (3S,8aR)-7-(6-amino-3-chloro-2-fluorophenyl)-5-oxo-1,2,3,5,8,8a-hexahydroindolizine-3-carboxylic acid (168 mg, 0.52 mmol, 1.0 equiv.) in DMF (5 mL) was added $K_2CO_3$ (143 mg, 1.03 mmol, 2.0 equiv.). The mixture was stirred at 25° C. for 0.5 h. To the resulting mixture was added 2-bromo-1-(3-(trifluoromethyl)-1-((2-(trimethylsilyl)ethoxy)methyl)-1H-pyrazol-4-yl)ethanone (200 mg, 0.52 mmol, 1.0 equiv.) and the resulting mixture was stirred 1.5 h. The solid was filtered off and the filtrate was concentrated. The residue was purified by Prep-HPLC with Mobile Phase A: Water (0.05% TFA), Mobile Phase B: ACN to yield 2-oxo-2-(3-(trifluoromethyl)-1-((2-(trimethylsilyl)ethoxy)methyl)-1H-pyrazol-4-yl)ethyl (3S,8aR)-7-(6-amino-3-chloro-2-fluorophenyl)-5-oxo-1,2,3,5,8,8a-hexahydroindolizine-3-carboxylate as a yellow oil. LC/MS: mass calculated for $C_{27}H_{31}ClF_4N_4O_5Si$: 630.17, measured: 631.25 [M+H]$^+$.

Step 2: (3S,8aR)-7-(6-amino-3-chloro-2-fluorophenyl)-3-(5-(3-(trifluoromethyl)-1-((2-(trimethylsilyl)ethoxy)methyl)-1H-pyrazol-4-yl)-1H-imidazol-2-yl)-2,3,8,8a-tetrahydroindolizin-5(1H)-one To a solution of 2-oxo-2-(3-(trifluoromethyl)-1-((2-(trimethylsilyl)ethoxy)methyl)-1H-pyrazol-4-yl)ethyl (3S,8aR)-7-(6-amino-3-chloro-2-fluorophenyl)-5-oxo-1,2,3,5,8,8a-hexahydroindolizine-3-carboxylate (220 mg, 0.35 mmol, 1.0 equiv.) in toluene (5 mL) were added AcOH (0.5 mL) and $NH_4OAc$ (269 mg, 3.49 mmol, 10.0 equiv.). The resulting mixture was heated at 100 ® C. for 3 h under nitrogen. After being cooled to room temperature. The resulting mixture was concentrated under vacuum. The residue was purified by silica gel chromatography (0-010% MeOH/DCM) to yield the (3S,8aR)-7-(6-amino-3-chloro-2-fluorophenyl)-3-(5-(3-(trifluoromethyl)-1-((2-(trimethylsilyl)ethoxy)methyl)-1H-pyrazol-4-yl)-1H-imidazol-2-yl)-2,3,8,8a-tetrahydroindolizin-5(1H)-one as a brown oil. LC/MS: mass calculated for $C_{27}H_{31}ClF_4N_6O_2Si$: 611.19, measured: 611.35 [M+H]$^+$.

Step 3: (3S,8aR)-7-(3-chloro-2-fluoro-6-(1H-tetrazol-1-yl)phenyl)-3-(5-(3-(trifluoromethyl)-1-((2-(trimethylsilyl)ethoxy)methyl)-1H-pyrazol-4-yl)-1H-imidazol-2-yl)-2,3,8,8a-tetrahydroindolizin-5(1H)-one To a solution of (3S,8aR)-7-(6-amino-3-chloro-2-fluorophenyl)-3-(5-(3-(trifluoromethyl)-1-((2-(trimethylsilyl)ethoxy)methyl)-1H-pyrazol-4-yl)-1H-imidazol-2-yl)-2,3,8,8a-tetrahydroindolizin-5(1H)-one (150 mg, 0.24 mmol, 1.0 equiv.) in HOAc (5 mL) were added trimethoxymethane (260 mg, 2.45 mmol, 10.0 equiv.) and $TMSN_3$ (260 mg, 2.45 mmol, 10.0 equiv.). The resulting mixture was maintained under nitrogen and stirred at 25° C. for 16 h. The residue was purified by prep-HPLC with Mobile Phase A: Water (0.05% TFA), Mobile Phase B: ACN to yield (3S,8aR)-7-(3-chloro-2-fluoro-6-(1H-tetrazol-1-yl)phenyl)-3-(5-(3-(trifluoromethyl)-1-((2-(trimethylsilyl)ethoxy)methyl)-1H-pyrazol-4-yl)-1H-imidazol-2-yl)-2,3,8,8a-tetrahydroindolizin-5(1H)-one as a brown oil. LC/MS: mass calculated for $C_{28}H_{30}ClF_4N_9O_2Si$: 663.19, measured: 665.25 $[M+H]^+$.

Step 4: (3S,8aR)-7-(3-chloro-2-fluoro-6-(1H-tetrazol-1-yl)phenyl)-3-(5-(3-(trifluoromethyl)-1H-pyrazol-4-yl)-1H-imidazol-2-yl)-2,3,8,8a-tetrahydroindolizin-5(1H)-one To a solution of (3S,8aR)-7-(3-chloro-2-fluoro-6-(1H-tetrazol-1-yl)phenyl)-3-(5-(3-(trifluoromethyl)-1-((2-(trimethylsilyl)ethoxy)methyl)-1H-pyrazol-4-yl)-1H-imidazol-2-yl)-2,3,8,8a-tetrahydroindolizin-5(1H)-one (130 mg, 0.196 mmol, 1.0 equiv.) in DCM (3 mL) was added TFA (3 mL). The resulting mixture was stirred at 25° C. for 2 h and then concentrated under vacuum. The residue was purified by reverse chromatography to yield the racemic product, which was further separated by chiral-HPLC to yield (3S,8aR)-7-(3-chloro-2-fluoro-6-(1H-tetrazol-1-yl)phenyl)-3-(5-(3-(trifluoromethyl)-1H-pyrazol-4-yl)-1H-imidazol-2-yl)-2,3,8,8a-tetrahydroindolizin-5(1H)-one as a white solid.

LC/MS: mass calculated for $C_{22}H_{16}ClF_4N_6O$: 533.11, measured (ES, m/z): 534.10 $[M+H]^+$. $^1$H NMR (400 MHz, DMSO-$d_6$) δ 13.51 (br, 1H), 11.92 (br, 1H), 9.83 (s, 1H), 8.09 (s, 1H), 7.97 (t, J=8.2 Hz, 1H), 7.70-7.72 (m, 1H), 6.99 (s, 1H), 5.66 (d, J=2.4 Hz, 1H), 4.98 (t, J=7.2 Hz, 1H), 3.98-4.22 (m, 1H), 2.18-2.38 (m, 4H), 1.93-2.12 (m, 2H). $^{19}$F NMR (376 MHz, DMSO-$d_6$) δ −60.01, −112.84.

Example 241 N-[4-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-6-(trifluoromethyl)-3-pyridyl]cyclopropanecarboxamide

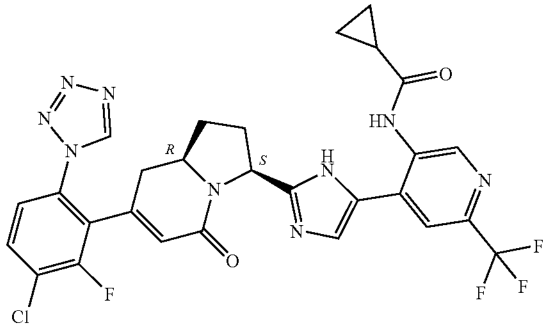

LC/MS: mass calculated for $C_{28}H_{22}ClF_4N_9O_2$: 627.15, measured (ES, m/z): 628.15 $[M+H]^+$. $^1$H NMR (300 MHz, DMSO-$d_6$) δ 12.52 (s, 1H), 9.80 (s, 1H), 9.63 (s, 1H), 8.18 (d, J=1.4 Hz, 2H), 7.96 (t, J=7.8 Hz, 1H), 7.70 (d, J=8.6 Hz, 1H), 7.19-7.45 (m, 1H), 5.67 (d, J=2.4 Hz, 1H), 5.09 (d, J=8.8 Hz, 1H), 3.65-3.82 (m, 1H), 2.48-2.75 (m, 2H), 2.23-2.41 (m, 1H), 2.00-2.18 (m, 2H), 1.82-1.99 (m, 1H), 1.72-1.80 (m, 1H), 0.83-0.94 (m, 4H). $^{19}$F NMR (282 MHz, DMSO-$d_6$) δ −65.37, −73.49, −112.81.

Example 242 N-[4 [2-[(3S,8aS)-7-[3-Chloro-2-fluoro-6-(tetrazol-1-yl)phenyl]-5-oxo-2,3,8,8a-tetrahydro-1H-indolizin-3-yl]-1H-imidazol-5-yl]-6-(trifluoromethyl)-3-pyridyl]cyclopropanecarboxamide

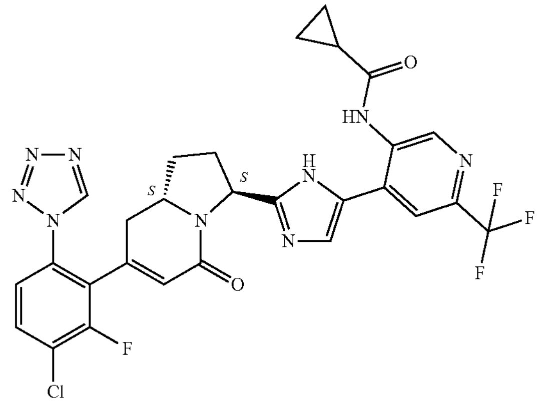

LC/MS: mass calculated for $C_{28}H_{22}ClF_4N_9O_2$: 627.15, measured (ES, m/z): 628.10 $[M+H]^+$. $^1$H NMR (300 MHz, DMSO-$d_6$) δ 12.89 (br, 1H), 12.82 (s, 1H), 9.82 (s, 1H), 9.67 (s, 1H), 8.21 (d, J=17.5 Hz, 2H), 7.97 (t, J=8.2 Hz, 1H), 7.70 (d, J=8.7 Hz, 1H), 7.22-7.41 (m, 1H), 5.71 (d, J=2.6 Hz, 1H), 5.07 (t, J=7.6 Hz, 1H), 4.01-4.18 (m, 1H), 2.31-2.46 (m, 2H), 2.20-2.28 (m, 1H), 1.93-2.08 (m, 2H), 1.61-1.78 (m, 2H), 0.79-0.95 (m, 4H). $^{19}$F NMR (282 MHz, DMSO-$d_6$) δ −65.54, −73.45, −113.38.

Example 243 N-[4-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-6-(trifluoromethyl)-3-pyridyl]-2,2,2-trideuterio-acetamide

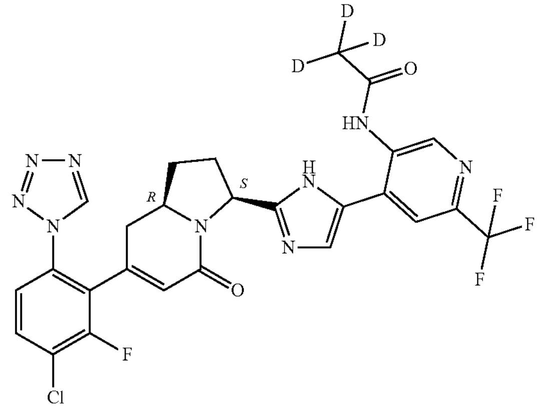

LC/MS: mass calculated for $C_{26}H_{17}ClD_3F_4N_9O_2$: 604.16, measured (ES, m/z): 605.15 $[M+H]^+$. $^1H$ NMR (300 MHz, DMSO-$d_6$) δ 12.71 (s, 1H), 12.31 (s, 1H), 9.82 (s, 1H), 9.66 (s, 1H), 8.19 (s, 2H), 7.97 (t, J=8.3 Hz, 1H), 7.71 (d, J=8.7 Hz, 1H), 5.70 (d, J=2.1 Hz, 1H), 5.07 (d, J=8.9 Hz, 1H), 3.66-3.81 (m, 1H), 2.54-2.73 (m, 2H), 2.23-2.36 (m, 1H), 2.13-2.20 (m, 1H), 2.03-2.12 (m, 1H), 1.87-1.99 (m, 1H). $^{19}F$ NMR (282 MHz, DMSO-$d_6$) δ −65.20, −73.44, −112.87.

Example 244 N-[4 [2-[(3S,8aS)-7-[3-Chloro-2-fluoro-6-(tetrazol-1-yl)phenyl]-5-oxo-2,3,8,8a-tetrahydro-1H-indolizin-3-yl]-1H-imidazol-5-yl]-6-(trifluoromethyl)-3-pyridyl]acetamide

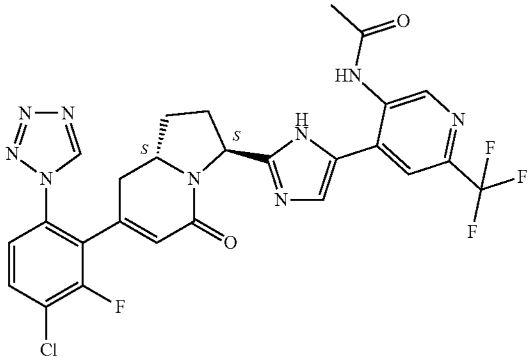

LC/MS: mass calculated for $C_{26}H_{20}ClF_4N_9O_2$: 601.14, measured (ES, m/z): 602.10 $[M+H]^+$. $^1H$ NMR (300 MHz, DMSO-$d_6$) δ 12.87 (s, 1H), 12.59 (s, 1H), 9.82 (s, 1H), 9.68 (s, 1H), 8.19 (d, J=12.2 Hz, 2H), 7.96 (t, J=8.3 Hz, 1H), 7.70 (d, J=8.7 Hz, 1H), 5.72 (d, J=2.5 Hz, 1H), 5.07 (t, J=7.4 Hz, 1H), 4.03-4.16 (m, 1H), 2.37-2.46 (m, 2H), 1.96-2.31 (m, 6H), 1.69-1.84 (m, 1H). $^{19}F$ NMR (282 MHz, DMSO-$d_6$) δ −65.56, −73.42, −113.17.

Example 245 N-[4-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-5-yl]-6-(trifluoromethyl)-3-pyridyl]acetamide

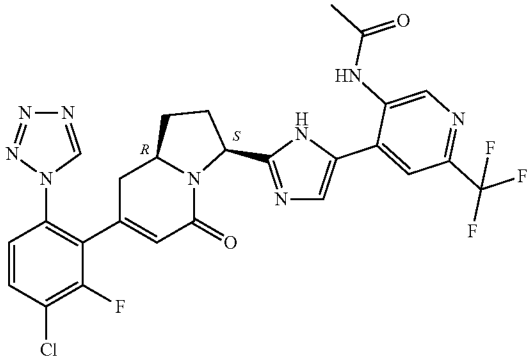

LC/MS: mass calculated for $C_{26}H_{20}ClF_4N_9O_2$: 601.14, measured (ES, m/z): 602.15 $[M+H]^+$. $^1H$ NMR (300 MHz, DMSO-$d_6$) δ 12.68 (s, 1H), 12.29 (s, 1H), 9.81 (s, 1H), 9.65 (s, 1H), 8.17 (d, J=3.1 Hz, 2H), 7.96 (t, J=8.3 Hz, 1H), 7.70 (d, J=8.6 Hz, 1H), 5.70 (d, J=2.1 Hz, 1H), 5.07 (d, J=8.8 Hz, 1H), 3.68-3.79 (m, 1H), 2.53-2.72 (m, 2H), 2.05-2.32 (m, 6H), 1.86-2.02 (m, 1H). $^{19}F$ NMR (282 MHz, DMSO-$d_6$) δ −65.57, −73.44, −112.86.

Example 246 N-[4-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-4-yl]-3-pyridyl]-2,2-difluoro-propanamide

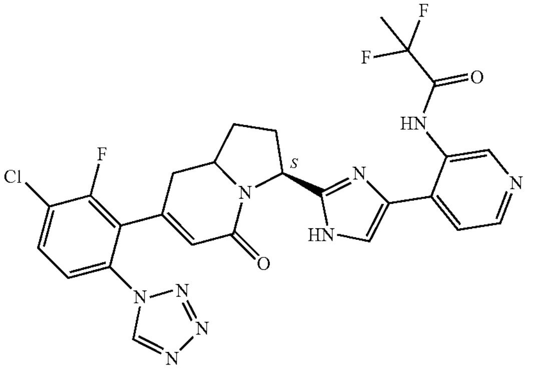

LC/MS: mass calculated for $C_{28}H_{21}ClF_3N_9O_2$: 583.15, measured (ES, m/z): 584.25 $[M+H]^+$. $^1H$ NMR (300 MHz, $CD_3OD$-$d_4$) δ 9.90 (s, 1H), 9.57 (s, 1H), 8.40-8.50 (m, 1H), 8.25-8.33 (m, 1H), 8.24 (s, 1H), 7.84 (t, J=7.8 Hz, 1H), 7.52-7.60 (m, 1H), 5.65-5.77 (m, 1H). 5.11-5.24 (m, 1H), 3.85-4.04 (m, 1H), 2.65-2.73 (m, 2H), 2.27-2.57 (m, 3H), 1.80-2.20 (m, 4H). $^{19}F$ NMR (282 MHz, $CD_3OD$-d4) δ −77.02, −99.20, −113.75.

Example 247 N-[5-[2-[(3S,8aS)-7-[3-Chloro-2-fluoro-6-(tetrazol-1-yl)phenyl]-5-oxo-2,3,8,8a-tetrahydro-1H-indolizin-3-yl]-1H-imidazol-4-yl]-1-methyl-pyrazol-4-yl]cyclopropanecarboxamide

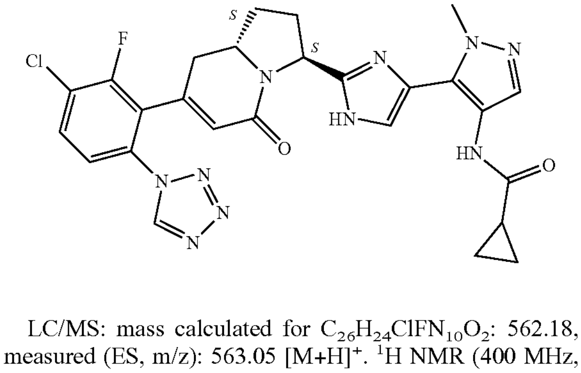

LC/MS: mass calculated for $C_{26}H_{24}ClFN_{10}O_2$: 562.18, measured (ES, m/z): 563.05 $[M+H]^+$. $^1H$ NMR (400 MHz, DMSO-$d_6$) δ 9.92 (br, 1H), 9.76-9.90 (m, 1H), 7.99 (t, J=8.2 Hz, 1H), 7.69-7.81 (m, 3H), 5.65-5.80 (m, 1H), 5.15 (t, J=7.5 Hz, 1H), 4.06-4.21 (m, 1H), 3.80-3.86 (m, 3H), 2.62-2.88 (m, 1H), 2.21-2.45 (m, 3H), 1.73-2.19 (m, 2H), 1.62-1.72 (m, 1H), 0.71-0.83 (m, 4H). $^{19}F$ NMR (282 MHz, $CD_3OD$-$d_4$) δ −77.02, −99.20, −113.75 (d, J=97.01 Hz). $^{19}F$ NMR (376 MHz, DMSO-$d_6$) δ −77.02, −99.20, −113.75.

Example 248 N-[2-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-4-yl]-3-thienyl]cyclopropanecarboxamide

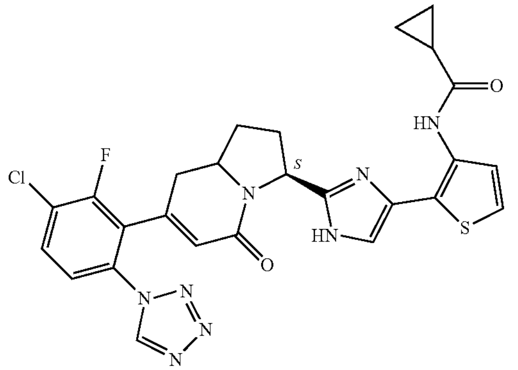

LC/MS: mass calculated for $C_{28}H_{22}ClFN_8O_2S$: 564.13, measured (ES, m/z): 565.10 $[M+H]^+$. $^1H$ NMR (300 MHz, DMSO-$d_6$) δ 11.68 (br, 1H), 9.84 (d, J=2.8 Hz, 1H), 7.99 (t, J=8.1 Hz, 1H), 7.73 (d, J=8.6 Hz, 2H), 7.15-7.31 (m, 1H), 6.67 (d, J=4.5 Hz, 1H), 5.68-5.79 (m, 1H), 5.02-5.19 (m, 1H), 3.63-3.85 (m, 1H), 2.85-3.04 (m, 1H), 1.86-2.16 (m, 4H), 1.72-1.84 (m, 1H), 0.81-0.94 (m, 4H). $^{19}F$ NMR (376 MHz, DMSO-$d_6$) δ-73.67, −112.74.

Example 249 N-(4-(2-((3S,8a*R)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)pyridin-3-yl)cyclopropanecarboxamide

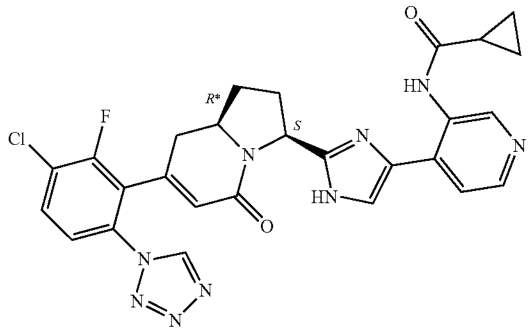

Step 1: 2-(3-bromopyridin-4-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (612 mg, 1.88 mmol, 1.0 equiv.) in DMF (10 mL) was added cesium carbonate (430 mg, 1.32 mmol, 0.7 equiv.). The mixture was stirred at 35° C. for 0.5 h. To the mixture was then added 2-bromo-1-(3-bromopyridin-4-yl)ethan-1-one (841 mg, 3.02 mmol, 1.6 equiv.) and the resulting mixture was stirred 1.5 h, then quenched with water (50 mL) and extracted with ethyl acetate (3×50 mL). The organic layers were combined, dried over anhydrous sodium sulfate, filtered, and concentrated. The residue was purified by silica gel chromatography (0-0100% PE/EA) to yield the 2-(3-bromopyridin-4-yl)-2-oxoethyl (3S)-7-(6-amino-3-chloro-2-fluorophenyl)-5-oxo-1,2,3,5,8,8a-hexahydroindolizine-3-carboxylate as a yellow oil. LC/MS: mass calculated for $C_{22}H_{18}BrClFN_3O_4$: 521.02, measured 522.00 $[M+H]^+$, 522.00 $[M+H+2]^+$.

Step 2: (3S)-7-(6-amino-3-chloro-2-fluorophenyl)-3-(4-(3-bromopyridin-4-yl)-1H-imidazol-2-yl)-2,3,8,8a-tetrahydroindolizin-5(1H)-one To a solution of 2-(3-bromopyridin-4-yl)-2-oxoethyl (3S)-7-(6-amino-3-chloro-2-fluorophenyl)-5-oxo-1,2,3,5,8,8a-hexahydroindolizine-3-carboxylate (581 mg, 1.11 mmol, 1.0 equiv.) in toluene (10 mL) and acetic acid (1 mL) was added ammonium acetate (857 mg, 11.12 mmol, 10.0 equiv.). The mixture was stirred at 110° C. for 2 h. After being cooled to room temperature, the reaction mixture was quenched with water (50 mL) and extracted with ethyl acetate (3×50 mL). The organic layers were combined, dried over anhydrous sodium sulfate, filtered, and concentrated. The residue was purified by flash column chromatography on silica gel (0→10% MeOH/DCM) to yield the (3S)-7-(6-amino-3-chloro-2-fluorophenyl)-3-(4-(3-bromopyridin-4-yl)-1H-imidazol-2-yl)-2,3,8,8a-tetrahydroindolizin-5(1H)-one as a yellow oil. LC/MS: mass calculated for $C_{22}H_{18}BrClFN_5O$: 501.04, measured: 501.95 $[M+H]^+$, 503.95 $[M+H+2]^+$.

Step 3: (3S)-3-(4-(3-bromopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of (3S)-7-(6-amino-3-chloro-2-fluorophenyl)-3-(4-(3-bromopyridin-4-yl)-1H-imidazol-2-yl)-2,3,8,8a-tetrahydroindolizin-5(1H)-one (406 mg, 0.81 mmol, 1.0 equiv.) in acetic acid (10 mL) were added azidotrimethylsilane (929 mg, 8.07 mmol, 10.0 equiv.) and trimethoxymethane (856 mg, 8.07 mmol, 10.0 equiv.). The reaction mixture was stirred at 65° C. for 2 h, diluted with water and extracted with EA. The combined extracts were washed with water, dried over $Na_2SO_4$, filtered and purified by silica gel chromatography (0→10% MeOH/DCM) to yield (3S)-3-(4-(3-bromopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow oil. LC/MS: mass calculated for $C_{23}H_{19}ClFN_9O$: 554.04, measured: 555.00 $[M+H]^+$, 557.00 $[M+H+2]^+$.

Step 4: (3S)-3-(4-(3-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of (3S)-3-(4-(3-bromopyridin-4-yl)-1H-imidazol-2-yl)-7-(3-chloro-2-fluoro-6-(1H-tetrazol-1-yl)phenyl)-2,3,8,8a-tetrahydroindolizin-5(1H one (313 mg, 0.56 mmol, 1.0 equiv.) in ethanol (4 mL) and $H_2O$ (1 mL) were added sodium azide (110 mg, 1.69 mmol, 3.0 equiv.), sodium ascorbate (89 mg, 0.45 mmol, 0.8 equiv.), (1R,2R)-N,N'-dimethyl-1,2-cyclohexanediamine (48 mg, 0.34 mmol, 0.6 equiv.), and copper sulfate pentahydrate (56 mg, 0.22 mmol, 0.4 equiv.). The mixture was stirred at room temperature for 2 h. The reaction was quenched with water (50 mL), extracted with ethyl acetate (3×50 mL). The combined extracts were washed with water, dried over $Na_2SO_4$, concentrated and purified by flash column chromatography on silica gel (0→10% MeOH/DCM) to yield (3S)-3-(4-(3-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow solid. LC/MS: mass calculated for $C_{23}H_{19}ClFN_9O$: 491.14, measured: 492.10 $[M+H]^+$.

Step 5: N-(4-(2-((3S,8a*R)-7-(3-chloro-2-fluoro-6-(1H-tetrazol-1-yl)phenyl)-5-oxo-1,2,3,5,8,8a-hexahydroindolizin-3-yl)-1H-imidazol-4-yl)pyridin-3-yl) cyclopropanecarboxamide To a solution of (3S)-3-(4-(3-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H one (206 mg, 0.42 mmol, 1.0 equiv.) in pyridine (4 mL) was added cyclopropanecarboxylic acid (180 mg, 2.09 mmol, 5.0 equiv.), followed by addition of EDCl (160 mg, 0.84 mmol, 2.0 equiv.). The reaction mixture was stirred at room temperature for 3 h and concentrated. The residue was re dissolved in methanol (4 mL) and ammonium hydroxide (0.4 mL) and stirred at room temperature for 1 h. The resulting mixture was then diluted with water and extracted with EA. The organic layers were combined, dried over anhydrous sodium sulfate, filtered and purified by prep-HPLC with (0→30% MeCN/$H_2O$) to yield N-(4-(2-((3S,8a*R)-7-(3-chloro-2-fluoro-6-(1H-tetrazol-1-yl)phenyl)-5-oxo-1,2,3,5,8,8a-hexahydroindolizin-3-yl)-1H-imidazol-4-yl)pyridin-3-yl) cyclopropanecarboxamide as a white solid.

LC/MS: mass calculated for $C_{27}H_{23}ClFN_9O_2$: 559.16, measured (ES, m/z): 560.10 $[M+H]^+$. $^1H$ NMR (300 MHz, DMSO-$d_6$) δ 12.52 (s, 1H), 12.10 (s, 1H), 9.82 (s, 1H), 9.45 (s, 1H), 8.20 (d, J=5.2 Hz, 1H), 7.85-8.06 (m, 2H), 7.62-7.78 (m, 2H), 5.67 (s, 1H), 5.08 (d, J=8.9 Hz, 1H), 3.58-3.86 (m, 1H), 2.56-2.80 (m, 2H), 2.01-2.36 (m, 3H), 1.80-2.00 (m, 1H), 1.57-1.80 (m, 1H), 0.72-0.99 (m, 4H). $^{19}F$ NMR (282 MHz, DMSO-$d_6$) δ-112.79.

Example 250 N-(4-(24(3S,8aS*)-7-(3-choro-2-fluoro-6-(1H-tetrazol-1-yl)phenyl)-5-oxo-1,2,3,5,8,8a-hexahydroindolizin-3-yl)-1H-imidazol-4-yl)pyridin-3-yl)cyclopropanecarboxamide

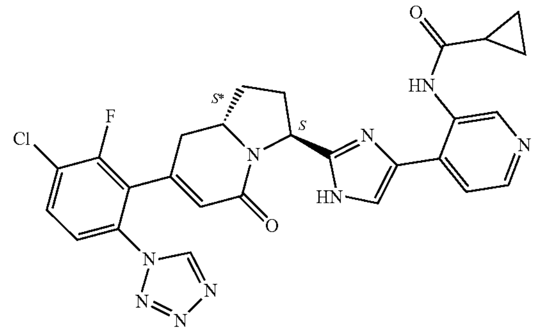

LC/MS: mass calculated for $C_{27}H_{23}ClFN_9O_2$: 559.16, measured (ES, m/z): 560.15 $[M+H]^+$. $^1H$ NMR (300 MHz, DMSO-$d_6$) δ 12.71 (s, 1H), 12.40 (s, 1H), 9.82 (s, 1H), 9.50 (s, 1H), 8.18 (d, J=5.2 Hz, 1H), 7.88-8.04 (m, 2H), 7.62-7.78 (m, 2H), 5.71 (d, J=2.7 Hz, 1H), 5.06 (t, J=7.5 Hz, 1H), 4.00-4.22 (m, 1H), 2.33-2.47 (m, 2H), 2.12-2.32 (m, 2H), 1.86-2.10 (m, 1H), 1.55-1.84 (m, 2H), 0.76-0.96 (m, 4H). $^{19}F$ NMR (282 MHz, DMSO-$d_6$) δ 113.38.

Example 251 Ethyl N-[3-[2-[(3S)-7-[3-chloro-2-fluoro-6-(tetrazol-1-yl)phenyl]-5-oxo-2,3,8,8a-tetrahydro-1H-indolizin-3-yl]-1H-imidazol-4-yl]-4-pyridyl]carbamate

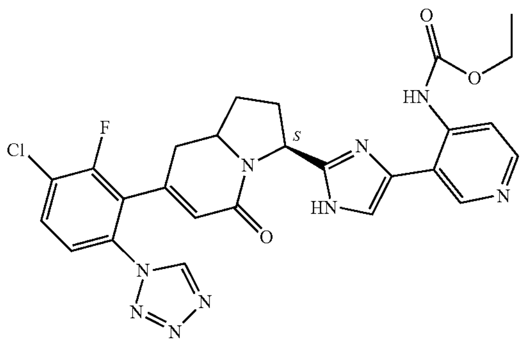

LC/MS: mass calculated for $C_{20}H_{23}ClFN_9O_3$: 563.16, measured (ES, m/z): 564.15 $[M+H]^+$. $^1H$ NMR (300 MHz, DMSO-$d_6$) δ 13.13-13.40 (m, 1H), 13.00 (br, 1H), 9.82 (s, 1H), 9.06-9.14 (m, 1H), 8.49-8.65 (m, 2H), 8.03 (s, 1H), 7.90-8.01 (m, 1H), 7.71 (d, J=8.7 Hz, 1H), 5.63-5.75 (m, 1H), 5.00-5.14 (m, 1H), 4.15-4.34 (m, 2H), 3.78-3.86 (m, 1H), 2.51-2.64 (m, 1H), 2.18-2.34 (m, 4H), 1.92-2.02 (m, 1H), 1.16-1.34 (m, 3H). $^{19}F$ NMR (282 MHz, DMSO-$d_6$) δ-73.88, −113.19.

Example 252 N-[3-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-4-yl]-4-pyridyl]cyclopropanecarboxamide

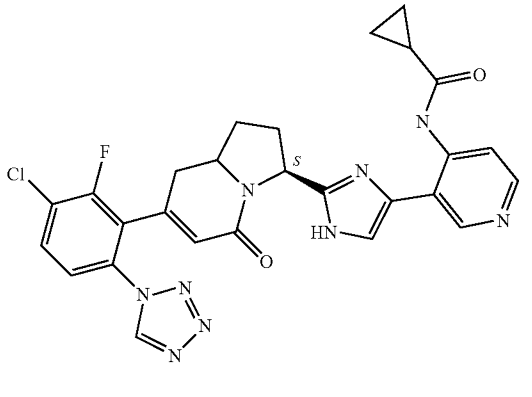

LC/MS: mass calculated for $C_{27}H_{23}ClFN_9O_2$: 559.16, measured (ES, m/z): 560.15 $[M+H]^+$. $^1H$ NMR (300 MHz, DMSO-$d_6$) δ 13.31-13.77 (m, 1H), 12.60-13.28 (m, 1H), 9.83 (s, 1H), 9.15 (s, 1H), 8.85 (d, J=6.3 Hz, 1H), 8.56 (d, J=6.0 Hz, 1H), 8.08 (s, 1H), 7.97 (t, J=8.2 Hz, 1H), 7.71 (d, J=8.7 Hz, 1H), 5.60-5.80 (m, 1H), 5.13 (d, J=8.7 Hz, 1H), 3.70-3.80 (m, 1H), 2.58-2.80 (m, 2H), 2.01-2.37 (m, 3H), 1.60-2.00 (m, 2H), 0.80-1.15 (m, 4H). $^{19}F$ NMR (282 MHz, DMSO-$d_6$) δ-74.42, −113.11.

Example 253 (3S)-3-[4-(4-Amino-3-pyridyl)-1H-imidazol-2-yl]-7-[3-chloro-2-fluoro-6-(tetrazol-1-yl)phenyl]-2,3,8,8a-tetrahydro-1H-indolizin-5-one

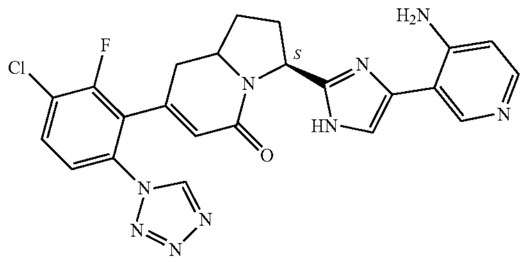

LC/MS: mass calculated for $C_{23}H_{19}ClFN_9O$: 491.14, measured (ES, m/z): 492.10 $[M+H]^+$. $^1H$ NMR (300 MHz, DMSO-$d_6$) δ 9.83 (s, 1H), 8.59 (s, 1H), 8.07 (d, J=7.0 Hz, 1H), 7.97 (t, J=8.1 Hz, 1H), 7.80 (s, 1H), 7.71 (d, J=8.7 Hz, 1H), 7.00 (d, J=6.9 Hz, 1H), 5.67 (d, J=2.4 Hz, 1H), 5.06 (d, J=8.8 Hz, 1H), 3.71-3.77 (m, 1H), 2.55-2.77 (m, 2H), 2.11-2.29 (m, 2H), 1.86-2.04 (m, 2H). $^{19}F$ NMR (282 MHz, DMSO-$d_6$) δ−74.24, −112.78.

Example 254 Ethyl N-[3-[2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-4-yl]-2-pyridyl]carbamate

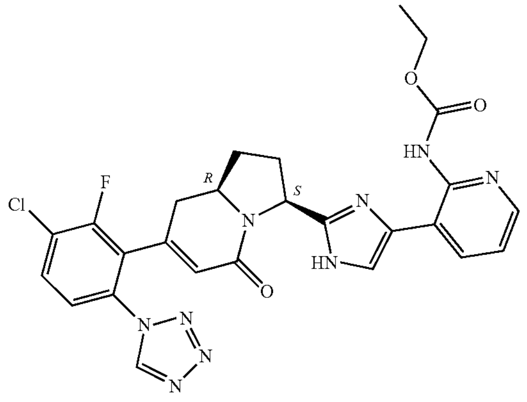

LC/MS: mass calculated for $C_{26}H_{23}ClFN_9O_3$: 563.16, measured (ES, m/z): 564.30 $[M+H]^+$. $^1H$ NMR (400 MHz, DMSO-$d_6$) δ 12.96 (br, 1H), 9.83 (s, 1H), 8.16-8.45 (m, 2H), 7.98 (t, J=8.2 Hz, 1H), 7.87 (s, 1H), 7.72 (d, J=8.7 Hz, 1H), 7.33 (t, J=6.0 Hz, 1H), 5.69 (s, 1H), 5.06 (d, J=8.7 Hz, 1H), 4.11-4.21 (m, 2H), 3.75-3.80 (m, 1H), 2.55-2.81 (m, 2H), 2.05-2.37 (m, 3H), 1.85-2.05 (m, 1H), 1.20 (t, J=7.1 Hz, 3H). $^{19}F$ NMR (376 MHz, DMSO-$d_6$) δ −74.11, −113.03.

Example 255 (3S)-7-[3-Chloro-2-fluoro-6-(tetrazol-1-yl)phenyl]-3-[4-(1-methyl-1,2,4-triazol-3-yl)-1H-imidazol-2-yl]-2,3,8,8a-tetrahydro-1H-indolizin-5-one

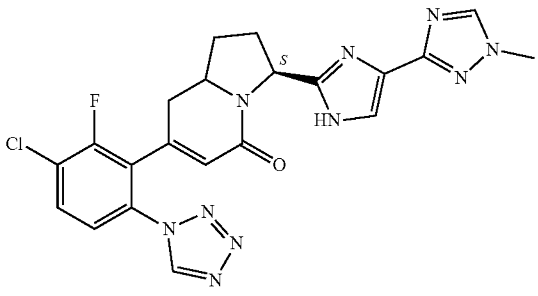

LC/MS: mass calculated for $C_{21}H_{18}ClFN_{10}O$: 480.13, measured (ES, m/z): 481.05 $[M+H]^+$. $^1H$ NMR (300 MHz, $CD_3OD$-$d_4$) δ 9.58 (s, 1H), 8.50 (s, 1H), 7.76-7.92 (m, 2H), 7.51-7.60 (m, 1H), 5.70-5.82 (m, 1H), 5.19-5.35 (m, 1H), 3.84-4.10 (m, 4H), 2.90-3.10 (m, 1H), 2.60-2.80 (m, 2H), 2.41-2.59 (m, 1H), 2.18-2.37 (m, 1H), 1.85-2.15 (m, 1H). $^{19}F$ NMR (282 MHz, $CD_3OD$-$d_4$) δ −77.11, −113.77.

Example 256 N-[4-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-4-yl]-3-pyridyl]-2,2,2-trideuterio-acetamide

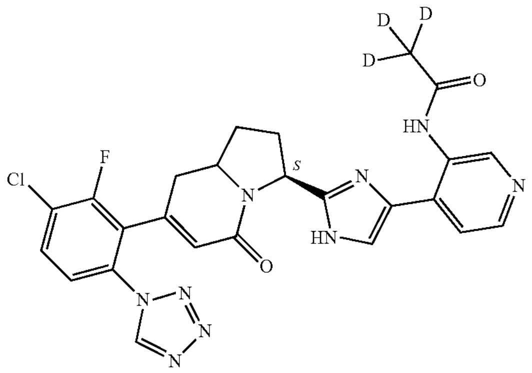

LC/MS: mass calculated for $C_{25}H_{18}ClD_3FN_9O_2$: 536.17, measured (ES, m/z): 537.25 $[M+H]^+$. $^1H$ NMR (300 MHz, DMSO-$d_6$) δ 12.85-13.35 (m, 1H), 12.35-12.80 (m, 1H), 9.84 (s, 1H), 9.66 (s, 1H), 8.48 (d, J=8.0 Hz, 1H), 8.29-8.37 (m, 1H), 8.22 (d, J=11.7 Hz, 1H), 7.98 (t, J=8.1 Hz, 1H), 7.72 (d, J=9.9 Hz, 1H), 5.72 (s, 1H), 5.10 (d, J=9.0 Hz, 1H), 3.72-3.76 (m, 1H), 2.55-2.67 (m, 2H), 2.40-2.49 (m, 1H), 2.16-2.36 (m, 2H), 2.03-2.15 (m, 1H), 1.87-2.02 (m, 1H). $^{19}F$ NMR (282 MHz, DMSO-$d_6$) δ −73.98, −113.05.

Example 257 N-[2-[2-[(3S,8aR)-7-[3-Chloro-2-fluoro-6-(tetrazol-1-yl)phenyl]-5-oxo-2,3,8,8a-tetrahydro-1H-indolizin-3-yl]-1H-imidazol-4-yl]-4-methoxy-phenyl]cyclopropanecarboxamide

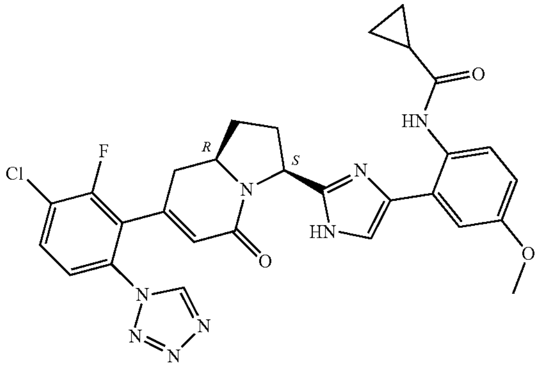

LC/MS: mass calculated for $C_{29}H_{26}ClFN_8O_3$: 588.18, measured (ES, m/z): 589.10 $[M+H]^+$. $^1H$ NMR (400 MHz, DMSO-$d_6$) δ 12.27 (s, 1H), 11.99 (s, 1H), 9.83 (s, 1H), 8.23 (d, J=9.0 Hz, 1H), 7.98 (t, J=8.2 Hz, 1H), 7.72 (d, J=8.7 Hz, 1H), 7.65 (s, 1H), 7.23 (d, J=2.9 Hz, 1H), 6.76 (dd, J=9.0, 2.9 Hz, 1H), 5.66 (d, J=2.6 Hz, 1H), 5.07 (d, J=9.0 Hz, 1H), 3.76 (s, 3H), 3.65-3.74 (m, 1H), 2.63-2.78 (m, 1H), 2.54-2.62 (m, 1H), 2.21-2.34 (m, 1H), 2.11-2.19 (m, 1H), 2.01-2.10 (m, 1H), 1.85-2.00 (m, 1H), 1.52-1.65 (m, 1H), 0.64-0.92 (m, 4H). $^{19}F$ NMR (376 MHz, DMSO-$d_6$) δ −112.48.

Example 258 (3S)-7-[3-Chloro-2-fluoro-6-(tetrazol-1-yl)phenyl]-3-[5-[3-(methylamino)-1H-indazol-6-yl]-1H-imidazol-2-yl]-2,3,8,8a-tetrahydro-1H-indolizin-5-one

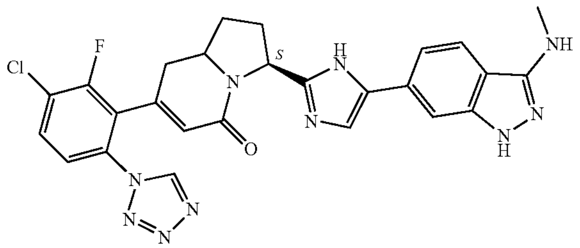

LC/MS: mass calculated for $C_{26}H_{22}ClFN_{10}O$: 544.17, measured (ES, m/z): 545.05 $[M+H]^+$. $^1H$ NMR (400 MHz, DMSO-$d_6$) δ 13.90-14.90 (m, 1H), 11.95 (br, 1H), 9.84 (s, 1H), 8.12 (s, 1H), 7.99 (t, J=8.0 Hz, 1H), 7.83 (d, J=11.2 Hz, 1H), 7.73 (d, J=12.8 Hz, 1H), 7.60-7.70 (m, 1H), 7.20-7.42 (m, 1H), 5.65-5.90 (m, 1H), 5.10-5.30 (m, 1H), 3.70-3.82 (m, 1H), 3.00 (t, J=15.3 Hz, 1H), 2.89 (s, 3H), 2.53-2.70 (m, 1H), 2.25-2.48 (m, 2H), 2.07-2.25 (m, 2H), 1.76-2.07 (m, 1H). $^{19}F$ NMR (376 MHz, DMSO-$d_6$) δ −74.29, 112.86.

Example 259 N-[4-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-4-yl]-1-methyl-pyrazol-3-yl]cyclopropanecarboxamide

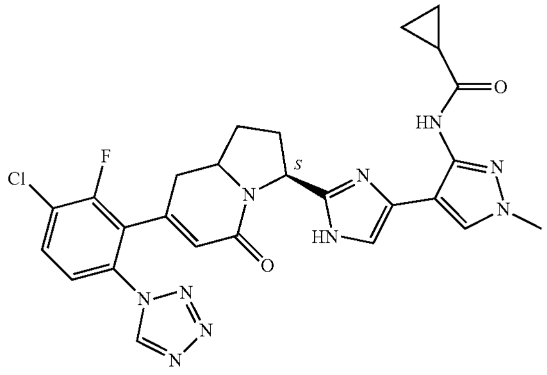

LC/MS: mass calculated for $C_{26}H_{24}ClFN_{10}O_2$: 562.18, measured (ES, m/z): 563.10 $[M+H]^+$. $^1H$ NMR (300 MHz, DMSO-$d_6$) δ 10.10-10.30 (m, 1H), 9.83 (s, 1H), 7.92-8.10 (m, 2H), 7.73 (d, J=8.7 Hz, 1H), 7.16 (s, 1H), 5.63-5.80 (m, 1H), 5.05-5.25 (m, 1H), 4.10-4.40 (m, 1H), 3.86 (s, 3H), 2.85-3.10 (m, 1H), 2.54-2.65 (m, 1H), 2.21-2.45 (m, 1H), 1.70-2.20 (m, 4H), 0.65-0.90 (m, 4H). $^{19}F$ NMR (282 MHz, DMSO-$d_6$) δ −74.08, −112.61.

Example 260 (3S)-7-[3-Chloro-2-fluoro-6-(tetrazol-1-yl)phenyl]-3-[4-[2-(methylamino)-3-pyridyl]-1H-imidazol-2-yl]-2,3,8,8a-tetrahydro-1H-indolizin-5-one

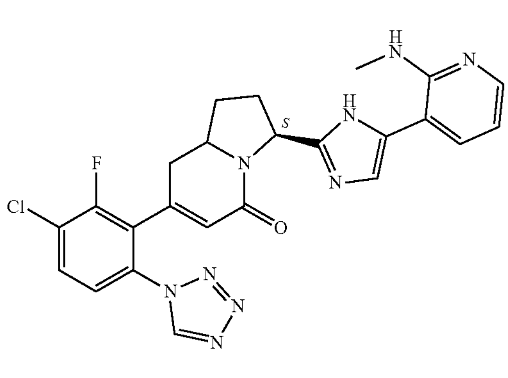

LC/MS: mass calculated for $C_{24}H_{21}ClFN_9O$: 505.15, measured (ES, m/z): 506.05 $[M+H]^+$. $^1H$ NMR (400 MHz, DMSO-$d_6$) δ 12.75 (br, 1H), 10.35-11.00 (m, 1H), 9.85 (s, 1H), 8.21-8.31 (m, 1H), 7.99 (t, J=8.4 Hz, 1H), 7.85-7.97 (m, 2H), 7.73 (d, J=8.6 Hz, 1H), 6.94 (t, J=6.8 Hz, 1H), 5.70-5.75 (m, 1H), 5.03-5.08 (m, 1H), 3.69-3.90 (m, 1H), 3.12 (s, 3H), 2.60-2.67 (m, 1H), 2.38-2.50 (m, 1H), 2.22-2.33 (m, 1H), 2.13-2.20 (m, 1H), 1.70-2.00 (m, 2H). $^{19}F$ NMR (376 MHz, DMSO-$d_6$) δ −74.23, −113.09.

Example 261: 6-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-5-yl]-1H-quinolin-2-one

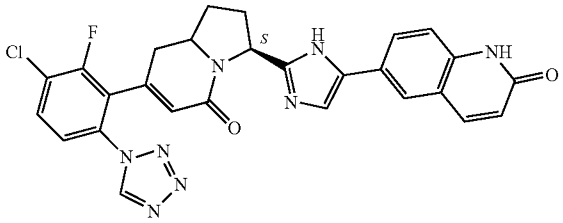

LC/MS: mass calculated for $C_{27}H_{20}ClFN_8O_2$: 542.14, measured (ES, m/z): 543.15 $[M+H]^+$. $^1H$ NMR (400 MHz, DMSO-$d_6$) δ 11.94 (br, 1H), 9.84 (s, 1H), 7.84-8.10 (m, 5H), 7.72 (d, J=13.2 Hz, 1H), 7.40 (d, J=8.6 Hz, 1H), 6.59 (d, J=9.6 Hz, 1H), 5.67-5.80 (m, 1H), 5.02-5.24 (m, 1H), 3.70-3.83 (m, 1H), 2.86-3.06 (m, 1H), 2.52-2.65 (m, 1H), 2.26-2.45 (m, 1H), 1.78-2.24 (m, 3H). $^{19}F$ NMR (376 MHz, DMSO-$d_6$) δ −73.82, −112.70.

Example 262: Ethyl N-[3-[2-[(3S,8aS)-7-[3-chloro-2-fluoro-6-(tetrazol-1-yl)phenyl]-5-oxo-2,3,8,8a-tetrahydro-1H-indolizin-3-yl]-1H-imidazol-4-yl]-2-pyridyl]carbamate

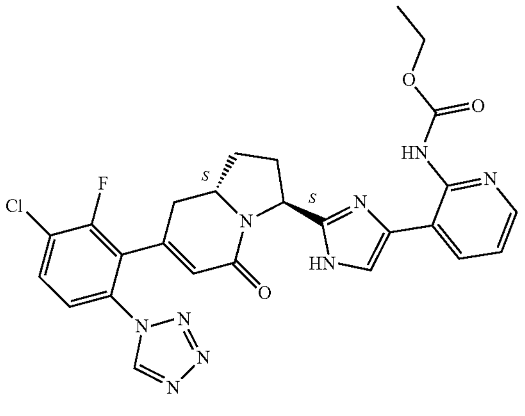

LC/MS: mass calculated for $C_{26}H_{23}ClFN_9O_3$: 563.16, measured (ES, m/z): 564.15 $[M+H]^+$. $^1H$ NMR (300 MHz, DMSO-$d_6$) δ 9.83 (s, 1H), 8.26-8.40 (m, 2H), 7.98 (t, J=8.2 Hz, 1H), 7.80 (s, 1H), 7.71 (d, J=8.7 Hz, 1H), 7.25-7.35 (m, 1H), 5.71 (d, J=2.4 Hz, 1H), 5.10 (t, J=7.3 Hz, 1H), 4.07-4.23 (m, 3H), 2.52-2.64 (m, 1H), 2.30-2.48 (m, 3H), 1.98-2.04 (m, 1H), 1.76-1.86 (m, 1H), 1.10-1.26 (m, 3H). $^{19}F$ NMR (282 MHz, DMSO-$d_6$) δ −73.90, −113.13.

Example 263: Ethyl N-[4-[2-[(3S,8aS)-7-[3-chloro-2-fluoro-6-(tetrazol-1-yl)phenyl]-5-oxo-2,3,8,8a-tetrahydro-1H-indolizin-3-yl]-1H-imidazol-4-yl]-3-pyridyl]carbamate

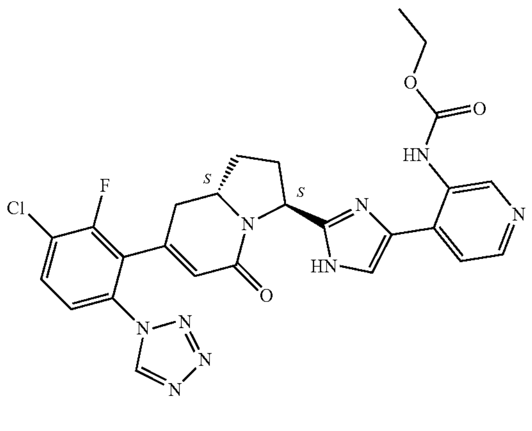

LC/MS: mass calculated for $C_{26}H_{23}ClFN_6O_3$: 563.16, measured (ES, m/z): 564.15 $[M+H]^+$. $^1H$ NMR (300 MHz, DMSO-$d_6$) δ 13.24 (br, 1H), 12.48 (br, 1H), 9.82 (s, 1H), 9.40 (s, 1H), 8.44 (d, J=5.4 Hz, 1H), 8.32 (s, 1H), 8.19 (d, J=5.7 Hz, 1H), 7.98 (t, J=8.2 Hz, 1H), 7.71 (d, J=8.7 Hz, 1H), 5.69 (s, 1H), 5.09 (t, J=7.2 Hz, 1H), 4.13-4.29 (m, 3H), 2.54-2.59 (m, 1H), 2.25-2.45 (m, 3H), 1.94-2.06 (m, 1H), 1.75-1.88 (m, 1H), 1.21-1.32 (m, 3H). $^{19}F$ NMR (282 MHz, DMSO-$d_6$) δ −74.01, −113.18.

Example 264: N-[2-[2-[(3S,8aS)-7-[3-Chloro-2-fluoro-6-(tetrazol-1-yl)phenyl]-5-oxo-2,3,8,8a-tetrahydro-1H-indolizin-3-yl]-1H-imidazol-4-yl]-5-methoxy-phenyl]cyclopropanecarboxamide

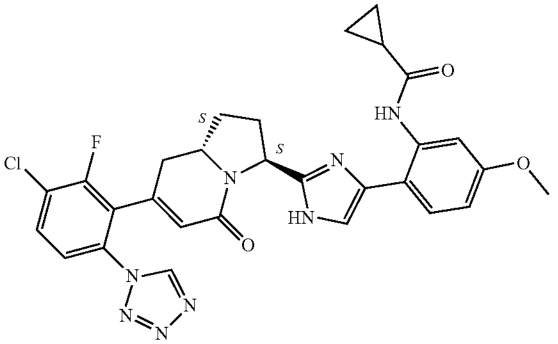

LC/MS: mass calculated for $C_{29}H_{26}ClFN_8O_3$: 588.18, measured (ES, m/z): 589.30 $[M+H]^+$. $^1H$ NMR (400 MHz, DMSO-$d_6$) δ 13.50-14.80 (m, 1H), 9.83 (s, 1H), 7.98 (t, J=8.4 Hz, 1H), 7.72 (d, J=8.7 Hz, 1H), 7.59 (s, 1H), 7.45 (d, J=8.5 Hz, 1H), 6.84 (br, 1H), 5.75 (d, J=2.6 Hz, 1H), 5.14 (t, J=8.1 Hz, 1H), 4.11-4.25 (m, 1H), 3.77 (s, 3H), 2.52-2.60 (m, 1H), 2.39-2.48 (m, 1H), 2.23-2.32 (m, 1H), 1.97-2.06 (m, 1H), 1.71-1.86 (m, 2H), 0.75-0.81 (m, 4H). $^{19F}$ NMR (376 MHz, DMSO-$d_6$) δ −74.15, −113.14.

Example 265: (3S,8aS)-7-[3-Chloro-2-fluoro-6-(tetrazol-1-yl)phenyl]-3-[5-[3-(methylamino)-1H-indazol-6-yl]-1H-imidazol-2-yl]-2,3,8,8a-tetrahydro-1H-indolizin-5-one

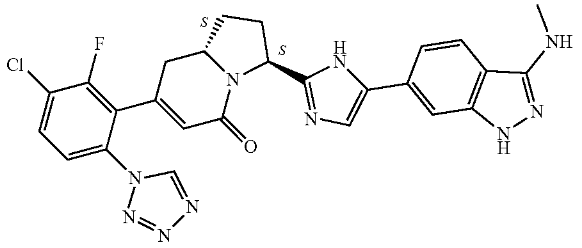

LC/MS: mass calculated for $C_{26}H_{22}ClFN_{10}O$: 544.17, measured (ES, m/z): 545.15 $[M+H]^+$. $^1H$ NMR (400 MHz, DMSO-$d_6$) δ14.60 (br, 1H), 11.87 (br, 1H), 9.85 (s, 1H), 8.11 (s, 1H), 8.00 (t, J=8.2 Hz, 1H), 7.82 (d, J=8.4 Hz, 1H), 7.73 (d, J=8.7 Hz, 1H), 7.65 (s, 1H), 7.29 (d, J=8.4 Hz, 1H), 5.77 (d, J=2.6 Hz, 1H), 5.15 (t, J=8.8 Hz, 1H), 4.13-4.29 (m, 1H), 2.88 (s, 3H), 2.53-2.67 (2H), 2.40-2.48 (m, 1H), 2.26-2.34 (m, 1H), 1.98-2.09 (m, 1H), 1.77-1.93 (m, 1H). $^{19}F$ NMR (376 MHz, DMSO-$d_6$) δ −74.11, −113.06.

Example 266: N-(2-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-5-methoxyphenyl)cyclopropanecarboxamide

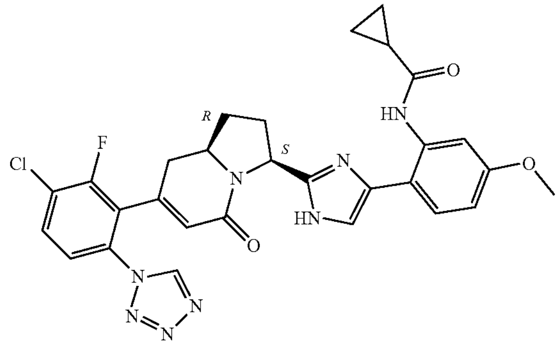

LC/MS: mass calculated for $C_{29}H_{26}ClFN_8O_3$: 588.18, measured (ES, m/z): 589.10 $[M+H]^+$. $^1H$ NMR (400 MHz, DMSO-$d_6$) δ 12.48 (s, 1H), 12.18 (s, 1H), 9.82 (s, 1H), 8.11 (s, 1H), 7.97 (t, J=8.2 Hz, 1H), 7.71 (d, J=8.8 Hz, 1H), 7.58 (d, J=8.6 Hz, 1H), 7.48 (s, 1H), 6.62 (d, J=11.6 Hz, 1H), 5.65 (s, 1H), 5.05 (d, J=9.0 Hz, 1H), 3.63-3.77 (m, 4H), 2.53-2.74 (m, 2H), 2.19-2.35 (m, 1H), 2.11-2.19 (m, 1H), 2.00-2.10 (m, 1H), 1.84-2.01 (m, 1H), 1.52-1.68 (m, 1H), 0.69-0.94 (m, 4H). $^{19}F$ NMR (376 MHz, DMSO-$d_6$) δ−112.57.

Example 267: N-[3-[2-[(3S,8aS)-7-[3-Chloro-2-fluoro-6-(tetrazol-1-yl)phenyl]-5-oxo-2,3,8,8a-tetrahydro-1H-indolizin-3-yl]-1H-imidazol-4-yl]-4-pyridyl]cyclopropanecarboxamide

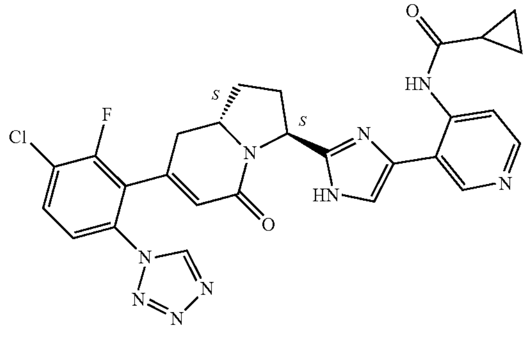

LC/MS: mass calculated for $C_{27}H_{23}ClFN_9O_2$: 559.16, measured (ES, m/z): 560.15 $[M+H]^+$. $^1H$ NMR (300 MHz, $CD_3OD$-$d_4$) δ 9.59 (s, 1H), 8.98-9.09 (m, 2H), 8.41 (d, J=6.9 Hz, 1H), 7.79-7.92 (m, 2H), 7.58 (d, J=8.7 Hz, 1H), 5.73 (d, J=2.3 Hz, 1H), 5.23 (t, J=7.8 Hz, 1H), 4.19-4.33 (m, 1H), 2.51-2.73 (m, 3H), 2.35-2.50 (m, 1H), 2.15-2.34 (m, 1H), 1.75-1.97 (m, 2H), 1.04-1.25 (m, 4H). $^{19}F$ NMR (282 MHz, $CD_3OD$-$d_4$) δ-77.02, −114.16.

Example 268: Ethyl N-[3-[2-[(3S,8aS)-7-[3-chloro-2-fluoro-6-(tetrazol-1-yl)phenyl]-5-oxo-2,3,8,8a-tetrahydro-1H-indolizin-3-yl]-1H-imidazol-4-yl]-4-pyridyl]carbamate

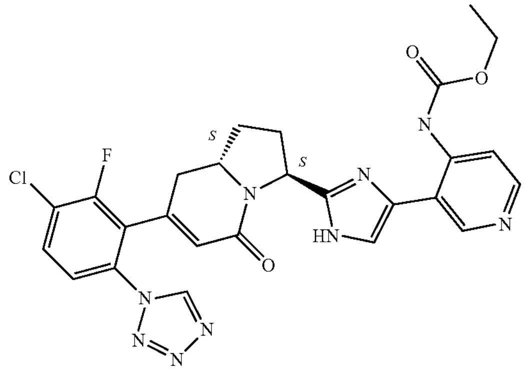

LC/MS: mass calculated for $C_{26}H_{23}ClFN_9O_3$: 563.16, measured (ES, m/z): 564.15 $[M+H]^+$. $^1H$ NMR (300 MHz, DMSO-$d_6$) δ 13.26 (br, 1H), 12.98 (br, 1H), 9.82 (s, 1H), 9.08 (s, 1H), 8.53 (br, 2H), 7.92-8.05 (m, 2H), 7.71 (d, J=8.7 Hz, 1H), 5.68 (d, J=2.3 Hz, 1H), 5.09 (t, J=7.0 Hz, 1H), 4.21-4.35 (m, 2H), 4.09-4.20 (m, 1H), 2.30-2.45 (m, 4H), 1.95-2.08 (m, 1H), 1.75-1.88 (m, 1H), 1.28 (t, J=7.0 Hz, 3H). $^{19}F$ NMR (282 MHz, DMSO-$d_6$) δ −73.74, −113.21.

Example 269: (3S,8aS)-7-[3-Chloro-2-fluoro-6-(tetrazol-1-yl)phenyl]-3-[5-[2-(methylamino)-3-pyridyl]-1H-imidazol-2-yl]-2,3,8,8a-tetrahydro-1H-indolizin-5-one

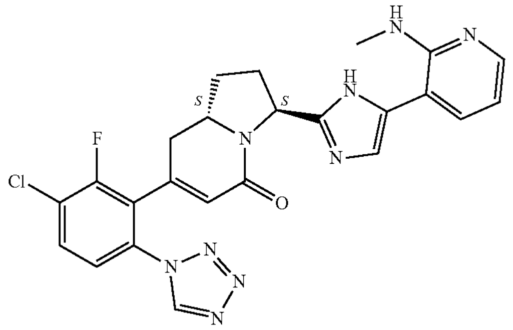

LC/MS: mass calculated for $C_{24}H_{21}ClFN_9O$: 505.15, measured (ES, m/z): 506.15 $[M+H]^+$. $^1H$ NMR (400 MHz, DMSO-$d_6$) δ 12.93 (br, 1H), 9.85 (s, 1H), 8.22 (d, J=7.3 Hz, 1H), 7.98 (t, J=8.2 Hz, 1H), 7.85-7.92 (m, 2H), 7.72 (d, J=8.7 Hz, 1H), 6.92 (t, J=6.8 Hz, 1H), 5.71 (d, J=2.5 Hz, 1H), 5.06 (t, J=7.5 Hz, 1H), 4.03-4.12 (m, 1H), 3.14 (s, 3H), 2.52-2.58 (m, 1H), 2.34-2.48 (m, 2H), 2.18-2.30 (m, 1H), 1.92-2.06 (m, 1H), 1.69-1.79 (m, 1H). $^{19}F$ NMR (376 MHz, DMSO-$d_6$) δ−74.05, −113.18.

Example 270: 6-[2-[(3S,8aS)-7-[3-Chloro-2-fluoro-6-(tetrazol-1-yl)phenyl]-5-oxo-2,3,8,8a-tetrahydro-1H-indolizin-3-yl]-1H-imidazol-5-yl]-1H-quinolin-2-one

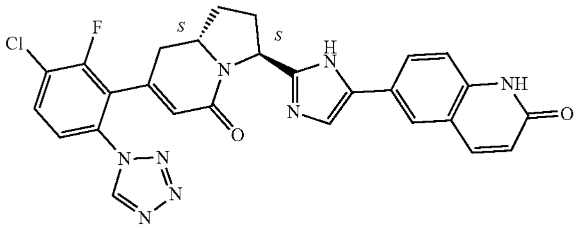

LC/MS: mass calculated for $C_{27}H_{20}ClFN_8O_2$: 542.14, measured (ES, m/z): 543.15 $[M+H]^+$. $^1H$ NMR (300 MHz, DMSO-$d_6$) δ 11.75 (s, 1H), 9.85 (s, 1H), 7.91-8.04 (m, 3H), 7.86 (d, J=8.2 Hz, 1H), 7.71 (d, J=8.7 Hz, 1H), 7.48 (br, 1H), 7.29 (d, J=8.6 Hz, 1H), 6.50 (d, J=9.6 Hz, 1H), 5.71 (d, J=2.5 Hz, 1H), 5.01 (t, J=7.3 Hz, 1H), 4.02-4.15 (m, 1H), 2.67-2.72 (m, 2H), 2.22-2.43 (m, 2H), 1.99-2.13 (m, 1H), 1.67-1.84 (m, 1H). $^{19}F$ NMR (282 MHz, DMSO-$d_6$) δ −113.08.

Example 271: N-(2-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-4-methoxyphenyl)cyclopropanecarboxamide

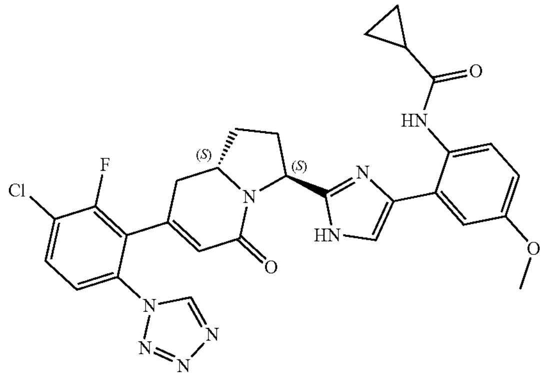

LC/MS: mass calculated for $C_{29}H_{26}ClFN_8O_3$: 588.18, measured: 589.05 $[M+H]^+$. $^1H$ NMR (400 MHz, DMSO-$d_6$) δ 9.83 (s, 1H), 7.98 (t, J=8.4 Hz, 1H), 7.65-7.74 (m, 2H), 7.14 (s, 1H), 6.76-7.06 (m, 1H), 5.73-5.77 (m, 1H), 5.12-5.15 (m, 1H), 4.13-4.18 (m, 1H), 3.77-3.82 (m, 3H), 2.53-2.69 (m, 1H), 2.37-2.47 (m, 2H), 2.22-2.35 (m, 1H), 1.95-2.05 (m, 1H), 1.73-1.86 (m, 1H), 1.59-1.72 (m, 1H), 0.68-0.84 (m, 4H). $^{19}F$ NMR (376 MHz, DMSO-$d_6$) δ −74.10, −113.17.

Example 272 (3S,8aS)-3-(4-(4-Aminopyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

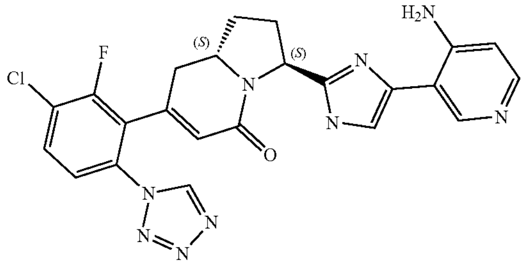

LC/MS: mass calculated for $C_{23}H_{19}ClFN_9O$: 491.14, measured: 492.10 $[M+H]^+$. $^1H$ NMR (300 MHz, DMSO-$d_6$) δ 9.80 (s, 1H), 8.49-8.54 (m, 1H), 8.05-8.09 (m, 1H), 7.89-8.00 (m, 1H), 7.78 (s, 1H), 7.65-7.71 (m, 1H), 6.99 (d, J=6.9 Hz, 1H), 5.69 (d, J=2.5 Hz, 1H), 5.06 (t, J=7.6 Hz, 1H), 4.06-4.12 (m, 1H), 2.36-2.56 (m, 3H), 2.21-2.26 (m, 1H), 1.95-2.02 (m, 1H), 1.67-1.83 (m, 1H). $^{19}F$ NMR (282 MHz, MHz, DMSO-$d_6$) δ −74.28, −113.09.

Example 273 6-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)quinazolin-2(1H)-one

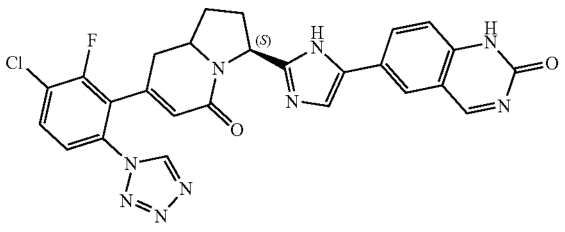

LC/MS: mass calculated for $C_{26}H_{19}ClFN_9O_2$:543.94, measured: 544.05 $[M+H]^+$. 1H NMR (300 MHz, Methanol-$d_4$) δ 9.61 (d, J=2.2 Hz, 1H), 7.80-7.92 (m, 1H), 7.78 (s, 1H), 7.64-7.74 (m, 2H), 7.57-7.62 (m, 1H), 7.04-7.11 (m, 1H), 5.68-5.80 (m, 2H), 5.12-5.33 (m, 1H), 3.98-4.44 (m, 1H), 3.01 (t, J=15.6 Hz, 1H), 2.62-2.81 (m, 1H), 2.46-2.60 (m, 1H), 2.25-2.43 (m, 2H), 1.90-2.09 (m, 1H).

Example 274 (3S,8aS)-7-(3-Chloro-2-fluoro-6-(1H-tetrazol-1-yl)phenyl)-3-(4-(1-methyl-1H-1,2,4-triazol-3-yl)-1H-imidazol-2-yl)-2,3,8,8a-tetrahydroindolizin-5(1H)-one

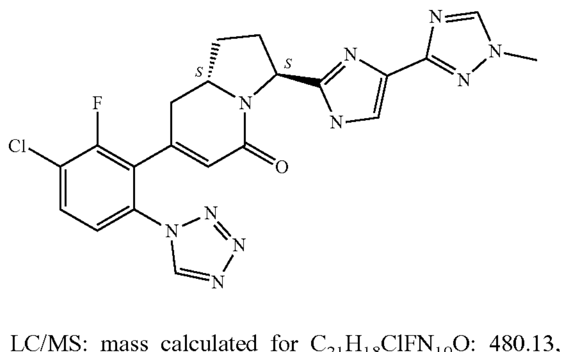

LC/MS: mass calculated for $C_{21}H_{18}ClFN_{10}O$: 480.13, measured: 481.10 $[M+H]^+$. $^1$H NMR (300 MHz, DMSO-$d_6$) δ 9.81 (s, 1H), 8.65 (s, 1H), 7.91-8.04 (m, 2H), 7.69 (d, J=8.7 Hz, 1H), 5.72 (d, J=2.4 Hz, 1H), 5.01-5.11 (m, 1H), 4.16-4.22 (m, 1H), 3.91-3.95 (m, 3H), 2.22-2.47 (m, 4H), 1.94-2.03 (m, 1H), 1.75-1.91 (m, 1H). $^{19}$F NMR (282 MHz, DMSO-$d_6$) δ −73.65, −113.09.

Example 275 N-(3-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-1-methyl-1H-pyrazol-4-yl)cyclopropanecarboxamide

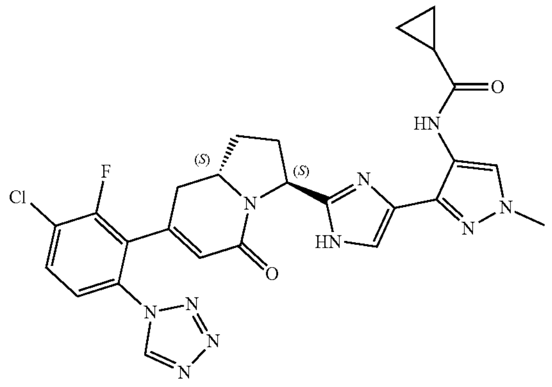

LC/MS: mass calculated for $C_{26}H_{24}ClFN_{10}O_2$: 562.18, measured: 563.10 $[M+H]^+$. $^1$H NMR (400 MHz, DMSO-$d_6$) δ 9.83 (s, 1H), 8.04 (s, 1H), 7.94-8.01 (m, 1H), 7.65-7.74 (m, 2H), 5.75 (s, 1H), 5.06-5.24 (m, 1H), 4.21-4.29 (m, 1H), 3.90 (s, 3H), 2.54-2.70 (m, 2H), 2.38-2.47 (m, 1H), 2.21-2.36 (m, 1H), 1.90-2.06 (m, 1H), 1.75-1.92 (m, 2H), 0.72-0.86 (m, 4H). $^{19}$F NMR (376 MHz, DMSO-$d_6$) δ −74.09, −113.09.

Example 276 N-(2-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-5-methoxyphenyl)cyclopropanecarboxamide

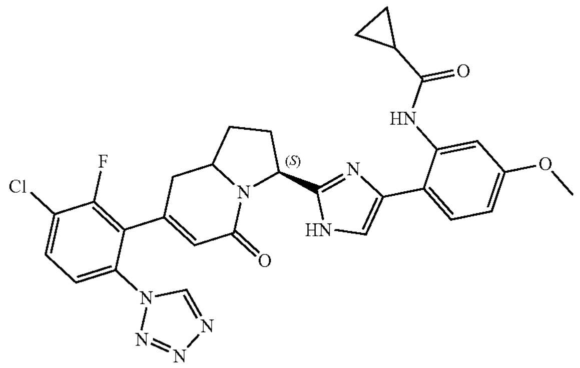

LC/MS: mass calculated for $C_{29}H_{26}ClFNeO_3$: 588.18, measured: 589.10 $[M+H]^+$. $^1$H NMR (300 MHz, DMSO-$d_6$) δ12.46-12.51 (m, 1H), 12.13-12.22 (m, 1H), 9.83 (s, 1H), 8.08-8.15 (m, 1H), 7.92-8.04 (m, 1H), 7.67-7.76 (m, 1H), 7.54-7.62 (m, 1H), 7.47-7.52 (m, 1H), 6.57-6.67 (m, 1H), 5.66 (s, 1H), 5.02-5.10 (m, 1H), 3.70-3.76 (m, 4H), 2.56-2.71 (m, 1H), 1.95-2.25 (m, 5H), 1.55-1.64 (m, 1H), 0.70-0.90 (m, 4H). $^{19}$F NMR (282 MHz, DMSO-$d_6$) δ −112.74, −113.37.

Example 277 6-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1,4-dihydro-2H-benzo[d][1,3]oxazin-2-one

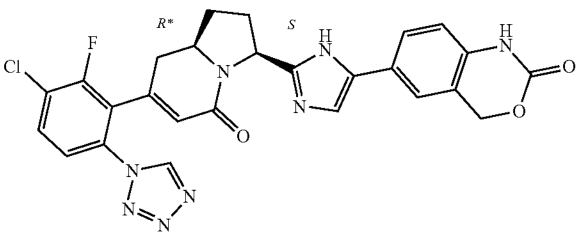

Step 1: 2-oxo-2-(2-oxo-1,4-dihydro-2H-benzo[d][1,3]oxazin-6-yl)ethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (192 mg, 0.59 mmol, 1.0 equiv.) in $CH_3CN$ (10 mL) was added $K_2CO_3$ (204 mg, 1.48 mmol, 2.5 equiv.), followed by 6-(2-chloroacetyl)benzo[d]oxazol-2(3H)-one (200 mg, 0.74 mmol, 1.3 equiv.) and the reaction mixture was stirred overnight at 40° C., quenched with water (10 mL), and extracted with ethyl acetate (3×50 mL). The combined organic layers were washed with brine (2×100 mL), dried over $Na_2SO_4$ and concentrated. The residue was purified by flash column chromatography on silica gel (0→25% EA/PE) to yield 2-oxo-2-(2-oxo-1,4-dihydro-2H-benzo[d][1,3]oxazin-6-yl)ethyl (3S)-7-(6-amino-3-chloro-2-fluorophenyl)-5-oxo-1,2,3,5,8,8a-hexahydroindolizine-3-carboxylate as a white solid. LC/MS: mass calculated for $C_{25}H_{21}ClFN_3O_6$: 513.11, measured 514.10 $[M+H]^+$.

Step 2: 6-(2-((3S)-7-(6-amino-3-chloro-2-fluorophenyl)-5-oxo-1,2,3,5,8,8a-hexahydroindolizin-3-yl)-1H-imidazol-5-yl)-1,4-dihydro-2H-benzo[d][1,3]oxazin-2-one To a solution of 2-oxo-2-(2-oxo-1,4-dihydro-2H-benzo[d][1,3]oxazin-6-yl)ethyl (3S)-7-(6-amino-3-chloro-2-fluorophenyl)-5-oxo-1,2,3,5,8,8a-hexahydroindolizine-3-carboxylate (502 mg, 0.98 mmol, 1.0 equiv.) in toluene (10 mL) and acetic acid (1 mL) was added ammonium acetate (753 mg, 9.77 mmol, 10.0 equiv.). The mixture was stirred at 110° C. for 2 h. After being cooled to room temperature, the reaction mixture was quenched with water (50 mL) and extracted with ethyl acetate (3×50 mL). The organic layers were combined, dried over anhydrous sodium sulfate, filtered, and concentrated. The residue was purified by silica gel chromatography (0→10% MeOH/DCM) to yield the 6-(2-((3S)-7-(6-amino-3-chloro-2-fluorophenyl)-5-oxo-1,2,3,5,8,8a-hexahydroindolizin-3-yl)-1H-imidazol-5-yl)-1,4-dihydro-2H-benzo[d][1,3]oxazin-2-one as a yellow solid. LC/MS: mass calculated for $C_{25}H_{21}ClFN_5O_3$: 493.13, measured: 494.10 $[M+H]^+$.

Step 3: 6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-1,4-dihydro-2H-benzo[d][1,3]oxazin-2-one To a solution of 6-(2-((3S)-7-(6-amino-3-chloro-2-fluorophenyl)-5-oxo-1,2,3,5,8,8a-hexahydroindolizin-3-yl)-1H-imidazol-5-yl)-1,4-dihydro-2H-benzo[d][1,3]oxazin-2-one (212 mg, 0.43 mmol, 1.0 equiv.) in acetic acid (5 mL) were added azidotrimethylsilane (496 mg, 4.30 mmol, 10.0 equiv.) and trimethoxymethane (457 mg, 4.30 mmol, 10.0 equiv.). The reaction mixture was stirred at room temperature overnight, diluted with water and extracted with EA. The organic layers were combined, dried over anhydrous sodium sulfate, filtered and concentrated. The residue was purified by prep-HPLC with (MeCN/$H_2O$ 0→30%) to yield 6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-1,4-dihydro-2H-benzo[d][1,3]oxazin-2-one as a white solid.

LC/MS: mass calculated for $C_{26}H_{20}ClFN_8O_3$: 546.13, measured: 547.10 $[M+H]^+$. $^1H$ NMR (300 MHz, DMSO-$d_6$) δ 11.73-11.79 (m, 1H), 10.10-10.15 (m, 1H), 9.84 (s, 1H), 7.91-8.01 (m, 1H), 7.67-7.75 (m, 1H), 7.56-7.65 (m, 2H), 7.33-7.39 (m, 1H), 6.82-6.90 (m, 1H), 5.66-5.73 (m, 1H), 5.30-5.36 (m, 2H), 4.94-5.03 (m, 1H), 3.65-3.82 (m, 1H), 3.50-3.53 (m, 1H), 2.65-2.80 (m, 1H), 2.06-2.20 (m, 2H), 1.90-1.98 (m, 2H). $^{19}F$ NMR (282 MHz, DMSO-$d_6$) δ −112.81, −112.91.

Example 278 (3S,8aS)-7-(3-Chloro-2-fluoro-6-(1H-tetrazol-1-yl)phenyl)-3-(5-(1,4-dihydro-2H-benzo[d][1,3]oxazin-6-yl)-1H-imidazol-2-yl)-2,3,8,8a-tetrahydroindolizin-5(1H)-one

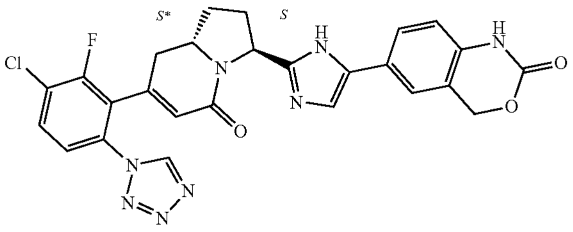

LC/MS: mass calculated for $C_{26}H_{20}ClFN_8O_3$: 546.13, measured: 547.15 $[M+H]^+$. $^1H$ NMR (300 MHz, DMSO-$d_6$) δ 11.89-11.94 (m, 1H), 10.10-10.15 (m, 1H), 9.84 (s, 1H), 7.92-8.03 (m, 1H), 7.65-7.74 (m, 1H), 7.55-7.64 (m, 2H), 7.33-7.38 (m, 1H), 6.80-6.88 (m, 1H), 5.69 (d, J=2.5 Hz, 1H), 5.29-5.35 (m, 2H), 4.92-5.02 (m, 1H), 4.05-4.15 (m, 1H), 3.48-3.54 (m, 1H), 2.20-2.45 (m, 3H), 1.99-2.05 (m, 1H), 1.63-1.74 (m, 1H). $^{19}F$ NMR (282 MHz, DMSO-$d_6$) δ −113.07, −218.48.

Example 279 N-(2-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-4-methoxyphenyl)cyclopropanecarboxamide

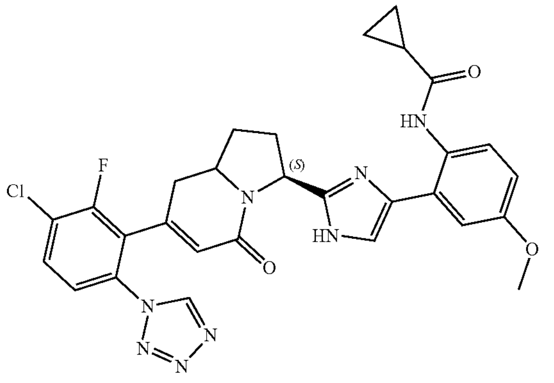

LC/MS: mass calculated for $C_{29}H_{26}ClFN_8O_3$: 588.18, measured: 589.15 $[M+H]^+$. $^1H$ NMR (300 MHz, DMSO-$d_6$) δ 9.83 (s, 1H), 7.93-8.03 (m, 1H), 7.64-7.78 (m, 3H), 7.15 (d, J=2.9 Hz, 1H), 6.96-7.04 (m, 1H), 5.68-5.80 (m, 1H), 5.20 (d, J=9.5 Hz, 1H), 3.68-3.82 (m, 4H), 2.85-2.98 (m, 1H), 2.52-2.67 (m, 1H), 2.27-2.47 (m, 1H), 2.03-2.22 (m, 2H), 1.83-1.99 (m, 1H), 1.64-1.77 (m, 1H), 0.71-0.79 (m, 4H). $^{19}F$ NMR (282 MHz, DMSO-$d_6$) δ −74.41, −112.58.

Example 280 6-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-3,4-dihydroquinolin-2(1H)-one

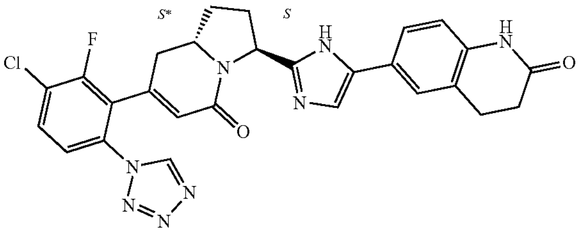

LC/MS: mass calculated for $C_{24}H_{20}ClF_2N_9O$: 253.14 measured: 545.1 $[M+H]^1$H NMR (300 MHz, DMSO-$d_6$) δ 11.71-12.26 (m, 1H), 10.05-10.11 (m, 1H), 9.85 (s, 1H), 7.98 (t, J=8.2 Hz, 1H), 7.71 (d, J=8.7 Hz, 1H), 7.50-7.55 (m, 1H), 7.43-7.50 (m, 1H), 7.32 (s, 1H), 6.82 (d, J=8.1 Hz, 1H), 5.69 (d, J=2.4 Hz, 1H), 4.93-5.03 (m, 1H), 4.01-4.16 (m, 1H), 3.40-3.52 (m, 1H), 2.91 (t, J=7.5 Hz, 2H), 2.19-2.49 (m, 5H), 1.97-2.10 (m, 1H), 1.62-1.82 (m, 1H). $^{19}F$ NMR (282 MHz, DMSO-$d_6$) δ −113.06, −218.29.

Example 281 6-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-3,4-dihydroquinolin-2(1H)-one

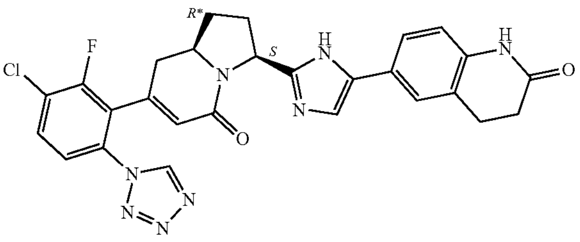

LC/MS: mass calculated for $C_{24}H_{20}ClF_2N_6O$: 253.14 measured: 545.1 $[M+H]^+$. $^1H$ NMR (300 MHz, DMSO-$d_6$) δ 12.17 (br, 1H), 10.07-10.12 (m, 1H), 9.85 (s, 1H), 7.91-8.03 (m, 1H), 7.72 (d, J=8.7 Hz, 1H), 7.45-7.59 (m, 2H), 7.38 (s, 1H), 6.85 (d, J=8.2 Hz, 1H), 5.68 (d, J=2.6 Hz, 1H), 5.02 (d, J=8.6 Hz, 1H), 3.65-3.77 (m, 1H), 2.87-2.97 (m, 2H), 2.71-2.87 (m, 1H), 2.51-2.57 (m, 2H), 2.45-2.48 (m, 1H), 1.93-2.25 (m, 4H). $^{19}F$ NMR (282 MHz, DMSO-$d_6$) δ −112.78, −218.42.

Example 282 (3S,8aR)-7-(3-Chloro-2-fluoro-6-(1H-tetrazol-1-yl)phenyl)-3-(5-(2-fluoro-6-(methylamino)pyridin-3-yl)-1H-imidazol-2-yl)-2,3,8,8a-tetrahydroindolizin-5(1H)-one

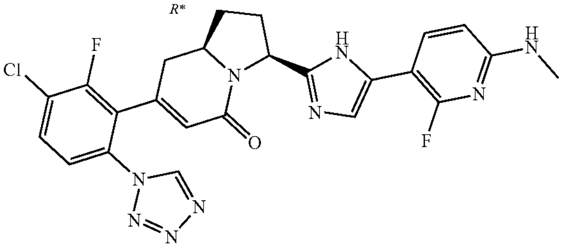

Step 1: 2-(2-fluoro-6-(methylamino)pyridin-3-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) in DMF (10 mL) was added cesium carbonate (120 mg, 0.37 mmol, 0.6 equiv.). The mixture was stirred at room temperature for 0.5 h. To the resulting mixture was added 2-bromo-1-(2-fluoro-6-(methylamino)pyridin-3-yl)ethan-1-one (152 mg, 0.62 mmol, 1.0 equiv.) and the mixture was maintained stirring for 1.5 h. The reaction was quenched with water (50 mL). The resulting mixture was extracted with ethyl acetate (3×50 mL). The organic layers were combined, dried over anhydrous sodium sulfate, filtered, and concentrated. The residue was purified by flash column chromatography on silica gel (0→30% MeOH/DCM) to yield 2-(2-fluoro-6-(methylamino)pyridin-3-yl)-2-oxoethyl (3S)-7-(6-amino-3-chloro-2-fluorophenyl)-5-oxo-1,2,3,5,8,8a-hexahydroindolizine-3-carboxylate as an yellow solid. LC/MS: mass calculated for $C_{23}H_{21}ClF_2N_4O_4$: 490.12, measured: 491.25 $[M+H]^+$.

Step 2: (3S)-7-(6-amino-3-chloro-2-fluorophenyl)-3-(5-(2-fluoro-6-(methylamino)pyridin-3-yl)-1H-imidazol-2-yl)-2,3,8,8a-tetrahydroindolizin-5(1H one To a solution of the 2-(2-fluoro-6-(methylamino)pyridin-3-yl)-2-oxoethyl (3S)-7-(6-amino-3-chloro-2-fluorophenyl)-5-oxo-1,2,3,5,8,8a-hexahydroindolizine-3-carboxylate (300 mg, 0.66 mmol) in toluene (10 mL) was added acetic acid (1 mL), followed by ammonium acetate (707 mg, 9.12 mmol). The resulting mixture was stirred at 100° C. for 2 h, then cooled to room temperature, and then concentrated. The residue was purified by silica gel chromatography (0→30% MeOH/DCM) to yield (3S)-7-(6-amino-3-chloro-2-fluorophenyl)-3-(5-(2-fluoro-6-(methylamino)pyridin-3-yl)-1H-imidazol-2-yl)-2,3,8,8a-tetrahydroindolizin-5(1H)-one as a yellow solid. LC/MS: mass calculated for $C_{23}H_{21}ClF_2N_6O$: 471.14, measured: 472.30 $[M+H]^+$.

Step 3: (3S,8aR)-7-(3-chloro-2-fluoro-6-(1H-tetrazol-1-yl)phenyl)-3-(5-(2-fluoro-6-(methylamino)pyridin-3-yl)-1H-imidazol-2-yl)-2,3,8,8a-tetrahydroindolizin-5(1H)-one To a solution of the (3S)-7-(6-amino-3-chloro-2-fluorophenyl)-3-(5-(2-fluoro-6-(methylamino)pyridin-3-yl)-1H-imidazol-2-yl)-2,3,8,8a-tetrahydroindolizin-5(1H)-one (200 mg, 0.42 mmol) in glacial acetic acid (5 mL) were added trimethoxymethane (1 mL) and azidotrimethylsilane (1 mL). The resulting mixture was stirred at 60° C. for 2 h and concentrated. The resulting residue was added to 2N HCl (aq.)/THF (v/v 1:1) (4 mL). The reaction mixture was stirred at 50° C. for 0.5 h and adjusted to pH 7.0 with $NaHCO_3$ (aq.), then concentrated under vacuum. The residue was purified by flash column chromatography on silica gel to yield the racemic product, which was further purified by prep-HPLC to yield the (3S,8aR)-7-(3-chloro-2-fluoro-6-(1H-tetrazol-1-yl)phenyl)-3-(5-(2-fluoro-6-(methylamino)pyridin-3-yl)-1H-imidazol-2-yl)-2,3,8,8a-tetrahydroindolizin-5(1H)-one as an white solid. LC/MS: mass calculated for $C_{24}H_{20}ClF_2N_9O$: 523.14, measured: 524.15 $[M+H]^+$. $^1H$ NMR (300 MHz, DMSO-$d_6$) δ 11.89-11.95 (m, 1H), 9.84 (s, 1H), 7.91-8.11 (m, 2H), 7.70 (d, J=8.7 Hz, 1H), 6.90-7.09 (m, 1H), 6.81 (d, J=5.1 Hz, 1H), 6.40 (d, J=8.3 Hz, 1H), 5.69 (d, J=2.5 Hz, 1H), 4.99 (t, J=7.2 Hz, 1H), 4.04-4.15 (m, 1H), 2.71-2.80 (m, 3H), 2.19-2.51 (m, 4H), 1.96-2.11 (m, 1H), 1.60-1.78 (m, 1H). $^{19}F$ NMR (282 MHz, DMSO-$d_6$) δ-70.36, −113.07, −218.48

Example 283 5-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)indolin-2-one

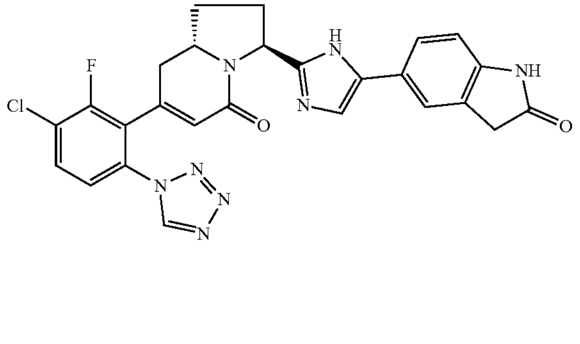 [SMILES: O=C1Cc2cc(-c3cnc([C@@H]4CC[C@H]5CC(c6c(-n7cnnn7)ccc(Cl)c6F)=CC(=O)N54)[nH]3)ccc2N1]

LC/MS: mass calculated for $C_{26}H_{20}ClFN_8O_2$: 530.14, measured: 531.05 $[M+H]^+$. $^1H$ NMR (400 MHz, Methanol-$d_4$) δ 9.59 (s, 1H), 7.84 (t, J=8.7 Hz, 1H), 7.53-7.61 (m, 3H), 7.38-7.42 (m, 1H), 6.96 (d, J=8.1 Hz, 1H), 5.76 (d, J=2.8 Hz, 1H), 5.13-5.18 (m, 1H), 4.22-4.35 (m, 1H), 3.60 (s, 2H), 2.52-2.74 (m, 3H), 2.39-2.46 (m, 1H), 2.09-2.23 (m, 1H), 1.79-1.94 (m, 1H). $^{19}F$ NMR (376 MHz, Methanol-$d_4$) δ −113.89.

Example 348: 5-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)indolin-2-one

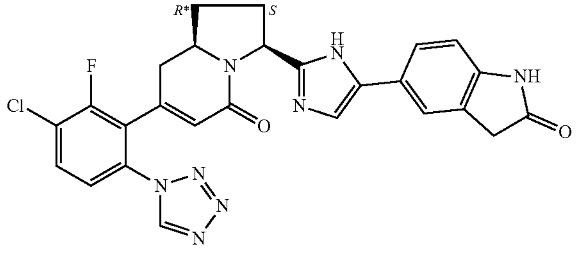

LC/MS: mass calculated for $C_{26}H_{20}ClFN_8O_2$: 530.14, measured: 531.05 $[M+H]^1H$ NMR (400 MHz, Methanol-$d_4$) δ 9.60 (s, 1H), 7.83 (t, J=8.7 Hz, 1H), 7.51-7.62 (m, 3H), 7.21 (s, 1H), 6.92 (d, J=8.1 Hz, 1H), 5.73 (d, J=2.8 Hz, 1H), 5.15 (d, J=9.0 Hz, 1H), 3.83-3.96 (m, 1H), 3.59 (s, 2H), 2.92-3.05 (m, 1H), 2.59-2.65 (m, 1H), 2.27-2.40 (m, 1H), 2.16-2.27 (m, 2H), 2.00-2.15 (m, 1H). $^{19}F$ NMR (376 MHz, Methanol-$d_4$) δ −113.31.

Example 285 (1 S,3S)-3-(4-(6-Amino-2-fluoropyridin-3-yl)-1H-imidazol-2-yl)-7-(3-chloro-2-fluoro-6-(1H-tetrazol-1-yl)phenyl)-1-methoxy-2,3,8,8a-tetrahydroindolizin-5(1H)-one

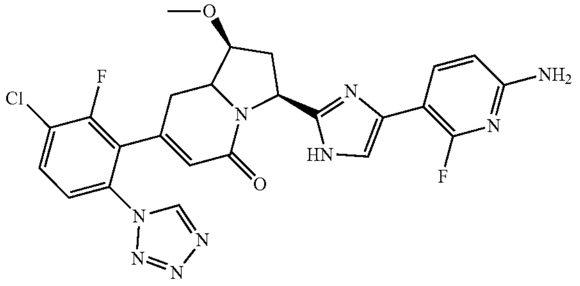 [SMILES: CO[C@H]1C[C@@H](c2nc(-c3ccc(N)nc3F)c[nH]2)N2C(=O)C=C(c3c(-n4cnnn4)ccc(Cl)c3F)CC12]

LC/MS: mass calculated for $C_{24}H_{20}ClF_2N_9O_2$:539.14, measured: 540.1 $[M+H]^+$. $^1H$ NMR (300 MHz, DMSO-$d_6$) (ppm) δ: 9.84 (s, 1H), 7.94-8.04 (m, 1H), 7.79-7.94 (m, 1H), 7.68-7.74 (m, 1H), 7.56 (s, 1H), 6.79 (br, 1H), 6.46 (d, J=8.3 Hz, 1H), 5.67-5.78 (m, 1H), 5.23 (d, J=10.0 Hz, 1H), 3.99-4.41 (m, 1H), 3.20-3.31 (m, 4H), 2.95-3.17 (m, 1H), 2.55-2.74 (m, 1H), 2.37-2.46 (m, 1H), 2.04-2.30 (m, 1H). $^{19}F$ NMR (282 MHz, DMSO-$d_6$) (ppm) δ: −69.23, −73.74, −112.72, −113.17.

Example 286 5-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1,3-dihydro-2H-benzo[d]imidazol-2-one

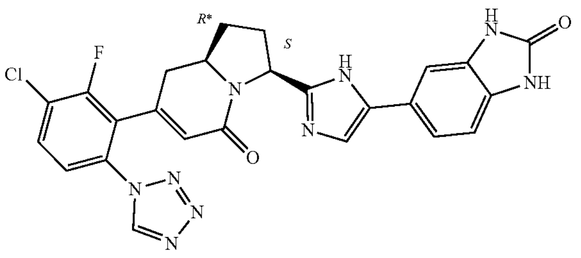

LC/MS: mass calculated For $C_{25}H_{19}ClFN_9O_2$: 531.13, measured: 532.10 $[M+H]^+$ $^1H$ NMR (400 MHz, Methanol-$d_4$) δ 9.59 (s, 1H), 7.83 (t, J=8.1 Hz, 1H), 7.52-7.59 (m, 1H), 7.34-7.43 (m, 2H), 7.21 (s, 1H), 7.05 (d, J=8.6 Hz, 1H), 5.74 (d, J=2.7 Hz, 1H), 5.04-5.15 (m, 1H), 4.30-4.41 (m, 1H), 2.45-2.71 (m, 3H), 2.33-2.45 (m, 1H), 2.12-2.25 (m, 1H), 1.75-1.89 (m, 1H). $^{19}F$ NMR (376 MHz, Methanol-$d_4$) δ −113.82.

Example 287 2-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-N-methylbenzamide

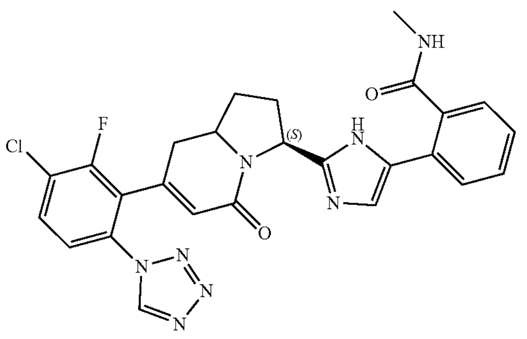

To a solution of 2-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)benzoic acid (50 mg, 0.096 mol) in DMF (2.0 mL) was added DIEA (40 mg), followed by addition of $CH_3NH_2$·HCl (130 mg, 1.932 mmol) and HATU (55 mg, 0.144 mmol). The mixture was stirred at room temperature for 3 h, diluted with water, and extracted with ethyl acetate (3×50 mL). The organic layers were combined, wash with brine three times, dried over anhydrous sodium sulfate, filtered, and concentrated under reduced pressure. The resulting residue was purified by reverse phase chromatography on C18 column (0~60% $CH_3CN/H_2O$ (0.05% TFA)) to yield the 2-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-4-yl)-N-methylbenzamide as a white solid.

LC/MS: mass calculated for $C_{26}H_{22}ClFN_8O_2$:532.2, measured: 533.20 $[M+H]^+$. $^1H$ NMR (300 MHz, Methanol-$d_4$) δ 9.60 (s, 1H), 7.80-7.90 (m, 1H), 7.46-7.74 (m, 5H), 7.38-7.43 (m, 1H), 5.77 (d, J=2.8 Hz, 1H), 5.26 (d, J=9.2 Hz, 1H), 3.87-4.38 (m, 1H), 2.93-3.09 (m, 1H), 2.87 (s, 3H), 2.63-2.79 (m, 1H), 2.04-2.53 (m, 1H), 2.21-2.40 (m, 2H), 1.92-2.16 (m, 1H). $^{19}F$ NMR (282 MHz, Methanol-$d_4$) δ −113.34, −113.91.

Example 288 2-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)-N,N-dimethylbenzamide

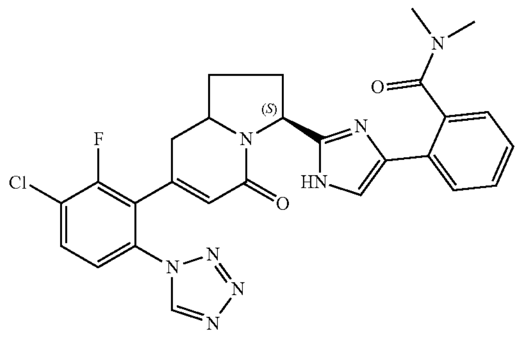

LC/MS: mass calculated for $C_{27}H_{24}ClFN_8O_2$:546.983, measured: 547.25 $[M+H]^+$. $^1H$ NMR (300 MHz, Methanol-$d_4$) δ 9.53 (s, 1H), 7.69-7.84 (m, 2H), 7.46-7.57 (m, 2H), 7.33 (t, J=7.5 Hz, 1H), 7.23 (d, J=7.6 Hz, 1H), 7.03 (s, 1H), 5.67 (s, 1H), 5.06-5.16 (m, 1H), 3.77-3.93 (m, 1H), 2.99-3.02 (m, 3H), 2.82-2.98 (m, 1H), 2.55-2.67 (m, 4H), 2.19-2.35 (m, 3H), 1.98-2.16 (m, 1H). $^{19}F$ NMR (282 MHz, Methanol-$d_4$) δ −113.37.

Example 289 (3S)-7-(3-Chloro-2-fluoro-6-(1H-tetrazol-1-yl)phenyl)-3-(4-(2-(dimethylamino)phenyl)-1H-imidazol-2-yl)-2,3,8,8a-tetrahydroindolizin-5(1H)-one

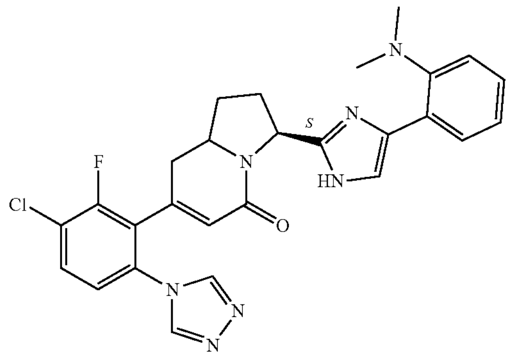

LC/MS: mass calculated for $C_{26}H_{24}ClFN_8O$: 518.17, measured: 519.1 $[M+H]^+$. $^1H$ NMR (300 MHz, DMSO-$d_6$) δ 11.72-12.08 (m, 1H), 9.82 (s, 1H), 7.91-8.08 (m, 2H), 7.66-7.76 (m, 1H), 7.49-7.58 (m, 1H), 7.02-7.25 (m, 3H), 5.66-5.79 (m, 1H), 5.00-5.15 (m, 1H), 3.69-4.17 (m, 1H), 2.59-2.82 (m, 5H), 1.97-2.50 (m, 6H), 1.66-0.89 (m, 1H). $^{19}F$ NMR (282 MHz, DMSO-$d_6$) δ −112.88, −113.05.

Example 290 2-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)benzamide

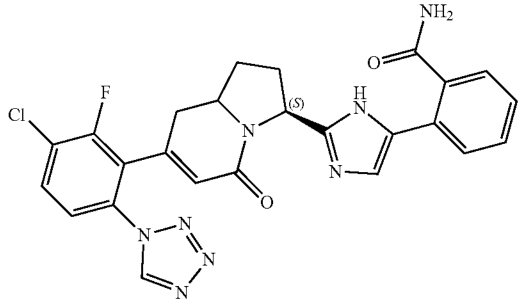

LC/MS: mass calculated for $C_{25}H_{20}ClFN_8O_2$: 518.93, measured: 519.10 $[M+H]^+$. $^1H$ NMR (300 MHz, Methanol-$d_4$) δ 9.59 (s, 1H), 7.79-7.90 (m, 1H), 7.70-7.78 (m, 1H), 7.52-7.71 (m, 6H), 5.78 (d, J=2.8 Hz, 1H), 5.31 (d, J=9.2 Hz, 1H), 3.91-4.05 (m, 1H), 2.85-3.04 (m, H), 2.69-2.77 (m, 1H), 2.47-2.63 (m, 1H), 2.24-2.41 (m, 2H), 1.94-2.09 (m, 1H). $^{19}F$ NMR (282 MHz, Methanol-$d_4$) δ −76.86, −113.49.

Example 291 (3S,8aS)-7-(3-Chloro-2-fluoro-6-(1H-tetrazol-1-yl)phenyl)-3-(5-(2-fluoro-6-(methylamino)pyridin-3-yl)-1H-imidazol-2-yl)-2,3,8,8a-tetrahydroindolizin-5(1H)-one

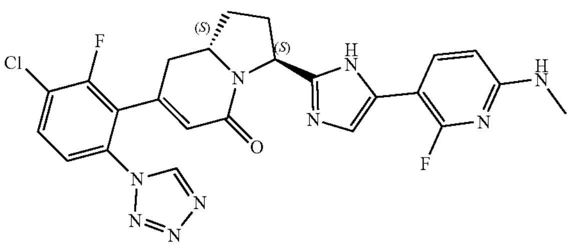

LC/MS: mass calculated for $C_{26}H_{22}ClFN_8O_3$: 523.14, measured: 524.25 $[M+H]^+$. $^1H$ NMR (400 MHz, Methanol-$d_4$) δ 9.58 (s, 1H), 7.99 (s, 1H), 7.82 (dd, J=8.7, 7.6 Hz, 1H), 7.55 (d, J=8.7 Hz, 1H), 7.12 (d, J=3.4 Hz, 1H), 6.42 (dd, J=8.4, 1.9 Hz, 1H), 5.73 (d, J=2.8 Hz, 1H), 5.12-5.18 (m, 1H), 3.83-3.94 (m, 1H), 2.94 (t, J=14.9 Hz, 1H), 2.88 (s, 3H), 2.59-2.65 (m, 1H), 2.26-2.37 (m, 1H), 2.17-2.39 (m, 2H), 1.99-2.11 (m, 1H). $^{19}F$ NMR (376 MHz, Methanol-$d_4$) δ −72.98, −113.30.

Example 292 5-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1,3-dihydro-2H-benzo[d]imidazol-2-one

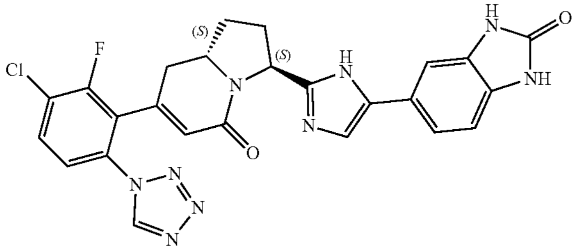

LC/MS: mass calculated For $C_2SH_{19}ClFN_9O_2$: 531.13, measured: 532.10 $[M+H]^+$. $^1H$ NMR (400 MHz, Methanol-$d_4$) δ 9.60 (s, 1H), 7.79-7.88 (m, 1H), 7.57 (d, J=8.7 Hz, 1H), 7.35-7.41 (m, 2H), 7.21 (s, 1H), 7.02-7.12 (m, 1H), 5.73 (d, J=2.8 Hz, 1H), 5.16 (d, J=8.9 Hz, 1H), 3.83-3.96 (m, 1H), 2.92-3.04 (m, 1H), 2.59-2.63 (m, 1H), 2.28-2.42 (m, 1H), 2.16-2.28 (m, 2H), 1.98-2.16 (m, 1H). $^{19}F$ NMR (376 MHz, Methanol-$d_4$) δ −113.82.

Example 293 N-(2-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl)methanesulfonamide

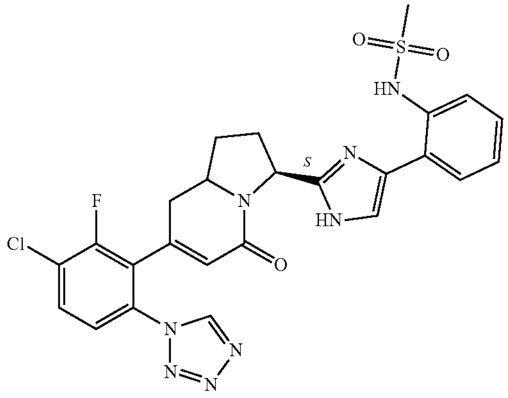

LC/MS: mass calculated for $C_{25}H_{22}ClFN_8O_3S$: 568.12, measured: 569.1 $[M+H]^+$. $^1H$ NMR (300 MHz, DMSO-$d_6$) δ12.50 (br, 1H), 9.83 (s, 1H), 7.98 (t, J=8.2 Hz, 1H), 7.67-7.76 (m, 3H), 7.49 (d, J=8.0 Hz, 1H), 7.13-7.37 (m, 2H), 5.66 (d, J=2.6 Hz, 1H), 5.06 (d, J=8.7 Hz, 1H), 3.61-3.74 (m, 1H), 2.75-2.94 (m, 4H), 2.53-2.57 (m, 1H), 1.94-2.31 (m, 4H). $^{19}F$ NMR (282 MHz, DMSO-$d_6$) δ −74.44, −112.61.

Example 294 (3S)-7-(3-Chloro-2-fluoro-6-(1H-tetrazol-1-yl)phenyl)-3-(5-(2-isopropoxyphenyl)-1H-imidazol-2-yl)-2,3,8,8a-tetrahydroindolizin-5(1H)-one

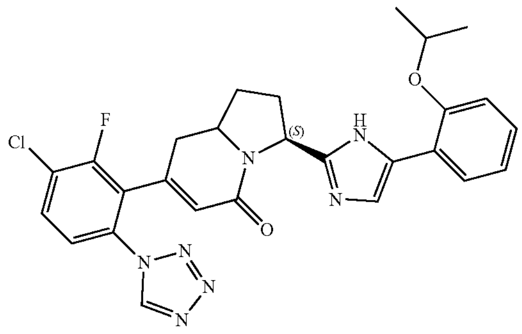

LC/MS: mass calculated for $C_{27}H_{25}ClFN_7O_2$:533.17, measured: 534.3 $[M+H]^+$. $^1H$ NMR (300 MHz, DMSO-$d_6$) δ (ppm): 9.84 (s, 1H), 8.00 (t, J=8.3 Hz, 1H), 7.65-7.79 (m, 3H), 7.36-7.48 (m, 1H), 7.22 (d, J=8.4 Hz, 1H), 7.10 (t, J=7.5 Hz, 1H), 5.75 (d, J=2.5 Hz, 1H), 5.20 (d, J=9.1 Hz, 1H), 4.72-4.86 (m, 1H), 3.69-3.83 (m, 1H), 2.89-3.07 (m, 1H), 2.55-2.60 (m, 1H), 2.36-2.46 (m, 1H), 1.87-2.21 (m, 3H), 1.34 (d, J=5.9 Hz, 6H). $^{19F}$ NMR (282 MHz, DMSO-$d_6$) δ (ppm): −73.86, −112.75.

Example 295 N-(2-(2-((3S,8aR*)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl)propionamide

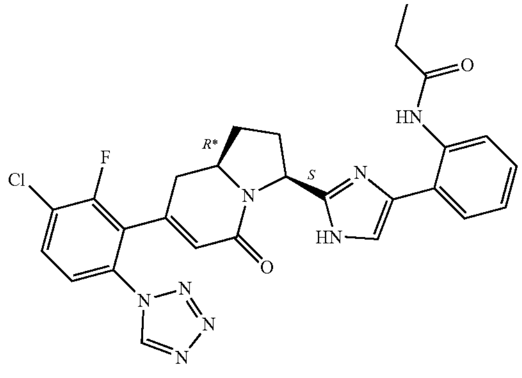

LC/MS: mass calculated for $C_{27}H_{24}ClFN_8O_2$:546.17, measured (ES, m/z): 547.20 $[M+H]^+$. $^1H$ NMR (300 MHz, DMSO-$d_6$) δ 12.26 (s, 1H), 12.15 (s, 1H), 9.83 (s, 1H), 8.44 (d, J=8.3 Hz, 1H), 7.92-8.03 (m, 1H), 7.63-7.76 (m, 2H), 7.59 (s, 1H), 7.17 (t, J=8.0 Hz, 1H), 7.03 (t, J=7.5 Hz, 1H), 5.69 (d, J=2.4 Hz, 1H), 5.05 (d, J=8.8 Hz, 1H), 3.66-3.81 (m, 1H), 2.52-2.77 (m, 2H), 1.88-2.43 (m, 6H), 1.01-1.16 (m, 3H). $^{19}F$ NMR (282 MHz, Methanol-$d_4$) δ 76.95, 113.38.

Example 296 N-(2-(24(3S,8aS*)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl)propionamide

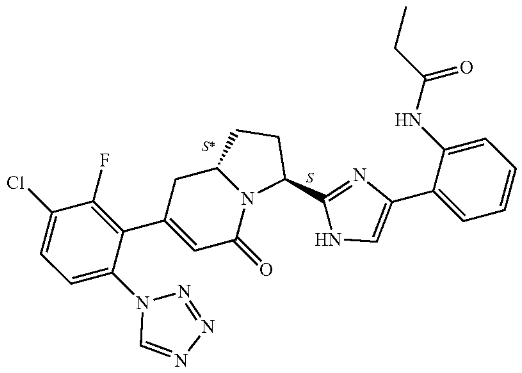

LC/MS: mass calculated for $C_{27}H_{24}ClFN_8O_2$: 546.17, measured (ES, m/z): 547.15 $[M+H]^+$. $^1H$ NMR (300 MHz, Chloroform-d) δ 8.93 (s, 1H), 8.47 (br, 1H), 7.62-7.74 (m, 1H), 7.49 (d, J=7.7 Hz, 1H), 7.30-7.36 (m, 2H), 7.25 (d, J=7.7 Hz, 1H), 7.10 (t, J=7.8 Hz, 1H), 5.75 (s, 1H), 5.29 (t, J=7.8 Hz, 1H), 4.01-4.21 (m, 1H), 2.75-2.93 (m, 1H), 2.40-2.64 (m, 6H), 1.73-1.87 (m, 1H), 1.24-1.35 (m, 4H). $^{19}F$ NMR (282 MHz, Methanol-$d_4$) δ−76.96, −113.92.

Example 297 6-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1H-benzo[d][1,3]oxazin-2(4H)-one

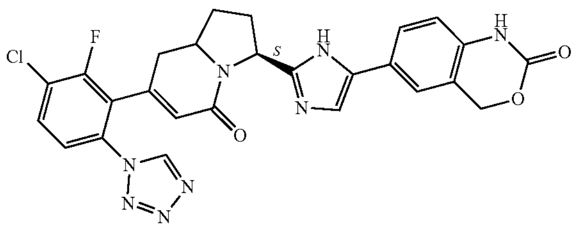

LC/MS: mass calculated for $C_{28}H_{20}ClFN_8O_3$: 546.13, measured (ES, m/z): 547.05$[M+H]^+$. $^1H$ NMR (300 MHz, Methanol-$d_4$) δ 9.60 (s, 1H), 7.80-7.93 (m, 1H), 7.70-7.85 (m, 1H), 7.50-7.70 (m, 3H), 7.04 (d, J=8.3 Hz, 1H), 5.73-5.81 (m, 1H), 5.37-5.44 (m, 2H), 5.20-5.36 (m, 1H), 3.95-4.01 (m, 1H), 2.92-3.07 (m, 1H), 2.67-2.82 (m, 2H), 2.45-2.62 (m, 1H), 2.21-2.43 (m, 1H), 1.96-2.13 (m, 1H). $^{19}F$ NMR (282 MHz, Methanol-$d_4$) δ −77.06, −113.49, −113.87.

Example 298 N-(2-(2-((3S,8aR*)-7-(3-Chloro-2-fluoro-6-(1H-tetrazol-1-yl)phenyl)-5-oxo-1,2,3,5,8,8a-hexahydroindolizin-3-yl)-1-methyl-1H-imidazol-4-yl)phenyl)cyclopropanecarboxamide

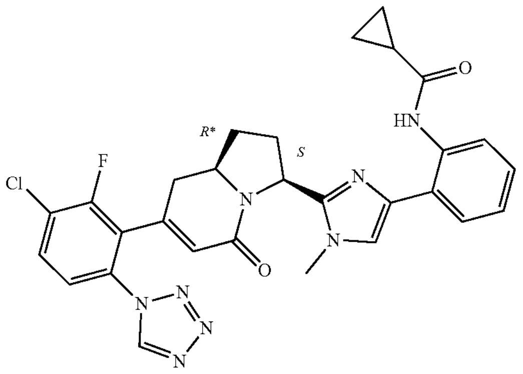

LC/MS: mass calculated for $C_{29}H_{26}ClFN_8O_2$: 572.19, measured (ES, m/z): 573.15 $[M+H]^+$. $^1H$ NMR (300 MHz, DMSO-$d_6$) δ 9.83 (s, 1H), 8.01-8.05 (m, 1H), 7.97 (t, J=8.2 Hz, 1H), 7.67-7.77 (m, 2H), 7.50 (d, J=7.6 Hz, 1H), 7.30-7.40 (m, 1H), 7.13-7.22 (m, 1H), 5.65 (d, J=2.3 Hz, 1H), 5.28 (d, J=9.3 Hz, 1H), 3.88 (s, 3H), 3.67-3.82 (m, 1H), 2.70-2.88 (m, 1H), 2.56-2.66 (m, 1H), 2.28-2.42 (m, 1H), 1.97-2.26 (m, 3H), 1.62-1.74 (m, 1H), 0.71-0.82 (m, 4H). $^{19}F$ NMR (282 MHz, DMSO-$d_6$) δ −74.72, −112.66.

Example 299 6-(2-((3S,8aS*)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1-methyl-1H-benzo[d]imidazol-2(3H)-one

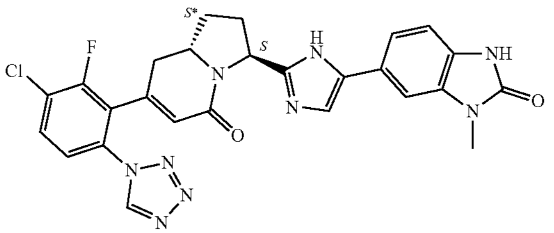

LC/MS: mass calculated for $C_{26}H_{21}ClFN_9O_2$: 545.15, measured (ES, m/z): 546.30$[M+H]^+$. $^1H$ NMR (400 MHz, DMSO-$d_6$) δ 10.88 (br, 1H), 9.83 (s, 1H), 7.96 (t, J=8.2 Hz, 1H), 7.70 (dd, J=8.7, 1.5 Hz, 1H), 7.33-7.42 (m, 3H), 6.92-7.04 (m, 1H), 5.70 (d, J=2.5 Hz, 1H), 4.97-5.07 (m, 1H), 4.06-4.20 (m, 1H), 3.31 (s, 3H), 2.16-2.43 (m, 3H), 1.95-2.08 (m, 2H), 1.68-1.80 (m, 1H). $^{19}F$ NMR (376 MHz, DMSO-$d_6$) δ −73.41, −113.07.

Example 300 6-(2-((3S,8aR*)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1-methyl-1H-benzo[d]imidazol-2(3H)-one

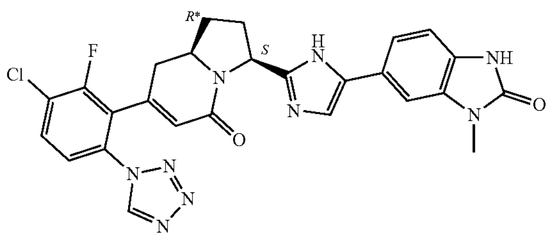

Step 1: 2-(2-fluoro-6-(methylamino)pyridin-3-yl)-2-oxoethyl (3S)-7-(6-amino-3-chloro-2-fluorophenyl)-5-oxo-1,2,3,5,8,8a-hexahydroindolizine-3-carboxylate Bromoacetic acid (1.0 g, 7.42 mmol, 1.1 equiv.) was added in portions to a stirred mixture of 1-methyl-1,3-dihydro-2H-benzo[d]imidazol-2-one (1.0 g, 14.91 mmol, 1.0 equiv.) in polyphosphoric acid (14 g) at room temperature under nitrogen atmosphere. The resulting mixture was stirred at 115° C. for 1.5 h. Upon the completion of the reaction, the mixture was poured into ice/water and stirred for 1 h. The precipitated solids were collected by filtration and washed with water (3×20 mL) and dried in vacuo to yield 6-(2-bromoacetyl)-1-methyl-1,3-dihydro-2H-benzo[d]imidazol-2-one (include 5-(2-bromoacetyl)-1-methyl-1,3-dihydro-2H-benzo[d]imidazol-2-one, about 40%) as a gray solid. LC/MS: mass calculated for $C_{10}H_9BrN_2O_2$: 267.98, measured: 269.10 [M+H], 271.10 $[M+H+2]^+$.

Step 2: 2-(3-methyl-2-oxo-2,3-dihydro-1H-benzo[d]imidazol-5-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (150 mg, 0.46 mmol, 1.0 equiv.) in acetonitrile (8 mL) was added potassium carbonate (127.7 mg, 0.92 mmol, 2.0 equiv.), followed by 6-(2-bromoacetyl)-1-methyl-1,3-dihydro-2H-benzo[d]imidazol-2-one (248 mg, 0.92 mmol, 2.0 equiv.) and the reaction mixture was stirred for 1.5 h. The resulting mixture was then diluted with water (20 mL) and extracted with EtOAc (3×20 mL). The combined organic layers were washed with brine (3×20 mL), dried over anhydrous $Na_2SO_4$. After filtration, the filtrate was concentrated under reduced pressure. The residue was purified by flash column chromatography on silica gel (0→25% EA/PE) to yield 2-(3-methyl-2-oxo-2,3-dihydro-1H-benzo[d]imidazol-5-yl)-2-oxoethyl (3S)-7-(6-amino-3-chloro-2-fluorophenyl)-5-oxo-1,2,3,5,8,8a-hexahydroindolizine-3-carboxylate (include 2-(1-methyl-2-oxo-2,3-dihydro-1H-benzo[d]imidazol-5-yl)-2-oxoethyl (3S)-7-(6-amino-3-chloro-2-fluorophenyl)-5-oxo-1,2,3,5,8,8a-hexahydroindolizine-3-carboxylate, as a yellow solid. LC/MS: mass calculated for $C_{25}H_{22}ClFN_4O_5$: 512.13, measured: 513.25 $[M+H]^+$.

Step 3: 6-(2-((3S)-7-(6-amino-3-chloro-2-fluorophenyl)-5-oxo-1,2,3,5,8,8a-hexahydroindolizin-3-yl)-1H-imidazol-5-yl)-1-methyl-1,3-dihydro-2H-benzo[d]imidazol-2-one To a stirred solution of 2-(3-methyl-2-oxo-2,3-dihydro-1H-benzo[d]imidazol-5-yl)-2-oxoethyl (3S)-7-(6-amino-3-chloro-2-fluorophenyl)-5-oxo-1,2,3,5,8,8a-hexahydroindolizine-3-carboxylate (149 mg, 0.29 mmol, 1.0 equiv.) in HOAc (1.5 mL) and toluene (15 mL) was added ammonium acetate (193 mg, 2.51 mmol, 5.0 equiv.) in portions at room temperature. The resulting mixture was stirred for 2 h at 90° C. and then concentrated under reduced pressure. The residue was purified by flash column chromatography on silica gel (0→20% MeOH/DCM) to yield 6-(2-((3S)-7-(6-amino-3-chloro-2-fluorophenyl)-5-oxo-1,2,3,5,8,8a-hexahydroindolizin-3-yl)-1H-imidazol-5-yl)-1-methyl-1,3-dihydro-2H-benzo[d]imidazol-2-one (include 5-(2-((3S)-7-(6-amino-3-chloro-2-fluorophenyl)-5-oxo-1,2,3,5,8,8a-hexahydroindolizin-3-yl)-1H-imidazol-5-yl)-1-methyl-1,3-dihydro-2H-benzo[d]imidazol-2-one) as a brown solid. LC/MS: mass calculated for $C_{25}H_{22}ClFN_6O_2$: 492.15, measured: 493.10 $[M+H]^+$.

Step 4: 6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-1-methyl-1,3-dihydro-2H-benzo[d]imidazol-2-one To a stirred mixture of 6-(2-((3S)-7-(6-amino-3-chloro-2-fluorophenyl)-5-oxo-1,2,3,5,8,8a-hexahydroindolizin-3-yl)-1H-imidazol-5-yl)-1-methyl-1,3-dihydro-2H-benzo[d]imidazol-2-one (50 mg, 0.10 mmol, 1.0 equiv.) and 5-(2-((3S)-7-(6-amino-3-chloro-2-fluorophenyl)-5-oxo-1,2,3,5,8,8a-hexahydroindolizin-3-yl)-1H-imidazol-5-yl)-1-methyl-1,3-dihydro-2H-benzo[d]imidazol-2-one (50 mg, 0.101 mmol, 1.00 equiv) in acetic acid (5.00 mL) were added trimethylorthoformate (0.5 mL) and $TMSN_3$ (0.5 mL) at room temperature. The resulting mixture was stirred for 2 h at 60° C., then concentrated under vacuum. The residue was purified by prep-HPLC with Mobile Phase A: Water (0.05% TFA), Mobile Phase B: ACN to yield a residue, which was purified by chiral-HPLC with MTBE (0.1% DEA): EtOH=50:50 to yield 6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-1-methyl-1,3-dihydro-2H-benzo[d]imidazol-2-one as a white solid.

LC/MS: mass calculated for $C_{26}H_{21}ClFN_9O_2$: 545.15, measured (ES, m/z): 546.30 $[M+H]^+$. $^1H$ NMR (400 MHz, DMSO-$d_6$) δ 11.71 (br, 1H), 10.76 (s, 1H), 9.82 (s, 1H), 7.96 (t, J=8.6, 7.8 Hz, 1H), 7.70 (dd, J=8.7, 1.4 Hz, 1H), 7.39 (d, J=14.1 Hz, 3H), 6.92 (d, J=8.1 Hz, 1H), 5.66 (d, J=2.6 Hz, 1H), 4.98 (d, J=8.6 Hz, 1H), 3.64-3.72 (m, 1H), 3.30 (s, 3H), 2.72-2.85 (m, 1H), 2.51-2.54 (m, 1H), 2.03-2.23 (m, 2H), 1.88-2.00 (m, 2H). $^{19}F$ NMR (376 MHz, DMSO-$d_6$) δ−73.40, −112.82.

Example 301 Methyl 2-(2-((3S,8aR*)-7-(3-chloro-2-fluoro-6-(1H-tetrazol-1-yl)phenyl)-5-oxo-1,2,3,5,8,8a-hexahydroindolizin-3-yl)-1H-imidazol-4-yl)phenylcarbamate

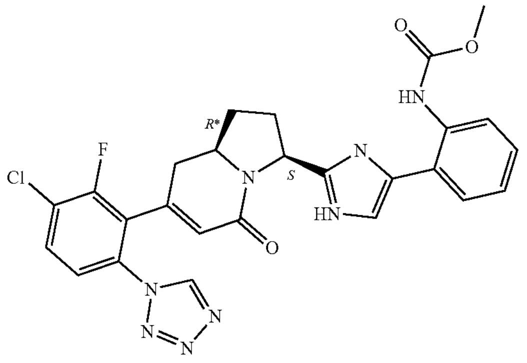

LC/MS: mass calculated for $C_{26}H_{22}ClFN_8O_3$: 548.15, measured (ES, m/z): 549.15$[M+H]^+$. 1H NMR (300 MHz, Methanol-$d_4$) δ 9.57 (s, 1H), 7.79-7.87 (m, 1H), 7.69-7.77 (m, 1H), 7.41-7.60 (m, 4H), 7.29 (t, J=7.5 Hz, 1H), 5.77 (d, J=2.6 Hz, 1H), 5.27 (d, J=9.7 Hz, 1H), 3.90-4.02 (m, 1H), 3.70 (s, 3H), 2.86-3.03 (m, 1H), 2.64-2.76 (m, 1H), 2.45-2.55 (m, 1H), 2.18-2.38 (m, 2H), 1.93-2.06 (m, 1H). $^{19}F$ NMR (282 MHz, Methanol-$d_4$) δ −77.23, 113.53.

Example 302 Methyl 2-(24(3S,8aS*)-7-(3-chloro-2-fluoro-6-(1H-tetrazol-1-yl)phenyl)-5-oxo-1,2,3,5,8,8a-hexahydroindolizin-3-yl)-1H-imidazol-4-yl)phenylcarbamate

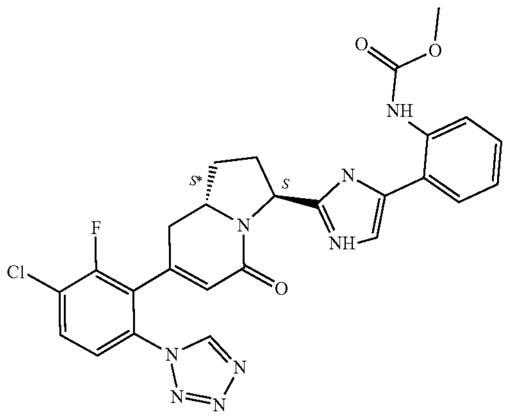

LC/MS: mass calculated for $C_{26}H_{22}ClFN_8O_3$: 548.15, measured (ES, m/z): 549.15$[M+H]^+$. 1H NMR (300 MHz, Methanol-$d_4$) δ 9.57 (s, 1H), 7.79-7.87 (m, 1H), Hz, 1H), 7.70 (d, J=8.1 Hz, 1H), 7.41-7.60 (m, 4H), 7.29 (t, J=7.5 Hz, 1H), 5.77 (d, J=2.6 Hz, 1H), 5.18-5.30 (m, 1H), 4.25-4.33 (m, 1H), 3.70 (s, 3H), 2.56-2.75 (m, 3H), 2.40-2.52 (m, 1H), 2.05-2.20 (m, 1H), 1.85-1.98 (m, 1H). $^{19}F$ NMR (282 MHz, Methanol-$d_4$) δ −77.09, −113.95.

Example 303 5-(24(3S,8aR*)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1-methyl-1H-benzo[d]imidazol-2(3H)-one

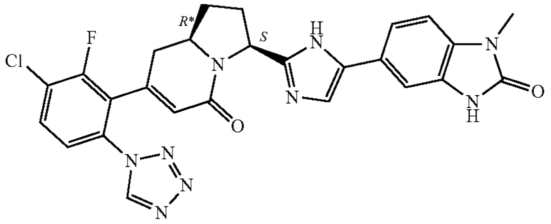

LC/MS: mass calculated for $C_{26}H_{21}ClFN_9O_2$: 545.15, measured (ES, m/z): 546.30 $[M+H]^+$. $^1H$ NMR (400 MHz, DMSO-$d_6$) δ11.91 (br, 1H), 10.84 (s, 1H), 9.82 (s, 1H), 7.96 (t, J=8.2 Hz, 1H), 7.69 (dd, J=8.7, 1.5 Hz, 1H), 7.31-7.39 (m, 3H), 7.05 (d, J=8.1 Hz, 1H), 5.68 (d, J=2.7 Hz, 1H), 4.97 (t, J=7.4 Hz, 1H), 4.04-4.13 (m, 1H), 3.26 (s, 3H), 2.20-2.44 (m, 4H), 1.98-2.07 (m, 1H), 1.64-1.74 (m, 1H). $^{19}F$ NMR (376 MHz, DMSO-$d_6$) δ −73.41, −113.04.

Example 304 N-(2-(2-((3S,8aS*)-7-(3-Chloro-2-fluoro-6-(1H-tetrazol-1-yl)phenyl)-5-oxo-1,2,3,5,8,8a-hexahydroindolizin-3-yl)-1-methyl-1H-imidazol-4-yl)phenyl)cyclopropanecarboxamide

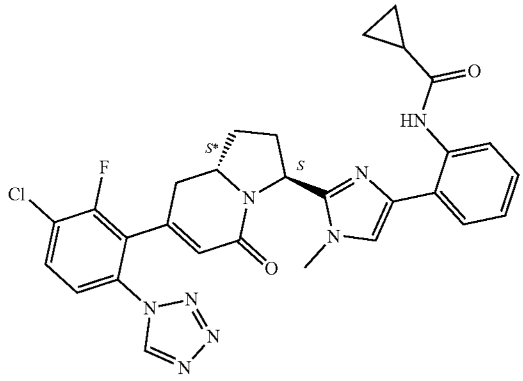

LC/MS: mass calculated for $C_{29}H_{26}ClFN_8O_2$: 572.19, measured (ES, m/z): 573.20 $[M+H]^+$. $^1H$ NMR (300 MHz, DMSO-$d_6$) δ 9.82 (s, 1H), 8.17-8.34 (m, 1H), 7.98 (t, J=8.2 Hz, 1H), 7.63-7.75 (m, 2H), 7.55 (d, J=7.7 Hz, 1H), 7.18-7.32 (m, 1H), 7.03-7.12 (m, 1H), 5.69 (s, 1H), 5.14-5.24 (m, 1H), 4.00-4.19 (m, 1H), 3.81 (s, 3H), 2.52-2.67 (m, 2H), 2.25-2.47 (m, 2H), 2.04-2.20 (m, 1H), 1.66-1.85 (m, 1H), 1.51-1.63 (m, 1H), 0.79-0.87 (m, 4H). $^{19}F$ NMR (282 MHz, DMSO-$d_6$) δ −74.20, −113.42.

Example 305 N-(2-(2-((3S,8aR*)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl)isobutyramide

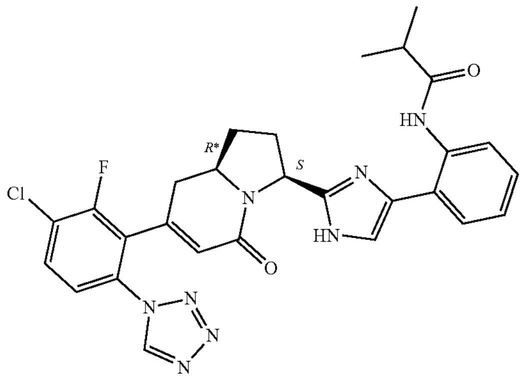

LC/MS: mass calculated for $C_{28}H_{26}ClFN_8O_2$: 560.19, measured (ES, m/z): 561.1 $[M+H]^+$. $^1H$ NMR (400 MHz, DMSO-$d_6$) δ 12.46 (s, 1H), 12.40 (s, 1H), 9.81 (s, 1H), 8.41-8.49 (m, 1H), 7.96 (t, J=8.2 Hz, 1H), 7.61-7.70 (m, 3H), 7.10-7.17 (m, 1H), 6.96-7.03 (m, 1H), 5.68 (d, J=2.8 Hz, 1H), 4.95-5.03 (m, 1H), 4.06-4.14 (m, 1H), 2.49-2.61 (m, 2H), 2.33-2.46 (m, 2H), 2.19-2.28 (m, 1H), 1.97-2.06 (m, 1H), 1.69-1.82 (m, 1H), 1.14 (t, J=6.5 Hz, 6H). $^{19}F$ NMR (376 MHz, DMSO-$d_6$) δ −73.49, −113.14.

Example 306 N-(2-(24(3S,8aS*)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl)acetamide

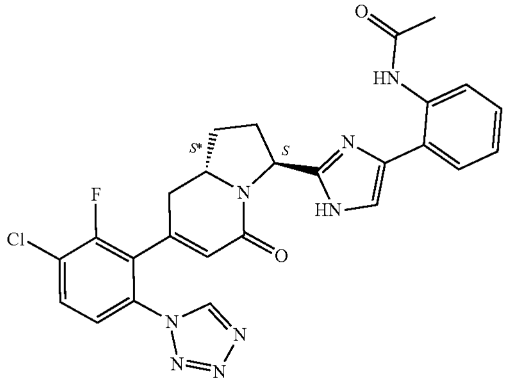

LC/MS: mass calculated for $C_{26}H_{22}ClFN_8O_2$:532.15, measured (ES, m/z): 533.10 $[M+H]^+$. $^1H$ NMR (300 MHz, DMSO-$d_6$) δ 12.30 (s, 1H), 12.15 (s, 1H), 9.84 (s, 1H), 8.35-8.42 (m, 1H), 7.98 (t, J=8.2 Hz, 1H), 7.72 (dd, J=8.7, 1.5 Hz, 1H), 7.58-7.70 (m, 2H), 7.19 (s, 1H), 7.05 (s, 1H), 5.67-5.75 (m, 1H), 5.07 (d, J=8.7 Hz, 1H), 3.66-3.80 (m, 1H), 2.51-2.68 (m, 2H), 1.85-2.34 (m, 7H). 19F NMR (282 MHz, DMSO-$d_6$) δ −74.16, −113.38.

Example 307 N-(2-(2-((3S,8aR)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl)cyclopropanecarboxamide

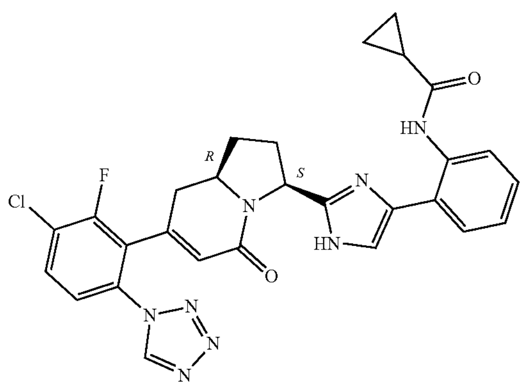

Step 1: 2-(2-nitrophenyl)-2-oxoethyl (3S)-7-(6-amino-3-chloro-2-fluorophenyl)-5-oxo-1,2,3,5,8,8a-hexahydroindolizine-3-carboxylate To a solution of the (3S)-7-(6-amino-3-chloro-2-fluorophenyl)-5-oxo-1,2,3,5,8,8a-hexahydroindolizine-3-carboxylic acid (200 mg, 0.62 mmol, 1.0 equiv.) in $CH_3CN$ (10 mL) was added 2-bromo-1-(2-nitrophenyl)ethan-1-one (158 mg, 0.62 mmol, 1.0 equiv.), followed by $K_2CO_3$ (196 mg, 1.42 mmol, 2.3 equiv.). The resulting mixture was stirred at room temperature. for 2 h, then was quenched with water and extracted with EA. The combined organic layer was washed with brine, dried over $Na_2SO_4$. The solids were filtered out. The resulting organic phase was concentrated under vacuum. The residue was purified by flash column chromatography on silica gel to yield 2-(2-nitrophenyl)-2-oxoethyl (3S)-7-(6-amino-3-chloro-2-fluorophenyl)-5-oxo-1,2,3,5,8,8a-hexahydroindolizine-3-carboxylate as a yellow solid.

Step 2: (3S)-7-(6-amino-3-chloro-2-fluorophenyl)-3-(4-(2-nitrophenyl)-1H-imidazol-2-yl)-2,3,8,8a-tetrahydroindolizin-5(1H)-one To a solution of the 2-(2-nitrophenyl)-2-oxoethyl (3S)-7-(6-amino-3-chloro-2-fluorophenyl)-5-oxo-1,2,3,5,8,8a-hexahydroindolizine-3-carboxylate (150 mg, 0.31 mmol, 1.0 equiv.) in toluene (10 mL) were added ammonium acetate (264 mg, 3.07 mmol, 10.0 equiv.) and HOAc (0.1 mL). The resulting mixture stirred at 110° C. for 2 h, then concentrated under vacuum. The residue was purified by silica gel chromatography (0→10% MeOH/DCM) to yield the (3S)-7-(6-amino-3-chloro-2-fluorophenyl)-3-(4-(2-nitrophenyl)-1H-imidazol-2-yl)-2,3,8,8a-tetrahydroindolizin-5(1H)-one as a yellow solid.

Step 3: (3S)-7-(3-chloro-2-fluoro-6-(1H-tetrazol-1-yl)phenyl)-3-(4-(2-nitrophenyl)-1H-imidazol-2-yl)-2,3,8,8a-tetrahydroindolizin-5(1H)-one To a solution of the (3S)-7-(6-amino-3-chloro-2-fluorophenyl)-3-(4-(2-nitrophenyl)-1H-imidazol-2-yl)-2,3,8,8a-tetrahydroindolizin-5(1H)-one (1.0 g, 2.14 mmol, 1.0 equiv.) in HOAc (30 mL) were added trimethoxymethane (2 mL) and azidotrimethylsilane (2 mL). The resulting mixture stirred at 60° C. for 2 h, then concentrated under vacuum. The residue was purified by flash column chromatography on silica gel (0→10% MeOH/DCM) to yield (3S)-7-(3-chloro-2-fluoro-6-(1H-tetrazol-1-yl)phenyl)-3-(4-(2-nitrophenyl)-1H-imidazol-2-yl)-2,3,8,8a-tetrahydroindolizin-5(1H)-one as a yellow solid.

Step 4: (3S)-3-(4-(2-aminophenyl)-1H-imidazol-2-yl)-7-(3-chloro-2-fluoro-6-(1H-tetrazol-1-yl)phenyl)-2,3,8,8a-tetrahydroindolizin-5(1H)-one Pd/C (50 mg) was added to a solution of the (3S)-7-(3-chloro-2-fluoro-6-(1H-tetrazol-1-yl)phenyl)-3-(4-(2-nitrophenyl)-1H-imidazol-2-yl)-2,3,8,8a-tetrahydroindolizin-5(1H)-one (220 mg, 0.42 mmol, 1.0 equiv.) in methanol (8 mL) and chlorobenzene (4 mL). The mixture was evacuated, filled with hydrogen and this process repeated three times. The resulting mixture was stirred 15 min at 25° C. LCMS showed the desired product was generated. Water was added and the mixture was extracted with EA. The organic layers were combined, dried over anhydrous sodium sulfate, filtered and concentrated to yield (3S)-3-(4-(2-aminophenyl)-1H-imidazol-2-yl)-7-(3-chloro-2-fluoro-6-(1H-tetrazol-1-yl)phenyl)-2,3,8,8a-tetrahydroindolizin-5(1H)-one as an yellow solid. LC/MS: mass calculated for C24H20ClFN8O: 490.14, measured: 491.10 $[M+H]^+$.

Step 5: N-(2-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)phenyl)cyclopropanecarboxamide To a solution of the (3S)-3-(4-(2-aminophenyl)-1H-imidazol-2-yl)-7-(3-chloro-2-fluoro-6-(1H-tetrazol-1-yl)phenyl)-2,3,8,8a-tetrahydroindolizin-5(1H)-one (150 mg, 0.31 mmol, 1.0 equiv.) in pyridine (5 mL) was added cyclopropanecarboxylic acid (131 mg, 1.53 mmol, 5.0 equiv.), followed by EDCl (95 mg, 0.61 mmol, 2.0 equiv.). The resulting mixture was stirred room temperature overnight, and concentrated. The residue was purified by HPLC and SFC to yield N-(2-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)phenyl)cyclopropanecarboxamide as a white solid.

LC/MS: mass calculated for $C_{28}H_{24}ClFN_8O_2$: 558.17, measured (ES, m/z): 559.10 $[M+H]^+$. $^1H$ NMR (300 MHz, DMSO-$d_6$) δ 12.34-12.78 (m, 2H), 9.83 (s, 1H), 8.29-8.49 (m, 1H), 7.92-8.04 (m, 1H), 7.71 (d, J=8.7 Hz, 1H), 7.60-7.69 (m, 2H), 6.97-7.25 (m, 2H), 5.71 (d, J=2.5 Hz, 1H), 5.07 (t, J=7.4 Hz, 1H), 4.06-4.16 (m, 1H), 2.44-2.62 (m, 2H), 2.20-2.43 (m, 2H), 1.95-2.11 (m, 1H), 1.54-1.85 (m, 2H), 0.78-0.88 (m, 4H). $^{19}F$ NMR (282 MHz, DMSO-$d_6$) δ −73.54, −74.98, −113.30.

Example 308 (3S,8aS*)-3-(4-(2-Aminophenyl)-1H-imidazol-2-yl)-7-(3-chloro-2-fluoro-6-(1H-tetrazol-1-yl)phenyl)-2,3,8,8a-tetrahydroindolizin-5(1H)-one

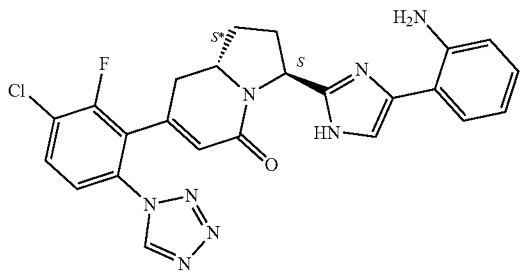

LC/MS: mass calculated for $C_{24}H_{20}ClFN_8O$: 490.14, measured (ES, m/z): 491.10 $[M+H]^+$. $^1H$ NMR (400 MHz, DMSO-$d_6$) δ 12.05 (s, 1H), 9.84 (s, 1H), 7.91-7.99 (m, 1H), 7.69 (dd, J=8.7, 1.5 Hz, 1H), 7.28-7.42 (m, 2H), 6.82-6.91 (m, 1H), 6.62 (dd, J=8.1, 1.3 Hz, 1H), 6.42-6.58 (m, 1H), 6.17 (s, 2H), 5.67 (d, J=2.7 Hz, 1H), 5.00 (t, J=7.1 Hz, 1H), 3.99-4.10 (m, 1H), 2.29-2.45 (m, 3H), 2.17-2.28 (m, 1H), 1.93-2.07 (m, 1H), 1.65-1.76 (m, 1H). $^{19}F$ NMR (376 MHz, DMSO-$d_6$) δ −73.40, −113.08.

Example 309 6-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)benzo[d]oxazol-2(3H)-one

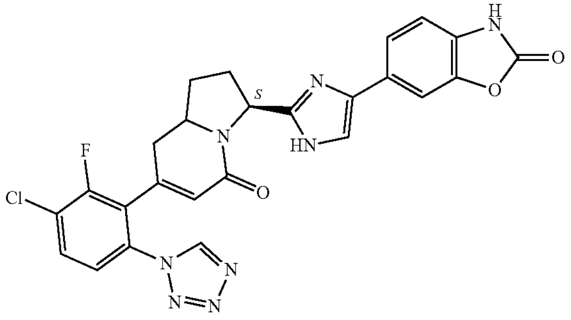

LC/MS: mass calculated for $C_{25}H_{18}ClFN_8O_3$: 532.12, measured (ES, m/z): 533.10 $[M+H]^+$. $^1H$ NMR (300 MHz, Methanol-$d_4$) δ 9.60 (s, 1H), 7.82-7.92 (m, 1H), 7.74-7.80 (m, 1H), 7.50-7.66 (m, 3H), 7.18-7.27 (m, 1H), 5.75-5.80 (m, 1H), 5.21-5.34 (m, 1H), 3.90-4.43 (m, 1H), 2.92-3.09 (m, 1H), 2.27-2.80 (m, 4H), 1.92-2.14 (m, 1H). $^{19}F$ NMR (282 MHz, Methanol-$d_4$) δ −76.91, −113.44, −113.92.

Example 310 (3S,8aR*)-3-(4-(2-Aminophenyl)-1H-imidazol-2-yl)-7-(3-chloro-2-fluoro-6-(1H-tetrazol-1-yl)phenyl)-2,3,8,8a-tetrahydroindolizin-5(1H)-one

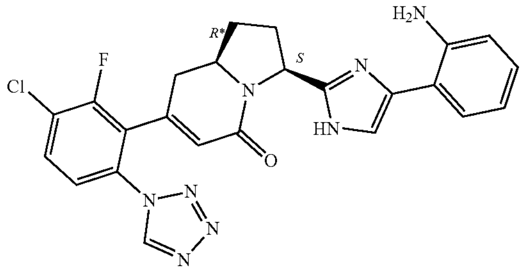

LC/MS: mass calculated for $C_{24}H_{20}ClFN_8O$: 490.14, measured (ES, m/z): 491.10 $[M+H]^+$. $^1H$ NMR (400 MHz, DMSO-$d_6$) δ 11.95 (s, 1H), 9.83 (s, 1H), 7.95 (t, J=8.2 Hz, 1H), 7.66-7.73 (m, 1H), 7.33-7.40 (m, 1H), 7.29-7.34 (m, 1H), 6.83-6.91 (m, 1H), 6.60-6.67 (m, 1H), 6.43-6.56 (m, 1H), 6.22 (s, 2H), 5.65 (d, J=2.6 Hz, 1H), 4.99 (d, J=8.6 Hz, 1H), 3.62-3.73 (m, 1H), 2.59-2.74 (m, 1H), 2.49-2.58 (m, 1H), 2.04-2.22 (m, 2H), 1.86-2.01 (m, 2H). $^{19}F$ NMR (376 MHz, DMSO-$d_6$) δ−73.41, −113.02.

Example 311 6-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-3,4-dihydroquinolin-2(1H)-one

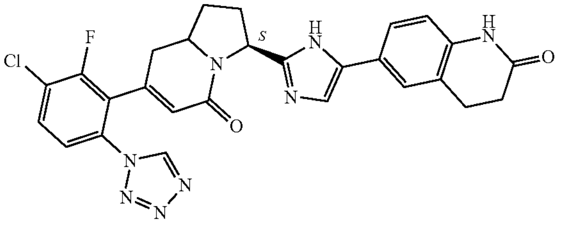

LC/MS: mass calculated for $C_{27}H_{22}ClFN_8O_2$: 544.15, measured (ES, m/z): 545.15 $[M+H]^+$. $^1H$ NMR (300 MHz, Methanol-$d_4$) δ 9.57 (s, 1H), 7.77-7.89 (m, 1H), 7.71 (s, 1H), 7.47-7.62 (m, 3H), 6.99 (d, J=8.3 Hz, 1H), 5.71-5.79 (m, 1H), 5.18-5.30 (m, 1H), 3.89-4.02 (m, 1H), 2.89-3.09 (m, 3H), 2.43-2.78 (m, 4H), 2.18-2.40 (m, 2H), 1.93-2.10 (m, 1H). $^{19}F$ NMR (282 MHz, Methanol-$d_4$) δ −76.98, −113.52, −113.92.

Example 312 5-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)-1H-benzo[d]imidazol-2(3H)-one

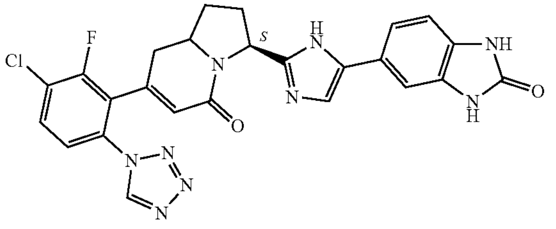

LC/MS: mass calculated for $C_{25}H_{19}ClFN_9O_2$: 531.13, measured (ES, m/z): 532.25 $[M+H]^+$. $^1$H NMR (300 MHz, DMSO-$d_6$) δ 11.68-12.21 (m, 1H), 10.05-10.71 (m, 2H), 9.84 (s, 1H), 7.91-8.03 (m, 1H), 7.69-7.74 (m, 1H), 7.29-7.36 (m, 2H), 6.85-7.21 (m, 2H), 5.62-5.73 (m, 1H), 4.93-5.03 (m, 1H), 3.71-4.09 (m, 1H), 2.67-2.82 (m, 1H), 2.53-2.64 (m, 1H), 1.89-2.39 (m, 4H). $^{19F}$ NMR (282 MHz, DMSO-$d_6$) δ−112.70.

Example 313 (3S)-3-(5-(3-Amino-1H-indazol-6-yl)-1H-imidazol-2-yl)-7-(3-chloro-2-fluoro-6-(1H-tetrazol-1-yl)phenyl)-2,3,8,8a-tetrahydroindolizin-5(1H)-one

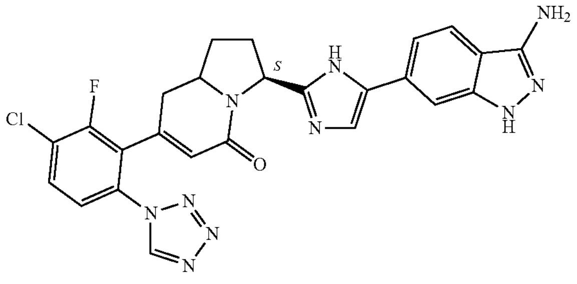

LC/MS: mass calculated for $C_{25}H_{20}ClFN_{10}O$: 530.15, measured (ES, m/z): 531.30 $[M+H]^+$. $^1$H NMR (400 MHz, DMSO-$d_6$) δ 12.04 (br, 1H), 9.82 (s, 1H), 8.11 (s, 1H), 7.91-8.05 (m, 1H), 7.81-7.90 (m, 1H), 7.59-7.81 (m, 2H), 7.23-7.46 (m, 1H), 5.61-5.85 (m, 1H), 5.10-5.26 (m, 1H), 3.67-4.10 (m, 1H), 2.90-2.98 (m, 1H), 2.51-2.68 (m, 1H), 2.23-2.44 (m, 2H), 2.07-2.19 (m, 1H), 1.77-2.05 (m, 1H). $^{19}$F NMR (376 MHz, DMSO-$d_6$) δ −74.31, −112.70.

Example 314 5-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)indolin-2-one

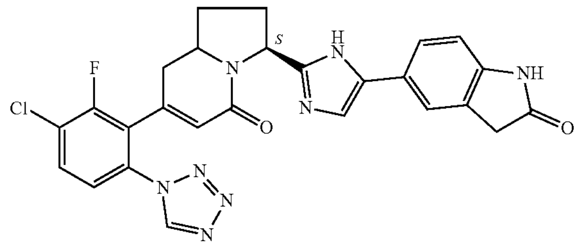

LC/MS: mass calculated for $C_{26}H_{20}ClFN_8O_2$: 530.14, measured (ES, m/z): 531.10 $[M+H]^+$. $^1$H NMR (400 MHz, DMSO-$d_6$) δ10.63 (s, 1H), 9.82 (s, 1H), 7.93-8.02 (m, 2H), 7.68-7.73 (m, 1H), 7.52-7.65 (m, 2H), 6.94 (d, J=8.0 Hz, 1H), 5.70-5.75 (m, 1H), 5.06-5.18 (m, 1H), 3.68-4.21 (m, 1H), 3.57 (s, 2H), 2.96 (t, J=15.2 Hz, 1H), 2.50-2.59 (m, 1H), 2.24-2.42 (m, 2H), 2.02-2.17 (m, 1H), 1.79-1.98 (m, 1H). $^{19}$F NMR (376 MHz, DMSO-$d_6$) δ −73.60, −112.72.

Example 315 (3S)-7-(3-Chloro-2-fluoro-6-(1H-tetrazol-1-yl)phenyl)-3-(5-(6-(dimethylamino)-2-fluoropyridin-3-yl)-1H-imidazol-2-yl)-2,3,8,8a-tetrahydroindolizin-5(1H)-one

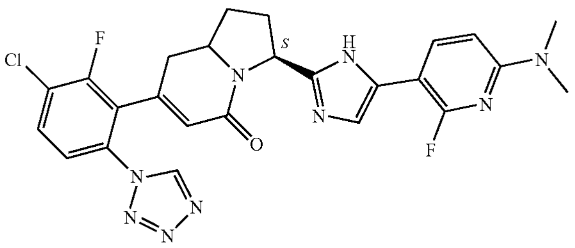

LC/MS: mass calculated for $C_{25}H_{22}ClF_2N_9O$: 537.16, measured (ES, m/z): 538.10 $[M+H]^+$. $^1$H NMR (300 MHz, DMSO-$d_6$) δ 9.83 (s, 1H), 7.93-8.06 (m, 2H), 7.62-7.77 (m, 2H), 6.71 (d, J=8.7 Hz, 1H), 5.67-5.79 (m, 1H), 5.10-5.21 (m, 1H), 3.69-4.25 (m, 1H), 3.02-3.10 (m, 7H), 2.54-2.62 (m, 1H), 2.30-2.45 (m, 1H), 1.95-2.20 (m, 3H). $^{19}$F NMR (282 MHz, DMSO-$d_6$) δ −67.65, −73.93, −112.68.

Example 316 Methyl (6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-3-yl)carbamate

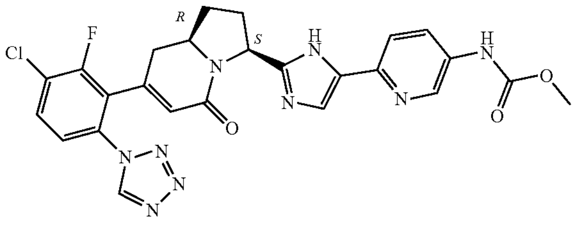

Step 1: 2-(5-((methoxycarbonyl)amino)pyridin-2-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (89 mg, 0.27 mmol, 1.0 equiv.) in DMF (3 mL) was added $Cs_2CO_3$ (107 mg, 0.33 mmol, 1.2 equiv.), followed by 6-(2-bromoacetyl)-1-methyl-1,3-dihydro-2H-benzo[d]imidazol-2-one (150 mg, 0.55 mmol, 2.0 equiv.). The resulting mixture was stirred 1.5 h, quenched with water (3×20 mL), dried over $Na_2SO_4$, and concentrated. The residue was purified by flash column chromatography on silica gel (0→20% MeOH/DCM) to yield 2-(5-((methoxycarbonyl)amino)pyridin-2-yl)-2-oxoethyl (3S)-7-(6-amino-3-chloro-2-fluorophenyl)-5-oxo-1,2,3,5,8,8a-hexahydroindolizine-3-carboxylate as a yellow oil. LC/MS: mass calculated for $C_{24}H_{22}ClFN_4O_6$: 516.12, measured: 517.20 $[M+H]^+$.

Step 2: methyl (6-(2-((3S)-7-(6-amino-3-chloro-2-fluorophenyl)-5-oxo-1,2,3,5,8,8a-hexahydroindolizin-3-yl)-1H-imidazol-5-yl)pyridin-3-yl)carbamate To a mixture of 2-(5-((methoxycarbonyl)amino)pyridin-2-yl)-2-oxoethyl (3S)-7-(6-amino-3-chloro-2-fluorophenyl)-5-oxo-1,2,3,5,8,8a-hexahydroindolizine-3-carboxylate (120 mg, 0.23 mmol, 1.0 equiv.) in toluene (5 mL) and acetic acid (0.2 mL) was added ammonium acetate (179 mg, 2.32 mmol, 10.0 equiv.). The reaction mixture was stirred at 100° C. for 2 h and concentrated under vacuum. The residue was purified by flash column chromatography on silica gel (0-20% MeOH/DCM) to yield methyl (6-(2-((3S)-7-(6-amino-3-chloro-2-fluorophenyl)-5-oxo-1,2,3,5,8,8a-hexahydroindolizin-3-yl)-1H-imidazol-5-yl)pyridin-3-yl)carbamate as a yellow oil. LC/MS: mass calculated for $C_{24}H_{22}ClFN_6O_3$: 496.14, measured: 497.25 $[M+H]^+$.

Step 3: methyl (6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-3-yl)carbamate To a stirred solution of methyl (6-(2-((3S)-7-(6-amino-3-chloro-2-fluorophenyl)-5-oxo-1,2,3,5,8,8a-hexahydroindolizin-3-yl)-1H-imidazol-5-yl)pyridin-3-yl)carbamate (110 mg, 0.22 mmol, 1.0 equiv.) in trimethylorthoformate (0.5 mL) and AcOH (5.00 mL) was added $TMSN_3$ (0.5 mL) at room temperature. The resulting mixture was stirred at 60° C. for 2 h, then concentrated under reduced pressure. The residue was purified by prep-HPLC to yield methyl (6-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-3-yl)carbamate as a yellow solid.

LC/MS: mass calculated for $C_{25}H_{21}ClFN_9O_3$: 549.14, measured (ES, m/z): 550.10 $[M+H]^+$. $^1H$ NMR (300 MHz, Methanol-$d_4$) δ 9.58 (s, 1H), 8.59 (d, J=2.5 Hz, 1H), 7.92-8.01 (m, 1H), 7.75-7.89 (m, 2H), 7.44-7.61 (m 2H), 5.73-5.75 (m, 1H), 5.13 (t, J=8.0 Hz, 1H), 4.27-4.41 (m, 1H), 3.75-3.89 (m, 3H), 2.35-2.67 (m, 4H), 2.01-2.27 (m, 2H), 1.75-1.97 (m, 1H). $^{19}F$ NMR (282 MHz, Methanol-$d_4$) δ −113.47, −113.82.

Example 317 (3S)-7-(3-Chloro-2-fluoro-6-(1H-tetrazol-1-yl)phenyl)-3-(4-(2-methoxyphenyl)-1H-imidazol-2-yl)-2,3,8,8a-tetrahydroindolizin-5(1H)-one

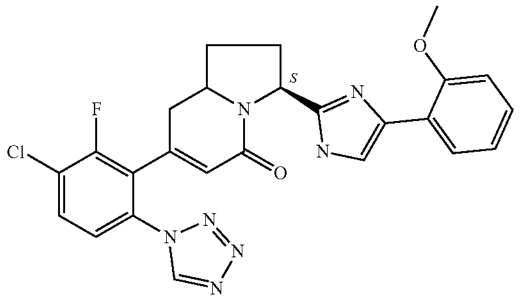

LC/MS: mass calculated for $C_{25}H_{21}ClFN_7O_2$: 505.14, measured (ES, m/z): 506.15 $[M+H]^+$. $^1H$ NMR (300 MHz, DMSO-$d_6$) δ 9.84 (s, 1H), 7.97-8.04 (m, 1H), 7.84-7.89 (m, 1H), 7.68-7.78 (m, 2H), 7.41-7.52 (m, 1H), 7.08-7.27 (m, 2H), 5.72-5.78 (m, 1H), 5.16-5.27 (m, 1H), 4.08-4.33 (m, 1H), 3.94 (s, 3H), 3.65-3.86 (m, 2H), 2.30-2.40 (m, 1H), 1.88-2.20 (m, 3H). $^{19}F$ NMR (282 MHz, DMSO-$d_6$) δ−73.81, −112.87.

Example 318 3-(4(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)phenyl)oxazolidin-2-one

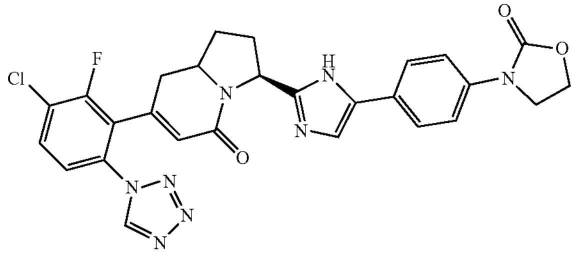 [SMILES: O=C1OCCN1c1ccc(-c2cnc([C@@H]3CCC4CC(c5c(-n6cnnn6)ccc(Cl)c5F)=CC(=O)N43)[nH]2)cc1]

LC/MS: mass calculated for $C_{27}H_{22}ClFN_8O_3$: 560.15, measured (ES, m/z): 561.15 $[M+H]^+$. $^1H$ NMR (400 MHz, DMSO-$d_6$) δ 9.84 (s, 1H), 7.93-8.09 (m, 2H), 7.67-7.91 (m, 5H), 5.65-5.80 (m, 1H), 5.10-5.25 (m, 1H), 4.47 (t, J=7.6 Hz, 2H), 4.12 (t, J=8.4 Hz, 2H), 3.65-3.85 (m, 1H), 2.99 (t, J=15.2 Hz, 1H), 2.53-2.66 (m, 1H), 2.25-2.47 (m, 1H), 2.06-2.20 (m, 2H), 1.80-2.04 (m, 1H). $^{19}F$ NMR (376 MHz, DMSO-$d_6$) δ −73.84, −112.70.

Example 319 Methyl (4-(2-((3S,8aS)-7-(3-Chloro-2-(difluoromethoxy)-6-fluorophenyl)-5-oxo-1,2,3,5,8,8a-hexahydroindolizin-3-yl)-1H-imidazol-5-yl)phenyl)carbamate

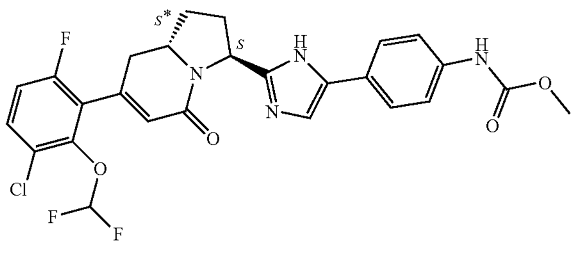

LC/MS: mass calculated for $C_{26}H_{22}ClF_3N_4O_4$: 546.13, measured (ES, m/z): 547.10 $[M+H]^+$. $^1H$ NMR (400 MHz, DMSO-$d_6$) δ11.96 (br, 1H), 9.63 (s, 1H), 7.70-7.84 (m, 1H), 7.56-7.69 (m, 2H), 7.29-7.55 (m, 4H), 7.09 (t, J=72.2 Hz, 1H), 5.91 (s, 1H), 5.07 (t, J=7.2 Hz, 1H), 4.20-4.40 (m, 1H), 3.67 (s, 3H), 2.57-2.75 (m, 2H), 2.25-2.44 (m, 2H), 2.00-2.20 (m, 1H), 1.70-1.85 (m, 1H). $^{19F}$ NMR (376 MHz, DMSO-$d_6$) δ −79.88, −112.76.

Example 320 Methyl (4-(2-((3S,8aS)-7-(3-Chloro-6-(difluoromethoxy)-2-fluorophenyl)-5-oxo-1,2,3,5,8,8a-hexahydroindolizin-3-yl)-1H-imidazol-5-yl)phenyl)carbamate

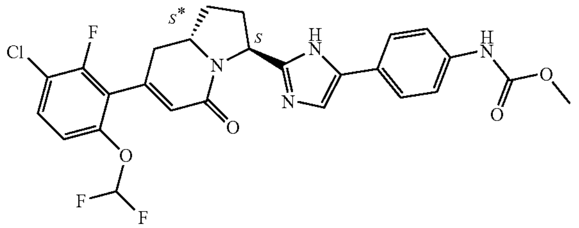

LC/MS: mass calculated for $C_{26}H_{22}ClF_3N_4O_4$: 546.13, measured (ES, m/z): 547.10 $[M+H]^+$. $^1H$ NMR (300 MHz, DMSO-$d_6$) δ 11.94 (br, 1H), 9.60 (s, 1H), 7.55-7.80 (m, 3H), 7.04-7.54 (m, 5H), 5.93 (s, 1H), 5.07 (t, J=7.1 Hz, 1H), 4.18-4.40 (m, 1H), 3.67 (s, 3H), 2.56-2.75 (m, 2H), 2.25-2.46 (m, 2H), 1.96-2.23 (m, 1H), 1.68-1.90 (m, 1H). $^{19}F$ NMR (282 MHz, DMSO-$d_6$) δ 82.53, −113.67.

Example 321 4-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)pyridine 1-oxide

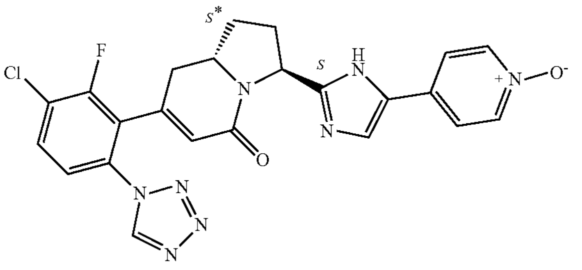

LC/MS: mass calculated for $C_{23}H_{20}ClFN_8O_2$: 492.12, measured (ES, m/z): 493.10 $[M+H]^+$. $^1H$ NMR (300 MHz, DMSO-$d_6$) δ 9.84 (s, 1H), 8.36-8.42 (m, 2H), 7.93-8.13 (m, 2H), 7.79-7.90 (m, 2H), 7.66-7.79 (m, 1H), 5.71 (d, J=2.6 Hz, 1H), 5.10 (d, J=9.3 Hz, 1H), 2.76-2.93 (m, 1H), 2.53-2.65 (m, 1H), 2.21-2.44 (m, 1H), 1.78-2.20 (m, 4H). $^{19}F$ NMR (282 MHz, DMSO-$d_6$) δ −74.31, −112.76.

Example 322 Methyl (6-(2-((3S,8aS)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)pyridin-3-yl)carbamate

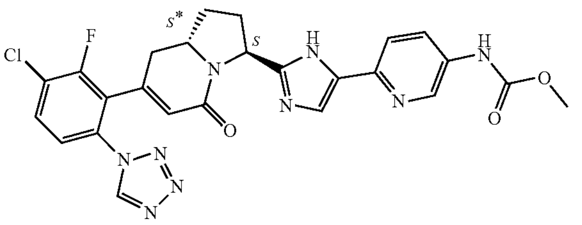

LC/MS: mass calculated for $C_{25}H_{21}ClFN_9O_3$: 549.14, measured (ES, m/z): 550.10 $[M+H]^+$. $^1H$ NMR (300 MHz, DMSO-$d_6$) δ (ppm): 11.86-12.26 (m, 1H), 9.76-9.90 (m, 2H), 8.52-8.64 (m, 1H), 7.92-8.02 (m, 1H), 7.83-7.91 (m, 1H), 7.65-7.82 (m, 2H), 7.45 (d, J=2.0 Hz, 1H), 5.63-7.73 (m, 1H), 4.96-5.10 (m, 1H), 3.66-3.76 (m, 4H), 2.58-2.84 (m, 2H), 1.90-2.25 (m, 4H). $^{19}F$ NMR (282 MHz, DMSO-$d_6$) δ −73.40, −112.83, −112.90.

Example 323 Methyl (4-(2-((3S,8aR)-7-(3-Chloro-2-(difluoromethoxy)-6-fluorophenyl)-5-oxo-1,2,3,5,8,8a-hexahydroindolizin-3-yl)-1H-imidazol-5-yl)phenyl)carbamate

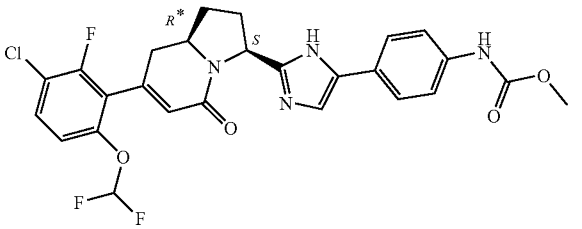

LC/MS: mass calculated for $C_{26}H_{22}ClF_3N_4O_4$: 546.13, measured (ES, m/z): 547.10 $[M+H]^+$. $^1H$ NMR (400 MHz, DMSO-$d_6$) δ11.79 (br, 1H), 9.59 (s, 1H), 7.60-7.78 (m, 3H), 7.45-7.57 (m, 1H), 7.28-7.45 (m, 3H), 7.17-7.24 (m, 1H), 5.97 (d, J=2.6 Hz, 1H), 5.07 (d, J=8.4 Hz, 1H), 3.90-3.99 (m, 1H), 3.64-3.69 (m, 3H), 2.92 (t, J=15.2 Hz, 1H), 2.59-2.67 (m, 1H), 1.97-2.28 (m, 4H). $^{19}F$ NMR (376 MHz, DMSO-$d_6$) δ −82.39, −113.33.

Example 324 Methyl (4-(2-((3S)-7-(3-Chloro-2-fluoro-6-(2,2,2-trifluoroethoxy)phenyl)-5-oxo-1,2,3,5,8,8a-hexahydroindolizin-3-yl)-1H-imidazol-5-yl)phenyl)carbamate

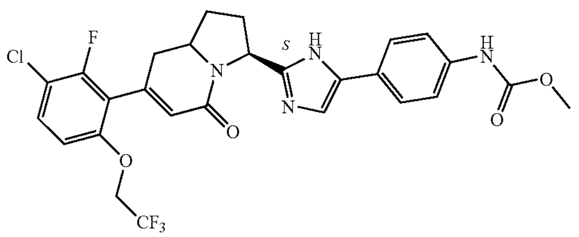

LC/MS: mass calculated for $C_{27}H_{23}ClF_4N_4O_4$: 578.13, measured (ES, m/z): 579.00 $[M+H]^+$. $^1H$ NMR (400 MHz, DMSO-$d_6$) δ14.53 (br, 1H), 9.92 (s, 1H), 7.89-8.10 (m, 1H), 7.53-7.79 (m, 5H), 7.15 (d, J=9.2 Hz, 1H), 5.80-6.20 (m, 1H), 5.15-5.35 (m, 1H), 4.75-5.10 (m, 2H), 3.84-4.43 (m, 1H), 3.69 (s, 3H), 2.58-3.09 (m, 2H), 1.75-2.43 (m, 4H). $^{19}F$ NMR (376 MHz, DMSO-$d_6$) δ −72.45, −73.73, −115.11.

Example 325 Methyl (5-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)carbamate

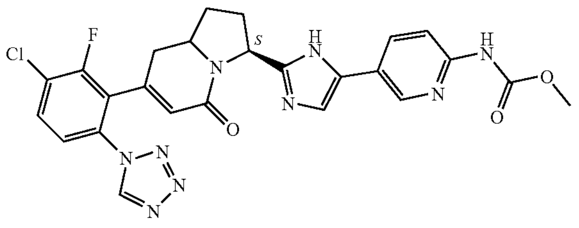

Step 1: methyl (5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)carbamate To a solution of the methyl (5-(2-((3S)-7-(6-amino-3-chloro-2-fluorophenyl)-5-oxo-1,2,3,5,8,8a-hexahydroindolizin-3-yl)-1H-imidazol-5-yl)pyridin-2-yl)carbamate (200 mg, 0.43 mmol, 1.0 equiv.) in acetic acid (5 mL) were added trimethoxymethane (1 mL) and azidotrimethylsilane (1 mL). The resulting mixture stirred 60° C. for 2 h, then concentrated. The residue was then purified by prep-HPLC to yield the methyl (5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)carbamate as a yellow solid.

LC/MS: mass calculated for $C_{25}H_{21}ClFN_9O_3$: 549.12, measured (ES, m/z): 550.05 $[M+H]^+$. $^1H$ NMR (400 MHz, DMSO-$d_6$) δ 10.48 (s, 1H), 9.86 (s, 1H), 8.71-8.77 (m, 1H), 8.19-8.23 (m, 1H), 8.08-8.11 (m, 1H), 7.91-8.01 (m, 2H), 7.72-7.78 (m, 1H), 5.73-5.80 (m, 1H), 5.31-5.40 (m, 1H), 3.82-4.32 (m, 1H), 3.71-3.78 (m, 3H), 3.00-3.21 (m, 1H), 2.67-3.22 (m, 1H), 2.28-2.31 (m, 1H), 1.78-2.21 (m, 3H). $^{19}F$ NMR (376 MHz, DMSO-$d_6$) δ −74.50, −112.50, −112.90.

Example 326 Methyl (6-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-5-yl)pyridin-3-yl)carbamate

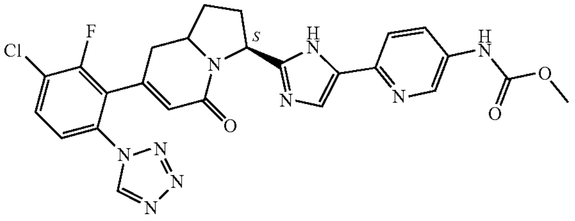

LC/MS: mass calculated for $C_{25}H_{21}ClFN_9O_3$: 549.14, measured (ES, m/z): 550.25 $[M+H]^+$. $^1H$ NMR (400 MHz, DMSO-$d_6$) δ 14.37 (br, 1H), 10.16 (s, 1H), 9.84 (s, 1H), 8.77-8.81 (m, 1H), 8.20 (d, J=4.1 Hz, 1H), 7.86-8.09 (m, 3H), 7.69-7.77 (m, 1H), 5.68-5.78 (m, 1H), 5.03-5.25 (m, 1H), 3.70-3.82 (m, 4H), 2.90-3.11 (m, 1H), 2.56-2.70 (m, 2H), 2.30-2.47 (m, 1H), 2.03-2.21 (m, 1H), 1.79-2.01 (m, 1H). $^{19}F$ NMR (376 MHz, DMSO-$d_6$) δ −74.36, −112.92.

Example 327 (1R,3S)-3-(4-(6-Amino-2-fluoropyridin-3-yl)-1H-imidazol-2-yl)-7-(3-chloro-2-fluoro-6-(1H-tetrazol-1-yl)phenyl)-1-methoxy-2,3,8,8a-tetrahydroindolizin-5(1H)-one

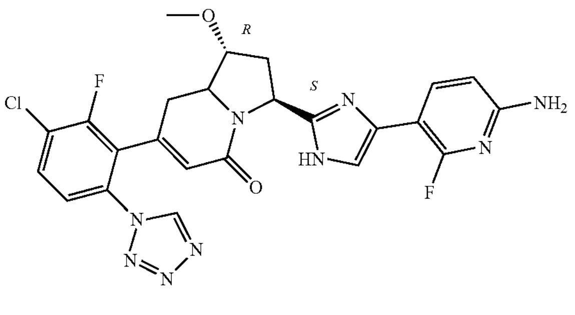

LC/MS: mass calculated for $C_{24}H_{20}ClF_2N_9O_2$: 539.14, measured (ES, m/z): 540.25 $[M+H]^+$. $^1H$ NMR (300 MHz, DMSO-$d_6$) δ 13.6-14.9 (m, 1H) 9.86 (s, 1H), 7.90-8.10 (m, 2H), 7.45-7.80 (m, 2H), 6.60-7.00 (m, 2H), 6.40-6.50 (m, 1H), 5.71-5.74 (m, 1H), 5.15-5.45 (m, 1H), 4.00-4.12 (m, 1H), 3.55-3.70 (m, 1H), 3.28-3.35 (m, 3H), 3.00-3.10 (m, 1H) 2.60-2.70 (m, 1H), 2.10-2.30 (m, 2H). $^{19}F$ NMR (282 MHz, DMSO-$d_6$) δ −69.04, −74.13, −112.63, 113.05.

Example 328 3-(5-(6-Amino-2-fluoropyridin-3-yl)-1H-imidazol-2-yl)-7-(3-chloro-2-fluoro-6-(1H-tetrazol-1-yl)phenyl)-2-methyl-2,3,8,8a-tetrahydroindolizin-5(1H)-one

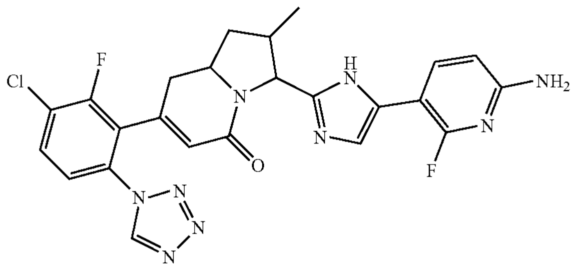 [SMILES: CC1CC2CC(c3c(-n4cnnn4)ccc(Cl)c3F)=CC(=O)N2C1c1ncc(-c2ccc(N)nc2F)[nH]1]

LC/MS: mass calculated for $C_{24}H_{20}ClF_2N_9O$: 523.14, measured (ES, m/z): 524.10 $[M+H]^+$. $^1H$ NMR (300 MHz, DMSO-$d_6$) δ 10.11 (s, 1H), 7.82-8.05 (m, 3H), 7.56-7.77 (m, 2H), 6.72-6.95 (m, 2H), 6.45-6.50 (m, 1H), 5.71 (d, J=2.6 Hz, 1H), 4.68-4.74 (m, 1H), 3.83-3.97 (m, 2H), 2.84-2.95 (m, 1H), 2.31-2.45 (m, 1H), 2.10-2.15 (m, 1H), 1.80-1.86 (m, 1H), 1.14-1.27 (m, 3H). $^{19}F$ NMR (282 MHz, DMSO-$d_6$) δ −112.62, −73.776.

Example 329 N-(2-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl) isobutyramide

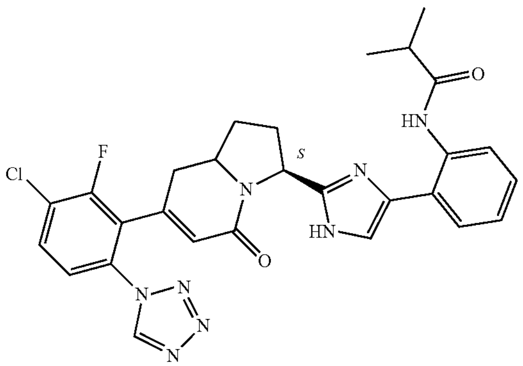

LC/MS: mass calculated for $C_{28}H_{26}ClFN_8O_2$: 560.19, measured (ES, m/z): 561.10 $[M+H]^+$. $^1H$ NMR (300 MHz, Methanol-$d_4$) δ 9.60 (s, 1H), 7.86-8.80 (m, 1H), 7.35-7.66 (m, 5H), 5.78-5.88 (m, 1H), 5.23-5.34 (m, 1H), 3.87-4.02 (m, 1H), 2.90-3.09 (m, 1H), 2.45-2.80 (m, 3H), 2.21-2.42 (m, 2H), 1.98-2.01 (m, 2H), 1.02-1.46 (m, 6H). $^{19}F$ NMR (282 MHz, Methanol-$d_4$) δ −76.96, −113.51, −113.94.

Example 330 N-(2-(2-((3S)-7-(3-Chloro-2-fluoro-6-(1H-tetrazol-1-yl)phenyl)-5-oxo-1,2,3,5,8,8a-hexahydroindolizin-3-yl)-1H-imidazol-4-yl)phenyl)cycloheptanecarboxamide

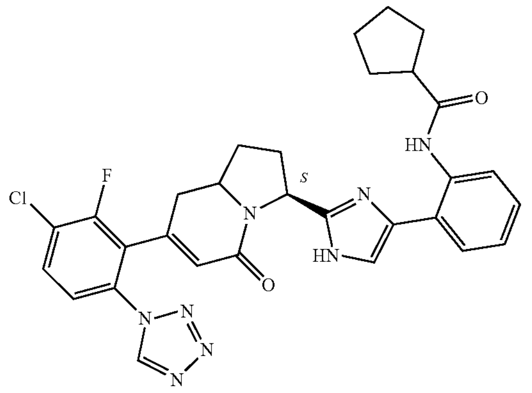

LC/MS: mass calculated for $C_{30}H_{28}ClFN_8O_2$: 586.20, measured (ES, m/z): 587.30 $[M+H]^+$. $^1H$ NMR (300 MHz, DMSO-$d_6$) δ 9.81-9.90 (m, 1H), 7.89-8.12 (m, 2H), 7.61-7.73 (m, 2H), 7.45-7.54 (m, 1H), 7.13-7.41 (m, 2H), 5.61-5.81 (m, 1H), 5.02-5.29 (m, 1H), 3.71-4.29 (m, 1H), 2.71-2.98 (m, 2H), 1.90-2.50 (m, 5H), 1.28-1.94 (m, 9H). $^{19}F$ NMR (282 MHz, DMSO-$d_6$) δ −74.29, −112.65, −113.07.

Example 331 (3S)-3-(4-(1H-1,2,4-Triazol-3-yl)-1H-imidazol-2-yl)-7-(3-chloro-2-fluoro-6-(1H-tetrazol-1-yl)phenyl)-2,3,8,8a-tetrahydroindolizin-5(1H)-one

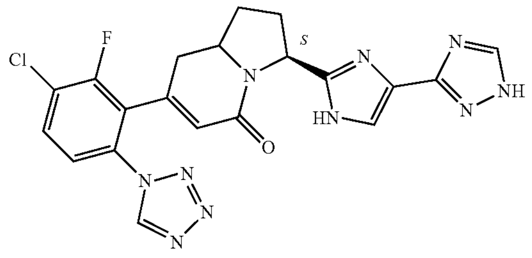

Step 1: 2-oxo-2-(1-((2-(trimethylsilyl)ethoxy)methyl)-1H-1,2,4-triazol-3-yl)ethyl (3S)-7-(6-amino-3-chloro-2-fluorophenyl)-5-oxo-1,2,3,5,8,8a-hexahydroindolizine-3-carboxylate To a solution of the (3S)-7-(6-amino-3-chloro-2-fluorophenyl)-5-oxo-1,2,3,5,8,8a-hexahydroindolizine-3-carboxylic acid (200 mg, 0.62 mmol, 1.3 equiv.) in $CH_3CN$ (10 mL) were added 2-bromo-1-(1-((2-(trimethylsilyl)ethoxy)methyl)-1H-1,2,4-triazol-3-yl)ethan-1-one (150 mg, 0.47 mmol, 1.0 equiv.) and $K_2CO_3$ (150 mg, 1.09 mmol, 2.3 equiv.). The resulting mixture was stirred at room temperature. for 5 h, then was quenched with water and extracted with EA. The combined organic layer was washed with brine, dried over $Na_2SO_4$. The solids were filtered out. The resulting organic phase was concentrated under vacuum. The residue was applied onto a silica gel column to yield 2-oxo-2-(1-((2-(trimethylsilyl)ethoxy)methyl)-1H-1,2,4-triazol-3-yl)ethyl (3S)-7-(6-amino-3-chloro-2-fluorophenyl)-5-oxo-1,2,3,5,8,8a-hexahydroindolizine-3-carboxylate as a yellow solid.

Step 2: 2-oxo-2-(1-((2-(trimethylsilyl)ethoxy)methyl)-1H-1,2,4-triazol-3-yl)ethyl (3S)-7-(6-amino-3-chloro-2-fluorophenyl)-5-oxo-1,2,3,5,8,8a-hexahydroindolizine-3-carboxylate To a solution of the 2-oxo-2-(1-((2-(trimethylsilyl)ethoxy)methyl)-1H-1,2,4-triazol-3-yl)ethyl (3S)-7-(6-amino-3-chloro-2-fluorophenyl)-5-oxo-1,2,3,5,8,8a-hexahydroindolizine-3-carboxylate (150 mg, 0.26 mmol) in toluene (10 mL) were added ammonium acetate (264 mg, 3.07 mmol) and HOAc (0.1 mL). The resulting mixture stirred at 110° C. for 2 h, then cooled to room temperature and concentrated under vacuum. The residue was purified by flash column chromatography on silica gel to yield the (3S)-7-(6-amino-3-chloro-2-fluorophenyl)-3-(5-(1-((2-(trimethylsilyl)ethoxy)methyl)-1H-1,2,4-triazol-3-yl)-1H-imidazol-2-yl)-2,3,8,8a-tetrahydroindolizin-5(1H)-one as a yellow solid.

Step 3: (3S)-3-(5-(1H-1,2,4-triazol-3-yl)-1H-imidazol-2-yl)-7-(6-amino-3-chloro-2-fluorophenyl)-2,3,8,8a-tetrahydroindolizin-5(1H)-one To a solution of the (3S)-7-(6-amino-3-chloro-2-fluorophenyl)-3-(5-(1-((2-(trimethylsilyl)ethoxy)methyl)-1H-1,2,4-triazol-3-yl)-1H-imidazol-2-yl)-2,3,8,8a-tetrahydroindolizin-5(1H)-one (100 mg, 0.18 mmol) in DCM (5 mL) was added TFA (3 mL). The resulting mixture stirred at room temperature. for 2 h, then concentrated to yield the (3S)-3-(5-(1H-1,2,4-triazol-3-yl)-1H-imidazol-2-yl)-7-(6-amino-3-chloro-2-fluorophenyl)-2,3,8,8a-tetrahydroindolizin-5(1H)-one as a yellow oil.

Step 4: (3S)-3-(4-(1H-1,2,4-triazol-3-yl)-1H-imidazol-2-yl)-7-(3-chloro-2-fluoro-6-(1H-tetrazol-1-yl)phenyl)-2,3,8,8a-tetrahydroindolizin-5(1H)-one To a stirred solution of (3S)-3-(5-(1H-1,2,4-triazol-3-yl)-1H-imidazol-2-yl)-7-(6-amino-3-chloro-2-fluorophenyl)-2,3,8,8a-tetrahydroindolizin-5(1H)-one (40 mg, 0.10 mmol, 1.0 equiv.) in AcOH (2.5 mL) were added azidotrimethylsilane (0.25 mL) and azidotrimethylsilane (0.25 mL) at room temperature. The mixture was stirred for 4 h at 60° C. and concentrated under reduced pressure. The residue was purified by reverse flash chromatography on C18 with the following conditions: mobile phase, A: TFA (0.05%) in water and B: ACN, 10% to 50% gradient in 20 min to yield (3S)-3-(4-(1H-1,2,4-triazol-3-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow solid.

LC/MS: mass calculated for $C_{20}H_{16}ClFN_{10}O$: 466.12, measured (ES, m/z): 467.10 $[M+H]^+$. $^1H$ NMR (400 MHz, DMSO-$d_6$) δ 9.80 (s, 1H), 8.69-8.73 (m, 1H), 7.95-8.04 (m, 2H), 7.68-7.69 (m, 1H), 5.69-5.73 (m, 1H), 5.12-5.19 (m, 1H), 2.99-3.02 (m, 1H), 2.52-2.55 (m, 1H), 2.16-2.35 (m, 2H), 1.75-2.16 (m, 4H). $^{19}F$ NMR (376 MHz, DMSO-$d_6$) δ −112.58, −112.64, −113.06.

Example 332 (3S)-3-(4-(1H-1,2,3-Triazol-5-yl)-1H-imidazol-2-yl)-7-(3-chloro-2-fluoro-6-(1H-tetrazol-1-yl)phenyl)-2,3,8,8a-tetrahydroindolizin-5(1H)-one

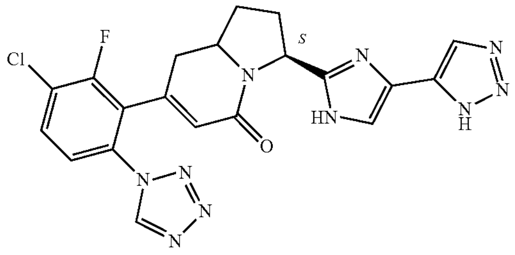

LC/MS: mass calculated for $C_{20}H_{16}ClFN_{10}O$: 466.12, measured (ES, m/z): 467.10 $[M+H]^+$. $^1H$ NMR (300 MHz, Methanol-$d_4$) δ 9.59 (s, 1H), 7.98-8.01 (m, 1H), 7.83-7.98 (m, 1H), 7.56-7.83 (m, 1H), 7.39-7.54 (m, 1H), 5.71-5.76 (m, 1H), 5.13-5.21 (m, 1H), 3.90-4.45 (m, 1H), 2.88-3.04 (m, 1H), 2.55-2.74 (m, 2H), 1.98-2.51 (m, 3H). $^{19}F$ NMR (282 MHz, Methanol-$d_4$) δ −113.33, −113.83.

Example 333 (3S)-3-(1H,1'H-[2,4'-Biimidazol]-2'-yl)-7-(3-chloro-2-fluoro-6-(1H-tetrazol-1-yl)phenyl)-2,3,8,8a-tetrahydroindolizin-5(1H)-one

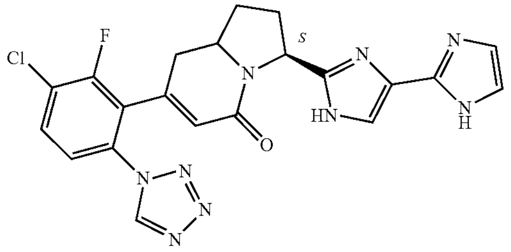

LC/MS: mass calculated for $C_{21}H_{17}ClFN_9O$: 465.12, measured (ES, m/z): 466.05 $[M+H]^+$. $^1H$ NMR (300 MHz, Methanol-$d_4$) δ 9.58 (s, 1H), 7.81 (t, J=8.7, 1H), 7.49-7.67 (m, 1H), 7.38-7.46 (m, 1H), 7.04-7.12 (m, 2H), 5.73 (d, J=2.9 Hz, 1H), 5.14 (d, J=8.3 Hz, 1H), 3.79-4.05 (m, 1H), 2.75-2.91 (m, 1H), 2.54-2.66 (m, 1H), 2.16-2.35 (m, 3H), 2.00-2.06 (m, 1H). $^{19}F$ NMR (282 MHz, Methanol-$d_4$) δ −77.02, −113.87.

Example 334 (3S)-7-(3-chloro-2-Fluoro-6-(1H-tetrazol-1-yl)phenyl)-3-(1-methyl-1H,1'H-[2,4'-biimidazol]-2'-yl)-2,3,8,8a-tetrahydroindolizin-5(1H)-one

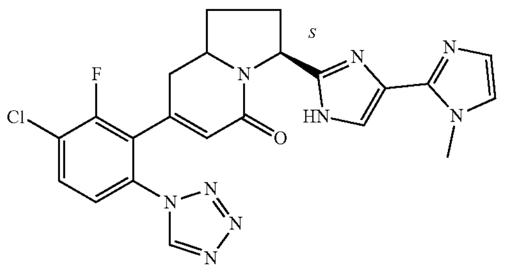

LC/MS: mass calculated for $C_{22}H_{19}ClFN_9O$: 479.14, measured (ES, m/z): 480.15 $[M+H]^+$. $^1H$ NMR (300 MHz, DMSO-$d_6$) δ 9.83 (s, 1H), 7.95-8.02 (m, 2H), 7.6-7.769 (m, 3H), 5.51-5.78 (m, 1H), 5.09-5.21 (m, 1H), 4.08-4.10 (m, 3H), 2.55-2.75 (m, 1H), 2.52-2.60 (m, 3H), 2.13-2.27 (m, 1H), 1.89-2.04 (m, 2H). $^{19}F$ NMR (282 MHz, DMSO-$d_6$) δ −74.21, −112.98.

Example 335 (3S,8aR)-3-(5-(6-Amino-2-chloropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one

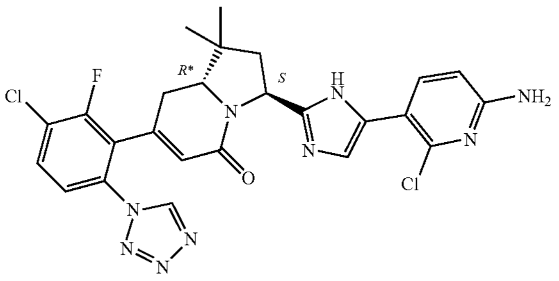

LC/MS: mass calculated for $C_{25}H_{22}Cl_2FN_9O$: 553.13, measured (ES, m/z): 554.10 $[M+H]^+$. $^1H$ NMR (300 MHz, DMSO-$d_6$) δ 9.86 (s, 1H), 7.93-8.05 (m, 1H), 7.68-7.77 (m, 1H), 7.40-7.50 (m, 1H), 6.48-6.55 (m, 2H), 5.70 (s, 1H), 4.89-4.95 (m, 1H), 3.77-3.90 (m, 1H), 2.06-2.40 (m, 3H), 1.90-2.03 (m, 1H), 1.04-1.08 (m, 3H), 0.91-0.95 (m, 3H). $^{19}F$ NMR (282 MHz, DMSO-$d_6$) δ −73.41, −112.93.

Example 336 (3S,8aR)-3-(5-(6-Amino-2-fluoropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one

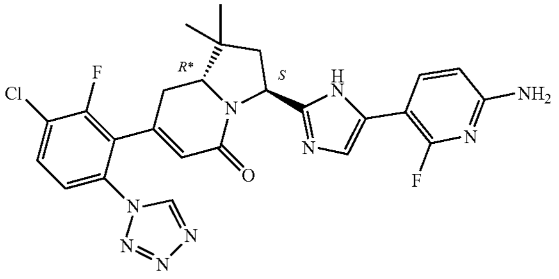

Step 1: 2-(6-acetamido-2-fluoropyridin-3-yl)-2-oxoethyl (3S)-7-(6-amino-3-chloro-2-fluorophenyl)-1,1-dimethyl-5-oxo-1,2,3,5,8,8a-hexahydroindolizine-3-carboxylate To a solution of (3S)-7-(6-amino-3-chloro-2-fluorophenyl)-1,1-dimethyl-5-oxo-1,2,3,5,8,8a-hexahydroindolizine-3-carboxylic acid (300 mg, 0.85 mmol, 1.0 equiv.) in N,N-dimethylformamide (10 mL) was added cesium carbonate (166 mg, 0.51 mmol, 0.6 equiv.), followed by N-(5-(2-bromoacetyl)-6-fluoropyridin-2-yl)acetamide (281 mg, 1.02 mmol, 1.2 equiv.). The resulting mixture was stirred for 1 h at room temperature, quenched with water and extracted with ethyl acetate. The combined organic layer was washed with brine, dried over $Na_2SO_4$ and concentrated. The residue was purified by silica gel chromatography (0→100% EA/PE) to yield 2-(6-acetamido-2-fluoropyridin-3-yl)-2-oxoethyl (3S)-7-(6-amino-3-chloro-2-fluorophenyl)-1,1-dimethyl-5-oxo-1,2,3,5,8,8a-hexahydroindolizine-3-carboxylate as a yellow solid. LC/MS: mass calculated for $C_{26}H_{25}ClF_2N_4O_5$: 546.15, measured: 547.25 $[M+H]^+$.

Step 2: N-(5-(2-((3S)-7-(6-amino-3-chloro-2-fluorophenyl)-1,1-dimethyl-5-oxo-1,2,3,5,8,8a-hexahydroindolizin-3-yl)-1H-imidazol-5-yl)-6-fluoropyridin-2-yl)acetamide To a solution of 2-(6-acetamido-2-fluoropyridin-3-yl)-2-oxoethyl (3S)-7-(6-amino-3-chloro-2-fluorophenyl)-1,1-dimethyl-5-oxo-1,2,3,5,8,8a-hexahydroindolizine-3-carboxylate (180 mg, 0.33 mmol, 1.0 equiv.) in toluene (10 mL) were added ammonium acetate (254 mg, 3.29 mmol, 10.0 equiv.) and acetic acid (0.5 mL). The reaction mixture was stirred for 2 h at 110° C., then cooled to room temperature, and concentrated. The residue was purified by flash column chromatography on silica gel (0→100% EA/PE) to yield N-(5-(2-((3S)-7-(6-amino-3-chloro-2-fluorophenyl)-1,1-dimethyl-5-oxo-1,2,3,5,8,8a-hexahydroindolizin-3-yl)-1H-imidazol-5-yl)-6-fluoropyridin-2-yl)acetamide as a brown solid. LC/MS: mass calculated for $C_{26}H_{25}ClF_2N_6O_2$: 526.17, measured: 527.15 $[M+H]^+$.

Step 3: N-(5-(2-((3S)-7-(3-chloro-2-fluoro-6-(1H-tetrazol-1-yl)phenyl)-1,1-dimethyl-5-oxo-1,2,3,5,8,8a-hexahydroindolizin-3-yl)-1H-imidazol-5-yl)-6-fluoropyridin-2-yl)acetamide To a solution of N-(5-(2-((3S)-7-(6-amino-3-chloro-2-fluorophenyl)-1,1-dimethyl-5-oxo-1,2,3,5,8,8a-hexahydroindolizin-3-yl)-1H-imidazol-5-yl)-6-fluoropyridin-2-yl)acetamide (150 mg, 0.29 mmol, 1.0 equiv.) in acetic acid (5 mL) were added azidotrimethylsilane (0.2 mL) and trimethoxymethane (0.2 mL). The reaction mixture was stirred at 60° C. for 16 h and then concentrated under reduced pressure. The residue was purified by silica gel chromatography (0→100% EA/PE) to yield N-(5-(2-((3S)-7-(3-chloro-2-fluoro-6-(1H-tetrazol-1-yl)phenyl)-1,1-dimethyl-5-oxo-1,2,3,5,8,8a-hexahydroindolizin-3-yl)-1H-imidazol-5-yl)-6-fluoropyridin-2-yl)acetamide as a brown solid. LC/MS: mass calculated for $C_{27}H_{24}ClF_2N_9O_2$: 579.17, measured: 580.25 $[M+H]^+$.

Step 4: (3S,8a*R)-3-(5-(6-amino-2-fluoropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one To a solution of N-(5-(2-((3S)-7-(3-chloro-2-fluoro-6-(1H-tetrazol-1-yl)phenyl)-1,1-dimethyl-5-oxo-1,2,3,5,8,8a-hexahydroindolizin-3-yl)-1H-imidazol-5-yl)-6-fluoropyridin-2-yl)acetamide (110 mg, 0.19 mmol, 1.0 equiv.) in tetrahydrofuran (4 mL) was added hydrochloric acid (2 N) (2 mL). The reaction mixture was stirred at 50° C. for 4 h, then concentrated. The residue was purified by reverse phase chromatography on C18 column (0→60% $CH_3CN/H_2O$) to yield (3S,8a*R)-3-(5-(6-amino-2-fluoropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one as a white solid.

LC/MS: mass calculated for $C_{25}H_{22}ClF_2N_9O$: 537.16, measured (ES, m/z): 538.10 $[M+H]^+$. $^1H$ NMR (300 MHz, DMSO-$d_6$) δ 11.92 (br, 1H), 9.85 (s, 1H), 7.98-8.05 (m, 2H), 7.69-7.75 (m, 1H), 7.02-7.08 (m, 1H), 6.35-6.41 (m, 1H), 6.23 (s, 1H), 5.67 (s, 1H), 4.85 (t, J=8.5 Hz, 1H), 3.80 (t, J=9.6 Hz, 1H), 2.25-2.35 (m, 2H), 2.06-2.18 (m, 1H), 1.96 (t, J=11.2 Hz, 1H), 1.02-1.06 (m, 3H), 0.90-0.93 (m, 3H). $^{19}F$ NMR (282 MHz, DMSO-$d_6$) δ −70.79, −73.40, −112.96.

Example 337 (3S,8aS)-3-(5-(6-Amino-2-fluoropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one

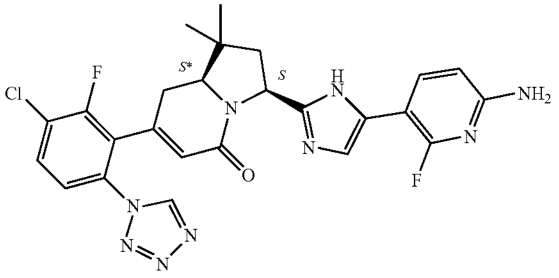

LC/MS: mass calculated for $C_{25}H_{22}ClF_2N_9O$: 537.16, measured (ES, m/z): 538.10 $[M+H]^+$. $^1H$ NMR (300 MHz, DMSO-$d_6$) δ 14.21 (br, 1H), 9.86 (s, 1H), 7.95-8.07 (m, 1H), 7.86 (t, J=9.4 Hz, 1H), 7.71-7.76 (m, 1H), 7.60 (s, 1H), 6.79-6.84 (m, 2H), 6.41-6.50 (m, 1H), 5.85 (d, J=2.6 Hz, 1H), 5.19 (d, J=10.2 Hz, 1H), 3.67 (d, J=6.5 Hz, 1H), 2.67 (s, 1H), 2.14-2.44 (m, 2H), 1.99 (d, J=13.2 Hz, 1H), 0.97-1.01 (m, 3H), 0.82-0.86 (m, 3H). $^{19}F$ NMR (282 MHz, DMSO-$d_6$) δ −73.68, −112.23.

Example 338 (3S,8aS)-3-(5-(6-Amino-2-chloropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one

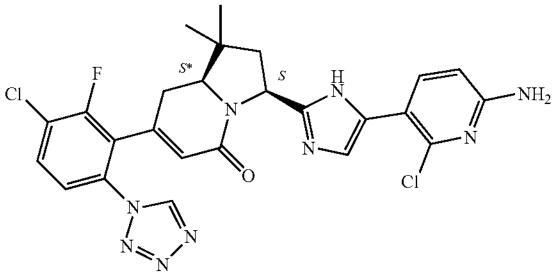

LC/MS: mass calculated for $C_{25}H_{22}Cl_2FN_6O$: 553.13, measured (ES, m/z): 554.05 $[M+H]^+$. $^1H$ NMR (300 MHz, DMSO-$d_6$) δ 14.25 (br, 1H), 9.85 (s, 1H), 7.98-8.04 (m, 1H), 7.74 (t, J=8.7 Hz, 1H), 7.65-7.70 (m, 2H), 6.80-6.84 (m, 2H), 6.52 (d, J=8.5 Hz, 1H), 5.85 (d, J=2.6 Hz, 1H), 5.19 (d, J=10.4 Hz, 1H), 3.41 (t, J=14.3 Hz, 1H), 2.67 (d, J=15.6 Hz, 1H), 2.36 (t, J=11.9 Hz, 1H), 2.20-2.26 (m, 1H), 1.99 (d, J=13.4 Hz, 1H), 0.98-1.01 (m, 3H), 0.82-0.87 (m, 3H). $^{19}F$ NMR (282 MHz, DMSO-$d_6$) δ −73.75, −112.16.

Example 339 (3S)-7-(3-Chloro-2-fluoro-6-(1H-tetrazol-1-yl)phenyl)-3-(4-(1-methyl-1H-1,2,3-triazol-5-yl)-1H-imidazol-2-yl)-2,3,8,8a-tetrahydroindolizin-5(1H)-one

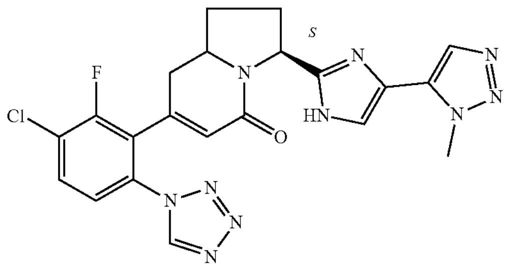

LC/MS: mass calculated for $C_{21}H_{18}ClFN_{10}O$: 480.13, measured (ES, m/z): 481.15 $[M+H]^+$. $^1H$ NMR (400 MHz, DMSO-$d_6$) δ 13.0 (br, 1H), 9.83 (s, 1H), 7.95-8.02 (m, 1H), 7.93-7.95 (m, 1H), 7.69-7.76 (m, 2H), 5.70 (d, J=2.7 Hz, 1H), 5.09 (d, J=9.0 Hz, 1H), 4.16-4.25 (m, 3H), 2.75-2.80 (m, 1H), 2.52-2.60 (m, 2H), 2.13-2.27 (m, 2H), 1.89-2.04 (m, 2H). $^{19}F$ NMR (376 MHz, DMSO-$d_6$) δ−74.61, −112.93.

Example 340 Methyl (4-(2-((3S,8aS)-7-(3-chloro-2-fluoro-6-(1H-tetrazol-1-yl) phenyl)-5-oxo-1,2,3,5,8,8a-hexahydroindolizin-3-yl)-1H-imidazol-5-yl)phenyl)carbamate

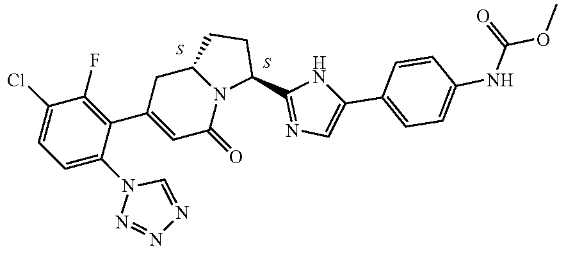

LC/MS: mass calculated for $C_{26}H_{22}ClFN_8O_3$: 548.15, measured (ES, m/z): 549.10 $[M+H]^+$. $^1H$ NMR (400 MHz, DMSO-$d_6$) δ 9.91 (br, 1H), 9.83 (s, 1H), 7.93-8.02 (m, 2H), 7.69-7.73 (m, 3H), 7.58-7.60 (m, 2H), 5.72 (d, J=2.8 Hz, 1H), 5.19 (d, J=9.8 Hz, 1H), 3.62-3.75 (m, 1H), 3.70-3.74 (m, 3H), 3.05-3.14 (m, 1H), 2.89-3.11 (m, 1H), 2.41-2.57 (m, 1H), 2.05-2.34 (m, 2H), 1.94-2.01 (m, 1H). $^{19}F$ NMR (376 MHz, DMSO-$d_6$) δ −112.69

Example 341 Methyl (4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)phenyl)carbamate

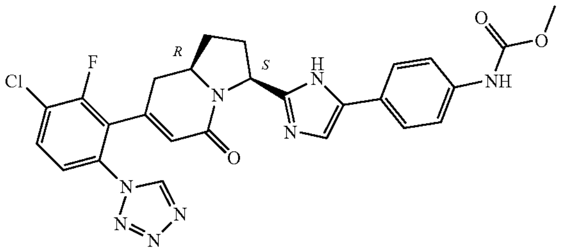

LC/MS: mass calculated for $C_{26}H_{22}ClFN_8O_3$: 548.15, measured (ES, m/z): 549.10 $[M+H]^+$. $^1H$ NMR (400 MHz, DMSO-$d_6$) δ 9.91 (br, 1H), 9.83 (s, 1H), 7.93-8.02 (m, 2H), 7.69-7.73 (m, 3H), 7.58-7.60 (m, 2H), 5.72 (d, J=2.8 Hz, 1H), 5.19 (d, J=9.8 Hz, 1H), 3.62-3.75 (m, 1H), 3.70-3.74 (m, 3H), 3.05-3.14 (m, 1H), 2.89-3.11 (m, 1H), 2.41-2.57 (m, 1H), 2.05-2.34 (m, 2H), 1.94-2.01 (m, 1H). $^{19}F$ NMR (376 MHz, DMSO-$d_6$) δ −112.69.

Example 342 4-[2-[(3S)-7-[3-Chloro-2-fluoro-6-(tetrazol-1-yl)phenyl]-5-oxo-2,3,8,8a-tetrahydro-1H-indolizin-3-yl]-1H-imidazol-4-yl]-2-fluoro-benzoic acid

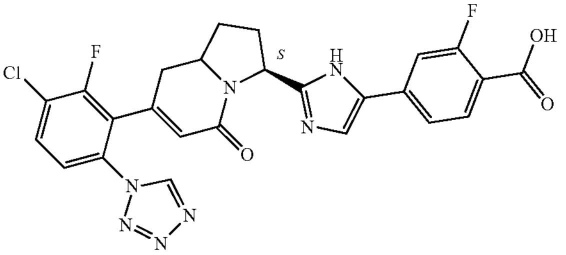

LC/MS: mass calculated for $C_{25}H_{18}ClF_2N_7O_3$: 537.15, measured (ES, m/z): 538.05 $[M+H]^+$. $^1H$ NMR (300 MHz, DMSO-$d_6$) δ 13.24 (br, 1H), 9.84 (s, 1H), 7.90-8.05 (m, 3H), 7.68-7.73 (m, 3H), 5.71-5.76 (m, 1H), 5.09-5.12 (m, 1H), 3.69-4.25 (m, 1H), 2.78-2.91 (m, 1H), 2.56-2.61 (m, 1H), 2.26-2.36 (m, 1H), 2.07-2.16 (m, 1H), 1.90-2.07 (m, 2H).

Example 344 (1*S,3S,8a*R)-3-(5-(6-Amino-2-fluoropyridin-3-yl)-1H-imidazol-2-yl)-7-(3-chloro-2-fluoro-6-(1H-tetrazol-1-yl)phenyl)-1-methyl-2,3,8,8a-tetrahydroindolizin-5(1H)-one

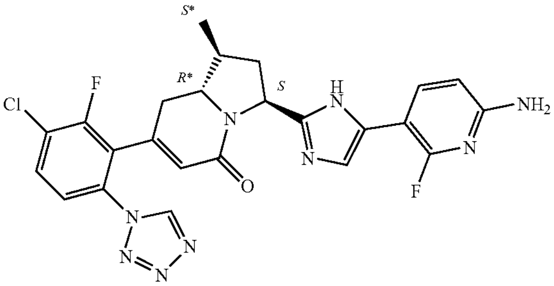

LC/MS: mass calculated for $C_{24}H_{20}ClF_2N_9O$: 523.14, measured (ES, m/z): 524.10 $[M+H]^+$. $^1H$ NMR (400 MHz, DMSO-$d_6$) δ 11.73 (s, 1H), 9.84 (s, 1H), 7.94-8.05 (m, 2H), 7.70 (d, J=8.3 Hz, 1H), 7.02 (s, 1H), 6.40 (d, J=8.4 Hz, 1H), 6.21 (s, 2H), 5.69 (s, 1H), 5.01-4.94 (m, 1H), 3.06-3.29 (m, 1H), 2.56-2.64 (m, 1H), 2.20-2.46 (m, 2H), 1.98-2.13 (m, 1H), 1.74-1.93 (m, 1H), 0.98 (d, J=2.7 Hz, 3H). $^{19}F$ NMR (376 MHz, DMSO-$d_6$) δ −70.85, −112.72.

Example 345 (1*R,3S,8a*R)-3-(5-(6-Amino-2-fluoropyridin-3-yl)-1H-imidazol-2-yl)-7-(3-chloro-2-fluoro-6-(1H-tetrazol-1-yl)phenyl)-1-methyl-2,3,8,8a-tetrahydroindolizin-5(1H)-one

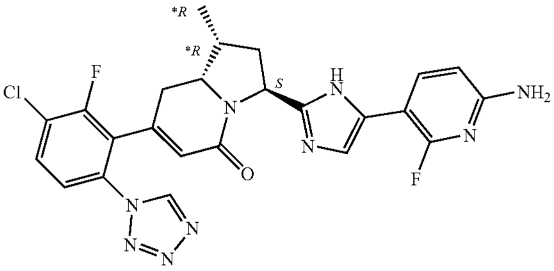

LC/MS: mass calculated for $C_{24}H_{20}ClF_2N_9O$: 523.14, measured (ES, m/z): 524.10 $[M+H]^+$. $^1H$ NMR (400 MHz, DMSO-$d_6$) δ 11.82 (br, 1H), 9.80 (s, 1H), 7.85-8.09 (m, 2H), 7.69 (d, J=8.6 Hz, 1H), 7.05 (d, J=3.8 Hz, 1H), 6.36 (d, J=8.7 Hz, 1H), 6.26 (s, 2H), 5.82 (s, 1H), 5.03 (t, J=8.5 Hz, 1H), 3.75-3.90 (m, 1H), 3.16-3.28 (m, 1H), 2.80-2.87 (m, 1H), 1.71-1.81 (m, 1H), 1.34-1.50 (m, 1H), 1.24 (s, 1H), 0.99 (d, J=6.4 Hz, 3H). $^{19}F$ NMR (376 MHz, DMSO-$d_6$) δ −70.77, −113.60.

Example 346 (1*S,3S,8a*S)-3-(5-(6-Amino-2-fluoropyridin-3-yl)-1H-imidazol-2-yl)-7-(3-chloro-2-fluoro-6-(1H-tetrazol-1-yl)phenyl)-1-methyl-2,3,8,8a-tetrahydroindolizin-5(1H)-one

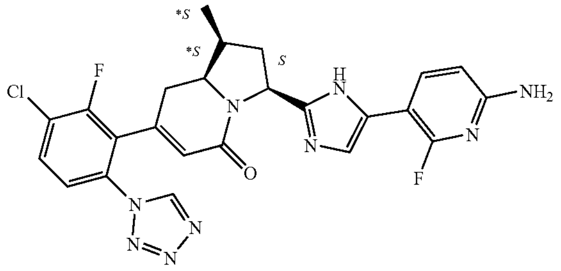

LC/MS: mass calculated for $C_{24}H_{20}ClF_2N_9O$: 523.14, measured (ES, m/z): 524.10 $[M+H]^+$. $^1H$ NMR (400 MHz, DMSO-$d_6$) δ 11.92 (br, 1H), 9.84 (s, 1H), 7.86-8.14 (m, 2H), 7.70 (d, J=8.7 Hz, 1H), 7.03 (s, 1H), 6.38 (d, J=8.2 Hz, 1H), 6.24 (s, 2H), 5.67 (d, J=2.3 Hz, 1H), 4.89 (t, J=8.3 Hz, 1H), 3.51-3.71 (m, 1H), 2.54-2.60 (m, 1H), 2.22-2.47 (m, 2H), 1.90-2.12 (m, 1H), 1.71-181 (m, 1H), 1.02 (d, J=6.3 Hz, 3H). $^{19}F$ NMR (376 MHz, DMSO-$d_6$) δ −70.78, −112.95.

Example 347 (3S)-3-(5-(6-Amino-2-chloropyridin-3-yl)-1H-imidazol-2-yl)-7-(3-chloro-2-fluoro-6-(1H-tetrazol-1-yl)phenyl)-1-methyl-2,3,8,8a-tetrahydroindolizin-5(1H)-one

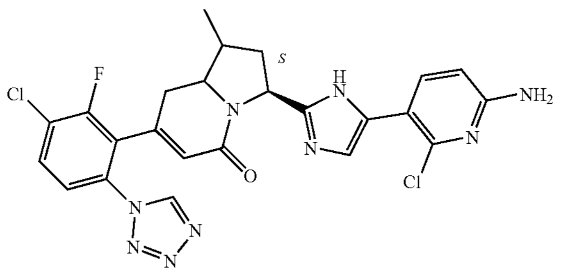

LC/MS: mass calculated for $C_{24}H_{20}Cl_2FN_9O$: 539.12, measured (ES, m/z): 540.10 $[M+H]^+$. $^1H$ NMR (300 MHz, DMSO-$d_6$) δ 11.77 (s, 1H), 9.85 (s, 1H), 7.92-8.10 (m, 2H), 7.72 (d, J=8.7 Hz, 1H), 6.99-7.07 (m, 1H), 6.36-6.48 (m, 1H), 6.25 (s, 2H), 5.72 (d, J=2.5 Hz, 1H), 4.98 (d, J=8.6 Hz, 1H), 3.20-3.31 (m, 1H), 2.27-2.35 (m, 2H), 2.01-2.12 (m, 1H), 1.81-1.94 (m, 1H), 0.98 (d, J=6.4 Hz, 3H). $^{19}F$ NMR (282 MHz, DMSO-$d_6$) δ−112.76.

Example 348 (3S)-3-(5-(6-Amino-2-fluoropyridin-3-yl)-1H-imidazol-2-yl)-7-(3-chloro-2-fluoro-6-(1H-tetrazol-1-yl)phenyl)-1-methyl-2,3,8,8a-tetrahydroindolizin-5(1H)-one

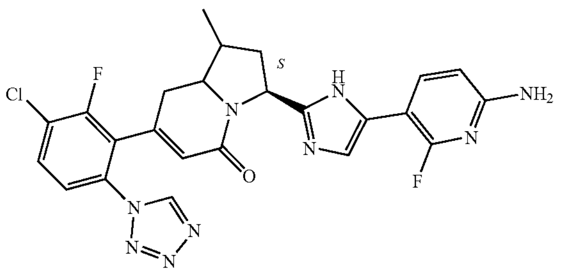

LC/MS: mass calculated for $C_{24}H_{20}ClF_2N_9O$: 523.14, measured (ES, m/z): 524.15 $[M+H]^+$. $^1H$ NMR (300 MHz, DMSO-$d_6$) δ 11.77 (s, 1H), 9.85 (s, 1H), 7.92-8.10 (m, 2H), 7.72 (d, J=8.7 Hz, 1H), 6.99-7.07 (m, 1H), 6.36-6.48 (m, 1H), 6.25 (s, 2H), 5.72 (d, J=2.5 Hz, 1H), 4.98 (d, J=8.6 Hz, 1H), 3.15-3.21 (m, 1H), 2.61-2.71 (m, 1H), 2.25-2.37 (m, 2H), 2.01-2.09 (m, 1H), 1.81-1.94 (m, 1H), 0.98 (d, J=6.4 Hz, 3H). $^{19}F$ NMR (282 MHz, DMSO-$d_6$) δ−70.78, −112.73.

Example 349 (3S)-3-(5-(6-Amino-2-chloropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one

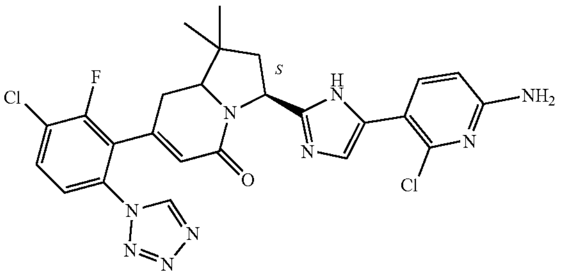

LC/MS: mass calculated for $C_{25}H_{22}Cl_2FN_9O$: 53.13, measured (ES, m/z): 576.10 $[M+Na]^+$. $^1H$ NMR (300 MHz, DMSO-$d_6$) δ 11.63 (s, 1H), 9.87 (s, 1H), 7.92-8.07 (m, 2H), 7.73 (d, J=8.6 Hz, 1H), 7.34 (d, J=1.9 Hz, 1H), 6.49 (d, J=8.5 Hz, 1H), 6.29 (s, 2H), 5.81 (d, J=2.5 Hz, 1H), 4.96 (t, J=5.8 Hz, 1H), 2.32-2.38 (m, 1H), 2.11-2.19 (m, 2H), 1.25 (s, 1H), 0.99 (s, 3H), 0.88 (s, 3H). $^{19}F$ NMR (282 MHz, DMSO-$d_6$) δ −73.40, −112.49.

Example 350 (3S)-3-(5-(6-Amino-2-fluoropyridin-3-yl)-1H-imidazol-2-yl)-7-(3-chloro-2-fluoro-6-(1H-tetrazol-1-yl)phenyl)-1,1-dimethyl-2,3,8,8a-tetrahydroindolizin-5(1H)-one

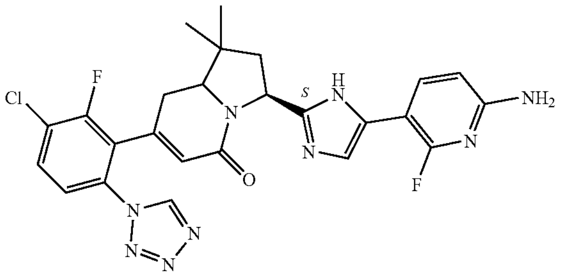

LC/MS: mass calculated for $C_{25}H_{22}ClF_2N_9O$: 537.16, measured (ES, m/z): 538.15 $[M+H]^+$. $^1H$ NMR (300 MHz, DMSO-$d_6$) δ 11.61 (s, 1H), 9.87 (s, 1H), 7.94-8.10 (m, 2H), 7.74 (d, J=8.6 Hz, 1H), 7.03 (s, 1H), 6.39 (d, J=9.1 Hz, 1H), 6.24 (s, 2H), 5.80 (s, 1H), 4.96 (d, J=8.7 Hz, 1H), 2.71-2.76 (m, 1H), 2.07-2.24 (m, 3H), 1.23-1.29 (m, 1H), 0.86 (s, 3H), 0.99 (s, 3H). $^{19}F$ NMR (282 MHz, DMSO-$d_6$) δ −70.81, −73.26, −112.47.

Example 351 (3S,8aR)-7-(3-Chloro-2-fluoro-6-(1H-tetrazol-1-yl)phenyl)-3-(5-(2-(trifluoromethyl)pyridin-4-yl)-1H-imidazol-2-yl)-2,3,8,8a-tetrahydroindolizin-5(1H)-one

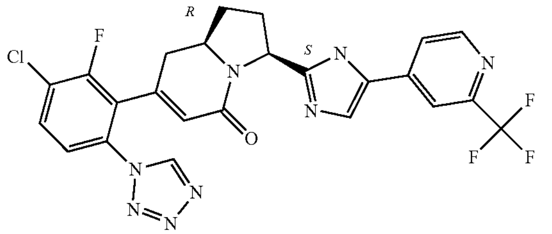

Step 1: 2-oxo-2-(2-(trifluoromethyl)pyridin-4-yl)ethyl (3S)-7-(6-amino-3-chloro-2-fluorophenyl)-5-oxo-1,2,3,5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (120 mg, 0.37 mmol, 1.0 equiv.) and $Cs_2CO_3$ (72 mg, 0.22 mmol, 0.6 equiv.) in DMF (2 mL) was maintained with stirring at room temperature for 10 min. 2-Bromo-1-(2-(trifluoromethyl)pyridin-4-yl)ethan-1-one (118 mg, 0.44 mmol, 1.2 equiv) was then added. The reaction mixture was stirred at room temperature overnight. The resulting mixture was poured into water (10 mL), filtered, and the solid was collected and dried to yield 2-oxo-2-(2-(trifluoromethyl)pyridin-4-yl)ethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{23}H_{18}ClF_4N_3O_4$: 511.09, measured: 534.11 $[M+Na]^+$.

Step 2: (3S)-7-(6-amino-3-chloro-2-fluorophenyl)-3-(5-(2-(trifluoromethyl)pyridin-4-yl)-1H-imidazol-2-yl)-2,3,8,8a-tetrahydroindolizin-5(1H)-one A mixture of (2-oxo-2-(2-(trifluoromethyl)pyridin-4-yl)ethyl (3S)-7-(6-amino-3-chloro-2-fluorophenyl)-5-oxo-1,2,3,5,8,8a-hexahydroindolizine-3-carboxylate (108 mg, 0.21 mmol, 1.0 equiv.) and $NH_4OAc$ (162 mg, 2.11 mmol, 10.0 equiv.) in AcOH (0.2 mL) and toluene (2 mL) was heated at 110° C. for 2 h with stirring. After being cooled to room temperature, the mixture was concentrated under reduced pressure and the residue was purified by flash column chromatography on silica gel (0-43% MeOH/DCM) to yield (3S)-7-(6-amino-3-chloro-2-fluorophenyl)-3-(5-(2-(trifluoromethyl)pyridin-4-yl)-1H-imidazol-2-yl)-2,3,8,8a-tetrahydroindolizin-5(1H)-one as a yellow solid. LC/MS: mass calculated for $C_{23}H_{18}ClF_4N_5O$: 491.11, measured: 492.10 $[M+H]^+$.

Step 3: (3S,8aR)-7-(3-chloro-2-fluoro-6-(1H-tetrazol-1-yl)phenyl)-3-(5-(2-(trifluoromethyl)pyridin-4-yl)-1H-imidazol-2-yl)-2,3,8,8a-tetrahydroindolizin-5(1H)-one To a solution of (3S)-7-(6-amino-3-chloro-2-fluorophenyl)-3-(5-(2-(trifluoromethyl)pyridin-4-yl)-1H-imidazol-2-yl)-2,3,8,8a-tetrahydroindolizin-5(1H)-one (98 mg, 0.20 mmol, 1.0 equiv.) in AcOH (5 mL) were added $TMSN_3$ (229 mg, 1.99 mmol, 10.0 equiv.) and trimethoxymethane (211 mg, 1.99 mmol, 10.0 equiv.). The mixture was heated at 60° C. for 8 h and then concentrated under reduced pressure. The residue was purified by prep-HPLC to yield (3S,8aR)-7-(3-chloro-2-fluoro-6-(1H-tetrazol-1-yl)phenyl)-3-(5-(2-(trifluoromethyl)pyridin-4-yl)-1H-imidazol-2-yl)-2,3,8,8a-tetrahydroindolizin-5(1H)-one as a white solid.

LC/MS: mass calculated for $C_{24}H_{17}ClF_4N_8O$: 544.11, measured (ES, m/z): 545.25 $[M+H]^+$. $^1H$ NMR (300 MHz, DMSO-$d_6$) δ 9.84 (s, 1H), 8.80 (d, J=5.2 Hz, 1H), 8.44-8.21 (m, 2H), 8.15-7.85 (m, 2H), 7.72 (d, J=8.7 Hz, 1H), 5.70 (d, J=2.6 Hz, 1H), 5.15 (d, J=9.2 Hz, 1H), 3.81-3.85 (m, 1H), 2.80-2.92 (m, 1H), 2.51-2.62 (m, 1H), 2.22-2.27 (m, 1H), 2.11-2.20 (m, 1H), 1.81-2.10 (m, 2H). $^{19}F$ NMR (282 MHz, DMSO-$d_6$) δ −66.62, −113.05.

Example 352 (3S,8aS)-3-(5-(6-Amino-2-chloropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

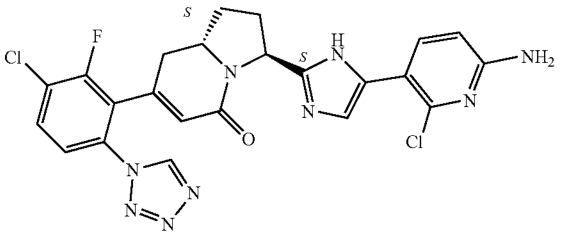

LC/MS: mass calculated for $C_{23}H_{18}Cl_2FN_9O$: 525.10, measured (ES, m/z): 548.10 $[M+Na]^+$. $^1H$ NMR (300 MHz, DMSO-$d_6$) δ 11.99 (s, 1H), 9.84 (s, 1H), 7.92-8.09 (m, 2H), 7.71 (d, J=8.7 Hz, 1H), 7.35 (d, J=2.0 Hz, 1H), 6.43-6.59 (m, 1H), 6.30 (s, 2H), 5.69 (d, J=2.6 Hz, 1H), 4.99 (t, J=7.1 Hz, 1H), 3.81-3.85 (m, 1H), 3.30-3.35 (m, 1H), 2.21-2.44 (m, 1H), 1.97-2.08 (m, 1H), 1.64-1.72 (m, 1H), 1.36-1.41 (m, 1H), 1.22-1.26 (m, 1H). $^{19}$F NMR (282 MHz, DMSO-$d_6$) δ −113.09.

Example 353 (3S,8aS)-7-(3-Chloro-2-fluoro-6-(1H-tetrazol-1-yl)phenyl)-3-(5-(2-(trifluoromethyl)pyridin-4-yl)-1H-imidazol-2-yl)-2,3,8,8a-tetrahydroindolizin-5(1H)-one

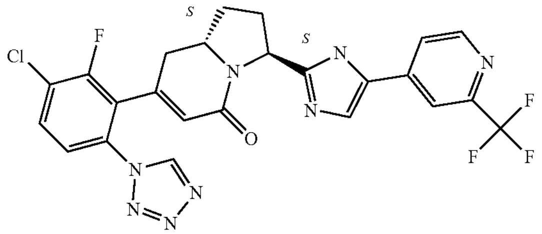

LC/MS: mass calculated for $C_{24}H_{17}ClF_4N_8O$: 544.11, measured (ES, m/z): 545.25 $[M+H]^+$. $^1$H NMR (300 MHz, DMSO-$d_6$) δ 9.84 (s, 1H), 8.80 (d, J=5.2 Hz, 1H), 8.44-8.21 (m, 2H), 8.15-7.85 (m, 2H), 7.72 (d, J=8.7 Hz, 1H), 5.70 (d, J=2.6 Hz, 1H), 5.15 (d, J=9.2 Hz, 1H), 4.04-4.14 (m, 1H), 2.80-2.92 (m, 1H), 2.51-2.62 (m, 1H), 2.22-2.27 (m, 1H), 2.11-2.20 (m, 1H), 1.81-2.10 (m, 2H). $^{19}$F NMR (282 MHz, DMSO-$d_6$) δ −66.62, −113.05.

Example 354 (3S,8aR)-3-(5-(6-Amino-2-chloropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

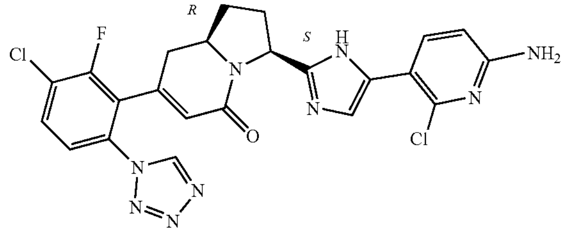

LC/MS: mass calculated for $C_{23}H_{18}Cl_2FN_9O$: 525.10, measured (ES, m/z): 548.10 $[M+Na]^+$. $^1$H NMR (300 MHz, DMSO-$d_6$) δ 11.99 (s, 1H), 9.84 (s, 1H), 7.92-8.09 (m, 2H), 7.71 (d, J=8.7 Hz, 1H), 7.35 (d, J=2.0 Hz, 1H), 6.43-6.59 (m, 1H), 6.30 (s, 2H), 5.69 (d, J=2.6 Hz, 1H), 4.99 (t, J=7.1 Hz, 1H), 4.04-4.14 (m, 1H), 3.30-3.35 (m, 1H), 2.21-2.44 (m, 1H), 1.97-2.08 (m, 1H), 1.64-1.72 (m, 1H), 1.36-1.41 (m, 1H), 1.22-1.26 (m, 1H). $^{19}$F NMR (282 MHz, DMSO-$d_6$) δ −113.09.

Example 355 Methyl (4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)phenyl)carbamate

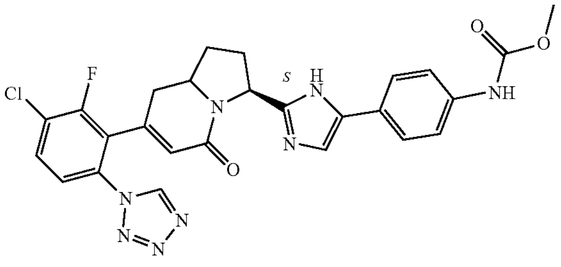

LC/MS: mass calculated for $C_{26}H_{22}ClFN_8O_3$: 548.15, measured (ES, m/z): 549.10 $[M+H]^+$. $^1$H NMR (400 MHz, DMSO-$d_6$) δ 9.91 (s, 1H), 9.83 (s, 1H), 7.93-8.02 (m, 2H), 7.69-7.73 (m, 3H), 7.58-7.60 (m, 2H), 5.72 (d, J=2.8 Hz, 1H), 5.19 (d, J=9.8 Hz, 1H), 3.62-3.75 (m, 1H), 3.72 (s, 3H), 3.05-3.14 (m, 1H), 2.89-3.11 (m, 1H), 2.41-2.57 (m, 1H), 2.05-2.34 (m, 2H), 1.94-2.01 (m, 1H). $^{19}$F NMR (376 MHz, DMSO-$d_6$) δ −112.69.

Example 356 (3R,8aR)-3-(5-(6-Amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

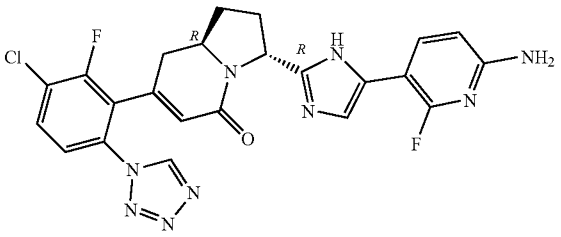

LC/MS: mass calculated for $C_{23}H_{18}ClF_2N_9O$: 509.13, measured (ES, m/z): 510.05 $[M+H]^+$. $^1$H NMR (300 MHz, DMSO-$d_6$) δ 11.95 (s, 1H), 9.84 (s, 1H), 7.83-8.11 (m, 2H), 7.71 (d, J=8.7 Hz, 1H), 7.04 (d, J=3.9 Hz, 1H), 6.39 (d, J=8.2 Hz, 1H), 6.27 (s, 1H), 5.69 (d, J=2.5 Hz, 1H), 4.99 (t, J=7.1 Hz, 1H), 3.60-3.71 (m, 1H), 3.61-3.71 (m, 1H), 2.11-2.20 (m, 3H), 1.87-1.92 (m, 2H). $^{19}$F NMR (282 MHz, DMSO-$d_6$) δ −70.73, −113.08.

Example 357 (3R,8aS)-3-(5-(6-Amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

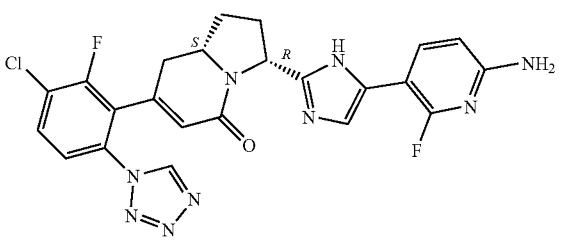

LC/MS: mass calculated for $C_{23}H_{18}ClF_2N_9O$: 509.13, measured (ES, m/z): 510.05 $[M+H]^+$. $^1H$ NMR (300 MHz, DMSO-$d_6$) δ 11.80 (s, 1H), 9.84 (s, 1H), 7.97-8.10 (m, 2H), 7.72 (d, J=8.7 Hz, 1H), 7.05 (d, J=3.9 Hz, 1H), 6.41 (d, J=8.2 Hz, 1H), 6.27 (s, 2H), 5.69 (d, J=2.5 Hz, 1H), 5.00 (d, J=8.3 Hz, 1H), 3.60-3.85 (m, 1H), 2.54-2.87 (m, 2H), 2.02-2.23 (m, 2H), 1.93-1.98 (m, 2H). $^{19}F$ NMR (282 MHz, DMSO-$d_6$) δ −70.78, −112.87.

Example 358 (3S,8aR)-3-(5-(6-Amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

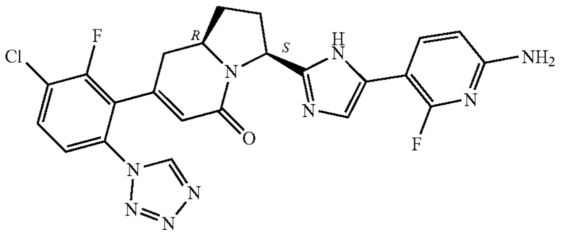

Step 1: 2-(6-acetamido-2-fluoropyridin-3-yl)-2-oxoethyl (3S)-7-(6-amino-3 chloro-2-fluorophenyl)-5-oxo-1,2,3,5,8,8a-hexahydroindolizine-3-carboxylate To a mixture of (3S)-7-(6-amino-3-chloro-2-fluorophenyl)-5-oxo-1,2,3,5,8,8a-hexahydroindolizine-3-carboxylic acid (180 mg, 0.55 mmol, 1.0 equiv.) and cesium carbonate (108 mg, 0.33 mmol, 0.6 equiv.) in N,N-dimethylformamide (5 mL) was added N-(5-(2-bromoacetyl)-6-fluoropyridin-2-yl)acetamide (183 mg, 0.67 mmol, 1.2 equiv.). The reaction mixture was stirred for 1 h at room temperature, then quenched with water and the solid was collected by filtration and dried under vacuum to yield 2-(6-acetamido-2-fluoropyridin-3-yl)-2-oxoethyl (3S)-7-(6-amino-3-chloro-2-fluorophenyl)-5-oxo-1,2,3,5,8,8a-hexahydroindolizine-3-carboxylate as a yellow solid. LC/MS: mass calculated for $C_{24}H_{21}ClF_2N_4O_5$: 518.12, measured: 519.10 $[M+H]^+$.

Step 2: N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl)acetamide To a solution of 2-(6-acetamido-2-fluoropyridin-3-yl)-2-oxoethyl (3S)-7-(6-amino-3-chloro-2-fluorophenyl)-5-oxo-1,2,3,5,8,8a-hexahydroindolizine-3-carboxylate (180 mg, 0.35 mmol, 1.0 equiv.) in toluene (5 mL) were added ammonium acetate (267 mg, 3.47 mmol, 10.0 equiv.) and acetic acid (0.5 mL). The reaction mixture was heated at 110° C. for 2 h. The excess solvent was removed under reduced pressure and the residue was purified by silica gel chromatography (0→100% EA/PE) to yield N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl)acetamide as a yellow solid. LC/MS: mass calculated for $C_{24}H_{21}ClF_2N_6O_2$: 498.14, measured: 499.15 $[M+H]^+$.

Step 3: N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide To a solution of N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl)acetamide (150 mg, 0.30 mmol, 1.0 equiv.) in glacial acetic acid (3 mL) were added azidotrimethylsilane (0.2 mL, 1.50 mmol, 5.0 equiv.) and trimethoxymethane (0.2 mL, 1.50 mmol, 5.0 equiv.). The reaction mixture was stirred at 50° C. overnight. The solvent was removed under reduced pressure and the residue was purified by silica gel chromatography (0→100% EA/PE) to yield N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide as a yellow solid. LC/MS: mass calculated for $C_{25}H_{20}ClF_2N_9O_2$: 551.14, measured: 574.15 $[M+Na]^+$.

Step 4: (3S,8aR)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide (110 mg, 0.20 mmol, 1.0 equiv) in tetrahydrofuran (4 mL) was added 4 N hydrochloric acid (1 mL). The reaction mixture was stirred at 50° C. for 4 h. The residue was purified by silica gel chromatography (0→100% EA/PE) to yield (3S)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid. The racemic mixture was separated by prep-chiral-HPLC separation. The collected fractions were combined and concentrated under vacuum to yield (3S,8aR)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC/MS: mass calculated for $C_{23}H_{18}ClF_2N_9O$: 509.13, measured (ES, m/z): 510.05 $[M+H]^+$. $^1H$ NMR (300 MHz, DMSO-$d_6$) δ 11.91 (s, 1H), 9.84 (s, 1H), 7.91-8.09 (m, 2H), 7.71 (d, J=8.7 Hz, 1H), 7.04 (s, 1H), 6.39 (d, J=8.2 Hz, 1H), 6.24 (s, 2H), 5.69 (d, J=2.4 Hz, 1H), 4.99 (t, J=7.1 Hz, 1H), 3.60-3.71 (m, 1H), 2.45-2.49 (m, 2H), 2.34-2.40 (m, 2H), 1.97-2.15 (m, 1H), 1.61-1.75 (m, 1H). $^{19}F$ NMR (282 MHz, DMSO-$d_6$) δ −70.76, −113.08.

Example 359 (3S,8aS)-3-(5-(6-Amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one

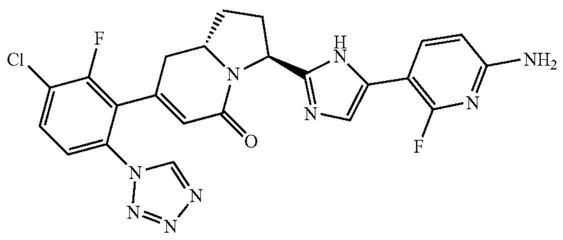 [SMILES: Nc1ccc(-c2cnc([C@@H]3CC[C@H]4CC(c5c(-n6cnnn6)ccc(Cl)c5F)=CC(=O)N43)[nH]2)c(F)n1]

LC/MS: mass calculated for $C_{23}H_{18}ClF_2N_9O$: 509.13, measured (ES, m/z): 510.05 $[M+H]^+$. $^1H$ NMR (300 MHz, DMSO-$d_6$) δ 11.91 (s, 1H), 9.84 (s, 1H), 7.91-8.09 (m, 2H), 7.71 (d, J=8.7 Hz, 1H), 7.04 (s, 1H), 6.39 (d, J=8.2 Hz, 1H), 6.24 (s, 2H), 5.69 (d, J=2.4 Hz, 1H), 4.99 (t, J=7.1 Hz, 1H), 4.04-4.14 (m, 1H), 2.45-2.49 (m, 2H), 2.34-2.40 (m, 2H), 1.97-2.15 (m, 1H), 1.61-1.75 (m, 1H). $^{19}F$ NMR (282 MHz, DMSO-$d_6$) δ −70.76, −113.08.

Example 360 (6S*,8aR*)-6-(5-(6-amino-2-fluoropyridin-3-yl)-1H-imidazol-2-yl)-2-(5-chloro-2-(1H-tetrazol-1-yl)phenyl)hexahydropyrrolo[1,2-a]pyrazine-1,4-dione

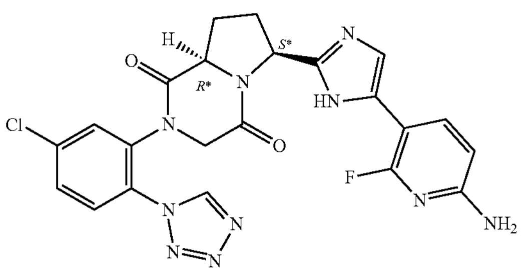 [SMILES: Nc1ccc(-c2cnc([C@@H]3CC[C@@H]4C(=O)N(c5cc(Cl)ccc5-n5cnnn5)CC(=O)N43)[nH]2)c(F)n1]

Step 1: Diethyl pyrrolidine-2,5-dicarboxylate

Diethyl-1-benzylpyrrolidine-2,5-dicarboxylate (5.0 g, 16.37 mmol) and Pd/C (500 mg) were dissolved in MeOH (50 mL) and the mixture was stirred at room temperature under $H_2$ for 2 h. The solid was filtered, and the solvent was removed under vacuum to yield diethyl pyrrolidine-2,5-dicarboxylate as a white solid. LC/MS: mass calculated for $C_{10}H_{17}NO_4$: 215.12, measured: 228.25 $[M+Na]^+$.

Step 2: Diethyl 1-(((benzyloxy)carbonyl)glycyl) pyrrolidine-2,5-dicarboxylate

Diethyl pyrrolidine-2,5-dicarboxylate (3.2 g, 14.86 mmol, 1.0 equiv.), EDCl (4.3 g, 22.30 mmol, 1.5 equiv.) and ((benzyloxy)carbonyl)glycine (3.7 g, 17.84 mmol, 1.2 equiv.) were dissolved in pyridine (60.0 mL) and the mixture was stirred at room temperature for 2 h. The solvent was removed under reduced pressure and the residue was purified by silica gel column chromatography (0→11% MeOH/DCM) to yield diethyl-1-(((benzyloxy)carbonyl)glycyl)pyrrolidine-2,5-dicarboxylate as a yellow solid. LC/MS: mass calculated for $C_{20}H_{26}N_2O_7$: 406.17, measured: 407.30 $[M+H]^+$.

Step 3: Ethyl 1,4-dioxooctahydropyrrolo[1,2-a]pyrazine-6-carboxylate

Diethyl-1-(((benzyloxy)carboyl)glycyl)pyrrolidine-2,5-dicarboxylate (5.1 g, 12.54 mmol) and Pd/C (510 mg) were dissolved in EtOH (50.0 mL) under $H_2$ and stirred at 50° C. for 3 h. The solid was filtered and the solvent removed under vacuum. The residue was purified silica gel column chromatography (0→11% MeOH/DCM) to yield ethyl 1,4-dioxooctahydropyrrolo[1,2-a]pyrazine-6-carboxylate as a white solid. LC/MS: mass calculated for $C_{10}H_{14}N_2O_4$: 226.23, measured (ES, m/z): 227.25 $[M+H]^+$.

Step 4: Ethyl 2-(5-chloro-2-nitrophenyl)-1,4-dioxooctahydropyrrolo[1,2-a]pyrazine-6-carboxylate tert-BuONa (630.8 mg, 6.56 mmol, 1.1 equiv.) was added to a solution of ethyl 1,4-dioxooctahydropyrrolo[1,2-a]pyrazine-6-carboxylate (1.4 g, 5.96 mmol, 1.0 equiv.) in DMA (12.0 mL) at 0° C. and the reaction mixture was stirred for 30 minutes. A solution of 4-chloro-2-fluoro-1-nitrobenzene (1.2 g, 7.16 mmol, 1.2 equiv.) in DMA (8.0 mL) was then added, the reaction mixture was stirred at room temperature for 2 h, then diluted with ice water (5 mL) and extracted with EA (150 mL). The organic layers were dried over anhydrous sodium sulfate, filtered, and concentrated under reduced pressure. The residue was purified by normal phase chromatography on silica gel (0→11% MeOH/DCM) to yield ethyl-2-(2-amino-5-chlorophenyl)-1,4-dioxooctahydropyrrolo[1,2-a]pyrazine-6-carboxylate as a yellow solid. LC/MS: mass calculated for $C_{16}H_{16}ClN_3O_6$: 381.07, measured (ES, m/z): 382.20 $[M+H]^+$.

Step 5: 2-(5-Chloro-2-nitrophenyl)-1,4-dioxooctahydropyrrolo[1,2-a]pyrazine-6-carboxylic acid Ethyl-2-(2-amino-5-chlorophenyl)-1,4-dioxooctahydropyrrolo[1,2-a]pyrazine-6-carboxylate (319 mg, 0.84 mmol, 1.0 equiv.), LiBr (726 mg, 8.34 mmol, 10.0 equiv.) and $Et_3N$ (253 mg, 2.51 mmol, 3.0 equiv.) were added to $CH_3CN$ (10.0 mL) and water (0.1 mL). The resulting mixture was stirred at room temperature for 2 h. Then the solvent was removed under vacuum and the pH was adjusted to 6 with HCl (2 M), and the resulting mixture extracted with EA (50 mL). The organic layer was separated and dried with $Na_2SO_4$, concentrated under vacuum to yield 2-(5-chloro-2-nitrophenyl)-1,4-dioxooctahydropyrrolo[1,2-a]pyrazine-6-carboxylic acid as a yellow solid. LC/MS: mass calculated for $C_{14}H_{12}ClN_3O_6$: 353.04, measured (ES, m/z): 354.00 $[M+H]^+$.

Step 6: 2-(6-Acetamido-2-fluoropyridin-3-yl)-2-oxoethyl 2-(5-chloro-2-nitrophenyl)-1,4-dioxooctahydropyrrolo[1,2-a]pyrazine-6-carboxylate 2-(5-Chloro-2-nitrophenyl)-1,4-dioxooctahydropyrrolo[1,2-a]pyrazine-6-carboxylic acid (200 mg, 0.56 mmol, 1.0 equiv.) and $K_2CO_3$ (78 mg, 0.56 mmol, 1.0 equiv.) were dissolved in $CH_3CN$ (8 mL), and the mixture was stirred at room temperature for 0.5 h. A solution of N-(5-(2-bromoacetyl)-6-fluoropyridin-2-yl)acetamide (171 mg, 0.62 mmol, 1.1 equiv.) in $CH_3CN$ (2.0 mL) was then added, the resulting mixture was stirred for another 2 h at room temperature and concentrated under reduced pressure. The residue was purified by normal phase chromatography on silica gel (EA/PE, 0→67%) to yield 2-(6-acetamido-2-fluoropyridin-3-yl)-2-oxoethyl 2-(5-chloro-2-nitrophenyl)-1,4-dioxooctahydropyrrolo[1,2-a]pyrazine-6-carboxylate as a yellow solid. LC/MS: mass calculated for $C_{23}H_{19}ClFN_5O_8$: 547.09, measured (ES, m/z): 570.20 $[M+Na]^+$.

Step 7: N-(5-(2-(2-(5-chloro-2-nitrophenyl)-1,4-dioxooctahydropyrrolo[1,2-a]pyrazin-6-yl)-1H-imidazol-5-yl)-6-fluoropyridin-2-yl)acetamide 2-(6-Acetamido-2-fluoropyridin-3-yl)-2-oxoethyl 2-(5-chloro-2-nitrophenyl)-1,4-dioxooctahydropyrrolo[1,2-a]pyrazine-6-carboxylate (170 mg, 0.31 mmol, 1.0 equiv.), ammonium acetate (478 mg, 6.2 mmol, 20.0 equiv.) and acetic acid (2.0 mL) were added to toluene (20.0 mL), and the reaction mixture was stirred at 90° C. for 1.5 h. The solvent was removed under vacuum and the residue was purified by silica gel column with (0→10% MeOH/DCM) to yield N-(5-(2-(2-(5-chloro-2-nitrophenyl)-1,4-dioxooctahydropyrrolo[1,2-a]pyrazin-6-yl)-1H-imidazol-5-yl)-6-fluoropyridin-2-yl)acetamide as a yellow solid. LC/MS: mass calculated for $C_{23}H_{19}ClFN_7O_5$: 527.11, measured (ES, m/z): 528.10 $[M+H]^+$.

Step 8: N-(5-(2-(2-(2-amino-5-chlorophenyl)-1,4-dioxooctahydropyrrolo[1,2-a]pyrazin-6-yl)-1H-imidazol-5-yl)-6-fluoropyridin-2-yl)acetamide N-(5-(2-(2-(5-chloro-2-nitrophenyl)-1,4-dioxooctahydropyrrolo[1,2-a]pyrazin-6-yl)-1H-imidazol-5-yl)-6-fluoropyridin-2-yl)acetamide (140 mg, 0.27 mmol, 1.0 equiv.), Fe (148 mg, 2.65 mmol, 10.0 equiv.) and $NH_4Cl$ (42 mg, 0.80 mmol, 3.0 equiv.) were added to MeOH (10.0 mL) and water (2.0 mL). The mixture was stirred at 60° C. for 30 min. The solid was filtered and the solvent was removed under vacuum to yield N-(5-(2-(2-(2-amino-5-chlorophenyl)-1,4-dioxooctahydropyrrolo[1,2-a]pyrazin-6-yl)-1H-imidazol-5-yl)-6-fluoropyridin-2-yl)acetamide as a residue, which was used in the next step without further purification. LC/MS: mass calculated for $C_{23}H_{21}ClFN_7O_3$: 497.14, measured (ES, m/z): 498.30 $[M+H]^+$.

Step 9: N-(5-(2-(2-(5-chloro-2-(1H-tetrazol-1-yl)phenyl)-1,4-dioxooctahydro pyrrolo[1,2-a]pyrazin-6-yl)-1H-imidazol-5-yl)-6-fluoropyridin-2-yl)acetamide N-(5-(2-(2-(2-amino-5-chlorophenyl)-1,4-dioxooctahydropyrrolo[1,2-a]pyrazin-6-yl)-1H-imidazol-5-yl)-6-fluoropyridin-2-yl)acetamide (117 mg, 0.24 mmol, 1.0 equiv.), $TMSN_3$ (135 mg, 1.18 mmol, 5.0 equiv.) and trimethoxymethane (124 mg, 1.18 mmol, 5.0 equiv.) were dissolved in AcOH (5.0 mL), and the mixture was stirred at room temperature overnight. The solvent was removed under vacuum and the residue was purified by reverse phase chromatography on C18 column with ($CH_3CN/H_2O$ (0.05% TFA): 0→60%) to yield N-(5-(2-(2-(5-chloro-2-(1H-tetrazol-1-yl)phenyl)-1,4-dioxooctahydropyrrolo[1,2-a]pyrazin-6-yl)-1H-imidazol-5-yl)-6-fluoropyridin-2-yl)acetamide as a yellow solid. LC/MS: mass calculated for $C_{24}H_{20}ClFN_{10}O_3$: 550.14, measured (ES, m/z): 551.35 $[M+H]^+$.

Step 10: (6S',8aR*)-6-(5-(6-Amino-2-fluoropyridin-3-yl)-1H-imidazol-2-yl)-2-(5-chloro-2-(1H-tetrazol-1-yl)phenyl)hexahydropyrrolo[1,2-a]pyrazine-1,4-dione N-(5-(2-(2-(5-chloro-2-(1H-tetrazol-1-yl)phenyl)-1,4-dioxooctahydropyrrolo[1,2-a]pyrazin-6-yl)-1H-imidazol-5-yl)-6-fluoropyridin-2-yl)acetamide (60.0 mg, 0.109 mmol) was dissolved in HCl (2 M, 2.5 mL) and THE (2.5 mL), and the mixture was stirred at 50° C. for 1 h. The solvent was removed under reduced pressure and the residue was purified by reverse phase chromatography on C18 column with $MeCN/H_2O$ (0.05% TFA) (0-60%) to yield 6-(5-(6-amino-2-fluoropyridin-3-yl)-1H-imidazol-2-yl)-2-(5-chloro-2-(1H-tetrazol-1-yl)phenyl)hexahydropyrrolo[1,2-a]pyrazine-1,4-dione as a yellow solid, which was further purified by chiral-HPLC (Column: CHIRAL ART Cellulose-SB, 2*25 cm, 5 um; Mobile Phase A: MTBE (0.5% 2M $NH_3$-MeOH)-HPLC, Mobile Phase B: EtOH—HPLC; Flow rate: 20 mL/min; Gradient: 50 B to 50 B in 11 min; 220/254 nm; RT1:5.525; RT2:10.237; Injection Volume: 3 ml; Number Of Runs: 2) to yield (6S',8aR*)-6-(5-(6-amino-2-fluoropyridin-3-yl)-1H-imidazol-2-yl)-2-(5-chloro-2-(1H-tetrazol-1-yl)phenyl)hexahydropyrrolo[1,2-a]pyrazine-1,4-dione as pink solid and (6R',8aR*)-6-(5-(6-amino-2-fluoropyridin-3-yl)-1H-imidazol-2-yl)-2-(5-chloro-2-(1H-tetrazol-1-yl)phenyl)hexahydropyrrolo[1,2-a]pyrazine-1,4-dione as an off-white solid.

LC/MS calculated for $C_{22}H_{18}ClFN_{10}O_2$ 508.1, measured 509.2 ($MH^+$). $^1H$ NMR (400 MHz, DMSO-$d_6$) δ 9.74 (s, 1H), 7.70-7.96 (m, 5H), 7.35-7.49 (m, 1H), 6.43 (dd, J=8.3, 2.0 Hz, 1H), 5.13 (s, 1H), 4.79-4.92 (m, 1H), 4.30-4.70 (m, 1H), 2.12-2.21 (m, 2H), 1.90-2.08 (m, 1H), 1.40-1.60 (m, 1H)/19F NMR (376 MHz, DMSO-$d_6$) δ −69.95, −73.69.

Example 361 (3S,8aR)-7-(3-chloro-2-fluoro-6-(1H-tetrazol-1-yl)phenyl)-3-(5-(2,3-dihydro-[1,4]dioxino[2,3-b]pyridin-8-yl)-1H-imidazol-2-yl)-2,3,8,8a-tetrahydroindolizin-5(1H)-one

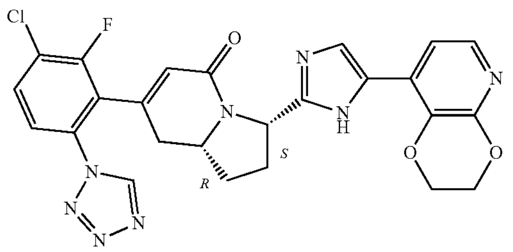

Step 1. (2,3-dihydro-[1,4]dioxino[2,3-b]pyridin-8-yl)boronic acid

To a mixture of 8-chloro-2,3-dihydro-[1,4]dioxino[2,3-b]pyridine (50 mg, 0.291 mmol, 1.0 equiv.) and 4,4,4',4',5,5,5',5'-octamethyl-2,2'-bi(1,3,2-dioxaborolane) (147.999 mg, 0.583 mmol, 2.0 equiv.) in 1,4-dioxane (1 mL) was added potassium acetate (85.798 mg, 0.874 mmol, 3.0 equiv.), X-Phos Pd G2 (11.464 mg, 0.031 mmol, 0.05 equiv.) and X-Phos (6.946 mg, 0.015 mmol, 0.05 equiv.). The reaction mixture was stirred at 100° C. for 3 h under $N_2$. The resulting mixture containing (2,3-dihydro-[1,4]dioxino[2,3-b]pyridin-8-yl)boronic acid was used in the next step without any further purification. LC/MS: mass calculated, for $C_7H_8BNO_4$: 181.05, measured: 182.10 $[M+H]^+$.

Step 2. (3S)-7-(6-amino-3-chloro-2-fluorophenyl)-3-(5-(2,3-dihydro-[1,4]dioxino[2,3-b]pyridin-8-yl)-1H-imidazol-2-yl)-2,3,8,8a-tetrahydroindolizin-5(1H)-one To a mixture of (2,3-dihydro-[1,4]dioxino[2,3-b]pyridin-8-yl)boronic acid (500 mg) in 1,4-dioxane (10 mL) was added (3S)-7-(6-amino-3-chloro-2-fluorophenyl)-3-(5-iodo-1H-imidazol-2-yl)-2,3,8,8a-tetrahydroindolizin-5(1H)-one (100 mg, 0.212 mmol, 1.0 equiv.), potassium carbonate (87.716 mg, 0.635 mmol, 3.0 equiv.), 1,1'bBis (di-t-butylphosphino)ferrocene palladium dichloride (13.788 mg, 0.021 mmol, 0.1 equiv.) and water (1 mL). The resulting mixture was maintained under nitrogen and stirred at 100° C. for 2 h, then cooled to room temperature. Water was added, the mixture was extracted with EA. The combined extracts were dried over anhydrous $Na_2SO_4$, then concentrated. The residue was purified by silica gel chromatography with MeOH/DCM (0%-8%) to yield (3S)-7-(6-amino-3-chloro-2-fluorophenyl)-3-(5-(2,3-dihydro-[1,4]dioxino[2,3-b]pyridin-8-yl)-1H-imidazol-2-yl)-2,3,8,8a-tetrahydroindolizin-5(1H)-one as a brown solid. LC/MS: mass calculated, for $C_{24}H_{21}ClFN_5O_3$: 481.13, measured: 482.10 $[M+H]^+$.

Step 3. (3S,8aR)-7-(3-chloro-2-fluoro-6-(1H-tetrazol-1-yl)phenyl)-3-(5-(2,3-dihydro-[1,4]dioxino[2,3-b]pyridin-8-yl)-1H-imidazol-2-yl)-2,3,8,8a-tetrahydroindolizin-5(1H)-one To a mixture of (3S)-7-(6-amino-3-chloro-2-fluorophenyl)-3-(5-(2,3-dihydro-[1,4]dioxino[2,3-b]pyridin-8-yl)-1H-imidazol-2-yl)-2,3,8,8a-tetrahydroindolizin-5(1H)-one (50 mg, 0.104 mmol, 1.0 equiv.) in acetic acid (5 mL) were added azidotrimethylsilane (2.5 mL) and trimethoxymethane (2.5 mL). The reaction mixture was stirred overnight at 50° C. The resulting mixture was concentrated under vacuum. The residue was purified by HPLC to yield (3S,8aR)-7-(3-chloro-2-fluoro-6-(1H-tetrazol-1-yl)phenyl)-3-(5-(2,3-dihydro-[1,4]dioxino[2,3-b]pyridin-8-yl)-1H-imidazol-2-yl)-2,3,8,8a-tetrahydroindolizin-5(1H)-one as a white solid.

LC/MS: mass calculated for $C_{25}H_{20}ClFN_8O_3$: 534.13, measured (ES, m/z): 535.10 $[M+H]^+$. $^1H$ NMR (400 MHz, Methanol-$d_4$) δ 9.57 (s, 1H), 7.78-7.84 (m, 1H), 7.51-7.71 (m. 4H), 5.73 (s, 1H), 5.12-5.25 (m, 1H), 4.35-4.58 (m, 4H), 3.83-3.97 (m, 1H), 2.73-2.98 (m, 1H), 2.56-2.67 (m, 1H), 2.13-2.41 (m, 3H), 1.97-2.11 (m, 1H). $^{19}F$ NMR (376 MHz, Methanol-$d_4$) δ −113.44.

Example 362 (3S,8aR*)-3-(5-(1H-pyrrolo[2,3-b]pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

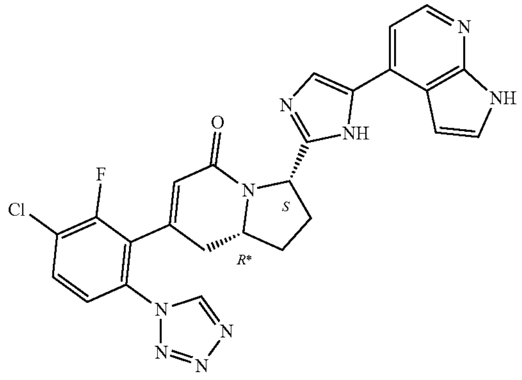

To a mixture of (3S)-3-(5-(1H-pyrrolo[2,3-b]pyridin-4-yl)-1H-imidazol-2-yl)-7-(6-amino-3-chloro-2-fluorophenyl)-2,3,8,8a-tetrahydroindolizin-5(1H)-one (90 mg, 0.194 mmol, 1.0 equiv.) in acetic acid (5 mL) were added azidotrimethylsilane (2.5 mL) followed by trimethoxymethane (2.5 mL). The reaction mixture was stirred at 50° C. overnight. The resulting mixture was concentrated under vacuum. The residue was purified by flash column chromatography on silica gel with MeOH/DCM (0-15%) to yield racemic product, which was further purified by chiral HPLC with (Hex:DCM=3:1)(0.1% DEA):EtOH=70:30 to yield (3S,8a*R)-3-(5-(1H-pyrrolo[2,3-b]pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid and (3S,8a*S)-3-(5-(1H-pyrrolo[2,3-b]pyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC/MS calculated for $C_{25}H_{19}ClFN_9O$: 515.15, measured 516.15 (MH)+. $^1H$ NMR (400 MHz, Methanol-$d_4$) δ 9.56 (s, 1H), 8.15 (d, J=5.2 Hz, 1H), 7.74-7.84 (m, 1H), 7.61 (s, 1H), 7.53 (dd, J=8.7, 1.6 Hz, 1H), 7.36-7.48 (m, 2H), 6.85 (d, J=3.6 Hz, 1H), 5.72 (d, J=2.8 Hz, 1H), 5.16-5.22 (m, 1H), 3.83-3.95 (m, 1H), 2.87-3.03 (m, 1H), 2.56-2.66 (m, 1H), 2.18-2.38 (m, 2H), 2.03-2.16 (m, 1H). $^{19}F$ NMR (376 MHz, Methanol-$d_4$) δ −113.29.

Example 363 (3S)-3-(5-(6-Amino-2-fluoropyridin-3-yl)-1H-imidazol-2-yl)-7-(3-chloro-2-fluoro-6-(1H-pyrazol-5-yl)phenyl)-2,3,8,8a-tetrahydroindolizin-5(1H)-one

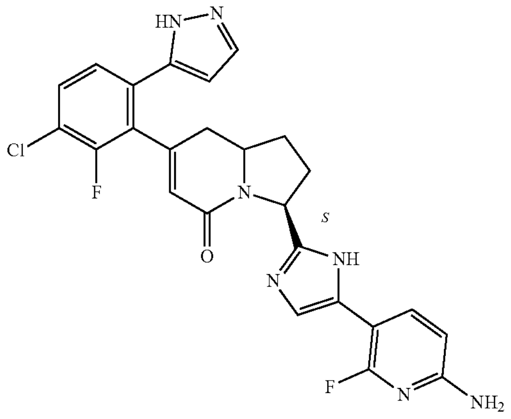

Step 1: Ethyl (3S)-7-(6-Bromo-3-chloro-2-fluorophenyl)-5-oxo-1,2,3,5,8,8a-hexahydroindolizine-3-carboxylate To a mixture of ethyl (3S)-7-(6-amino-3-chloro-2-fluorophenyl)-5-oxo-1,2,3,5,8,8a-hexahydroindolizine-3-carboxylate (1.0 g, 2.83 mmol, 1.0 equiv.) and $CuBr_2$ (633 mg, 2.83 mmol, 1.0 equiv.) in ACN (15 mL) was added at 0° C. tert-butyl nitrite (438 mg, 4.24 mmol, 1.5 equiv.). The resulting mixture was maintained under nitrogen and stirred at room temperature for 1 h. The reaction was quenched with water (100 mL). The resulting mixture was extracted with ethyl acetate (3×100 mL). The organic layers were combined, dried over anhydrous sodium sulfate, filtered, and concentrated. The residue was purified by silica gel chromatography (0-55% ethyl acetate/petroleum ether) to yield the ethyl (3S)-7-(6-bromo-3-chloro-2-fluorophenyl)-5-oxo-1,2,3,5,8,8a-hexahydroindolizine-3-carboxylate as a yellow solid. LC/MS: mass calculated for $C_{17}H_{16}BrClFNO_3$, measured: 416.15 [M+H], 418.15 $[M+H+2]^+$.

Step 2: (3S)-7-(6-Bromo-3-chloro-2-fluorophenyl)-5-oxo-1,2,3,5,8,8a-hexahydroindolizine-3-carboxylic acid To a solution of ethyl (3S)-7-(6-bromo-3-chloro-2-fluorophenyl)-5-oxo-1,2,3,5,8,8a-hexahydroindolizine-3-carboxylate (490 mg, 1.17 mmol, 1.0 equiv.) in THE/$H_2O$ (3:1, 8 mL) was added $LiOH \cdot H_2O$ (99 mg, 2.35 mmol, 2.0 equiv.). The resulting mixture was stirred at room temperature for 2 h. The reaction was concentrated and adjusted pH to 2.0-3.0 with 1N HCl. The resulting mixture was extracted with ethyl acetate (3×100 mL). The organic layers were combined, dried over anhydrous sodium sulfate, filtered and concentrated to yield the (3S)-7-(6-bromo-3-chloro-2-fluorophenyl)-5-oxo-1,2,3,5,8,8a-hexahydroindolizine-3-carboxylic acid as a yellow solid. LC/MS: mass calculated for $C_{15}H_{12}BrClFNO_3$: 386.97, measured: 388.10 $[M+H]^+$, 390.10 $[M+H+2]^+$.

Step 3: 2-(6-Amino-2-fluoropyridin-3-yl)-2-oxoethyl (3S)-7-(6-bromo-3-chloro-2-fluorophenyl)-5-oxo-1,2,3,5,8,8a-hexahydroindolizine-3-carboxylate To a solution of (3S)-7-(6-bromo-3-chloro-2-fluorophenyl)-5-oxo-1,2,3,5,8,8a-hexahydroindolizine-3-carboxylic acid (560 mg, 1.44 mmol, 1.0 equiv.) in DMF (8 mL) was added $K_2CO_3$ (199 mg, 1.44 mmol, 1.0 equiv), the mixture was stirred at room temperature for 20 min. 1-(6-Amino-2-fluoropyridin-3-yl)-2-bromoethan-1-one (504 mg, 2.16 mmol, 1.5 equiv.) was then added. The resulting mixture was stirred at room temperature for 3 h. The reaction was quenched with water (100 mL), extracted with ethyl acetate (3×100 mL). The organic layers were wash with water and brine, combined, dried over anhydrous sodium sulfate, filtered, and concentrated. The residue was purified by silica gel chromatography (0-20% ethyl DCM/MeOH) to yield the 2-(6-amino-2-fluoropyridin-3-yl)-2-oxoethyl (3S)-7-(6-bromo-3-chloro-2-fluorophenyl)-5-oxo-1,2,3,5,8,8a-hexahydroindolizine-3-carboxylate as a yellow solid. LC/MS: mass calculated for $C_{22}H_{17}BrClF_2N_3O_4$: 539.01, measured: 540.00 $[M+H]^+$, 542.00 $[M+H+2]^+$.

Step 4: (3S)-3-(4-(6-Amino-2-fluoropyridin-3-yl)-1H-imidazol-2-yl)-7-(6-bromo-3-chloro-2-fluorophenyl)-2,3,8,8a-tetrahydroindolizin-5(1H)-one To a solution of 2-(6-amino-2-fluoropyridin-3-yl)-2-oxoethyl (3S)-6-(6-bromo-3-chloro-2-fluorophenyl)-5-oxo-1,2,3,5,8,8a-hexahydroindolizine-3-carboxylate (810 mg, 1.49 mmol, 1.0 equiv.) in toluene/AcOH (10:1, 22 mL) was added $NH_4OAc$ (1.2 g, 15.56 mmol, 10.0 equiv.). The resulting mixture was maintained under nitrogen and stirred at 110° C. for 1 h. The reaction was concentrated, and the residue was purified by silica gel chromatography (0-100% ethyl acetate/petroleum ether) to yield the (3S)-3-(4-(6-amino-2-fluoropyridin-3-yl)-1H-imidazol-2-yl)-7-(6-bromo-3-chloro-2-fluorophenyl)-2,3,8,8a-tetrahydroindolizin-5(1H)-one as a yellow solid. LC/MS: mass calculated for $C_{22}H_{17}BrClF_2N_5O$: 519.03, measured: 520.00 $[M+H]^+$, 521.95 $[M+H+2]^+$.

Step 5: (3S)-3-(4-(6-Amino-2-fluoropyridin-3-yl)-1H-imidazol-2-yl)-7-(3-chloro-2-fluoro-6-(1-(tetrahydro-2H-pyran-2-yl)-1H-pyrazol-5-yl)phenyl)-2,3,8,8a-tetrahydroindolizin-5(1H)-one To a solution of (3S)-3-(4-(6-amino-2-fluoropyridin-3-yl)-1H-imidazol-2-yl)-7-(6-bromo-3-chloro-2-fluorophenyl)-2,3,8,8a-tetrahydroindolizin-5(1H)-one (100 mg, 0.19 mmol, 1.0 equiv.) in 1,4-dioxane/$H_2O$ (4:1, 5 mL) were added 1-(tetrahydro-2H-pyran-2-yl)-4-(4,4,5,5-tetramethyl-1,3,2-dioxaborolan-2-yl)-1H-pyrazole (267 mg, 0.96 mmol, 5.0 equiv.), $Cs_2O_3$ (125 mg, 0.38 mmol, 2.0 equiv.), and $Pd(PPh_3)_4$ (22 mg, 0.01 mmol, 0.1 equiv.). The resulting mixture was maintained under nitrogen and stirred at 100° C. for 3 h. After cooling to room temperature, the reaction was quenched with water (50 mL). The resulting mixture was extracted with ethyl acetate (3×50 mL). The organic layers were combined, dried over anhydrous sodium sulfate, filtered, and concentrated. The residue was purified by silica gel chromatography (0-20% ethyl acetate/petroleum ether) to yield the (3S)-3-(5-(6-amino-2-fluoropyridin-3-yl)-1H-imidazol-2-yl)-7-(3-chloro-2-fluoro-6-(1-(tetrahydro-2H-pyran-2-yl)-1H-pyrazol-4-yl)phenyl)-2,3,8,8a-tetrahydroindolizin-5(1H)-one as a yellow oil. LC/MS: mass calculated for $C_{30}H_{28}ClF_2N_7O_2$: 591.20, measured: 592.15 $[M+H]^+$.

Step 6: (3S)-3-(4-(6-Amino-2-fluoropyridin-3-yl)-1H-imidazol-2-yl)-7-(3-chloro-2-fluoro-6-(1H-pyrazol-5-yl)phenyl)-2,3,8,8a-tetrahydroindolizin-5(1H)-one To a solution of (3S)-3-(5-(6-amino-2-fluoropyridin-3-yl)-1H-imidazol-2-yl)-7-(3-chloro-2-fluoro-6-(1-(tetrahydro-2H-pyran-2-yl)-1H-pyrazol-4-yl)phenyl)-2,3,8,8a-tetrahydroindolizin-5(1H)-one (100 mg, 0.16 mmol, 1.0 equiv.) in DCM (5 mL) at 0° C. was added TFA (1 mL). The resulting mixture was stirred at room temperature for 3 h. The reaction was concentrated and purified by reverse phase chromatography on C18 column (0-70% ACN/Water-0.05% $NH_4HCO_3$) to yield the (3S)-3-(5-(6-amino-2-fluoropyridin-3-yl)-1H-imidazol-2-yl)-7-(3-chloro-2-fluoro-6-(1H-pyrazol-4-yl)phenyl)-2,3,8,8a-tetrahydroindolizin-5(1H)-one as a white solid.

LC/MS: mass calculated for $C_{25}H_{20}ClF_2N_7O$: 507.14, measured: 508.10 $[M+H]^+$. $^1H$ NMR (400 MHz, DMSO-$d_6$) δ13.09 (s, 1H), 12.00 (br, 1H), 7.99 (t, J=9.3 Hz, 1H), 7.75 (s, 1H), 7.64 (t, J=7.9 Hz, 1H), 7.56 (d, J=8.7 Hz, 1H), 7.13 (s, 1H), 6.56 (s, 1H), 6.38 (dd, J=8.2, 2.1 Hz, 1H), 6.32-6.35 (m, 2H), 5.75 (s, 1H), 5.08 (d, J=8.6 Hz, 1H), 3.96-4.00 (m, 1H), 2.67-2.80 (m, 1H), 2.36-2.46 (m, 1H), 2.11-2.23 (m, 1H), 1.92-2.11 (m, 3H). $^{19}F$ NMR (376 MHz, DMSO-$d_6$) δ−70.51, −73.44, −116.74.

Example 364 (3S)-3-(4-(6-Amino-2-fluoropyridin-3-yl)-1H-imidazol-2-yl)-7-(3-chloro-2-fluoro-6-(1H-imidazol-5-yl)phenyl)-2,3,8,8a-tetrahydroindolizin-5(1H)-one

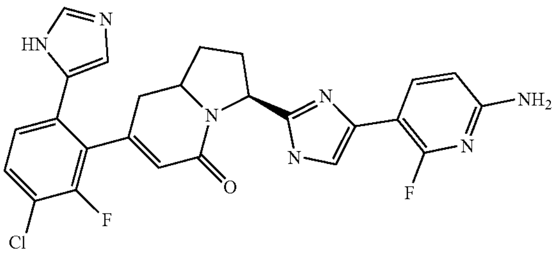 [SMILES: Nc1ccc(-c2c[nH]c([C@@H]3CCC4CC(c5c(-c6cnc[nH]6)ccc(Cl)c5F)=CC(=O)N43)n2)c(F)n1]

Step 1: (3S)-3-(4-(6-Amino-2-fluoropyridin-3-yl)-1H-imidazol-2-yl)-7-(3-chloro-2-fluoro-6-(1-trityl-1H-imidazol-5-yl)phenyl)-2,3,8,8a-tetrahydroindolizin-5(1H)-one To a solution of (3S)-3-(4-(6-amino-2-fluoropyridin-3-yl)-1H-imidazol-2-yl)-7-(6-bromo-3-chloro-2-fluorophenyl)-2,3,8,8a-tetrahydroindolizin-5(1H)-one (100 mg, 0.19 mmol, 1.0 equiv.) in 1,4-dioxane/$H_2O$ (4:1, 5 mL) were added (1-trityl-1H-imidazol-5-yl)boronic acid (340 mg, 0.96 mmol, 5.0 equiv.), $Cs_2O_3$ (125 mg, 0.38 mmol, 2.0 equiv.), and $Pd(PPh_3)_4$ (22 mg, 0.01 mmol, 0.1 equiv.). The resulting mixture was maintained under nitrogen and stirred at 100° C. for 3 h. After cooling to room temperature, the reaction was quenched with water (10 mL). The resulting mixture was extracted with ethyl acetate (3×10 mL). The organic layers were combined, dried over anhydrous sodium sulfate, filtered, and concentrated. The residue was purified by silica gel chromatography (0-15% DCM/MeOH) to yield the (3S)-3-(4-(6-amino-2-fluoropyridin-3-yl)-1H-imidazol-2-yl)-7-(3-chloro-2-fluoro-6-(1-trityl-1H-imidazol-5-yl)phenyl)-2,3,8,8a-tetrahydroindolizin-5(1H)-one as an off-white solid. LC/MS: mass calculated for $C_{44}H_{34}ClF_2N_7O$: 749.25, measured: 750.25 $[M+H]^+$.

Step 2: (3S)-3-(4-(6-Amino-2-fluoropyridin-3-yl)-1H-imidazol-2-yl)-7-(3-chloro-2-fluoro-6-(1H-imidazol-5-yl)phenyl)-2,3,8,8a-tetrahydroindolizin-5(1H)-one To a solution of (3S)-3-(4-(6-amino-2-fluoropyridin-3-yl)-1H-imidazol-2-yl)-7-(3-chloro-2-fluoro-6-(1-trityl-1H-imidazol-5-yl)phenyl)-2,3,8,8a-tetrahydroindolizin-5(1H)-one (120 mg, 0.16 mmol, 1.0 equiv.) in DCM (5 mL) at 0° C. was added TFA (0.1 mL). The resulting mixture was stirred at room temperature for 3 h. The reaction was concentrated and purified by reverse phase chromatography on C18 column (0-80% ACN/Water-0.05% $NH_4HCO_3$) to yield the (3S)-3-(4-(6-amino-2-fluoropyridin-3-yl)-1H-imidazol-2-yl)-7-(3-chloro-2-fluoro-6-(1H-imidazol-5-yl)phenyl)-2,3,8,8a-tetrahydroindolizin-5(1H)-one as a white solid.

LC/MS: mass calculated for $C_{25}H_{20}ClF_2N_7O$: 507.14, measured: 508.10 $[M+H]^+$. $^1H$ NMR (400 MHz, DMSO-$d_6$) δ 12.35 (br, 1H), 7.99 (t, J=9.3 Hz, 1H), 7.79 (s, 1H), 7.64 (d, J=8.7 Hz, 1H), 7.63-7.55 (m, 1H), 7.48 (s, 1H), 7.15 (s, 1H), 6.38 (dd, J=8.3, 2.1 Hz, 1H), 6.33-6.36 (m, 2H), 5.78 (d, J=2.6 Hz, 1H), 5.09 (d, J=8.8 Hz, 1H), 3.97-4.10 (m, 1H), 2.72-2.85 (m, 1H), 2.41-2.50 (m, 1H), 2.13-2.28 (m, 1H), 1.88-2.13 (m, 3H). $^{19}F$ NMR (376 MHz, DMSO-$d_6$) δ −70.45, −73.43, −117.13.

Example 365 (3S)-3-(5-(7H-pyrrolo[2,3-d]pyrimidin-5-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one

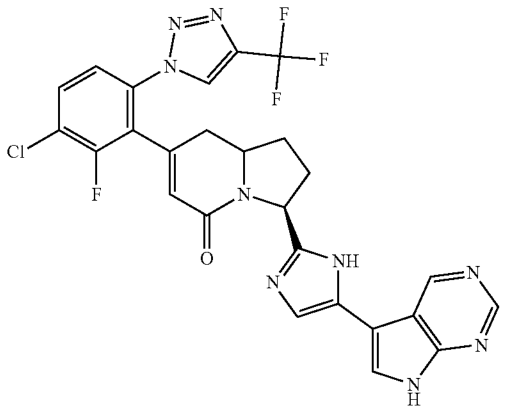 [SMILES: O=C1C=C(c2c(-n3cc(C(F)(F)F)nn3)ccc(Cl)c2F)CC2CC[C@@H](c3ncc(-c4c[nH]c5ncncc45)[nH]3)N12]

Step 1. Ethyl (3S)-7-(6-azido-3-chloro-2-fluorophenyl)-5-oxo-1,2,3,5,8,8a-hexahydroindolizine-3-carboxylate To a solution of ethyl (3S)-7-(6-amino-3-chloro-2-fluorophenyl)-5-oxo-1,2,3,5,8,8a-hexahydroindolizine-3-carboxylate (1 g, 2.835 mmol, 1.0 equiv.) in acetonitrile (15 mL) was added azidotrimethylsilane (0.490 g, 4.252 mmol, 1.5 equiv.), followed by the addition of tert-butyl nitrite (0.438 g, 4.252 mmol, 1.5 equiv.). The reaction mixture was stirred at room temperature for 1 h. The resulting mixture was concentrated under vacuum. The residue was purified by silica gel chromatography with EA/PE (0%-45%) to yield ethyl (3S)-7-(6-azido-3-chloro-2-fluorophenyl)-5-oxo-1,2,3,5,8,8a-hexahydroindolizine-3-carboxylate as a light yellow solid. LC/MS: mass calculated, for $C_{17}H_{16}ClFN_4O_3$: 378.09, measured: 379.20 $[M+H]^+$.

Step 2. ethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate To a solution of ethyl (3S)-7-(6-azido-3-chloro-2-fluorophenyl)-5-oxo-1,2,3,5,8,8a-hexahydroindolizine-3-carboxylate (1 g, 2.640 mmol, 1.0 equiv) and 4,4,4-trifluorobut-2-ynoic acid (1.822 g, 13.200 mmol, 5.0 equiv) in acetonitrile (15 mL) was added cuprous oxide (0.151 g, 1.056 mmol, 0.4 equiv). The reaction mixture was stirred at 80° C. for 2 h under $N_2$. The solid was filtered out, and the resulting mixture was concentrated under vacuum. The residue was purified by silica gel chromatography on EA/PE (0%-70%) to yield ethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate as a light yellow solid. LC/MS: mass calculated, for $C_{20}H_{17}ClF_4N_4O_3$: 472.09, measured: 473.10 $[M+H]^+$.

Step 3. (3R)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carbaldehyde To a solution of ethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate (1.1 g, 2.326 mmol, 1.0 equiv) in dichloromethane (20 mL) was added diisobutylaluminium hydride (4.653 mL, 1 M in DCM, 4.653 mmol, 3.0 equiv) in batches at −78° C. under $N_2$. The reaction mixture was stirred for 2 h, quenched with potassium sodium tartrate solution, and the mixture was extracted with EA. The combined extracts were dried over anhydrous $Na_2SO_4$. The resulting mixture was concentrated under vacuum. The residue was purified by silica gel chromatography with MeOH/DCM (0%-55%) to yield (3R)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carbaldehyde as a light yellow solid. LC/MS: mass calculated, for $C_{18}H_{13}ClF_4N_4O_2$: 428.07, measured: 429.05 $[M+H]^+$.

Step 4. (3S)-7-(3-chloro-2-fluoro-6-(4-(trifluoromethyl)-1H-1,2,3-triazol-1-yl)phenyl)-3-(1H-imidazol-2-yl)-2,3,8,8a-tetrahydroindolizin-5(1H)-one To a solution of (3R)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carbaldehyde (0.64 g, 1.493 mmol, 1.0 equiv.) in methanol (10 mL) and ammonium hydroxide (10 mL) was added glyoxal (2.166 g, 14.926 mmol, 10.0 equiv., 40% in water) in portions. The mixture was stirred at room temperature for 48 h. The resulting mixture was concentrated, then EA was added, washed with brine, dried over anhydrous $Na_2SO_4$, and concentrated under reduced pressure. The residue was purified by flash column chromatography on silica gel with MeOH/DCM (0-6%) to yield (3S)-7-(3-chloro-2-fluoro-6-(4-(trifluoromethyl)-1H-1,2,3-triazol-1-yl)phenyl)-3-(1H-imidazol-2-yl)-2,3,8,8a-tetrahydroindolizin-5(1H)-one as a yellow solid. LC/MS: mass calculated, for $C_{20}H_{15}ClF_4N_6O$: 466.09, measured: 467.00 $[M+H]^+$.

Step 5. (3S)-7-(3-chloro-2-fluoro-6-(4-(trifluoromethyl)-1H-1,2,3-triazol-1-yl)phenyl)-3-(5-iodo-1H-imidazol-2-yl)-2,3,8,8a-tetrahydroindolizin-5(1H)-one To a solution of (3S)-7-(3-chloro-2-fluoro-6-(4-(trifluoromethyl)-1H-1,2,3-triazol-1-yl)phenyl)-3-(1H-imidazol-2-yl)-2,3,8,8a-tetrahydroindolizin-5(1H)-one (250 mg, 0.536 mmol, 1.0 equiv.) in DCM (10 mL) was added N-iodosuccinimide (240.977 mg, 1.071 mmol, 2.0 equiv.). The reaction mixture was stirred at room temperature for 10 min. Water was added, the mixture was extracted with EA. The combined extracts were washed with water, dried over anhydrous $Na_2SO_4$ and concentrated. EtOH (10 mL), $H_2O$ (10 mL) and sodium sulfite (1.35 g, 10.711 mmol, 20.0 equiv.) was added to residue. The mixture was stirred overnight at 95° C., then cooled to room temperature. Water was added, the mixture was extracted with EA. The combined extracts were dried over anhydrous $Na_2SO_4$ and concentrated under reduced pressure. The residue was purified by flash column chromatography on silica gel with MeOH/DCM (0-4%) to yield (3S)-7-(3-chloro-2-fluoro-6-(4-(trifluoromethyl)-1H-1,2,3-triazol-1-yl)phenyl)-3-(5-iodo-1H-imidazol-2-yl)-2,3,8,8a-tetrahydroindolizin-5(1H)-one as an off-white solid. LC/MS: mass calculated, for $C_{20}H_{14}ClF_4IN_6O$: 591.99, measured: 592.95 $[M+H]^+$.

Step 6. (3S)-7-(3-chloro-2-fluoro-6-(4-(trifluoromethyl)-1H-1,2,3-triazol-1-yl)phenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one To a mixture of (3S)-7-(3-chloro-2-fluoro-6-(4-(trifluoromethyl)-1H-1,2,3-triazol-1-yl)phenyl)-3-(5-iodo-1H-imidazol-2-yl)-2,3,8,8a-tetrahydroindolizin-5(1H)-one (100 mg, 0.169 mmol, 1.0 equiv.) and 5-(4,4,5,5-tetramethyl-1,3,2-dioxaborolan-2-yl)-7-((2-(trimethylsilyl)ethoxy)methyl)-7H-pyrrolo[2,3-d]pyrimidine (316.632 mg, 0.844 mmol, 5.0 equiv.) in 1,4-dioxane (10 mL) and water (1 mL) was added potassium carbonate (69.952 mg, 0.506 mmol, 3.0 equiv.) and 1,1'-bis (di-t butylphosphino)ferrocene palladium dichloride (10.996 mg, 0.017 mmol, 0.1 equiv.). The resulting mixture was maintained under nitrogen and stirred at 100° C. for 2 h. After cooling to room temperature, the reaction was quenched with water and the mixture was extracted with EA. The combined extracts were dried over anhydrous $Na_2SO_4$ and concentrated. The residue was purified by flash column chromatography on silica gel with MeOH/DCM (0-5%) to yield (3S)-7-(3-chloro-2-fluoro-6-(4-(trifluoromethyl)-1H-1,2,3-triazol-1-yl)phenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one as a brown solid. LC/MS: mass calculated, for $C_{32}H_{32}ClF_4N_9O_2Si$: 713.21, measured: 714.15 $[M+H]^+$.

Step 7. (3S)-3-(5-(7H-pyrrolo[2,3-d]pyrimidin-5-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one A solution of (3S)-7-(3-chloro-2-fluoro-6-(4-(trifluoromethyl)-1H-1,2,3-triazol-1-yl)phenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one (110 mg, 0.154 mmol, 1.0 equiv.) in dichloromethane (6 mL) and trifluoroacetic acid (2 mL) was stirred at room temperature for 1 h. The resulting mixture was concentrated under vacuum. To the resulting residue in methanol (6 mL) was added ammonia solution (1 mL, 7.0 M in methanol) and the mixture stirred at room temperature for 10 min. The resulting mixture was extracted with EA two times. The combined extracts were dried over anhydrous $Na_2SO_4$, then concentrated. The residue was purified by reverse phase chromatography with $CH_3CN$/water (5%-45%) to yield (3S)-3-(5-(7H-pyrrolo[2,3-d]pyrimidin-5-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one as a grey solid.

$^1H$ NMR (400 MHz, Methanol-$d_4$) δ 9.23 (s, 1H), 9.00 (d, J=1.0 Hz, 1H), 8.76 (s, 1H), 7.74-7.83 (m, 2H), 7.54 (dd, J=8.6, 1.6 Hz, 1H), 7.37 (s, 1H), 5.71 (d, J=2.8 Hz, 1H), 5.18 (d, J=9.0 Hz, 1H), 3.82-3.99 (m, 1H), 2.92-3.06 (m, 1H), 2.54-2.72 (m, 1H), 2.19-2.45 (m, 3H), 2.01-2.18 (m, 1H). $^{19}F$ NMR (376 MHz, Methanol-$d_4$) δ −62.60, −113.48, −114.01.

Example 366 (3S)-3-(5-(5-chloro-1H-pyrazol-4-yl)-1H-imidazol-2-yl)-7-(3-chloro-2-fluoro-6-(1H-tetrazol-1-yl)phenyl)-2,3,8,8a-tetrahydroindolizin-5(1H)-one

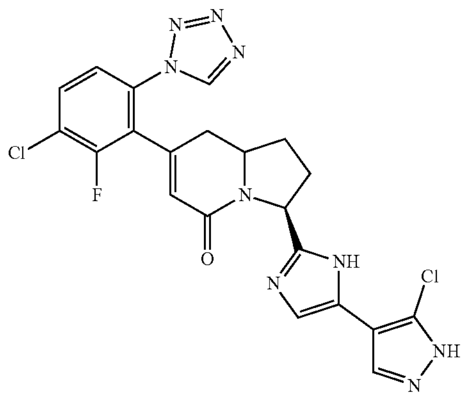 [SMILES: O=C1C=C(c2c(-n3cnnn3)ccc(Cl)c2F)CC2CC[C@@H](c3ncc(-c4cn[nH]c4Cl)[nH]3)N12]

To a mixture of (3S)-7-(6-amino-3-chloro-2-fluorophenyl)-3-(5-(5-chloro-1H-pyrazol-4-yl)-1H-imidazol-2-yl)-2,3,8,8a-tetrahydroindolizin-5(1H)-one (40 mg) in acetic acid (1 mL) was added azidotrimethylsilane (0.5 mL) and trimethoxymethane (0.5 mL). The reaction mixture was stirred overnight at 50° C. The resulting mixture was then concentrated under vacuum. The residue was purified by HPLC with Mobile Phase A: Water (0.05% TFA), Mobile Phase B: MeOH to yield (3S)-3-(5-(5-chloro-1H-pyrazol-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

$^1$H NMR (400 MHz, Methanol-$d_4$) δ 9.58 (s, 1H), 8.08 (s, 1H), 7.79-7.89 (m, 1H), 7.52-7.67 (m, 2H), 5.75 (d, J=2.8 Hz, 1H), 5.26 (d, J=10.1 Hz, 1H), 3.87-4.02 (m, 1H), 2.88-3.03 (m, 1H), 2.65-2.76 (m, 1H), 2.42-2.59 (m, 1H), 2.28-2.38 (m, 1H), 2.18-2.26 (m, 1H), 1.89-2.05 (m, 1H). $^{19}$F NMR (376 MHz, Methanol-$d_4$) −113.58.

Example 367 N-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methanesulfonamide

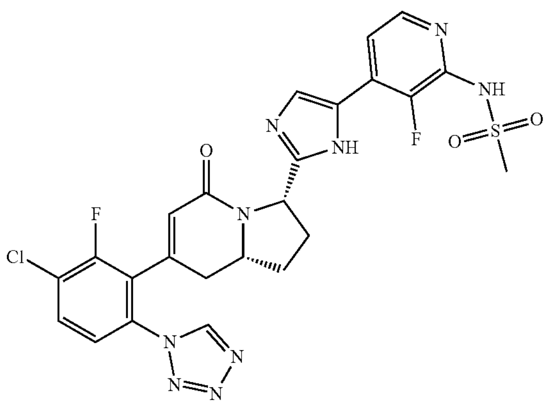 [SMILES: CS(=O)(=O)Nc1nccc(-c2cnc([C@@H]3CC[C@@H]4CC(c5c(-n6cnnn6)ccc(Cl)c5F)=CC(=O)N43)[nH]2)c1F]

To a mixture of N-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)methanesulfonamide (77 mg, 0.14 mmol, 1.0 equiv) in AcOH (3 mL) were added trimethoxymethane (153 mg, 1.44 mmol, 10 equiv) and $TMSN_3$ (166 mg, 1.44 mmol, 10.0 eq.). The mixture was then stirred at room temperature overnight. The mixture was concentrated. The residue was applied onto a C18 column (mobile phase: $CH_3CN$ (0.1% TFA) & $H_2O$ (0.1% TFA)) & Chiral-HPLC ((R,R) WHELK-O1, 4.6*50 mm, 3.5 um; Mobile Phase A: MtBE (0.1% DEA): Mobile phase B: EtOH=70:30, Flow rate: 1 mL/min; to yield N-(4-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)methanesulfonamide as a white solid.

LC/MS: mass calculated for $C_{24}H_{20}ClF_2N_9O_3S$: 587.11, measured: 588.10 $[M+H]^+$. $^1$H NMR (400 MHz, DMSO-$d_6$) δ 12.30 (s, 1H), 10.55 (s, 1H), 9.84 (s, 1H), 8.12 (s, 1H), 7.93-8.01 (m, 1H), 7.71 (dd, J=8.7, 1.5 Hz, 1H), 7.68 (s, 1H), 7.56 (s, 1H), 5.70 (d, J=2.7 Hz, 1H), 5.04 (d, J=8.7 Hz, 1H), 3.69-3.77 (m, 1H), 3.39 (s, 3H), 2.67-2.75 (m, 1H), 2.49-2.56 (m, 1H), 2.16-2.23 (m, 1H), 2.06-2.12 (m, 1H), 1.93-1.99 (m, 2H). $^{19}$F NMR (376 MHz, DMSO-$d_6$) δ−112.85, −135.33.

Example 368 (3S)-7-(3-chloro-2-fluoro-6-(1H-tetrazol-1-yl)phenyl)-3-(5-(2-fluoro-6-(methylamino)pyridin-3-yl)-1H-imidazol-2-yl)-2,3,8,8a-tetrahydroindolizin-5(1H)-one

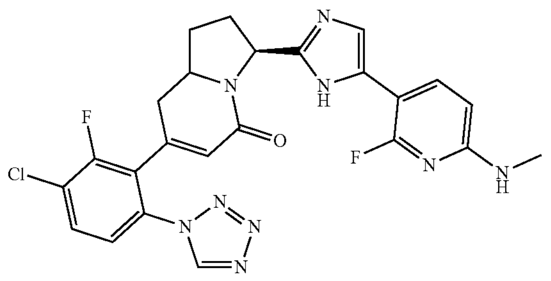 [SMILES: CNc1ccc(-c2cnc([C@@H]3CCC4CC(c5c(-n6cnnn6)ccc(Cl)c5F)=CC(=O)N43)[nH]2)c(F)n1]

Step 1: (3S)-7-(6-Amino-3-chloro-2-fluorophenyl)-3-(4-(3-nitropyridin-4-yl)-1H-imidazol-2-yl)-2,3,8,8a-tetrahydroindolizin-5(1H)-one To a solution of 6-fluoro-5-iodopyridin-2-amine (4 g, 16.80 mmol) in tetrahydrofuran (50 mL) was added NaH (806.6 mg, 20.168 mmol) at 0° C., after 30 min was added $CH_3I$ (3.578 g, 25.21 mmol). The resulting mixture was stirred at 0° C. for 2 h. The residue was purified by silica gel chromatography (0-50% ethyl acetate/petroleum ether) to yield (3S)-7-(6-amino-3-chloro-2-fluorophenyl)-3-(4-(3-nitropyridin-4-yl)-1H-imidazol-2-yl)-2,3,8,8a-tetrahydroindolizin-5(1H)-one as a yellow solid. LC/MS: mass calculated for $C_6H_6FIN_2$: 251.96, measured: 253.03 $[M+H]^+$.

Step 2: 1-(2-fluoro-6-(methylamino)pyridin-3-yl)ethan-1-one

To a solution of the 6-fluoro-5-iodopyridin-2-amine (1.5 g, 5.95 mmol) in 1,4-dioxane (30 mL) was added tributyl (1-ethoxyvinyl)stannane (4.3 g, 11.903 mmol), tetrakis(triphenylphosphine) palladium(0) (687.7 mg, 0.6 mmol). The resulting mixture was stirred at 100° C. overnight. The residue was purified by silica gel chromatography (0-50% ethyl acetate/petroleum ether) to yield 1-(2-fluoro-6-(methylamino)pyridin-3-yl)ethan-1-one as an yellow solid. LC/MS: mass calculated for $C_8H_9FN_2O$: 168.07, measured: 169.1 $[M+H]^+$.

Step 3: 1-(2-fluoro-6-(methylamino)pyridin-3-yl) ethan-1-one

To a solution of the 1-(2-fluoro-6-(methylamino)pyridin-3-yl)ethan-1-one (800 mg, 4.757 mmol) in glacial acetic acid (20 mL) and HBr (2 mL) was added pyridinium tribromide (380.1 mg, 2.4 mmol). The resulting mixture was stirred at room temperature for 2 h. The organic layers were combined, dried over anhydrous sodium sulfate, filtered and concentrated to yield 1-(2-fluoro-6-(methylamino)pyridin-3-yl)ethan-1-one as a yellow solid. LC/MS: mass calculated for $C_8H_8BrFN_2O$: 245.98, measured: 247.1 $[M+H]^+$.

Step 4: 2-(2-fluoro-6-(methylamino)pyridin-3-yl)-2-oxoethyl (3S)-7-(6-amino-3-chloro-2-fluorophenyl)-5-oxo-1,2,3,5,8,8a-hexahydroindolizine-3-carboxylate To a solution of the methyl 1-(2-fluoro-6-(methylamino) pyridin-3-yl)ethan-1-one (152.2 mg, 0.616 mmol) in N,N-dimethylformamide (10 mL) were added cesium carbonate (120.4 mg, 0.370 mmol), and (3S)-7-(6-amino-3-chloro-2-fluorophenyl)-5-oxo-1,2,3,5,8,8a-hexahydroindolizine-3-carboxylic acid (200 mg, 0.616 mmol). The resulting mixture was stirred at 30° C. for 2 h. The organic layers were combined, dried over anhydrous sodium sulfate, filtered and concentrated. The residue was purified by silica gel chromatography (0-30% methanol/dichloromethane)) to yield 2-(2-fluoro-6-(methylamino)pyridin-3-yl)-2-oxoethyl (3S)-7-(6-amino-3-chloro-2-fluorophenyl)-5-oxo-1,2,3,5,8,8a-hexahydroindolizine-3-carboxylate as an yellow solid. LC/MS: mass calculated for $C_{23}H_{21}ClF_2N_4O_4$: 490.12, measured: 491.1 $[M+H]^+$.

Step 5: (3S)-7-(6-amino-3-chloro-2-fluorophenyl)-3-(5-(2-fluoro-6-(methylamino)pyridin-3-yl)-1H-imidazol-2-yl)-2,3,8,8a-tetrahydroindolizin-5(1H one To a solution of the (3S)-2-(6-(methoxycarbonylamino) pyridin-3-yl)-2-oxoethyl 7-(6-amino-3-chloro-2-fluorophenyl)-5-oxo-1,2,3,5,8,8a-hexahydroindolizine-3-carboxylate (300 mg, 0.661 mmol) in toluene (10 mL) was added glacial acetic acid (1 mL), ammonium acetate (706.6 mg, 9.2 mmol). The resulting mixture was stirred at 100° C. for 2 h. The organic layers were combined, dried over anhydrous sodium sulfate, filtered and concentrated. The residue was purified by silica gel chromatography (0-30% methanol/dichloromethane)) to yield (3S)-7-(6-amino-3-chloro-2-fluorophenyl)-3-(5-(2-fluoro-6-(methylamino)pyridin-3-yl)-1H-imidazol-2-yl)-2,3,8,8a-tetrahydroindolizin-5(1H)-one as an yellow solid. LC/MS: mass calculated for $C_{23}H_{21}ClF_2N_8O$: 471.14, measured: 472.3$[M+H]^+$.

Step 6: (3S)-7-(3-chloro-2-fluoro-6-(1H-tetrazol-1-yl)phenyl)-3-(5-(2-fluoro-6-(methylamino)pyridin-3-yl)-1H-imidazol-2-yl)-2,3,8,8a-tetrahydroindolizin-5 (1H)-one To a solution of the (3S)-7-(6-amino-3-chloro-2-fluorophenyl)-3-(5-(2-fluoro-6-(methylamino)pyridin-3-yl)-1H-imidazol-2-yl)-2,3,8,8a-tetrahydroindolizin-5(1H)-one (200 mg, 0.425 mmol) in glacial acetic acid (5 mL) were added trimethoxymethane (1 mL), and azidotrimethylsilane (1 mL). The resulting mixture stirred at 60° C. for 2 h and concentrated. The resulting residue was added to 2N HCl (aq.)/THF (1:1) (4 mL). The mixture was stirred at 50° C. for 0.5 h. The pH value was 7.0 used $NaHCO_3$ (aq.), the resulting mixture concentrated. The residue was purified by silica gel column then purified by Prep-HPLC to yield the (3S)-7-(3-chloro-2-fluoro-6-(1H-tetrazol-1-yl)phenyl)-3-(5-(2-fluoro-6-(methylamino)pyridin-3-yl)-1H-imidazol-2-yl)-2,3,8,8a-tetrahydroindolizin-5(1H)-one as an white solid.

LC/MS: mass calculated for $C_{24}H_{20}ClF_2N_9O$: 523.14, measured: 524.15 $[M+H]^+$. $^1H$ NMR (300 MHz, DMSO-$d_6$) δ 11.92 (s, 1H), 9.84 (s, 1H), 7.91-8.11 (m, 2H), 7.70 (dd, J=8.7, 1.5 Hz, 1H), 6.90-7.09 (m, 1H), 6.81 (d, J=5.1 Hz, 1H), 6.40 (dd, J=8.3, 2.2 Hz, 1H), 5.69 (d, J=2.5 Hz, 1H), 4.99 (t, J=7.2 Hz, 1H), 4.04-4.15 (m, 1H), 2.76 (d, J=4.8 Hz, 3H), 2.19-2.51 (m, 4H), 1.96-2.11 (m, 1H), 1.60-1.78 (m, 1H). $^{19}F$ NMR (282 MHz, DMSO-$d_6$) δ −70.36, −113.07, −218.48

Example 369 N-(2-(2-((3S,8aR)-7-(3-chloro-2-fluoro-6-(1H-tetrazol-1-yl)phenyl)-5-oxo-1,2,3,5,8,8a-hexahydroindolizin-3-yl)-1H-imidazol-4-yl)phenyl)cyclopropanecarboxamide

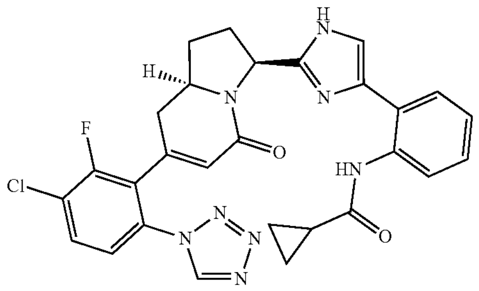 [SMILES: O=C(Nc1ccccc1-c1c[nH]c([C@@H]2CC[C@@H]3CC(c4c(-n5cnnn5)ccc(Cl)c4F)=CC(=O)N32)n1)C1CC1]

To a solution of the (3S)-3-(4-(2-aminophenyl)-1H-imidazol-2-yl)-7-(3-chloro-2-fluoro-6-(1H-tetrazol-1-yl)phenyl)-2,3,8,8a-tetrahydroindolizin-5(1H)-one (150 mg, 0.306 mmol) in pyridine (5 mL) were added cyclopropanecarboxylic acid (131.522 mg, 1.528 mmol), and EDCl (94.867 mg, 0.611 mmol). The resulting mixture was stirred room temperature overnight. The residue was purified by HPLC and SFC to yield N-(2-(2-((3S,8aS)-7-(3-chloro-2-fluoro-6-(1H-tetrazol-1-yl)phenyl)-5-oxo-1,2,3,5,8,8a-hexahydroindolizin-3-yl)-1H-imidazol-4-yl)phenyl)cyclopropanecarboxamide as a white solid.

LC/MS: mass calculated for $C_{28}H_{24}ClFN_8O_2$: 558.17, measured: 559.1 $[M+H]^+$. $^1H$ NMR (300 MHz, DMSO-$d_6$) δ 12.56 (m, 2H), 9.83 (s, 1H), 8.38 (d, 1H), 7.92-8.04 (m, 1H), 7.63-7.73 (m, 3H), 6.97-7.25 (m, 2H), 5.71 (d, J=2.5 Hz, 1H), 5.07 (t, J=7.4 Hz, 1H), 4.06-4.16 (m, 1H), 2.44-2.62 (m, 2H), 2.20-2.43 (m, 2H), 1.95-2.11 (m, 1H), 1.54-1.85 (m, 2H), 0.78-0.88 (m, 4H). $^{19}F$ NMR (282 MHz, DMSO) δ −73.54, −74.98, −113.30.

Example 370 N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-4-yl)pyridin-3-yl) cyclopropanecarboxamide

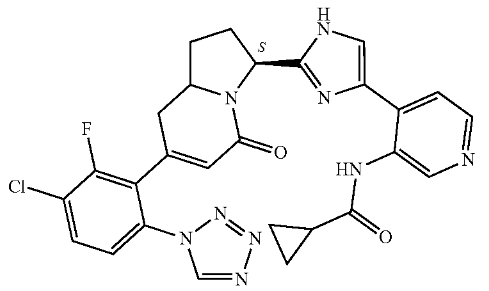

Step 1: 3-bromo-N-methoxy-N-methylnicotinamide

To a solution of 3-bromoisonicotinic acid (20.3 g, 100.493 mmol, 1.0 eq.) in DCM (250 mL) were added HOBt (14.937 g, 110.542 mmol, 1.1 eq.), N,O-dimethylhydroxylamine hydrochloride (14.704 g, 150.739 mmol, 1.5 eq.), EDCl (21.191 g, 110.542 mmol, 1.1 eq.), and TEA (40.675 g, 401.97 mmol, 4.0 eq.). The reaction mixture was stirred at room temperature overnight. The mixture was quenched with water (500 mL) and extracted with ethyl acetate (3×500 mL). The organic layers were combined, dried over anhydrous sodium sulfate, filtered and concentrated. The residue was purified by silica gel chromatography (0-50% ethyl acetate/petroleum ether) to yield the 3-bromo-N-methoxy-N-methylnicotinamide as a yellow oil. LC/MS: mass calculated for $C_8H_9BrN_2O_2$: 243.98, measured: 244.90, 246.90 $[M+H, M+H+2]^+$.

Step 2: 1-(3-bromopyridin-4-yl)ethan-1-one

To a solution of 3-bromo-N-methoxy-N-methylisonicotinamide (16.6 g, 67.73 mmol, 1.0 eq.) in THE (200 mL) was added methylmagnesium bromide (135.5 mL, 135.5 mmol, 2.0 eq.) at 0° C. under an atmosphere of nitrogen. The reaction mixture was stirred at 0° C. for 4 h. The reaction was quenched with $NH_4Cl$ solution (50 mL) and extracted with EA twice (100 mL×2), dried over $Na_2SO_4$, and concentrated to dryness. The residue was purified by silica gel chromatography (0-50% ethyl acetate/petroleum ether) to yield the 1-(3-bromopyridin-4-yl)ethan-1-one as a yellow oil. LC/MS: mass calculated for $C_7H_8BrNO$: 198.96, measured: 199.90, 201.90 $[M+H, M+H+2]^+$.

Step 3: 2-bromo-1-(3-bromopyridin-4-yl)ethan-1-one

To a solution of 1-(3-bromopyridin-4-yl)ethan-1-one (2.5 g, 12.498 mmol, 1.0 eq.) in acetic acid (30 mL) were added saturated HBr solution in acetic acid (33%, 3 mL), and bromine (1.798 g, 11.248 mmol, 0.9 eq.). The mixture was stirred at room temperature for 2 h. The reaction was concentrated to yield 2-bromo-1-(3-bromopyridin-4-yl)ethan-1-one as a yellow solid. LC/MS: mass calculated for $C_7H_5Br_2NO$: 276.87, measured 277.85, 279.85 $[M+H, M+H+2]^+$.

Step 4: 2-(3-bromopyridin-4-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(3-chloro-2-fluoro-6-(1H-tetrazol-1-yl)phenyl)-5-oxo-1,2,3,5,8,8a-hexahydroindolizine-3-carboxylic acid (502.3 mg, 1.547 mmol, 1.0 eq.) in DMF (10 mL) were added 2-bromo-1-(3-bromopyridin-4-yl)ethan-1-one (690.3 mg, 2.4 mmol, 1.6 eq.), and cesium carbonate (503.9 mg, 1.5 mmol, 0.7 eq.). The mixture was stirred at 35° C. for 2 h. The reaction was quenched with water (50 mL). The resulting mixture was extracted with ethyl acetate (3x50 mL). The organic layers were combined, dried over anhydrous sodium sulfate, filtered and concentrated. The residue was purified by silica gel chromatography (0-100% PE/EA) to yield the 2-(3-bromopyridin-4-yl)-2-oxoethyl (3S)-7-(6-amino-3-chloro-2-fluorophenyl)-5-oxo-1,2,3,5,8,8a-hexahydroindolizine-3-carboxylate as a yellow oil. LC/MS: mass calculated for $C_{22}H_{18}BrClFN_3O_4$: 521.02, measured 521.95, 523.95 $[M+H, M+H+2]^+$.

Step 5: (3S)-7-(6-amino-3-chloro-2-fluorophenyl)-3-(4-(3-bromopyridin-4-yl)-1H-imidazol-2-yl)-2,3,8,8a-tetrahydroindolizin-5(1H)-one To a solution of 2-(3-bromopyridin-4-yl)-2-oxoethyl (3S)-7-(6-amino-3-chloro-2-fluorophenyl)-5-oxo-1,2,3,5,8,8a-hexahydroindolizine-3-carboxylate (612.4 mg, 1.171 mmol, 1.0 eq.) in toluene (10 mL) and acetic acid (1 mL) was added ammonium acetate (903 mg, 11.7 mmol, 10.0 eq.). The mixture was stirred at 110° C. for 2 h. After cooling to room temperature, the reaction was quenched with water (50 mL). The resulting mixture was extracted with ethyl acetate (3×50 mL). The organic layers were combined, dried over anhydrous sodium sulfate, filtered and concentrated. The residue was purified by silica gel chromatography (0-10% DCM/methanol) to yield the (3S)-7-(6-amino-3-chloro-2-fluorophenyl)-3-(4-(3-bromopyridin-4-yl)-1H-imidazol-2-yl)-2,3,8,8a-tetrahydroindolizin-5(1H)-one as a yellow oil. LC/MS: mass calculated for $C_{22}H_{18}BrClFN_5O$: 501.04, measured: 502.10, 504.10 $[M+H, M+H+2]^+$.

Step 6: (3S)-3-(4-(3-bromopyridin-4-yl)-1H-imidazol-2-yl)-7-(3-chloro-2-fluoro-6-(1H-tetrazol-1-yl) phenyl)-2,3,8,8a-tetrahydroindolizin-5(1H)-one acid To a solution of (3S)-7-(6-amino-3-chloro-2-fluorophenyl)-3-(4-(3-bromopyridin-4-yl)-1H-imidazol-2-yl)-2,3,8,8a-tetrahydroindolizin-5(1H)-one (412.3 mg, 0.820 mmol, 1.0 eq.) in acetic acid (10 mL) were added azidotrimethylsilane (944.785 mg, 8.201 mmol, 10.0 eq.), and trimethoxymethane (870.2 mg, 8.201 mmol, 10.0 eq.). The reaction mixture was stirred at 65° C. for 2 h. The reaction mixture was diluted with water and extracted with EA. The combined extracts were washed with water, dried over $Na_2SO_4$, filtered and purified by silica gel chromatography (0-10% DCM/methanol) to yield (3S)-3-(4-(3-bromopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one acid as a yellow oil. LC/MS: mass calculated for $C_{23}H_{19}ClFN_9O$: 554.04, measured 555.00, 557.00 $[M+H, M+H+2]^+$.

Step 7: (3S)-3-(4-(3-aminopyridin-4-yl)-1H-imidazol-2-yl)-7-(3-chloro-2-fluoro-6-(1H-tetrazol-1-yl) phenyl)-2,3,8,8a-tetrahydroindolizin-5(1H)-one To a solution of (3S)-3-(4-(3-bromopyridin-4-yl)-1H-imidazol-2-yl)-7-(3-chloro-2-fluoro-6-(1H-tetrazol-1-yl)phenyl)-2,3,8,8a-tetrahydroindolizin-5(1H one (215.6 mg, 0.388 mmol, 1.0 eq.) in ethanol (4 mL) and $H_2O$ (1 mL), were added sodium azide (75.6 mg, 1.164 mmol, 3.0 eq.), sodium ascorbate (61.5 mg, 0.3 mmol, 0.8 eq.), (1R,2R)-N, N'-Dimethyl-1,2-cyclohexanediamine (33.1 mg, 0.233 mmol, 0.6 eq.), and copper sulfate pentahydrate (38.7 mg, 0.16 mmol, 0.4 eq.). The mixture was stirred at room temperature for 2 h. The reaction was quenched with water (50 mL), extracted with ethyl acetate (3×50 mL). The combined extracts were washed with water, dried over $Na_2SO_4$, filtered and purified by silica gel chromatography (0-10% DCM/methanol) to yield (3S)-3-(4-(3-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a yellow solid. LC/MS: mass calculated for $C_{23}H_{19}ClFN_9O$: 491.14, measured: 492.10 $[M+H]^+$.

Step 8: N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-4-yl)pyridin-3-yl) cyclopropanecarboxamide To a solution of (3S)-3-(4-(3-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one (75.8 mg, 0.154 mmol, 1.0 eq.) in pyridine (2 mL) were added cyclopropanecarboxylic acid (66.3 mg, 0.770 mmol, 5.0 eq.), and EDCl (59.1 mg, 0.308 mmol, 2.0 eq.). The reaction mixture was stirred at room temperature for 3 h. The reaction was diluted with water and extracted with EA. The organic layers were combined, dried over anhydrous sodium sulfate, filtered and purified by pre-HPLC with $MeCN/H_2O$ (0-30%) to yield N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-4-yl)pyridin-3-yl)cyclopropanecarboxamide as a white solid.

LC/MS: mass calculated for $C_{27}H_{23}ClFN_9O_2$: 559.16, measured: 560.15 $[M+H]^+$. $^1H$ NMR (300 MHz, DMSO-$d_6$) δ 12.51 (s, 1H), 12.10 (s, 1H), 9.83 (s, 1H), 9.46 (s, 1H), 8.17-8.25 (m, 1H), 7.88-8.04 (m, 2H), 7.67-7.77 (m, 2H), 5.68 (s. 1H), 5.04-5.13 (m, 1H), 3.70-3.76 (m, 1H), 2.55-2.65 (m, 2H), 2.09-2.29 (m, 3H), 1.72-2.02 (m, 1H), 1.66-1.72 (m, 1H), 0.79-0.91 (m, 4H). $^{19}F$ NMR (282 MHz, DMSO-$d_6$) δ−112.79, −113.11, −113.38.

Example 371 (3S,8aR)-7-(3-chloro-2-fluoro-6-(1H-tetrazol-1-yl)phenyl)-3-(5-(5-chloro-2-fluoropyridin-4-yl)-1H-imidazol-2-yl)-2,3,8,8a-tetrahydroindolizin-5(1H)-one

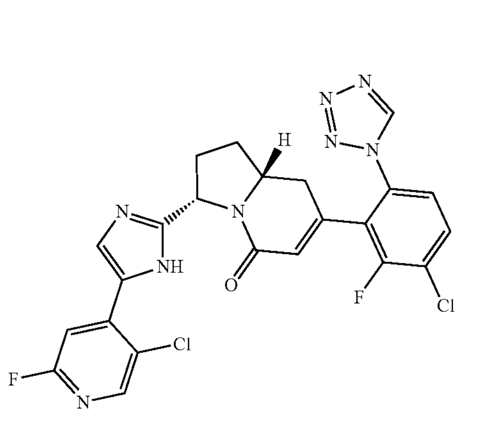 [SMILES: O=C1C=C(c2c(-n3cnnn3)ccc(Cl)c2F)C[C@H]2CC[C@@H](c3ncc(-c4cc(F)ncc4Cl)[nH]3)N12]

Step 1: (3S)-7-(3-chloro-2-fluoro-6-(1H-tetrazol-1-yl)phenyl)-3-(5-(5-chloro-2-fluoropyridin-4-yl)-1H-imidazol-2-yl)-2,3,8,8a-tetrahydroindolizin-5(1H)-one To a solution of 2-(5-chloro-2-fluoropyridin-4-yl)-2-oxoethyl 2-(6-amino-3-chloro-2-fluorophenyl)-4-oxo-6,7,8,9-tetrahydro-4H-pyrido[1,2-a]pyrimidine-6-carboxylate (200 mg, 0.4 mmol, 1.0 eq) in toluene/HOAc (4:1) (5.0 mL) was added $NH_4OAc$ (370 mg, 4.8 mmol, 11.9 eq). The resulting mixture was stirred at 60° C. overnight. After cooling to room temperature, the reaction mixture was concentrated and purified with silica gel column to yield (3S)-7-(3-chloro-2-fluoro-6-(1H-tetrazol-1-yl)phenyl)-3-(5-(5-chloro-2-fluoropyridin-4-yl)-1H-imidazol-2-yl)-2,3,8,8a-tetrahydroindolizin-5(1H)-one as a light yellow solid.

Step 2: (3S,8aR)-7-(3-chloro-2-fluoro-6-(1H-tetrazol-1-yl)phenyl)-3-(5-(5-chloro-2-fluoropyridin-4-yl)-1H-imidazol-2-yl)-2,3,8,8a-tetrahydroindolizin-5 (1H)-one (3S)-7-(6-Amino-3-chloro-2-fluorophenyl)-3-(5-(5-chloro-2-fluoropyridin-4-yl)-1H-imidazol-2-yl)-2,3,8,8a-tetrahydroindolizin-5(1H)-one (160 mg, 0.3 mmol, 1.0 eq.) was dissolved in HOAc (5.0 mL). Then trimethoxymethane (3.0 mL) and $TMSN_3$ (3.0 mL) were added, and the mixture was stirred for 6 h at room temperature. The mixture was concentrated. The resulting residue was purified by Prep-HPLC & Chiral-HPLC to yield (3S,8aR)-7-(3-chloro-2-fluoro-6-(1H-tetrazol-1-yl)phenyl)-3-(5-(5-chloro-2-fluoropyridin-4-yl)-1H-imidazol-2-yl)-2,3,8,8a-tetrahydroindolizin-5(1H)-one.

LC/MS: (ES, m/z): 529.05 $[M+H]^+$. $^1H$ NMR (400 MHz, DMSO-$d_6$) δ 9.82 (s, 1H), 8.31 (s, 1H), 7.93-8.01 (m, 2H), 7.67-7.75 (m, 2H), 5.67 (d, J=2.8 Hz, 1H), 5.05 (d, J=8.7 Hz, 1H), 3.67-3.80 (m, 1H), 2.69-2.82 (m, 2H), 2.07-2.26 (m, 2H), 1.89-2.05 (m, 2H). $^{19}F$ NMR (376 MHz, DMSO-$d_6$) δ −72.71, −74.16, −113.02.

Example 372 (3S,8aR)-3-(5-(2-aminopyridin-4-yl)-4-chloro-1H-imidazol-2-yl)-7-(3-chloro-2-fluoro-6-(1H-tetrazol-1-yl)phenyl)-2,3,8,8a-tetrahydroindolizin-5(1H)-one

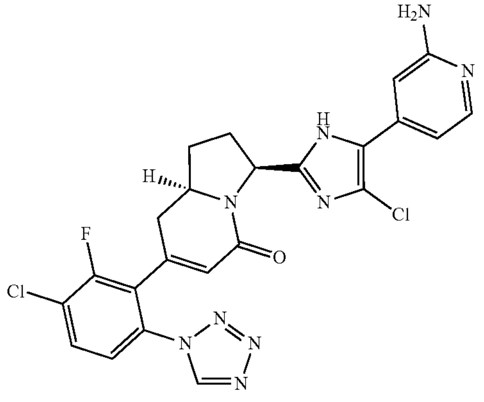 [SMILES: Nc1cc(-c2[nH]c([C@@H]3CC[C@@H]4CC(c5c(-n6cnnn6)ccc(Cl)c5F)=CC(=O)N43)nc2Cl)ccn1]

Step 1: N-(4-bromopyridin-2-yl)acetamide

To a solution of 4-bromopyridin-2-amine (3 g, 17.340 mmol, 1.0 equiv) in DCM (30 mL) were added $Ac_2O$ (3.54 g, 34.680 mol, 2.0 equiv) and $Et_3N$ (3.51 g, 34.680 mmol, 2.0 equiv). The reaction mixture was stirred overnight at room temperature. The reaction was quenched with water and extracted with ethyl acetate. The combined organic layer was washed with brine, dried over $Na_2SO_4$ and concentrated. The residue was purified by silica gel chromatography (0-50% EtOAc/petroleum ether) to yield N-(4-bromopyridin-2-yl)acetamide as a yellow solid.

Step 2: 2-(4-(1-ethoxyvinyl)pyridin-2-yl)propan-2-ol

Under an inert atmosphere of nitrogen, to a solution of N-(4-bromopyridin-2-yl)acetamide (500.0 mg, 2.325 mmol, 1.0 equiv) in 1,4-dioxane (10 mL) were added tributyl(1-ethoxyvinyl)stannane (1.008 g, 2.790 mmol, 1.2 equiv) and $Pd(PPh_3)_4$ (268.7 mg, 0.233 mmol, 0.1 equiv). The reaction mixture was stirred for 8 h at 100° C. The reaction was concentrated under vacuum to yield 2-(4-(1-ethoxyvinyl)pyridin-2-yl)propan-2-ol as a yellow oil.

Step 3: N-(4-(2-bromoacetyl)pyridin-2-yl)acetamide

To a solution of methyl 6-chloro-5-(1-ethoxyvinyl)picolinate (400 mg, 1.939 mmol, 1.0 equiv) in THE (6 mL) with $H_2O$ (3 mL) at 0° C. was added NBS (345.5 mg, 1.939 mmol, 1.0 equiv). The reaction mixture was stirred for 1 h at room temperature. The reaction was quenched with brine, extracted with EA three times. The combined organic layers were concentrated under vacuum, then the residue was purified on flash chromatography by silica gel (EA/PE: 0%-3%) to yield N-(4-(2-bromoacetyl)pyridin-2-yl)acetamide as a yellow solid.

Step 4: 2-(2-acetamidopyridin-4-yl)-2-oxoethyl (3S)-7-(6-amino-3-chloro-2-fluorophenyl)-5-oxo-1,2,3,5,8,8a-hexahydroindolizine-3-carboxylate To a solution of (3S)-7-(6-amino-3-chloro-2-fluorophenyl)-5-oxo-1,2,3,5,8,8a-hexahydroindolizine-3-carboxylic acid (250 mg, 0.770 mmol, 1.0 equiv) in DMF (5 mL) were added N-(4-(2-bromoacetyl)pyridin-2-yl)acetamide (237.5 mg, 0.92 mmol, 1.2 equiv) and $Cs_2CO_3$ (150.5 mg, 0.46 mmol, 0.6 equiv). The reaction mixture was stirred overnight at room temperature. The reaction was quenched with water and extracted with ethyl acetate. The combined organic layer was washed with brine, dried over $Na_2SO_4$ and concentrated. The residue was purified by silica gel chromatography (0-30% MeOH/DCM) to yield 2-(2-acetamidopyridin-4-yl)-2-oxoethyl (3S)-7-(6-amino-3-chloro-2-fluorophenyl)-5-oxo-1,2,3,5,8,8a-hexahydroindolizine-3-carboxylate as a yellow oil.

Step 5: N-(4-(2-((3S)-7-(6-amino-3-chloro-2-fluorophenyl)-5-oxo-1,2,3,5,8,8a-hexahydroindolizin-3-yl)-1H-imidazol-5-yl)pyridin-2-yl)acetamide To a solution of 2-(2-acetamidopyridin-4-yl)-2-oxoethyl (3S)-7-(6-amino-3-chloro-2-fluorophenyl)-5-oxo-1,2,3,5,8,8a-hexahydroindolizine-3-carboxylate (200 mg, 0.399 mmol, 1.0 equiv) in toluene (5.0 mL) with $CH_3COOH$ (0.5 mL) was added $NH_4OAc$ (307.8 mg, 3.99 mmol, 10 equiv). The reaction mixture was stirred for 2 h at 110° C. The reaction was quenched with water and extracted with ethyl acetate. The combined organic layer was washed with brine, dried over $Na_2SO_4$ and concentrated. The residue was purified by silica gel chromatography (0-30% MeOH/DCM) to yield N-(4-(2-((3S)-7-(6-amino-3-chloro-2-fluorophenyl)-5-oxo-1,2,3,5,8,8a-hexahydroindolizin-3-yl)-1H-imidazol-5-yl)pyridin-2-yl)acetamide as a yellow oil.

Step 6: N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide To a solution of N-(4-(2-((3S)-7-(6-amino-3-chloro-2-fluorophenyl)-5-oxo-1,2,3,5,8,8a-hexahydroindolizin-3-yl)-1H-imidazol-5-yl)pyridin-2-yl)acetamide (100 mg, 0.208 mmol, 1.0 equiv) in HOAc (3 mL) were added $TMSN_3$ (239.6 mg, 2.079 mmol, 10.0 equiv) and trimethoxymethane (220.6 mg, 2.08 mmol, 10.0 equiv). The reaction mixture was stirred overnight at room temperature, quenched with water and extracted with ethyl acetate. The combined organic layer was washed with brine, dried over $Na_2SO_4$ and concentrated. The residue was purified by silica gel chromatography (0-20% MeOH/DCM) to yield N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide as a yellow solid.

Step 7: N-(4-(4-chloro-2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide To a mixture of N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide (200 mg, 0.375 mmol, 1.0 equiv) in DMF (8 mL) was added NCS (50 mg, 0.374 mmol, 1.0 equiv) and the mixture was stirred at room temperature for 2 h. The reaction was quenched with water (50 mL) and extracted with ethyl acetate (100 mL×3). The combined organic layer was washed with brine, dried over $Na_2SO_4$ and concentrated. The residue was purified by silica gel chromatography (0-20% MeOH/DCM) to yield N-(4-(4-chloro-2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide as a yellow solid. MS (ESI): mass calculated for C25H20Cl2FN9O2 567.11 m/z, measured 568.20$[M+H]^+$.

Step 8: (3S)-3-(5-(2-aminopyridin-4-yl)-4-chloro-1H-imidazol-2-yl)-7-(3-chloro-2-fluoro-6-(1H-tetrazol-1-yl)phenyl)-2,3,8,8a-tetrahydroindolizin-5(1H)-one To a solution of N-(4-(4-chloro-2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide (150 mg, 0.264 mmol, 1.0 equiv) in THE (2 mL) was added 2N HCl (2 mL). The reaction mixture was stirred for 2 h at 70° C. The mixture was concentrated under vacuum and purified by C18 column (eluent: 5% to 50% (v/v) $CH_3CN$ and $H_2O$ containing 0.05% $NH_4HCO_3$) to yield (3S)-3-(5-(2-aminopyridin-4-yl)-4-chloro-1H-imidazol-2-yl)-7-(3-chloro-2-fluoro-6-(1H-tetrazol-1-yl)phenyl)-2,3,8,8a-tetrahydroindolizin-5(1H)-one as a yellow solid. MS (ESI): mass calculated for C23H18C12FN9O 525.10 m/z, measured 526.20$[M+H]^+$.

Step 9: (3S,8aR)-3-(5-(2-aminopyridin-4-yl)-4-chloro-1H-imidazol-2-yl)-7-(3-chloro-2-fluoro-6-(1H-tetrazol-1-yl)phenyl)-2,3,8,8a-tetrahydroindolizin-5(1H)-one (3S)-3-(5-(2-Aminopyridin-4-yl)-4-chloro-1H-imidazol-2-yl)-7-(3-chloro-2-fluoro-6-(1H-tetrazol-1-yl)phenyl)-2,3, 8,8a-tetrahydroindolizin-5(1H)-one (100 mg, 0.190 mmol) was purified by SFC to yield (3S,8aR)-3-(5-(2-aminopyridin-4-yl)-4-chloro-1H-imidazol-2-yl)-7-(3-chloro-2-fluoro-6-(1H-tetrazol-1-yl)phenyl)-2,3,8,8a-tetrahydroindolizin-5(1H)-one as a yellow solid.

LC/MS: (ES, m/z): 526.20 $[M+H]^+$. $^1H$ NMR (300 MHz, DMSO-$d_6$) δ 12.74 (s, 1H), 9.84 (s, 1H), 7.92-8.03 (m, 2H), 7.72 (dd, J=8.7, 1.5 Hz, 1H), 6.74-6.84 (m, 2H), 6.03 (d, J=4.5 Hz, 2H), 5.67 (d, J=2.5 Hz, 1H), 4.96 (d, J=8.4 Hz, 1H), 3.64-3.76 (m, 1H), 2.53-2.73 (m, 2H), 1.83-2.30 (m, 4H). $^{19}F$ NMR (282 MHz, DMSO-$d_6$) δ −112.832.

Example 373 5-(2-(7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxylic acid

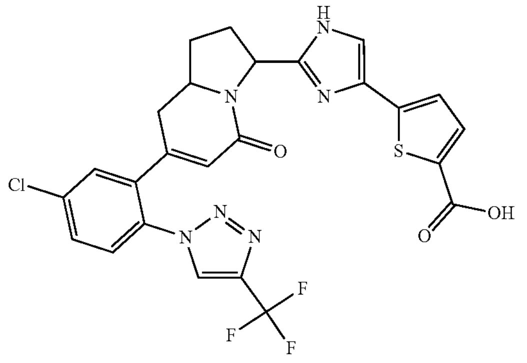 [SMILES: O=C(O)c1ccc(-c2c[nH]c(C3CCC4CC(c5cc(Cl)ccc5-n5cc(C(F)(F)F)nn5)=CC(=O)N43)n2)s1]

Step 1: 2-(5-(ethoxycarbonyl)thiophen-2-yl)-2-oxoethyl 7-(5-chloro-2-(4-(trifluoromethyl)-1H-1,2,3-triazol-1-yl)phenyl)-5-oxo-1,2,3,5,8,8a-hexahydroindolizine-3-carboxylate Into a 50-mL round-bottom flask, was placed 7-(5-chloro-2-(4-(trifluoromethyl)-1H-1,2,3-triazol-1-yl)phenyl)-5-oxo-1,2,3,5,8,8a-hexahydroindolizine-3-carboxylic acid (250 mg, 0.586 mmol, 1.0 equiv.) and $K_2CO_3$ (121.2 mg, 0.879 mmol, 1.2 equiv.) in $CH_3CN$ (20 mL), and the mixture was stirred at room temperature for 0.5 hour. To the resulting mixture was then added ethyl 5-(2-bromoacetyl)thiophene-2-carboxylate (194.8 mg, 0.7 mmol, 1.2 equiv.). The mixture was stirred at room temperature for 4 hours. The mixture was quenched by water, extracted with DCM. The organic layer was concentrated under vacuum, dried over $Na_2SO_4$, filtered, and evaporated to dryness. The residue was purified by silica gel with DCM/MeOH (20:1). The collected fractions were combined and concentrated under vacuum to yield 2-(5-(ethoxycarbonyl)thiophen-2-yl)-2-oxoethyl 7-(5-chloro-2-(4-(trifluoromethyl)-1H-1,2,3-triazol-1-yl)phenyl)-5-oxo-1,2,3,5,8,8a-hexahydroindolizine-3-carboxylate as a yellow solid. Mass spectrum (ESI, m/z): calculated for $C_{27}H_{22}ClF_3N_4O_6S$: 623.09 [M+H], measured: 623.00.

Step 2: ethyl 5-(2-(7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxylate Into a 100-mL round-bottom flask, was placed 2-(5-(ethoxycarbonyl)thiophen-2-yl)-2-oxoethyl 7-(5-chloro-2-(4-(trifluoromethyl)-1H-1,2,3-triazol-1-yl)phenyl)-5-oxo-1,2,3,5,8,8a-hexahydroindolizine-3-carboxylate (170 mg, 0.273 mmol, 1.0 equiv.) and $NH_4OAc$ (210.2 mg, 2.7 mmol, 10.0 equiv.) in toluene (30 mL) and HOAc (3 mL) was added. The mixture was stirred at 100° C. for 5 hours. The mixture was quenched by water, extracted with DCM. The organic layer was concentrated under vacuum. The residue was purified by silica gel with DCM/MeOH (20:1). The collected fractions were combined and concentrated under vacuum to yield ethyl 5-(2-(7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxylate as a yellow solid. Mass spectrum (ESI, m/z): calculated for $C_{27}H_{22}ClF_3N_6O_3S$: 603.11 [M+H], measured: 603.05.

Step 3: 5-(2-(7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxylic acid hydrochloride Into a 50-mL round-bottom flask, was placed ethyl 5-(2-(7-(5-chloro-2-(4-(trifluoromethyl)-1H-1,2,3-triazol-1-yl)phenyl)-5-oxo-1,2,3,5,8,8a hexahydroindolizin-3-yl)-1H-imidazol-4-yl)thiophene-2-carboxylate (160 mg, 0.26 mmol, 1.0 equiv.) in THE (15 mL) and $H_2O$ (3 mL). NaOH (53.0 mg 1.3 mmol 5.0 equiv.) was then added. The mixture was stirred at 50° C. for 2 days. The mixture was concentrated. The residue was purified by Prep-HPLC with the following conditions: Column, Sun Fire Prep C18, 5 um, 19*100 mm; mobile phase, Water of 0.05% HCl and $CH_3CN$ (60% $CH_3CN$ up to 95% in 10 min, up to 100% in 2 min, down to 60% in 1 min; Detector, 220 nm, 254 nm. to yield 5-(2-(7-(5-chloro-2-(4-(trifluoromethyl)-1H-1,2,3-triazol-1-yl)phenyl)-5-oxo-1,2,3,5,8,8a-hexahydroindolizin-3-yl)-1H-imidazol-4-yl)thiophene-2-carboxylic acid hydrochloride as a white solid.

$^1H$-NMR (400 MHz, DMSO-d6) δ (ppm): 9.37 (s, 1H), 7.79 (s, 1H), 7.73-7.83 (m, 4H), 7.60 (s, 1H), 5.63 (s, 1H), 5.16 (d, J=9.6 Hz, 1H), 3.69-3.78 (m, 1H), 2.89-2.93 (m, 1H), 2.28-2.35 (m, 2H), 2.02-2.21 (m, 2H), 1.88-2.01 (m, 1H). $^{19}F$-NMR (376 MHz, DMSO-$d_6$) δ (ppm): −59.49. Mass spectrum (ESI, m/z): calculated for $C_{25}H_{18}ClF_3N_6O_3S$: 575.1 [M+H], measured: 575.05.

Example 374 7-(3-chloro-2-fluoro-6-(1H-tetrazol-1-yl)phenyl)-3-(5-(7-methyl-5H-cyclopenta[b]pyridin-4-yl)-1H-imidazol-2-yl)-2,3,8,8a-tetrahydroindolizin-5(1H)-one

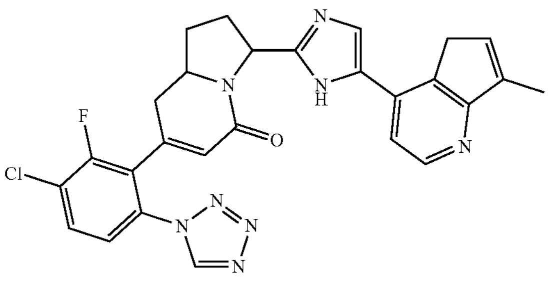 [SMILES: CC1=CCc2c(-c3cnc(C4CCC5CC(c6c(-n7cnnn7)ccc(Cl)c6F)=CC(=O)N54)[nH]3)ccnc21]

Step 1: 4-chloro-5,6-dihydro-7H-cyclopenta[b]pyridin-7-one

To a solution of 4-chloro-6,7-dihydro-5H-cyclopenta[b]pyridin-7-ol (4.0 g, 23.58 mmol, 1.0 equiv.) in DCM (40 mL) was added $MnO_2$ (26.4 g, 303.67 mmol, 12.876 equiv.). The mixture was stirred at room temperature for 16 h. The mixture was added water and the aqueous layer was extracted with DCM twice. The organic phases were combined, washed with water, concentrated to yield 4-chloro-5,6-dihydro-7H-cyclopenta[b]pyridin-7-one as a yellow solid.

Step 2: 4-chloro-7-methyl-6,7-dihydro-5H-cyclopenta[b]pyridin-7-ol

To a solution of 4-chloro-5,6-dihydro-7H-cyclopenta[b]pyridin-7-one (300 mg, 1.79 mmol, 1.0 equiv.) in THE (10 mL) was added MeBrMg (6 mL, 1.0 M) dropwise at 0° C. and the mixture was stirred at room temperature for 16 h. The mixture was quenched with water and the mixture was extracted with EtOAc twice. The organic phases were combined, washed with $H_2O$, concentrated to yield 4-chloro-7-methyl-6,7-dihydro-5H-cyclopenta[b]pyridin-7-ol as a yellow solid.

Step 3: 4-(1-ethoxyvinyl)-7-methyl-6,7-dihydro-5H-cyclopenta[b]pyridin-7-ol

To a solution of 4-chloro-7-methyl-6,7-dihydro-5H-cyclopenta[b]pyridin-7-ol (600 mg, 3.27 mmol, 1.0 equiv.) in 1,4-dioxane (10 mL) were added tributyl(1-ethoxyvinyl) stannane (2.0 mL), X-Phos (156 mg, 0.33 mmol, 1.8 equiv.) and X-Phos-Pd-G3 (277 mg, 0.33 mmol, 0.1 equiv.). The mixture was stirred at 80° C. for 1 h under $N_2$. The reaction was quenched with $H_2O$ and the aqueous layer was extracted with EtOAc. The organic phases were combined, washed with $H_2O$, concentrated, and purified by silica gel column chromatography (120 g, EA/PE: 1/25) to yield 4-(1-ethoxyvinyl)-7-methyl-6,7-dihydro-5H-cyclopenta[b]pyridin-7-ol as a yellow solid.

Step 4: 2-bromo-1-(7-hydroxy-7-methyl-6,7-dihydro-5H-cyclopenta[b]pyridin-4-yl)ethan-1-one To a solution of 4-(1-ethoxyvinyl)-7-methyl-6,7-dihydro-5H-cyclopenta[b]pyridin-7-ol (700 mg, 3.19 mmol, 1.0 equiv.) in THE (10 mL) and $H_2O$ (4 mL) was added NBS (512 mg, 2.89 mmol, 0.9 equiv.). The mixture was stirred at room temperature 1 h. The reaction was quenched with $H_2O$ and the aqueous layer was extracted with EtOAc twice. The organic phases were combined, washed with $H_2O$ and concentrated to yield 2-bromo-1-(7-hydroxy-7-methyl-6,7-dihydro-5H-cyclopenta[b]pyridin-4-yl)ethan-1-one as a yellow solid.

Step 5: 2-(7-hydroxy-7-methyl-6,7-dihydro-5H-cyclopenta[b]pyridin-4-yl)-2-oxoethyl 7-(6-amino-3-chloro-2-fluorophenyl)-5-oxo-1,2,3,5,8,8a-hexahydroindolizine-3-carboxylate To a solution of 2-bromo-1-(7-hydroxy-7-methyl-6,7-dihydro-5H-cyclopenta[b]pyridin-4-yl)ethan-1-one (858 mg, 3.176 mmol, 2.0 equiv.) in $CH_3CN$ (10 mL) were added 7-(6-amino-3-chloro-2-fluorophenyl)-5-oxo-1,2,3,5,8,8a-hexahydroindolizine-3-carboxylic acid (516 mg, 1.589 mmol, 1.0 equiv.) and $K_2CO_3$ (220 mg, 1.592 mmol). The mixture was stirred at room temperature 1 h. The reaction was quenched with $H_2O$ and the aqueous layer was extracted with EtOAc twice. The organic phases were combined, washed with $H_2O$, concentrated, and purified by silica gel column chromatography (120 g, PE/EA: 1/30) to yield 2-(7-hydroxy-7-methyl-6,7-dihydro-5H-cyclopenta[b]pyridin-4-yl)-2-oxoethyl 7-(6-amino-3-chloro-2-fluorophenyl)-5-oxo-1,2,3,5,8,8a-hexahydroindolizine-3-carboxylate as a yellow solid.

Step 6: (3S)-7-(6-amino-3-chloro-2-fluorophenyl)-3-(5-(7-hydroxy-7-methyl-6,7-dihydro-5H-cyclopenta[b]pyridin-4-yl)-1H-imidazol-2-yl)-2,3,8,8a-tetrahydroindolizin-5(1H)-one To a solution of 2-(7-hydroxy-7-methyl-6,7-dihydro-5H-cyclopenta[b]pyridin-4-yl)-2-oxoethyl 7-(6-amino-3-chloro-2-fluorophenyl)-5-oxo-1,2,3,5,8,8a-hexahydroindolizine-3-carboxylate (800 mg, 1.557 mmol, 1.0 equiv.) in toluene (2 mL) were added $NH_4OAc$ (1.2 g, 15.57 mmol, 10.0 equiv.) and AcOH (0.3 mL). The mixture was stirred at 110° C. for 2 h. The reaction was quenched with $H_2O$ and the aqueous layer was extracted with EtOAc twice. The organic phases were combined, washed with $H_2O$, concentrated, and purified by silica gel column chromatography (120 g, MeOH/DCM: 1/25) to yield (3S)-7-(6-amino-3-chloro-2-fluorophenyl)-3-(5-(7-hydroxy-7-methyl-6,7-dihydro-5H-cyclopenta[b]pyridin-4-yl)-1H-imidazol-2-yl)-2,3,8,8a-tetrahydroindolizin-5(1H)-one as a yellow solid.

Step 7: 4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-7-methyl-6,7-dihydro-5H-cyclopenta[b]pyridin-7-yl acetate To a solution of (4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl) methyl acetate (530 mg, 1.07 mmol, 1.0 equiv.) in HOAc (5 mL) was added trimethoxymethane (2.4 mL, 20 equiv.) followed by addition of $TMSN_3$ (2.8 mL, 20 equiv). The resulting mixture was stirred at 60° C. for 1 h, then concentrated under reduced pressure and the residue was purified by C18 reversal column chromatography (eluent: 5% to 70% (v/v) $CH_3CN$ and $H_2O$ with 0.05% $NH_4HCO_3$) to yield 4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-7-methyl-6,7-dihydro-5H-cyclopenta[b]pyridin-7-yl acetate as a yellow solid.

Step 8: (3S)-7-(3-chloro-2-fluoro-6-(1H-tetrazol-1-yl)phenyl)-3-(5-(7-methyl-5H-cyclopenta[b]pyridin-4-yl)-1H-imidazol-2-yl)-2,3,8,8a-tetrahydroindolizin-5(1H)-one A solution of 4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-7-methyl-6,7-dihydro-5H-cyclopenta[b]pyridin-7-yl acetate (550 mg, 0.93 mmol, 1 equiv.) in THE (6 mL) and 4N HCl (2 mL) was stirred at 50° C. for 1 h. The mixture was concentrated and purified by C18 gel chromatography (eluent: 5% to 70% (v/v) $CH_3CN$ and $H_2O$ with 0.05% $NH_4HCO_3$) to yield (3S)-7-(3-chloro-2-fluoro-6-(1H-tetrazol-1-yl)phenyl)-3-(5-(7-methyl-5H-cyclopenta

[b]pyridin-4-yl)-1H-imidazol-2-yl)-2,3,8,8a-tetrahydroindolizin-5(1H)-one as a white solid.

LC/MS: mass calculated for $C_{27}H_{22}ClFN_8O$: 528.16, measured: 529.15 $[M+H]^+$. $^1H$ NMR (400 MHz, DMSO-$d_6$) δ 12.20 (s, 1H), 9.84 (s, 1H), 8.39 (d, J=5.3 Hz, 1H), 7.97 (t, J=8.2 Hz, 1H), 7.71 (d, J=8.7 Hz, 1H), 7.66 (d, J=1.9 Hz, 1H), 7.59 (d, J=5.3 Hz, 1H), 6.66 (d, J=2.1 Hz, 1H), 5.68 (d, J=2.7 Hz, 1H), 5.03 (d, J=8.4 Hz, 1H), 3.69-3.78 (m, 1H), 3.47-3.55 (m, 2H), 2.67-2.79 (m, 1H), 2.53-2.59 (m, 1H), 2.01-2.22 (m, 6H), 1.94-1.98 (m, 1H). $^{19}$FNMR (376 MHz, DMSO-$d_6$) δ −112.95.

Example 376 (3S,8aR)-3-(5-(6-amino-2-fluoropyridin-3-yl)-1H-imidazol-2-yl)-7-(5-chloro-2-(1H-tetrazol-1-yl)phenyl)hexahydroindolizin-5(1H)-one

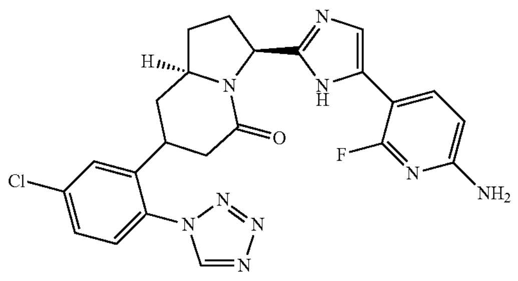 [SMILES: Nc1ccc(-c2cnc([C@@H]3CC[C@@H]4CC(c5cc(Cl)ccc5-n5cnnn5)CC(=O)N43)[nH]2)c(F)n1]

To a solution of (3S,8aR)-3-(5-(6-amino-2-fluoropyridin-3-yl)-1H-imidazol-2-yl)-7-(5-chloro-2-(1H-tetrazol-1-yl) phenyl)-2,3,8,8a-tetrahydroindolizin-5(1H)-one (0.1 g, 0.203 mmol, 1.0 equiv.) in EA (10 mL) were added $PtO_2$ (0.014 g, 0.061 mmol, 0.3 equiv.) and TFA (0.030 mL, 0.407 mmol, 2.0 equiv.) and the mixture was stirred overnight at room temperature under $H_2$ (10 atm.). The solid was filtered out. The filtrate was concentrated under vacuum and the residue was purified by reverse phase chromatography on C18 (80 g, MeCN/$H_2O$ (0.05% $CF_3COOH$): 0>>>45%) and separated by Chiral-HPLC (Column: CHIRALPAK IA-3, 4.6*50 mm, 3.0 um; Mobile Phase: Hex (0.1% DEA): EtOH=60:40; Flow rate: 1 mL/min) to yield (3S,8aR)-3-(5-(6-amino-2-fluoropyridin-3-yl)-1H-imidazol-2-yl)-7-(5-chloro-2-(1H-tetrazol-1-yl)phenyl)hexahydroindolizin-5 (1H)-one as a white solid.

LC-MS (ES, m/z): 494.10 $[M+H]^+$. $^1H$ NMR: (400 MHz, DMSO-$d_6$) δ 11.53 (s, 1H), 9.83 (s, 1H), 7.95-8.04 (m, 1H), 7.78 (s, 1H), 7.48-7.60 (m, 2H), 6.95-7.05 (m, 1H), 6.29-6.37 (m, 1H), 6.15-6.25 (m, 2H), 4.92 (d, J=8.7 Hz, 1H), 3.42-3.56 (m, 1H), 2.68-2.79 (m, 1H), 2.25-2.42 (m, 2H), 1.99-2.16 (m, 3H), 1.89-1.98 (m, 1H), 1.79-1.87 (m, 1H), 1.66-1.78 (m, 1H). $^{19}$F NMR: (376 MHz, DMSO-$d_6$) δ−70.75.

Example 378 (3S,7R,8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)hexahydroindolizin-5(1H)-one

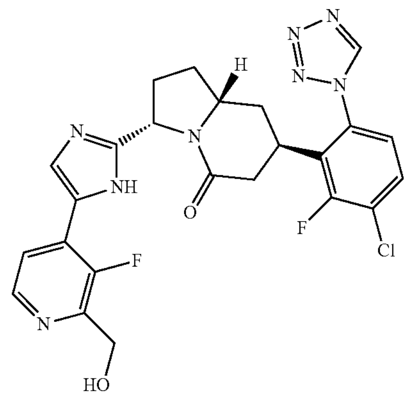 [SMILES: O=C1C[C@H](c2c(-n3cnnn3)ccc(Cl)c2F)C[C@H]2CC[C@@H](c3ncc(-c4ccnc(CO)c4F)[nH]3)N12]

Step 1: (8aR)-7-(3-chloro-2-fluoro-6-(1H-tetrazol-1-yl)phenyl)-5-oxooctahydroindolizine-3-carboxylic acid To a solution of (8aR)-7-(3-chloro-2-fluoro-6-(1H-tetrazol-1-yl)phenyl)-5-oxo-1,2,3,5,8,8a-hexahydroindolizine-3-carboxylic acid (0.5 g, 1.324 mmol, 1.0 equiv.) in EA (20 mL) were added $PtO_2$ (0.090 g, 0.397 mmol, 0.3 equiv.) and TFA (0.197 mL, 2.647 mmol, 2.0 equiv.) and the mixture was stirred overnight at room temperature under $H_2$ (15 atm.). The solid was filtered out. The filtrate was concentrated under vacuum and the residue was purified by reverse phase chromatography on C18 (80 g, MeCN/$H_2O$ (0.05% $CF_3COOH$): 0>>>45%) to yield (8aR)-7-(3-chloro-2-fluoro-6-(1H-tetrazol-1-yl)phenyl)-5-oxooctahydroindolizine-3-carboxylic acid as a yellow solid. LC-MS (ES, m/z): 380.15 $[M+H]^+$.

Step 2: 2-(2-(((tert-butyldimethylsilyl)oxy)methyl)-3-fluoropyridin-4-yl)-2-oxoethyl (8aR)-7-(3-chloro-2-fluoro-6-(1H-tetrazol-1-yl)phenyl)-5-oxooctahydroindolizine-3-carboxylate To a mixture of (8aR)-7-(3-chloro-2-fluoro-6-(1H-tetrazol-1-yl)phenyl)-5-oxooctahydroindolizine-3-carboxylic acid (0.15 g, 0.395 mmol, 1.0 equiv.) and $Cs_2CO_3$ (0.077 g, 0.237 mmol, 0.6 equiv.) in DMF (5 mL) was added 2-bromo-1-(2-(((tert butyldimethylsilyl)oxy)methyl)-3-fluoropyridin-4-yl)ethan-1-one (0.3 g) and the mixture was stirred at room temperature for 2 h. The mixture was diluted with $H_2O$, extracted with ethyl acetate twice. The combined organic layers were washed with brine, dried over $Na_2SO_4$, concentrated and purified by silica gel chromatography (0-3% MeOH/DCM) to yield 2-(2-(((tert-butyldimethylsilyl)oxy)methyl)-3-fluoropyridin-4-yl)-2-oxoethyl (8aR)-7-(3-chloro-2-fluoro-6-(1H-tetrazol-1-yl)phenyl)-5-oxooctahydroindolizine-3-carboxylate as a yellow solid. LC-MS: (ES, m/z): 661.20 $[M+H]^+$.

Step 3: (8aR)-3-(5-(2-(((tert-butyldimethylsilyl)oxy)methyl)-3-fluoropyridin-4-yl)-1H-imidazol-2-yl)-7-(3-chloro-2-fluoro-6-(1H-tetrazol-1-yl)phenyl)hexahydroindolizin-5(1H)-one To a solution of 2-(2-(((tert-butyldimethylsilyl)oxy)methyl)-3-fluoropyridin-4-yl)-2-oxoethyl (8aR)-7-(3-chloro-2-fluoro-6-(1H-tetrazol-1-yl)phenyl)-5-oxooctahydroindolizine-3-carboxylate (0.1 g, 0.151 mmol, 1.0 equiv.) in toluene (5 mL) were added $NH_4OAc$ (0.117 g, 1.512 mmol, 10 equiv.) and AcOH (0.1 mL) and the mixture was stirred for 1 h at 100° C. The solvent was evaporated under vacuum and purified by reverse phase chromatography on C18 (0-50% $ACN/H_2O$) to yield (8aR)-3-(5-(2-(((tert-butyldimethylsilyl)oxy)methyl)-3-fluoropyridin-4-yl)-1H-imidazol-2-yl)-7-(3-chloro-2-fluoro-6-(1H-tetrazol-1-yl)phenyl)hexahydroindolizin-5(1H)-one as a yellow solid. LC-MS: (ES, m/z): 641.40 $[M+H]^+$.

Step 4: (3R',8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)hexahydroindolizin-5(1H)-one To a solution of (8aR)-3-(5-(2-(((tert-butyldimethylsilyl)oxy)methyl)-3-fluoropyridin-4-yl)-1H-imidazol-2-yl)-7-(3-chloro-2-fluoro-6-(1H-tetrazol-1-yl)phenyl)hexahydroindolizin-5(1H)-one (50 mg, 0.078 mmol, 1.0 equiv.) in THE (1 mL) was added $Et_3N{\cdot}3HF$ (1 mL) at room temperature and the solution was stirred for 2 h at room temperature. The solution was concentrated under vacuum and purified by reverse phase chromatography on C18 (80 g, $MeCN/H_2O$ (0.05% $CF_3COOH$): 0>>>45%) to yield (8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)hexahydroindolizin-5(1H)-one. The racemic product was separated by Chiral-HPLC (Column: (R,R) WHELK-01, 4.6*50 mm, 3.5 um; Mobile Phase: Hex (0.1% DEA): EtOH=50:50; Flow rate: 1 mL/min) to yield (3R',8aR)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)hexahydroindolizin-5(1H)-one as a white solid.

LC-MS: (ES, m/z): 527.15 $[M+H]^+$. $^1H$-NMR: (400 MHz, DMSO-$d_6$) δ 12.21 (s, 1H), 9.85 (s, 1H), 8.28-8.40 (m, 1H), 7.85-7.92 (m, 1H), 7.76-7.84 (m, 1H), 7.47-7.57 (m, 2H), 5.24-5.28 (m, 1H), 4.96 (d, J=8.5 Hz, 1H), 4.61 (s, 2H), 3.44-3.54 (m, 1H), 2.72-2.84 (m, 1H), 2.40-2.45 (m, 2H), 2.14-2.23 (m, 2H), 2.04-2.12 (m, 1H), 1.76-2.03 (m, 3H). $^{19}F$-NMR: (376 MHz, DMSO-$d_6$) δ −111.74, −130.10.

Example 379 (3S,8aR)-3-(5-(7H-pyrrolo[2,3-d]pyrimidin-5-yl)-1H-imidazol-2-yl)-7-(3-chloro-2-fluoro-6-(1H-tetrazol-1-yl)phenyl)-2,3,8,8a-tetrahydroindolizin-5(1H)-one

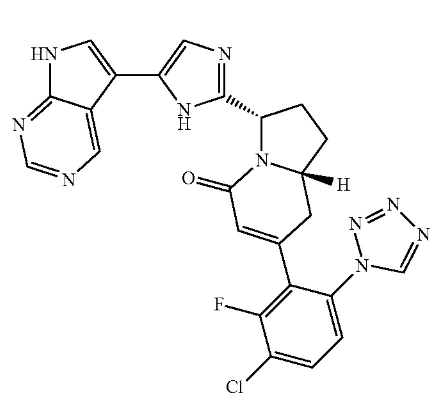 [SMILES: O=C1C=C(c2c(-n3cnnn3)ccc(Cl)c2F)C[C@H]2CC[C@@H](c3ncc(-c4c[nH]c5ncncc45)[nH]3)N12]

Step 1: 5-bromo-7-((2-(trimethylsilyl)ethoxy)methyl)-7H-pyrrolo[2,3-d]pyrimidine To a solution of 5-bromo-7H-pyrrolo[2,3-d]pyrimidine (0.5 g, 2.525 mmol, 1.0 equiv.) in N,N-dimethylformamide (10 mL) was added sodium hydride (0.131 g, 3.282 mmol, 1.3 equiv.) at 0° C. The reaction mixture was stirred 0.5 h. Then, 2-(trimethylsilyl)ethoxymethyl chloride (0.505 g, 3.030 mmol, 1.2 equiv.) was added and the reaction mixture was stirred at room temperature. for 2 h. Water was added, the mixture was extracted with EA. The combined extracts were washed with water, saturated brine, and dried over anhydrous $Na_2SO_4$, then concentrated and the resulting residue purified by chromatography on EA/PE (0-20%) to yield 5-bromo-7-((2-(trimethylsilyl)ethoxy)methyl)-7H-pyrrolo[2,3-d]pyrimidine as a yellow oil. LC-MS: (ES, m/z): 327.95 $[M+H]^+$, 329.95 $[M+H+2]^+$.

Step 2: 5-(4,4,5,5-tetramethyl-1,3,2-dioxaborolan-2-yl)-7-((2-(tri methylsilyl)ethoxy)methyl)-7H-pyrrolo[2,3-d]pyrimidine To a mixture of 5-bromo-7-((2-(trimethylsilyl)ethoxy)methyl)-7H-pyrrolo[2,3-d]pyrimidine (0.53 g, 1.614 mmol, 1.0 equiv) and 4,4,4',4',5,5,5',5'-octamethyl-2,2'-bi(1,3,2-dioxaborolane) (0.820 g, 3.229 mmol, 2.0 equiv.) in 1,4-dioxane (10 mL) were added potassium acetate (0.475 g, 4.843 mmol, 3.0 equiv.) and 1,1'-bis(diphenylphosphino)ferrocene-palladium(II)dichloride dichloromethane complex (0.132 g, 0.161 mmol, 0.1 equiv.). The reaction mixture was stirred at 100° C. for 3 h under $N_2$. Water was added, the mixture was extracted with EA. The combined extracts were washed with water, saturated brine and dried over anhydrous $Na_2SO_4$, then concentrated to yield 5-(4,4,5,5-tetramethyl-1,3,2-dioxaborolan-2-yl)-7-((2-(trimethylsilyl)ethoxy)methyl)-7H-pyrrolo[2,3-d]pyrimidine as a black oil. LC-MS (ES, m/z): 376.20 $[M+H]^+$.

Step 3: (3S)-7-(6-amino-3-chloro-2-fluorophenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one To a mixture of (3S)-7-(6-amino-3-chloro-2-fluorophenyl)-3-(5-iodo-1H-imidazol-2-yl)-2,3,8,8a-tetrahydroindolizin-5(1H)-one (100 mg, 0.212 mmol, 1.0 equiv.) and 5-(4,4,5,5-tetramethyl-1,3,2-dioxaborolan-2-yl)-7-((2-(trimethylsilyl)ethoxy)methyl)-7H-pyrrolo[2,3-d]pyrimidine (397.0 mg, 1.0 mmol, 5.0 equiv.) in 1,4-dioxane (10 mL) and water (1 mL) were added potassium carbonate (87.716 mg, 0.635 mmol, 3.0 equiv.) and 1,1'-bis (di-t-butylphosphino)ferrocene palladium dichloride (13.8 mg, 0.021 mmol, 0.1 equiv.). The resulting mixture was maintained under nitrogen and stirred at 100° C. for 3 h. After cooling to room temperature, the reaction was quenched with water and the mixture was extracted with EA. The combined extracts were dried over anhydrous $Na_2SO_4$, then concentrated and the resulting residue purified by chromatography on MeOH/DCM (0-8%) to yield (3S)-7-(6-amino-3-chloro-2-fluorophenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one as a brown solid. LC-MS(ES, m/z): 594.25 $[M+H]^+$.

Step 4: (3S)-7-(3-chloro-2-fluoro-6-(1H-tetrazol-1-yl)phenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one To a mixture of (3S)-7-(6-amino-3-chloro-2-fluorophenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one (90 mg, 0.151 mmol, 1.0 equiv.) in acetic acid (5 mL) were added azidotrimethylsilane (2.5 mL) and trimethoxymethane (2.5 mL). The reaction mixture was stirred overnight at 50° C. The resulting mixture was concentrated under vacuum to yield (3S)-7-(3-chloro-2-fluoro-6-(1H-tetrazol-1-yl)phenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one as a brown solid. LC-MS(ES, m/z): 647.15 $[M+H]^+$.

Step 5: (3S,8aR)-3-(5-(7H-pyrrolo[2,3-d]pyrimidin-5-yl)-1H-imidazol-2-yl)-7-(3-chloro-2-fluoro-6-(1H-tetrazol-1-yl)phenyl)-2,3,8,8a-tetrahydroindolizin-5 (1H one A solution of (3S)-7-(3-chloro-2-fluoro-6-(1H-tetrazol-1-yl)phenyl)-3-(5-(7-((2-(trimethylsilyl)ethoxy)methyl)-7H-pyrrolo[2,3-d]pyrimidin-5-yl)-1H-imidazol-2-yl)-2,3,8,8a-tetrahydroindolizin-5(1H)-one (100 mg) in dichloromethane (10 mL) and trifluoroacetic acid (2 mL) was stirred at room temperature for 1 h. The resulting mixture was concentrated under vacuum. The residue was dissolved into ammonia solution (5 mL, 2 M in methanol) and stirred at room temperature. for 5 min. The resulting mixture was extracted with EA two times. The combined extracts were dried over anhydrous $Na_2SO_4$, then concentrated. The residue was purified by silica gel column chromatography on MeOH/DCM (0-15%) yield a racemic product, which was purified by Chiral-HPLC with (Hex:DCM=3:1)(0.1% DEA): EtOH=70:30 to yield (3S,8a*R)-3-(5-(7H-pyrrolo[2,3-d]pyrimidin-5-yl)-1H-imidazol-2-yl)-7-(3-chloro-2-fluoro-6-(1H-tetrazol-1-yl)phenyl)-2,3,8,8a-tetrahydroindolizin-5 (1H)-one as an off-white solid and (3S,8a'S)-3-(5-(7H-pyrrolo[2,3-d]pyrimidin-5-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC-MS(ES, m/z): 517.10 $[M+H]^+$. $^1$H-NMR: (400 MHz, Methanol-$d_4$) δ 9.58 (s, 1H), 9.23 (s, 1H), 8.75 (s, 1H), 7.72-7.83 (m, 2H), 7.52-7.59 (m, 1H), 7.35 (s, 1H), 5.72 (d, J=2.8 Hz, 1H), 5.09-5.19 (m, 1H), 3.82-3.94 (m, 1H), 2.86-3.05 (m, 1H), 2.56-2.64 (m, 1H), 2.28-2.40 (m, 1H), 2.19-2.27 (m, 2H), 2.03-2.16 (m, 1H). $^{19}$F-NMR: (376 MHz, Methanol-$d_4$) δ −113.29.

Example 380 (3S,8aR)-3-(5-(2-amino-3-chloropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

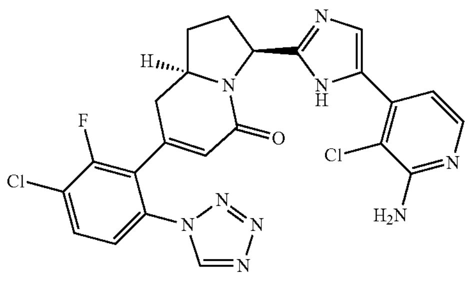 [SMILES: Nc1nccc(-c2cnc([C@@H]3CC[C@@H]4CC(c5c(-n6cnnn6)ccc(Cl)c5F)=CC(=O)N43)[nH]2)c1Cl]

Step 1: N-(3-chloro-4-iodopyridin-2-yl)acetamide

A solution of 3-chloro-4-iodopyridin-2-amine (2 g, 7.9 mmol, 1.0 equiv.) in acetic anhydride (20 mL) was stirred at 80° C. for 1 h. The resulting mixture was concentrated under vacuum. The residue was purified by silica gel chromatography (60-80% ethyl acetate/petroleum ether) to yield N-(3-chloro-4-iodopyridin-2-yl)acetamide as a white solid. LC-MS(ES, m/z): 297.1 $[M+H]^+$.

Step 2: N-(3-chloro-4-(1-ethoxyvinyl)pyridin-2-yl) acetamide

To a solution of N-(4-chloro-3-cyanopyridin-2-yl)acetamide (1 g, 3.4 mmol, 1.0 equiv.) in 1,4-dioxane (20 mL) were added tributyl(1-ethoxyvinyl)stannane (2.4 g, 6.7 mmol, 2.0 equiv.) and $Pd(PPh_3)_4$ (389.7 mg, 0.3 mmol, 0.1 equiv.). The resulting mixture was stirred at 100° C. for 5 hrs. The resulting mixture was concentrated. The residue was purified by silica gel chromatography (70-90% ethyl acetate/petroleum ether) to yield N-(3-chloro-4-(1-ethoxyvinyl)pyridin-2-yl)acetamide as a yellow solid. LC-MS(ES, m/z): 241.3 $[M+H]^+$.

Step 3: N-(4-(2-bromoacetyl)-3-chloropyridin-2-yl) acetamide

To a solution of N-(3-chloro-4-(1-ethoxyvinyl)pyridin-2-yl)acetamide (200 mg, 0.8 mmol, 1.0 equiv.) in THE (4 mL) and $H_2O$ (1 mL) was added NBS (133.1 mg, 0.7 mmol, 0.9 equiv.). The resulting mixture was stirred at 25° C. for 1 h. The resulting mixture was extracted with ethyl acetate (50 mL). The organic layers were combined, dried over anhydrous sodium sulfate, filtered and concentrated to yield N-(4-(2-bromoacetyl)-3-chloropyridin-2-yl)acetamide as a yellow oil. LC-MS(ES, m/z): 291.0 $[M+H]^+$.

Step 4: 2-(2-acetamido-3-chloropyridin-4-yl)-2-oxoethyl (8aR)-7-(6-amino-3-chloro-2-fluorophenyl)-5-oxo-1,2,3,5,8,8a-hexahydroindolizine-3-carboxylate To a solution of (8aR)-7-(6-amino-3-chloro-2-fluorophenyl)-5-oxo-1,2,3,5,8,8a-hexahydroindolizine-3-carboxylic acid (200 mg, 0.6 mmol, 1.0 equiv.) in ACN (4 mL) was added $K_2CO_3$ (102.1 mg, 0.7 mmol, 1.2 equiv.). The resulting mixture was stirred at 25° C. for 0.5 h. N-(4-(2-bromoacetyl)-3-chloropyridin-2-yl)acetamide (179.5 mg, 0.6 mmol, 1.0 equiv.) was then added in portions. The resulting mixture was stirred at 25° C. for 1 h. The resulting mixture was concentrated. The residue was purified by silica gel chromatography (0-20% MeOH/DCM) to yield 2-(2-acetamido-3-chloropyridin-4-yl)-2-oxoethyl (8aR)-7-(6-amino-3-chloro-2-fluorophenyl)-5-oxo-1,2,3,5,8,8a-hexahydroindolizine-3-carboxylate as a yellow solid. LC-MS (ES, m/z): 535.3 $[M+H]^+$.

Step 5: N-(4-(2-((8aR)-7-(6-amino-3-chloro-2-fluorophenyl)-5-oxo-1,2,3,5,8,8a-hexahydroindolizin-3-yl)-1H-imidazol-5-yl)-3-chloropyridin-2-yl)acetamide To a solution of 2-(2-acetamido-3-chloropyridin-4-yl)-2-oxoethyl (8aR)-7-(6-amino-3-chloro-2-fluorophenyl)-5-oxo-1,2,3,5,8,8a-hexahydroindolizine-3-carboxylate (200 mg, 0.4 mmol, 1.0 equiv.) in acetic acid (0.3 mL) and toluene (3 mL) was added ammonium acetate (575.9 mg, 7.5 mmol, 20.0 equiv.). The resulting mixture was stirred at 100° C. for 1 h. The resulting mixture was concentrated under vacuum. The residue was purified by silica gel chromatography (0-20% MeOH/DCM) to yield N-(4-(2-((8aR)-7-(6-amino-3-chloro-2-fluorophenyl)-5-oxo-1,2,3,5,8,8a-hexahydroindolizin-3-yl)-1H-imidazol-5-yl)-3-chloropyridin-2-yl)acetamide as a yellow solid. LC-MS(ES, m/z): 515.3 $[M+H]^+$.

Step 6: N-(3-chloro-4-(2-((8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide To a solution of N-(4-(2-((8aR)-7-(6-amino-3-chloro-2-fluorophenyl)-5-oxo-1,2,3,5,8,8a-hexahydroindolizin-3-yl)-1H-imidazol-5-yl)-3-chloropyridin-2-yl)acetamide (50 mg, 0.09 mmol, 1.0 equiv.) in HOAc (2 mL) were added $TMSN_3$ (1 mL) and trimethoxymethane (1 mL). The resulting mixture was stirred at 25° C. for 4 hrs. The resulting mixture was concentrated to yield N-(3-chloro-4-(2-((8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl) acetamide as a yellow oil. LC-MS(ES, m/z): 658.3 $[M+H]^+$.

Step 7: (3R',8aR)-3-(5-(2-amino-3-chloropyridin-4-yl)-1H-imidazol-2-yl)-7-(3-chloro-2-fluoro-6-(1H-tetrazol-1-yl)phenyl)-2,3,8,8a-tetrahydroindolizin-5 (1H one To a solution of N-(3-chloro-4-(2-((8aR)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl) acetamide (40 mg, 0.07 mmol, 1.0 equiv.) in THE (1 mL) was added HCl (1 mL, 2 mmol, 2 M). The resulting mixture was stirred at 70° C. for 1 h. The residue was purified by reverse phase chromatography with ACN/water (0.05% TFA) (40-60%) and chiral-HPLC to yield (3R',8aR)-3-(5-(2-amino-3-chloropyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

LC-MS(ES, m/z): 526.15 $[M+H]^+$. $^1H$ NMR (400 MHz, DMSO-$d_6$) δ 12.48-12.63 (m, 1H), 9.85 (s, 1H), 7.97-7.99 (m, 1H), 7.91-7.93 (m, 2H), 7.72 (dd, J=8.7, 1.5 Hz, 1H), 7.32 (d, J=5.7 Hz, 1H), 6.77-6.85 (m, 2H), 5.70 (d, J=2.7 Hz, 1H), 5.04 (d, J=8.8 Hz, 1H), 3.75-3.79 (m, 1H), 2.72-2.74 (m, 1H), 2.56-2.58 (m, 1H), 2.11-2.26 (m, 2H), 1.89-1.98 (m, 2H). $^{19}F$ NMR (376 MHz, DMSO-$d_6$) δ–112.88.

Example 381 (3S)-7-(3-chloro-2-fluoro-6-(1H-tetrazol-1-yl)phenyl)-3-(5-(5-methyl-1H-pyrrolo[2,3-c]pyridin-3-yl)-1H-imidazol-2-yl)-2,3,8,8a-tetrahydroindolizin-5(1H)-one

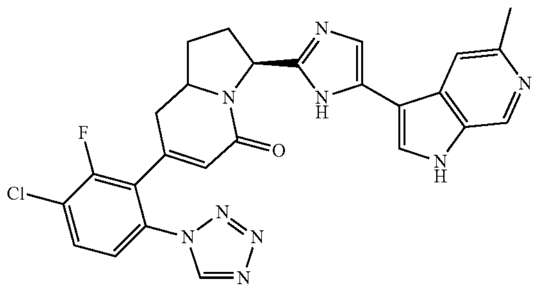 [SMILES: Cc1cc2c(-c3cnc([C@@H]4CCC5CC(c6c(-n7cnnn7)ccc(Cl)c6F)=CC(=O)N54)[nH]3)c[nH]c2cn1]

Step 1: 3-bromo-5-methyl-1H-pyrrolo[2,3-c]pyridine

To a solution of 5-methyl-1H-pyrrolo[2,3-c]pyridine (1 g, 7.6 mmol, 1.0 equiv) in acetonitrile (15 mL) was added N-bromosuccinimide (1.347 g, 7.566 mmol, 1.0 equiv). The reaction mixture stirred for 2 h at room temperature, then concentrated under vacuum. The residue was purified by silica gel chromatography with MeOH/DCM (0-12%) to yield 3-bromo-5-methyl-1H-pyrrolo[2,3-c]pyridine as an off-white solid. LC/MS(ES, m/z): 211.00 $[M+H]^+$, 213.00 $[M+H+2]^+$.

Step 2: 5-bromo-7-((2-(trimethylsilyl)ethoxy)methyl)-7H-pyrrolo[2,3-d]pyrimidine To a solution of 3-bromo-5-methyl-1H-pyrrolo[2,3-c]pyridine (1.4 g, 6.633 mmol, 1.0 equiv.) in N,N-Dimethylformamide (10 mL) was added sodium hydride (0.345 g, 8.623 mmol, 1.3 equiv., 60%) at 0° C. The reaction mixture was stirred 0.5 h. To the mixture was then added a solution of 2-(trimethylsilyl)ethoxymethyl chloride (1.327 g, 7.960 mmol, 1.2 equiv.) in N,N-dimethylformamide (10 mL) and the reaction mixture was stirred at room temperature. for 1 h. The reaction was quenched by water, the mixture was extracted with EA. The combined extracts were washed with water, saturated brine and dried over anhydrous $Na_2SO_4$. After concentration, the residue was purified by silica gel chromatography on EA/PE (0-70%) to yield 5-bromo-7-((2-(trimethylsilyl)ethoxy)methyl)-7H-pyrrolo[2,3-d]pyrimidine as a yellow oil. LC/MS(ES, m/z): 341.00 $[M+H]^+$, 343.00 $[M+H+2]^+$.

Step 3: 5-methyl-3-(4,4,5,5-tetramethyl-1,3,2-dioxaborolan-2-yl)-1-((2-(trimethylsilyl)ethoxy)methyl)-1H-pyrrolo[2,3-c]pyridine Under an atmosphere of nitrogen, to a mixture of 3-bromo-5-methyl-1-((2-(trimethylsilyl)ethoxy)methyl)-1H-pyrrolo[2,3-c]pyridine (1.7 g, 4.981 mmol, 1.0 equiv.) and 4,4,4',4',5,5,5',5'-octamethyl-2,2'-bi(1,3,2-dioxaborolane) (2.530 g, 9.961 mmol, 2.0 equiv.) in 1,4-dioxane (30 mL) were added potassium acetate (1.466 g, 14.942 mmol, 3.0 equiv.) and 1,1'-bis(diphenylphosphino)ferrocene-palladium(II)dichloride dichloromethane complex (0.407 g, 0.498 mmol, 0.1 equiv.). The reaction mixture was stirred at 100° C. for 3 h under $N_2$, then cooled to room temperature. Water was added, the mixture was extracted with EA. The combined extracts were dried over anhydrous $Na_2SO_4$, concentrated. The residue was purified by silica gel chromatography with MeOH/DCM (0%-6%) to yield 5-methyl-3-(4,4,5,5-tetramethyl-1,3,2-dioxaborolan-2-yl)-1-((2-(trimethylsilyl)ethoxy)methyl)-1H-pyrrolo[2,3-c]pyridine as brown oil. LC/MS(ES, m/z): 389.35 $[M+H]^+$.

Step 4: (3S)-7-(6-amino-3-chloro-2-fluorophenyl)-3-(5-(5-methyl-1-((2-(trimethylsilyl)ethoxy)methyl)-1H-pyrrolo[2,3-c]pyridin-3-yl)-1H-imidazol-2-yl)-2,3,8,8a-tetrahydroindolizin-5(1H)-one Under at atmosphere of nitrogen, to a mixture of (3S)-7-(6-amino-3-chloro-2-fluorophenyl)-3-(5-iodo-1H-imidazol-2-yl)-2,3,8,8a-tetrahydroindolizin-5(1H)-one (100 mg, 0.212 mmol, 1.0 equiv.) in 1,4-dioxane (10 mL) and water (1 mL) were added 5-methyl-3-(4,4,5,5-tetramethyl-1,3,2-dioxaborolan-2-yl)-1-((2-(trimethylsilyl)ethoxy)methyl)-1H-pyrrolo[2,3-c]pyridine (410.8 mg, 1.058 mmol, 5.0 equiv.), potassium carbonate (87.7 mg, 0.635 mmol, 3.0 equiv.) and 1,1'-bis (di-t butylphosphino)ferrocene palladium dichloride (13.8 mg, 0.021 mmol, 0.1 equiv.). The resulting mixture was maintained under nitrogen and stirred at 100° C. for 3 h, then cooled to room temperature. Water was added, the mixture was extracted with EA. The combined extracts were dried over anhydrous $Na_2SO_4$, concentrated. The residue was purified by silica gel chromatography with MeOH/DCM (0%-15%) to yield (3S)-7-(6-amino-3-chloro-2-fluorophenyl)-3-(5-(5-methyl-1-((2-(trimethylsilyl)ethoxy)methyl)-1H-pyrrolo[2,3-c]pyridin-3-yl)-1H-imidazol-2-yl)-2,3,8,8a-tetrahydroindolizin-5(1H one as a brown solid. LC/MS(ES, m/z): 607.15 $[M+H]^+$.

Step 5: (3S)-7-(3-chloro-2-fluoro-6-(1H-tetrazol-1-yl)phenyl)-3-(5-(5-methyl-1-((2-(trimethylsilyl)ethoxy)methyl)-1H-pyrrolo[2,3-c]pyridin-3-yl)-1H-imidazol-2-yl)-2,3,8,8a-tetrahydroindolizin-5(1H)-one To a mixture of (3S)-7-(6-amino-3-chloro-2-fluorophenyl)-3-(5-(5-methyl-1-((2-(trimethylsilyl)ethoxy)methyl)-1H-pyrrolo[2,3-c]pyridin-3-yl)-1H-imidazol-2-yl)-2,3,8,8a-tetrahydroindolizin-5(1H)-one (110 mg, 0.181 mmol, 1.0 equiv.) in acetic acid (5 mL) were added azidotrimethylsilane (2.5 mL) and trimethoxymethane (2.5 mL). The reaction mixture was stirred overnight at 50° C. The resulting mixture was concentrated under vacuum to yield (3S)-7-(3-chloro-2-fluoro-6-(1H-tetrazol-1-yl)phenyl)-3-(5-(5-methyl-1-((2-(trimethylsilyl)ethoxy)methyl)-1H-pyrrolo[2,3-c]pyridin-3-yl)-1H-imidazol-2-yl)-2,3,8,8a-tetrahydroindolizin-5(1H)-one as a brown solid. LC/MS(ES, m/z): 660.15 $[M+H]^+$.

Step 6: (3S)-7-(3-chloro-2-fluoro-6-(1H-tetrazol-1-yl)phenyl)-3-(5-(5-methyl-1H-pyrrolo[2,3-c]pyridin-3-yl)-1H-imidazol-2-yl)-2,3,8,8a-tetrahydroindolizin-5(1H) one A solution of (3S)-7-(3-chloro-2-fluoro-6-(1H-tetrazol-1-yl)phenyl)-3-(5-(5-methyl-1-((2-(trimethylsilyl)ethoxy)methyl)-1H-pyrrolo[2,3-c]pyridin-3-yl)-1H-imidazol-2-yl)-2,3,8,8a-tetrahydroindolizin-5(1H)-one (150 mg) in dichloromethane (10 mL) and trifluoroacetic acid (5 mL) was stirred at room temperature for 3 h. The resulting mixture was concentrated under vacuum. The residue was purified by reverse phase chromatography with $CH_3CN$/water (5%-38%) to yield the product which was purified by HPLC to yield (3S)-7-(3-chloro-2-fluoro-6-(1H-tetrazol-1-yl)phenyl)-3-(5-(5-methyl-1H-pyrrolo[2,3-c]pyridin-3-yl)-1H-imidazol-2-yl)-2,3,8,8a-tetrahydroindolizin-5(1H)-one as an off-white solid.

LC/MS(ES, m/z): 530.15 $[M+H]^+$. $^1H$ NMR: (300 MHz, Methanol-$d_4$) δ 9.58 (s, 1H), 8.57 (s, 1H), 7.74-7.89 (m, 2H), 7.64 (s, 1H), 7.50-7.58 (m, 1H), 7.23 (s, 1H), 5.72 (d, J=2.8 Hz, 1H), 5.07-5.20 (m, 1H), 3.79-3.98 (m, 1H), 2.89-3.10 (m, 1H), 2.52-2.66 (m, 4H), 1.98-2.46 (m, 4H). $^{19}F$ NMR: (286 MHz, Methanol-$d_4$) δ −113.32.

Example 382 (3R,8aS)-3-(5-(2-amino-3-methoxypyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

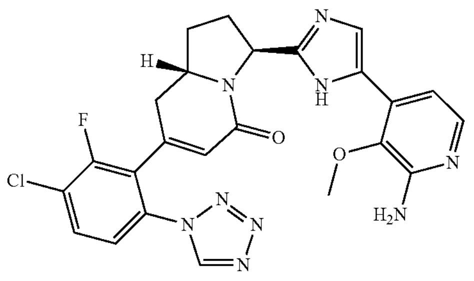 [SMILES: COc1c(-c2cnc([C@@H]3CC[C@H]4CC(c5c(-n6cnnn6)ccc(Cl)c5F)=CC(=O)N43)[nH]2)ccnc1N]

Step 1: N-(4-chloro-3-methoxypyridin-2-yl)acetamide

4-Chloro-3-methoxypyridin-2-amine (400 mg, 2.52 mmol, 1.0 equiv.) in acetic anhydride (15 mL) was stirred at room temperature for 2 h. The mixture was concentrated under reduced pressure. The mixture was added EA (50 mL) and then washed by $NaHCO_3$ (50 mL×3). The organic layers were combined, dried over anhydrous sodium sulfate, filtered, and concentrated to yield a N-(4-chloro-3-methoxypyridin-2-yl)acetamide. LC/MS: mass calculated for $C_8H_9ClN_2O_2$: 200.622, measured: 201.20 $[M+H]^+$ Step 2: N-(4-(1-ethoxyvinyl)-3-methoxypyridin-2-yl)acetamide N-(4-chloro-3-methoxypyridin-2-yl)acetamide (300 mg, 1.50 mmol, 1.0 equiv.), tributyl(1-ethoxyvinyl)stannane (810 mg, 2.24 mmol, 1.5 equiv.), and bis(triphenylphosphine)palladium(II) chloride (105 mg, 0.15 mmol, 0.1 equiv.) were dissolved in 1,4-dioxane (15 mL). The flask was evacuated and flushed three times with nitrogen and the mixture was stirred 2 h at 100° C. under an atmosphere of nitrogen. After cooling to room temperature, the reaction was quenched with water (50 mL). The resulting mixture was extracted with ethyl acetate (3×50 mL). The organic layers were combined, dried over anhydrous sodium sulfate, filtered and concentrated. The residue was purified by silica gel chromatography (0-50% ethyl acetate/petroleum ether) to yield the N-(4-(1-ethoxyvinyl)-3-methoxypyridin-2-yl)

acetamide as a yellow oil. LC/MS: mass calculated for $C_{12}H_{16}N_2O_3$: 236.267, measured: 237.25 [M+H]$^+$ Step 3: N-(4-(2-bromoacetyl)-3-methoxypyridin-2-yl)acetamide To a solution of N-(4-(1-ethoxyvinyl)-3-methoxypyridin-2-yl)acetamide (250 mg, 1.06 mmol, 1.0 equiv.) in tetrahydrofuran (12 mL) was added N-bromosuccinimide (170 mg, 0.95 mmol, 0.9 equiv.). The resulting mixture was stirred at room temperature for 1 h. The reaction was quenched with water (50 mL). The resulting mixture was extracted with ethyl acetate (3×50 mL). The organic layers were combined, dried over anhydrous sodium sulfate, filtered, and concentrated to yield N-(4-(2-bromoacetyl)-3-methoxypyridin-2-yl)acetamide. LC/MS: mass calculated for $C_{10}H_{11}BrN_2O_3$: 287.11, measured: 289.15 [M+H]$^+$.

Step 4: 2-(2-acetamido-3-methoxypyridin-4-yl)-2-oxoethyl (3S,8aS)-7-(3-chloro-2-fluoro-6-(1H-tetrazol-1-yl)phenyl)-5-oxo-1,2,3,5,8,8a-hexahydroindolizine-3-carboxylate (3S,8aS)-7-(3-chloro-2-fluoro-6-(1H-tetrazol-1-yl)phenyl)-5-oxo-1,2,3,5,8,8a-hexahydroindolizine-3-carboxylic acid (180 mg, 0.48 mmol, 1.0 equiv.) in acetonitrile (20 mL) was added potassium carbonate (132 mg, 0.95 mmol, 2.0 equiv.). The resulting mixture was stirred at room temperature for 0.5 h, and then N-(4-(2-bromoacetyl)-3-methoxypyridin-2-yl)acetamide (164 mg, 0.57 mmol, 1.2 equiv.) was added. The resulting mixture was stirred at room temperature for 1 h. The mixture was concentrated under reduced pressure and then purified by silica gel chromatography (0-50% ethyl acetate/petroleum ether) to yield 2-(2-acetamido-3-methoxypyridin-4-yl)-2-oxoethyl (3S,8 aS)-7-(3-chloro-2-fluoro-6-(1H-tetrazol-1-yl)phenyl)-5-oxo-1, 2, 3, 5, 8, 8a-hexahydroindolizine-3-carboxylate as a yellow oil. LC/MS: mass calculated for $C_{26}H_{23}ClFN_7O_6$: 583.956, measured: 584.10 [M+H]$^+$ Step 5: N-(4-(2-((3S,8aS)-7-(3-chloro-2-fluoro-6-(1H-tetrazol-1-yl)phenyl)-5-oxo-1,2,3, 5,8,8a-hexahydroindolizin-3-yl)-1H-imidazol-5-yl)-3-methoxypyridin-2-yl)acetamide To a mixture of 2-(2-acetamido-3-methoxypyridin-4-yl)-2-oxoethyl (3S,8aS)-7-(3-chloro-2-fluoro-6-(1H-tetrazol-1-yl)phenyl)-5-oxo-1,2,3,5,8,8a-hexahydroindolizine-3-carboxylate (160 mg, 0.27 mmol, 1.0 equiv.) in toluene (5 mL) and acetic acid (0.5 mL) was added ammonium acetate (211 mg, 2.74 mmol, 20.0 equiv.). The resulting mixture was stirred at 100° C. for 1 h. The mixture was concentrated under reduced pressure and then purified by silica gel chromatography (0-50% ethyl acetate/petroleum ether) to yield N-(4-(2-((3S,8aS)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-methoxypyridin-2-yl)acetamide as a yellow oil. LC/MS: mass calculated for $C_{26}H_{23}ClFN_9O_3$: 563.971, measured: 564.30 [M+H]$^+$ Step 5: (3R*,8aS)-3-(5-(2-amino-3-methoxypyridin-4-yl)-1H-imidazol-2-yl)-7-(3-chloro-2-fluoro-6-(1H-tetrazol-1-yl)phenyl)-2,3,8,8a-tetrahydroindolizin-5 (1H one To a mixture of N-(4-(2-((8aS)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-methoxypyridin-2-yl)acetamide (100 mg, 0.18 mmol, 1.0 equiv.) in tetrahydrofuran (5 mL) was added 2M hydrochloric acid (5 mL). The resulting mixture was stirred at 70° C. for 1 h. The mixture was concentrated under reduced pressure and then purified by Prep-HPLC to yield 3-(5-(2-amino-3-methoxypyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid which was further separated by Chiral-HPLC to yield (3R',8aS)-3-(5-(2-amino-3-methoxypyridin-4-yl)-1H-imidazol-2-yl)-7-(3-chloro-2-fluoro-6-(1H-tetrazol-1-yl) phenyl)-2,3,8,8a-tetrahydroindolizin-5(1H)-one as a white solid.

LC/MS: mass calculated for $C_{24}H_{21}ClFN_9O_2$: 521.934, measured: 522.05 [M+H]$^+$ $^1H$ NMR (400 MHz, DMSO-$d_6$) δ 11.95-12.03 (m, 1H), 9.84 (d, J=3.3 Hz, 1H), 7.89-8.05 (m, 1H), 7.62-7.79 (m, 2H), 7.67 (d, J=5.3 Hz, 1H), 7.14 (d, J=5.3 Hz, 1H), 5.66-5.75 (m, 3H), 4.99-5.11 (m, 1H), 3.68-3.74 (m, 1H), 3.56-3.64 (m, 3H), 2.71-2.81 (m, 1H), 2.55-2.57 (m, 1H), 2.05-2.23 (m, 2H), 1.93-2.04 (m, 2H). $^{19}F$ NMR (376 MHz, DMSO-$d_6$) δ −112.87.

Example 383 6-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-7-fluoroindolin-2-one

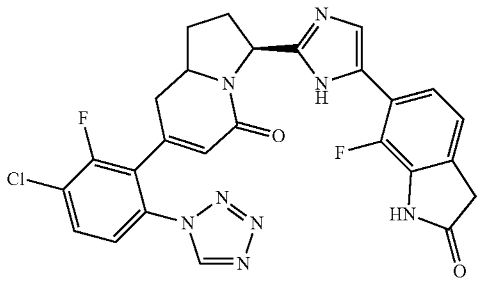 [SMILES: O=C1Cc2ccc(-c3cnc([C@@H]4CCC5CC(c6c(-n7cnnn7)ccc(Cl)c6F)=CC(=O)N54)[nH]3)c(F)c2N1]

Step 1: 6-bromo-7-fluoroindolin-2-one

To a solution of 6-bromo-7-fluoroindolin-2,3-dione (2.80 g, 11.48 mmol) in ethanol (50 mL) was added hydrazine hydrate (85%, 0.5 mL) under nitrogen. After the mixture was refluxed for 30 min, a yellow participate was formed and collected by filtration. The yellow precipitate was then dissolved in anhydrous ethanol (50 mL), and t-BuOK (4.03 g, 35.90 mmol) was added. The mixture was refluxed under nitrogen for 2 h before pouring into water. The mixture was acidified with dilute HCl to pH=2 and extracted with EA. The combined organic phase was washed with water, brine, dried with $Na_2SO_4$, and concentrated under reduced pressure. The residue was purified by column chromatography (silica gel; eluent: PE:EA=5:1) to yield 6-bromo-7-fluoroindolin-2-one as a light-yellow solid. MS (ESI): mass calculated for $C_8H_5BrFNO$ 228.95 m/z, measured 230.00[M+H]$^+$.

Step 2: 7-fluoro-6-(4,4,5,5-tetramethyl-1,3,2-dioxaborolan-2-yl)indolin-2-one

Under an inert atmosphere of nitrogen, to a solution of 6-bromo-7-fluoroindolin-2-one (500 mg, 2.174 mmol, 1.0 equiv) in 1,4-dioxane (10 mL), were added 4,4,4',4',5,5,5', 5'-octamethyl-2,2'-bi(1,3,2-dioxaborolane (828 mg, 3.261 mmol, 1.5 equiv), Pd(dppf)$Cl_2$ (159 mg, 0.217 mmol, 0.1 equiv), and KOAc (427 mg, 4.351 mmol, 2 equiv). The reaction mixture was stirred for 2 h at 90° C. The reaction was concentrated to dryness under reduced pressure to yield a residue, which was purified by column chromatography on silica gel with EA/PE (0-100%) to yield 7-fluoro-6-(4,4,5,5-tetramethyl-1,3,2-dioxaborolan-2-yl)indolin-2-one as a yellow solid. MS (ESI): mass calculated for $C_{14}H_{17}BFNO_3$ 277.13 m/z, measured 278.15[M+H]$^+$.

Step 3: 6-(2-((3S)-7-(6-amino-3-chloro-2-fluorophenyl)-5-oxo-1,2,3,5,8,8a-hexahydroindolizin-3-yl)-1H-imidazol-5-yl)-7-fluoroindolin-2-one Under an inert atmosphere of nitrogen, to a solution of (3S)-7-(6-amino-3-chloro-2-fluorophenyl)-3-(5-iodo-1H-imidazol-2-yl)-2,3,8,8a-tetrahydroindolizin-5(1H)-one (200 mg, 0.423 mmol, 1.0 equiv) in 1,4-dioxane (5 mL) with $H_2O$ (0.5 mL), were added 7-fluoro-6-(4,4,5,5-tetramethyl-1,3,2-dioxaborolan-2-yl)indolin-2-one (176 mg, 0.635 mmol, 1.5 equiv), Pd(dppf)$Cl_2$ (40 mg, 0.055 mmol, 0.1 equiv), $K_2CO_3$ (117 mg, 0.847 mmol, 2 equiv). The reaction mixture was stirred for 2 h at 90° C. The reaction was concentrated to dryness under reduced pressure to yield a residue, which was purified by column chromatography on silica gel with MeOH/DCM (0-15%) to yield 6-(2-((3S)-7-(6-amino-3-chloro-2-fluorophenyl)-5-oxo-1,2,3,5,8,8a-hexahydroindolizin-3-yl)-1H-imidazol-5-yl)-7-fluoroindolin-2-one as a yellow solid. MS (ESI): mass calculated for $C_{25}H_{20}ClF_2NSO_2$ 495.13 m/z, measured 496.05[M+H]$^+$.

Step 4: 6-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-7-fluoroindolin-2-one To a solution of 6-(2-((3S)-7-(6-amino-3-chloro-2-fluorophenyl)-5-oxo-1,2,3,5,8,8a-hexahydroindolizin-3-yl)-1H-imidazol-5-yl)-7-fluoroindolin-2-one (60 mg, 1.121 mmol, 1.0 equiv) in AcOH (3 mL) were added $TMSN_3$ (139 mg, 1.207 mmol, 10 equiv), and trimethoxymethane (128 mg, 1.206 mmol, 10 equiv). The reaction mixture was stirred for overnight at room temperature. The mixture was concentrated under vacuum and purified by C18 column (eluent: 5% to 50% (v/v) $CH_3CN$ and $H_2O$ with 0.05% $NH_4HCO_3$) to yield 6-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-7-fluoroindolin-2-one as an off-white solid.

LC/MS: mass calculated for $C_{25}H_{19}ClF_2N_8O_2$: 548.13, measured: 549.10 [M+H]$^+$. LC-MS: (ES, m/z): 549.10 [M+H]$^+$; $^1$H-NMR: $^1$H NMR (300 MHz, DMSO-$d_6$) δ 11.95 (s, 1H), 10.87 (s, 1H), 9.84 (s, 1H), 7.92-8.03 (m, 1H), 7.72 (d, J=8.7 Hz, 1H), 7.55-7.66 (m, 1H), 7.31 (s, 1H), 7.08 (d, J=7.9 Hz, 1H), 5.67-5.69 (m, 1H), 5.02 (d, J=8.3 Hz, 1H), 3.66-3.76 (m, 1H), 3.57 (s, 2H), 2.47-2.53 (m, 2H), 2.07-2.23 (m, 2H), 1.92-2.02 (m, 2H). $^{19}$F NMR (282 MHz, DMSO-$d_6$) δ−112.87, −135.48.

Example 384 (3S,8aR)-7-(3-chloro-2-fluoro-6-(1H-tetrazol-1-yl)phenyl)-3-(5-(7-fluoro-1H-indol-6-yl)-1H-imidazol-2-yl)-2,3,8,8a-tetrahydroindolizin-5(1H)-one

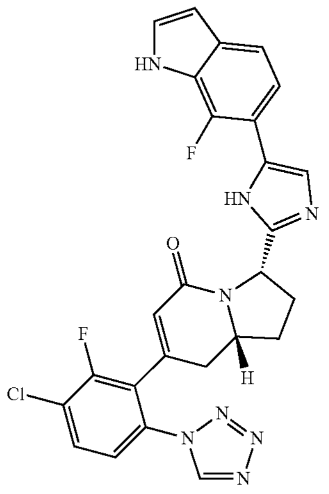 [SMILES: O=C1C=C(c2c(-n3cnnn3)ccc(Cl)c2F)C[C@H]2CC[C@@H](c3ncc(-c4ccc5cc[nH]c5c4F)[nH]3)N12]

Step 1: 7-fluoro-6-(4,4,5,5-tetramethyl-1,3,2-dioxaborolan-2-yl)-1H-indole

Under an inert atmosphere of nitrogen, to a solution of 6-bromo-7-fluoro-1H-indole (300 mg, 1.402 mmol, 1.0 equiv) in 1,4-dioxane (5 mL), were added 4,4,4',4',5,5,5',5'-octamethyl-2,2'-bi(1,3,2-dioxaborolane (534 mg, 2.103 mmol, 1.5 equiv), Pd(dppf)$Cl_2$ (103 mg, 0.141 mmol, 0.1 equiv), and KOAc (275 mg, 2.802 mmol, 2 equiv). The reaction mixture was stirred for 2 h at 90° C. The reaction was concentrated to dryness under reduced pressure to yield a residue, which was purified by column chromatography on silica gel with EA/PE (0-50%) to yield 7-fluoro-6-(4,4,5,5-tetramethyl-1,3,2-dioxaborolan-2-yl)-1H-indole as a yellow solid. MS (ESI): mass calculated for $C_{14}H_{17}BFNO_2$ 261.13 m/z, measured 262.10[M+H]$^+$.

Step 2: (3S,8aR)-7-(6-amino-3-chloro-2-fluorophenyl)-3-(5-(7-fluoro-1H-indol-6-yl)-1H-imidazol-2-yl)-2,3,8,8a-tetrahydroindolizin-5(1H)-one Under an inert atmosphere of nitrogen, to a solution of (3S)-7-(6-amino-3-chloro-2-fluorophenyl)-3-(5-iodo-1H-imidazol-2-yl)-2,3,8,8a-tetrahydroindolizin-5(1H)-one (100 mg, 0.212 mmol, 1.0 equiv) in 1,4-dioxane (5 mL) with $H_2O$ (0.5 mL), were added 7-fluoro-6-(4,4,5,5-tetramethyl-1,3,2-dioxaborolan-2-yl)-1H-indole (83 mg, 0.318 mmol, 1.5 equiv), Pd(dppf)$Cl_2$ (15 mg, 0.020 mmol, 0.1 equiv), $K_2CO_3$ (58 mg, 0.420 mmol, 2 equiv). The reaction mixture was stirred for 2 h at 90° C. The reaction was concentrated to dryness under reduced pressure to yield a residue, which was purified by column chromatography on silica gel with MeOH/DCM (0-15%) to yield (3S,8aR)-7-(6-amino-3-chloro-2-fluorophenyl)-3-(5-(7-fluoro-1H-indol-6-yl)-1H-imidazol-2-yl)-2,3,8,8a-tetrahydroindolizin-5(1H)-one as a yellow solid. MS (ESI): mass calculated for $C_{25}H_{20}ClF_2N_5O$ 479.13 m/z, measured 480.10[M+H]$^+$.

Step 3: (3S,8aR)-7-(3-chloro-2-fluoro-6-(1H-tetrazol-1-yl)phenyl)-3-(5-(7-fluoro-1H-indol-6-yl)-1H-imidazol-2-yl)-2,3,8,8a-tetrahydroindolizin-5(1H)-one To a solution of (3S)-7-(6-amino-3-chloro-2-fluorophenyl)-3-(5-(7-fluoro-1H-indol-6-yl)-1H-imidazol-2-yl)-2,3,8,8a-tetrahydroindolizin-5(1H)-one (100 mg, 0.208 mmol, 1.0 equiv) in AcOH (5 mL) were added $TMSN_3$ (240 mg, 2.083 mmol, 10 equiv), and trimethoxymethane (221 mg, 2.083 mmol, 10 equiv). The reaction mixture was stirred for overnight at room temperature. The residue was purified by preparative HPLC using a (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 33 B to 63 B in 7 min; 254 nm) to yield (3S,8aR)-7-(3-chloro-2-fluoro-6-(1H-tetrazol-1-yl)phenyl)-3-(5-(7-fluoro-1H-indol-6-yl)-1H-imidazol-2-yl)-2,3,8,8a-tetrahydroindolizin-5(1H)-one as a white solid.

MS (ESI): mass calculated for $C_{26}H_{19}ClF_2N_8O$ 532.13 m/z, measured 533.10 $[M+H]^+$. LC-MS: (ES, m/z): 533.10 $[M+H]^+$. H-NMR: $^1H$ NMR (300 MHz, DMSO-$d_6$) δ 11.85 (s, 1H), 11.49 (s, 1H), 9.85 (s, 1H), 7.98 (t, J=8.2 Hz, 1H), 7.63-7.77 (m, 2H), 7.30-7.46 (m, 3H), 6.48 (s, 1H), 5.70 (d, J=2.6 Hz, 1H), 5.04-5.07 (m, 1H), 3.66-3.76 (m, 1H), 2.73-2.83 (m, 1H), 2.52-2.60 (m, 1H), 1.99-2.24 (m, 4H). F-NMR: $^{19}F$ NMR (282 MHz, DMSO-$d_6$) δ −112.84, −135.54.

Example 385 (3S,8aR)-3-(5-(1H-pyrrolo[3,2-c]pyridin-3-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one

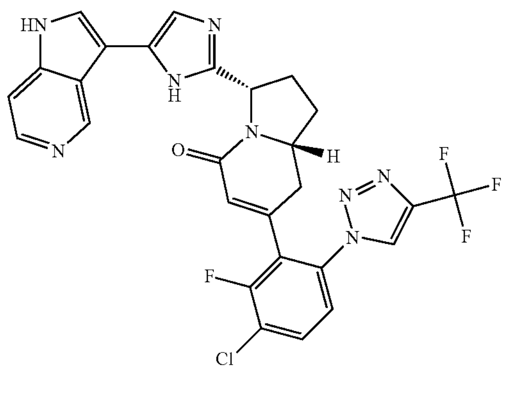 [SMILES: O=C1C=C(c2c(-n3cc(C(F)(F)F)nn3)ccc(Cl)c2F)C[C@H]2CC[C@@H](c3ncc(-c4c[nH]c5ccncc45)[nH]3)N12]

Step 1: ethyl (3S)-7-(6-azido-3-chloro-2-fluorophenyl)-5-oxo-1,2,3,5,8,8a-hexahydroindolizine-3-carboxylate To a solution of ethyl (3S)-7-(6-amino-3-chloro-2-fluorophenyl)-5-oxo-1,2,3,5,8,8a-hexahydroindolizine-3-carboxylate (1 g, 2.835 mmol, 1.0 equiv.) in acetonitrile (15 mL) was added azidotrimethylsilane (0.490 g, 4.252 mmol, 1.5 equiv.), followed by the addition of tart-butyl nitrite (0.438 g, 4.252 mmol, 1.5 equiv.). The reaction mixture was stirred at room temperature for 1 h. The resulting mixture was concentrated under vacuum. The residue was purified by silica gel chromatography with EA/PE (0%-45%) to yield ethyl (3S)-7-(6-azido-3-chloro-2-fluorophenyl)-5-oxo-1,2,3,5,8,8a-hexahydroindolizine-3-carboxylate as a light yellow solid. LC-MS(ES, m/z): 379.20 $[M+H]^+$.

Step 2: ethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate To a solution of ethyl (3S)-7-(6-azido-3-chloro-2-fluorophenyl)-5-oxo-1,2,3,5,8,8a-hexahydroindolizine-3-carboxylate (1 g, 2.640 mmol, 1.0 equiv) and 4,4,4-trifluorobut-2-ynoic acid (1.822 g, 13.200 mmol, 5.0 equiv) in acetonitrile (15 mL) was added cuprous oxide (0.151 g, 1.056 mmol, 0.4 equiv). The reaction mixture was stirred at 80° C. for 2 h under $N_2$. The solid was filtered out, and the resulting mixture was concentrated under vacuum. The residue was purified by silica gel chromatography on EA/PE (0%-70%) to yield ethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate as a light yellow solid (1.2 g, 96.1% yield). LC-MS(ES, m/z): 473.10 $[M+H]^+$.

Step 3: (3R)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carbaldehyde To a solution of ethyl (3S)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carboxylate (1.1 g, 2.326 mmol, 1.0 equiv) in dichloromethane (20 mL) was added diisobutylaluminium hydride (4.6 mL, 1 M in DCM, 4.653 mmol, 3.0 equiv.) in batches at −78° C. under $N_2$. The reaction mixture was stirred for 2 h. The reaction was quenched with potassium sodium tartrate solution, and the mixture was extracted with EA. The combined extracts were dried over anhydrous $Na_2SO_4$. The resulting mixture was concentrated under vacuum. The residue was purified by silica gel chromatography with MeOH/DCM (0%-55%) to yield (3R)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carbaldehyde as a light yellow solid. LC-MS(ES, m/z): 429.05 $[M+H]^+$.

Step 4: (3S)-7-(3-chloro-2-fluoro-6-(4-(trifluoromethyl)-1H-1,2,3-triazol-1-yl)phenyl)-3-(1H-imidazol-2-yl)-2,3,8,8a-tetrahydroindolizin-5(1H)-one To a solution of (3R)-7-(3-chloro-2-fluoro-6-(4-(trifluoromethyl)-1H-1,2,3-triazol-1-yl)phenyl)-5-oxo-1,2,3,5,8,8a-hexahydroindolizine-3-carbaldehyde (0.64 g, 1.493 mmol, 1.0 equiv.) in methanol (10 mL) and ammonium hydroxide (10 mL) was added glyoxal (2.166 g, 14.926 mmol, 10.0 equiv., 40% in water) in batches. The mixture was stirred at room temperature for 48 h. The resulting mixture was concentrated, then EA was added, washed with brine and dried over anhydrous $Na_2SO_4$, concentrated, and the residue purified by chromatography on MeOH/DCM (0-6%) to yield (3S)-7-(3-chloro-2-fluoro-6-(4-(trifluoromethyl)-1H-1,2,3-triazol-1-yl)phenyl)-3-(1H-imidazol-2-yl)-2,3,8,8a-tetrahydroindolizin-5(1H)-one as a yellow solid. LC-MS(ES, m/z): 467.00 $[M+H]^+$.

Step 5: (3S)-7-(3-chloro-2-fluoro-6-(4-(trifluoromethyl)-1H-1,2,3-triazol-1-yl)phenyl)-3-(5-iodo-1H-imidazol-2-yl)-2,3,8,8a-tetrahydroindolizin-5(1H)-one To a solution of (3S)-7-(3-chloro-2-fluoro-6-(4-(trifluoromethyl)-1H-1,2,3-triazol-1-yl)phenyl)-3-(1H-imidazol-2-yl)-2,3,8,8a-tetrahydroindolizin-5(1H)-one (250 mg, 0.536 mmol, 1.0 equiv.) in DCM (10 mL) was added N-iodosuccinimide (241 mg, 1.071 mmol, 2.0 equiv.). The reaction mixture was stirred at room temperature for 10 min. Water was added, the mixture was extracted with EA. The combined extracts were washed with water, dried over anhydrous $Na_2SO_4$, concentrated. EtOH (10 mL), $H_2O$ (10 mL) and sodium sulfite (1.35 g, 10.711 mmol, 20.0 equiv.) was added to residue. The mixture was stirred overnight at 95° C., then cooled to room temperature. Water was added, the mixture was extracted with EA. The combined extracts were dried over anhydrous $Na_2SO_4$, then concentrated. The resulting residue was purified by chromatography on MeOH/DCM (0-4%) to yield (3S)-7-(3-chloro-2-fluoro-6-(4-(trifluoromethyl)-1H-1,2,3-triazol-1-yl)phenyl)-3-(5-iodo-1H-imidazol-2-yl)-2,3,8,8a-tetrahydroindolizin-5(1H)-one as an off-white solid. LC-MS(ES, m/z): 592.95 $[M+H]^+$.

Step 6: tert-butyl 3-(2-((3S)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)-1H-pyrrolo[3,2-c]pyridine-1-carboxylate To a mixture of (3S)-7-(3-chloro-2-fluoro-6-(4-(trifluoromethyl)-1H-1,2,3-triazol-1-yl)phenyl)-3-(5-iodo-1H-imidazol-2-yl)-2,3,8,8a-tetrahydroindolizin-5(1H)-one (100 mg, 0.169 mmol, 1.0 equiv.) and tert-butyl 3-(4,4,5,5-tetramethyl-1,3,2-dioxaborolan-2-yl)-1H-pyrrolo[3,2-c]pyridine-1-carboxylate (116.1 mg, 0.337 mmol, 2.0 equiv.) in 1,4-dioxane (10 mL) and water (1 mL) were added potassium carbonate (69.9 mg, 0.506 mmol, 3.0 equiv.) and 1,1'-bis (di-t-butylphosphino)ferrocene palladium dichloride (11 mg, 0.017 mmol, 0.1 equiv.). The resulting mixture was maintained under nitrogen and stirred at 100° C. for 2 h. After cooling to room temperature, the reaction was quenched with water and the mixture was extracted with EA. The combined extracts were dried over anhydrous $Na_2SO_4$, then concentrated. The resulting residue was purified by chromatography on MeOH/DCM (0-5%) to yield tert-butyl 3-(2-((3S)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)-1H-pyrrolo[3,2-c]pyridine-1-carboxylate as a yellow solid. LC-MS(ES, m/z): 683.10 $[M+H]^+$.

Step 7: (3S,8aR)-3-(5-(1H-pyrrolo[3,2-c]pyridin-3-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one A solution of tert-butyl 3-(2-((3S)-7-(3-chloro-2-fluoro-6-(4-(trifluoromethyl)-1H-1,2,3-triazol-1-yl)phenyl)-5-oxo-1,2,3,5,8,8a-hexahydroindolizin-3-yl)-1H-imidazol-5-yl)-1H-pyrrolo[3,2-c]pyridine-1-carboxylate (96 mg, 0.141 mmol, 1.0 equiv.) in dichloromethane (6 mL) and trifluoroacetic acid (3 mL) was stirred at room temperature for 1 h. The resulting mixture was concentrated under vacuum. The resulting mixture was concentrated under vacuum. The residue was purified by reverse phase chromatography with $CH_3CN$/water (5%-45%) to yield the racemic product, which was purified by Chiral-H PLC with Hex (0.1% DEA):EtOH=70:30 to yield (3S,8a*R)-3-(5-(1H-pyrrolo[3,2-c]pyridin-3-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one as a white solid and (3S,8a*S)-3-(5-(1H-pyrrolo[3,2-c]pyridin-3-yl)-1H-imidazol-2-yl)-7-(3-chloro-2-fluoro-6-(4-(trifluoromethyl)-1H-1,2,3-triazol-1-yl)phenyl)-2,3,8,8a-tetrahydroindolizin-5(1H)-one as an off-white solid.

LC-MS(ES, m/z): 583.05 $[M+H]^+$. $^1$H NMR: (400 MHz, Methanol-$d_4$) δ 8.95-9.12 (m, 2H), 8.18 (d, J=5.9 Hz, 1H), 7.75-7.86 (m, 1H), 7.68 (s, 1H), 7.54 (dd, J=8.7, 1.6 Hz, 1H), 7.47 (dd, J=5.9, 1.1 Hz, 1H), 7.28 (s, 1H), 5.71 (d, J=2.8 Hz, 1H), 5.13-5.26 (m, 1H), 3.84-3.95 (m, 1H), 2.93-3.06 (m, 1H), 2.56-2.65 (m, 1H), 2.18-2.40 (m, 3H), 2.03-2.16 (m, 1H). $^{19}$F-NMR: (376 MHz, Methanol-$d_4$) δ −62.60, −113.43.

Example 386 (3S,8aR)-7-(3-chloro-2-fluoro-6-(1H-tetrazol-1-yl)phenyl)-3-(5-(2,3-dihydrofuro[2,3-b]pyridin-4-yl)-1H-imidazol-2-yl)-2,3,8,8a-tetrahydroindolizin-5(1H)-one

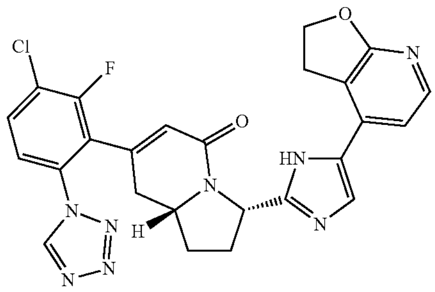 [SMILES: O=C1C=C(c2c(-n3cnnn3)ccc(Cl)c2F)C[C@H]2CC[C@@H](c3ncc(-c4ccnc5c4CCO5)[nH]3)N12]

A mixture of (3S,8aR)-7-(6-amino-3-chloro-2-fluorophenyl)-3-(5-(2,3-dihydrofuro[2,3-b]pyridin-4-yl)-1H-imidazol-2-yl)-2,3,8,8a-tetrahydroindolizin-5(1H)-one (80 mg, 0.172 mmol, 1.0 equiv.), trimethoxymethane (2 ml), azidotrimethylsilane (2 ml) and acetic acid (3 ml) was stirred at room temperature overnight. The reaction was concentrated and purified by reversal phase chromatography (0.05% TFA, $CH_3CN$/water, 0%-55%) to yield 7-(3-chloro-2-fluoro-6-(1H-tetrazol-1-yl)phenyl)-3-(5-(2,3-dihydrofuro[2,3-b]pyridin-4-yl)-1H-imidazol-2-yl)-2,3,8,8a-tetrahydroindolizin-5(1H)-one (36 mg) as a white solid, which was separated by Chiral HPLC (Column: CHIRALPAK IE-3, 4.6*50 mm, 3 um; Mobile Phase A: MTBE (0.3% Isopropylamine): EtOH=70:30: Flow rate: 1 mL/min) to yield (3R,8aS)-7-(3-chloro-2-fluoro-6-(1H-tetrazol-1-yl)phenyl)-3-(5-(2,3-dihydrofuro[2,3-b]pyridin-4-yl)-1H-imidazol-2-yl)-2,3,8,8a-tetrahydroindolizin-5(1H)-one as a white solid.

LC/MS: mass calculated. for $C_{25}H_{20}ClFN_8O_2$:518.14, measured: 519.05$[M+H]^+$. $^1$H NMR (300 MHz, DMSO-$d_6$) δ 12.57-12.23 (m, 1H), 9.84 (s, 1H), 7.97 (dd, J=8.7, 7.8 Hz, 1H), 7.84 (d, J=5.5 Hz, 1H), 7.72 (dd, J=8.7, 1.5 Hz, 1H), 7.59 (d, J=2.1 Hz, 1H), 7.24 (d, J=5.5 Hz, 1H), 5.70 (d, J=2.4 Hz, 1H), 5.02 (d, J=8.2 Hz, 1H), 4.60 (t, J=8.6 Hz, 2H), 3.81-3.68 (m, 1H), 3.43 (t, J=8.7 Hz, 2H), 2.75-2.53 (m, 2H), 2.27-1.87 (m, 4H). $^{19}$F NMR (282 MHz, DMSO-$d_6$) δ −113.04.

Example 387 (3S,8aR)-7-(3-chloro-2-fluoro-6-(1H-tetrazol-1-yl)phenyl)-3-(5-(thieno[3,2-b]pyridin-7-yl)-1H-imidazol-2-yl)-2,3,8,8a-tetrahydroindolizin-5(1H)-one

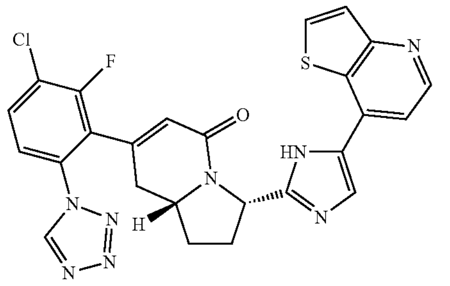 [SMILES: O=C1C=C(c2c(-n3cnnn3)ccc(Cl)c2F)C[C@H]2CC[C@@H](c3ncc(-c4ccnc5ccsc45)[nH]3)N12]

Step 1: 7-bromothieno[3,2-b]pyridine

With an inert atmosphere of nitrogen, a mixture of thieno[3,2-b]pyridin-7-01 (1.5 g, 9.922 mmol, 1.00 equiv), $POBr_3$ (14.2 g, 49.53 mmol, 5 equiv), the reaction mixture was stirred at 65° C. for 6 h. NaOH (aq.) (50 mL), water (50 mL) and chloroform (50 mL) were added. The phases were separated and the aqueous phase was extracted with more chloroform (2×50 mL). The organic phase was dried ($Na_2SO_4$) and filtered and concentrated. The residue was applied onto a silica gel column (80 g, EtOAc/PE: 1/3) to yield 7-bromothieno[3,2-b]pyridine as a yellow solid. MS (ESI): mass calculated for $C_7H_4BrNS$ 212.92 m/z, measured 213.95 $[M+H]^+$.

Step 2: 7-(1-ethoxyvinyl)thieno[3,2-b]pyridine

Under an inert atmosphere of nitrogen, a mixture of 7-bromothieno[3,2-b]pyridine (800 mg, 3.737 mmol, 1.00 equiv), tributyl(1-ethoxyvinyl)stannane (1.8 g, 4.984 mmol, 1.3 equiv), $Pd(PPh_3)_2Cl_2$ (262 mg, 0.373 mmol, 0.1 equiv) in 1,4-dioxane (15 mL) was stirred at 90° C. for 2 h and then concentrated. The residue was applied onto a silica gel column (80 g, EtOAc/PE: 1/10) to yield 7-(1-ethoxyvinyl)thieno[3,2-b]pyridine as a yellow oil. MS (ESI): mass calculated for C11H11 NOS 205.06 m/z, measured 206.05 $[M+H]^+$.

Step 3: 2-bromo-1-(thieno[3,2-b]pyridin-7-yl)ethan-1-one

To a mixture of 7-(1-ethoxyvinyl)thieno[3,2-b]pyridine (310 mg, 1.510 mmol, 1.0 equiv) in THE (6 mL) with $H_2O$ (3 mL) was added NBS (269 mg, 1.511 mmol, 1.0 equiv), and the mixture was stirred at room temperature for 30 min. The reaction was quenched with water (50 mL) and extracted with ethyl acetate (100 mL×3). The combined organic layer was washed with brine, dried over $Na_2SO_4$ and concentrated to yield 2-bromo-1-(thieno[3,2-b]pyridin-7-yl)ethan-1-one as a yellow solid. MS (ESI): mass calculated for $C_9H_6BrNOS$ 254.94 m/z, measured 276.05 $[M+H]^+$.

Step 4: 2-oxo-2-(thieno[3,2-b]pyridin-7-yl)ethyl (3S)-7-(6-amino-3-chloro-2-fluorophenyl)-5-oxo-1,2,3,5,8,8a-hexahydroindolizine-3-carboxylate To a mixture of (3R)-7-(6-amino-3-chloro-2-fluorophenyl)-5-oxo-1,2,3,5,8,8a-hexahydroindolizine-3-carboxylic acid (250 mg, 0.770 mmol, 1.0 equiv) in DMF (10 mL) was added $Cs_2CO_3$ (151 mg, 0.463 mmol, 0.6 equiv), and the resulting mixture was stirred at room temperature for 30 min. 2-Bromo-1-(thieno[3,2-b]pyridin-7-yl)ethan-1-one (296 mg, 1.156 mmol, 1.5 equiv) was then added, and the mixture was stirred at room temperature for 2 h. The reaction was quenched with water (200 mL) and extracted with ethyl acetate (300 mL×3). The combined organic layer was washed with brine, dried over $Na_2SO_4$ and concentrated. The residue was purified by silica gel chromatography (0-20% MeOH/DCM) to yield 2-oxo-2-(thieno[3,2-b]pyridin-7-yl)ethyl (3S)-7-(6-amino-3-chloro-2-fluorophenyl)-5-oxo-1,2,3,5,8,8a-hexahydroindolizine-3-carboxylate as a yellow solid. MS (ESI): mass calculated for $C_{24}H_{19}ClFN_3O_4S$ 499.08 m/z, measured 500.00$[M+H]^+$.

Step 5: (3S)-7-(6-amino-3-chloro-2-fluorophenyl)-3-(5-(thieno[3,2-b]pyridin-7-yl)-1H-imidazol-2-yl)-2,3,8,8a-tetrahydroindolizin-5(1H)-one To a solution of 2-oxo-2-(thieno[3,2-b]pyridin-7-yl)ethyl (3S)-7-(6-amino-3-chloro-2-fluorophenyl)-5-oxo-1,2,3,5,8,8a-hexahydroindolizine-3-carboxylate (250 mg, 0.500 mmol, 1.0 equiv) in toluene (10.0 mL) with $CH_3COOH$ (1 mL) was added $NH_4OAc$ (385 mg, 5.0 mmol, 10 equiv). The reaction mixture was stirred for 2 h at 110° C. The reaction was concentrated to dryness under reduced pressure to yield a residue, which was purified by column chromatography on silica gel with MeOH/DCM (0-15%) to yield (3S)-7-(6-amino-3-chloro-2-fluorophenyl)-3-(5-(thieno[3,2-b]pyridin-7-yl)-1H-imidazol-2-yl)-2,3,8,8a-tetrahydroindolizin-5(1H)-one as a yellow solid. MS (ESI): mass calculated for $C_{24}H_{19}ClFN_5OS$ 479.10 m/z, measured 480.20$[M+H]^+$.

Step 6: (3S,8aR)-7-(3-chloro-2-fluoro-6-(1H-tetrazol-1-yl)phenyl)-3-(5-(thieno[3,2-b]pyridin-7-yl)-1H-imidazol-2-yl)-2,3,8,8a-tetrahydroindolizin-5(1H)-one To a solution of (3S)-7-(6-amino-3-chloro-2-fluorophenyl)-3-(5-(thieno[3,2-b]pyridin-7-yl)-1H-imidazol-2-yl)-2,3,8,8a-tetrahydroindolizin-5(1H one (180 mg, 0.375 mmol, 1.0 equiv) in HOAc (5 mL) were added $TMSN_3$ (432 mg, 3.750 mmol, 10.0 equiv), and trimethoxymethane (398 mg, 3.750 mmol, 10.0 equiv). The reaction mixture was stirred overnight at room temperature. The reaction was concentrated to dryness under reduced pressure to yield a residue, which was purified by column chromatography on silica gel with MeOH/DCM (0-15%) to yield (3S)-7-(3-chloro-2-fluoro-6-(1H-tetrazol-1-yl)phenyl)-3-(5-(thieno[3,2-b]pyridin-7-yl)-1H-imidazol-2-yl)-2,3,8,8a-tetrahydroindolizin-5(1H)-one as a yellow solid. The yellow solid was further purified by preparative HPLC to yield (3S,8aR)-7-(3-chloro-2-fluoro-6-(1H-tetrazol-1-yl)phenyl)-3-(5-(thieno[3,2-b]pyridin-7-yl)-1H-imidazol-2-yl)-2,3,8,8a-tetrahydroindolizin-5(1H)-one as a white solid.

MS (ESI): mass calculated for $C_{25}H_{18}ClFN_8OS$ 532.10 m/z, measured 533.05$[M+H]^+$. LC-MS: (ES, m/z): 533.05 $[M+H]^+$ $^1$H-NMR: $^1$H NMR (300 MHz, DMSO-$d_6$) δ 12.44 (s, 1H), 9.85 (s, 1H), 8.59 (d, J=4.9 Hz, 1H), 8.08 (d, J=5.6 Hz, 1H), 7.92-8.03 (m, 2H), 7.65-7.77 (m, 2H), 7.53 (d, J=5.6 Hz, 1H), 5.69 (d, J=2.7 Hz, 1H), 5.07 (d, J=6.5 Hz, 1H), 3.73-3.83 (m, 1H), 2.90 (t, J=15.3 Hz, 1H), 2.57-2.64 (m, 1H), 2.18-2.26 (m, 3H), 1.99-2.03 (m, 1H). $^{19}$F NMR (282 MHz, DMSO-$d_6$) δ-112.808

Example 388 (3S,8aR)-7-(3-chloro-2-fluoro-6-(1H-tetrazol-1-yl)phenyl)-3-(5-(6-methoxy-1H-pyrrolo[3,2-c]pyridin-3-yl)-1H-imidazol-2-yl)-2,3,8,8a-tetrahydroindolizin-5(1H)-one

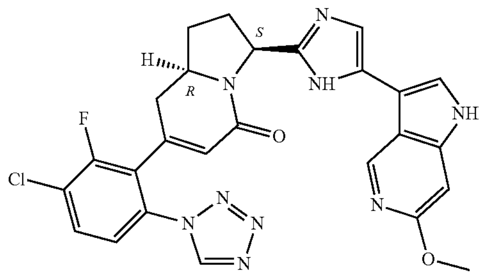

Step 1: 3-bromo-6-methoxy-1H-pyrrolo[3,2-c]pyridine

A mixture of 7-fluoro-1H-pyrrolo[3,2-c]pyridine (1.0 g, 7.3 mmol, 1.0 equiv) in THE 15 mL was flowed added NBS (1.3 g, 7.304 mmol, 1.0 equiv) was stirred at room temperature for 1 h. The mixture was concentrated under vacuum. The residue was dissolved by the addition of $H_2O$. The resulting solution was extracted with of ethyl acetate (3×15 mL). The organic layers were combined, washed with brine, dried and concentrated. The residue was purified by silica gel chromatography (0-50% PE/EA) to yield 3-bromo-6-methoxy-1H-pyrrolo[3,2-c]pyridine as a yellow solid. LC/MS: mass calculated for $C_8H_7BrN_2O$: 225.97, measured: 226.95 $[M+H+2]^+$.

Step 2: 3-bromo-6-methoxy-1-((2-(trimethylsilyl)ethoxy)methyl)-1H-pyrrolo[3,2-c]pyridine 3-Bromo-6-methoxy-1H-pyrrolo[3,2-c]pyridine (600 mg, 2.642 mmol, 1.0 eq.) in DMF (5 mL). The mixture was stirred at 15 min for 0° C. NaH (159 mg, 3.975 mmol, 1.5 eq., 60%) was then added, and the reaction mixture was stirred at 30 min for 0° C. SEMCl (661 mg, 3.965 mmol, 1.5 eq.) was added then added and the mixture stirred at room temperature for 2 h. The reaction was quenched with water (20 mL). The resulting mixture was extracted with ethyl acetate (3×10 mL) then washed with water (3×5 mL). The organic layers were combined, dried over anhydrous sodium sulfate, filtered and concentrated. The residue was purified by silica gel chromatography (0-30% PE/EA) to yield 3-bromo-6-methoxy-1-((2-(trimethylsilyl)ethoxy)methyl)-1H-pyrrolo[3,2-c]pyridine as a white solid. LC/MS: mass calculated for $C_{14}H_{21}BrN_2O_2Si$: 356.06, measured: 357.05 $[M+H]^+$.

Step 3: 2-chloro-1-(6-methoxy-1-((2-(trimethylsilyl)ethoxy)methyl)-1H-pyrrolo[3,2-c]pyridin-3-yl)ethan-1-one To a solution of 3-bromo-6-methoxy-1-((2-(trimethylsilyl)ethoxy)methyl)-1H-pyrrolo[3,2-c]pyridine (200.0 mg, 0.056 mmol, 1.0 equiv.) in dry tetrahydrofuran (5 mL) under nitrogen was added n-butyllithium (0.3 mL, 0.75 mmol, 2.5 M, 1.2 equiv.) at −78° C. and the solution was stirred for 1.0 h at this temperature under $N_2$. A solution of 1-chloro-3-(methoxy(methyl)amino)propan-2-one (80 mg, 0.58 mmol, 1.1 equiv. in dry THE (1 mL) was added dropwise −78° C. and the solution was allowed stirred at −78° C. for 1 h. The solution was quenched with diluted with water, extracted with EA, the combined organic phase was washed with water and brine, dried over $Na_2SO_4$, after filtration and concentration, the residue was purified with silica gel column (EA:PE=0% to 50%) to yield 2-chloro-1-(6-methoxy-1-((2-(trimethylsilyl)ethoxy)methyl)-1H-pyrrolo[3,2-c]pyridin-3-yl)ethan-1-one as a yellow solid. LC/MS: mass calculated for $C_{16}H_{23}ClN_2O_3Si$: 354.12, measured: 355.10 $[M+H]^+$.

Step 4: 2-(6-methoxy-1-((2-(trimethylsilyl)ethoxy)methyl)-1H-pyrrolo[3,2-c]pyridin-3-yl)-2-oxoethyl (3S)-7-(6-amino-3-chloro-2-fluorophenyl)-5-oxo-1,2,3, 5,8,8a-hexahydroindolizine-3-carboxylate (3S)-7-(6-amino-3-chloro-2-fluorophenyl)-5-oxo-1,2,3,5,8,8a-hexahydroindolizine-3-carboxylic acid (130 mg, 0.400 mmol, 1.0 equiv) in $CH_3CN$ (3 mL) was added $K_2CO_3$ (102 mg, 0.738 mmol, 2.0 eq.), the solution was stirred for 20 min at room temperature. To the resulting mixture was then added 2-chloro-1-(6-methoxy-1-((2-(trimethylsilyl)ethoxy)methyl)-1H-pyrrolo[3,2-c]pyridin-3-yl)ethan-1-one (172 mg, 0.553 mmol, 1.5 eq.). The resulting solution was stirred for overnight at room temperature. The mixture was concentrated under vacuum. The residue was applied onto a silica gel column (DCM/MeOH) to yield 2-(6-methoxy-1-((2-(trimethylsilyl)ethoxy)methyl)-1H-pyrrolo[3,2-c]pyridin-3-yl)-2-oxoethyl (3S)-7-(6-amino-3-chloro-2-fluorophenyl)-5-oxo-1,2,3,5,8,8a-hexahydroindolizine-3-carboxylate as a brown solid. LC/MS: mass calculated for $C_{31}H_{38}ClFN_4O_6Si$: 642.21, measured: 643.40 $[M+H]^+$.

Step 5: (3S)-7-(6-amino-3-chloro-2-fluorophenyl)-3-(5-(6-methoxy-1-((2-(trimethylsilyl)ethoxy)methyl)-1H-pyrrolo[3,2-c]pyridin-3-yl)-1H-imidazol-2-yl)-2,3,8,8a-tetrahydroindolizin-5(1H)-one 2-(6-Methoxy-1-((2-(trimethylsilyl)ethoxy)methyl)-1H-pyrrolo[3,2-c]pyridin-3-yl)-2-oxoethyl (3S)-7-(6-amino-3-chloro-2-fluorophenyl)-5-oxo-1,2,3,5,8,8a-hexahydroindolizine-3-carboxylate (127 mg, 0.197 mmol, 1.0 equiv) was dissolved in HOAc (0.3 mL) and toluene (3 mL). To the resulting solution was then added $CH_3COONH_4$ (304 mg, 3.949 mmol, 10 eq.). The mixture was stirred at 110° C. for 1.5 h. The mixture was concentrated. The residue was applied onto a silica gel column (DCM/MeOH) to yield (3S)-7-(6-amino-3-chloro-2-fluorophenyl)-3-(5-(6-m ethoxy-1-((2-(trimethylsilyl)ethoxy)methyl)-1H-pyrrolo[3,2-c]pyridin-3-yl)-1H-imidazol-2-yl)-2,3,8,8a-tetrahydroindolizin-5(1H)-one as a yellow solid. LC/MS: mass calculated for $C_{31}H_{36}ClFN_6O_3Si$: 622.23, measured: 623.45 $[M+1]^+$.

Step 6: (3S)-7-(3-chloro-2-fluoro-6-(1H-tetrazol-1-yl)phenyl)-3-(5-(6-methoxy-1-((2-(trimethylsilyl)ethoxy)methyl)-1H-pyrrolo[3,2-c]pyridin-3-yl)-1H-imidazol-2-yl)-2,3,8,8a-tetrahydroindolizin-5(1H)-one To a mixture of (3S)-7-(6-amino-3-chloro-2-fluorophenyl)-3-(5-(6-methoxy-1-((2-(trimethylsilyl)ethoxy)methyl)-1H-pyrrolo[3,2-c]pyridin-3-yl)-1H-imidazol-2-yl)-2,3,8,8a-tetrahydroindolizin-5(1H)-one (80 mg, 0.128 mmol, 1.0 equiv) in AcOH (3 mL) were added trimethoxymethane (136 mg, 1.282 mmol, 10 eq.) and $TMSN_3$ (148 mg, 1.285 mmol, 10 eq.). The mixture was stirred at room temperature for overnight. The mixture was concentrated. The residue was applied onto a silica gel column (DCM/MeOH) to yield (3S)-7-(3-chloro-2-fluoro-6-(1H-tetrazol-1-yl)phenyl)-3-(5-(6-methoxy-1-((2-(trimethylsilyl)ethoxy)methyl)-1H-pyrrolo[3,2-c]pyridin-3-yl)-1H-imidazol-2-yl)-2,3,8,8a-tetrahydroindolizin-5(1H)-one as a yellow solid. LC/MS: mass calculated for $C_{32}H_{35}ClFN_9O_3Si$: 675.23, measured: 676.15 $[M+1]^+$.

Step 7: (3S,8aR)-7-(3-chloro-2-fluoro-6-(1H-tetrazol-1-yl)phenyl)-3-(5-(6-methoxy-1H-pyrrolo[3,2-c]pyridin-3-yl)-1H-imidazol-2-yl)-2,3,8,8a-tetrahydroindolizin-5(1H)-one To a solution of (3S)-7-(3-chloro-2-fluoro-6-(1H-tetrazol-1-yl)phenyl)-3-(5-(6-methoxy-1-((2-(trimethylsilyl)ethoxy)methyl)-1H-pyrrolo[3,2-c]pyridin-3-yl)-1H-imidazol-2-yl)-2,3,8,8a-tetrahydroindolizin-5(1H)-one (58 mg, 0.086 mmol, 1.0 equiv.) in DCM (1.5 mL) was added TFA (0.5 mL). The mixture was stirred at 30° C. for 1 h. The mixture was concentrated. MeOH (1 mL) and $NH_4OH$ (0.1 mL) were then added. The mixture was stirred at 25° C. for 1 h. The mixture was concentrated. The residue was applied onto a C18 column to yield (3S,8aR)-7-(3-chloro-2-fluoro-6-(1H-tetrazol-1-yl)phenyl)-3-(5-(6-methoxy-1H-pyrrolo[3,2-c]pyridin-3-yl)-1H-imidazol-2-yl)-2,3,8,8a-tetrahydroindolizin-5(1H)-one as a white solid.

LC/MS: mass calculated for $C_{26}H_{21}ClFN_9O_2$: 545.15, measured: 546.15 $[M+H]^+$. $^1H$ NMR (400 MHz, DMSO-$d_6$) δ 11.68 (s, 1H), 11.04 (s, 1H), 9.83 (s, 1H), 8.85 (s, 1H), 7.96 (t, J=8.2 Hz, 1H), 7.71 (d, J=8.7 Hz, 1H), 7.47 (d, J=2.1 Hz, 1H), 7.31 (d, J=1.9 Hz, 1H), 6.63 (s, 1H), 5.67 (d, J=2.8 Hz, 1H), 5.00 (d, J=8.3 Hz, 1H), 3.87 (s, 3H), 3.65-3.75 (m, 1H), 2.79 (t, J=15.3 Hz, 1H), 2.53-2.57 (m, 1H), 1.92-2.21 (m, 4H). $^{19}F$ NMR (376 MHz, DMSO-$d_6$) δ−112.62.

Example 389 (3S,8aR)-3-(5-(2-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one

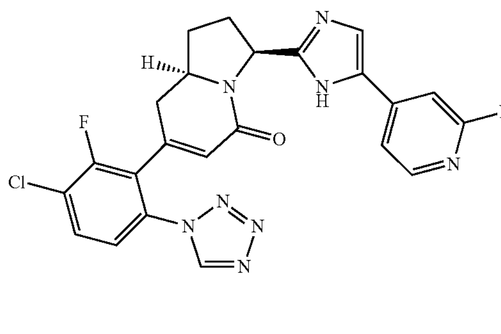

Step 1: N-(4-bromopyridin-2-yl)acetamide

To 4-bromopyridin-2-amine (2 g, 11.560 mmol, 1.0 equiv) was added $Ac_2O$ (20 mL) and the resulting mixture was stirred at room temperature overnight. The resulting mixture was concentrated to dryness under reduced pressure, and the residue was washed with dilute $NaHCO_3$ (aq) to pH=7 and extracted with EA. The combined organic phase was washed with water, brine, dried with $Na_2SO_4$, then purified by column chromatography on silica gel with EA/PE (0-100%) to yield N-(4-bromopyridin-2-yl)acetamide as a yellow solid. MS (ESI): mass calculated for $C_7H_7BrN_2O$ 213.97 m/z, measured 215.00$[M+H]^+$.

Step 2: N-(4-(1-ethoxyvinyl)pyridin-2-yl)acetamide

Under an inert atmosphere of nitrogen, a mixture of N-(4-bromopyridin-2-yl)acetamide (1 g, 4.650 mmol, 1.00 equiv), tributyl(1-ethoxyvinyl)stannane (2.2 g, 6.092 mmol, 1.3 equiv), and $Pd(PPh_3)_2Cl_2$ (326 mg, 0.464 mmol, 0.1 equiv) in 1,4-dioxane (15 mL) was stirred at 90° C. for 2 h. The resulting mixture was then concentrated and the residue was applied onto a silica gel column (80 g, EtOAc/PE: 1/10) to yield N-(4-(1-ethoxyvinyl)pyridin-2-yl)acetamide as a yellow oil. MS (ESI): mass calculated for $C_{11}H_{14}N_2O_2$ 206.11 m/z, measured 207.15 $[M+H]^+$.

Step 3: N-(4-(2-bromoacetyl)pyridin-2-yl)acetamide

To a mixture of N-(4-(1-ethoxyvinyl)pyridin-2-yl)acetamide (400 mg, 1.939 mmol, 1.0 equiv) in THE (6 mL) with water (3 mL) was added NBS (345 mg, 1.938 mmol, 1.0 equiv), and the mixture was stirred at room temperature for 30 min. The reaction was quenched with water (50 mL) and extracted with ethyl acetate (100 mL×3). The combined organic layer was washed with brine, dried over $Na_2SO_4$ and concentrated to yield N-(4-(2-bromoacetyl)pyridin-2-yl)acetamide as a yellow solid. MS (ESI): mass calculated for $C_9H_9BrN_2O_2$ 255.98 m/z, measured 258.95 $[M+H+2]^+$.

Step 4: 2-(6-acetamidopyridin-3-yl)-2-oxoethyl (3R)-7-(6-amino-3-chloro-2-fluorophenyl)-5-oxo-1,2,3,5,8,8a-hexahydroindolizine-3-carboxylate To a mixture of (3R)-7-(6-amino-3-chloro-2-fluorophenyl)-5-oxo-1,2,3,5,8,8a-hexahydroindolizine-3-carboxylic acid (300 mg, 0.924 mmol, 1.0 equiv) in DMF (5 mL) was added $Cs_2CO_3$ (181 mg, 0.556 mmol, 0.6 equiv) and stirred at room temperature for 30 min. N-(4-(2-bromoacetyl)pyridin-2-yl)acetamide (475 mg, 1.848 mmol, 2 equiv) was then added, and the resulting mixture was stirred at room temperature for 2 h. The reaction was quenched with water (200 mL) and extracted with ethyl acetate (300 mL×3). The combined organic layer was washed with brine, dried over $Na_2SO_4$ and concentrated. The residue was purified by silica gel chromatography (0-20% MeOH/DCM) to yield 2-(6-acetamidopyridin-3-yl)-2-oxoethyl (3R)-7-(6-amino-3-chloro-2-fluorophenyl)-5-oxo-1,2,3,5,8,8a-hexahydroindolizine-3-carboxylate as a yellow solid. MS (ESI): mass calculated for $C_{24}H_{22}ClFN_4O_5$ 500.13 m/z, measured 501.15$[M+H]^+$.

Step 5: N-(4-(2-((3S)-7-(6-amino-3-chloro-2-fluorophenyl)-5-oxo-1,2,3,5,8,8a-hexahydroindolizin-3-yl)-1H-imidazol-5-yl)pyridin-2-yl)acetamide To a solution of 2-(2-acetamidopyridin-4-yl)-2-oxoethyl (3R)-7-(6-amino-3-chloro-2-fluorophenyl)-5-oxo-1,2,3,5,8,8a-hexahydroindolizine-3-carboxylate (350 mg, 0.7 mmol, 1.0 equiv) in toluene (10.0 mL) with $CH_3COOH$ (1 mL) was added $NH_4OAc$ (539 mg, 6.993 mmol, 10 equiv). The reaction mixture was stirred for 2 h at 110° C. The reaction was concentrated to dryness under reduced pressure to yield a residue, which was purified by column chromatography on silica gel with MeOH/DCM (0-15%) to yield N-(4-(2-((3S)-7-(6-amino-3-chloro-2-fluorophenyl)-5-oxo-1,2,3, 5,8,8a-hexahydroindolizin-3-yl)-1H-imidazol-5-yl)pyridin-2-yl) acetamide as a yellow solid. MS (ESI): mass calculated for $C_{24}H_{22}ClFN_6O_2$ 480.15 m/z, measured 481.15[M+H]$^+$.

Step 6: N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl) acetamide To a solution of N-(4-(2-((3S)-7-(6-amino-3-chloro-2-fluorophenyl)-5-oxo-1,2,3,5,8,8a-hexahydroindolizin-3-yl)-1H-imidazol-5-yl)pyridin-2-yl)acetamide (200 mg, 0.416 mmol, 1.0 equiv) in AcOH (5 mL) were added $TMSN_3$ (479 mg, 4.158 mmol, 10.0 equiv), and trimethoxymethane (441 mg, 4.156 mmol, 10.0 equiv). The reaction mixture was stirred overnight at room temperature. The reaction was concentrated to dryness under reduced pressure to yield a residue, which was purified by column chromatography on silica gel with MeOH/DCM (0-15%) to yield N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide as a yellow solid. MS (ESI): mass calculated for $C_{25}H_{21}ClFN_9O_2$ 533.15 m/z, measured 534.10[M+H]$^+$.

Step 7: (3S,8aR)-3-(5-(2-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one To a solution of N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)pyridin-2-yl)acetamide (130 mg, 0.243 mmol, 1.0 equiv) in THE (5 mL) was added 4N HCl (2 mL). The reaction mixture was stirred 2 h at 70° C. The mixture was concentrated under vacuum and purified by C18 column (eluent: 5% to 60% (v/v) $CH_3CN$ and $H_2O$ with 0.05% $NH_4HCO_3$) to yield (3S)-3-(5-(2-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one. The residue was further purified by preparative HPLC (Column: CHIRALPAK IA-3, 4.6*50 mm, 3 um; Mobile Phase A: MtBE (0.1% DEA): EtOH=50:50; Flow rate: 1 mL/min; Gradient: 20 B to 20 B in 14 min; 220/254 nm) to yield (3S,8aR)-3-(5-(2-aminopyridin-4-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid.

MS (ESI): mass calculated for $C_{23}H_{19}ClFN_9O$ 491.14 m/z, measured 492.05[M+H]$^+$. LC-MS: (ES, m/z): 492.05 [M+H]$^+$ $^1$H NMR (300 MHz, DMSO-$d_6$) δ 11.91 (s, 1H), 9.84 (s, 1H), 7.87-8.03 (m, 1H), 7.83 (d, J=5.3 Hz, 1H), 7.72 (d, J=8.7 Hz, 1H), 7.51 (d, J=2.1 Hz, 1H), 6.78-6.87 (m, 2H), 5.76 (s, 2H), 5.69 (d, J=2.6 Hz, 1H), 4.99 (d, J=8.5 Hz, 1H), 3.71 (s, 1H), 2.72 (t, J=15.4 Hz, 1H), 2.42-2.52 (m, 1H) 2.15-2.20 (m, 1H), 2.03-2.18 (m, 1H), 1.83-1.97 (m, 2H). $^{19}$F NMR (282 MHz, DMSO-$d_6$) δ-112.91.

Example 390 (3S,8aR)-7-(3-chloro-2-fluoro-6-(1H-tetrazol-1-yl)phenyl)-3-(5-(2-(ethylamino)-3-fluoropyridin-4-yl)-1H-imidazol-2-yl)-2,3,8,8a-tetrahydroindolizin-5(1H)-one

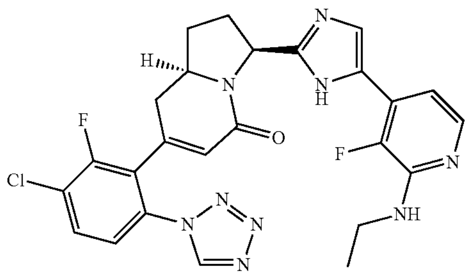 [SMILES: CCNc1nccc(-c2cnc([C@@H]3CC[C@@H]4CC(c5c(-n6cnnn6)ccc(Cl)c5F)=CC(=O)N43)[nH]2)c1F]

Step 1: N-ethyl-N-(3-fluoro-4-iodopyridin-2-yl)acetamide

Under an inert atmosphere of nitrogen, to a mixture of N-(3-fluoro-4-iodopyridin-2-yl)acetamide (2 g, 7.142 mmol, 1.00 equiv) in THE (20 mL) was added NaH (314 mg, 7.851 mmol, 1.1 equiv, 60%) at 0° C. for 30 min. followed by addition of iodoethane (5.6 g, 35.905 mmol, 5 equiv). The reaction mixture was stirred at 60° C. for 2 h. The reaction was quenched with ice water (100 mL) and extracted with ethyl acetate (200 mL×3). The combined organic layer was washed with brine, dried over $Na_2SO_4$ and concentrated. The residue was purified by silica gel chromatography (0-100% EA/PE) to yield N-ethyl-N-(3-fluoro-4-iodopyridin-2-yl)acetamide as a yellow solid. MS (ESI): mass calculated for $C_9H_{10}FIN_2O$ 307.98 m/z, measured 308.95[M+H]$^+$.

Step 2: N-(4-(1-ethoxyvinyl)-3-fluoropyridin-2-yl)-N-ethylacetamide

Under an inert atmosphere of nitrogen, a mixture of N-ethyl-N-(3-fluoro-4-iodopyridin-2-yl)acetamide (1 g, 3.246 mmol, 1.00 equiv), tributyl(1-ethoxyvinyl)stannane (1.5 g, 4.153 mmol, 1.3 equiv), $Pd(PPh_3)_2Cl_2$ (228 mg, 0.325 mmol, 0.1 equiv) in 1,4-dioxane (15 mL) was stirred at 90° C. for 2 h. Concentrated. The residue was applied onto a silica gel column (80 g, EtOAc/PE: 1/10) to yield N-(4-(1-ethoxyvinyl)-3-fluoropyridin-2-yl)-N-ethylacetamide as a yellow oil. MS (ESI): mass calculated for $C_{13}H_{17}FN_2O_2$ 252.13 m/z, measured 253.05 [M+H]$^+$.

Step 3: N-(4-(2-bromoacetyl)-3-fluoropyridin-2-yl)-N-ethylacetamide

To a mixture of N-(4-(1-ethoxyvinyl)-3-fluoropyridin-2-yl)-N-ethylacetamide (400 mg, 1.586 mmol, 1.0 equiv) in THE (6 mL) with $H_2O$ (3 mL) was added NBS (282 mg, 1.584 mmol, 1.0 equiv) and the resulting mixture was stirred at room temperature for 30 min. The reaction was quenched with water (50 mL) and extracted with ethyl acetate (100 mL×3). The combined organic layer was washed with brine, dried over $Na_2SO_4$, and concentrated to yield N-(4-(2-bromoacetyl)-3-fluoropyridin-2-yl)-N-ethylacetamide as a yellow solid. MS (ESI): mass calculated for $C_{11}H_{12}BrFN_2O_2$ 302.01 m/z, measured 305.00 [M+H+2]$^+$.

Step 4: 2-(2-(N-ethylacetamido)-3-fluoropyridin-4-yl)-2-oxoethyl (3R)-7-(6-amino-3-chloro-2-fluorophenyl)-5-oxo-1,2,3,5,8,8a-hexahydroindolizine-3-carboxylate To a mixture of (3R)-7-(6-amino-3-chloro-2-fluorophenyl)-5-oxo-1,2,3,5,8,8a-hexahydroindolizine-3-carboxylic acid (300 mg, 0.924 mmol, 1.0 equiv) in DMF (5 mL) was added $Cs_2CO_3$ (181 mg, 0.556 mmol, 0.6 equiv) and the resulting mixture was stirred at room temperature for 30 min. N-(4-(2-bromoacetyl)-3-fluoropyridin-2-yl)-N-ethylacetamide (560 mg, 1.847 mmol, 2 equiv) was then added, and the resulting mixture was stirred at room temperature for 2 h. The reaction was quenched with water (200 mL) and extracted with ethyl acetate (300 mL×3). The combined organic layer was washed with brine, dried over $Na_2SO_4$ and concentrated. The residue was purified by silica gel chromatography (0-20% MeOH/DCM) to yield 2-(2-(N-ethylacetamido)-3-fluoropyridin-4-yl)-2-oxoethyl (3R)-7-(6-amino-3-chloro-2-fluorophenyl)-5-oxo-1,2,3,5,8,8a-hexahydroindolizine-3-carboxylate as a yellow solid. MS (ESI): mass calculated for $C_{26}H_{25}ClF_2N_4O_5$ 546.15 m/z, measured 547.10[M+H]$^+$.

Step 5: N-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-N-ethylacetamide To a solution of 2-(2-(N-ethylacetamido)-3-fluoropyridin-4-yl)-2-oxoethyl (3R)-7-(6-amino-3-chloro-2-fluorophenyl)-5-oxo-1,2,3,5,8,8a-hexahydroindolizine-3-carboxylate (350 mg, 0.640 mmol, 1.0 equiv) in toluene (10 mL) with $CH_3COOH$ (1 mL) was added $NH_4OAc$ (493 mg, 6.396 mmol, 10 equiv). The reaction mixture was stirred for 2 h at 110° C. The reaction was concentrated to dryness under reduced pressure to yield a residue, which was purified by column chromatography on silica gel with MeOH/DCM (0-15%) to yield N-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-N-ethylacetamide as a yellow solid. MS (ESI): mass calculated for $C_{26}H_{25}ClF_2N_6O_2$ 526.17 m/z, measured 527.10[M+H]$^+$.

Step 6: N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-N-ethylacetamide To a solution of N-(4-(2-((3S)-7-(6-amino-3-chloro-2-fluorophenyl)-5-oxo-1,2,3,5,8,8a-hexahydroindolizin-3-yl)-1H-imidazol-5-yl)-3-fluoropyridin-2-yl)-N-ethylacetamide (180 mg, 0.342 mmol, 1.0 equiv) in AcOH (5 mL) were added $TMSN_3$ (394 mg, 3.420 mmol, 10.0 equiv), and trimethoxymethane (362 mg, 3.411 mmol, 10.0 equiv). The reaction mixture was stirred overnight at room temperature. The reaction was concentrated to dryness under reduced pressure to yield a residue, which was purified by column chromatography on silica gel with MeOH/DCM (0-15%) to yield N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-N-ethylacetamide as a yellow solid. MS (ESI): mass calculated for $C_{27}H_{24}ClF_2N_9O_2$ 579.17 m/z, measured 580.15[M+H]$^+$.

Step 7: (3S,8aR)-7-(3-chloro-2-fluoro-6-(1H-tetrazol-1-yl)phenyl)-3-(5-(2-(ethylamino)-3-fluoropyridin-4-yl)-1H-imidazol-2-yl)-2,3,8,8a-tetrahydroindolizin-5(1H)-one To a solution of N-(4-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-3-fluoropyridin-2-yl)-N-ethylacetamide (130 mg, 0.224 mmol, 1.0 equiv) in THE (5 mL) was added 4N HCl (2 mL). The reaction mixture was stirred 2 h at 70° C. The mixture was concentrated under vacuum and purified by C18 column (eluent: 5% to 60% (v/v) $CH_3CN$ and $H_2O$ with 0.05% $NH_4HCO_3$) to yield (3S)-7-(3-chloro-2-fluoro-6-(1H-tetrazol-1-yl)5-(2-(ethylamino)-3-fluoropyridin-4-yl)-1H-imidazol-2-yl)-2,3,8,8a-tetrahydroindolizin-5(1H)-one, which was further purified by preparative HPLC (Column: CHIRALPAK ID-3, 4.6*50 mm, 3 μm; Mobile Phase phenyl)-3-(A: MtBE (0.1% DEA): EtOH=70:30; Flow rate: 1 mL/min; Gradient: 20 B to 20 B in 14 min; 220/254 nm) to yield (3S,8aR)-7-(3-chloro-2-fluoro-6-(1H-tetrazol-1-yl)phenyl)-3-(5-(2-(ethylamino)-3-fluoropyridin-4-yl)-1H-imidazol-2-yl)-2,3,8,8a-tetrahydroindolizin-5(1H)-one as a white solid.

MS (ESI): mass calculated for $C_{25}H_{22}ClF_2N_9O$ 537.16 m/z, measured 538.20[M+H]$^+$. LC-MS: (ES, m/z): 538.20 [M+H]$^+$ $^1$H NMR (300 MHz, DMSO-$d_6$) δ 12.09 (s, 1H), 9.81 (s, 1H), 7.89-8.01 (m, 1H), 7.76 (d, J=5.3 Hz, 1H), 7.69 (d, J=8.7 Hz, 1H), 7.41 (dd, J=3.9, 2.1 Hz, 1H), 7.05 (t, J=5.1 Hz, 1H), 6.37-6.47 (m, 1H), 5.67 (d, J=2.6 Hz, 1H), 5.00 (d, J=8.4 Hz, 1H), 3.63-3.74 (m, 1H), 3.36 (dd, J=7.3, 5.8 Hz, 2H), 2.67-2.78 (m, 1H), 2.49-2.54 (m, 1H), 2.04-2.21 (m, 2H), 1.92-1.99 (m, 2H), 1.13 (t, J=7.1 Hz, 3H). $^{19}$F NMR (282 MHz, DMSO-$d_6$) δ−112.85, −112.94, −143.17, −143.59.

Example 391 (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-8a-methyl-2,3,8,8a-tetrahydroindolizin-5(1H)-one

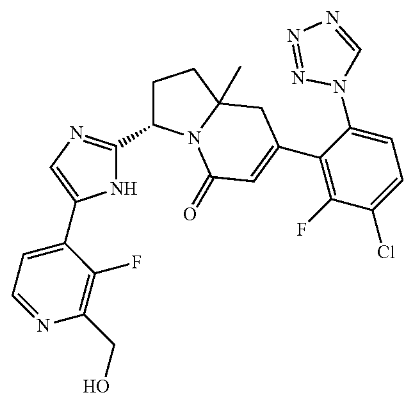 [SMILES: CC12CC[C@@H](c3ncc(-c4ccnc(CO)c4F)[nH]3)N1C(=O)C=C(c1c(-n3cnnn3)ccc(Cl)c1F)C2]

Step 1: (S)-2-(5-(ethoxycarbonyl)pyrrolidin-2-ylidene)malonate

A mixture of ethyl (S)-5-thioxopyrrolidine-2-carboxylate (3.2 g, 18.472 mmol, 1.0 equiv.), bis(methoxycarbonyl)methylidene-imino-azanium (3.797 g, 24.014 mmol, 1.3 equiv.) and Grubbs Catalyst 1st Generation (1.524 g, 1.847 mmol, 0.1 equiv.) in benzene (45 mL) was stirred at 90° C. under nitrogen atmosphere for 2 h. The mixture was concentrated and purified by silica gel chromatography (0-80% EtOAc/petroleum ether) to yield dimethyl (S)-2-(5-(ethoxycarbonyl)pyrrolidin-2-ylidene)malonate as a light red oil. LC/MS: mass calculated for $C_{12}H_{17}NO_6$: 271.11, measured: 272.15 [M+H]$^+$.

Step 2: 1-(tert-butyl) 2-ethyl (S)-5-(1,3-dimethoxy-1,3-dioxopropan-2-ylidene)pyrrolidin-1,2-dicarboxylate To a solution of dimethyl (S)-2-(5-(ethoxycarbonyl)pyrrolidin-2-ylidene)malonate (5.7 g, 21.013 mmol, 1.0 equiv.), triethylamine (7.3 mL, 52.5 mmol, 2.50 equiv.) and DMAP (0.257 g, 2.101 mmol, 0.10 equiv.) in dichloromethane (100 mL) was added $Boc_2O$ (6.879 g, 31.519 mmol, 1.50 equiv.) and the mixture was stirred overnight at room temperature. The solution was concentrated and the residue was purified by silica gel chromatography (0-50% EtOAc/petroleum ether) to yield 1-(tert butyl) 2-ethyl (S)-5-(1,3-dimethoxy-1,3-dioxopropan-2-ylidene)pyrrolidine-1,2-dicarboxylate as a light red oil. LC/MS: mass calculated for $C_{17}H_{25}NO_8$: 371.16, measured: 372.30 $[M+H]^+$.

Step 3: 1-(tert-butyl) 2-ethyl (2S)-5-(1,3-dimethoxy-1,3-dioxopropan-2-yl)-5-methylpyrrolidine-1,2-dicarboxylate Under an atmosphere of nitrogen, to a suspension of cuprous iodide (9.231 g, 48.468 mmol, 2.0 equiv.) in anhydrous diethyl ether (150 mL) at −50° C. was added methylmagnesium bromide (32.3 mL, 96.9 mmol, 4.0 equiv., 3 mL) over a period of 15 min. After the addition was completed, the reaction mixture was gradually warmed room temperature and stirred for 40 min. Then the temperature of the mixture was lowered to −50° C., a diethyl ether solution (30 mL) of 1-(tert-butyl) 2-ethyl (S)-5-(1,3-dimethoxy-1,3-dioxopropan-2-ylidene)pyrrolidine-1,2-dicarboxylate (9.3 g, 24.234 mmol, 1.0 equiv.) was added. The reaction mixture was allowed to slowly warm to room temperature and then stirred for 1 h. Aqueous saturated $NH_4Cl$ solution was added to quench the reaction. The mixture was filtered, and the filtrate was extracted with ethyl acetate twice. The organic layers were combined, washed with brine, dried over anhydrous sodium sulfate and concentrated. The residue was purified by silica gel chromatography (0-40% ethyl acetate/petroleum ether) to yield 1-(tert-butyl) 2-ethyl (2S)-5-(1,3-dimethoxy-1,3-dioxopropan-2-yl)-5-methylpyrrolidine-1,2-dicarboxylate as a light yellow oil. LC/MS: mass calculated for $C_{18}H_{29}NO_8$: 387.19, measured: 410.05 $[M+Na]^+$.

Step 4: 1-(tert-butyl) 2-ethyl (2S)-5-(2-methoxy-2-oxoethyl)-5-methylpyrrolidine-1,2-dicarboxylate To a solution of 1-(tert-butyl) 2-ethyl (2S)-5-(1,3-dimethoxy-1,3-dioxopropan-2-yl)-5-methylpyrrolidine-1,2-dicarboxylate (1.5 g, 3.872 mmol, 1.0 equiv.) in DMSO (15 mL) was added LiCl (1.641 g, 38.717 mmol, 10.0 equiv.) and $H_2O$ (0.2 mL). The reaction mixture was heated at 130° C. for 6 h. The solution was diluted with water and extracted with ethyl acetate (2×50 mL). The combined organic layers were washed with water and brine, dried over anhydrous sodium sulfate and concentrated. The residue was purified by silica gel chromatography (0-60% EtOAc/petroleum ether) to yield 1-(tert-butyl) 2-ethyl (2S)-5-(2-methoxy-2-oxoethyl)-5-methylpyrrolidine-1,2-dicarboxylate as a light red oil. LC/MS: mass calculated for $C_{16}H_{27}NO_6$: 329.18, measured: 330.20 $[M+H]^+$. LC/MS: (ES, m/z): 330.20 $[M+H]^+$.

Step 5: ethyl (2S)-5-(2-methoxy-2-oxoethyl)-5-methylpyrrolidine-2-carboxylate

To a solution of 1-(tert-butyl) 2-ethyl (2S)-5-(2-methoxy-2-oxoethyl)-5-methylpyrrolidine-1,2-dicarboxylate (1.4 g, 4.250 mmol, 1.0 equiv.) in DCM (15 mL) was added trifluoroacetic acid (5 mL) at room temperature and the solution was stirred for 1 h at room temperature. The solution was concentrated and dissolved into dichloromethane. The pH value of the solution was adjusted to 8 and the solution was concentrated. The residue was purified by silica gel chromatography (0-10% methanol/dichloromethane) to yield ethyl (2S)-5-(2-methoxy-2-oxoethyl)-5-methylpyrrolidine-2-carboxylate as a light red oil. LC/MS: mass calculated for $C_{11}H_{19}NO_4$: 229.13, measured: 230.00 $[M+H]^+$.

Step 6: ethyl (2S)-1-(3-ethoxy-3-oxopropanoyl)-5-(2-methoxy-2-oxoethyl)-5-methyl pyrrolidine-2-carboxylate A mixture of ethyl (2S)-5-(2-methoxy-2-oxoethyl)-5-methylpyrrolidine-2-carboxylate (980 mg, 4.274 mmol, 1.0 equiv.), 3-ethoxy-3-oxopropanoic acid (1.129 g, 8.549 mmol, 2.0 equiv.), $T_3P$ (8.160 g, 12.823 mmol, 3.0 equiv., 50 wt % in EA) and triethylamine (2.4 mL, 17.1 mmol, 4.0 equiv.) in ethyl acetate (15 mL) was stirred at room temperature for overnight. The solution was washed with water and brine, dried over anhydrous sodium sulfate and concentrated. The residue was purified by silica gel chromatography (0-5% methanol/dichloromethane) to yield ethyl (2S)-1-(3-ethoxy-3-oxopropanoyl)-5-(2-methoxy-2-oxoethyl)-5-methylpyrrolidine-2-carboxylate as a light yellow oil. LC/MS: mass calculated for $C_{16}H_{25}NO_7$: 343.16, measured: 344.15 $[M+H]^+$.

Step 7: diethyl (3S)-8a-methyl-5,7-dioxooctahydroindolizine-3,8-dicarboxylate

To a solution of ethyl (2S)-1-(3-ethoxy-3-oxopropanoyl)-5-(2-methoxy-2-oxoethyl)-5-methylpyrrolidine-2-carboxylate (1.3 g, 3.786 mmol, 1.0 equiv.) in ethanol (20 mL) was added sodium ethanolate (5.6 mL, 15.1 mmol, 4.0 equiv., 21% in EtOH) and the mixture was stirred for 1 h at 90° C. After allowing to cool to 20° C., the mixture was concentrated by Rotary Evaporator. The residue was acidified with 1N HCl and extracted with ethyl acetate twice. The combined organic layers were washed with brine, dried over anhydrous sodium sulfate and concentrated to yield diethyl (3S)-8a-methyl-5,7-dioxooctahydroindolizine-3,8-dicarboxylate as a light yellow oil (1.2 g). LC/MS: mass calculated for $C_{15}H_{21}NO_6$: 311.14, measured: 312.00 $[M+H]^+$.

Step 8: ethyl (3S)-8a-methyl-5,7-dioxooctahydroindolizine-3-carboxylate

A mixture of diethyl (3S)-8a-methyl-5,7-dioxooctahydroindolizine-3,8-dicarboxylate (1.2 g, 3.854 mmol, 1.0 equiv.) in acetic acid (10 mL) and water (1 mL) was stirred at 100° C. for 1 h. The mixture was concentrated to yield ethyl (3S)-8a-methyl-5,7-dioxooctahydroindolizine-3-carboxylate as a light red oil (950 mg). LC/MS: mass calculated for $C_{12}H_{17}NO_4$: 239.12, measured: 240.10 $[M+H]^+$.

Step 9: ethyl (3S)-8a-methyl-5-oxo-7-(((trifluoromethyl)sulfonyl)oxy)-1,2,3,5,8,8a-hexahydroindolizine-3-carboxylate To a solution of ethyl (3S)-8a-methyl-5,7-dioxooctahydroindolizine-3-carboxylate (900 mg, 3.761 mmol, 1.0 equiv.) and triethylamine (1.3 mL, 9.4 mmol, 2.50 equiv.) in dichloromethane (15 mL) was added N-phenyl-bis(trifluoromethanesulfonimide) (2.016 g, 5.642 mmol, 1.50 equiv.)

and the mixture was stirred for 2 h at room temperature. The solution was diluted with water and extracted with dichloromethane twice. The combined organic layers were washed with brine, dried over anhydrous sodium sulfate and concentrated. The residue was purified by silica gel chromatography (0-5% methanol/dichloromethane) to yield ethyl (3S)-8a-methyl-5-oxo-7-(((trifluoromethyl)sulfonyl)oxy)-1,2,3,5,8,8a-hexahydroindolizine-3-carboxylate as a light yellow oil. LC/MS: mass calculated for $C_{13}H_{18}F_3NO_6S$: 371.07, measured: 372.05 $[M+H]^+$.

Step 10: ethyl (3S)-7-(6-amino-3-chloro-2-fluorophenyl)-8a-methyl-5-oxo-1,2,3,5,8,8a-hexahydroindolizine-3-carboxylate A mixture of ethyl (3S)-8a-methyl-5-oxo-7-(((trifluoromethyl)sulfonyl)oxy)-1,2,3,5,8,8a-hexahydroindolizine-3-carboxylate (280 mg, 0.754 mmol, 1.00 equiv.), 6-amino-3-chloro-2-fluorophenylboronic acid (285.6 mg, 1.508 mmol, 2.0 equiv.), potassium phosphate (480.1 mg, 2.262 mmol, 3.00 equiv.) and $Pd(dppf)Cl_2 \cdot CH_2C_{12}$ (57 mg, 0.075 mmol, 0.10 equiv.) in 1,4-dioxane (5.0 mL) and water (1 mL) was stirred for 2 h at 90° C. After cooling to room temperature, the solution was diluted with water and extracted with ethyl acetate twice. The combined organic layers were washed with brine, dried over anhydrous sodium sulfate and concentrated. The residue was purified by silica gel chromatography (0-5% methanol/dichloromethane) to yield ethyl (3S)-7-(6-amino-3-chloro-2-fluorophenyl)-8a-methyl-5-oxo-1,2, 3,5,8,8a-hexahydroindolizine-3-carboxylate as a light yellow solid. LC/MS: mass calculated for $C_{18}H_{20}ClFN_2O_3$: 366.11, measured: 367.10 $[M+H]^+$.

Step 11: (3S)-7-(6-amino-3-chloro-2-fluorophenyl)-8a-methyl-5-oxo-1,2,3,5,8,8a-hexahydroindolizine-3-carboxylic acid To a solution of ethyl (3S)-7-(6-amino-3-chloro-2-fluorophenyl)-8a-methyl-5-oxo-1,2,3,5,8,8a-hexahydroindolizine-3-carboxylate (260 mg, 0.709 mmol, 1.0 equiv.) in methanol (5 mL) was added aqueous LiOH solution (2.0 mL, 3M) and the solution was stirred at room temperature for 1 h. The solution was concentrated to 2 mL and then diluted with water. The pH value of the solution was adjusted to 3 and extracted with ethyl acetate twice. The organic layers were washed with brine, dried over anhydrous sodium sulfate, and concentrated to yield (3S)-7-(6-amino-3-chloro-2-fluorophenyl)-8a-methyl-5-oxo-1,2,3,5,8,8a-hexahydroindolizine-3-carboxylic acid as a brown solid, which used in the next step without further purification. LC/MS: mass calculated for $C_{16}H_{16}ClFN_2O_3$: 338.08, measured: 339.05 $[M+H]^+$.

Step 12: 2-(3-fluoro-2-(hydroxymethyl)pyridin-4-yl)-2-oxoethyl (3S)-7-(6-amino-3-chloro-2-fluorophenyl)-8a-methyl-5-oxo-1,2,3,5,8,8a-hexahydroindolizine-3-carboxylate A mixture of (3S)-7-(6-amino-3-chloro-2-fluorophenyl)-8a-methyl-5-oxo-1,2,3,5,8,8a-hexahydroindolizine-3-carboxylic acid (220 mg, 0.649 mmol, 1.00 equiv.) and potassium carbonate (89.7 mg, 0.649 mmol, 1.00 equiv.) in DMF (2.0 mL) was stirred for 15 min at room temperature. 2-Bromo-1-(3-(((tert-butyldimethylsilyl)oxy)methyl)-2-fluorophenyl)ethan-1-one (268 mg, 0.97 mmol, 1.50 equiv.) was added and the mixture was stirred at room temperature for 1 h. The reaction was diluted with water and extracted with ethyl acetate twice. The combined organic layers were washed with water and brine, dried over anhydrous sodium sulfate and concentrated. The residue was purified by reverse phase chromatography on C18 (80, $MeCN/H_2O$: 0>>>50%) to yield 2-(3-fluoro-2-(hydroxymethyl)pyridin-4-yl)-2-oxoethyl (3S)-7-(6-amino-3-chloro-2-fluorophenyl)-8a-methyl-5-oxo-1,2,3, 5,8,8a-hexahydroindolizine-3-carboxylate as a light yellow solid. LC/MS: mass calculated for $C_{24}H_{22}ClF_2N_3O_5$: 505.12, measured: 506.15 $[M+H]^+$.

Step 13: (3S)-7-(6-amino-3-chloro-2-fluorophenyl)-3-(5-(3-fluoro-2-(hydroxymethyl)pyridin-4-yl)-1H-imidazol-2-yl)-8a-methyl-2,3,8,8a-tetrahydroindolizin-5(1H)-one A mixture of 2-(3-fluoro-2-(hydroxymethyl)pyridin-4-yl)-2-oxoethyl (3S)-7-(6-amino-3-chloro-2-fluorophenyl)-8a-methyl-5-oxo-1,2,3,5,8,8a-hexahydroindolizine-3-carboxylate (50 mg, 0.1 mmol, 1.0 equiv.), ammonium acetate (76.1 mg, 0.99 mmol, 10.0 equiv.) and glacial acetic acid (6 mg, 0.1 mmol, 1.0 equiv.) in toluene (2 mL) was stirred at 110° C. for 2 h. The reaction was concentrated and the residue was purified by reverse phase chromatography on C18 (80 g, $MeCN/H_2O$ (0.05% $CF_3COOH$): 0>>>50%) to yield (3S)-7-(6-amino-3-chloro-2-fluorophenyl)-3-(5-(3-fluoro-2-(hydroxymethyl)pyridin-4-yl)-1H-imidazol-2-yl)-8a-methyl-2,3,8,8a-tetrahydroindolizin-5(1H)-one as a light yellow solid. LC/MS: mass calculated for $C_{24}H_{22}ClF_2N_5O_2$: 485.14, measured: 486.25 $[M+H]^+$.

Step 14: (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-8a-methyl-2,3,8,8a-tetrahydroindolizin-5(1H)-one A mixture of (3S)-7-(6-amino-3-chloro-2-fluorophenyl)-3-(5-(3-fluoro-2-(hydroxymethyl)pyridin-4-yl)-1H-imidazol-2-yl)-8a-methyl-2,3,8,8a-tetrahydroindolizin-5(1H)-one (20 mg, 0.041 mmol, 1.0 equiv.), azidotrimethylsilane (0.2 mL) and trimethoxymethane (0.2 mL) in glacial acetic acid (0.2 mL) was stirred at room temperature overnight. The mixture was concentrated under reduced pressure and the residue was purified by reverse phase chromatography on C18 (40 g, $MeCN/H_2O$ (0.05% $CF_3COOH$): 0>>>50%) to yield (3S)-7-(3-chloro-2-fluoro-6-(1H-tetrazol-1-yl)phenyl)-3-(5-(3-fluoro-2-(hydroxymethyl)pyridin-4-yl)-1H-imidazol-2-yl)-8a-methyl-2,3,8,8a-tetrahydroindolizin-5 (1H)-one as a light yellow solid.

LC/MS: mass calculated for $C_{25}H_{21}ClF_2N_8O_2$: 538.14, measured: 539.15 $[M+H]^+$. $^1H$ NMR: (300 MHz, methanol-$d_4$): δ 9.53-9.59 (m, 1H), 8.27-8.60 (m, 2H), 7.92-7.98 (m, 1H), 7.79-7.86 (m, 1H), 7.46-7.60 (m, 1H), 5.73-5.82 (m, 1H), 5.13-5.23 (m, 1H), 4.99-5.07 (m, 2H), 2.78-3.03 (m, 1H), 2.65-2.76 (m, 1H), 2.46-2.59 (m, 1H), 2.17-2.36 (m, 1H), 1.98-2.13 (m, 2H), 1.23-1.45 (m, 3H).

Example 392: (3S,8aR)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one
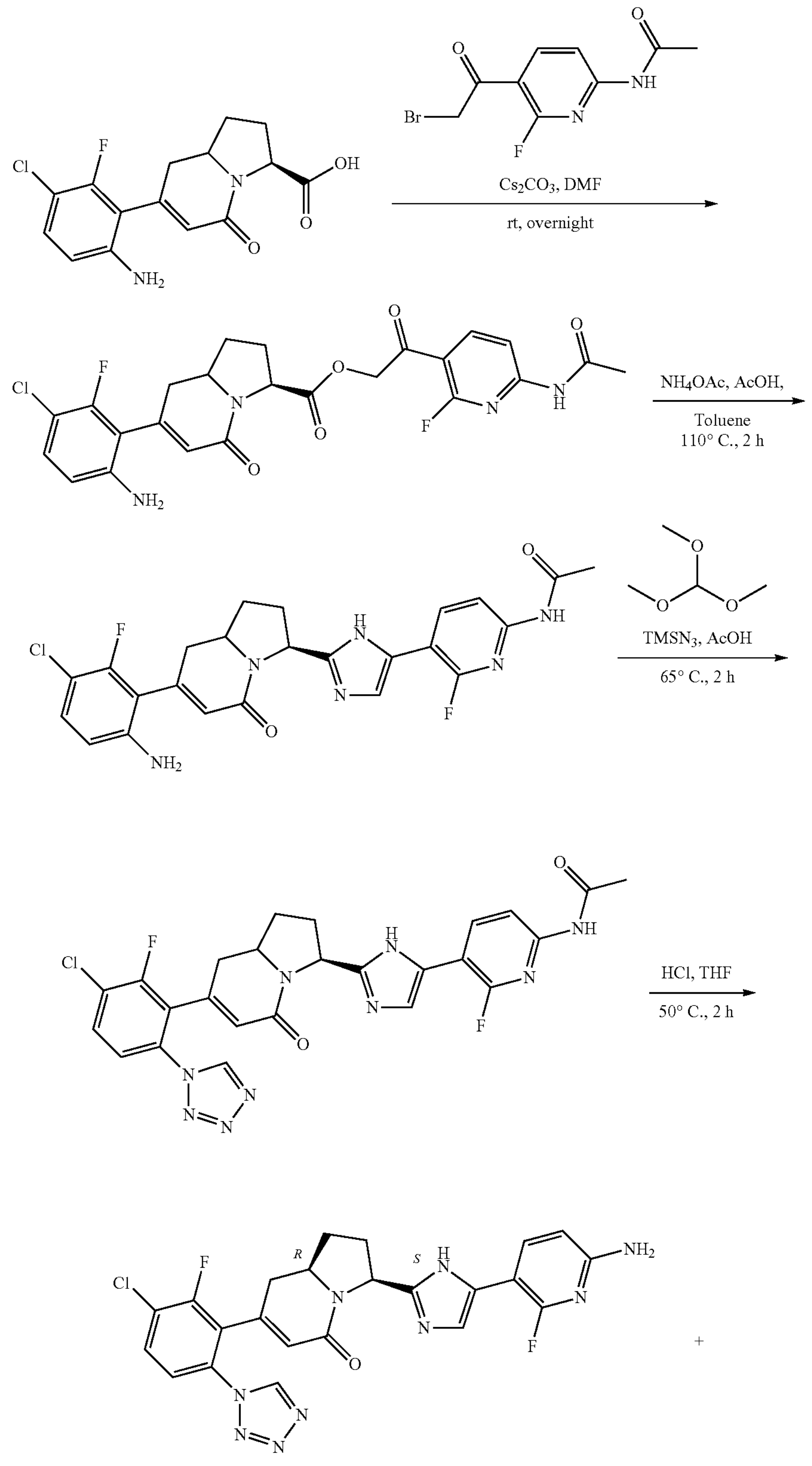

-continued

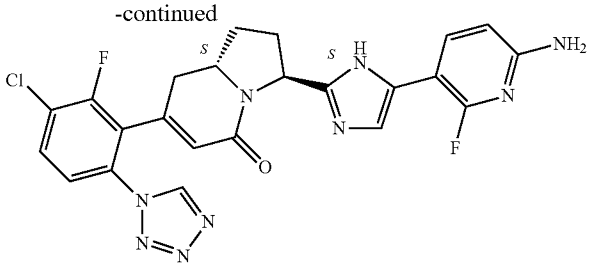

Step 1: (3S)-2-(6-acetamido-2-fluoropyridin-3-yl)-2-oxoethyl 7-(6-amino-3-chloro-2-fluorophenyl)-5-oxo-1,2,3, 5,8,8a-hexahydroindolizine-3-carboxylate A mixture of (3S)-7-(6-amino-3-chloro-2-fluorophenyl)-5-oxo-1,2,3,5,8,8a-hexahydroindolizine-3-carboxylic acid (500 mg, 1.540 mmol, 1.00 equiv) and $Cs_2CO_3$ (301 mg, 0.924 mmol, 0.60 equiv) in DMF (8 mL) was stirred at room temperature for 10 min. N-(5-(2-bromoacetyl)-6-fluoropyridin-2-yl)acetamide (508 mg, 1.848 mmol, 1.20 equiv) was then added. The reaction mixture was stirred at room temperature overnight, then poured into water (100 mL) and filtered. The solid was collected to yield (3S)-2-(6-acetamido-2-fluoropyridin-3-yl)-2-oxoethyl 7-(6-amino-3-chloro-2-fluorophenyl)-5-oxo-1,2,3,5,8,8a-hexahydroindolizine-3-carboxylate as yellow solid. LC/MS: mass calculated for $C_{24}H_{21}ClF_2N_4O_5$: 518.12, measured: 541.05 $[M+Na]^+$.

Step 2: N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl)acetamide A mixture of (3S)-2-(6-acetamido-2-fluoropyridin-3-yl)-2-oxoethyl 7-(6-amino-3-chloro-2-fluorophenyl)-5-oxo-1,2,3,5,8,8a-hexahydroindolizine-3-carboxylate (450 mg, 0.867 mmol, 1.00 equiv) and $NH_4OAc$ (668 mg, 8.672 mmol, 10.00 equiv) in AcOH (0.5 mL) and toluene (10 mL) was stirred at 110° C. for 2 h, then concentrated. The resulting residue was applied onto a silica gel column (40 g, MeOH/DCM: 1/12) to yield N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl)acetamide as yellow solid. LC/MS: mass calculated for $C_{24}H_{21}ClF_2N_6O_2$: 498.14, measured: 499.10 $[M+H]^+$.

Step 3: N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide A mixture of N-(5-(2-((3S)-7-(6-amino-3-chloro-2-fluorophenyl)-5-oxo-1,2,3,5,8,8a-hexahydroindolizin-3-yl)-1H-imidazol-5-yl)-6-fluoropyridin-2-yl)acetamide (400 mg, 0.802 mmol, 1.00 equiv), trimethylsilylazide ($TMSN_3$) (924 mg, 8.017 mmol, 10.00 equiv) and trimethoxymethane (851 mg, 8.017 mmol, 10.00 equiv) in AcOH (10 mL) was stirred at 65° C. for 2 h, then concentrated. The resulting residue was applied onto a silica gel column (40 g, MeOH/DCM: 1/12) to yield N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide as yellow solid. LC/MS: mass calculated for $C_{25}H_{20}ClF_2N_9O_2$: 551.14, measured: 552.10 $[M+H]^+$.

Step 4: (3S,8aR)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H) one A mixture of N-(5-(2-((3S)-7-(3-chloro-2-fluoro-6-(1H-tetrazol-1-yl)phenyl)-5-oxo-1,2,3,5,8,8a-hexahydroindolizin-3-yl)-1H-imidazol-5-yl)-6-fluoropyridin-2-yl)acetamide (330 mg, 0.598 mmol, 1.00 equiv) in THE (5 mL) and HCl (5 mL, 4M) was stirred at 50° C. for 2 h, then concentrated. The resulting residue was applied onto a C18 reverse phase column (330 g, ACN/$H_2O$ (0.05% $NH_4HCO_3$): 5%>>>40%>>>45%) to yield (3S)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one as light yellow solid. The collected light yellow solid was purified by prep-chiral-HPLC (CHIRALPAK IC-3, 0.46*5 cm; 3 um, (Hex:DCM=1:1)(0.1% DEA):EtOH=50:50, 25° C.) to yield: (3S,8aR)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid, LC/MS (ES, m/z): mass calculated for $C_{23}H_{18}ClF_2N_9O$: 509.13, measured: 510.05 $[M+H]^+$;

$^1$H-NMR (400 MHz, DMSO-$d_6$) δ 11.60-12.02 (m, 1H), 9.84 (s, 1H), 7.88-8.11 (m, 2H), 7.72 (dd, J=8.6, 1.5 Hz, 1H), 7.04 (s, 1H), 6.33-6.49 (m, 1H), 6.25 (s, 2H), 5.70 (d, J=2.6 Hz, 1H), 4.99 (d, J=8.5 Hz, 1H), 3.60-3.90 (m, 1H), 2.71 (t, J=14.8 Hz, 1H), 1.85-2.27 (m, 5H). $^{19}$F NMR (376 MHz, DMSO-$d_6$) δ −70.81, −112.88.

and (3S,8aS)-3-(5-(6-amino-2-fluoropyridin-3-yl)-1H-imidazol-2-yl)-7-(3-chloro-2-fluoro-6-(1H-tetrazol-1-yl)phenyl)-2,3,8,8a-tetrahydroindolizin-5(1H)-one as a white solid, LC/MS: mass calculated for $C_{23}H_{18}ClF_2N_9O$: 509.13, measured: 510.05 $[M+H]^+$.

BIOLOGICAL AND FORMULATION EXAMPLES

Biological Example 1: Factor XIa Inhibition Assay Utilizing a Fluorophore-Quencher Pair Peptide Substrate A fluorescence intensity (FLINT) based assay was used to monitor inhibition of Factor XIa. The peptide substrate, 5Fam-KLTRAETV-$K_5$Tamra (purchased from New England Peptide) was chosen based on the FXI sequence. Conversion of zymogen FXI to its activated form, FXIa, occurs by proteolytic cleavage by FXIa at two sites, Arg146 and Arg180. The custom peptide used in this assay was based on the Arg146 cleavage site of FXI. The peptide substrate was designed with a fluorophore-quencher pair, where the fluorescence is quenched until FXIa cleaves the 8-mer peptide after the Arg residue. The substrate $K_M$ was fit to a substrate inhibition model whereby $k_{cat}$=0.86 $s^{-1}$, $K_M$=12.4 μM, $K_i$=61.6 μM with an enzymatic efficiency, and $k_{cat}/K_M$=69523 $M^{-1}$ $s^{-1}$.

The Factor XIa FLINT assay was used with the following 5Fam-KLTRAETV-K5Tamra assay buffer: 50 mM Tris, pH 7.5, 100 mM NaCl, 5 mM $CaCl_2$), 0.1 mg/mL BSA, 0.03% CHAPS. Assay buffer was prepared by mixing all ingredients fresh. 5Fam-KLTRAETV-K5Tamra peptide substrate was first prepared at 10 mM in 100% DMSO, then diluted to 3 mM in 100% DMSO. Assay buffer was then added directly to the 3 mM stock of substrate to prepare the 30 μM 2× working concentration (15 μM final concentration). The 2×Factor XIa stock solution was prepared by diluting 6.562 μM stock in 1× assay buffer for a 200 μM working stock solution (100 μM final concentration).

Test compound(s) were run in an 11-point, 3-fold serial dilution with a final top compound concentration of 100 nM. Final DMSO in assay was 2%. FXIa was preincubated with compound for 30-minutes and then substrate was added to initiate the reaction. The assay was run with kinetic (KIN) reads at 5 min intervals over 30 minutes. The time course was linear using 100 μM FXIa greater than 30 minutes. More specifically, the assay was run as follows:

- 100 nL of 0.01 mM test compound was dispensed into black 384 well non-binding Greiner BioOne 784900 plate for 0.1 μM final concentration;
- 5 μL of 1× assay buffer was dispensed to column 24 (low control) and 5 μL 2× Factor XIa solution was dispensed to columns 1-23 (column 23 high control);
- the plate was centrifuged with a "cover" plate at 500 rpm for 1 min
- the plate was pre-incubated for 30 minutes at room temperature with plate covered;
- 5 μL of 2×5Fam-KLTRAETV-K5Tamra peptide substrate was dispensed into the entire plate, columns 1-24;
- the plate was centrifuged with a "cover" plate at 500 rpm for 1 min;
- the plate was read monitoring fluorescence intensity on the BMG PHERAStar at room temperature, using fluorescence module 485 nm/520 nm.

Percent inhibition ($IC_{50}$) curves were generated per compound tested, and data was analyzed using a 4-parameter logistic fit using GeneData Screener. The relative fluorescence unit (RFU) values were normalized to percent inhibition using the following equation:

$$\% \text{ inhibition}=((HC-LC)-(\text{compound}-LC)/(HC-LC))*100$$

where LC—low control=mean signal of no Factor XIa or 100% inhibition of Factor XIa; HC—high control=mean signal of Factor XIa+5Fam-KLTRAETV-K5Tamra peptide substrate with DMSO only.

An 11-point dose response curve for the test compound(s) was generated using GENDATA to determine $IC_{50}$ value based on the following equation:

$$Y=\text{Bottom}+(\text{Top}-\text{Bottom})/(1+10\hat{}((\log IC_{50}-X)*\text{HillSlope}))$$

where Y is the % inhibition in the presence of X inhibitor concentration, Top=high control=mean signal of Factor XIa+5Fam-KLTRAETV $K_5$Tamra peptide substrate with DMSO only; Bottom=low control−mean signal of no Factor XIa or 100% inhibition of Factor XIa; HillSlope—Hill coefficient; and $IC_{50}$=concentration of compound with 50% inhibition in relation to top/high control.

Biological Example 2: Kallikrein Inhibition Assay Utilizing a Quenched AMC Peptide Substrate A fluorescence intensity (FLINT) based assay was used to monitor inhibition of human plasma kallikrein. The peptide substrate, Z-Gly-Pro-Arg-AMC (Purchased from Bachem; Catalog #I-1150) was chosen based on its relatively low $K_M$ for kallikrein which enables running the assay at lower substrate concentrations to control background fluorescence. The kinetic parameters for this substrate were determined by fitting titration data to the Michaelis-Menten equation yielding a $K_M$=40 μM, $k_{cat}$=0.76 $s^{-1}$, and $k_{cat}/K_M$=18932 $M^{-1}s^{-1}$.

The Kallikrein FLINT assay was used with the following Z-Gly-Pro-Arg-AMC assay buffer: 50 mM Tris, pH 7.5, 100 mM NaCl, 5 mM $CaCl_2$), 0.1 mg/mL BSA, 0.03% CHAPS. Assay buffer was prepared by mixing all ingredients fresh. 2× Z-Gly-Pro-Arg-AMC peptide substrate was prepared by diluting 10 mM stock into 1× assay buffer for a 100 μM working concentration (50 μM final concentration). The 2× kallikrein stock solution was prepared by diluting 14.76 μM stock in 1× assay buffer for a 4 nM working stock solution (2 nM final concentration).

Test compound(s) were run in an 11-point, 3-fold serial dilution with a final top compound concentration of 1 μM. Final DMSO in assay was 2%. Plasma kallikrein was pre-incubated for 30-minute with compound and then 50 μM substrate was added to initiate the reaction. The assay was run with kinetic (KIN) reads at 5 min intervals over 30 minutes. The time course was linear using 2 nM kallikrein greater than 30 minutes. More specifically, the assay was run as follows:

- 100 nL of 0.1 mM test compound was dispensed into black 384-well non-binding Greiner BioOne 784900 plate for 1 μM final concentration;
- 5 μL of 1× assay buffer was dispensed to columns 24 (low control) and 5 μL 2× human kallikrein enzyme solution was dispensed to columns 1-23 (column 23 high control);
- the plate was centrifuged with a "cover" plate at 500 rpm for 1 min
- the plate was pre-incubated for 30 minutes at room temperature with plate covered;
- 5 μL of 2× Z-Gly-Pro-Arg-AMC peptide substrate was dispensed into the entire plate, columns 1-24;
- the plate was centrifuged with a "cover" plate at 500 rpm for 1 min;
- the plate was read monitoring fluorescence intensity on the BMG PHERAStar at room temperature, using fluorescence module 340 nm/440 nm.

Percent inhibition ($IC_{50}$) curves were generated per compound tested, and data was analyzed using a 4-parameter logistic fit using GeneData Screener. The relative fluorescence unit (RFU) values were normalized to percent inhibition using the following equation:

$$\% \text{ inhibition}=((HC-LC)-(\text{compound}-LC)\backslash(HC-LC))*100$$

where LC—low control=mean signal of human kallikrein enzyme or 100% inhibition of human kallikrein enzyme; HC—high control=mean signal of Factor XIa+Z-Gly-Pro-Arg-AMC peptide substrate with DMSO only.

An 11-point dose response curve for the test compound(s) was generated using GENDATA to determine $IC_{50}$ value based on the following equation:

$$Y=\text{Bottom}+(\text{Top}-\text{Bottom})/(1+10\^{}((\log IC_{50}-X)*\text{HillSlope}))$$

where Y is the % inhibition in the presence of X inhibitor concentration, Top=high control=mean signal of human kallikrein enzyme+Z-Gly-Pro-Arg-AMC peptide substrate with DMSO only; Bottom=low control–mean signal of no human kallikrein enzyme or 100% inhibition of human kallikrein enzyme; HillSlope—Hill coefficient; and $IC_{50}$=concentration of compound with 50% inhibition in relation to top/high control.

Representative compounds of the present invention were tested according to the procedure described in Biological Example 1 and Biological Example 2 above, with results as listed in Table 3, below.

TABLE 3

Biological Activity, Representative Compounds of Formula (I)

| Example | FXIa Kin Inh $IC_{50}$ (nM) | Kallikrein Kin Inh $IC_{50}$ (nM) |
|---|---|---|
| 1 | 12.6 | 67.9 |
| 2 | 1.9 | 9.3 |
| 3 | 3.9 | 5.4 |
| 4 | 91.7 | 867.4 |
| 5 | 4.2 | 48.8 |
| 6 | 0.6 | 6.6 |
| 7 | 6.4 | 70.1 |
| 8 | 3.7 | 17.7 |
| 9 | 2.1 | 8.5 |
| 10 | 36.1 | 26.8 |
| 11 | 11.4 | 30.5 |
| 12 | 2.7 | 35.5 |
| 13 | 4.2 | 68.6 |
| 14 | 3.8 | 6.5 |
| 15 | 3.7 | 27.5 |
| 16 | 61.0 | 330.1 |
| 17 | 3.0 | 29.0 |
| 18 | 82.1 | 465.3 |
| 19 | 2.4 | 7.4 |
| 20 | 1.0 | 9.5 |
| 21 | 6.3 | 65.5 |
| 22 | 47.8 | 102.9 |
| 23 | 50.1 | 264.7 |
| 24 | 74.4 | 92.0 |
| 25 | >100 | 479.7 |
| 26 | >100 | 269.6 |
| 27 | >100 | 118.1 |
| 28 | 1.3 | 9.4 |
| 29 | 57.9 | 307.0 |
| 30 | 2.1 | 4.4 |
| 31 | 0.7 | 1.8 |
| 32 | 1.5 | 2.9 |
| 33 | 3.9 | 33.2 |
| 34 | 0.6 | 32.8 |
| 35 | 60.1 | 244.6 |
| 36 | 5.1 | 33.7 |
| 37 | 1.3 | 55.8 |
| 38 | 2.1 | 2.6 |
| 39 | 95.6 | 136.5 |
| 40 | 0.8 | 6.4 |
| 41 | 44.7 | 54.2 |
| 42 | 1.0 | 4.6 |
| 43 | 2.1 | 4.0 |
| 44 | 1.8 | 11.4 |
| 45 | 4.4 | 41.3 |
| 46 | 5.4 | 35.5 |
| 47 | 5.7 | 42.6 |
| 48 | 22.5 | 72.4 |
| 49 | 31.3 | 11.4 |
| 50 | 19.8 | 31.6 |
| 51 | 3.8 | 4.4 |
| 52 | 3.2 | 9.5 |
| 53 | 1.7 | 2.8 |
| 54 | 0.8 | 67.9 |
| 56 | 35.2 | 59.2 |
| 57 | 20.2 | 105.8 |
| 58 | 0.7 | 49.2 |
| 59 | 3.1 | 12.0 |
| 61 | 0.5 | 44.4 |
| 63 | 6.9 | 6.2 |
| 64 | 11.5 | 156.3 |
| 65 | 45.4 | 419.9 |
| 66 | 55.0 | 25.9 |
| 67 | 10.7 | 85.7 |
| 68 | 30.0 | 58.0 |
| 69 | 0.3 | 3.8 |
| 70 | 0.3 | 2.6 |
| 71 | 13.8 | 19.4 |
| 72 | 6.5 | 2.3 |
| 73 | 0.6 | 2.7 |
| 74 | 2.6 | 4.9 |
| 75 | 4.3 | 38.3 |
| 76 | 0.7 | 1.9 |
| 77 | 1.3 | 5.0 |
| 78 | 40.9 | 136.5 |
| 79 | 7.5 | 12.2 |
| 80 | 1.3 | 11.2 |
| 81 | 0.7 | 1.8 |
| 83 | 17.4 | 57.5 |
| 84 | 0.3 | 3.0 |
| 85 | 11.1 | 8.9 |
| 86 | 4.6 | 3.2 |
| 87 | 0.9 | 1.6 |
| 88 | 1.5 | 1.9 |
| 89 | 5.8 | 7.4 |
| 90 | 0.5 | 5.5 |
| 92 | 3.7 | 6.0 |
| 93 | 10.3 | 3.1 |
| 94 | 12.3 | 121.5 |
| 95 | 3.5 | 23.9 |
| 96 | 5.4 | 2.6 |
| 97 | 1.6 | 4.6 |
| 98 | 0.6 | 9.0 |
| 99 | 2.3 | 3.2 |
| 100 | 1.9 | 5.1 |
| 101 | 0.6 | 1.9 |
| 102 | 10.3 | 9.6 |
| 103 | 1.6 | 53.1 |
| 104 | 16.6 | 35.4 |
| 105 | 62.9 | 125.1 |
| 106 | 11.0 | 27.0 |
| 107 | 0.7 | 6.5 |
| 108 | 2.9 | 5.7 |
| 109 | 4.8 | 35.8 |
| 110 | 11.0 | 6.9 |
| 111 | 2.9 | 3.8 |
| 112 | 9.6 | 20.6 |
| 113 | 3.2 | 27.3 |
| 114 | 9.4 | 55.9 |
| 115 | 1.5 | 1.9 |
| 116 | 8.3 | 64.4 |
| 117 | 2.9 | 24.8 |
| 118 | 0.4 | 1.7 |
| 119 | 0.6 | 11.7 |
| 120 | 4.5 | 67.7 |
| 121 | 0.7 | 16.9 |
| 122 | 4.0 | 53.1 |
| 123 | 0.4 | 8.6 |
| 124 | 0.4 | 11.6 |
| 125 | 0.5 | 9.6 |
| 126 | 0.5 | 4.6 |
| 127 | 10.9 | 12.9 |
| 128 | 6.1 | 12.8 |
| 129 | 0.4 | 5.4 |
| 130 | 3.5 | 12.7 |
| 131 | 0.9 | 11.7 |
| 132 | 0.4 | 6.8 |

TABLE 3-continued

Biological Activity, Representative Compounds of Formula (I)

| Example | FXIa Kin Inh $IC_{50}$ (nM) | Kallikrein Kin Inh $IC_{50}$ (nM) |
|---|---|---|
| 133 | 0.7 | 7.5 |
| 134 | 0.4 | 1.1 |
| 135 | 22.5 | 15.5 |
| 136 | 4.8 | 6.3 |
| 137 | 4.6 | 7.7 |
| 138 | 32.0 | 138.0 |
| 139 | 29.1 | 22.0 |
| 140 | 2.9 | 6.2 |
| 141 | 10.8 | 13.0 |
| 142 | 6.2 | 10.7 |
| 143 | 2.4 | 33.0 |
| 144 | 3.1 | 43.5 |
| 145 | 0.6 | 7.7 |
| 146 | 0.5 | 7.3 |
| 147 | 0.5 | 7.8 |
| 148 | 0.6 | 8.6 |
| 149 | 0.5 | 7.6 |
| 150 | 0.6 | 8.6 |
| 151 | 0.6 | 8.9 |
| 152 | 0.7 | 1.0 |
| 153 | 0.5 | 8.1 |
| 154 | 0.4 | 5.7 |
| 155 | 4.9 | 52.4 |
| 156 | 13.8 | 19.1 |
| 157 | 2.0 | 6.8 |
| 158 | 1.0 | 7.8 |
| 159 | 5.4 | 22.2 |
| 160 | 8.4 | 27.8 |
| 161 | 0.5 | 1.9 |
| 162 | 4.2 | 30.6 |
| 163 | 7.4 | 28.8 |
| 164 | 4.3 | 16.6 |
| 165 | 8.0 | 122.9 |
| 166 | 0.8 | 6.6 |
| 167 | 31.0 | 371.5 |
| 168 | 0.8 | 4.9 |
| 169 | 42.3 | 40.1 |
| 170 | 17.9 | 31.8 |
| 171 | 4.1 | 31.7 |
| 172 | 3.6 | 6.1 |
| 173 | 1.7 | 7.0 |
| 174 | 18.1 | 25.9 |
| 175 | 9.5 | 30.3 |
| 176 | 4.0 | 28.5 |
| 177 | 3.1 | 21.6 |
| 178 | 0.4 | 1.1 |
| 179 | 0.5 | 1.4 |
| 180 | 8.6 | 33.2 |
| 181 | 8.3 | 17.8 |
| 182 | 0.4 | 14.1 |
| 183 | 0.6 | 3.8 |
| 184 | 7.3 | 210.0 |
| 185 | 6.5 | 33.9 |
| 186 | 4.6 | 35.1 |
| 187 | 3.7 | 4.1 |
| 188 | 17.2 | 7.8 |
| 189 | 1.8 | 16.7 |
| 190 | 1.2 | 9.4 |
| 191 | 3.8 | 34.3 |
| 192 | 5.4 | 29.5 |
| 193 | 0.4 | 14.3 |
| 194 | 2.2 | 16.8 |
| 195 | 0.5 | 22.1 |
| 196 | 0.6 | 3.4 |
| 197 | 4.1 | 6.0 |
| 198 | 30.5 | 14.3 |
| 199 | 1.3 | 15.6 |
| 200 | 4.4 | 24.4 |
| 201 | 9.1 | 6.9 |
| 202 | 0.6 | 1.5 |
| 203 | 0.9 | 2.5 |
| 204 | 29.1 | 24.5 |
| 205 | 3.3 | 12.5 |
| 206 | 10.6 | 9.5 |
| 207 | 2.5 | 7.7 |

TABLE 3-continued

Biological Activity, Representative Compounds of Formula (I)

| Example | FXIa Kin Inh $IC_{50}$ (nM) | Kallikrein Kin Inh $IC_{50}$ (nM) |
|---|---|---|
| 208 | 4.6 | 7.8 |
| 209 | 46.5 | 37.9 |
| 210 | 9.3 | 20.7 |
| 211 | 0.2 | 0.8 |
| 212 | 20.5 | 90.9 |
| 213 | 39.4 | 197.1 |
| 214 | 1.4 | 1.7 |
| 215 | >100 | 117.2 |
| 216 | 19.6 | 27.4 |
| 217 | 4.5 | 32.6 |
| 218 | 0.3 | 0.7 |
| 219 | 2.1 | 1.9 |
| 220 | 5.0 | 9.7 |
| 221 | 2.3 | 7.7 |
| 222 | 1.8 | 12.6 |
| 223 | 15.9 | 138.3 |
| 224 | 0.5 | 8.0 |
| 225 | 2.6 | 16.6 |
| 226 | 10.2 | 38.4 |
| 227 | 3.5 | 11.4 |
| 228 | 18.8 | 162.2 |
| 229 | 54.9 | 342.3 |
| 230 | 0.4 | 11.1 |
| 231 | 37.1 | 84.6 |
| 232 | >100 | 17.8 |
| 233 | 24.2 | 6.7 |
| 234 | 1.0 | 0.6 |
| 235 | 4.7 | 21.1 |
| 236 | 5.3 | 21.6 |
| 237 | 5.6 | 1.5 |
| 238 | 0.2 | 0.7 |
| 239 | 1.5 | 15.9 |
| 240 | 0.6 | 12.9 |
| 241 | 3.3 | 14.9 |
| 242 | 10.8 | 18.7 |
| 243 | 52.0 | 653.0 |
| 244 | >100 | 730.1 |
| 245 | 76.8 | 558.1 |
| 246 | 1.8 | 141.2 |
| 247 | 0.7 | 15.6 |
| 248 | 1.0 | 1.5 |
| 249 | 0.2 | 0.4 |
| 250 | 0.2 | 0.7 |
| 251 | 32.2 | 226.4 |
| 252 | 0.6 | 4.5 |
| 253 | >100 | >1 μM |
| 254 | 16.7 | 150.4 |
| 255 | >100 | >1 μM |
| 256 | 1.4 | 67.5 |
| 257 | 0.5 | 0.7 |
| 258 | 0.3 | 0.8 |
| 259 | 2.7 | 21.0 |
| 260 | >100 | 462.2 |
| 261 | 0.3 | 0.7 |
| 262 | 45.8 | 149.7 |
| 263 | 2.3 | 33.7 |
| 264 | 1.1 | 2.1 |
| 265 | 0.4 | 1.0 |
| 266 | 0.9 | 1.1 |
| 267 | 1.0 | 9.0 |
| 268 | 68.1 | 285.5 |
| 269 | >100 | 792.7 |
| 270 | 0.2 | 0.4 |
| 271 | 0.8 | 0.9 |
| 272 | >100 | >1 μM |
| 273 | 0.5 | 2.0 |
| 274 | >100 | >1 μM |
| 275 | 24.4 | 15.6 |
| 276 | 0.6 | 1.2 |
| 277 | 0.2 | 1.1 |
| 278 | 0.5 | 1.9 |
| 279 | 0.9 | 1.5 |
| 280 | 0.6 | 1.2 |
| 281 | 0.3 | 0.8 |
| 282 | 1.2 | 9.0 |

TABLE 3-continued

Biological Activity, Representative Compounds of Formula (I)

| Example | FXIa Kin Inh $IC_{50}$ (nM) | Kallikrein Kin Inh $IC_{50}$ (nM) |
|---|---|---|
| 283 | 3.5 | 5.9 |
| 284 | 1.3 | 3.5 |
| 285 | 9.1 | 206.6 |
| 286 | 1.5 | 1.1 |
| 287 | ~30.4 | 379.8 |
| 288 | >200 | 1.1 μM |
| 289 | >200 | 491.7 |
| 290 | 134.0 | 1.2 μM |
| 291 | 0.5 | 7.4 |
| 292 | 0.3 | 0.7 |
| 293 | 79.7 | 1.2 μM |
| 294 | 77.0 | 46.2 |
| 295 | 0.7 | 2.6 |
| 296 | 0.6 | 5.4 |
| 297 | 0.3 | 1.0 |
| 298 | >100 | 1.05 μM |
| 299 | 5.2 | 5.6 |
| 300 | 1.4 | 2.0 |
| 301 | 3.1 | 17.7 |
| 302 | 10.4 | 29.1 |
| 303 | 0.9 | 4.4 |
| 304 | >100 | 322.9 |
| 305 | 0.7 | 1.7 |
| 306 | 0.5 | 11.8 |
| 307 | 0.3 | 0.7 |
| 308 | 92.7 | >100 |
| 309 | 1.9 | 1.3 |
| 310 | 33.6 | >100 |
| 311 | 0.3 | 0.7 |
| 312 | 0.3 | 0.6 |
| 313 | 0.2 | 0.6 |
| 314 | 1.0 | 3.2 |
| 315 | 31.1 | 34.8 |
| 316 | 5.0 | 25.5 |
| 317 | 5.3 | 12.9 |
| 318 | 54.1 | 71.5 |
| 319 | 2.2. μM | 454.6 |
| 320 | 23.5 | 3.8 |
| 321 | 78.7 | 342.5 |
| 322 | 0.8 | 10.3 |
| 323 | 18.9 | 36.3 |
| 324 | 14.3 | 95.0 |
| 325 | 1.2 | 7.0 |
| 326 | 1.0 | 12.4 |
| 327 | 0.6 | 9.5 |
| 328 | 3.4 | 45.9 |
| 329 | 0.5 | 1.3 |
| 330 | 0.9 | 2.4 |
| 331 | 347.1 | 2.4 μM |
| 332 | 85.8 | 542.3 |
| 333 | 282.4 | 1.1 μM |
| 334 | 210.9 | 7.3 μM |
| 335 | 5.7 | 22.7 |
| 336 | 9.3 | 47.9 |
| 337 | 1.5 | 12.7 |
| 338 | 1.0 | 8.4 |
| 339 | 134.3 | 2.05 μM |
| 340 | 0.3 | 1.9 |
| 341 | 0.2 | 1.3 |
| 342 | 22.6 | 405.1 |
| 344 | 202.3 | 1.3 μM |
| 345 | 2.6 | 14.5 |
| 346 | 1.3 | 8.2 |
| 347 | 0.6 | 5.5 |
| 348 | 0.5 | 6.4 |
| 349 | 0.6 | 5.6 |
| 350 | 1.3 | 18.5 |
| 351 | 2.7 | 7.8 |
| 352 | 0.3 | 4.9 |
| 353 | 12.9 | 17.5 |
| 354 | 0.2 | 2.6 |
| 355 | 0.2 | 1.4 |
| 356 | 7.4 μM | >10 μM |
| 357 | 64.1 | 2.3 μM |
| 358 | 0.3 | 6.8 |
| 359 | 0.5 | 11 |
| 360 | 12.0 | 110.0 |
| 361 | 0.7 | 6.1 |
| 362 | 0.1 | 2.5 |
| 363 | >100 | >1 μM |
| 364 | 87.0 | 610.0 |
| 365 | 2.7 | 7.3 |
| 366 | 1.4 | 19.0 |
| 367 | 0.4 | 7.5 |
| 368 | 0.7 | 7.4 |
| 369 | 0.2 | 0.5 |
| 370 | 0.2 | 0.9 |
| 371 | 36.3 | 56.5 |
| 372 | 0.3 | 1.2 |
| 373 | 0.7 | 39.6 |
| 374 | 0.8 | 1.5 |
| 376 | 7.3 | 208.7 |
| 378 | 14.5 | 114.6 |
| 379 | 0.6 | 2.2 |
| 380 | 0.8 | 4.2 |
| 381 | 17.1 | 13.6 |
| 382 | 1.4 | 27.7 |
| 383 | 3.1 | 12.6 |
| 384 | 1.7 | 6.6 |
| 385 | 3.6 | 26.8 |
| 386 | 1.3 | 9.5 |
| 387 | 1.3 | 3.8 |
| 388 | 0.5 | 1.9 |
| 389 | 1.4 | 12.4 |
| 390 | 0.4 | 1.3 |
| 391 | 33.3 | 35.4 |

Formulation Example 1

Solid, Oral Dosage Form—Prophetic Example

As a specific embodiment of an oral composition, 100 mg of any of Compound ID No. 354, prepared as described in Example 354, above is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

Throughout this application, various publications are cited. The disclosure of these publications is hereby incorporated by reference into this application to describe more fully the state of the art to which this invention pertains.

What is claimed:

1. A compound of formula (I)

(I)

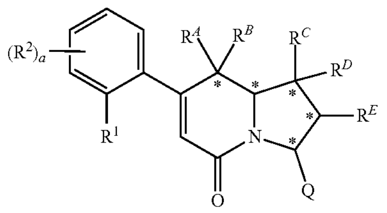

wherein $R^1$ is selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, —$NR^{A'}R^{B'}$, —C(O)—$C_{1-4}$alkyl, $C_{3-6}$cycloalkyl, phenyl and 5 to 6 membered heterocyclyl;

wherein the $C_{3-6}$cycloalkyl, phenyl or 5 to 6 membered heterocyclyl is optionally substituted with one or more substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy, —C(O)OH, —C(O)O—($C_{1-4}$alkyl), —$NR^{A'}NR^{B'}$, —($C_{1-4}$alkyl-$NR^{A'}R^{B'}$, $C_{3-7}$cycloalkyl and 5 to 6 membered heterocyclyl; and wherein $R^{A'}$ and $R^{B'}$ are each independently selected from the group consisting of hydrogen and $C_{1-4}$alkyl;

a is an integer from 0 to 3;

each $R^2$ is independently selected from the group consisting of chloro, fluoro, methyl and methoxy;

$R^A$ and $R^B$ are each independently selected from the group consisting of hydrogen and halogen;

alternatively, $R^A$ and $R^B$ are taken together with the carbon atom to which they are bound to form oxo;

$R^C$ is selected from the group consisting of hydrogen and $C_{1-4}$alkyl;

$R^D$ is selected from the group consisting of hydrogen, $C_{1-4}$alkyl and $C_{1-4}$alkoxy;

$R^E$ is selected from the group consisting of hydrogen and $C_{1-4}$alkyl;

Q is selected from the group consisting of (a)

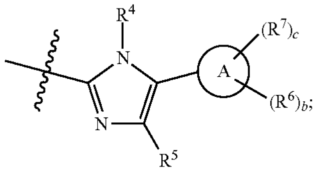

and (b)

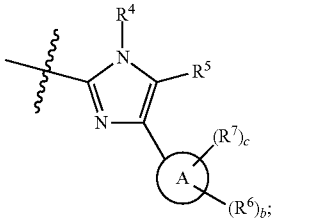

wherein $R^4$ is selected from the group consisting of hydrogen and $C_{1-4}$alkyl;

$R^5$ is selected from the group consisting of hydrogen, halogen and $C_{1-4}$alkyl;

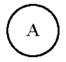

is selected from the group consisting of phenyl, 5-6 membered heteroaryl, and 9 to 10 membered heterocyclyl;

b is an integer from 0 to 1;

$R^6$ is selected from the group consisting of $C_{3-6}$cycloalkyl, —O—($C_{1-2}$alkylene)-$C_{3-6}$cycloalkyl, —C(O)—($C_{3-6}$cycloalkyl), —NH—($C_{3-6}$cycloalkyl), —NH—C(O)—($C_{3-6}$cycloalkyl), —C(O)—NH—($C_{3-6}$cycloalkyl), 4-6 membered heterocycloalkyl, —O—($C_{1-2}$alkylene)-(4-6 membered heterocycloalkyl), —C(O)-(4-6 membered heterocycloalkyl), —NH-(4-6 membered heterocycloalkyl), —C(O)—NH-(4-6 membered heterocycloalkyl), —NH—C(O)-(4-6 membered heterocycloalkyl), 5-6 membered heteroaryl, —O—($C_{1-2}$alkylene)-(5-6 membered heteroaryl), —C(O)-(5-6 membered heteroaryl), —NH-(5-6 membered heteroaryl), —NH—C(O)-(5-6 membered heteroaryl), —C(O)—NH-(5-6 membered heteroaryl), 2-oxa-6-azaspiro[3.3]hept-6-yl, 6-oxa-2-azaspiro[3.4]octan-2-yl, and 7-oxa-2-azaspiro[3.5]nonan-2-yl;

wherein the $C_{3-6}$cycloalkyl, 4-6 membered heterocycloalkyl, or 5-6 membered heteroaryl, whether alone or as part of a substituent group is optionally substituted with one or more substituents independently selected from the group consisting of halogen, $C_{1-4}$alkyl, hydroxy, oxo, cyano and $NR^PR^Q$;

wherein $R^P$ and $R^Q$ are each independently selected from the group consisting of hydrogen and $C_{1-4}$alkyl;

c is an integer from 0 to 3;

each $R^7$ is independently selected from the group consisting of halogen, $C_{1-4}$alkyl, fluorinated $C_{1-4}$alkyl, hydroxy substituted $C_{1-6}$alkyl, hydroxy substituted fluorinated $C_{1-2}$alkyl, cyano, $C_{1-4}$alkoxy, fluorinated $C_{1-2}$alkoxy, hydroxy substituted $C_{1-4}$alkoxy, —($C_{1-2}$alkylene)- O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-6}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-4}$alkyl), —C(O)—$NR^K$—$SO_2$—($C_{1-2}$alkyl), —($C_{1-2}$alkyene)-O—P(O)$(OH)_2$, and —($C_{1-2}$alkyene)-O—($C_{1-2}$alkylene)-P(O)$(OH)_2$; wherein $R^K$ and $R^L$ are each independently selected from hydrogen and $C_{1-4}$alkyl;

and wherein the heterocyclyl, heteroaryl or heterocycloalkyl present as any part of the

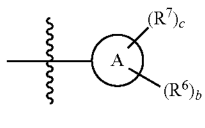

group contains a nitrogen atom, then said heterocyclyl, heteroaryl or heterocycloalkyl may be further substituted to form an N-oxide;

provided that when $R^1$ is 1,2,3,4-tetrazol-1-yl, a is 2, and the two $R^2$ groups are 2-fluoro and 3-chloro, then Q is other than (a)

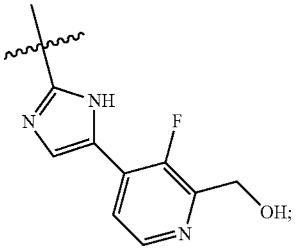

(b)

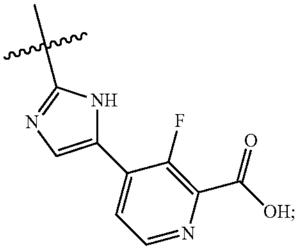

or (c)

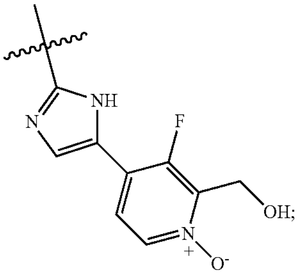

or a tautomer, stereoisomer, isotopologue, or pharmaceutically acceptable salt thereof.

2. The compound of claim 1, wherein $R^1$ is selected from the group consisting of halogen, $C_{1-4}$alkyl, fluorinated $C_{1-4}$alkyl, $C_{1-4}$alkoxy, fluorinated $C_{1-4}$alkoxy, phenyl and 5 to 6 membered heterocyclyl; wherein the phenyl or 5 to 6 membered heterocyclyl is optionally substituted with one or more substituents independently selected from the group consisting of halogen, $C_{1-4}$alkyl, fluorinated $C_{1-4}$alkyl, $C_{1-4}$alkoxy, and fluorinated $C_{1-4}$alkoxy;

a is an integer from 0 to 2;

each $R^2$ is independently selected from the group consisting of chloro, fluoro, and methyl;

$R^A$ and $R^B$ are each independently selected from the group consisting of hydrogen and halogen;

alternatively, $R^A$ and $R^B$ are taken together with the carbon atom to which they are bound to form oxo;

$R^C$ is selected from the group consisting of hydrogen and $C_{1-4}$alkyl;

$R^D$ is selected from the group consisting of hydrogen, $C_{1-4}$alkyl and $C_{1-4}$alkoxy;

$R^E$ is selected from the group consisting of hydrogen and $C_{1-4}$alkyl;

Q is selected from the group consisting of (a)

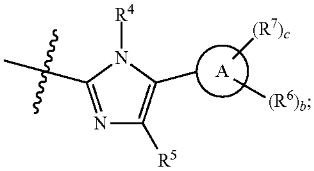

and (b)

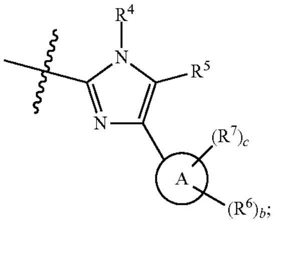

wherein $R^4$ is selected from the group consisting of hydrogen and $C_{1-4}$alkyl;

$R^5$ is selected from the group consisting of hydrogen, halogen and $C_{1-4}$alkyl;

b is an integer from 0 to 1;

$R^6$ is selected from the group consisting of $C_{3-6}$cycloalkyl, —O—($C_{1-2}$alkylene)-$C_{3-6}$ cycloalkyl, —NH—($C_{3-6}$cycloalkyl), —NH—C(O)—($C_{3-6}$cycloalkyl), 4-6 membered heterocycloalkyl, —O—($C_{1-2}$alkylene)-(4-6 membered heterocycloalkyl), —C(O)-(4-6 membered heterocycloalkyl), —NH-(4-6 membered heterocycloalkyl), —C(O)—NH-(4-6 membered heterocycloalkyl), 5-6 membered heteroaryl, —O—($C_{1-2}$alkylene)-(5-6 membered heteroaryl), —NH—C(O)-(5-6 membered heteroaryl), and 2-oxa-6-azaspiro[3.3]hept-6-yl;

wherein the $C_{3-6}$cycloalkyl, 4-6 membered heterocycloalkyl, or 5-6 membered heteroaryl, whether alone or as part of a substituent group is optionally substituted with one to two substituents independently selected from the group consisting of halogen, $C_{1-2}$alkyl, hydroxy, oxo, cyano and $NR^PR^Q$;

wherein $R^P$ and $R^Q$ are each independently selected from the group consisting of hydrogen and $C_{1-4}$alkyl;

c is an integer from 0 to 2;

each $R^7$ is independently selected from the group consisting of halogen, $C_{1-2}$alkyl, fluorinated $C_{1-2}$ alkyl, hydroxy substituted $C_{1-6}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^L$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-5}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-2}$alkyl), —C(O)—$NR^K$—$SO_2$—($C_{1-2}$alkyl), —($C_{1-2}$alkyene)-O—P(O)$(OH)_2$, and —($C_{1-2}$alkyene)-

O—($C_{1-2}$alkylene)-P(O)(OH)$_2$; wherein $R^K$ and $R^L$ are each independently selected from hydrogen and $C_{1-4}$alkyl;

provided that when $R^1$ is 1,2,3,4-tetrazol-1-yl, a is 2, and the two $R^2$ groups are 2-fluoro and 3-chloro, then Q is other than (a)

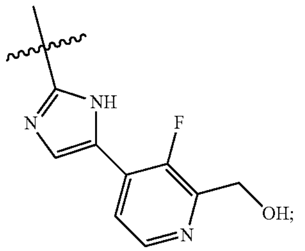

(b)

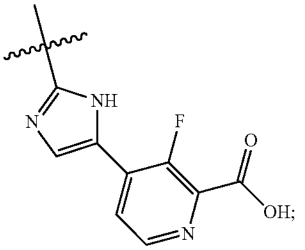

or (c)

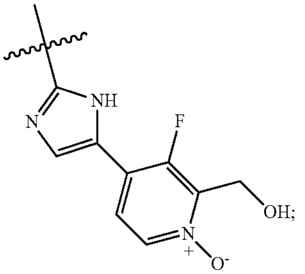

or a tautomer, stereoisomer, isotopologue, or pharmaceutically acceptable salt thereof.

3. The compound of claim 1, wherein $R^1$ is selected from the group consisting of fluorinated $C_{1-2}$alkyl, fluorinated $C_{1-2}$alkoxy, and 5-membered nitrogen containing heteroaryl; wherein the 5-membered nitrogen containing heteroaryl is optionally substituted with halogen or fluorinated $C_{1-2}$alkyl;

a is an integer from 1 to 2;

each $R^2$ is independently selected from the group consisting of chloro, fluoro and methyl;

$R^A$ and $R^B$ are each independently selected from the group consisting of hydrogen and halogen; alternatively, $R^A$ and $R^B$ are taken together with the carbon atom to which they are bound to form oxo;

$R^C$ is selected from the group consisting of hydrogen and $C_{1-2}$alkyl;

$R^D$ is selected from the group consisting of hydrogen, $C_{1-2}$alkyl and $C_{1-2}$alkoxy;

$R^E$ is selected from the group consisting of hydrogen and $C_{1-2}$alkyl;

Q is selected from the group consisting of (a)

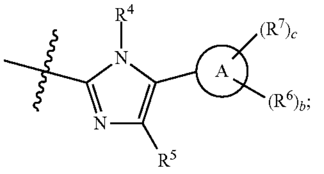

and (b)

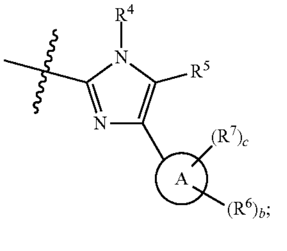

wherein $R^4$ is selected from the group consisting of hydrogen and $C_{1-2}$alkyl;

$R^5$ is selected from the group consisting of hydrogen, halogen and $C_{1-2}$alkyl;

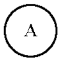

is selected from the group consisting of phenyl, 5 to 6 membered heteroaryl, and 9 to 10 membered heterocyclyl;

b is an integer from 0 to 1;

$R^6$ is selected from the group consisting of $C_{3-6}$cycloalkyl, —NH—C(O)—$C_{3-6}$cycloalkyl, 4-6 membered heterocycloalkyl, —O—($C_{1-2}$alkylene)-(4-6 membered heterocycloalkyl), —C(O)-(4-6 membered heterocycloalkyl), —NH-(4-6 membered heterocycloalkyl), —C(O)—NH-(5-6 membered heterocycloalkyl), 5-6 membered heteroaryl, —O—($C_{1-2}$alkylene)-(5-6 membered heteroaryl), —NH—C(O)-(5-6 membered heteroaryl), and 2-oxa-6-azaspiro[3.3]hept-6-yl;

wherein the $C_{3-5}$cycloalkyl, 4-6 membered heterocycloalkyl, or 5-6 membered heteroaryl, whether alone or as part of a substituent group is optionally substituted with one to two substituents independently selected from the group consisting of halogen, $C_{1-2}$alkyl, hydroxy, oxo, cyano, and $NR^PR^Q$; wherein $R^P$ and $R^Q$ are each independently selected from the group consisting of hydrogen and $C_{1-4}$alkyl;

c is an integer from 0 to 2;

each $R^7$ is independently selected from the group consisting of halogen, $C_{1-2}$alkyl, fluorinated $C_{1-2}$alkyl, hydroxy substituted $C_{1-6}$alkyl, hydroxy substituted fluorinated $C_{1-2}$alkyl, cyano substituted $C_{1-2}$alkyl, $C_{1-4}$alkoxy, fluorinated $C_{1-2}$alkoxy, hydroxy substituted $C_{1-4}$alkoxy, —($C_{1-2}$alkylene)-O—($C_{1-4}$alkyl), oxo, —C(O)OH, —C(O)O—($C_{1-2}$alkyl), —$NR^KR^L$, —$NR^K$-(hydroxy substituted $C_{1-4}$alkyl), —$NR^K$—($C_{1-2}$alkylene)-O—($C_{1-2}$alkyl), —C(O)—$NR^KR^L$, —C(O)—$NR^K$—O—($C_{1-4}$alkyl), —C(O)—$NR^K$—($C_{1-2}$alkylene)-O—($C_{1-2}$alkyl), —($C_{1-2}$alkylene)-C(O)—$NR^KR^L$, —$NR^K$—C(O)—($C_{1-4}$alkyl), —$NR^K$—C(O)-(fluorinated $C_{1-2}$alkyl), —$NR^K$—C(O)O—($C_{1-4}$alkyl), —$NR^K$—C(O)—$C_{3-6}$cycloalkyl, —($C_{1-2}$alkylene)-$NR^K$—C(O)—($C_{1-4}$alkyl), —($C_{1-2}$alkylene)-$NR^K$—C(O)O—($C_{1-4}$alkyl), —($C_{1-2}$alkylene)-O—C(O)-(amino substituted $C_{1-4}$alkyl), —$NR^K$—$SO_2$—($C_{1-2}$alkyl), —C(O)—$NR^K$—$SO_2$—($C_{1-2}$alkyl), —($C_{1-2}$alkyene)-O—P(O)$(OH)_2$, and —($C_{1-2}$alkyene)-O—($C_{1-2}$alkylene)-P(O)$(OH)_2$; wherein $R^K$ and $R^L$ are each independently selected from hydrogen and $C_{1-2}$alkyl;

and wherein the heterocyclyl, heteroaryl or heterocycloalkyl present as any part of the

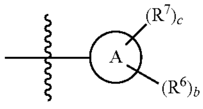

group contains a nitrogen atom, then said heterocyclyl, heteroaryl or heterocycloalkyl may be further substituted to form an N-oxide;

provided that when $R^1$ is 1,2,3,4-tetrazol-1-yl, a is 2, and the two $R^2$ groups are 2-fluoro and 3-chloro, then Q is other than (a)

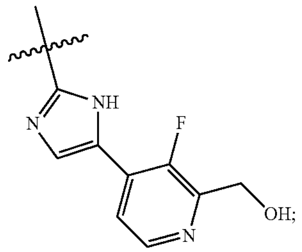

(b)

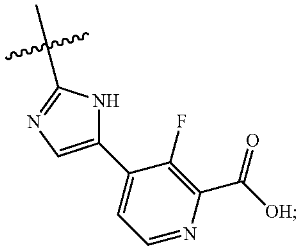

or (c)

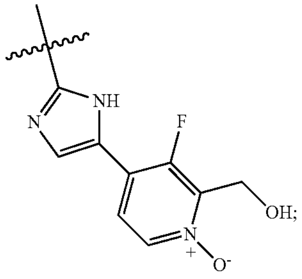

or a tautomer, stereoisomer, isotopologue, or pharmaceutically acceptable salt thereof.

4. The compound of claim 1, wherein $R^1$ is selected from the group consisting of difluoromethyl, difluoro-methoxy, 2,2,2-trifluoro-ethoxy, pyrazol-5-yl, imidazol-5-yl, 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, 3-chloro, 5-chloro and 3-methyl;

$R^A$ and $R^B$ are each independently selected from the group consisting of hydrogen, deuterium, and fluoro; alternatively, $R^A$ and $R^B$ are taken together with the carbon atom to which they are bound to form oxo;

$R^C$ is selected from the group consisting of hydrogen, deuterium, and methyl;

$R^D$ is selected from the group consisting of hydrogen, deuterium, methyl, S*-methyl, R*-methyl, S-methoxy, and R-methoxy;

$R^E$ is selected from the group consisting of hydrogen and methyl;

Q is selected from the group consisting of (a)

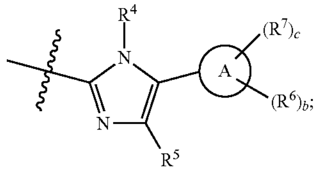

and (b)

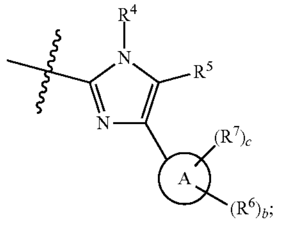

wherein $R^4$ is selected from the group consisting of hydrogen, deuterium, and methyl;

$R^5$ is selected from the group consisting of hydrogen, fluoro, chloro, bromo, and methyl;

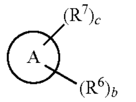

is selected from the group consisting of 2-methoxy-phenyl, 2-(isopropyloxy)-phenyl, 3-fluoro-4-carboxy-phenyl, 2-amino-phenyl, 2-(dimethyl-amino)-phenyl, 2-(amino-carbonyl)-phenyl, 2-fluoro-4-(amino-carbonyl)-phenyl, 2-fluoro-3-(amino-carbonyl)-phenyl, 3-(amino-carbonyl)-4-fluoro-phenyl, 3-fluoro-4-(amino-carbonyl)-phenyl, 2-(methyl-amino-carbonyl)-phenyl, 2-(dimethyl-amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 4-(1R-(methyl-carbonyl-amino)-ethyl)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl, 2-(methyl-sulfonyl-amino)-phenyl, 4-(oxazolidin-3-yl-2-one)-phenyl;

2-carboxy-thien-5-yl, 2-carboxy-3-fluoro-thien-5-yl, 2-(amino-carbonyl)-thien-4-yl, 2-(amino-carbonyl)- thien-5-yl, 2-(amino-carbonyl)-3-fluoro-thien-4-yl, 2-(amino-carbonyl)-3-fluoro-thien-5-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 4-chloro-pyrazol-3-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, 1-methyl-3-(cyclopropyl-carbonyl-amino)-pyrazol-4-yl, 1-methyl-4-(cyclopropyl-carbonyl-amino)-pyrazol-5-yl, imidazol-2-yl, 2-(trifluoro-methyl)-imidazol-4-yl, 1-methyl-imidazol-2-yl, 4-(hydroxy-methyl)-thiazol-2-yl, 2-(hydroxy-methyl)-thiazol-4-yl, 2-(amino-carbonyl)-thiazol-5-yl, 1,2,4-triazol-3-yl, 1,2,3-triazol-5-yl, 1-methyl-(1,2,4-triazol-3-yl), 1-methyl-1,2,3-triazol-5-yl;

3-fluoro-pyridin-4-yl-2-one, 3-fluoro-pyridin-4-yl, 2-fluoro-5-chloro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R*-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1S-hydroxy-ethyl)-3-fluoro-pyridin-4-yl, 2-(1R-(hydroxy-methyl)-ethyl)-3-fluoro-pyridin-4-yl, 2-(1S*-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S*-cyano-ethyl)-3-fluoro-pyridin-4-yl, 2-(1R*-cyano-ethyl)-3-fluoro-pyridin-4-yl, 4-amino-pyridin-3-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-amino-6-(trifluoro-methyl)-pyridin-5-yl, 2-(methyl-amino)-pyridin-3-yl, 2-fluoro-6-(methyl-amino)-pyridin-3-yl, 2-fluoro-6-(dimethyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R*-hydroxy-n-propyl)-3-fluoro-pyridin-4-yl, 2-fluoro-4-deutero-6-amino-pyridin-3-yl, 2-fluoro-5-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-4-yl, 2-(amino-carbonyl)-pyridin-5-yl, 2-(amino-carbonyl)-3-fluoro-pyridin-3-yl, 2-chloro-6-(amino-carbonyl)-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 3-chloro-6-(methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 4-(ethoxy-carbonyl-amino)-pyridin-3-yl, 2-(ethoxy-carbonyl-amino-methyl)-3-fluoro-pyridin-4-yl, 3-(methyl-carbonyl-amino)-6-(trifluoro-methyl)-pyridin-4-yl, 3-(d3-methyl-carbonyl-amino)-6-(trifluoro-methyl)-pyridin-4-yl, 2-(1S-amino-isopropyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(2-cyano-cycloprop-1-yl)-3-fluoro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(oxetan-3-yl)-3-fluoro-pyridin-4-yl, 2-(3-cyano-oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(pyrrolidin-1-yl-2-one)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-2-yl, 2-(pyrazol-5-yl)-pyridin-4-yl, 2-(pyrazol-5-yl)-3-fluoro-pyridin-4-yl, 2-(5-amino-pyrazol-1-yl)-pyridin-4-yl, 2-(3-amino-pyrazol-1-yl)-3-fluoro-pyridin-4-yl, 2-(5-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 2-(1,2,3-triazol-1-yl)-pyridin-4-yl, 1-(1,2,5-triazol-1-yl)-pyridin-4-yl, 2-(1,2,3-triazol-1-yl)-3-fluoro-pyridin-4-yl, 2-(1,3,4-triazol-1-yl)-3-fluoro-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1R*-oxazol-2-yl-ethoxy)-3-fluoro-pyridin-4-yl, 2-(1S*-oxazol-2-yl-ethoxy)-3-fluoro-pyridin-4-yl, 2-(1S-(1,3,4-oxadiazol-2-yl)-ethoxy)-3-fluoro-pyridin-4-yl, 2-(3,3-difluoro-azetin-1-yl-carbonyl)-3-fluoro-pyridin-4-yl, 2-fluoro-6-(bicyclo[1.1.1]pentanyl-amino)-pyridin-3-yl, 2-(bicyclo[1.1.1]pentanyl-amino)-3-fluoro-pyridin-3-yl, 2-(bicyclo[1.1.1]pentanyl-amino-carbonyl)-3-fluoro-pyridin-3-yl, 3-(cyclopropyl-carbonyl-amino)-6-(trifluoro-methyl)-pyridin-4-yl, 2-(3-methyl-isoxazol-5-yl-carbonyl-amino)-3-fluoro-pyridin-4-yl, pyridin-4-yl-2-one, pyridin-4-yl-N-oxide, 2-(hydroxy-methyl)-3-fluoro-pyridin-4-yl-N-oxide indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-b]pyridin-5-yl, 1H-pyrrolo[2,3-c]pyridin-3-yl, 5-methyl-1H-pyrrolo[2,3-c]pyridin-3-yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, and 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

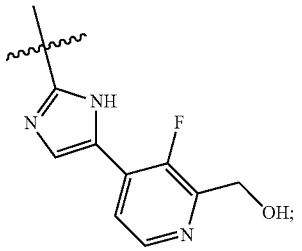

(b)

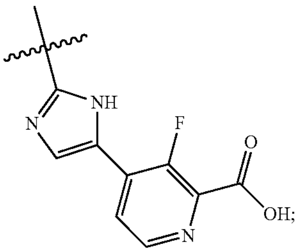

or (c)

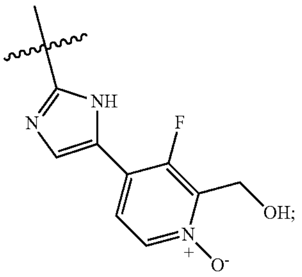

or a tautomer, stereoisomer, isotopologue, or pharmaceutically acceptable salt thereof.

5. The compound of claim 1, wherein $R^1$ is selected from the group consisting of 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is selected from the group consisting of hydrogen, and methyl;

$R^D$ is selected from the group consisting of hydrogen, methyl, S*-methyl, R*-methyl, S-methoxy, and R-methoxy;

$R^E$ is hydrogen;

Q is selected from the group consisting of (a)

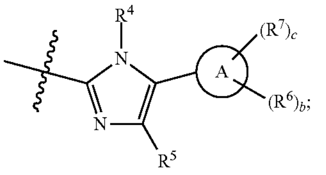

and (b)

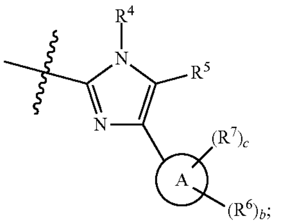

wherein $R^4$ is hydrogen;

$R^5$ is selected from the group consisting of hydrogen, deuterium, fluoro, chloro, bromo, and methyl;

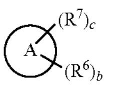

is selected from the group consisting of 2-methoxy-phenyl, 2-fluoro-4-(amino-carbonyl)-phenyl, 2-fluoro-3-(amino-carbonyl)-phenyl, 3-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 2-(methoxy-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl;

2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 2-(methyl-sulfonyl-amino-carbonyl)-3-fluoro-thien-5-yl, 3-(trifluoro-methyl)-pyrrol-4-yl, 3-fluoro-pyrazol-4-yl, 3-chloro-pyrazol-4-yl, 3-methoxy-pyrazol-4-yl, 3-(trifluoromethyl)-pyrazol-4-yl, 5-chloro-pyrazol-4-yl, 2-(amino-carbonyl)-thiazol-5-yl;

3-fluoro-pyridin-4-yl-2-one, 3-fluoro-pyridin-4-yl, 2-(difluoromethoxy)-pyridin-4-yl, 2-(trifluoro-methyl)-pyridin-4-yl, 2-(cyano-methyl)-3-fluoro-pyridin-4-yl, 2-(methoxy-methyl)-3-fluoro-pyridin-4-yl, 2-carboxy-3-fluoro-pyridin-4-yl, 2-(methoxy-carbonyl)-3-fluoro-pyridin-4-yl, 2-(hydroxy-methyl)-3-fluoro-pyridin-4-yl, 2-(hydroxy-d2-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-chloro-6-(hydroxy-methyl)-pyridin-3-yl, 2-fluoro-6-(hydroxy-methyl)-pyridin-3-yl, 2-(hydroxy-d2-methyl)-3-chloro-pyridin-4-yl, 2-(1R*-hydroxy-ethyl)-3-fluoro-pyridin-4-yl, 2-(1S*-hydroxy-ethyl)-3-fluoro-pyridin-4-yl, 2-(1R-hydroxy-ethyl)-3-fluoro-pyridin-4-yl, 2-(1S-hydroxy-ethyl)-3-fluoro-pyridin-4-yl, 2-(1R-(hydroxy-methyl)-ethyl)-3-fluoro-pyridin-4-yl, 2-(1S*-hydroxy-2,2-difluoro-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(1,1-difluoro-2-hydroxy-ethyl)-3-fluoro-pyridin-4-yl, 2-(2-methyl-2-hydroxy-n-propyl-oxy)-3-fluoro-pyridin-4-yl, 2-(1S*-cyano-ethyl)-3-fluoro-pyridin-4-yl, 2-(1R*-cyano-ethyl)-3-fluoro-pyridin-4-yl, 2-chloro-6-amino-pyridin-3-yl, 3-chloro-6-amino-pyridin-4-yl, 2-amino-3-methyl-pyridin-4-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(1,1-dimethyl-2-hydroxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-(3,3,3-trifluoro-2R*-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(N-ethyl-N-2-hydroxy-ethyl-amino)-3-fluoro-pyridin-4-yl, 2-(amino-carbonyl)-pyridin-5-yl, 2-(amino-carbonyl)-3-fluoro-pyridin-3-yl, 2-(2-methoxy-ethyl-amino-carbonyl)-3-fluoro-pyridin-4-yl, 2-(methoxy-amino-carbonyl)-3-fluoro-pyridin-4-yl, 2-(amino-carbonyl-methyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(methyl-carbonyl-amino-methyl)-3-fluoro-pyridin-4-yl, 2-(ethoxy-carbonyl-amino)-pyridin-3-yl, 2-(ethoxy-carbonyl-amino-methyl)-3-fluoro-pyridin-4-yl, 2-(1S-amino-isopropyl-carbonyl-oxo-methyl)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl)-3-chloro-pyridin-4-yl, 2-(1-hydroxy-cycloprop-1-yl)-3-fluoro-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(oxetan-3-yl)-3-fluoro-pyridin-4-yl, 2-(azetidin-1-yl)-3-fluoro-pyridin-4-yl, 2-(3-cyano-azetidin-1-yl)-3-fluoro-pyridin-4-yl, 2-(S-tetrahydrofuran-3-yl-amino)-3-fluoro-pyridin-4-yl, 2-(3S-hydroxy-piperidin-1-yl)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(3-amino-pyrazol-1-yl)-3-fluoro-pyridin-4-yl, 2-(3-amino-pyrazol-1-yl)-pyridin-4-yl, 2-(imidazol-2-yl)-3-fluoro-pyridin-4-yl, 1-(1,2,5-triazol-1-yl)-pyridin-4-yl, 2-(1,2,4-triazol-1-yl)-3-fluoro-pyridin-4-yl, 2-(oxazolidin-3-yl-2-one)-3-fluoro-pyridin-4-yl, 2-(2-oxa-6-azaspiro[3.3]hept-6-yl)-3-fluoro-pyridin-4-yl, 2-(dioxan-2S-yl-ethoxy)-3-fluoro-pyridin-4-yl, 2-(1S*-oxazol-2-yl-ethoxy)-3-fluoro-pyridin-4-yl, 2-(1S-(1,3,4-oxadiazol-2-yl)-ethoxy)-3-fluoro-pyridin-4-yl, 2-(bicyclo[1.1.1]pentanyl-amino)-3-fluoro-pyridin-3-yl, 3-(cyclopropyl-carbonyl-amino)-6-(trifluoro-methyl)-pyridin-4-yl, 2-(3-methyl-isoxazol-5-yl-carbonyl-amino)-3-fluoro-pyridin-4-yl, pyridin-4-yl-2-one;

indol-3-yl, indol-6-yl, indol-5-yl, indol-5-yl-2-one, 7-fluoro-indol-6-yl, indazol-5-yl, indazol-4-yl, 3-(methyl-amino)-indazol-6-yl, 3-amino-indazol-6-yl, indolin-5-yl-2-one, 6-methyl-indolin-7-yl-2-one, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, 3-amino-benzisoxazol-5-yl, benzoxazol-6-yl-2-one, quinolin-5-yl-2-one, quinolin-6-yl-2-one, 3,4-dihydro-2H-quinolin-6-yl-2-one, quinazolin-6-yl-2-one, 6-methyl-quinoxalin-5-yl-2(1H)-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-b]pyridin-3-yl, 1H-pyrrolo[2,3-c]pyridin-3-yl, 1H-pyrrolo[2,3-c]pyridin-3yl, 1H-pyrrolo[3,2-c]pyridin-3-yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1H-pyrazolo[3,4-b]pyridin-5-yl, 1,4-dihydro-2H-benzo[d][1,3]oxazin-6-yl-2-one, 5-fluoro-1,4-dihydro-2H-benzo[d][1,3]oxazin-6-yl-2-one, 2,3-dihydro-[1,4]dioxino[2,3-b]pyridin-8-yl, and 7-methyl-6,7-dihydro-5H-cyclopenta[b]pyridin-4-yl-7-ol;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

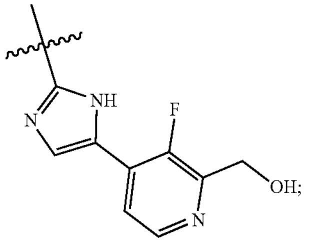

or (b)

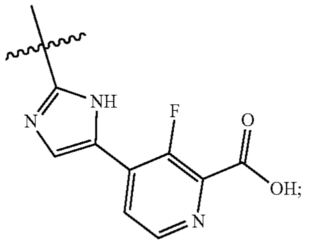

or a tautomer, stereoisomer, isotopologue, or pharmaceutically acceptable salt thereof.

6. The compound of claim 1, wherein $R^1$ is selected from the group consisting of 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is selected from the group consisting of hydrogen, and methyl;

$R^D$ is selected from the group consisting of hydrogen, methyl, S*-methyl, and R-methoxy;

$R^E$ is hydrogen;

Q is selected from the group consisting of (a)

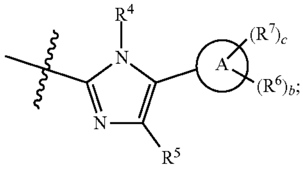

and (b)

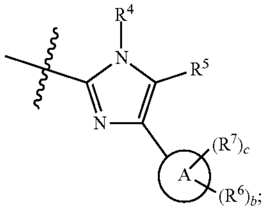

wherein $R^4$ is hydrogen;

$R^5$ is selected from the group consisting of hydrogen, deuterium, fluoro, and chloro;

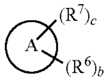

is selected from the group consisting of 2-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl;

2-carboxy-thien-5-yl, 2-carboxy-3-fluoro-thien-5-yl, 2-(amino-carbonyl)-thien-4-yl, 2-(amino-carbonyl)-thien-5-yl, 2-(amino-carbonyl)-3-fluoro-thien-4-yl, 3-(cyclopropyl-carbonyl-amino)-thien-2-yl, 3-(trifluoro-methyl)-pyrrol-4-yl, 3-chloro-pyrazol-4-yl, 3-(trifluoromethyl)-pyrazol-4-yl, 5-chloro-pyrazol-4-yl, 1-methyl-4-(cyclopropyl-carbonyl-amino)-pyrazol-5-yl, 2-(amino-carbonyl)-thiazol-5-yl;

2-carboxy-3-fluoro-pyridin-4-yl, 2-(hydroxy-methyl)-3-fluoro-pyridin-4-yl, 2-(2-hydroxy-ethyloxy)-pyridin-4-yl, 2-(2-hydroxy-n-propyl-oxy)-3-fluoro-pyridin-4-yl, 2-(2-hydroxy-2-methyl-n-propyl-oxy)-3-fluoro-pyridin-4-yl, 2-(hydroxy-d2-methyl)-3-chloro-pyridin-4-yl, 2-(1R-(hydroxy-methyl)-ethyl)-3-fluoro-pyridin-4-yl, 2-(1R*-hydroxy-2,2-difluoro-ethyl)-3-fluoro-pyridin-4-yl, 2-(3-hydroxy-3-methyl-n-butyl)-3-fluoro-pyridin-3-yl, 2-(2-methyl-2-hydroxy-n-propyl-oxy)-3-fluoro-pyridin-4-yl, 2-chloro-6-amino-pyridin-3-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-amino-3-methoxy-pyridin-4-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-(3,3,3-trifluoro-2S*-hydroxy-n-propyl)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 2-(methoxy-amino-carbonyl)-3-fluoro-pyridin-4-yl, 3-(trifluoromethyl-carbonyl-amino)-pyridin-4-yl, 3-(d3-methyl-carbonyl-amino)-pyridin-4-yl, 5-(methoxy-carbonyl-amino)-pyridin-2-yl, 2-(methoxy-carbonyl-amino)-pyridin-5-yl, 2-(methoxy-carbonyl-amino)-pyridin-4-yl, 2-(methoxy-carbonyl-amino)-3-fluoro-pyridin-4-yl, 2-(ethoxy-carbonyl-amino)-pyridin-3-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(phosphono-methoxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(3-cyano-azetidin-1-yl)-3-fluoro-pyridin-4-yl, 2-(S-tetrahydrofuran-3-yl-amino)-3-fluoro-pyridin-4-yl, 2-(pyrazol-1-yl)-pyridin-4-yl, 2-(pyrazol-5-yl)-pyridin-4-yl, 2-(pyrazol-5-yl)-3-fluoro-pyridin-4-yl, 2-(imidazol-2-yl)-3-fluoro-pyridin-4-yl, 1-(1,2,5-triazol-1-yl)-pyridin-4-yl, 2-(dioxan-2S-yl-ethoxy)-3-fluoro-pyridin-4-yl, pyridin-4-yl-2-one;

indol-5-yl-2-one, 7-fluoro-indol-6-yl, indazol-5-yl, 3-(methyl-amino)-indazol-6-yl, 3-amino-indazol-6-yl, benzimidiazol-5-yl, 2-methyl-benzimidazol-6-yl, benzimidazol-5-yl-2-one, 1-methyl-benzimidazol-6-yl-2-one, 1-methyl-benzimidazol-5-yl-2-one, benzoxazol-6-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 2,3-dihydrofuro[2,3-b]pyridin-4-yl, thieno[3,2-b]pyridin-7-yl, 1H-pyrrolo[2,3-b]pyridin-4-yl, 1H-pyrrolo[2,3-c]pyridin-3-yl, 1H-pyrrolo[2,3-c]pyridin-3yl, 6-methoxy-1H-pyrrolo[3,2-c]pyridin-3-yl, 7H-pyrrolo[2,3-d]pyrimidin-5-yl, 1H-pyrazolo[3,4-b]pyridin-4-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

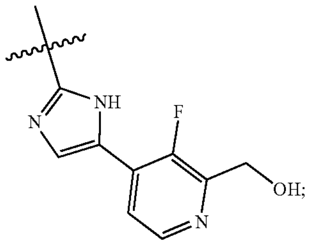

or (b)

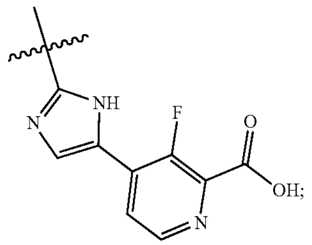

or a tautomer, stereoisomer, isotopologue, or pharmaceutically acceptable salt thereof.

7. The compound of claim 1, wherein $R^1$ is selected from the group consisting of 4-chloro-1,2,3-triazol-1-yl, 4-(trifluoromethyl)-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is selected from the group consisting of hydrogen, and methyl;

$R^D$ is selected from the group consisting of hydrogen, methyl, and R-methoxy;

$R^E$ is hydrogen;

Q is selected from the group consisting of (a)

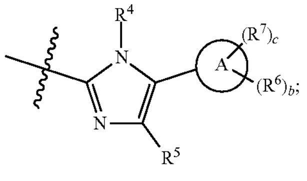

and (b)

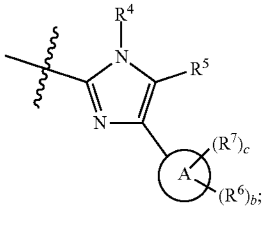

wherein $R^4$ is hydrogen;

$R^5$ is selected from the group consisting of hydrogen, deuterium, fluoro, and chloro;

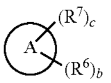

is selected from the group consisting of 2-fluoro-4-(amino-carbonyl)-phenyl, 2-(ethyl-carbonyl-amino)-phenyl, 2-(methyl-carbonyl-amino)-phenyl, 2-(isopropyl-carbonyl-amino)-phenyl, 4-(methoxy-carbonyl-amino)-phenyl, 2-(cyclopropyl-carbonyl-amino)-phenyl, 2-(cyclopentyl-carbonyl-amino)-phenyl, 2-(cyclopropyl-carbonyl-amino)-5-methoxy-phenyl, 2-(cyclopropyl-carbonyl-amino)-4-methoxy-phenyl;

2-carboxy-thien-5-yl, 2-carboxy-3-fluoro-thien-5-yl, 2-(amino-carbonyl)-thien-4-yl, 2-(amino-carbonyl)-thien-5-yl, 3-(trifluoro-methyl)-pyrrol-4-yl, 3-chloro-pyrazol-4-yl, 3-(trifluoromethyl)-pyrazol-4-yl, 1-methyl-4-(cyclopropyl-carbonyl-amino)-pyrazol-5-yl, 2-(amino-carbonyl)-thiazol-5-yl;

2-carboxy-3-fluoro-pyridin-4-yl, 2-(hydroxy-methyl)-3-fluoro-pyridin-4-yl, 2-(1R-(hydroxy-methyl)-ethyl)-3-fluoro-pyridin-4-yl, 2-(2-methyl-2-hydroxy-n-propyl-oxy)-3-fluoro-pyridin-4-yl, 2-fluoro-6-amino-pyridin-3-yl, 2-amino-3-fluoro-pyridin-4-yl, 2-fluoro-5-deutero-6-amino-pyridin-3-yl, 2-fluoro-6-(methyl-amino)-pyridin-3-yl, 2-amino-pyridin-4-yl, 2-amino-3-chloro-pyridin-4-yl, 2-chloro-6-amino-pyridin-3-yl, 2-(ethyl-amino)-3-fluoro-pyridin-4-yl, 2-(methoxy-ethyl-amino)-3-fluoro-pyridin-4-yl, 2-(2-methyl-2-hydroxy-n-propyl-amino)-3-fluoro-pyridin-4-yl, 2-fluoro-4-deutero-6-amino-pyridin-3-yl, 2-fluoro-4,5-dideutero-6-amino-pyridin-3-yl, 2-fluoro-4,5-dideutero-6-(methyl-amino)-pyridin-3-yl, 2-(methyl-amino)-3-fluoro-pyridin-4-yl, 5-(methoxy-carbonyl-amino)-pyridin-2-yl, 2-(methoxy-carbonyl-amino)-3-fluoro-pyridin-4-yl, 2-(methyl-sulfonyl-amino)-pyridin-4-yl, 2-(methyl-sulfonyl-amino)-3-fluoro-pyridin-4-yl, 2-(phosphono-oxy-methyl)-3-fluoro-pyridin-4-yl, 2-(1-hydroxy-cycloprop-1-yl)-pyridin-4-yl, 2-(1-hydroxy-cycloprop-1-yl-methoxy)-3-fluoro-pyridin-4-yl, 3-(cyclopropyl-carbonyl-amino)-pyridin-4-yl, 4-(cyclopropyl-carbonyl-amino)-pyridin-3-yl, 2-(S-tetrahydrofuran-3-yl-amino)-3-fluoro-pyridin-4-yl, 2-(pyrazol-5-yl)-pyridin-4-yl, 1-(1,2,5-triazol-1-yl)-pyridin-4-yl;

3-(methyl-amino)-indazol-6-yl, 3-amino-indazol-6-yl, benzimidazol-5-yl-2-one, quinolin-5-yl-2-one, quinolin-6-yl-2-one, 3,4-dihydro-2H-quinolin-6-yl-2-one, quinazolin-6-yl-2-one, 7-methyl-5H-cyclopenta[b]pyridin-4-yl, 1H-pyrrolo[2,3-b]pyridin-4-yl, 6-methoxy-1H-pyrrolo[3,2-c]pyridin-3-yl, 7H-pyrrolo[2,3-d]pyrimidin-5-yl, 1,4-dihydro-2H-benzo[d][1,3]oxazin-6-yl-2-one, 5-fluoro-1,4-dihydro-2H-benzo[d][1,3]oxazin-6-yl-2-one, and 2,3-dihydro-[1,4]dioxino[2,3-b]pyridin-8-yl;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (a)

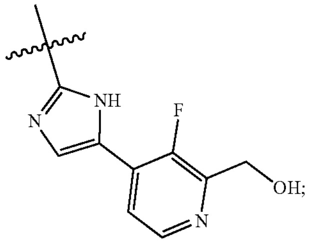

or (b)

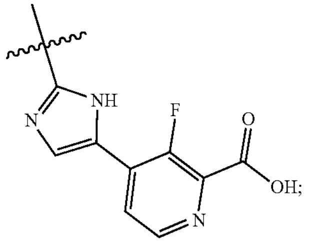

or a tautomer, stereoisomer, isotopologue, or pharmaceutically acceptable salt thereof.

8. The compound of claim 1, wherein $R^1$ is selected from the group consisting of 4-chloro-1,2,3-triazol-1-yl, and 1,2,3,4-tetrazol-1-yl;

a is an integer from 1 to 2;

each $R^2$ is independently selected from the group consisting of 2-fluoro, and 3-chloro;

$R^A$ and $R^B$ are each hydrogen;

$R^C$ is hydrogen;

$R^D$ is hydrogen;

$R^E$ is hydrogen;

Q is selected from the group consisting of (a)

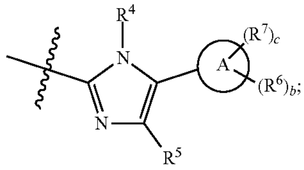

and (b)

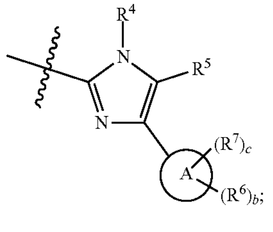

wherein $R^4$ is hydrogen;

$R^5$ is selected from the group consisting of hydrogen, deuterium, fluoro, and chloro;

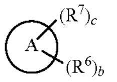

is selected from the group consisting of 4-(methoxy-carbonyl-amino)-phenyl, 2-(cyclopropyl-carbonyl-amino)-phenyl;

2-carboxy-thien-5-yl, 2-(amino-carbonyl)-thien-4-yl, 2-(amino-carbonyl)-thien-5-yl, 3-(trifluoro-methyl)-pyrrol-4-yl, 2-(amino-carbonyl)-thiazol-5-yl;

2-carboxy-3-fluoro-pyridin-4-yl, 2-fluoro-6-amino-pyridin-3-yl, 2-amino-3-fluoro-pyridin-4-yl, 2-fluoro-5-deutero-6-amino-pyridin-3-yl, 2-amino-pyridin-4-yl, 2-chloro-6-amino-pyridin-3-yl, 2-(ethyl-amino)-3-fluoro-pyridin-4-yl, 2-(2-methyl-2-hydroxy-n-propyl-amino)-3-fluoro-pyridin-4-yl, 2-fluoro-4,5-dideutero-6-amino-pyridin-3-yl, 2-(methyl-amino)-3-fluoro-pyridin-4-yl, 2-(methyl-sulfonyl-amino)-3-fluoro-pyridin-4-yl 2-(1-hydroxy-cycloprop-1-yl)-pyridin-4-yl, 3-(cyclopropyl-carbonyl-amino)-pyridin-4-yl;

3-(methyl-amino)-indazol-6-yl, 3-amino-indazol-6-yl, benzimidazol-5-yl-2-one, 2H-quinolin-6-yl-2-one, 3,4-dihydro-2H-quinolin-6-yl-2-one, 1H-pyrrolo[2,3-b]pyridin-4-yl, 1,4-dihydro-2H-benzo[d][1,3]oxazin-6-yl-2-one, and 5-fluoro-1,4-dihydro-2H-benzo[d][1,3]oxazin-6-yl-2-one;

and wherein one or both of (i) the hydrogen atom bound to the phenyl ring at the meta-position to $R^1$ and (ii) the hydrogen atom bound to the 8a-position of the 2,3,8,8a-tetrahydroindolizin-5(1H)-one are optionally deuterium;

provided that when $R^1$ is 1,2,3,4-tetrazol-1-yl, a is 2, and the two $R^2$ groups are 2-fluoro and 3-chloro, then Q is other than (b)

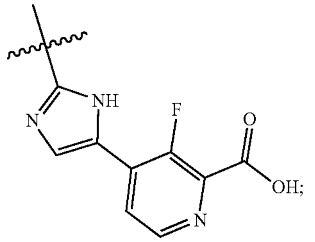

or a tautomer, stereoisomer, isotopologue, or pharmaceutically acceptable salt thereof.

9. The compound of claim 1, wherein $R^1$ is 1,2,3,4-tetrazol-1-yl;

a is 2;

the two $R^2$ are 2-fluoro, and 3-chloro;

$R^A$ and $R^B$ are each hydrogen;

$R^C$ is hydrogen;

$R^D$ is hydrogen;

$R^E$ is hydrogen;

Q is selected from the group consisting of (a)

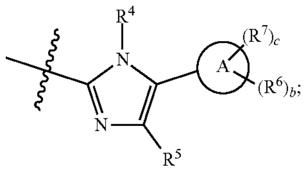

and

-continued (b)

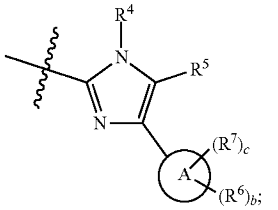

wherein $R^4$ is hydrogen;

$R^5$ is selected from the group consisting of hydrogen, and chloro;

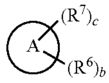

is selected from the group consisting of 4-(methoxy-carbonyl-amino)-phenyl, 2-(cyclopropyl-carbonyl-amino)-phenyl, 2-(amino-carbonyl)-thien-5-yl, 2-(amino-carbonyl)-thiazol-5-yl, 2-chloro-6-amino-pyridin-3-yl, 3-(cyclopropyl-carbonyl-amino)-pyridin-4-yl, 3-amino-indazol-6-yl, 2H-quinolin-6-yl-2-one, 1H-pyrrolo[2,3-b]pyridin-4-yl, and 1,4-dihydro-2H-benzo[d][1,3]oxazin-6-yl-2-one;

or a tautomer, stereoisomer, isotopologue, or pharmaceutically acceptable salt thereof.

10. The compound of claim 1, selected from the group consisting of (3S,8aR)-3-[5-(6-amino-2-fluoro-3-pyridyl)-1H-imidazol-2-yl]-7-[3-chloro-2-fluoro-6-(tetrazol-1-yl)phenyl]-2,3,8,8a-tetrahydro-1H-indolizin-5-one;

(3S,8aR)-3-[5-(6-amino-2-chloro-3-pyridyl)-1H-imidazol-2-yl]-7-[3-chloro-2-fluoro-6-(tetrazol-1-yl)phenyl]-2,3,8,8a-tetrahydro-1H-indolizin-5-one;

(3S,8aR)-7-[3-chloro-2-fluoro-6-(tetrazol-1-yl)phenyl]-3-[5-[3-fluoro-2-(2-hydroxy-2-methyl-propoxy)-4-pyridyl]-1H-imidazol-2-yl]-2,3,8,8a-tetrahydro-1H-indolizin-5-one;

(3S,8aR)-7-[3-chloro-2-fluoro-6-(tetrazol-1-yl)phenyl]-3-[5-[3-fluoro-2-(1-hydroxycyclopropyl)-4-pyridyl]-1H-imidazol-2-yl]-2,3,8,8a-tetrahydro-1H-indolizin-5-one;

(3S,8aR)-3-[5-(2-amino-3-fluoro-4-pyridyl)-1H-imidazol-2-yl]-7-[3-chloro-2-fluoro-6-(tetrazol-1-yl)phenyl]-2,3,8,8a-tetrahydro-1H-indolizin-5-one;

(3S,8aR)-7-[3-chloro-2-fluoro-6-(tetrazol-1-yl)phenyl]-3-[4-fluoro-5-[3-fluoro-2-(hydroxymethyl)-4-pyridyl]-1H-imidazol-2-yl]-2,3,8,8a-tetrahydro-1H-indolizin-5-one;

(3S,8aR)-7-[5-chloro-2-(tetrazol-1-yl)phenyl]-3-[4-fluoro-5-[3-fluoro-2-(hydroxymethyl)-4-pyridyl]-1H-imidazol-2-yl]-2,3,8,8a-tetrahydro-1H-indolizin-5-one;

(3S*,8aR)-3-[5-(2-amino-3-fluoro-4-pyridyl)-1H-imidazol-2-yl]-7-[5-chloro-2-(tetrazol-1-yl)phenyl]-2,3,8,8a-tetrahydro-1H-indolizin-5-one;

methyl N-[4-[2-[(3S,8aR)-7-[3-chloro-2-fluoro-6-(tetrazol-1-yl)phenyl]-5-oxo-2,3,8,8a-tetrahydro-1H-indolizin-3-yl]-1H-imidazol-5-yl]-3-fluoro-2-pyridyl]carbamate;

(3S,8aR)-7-[3-chloro-2-fluoro-6-(tetrazol-1-yl)phenyl]-3-[5-(2,3-dihydro-[1,4]dioxino[2,3-b]pyridin-8-yl)-1H-imidazol-2-yl]-2,3,8,8a-tetrahydro-1H-indolizin-5-one;

and tautomers, isotopologues and pharmaceutically acceptable salts thereof.

11. The compound of claim 1 selected from the group consisting (a) a compound of formula (Ix)

(Ix)

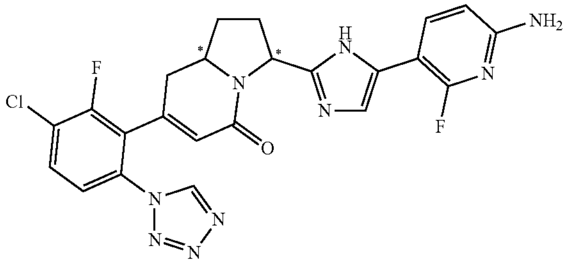

(b) a compound of formula (Iy)

(Iy)

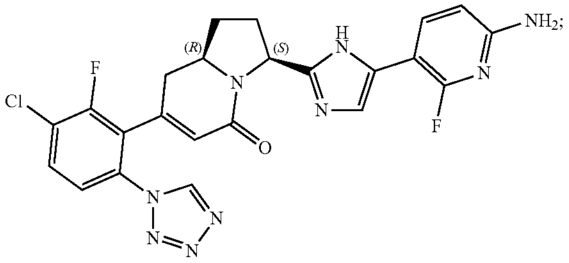

(c) a compound of formula (Iz)

(Iz)

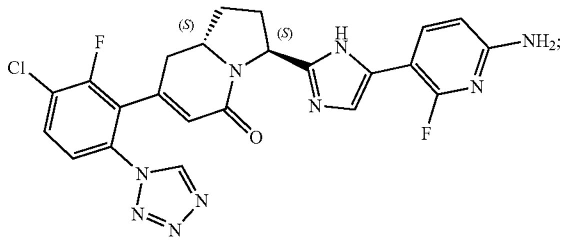

and tautomers, isotopologues, and pharmaceutically acceptable salts thereof.

12. A compound of formula (II)

(II)

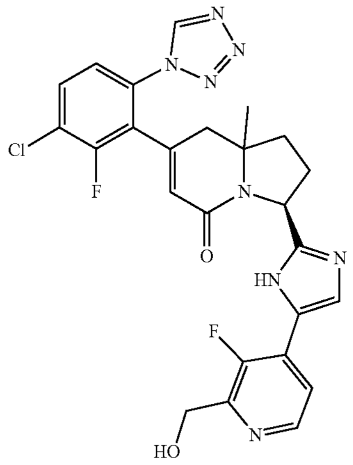

and tautomers, stereoisomers, isotopologues, and pharmaceutically acceptable salts thereof.

13. A compound selected from the group consisting of (a) a compound of formula (III)

(III)

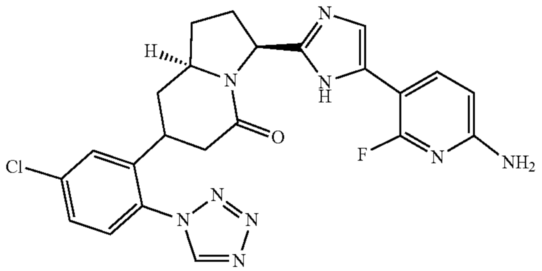

and tautomers, stereoisomers, isotopologues, and pharmaceutically acceptable salts thereof;

(b) a compound of formula (IV)

(IV)

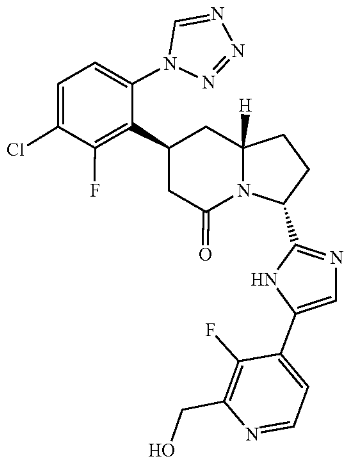

and tautomers, stereoisomers, isotopologues, and pharmaceutically acceptable salts thereof.

14. A pharmaceutical composition comprising a pharmaceutically acceptable carrier and a compound of claim 1.

* * * * *